(12) United States Patent
Kim et al.

(10) Patent No.: US 9,732,126 B2
(45) Date of Patent: Aug. 15, 2017

(54) METHOD FOR CRYSTALLIZATION OF TRX-TXNIP COMPLEX MUTEIN AND 3D STRUCTURE THEREOF

(71) Applicant: KOREA RESEARCH INSTITUTE OF BIOSCIENCE AND BIOTECHNOLOGY, Daejeon (KR)

(72) Inventors: Myung Hee Kim, Daejeon (KR); Jung Won Hwang, Daejeon (KR); Tae Kwang Oh, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 14/414,370

(22) PCT Filed: Jul. 12, 2013

(86) PCT No.: PCT/KR2013/006286
§ 371 (c)(1),
(2) Date: Jan. 12, 2015

(87) PCT Pub. No.: WO2014/011003
PCT Pub. Date: Jan. 16, 2014

(65) Prior Publication Data
US 2015/0284436 A1 Oct. 8, 2015

(30) Foreign Application Priority Data

Jul. 12, 2012 (KR) ........................ 10-2012-0076310

(51) Int. Cl.
*C07K 14/47* (2006.01)
*G01N 33/574* (2006.01)
*C12N 9/02* (2006.01)
*G01N 33/53* (2006.01)

(52) U.S. Cl.
CPC .......... *C07K 14/47* (2013.01); *C07K 14/4702* (2013.01); *C12N 9/0051* (2013.01); *C12Y 108/01008* (2013.01); *G01N 33/5308* (2013.01); *G01N 33/57484* (2013.01); *C07B 2200/13* (2013.01); *G01N 2500/02* (2013.01); *G01N 2500/04* (2013.01)

(58) Field of Classification Search
None
See application file for complete search history.

(56) References Cited

U.S. PATENT DOCUMENTS

| 2005/0143402 | A1* | 6/2005 | Cheetham | C12N 9/1205 514/266.21 |
| 2011/0097317 | A1 | 4/2011 | Berk | |
| 2012/0058105 | A1* | 3/2012 | Ng | G01N 33/6893 424/130.1 |

OTHER PUBLICATIONS

Wiencek, J. M. Ann. Rev. Biomed. Eng. 1999, 1, 505-534.*
Fould et al., "Mutagenic analysis in a pure molecular system shows that thioredoxin-interacting protein residue Cys247 is necessary and sufficient for a mixed disulfide formation with thioredoxin," Protein Science, 21: 1323-1333 (2012).
Polekhina et al., "Crystallization and preliminary X-ray analysis of the N-terminal domain of human thioredoxin-interacting protein," Acta Crystallographica Section F: Structural Biology and Crystallization Communications, 67: 613-617 (2011).
Yoshihara et al., "Disruption of TBP-2 ameliorates insulin sensitivity and secretion without affecting obesity," Nature Communications, 1: 1-12 (2010).
Kalnine et al., "*Homo sapiens* thioredoxin [synthetic construct]," Protein—NCBI GenBank accession No. AAP36296 (2003).
Powis et al., "Thioredoxin signaling as a target for cancer therapy," Current Opinion in Pharmacology, 7: 392-397 (2007).
Mukherjee et al., "The thioredoxin system: a key target in tumour and endothelial cells," British Institute of Radiology (2014) abstract only.
Schulze et al., "Hyperglycemia Promotes Oxidative Stress through Inhibition of Thioredoxin Function by Thioredoxin-interacting Protein," Journal of Biological Chemistry, 279: 30369-30374 (2004).
Dunn et al., "The Emerging Role of the Thioredoxin System in Angiogenesis," Arteriosclerosis, Thrombosis, and Vascular Biology, 30: 2089-2098 (2010).
Spindel et al., "Thioredoxin Interacting Protein: Redox Dependent and Independent Regulatory Mechanisms," Antioxidants & Redox Signaling, 16: 587-596 (2012).
Shin et al., "hnRNP G elicits tumor suppressive activity in part by upregulating the expression of Txnip," Biochemical and Biophysical Research Communications, 372: 880-885 (2008).
Sheth et al., "Hepatocellular carcinoma in Txnip-deficient mice," Oncogene, 25: 3528-3536 (2006).
Matsuoka et al., "Involvement of thioredoxin-binding protein 2 in the antitumor activity of CD437," Cancer Science, 99: 2485-2490 (2008).
Muoio, "TXNIP Links Redox Circuitry to Glucose Control," Cell Metabolism, 5: 412-414 (2007).
Minn et al., "Thioredoxin-Interacting Protein Is Stimulated by Glucose through a Carbohydrate Response Element and Induces B-Cell Apoptosis," Endocrinology, 146: 2397-2405 (2005).
Stoltzman et al., "Glucose sensing by MondoA:Mlx complexes: A role for hexokinases and direct regulation of thioredoxin-interacting protein expression," Proceedings of the National Academy of Sciences, 105: 5912-6917 (2008).
Chen et al., "Thioredoxin-interacting protein deficiency induces Akt/Bcl-xL signaling and pancreatic beta-cell mass and protects against diabetes," The FASEB Journal, 322: 3581-3594 (2008).
Parikh et al., "TXNIP Regulates Peripheral Glucose Metabolism in Humans," PLoS Medicine, 4: 0868-0879, e158 (2007).
International Search Report issued in corresponding International Patent Application No. PCT/KR2013/006286 dated Oct. 15, 2013.

* cited by examiner

*Primary Examiner* — Suzanne M Noakes
(74) *Attorney, Agent, or Firm* — Morgan, Lewis & Bockius LLP

(57) ABSTRACT

The present invention relates to a modified TXNIP protein, a method for preparing the modified TXNIP protein, a polynucleotide encoding the modified protein, an expression vector including the polynucleotide, a transformant introduced with the expression vector, a method for crystallizing a modified TRX-TXNIP complex using the modified TXNIP protein, and a method for screening a substance regulating interaction between TRX and TXNIP, an inhibitor of TRX activity, or a substance regulating TXNIP function.

10 Claims, 41 Drawing Sheets

(SEQ ID NO: 1) Hs
(SEQ ID NO: 25) Mm
(SEQ ID NO: 26) Ss
(SEQ ID NO: 27) Dr

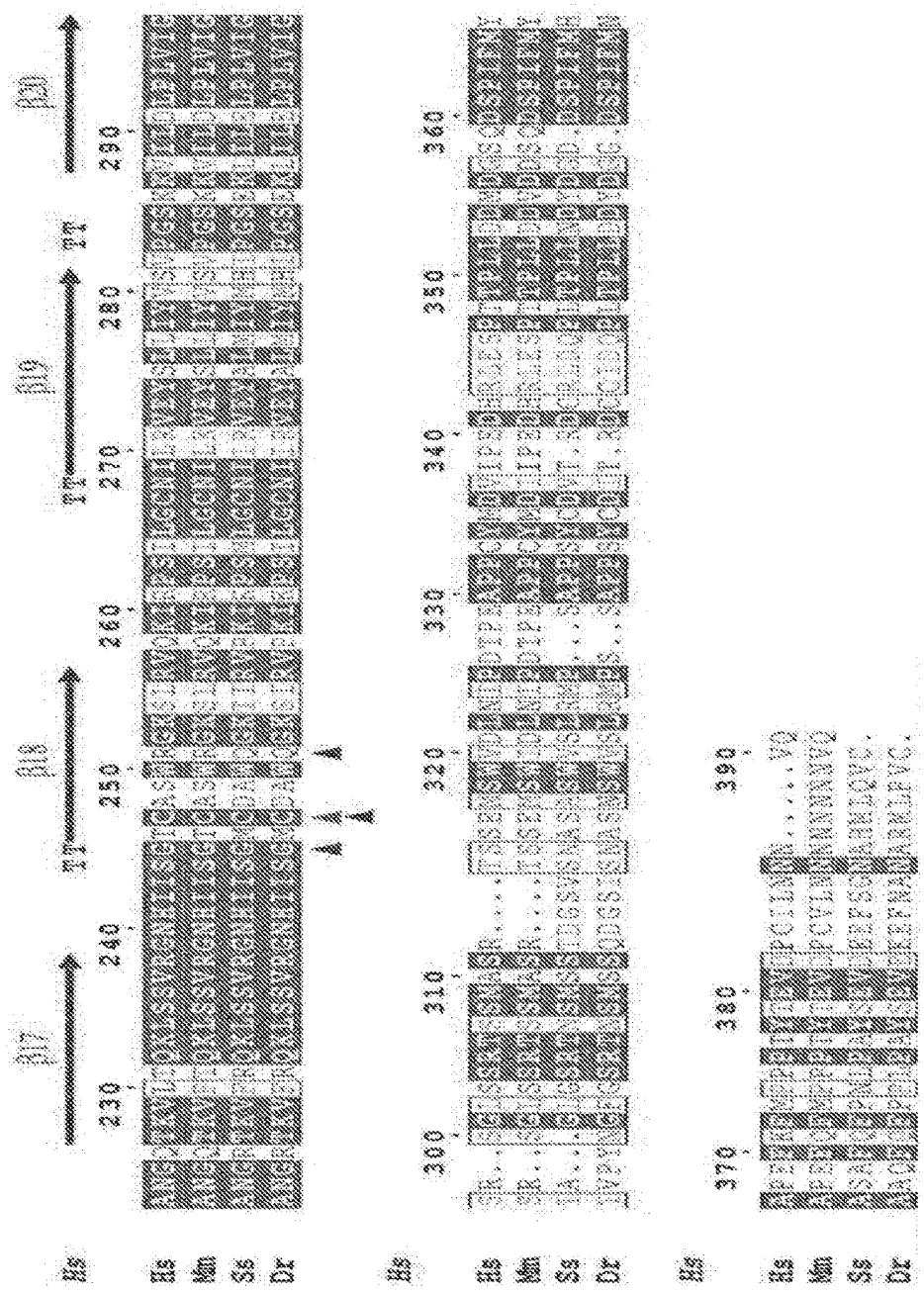
FIG. 13-continued

US 9,732,126 B2

METHOD FOR CRYSTALLIZATION OF TRX-TXNIP COMPLEX MUTEIN AND 3D STRUCTURE THEREOF

SEQUENCE LISTING SUBMISSION VIA EFS WEB

A computer readable text file, entitled "SequenceListing.txt," created on or about Mar. 23, 2017 with a file size of about 21 kb contains the sequence listing for this application and is hereby incorporated by reference in its entirety.

BACKGROUND OF THE INVENTION

1. Field of the Invention

The present invention relates to a modified TXNIP (thioredoxin-interacting protein) protein, a method for preparing the modified TXNIP protein, a polynucleotide encoding the modified protein, an expression vector comprising the polynucleotide, a transformant introduced with the expression vector, a method for crystallizing a modified TRX(thioredoxin)-TXNIP complex using the modified TXNIP protein, and a method for screening a substance regulating interaction between TRX and TXNIP, an inhibitor of TRX activity, and a substance regulating TXNIP function, using the crystal structure of the TRX-TXNIP complex mutein.

2. Description of the Related Art

TRX, which is up-regulated in many cancers, is involved in a wide range of cell signaling processes comprising cellular immune response, in response to a variety of oxidative stresses, and thus TRX is an important protein that has received much attention from the world's major pharmaceutical companies as an attractive target for anticancer drugs (Powis, G. et al., 2007 *Current Opinion in Pharmacology* 7:392, Mukherjee, A. et al., 2008 *The British Journal of Radiology* 81:S57). TXNIP, the only currently known endogenous inhibitor of TRX, inhibits interaction between TRX and a range of proteins involved in cell signaling as well as redox-potential activity of TRX. Therefore, studies have been actively conducted on TRX-TXNIP roles in cancers and metabolic diseases (Schulze, P. C. et al., 2004 *J Biol Chem* 279:30369, Dunn, L. L. et al., 2010 *Arteriosclerosis, Thrombosis, and Vascular Biology* 30:2089, Spindel, O. N. et al., 2012 *Antioxidants & Redox Signaling* 16:587), which is strongly supported by the experimental results that TXNIP is strongly down-regulated in a variety of tumor cells and tissues (Shin, K. H. et al., 2008 *Biochem Biophys Res Commun* 372:880), and TXNIP knockout mice have an increased incidence of hepatocellular carcinoma (Sheth, S. S. et al., 2006 *Oncogene* 25:3528). The function of TXNIP as the tumor suppressor inhibiting TRX activity is well-known in the research related to inhibition of TRX-ASK1 (apoptosis signal-regulating kinase 1) interaction by TXNIP. That is, TXNIP-TRX interaction inhibits TRX-ASK1 interaction, leading to increased levels of reactive oxygen species (ROS) and promotion of cell apoptosis by ASK1 (Matsuoka, S. et al., 2008 *Cancer Science* 99:2485).

In addition to its function as an endogenous inhibitor of TRX, TXNIP is correlated with glucose levels (Muoio, D. M. 2007 *Cell Metabolism* 5:412, Parikh, H. et al., 2007 *PLoS Medicine* 4:2158). Glucose stimulates TXNIP transcription through a carbohydrate-response element present in the TXNIP promoter (Minn, A. H. et al., 2005 *Endocrinology* 146:2397) and its association with transcription factors MLX (max-like protein X) and MondoA (Stoltzman, C. A. et al., 2008 *Proc Natl Acad Sci USA* 105:6912). An elevated level of TXNIP has led to a reduction in the number of pancreatic beta-cells, insulin secretion, and peripheral glucose uptake (Parikh, H. et al., 2007 *PLoS Medicine* 4:2158, 23). By contrast, TXNIP deficiency protected against beta-cell apoptosis, and enhanced insulin sensitivity (Yoshihara, E. et al., 2010 *Nature Communications* 1:127, Chen, J. et al., 2008 *FASEB Journal* 22:3581). Despite considerable efforts to identify TXNIP characteristics and molecular mechanism of TRX regulation by TXNIP which are involved in metabolic diseases as well as cancers, understanding of TXNIP and regulation mechanism of TXNIP-TRX has reached a limit, because of a lack of their structural information.

Recent studies change their approach from a random approach to exploration of a number of anticancer drug candidates and therapeutic candidates to a new approach to development of effective therapeutic agents by exploration of target proteins, investigation of structure and reaction mechanism of the target proteins, and design and development of drug candidates through more efficient and scientific protein engineering. To design and develop drug candidates, investigation of their three-dimensional structures is essential. To investigate the three-dimensional structures, the priority is to acquire the protein in a stable form. However, the three-dimensional structure of the TXNIP protein, for all its importance, has not been revealed yet, because the TXNIP protein is a redox protein containing 11 cysteines, making it difficult to handle during production.

Accordingly, the present inventors have made many efforts to investigate the three-dimensional structure of the TXNIP protein. As a result, the present inventors have established a method for preparing a stable TRX-TXNIP complex having a purity of 90% or more, through various types of engineering, and they prepared a complex crystal of a TRX protein and a modified TXNIP protein, activity of which has no significant difference from that of the wild-type and demonstrated interaction between TRX and TXNIP at the protein level. Consequently, they have found that a substance capable of regulating the activities of TRX and TXNIP or interaction there between can be developed, based on the protein structure, thereby completing the present invention.

SUMMARY OF THE INVENTION

An object of the present invention is to provide a method for crystallizing a modified TRX-TXNIP complex, comprising a modified TXNIP protein and a modified TRX protein.

Another object of the present invention is to provide a crystal of the modified TXNIP protein, and a crystal of the modified TRX-TXNIP complex.

Still another object of the present invention is to provide a modified TXNIP protein, a polynucleotide encoding the protein, an expression vector comprising the polynucleotide, and a transformant introduced with the expression vector.

Still another object of the present invention is to provide a method for preparing the modified TXNIP protein.

Still another object of the present invention is to provide a method for screening a substance regulating interaction between TRX and TXNIP, by utilizing the three-dimensional structure of the modified TXNIP protein or the modified TRX-TXNIP complex.

Still another object of the present invention is to provide a method for screening an inhibitor of TRX activity, by utilizing the three-dimensional structure of the modified TXNIP protein or the modified TRX-TXNIP complex.

Still another object of the present invention is to provide a method for screening a substance regulating TXNIP function, by utilizing the three-dimensional structure of the modified TXNIP protein or the modified TRX-TXNIP complex.

BRIEF DESCRIPTION OF THE DRAWINGS

FIG. 6c shows that native T-TXNIP and its mutants were indistinguishable from full-length TXNIP in their ability to inhibit endogenous TRX. The TRX activity was analyzed by the insulin disulfide reduction assay. The data are expressed as mean±S.D. of all three independent experiments;

Figure 9A:
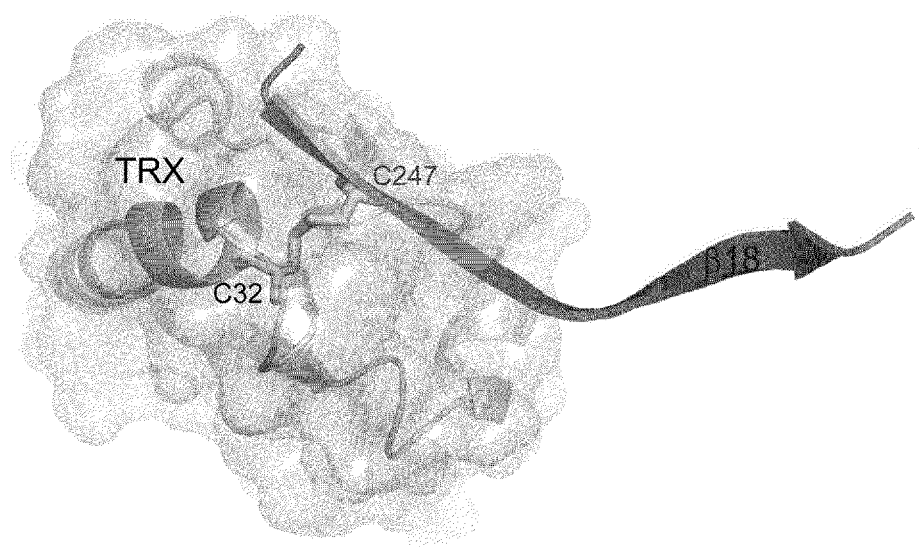
FIG. 9a shows the critical β-strand (β18, dark gray) of TXNIP interacting with TRX (transparent surface). The cleft formed by residues in the active site of TRX is shown in transparent gray under C247. The intermolecular disulfide-forming TRX Cys32 and TXNIP Cys247 residues are shown with stick atom models.
Figure 9B:
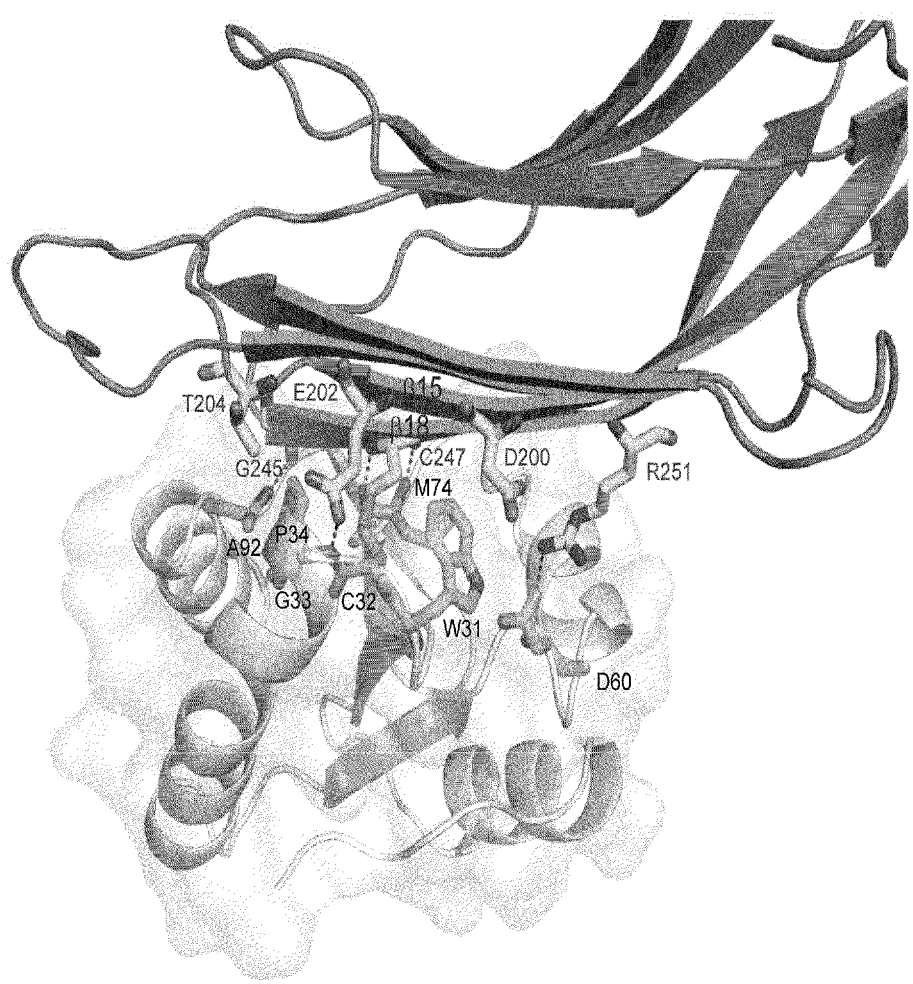
FIG. 9b shows a detailed stick depiction of the interactions between TRX (transparent surface) and TXNIP (upper). The backbone-backbone interactions between TRX Met74 and TXNIP Cys247, and TRX Ala92 and TXNIP Gly245, are displayed as short dashed lines. The salt bridge between TRX Asp60 and TXNIP Arg251; and the hydrogen bond between TRX Gly33 and TXNIP Glu202 are also shown as short dashed lines. Strands β15 and β18 in TXNIP are also indicated.
Figure 9C:
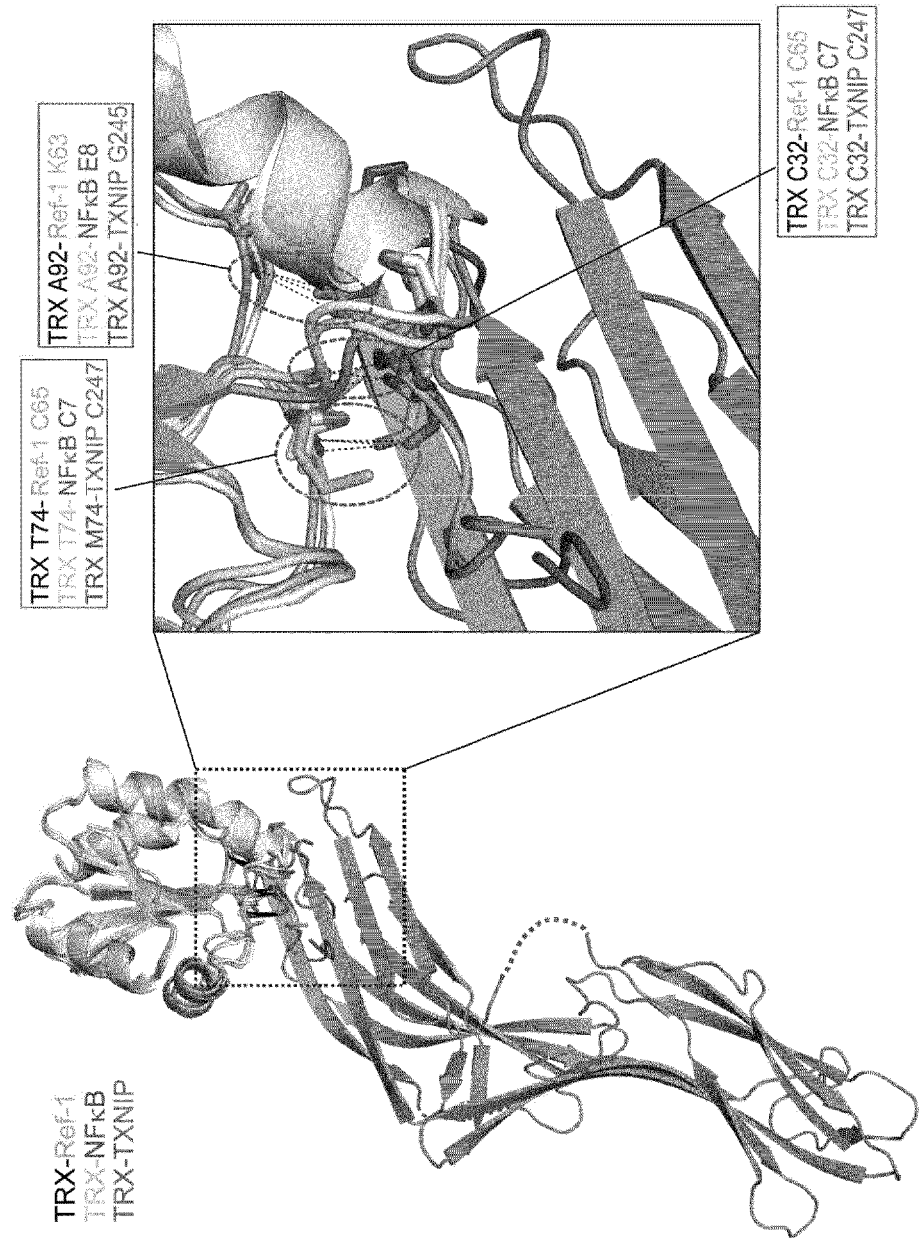
FIG. 9c shows superimposition of TRX-interacting substrates. Complexes of TRX and Ref-1 (PDB ID 1CQG); TRX and NF-κB (PDB ID 1MDI); and TRX and TXNIP are displayed. The consensus backbone-backbone interactions stabilizing intermolecular disulfides in each complex are depicted as black dashed lines in red circles.
Figure 9D:
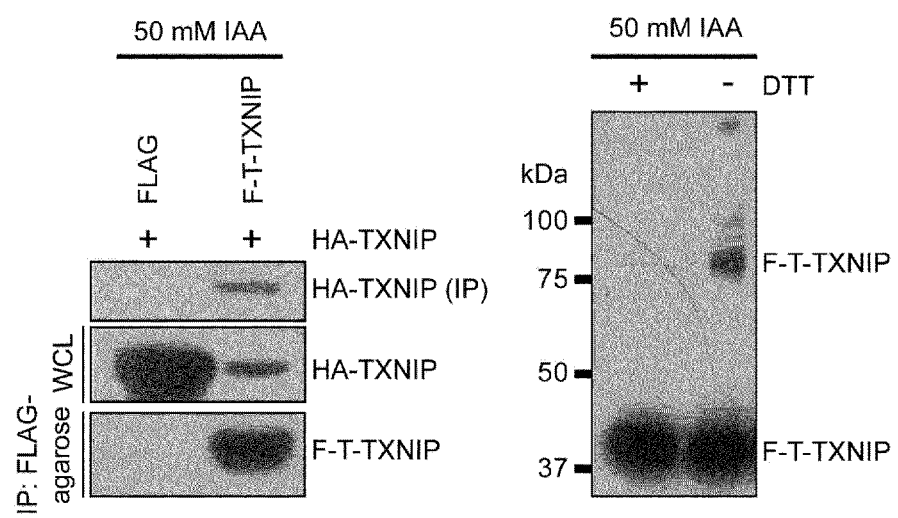
FIG. 9d shows in vivo interprotomer interaction between TXNIP molecules. Assays were performed using lysates from HEK 293T cells transfected with FLAG-tagged or HA-tagged TXNIP-expressing plasmid after cell disruption with lysis buffer containing 50 mM IAA. (Left) Immobilized proteins on FLAG-agarose beads were visualized by Western blot analysis using anti-FLAG or anti-HA antibodies. (Right) Immobilized proteins on FLAG-agarose beads were fractionated by SDS-PAGE under reduced and non-reduced conditions and visualized by Western blot analysis using anti-FLAG antibody. F, FLAG.
Figure 9E:
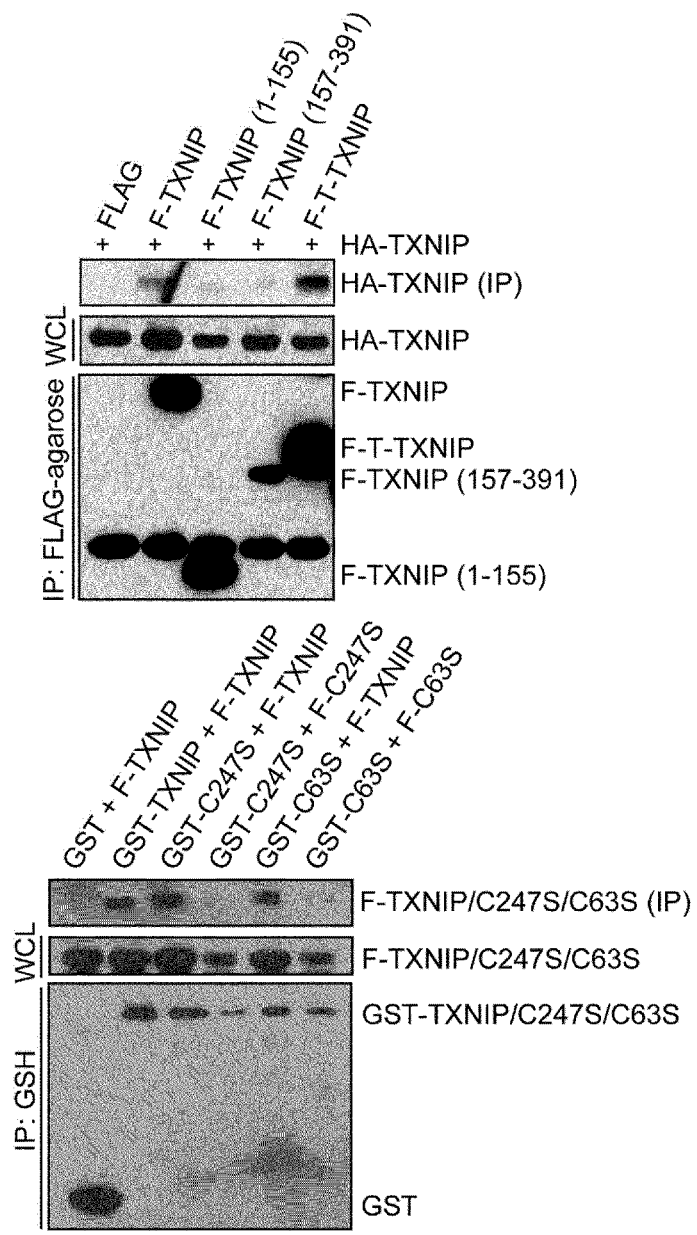
FIG. 9e shows that TXNIP molecules form interprotomer disulfide bonds via Cys63 and Cys247. (Left) TXNIP molecules interact with each other through their N- and C-terminal domains. (Right) The Cys63 and Cys247 residues are critical for the interaction between TXNIP molecules. Coimmunoprecipitation assays were performed using lysates from 293T cells transfected with combinations of FLAG-tagged or HA-tagged TXNIP plasmids and GST-tagged or FLAG-tagged TXNIP plasmids. Immobilized proteins on FLAG-agarose beads or glutathione beads were visualized by Western blot analysis using anti-HA, anti-FLAG, or anti-GST antibodies. One percent of WCL was used as the input.
Figure 9F:
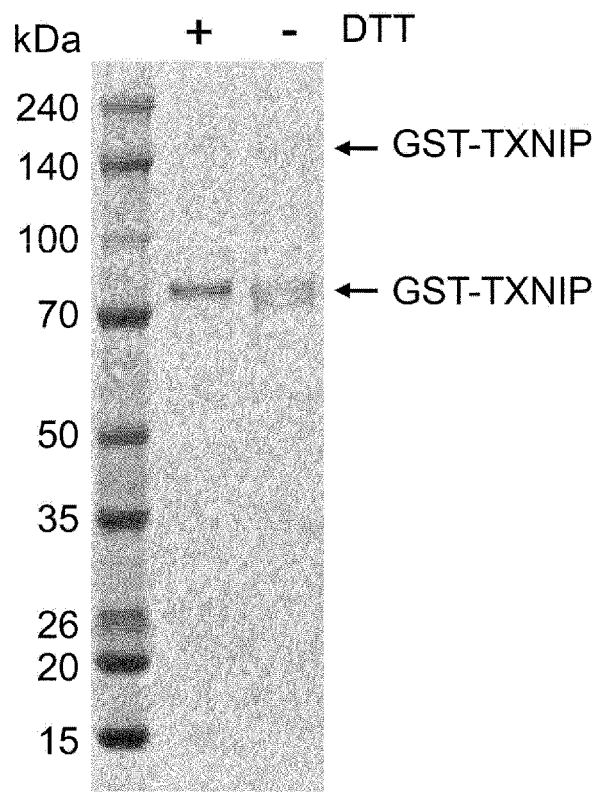
FIG. 9f shows that TXNIP molecules interact with each other in the redox dependent manner. Pull-down assays were performed using lysates from HEK 293T cells transfected with plasmid expressing GST-fused TXNIP. (a) Immobilized proteins on glutathione beads were fractionated by SDS-PAGE and (b) analyzed by western blotting using anti-GST antibody.
Figure 9F:
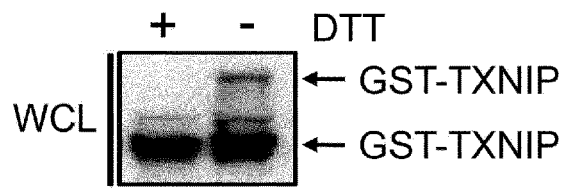
Figure 9G:
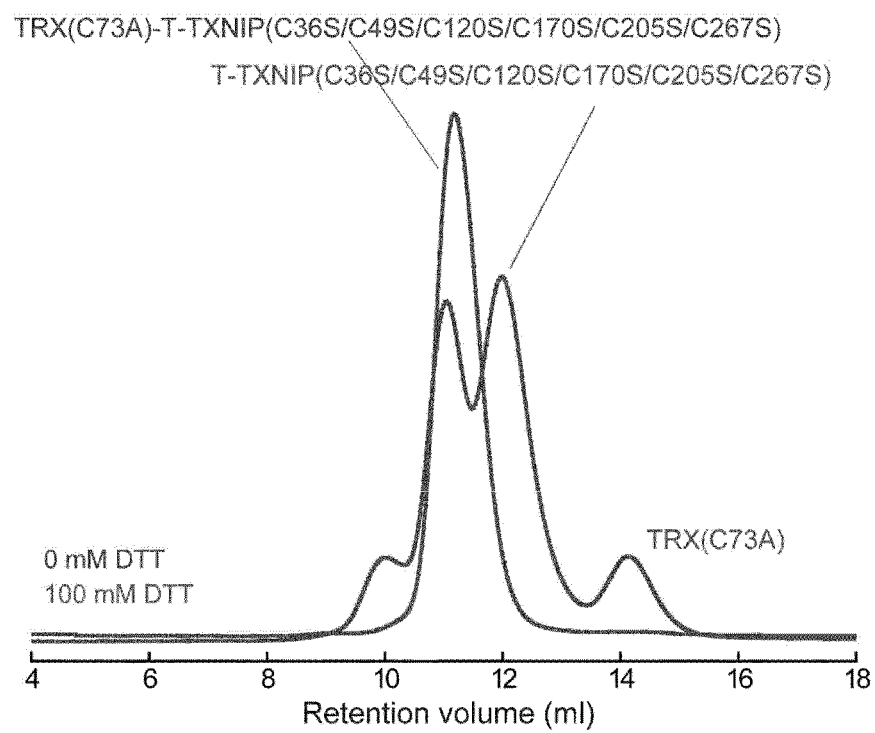
FIG. 9g shows the results of T-TXNIP(C36S/C49S/C120S/C170S/C205S/C267S) isolation.
Figure 9H:
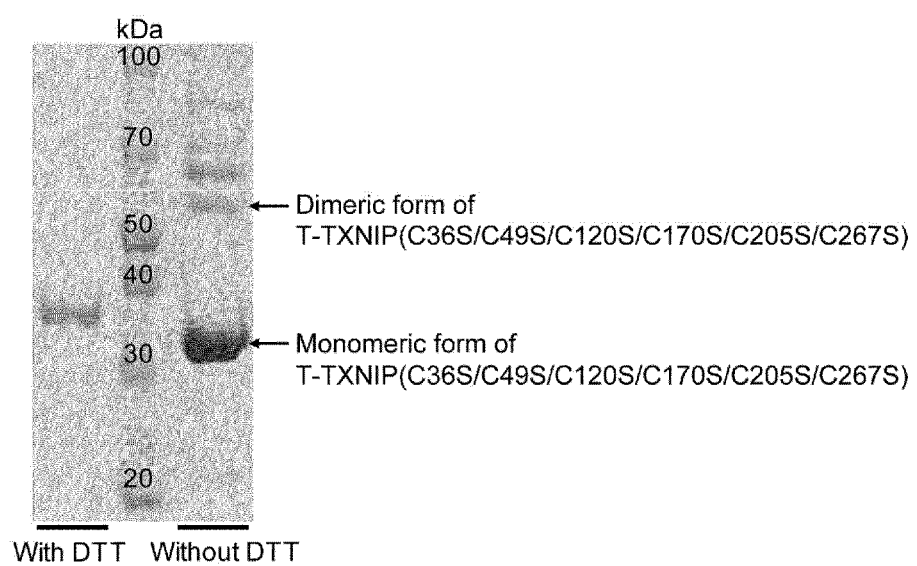
Figure 9I:
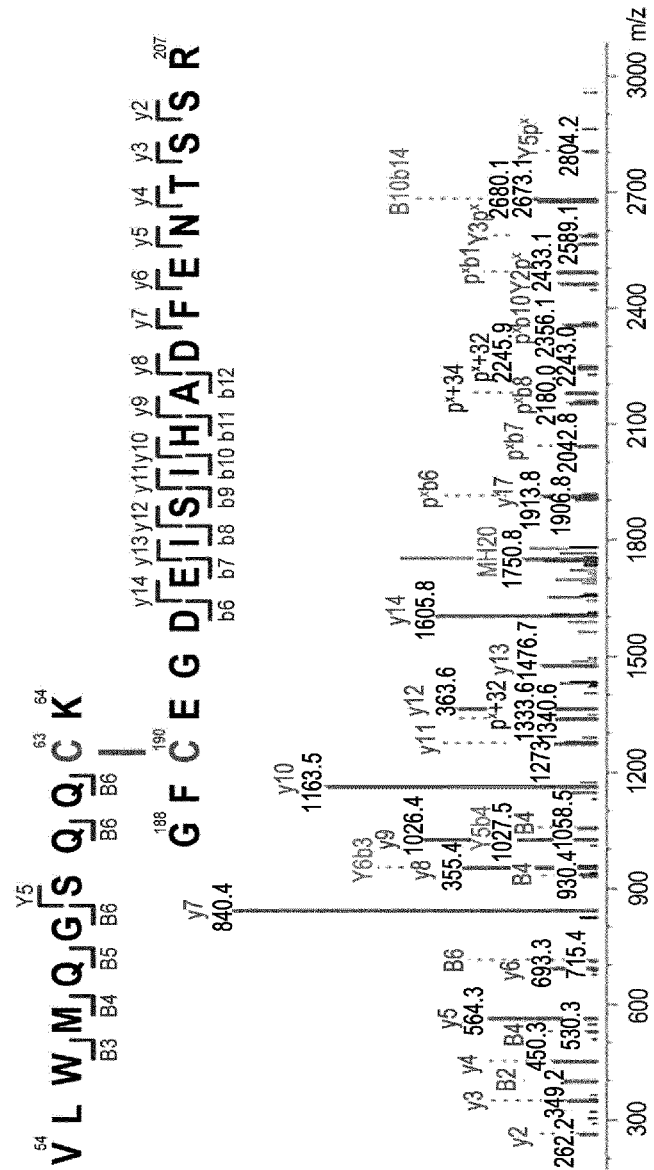
Figure 9J:
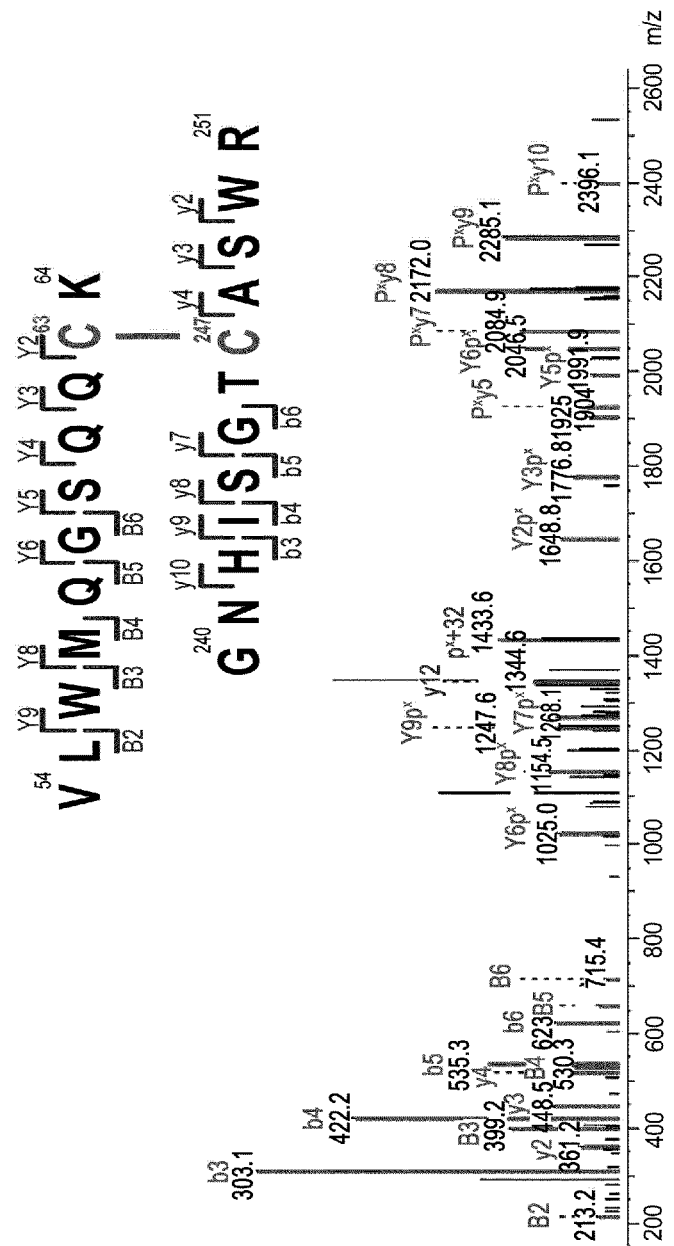
Figure 9K:
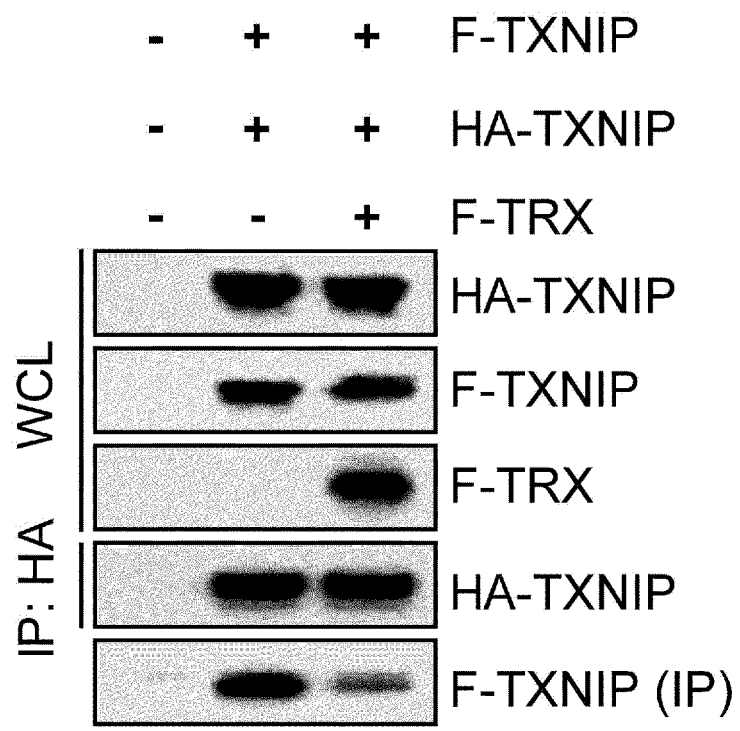
Figure 10A:
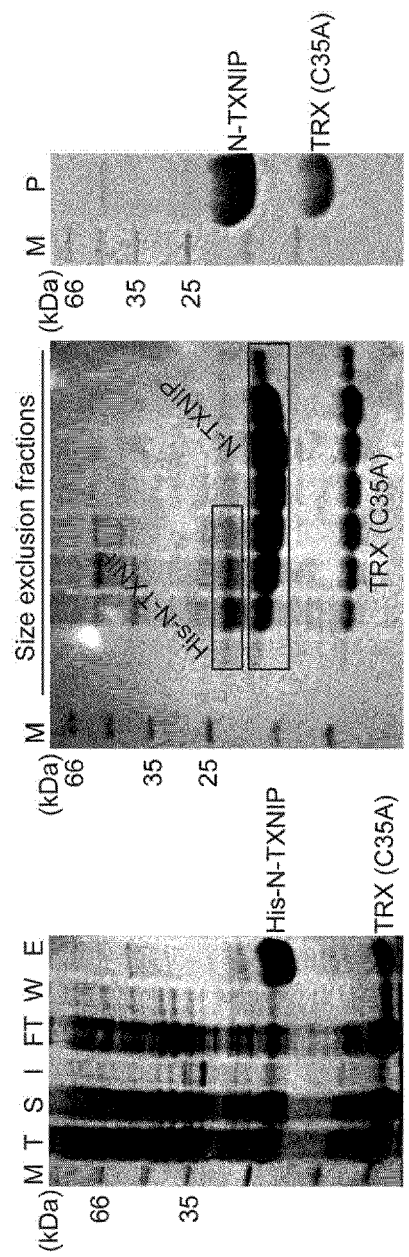
Figure 12A:
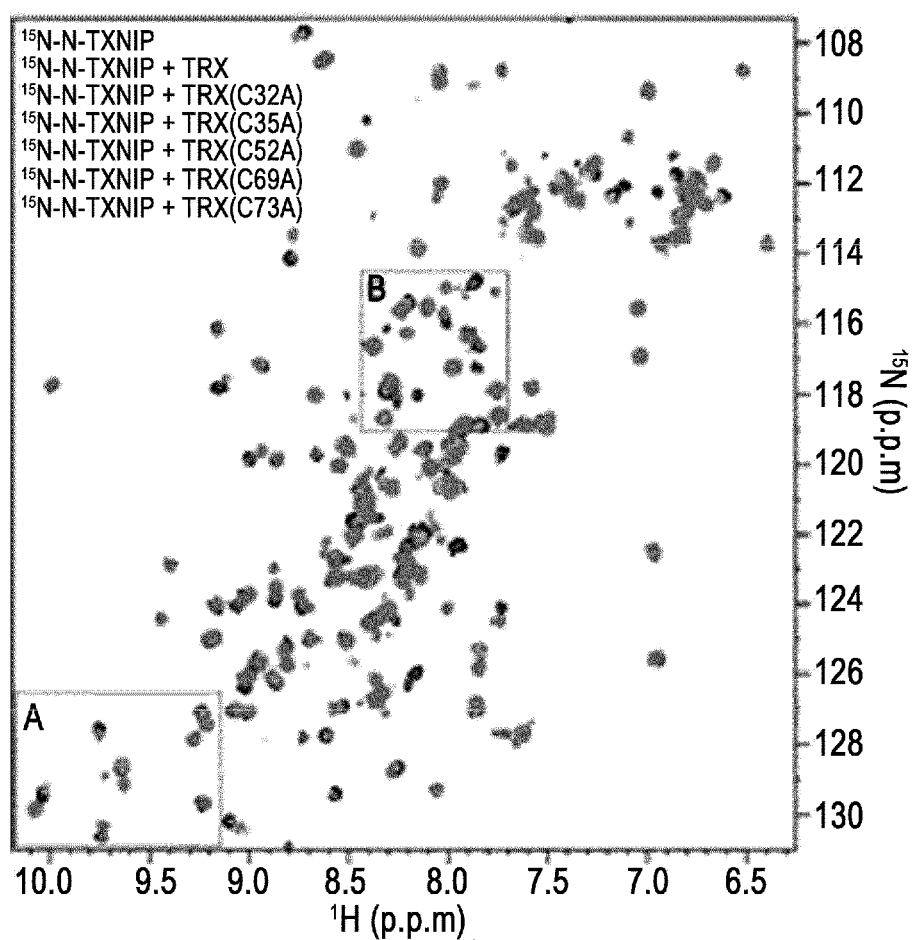
Figure 12B:
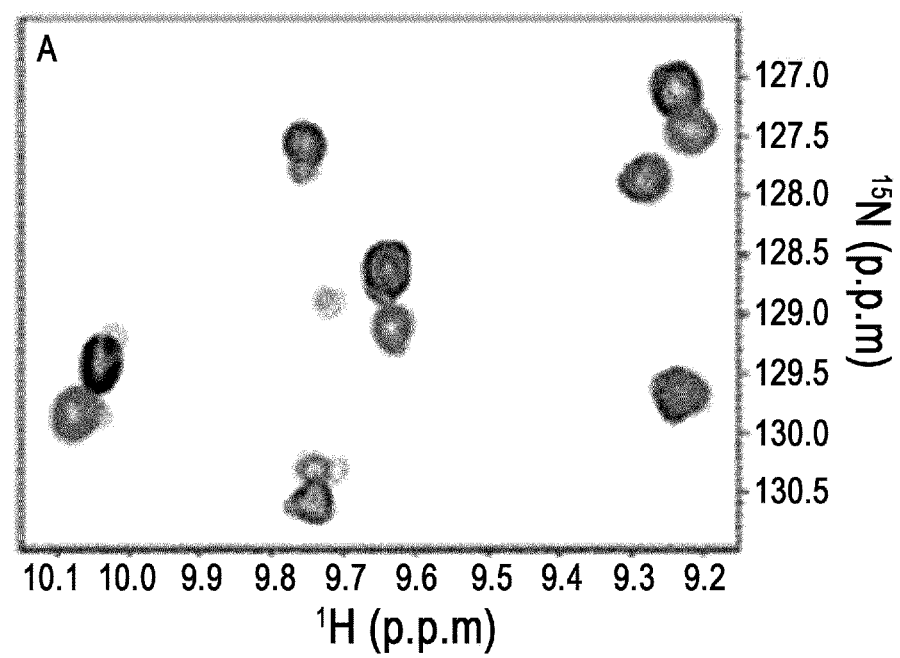
Figure 12C:
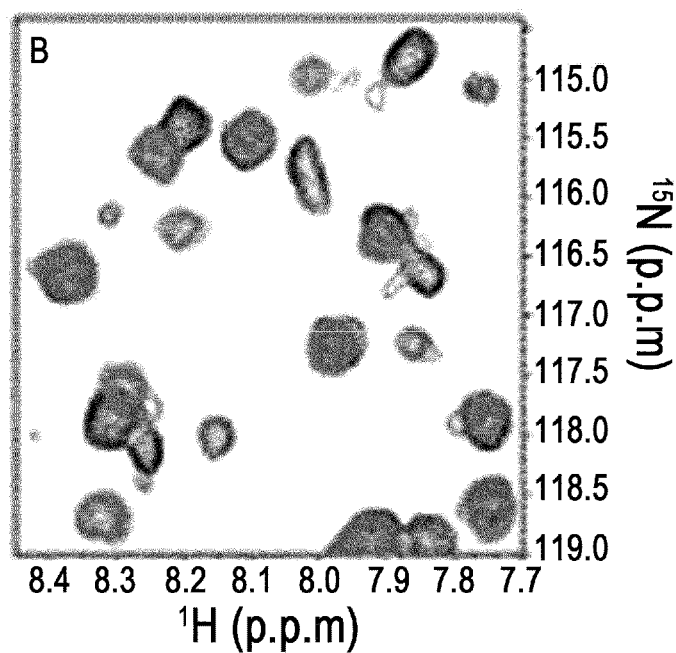
Figure 13:
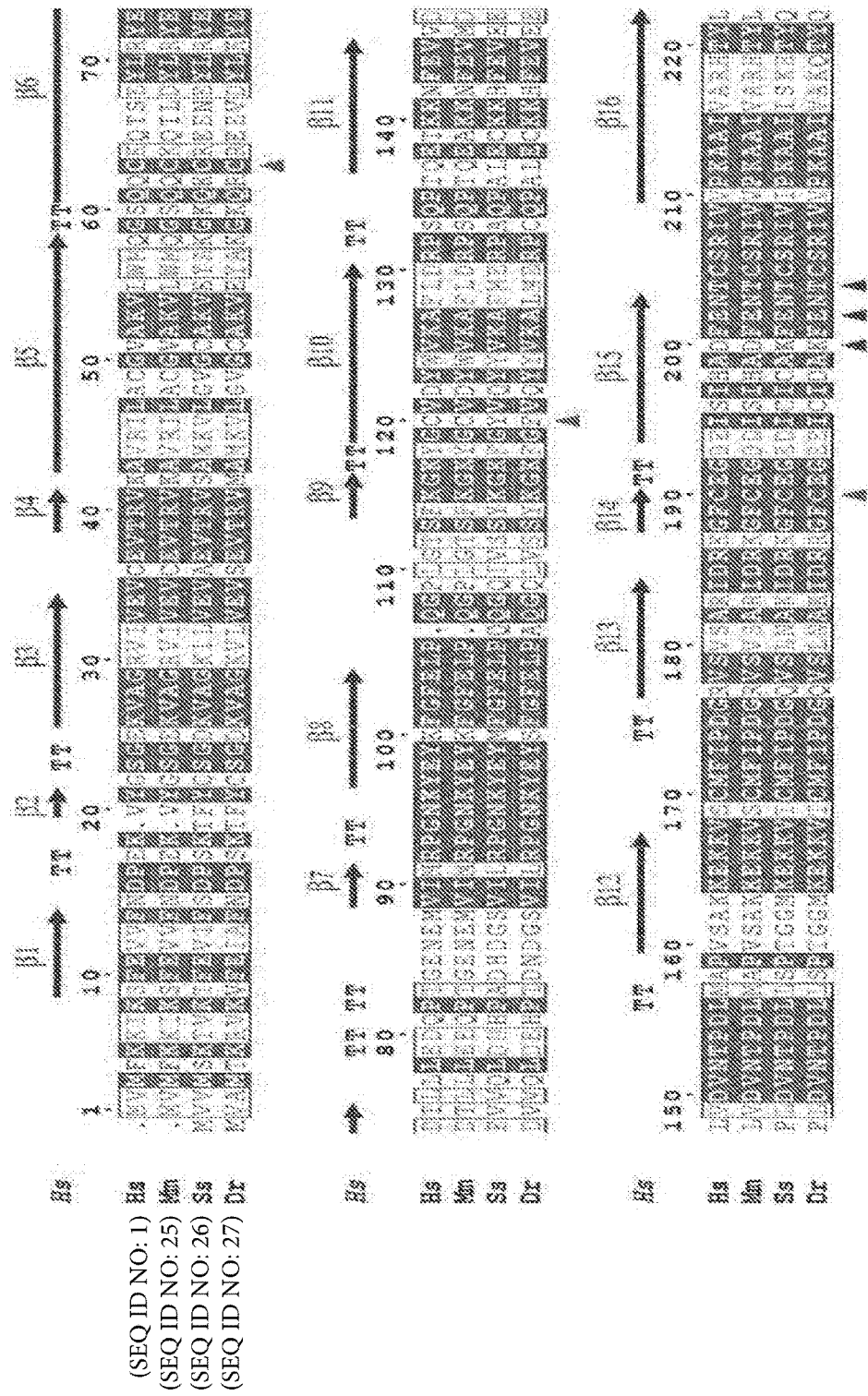
Figure 14:
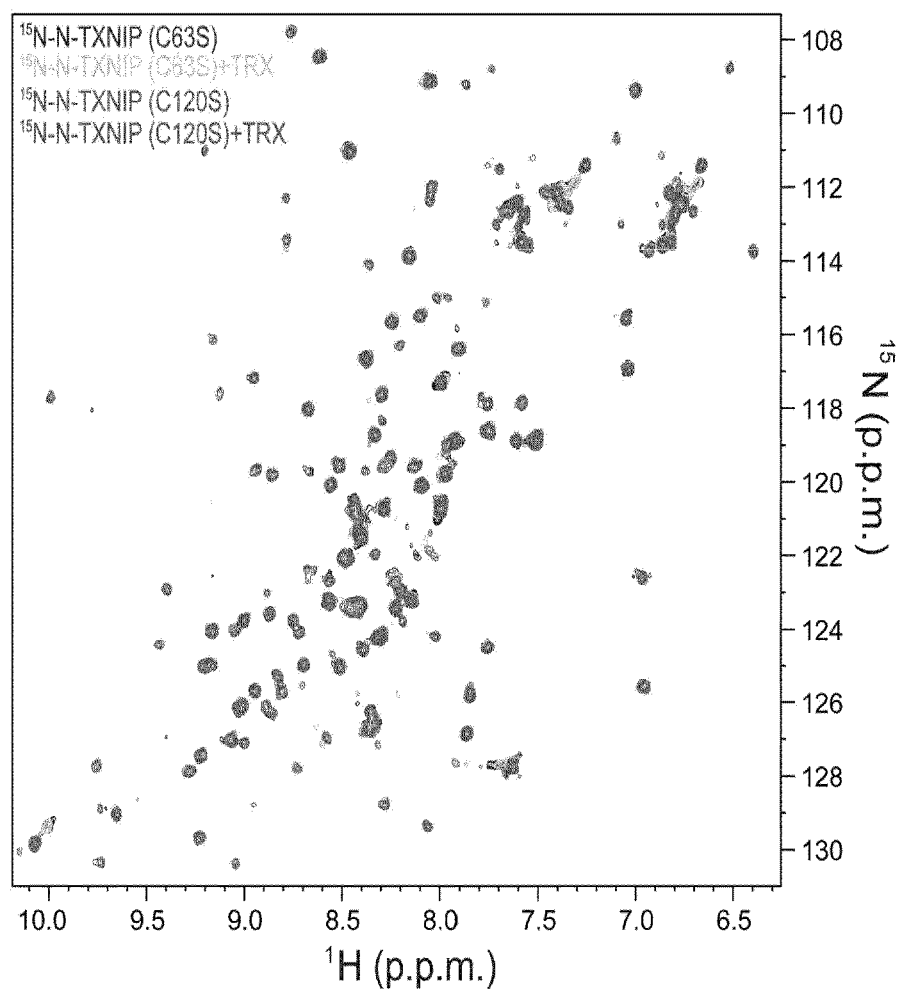
Figure 15A:
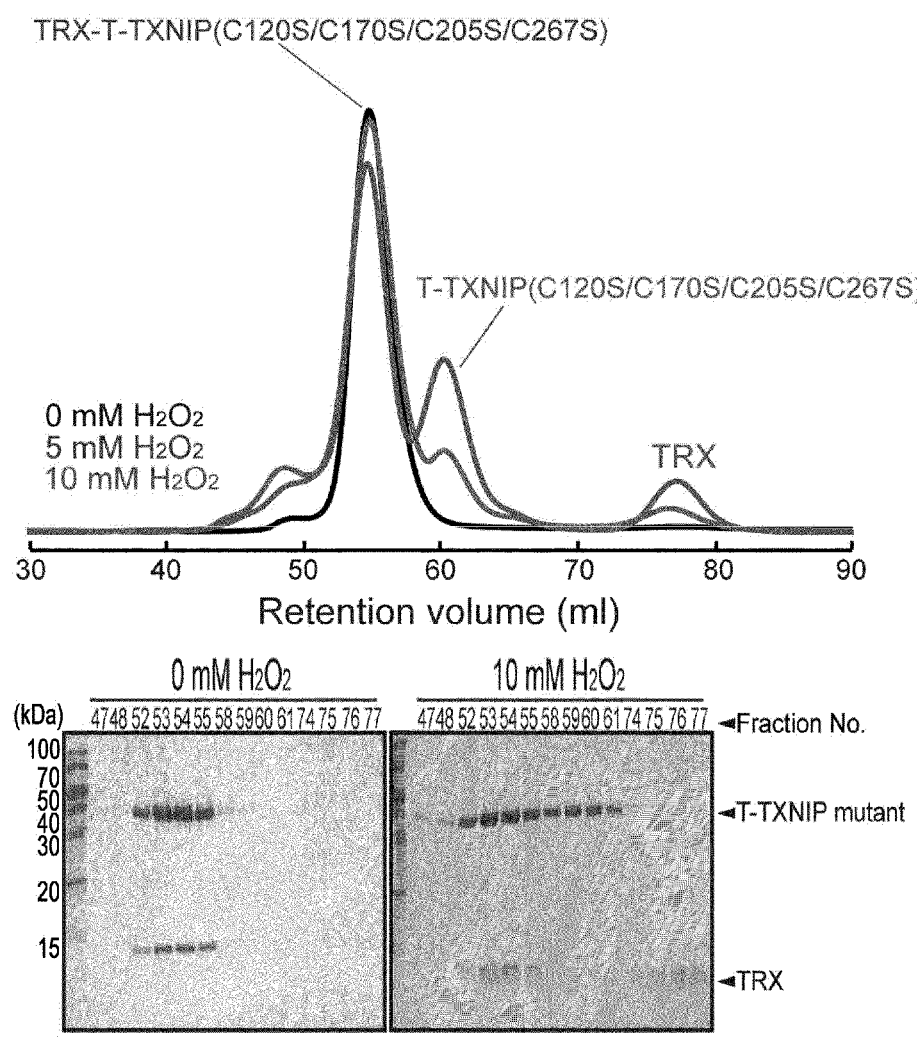
Figure 15B:
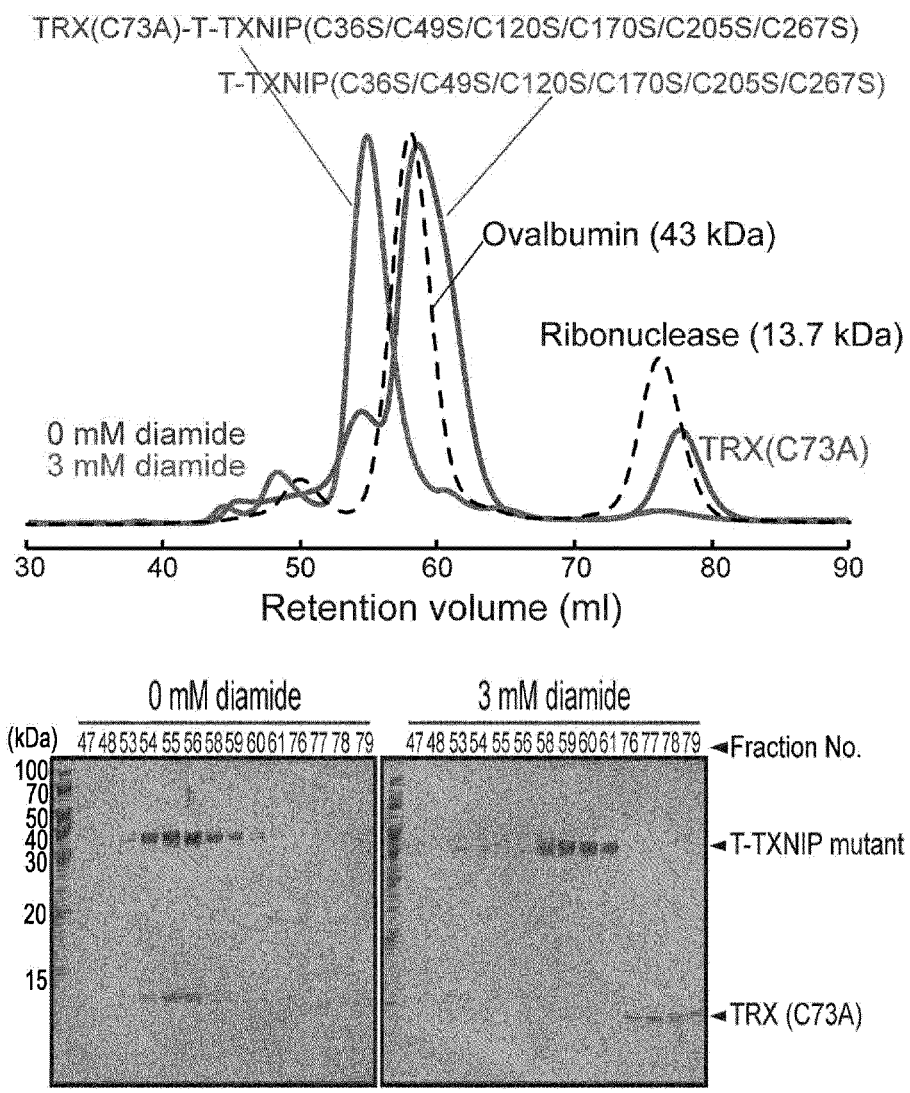
Figure 15C:
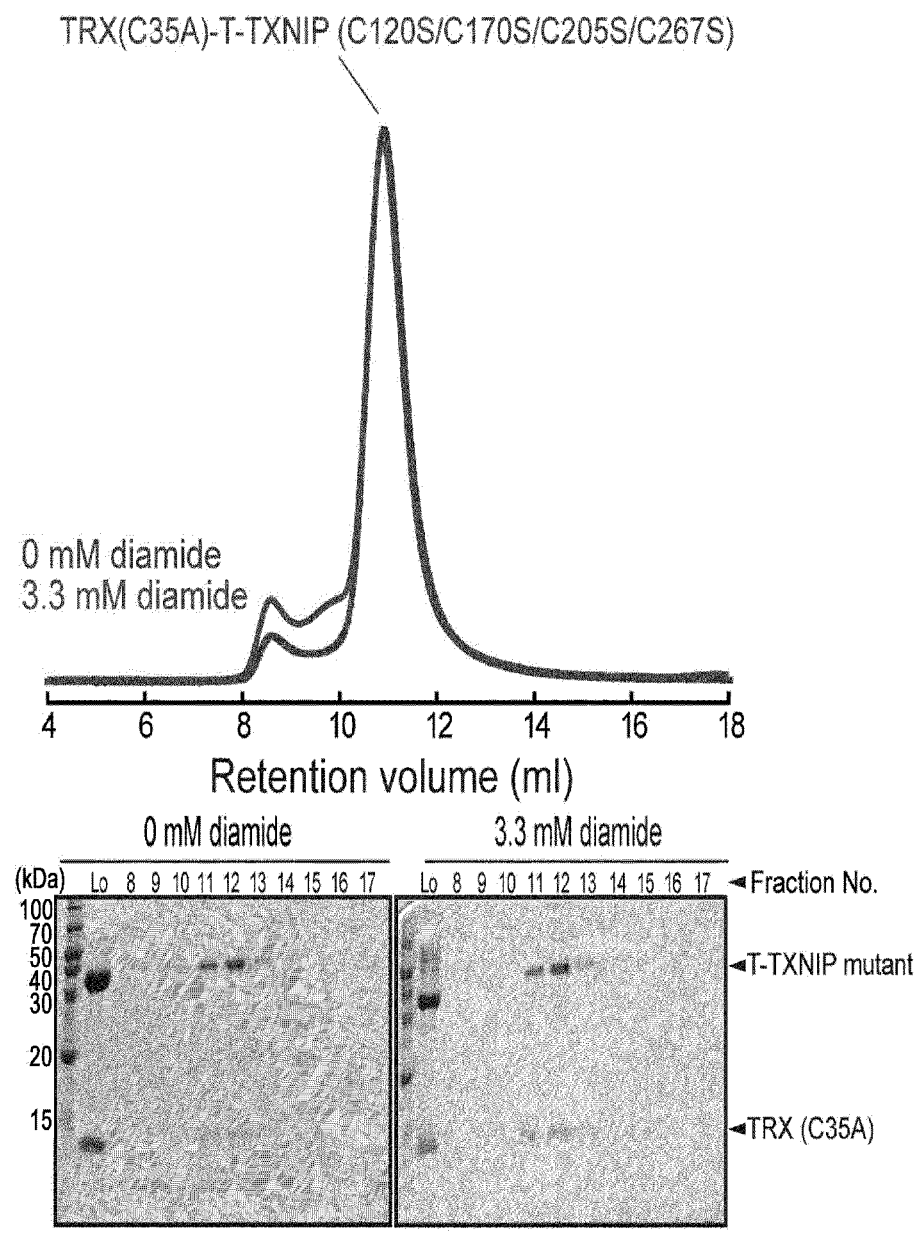
Figure 15D:
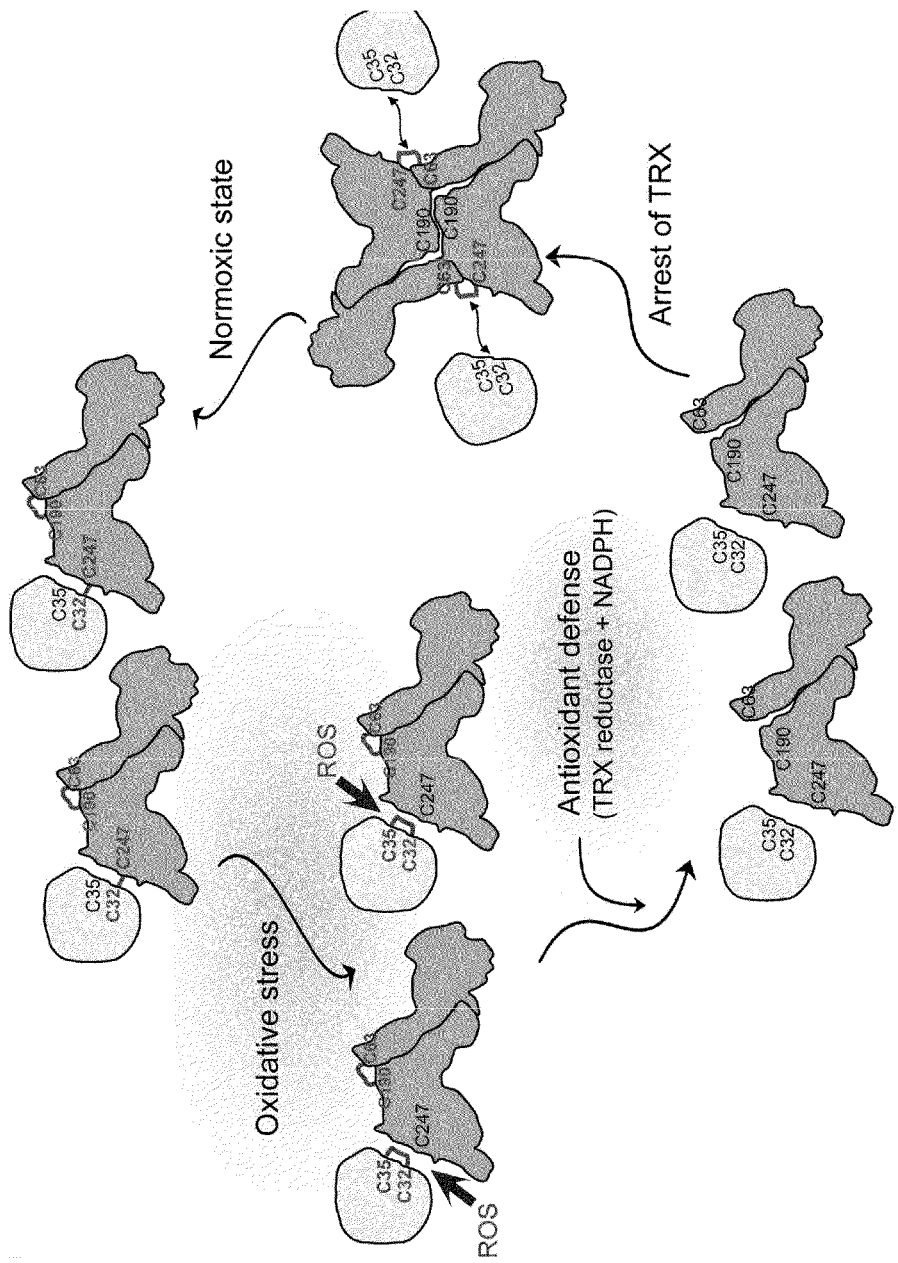
Figure 16:
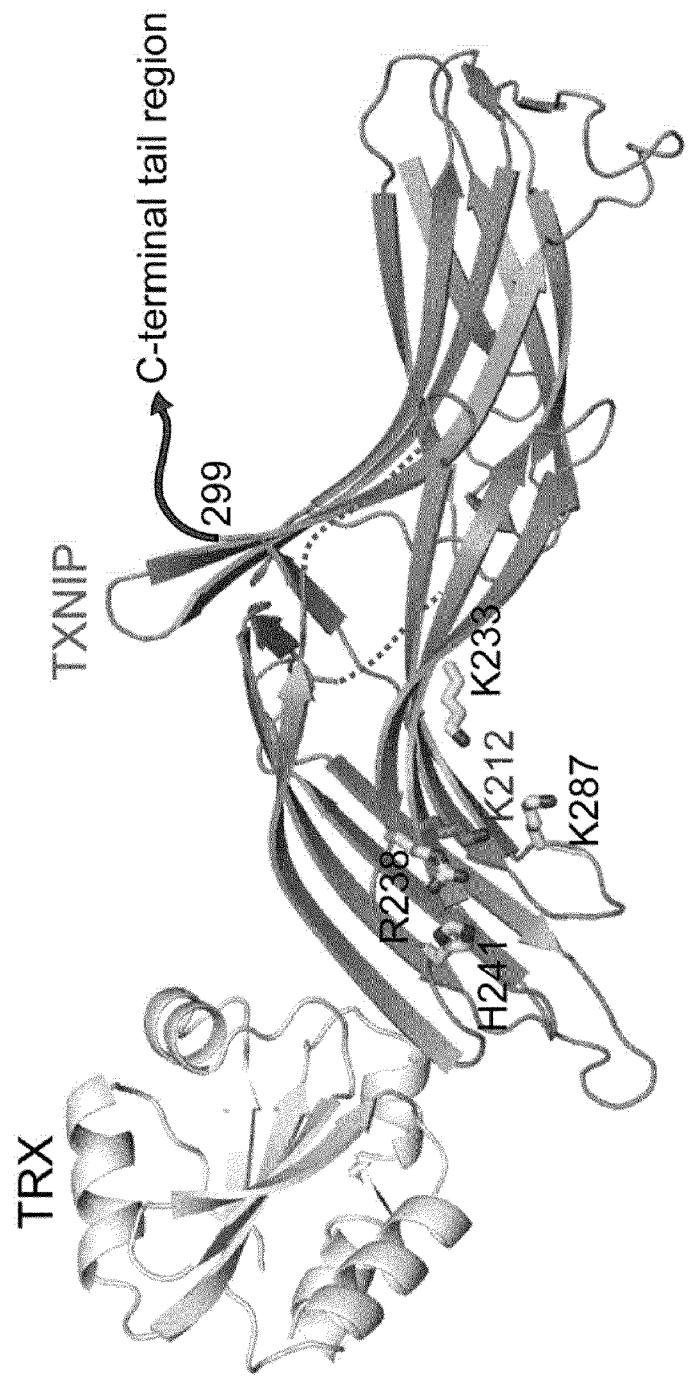

TRX(C73A)-T-TXNIP(C36S/C49S/C120S/C170S/C205S/C267S) complex was incubated with 100 mM DTT and subjected to size exclusion chromatography to isolate T-TXNIP(C36S/C49S/C120S/C170S/C205S/C267S) from remained protein complex and TRX. The fractions containing T-TXNIP (C36S/C49S/C120S/C170S/C205S/C267S) were collected and dialyzed against 50 mM Tris-HCl (pH 8.0), 500 mM NaCl and 10% glycerol to induce the formation of disulfide bonds between TXNIP molecules;

FIG. 9h shows the results of SDS-PAGE analysis of the interprotomer-interacting TXNIP molecules. Reducing and non-reducing protein samples were fractionated on SDS-PAGE. The bands ~32 kDa and ~60 kDa were analyzed as monomeric and dimeric T-TXNIP(C36S/C49S/C120S/C170S/C205S/C267S), respectively. The rest of high molecular bands were analyzed as non-specific aggregates of TXNIP molecules. No disulfide bonds were detected from the bands;

FIG. 9i shows interdomain disulfide bond between Cys63 and Cys190. Protein band ~32 kDa on SDS-PAGE was subjected to a proteomic analysis. Interdomain disulfide bond between Cys63 and Cys190 was identified from the MS/MS spectra as '$^{54}$VLWMQGSQQCK$^{64}$', '$^{188}$GFCEGDEISIHADFENTSSR$^{207}$'. The ion types of matched peaks were written in b- and y-ions;

FIG. 9j shows the result of proteomic analysis of the interaction between TXNIP molecules. The interprotomer-interacting TXNIP molecules fractionated by SDS-PAGE under non-reducing condition were subjected to the proteomic analysis. The MS/MS spectra show the interprotomer disulfide bond between Cys63 and Cys247 identified as "$^{54}$VLWMQGSQQCK$^{64}$-$^{240}$GNHISGTCASWR$^{251}$";

FIG. 9k shows that TRX diminishes the interaction between TXNIP molecules. Coimmunoprecipitation assays were performed using lysates from 293T cells transfected with FLAG-tagged TXNIP, HA-tagged TXNIP, and FLAG-tagged TRX-expressing plasmids Immobilized proteins or HA-agarose beads were detected using anti-HA, anti-FLAG antibodies. HA-tagged TXNIP, FLAG-tagged TXNIP, and FLAG-tagged TRX were detected by using anti-HA and FLAG antibodies;

FIG. 10 shows interaction between N-TXNIP and TRX. (A) N-TXNIP was co-expressed and co-purified with TRX (C35A)(SEQ ID NO:3) and analyzed by SDS-PAGE. M, molecular weight size marker; T, total cell lysate; S, soluble fraction; I, insoluble fraction; FT, flow-through fraction; W, wash fraction; E, hexahistidine-tagged N-TXNIP eluted from the Ni-NTA column; N-TXNIP, tag-free N-TXNIP obtained by treatment with recombinant TEV protease; P, purified protein. (B) NMR-titration experiments are shown. Representative $^{15}$N-HSQC NMR spectra from N-TXNIP after addition of different amounts of TRX are shown. Inset, chemical shift perturbations upon addition of 0, 0.2, 0.5, 1, 1.5 and 2 molar equivalents of TRX;

FIG. 11 shows that the interaction between TRX and TXNIP involves disulfide bond switching. (A) Ribbon representation of N-TXNIP displaying the intramolecular disulfide bond between Cys63 and Cys120 is shown. Locations of other cysteine residues are shown. (B) TXNIP undergoes disulfide bond switching via a significant Cys63-mediated conformational change. The structure of N-TXNIP is superimposed onto the T-TXNIP structure. The β-strands and cysteine residues in T-TXNIP are indicated in green. The interdomain disulfide bond between Cys63 and Cys190 is displayed. The intramolecular disulfide bond between Cys63 and Cys190 in N-TXNIP is indicated in magenta. (C) An interdomain disulfide bond is formed in TXNIP between N-TXNIP Cys63 and C-TXNIP Cys190. The disulfide bond is located at the center of the interdomain interface. Residues involved in the interface between N-TXNIP and C-TXNIP are depicted using stick representations with magenta and green carbon atoms, respectively. Strands β5, β6 and β14 are indicated. (D) interaction between the TXNIP domains is shown. Interdomain interactions between the N-terminal strand β6 and the C-terminal strand β19 are displayed;

FIG. 12 shows that TRX interacts with N-TXNIP via its active cysteine residue. Interaction between N-TXNIP and TRX was analyzed by monitoring $^1$H-$^{15}$N HSQC spectra of $^{15}$N-labeled N-TXNIP, after addition of modified TRX protein. There were no significant chemical shift changes when C32A or C35A TRX mutants were added, whereas C62A, C69A and C73A mutants caused a chemical shift similar to the wild-type TRX. Inset A and B was magnified for visualization convenience;

FIG. 13 shows structure-related functional sequence conservation in TXNIP and homologous proteins. Shown above the alignments are elements of the secondary structure of TXNIP. The numbering shown is from human TXNIP (SEQ ID NO: 1). 63, 120, 190 and 247 amino acid residues indicated by triangles are functional cysteine residues in TXNIP. As shown in figure, while Cys63, Cys190 and Cys247 are strictly conserved, Cys120 are not. The rest triangles indicate residues critical for interaction with TRX. Strictly conserved residues are highlighted with inverted boxes. Biological sources and accession codes for the sequences are: Hs, *Homo sapiens* (gi:171184421); Mm, *Mus musculus* (gi:254553444); Ss, *Salmo salar* (gi:223647818); Dr, *Danio rerio* (gi:41056117). Sequence alignments were assembled using CLUSTALW, and visualized using ESPript software, both located on the ExPASy Proteomics Server (au.expasy.org/);

FIG. 14 shows that TRX interacts with a disulfide bond involving TXNIP Cys63. $^1$H-$^{15}$N HSQC NMR experiments using $^{15}$N-labeled N-TXNIP modified proteins and TRX were performed. There were no significant chemical shift changes when TRX was added to C63S and C120S modified proteins of N-TXNIP compared with the spectra for each modified protein without TRX;

FIGS. 15a to c show that ROS directly affect the intermolecular disulfide bond between TRX and TXNIP. In detail, the TRX-T-TXNIP(C120S/C170S/C205S/C267S) (SEQ ID NO: 6) complex was incubated with $H_2O_2$ at 37° C. for 30 minutes (a). The TRX(C73A)-T-TXNIP(C36S/C49S/C120S/C170S/C205S/C267S) complex was incubated with diamide at 37° C. for 30 minutes. The reaction products were injected onto a HiLoad™ 16/60 Superdex™ 75 gel filtration column at room temperature (b). The TRX Cys35 residue is essential for dissociation between TRX and TXNIP. The TRX(C35A)(SEQ ID NO:3)-T-TXNIP(C120S/C170S/C205S/C267S)(SEQ ID NO: 6) complex was incubated with diamide at 37° C. for 60 minutes and the reaction products were injected onto the Superdex™ 75 10/300 GL gel filtration column (c). Eluted T-TXNIP and TRX after the ROS treatments are indicated for each reaction. All eluted proteins were analyzed by SDS-PAGE;

FIG. 15D shows a proposed molecular mechanism of the negative regulation of TRX by TXNIP; and FIG. 16 shows location of the ubiquitinated residue Lys212 in the TXNIP structure complexed with TRX. The Lys212 residue is located in the highly basic C-terminal region, which forms a deeply curved □beta-sandwich domain, and is depicted as a dark stick. The residues with positive electrostatic potential in C-TXNIP are displayed with light sticks.

DETAILED DESCRIPTION OF THE PREFERRED EMBODIMENTS

In one aspect, the present invention provides a method for crystallizing a modified TRX-TXNIP complex comprising a modified TXNIP protein and a modified TRX protein.

Specifically, the method for crystallizing the modified TRX-TXNIP complex comprises the steps of: (a) co-expressing the modified TXNIP protein, which is prepared by deleting 2 amino acids at the N-terminus and 74 amino acids at the C-terminus, and substituting serines (Ser) for cysteines (Cys) at positions 170, 205, and 267 in an amino acid sequence of SEQ ID NO: 1 of TXNIP protein, and the modified TRX protein represented by SEQ ID NO: 3; and (b) crystallizing the modified TXNIP protein and the modified TRX protein; but is not limited thereto. The modified TXNIP protein may be a modified protein further comprising a substitution of serine for cysteine at position 120, but is not limited thereto.

In the crystallizing method, Step (a) may include a step of purifying the expressed proteins, and purification of the proteins may be conducted by a known purification method such as affinity chromatography, etc.

As used herein, the term "TRX protein" is a redox-active protein which functions as a defense protein in response to a variety of oxidative stresses and plays pivotal roles in intra- and extracellular signaling pathways. With respect to the objects of the present invention, TRX means a protein that interacts with TXNIP, but is not limited thereto. TRX is preferably human TRX, but is not limited thereto. The amino acid sequence and nucleotide sequence of the TRX protein can be obtained from the known database such as NCBI GenBank, and preferably, an amino acid sequence of SEQ ID NO: 2 and a nucleotide sequence of SEQ ID NO: 10, but is not limited thereto.

As used herein, the term "modified TRX protein" means a protein prepared by substitution, insertion, deletion, or alteration of one or more amino acids in the wild-type TRX protein. With respect to the objects of the present invention, modified TRX protein means a protein modified in order to prevent further reactions after interaction with TXNIP, but is not limited thereto. The modified TRX protein comprises any modified TRX protein without limitation, as long as it is a soluble, or a soluble and crystalline protein, but is not limited thereto. The modified TRX protein is preferably a protein prepared by substitution of alanine (Ala) for cysteine (Cys) at position 35 in the wild-type TRX protein, but is not limited thereto. In the present invention, TRX protein having a substitution of alanine for cysteine at position 35 was designated as TRX(C35A)(SEQ ID NO:3). This modified TRX protein may be a protein having the amino acid sequence of SEQ ID NO: 3, and it may also be a protein having an amino acid sequence having 70% or more homology, preferably 80% or more homology, more preferably 95% or more homology, or much more preferably 98% or more homology thereto, in which it is apparent that a protein having an amino acid sequence in which a part thereof is deleted, altered, substituted, or added is also included in the scope of the present invention, as long as it substantially has an activity to form a crystal, together with the modified TXNIP protein. In one embodiment of the present invention, a modified TRX protein was prepared by substitution of alanine for cysteine at position 35 in TRX protein having the amino acid sequence of SEQ ID NO: 2, and then used for the preparation of a modified TRX-TXNIP complex crystal, together with the modified TXNIP protein.

As used herein, the term "TXNIP protein" means a protein that is able to interact with TRX protein, and interacts with TRX to inhibit TRX activity. The TXNIP protein acts as a tumor suppressor protein in cancer and its expression is down-regulated in a variety of tumor cells. TXNIP interacts with TRX which is up-regulated in tumor cells to inhibit its activity, thereby exhibiting an anticancer effect, but is not limited thereto. The anticancer activity of TXNIP may be exemplified by an anticancer activity through inhibition of binding between TRX and ASK1, but is not limited thereto. The TXNIP protein may be preferably human TXNIP protein (SEQ ID NO: 1), but is not limited thereto. The amino acid sequence and nucleotide sequence of the TXNIP protein can be obtained from a known database such as NCBI GenBank, and preferably, an amino acid sequence of SEQ ID NO: 1 and a nucleotide sequence of SEQ ID NO: 9.

As used herein, the term "modified TXNIP protein" means a protein prepared by substitution, insertion, deletion or alteration of one or more amino acids in the wild-type TXNIP protein. With respect to the objects of the present invention, the modified TXNIP protein is any protein without limitation, as long as it is able to form a complex with the wild-type or modified TRX protein and has alteration of one or more amino acids in the amino acid sequence encoding the wild-type TXNIP protein. The modified TXNIP protein may be preferably a protein prepared by deletion of 2 amino acids at the N-terminus and 74 amino acids at the C-terminus, and substitution of serines for cysteines at positions 170, 205, and 267 in the wild-type TXNIP protein (e.g. SEQ ID NO: 4 and 5, respectively), but is not limited thereto. Further, the modified TXNIP protein comprises a protein prepared by further substitution of serine for cysteine at position 120, in addition to substitution of serines for cysteines at positions 170, 205, and 267 (e.g. SEQ ID NO: 6). Through the alteration of the length and partial sequences of the wild-type TXNIP protein, the modified TXNIP protein becomes more prone to crystallization than the wild-type TXNIP protein, which could not be crystallized together with TRX protein.

The modified TXNIP protein prepared by deletions of 2 amino acids at the N-terminus and 74 amino acids at the C-terminus in the wild-type TXNIP protein was designated as T-TXNIP, and represented by SEQ ID NO: 4.

Further, the modified TXNIP protein prepared by substitutions of serines for cysteines at positions 170, 205, and 267 based on the wild-type TXNIP protein represented by the amino acid sequence of SEQ ID NO: 1 in T-TXNIP was designated as T-TXNIP(C170S/C205S/C267S), and represented by SEQ ID NO: 5.

Furthermore, the modified TXNIP protein prepared by further substitution of serine for cysteine at position 120 in T-TXNIP(C170S/C205S/C267S)(SEQ ID NO: 5) was designated as T-TXNIP(C120S/C170S/C205S/C267S), and represented by SEQ ID NO: 6.

In one embodiment of the present invention, in order to prepare a crystal of the modified TXNIP protein and TRX (C35A)(SEQ ID NO:3) complex, T-TXNIP(C170S/C205S/C267S)(SEQ ID NO: 5) and T-TXNIP(C120S/C170S/C205S/C267S)(SEQ ID NO: 6) were used as the modified TXNIP protein, respectively. Like the wild-type TXNIP protein, the T-TXNIP(C170S/C205S/C267S)(SEQ ID NO: 5) and T-TXNIP(C120S/C170S/C205S/C267S)(SEQ ID NO: 6) proteins effectively inhibited the activity of TRX protein, suggesting that their activities are not affected by the substitution of serines for cysteine residues (FIG. 6c).

As used herein, the term "TRX-TXNIP complex" means a complex formed by interaction between TRX protein and TXNIP protein. Preferably, it may be a complex formed through an intermolecular disulfide bond between the cysteine residue (Cys32) at position 32 of TRX protein and the cysteine residue (Cys247) at position 247 of TXNIP protein, but is not limited thereto.

As used herein the term "modified TRX-TXNIP complex" means a protein complex formed by interaction between the modified TRX protein and the modified TXNIP protein. The modified TRX-TXNIP complex means a complex formed through an intermolecular disulfide bond between the cysteine residue at position 32 of the modified TRX protein and the cysteine residue at position 247 of the modified TXNIP protein, but is not limited thereto. The modified TRX-TXNIP complex may be preferably a modified complex formed by interaction between TRX(C35A)(SEQ ID NO:3) and T-TXNIP(C170S/C205S/C267S)(SEQ ID NO: 5), or a modified complex formed by interaction between TRX (C35A)(SEQ ID NO:3) and T-TXNIP(C120S/C170S/C205S/C267S) (SEQ ID NO: 6), but is not limited thereto. The modified TRX-TXNIP complex of the present invention is formed by interaction between the modified TXNIP protein and the modified TRX protein, in which the modified TXNIP protein can be easily crystallized due to modification of the TXNIP protein, of which crystallization trials have been unsuccessful, without affecting its activity. The modified TRX-TXNIP complex is a protein capable of forming its crystal structure. Thus, it provides an advantage in that the interaction between TRX and TXNIP can be analyzed through its three-dimensional structure. In one embodiment of the present invention, the modified TRX-TXNIP complex was used to prepare two crystals, COM1 (TRX(C35A) and T-TXNIP(C120S/C170S/C205S/C267S)(SEQ ID NO: 6)) and COM2 (TRX(C35A)(SEQ ID NO:3) and T-TXNIP (C170S/C205S/C267S)(SEq ID NO: 5)). Their structures were examined (in Example 6, Experimental Example 1 and FIG. 5). Like the wild-type TXNIP protein, the modified TXNIP protein of the present invention exhibits TRX-inhibitory activity (FIG. 6c), and thus it can be understood that the modified TRX-TXNIP complex of the present invention represents the wild-type TRX-TXNIP complex.

As used herein, the term "interaction between TRX protein and TXNIP protein" means interaction by a disulfide bond between Cys32 of TRX protein and Cys247 of TXNIP protein, but is not limited thereto. The interaction between TRX protein and TXNIP protein, particularly, the β18 strand of TXNIP in combination with β15 is a critical component of the interaction, and intermolecular backbone-backbone interactions between TRX and the β18 strand of T-TXNIP contributes to stabilization of the disulfide bond between C32 of TRX and C247 of TXNIP. Further, Arg251 (Arginine, R) of TXNIP protein forms a salt bridge with Asp60 (aspartic acid, D) of TRX protein, which further contributes to stabilization of the interaction (FIG. 9 b).

In the present invention, the mechanism by which interaction between TRX protein and TXNIP protein is regulated, was demonstrated by using the crystal structure investigated in the present invention. In detail, the interaction between TRX protein and TXNIP protein is caused by disulfide bond switching. A head-to-tail interprotomer disulfide bond between Cys63 and Cys247 of TXNIP is present in TXNIP proteins, and when TRX approaches and interacts with TXNIP, disruption of the interprotomer disulfide bond occurs, and a disulfide bond between TRX Cys32 and TXNIP Cys247 is formed, and a disulfide bond between Cys63 and Cys190 in the TXNIP protein is formed, leading to S-shaped conformation of TXNIP protein (FIGS. 9 to 15).

The crystallization method preferably comprises the step of co-expressing the modified TRX protein and the modified TXNIP protein, but is not limited thereto.

Since TXNIP protein is not expressed as a soluble protein without TRX protein, co-expression of the modified TRX protein and the modified TXNIP protein is preferred in order to prepare the modified TRX-TXNIP complex in soluble form. Such co-expression may be performed by expressing them in a single vector, a single cell or separate individual vectors, and the proteins thus expressed may be purified, followed by crystallization. In one embodiment of the present invention, a two-promoter vector system capable of co-expressing the modified TRX protein and the modified TXNIP protein was used to prepare a vector comprising polynucleotides encoding each of the two proteins in a single vector (Example 1).

As used herein, the phrase "expressed in soluble form" means that a protein having low solubility is expressed in soluble form. Expression in soluble form is a prerequisite for crystallization of a protein. Most proteins form crystals readily when they are in water-soluble form, and therefore, this step is required for the subsequent crystallization step.

As used herein, the phrase "allowing crystallization" or "having crystallinity" means that, in order to prepare a protein in a form suitable for X-ray analysis of its tertiary structure, mutations are introduced into the protein molecule so as to form solid particles having a uniform shape and size from a uniform liquid or to further stabilize the crystal of the protein. The three-dimensional structure of a protein is very important for the understanding of in vivo actions of the protein and development of therapeutic drugs. That is, since an understanding of the arrangement and three-dimensional structure of atoms constituting a protein as a macromolecule makes it possible to analyze the three-dimensional structure of the modified TRX-TXNIP complex and to provide a platform for development of new drugs for inhibiting interaction between TRX protein and TXNIP protein, it is a common issue in biological and medical fields. However, it was very difficult to demonstrate the three-dimensional structure of the TRX-TXNIP complex. A crystal structure of the TRX-TXNIP complex should be first prepared in order to analyze the three-dimensional structure of the complex, and the protein complex should be prepared in soluble form in order to prepare its stable crystal structure. In order to acquire such protein, the present inventors expressed both the modified TRX protein and the modified TXNIP protein, and prepared modified TRX and TXNIP proteins by substitution of cysteine residues in the amino acid sequence(s) of TRX or/and TXNIP protein, and then prepared the modified TRX-TXNIP complex which serves as a stable TRX-TXNIP complex, using the modified proteins.

The crystallization of Step (b) may be carried out by a variety of known crystallization methods, preferably, by a vapor diffusion method. The vapor diffusion method may be a sitting drop vapor diffusion method or a hanging-drop vapor diffusion method, and more preferably, the sitting drop vapor diffusion method, but is not limited thereto.

As used herein, the term "sitting drop vapor diffusion method" refers to a crystallization method in which, when a microdrop of mother liquor and a much larger reservoir solution exist separately in a closed system, transport of either water or other volatile agent occurs between them, leading to a supersaturated state of protein, and in such a thermodynamically metastable state, proteins are precipitated depending on the precipitant. While the protein precipitation slowly occurs, stable crystals are formed and the precipitant functions to lower the solubility of the concentrated protein solution, and proteins congregate to form crystals in order to reduce an adsorption layer around protein molecules. The reservoir solution contains a mixture of the precipitant, buffer, salt, and detergent at different concentrations. Droplets are usually formed by mixing the protein solution with the reservoir solution of various conditions at a ratio of 1:1, and the droplets thus formed are placed on a microbridge, and sealed. At this time, there is a difference in the concentration between the proteins in the droplets and the reservoir solution, and thus the proteins do not begin as crystals. They are equilibrated while sealed, and crystals are formed under the specific conditions by the above described principle. In the sitting drop vapor diffusion method, the type and proper concentration of the salt, the buffer and the surfactant as well as the precipitant in the reservoir solution, pH of the solution, and the experimental temperature vary depending on the type of protein, and in some cases, they become very important factors in crystal formation of proteins.

As used herein, the term "hanging-drop vapor diffusion method" is a protein crystallization method, which provides crystals having a size sufficient for protein structural analysis. In the hanging-drop vapor diffusion method, a reagent containing a sample and a pure liquid reagent are placed on the top of the reservoir under vapor equilibration. To achieve equilibrium of the sample having a lower reagent concentration than the reservoir, water contained in the sample eventually ends up in the reservoir. Water contained in the sample is removed until the concentration is approximately the same as that in the liquid reagent, and finally, protein crystals reaching the equilibration can be obtained.

In one embodiment of the present invention, the sitting drop vapor diffusion method was used to obtain N-TXNIP, COM1, and COM2 crystals (Example 6).

In another aspect, the present invention provides a crystal of the modified TXNIP protein or the modified TRX-TXNIP complex.

The modified TXNIP protein is the same as described above. The modified TXNIP protein is preferably N-TXNIP (K5A/K6A) protein (SEQ ID NO: 8), and the modified TRX-TXNIP complex is TRX(C35A)(SEQ ID NO:3)-T-TXNIP(C120S/C170S/C205S/C267S)(SEQ ID NO: 6) complex (COM1) and TRX(C35A)(SEQ ID NO:3)-T-TX-NIP(C170S/C205S/C267S)(SEQ ID NO: 5) complex (COM2), but are not limited thereto.

There are many different methods for analyzing a protein's crystal structure, and two main methods are NMR spectroscopy and X-ray crystallography. NMR Spectroscopy is based on the principle of predicting a distance between particular atoms in a molecule by analyzing signal changes due to chemical factor which can be detected in the NMR spectrum of a molecule. Data of the chemical shift obtained by the NMR test is analyzed to obtain a set of the distances between labeled atoms in one protein, and a model or a set of models satisfying information about all distances determined by the experiment is produced. Thus, there is a disadvantage of requiring collection and analysis of a large amount of data. Meanwhile, X-ray crystallography is based on the principle of obtaining the result by analyzing x-ray scattered by electron cloud surrounding an atom of the crystal in an x-ray generator. X-ray diffraction patterns from protein crystals are regular because the individual protein molecules are arranged in a regular lattice. Based on this principle, X-ray crystallography is a method of analyzing a protein structure by producing an electron density map of the protein using x-ray scattered and reflected from the protein crystals. However, there is a disadvantage of requiring pure protein samples and protein crystallization. In the present invention, the TXNIP protein of which crystallization trials have been unsuccessful was properly modified to prepare crystals of N-TXNIP protein, COM1, and COM2.

In the present invention, to provide three-dimensional crystal structures of N-TXNIP(K5A/K6A) protein (SEQ ID NO: 8), COM1, and COM2, diffraction patterns were obtained using an x-ray image plate, and phase information was obtained by multiple anomalous dispersion (MAD) using Se-Met (selenium-methionine). An electron density map was obtained from the x-ray diffraction patterns and phase information, and atomic coordinates were derived therefrom so as to obtain the three-dimensional structures. The crystal of N-TXNIP(K5A/K6A) protein (SEQ ID NO: 8) of the present invention is preferably a crystal having an amino acid sequence represented by SEQ ID NO: 8 and having a space group of $P2_12_12_1$ and a unit-cell dimension of a=37.43 Å, b=56.62 Å, and c=67.66 Å, and $\alpha=\beta=\gamma=90°$, but is not limited thereto (Table 8). The N-TXNIP(K5A/K6A) protein (SEQ ID NO: 8) has atomic coordinates shown in Table 9.

Further, the crystal of COM1 of the present invention is preferably a crystal of complex of the modified TXNIP protein represented by SEQ ID NO: 6 and the modified TRX protein represented by SEQ ID NO: 3, and having a space group of $P2_1$ and a unit-cell dimension of a=80.14 Å, b=64.02 Å, c=88.30 Å, $\alpha=\gamma=90°$ and $\beta=91.28°$, but is not limited thereto (Table 8). The COM1 complex has atomic coordinates shown in Table 10, and the atomic coordinates and the structure-factor amplitudes thereof were deposited in PDB (Protein Data Bank) under accession code of 4LL1.

The crystal of COM2 of the present invention is preferably a complex crystal of the modified TXNIP protein represented by SEQ ID NO: 5 and the modified TRX protein represented by SEQ ID NO: 3, and having a space group of $P2_1$ and a unit-cell dimension of a=79.83 Å, b=64.99 Å, c=88.42 Å, $\alpha=\gamma=90°$, and $\beta=90.88°$, but is not limited thereto (Table 8). The COM2 complex has atomic coordinates shown in Table 11, and the atomic coordinates and the structure-factor amplitudes thereof were deposited in PDB (Protein Data Bank) under accession code of 4LL4.

As used herein, the term "space group" means the symmetry of a unit cell of a crystal, and combinations of symmetry elements form symmetry groups. This space is used interchangeably with the space group.

As used herein, the term "unit-cell dimension" is also called lattice parameter, and the unit-cell is the simplest minimum repeating unit constituting the space group, and defined by three crystallographic axes, the lengths of the three vectors (a, b, c) and the inter-axial angles ($\alpha$, $\beta$, $\gamma$).

The phase information can be obtained by multiple isomorphous replacement, multiwavelength anomalous dispersion, molecular replacement, or the like. First, multiple isomorphous replacement is a technique of obtaining the phase information by replacing crystals with heavy metals, and collecting and analyzing the data. Second, multiwavelength anomalous dispersion is a widely used technique of obtaining phase information by collecting data using the anomalous dispersion at different wavelengths, in which a specific metal or atom in the crystal is used instead of heavy metals. That is, without the need for collecting data of many crystals, data can be easily obtained from one crystal using a selenium atom by replacing the amino acid methionine with selenomethionine (Se-Met) using a molecular biological method. However, this method has a disadvantage in that data should be obtained from a radiation beam. Third, molecular replacement is a method of solving the phase problem from a known similar structure, and it is widely used as the number of known structures is increasing. Data is collected from each structure, and then refinement is conducted to fit our model against the data. This procedure is performed using known programs (CCP4, Coot, Quanta, CNS, etc.), and standardization of each angle, bond length, etc. is required. In this process, a procedure for fitting the model to the obtained electron density map is performed repeatedly by computer and by eye. In the analysis step after refinement of the structure, a lot of information can be derived from the structure with interpretation. In this analysis step, the mechanism of action can be studied, based on the structure. The studies on the correct mechanism of action provide information needed for development of new drugs. Further, the directly related residues can be identified through the structure of the complex of the protein and its regulator, and therefore, important information is provided for the next step for studying the regulator.

In the present invention, phase information of human N-TXNIP(K5A/K6A) (SEQ ID NO: 8), COM1, and COM2 structures was obtained by multiple anomalous dispersion (MAD), and SOLVE and RESOLVE programs were used for calculation thereof, and COOT and REFMAC5 programs were used for refinement of the structures. The atomic coordinates and the structure-factor amplitudes of N-TXNIP (K5A/K6A) (SEQ ID NO: 8), COM1, and COM2 thus obtained are shown in Tables 9 to 11, respectively and their three-dimensional structures are shown in FIGS. 5 to 9, 11, and 16, respectively.

In still another aspect, the present invention provides a modified TXNIP protein, a polynucleotide encoding the modified TXNIP protein, an expression vector comprising the polynucleotide, and a transformant introduced with the expression vector.

The modified TXNIP protein is the same as described above.

The expression vector comprising the polynucleotide encoding the modified TXNIP protein provided in the present invention may be, but is not particularly limited to, a vector capable of replicating and/or expressing the polynucleotide in eukaryotic or prokaryotic cells comprising mammalian cells (e.g., human, monkey, rabbit, rat, hamster, mouse cells, etc.), plant cells, yeast cells, insect cells, or bacteria cells (e.g., *E. coli*, etc.), preferably, a vector which is operably linked to a suitable promoter to express the polynucleotide in the host cells and comprises at least one selection marker. More preferably, it may be in the form of a phage, a plasmid, a cosmid, a mini-chromosome, a virus, a retrovirus vector to which the polynucleotide is introduced.

The expression vector comprising the polynucleotide encoding the modified TXNIP protein may be an expression vector further comprising a polynucleotide encoding the wild-type or modified TRX protein. Since the modified TXNIP protein is not expressed as a soluble protein without a TRX protein, the expression vector comprising the polynucleotide encoding the modified TXNIP protein may be introduced, together with the expression vector comprising the polynucleotide encoding the wild-type or modified TRX protein, or a single expression vector comprising both the polynucleotides encoding the wild-type or modified TRX protein and the polynucleotide encoding the modified TXNIP protein may be introduced to express both the TRX protein and the modified TXNIP protein.

As used herein, the term "transformant" refers to a host cell transformed with the vector, and means a transformant capable of producing a large amount of soluble, or soluble and crystalline N-TXNIP(K5A/K6A) (SEQ ID NO: 8), COM1 or COM2 proteins of the present invention, and also comprises a transformant which is introduced with the N-TXNIP(K5A/K6A) (SEQ ID NO: 8), COM1 or COM2 protein and thus is used to screen candidates for new drug development through NMR, etc, but is not limited thereto. The transformant introduced with the expression vector provided in the present invention may be, but is not particularly limited to, bacterial cells such as *E. coli, Streptomyces, Salmonella typhimurium*, etc.; yeast cells; fungus cells such as *Pichia pastoris*; insect cells such as *Drosophila, Spodoptera* Sf9 cell, etc; animal cells such as CHO, COS, NSO, 293T, Bowes melanoma cells, etc.; or plants cells, which are transformed by introduction of the expression vector.

As used herein, the term "introduction" refers to delivery of the vector comprising the polynucleotide encoding the modified TXNIP protein into a host cell. This introduction may be performed by various methods known in the art, comprising calcium phosphate-DNA coprecipitation, DEAE dextran-mediated transfection, polybrene-mediated transfection, electroporation, microinjection, liposome fusion, lipofection and protoplast fusion. Further, the term "transfection" means delivery of a desired material into a cell by means of infection using viral particles. In addition, the vector may be introduced into a host cell by gene bombardment. In the present invention, the introduction may be used interchangeably with transformation.

In still another aspect, the present invention provides a method for preparing the modified TXNIP protein.

The modified TXNIP protein is the same as described above.

A method of preparing T-TXNIP(C170S/C205S/C267S) (SEQ ID NO: 5) among the modified TXNIP proteins may include the steps of deleting 2 amino acids at the N-terminus and 74 amino acids at the C-terminus in the amino acid sequence of SEQ ID NO: 1 of the TXNIP protein, and substituting serines (Ser) for cysteines (Cys) at positions 170, 205, and 267 based on the amino acid sequence of SEQ ID NO: 1. Further, a method of preparing T-TXNIP(C120S/C170S/C205S/C267S)(SEQ ID NO: 6) among the modified TXNIP proteins may include the steps of deleting 2 amino acids at the N-terminus and 74 amino acids at the C-terminus in the amino acid sequence of SEQ ID NO: 1 of the TXNIP protein, and substituting serines (Ser) for cysteines (Cys) at positions 120, 170, 205, and 267, but is not limited thereto.

Further, a method preparing N-TXNIP(K5A/K6A) (SEQ ID NO: 8) may include the steps of comprising only the amino acids at position 3 to 156 in the amino acid sequence of SEQ ID NO: 1, and substituting alanines for lysines at positions 5 and 6, but is not limited thereto.

In still another aspect, the present invention provides a method for screening a substance candidate regulating the interaction between TRX and TXNIP by utilizing the tertiary structure of the modified TXNIP protein or the modified TRX-TXNIP complex.

Preferably, the method may include: (a) producing or selecting a candidate regulating interaction between TRX and TXNIP using a tertiary structure of N-TXNIP (the N-terminal domain of thioredoxin-interacting protein) having the atomic coordinates shown in Table 9; a tertiary structure of the modified TRX-TXNIP complex having the atomic coordinates shown in Table 10; or a tertiary structure of the modified TRX-TXNIP complex having the atomic coordinates shown in Table 11; and (b) examining whether the candidate produced or selected in Step (a) regulates interaction between TRX and TXNIP.

The modified TXNIP protein and the modified TRX-TXNIP complex are the same as described above.

The modified TXNIP protein is preferably N-TXNIP (K5A/K6A) (SEQ ID NO: 8), and the modified TRX-TXNIP complex is preferably COM1 or COM2, but is not limited thereto. The atomic coordinates of N-TXNIP and the modified TRX-TXNIP complexes can be obtained by atomic coordinates of the proteins shown in Tables 9 to 11. The atomic coordinates of N-TXNIP(K5A/K6A) (SEQ ID NO: 8) is shown in Table 9, the atomic coordinates of COM1 is shown in Table 10, and the atomic coordinates of COM2 is shown in Table 11.

Further, the atomic coordinates for N-TXNIP(K5A/K6A) (SEQ ID NO: 8), COM1 or COM2 can be stored in media for consecutive use in a calculating apparatus such as a computer. Typically, the coordinates can be stored in media (e.g., floppy disks, hard disks, compact disks, magneto-optical media, or electronic media) useful for storing large amounts of data, such as magnetic or optical media. Those skilled in the structural/computational chemistry are used to selecting the computer, storage media, networking, and another device or technique.

Based on the three-dimensional structure of N-TXNIP (K5A/K6A) (SEQ ID NO: 8), COM1 or COM2 demonstrated in the present invention, information about various protein sites comprising binding sites can be provided by using computer readable media containing the data of the atomic coordinates and/or three-dimensional structure. Through these procedures, reaction patterns of numerous drug candidates can be predicted without practical experiments, and only the resulting selected substances are subjected to experiments, leading to economic improvement in new drug development.

Further, step (a) of the screening method may include the steps of entering the data of the atomic coordinates for the tertiary structures of the proteins into a computer, together with a proper software program; and obtaining a three-dimensional protein structure for visualization and additional computer manipulation, but is not limited thereto. When the tertiary structure of TXNIP, TRX, or complex thereof is designed using the atomic coordinates shown in Tables 9 to 11, amino acids can be appropriately modified within the scope without causing a large structural change, such as substitution of the amino acids which are the same as in the wild-type for the modification of the wild-type protein, but is not limited thereto.

If all or part of the tertiary structure of the N-TXNIP (K5A/K6A) (SEQ ID NO: 8), COM1 or COM2 is used, a candidate capable of regulating interaction between TRX and TXNIP can be specifically selected or produced. That is, based on the tertiary structure, a substance capable of regulating the interaction can be designed, and a candidate substance can be selected by examining whether the known substances are able to regulate the interaction. Further, it is known that binding of TXNIP protein to TRX protein inhibits TRX activity. It is also known that TRX protein is up-regulated in tumor cells to promote tumorigenesis. Therefore, the candidates can be determined as anticancer therapeutic agents having anticancer effects on tumors by examining whether the candidates promote the interaction between TRX and TXNIP, compared to control group treated with no candidates. Further, when TXNIP protein is over-expressed, insulin sensitivity is reduced and blood glucose level is increased. Therefore, the candidates can be determined as diabetes therapeutic agents that function to lower blood glucose levels in diabetes by examining whether the candidates diminish the interaction between TRX and TXNIP, compared to control group treated with no candidates.

In still another embodiment, the present invention provides a method for screening an inhibitor of TRX activity using the tertiary structure of the modified TXNIP protein or the modified TRX-TXNIP complex.

The method for screening an inhibitor of TRX activity may preferably include (a) producing or selecting a candidate peptide of inhibiting TRX activity or a TRX-binding compound using the tertiary structure of N-TXNIP (the N-terminal domain of thioredoxin-interacting protein) having the atomic coordinates shown in Table 9; the tertiary structure of the modified TRX(thioredoxin)-TXNIP(thioredoxin-interacting protein) complex having the atomic coordinates shown in Table 10; or the tertiary structure of the modified TRX-TXNIP complex having the atomic coordinates shown in Table 11; and (b) examining whether the candidate peptide or compound produced or selected in Step (a) inhibits TRX activity; but is not limited thereto.

In particular, the method for screening an inhibitor of TRX activity may be used to produce a candidate peptide or compound inhibiting TRX activity, on the basis of one or more amino acid sequences selected from the group consisting of the amino acid sequences of β18 and β15 strands of T-TXNIP which are located in the center of the interaction interface between TRX and TXNIP, and combinations thereof, using the tertiary structure of N-TXNIP (the N-terminal domain of thioredoxin-interacting protein) having the atomic coordinates shown in Table 9; the tertiary structure of the modified TRX(thioredoxin)-TXNIP(thioredoxin-interacting protein) complex having the atomic coordinates shown in Table 10; or the tertiary structure of the modified TRX-TXNIP complex having the atomic coordinates shown in Table 11, but is not limited thereto.

In the present invention, the tertiary structures of N-TXNIP(K5A/K6A) (SEQ ID NO: 8); and the modified TRX-TXNIP complex were investigated. It was confirmed that β18 and β15 strands of T-TXNIP are located in the center of the interaction interface between TRX and TXNIP. Therefore, a peptide of inhibiting TRX activity can be synthesized or designed using the amino acid sequences of T-TXNIP β18 and β15 strands involved in the interaction with TRX or/and combinations thereof. In addition, a compound that binds to TRX and regulates its activity can be designed or/and synthesized using information about of β18 and β15 strands in the interaction interface between TRX and TXNIP. Preferably, the compound may be a small compound, but is not limited thereto. It is also known that binding of the TXNIP protein to TRX inhibits TRX activity. Therefore, when a peptide or a compound binding to TRX is synthesized using the information about the interaction interface between TRX and TXNIP, it can be a substance that binds to TRX and regulates its activity, like the TXNIP, but is not limited thereto.

The inhibition of TRX activity may include inhibition of Redox-potential of TRX or inhibition of interaction with a protein that is known to interact with TRX, but is not limited thereto.

By the method for screening an inhibitor of TRX activity, it is possible to further screen a substance having a TRX-inhibitory activity stronger than the TRX inhibitor screened in Step (b) using the designed tertiary structures. In such a manner, it is possible to investigate a substance having a higher TRX-inhibitory activity.

A step of determining the screened peptide or compound as an anticancer agent when the TRX-binding ability of the peptide or compound is higher than that of TXNIP may be further included.

In still another aspect, the present invention provides a method for screening a substance regulating TXNIP function using the tertiary structure of the modified TXNIP protein or modified TRX-TXNIP complex.

The method for screening a substance regulating TXNIP function may preferably include: (a) producing or selecting a candidate regulating TXNIP function using a tertiary structure of N-TXNIP (the N-terminal domain of thioredoxin-interacting protein) having the atomic coordinates shown in Table 9; a tertiary structure of the modified TRX(thioredoxin)-TXNIP(thioredoxin-interacting protein) complex having the atomic coordinates shown in Table 10; or a tertiary structure of the modified TRX-TXNIP complex having the atomic coordinates shown in Table 11; and (b) examining whether the candidate produced or selected in Step (a) regulates TXNIP function; but is not limited thereto. Further, the method may further include the step of determining the candidate regulating TXNIP function as a therapeutic agent for diabetes when the candidate reduces or inhibits TXNIP activity, compared to control group treated with no candidates.

Hereinafter, the present invention will be described in more detail with reference to the following Examples. However, these Examples are for illustrative purposes only, and the invention is not intended to be limited by these Examples.

Example 1: DNA Cloning

Since TXNIP could not be expressed as a soluble protein without TRX, plasmids co-expressing human TRX and TXNIP were constructed using a two-promoter vector system. Further, T-TXNIP (residues 3-317) with an N-terminal hexahistidine-tag containing an integrated rTEV protease cleavage site was cloned into pProEX HTa plasmid (Invitrogen), which expresses tag-free human TRX under the control of the T7 promoter. A plasmid co-expressing TRX (C35A)(SEQ ID NO:3) which was prepared by substituting alanine for cysteine at position 35 of human TRX and N-TXNIP was constructed by cloning N-TXNIP(residues 3-156) with an N-terminal hexahistidine-tag containing the integrated rTEV protein cleavage site into pPROEX-HTa plasmid (Invitrogen) which expresses tag-free human TRX (C35A)(SEQ ID NO:3) under the control of the T7 promoter using the two-promoter vector system. N-TXNIP was subcloned into the pHis-Parallel1 expression vector, which is a protein expression vector encoding an N-terminal hexahistidine tag with an rTEV protease cleavage site. For NMR experiments, TRX was subcloned into pET21 vector, which contains a C-terminal hexahistidine-tag. Cloning of T-TXNIP and TRX is described in more detail below.

Example 1-1: Amplification of T-TXNIP Gene

To synthesize and amplify T-TXNIP gene (T-TXNIP(3-317)) starting from amino acid 3 as the N-terminus and ending at amino acid 317 by PCR, two oligonucleotides were designed as follows and synthesized using a DNA synthesizer (Table 1).

TABLE 1

| | Sequence (5'→3') | SEQ ID NO. |
|---|---|---|
| Forward primer | CAT GCC ATG GTC AAG AAG ATC AAG | 11 |
| Reverse primer | ATA AGA ATG CGG CCG CTC ACA TCT CAG AGC TGG | 12 |

The forward primer contains a base sequence corresponding to the NcoI restriction enzyme recognition site, which is underlined. The reverse primer has a stop codon, which is indicated in italics and the restriction enzyme NotI recognition site underlined.

Human-derived TXNIP gene was used as a template to carry out PCR by the following procedure: 1 µl of TXNIP DNA, 1 µl of 10 mM dNTP (final concentration: 0.2 mM), 1 µl each of forward and reverse primers (final concentration: 0.2 µM), 0.5 µl of Taq DNA polymerase (5 U/µl, NEB, USA), and 5 µl of PCR buffer (NEB) are added to 40.5 µl of distilled water to prepare a reaction solution. After reaction was allowed at 95° C. for 3 minutes, 30 cycles of 95° C. for 30 seconds; 55° C. for 45 seconds; 72° C. for 1 minute and 30 seconds were performed. The reaction solution was separated on a 1% agarose gel by electrophoresis, and a desired DNA fragment was extracted and dissolved in 40 µl of distilled water (hereinafter, referred to as T-Txnip N/N).

Example 1-2: Construction of T-TXNIP-Containing Expression Vector

Plasmid pPROEX was completely cleaved with restriction enzymes, NcoI and NotI, and separated on a 1% agarose gel. 0.5 µg of T-TXNIP N/N and 0.6 µg of the plasmid vector pPROEX N/N were put in a reaction tube, and then 1 µl of 10× ligation solution (500 mM tris-HCl, pH 7.8, 100 mM magnesium chloride, 100 mM DTT, 10 mM ATP) and 10 U of T4 DNA ligase were added thereto and distilled water was added to a final volume of 10 µl, and allowed to react at 4° C. for 12 hours. This reaction solution was added to E. coli DH5α cell for transformation, and plated on a 100(g/ml LB-ampicillin medium to select E. coli transformants. Plasmids were extracted therefrom, and acquisition of pPROEX-T-TXNIP was confirmed by using restriction enzyme and sequencing. The nucleotide sequences of the N-TXNIP and T-TXNIP genes cloned into the recombinant plasmids were analyzed in accordance with the method of Sanger et al. (Sanger, F. et al., 1977 PNAS USA 74:5463) using a Big-Dye Cycle Sequencing System (Applied Biosystems, U.S.A) and a ABI 377 DNA sequencer.

Example 1-3: Amplification of TRX Gene

To synthesize and amplify TRX gene by PCR, two oligonucleotides were designed as follows and synthesized using a DNA synthesizer (Table 2).

TABLE 2

| | Sequence (5'→3') | SEQ ID NO. |
|---|---|---|
| Forward primer | GGA ATT C<u>CA TAT G</u>GT GAA GCA GAT | 13 |
| Reverse primer | CCG <u>CTC GAG</u> *TCA* GAC TAA TTC ATT AAT | 14 |

The forward primer contains a base sequence corresponding to the NdeI restriction enzyme recognition site (underlined), and the reverse primer contains a stop codon (in italics) and a base sequence corresponding to the restriction enzyme XhoI recognition site (underlined).

Human-derived TRX gene was used as a template to carry out PCR by the following procedure: 40.5 µl of distilled water was added to 1 µl of Trx DNA, 1 µl of 10 mM dNTP (final concentration: 0.2 mM), 1 µl each of forward and reverse primers (final concentration: 0.2 µM), 0.5 µl of Taq DNA polymerase (5 U/µl, NEB, USA), 5 µl of PCR buffer (NEB) to prepare a reaction solution. After reaction was allowed at 95° C. for 3 minutes, 30 cycles of 95° C. for 30 seconds; 55° C. for 45 seconds; 72° C. for 30 seconds were performed. The reaction solution was separated on a 1% agarose gel by electrophoresis, and a desired DNA fragment was extracted and dissolved in 40 µl of distilled water (hereinafter, referred to as Trx N/X).

Example 1-4: Construction of Expression Vector Containing T-TXNIP and TRX

Since TXNIP could not be expressed as a soluble protein without TRX protein, plasmids co-expressing human TRX and T-TXNIP were constructed using a two-promoter vector system as follows:

Recombinant plasmid pPROEX-T-TXNIP was completely cleaved with restriction enzymes, NdeI and XhoI, and separated on a 1% agarose gel. 0.3 µg of Trx N/X and 0.2 µg of the plasmid vector pPROEX-T-XNIP N/X were put in a reaction tube, and then 1 µl of 10× ligation solution (500 mM tris-HCl, pH 7.8, 100 mM magnesium chloride, 100 mM DTT, 10 mM ATP) and 10 U of T4 DNA ligase were added thereto and distilled water was added to a final volume of 10 µl, and allowed to react at 4° C. for 12 hours. This reaction solution was added to *E. coli* DH5α cells for transformation, and plated on a 100 µg/ml LB-ampicillin medium to select *E. coli* transformants. Plasmids were extracted therefrom, and acquisition of pPROEX-T-TXNIP-TRX was confirmed by using restriction enzyme and sequencing. The nucleotide sequence of the TXNIP gene cloned into the recombinant plasmid was analyzed in accordance with the method of Sanger et al. (Sanger, F. et al., 1977 *PNAS USA* 74:5463) using a Big-Dye Cycle Sequencing System (Applied Biosystems, USA) and a ABI 377 DNA sequencer.

Figure 1:
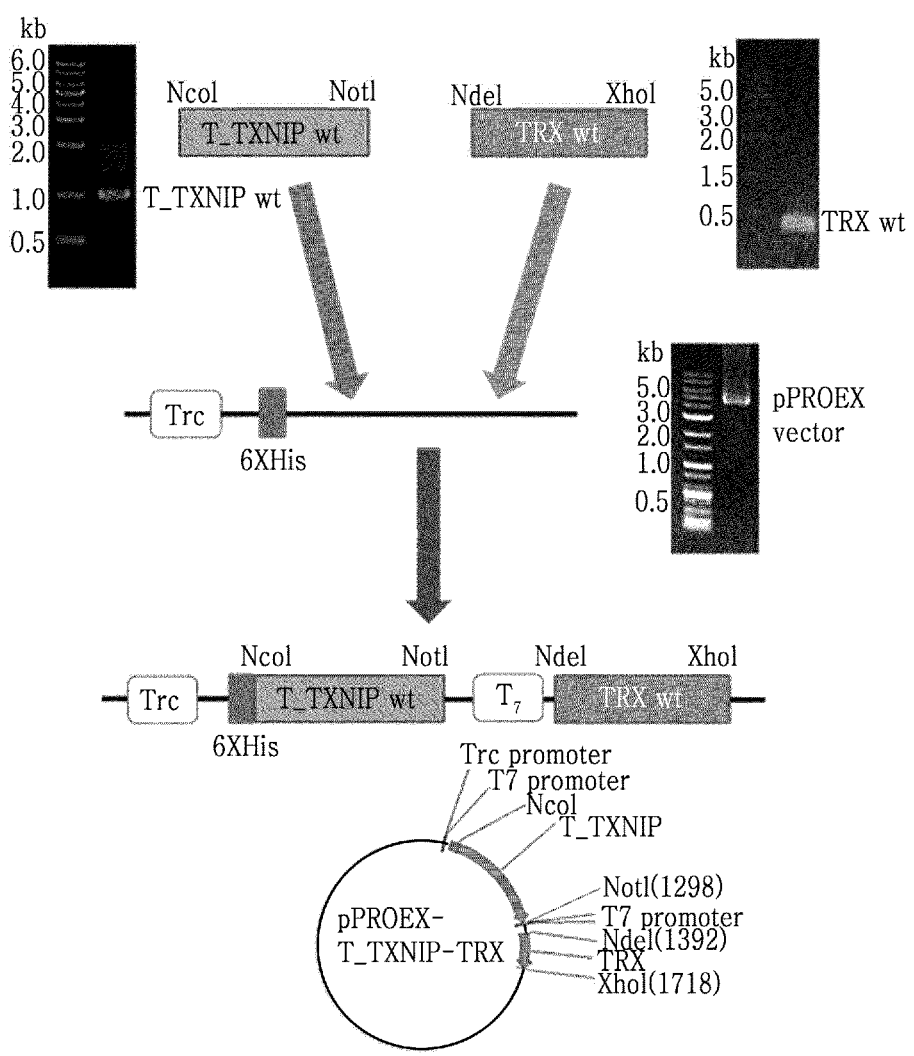
FIG. 1 illustrates cloning of the TXNIP gene and TRX gene into an *E. coli* expression vector, pPROEX-T-TXNIP-TRX.

The series of the procedures is shown in the diagram of FIG. 1.

Example 2: DNA Mutagenesis

Example 2-1: TRX Mutagenesis

To substitute alanine for cysteine at position 35 of TRX gene, two oligonucleotides were designed as follows and synthesized using a DNA synthesizer (Table 3).

TABLE 3

| | Sequence(5'→3') | SEQ ID NO. |
|---|---|---|
| Forward primer | CAG CCA CGT GGT GTG GGC <u>CTG</u> <u>C</u>CA AAA TGA TCA AGC CTT TC | 15 |
| Reverse primer | GAA AGG CTT GAT CAT TTT G<u>GC</u> <u>A</u>GG CCC ACA CCA CGT GGC TG | 16 |

The forward and reverse primers contain sequences (underlined) encoding the amino acids substituted with alanine (Ala) for cysteine (Cys). The expression vector pPROEX-T-TXNIP-TRX prepared in Example 1-4 was used as a template to carry out site-directed mutagenesis by the following procedure: 40.5 µl of distilled water was added to 0.5 µl of pPROEX-T-TXNIP-TRX, 1 µl of 100 mM dNTP, 1 µl each of forward and reverse primers (final concentration: 0.2 µM), 1 µl of pfu DNA polymerase (2.5 U/µl, Stratagene, USA), 5 µl of mutagenesis buffer (Stratagene, USA) to prepare a reaction solution. After reaction was allowed at 95° C. for 30 seconds, 18 cycles of 95° C. for 30 seconds; 55° C. for 60 seconds; 68° C. for 8 minutes were performed. After completion of the reaction, 1 µl of DpnI (NEB, USA) was added to the reaction solution, and allowed to react at 37° C. for 1 hour to remove pPROEX-T-TXNIP-TRX used as the template. This reaction solution was added to *E. coli* DH5α cell for transformation, and plated on a 100 µg/ml LB-ampicillin medium to select *E. coli* transformants. Plasmids were extracted therefrom, and the nucleotide sequence of TRX gene undergoing mutagenesis was examined.

Example 2-2: T-TXNIP Mutagenesis

To substitute serine for cysteine at position 120 of TXNIP gene, two oligonucleotides were designed as follows and synthesized using a DNA synthesizer (Table 4).

TABLE 4

| | Sequence(5'→3') | SEQ ID NO. |
|---|---|---|
| Forward primer | TTC AAA GGA AAA TAT GGG <u>TCT</u> GTA GAC TAC TGG GTG AAG | 17 |
| Reverse primer | CTT CAC CCA GTA GTC TAC <u>AGA</u> CCC ATA TTT TCC TTT GAA | 18 |

The forward and reverse primers contain sequences (underlined) encoding the amino acids substituted with serine for cysteine. In addition, for substitution of serine for cysteine at position 170 of TXNIP gene, the primers of SEQ ID NOs. 19 and 20 of the following Table 5 were synthesized. For substitution of serine for cysteine at position 205 of TXNIP gene, the primers of SEQ ID NOs. 21 and 22 of the following Table 6 were synthesized. For substitution of serine for cysteine at position 267 of TXNIP gene, the primers of SEQ ID NOs. 23 and 24 of the following Table 7 were synthesized.

TABLE 5

| | Sequence (5'→3') | SEQ ID NO. |
|---|---|---|
| Forward primer | AAA GAA AAG AAA GTT TCC <u>TCC</u> ATG TTC ATT CCT GAT GGG | 19 |

TABLE 5-continued

| | Sequence(5'→3') | SEQ ID NO. |
|---|---|---|
| Reverse primer | CCC ATC AGG AAT GAA CAT GGA GGA AAC TTT CTT TTC | 20 |

TABLE 6

| | Sequence(5'→3') | SEQ ID NO. |
|---|---|---|
| Forward primer | GCT GAC TTT GAG AAT ACA TCT TCC CGA ATT GTG GTC CCC | 21 |
| Reverse primer | GGG GAC CAC AAT TCG GGA AGA TGT ATT CTC AAA GTC AGC | 22 |

TABLE 7

| | Sequence(5'→3') | SEQ ID NO. |
|---|---|---|
| Forward primer | AGG CCT TCT ATC CTG GGC TCC AAC ATC TTC GA GTT GAA | 23 |
| Reverse primer | TTC AAC TCG AAG GAT GTT GGA GCC CAG GAT AGA AGG CCT | 24 |

The expression vector pPROEX-T-TXNIP-TRX(C35A) prepared by TRX mutagenesis was used as a template to carry out site-directed mutagenesis by the following procedure: 40.5 µl of distilled water was added to 0.5 µl of pPROEX-T-TXNIP-TRX(C35A), 1 µl of 100 mM dNTP, 1 µl each of forward and reverse primers of Table 4 (final concentration: 0.2 µM), 1 µl of pfu DNA polymerase (2.5 U/µl, Stratagene, USA), 5 µl of mutagenesis buffer (Stratagene, USA) to prepare a reaction solution. After reaction was allowed at 95° C. for 30 seconds, 18 cycles of 95° C. for 30 seconds; 55° C. for 60 seconds; and 68° C. for 8 minutes were performed. After completion of the reaction, 1 µl of DpnI (NEB, USA) was added to the reaction solution, and allowed to react at 37° C. for 1 hour to remove pPROEX-T-TXNIP-TRX(C35A) used as the template. This reaction solution was added to E. coli DH5α cell for transformation, and plated on a 100 µg/ml LB-ampicillin medium to select E. coli transformants. Plasmids were extracted therefrom, and the nucleotide sequence of Txnip gene undergoing mutagenesis was examined. To obtain pPROEX-T-TXNIP(C120,170S)-TRX(C35A), pPROEX-T-TXNIP(C120S)-TRX(C35A) as a template and the primers of Table 5 were used. pPROEX-T-TXNIP(C120,170S)-TRX(C35A) as a template and the primers of Table 6 were used to obtain pPROEX-T-TXNIP(C120,170,205S)-TRX(C35A). pPROEX-T_TXNIPC120,170,205S-TRXC35A as a template and the primers of Table 7 were used to obtain pPROEX-T-TXNIP(C120,170,205,267S)-TRX(C35A). The nucleotide sequences thereof were examined in the same manner as in Example 1-4.

Figure 2:
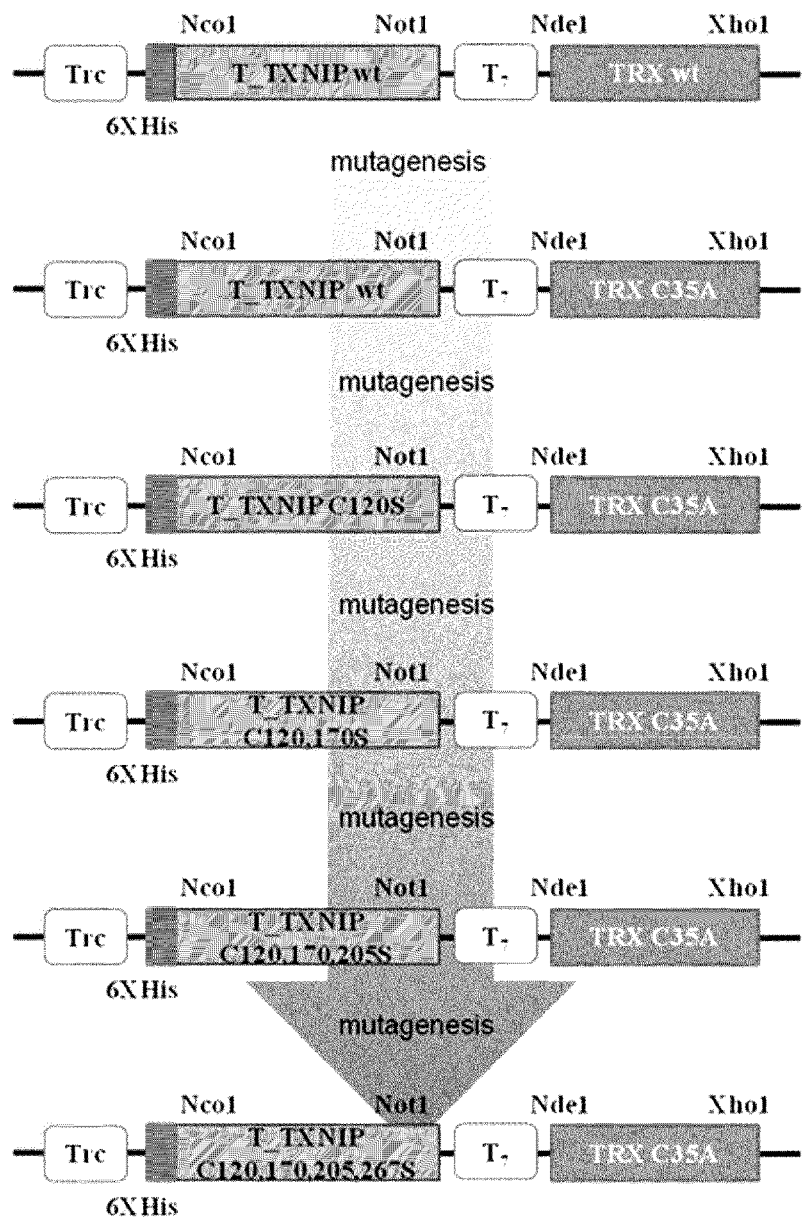
FIG. 2 illustrates mutagenesis of non-specific cysteines.
Figure 3:
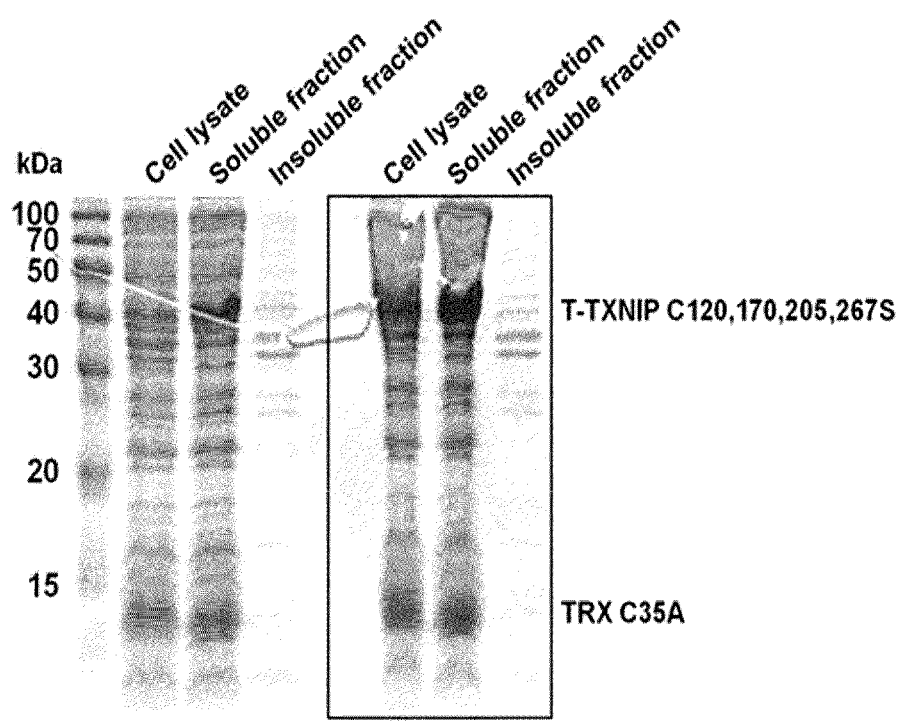
FIG. 3 shows the results of SDS-polyacrylamide gel electrophoresis of a cell pellet which was obtained by culturing *E. coli* transformed with mutation-induced pPROEX-T-TXNIP (C120,170,205,267S)(SEQ ID NO: 6)-TRX(C35A)(SEQ ID NO:3)
Figure 4:
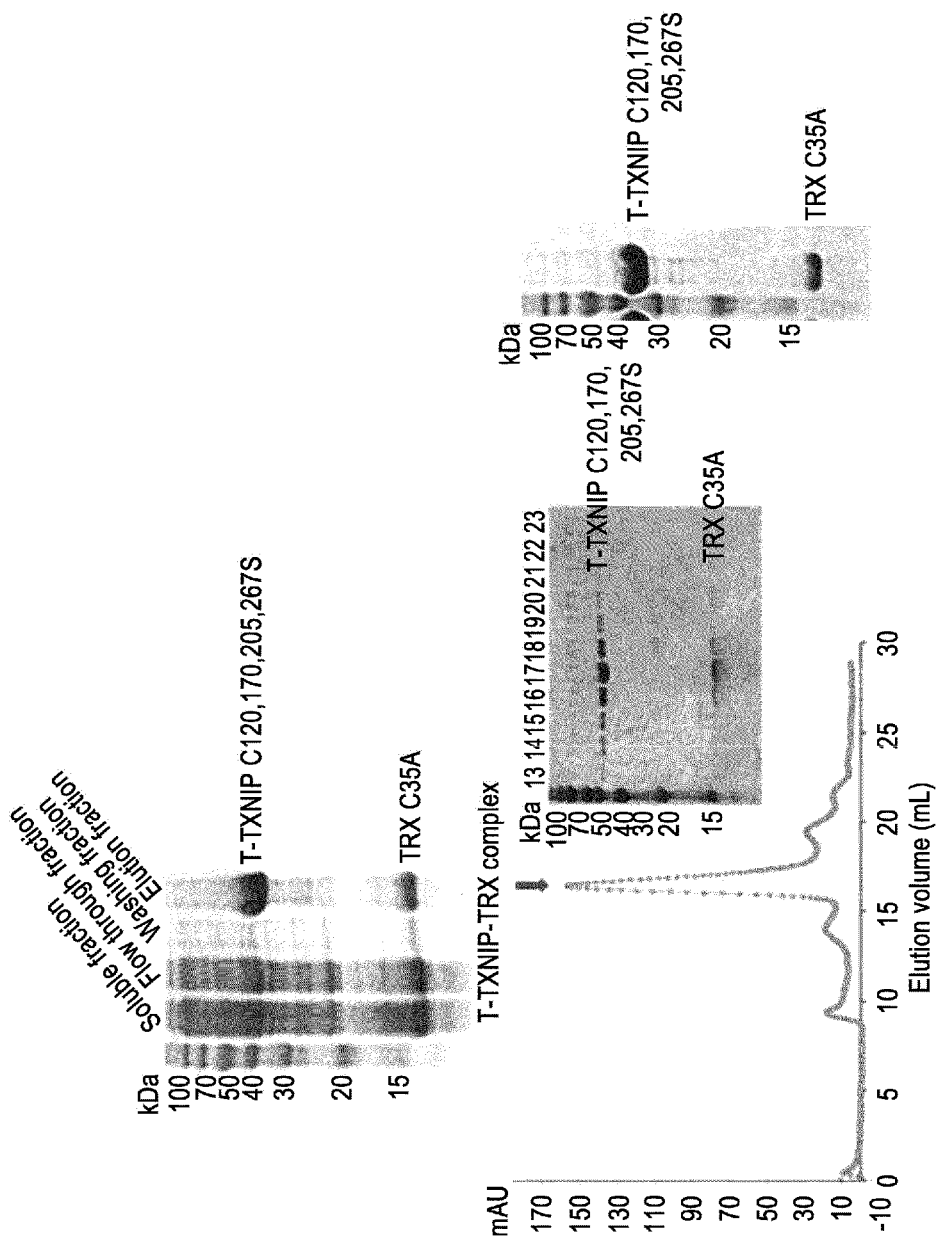
FIG. 4 shows the results of SDS-polyacrylamide gel electrophoresis of T-TXNIP-TRX purified from the cell pellet which was obtained by culturing *E. coli* transformed with mutation-induced pPROEX-T-TXNIP(C120,170,205, 267S)(SEQ ID NO: 6)-TRX(C35A)(SEQ ID NO:3)

A series of the mutagenesis procedures is shown in the diagram of FIG. 2.

Example 3: Protein Expression and Purification

Expression of TRX and T-TXNIP complex, their modified complexes, and TRX(C35A)-N-TXNIP complex was induced with 0.5 mM IPTG in E. coli Rosetta-Gami™ (DE3) cells at 21° C. for 40 hours. Expression of the N-TXNIP(K5A/K6A) mutant was induced with 0.5 mM IPTG in E. coli C41(DE3) cells at 21° C. for 16 hours. Recombinant proteins were purified by Ni-NTA affinity chromatography, treated with rTEV protease to remove hexahistidine-tags and further purified by size-exclusion chromatography and additional Ni-NTA affinity chromatography. The purified proteins were dialyzed against 50 mM Tris-HCl (pH 7.0). A selenomethionine (SeMet)-substituted complex of TRX(C35A)(SEQ ID NO:3) and T-TXNIP (C120S/C170S/C205S/C267S)(SEQ ID NO: 6), and SeMet-substituted N-TXNIP(K5A/K6A) were expressed in the methionine auxotroph E. coli B834(DE3) (Novagen) grown in minimal medium supplemented with 50 mg/ml SeMet under the same conditions as the cells containing the native plasmid. The SeMet-substituted proteins were purified as for the native proteins. TRX and its modified protein were expressed in E. coli C41 (DE3) using 0.5 mM IPTG at 21° C. for 18 hours and purified by Ni-NTA agarose affinity and size-exclusion chromatography. The proteins were then dialyzed against 50 mM potassium phosphate (pH 6.6) for NMR experiments. E. coli C41 (DE3) transformed with plasmids encoding N-TXNIP or its modified protein were grown in M9 minimal medium enriched with ($^{15}$NH$_4$)$_2$SO$_4$ (99% $^{15}$N; Cambridge Isotope Laboratory, Inc.) as the sole nitrogen source. All $^{15}$N-labeled proteins were purified using Ni-NTA affinity chromatography. The proteins were then treated with rTEV protease to remove the hexahistidine-tags and dialyzed against 50 mM potassium phosphate (pH 6.6) as a final step before NMR.

Example 3-1: Expression of T-TXNIP(C120,170,205,267S) and TRX(C35A) in E. coli

The expression vector pPROEX-T-TXNIP(C120,170, 205S,C267S)-TRX(C35A) prepared in Example 2-1 was transformed into a host cell, E. coli Rosetta-Gami(DE3) (Novagen Inc.). The transformed E. coli strain was cultured with shaking in 100 µg/ml LB-ampicillin-containing LB medium (1% bactotrypton, 0.5% yeast extract, 1% sodium chloride) for 12 hours, and then 2 ml thereof was transferred to 50 ml of LB medium (containing 100 ug/ml ampicillin). When absorbance at 600 nm was about 0.4-0.6, the culture temperature was reduced from 37° C. to 21° C., and the IPTG was added to a final concentration of 0.5 mM, followed by culture for about 40 hours. 10 ml of E. coli was taken and centrifuged at 6,500 rpm for 10 minutes to obtain a cell pellet, which was suspended in a buffer solution containing 50 mM Tris pH 8.0, 500 mM sodium chloride, 10% glycerol, and 1 mM DTT. Cells were disrupted using an ultrasonicator (VCX 500, Sonics, USA) on ice. This solution was centrifuged using a centrifuge at 16,000 rpm for 30 minutes, and then the supernatant and pellet were subjected to 15% SDS-polyacrylamide gel electrophoresis in accordance with the method of Laemmli et al., (1970 Nature 227: 680), and then proteins were stained with Coomassie Brilliant Blue for analysis.

Example 3-2: Purification of T-TXNIP(C120,170,205,267S) and TRX(C35A) Protein

E. coli in which T-TXNIP(C120,170,205,267S) and TRX (C35A) were expressed by the method in Example 2-1, was cultured in a 2-liter volume, and then centrifuged at 6,000 rpm for 10 minutes using a centrifuge to obtain an *E. coli* cell pellet, which was suspended in a buffer solution containing 50 mM Tris pH 8.0, 500 mM sodium chloride, 10% glycerol, and 1 mM DTT. Cells were disrupted using an ultrasonicator (VCX 500, Sonics, USA) on ice. This solution was centrifuged using a centrifuge at 16,000 rpm for 60 minutes, and then the supernatant was used in the following procedure:

The supernatant thus obtained was bound to Ni-NTA resin (Quiagen, USA) previously equilibrated with the buffer solution, and then Ni-NTA column was washed with a buffer solution containing 50 mM Tris pH 8.0, 500 mM sodium chloride, 10% glycerol, 1 mM DTT, and 30 mM Imidazole. Elution was carried out using a buffer solution containing 50 mM Tris pH 8.0, 500 mM sodium chloride, 10% glycerol, 1 mM DTT, and 250 mM Imidazole, and then SDS-PAGE was performed to collect only T-TXNIP(C120,170,205,267S) (SEQ ID NO: 6) and TRX(C35A)(SEQ ID NO:3) proteins, which were used in the following procedure: The T-TXNIP (C120,170,205,267S)(SEQ ID NO: 6) and TRX(C35A) (SEQ ID NO:3) proteins obtained in the above procedure were concentrated to 1 ml, and applied to a size-exclusion chromatography column (Superdex™ 200, 10/30 GL, GE) equilibrated with a buffer solution containing 50 mM Tris pH 8.0, 500 mM sodium chloride, 10% glycerol, and 2 mM DTT. Proteins were separated according to their molecular weight, and analyzed by electrophoresis, thereby collecting only T-TXNIP(C120,170,205,267S)(SEQ ID NO: 6) and TRX(C35A)(SEQ ID NO:3) proteins.

Example 4: Size-Exclusion Chromatography

A Superdex™ 200 10/300 GL gel filtration column (GE Healthcare) installed on an Acta purifier FPLC system (GE Healthcare) was equilibrated with 50 mM Tris-HCl (pH 8.0), 500 mM NaCl, and 10% glycerol at a flow rate of 0.4 ml/min at room temperature. Purified TRX-T-TXNIP and its mutants were injected onto the column Ovalbumin was used as a molecular weight standard.

Example 5: GST Pull-Down Assay and Coimmunoprecipitation Assay

To test the in vivo interprotomer interaction between TXNIP molecules, HEK 293T cells were transfected with plasmids expressing HA-tagged-TXNIP and FLAG-tagged T-TXNIP. 24 hours later, the cells were harvested and lysed in the 50 mM iodoacetamide-containing buffer [0.5% Triton X-100, 150 mM NaCl, 10% glycerol, 1 mM NaF, 1 mM AEBSF, 2 μg/mL leupeptin, 5 μg/mL aprotinin and 20 mM HEPES (pH 7.2)]. After centrifugation at 16,000 rpm for 20 minutes, the supernatant was incubated with anti-FLAG M2 agarose (Sigma) at 4° C. for 12 hours. The immobilized proteins were collected by centrifugation and washed three times with the lysis buffer. The bound proteins were subjected to SDS-PAGE under reduced and non-reduced conditions. For the assay demonstrating the TXNIP-TXNIP interaction, HEK 293T cells were transfected with combinations of expression plasmids. 24 hours later, the cells were harvested and lysed in the lysis buffer. After centrifugation at 16,000 g for 20 minutes, the supernatants were incubated at 4° C. for 12 hours with monoclonal anti-FLAG M2 agarose beads (Sigma) for immunoprecipitation, or with glutathione-conjugated sepharose beads (GE Healthcare) for pull-down assay. The immobilized proteins were collected by centrifugation and washed three times with lysis buffer. Bound proteins or WCLs were eluted by boiling in SDS sample buffer. To detect HA-tagged proteins, FLAG-tagged proteins or GST-fused proteins, the rabbit polyclonal anti-HA antibody (Santa Cruz Biotechnology), rabbit polyclonal anti-FLAG antibody (Santa Cruz Biotechnology) or rabbit polyclonal anti-GST antibody (Santa Cruz Biotechnology) was used and then HRP (horseradish peroxidase)-conjugated secondary antibody (Santa Cruz Biotechnology) was used to visualize the specific target bands in the membrane.

For immunoprecipitation assay showing the effect of TRX on the TXNIP-TXNIP interaction, the transfected HEK 293T cells were harvested and lysed in lysis buffer containing 0.5% Triton X-100, 150 mM NaCl, 10% glycerol and 20 mM HEPES (pH 7.2) supplemented with complete protease inhibitor cocktail (Roche). After incubation at 4° C. for 30 minutes, lysate was centrifuged at 16,000 g for 20 minutes. The supernatants were then precleared by incubation at 4° C. for 2 hours with 20 μl of protein G-sepharose beads (GE Healthcare) and centrifuged at 10,000 g for 5 minutes. The precleared lysate was incubated at 4° C. for 14 hours with the rabbit polyclonal anti-HA antibody (Santa Cruz Biotechnology), followed by further incubation at 4° C. for 5 hours with protein G-sepharose beads. After immunoprecipitation, the beads were washed five times with lysis buffer. Bound proteins or WCLs were eluted by boiling in LDS-PAGE loading buffer. To detect HA-tagged proteins or FLAG-tagged proteins, the mouse monoclonal anti-HA antibody (Abcam) or the mouse anti-FLAG antibody (Sigma) was used and then HRP (horseradish peroxidase)-conjugated secondary antibody (Santa Cruz Biotechnology) or peroxidase-conjugated light chain specific secondary antibody (Jackson ImmunoResearch Laboratories. Inc) was used to visualize the specific target bands in the membrane.

Example 6: Crystallization and Structure Determination

Because N-TXNIP was not crystallized, N-TXNIP(K5A/K6A)(SEQ ID NO: 8) with reduced surface entropy was crystallized using the sitting drop vapor-diffusion method at 21° C. The best crystals were obtained with sodium-potassium phosphate (0.75 M) and 0.1 M HEPES-Na (pH 7.5). Diffraction data were collected at beamline 4A of Pohang Accelerator Laboratory (PAL) at a resolution of 1.6 Å. SeMet-substituted K5A/K6A crystals were grown under the same crystallization conditions as for the wild-type protein (native protein).

Multiple-wavelength anomalous diffraction (MAD) data for the SeMet-substituted crystals were collected at beamline 6 C of PAL at a resolution of 1.8 Å. The TRX(C35A) (SEQ ID NO:3) and T-TXNIP(C120S/C170S/C205S/C267S)(SEQ ID NOL 6) complex crystals were optimized in 0.16 M sodium citrate and 16% PEG 3350, and diffraction data were collected at a resolution of 2.0 Å at PAL beamline 4A. SeMet-substituted crystals were grown under 0.2 M sodium citrate and 20% PEG 3,350. MAD data were collected at a resolution of 3.0 Å at PAL beamline 6 C. Crystals of the TRX(C35A)(SEQ ID NO:3) and T-TXNIP(C170S/C205S/C267S)(SEQ ID NO: 5) complex were optimized using conditions similar to those for the other complex, and diffraction data were collected at a resolution of 2.7 Å at PAL beamline 4A. All data were processed with the HKL2000 package. The N-TXNIP(K5A/K6A) (SEQ ID NO: 8) structure was determined by analyzing anomalous signals from Se atoms with the program SOLVE55. Density modification and subsequent automated model building were carried out using RESOLVE. The N-TXNIP(K5A/K6A) (SEQ ID NO: 8) crystal structure was solved at a resolution of 1.6 Å using the molecular replacement method (MR) with the program MOLREP, based on the partially refined structure of the SeMet crystal. The SeMet-substituted TRX(C35A)(SEQ ID NO:3) and T-TXNIP(C120S/C170S/C205S/C267S)(SEQ ID NO: 6) structure was determined using SOLVE, and subsequent automated model building was carried out using RESOLVE. The complex structure at a resolution of 2.0 Å was solved by MR using the partially refined SeMet complex structure. The TRX (C35A)(SEQ ID NO:3) and T-TXNIP(C170S/C205S/C267S)(SEQ ID NO: 5) complex structure was determined by MR using the TRX(C35A)(SEQ ID NO:3) and T-TXNIP (C120S/C170S/C205S/C267S)(SEQ ID NO: 6) complex model. All structures were revised using COOT and refined with REFMAC5.

All crystallographic data investigated by the method are summarized in the following Table 8. Further, the atomic coordinates of N-TXNIP(K5A/K6A) (SEQ ID NO: 8), COM1, and COM2 are summarized in the following Tables 9, 10, and 11, respectively.

TABLE 8

|  | SeMet_N-TXNIP | | | N-TXN P |
|---|---|---|---|---|
| Data collection | | | | |
| Space group | $P2_12_12_1$ | | | $P2_12_12_1$ |
| Cell dimensions | | | | |
| a, b, c (Å) | 37.30, 56.86, 67.80 | | | 37.43, 56.62, 67.66 |
| α, β, γ(°) | 90, 90, 90 | | | 90, 90, 90 |
|  | Peak | Inflection | Remote | |
| Wavelength | 0.9795 | 0.9796 | 0.9840 | 1.0000 |
| Resolution (Å) | 50-1.8 (1.86-1.8) | 50-1.8 (1.86-1.8) | 50-1.8 (1.86-1.8) | 50-1.6 (1.66-1.6)* |
| No. total reflections | 139,452 | 189,441 | 140,939 | 114,345 |
| No. unique reflections | 13,873 | 13,947 | 13,975 | 18,976 |
| Redundancy | 10.1 (7.2) | 13.6 (11.5) | 10.1 (5.9) | 6.0 (4.3) |
| Completeness (%) | 99.9 (99.6) | 100 (99.9) | 99.7 (97.5) | 97.0 (90.5) |
| $R_{sym}$ (%)[a] | 11.7 (66.8) | 9.1 (57.9) | 9.2 (77.8) | 8.3 (41.6) |
| I/σI | 15.15 (2.7) | 35.41 (3.69) | 24.36 (1.93) | 27.12 (2.28) |
| Refinement | | | | |
| Resolution (Å) | | | | 18.0-1.6 |
| $R_{work}/R_{free}$[b,c] | | | | 0.171/0.227 |
| R.m.s. deviations | | | | |
| Bond lengths (Å) | | | | 0.008 |
| Bond angles. (°) | | | | 1.129 |
| No. atoms[d] | | | | |
| Protein | | | | 1,203 |
| Waters | | | | 100 |
| Average B-factors (Å$^2$) | | | | |
| Protein | | | | 23.90 |
| Water | | | | 39.32 |
| Geometry (%) | | | | |
| Favored region | | | | 90.6 |
| Allowed region | | | | 9.4 |
| PDB ID | | | | 3ZXM |

|  | SeMet_Com1 | | | Com1 | Com2 |
|---|---|---|---|---|---|
| Data collection | | | | | |
| Space group | $P2_1$ | | | $P2_1$ | $P2_1$ |
| Cell dimensions | | | | | |
| a, b, c(Å) | 80.26, 61.34, 86.82 | | | 80.14, 64.02, 88.30 | 79.83, 64.99, 88.42 |
| α, β, γ(°) | 90, 90.74, 90 | | | 90, 91.28, 90 | 90, 90.88, 90 |
|  | Peak | Inflection | Remote | | |
| Wavelength | 0.9796 | 0.9798 | 0.9720 | 1.1000 | 1.1000 |
| Resolution (Å) | 50-3.0 (3.11-3.0) | 50-3.0 (3.11-3.0) | 50-3.0 (3.11-3.0) | 50-2.0 (2.07.2.0) | 50-2.7 (2.8-2.7) |
| No. total reflections | 103,337 | 102,172 | 101,165 | 383,487 | 167,343 |
| No. unique reflections | 17,243 | 17,243 | 17,183 | 58,935 | 24,910 |
| Redundancy | 6.0 (5.0) | 5.9 (4.9) | 5.9 (4.9) | 6.5 (5.0) | 6.7 (6.1) |
| Completeness (%) | 99.0 (98.0) | 99.0 (98.4) | 98.9 (98.0) | 96.6 (79.1) | 99.9 (100) |
| $R_{sym}$ (%)[a] | 9.6 (30.8) | 9.5 (33.1) | 95 (37.2) | 5.4 (38.9) | 9.1 (54.9) |
| I/σI | 24.33 (4.81) | 23.28 (4.57) | 21.11 (3.85) | 39.83 (2.65) | 24.06 (2.81) |
| Refinement | | | | | |
| Resolution (Å) | | | | 30.0-2.0 | 40.0-2.7 |
| $R_{work}/R_{free}$[b,c] | | | | 0.22/0.288 | 0.196/0.264 |

TABLE 8-continued

| R.m.s. deviations | | |
|---|---|---|
| Bond lengths (Å) | 0.015 | 0.022 |
| Bond angles (°) | 1.594 | 2.148 |
| No. atoms[d] | | |
| Protein | 6,011 | 6,015 |
| Waters | 248 | 59 |
| Average B-factors (Å$^2$) | | |
| Protein | 52.77 | 57.06 |
| Water | 52.33 | 52.92 |
| Geometry (%) | | |
| Favored region | 92.1 | 86.8 |
| Allowed region | 7.9 | 13.1 |
| PDB ID | 3ZY8 | 3ZY9 |

TABLE 9

Atomic coordinates for N-TXNIP(K5A/K6A) protein (SEQ ID NO: 8)

```
HEADER    ----              XX-XXX-9-XXXX
COMPND  --REMARK 3
REMARK   3  REFINEMENT.
REMARK   3    PROGRAM:     REFMAC 5.2.0019
REMARK   3    AUTHOHS:     MURSHUDOV, VAGIN, DODSON
REMARK   3
REMARK   3    REFINEMENT TARGET: MAXIMUM LIKELIHOOD
REMARK   3
REMARK   3  DATA USED IN REFINEMENT.
REMARK   3    RESOLUTION RANGE HIGH    (ANGSTROMS):  1.60
REMARK   3    RESOLUTION RANGE LOW     (ANGSTROMS): 18.78
REMARK   3    DATA CUTOFF        (SIGMA(F)): NONE
REMARK   3    COMPLETENESS FOR RANGE     (%): 97.02
REMARK   3    NUMBER OF REFLECTIONS:      17968
REMARK   3
REMARK   3  FIT TO DATA USED IN REFINEMENT.
REMARK   3    CROSS-VALIDATION METHOD:    THROUGHOUT
REMARK   3    FREE R VALUE TEST SET SELECTION:   RANDOM
REMARK   3    R VALUE   (WORKING + TEST SET): 0.17423
REMARK   3    R VALUE        (WORKING SET): 0.17136
REMARK   3    FREE R VALUE:        0.22711
REMARK   3    FREE R VALUE TEST SET SIZE    (%): 5.1
REMARK   3    FREE R VALUE TEST SET COUNT:      972
REMARK   3
REMARK   3  FIT IN THE HIGHEST RESOLUTION, BIN.
REMARK   3    TOTAL NUMBER OF BINS USED:          20
REMARK   3    BIN RESOLUTION RANGE HIGH:       1.602
REMARK   3    BIN RESOLUTION RANGE LOW:        1.644
REMARK   3    REFLECTION IN BIN       (WORKING SET): 1164
REMARK   3    BIB COMPLETENESS (WORKING + TEST) (%): 86.99
REMARK   3    BIN R VALUE         (WORKING SET): 0.175
REMARK   3    BIN FREE R VALUE SET COUNT:         66
REMARK   3    BIN FREE R VALUE:             0.278
REMARK   3
REMARK   3  NUMBER OF NON-HYDROGEN ATOMS USED IN REFINEMENT.
REMARK   3    ALL ATOMS:            1309
REMARK   3
REMARK   3  B VALUES.
REMARK   3    FROM WILSON PLOT       (A**2): NULL
REMARK   3    MEAN B VALUE    (OVERALL., A**2): 25.152
REMARK   3    OVERALL ANISOTROPIC B VALUE.
REMARK   3     B11 (A**2):   -0.52
REMARK   3     B22 (A**2):    1.57
REMARK   3     B33 (A**2):   -1.05
REMARK   3     B12 (A**2):    0.00
REMARK   3     B13 (A**2):    0.00
REMARK   3     B23 (A**2):    0.00
REMARK   3
REMARK   3  ESTIMATED OVERALL COORDINATE ERROR.
REMARK   3    ESU BASED ON R VALUE          (A): 0.130
REMARK   3    ESU BASED ON FREE R VALUE     (A): 0.101
REMARK   3    ESU BASED ON MAXIMUM LIKELIHOOD    (A): 0.062
REMARK   3    ESU FOR B VALUES BASED ON MAXIMUM LIKELIHOOD (A**2): 3.815
REMARK   3
REMARK   3  CORRELATION COEFFICIENTS.
```

TABLE 9-continued

Atomic coordinates for N-TXNIP(K5A/K6A) protein (SEQ ID NO: 8)

```
REMARK   3   CORRELATION COEFFICIENTS FO-FC:       0.962
REMARK   3   CORRELATION COEFFICIENTS FO-FC FREE:  0.946
REMARK   3
REMARK   3   RMS DEVIATIONS FROM IDEAL VALUES      COUNT    RMS    WEIGHT
REMARK   3    BOND LENGTHS REFINED ATOMS        (A):   1236; 0.008; 0.022
REMARK   3    BOND ANGLES REFINED ATOMS     (DEGREES): 1673; 1.129; 1.973
REMARK   3    TORSION ANGLES, PERIOD 1     (DEGREES):   154; 6.455; 5.000
REMARK   3    TORSION ANGLES, PERIOD 2     (DEGREES):    56; 30.081; 25.000
REMARK   3    TORSION ANGLES, PERIOD 3     (DEGREES):   216; 11.963; 15.000
REMARK   3    TORSION ANGLES, PERIOD 4     (DEGREES):     6; 14.421; 15.000
REMARK   3    CHIRAL-CENTER RESTRINTS       (A**3):    180; 0.075; 0.200
REMARK   3    GENERAL PLANES REFINED ATOMS     (A):    939; 0.004; 0.020
REMARK   3    NON-BONDED CONTACTS REFINED ATOMS (A):   470; 0.189; 0.200
REMARK   3    NON-BONDED TORSION REFINED ATOMS  (A):   844; 0.304; 0.200
REMARK   3    H-BOND (X . . . Y) REFINED ATOMS  (A):    80; 0.103; 0.200
REMARK   3    SYMMETRY VDW REFINED ATOMS        (A):    55; 0.244; 0.200
REMARK   3    SYMMETRY H-BOND REFINED ATOMS     (A):    10; 0.127; 0.200
REMARK   3
REMARK   3   ISOTROPIC THERMAL FACTOR RESTRAINTS.       COUNT   RMS    WEIGHT
REMARK   3    MAIN-CHAIN BOND REFINED ATOMS  (A**2):    789; 2.624; 3.000
REMARK   3    MAIN-CHAIN ANGEL REFINED ATOMS (A**2):   1233; 3.504; 5.000
REMARK   3    SIDE-CHAIN BOND REFINED ATOMS  (A**2):    520; 5.721; 8.000
REMARK   3    SIDE-CHAIN ANGEL REFINED ATOMS (A**2):    440; 7.977; 11.000
REMARK   3
REMARK   3   NCS RESTRAINTS STATISTICS
REMARK   3    NUMBER OF NCS GROUPS: NULL
REMARK   3
REMARK   3
REMARK   3   TLS DETAILS
REMARK   3    NUMBER OF TLS GROUPS:   1
REMARK   3    ATOM RECORD CONTAINS SUM OF TLS AND RESIDUAL B FACTORS
REMARK   3    ANISOU RECORD CONTAINS SUM OF TLS AND RESIDUAL B FACTORS
REMARK   3
REMARK   3    TLS GROUP:   1
REMARK   3     NUMBER OF COMPONENTS GROUP:    1
REMARK   3     COMPONENTS       C SSSEQI  TO  C SSSEQI
REMARK   3     RESIDUE RANGE:   A    4      A   154
REMARK   3     ORIGIN FOR THE GROUP (A):   16.6030  -1.6540  1.9700
REMARK   3     T TENSOR
REMARK   3      T11: -0.0181  T22:   0.0051
REMARK   3      T33: -0.0419  T12:   0.0000
REMARK   3      T13: -0.0027  T23:   0.0000
REMARK   3     L TENSOR
REMARK   3      L11:  0.9770  L22:   0.3478
REMARK   3      L33:  0.4541  L12:  -0.4797
REMARK   3      L13:  0.3257  L23:   0.1286
REMARK   3     S TENSOR
REMARK   3      S11: -0.0141  S12:  -0.0378 S13: -0.0250
REMARK   3      S21:  0.0094  S22:   0.0361 S23: -0.0045
REMARK   3      S31:  0.0003  S32:  -0.0356 S33: -0.0220
REMARK   3
REMARK   3
REMARK   3   BULK SOLVENT MODELLING.
REMARK   3    METHOD USED: MASK
REMARK   3    PARAMETERG FOR MASK CALCULATION
REMARK   3    VDW PROBE RADIUS:    1.20
REMARK   3    ION PROBE RADIUS:    0.80
REMARK   3    SHRINKAGE RADIUS:    0.80
REMARK   3
REMARK   3   OTHER REFINEMENT REMARKS: NULL
REMARK   3
LINK         ILE A  46                 ALA A  48
SSBOND   1 CYS A   63    CYS A  120
CRYST1   37.431  56.621  67.660  90.00  90.00  90.00 P 21 21 21
SCALE1      0.026716  0.000000  0.000000     0.000000
SCALE2      0.000000  0.017661  0.000000     0.000000
SCALE3      0.000000  0.000000  0.014780     0.000000
ATOM     1  N   VAL A   4       6.588  -4.946 -16.753  1.00  32.49          N
ANISOU   1  N   VAL A   4     4054  4600  3690   269  -313  -344       N
ATOM     2  CA  VAL A   4       6.134  -6.49  -16.022  1.00  31.87          C
ANISOU   2  CA  VAL A   4     3965  4455  3688   228  -358   -39       C
ATOM     3  CB  VAL A   4       7.210  -6.722  15.069  1.00  32.41          C
ANISOU   3  CB  VAL A   4     4044  4481  3799   200  -345  -355       C
ATOM     4  CG1 VAL A   4       7.622  -5.706 -14.039  1.00  35.34          C
ANISOU   4  CG1 VAL A   4     4423  4852  4154   166  -283  -287       C
ATOM     5  CG2 VAL A   4       6.691  -7.985 -14.381  1.00  34.48          C
ANISOU   5  CG2 VAL A   4     4292  4674  4133   160  -394  -373       C
ATOM     6  C   VAL A   4       4.865  -5.845 -15.239  1.00  30.08          C
```

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 6 | C | VAL | A | 4 | 3720 | 4204 | 3504 | 180 | −356 | −335 | C |
| ATOM | 7 | O | VAL | A | 4 | 4.907 | −5.176 | −14.198 | 1.00 | 27.32 | | O |
| ANISOU | 7 | O | VAL | A | 4 | 3374 | 3844 | 3164 | 143 | −312 | −280 | O |
| ATOM | 8 | N | ALA | A | 5 | 3.737 | −6.341 | −15.750 | 1.00 | 29.02 | | N |
| ANISOU | 8 | N | ALA | A | 5 | 3566 | 4065 | 3395 | 183 | −407 | −372 | N |
| ATOM | 9 | CA | ALA | A | 5 | 2.432 | −6.086 | −15.149 | 1.00 | 28.65 | | C |
| ANISOU | 9 | CA | ALA | A | 5 | 3495 | 4005 | 3387 | 143 | −408 | −341 | C |
| ATOM | 10 | CB | ALA | A | 5 | 2.239 | −6.931 | −13.873 | 1.00 | 28.88 | | C |
| ANISOU | 10 | CB | ALA | A | 5 | 3506 | 3970 | 3496 | 83 | −419 | −314 | C |
| ATOM | 11 | C | ALA | A | 5 | 2.274 | −4.588 | −14.858 | 1.00 | 27.43 | | C |
| ANISOU | 11 | C | ALA | A | 5 | 3348 | 3889 | 3184 | 144 | −347 | −286 | C |
| ATOM | 12 | O | ALA | A | 5 | 1.969 | −4.183 | −13.729 | 1.00 | 28.15 | | O |
| ANISOU | 12 | O | ALA | A | 5 | 3433 | 3963 | 3298 | 104 | −316 | −237 | O |
| ATOM | 13 | N | ALA | A | 6 | 2.528 | −3.783 | −15.892 | 1.00 | 23.33 | | N |
| ANISOU | 13 | N | ALA | A | 6 | 2844 | 3424 | 2597 | 194 | −331 | −294 | N |
| ATOM | 14 | CA | ALA | A | 6 | 2.424 | −2.321 | −15.834 | 1.00 | 22.79 | | C |
| ANISOU | 14 | CA | ALA | A | 6 | 2784 | 3390 | 2484 | 202 | −280 | −246 | C |
| ATOM | 15 | CB | ALA | A | 6 | 1.225 | −1.881 | −15.007 | 1.00 | 23.29 | | C |
| ANISOU | 15 | CB | ALA | A | 6 | 2829 | 3442 | 2577 | 167 | −272 | −213 | C |
| ATOM | 16 | C | ALA | A | 6 | 3.676 | −1.631 | −15.330 | 1.00 | 20.74 | | C |
| ANISOU | 16 | C | ALA | A | 6 | 2546 | 3129 | 2204 | 198 | −228 | −205 | C |
| ATOM | 17 | O | ALA | A | 6 | 3.832 | −0.431 | −15.538 | 1.00 | 20.05 | | O |
| ANISOU | 17 | O | ALA | A | 6 | 2469 | 3070 | 2079 | 214 | −192 | −170 | O |
| ATOM | 18 | N | ILE | A | 7 | 4.549 | −2.365 | −14.641 | 1.00 | 19.41 | | N |
| ANISOU | 18 | N | ILE | A | 7 | 2385 | 2924 | 2066 | 174 | −228 | −208 | N |
| ATOM | 19 | CA | ILE | A | 7 | 5.692 | −1.733 | −13.981 | 1.00 | 17.30 | | C |
| ANISOU | 19 | CA | ILE | A | 7 | 2133 | 2649 | 1789 | 163 | −183 | −169 | C |
| ATOM | 20 | CB | ILE | A | 7 | 6.048 | 2.400 | −12.633 | 1.00 | 16.07 | | C |
| ANISOU | 20 | CB | ILE | A | 7 | 1977 | 2443 | 1684 | 118 | −182 | −158 | C |
| ATOM | 21 | CG1 | ILE | A | 7 | 4.789 | −2.569 | −11.754 | 1.00 | 16.35 | | C |
| ANISOU | 21 | CG1 | ILE | A | 7 | 1993 | 2457 | 1761 | 83 | −193 | −143 | C |
| ATOM | 22 | CD1 | ILE | A | 7 | 4.031 | −1.269 | −11.449 | 1.00 | 17.42 | | C |
| ANISOU | 22 | CD1 | ILE | A | 7 | 2128 | 2616 | 1877 | 83 | −165 | −108 | C |
| ATOM | 23 | CG2 | ILE | A | 7 | 7.149 | −1.615 | −11.916 | 1.00 | 15.68 | | C |
| ANISOU | 23 | CG2 | ILE | A | 7 | 1943 | 2388 | 1625 | 108 | −139 | −212 | C |
| ATOM | 24 | C | ILE | A | 7 | 6.908 | −1.639 | −14.905 | 1.00 | 17.78 | | C |
| ANISOU | 24 | C | ILE | A | 7 | 2207 | 2743 | 1806 | 204 | −171 | −177 | C |
| ATOM | 25 | O | ILE | A | 7 | 7.391 | −2.639 | −15.425 | 1.00 | 21.43 | | O |
| ANISOU | 25 | O | ILE | A | 7 | 2668 | 3207 | 2265 | 225 | −199 | −219 | O |
| ATOM | 26 | N | LYS | A | 8 | 7.373 | −0.408 | −15.093 | 1.00 | 16.91 | | N |
| ANISOU | 26 | N | LYS | A | 8 | 2104 | 2659 | 1664 | 216 | −130 | −134 | N |
| ATOM | 27 | CA | LYS | A | 8 | 8.517 | −0.098 | −15.946 | 1.00 | 17.18 | | C |
| ANISOU | 27 | CA | LYS | A | 8 | 2141 | 2733 | 1654 | 254 | −108 | −122 | C |
| ATOM | 28 | CB | LYS | A | 8 | 8.326 | 1.306 | −16.534 | 1.00 | 19.14 | | C |
| ANISOU | 28 | CB | LYS | A | 8 | 2387 | 3017 | 1867 | 276 | −76 | −75 | C |
| ATOM | 29 | CG | LYS | A | 8 | 9.415 | 1.804 | −17456 | 1.00 | 22.55 | | C |
| ANISOU | 29 | CG | LYS | A | 8 | 2815 | 3498 | 2254 | 315 | −47 | −43 | C |
| ATOM | 30 | CD | LYS | A | 8 | 9.080 | 3.212 | −17.917 | 1.00 | 25.27 | | C |
| ANISOU | 30 | CD | LYS | A | 8 | 3156 | 3868 | 2577 | 330 | −19 | 13 | C |
| ATOM | 31 | CE | LYS | A | 8 | 10.194 | 3.815 | −18.760 | 1.00 | 28.39 | | C |
| ANISOU | 31 | CE | LYS | A | 8 | 3540 | 4311 | 2935 | 364 | 16 | 63 | C |
| ATOM | 32 | NZ | LYS | A | 8 | 11.406 | 4.090 | −17.945 | 1.00 | 37.63 | | N |
| ANISOU | 32 | NZ | LYS | A | 8 | 4709 | 5445 | 4142 | 328 | 42 | 98 | N |
| ATOM | 33 | C | LYS | A | 8 | 9.852 | −0.178 | −15.203 | 1.00 | 16.34 | | C |
| ANISOU | 33 | C | LYS | A | 8 | 2041 | 2602 | 1567 | 233 | −84 | −102 | C |
| ATOM | 34 | O | LYS | A | 8 | 10.866 | −0.605 | −15.764 | 1.00 | 18.18 | | O |
| ANISOU | 34 | O | LYS | A | 8 | 2273 | 2860 | 1776 | 260 | −82 | −113 | O |
| ATOM | 35 | N | ASER | A | 9 | 9.837 | 0.244 | −13.944 | 0.50 | 14.34 | | N |
| ANISOU | 35 | N | ASER | A | 9 | 1792 | 2304 | 1351 | 188 | −69 | −76 | N |
| ATOM | 36 | N | BSER | A | 9 | 9.862 | 0.267 | −13.947 | 0.50 | 14.82 | | N |
| ANISOU | 36 | N | BSER | A | 9 | 1853 | 2365 | 1411 | 188 | −68 | −75 | N |
| ATOM | 37 | CA | ASER | A | 9 | 11.025 | 0.264 | −13.120 | 0.50 | 13.92 | | C |
| ANISOU | 37 | CA | ASER | A | 9 | 1745 | 2227 | 1320 | 165 | −50 | −57 | C |
| ATOM | 38 | CA | BSER | A | 9 | 11.072 | 0.251 | −13.132 | 0.50 | 14.95 | | C |
| ANISOU | 38 | CA | BSER | A | 9 | 1874 | 2357 | 1449 | 166 | −49 | −57 | C |
| ATOM | 39 | CB | ASER | A | 9 | 11.864 | 1.503 | −13.423 | 0.50 | 14.63 | | C |
| ANISOU | 39 | CB | ASER | A | 9 | 1831 | 2335 | 1392 | 175 | −13 | −8 | C |
| ATOM | 40 | CB | BSER | A | 9 | 12.050 | 1.350 | −13.567 | 0.50 | 15.54 | | C |
| ANISOU | 40 | CB | BSER | A | 9 | 1946 | 2456 | 1503 | 180 | −14 | −11 | C |
| ATOM | 41 | OG | ASER | A | 9 | 13.063 | 1.502 | −12.674 | 0.50 | 14.78 | | O |
| ANISOU | 41 | OG | ASER | A | 9 | 1851 | 2330 | 1434 | 154 | 2 | 7 | O |
| ATOM | 42 | OG | BSER | A | 9 | 11.567 | 2.638 | −13.229 | 0.50 | 19.95 | | O |
| ANISOU | 42 | OG | BSER | A | 9 | 2506 | 3002 | 2072 | 166 | 4 | 27 | O |
| ATOM | 43 | C | ASER | A | 9 | 10.602 | 0.254 | −11.664 | 0.50 | 12.92 | | C |
| ANISOU | 43 | C | ASER | A | 9 | 1621 | 2052 | 1236 | 122 | −52 | −51 | C |
| ATOM | 44 | C | BSER | A | 9 | 10.720 | 0.402 | −11.661 | 0.50 | 13.66 | | C |
| ANISOU | 44 | C | BSER | A | 9 | 1715 | 2146 | 1328 | 122 | −47 | −46 | C |
| ATOM | 45 | O | ASER | A | 9 | 9.519 | 0.735 | −11.318 | 0.50 | 12.43 | | O |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 45 | O | ASER | A | 9 | 1558 | 1984 | 1182 | 111 | −54 | −42 | O |
| ATOM | 46 | O | BSER | A | 9 | 9.810 | 1.153 | −11.304 | 0.50 | 13.98 | | O |
| ANISOU | 46 | O | BSER | A | 9 | 1756 | 2182 | 1375 | 112 | −43 | −29 | O |
| ATOM | 47 | N | PHE | A | 10 | 11.455 | −0.322 | −10.823 | 1.00 | 13.57 | | N |
| ANISOU | 47 | N | PHE | A | 10 | 1707 | 2107 | 1343 | 102 | −51 | −54 | N |
| ATOM | 48 | CA | PHE | A | 10 | 11.222 | −0.367 | −9.386 | 1.00 | 12.00 | | C |
| ANISOU | 48 | CA | PHE | A | 10 | 1624 | 1985 | 1292 | 68 | −50 | −45 | C |
| ATOM | 49 | CB | PHE | A | 10 | 10.333 | −1.572 | −9.034 | 1.00 | 13.74 | | C |
| ANISOU | 49 | CB | PHE | A | 10 | 1723 | 2074 | 1423 | 53 | −80 | −68 | C |
| ATOM | 50 | CG | PHE | A | 10 | 9.907 | −1.619 | −7.586 | 1.00 | 13.93 | | C |
| ANISOU | 50 | CG | PHE | A | 10 | 1743 | 2074 | 1476 | 25 | −76 | −49 | C |
| ATOM | 51 | CD1 | PHE | A | 10 | 9.568 | −0.457 | −6.903 | 1.00 | 14.02 | | C |
| ANISOU | 51 | CD1 | PHE | A | 10 | 1756 | 2090 | 1481 | 21 | −56 | −24 | C |
| ATOM | 52 | CE1 | PHE | A | 10 | 9.162 | −0.503 | −5.563 | 1.00 | 14.76 | | C |
| ANISOU | 52 | CE1 | PHE | A | 10 | 2092 | 2421 | 1840 | 5 | −52 | −8 | C |
| ATOM | 53 | CZ | PHE | A | 10 | 9.085 | −1.722 | −4.907 | 1.00 | 14.49 | | C |
| ANISOU | 53 | CZ | PHE | A | 10 | 1800 | 2123 | 1584 | −12 | −65 | −8 | C |
| ATOM | 54 | CE2 | PHE | A | 10 | 9.413 | −2.887 | −5.583 | 1.00 | 16.25 | | C |
| ANISOU | 54 | CE2 | PHE | A | 10 | 2021 | 2331 | 1823 | −15 | −87 | −30 | C |
| ATOM | 55 | CD2 | PHE | A | 10 | 9.805 | −2.837 | −6.916 | 1.00 | 15.39 | | C |
| ANISOU | 55 | CD2 | PHE | A | 10 | 1920 | 2234 | 1694 | 5 | −94 | −56 | C |
| ATOM | 56 | C | PHE | A | 10 | 12.601 | −0.514 | −8.773 | 1.00 | 14.48 | | C |
| ANISOU | 56 | C | PHE | A | 10 | 1828 | 2169 | 1502 | 59 | −38 | −38 | C |
| ATOM | 57 | O | PHE | A | 10 | 13.280 | −1.523 | −9.006 | 1.00 | 14.39 | | O |
| ANISOU | 57 | O | PHE | A | 10 | 1818 | 2158 | 1494 | 65 | −49 | −60 | O |
| ATOM | 58 | N | GLU | A | 11 | 13.045 | 0.503 | −8.038 | 1.00 | 12.99 | | N |
| ANISOU | 58 | N | GLU | A | 11 | 1643 | 1970 | 1323 | 47 | −18 | −12 | N |
| ATOM | 59 | CA | GLU | A | 11 | 14.418 | 0.489 | −7.527 | 1.00 | 15.14 | | C |
| ANISOU | 59 | CA | GLU | A | 11 | 1916 | 2230 | 1607 | 40 | −8 | −6 | C |
| ATOM | 60 | CB | GLU | A | 11 | 15.387 | 10.53 | −8.567 | 1.00 | 17.78 | | C |
| ANISOU | 60 | CB | GLU | A | 11 | 2244 | 2589 | 1924 | 58 | 9 | 12 | C |
| ATOM | 61 | CG | GLU | A | 11 | 15.252 | 2.542 | −8.843 | 1.00 | 21.55 | | C |
| ANISOU | 61 | CG | GLU | A | 11 | 2718 | 3068 | 2402 | 59 | 25 | 48 | C |
| ATOM | 62 | CD | GLU | A | 11 | 16.203 | 3.044 | −9.929 | 1.00 | 30.13 | | C |
| ANISOU | 62 | CD | GLU | A | 11 | 3790 | 4185 | 3474 | 77 | 45 | 79 | C |
| ATOM | 63 | OE1 | GLU | A | 11 | 17.220 | 2.372 | −10.219 | 1.00 | 33.09 | | O |
| ANISOU | 63 | OE1 | GLU | A | 11 | 4156 | 4577 | 3839 | 86 | 50 | 74 | O |
| ATOM | 64 | OE2 | GLU | A | 11 | 15.927 | 4.132 | −10.487 | 1.00 | 39.30 | | O |
| ANISOU | 64 | OE2 | GLU | A | 11 | 4946 | 5355 | 4632 | 84 | 57 | 113 | O |
| ATOM | 65 | C | GLU | A | 11 | 14.585 | 1.238 | −6.219 | 1.00 | 14.75 | | C |
| ANISOU | 65 | C | GLU | A | 11 | 1871 | 2155 | 1580 | 22 | −2 | 8 | C |
| ATOM | 66 | O | GLU | A | 11 | 13.833 | 2.158 | −5.941 | 1.00 | 13.74 | | O |
| ANISOU | 66 | O | GLU | A | 11 | 1744 | 2023 | 1452 | 22 | 0 | 19 | O |
| ATOM | 67 | N | VAL | A | 12 | 15.581 | 0.820 | −5.438 | 1.00 | 13.52 | | N |
| ANISOU | 67 | N | VAL | A | 12 | 1715 | 1984 | 1438 | 13 | −2 | 3 | N |
| ATOM | 68 | CA | VAL | A | 12 | 16.050 | 1.549 | −4.265 | 1.00 | 14.45 | | C |
| ANISOU | 68 | CA | VAL | A | 12 | 1834 | 2081 | 1574 | 3 | −1 | 10 | C |
| ATOM | 69 | CB | VAL | A | 12 | 16.468 | 0.574 | −3.122 | 1.00 | 14.14 | | C |
| ANISOU | 69 | CB | VAL | A | 12 | 1797 | 2031 | 1545 | −4 | −9 | −3 | C |
| ATOM | 70 | CG1 | VAL | A | 12 | 17.154 | 1.317 | −1.974 | 1.00 | 14.70 | | C |
| ANISOU | 70 | CG1 | VAL | A | 12 | 1868 | 2086 | 1630 | −6 | −11 | −3 | C |
| ATOM | 71 | CG2 | VAL | A | 12 | 15.263 | −0.195 | −2.009 | 1.00 | 15.84 | | C |
| ANISOU | 71 | CG2 | VAL | A | 12 | 2012 | 2248 | 1757 | −7 | −17 | −6 | C |
| ATOM | 72 | C | VAL | A | 12 | 17.249 | 2.408 | −4.697 | 1.00 | 14.98 | | C |
| ANISOU | 72 | C | VAL | A | 12 | 1895 | 2146 | 1653 | 3 | 10 | 27 | C |
| ATOM | 73 | O | VAL | A | 12 | 18.189 | 1.905 | −5.290 | 1.00 | 15.54 | | O |
| ANISOU | 73 | O | VAL | A | 12 | 1958 | 2229 | 1719 | 7 | 16 | 29 | O |
| ATOM | 74 | N | VAL | A | 13 | 17.197 | 3.705 | −4.420 | 1.00 | 15.10 | | N |
| ANISOU | 74 | N | VAL | A | 13 | 1908 | 2143 | 1685 | 0 | 9 | 41 | N |
| ATOM | 75 | CA | VAL | A | 13 | 18.279 | 4.615 | −4.793 | 1.00 | 16.01 | | C |
| ANISOU | 75 | CA | VAL | A | 13 | 2010 | 2248 | 1824 | −6 | 15 | 66 | C |
| ATOM | 76 | CB | VAL | A | 13 | 17.807 | 5.655 | −5.872 | 1.00 | 17.13 | | C |
| ANISOU | 76 | CB | VAL | A | 13 | 2147 | 2397 | 1986 | 1 | 25 | 99 | C |
| ATOM | 77 | CG1 | VAL | A | 13 | 18.910 | 6.668 | −6.190 | 1.00 | 23.67 | | C |
| ANISOU | 77 | CG1 | VAL | A | 13 | 2956 | 3209 | 2831 | −9 | 30 | 137 | C |
| ATOM | 78 | CG2 | VAL | A | 13 | 17.354 | 4.955 | −7.140 | 1.00 | 19.50 | | C |
| ANISOU | 78 | CG2 | VAL | A | 13 | 2445 | 2739 | 2225 | 19 | 38 | 103 | C |
| ATOM | 79 | C | VAL | A | 13 | 18.745 | 5.349 | −3.538 | 1.00 | 15.69 | | C |
| ANISOU | 79 | C | VAL | A | 13 | 1971 | 2173 | 1819 | −15 | −2 | 57 | C |
| ATOM | 80 | O | VAL | A | 13 | 17.966 | 6.075 | −2.927 | 1.00 | 17.64 | | O |
| ANISOU | 80 | O | VAL | A | 13 | 2227 | 2403 | 2073 | −9 | −16 | 47 | O |
| ATOM | 81 | N | PHE | A | 14 | 19.998 | 5.147 | −3.141 | 1.00 | 15.15 | | N |
| ANISOU | 81 | N | PHE | A | 14 | 1891 | 2095 | 1769 | −24 | −5 | 55 | N |
| ATOM | 82 | CA | PHE | A | 14 | 20.545 | 5.875 | −1.992 | 1.00 | 15.41 | | C |
| ANISOU | 82 | CA | PHE | A | 14 | 1922 | 2094 | 1839 | −29 | −28 | 40 | C |
| ATOM | 83 | CB | PHE | A | 14 | 21.745 | 5.151 | −1.374 | 1.00 | 15.63 | | C |
| ANISOU | 83 | CB | PHE | A | 14 | 1941 | 2123 | 1874 | −35 | −32 | 26 | C |
| ATOM | 84 | CG | PHE | A | 14 | 21.410 | 3.787 | −0.828 | 1.00 | 15.36 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 84 | CG | PHE | A | 14 | 1921 | 2111 | 1805 | −25 | −28 | 3 | C |
| ATOM | 85 | CD1 | PHE | A | 14 | 20.620 | 3.644 | 0.322 | 1.00 | 14.03 | | C |
| ANISOU | 85 | CD1 | PHE | A | 14 | 1767 | 1942 | 1623 | 13 | −41 | −20 | C |
| ATOM | 86 | CE1 | PHE | A | 14 | 20.295 | 2.368 | 0.815 | 1.00 | 17.03 | | C |
| ANISOU | 86 | CE1 | PHE | A | 14 | 2154 | 2340 | 1977 | −6 | −37 | −29 | C |
| ATOM | 87 | CZ | PHE | A | 14 | 20.756 | 1.233 | 0.148 | 1.00 | 16.73 | | C |
| ANISOU | 87 | CZ | PHE | A | 14 | 2114 | 2314 | 1930 | −12 | −26 | −24 | C |
| ATOM | 88 | CE2 | PHE | A | 14 | 21.536 | 1.376 | −0.997 | 1.00 | 15.44 | | C |
| ANISOU | 88 | CE2 | PHE | A | 14 | 1939 | 2155 | 1774 | −18 | −15 | −10 | C |
| ATOM | 89 | CD2 | PHE | A | 14 | 21.861 | 2.647 | −1.473 | 1.00 | 17.44 | | C |
| ANISOU | 89 | CD2 | PHE | A | 14 | 2181 | 2397 | 2049 | −25 | −13 | 7 | C |
| ATOM | 90 | C | PHE | A | 14 | 20.915 | 7.286 | −2.436 | 1.00 | 17.35 | | C |
| ANISOU | 90 | C | PHE | A | 14 | 2153 | 2310 | 2129 | −39 | −35 | 69 | C |
| ATOM | 91 | O | PHE | A | 14 | 21.386 | 7.485 | −3.567 | 1.00 | 10.14 | | O |
| ANISOU | 91 | O | PHE | A | 14 | 2361 | 2547 | 2363 | −47 | −16 | 109 | O |
| ATOM | 92 | N | ASN | A | 15 | 20.689 | 8.259 | −1.555 | 1.00 | 16.86 | | N |
| ANISOU | 92 | N | ASN | A | 15 | 2096 | 2211 | 2098 | −36 | −64 | 50 | N |
| ATOM | 93 | CA | ASN | A | 15 | 20.919 | 9.665 | −1.897 | 1.00 | 18.89 | | C |
| ANISOU | 93 | CA | ASN | A | 15 | 2341 | 2427 | 2410 | −46 | −80 | 75 | C |
| ATOM | 94 | CB | ASN | A | 15 | 20.483 | 10.563 | −0.742 | 1.00 | 19.39 | | C |
| ANISOU | 94 | CB | ASN | A | 15 | 2417 | 2451 | 2499 | −31 | −121 | 35 | C |
| ATOM | 95 | CG | ASN | A | 15 | 18.974 | 10.595 | −0.571 | 1.00 | 20.87 | | C |
| ANISOU | 95 | CG | ASN | A | 15 | 2629 | 2656 | 2644 | −5 | −120 | 17 | C |
| ATOM | 96 | OD1 | ASN | A | 15 | 18.230 | 10.178 | −1.458 | 1.00 | 24.30 | | O |
| ANISOU | 96 | OD1 | ASN | A | 15 | 3067 | 3122 | 3043 | −4 | −92 | 39 | O |
| ATOM | 97 | ND2 | ASN | A | 15 | 18.518 | 11.115 | 0.558 | 1.00 | 22.68 | | N |
| ANISOU | 97 | ND2 | ASN | A | 15 | 2871 | 2870 | 2878 | 19 | −154 | −27 | N |
| ATOM | 98 | C | ASN | A | 15 | 22.360 | 9.938 | −2.292 | 1.00 | 20.97 | | C |
| ANISOU | 98 | C | ASN | A | 15 | 2573 | 2675 | 2722 | −70 | −78 | 109 | C |
| ATOM | 99 | O | ASN | A | 15 | 22.628 | 10.713 | −3.219 | 1.00 | 22.32 | | O |
| ANISOU | 99 | O | ASN | A | 15 | 2722 | 2832 | 2926 | −83 | −70 | 159 | O |
| ATOM | 100 | N | ASP | A | 16 | 23.281 | 9.298 | −1.573 | 1.00 | 20.29 | | N |
| ANISOU | 100 | N | ASP | A | 16 | 2479 | 2591 | 2638 | −75 | −86 | 85 | N |
| ATOM | 101 | CA | ASP | A | 16 | 24.679 | 9.238 | −1.979 | 1.00 | 21.87 | | C |
| ANISOU | 101 | CA | ASP | A | 16 | 2646 | 2792 | 2872 | −96 | −78 | 116 | C |
| ATOM | 102 | CB | ASP | A | 16 | 25.604 | 9.780 | −0.888 | 1.00 | 21.90 | | C |
| ANISOU | 102 | CB | ASP | A | 16 | 2636 | 2752 | 2935 | −106 | −119 | 90 | C |
| ATOM | 103 | CG | ASP | A | 16 | 27.059 | 9.855 | −1.339 | 1.00 | 25.94 | | C |
| ANISOU | 103 | CG | ASP | A | 16 | 3104 | 3262 | 3491 | −132 | −112 | 130 | C |
| ATOM | 104 | OD1 | ASP | A | 16 | 27.396 | 9.317 | −2.422 | 1.00 | 27.05 | | O |
| ANISOU | 104 | OD1 | ASP | A | 16 | 3227 | 3445 | 3604 | −135 | −71 | 175 | O |
| ATOM | 105 | OD2 | ASP | A | 16 | 27.870 | 10.454 | −0.599 | 1.00 | 28.91 | | O |
| ANISOU | 105 | OD2 | ASP | A | 16 | 3461 | 3596 | 3929 | −145 | −150 | 115 | O |
| ATOM | 106 | C | ASP | A | 16 | 25.011 | 7.787 | −2.285 | 1.00 | 21.78 | | C |
| ANISOU | 106 | C | ASP | A | 16 | 2637 | 2835 | 2806 | 87 | 47 | 112 | C |
| ATOM | 107 | O | ASP | A | 16 | 25.268 | 7.003 | −1.368 | 1.00 | 20.90 | | O |
| ANISOU | 107 | O | ASP | A | 16 | 2536 | 2729 | 2676 | −80 | −58 | 73 | O |
| ATOM | 108 | N | PRO | A | 17 | 24.994 | 7.423 | −3.576 | 1.00 | 22.88 | | N |
| ANISOU | 108 | N | PRO | A | 17 | 2765 | 3013 | 2916 | −84 | −13 | 152 | N |
| ATOM | 109 | CA | PRO | A | 17 | 25.234 | 6.046 | −4.003 | 1.00 | 24.02 | | C |
| ANISOU | 109 | CA | PRO | A | 17 | 2913 | 3207 | 3008 | −69 | 11 | 143 | C |
| ATOM | 110 | CB | PRO | A | 17 | 25.038 | 6.105 | −5.523 | 1.00 | 24.92 | | C |
| ANISOU | 110 | CB | PRO | A | 17 | 3013 | 3360 | 3094 | −58 | 42 | 189 | C |
| ATOM | 111 | CG | PRO | A | 17 | 25.210 | 7.521 | −5.877 | 1.00 | 27.39 | | C |
| ANISOU | 111 | CG | PRO | A | 17 | 3303 | 3646 | 3460 | −76 | 40 | 238 | C |
| ATOM | 112 | CD | PRO | A | 17 | 24.699 | 8.303 | 4.722 | 1.00 | 25.88 | | C |
| ANISOU | 112 | CD | PRO | A | 17 | 3130 | 3395 | 3309 | −87 | 4 | 206 | C |
| ATOM | 113 | C | PRO | A | 17 | 26.630 | 5.531 | −3.661 | 1.00 | 22.75 | | C |
| ANISOU | 113 | C | PRO | A | 17 | 2729 | 3054 | 2861 | −76 | 10 | 140 | C |
| ATOM | 114 | O | PRO | A | 17 | 26.843 | 4.320 | −3.631 | 1.00 | 23.57 | | O |
| ANISOU | 114 | O | PRO | A | 17 | 2842 | 3187 | 2926 | −61 | 19 | 117 | O |
| ATOM | 115 | N | GLU | A | 18 | 27.562 | 6.430 | −3.372 | 1.00 | 21.14 | | N |
| ANISOU | 115 | N | GLU | A | 18 | 2495 | 2819 | 2716 | −97 | −4 | 161 | N |
| ATOM | 116 | CA | GLU | A | 18 | 28.923 | 6.016 | −3.035 | 1.00 | 19.85 | | C |
| ANISOU | 116 | CA | GLU | A | 18 | 2306 | 2665 | 2572 | −104 | −7 | 160 | C |
| ATOM | 117 | CB | GLU | A | 18 | 29.964 | 6.934 | −3.702 | 1.00 | 21.11 | | C |
| ANISOU | 117 | CB | GLU | A | 18 | 2414 | 2820 | 2788 | −126 | 1 | 223 | C |
| ATOM | 118 | CG | GLU | A | 18 | 29.778 | 7.168 | −5.223 | 1.00 | 27.34 | | C |
| ANISOU | 118 | CG | GLU | A | 18 | 3182 | 3650 | 3555 | −119 | 40 | 287 | C |
| ATOM | 119 | CD | GLU | A | 18 | 29.338 | 5.926 | −5.993 | 1.00 | 34.89 | | C |
| ANISOU | 119 | CD | GLU | A | 18 | 4160 | 4670 | 4428 | −83 | 70 | 273 | C |
| ATOM | 120 | OE1 | GLU | A | 18 | 28.459 | 6.062 | −6.870 | 1.00 | 36.47 | | O |
| ANISOU | 120 | OE1 | GLU | A | 18 | 4370 | 4892 | 4595 | −68 | 87 | 292 | O |
| ATOM | 121 | OE2 | GLU | A | 18 | 29.855 | 4.821 | −5.716 | 1.00 | 39.98 | | O |
| ANISOU | 121 | OE2 | GLU | A | 18 | 4809 | 5340 | 5041 | −68 | 72 | 240 | O |
| ATOM | 122 | C | GLU | A | 18 | 29.178 | 5.930 | −1.529 | 1.00 | 18.27 | | C |
| ANISOU | 122 | C | GLU | A | 18 | 2119 | 2432 | 2392 | −106 | −43 | 107 | C |
| ATOM | 123 | O | GLU | A | 18 | 30.242 | 5.486 | −1.104 | 1.00 | 18.46 | | O |

TABLE 9-continued

Atomic coordinates for N-TXNIP(K5A/K6A) protein (SEQ ID NO: 8)

| | | | | | | | | | | | | | |
|---|---|---|---|---|---|---|---|---|---|---|---|---|---|
| ANISOU | 123 | O | GLU | A | 18 | 2125 | 2463 | 2427 | −108 | −49 | 97 | | O |
| ATOM | 124 | N | LYS | A | 19 | 28.214 | 6.359 | −0.716 | 1.00 | 17.05 | | | N |
| ANISOU | 124 | N | LYS | A | 19 | 1994 | 2246 | 2240 | −100 | −69 | 72 | | N |
| ATOM | 125 | CA | LYS | A | 19 | 28.458 | 6.397 | 0.725 | 1.00 | 15.43 | | | C |
| ANISOU | 125 | CA | LYS | A | 19 | 1797 | 2015 | 2050 | −94 | −106 | 22 | | C |
| ATOM | 126 | CB | LYS | A | 19 | 27.375 | 7.192 | 1.448 | 1.00 | 16.61 | | | C |
| ANISOU | 126 | CB | LYS | A | 19 | 1972 | 2133 | 2206 | −83 | −134 | −8 | | C |
| ATOM | 127 | CG | LYS | A | 19 | 27.651 | 7.408 | 2.928 | 1.00 | 18.66 | | | C |
| ANISOU | 127 | CG | LYS | A | 19 | 2237 | 2372 | 2481 | −67 | −178 | −62 | | C |
| ATOM | 128 | CD | LYS | A | 19 | 26.716 | 8.469 | 3.476 | 1.00 | 25.64 | | | C |
| ANISOU | 128 | CD | LYS | A | 19 | 3139 | 3223 | 3381 | −53 | −211 | −89 | | C |
| ATOM | 129 | CE | LYS | A | 19 | 26.783 | 8.547 | 4.987 | 1.00 | 31.48 | | | C |
| ANISOU | 129 | CE | LYS | A | 19 | 3889 | 3957 | 4114 | −21 | −253 | −150 | | C |
| ATOM | 130 | NZ | LYS | A | 19 | 27.995 | 9.272 | 5.443 | 1.00 | 36.83 | | | N |
| ANISOU | 130 | NZ | LYS | A | 19 | 4538 | 4593 | 4861 | −33 | −298 | −169 | | N |
| ATOM | 131 | C | LYS | A | 19 | 28.567 | 4.992 | 1.320 | 1.00 | 15.16 | | | C |
| ANISOU | 131 | C | LYS | A | 19 | 1780 | 2015 | 1963 | −74 | −97 | −9 | | C |
| ATOM | 132 | O | LYS | A | 19 | 27.782 | 4.099 | 0.975 | 1.00 | 17.57 | | | O |
| ANISOU | 132 | O | LYS | A | 19 | 2109 | 2349 | 2219 | −61 | −75 | −10 | | O |
| ATOM | 133 | N | VAL | A | 20 | 29.571 | 4.818 | 2.179 | 1.00 | 14.82 | | | N |
| ANISOU | 133 | N | VAL | A | 20 | 1725 | 1967 | 1940 | −73 | −119 | −32 | | N |
| ATOM | 134 | CA | VAL | A | 20 | 29.740 | 3.623 | 3.005 | 1.00 | 15.67 | | | C |
| ANISOU | 134 | CA | VAL | A | 20 | 1848 | 2098 | 2006 | −52 | −119 | −63 | | C |
| ATOM | 135 | CB | VAL | A | 20 | 31.183 | 3.075 | 2.887 | 1.00 | 16.55 | | | C |
| ANISOU | 135 | CB | VAL | A | 20 | 1931 | 2226 | 2130 | −57 | −115 | −56 | | C |
| ATOM | 136 | CG1 | VAL | A | 20 | 31.391 | 1.885 | 3.786 | 1.00 | 16.32 | | | C |
| ANISOU | 136 | CG1 | VAL | A | 20 | 1919 | 2218 | 2063 | −33 | −119 | −86 | | C |
| ATOM | 137 | CG2 | VAL | A | 20 | 31.483 | 2.698 | 1.450 | 1.00 | 21.13 | | | C |
| ANISOU | 137 | CG2 | VAL | A | 20 | 2495 | 2835 | 2700 | −65 | −78 | −13 | | C |
| ATOM | 138 | C | VAL | A | 20 | 29.453 | 4.077 | 4.444 | 1.00 | 16.95 | | | C |
| ANISOU | 138 | C | VAL | A | 20 | 2024 | 2242 | 2173 | −33 | −158 | −108 | | C |
| ATOM | 139 | O | VAL | A | 20 | 30.007 | 5.081 | 4.904 | 1.00 | 18.76 | | | O |
| ANISOU | 139 | O | VAL | A | 20 | 2236 | 2440 | 2453 | −40 | −193 | −124 | | O |
| ATOM | 140 | N | TYR | A | 21 | 28.594 | 3.341 | 5.142 | 1.00 | 15.63 | | | N |
| ANISOU | 140 | N | TYR | A | 21 | 1885 | 2096 | 1956 | −8 | −154 | −128 | | N |
| ATOM | 141 | CA | TYR | A | 21 | 27.983 | 3.853 | 6.384 | 1.00 | 16.55 | | | C |
| ANISOU | 141 | CA | TYR | A | 21 | 2017 | 2208 | 2064 | 20 | −185 | −165 | | C |
| ATOM | 142 | CB | TYR | A | 21 | 26.481 | 3.516 | 6.411 | 1.00 | 16.74 | | | C |
| ANISOU | 142 | CB | TYR | A | 21 | 2067 | 2252 | 2042 | 35 | −166 | −158 | | C |
| ATOM | 143 | CG | TYR | A | 21 | 25.753 | 4.019 | 5.188 | 1.00 | 16.82 | | | C |
| ANISOU | 143 | CG | TYR | A | 21 | 2080 | 2249 | 2063 | 14 | −147 | −129 | | C |
| ATOM | 144 | CD1 | TYR | A | 21 | 25.669 | 3.235 | 4.031 | 1.00 | 15.29 | | | C |
| ANISOU | 144 | CD1 | TYR | A | 21 | 1886 | 2070 | 1855 | −4 | −112 | −96 | | C |
| ATOM | 145 | CE1 | TYR | A | 21 | 25.009 | 3.698 | 2.884 | 1.00 | 15.54 | | | C |
| ANISOU | 145 | CE1 | TYR | A | 21 | 1918 | 2095 | 1891 | −17 | −95 | −70 | | C |
| ATOM | 146 | CZ | TYR | A | 21 | 24.452 | 4.971 | 2.894 | 1.00 | 17.01 | | | C |
| ANISOU | 146 | CZ | TYR | A | 21 | 2105 | 2257 | 2101 | −18 | −112 | −72 | | C |
| ATOM | 147 | OH | TYR | A | 21 | 23.810 | 5.443 | 1.782 | 1.00 | 18.34 | | | O |
| ANISOU | 147 | OH | TYR | A | 21 | 2274 | 2421 | 2272 | −29 | −96 | −44 | | O |
| ATOM | 148 | CE2 | TYR | A | 21 | 24.529 | 5.770 | 4.027 | 1.00 | 16.70 | | | C |
| ANISOU | 148 | CE2 | TYR | A | 21 | 2067 | 2196 | 2080 | −2 | −149 | −107 | | C |
| ATOM | 149 | CD2 | TYR | A | 21 | 25.180 | 5.296 | 5.166 | 1.00 | 16.77 | | | C |
| ANISOU | 149 | CD2 | TYR | A | 21 | 2076 | 2216 | 2082 | 15 | −167 | −137 | | C |
| ATOM | 150 | C | TYR | A | 21 | 28.655 | 3.316 | 7.638 | 1.00 | 17.24 | | | C |
| ANISOU | 150 | C | TYR | A | 21 | 2103 | 2313 | 2135 | 46 | −206 | −198 | | C |
| ATOM | 151 | O | TYR | A | 21 | 29.032 | 2.158 | 7.689 | 1.00 | 18.73 | | | O |
| ANISOU | 151 | O | TYR | A | 21 | 2294 | 2527 | 2297 | 50 | −187 | −187 | | O |
| ATOM | 152 | N | GLY | A | 22 | 28.780 | 4.169 | 8.651 | 1.00 | 18.17 | | | N |
| ANISOU | 152 | N | GLY | A | 22 | 2218 | 2417 | 2268 | 69 | −240 | −230 | | N |
| ATOM | 153 | CA | GLY | A | 22 | 29.347 | 3.783 | 9.934 | 1.00 | 18.63 | | | C |
| ANISOU | 153 | CA | GLY | A | 22 | 2275 | 2498 | 2305 | 104 | −274 | −275 | | C |
| ATOM | 154 | C | GLY | A | 22 | 28.332 | 3.851 | 11.058 | 1.00 | 18.97 | | | C |
| ANISOU | 154 | C | GLY | A | 22 | 2338 | 2571 | 2298 | 154 | −287 | −302 | | C |
| ATOM | 155 | O | GLY | A | 22 | 27.162 | 4.200 | 10.843 | 1.00 | 18.50 | | | O |
| ANISOU | 155 | O | GLY | A | 22 | 2294 | 2514 | 2222 | 159 | −277 | −293 | | O |
| ATOM | 156 | N | SER | A | 23 | 28.786 | 3.515 | 12.259 | 1.00 | 19.56 | | | N |
| ANISOU | 156 | N | SER | A | 23 | 2411 | 2675 | 2344 | 194 | −310 | −334 | | N |
| ATOM | 157 | CA | SER | A | 23 | 27.923 | 3.492 | 13.430 | 1.00 | 20.71 | | | C |
| ANISOU | 157 | CA | SER | A | 23 | 2572 | 2866 | 2432 | 252 | −320 | −356 | | C |
| ATOM | 158 | CB | SER | A | 23 | 28.740 | 3.183 | 14.691 | 1.00 | 20.84 | | | C |
| ANISOU | 158 | CB | SER | A | 23 | 2581 | 2915 | 2424 | 298 | −350 | −392 | | C |
| ATOM | 159 | OG | SER | A | 23 | 29.391 | 1.932 | 14.568 | 1.00 | 25.56 | | | O |
| ANISOU | 159 | OG | SER | A | 23 | 3174 | 3530 | 3008 | 284 | −320 | −359 | | O |
| ATOM | 160 | C | SER | A | 23 | 27.166 | 4.979 | 13.610 | 1.00 | 20.80 | | | C |
| ANISOU | 160 | C | SER | A | 23 | 25.89 | 2859 | 2455 | 273 | −353 | −391 | | C |
| ATOM | 161 | O | SER | A | 23 | 27.746 | 5.883 | 13.514 | 1.00 | 20.33 | | | O |
| ANISOU | 161 | O | SER | A | 23 | 2519 | 2753 | 2454 | 263 | −397 | −427 | | O |
| ATOM | 162 | N | GLY | A | 24 | 25.865 | 4.669 | 13.855 | 1.00 | 20.34 | | | N |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 162 | N | GLY | A | 24 | 2545 | 2837 | 2346 | 301 | −332 | −377 | N |
| ATOM | 163 | CA | GLY | A | 24 | 25.008 | 5.798 | 14.192 | 1.00 | 21.49 | | C |
| ANISOU | 163 | CA | GLY | A | 24 | 2698 | 2981 | 2487 | 336 | −362 | −412 | C |
| ATOM | 164 | C | GLY | A | 24 | 24.622 | 6.688 | 13.034 | 1.00 | 22.79 | | C |
| ANISOU | 164 | C | GLY | A | 24 | 2866 | 3087 | 2704 | 292 | −351 | −401 | C |
| ATOM | 165 | O | GLY | A | 24 | 23.904 | 7.673 | 13.229 | 1.00 | 24.17 | | O |
| ANISOU | 165 | O | GLY | A | 24 | 3048 | 3253 | 2881 | 320 | −388 | −431 | O |
| ATOM | 166 | N | GLU | A | 25 | 25.086 | 6.346 | 11.833 | 1.00 | 20.69 | | N |
| ANISOU | 166 | N | GLU | A | 25 | 2594 | 2789 | 2480 | 230 | −332 | −357 | N |
| ATOM | 167 | CA | GLU | A | 25 | 24.860 | 7.191 | 10.667 | 1.00 | 19.39 | | C |
| ANISOU | 167 | CA | GLU | A | 25 | 2427 | 2572 | 2367 | 189 | −330 | −339 | C |
| ATOM | 168 | CB | GLU | A | 25 | 26.003 | 7.048 | 9.658 | 1.00 | 19.75 | | C |
| ANISOU | 168 | CB | GLU | A | 25 | 2454 | 2582 | 2469 | 133 | −318 | −308 | C |
| ATOM | 169 | CG | GLU | A | 25 | 27.318 | 7.601 | 10.181 | 1.00 | 22.49 | | C |
| ANISOU | 169 | CG | GLU | A | 25 | 2779 | 2896 | 2868 | 132 | −366 | −345 | C |
| ATOM | 170 | CD | GLU | A | 25 | 28.452 | 7.561 | 9.168 | 1.00 | 25.38 | | C |
| ANISOU | 170 | CD | GLU | A | 25 | 3120 | 3231 | 3293 | 78 | −354 | −308 | C |
| ATOM | 171 | OE1 | GLU | A | 25 | 28.364 | 6.817 | 8.175 | 1.00 | 27.73 | | O |
| ANISOU | 171 | OE1 | GLU | A | 25 | 3416 | 3545 | 3574 | 50 | −304 | −258 | O |
| ATOM | 172 | OE2 | GLU | A | 25 | 29.450 | 8.285 | 9.384 | 1.00 | 38.20 | | O |
| ANISOU | 172 | OE2 | GLU | A | 25 | 4719 | 4816 | 4981 | 67 | −397 | −331 | O |
| ATOM | 173 | C | GLU | A | 25 | 23.513 | 6.922 | 10.018 | 1.00 | 19.25 | | C |
| ANISOU | 173 | C | GLU | A | 25 | 2425 | 2576 | 2315 | 184 | −289 | −301 | C |
| ATOM | 174 | O | GLU | A | 25 | 22.993 | 5.806 | 10.072 | 1.00 | 20.29 | | O |
| ANISOU | 174 | O | GLU | A | 25 | 2562 | 2751 | 2397 | 187 | −251 | −271 | O |
| ATOM | 175 | N | LYS | A | 26 | 22.851 | 7.970 | 9.422 | 1.00 | 20.46 | | N |
| ANISOU | 175 | N | LYS | A | 26 | 2581 | 2693 | 2499 | 175 | −301 | −302 | N |
| ATOM | 176 | CA | LYS | A | 26 | 21.688 | 7.886 | 8.694 | 1.00 | 20.50 | | C |
| ANISOU | 176 | CA | LYS | A | 26 | 2597 | 2712 | 2479 | 168 | −267 | −268 | C |
| ATOM | 177 | CB | LYS | A | 26 | 21.022 | 9.262 | 8.597 | 1.00 | 22.73 | | C |
| ANISOU | 177 | CB | LYS | A | 26 | 2886 | 2962 | 2788 | 184 | −298 | −290 | C |
| ATOM | 178 | CG | LYS | A | 26 | 19.572 | 9.211 | 8.116 | 1.00 | 25.36 | | C |
| ANISOU | 178 | CG | LYS | A | 26 | 3231 | 3321 | 3083 | 191 | −268 | −265 | C |
| ATOM | 179 | CD | LYS | A | 26 | 18.906 | 10.590 | 8.145 | 1.00 | 31.75 | | C |
| ANISOU | 179 | CD | LYS | A | 26 | 4048 | 4100 | 3915 | 216 | −304 | −293 | C |
| ATOM | 180 | CE | LYS | A | 26 | 19.462 | 11.514 | 7.070 | 1.00 | 39.38 | | C |
| ANISOU | 180 | CE | LYS | A | 26 | 5008 | 4006 | 4950 | 173 | −318 | −274 | C |
| ATOM | 181 | NZ | LYS | A | 26 | 18.856 | 12.876 | 7.140 | 1.00 | 45.68 | | N |
| ANISOU | 181 | NZ | LYS | A | 26 | 5814 | 5755 | 5788 | 199 | −359 | −302 | N |
| ATOM | 182 | C | LYS | A | 26 | 21.889 | 7.315 | 7.291 | 1.00 | 19.81 | | C |
| ANISOU | 182 | C | LYS | A | 26 | 2504 | 2613 | 2409 | 115 | −225 | −215 | C |
| ATOM | 183 | O | LYS | A | 26 | 22.774 | 7.748 | 6.554 | 1.00 | 19.96 | | O |
| ANISOU | 183 | O | LYS | A | 26 | 2510 | 2593 | 2480 | 81 | −231 | −202 | O |
| ATOM | 184 | N | VAL | A | 27 | 21.062 | 6.334 | 6.945 | 1.00 | 17.26 | | N |
| ANISOU | 184 | N | VAL | A | 27 | 2189 | 2327 | 2042 | 111 | −186 | −184 | N |
| ATOM | 185 | CA | VAL | A | 27 | 21.003 | 5.806 | 5.578 | 1.00 | 16.15 | | C |
| ANISOU | 185 | CA | VAL | A | 27 | 2046 | 2182 | 1909 | 72 | −151 | −141 | C |
| ATOM | 186 | CB | VAL | A | 27 | 20.875 | 4.277 | 5.558 | 1.00 | 15.51 | | C |
| ANISOU | 186 | CB | VAL | A | 27 | 1966 | 2135 | 1791 | 67 | −121 | −120 | C |
| ATOM | 187 | CG1 | VAL | A | 27 | 20.752 | 3.784 | 4.122 | 1.00 | 14.92 | | C |
| ANISOU | 187 | CG1 | VAL | A | 27 | 1890 | 2058 | 1722 | 37 | −93 | −87 | C |
| ATOM | 188 | CG2 | VAL | A | 27 | 22.054 | 3.618 | 6.280 | 1.00 | 15.97 | | C |
| ANISOU | 188 | CG2 | VAL | A | 27 | 2017 | 2199 | 1850 | 72 | −129 | −133 | C |
| ATOM | 189 | C | VAL | A | 27 | 19.741 | 6.400 | 4.998 | 1.00 | 18.14 | | C |
| ANISOU | 189 | C | VAL | A | 27 | 2306 | 2434 | 2153 | 76 | −143 | −129 | C |
| ATOM | 190 | O | VAL | A | 27 | 18.655 | 6.146 | 5.518 | 1.00 | 18.55 | | O |
| ANISOU | 190 | O | VAL | A | 27 | 2366 | 2518 | 2165 | 101 | −137 | −132 | O |
| ATOM | 191 | N | ALA | A | 28 | 19.895 | 7.242 | 3.971 | 1.00 | 17.60 | | N |
| ANISOU | 191 | N | ALA | A | 28 | 2233 | 2331 | 2122 | 53 | −145 | −113 | N |
| ATOM | 192 | CA | ALA | A | 28 | 18.772 | 7.950 | 3.336 | 1.00 | 18.03 | | C |
| ANISOU | 192 | CA | ALA | A | 28 | 2296 | 2382 | 2174 | 58 | −141 | −101 | C |
| ATOM | 193 | CB | ALA | A | 28 | 18.868 | 9.457 | 3.608 | 1.00 | 20.95 | | C |
| ANISOU | 193 | CB | ALA | A | 28 | 2667 | 2708 | 2590 | 69 | −180 | −122 | C |
| ATOM | 194 | C | ALA | A | 28 | 18.701 | 7.665 | 1.878 | 1.00 | 16.11 | | C |
| ANISOU | 194 | C | ALA | A | 28 | 2047 | 2140 | 1933 | 29 | −110 | −59 | C |
| ATOM | 195 | O | ALA | A | 28 | 19.723 | 7.548 | 1.202 | 1.00 | 16.68 | | O |
| ANISOU | 195 | O | ALA | A | 28 | 2106 | 2200 | 2030 | 6 | −101 | −39 | O |
| ATOM | 196 | N | GLY | A | 29 | 17.484 | 7.576 | 1.366 | 1.00 | 14.36 | | N |
| ANISOU | 196 | N | GLY | A | 29 | 1833 | 1939 | 1684 | 36 | −94 | −47 | N |
| ATOM | 197 | CA | GLY | A | 29 | 17.305 | 7.280 | −0.039 | 1.00 | 13.80 | | C |
| ANISOU | 197 | CA | GLY | A | 29 | 1759 | 1878 | 1607 | 18 | −68 | −13 | C |
| ATOM | 198 | C | GLY | A | 29 | 15.873 | 7.430 | −0.465 | 1.00 | 14.37 | | C |
| ANISOU | 198 | C | GLY | A | 29 | 1838 | 1968 | 1652 | 30 | −60 | −6 | C |
| ATOM | 199 | O | GLY | A | 29 | 15.046 | 7.995 | 0.253 | 1.00 | 15.17 | | O |
| ANISOU | 199 | O | GLY | A | 29 | 1948 | 2071 | 1746 | 52 | −75 | −24 | O |
| ATOM | 200 | N | ARG | A | 30 | 15.592 | 6.914 | −1.657 | 1.00 | 13.36 | | N |
| ANISOU | 200 | N | ARG | A | 30 | 1707 | 1859 | 1509 | 20 | −39 | 17 | N |
| ATOM | 201 | CA | ARG | A | 30 | 14.239 | 6.881 | −2.195 | 1.00 | 12.14 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 201 | CA | ARG | A | 30 | 1557 | 1727 | 1328 | 31 | −31 | 23 | C |
| ATOM | 202 | CB | ARG | A | 30 | 14.044 | 7.987 | −3.234 | 1.00 | 14.21 | | C |
| ANISOU | 202 | CB | ARG | A | 30 | 1819 | 1977 | 1604 | 33 | −29 | 48 | C |
| ATOM | 203 | CG | ARG | A | 30 | 14.022 | 9.402 | −2.600 | 1.00 | 17.51 | | C |
| ANISOU | 203 | CG | ARG | A | 30 | 2240 | 2357 | 2056 | 42 | −52 | 43 | C |
| ATOM | 204 | CD | ARG | A | 30 | 14.314 | 10.388 | −3.820 | 1.00 | 24.84 | | C |
| ANISOU | 204 | CD | ARG | A | 30 | 3162 | 3265 | 3010 | 37 | −47 | 81 | C |
| ATOM | 205 | NE | ARG | A | 30 | 15.592 | 10.172 | −4.503 | 1.00 | 22.60 | | O |
| ANISOU | 205 | NE | ARG | A | 30 | 2862 | 2979 | 2746 | 18 | −33 | 111 | N |
| ATOM | 206 | CZ | ARG | A | 30 | 15.935 | 10.748 | −5.650 | 1.00 | 30.94 | | C |
| ANISOU | 206 | CZ | ARG | A | 30 | 3905 | 4034 | 3818 | 11 | −19 | 157 | C |
| ATOM | 207 | NH1 | ARG | A | 30 | 15.096 | 11.584 | −6.256 | 1.00 | 29.63 | | N |
| ANISOU | 207 | NH1 | ARG | A | 30 | 3743 | 3865 | 3652 | 24 | −20 | 179 | N |
| ATOM | 208 | NH2 | ARG | A | 30 | 17.117 | 10.492 | −6.194 | 1.00 | 31.03 | | N |
| ANISOU | 208 | NH2 | ARG | A | 30 | 3890 | 4052 | 3842 | −4 | −4 | 187 | N |
| ATOM | 209 | C | ARG | A | 30 | 13.958 | 5.537 | −2.841 | 1.00 | 12.39 | | C |
| ANISOU | 209 | C | ARG | A | 30 | 1586 | 1789 | 1335 | 23 | −16 | 27 | C |
| ATOM | 210 | O | ARG | A | 30 | 14.861 | 4.919 | −3.435 | 1.00 | 13.49 | | O |
| ANISOU | 210 | O | ARG | A | 30 | 1720 | 1930 | 1476 | 13 | −7 | 33 | O |
| ATOM | 211 | N | VAL | A | 31 | 12.707 | 5.086 | −2.738 | 1.00 | 11.59 | | N |
| ANISOU | 211 | N | VAL | A | 31 | 1484 | 1708 | 1210 | 30 | −15 | 22 | N |
| ATOM | 212 | CA | VAL | A | 31 | 12.228 | 3.991 | −3.580 | 1.00 | 12.02 | | C |
| ANISOU | 212 | CA | VAL | A | 31 | 1534 | 1784 | 1250 | 25 | −10 | 24 | C |
| ATOM | 213 | CB | VAL | A | 31 | 11.262 | 3.037 | −2.827 | 1.00 | 11.50 | | C |
| ANISOU | 213 | CB | VAL | A | 31 | 1461 | 1732 | 1175 | 23 | −14 | 18 | C |
| ATOM | 214 | CG1 | VAL | A | 31 | 10.746 | 1.950 | −3.763 | 1.00 | 12.61 | | C |
| ANISOU | 214 | CG1 | VAL | A | 31 | 1594 | 1885 | 1312 | 15 | −18 | 16 | C |
| ATOM | 215 | CG2 | VAL | A | 31 | 11.915 | 2.414 | −1.598 | 1.00 | 13.19 | | C |
| ANISOU | 215 | CG2 | VAL | A | 31 | 1675 | 1940 | 1398 | 18 | −16 | 13 | C |
| ATOM | 216 | C | VAL | A | 31 | 11.518 | 4.668 | −4.757 | 1.00 | 12.39 | | C |
| ANISOU | 216 | C | VAL | A | 31 | 1581 | 1843 | 1285 | 35 | −6 | 35 | C |
| ATOM | 217 | O | VAL | A | 31 | 10.668 | 5.530 | −4.557 | 1.00 | 13.55 | | O |
| ANISOU | 217 | O | VAL | A | 31 | 1730 | 1990 | 1428 | 47 | −9 | 39 | O |
| ATOM | 218 | N | ILE | A | 32 | 11.891 | 4.309 | −5.980 | 1.00 | 11.21 | | N |
| ANISOU | 218 | N | ILE | A | 32 | 1428 | 1706 | 1125 | 37 | 1 | 41 | N |
| ATOM | 219 | CA | ILE | A | 32 | 11.331 | 4.971 | −7.155 | 1.00 | 14.31 | | C |
| ANISOU | 219 | CA | ILE | A | 32 | 1819 | 2116 | 1502 | 52 | 5 | 56 | C |
| ATOM | 220 | CB | ILE | A | 32 | 12.439 | 5.711 | −7.957 | 1.00 | 16.08 | | C |
| ANISOU | 220 | CB | ILE | A | 32 | 2039 | 2339 | 1732 | 56 | 19 | 84 | O |
| ATOM | 221 | CG1 | ILE | A | 32 | 13.125 | 6.750 | −7.054 | 1.00 | 19.72 | | C |
| ANISOU | 221 | CG1 | ILE | A | 32 | 2502 | 2761 | 2229 | 45 | 16 | 96 | C |
| ATOM | 222 | CD1 | ILE | A | 32 | 14.373 | 7.370 | −7.629 | 1.00 | 21.80 | | C |
| ANISOU | 222 | CD1 | ILE | A | 32 | 2755 | 3016 | 2513 | 40 | 28 | 130 | C |
| ATOM | 223 | CG2 | ILE | A | 32 | 11.877 | 6.365 | −9.220 | 1.00 | 15.53 | | C |
| ANISOU | 223 | CG2 | ILE | A | 32 | 1956 | 2293 | 1641 | 77 | 27 | 107 | C |
| ATOM | 224 | C | ILE | A | 32 | 10.598 | 3.951 | −8.019 | 1.00 | 14.68 | | C |
| ANISOU | 224 | C | ILE | A | 32 | 1860 | 2191 | 1525 | 60 | −1 | 40 | C |
| ATOM | 225 | O | ILE | A | 32 | 11.124 | 2.870 | −8.322 | 1.00 | 14.11 | | O |
| ANISOU | 225 | O | ILE | A | 32 | 1786 | 2125 | 1450 | 58 | −6 | 24 | O |
| ATOM | 226 | N | VAL | A | 33 | 9.372 | 4.300 | −8.382 | 1.00 | 13.68 | | N |
| ANISOU | 226 | N | VAL | A | 33 | 1731 | 2080 | 1385 | 72 | −6 | 41 | N |
| ATOM | 227 | CA | VAL | A | 33 | 8.534 | 3.483 | −9.259 | 1.00 | 12.83 | | C |
| ANISOU | 227 | CA | VAL | A | 33 | 1616 | 1998 | 1260 | 82 | −20 | 23 | C |
| ATOM | 228 | CB | VAL | A | 33 | 7.229 | 3.007 | −8.528 | 1.00 | 14.16 | | C |
| ANISOU | 228 | CB | VAL | A | 33 | 1776 | 2157 | 1439 | 71 | −34 | 11 | C |
| ATOM | 229 | CG1 | VAL | A | 33 | 6.529 | 1.919 | −9.310 | 1.00 | 16.20 | | C |
| ANISOU | 229 | CG1 | VAL | A | 33 | 2021 | 2440 | 1693 | 74 | −57 | −13 | C |
| ATOM | 230 | CG2 | VAL | A | 33 | 7.524 | 2.526 | −7.103 | 1.00 | 14.25 | | C |
| ANISOU | 230 | CG2 | VAL | A | 33 | 1785 | 2155 | 1474 | 49 | −34 | 12 | C |
| ATOM | 231 | C | VAL | A | 33 | 8.175 | 1.275 | −10.530 | 1.00 | 13.85 | | C |
| ANISOU | 231 | C | VAL | A | 33 | 1745 | 2158 | 1361 | 110 | −14 | 37 | C |
| ATOM | 232 | O | VAL | A | 33 | 7.858 | 5.472 | −10.474 | 1.00 | 14.97 | | O |
| ANISOU | 232 | O | VAL | A | 33 | 1890 | 2294 | 1503 | 117 | −5 | 60 | O |
| ATOM | 233 | N | GLU | A | 34 | 8.259 | 3.602 | −11.674 | 1.00 | 13.50 | | N |
| ANISOU | 233 | N | GLU | A | 34 | 1596 | 2142 | 1293 | 130 | −21 | 21 | N |
| ATOM | 234 | CA | GLU | A | 34 | 7.754 | 4.125 | −12.941 | 1.00 | 15.44 | | C |
| ANISOU | 234 | CA | GLU | A | 34 | 1038 | 2427 | 1504 | 163 | −20 | 30 | C |
| ATOM | 235 | CB | GLU | A | 34 | 8.888 | 4.463 | −13.919 | 1.00 | 15.98 | | C |
| ANISOU | 235 | CB | GLU | A | 34 | 2004 | 2522 | 1547 | 188 | 0 | 55 | C |
| ATOM | 236 | CG | GLU | A | 34 | 9.868 | 5.497 | −13.404 | 1.00 | 21.82 | | C |
| ANISOU | 236 | CG | GLU | A | 34 | 2745 | 3235 | 2310 | 172 | 25 | 100 | C |
| ATOM | 237 | CD | GLU | A | 34 | 11.003 | 5.766 | −14.369 | 1.00 | 27.54 | | C |
| ANISOU | 237 | CD | GLU | A | 34 | 3458 | 3991 | 3013 | 194 | 47 | 135 | C |
| ATOM | 238 | OE1 | GLU | A | 34 | 11.362 | 4.866 | −15.157 | 1.00 | 36.78 | | O |
| ANISOU | 238 | OE1 | GLU | A | 34 | 4623 | 5201 | 4150 | 220 | 43 | 113 | O |
| ATOM | 239 | OE2 | GLU | A | 34 | 11.549 | 6.887 | −14.335 | 1.00 | 36.57 | | O |
| ANISOU | 239 | OE2 | GLU | A | 34 | 4598 | 5121 | 4176 | 188 | 67 | 185 | O |
| ATOM | 240 | C | GLU | A | 34 | 6.866 | 8.059 | 18.545 | 1.00 | 15.07 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 240 | C | GLU | A | 34 | 1882 | 2401 | 1443 | 175 | −50 | −12 | C |
| ATOM | 241 | O | GLU | A | 34 | 7.128 | 1.867 | −13.398 | 1.00 | 15.56 | | O |
| ANISOU | 241 | O | GLU | A | 34 | 1941 | 2452 | 1518 | 167 | −69 | −44 | O |
| ATOM | 242 | N | VAL | A | 35 | 5.806 | 3.491 | −14.221 | 1.00 | 15.29 | | N |
| ANISOU | 242 | N | VAL | A | 35 | 1904 | 2458 | 1449 | 198 | −57 | −12 | N |
| ATOM | 243 | CA | VAL | A | 35 | 4.871 | 2.565 | −14.849 | 1.00 | 15.32 | | C |
| ANISOU | 243 | CA | VAL | A | 35 | 1896 | 2480 | 1444 | 212 | −92 | −55 | C |
| ATOM | 244 | CB | VAL | A | 35 | 3.492 | 2.586 | −14.145 | 1.00 | 14.95 | | C |
| ANISOU | 244 | CB | VAL | A | 35 | 1838 | 2419 | 1423 | 190 | −107 | −59 | C |
| ATOM | 245 | CG1 | VAL | A | 35 | 3.653 | 2.244 | −12.681 | 1.00 | 16.79 | | C |
| ANISOU | 245 | CG1 | VAL | A | 35 | 2072 | 2610 | 1699 | 148 | −102 | −50 | C |
| ATOM | 246 | CG2 | VAL | A | 35 | 2.809 | 3.951 | −14.304 | 1.00 | 15.26 | | C |
| ANISOU | 246 | CG2 | VAL | A | 35 | 1881 | 2477 | 1443 | 207 | −89 | −27 | C |
| ATOM | 247 | C | VAL | A | 35 | 4.677 | 2.850 | −16.342 | 1.00 | 16.79 | | C |
| ANISOU | 247 | C | VAL | A | 35 | 2080 | 2721 | 1579 | 264 | −97 | −60 | C |
| ATOM | 248 | O | VAL | A | 35 | 4.874 | 3.975 | −16.795 | 1.00 | 18.44 | | O |
| ANISOU | 248 | O | VAL | A | 35 | 2292 | 2952 | 1762 | 285 | −70 | −19 | O |
| ATOM | 249 | N | CYS | A | 36 | 4.265 | 1.834 | −17.090 | 1.00 | 18.97 | | N |
| ANISOU | 249 | N | CYS | A | 36 | 2346 | 3018 | 1843 | 286 | −134 | −110 | N |
| ATOM | 250 | CA | CYS | A | 36 | 3.977 | 1.989 | −18.524 | 1.00 | 20.27 | | C |
| ANISOU | 250 | CA | CYS | A | 36 | 2506 | 3244 | 1058 | 344 | −145 | −125 | C |
| ATOM | 251 | CB | CYS | A | 36 | 4.425 | 0.761 | −19.299 | 1.00 | 21.39 | | C |
| ANISOU | 251 | CB | CYS | A | 36 | 2644 | 3407 | 2077 | 377 | −181 | −182 | C |
| ATOM | 252 | SG | CYS | A | 36 | 6.173 | 0.604 | −19.445 | 1.00 | 31.26 | | S |
| ANISOU | 252 | SG | CYS | A | 36 | 3903 | 4670 | 3306 | 393 | −152 | −166 | S |
| ATOM | 253 | C | CYS | A | 36 | 2.503 | 2.214 | −10.804 | 1.00 | 20.81 | | C |
| ANISOU | 253 | C | CYS | A | 36 | 2562 | 3327 | 2017 | 353 | −169 | −138 | C |
| ATOM | 254 | O | CYS | A | 36 | 2.127 | 2.566 | −19.919 | 1.00 | 22.36 | | O |
| ANISOU | 254 | O | CYS | A | 36 | 2754 | 3576 | 2165 | 403 | −175 | −143 | O |
| ATOM | 255 | N | GLU | A | 37 | 1.669 | 1.966 | −17.802 | 1.00 | 20.88 | | N |
| ANISOU | 255 | N | GLU | A | 37 | 2563 | 3295 | 2076 | 308 | −182 | −143 | N |
| ATOM | 256 | CA | GLU | A | 37 | 0.240 | 2.195 | −17.912 | 1.00 | 21.55 | | C |
| ANISOU | 256 | CA | GLU | A | 37 | 2632 | 3392 | 2164 | 310 | −202 | −151 | C |
| ATOM | 257 | CB | GLU | A | 37 | −0.451 | 1.023 | −18.592 | 1.00 | 23.34 | | C |
| ANISOU | 257 | CB | GLU | A | 37 | 2838 | 3629 | 2399 | 325 | −259 | −214 | C |
| ATOM | 258 | CG | GLU | A | 37 | −0.246 | −0.296 | −17.888 | 1.00 | 24.03 | | C |
| ANISOU | 258 | CG | GLU | A | 37 | 2918 | 3666 | 2547 | 284 | −290 | −245 | C |
| ATOM | 259 | CD | GLU | A | 37 | −0.582 | −1.474 | −18.768 | 1.00 | 29.01 | | C |
| ANISOU | 259 | CD | GLU | A | 37 | 3533 | 4302 | 3186 | 308 | −353 | −314 | C |
| ATOM | 260 | OE1 | GLU | A | 37 | −0.715 | −1.272 | −19.989 | 1.00 | 29.26 | | O |
| ANISOU | 260 | OE1 | GLU | A | 37 | 3566 | 4386 | 3164 | 366 | −369 | −343 | O |
| ATOM | 261 | OE2 | GLU | A | 37 | −0.703 | −2.601 | −18.243 | 1.00 | 37.10 | | O |
| ANISOU | 261 | OE2 | GLU | A | 37 | 4545 | 5278 | 4273 | 272 | −390 | −341 | O |
| ATOM | 262 | C | GLU | A | 37 | −0.366 | 2.430 | −16.538 | 1.00 | 20.31 | | C |
| ANISOU | 262 | C | GLU | A | 37 | 2468 | 3196 | 2054 | 261 | −191 | −126 | C |
| ATOM | 263 | O | GLU | A | 37 | 0.238 | 2.079 | −15.504 | 1.00 | 20.08 | | O |
| ANISOU | 263 | O | GLU | A | 37 | 2443 | 3125 | 2059 | 228 | 179 | 114 | O |
| ATOM | 264 | N | VAL | A | 38 | −1.553 | 3.033 | −16.534 | 1.00 | 19.82 | | N |
| ANISOU | 264 | N | VAL | A | 38 | 2393 | 3151 | 1989 | 266 | −194 | −116 | N |
| ATOM | 265 | CA | VAL | A | 38 | −2.265 | 3.346 | −15.288 | 1.00 | 20.63 | | C |
| ANISOU | 265 | CA | VAL | A | 38 | 2485 | 3231 | 2124 | 231 | −182 | −90 | C |
| ATOM | 266 | CB | VAL | A | 38 | −3.651 | 3.969 | −15.545 | 1.00 | 22.32 | | C |
| ANISOU | 266 | CB | VAL | A | 38 | 2681 | 3476 | 2324 | 250 | −191 | −86 | C |
| ATOM | 267 | CG1 | VAL | A | 38 | −4.324 | 4.324 | −14.223 | 1.00 | 22.86 | | C |
| ANISOU | 267 | CG1 | VAL | A | 38 | 2736 | 3530 | 2420 | 222 | −176 | −58 | C |
| ATOM | 268 | CG2 | VAL | A | 38 | −3.534 | 5.196 | −16.419 | 1.00 | 25.81 | | C |
| ANISOU | 268 | CG2 | VAL | A | 38 | 3141 | 3950 | 2714 | 295 | −171 | −65 | C |
| ATOM | 269 | C | VAL | A | 38 | −2.437 | 2.102 | −14.421 | 1.00 | 20.70 | | O |
| ANISOU | 269 | C | VAL | A | 38 | 2473 | 3205 | 2187 | 187 | −204 | −105 | C |
| ATOM | 270 | O | VAL | A | 38 | −2.915 | 1.067 | −14.891 | 1.00 | 21.47 | | O |
| ANISOU | 270 | O | VAL | A | 38 | 2549 | 3301 | 2307 | 183 | −246 | −141 | O |
| ATOM | 271 | N | THR | A | 39 | −2.030 | 2.211 | −13.157 | 1.00 | 18.40 | | N |
| ANISOU | 271 | N | THR | A | 39 | 2186 | 2885 | 1920 | 156 | −179 | −76 | N |
| ATOM | 272 | CA | THR | A | 39 | −2.146 | 1.100 | −12.216 | 1.00 | 20.28 | | C |
| ANISOU | 272 | CA | THR | A | 39 | 2403 | 3092 | 2210 | 114 | −193 | −76 | C |
| ATOM | 273 | CB | THR | A | 39 | −0.927 | 0.127 | −12.321 | 1.00 | 20.75 | | C |
| ANISOU | 273 | CB | THR | A | 39 | 2477 | 3120 | 2286 | 103 | −204 | −97 | C |
| ATOM | 274 | OG1 | THR | A | 39 | −1.137 | −1.020 | −11.489 | 1.00 | 21.77 | | O |
| ANISOU | 274 | OG1 | THR | A | 39 | 2584 | 3217 | 2472 | 63 | −223 | −94 | O |
| ATOM | 275 | CG2 | THR | A | 39 | 0.362 | 0.811 | −11.933 | 1.00 | 20.26 | | C |
| ANISOU | 275 | CG2 | THR | A | 39 | 2447 | 3049 | 2202 | 108 | −166 | −77 | C |
| ATOM | 276 | C | THR | A | 39 | −2.348 | 1.625 | −10.795 | 1.00 | 20.28 | | C |
| ANISOU | 276 | C | THR | A | 39 | 2399 | 3087 | 2221 | 95 | −163 | −35 | C |
| ATOM | 277 | O | THR | A | 39 | −1.807 | 2.672 | −10.429 | 1.00 | 19.73 | | O |
| ANISOU | 277 | O | THR | A | 39 | 2354 | 3019 | 2126 | 109 | −132 | −16 | O |
| ATOM | 278 | N | ARG | A | 40 | −3.156 | 0.900 | −10.024 | 1.00 | 20.84 | | N |
| ANISOU | 278 | N | ARG | A | 40 | 2435 | 3154 | 2331 | 67 | −175 | −21 | N |
| ATOM | 279 | CA | ARG | A | 40 | −3.516 | 1.274 | −8.659 | 1.00 | 21.54 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 279 | CA | ARG | A | 40 | 2509 | 3250 | 2424 | 56 | −148 | 19 | C |
| ATOM | 280 | CB | ARG | A | 40 | −4.959 | 0.840 | −8.396 | 1.00 | 23.54 | | C |
| ANISOU | 280 | CB | ARG | A | 40 | 2713 | 3527 | 2705 | 42 | −164 | 36 | C |
| ATOM | 281 | CG | ARG | A | 40 | −5.602 | 1.384 | −7.145 | 1.00 | 29.94 | | C |
| ANISOU | 281 | CG | ARG | A | 40 | 3501 | 4368 | 3506 | 46 | −136 | 78 | C |
| ATOM | 282 | CD | ARG | A | 40 | −7.110 | 1.297 | −7.328 | 1.00 | 37.27 | | C |
| ANISOU | 282 | CD | ARG | A | 40 | 4382 | 5332 | 4447 | 45 | −151 | 81 | C |
| ATOM | 283 | NE | ARG | A | 40 | −7.859 | 2.071 | −6.339 | 1.00 | 45.67 | | N |
| ANISOU | 283 | NE | ARG | A | 40 | 5426 | 6442 | 5485 | 66 | −123 | 126 | N |
| ATOM | 284 | CZ | ARG | A | 40 | −8.565 | 1.538 | −5.350 | 1.00 | 47.84 | | C |
| ANISOU | 284 | CZ | ARG | A | 40 | 5652 | 6742 | 5785 | 48 | −115 | 171 | C |
| ATOM | 285 | NH1 | ARG | A | 40 | −8.630 | 0.218 | −5.204 | 1.00 | 48.90 | | N |
| ANISOU | 285 | NH1 | ARG | A | 40 | 5750 | 6850 | 5978 | 4 | −135 | 190 | N |
| ATOM | 286 | NH2 | ARG | A | 40 | −9.209 | 2.327 | −4.501 | 1.00 | 49.03 | | N |
| ANISOU | 286 | NH2 | ARG | A | 40 | 5786 | 6944 | 5901 | 79 | −89 | 199 | N |
| ATOM | 287 | C | ARG | A | 40 | −2.573 | 0.593 | −7.679 | 1.00 | 20.39 | | C |
| ANISOU | 287 | C | ARG | A | 40 | 2370 | 3074 | 2304 | 30 | −137 | 33 | C |
| ATOM | 288 | O | ARG | A | 40 | −2.427 | −0.635 | −7.693 | 1.00 | 21.55 | | O |
| ANISOU | 288 | O | ARG | A | 40 | 2500 | 3194 | 2493 | 2 | −161 | 27 | O |
| ATOM | 289 | N | VAL | A | 41 | −1.937 | 1.398 | −6.831 | 1.00 | 17.85 | | N |
| ANISOU | 289 | N | VAL | A | 41 | 2070 | 2754 | 1958 | 42 | −106 | 49 | N |
| ATOM | 290 | CA | VAL | A | 41 | −0.955 | 0.901 | −5.862 | 1.00 | 18.60 | | C |
| ANISOU | 290 | CA | VAL | A | 41 | 2174 | 2825 | 2069 | 24 | −94 | 62 | C |
| ATOM | 291 | CB | VAL | A | 41 | 0.416 | 1.590 | −6.042 | 1.00 | 17.64 | | C |
| ANISOU | 291 | CB | VAL | A | 41 | 2095 | 2683 | 1923 | 39 | −79 | 46 | C |
| ATOM | 292 | CG1 | VAL | A | 41 | 1.385 | 1.162 | −4.927 | 1.00 | 17.64 | | C |
| ANISOU | 292 | CG1 | VAL | A | 41 | 2103 | 3663 | 1037 | 25 | −67 | 58 | C |
| ATOM | 293 | CG2 | VAL | A | 41 | 0.998 | 1.236 | −7.408 | 1.00 | 19.23 | | C |
| ANISOU | 293 | CG2 | VAL | A | 41 | 2312 | 2870 | 2123 | 42 | −96 | 16 | C |
| ATOM | 294 | C | VAL | A | 41 | −1.470 | 1.072 | −4.430 | 1.00 | 18.11 | | C |
| ANISOU | 294 | C | VAL | A | 41 | 2090 | 2787 | 2005 | 25 | −74 | 99 | C |
| ATOM | 295 | O | VAL | A | 41 | −1.847 | 2.183 | −4.020 | 1.00 | 19.82 | | O |
| ANISOU | 295 | O | VAL | A | 41 | 2312 | 3032 | 2188 | 55 | −57 | 106 | O |
| ATOM | 296 | N | LYS | A | 42 | −1.489 | −0.034 | −3.685 | 1.00 | 17.92 | | N |
| ANISOU | 296 | N | LYS | A | 42 | 2039 | 2755 | 2016 | −2 | −77 | 125 | N |
| ATOM | 297 | CA | LYS | A | 42 | −1.914 | −0.044 | −2.279 | 1.00 | 20.08 | | C |
| ANISOU | 297 | CA | LYS | A | 42 | 2286 | 3060 | 2285 | 2 | −55 | 169 | C |
| ATOM | 298 | CB | LYS | A | 42 | −2.276 | −1.470 | −1.859 | 1.00 | 20.84 | | C |
| ANISOU | 298 | CB | LYS | A | 42 | 2338 | 3145 | 2434 | −36 | −67 | 208 | C |
| ATOM | 299 | CG | LYS | A | 42 | −2.638 | −1.669 | −0.386 | 1.00 | 27.16 | | C |
| ANISOU | 299 | CG | LYS | A | 42 | 3104 | 3984 | 3231 | −32 | −42 | 264 | C |
| ATOM | 300 | CD | LYS | A | 42 | −3.487 | −2.923 | −0.199 | 1.00 | 37.50 | | C |
| ANISOU | 300 | CD | LYS | A | 42 | 4356 | 5292 | 4602 | −71 | −56 | 314 | C |
| ATOM | 301 | CE | LYS | A | 42 | −2.856 | −4.169 | −0.827 | 1.00 | 35.12 | | C |
| ANISOU | 301 | CE | LYS | A | 42 | 4060 | 4923 | 4363 | −112 | −90 | 298 | C |
| ATOM | 302 | NZ | LYS | A | 42 | −3.770 | −5.353 | −0.712 | 1.00 | 41.42 | | N |
| ANISOU | 302 | NZ | LYS | A | 42 | 4801 | 5712 | 5238 | −153 | −112 | 347 | N |
| ATOM | 303 | C | LYS | A | 42 | −0.866 | 0.539 | −1.335 | 1.00 | 19.59 | | C |
| ANISOU | 303 | C | LYS | A | 42 | 2253 | 2998 | 2193 | 23 | −33 | 167 | C |
| ATOM | 304 | O | LYS | A | 42 | −1.191 | 1.367 | −0.470 | 1.00 | 20.27 | | O |
| ANISOU | 304 | O | LYS | A | 42 | 2335 | 3121 | 2244 | 55 | −15 | 179 | O |
| ATOM | 305 | N | ALA | A | 43 | 0.382 | 0.095 | −1.495 | 1.00 | 16.37 | | N |
| ANISOU | 305 | N | ALA | A | 43 | 1873 | 2548 | 1798 | 8 | −38 | 149 | N |
| ATOM | 306 | CA | ALA | A | 43 | 1.459 | 0.478 | −0.592 | 1.00 | 16.89 | | C |
| ANISOU | 306 | CA | ALA | A | 43 | 1964 | 2609 | 1845 | 24 | −22 | 146 | C |
| ATOM | 307 | CB | ALA | A | 43 | 1.371 | −0.320 | 0.723 | 1.00 | 17.19 | | C |
| ANISOU | 307 | CB | ALA | A | 43 | 1973 | 2667 | 1893 | 18 | −11 | 188 | C |
| ATOM | 308 | C | ALA | A | 43 | 2.819 | 0.267 | −1.231 | 1.00 | 15.23 | | C |
| ANISOU | 308 | C | ALA | A | 43 | 1788 | 2354 | 1646 | 11 | −30 | 115 | C |
| ATOM | 309 | O | ALA | A | 43 | 2.976 | −0.582 | −2.116 | 1.00 | 15.69 | | O |
| ANISOU | 309 | O | ALA | A | 43 | 1845 | 2386 | 1732 | −11 | −48 | 103 | O |
| ATOM | 310 | N | VAL | A | 44 | 3.783 | 1.074 | −0.796 | 1.00 | 14.55 | | N |
| ANISOU | 310 | N | VAL | A | 44 | 1729 | 2261 | 1538 | 30 | −20 | 100 | N |
| ATOM | 311 | CA | VAL | A | 44 | 5.196 | 0.780 | −1.010 | 1.00 | 13.74 | | C |
| ANISOU | 311 | CA | VAL | A | 44 | 1651 | 2123 | 1446 | 19 | −23 | 82 | C |
| ATOM | 312 | CB | VAL | A | 44 | 5.924 | 1.860 | −1.849 | 1.00 | 15.01 | | C |
| ANISOU | 312 | CB | VAL | A | 44 | 1842 | 2267 | 1595 | 32 | −23 | 56 | C |
| ATOM | 313 | CG1 | VAL | A | 44 | 7.426 | 1.583 | −1.885 | 1.00 | 14.01 | | C |
| ANISOU | 313 | CG1 | VAL | A | 44 | 1733 | 2111 | 1478 | 22 | −22 | 44 | C |
| ATOM | 314 | CG2 | VAL | A | 44 | 5.380 | 1.887 | −3.276 | 1.00 | 16.11 | | C |
| ANISOU | 314 | CG2 | VAL | A | 44 | 1980 | 2407 | 1734 | 29 | −32 | 47 | C |
| ATOM | 315 | C | VAL | A | 44 | 5.807 | 0.643 | 0.385 | 1.00 | 15.82 | | C |
| ANISOU | 315 | C | VAL | A | 44 | 1914 | 2393 | 1704 | 27 | −13 | 94 | C |
| ATOM | 316 | O | VAL | A | 44 | 5.711 | 1.551 | 1.216 | 1.00 | 16.63 | | O |
| ANISOU | 316 | O | VAL | A | 44 | 2020 | 2517 | 1781 | 56 | −6 | 93 | O |
| ATOM | 317 | N | ARG | A | 45 | 6.382 | −0.522 | 0.054 | 1.00 | 14.09 | | N |
| ANISOU | 317 | N | ARG | A | 45 | 1689 | 2156 | 1508 | 7 | −16 | 105 | N |
| ATOM | 318 | CA | ARG | A | 45 | 6.952 | −0.798 | 1.967 | 1.00 | 17.12 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 318 | CA | ARG | A | 45 | 2071 | 2550 | 1886 | 16 | −8 | 120 | C |
| ATOM | 319 | CB | ARG | A | 45 | 6.310 | −2.044 | 2.572 | 1.00 | 17.95 | | C |
| ANISOU | 319 | CB | ARG | A | 45 | 2142 | 2667 | 2013 | −1 | −6 | 165 | C |
| ATOM | 320 | CG | ARG | A | 45 | 4.830 | −1.900 | 2.895 | 1.00 | 20.65 | | C |
| ANISOU | 320 | CG | ARG | A | 45 | 2448 | 3051 | 2346 | 7 | 2 | 199 | C |
| ATOM | 321 | CD | ARG | A | 45 | 4.261 | −3.212 | 3.450 | 1.00 | 23.91 | | C |
| ANISOU | 321 | CD | ARG | A | 45 | 2821 | 3470 | 2793 | −16 | 3 | 254 | C |
| ATOM | 322 | NE | ARG | A | 45 | 4.127 | −4.234 | 2.409 | 1.00 | 27.68 | | N |
| ANISOU | 322 | NE | ARG | A | 45 | 3292 | 3901 | 3325 | −56 | −22 | 250 | N |
| ATOM | 323 | CZ | ARG | A | 45 | 4.865 | −5.340 | 2.313 | 1.00 | 31.32 | | C |
| ANISOU | 323 | CZ | ARG | A | 45 | 3756 | 4318 | 3825 | −80 | −37 | 251 | C |
| ATOM | 324 | NH1 | ARG | A | 45 | 5.801 | −5.611 | 3.215 | 1.00 | 31.25 | | N |
| ANISOU | 324 | NH1 | ARG | A | 45 | 3758 | 4309 | 3808 | −71 | −27 | 264 | N |
| ATOM | 325 | NH2 | ARG | A | 45 | 4.651 | −6.188 | 1.311 | 1.00 | 29.35 | | N |
| ANISOU | 325 | NH2 | ARG | A | 45 | 3501 | 4027 | 3625 | −109 | −67 | 238 | N |
| ATOM | 326 | C | ARG | A | 45 | 8.447 | −1.024 | 1.856 | 1.00 | 16.66 | | C |
| ANISOU | 326 | C | ARG | A | 45 | 2035 | 2457 | 1836 | 9 | −12 | 98 | C |
| ATOM | 327 | O | ARG | A | 45 | 8.946 | −1.441 | 0.794 | 1.00 | 15.96 | | O |
| ANISOU | 327 | O | ARG | A | 45 | 1958 | 2340 | 1766 | −9 | −22 | 80 | O |
| ATOM | 328 | N | ILE | A | 46 | 9.166 | −0.757 | 2.947 | 1.00 | 15.77 | | N |
| ANISOU | 328 | N | ILE | A | 46 | 1930 | 2355 | 1708 | 28 | −6 | 97 | N |
| ATOM | 329 | CA | ILE | A | 46 | 10.564 | −1.193 | 3.023 | 1.00 | 16.67 | | C |
| ANISOU | 329 | CA | ILE | A | 46 | 2060 | 2442 | 1834 | 20 | −10 | 82 | C |
| ATOM | 330 | CB | ILE | A | 46 | 11.602 | −0.038 | 2.977 | 1.00 | 18.95 | | C |
| ANISOU | 330 | CB | ILE | A | 46 | 2371 | 2717 | 2113 | 35 | −14 | 49 | C |
| ATOM | 331 | CG1 | ILE | A | 46 | 11.422 | 0.930 | 4.145 | 1.00 | 20.55 | | C |
| ANISOU | 331 | CG1 | ILE | A | 46 | 2574 | 2947 | 2289 | 70 | −14 | 42 | C |
| ATOM | 332 | CD1 | ILE | A | 46 | 12.707 | 1.674 | 4.476 | 1.00 | 23.82 | | C |
| ANISOU | 332 | CD1 | ILE | A | 46 | 3004 | 3340 | 2706 | 82 | −26 | 11 | C |
| ATOM | 333 | CG2 | ILE | A | 46 | 11.606 | 0.659 | 1.595 | 1.00 | 20.98 | | C |
| ANISOU | 333 | CG2 | ILE | A | 46 | 2640 | 2955 | 2377 | 25 | −17 | 32 | C |
| ATOM | 334 | C | ILE | A | 46 | 10.888 | −2.110 | 4.189 | 1.00 | 15.64 | | C |
| ANISOU | 334 | C | ILE | A | 46 | 1917 | 2322 | 1705 | 24 | −6 | 108 | C |
| ATOM | 335 | O | ILE | A | 46 | 10.218 | −2.106 | 5.239 | 1.00 | 15.32 | | O |
| ANISOU | 335 | O | ILE | A | 46 | 1857 | 2319 | 1643 | 44 | 3 | 136 | O |
| ATOM | 336 | N | LEU | A | 47 | 11.927 | −2.906 | 3.975 | 1.00 | 14.03 | | N |
| ANISOU | 336 | N | LEU | A | 47 | 1722 | 2089 | 1522 | 9 | −18 | 100 | N |
| ATOM | 337 | CA | LEU | A | 47 | 12.535 | −3.715 | 5.027 | 1.00 | 14.39 | | C |
| ANISOU | 337 | CA | LEU | A | 47 | 1761 | 2139 | 1569 | 14 | −11 | 120 | C |
| ATOM | 338 | CB | LEU | A | 47 | 12.152 | −5.190 | 4.871 | 1.00 | 16.84 | | C |
| ANISOU | 338 | CB | LEU | A | 47 | 2053 | 2429 | 1915 | −11 | −17 | 154 | C |
| ATOM | 339 | CG | LEU | A | 47 | 12.837 | −6.208 | 5.795 | 1.00 | 20.80 | | C |
| ANISOU | 339 | CG | LEU | A | 47 | 2549 | 2926 | 2428 | −9 | −17 | 180 | C |
| ATOM | 340 | CD1 | LEU | A | 47 | 12.486 | −5.970 | 7.271 | 1.00 | 20.60 | | C |
| ANISOU | 340 | CD1 | LEU | A | 47 | 2505 | 2953 | 2368 | 22 | 1 | 218 | C |
| ATOM | 341 | CD2 | LEU | A | 47 | 12.505 | −7.642 | 5.383 | 1.00 | 22.84 | | C |
| ANISOU | 341 | CD2 | LEU | A | 47 | 2792 | 3148 | 2739 | −39 | −32 | 208 | C |
| ATOM | 342 | C | LEU | A | 47 | 14.086 | −3.532 | 4.893 | 1.00 | 13.22 | | C |
| ANISOU | 342 | C | LEU | A | 47 | 1634 | 1967 | 1421 | 17 | −17 | 86 | C |
| ATOM | 343 | O | LEU | A | 47 | 14.611 | −3.869 | 3.856 | 1.00 | 14.18 | | O |
| ANISOU | 343 | O | LEU | A | 47 | 1767 | 2058 | 1563 | −1 | −25 | 67 | O |
| ATOM | 344 | N | ALA | A | 48 | 14.656 | −2.956 | 5.917 | 1.00 | 12.50 | | N |
| ANISOU | 344 | N | ALA | A | 48 | 1548 | 1895 | 1307 | 44 | −16 | 76 | N |
| ATOM | 345 | CA | ALA | A | 48 | 16.104 | −2.740 | 5.919 | 1.00 | 13.71 | | C |
| ANISOU | 345 | CA | ALA | A | 48 | 1716 | 2029 | 1464 | 46 | −24 | 46 | C |
| ATOM | 346 | CB | ALA | A | 48 | 10.431 | −1.278 | 0.178 | 1.00 | 15.24 | | C |
| ANISOU | 346 | CB | ALA | A | 48 | 1919 | 2229 | 1643 | 67 | −31 | 14 | C |
| ATOM | 347 | C | ALA | A | 48 | 16.705 | −3.614 | 6.997 | 1.00 | 15.67 | | C |
| ANISOU | 347 | C | ALA | A | 48 | 1959 | 2289 | 1708 | 59 | −24 | 62 | C |
| ATOM | 348 | O | ALA | A | 48 | 16.264 | −3.576 | 8.141 | 1.00 | 17.60 | | O |
| ANISOU | 348 | O | ALA | A | 48 | 2191 | 2569 | 1925 | 86 | −18 | 82 | O |
| ATOM | 349 | N | CYS | A | 49 | 17.691 | −4.424 | 6.632 | 1.00 | 15.97 | | N |
| ANISOU | 349 | N | CYS | A | 49 | 2002 | 2299 | 1766 | 45 | −29 | 56 | N |
| ATOM | 350 | CA | CYS | A | 49 | 18.227 | −5.403 | 7.563 | 1.00 | 15.94 | | C |
| ANISOU | 350 | CA | CYS | A | 49 | 1993 | 2302 | 1762 | 56 | −30 | 77 | C |
| ATOM | 351 | CB | CYS | A | 49 | 17.725 | −6.797 | 7.222 | 1.00 | 19.04 | | C |
| ANISOU | 351 | CB | CYS | A | 49 | 2376 | 2674 | 2186 | 33 | −31 | 112 | C |
| ATOM | 352 | SG | CYS | A | 49 | 15.994 | −7.048 | 7.610 | 1.00 | 25.28 | | S |
| ANISOU | 352 | SG | CYS | A | 49 | 3141 | 3487 | 2976 | 29 | −20 | 165 | S |
| ATOM | 353 | C | CYS | A | 49 | 19.732 | −5.445 | 7.566 | 1.00 | 15.70 | | C |
| ANISOU | 353 | C | CYS | A | 49 | 1973 | 2257 | 1736 | 60 | −39 | 47 | C |
| ATOM | 354 | O | CYS | A | 49 | 20.371 | −5.164 | 6.552 | 1.00 | 15.85 | | O |
| ANISOU | 354 | O | CYS | A | 49 | 2000 | 2252 | 1770 | 45 | −43 | 20 | O |
| ATOM | 355 | N | GLY | A | 50 | 20.285 | −5.781 | 8.727 | 1.00 | 16.80 | | N |
| ANISOU | 355 | N | GLY | A | 50 | 2108 | 2416 | 1860 | 84 | −41 | 56 | N |
| ATOM | 356 | CA | GLY | A | 50 | 21.690 | −8.140 | 8.831 | 1.00 | 15.88 | | C |
| ANISOU | 356 | CA | GLY | A | 50 | 1997 | 2286 | 1750 | 89 | −50 | 36 | C |
| ATOM | 357 | C | GLY | A | 50 | 21.697 | −7.552 | 9.383 | 1.00 | 18.14 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 357 | C | GLY | A | 50 | 2277 | 2571 | 2044 | 92 | −48 | 75 | C |
| ATOM | 358 | O | GLY | A | 50 | 21.348 | −7.751 | 10.548 | 1.00 | 19.43 | | O |
| ANISOU | 358 | O | GLY | A | 50 | 2430 | 2768 | 2185 | 117 | −42 | 106 | O |
| ATOM | 359 | N | VAL | A | 51 | 22.058 | −8.519 | 8.535 | 1.00 | 19.29 | | N |
| ANISOU | 359 | N | VAL | A | 51 | 2427 | 2678 | 2222 | 71 | −55 | 75 | N |
| ATOM | 360 | CA | VAL | A | 51 | 21.939 | −9.949 | 8.857 | 1.00 | 21.80 | | C |
| ANISOU | 360 | CA | VAL | A | 51 | 2740 | 2980 | 2564 | 69 | −59 | 114 | C |
| ATOM | 361 | CB | VAL | A | 51 | 21.202 | −10.753 | 7.732 | 1.00 | 20.79 | | C |
| ANISOU | 361 | CB | VAL | A | 51 | 2611 | 2809 | 2478 | 38 | −69 | 123 | C |
| ATOM | 362 | CG1 | VAL | A | 51 | 21.109 | −12.246 | 8.083 | 1.00 | 29.15 | | C |
| ANISOU | 362 | CG1 | VAL | A | 51 | 3662 | 3838 | 3574 | 34 | −81 | 164 | C |
| ATOM | 363 | CG2 | VAL | A | 51 | 19.811 | −10.156 | 7.468 | 1.00 | 26.42 | | C |
| ANISOU | 363 | CG2 | VAL | A | 51 | 3315 | 3534 | 3189 | 24 | −60 | 138 | C |
| ATOM | 364 | C | VAL | A | 51 | 23.316 | −10.550 | 9.103 | 1.00 | 21.95 | | C |
| ANISOU | 364 | C | VAL | A | 51 | 2765 | 2988 | 2586 | 83 | −69 | 99 | C |
| ATOM | 365 | O | VAL | A | 51 | 24.227 | −10.375 | 8.308 | 1.00 | 21.83 | | O |
| ANISOU | 365 | O | VAL | A | 51 | 2759 | 2958 | 2577 | 79 | −76 | 59 | O |
| ATOM | 366 | N | ALA | A | 52 | 23.458 | −11.268 | 10.212 | 1.00 | 23.66 | | N |
| ANISOU | 366 | N | ALA | A | 52 | 2974 | 3219 | 2797 | 103 | −68 | 136 | N |
| ATOM | 367 | CA | ALA | A | 52 | 24.714 | −11.946 | 10.520 | 1.00 | 24.66 | | C |
| ANISOU | 367 | CA | ALA | A | 52 | 3106 | 3337 | 2927 | 119 | −78 | 126 | C |
| ATOM | 368 | CB | ALA | A | 52 | 24.745 | −12.362 | 11.976 | 1.00 | 26.49 | | C |
| ANISOU | 368 | CB | ALA | A | 52 | 3327 | 3603 | 3137 | 150 | −72 | 171 | C |
| ATOM | 369 | C | ALA | A | 52 | 24.896 | −13.150 | 9.622 | 1.00 | 25.64 | | C |
| ANISOU | 369 | C | ALA | A | 52 | 3237 | 3408 | 3098 | 101 | −95 | 127 | C |
| ATOM | 370 | O | ALA | A | 52 | 23.997 | −13.992 | 9.518 | 1.00 | 25.92 | | O |
| ANISOU | 370 | O | ALA | A | 52 | 3265 | 3415 | 3167 | 85 | −100 | 25.92 | O |
| ATOM | 371 | N | LYS | A | 53 | 26.057 | −13.240 | 8.971 | 1.00 | 25.49 | | N |
| ANISOU | 371 | N | LYS | A | 53 | 3228 | 3375 | 3082 | 107 | −106 | 82 | N |
| ATOM | 372 | CA | LYS | A | 53 | 26.426 | −14.384 | 8.137 | 1.00 | 25.85 | | C |
| ANISOU | 372 | CA | LYS | A | 53 | 3282 | 3375 | 3165 | 102 | −127 | 70 | C |
| ATOM | 373 | CB | LYS | A | 53 | 27.401 | −13.960 | 7.037 | 1.00 | 25.00 | | C |
| ANISOU | 373 | CB | LYS | A | 53 | 3181 | 3269 | 3047 | 107 | −131 | 13 | C |
| ATOM | 374 | CG | LYS | A | 53 | 26.905 | −12.862 | 6.099 | 1.00 | 28.93 | | C |
| ANISOU | 374 | CG | LYS | A | 53 | 3679 | 3780 | 3533 | 89 | −119 | −10 | C |
| ATOM | 375 | CD | LYS | A | 53 | 28.036 | −12.357 | 5.205 | 1.00 | 31.42 | | C |
| ANISOU | 375 | CD | LYS | A | 53 | 3993 | 4110 | 3834 | 98 | −117 | −52 | C |
| ATOM | 376 | CE | LYS | A | 53 | 28.637 | −13.342 | 4.088 | 1.00 | 35.41 | | C |
| ANISOU | 376 | CE | LYS | A | 53 | 4505 | 4592 | 4357 | 109 | −136 | −78 | C |
| ATOM | 377 | NZ | LYS | A | 53 | 27.382 | −13.277 | 2.967 | 1.00 | 37.83 | | N |
| ANISOU | 377 | NZ | LYS | A | 53 | 4816 | 4887 | 4672 | 96 | −141 | −88 | N |
| ATOM | 378 | C | LYS | A | 53 | 27.105 | −15.426 | 9.015 | 1.00 | 25.56 | | C |
| ANISOU | 378 | C | LYS | A | 53 | 3245 | 3329 | 3139 | 124 | −137 | 95 | C |
| ATOM | 379 | O | LYS | A | 53 | 27.773 | −15.070 | 9.986 | 1.00 | 26.10 | | O |
| ANISOU | 379 | O | LYS | A | 53 | 3309 | 3434 | 3175 | 147 | −128 | 100 | O |
| ATOM | 380 | N | VAL | A | 54 | 26.944 | −16.703 | 8.672 | 1.00 | 23.02 | | N |
| ANISOU | 380 | N | VAL | A | 54 | 2926 | 2957 | 2863 | 119 | −160 | 110 | N |
| ATOM | 381 | CA | VAL | A | 54 | 27.588 | −17.788 | 9.400 | 1.00 | 22.34 | | C |
| ANISOU | 381 | CA | VAL | A | 54 | 2841 | 2853 | 2795 | 140 | −173 | 136 | C |
| ATOM | 382 | CB | VAL | A | 54 | 26.573 | −18.875 | 9.810 | 1.00 | 23.14 | | C |
| ANISOU | 382 | CB | VAL | A | 54 | 2932 | 2911 | 2948 | 125 | −186 | 203 | C |
| ATOM | 383 | CG1 | VAL | A | 54 | 27.267 | −20.009 | 10.557 | 1.00 | 25.35 | | C |
| ANISOU | 383 | CG1 | VAL | A | 54 | 3212 | 3169 | 3251 | 148 | −201 | 236 | C |
| ATOM | 384 | CG2 | VAL | A | 54 | 25.445 | −18.269 | 10.655 | 1.00 | 25.01 | | C |
| ANISOU | 384 | CG2 | VAL | A | 54 | 3149 | 3187 | 3166 | 114 | −158 | 260 | C |
| ATOM | 385 | C | VAL | A | 54 | 28.680 | −18.395 | 8.520 | 1.00 | 19.88 | | C |
| ANISOU | 385 | C | VAL | A | 54 | 2543 | 2513 | 2497 | 157 | −197 | 84 | C |
| ATOM | 386 | O | VAL | A | 54 | 28.421 | −18.705 | 7.382 | 1.00 | 21.11 | | O |
| ANISOU | 386 | O | VAL | A | 54 | 2706 | 2632 | 2682 | 147 | −219 | 53 | O |
| ATOM | 387 | N | LEU | A | 55 | 29.899 | −18.455 | 9.052 | 1.00 | 18.54 | | N |
| ANISOU | 387 | N | LEU | A | 55 | 2374 | 2366 | 2303 | 186 | −196 | 71 | N |
| ATOM | 388 | CA | LEU | A | 55 | 31.041 | −18.981 | 8.315 | 1.00 | 18.48 | | C |
| ANISOU | 388 | CA | LEU | A | 55 | 2377 | 2345 | 2301 | 209 | −216 | 22 | C |
| ATOM | 389 | CB | LEU | A | 55 | 31.920 | −17.846 | 7.761 | 1.00 | 18.51 | | C |
| ANISOU | 389 | CB | LEU | A | 55 | 2376 | 2397 | 2262 | 215 | −199 | −28 | C |
| ATOM | 390 | CG | LEU | A | 55 | 33.195 | −18.261 | 7.001 | 1.00 | 21.44 | | C |
| ANISOU | 390 | CG | LEU | A | 55 | 2749 | 2770 | 2628 | 244 | −213 | −76 | C |
| ATOM | 391 | CD1 | LEU | A | 55 | 32.888 | −18.969 | 5.675 | 1.00 | 21.75 | | C |
| ANISOU | 391 | CD1 | LEU | A | 55 | 2798 | 2772 | 2693 | 249 | −238 | −108 | C |
| ATOM | 392 | CD2 | LEU | A | 55 | 34.125 | −17.073 | 6.777 | 1.00 | 24.76 | | C |
| ANISOU | 392 | CD2 | LEU | A | 55 | 3154 | 3245 | 3008 | 248 | −192 | −105 | C |
| ATOM | 393 | C | LEU | A | 55 | 31.867 | −19.904 | 9.200 | 1.00 | 19.35 | | C |
| ANISOU | 393 | C | LEU | A | 55 | 2488 | 2446 | 2419 | 238 | −228 | 43 | C |
| ATOM | 394 | O | LEU | A | 55 | 32.351 | −19.500 | 10.263 | 1.00 | 20.37 | | O |
| ANISOU | 394 | O | LEU | A | 55 | 2609 | 2617 | 2514 | 254 | −212 | 62 | O |
| ATOM | 395 | N | TRP | A | 56 | 32.018 | −21.146 | 8.752 | 1.00 | 19.09 | | N |
| ANISOU | 395 | N | TRP | A | 56 | 2465 | 2358 | 2430 | 250 | −261 | 38 | N |
| ATOM | 396 | CA | TRP | A | 56 | 32.852 | −22.109 | 9.447 | 1.00 | 19.36 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 396 | CA | TRP | A | 56 | 2502 | 2376 | 2476 | 281 | −278 | 54 | C |
| ATOM | 397 | CB | TRP | A | 56 | 32.171 | −23.469 | 9.497 | 1.00 | 17.43 | | C |
| ANISOU | 397 | CB | TRP | A | 56 | 2263 | 2056 | 2304 | 275 | −312 | 94 | C |
| ATOM | 398 | CG | TRP | A | 56 | 30.845 | −23.490 | 10.167 | 1.00 | 17.29 | | C |
| ANISOU | 398 | CG | TRP | A | 56 | 2232 | 2024 | 2312 | 242 | −300 | 168 | C |
| ATOM | 399 | CD1 | TRP | A | 56 | 29.650 | −23.078 | 9.647 | 1.00 | 16.71 | | C |
| ANISOU | 399 | CD1 | TRP | A | 56 | 2153 | 1940 | 2256 | 205 | −296 | 175 | C |
| ATOM | 400 | NE1 | TRP | A | 56 | 28.636 | −23.308 | 10.555 | 1.00 | 16.80 | | N |
| ANISOU | 400 | NE1 | TRP | A | 56 | 2147 | 1946 | 2292 | 185 | −284 | 259 | N |
| ATOM | 401 | CE2 | TRP | A | 56 | 29.172 | −23.863 | 11.688 | 1.00 | 19.13 | | C |
| ANISOU | 401 | NE1 | TRP | A | 56 | 2436 | 2250 | 2583 | 210 | −280 | 310 | C |
| ATOM | 402 | CD2 | TRP | A | 56 | 30.560 | −24.013 | 11.470 | 1.00 | 19.10 | | C |
| ANISOU | 402 | CD2 | TRP | A | 56 | 2449 | 2254 | 2556 | 246 | −292 | 253 | C |
| ATOM | 403 | CE3 | TRP | A | 56 | 31.351 | −24.576 | 12.484 | 1.00 | 18.21 | | C |
| ANISOU | 403 | CE3 | TRP | A | 56 | 2334 | 2151 | 2433 | 280 | −292 | 288 | C |
| ATOM | 404 | CZ3 | TRP | A | 56 | 30.737 | −24.980 | 13.666 | 1.00 | 16.23 | | C |
| ANISOU | 404 | CZ3 | TRP | A | 56 | 2065 | 1906 | 2195 | 279 | −279 | 383 | C |
| ATOM | 405 | CH2 | TRP | A | 56 | 29.347 | −24.826 | 13.849 | 1.00 | 19.04 | | C |
| ANISOU | 405 | CH2 | TRP | A | 56 | 2401 | 2258 | 2575 | 243 | −264 | 444 | C |
| ATOM | 406 | CZ2 | TRP | A | 56 | 28.551 | −24.275 | 12.873 | 1.00 | 17.63 | | C |
| ANISOU | 406 | CZ2 | TRP | A | 56 | 2224 | 2065 | 2408 | 207 | −266 | 407 | C |
| ATOM | 407 | C | TRP | A | 56 | 34.173 | −22.248 | 8.709 | 1.00 | 21.49 | | C |
| ANISOU | 407 | C | TRP | A | 56 | 2778 | 2658 | 2729 | 315 | −291 | −11 | C |
| ATOM | 408 | O | TRP | A | 56 | 34.187 | −22.589 | 7.531 | 1.00 | 21.01 | | O |
| ANISOU | 408 | O | TRP | A | 56 | 2726 | 2571 | 2687 | 320 | −313 | −56 | O |
| ATOM | 409 | N | MET | A | 57 | 35.275 | −21.964 | 9.399 | 1.00 | 24.92 | | N |
| ANISOU | 409 | N | MET | A | 57 | 3206 | 3138 | 3126 | 341 | −279 | −16 | N |
| ATOM | 410 | CA | MET | A | 57 | 36.618 | −22.114 | 8.829 | 1.00 | 28.83 | | C |
| ANISOU | 410 | CA | MET | A | 57 | 3700 | 3652 | 3602 | 276 | −289 | −70 | C |
| ATOM | 411 | CB | MET | A | 57 | 37.075 | −20.834 | 8.122 | 1.00 | 29.26 | | C |
| ANISOU | 411 | CB | MET | A | 57 | 3740 | 3763 | 3614 | 368 | −264 | −112 | C |
| ATOM | 412 | CG | MET | A | 57 | 36.524 | −20.651 | 6.720 | 1.00 | 26.41 | | C |
| ANISOU | 412 | CG | MET | A | 57 | 3384 | 3390 | 3262 | 354 | −268 | −146 | C |
| ATOM | 413 | SD | MET | A | 57 | 37.293 | −19.266 | 5.856 | 1.00 | 32.76 | | S |
| ANISOU | 413 | SD | MET | A | 57 | 4165 | 4263 | 4019 | 352 | −238 | −184 | S |
| ATOM | 414 | CE | MET | A | 57 | 38.858 | −19.989 | 5.372 | 1.00 | 32.03 | | C |
| ANISOU | 414 | CE | MET | A | 57 | 4065 | 4103 | 3013 | 407 | −254 | −226 | C |
| ATOM | 415 | C | MET | A | 57 | 37.612 | −22.471 | 9.921 | 1.00 | 31.83 | | C |
| ANISOU | 415 | C | MET | A | 57 | 4075 | 4053 | 3965 | 409 | −290 | −54 | C |
| ATOM | 416 | O | MET | A | 57 | 37.387 | −22.161 | 11.090 | 1.00 | 31.33 | | O |
| ANISOU | 416 | O | MET | A | 57 | 4004 | 4012 | 3886 | 405 | −274 | −10 | O |
| ATOM | 417 | N | GLN | A | 58 | 38.704 | −23.127 | 9.527 | 1.00 | 34.26 | | N |
| ANISOU | 417 | N | GLN | A | 58 | 4385 | 4358 | 4274 | 447 | −310 | −90 | N |
| ATOM | 418 | CA | GLN | A | 58 | 39.762 | −23.550 | 10.461 | 1.00 | 87.53 | | C |
| ANISOU | 418 | CA | GLN | A | 58 | 4795 | 4793 | 4673 | 485 | −316 | −80 | C |
| ATOM | 419 | CB | GLN | A | 58 | 40.447 | −22.335 | 11.102 | 1.00 | 38.18 | | C |
| ANISOU | 419 | CB | GLN | A | 58 | 4854 | 4949 | 4704 | 484 | −288 | −88 | C |
| ATOM | 420 | CG | GLN | A | 58 | 41.120 | −21.396 | 10.117 | 1.00 | 40.46 | | C |
| ANISOU | 420 | CG | GLN | A | 58 | 5125 | 5280 | 4968 | 479 | −275 | −141 | C |
| ATOM | 421 | CD | GLN | A | 58 | 41.775 | −20.207 | 10.801 | 1.00 | 43.85 | | C |
| ANISOU | 421 | CD | GLN | A | 58 | 5529 | 5771 | 5362 | 474 | −255 | −147 | C |
| ATOM | 422 | OE1 | GLN | A | 58 | 41.704 | −20.058 | 12.024 | 1.00 | 48.96 | | O |
| ANISOU | 422 | OE1 | GLN | A | 58 | 6174 | 6433 | 5996 | 479 | −254 | −119 | O |
| ATOM | 423 | NE2 | GLN | A | 58 | 42.418 | −19.354 | 10.010 | 1.00 | 45.42 | | N |
| ANISOU | 423 | NE2 | GLN | A | 58 | 5705 | 6008 | 5547 | 466 | −244 | −182 | N |
| ATOM | 424 | C | GLN | A | 58 | 39.247 | −24.509 | 11.541 | 1.00 | 38.72 | | C |
| ANISOU | 424 | C | GLN | A | 58 | 4955 | 4902 | 4856 | 491 | −329 | −15 | C |
| ATOM | 425 | O | GLN | A | 58 | 39.809 | −24.587 | 12.640 | 1.00 | 39.91 | | O |
| ANISOU | 425 | O | GLN | A | 58 | 5099 | 5082 | 4984 | 515 | −323 | 12 | O |
| ATOM | 426 | N | GLY | A | 59 | 38.179 | −25.236 | 11.223 | 1.00 | 39.44 | | N |
| ANISOU | 426 | N | GLY | A | 59 | 5060 | 4927 | 5001 | 470 | −347 | 12 | N |
| ATOM | 427 | CA | GLY | A | 59 | 37.613 | −26.223 | 12.141 | 1.00 | 40.38 | | C |
| ANISOU | 427 | CA | GLY | A | 59 | 5182 | 4997 | 5162 | 471 | −361 | 86 | C |
| ATOM | 428 | C | GLY | A | 59 | 36.680 | −25.676 | 13.205 | 1.00 | 40.55 | | C |
| ANISOU | 428 | C | GLY | A | 59 | 5190 | 5047 | 5168 | 446 | −330 | 157 | C |
| ATOM | 429 | O | GLY | A | 59 | 36.314 | −26.400 | 14.132 | 1.00 | 41.74 | | O |
| ANISOU | 429 | O | GLY | A | 59 | 5338 | 5177 | 5345 | 452 | −334 | 230 | O |
| ATOM | 430 | N | SER | A | 60 | 36.292 | −24.406 | 13.083 | 1.00 | 38.81 | | N |
| ANISOU | 430 | N | SER | A | 60 | 4961 | 4877 | 4907 | 421 | −300 | 189 | N |
| ATOM | 431 | CA | SER | A | 60 | 35.325 | −23.804 | 14.004 | 1.00 | 38.17 | | C |
| ANISOU | 431 | CA | SER | A | 60 | 4867 | 4829 | 4807 | 401 | −271 | 199 | C |
| ATOM | 432 | CB | SER | A | 60 | 36.028 | −23.267 | 15.262 | 1.00 | 39.28 | | C |
| ANISOU | 432 | CB | SER | A | 60 | 4996 | 5043 | 4886 | 436 | −252 | 213 | C |
| ATOM | 433 | OG | SER | A | 60 | 36.491 | −21.939 | 15.077 | 1.00 | 42.67 | | O |
| ANISOU | 433 | OG | SER | A | 60 | 5419 | 5530 | 5266 | 433 | −236 | 154 | O |
| ATOM | 434 | C | SER | A | 60 | 34.484 | −22.709 | 13.344 | 1.00 | 36.44 | | C |
| ANISOU | 434 | C | SER | A | 60 | 4645 | 4626 | 4574 | 362 | −252 | 174 | C |
| ATOM | 435 | O | SER | A | 60 | 34.775 | −22.263 | 12.230 | 1.00 | 33.82 | | O |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 435 | O | SER | A | 60 | 4319 | 4292 | 4240 | 352 | −257 | 111 | O |
| ATOM | 436 | N | GLN | A | 61 | 33.436 | −22.284 | 14.038 | 1.00 | 35.40 | | N |
| ANISOU | 436 | N | GLN | A | 61 | 4502 | 4517 | 4433 | 345 | −230 | 229 | N |
| ATOM | 437 | CA | GLN | A | 61 | 32.588 | −21.214 | 13.549 | 1.00 | 35.71 | | C |
| ANISOU | 437 | CA | GLN | A | 61 | 4537 | 4575 | 4457 | 312 | −212 | 211 | C |
| ATOM | 438 | CB | GLN | A | 61 | 31.236 | −21.266 | 14.245 | 1.00 | 36.51 | | C |
| ANISOU | 438 | CB | GLN | A | 61 | 4625 | 4680 | 4569 | 294 | −195 | 288 | C |
| ATOM | 439 | CG | GLN | A | 61 | 30.135 | −20.659 | 13.432 | 1.00 | 40.44 | | C |
| ANISOU | 439 | CG | GLN | A | 61 | 5121 | 5164 | 5079 | 545 | −188 | 276 | C |
| ATOM | 440 | CD | GLN | A | 61 | 28.968 | −20.225 | 14.277 | 1.00 | 48.35 | | C |
| ANISOU | 440 | CD | GLN | A | 61 | 6104 | 6204 | 6064 | 246 | −162 | 341 | C |
| ATOM | 441 | OE1 | GLN | A | 61 | 28.891 | −20.523 | 15.469 | 1.00 | 52.99 | | O |
| ANISOU | 441 | OE1 | GLN | A | 61 | 6678 | 6825 | 6633 | 271 | −150 | 404 | O |
| ATOM | 442 | NE2 | GLN | A | 61 | 28.044 | −19.509 | 13.660 | 1.00 | 53.19 | | N |
| ANISOU | 442 | NE2 | GLN | A | 61 | 6714 | 6818 | 6678 | 215 | −153 | 327 | N |
| ATOM | 443 | C | GLN | A | 61 | 33.263 | −19.865 | 13.789 | 1.00 | 35.79 | | C |
| ANISOU | 443 | C | GLN | A | 61 | 4542 | 4653 | 4405 | 324 | −193 | 163 | C |
| ATOM | 444 | O | GLN | A | 61 | 33.561 | −19.505 | 14.930 | 1.00 | 36.83 | | O |
| ANISOU | 444 | O | GLN | A | 61 | 4664 | 4836 | 4495 | 352 | −182 | 182 | O |
| ATOM | 445 | N | GLN | A | 62 | 33.499 | −19.129 | 12.710 | 1.00 | 34.86 | | N |
| ANISOU | 445 | N | GLN | A | 62 | 4428 | 4535 | 4283 | 306 | −193 | 103 | N |
| ATOM | 446 | CA | GLN | A | 62 | 34.238 | −17.868 | 12.774 | 1.00 | 34.71 | | C |
| ANISOU | 446 | CA | GLN | A | 62 | 4400 | 4567 | 4220 | 312 | −181 | 56 | C |
| ATOM | 447 | CB | GLN | A | 62 | 35.246 | −17.775 | 11.627 | 1.00 | 33.60 | | C |
| ANISOU | 447 | CB | GLN | A | 62 | 4261 | 4420 | 4086 | 312 | −191 | −2 | C |
| ATOM | 448 | CG | GLN | A | 62 | 36.234 | −18.940 | 11.575 | 1.00 | 33.97 | | C |
| ANISOU | 448 | CG | GLN | A | 62 | 4313 | 4447 | 4148 | 343 | −211 | −10 | C |
| ATOM | 449 | CD | GLN | A | 62 | 37.137 | −19.030 | 12.802 | 1.00 | 33.64 | | C |
| ANISOU | 449 | CD | GLN | A | 62 | 4262 | 4441 | 4078 | 379 | −214 | 0 | C |
| ATOM | 450 | OE1 | GLN | A | 62 | 37.253 | −18.083 | 13.585 | 1.00 | 36.58 | | O |
| ANISOU | 450 | OE1 | GLN | A | 62 | 4622 | 4859 | 4416 | 384 | −203 | −2 | O |
| ATOM | 451 | NE2 | GLN | A | 62 | 37.787 | −20.176 | 12.969 | 1.00 | 38.09 | | N |
| ANISOU | 451 | NE2 | GLN | A | 62 | 4832 | 4983 | 4657 | 409 | −232 | 8 | N |
| ATOM | 452 | C | GLN | A | 62 | 33.292 | −16.674 | 12.789 | 1.00 | 35.62 | | C |
| ANISOU | 452 | C | GLN | A | 62 | 4510 | 4707 | 4318 | 288 | −193 | 57 | C |
| ATOM | 453 | O | GLN | A | 62 | 33.219 | −15.955 | 13.791 | 1.00 | 35.97 | | O |
| ANISOU | 453 | O | GLN | A | 62 | 4545 | 4796 | 4326 | 304 | −154 | 66 | O |
| ATOM | 454 | N | CYS | A | 63 | 32.585 | −16.457 | 11.679 | 1.00 | 36.04 | | N |
| ANISOU | 454 | N | CYS | A | 63 | 4569 | 4733 | 4393 | 256 | −160 | 44 | N |
| ATOM | 455 | CA | CYS | A | 63 | 31.386 | −15.628 | 11.704 | 1.00 | 36.00 | | C |
| ANISOU | 455 | CA | CYS | A | 63 | 4561 | 4739 | 4370 | 232 | −145 | 60 | C |
| ATOM | 456 | CB | CYS | A | 63 | 30.900 | −15.269 | 10.296 | 1.00 | 33.72 | | C |
| ANISOU | 456 | CB | CYS | A | 63 | 4277 | 4424 | 4110 | 201 | −144 | 32 | C |
| ATOM | 457 | SG | CYS | A | 63 | 32.056 | −14.281 | 9.312 | 1.00 | 36.28 | | S |
| ANISOU | 457 | SG | CYS | A | 63 | 4596 | 4768 | 4420 | 199 | −142 | −31 | S |
| ATOM | 458 | C | CYS | A | 63 | 30.370 | −16.486 | 12.437 | 1.00 | 36.95 | | C |
| ANISOU | 458 | C | CYS | A | 63 | 4679 | 4846 | 4516 | 232 | −142 | 127 | C |
| ATOM | 459 | O | CYS | A | 63 | 29.974 | −17.566 | 11.959 | 1.00 | 32.30 | | O |
| ANISOU | 459 | O | CYS | A | 63 | 4095 | 4206 | 3972 | 219 | −156 | 150 | O |
| ATOM | 460 | N | LYS | A | 64 | 29.991 | −16.023 | 13.622 | 1.00 | 39.37 | | N |
| ANISOU | 460 | N | LYS | A | 64 | 4974 | 5197 | 4786 | 251 | −128 | 160 | N |
| ATOM | 461 | CA | LYS | A | 64 | 29.180 | −16.817 | 14.530 | 1.00 | 42.44 | | C |
| ANISOU | 461 | CA | LYS | A | 64 | 5352 | 5590 | 5182 | 260 | −121 | 236 | C |
| ATOM | 462 | CB | LYS | A | 64 | 29.545 | −16.520 | 15.985 | 1.00 | 43.65 | | C |
| ANISOU | 462 | CB | LYS | A | 64 | 5495 | 5809 | 5282 | 306 | −111 | 258 | C |
| ATOM | 463 | CG | LYS | A | 64 | 30.862 | −17.152 | 16.405 | 1.00 | 44.11 | | C |
| ANISOU | 463 | CG | LYS | A | 64 | 5557 | 5869 | 5335 | 339 | −126 | 246 | C |
| ATOM | 464 | CD | LYS | A | 64 | 31.253 | −16.754 | 17.814 | 1.00 | 49.60 | | C |
| ANISOU | 464 | CD | LYS | A | 64 | 6241 | 6636 | 5969 | 390 | −120 | 258 | C |
| ATOM | 465 | CE | LYS | A | 64 | 32.618 | −17.323 | 18.182 | 1.00 | 50.94 | | C |
| ANISOU | 465 | CE | LYS | A | 64 | 6414 | 6809 | 6133 | 423 | −137 | 240 | C |
| ATOM | 466 | NZ | LYS | A | 64 | 33.680 | −16.893 | 17.226 | 1.00 | 49.23 | | N |
| ANISOU | 466 | NZ | LYS | A | 64 | 6206 | 6569 | 5930 | 407 | −153 | 161 | N |
| ATOM | 467 | C | LYS | A | 64 | 27.687 | −16.650 | 14.280 | 1.00 | 43.45 | | C |
| ANISOU | 467 | C | LYS | A | 64 | 5472 | 5710 | 5327 | 230 | −108 | 273 | C |
| ATOM | 468 | O | LYS | A | 64 | 26.870 | −17.370 | 14.857 | 1.00 | 45.88 | | O |
| ANISOU | 468 | O | LYS | A | 64 | 5465 | 6015 | 5653 | 229 | −102 | 346 | O |
| ATOM | 469 | N | GLY | A | 65 | 27.341 | −15.717 | 13.398 | 1.00 | 43.45 | | N |
| ANISOU | 469 | N | GLY | A | 65 | 5479 | 5708 | 5325 | 206 | −105 | 228 | N |
| ATOM | 470 | CA | GLY | A | 65 | 25.954 | −15.457 | 13.046 | 1.00 | 42.78 | | C |
| ANISOU | 470 | CA | GLY | A | 65 | 5385 | 5616 | 5253 | 177 | −95 | 254 | C |
| ATOM | 471 | C | GLY | A | 65 | 25.154 | −14.981 | 14.239 | 1.00 | 43.41 | | C |
| ANISOU | 471 | C | GLY | A | 65 | 5446 | 5756 | 5292 | 199 | −73 | 304 | C |
| ATOM | 472 | O | GLY | A | 65 | 25.566 | −14.071 | 14.966 | 1.00 | 44.96 | | O |
| ANISOU | 472 | O | GLY | A | 65 | 5642 | 6007 | 5435 | 232 | −66 | 279 | O |
| ATOM | 473 | N | GLY | A | 66 | 24.015 | −15.624 | 14.452 | 1.00 | 42.92 | | N |
| ANISOU | 473 | N | GLY | A | 66 | 5365 | 5685 | 5256 | 185 | −65 | 374 | N |
| ATOM | 474 | CA | GLY | A | 66 | 23.102 | −15.209 | 15.489 | 1.00 | 41.54 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 474 | CA | GLY | A | 66 | 5167 | 5574 | 5041 | 207 | −40 | 429 | C |
| ATOM | 475 | C | GLY | A | 66 | 22.163 | −14.150 | 14.956 | 1.00 | 39.51 | | C |
| ANISOU | 475 | C | GLY | A | 66 | 4908 | 5332 | 4770 | 190 | −31 | 408 | C |
| ATOM | 476 | O | GLY | A | 66 | 21.705 | −14.227 | 13.815 | 1.00 | 40.36 | | O |
| ANISOU | 476 | O | GLY | A | 66 | 5023 | 5390 | 4922 | 148 | −40 | 384 | O |
| ATOM | 477 | N | SER | A | 67 | 21.900 | −13.149 | 15.787 | 1.00 | 37.41 | | N |
| ANISOU | 477 | N | SER | A | 67 | 4634 | 5137 | 4442 | 227 | −15 | 399 | N |
| ATOM | 478 | CA | SER | A | 67 | 20.776 | −12.252 | 15.574 | 1.00 | 34.09 | | C |
| ANISOU | 478 | CA | SER | A | 67 | 4205 | 4743 | 4006 | 220 | −3 | 396 | C |
| ATOM | 479 | CB | SER | A | 67 | 20.242 | −11.744 | 16.916 | 1.00 | 35.01 | | C |
| ANISOU | 479 | CB | SER | A | 67 | 4299 | 4949 | 4055 | 275 | 17 | 433 | C |
| ATOM | 480 | OG | SER | A | 67 | 19.696 | −12.808 | 17.672 | 1.00 | 39.48 | | O |
| ANISOU | 480 | OG | SER | A | 67 | 4835 | 5537 | 4630 | 284 | 35 | 531 | O |
| ATOM | 481 | C | SER | A | 67 | 21.112 | −11.084 | 14.665 | 1.00 | 30.63 | | C |
| ANISOU | 481 | C | SER | A | 67 | 3790 | 4285 | 3561 | 206 | −15 | 310 | C |
| ATOM | 482 | O | SER | A | 67 | 22.283 | −10.786 | 14.424 | 1.00 | 31.41 | | O |
| ANISOU | 482 | O | SER | A | 67 | 3909 | 4368 | 3658 | 211 | −30 | 253 | O |
| ATOM | 483 | N | AGLU | A | 68 | 20.061 | −10.436 | 14.169 | 0.50 | 29.14 | | N |
| ANISOU | 483 | N | AGLU | A | 68 | 3597 | 4101 | 3373 | 189 | −7 | 308 | N |
| ATOM | 484 | N | BGLU | A | 68 | 20.074 | −10.427 | 14.162 | 0.50 | 29.24 | | N |
| ANISOU | 484 | N | BGLU | A | 68 | 3610 | 4114 | 3886 | 189 | −7 | 307 | N |
| ATOM | 485 | CA | AGLU | A | 68 | 20.176 | −9.245 | 13.337 | 0.50 | 26.36 | | C |
| ANISOU | 485 | CA | AGLU | A | 68 | 3264 | 3736 | 3016 | 177 | −16 | 239 | C |
| ATOM | 486 | CA | BGLU | A | 68 | 20.244 | −9.285 | 13.275 | 0.50 | 26.57 | | C |
| ANISOU | 486 | CA | BGLU | A | 68 | 3292 | 3759 | 3046 | 175 | −17 | 237 | C |
| ATOM | 487 | CB | AGLU | A | 68 | 18.797 | −9.285 | 12.813 | 0.50 | 26.79 | | C |
| ANISOU | 487 | CB | AGLU | A | 68 | 3308 | 3794 | 3077 | 158 | −5 | 255 | C |
| ATOM | 488 | CB | BGLU | A | 68 | 18.970 | −9.043 | 12.460 | 0.50 | 26.83 | | C |
| ANISOU | 488 | CB | BGLU | A | 68 | 3318 | 3778 | 3099 | 144 | −10 | 250 | C |
| ATOM | 489 | CG | AGLU | A | 68 | 18.135 | −9.816 | 11.860 | 0.50 | 27.80 | | C |
| ANISOU | 489 | CG | AGLU | A | 68 | 3428 | 3870 | 3262 | 110 | −8 | 288 | C |
| ATOM | 490 | CG | BGLU | A | 68 | 18.662 | −10.177 | 11.484 | 0.50 | 28.00 | | C |
| ANISOU | 490 | CG | BGLU | A | 68 | 3464 | 3868 | 3308 | 99 | −17 | 274 | C |
| ATOM | 491 | CD | AGLU | A | 68 | 16.635 | −9.605 | 11.762 | 0.50 | 27.50 | | C |
| ANISOU | 491 | CD | AGLU | A | 68 | 3369 | 3854 | 3227 | 99 | 5 | 326 | C |
| ATOM | 492 | CD | BGLU | A | 68 | 17.345 | −10.010 | 10.755 | 0.50 | 28.16 | | C |
| ANISOU | 492 | CD | BGLU | A | 68 | 3473 | 3878 | 3349 | 71 | −13 | 289 | C |
| ATOM | 493 | OE1 | AGLU | A | 68 | 15.965 | −9.563 | 12.816 | 0.50 | 30.52 | | O |
| ANISOU | 493 | OE1 | AGLU | A | 68 | 3725 | 4293 | 3576 | 128 | 23 | 377 | O |
| ATOM | 494 | OE1 | BGLU | A | 68 | 16.811 | −8.878 | 10.704 | 0.50 | 31.11 | | O |
| ANISOU | 494 | OE1 | BGLU | A | 68 | 3848 | 4283 | 3691 | 82 | −5 | 267 | O |
| ATOM | 495 | OE2 | AGLU | A | 68 | 16.125 | −9.485 | 10.630 | 0.50 | 29.18 | | O |
| ANISOU | 495 | OE2 | AGLU | A | 68 | 3587 | 4030 | 3470 | 66 | −3 | 306 | O |
| ATOM | 496 | OE2 | BGLU | A | 68 | 16.845 | −11.023 | 10.221 | 0.50 | 27.72 | | O |
| ANISOU | 496 | OE2 | BGLU | A | 68 | 3406 | 3782 | 3344 | 39 | −22 | 320 | O |
| ATOM | 497 | C | AGLU | A | 68 | 20.786 | −8.080 | 14.106 | 0.50 | 24.30 | | C |
| ANISOU | 497 | C | AGLU | A | 68 | 3009 | 3519 | 2704 | 222 | −23 | 191 | C |
| ATOM | 498 | C | BGLU | A | 68 | 20.656 | −8.031 | 14.037 | 0.50 | 24.45 | | C |
| ANISOU | 498 | C | BGLU | A | 68 | 3028 | 3537 | 2724 | 219 | −22 | 192 | C |
| ATOM | 499 | O | AGLU | A | 68 | 20.689 | −8.009 | 15.337 | 0.50 | 24.85 | | O |
| ANISOU | 499 | O | AGLU | A | 68 | 3067 | 3648 | 2729 | 269 | −17 | 213 | O |
| ATOM | 500 | O | BGLU | A | 68 | 20.303 | −7.857 | 15.206 | 0.50 | 24.85 | | O |
| ANISOU | 500 | O | BGLU | A | 68 | 3139 | 3725 | 2805 | 265 | −13 | 217 | O |
| ATOM | 501 | N | TYR | A | 69 | 21.426 | −7.179 | 13.365 | 1.00 | 10.08 | | N |
| ANISOU | 501 | N | TYR | A | 69 | 2480 | 2943 | 2167 | 208 | −38 | 127 | N |
| ATOM | 502 | CA | TYR | A | 69 | 21.886 | −5.901 | 13.905 | 1.00 | 19.08 | | C |
| ANISOU | 502 | CA | TYR | A | 69 | 2372 | 2857 | 2021 | 243 | −53 | 74 | C |
| ATOM | 503 | CB | TYR | A | 69 | 23.174 | −5.471 | 13.192 | 1.00 | 18.87 | | C |
| ANISOU | 503 | CB | TYR | A | 69 | 2359 | 2788 | 2023 | 222 | −72 | 19 | C |
| ATOM | 504 | CG | TYR | A | 69 | 24.415 | −6.143 | 13.729 | 1.00 | 21.57 | | C |
| ANISOU | 504 | CG | TYR | A | 69 | 2700 | 3132 | 2364 | 238 | −82 | 14 | C |
| ATOM | 505 | CD1 | TYR | A | 69 | 24.770 | −7.424 | 13.318 | 1.00 | 25.05 | | C |
| ANISOU | 505 | CD1 | TYR | A | 69 | 3142 | 3544 | 2830 | 216 | −74 | 44 | C |
| ATOM | 506 | CE1 | TYR | A | 69 | 25.913 | −8.053 | 13.826 | 1.00 | 26.72 | | C |
| ANISOU | 506 | CE1 | TYR | A | 69 | 3353 | 3760 | 3040 | 234 | −84 | 39 | C |
| ATOM | 507 | CZ | TYR | A | 69 | 26.701 | −7.382 | 14.750 | 1.00 | 26.47 | | C |
| ANISOU | 507 | CZ | TYR | A | 69 | 3318 | 3761 | 2979 | 272 | −101 | 3 | C |
| ATOM | 508 | OH | TYR | A | 69 | 27.832 | −7.973 | 15.264 | 1.00 | 26.89 | | O |
| ANISOU | 508 | OH | TYR | A | 69 | 3370 | 3821 | 3029 | 292 | −112 | −3 | O |
| ATOM | 509 | CE2 | TYR | A | 69 | 26.364 | −6.110 | 15.165 | 1.00 | 27.21 | | C |
| ANISOU | 509 | CE2 | TYR | A | 69 | 3410 | 3880 | 3050 | 294 | −113 | −31 | C |
| ATOM | 510 | CD2 | TYR | A | 69 | 25.223 | −5.498 | 14.659 | 1.00 | 22.30 | | C |
| ANISOU | 510 | CD2 | TYR | A | 69 | 2790 | 3252 | 2430 | 278 | −103 | −25 | C |
| ATOM | 511 | C | TYR | A | 69 | 20.833 | −4.830 | 13.669 | 1.00 | 17.26 | | C |
| ANISOU | 511 | C | TYR | A | 69 | 2141 | 2640 | 1778 | 245 | −50 | 61 | C |
| ATOM | 512 | O | TYR | A | 69 | 20.781 | −3.826 | 14.376 | 1.00 | 19.05 | | O |
| ANISOU | 512 | O | TYR | A | 69 | 2367 | 2900 | 1971 | 286 | −63 | 28 | O |
| ATOM | 513 | N | LEU | A | 70 | 20.017 | −5.042 | 12.642 | 1.00 | 15.97 | | N |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 513 | N | LEU | A | 70 | 1978 | 2447 | 1644 | 205 | −38 | 82 | N |
| ATOM | 514 | CA | LEU | A | 70 | 19.083 | −4.036 | 12.151 | 1.00 | 16.35 | | C |
| ANISOU | 514 | CA | LEU | A | 70 | 2027 | 2497 | 1688 | 200 | −37 | 67 | C |
| ATOM | 515 | CB | LEU | A | 70 | 19.775 | −3.119 | 11.114 | 1.00 | 15.03 | | C |
| ANISOU | 515 | CB | LEU | A | 70 | 1877 | 2284 | 1549 | 175 | −53 | 14 | C |
| ATOM | 516 | CG | LEU | A | 70 | 18.914 | −2.174 | 10.247 | 1.00 | 13.73 | | C |
| ANISOU | 516 | CG | LEU | A | 70 | 1717 | 2106 | 1393 | 159 | −52 | 2 | C |
| ATOM | 517 | CD1 | LEU | A | 70 | 18.398 | −0.978 | 11.040 | 1.00 | 18.76 | | C |
| ANISOU | 517 | CD1 | LEU | A | 70 | 2353 | 2777 | 1998 | 202 | −63 | −23 | C |
| ATOM | 518 | CD2 | LEU | A | 70 | 19.671 | −1.680 | 9.021 | 1.00 | 15.83 | | C |
| ANISOU | 518 | CD2 | LEU | A | 70 | 1995 | 2324 | 1696 | 126 | −60 | −28 | C |
| ATOM | 519 | C | LEU | A | 70 | 17.914 | −4.754 | 11.502 | 1.00 | 17.210 | | C |
| ANISOU | 519 | C | LEU | A | 70 | 2126 | 2597 | 1817 | 168 | −19 | 115 | C |
| ATOM | 520 | O | LEU | A | 70 | 18.105 | −5.700 | 10.727 | 1.00 | 17.06 | | O |
| ANISOU | 520 | O | LEU | A | 70 | 2109 | 2538 | 1837 | 132 | −18 | 131 | O |
| ATOM | 521 | N | ARG | A | 71 | 16.704 | −4.330 | 11.855 | 1.00 | 17.46 | | N |
| ANISOU | 521 | N | ARG | A | 71 | 2143 | 2668 | 1824 | 187 | −8 | 137 | N |
| ATOM | 522 | CA | ARG | A | 71 | 15.510 | −4.752 | 11.141 | 1.00 | 19.08 | | C |
| ANISOU | 522 | CA | ARG | A | 71 | 2335 | 2863 | 2051 | 155 | 5 | 175 | C |
| ATOM | 523 | CB | ARG | A | 71 | 14.963 | −6.080 | 11.669 | 1.00 | 19.32 | | C |
| ANISOU | 523 | CB | ARG | A | 71 | 2338 | 2908 | 2093 | 148 | 19 | 247 | C |
| ATOM | 524 | CG | ARG | A | 71 | 13.768 | −6.582 | 10.877 | 1.00 | 21.01 | | C |
| ANISOU | 524 | CG | ARG | A | 71 | 2535 | 3104 | 2344 | 110 | 25 | 285 | C |
| ATOM | 525 | CD | ARG | A | 71 | 13.191 | −7.858 | 11.454 | 1.00 | 25.89 | | C |
| ANISOU | 525 | CD | ARG | A | 71 | 3119 | 3733 | 2985 | 101 | 36 | 365 | C |
| ATOM | 526 | NE | ARG | A | 71 | 12.212 | −8.444 | 10.540 | 1.00 | 33.65 | | N |
| ANISOU | 526 | NE | ARG | A | 71 | 4085 | 4680 | 4020 | 56 | 32 | 392 | N |
| ATOM | 527 | CZ | ARG | A | 71 | 12.497 | −9.318 | 9.576 | 1.00 | 36.44 | | C |
| ANISOU | 527 | CZ | ARG | A | 71 | 4448 | 4966 | 4432 | 14 | 11 | 382 | C |
| ATOM | 528 | NH1 | ARG | A | 71 | 13.747 | −9.727 | 9.373 | 1.00 | 36.36 | | N |
| ANISOU | 528 | NH1 | ARG | A | 71 | 4463 | 4918 | 4435 | 12 | −3 | 349 | N |
| ATOM | 529 | NH2 | ARG | A | 71 | 11.523 | −9.782 | 8.800 | 1.00 | 35.64 | | N |
| ANISOU | 529 | NH2 | ARG | A | 71 | 4328 | 4836 | 4377 | −21 | 1 | 402 | N |
| ATOM | 530 | C | ARG | A | 71 | 14.463 | −3.664 | 11.250 | 1.00 | 19.76 | | C |
| ANISOU | 530 | C | ARG | A | 71 | 2416 | 2986 | 2108 | 178 | 9 | 166 | C |
| ATOM | 531 | O | ARG | A | 71 | 13.762 | −3.553 | 12.260 | 1.00 | 21.63 | | O |
| ANISOU | 531 | O | ARG | A | 71 | 2631 | 3283 | 2304 | 218 | 21 | 196 | O |
| ATOM | 532 | N | TYR | A | 72 | 14.379 | −2.860 | 10.197 | 1.00 | 19.18 | | N |
| ANISOU | 532 | N | TYR | A | 72 | 2358 | 2877 | 2051 | 157 | 0 | 127 | N |
| ATOM | 533 | CA | TYR | A | 72 | 13.509 | −1.705 | 10.164 | 1.00 | 18.22 | | C |
| ANISOU | 533 | CA | TYR | A | 72 | 2236 | 2780 | 1906 | 179 | −1 | 110 | C |
| ATOM | 534 | CB | TYR | A | 72 | 14.337 | −0.446 | 9.911 | 1.00 | 18.56 | | C |
| ANISOU | 534 | CB | TYR | A | 72 | 2304 | 2797 | 1951 | 189 | −23 | 47 | C |
| ATOM | 535 | CG | TYR | A | 72 | 18.532 | 0.787 | 9.570 | 1.00 | 20.17 | | C |
| ANISOU | 535 | CG | TYR | A | 72 | 2513 | 3006 | 2146 | 204 | −30 | 23 | C |
| ATOM | 536 | CD1 | TYR | A | 72 | 12.674 | 1.368 | 10.503 | 1.00 | 26.07 | | C |
| ANISOU | 536 | CD1 | TYR | A | 72 | 3248 | 3809 | 2849 | 255 | −30 | 24 | C |
| ATOM | 537 | CE1 | TYR | A | 72 | 11.924 | 2.505 | 10.187 | 1.00 | 29.88 | | C |
| ANISOU | 537 | CE1 | TYR | A | 72 | 3736 | 4293 | 3323 | 272 | −39 | 0 | C |
| ATOM | 538 | CZ | TYR | A | 72 | 12.031 | 3.069 | 8.923 | 1.00 | 25.69 | | C |
| ANISOU | 538 | CZ | TYR | A | 72 | 3222 | 3708 | 2831 | 236 | −46 | −19 | C |
| ATOM | 539 | OH | TYR | A | 72 | 11.297 | 4.197 | 8.606 | 1.00 | 27.75 | | O |
| ANISOU | 539 | OH | TYR | A | 72 | 3488 | 3968 | 3086 | 254 | −57 | −40 | O |
| ATOM | 540 | CE2 | TYR | A | 72 | 12.878 | 2.511 | 7.983 | 1.00 | 24.35 | | C |
| ANISOU | 540 | CE2 | TYR | A | 72 | 3061 | 3489 | 2701 | 186 | −44 | −15 | C |
| ATOM | 541 | CD2 | TYR | A | 72 | 13.622 | 1.371 | 8.310 | 1.00 | 19.75 | | C |
| ANISOU | 541 | CD2 | TYR | A | 72 | 2474 | 2906 | 2125 | 172 | −30 | 3 | C |
| ATOM | 542 | C | TYR | A | 72 | 12.476 | −1.916 | 9.072 | 1.00 | 18.95 | | C |
| ANISOU | 542 | C | TYR | A | 72 | 2321 | 2854 | 2025 | 142 | 7 | 131 | C |
| ATOM | 543 | O | TYR | A | 72 | 12.824 | −2.111 | 7.904 | 1.00 | 17.30 | | O |
| ANISOU | 543 | O | TYR | A | 72 | 2126 | 2597 | 1852 | 104 | 1 | 115 | O |
| ATOM | 544 | N | GLU | A | 73 | 11.208 | −1.895 | 9.469 | 1.00 | 19.95 | | N |
| ANISOU | 544 | N | GLU | A | 73 | 2424 | 3027 | 2131 | 158 | 21 | 166 | N |
| ATOM | 545 | CA | GLU | A | 73 | 10.092 | −2.071 | 8.544 | 1.00 | 23.18 | | C |
| ANISOU | 545 | CA | GLU | A | 73 | 2819 | 3425 | 2562 | 128 | 26 | 187 | C |
| ATOM | 546 | CB | GLU | A | 73 | 9.235 | −3.276 | 8.952 | 1.00 | 26.10 | | C |
| ANISOU | 546 | CB | GLU | A | 73 | 3151 | 3819 | 2946 | 114 | 41 | 258 | C |
| ATOM | 547 | CG | GLU | A | 73 | 9.760 | −4.621 | 8.513 | 1.00 | 32.38 | | C |
| ANISOU | 547 | CG | GLU | A | 73 | 3945 | 4565 | 3793 | 71 | 34 | 279 | C |
| ATOM | 548 | CD | GLU | A | 73 | 8.913 | −5.786 | 9.013 | 1.00 | 36.59 | | C |
| ANISOU | 548 | CD | GLU | A | 73 | 4435 | 5116 | 4350 | 57 | 45 | 356 | C |
| ATOM | 549 | OE1 | GLU | A | 73 | 8.726 | −5.909 | 10.243 | 1.00 | 43.24 | | O |
| ANISOU | 549 | OE1 | GLU | A | 73 | 5254 | 6014 | 5160 | 90 | 63 | 402 | O |
| ATOM | 550 | OE2 | GLU | A | 73 | 8.453 | −6.590 | 8.171 | 1.00 | 44.28 | | O |
| ANISOU | 550 | OE2 | GLU | A | 73 | 5397 | 6048 | 5379 | 13 | 33 | 373 | O |
| ATOM | 551 | C | GLU | A | 73 | 9.229 | −0.825 | 8.575 | 1.00 | 22.22 | | C |
| ANISOU | 551 | C | GLU | A | 73 | 2697 | 3337 | 2409 | 159 | 26 | 168 | C |
| ATOM | 552 | O | GLU | A | 73 | 8.947 | −0.286 | 9.654 | 1.00 | 23.60 | | O |

TABLE 9-continued

Atomic coordinates for N-TXNIP(K5A/K6A) protein (SEQ ID NO: 8)

| | | | | | | | | | | | | | |
|---|---|---|---|---|---|---|---|---|---|---|---|---|---|
| ANISOU | 552 | O | GLU | A | 73 | 2862 | 3566 | 2539 | 210 | 31 | 169 | | O |
| ATOM | 553 | N | ASP | A | 74 | 8.796 | −0.366 | 7.403 | 1.00 | 21.01 | | | N |
| ANISOU | 553 | N | ASP | A | 74 | 2553 | 3153 | 2275 | 136 | 20 | 149 | | N |
| ATOM | 554 | CA | ASP | A | 74 | 7.900 | 0.782 | 7.346 | 1.00 | 21.37 | | | C |
| ANISOU | 554 | CA | ASP | A | 74 | 2598 | 3227 | 2295 | 165 | 19 | 134 | | C |
| ATOM | 555 | CB | ASP | A | 74 | 8.685 | 2.090 | 7.477 | 1.00 | 21.24 | | | C |
| ANISOU | 555 | CB | ASP | A | 74 | 2612 | 3193 | 2265 | 194 | 1 | 77 | | C |
| ATOM | 556 | CG | ASP | A | 74 | 7.920 | 3.158 | 8.244 | 1.00 | 28.94 | | | C |
| ANISOU | 556 | CG | ASP | A | 74 | 3581 | 4216 | 3197 | 251 | −4 | 62 | | C |
| ATOM | 557 | OD1 | ASP | A | 74 | 6.684 | 3.039 | 8.404 | 1.00 | 31.06 | | | O |
| ANISOU | 557 | OD1 | ASP | A | 74 | 3825 | 4532 | 3445 | 265 | 11 | 93 | | O |
| ATOM | 558 | OD2 | ASP | A | 74 | 8.566 | 4.19 | 8.708 | 1.00 | 34.38 | | | O |
| ANISOU | 558 | OD2 | ASP | A | 74 | 4290 | 4897 | 3875 | 285 | −20 | 15 | | O |
| ATOM | 559 | C | ASP | A | 74 | 7.119 | 0.818 | 6.048 | 1.00 | 19.95 | | | C |
| ANISOU | 559 | C | ASP | A | 74 | 2417 | 3024 | 2140 | 132 | 18 | 136 | | C |
| ATOM | 560 | O | ASP | A | 74 | 7.528 | 0.223 | 5.052 | 1.00 | 20.93 | | | O |
| ANISOU | 560 | O | ASP | A | 74 | 2550 | 3104 | 2300 | 92 | 12 | 132 | | O |
| ATOM | 561 | N | THR | A | 75 | 5.987 | 1.514 | 6.082 | 1.00 | 19.23 | | | N |
| ANISOU | 561 | N | THR | A | 75 | 2312 | 2968 | 2026 | 156 | 22 | 140 | | N |
| ATOM | 562 | CA | THR | A | 75 | 5.242 | 1.851 | 4.885 | 1.00 | 18.41 | | | C |
| ANISOU | 562 | CA | THR | A | 75 | 2210 | 2848 | 1938 | 137 | 18 | 134 | | C |
| ATOM | 563 | CB | THR | A | 75 | 3.728 | 1.649 | 5.099 | 1.00 | 19.43 | | | C |
| ANISOU | 563 | CB | THR | A | 75 | 2301 | 3029 | 2054 | 146 | 30 | 173 | | C |
| ATOM | 564 | OG1 | THR | A | 75 | 3.485 | 0.271 | 5.423 | 1.00 | 23.03 | | | O |
| ANISOU | 564 | OG1 | THR | A | 75 | 2723 | 3493 | 2533 | 118 | 39 | 224 | | O |
| ATOM | 565 | CG2 | THR | A | 75 | 2.942 | 2.000 | 3.650 | 1.00 | 22.20 | | | C |
| ANISOU | 565 | CG2 | THR | A | 75 | 2659 | 3372 | 2426 | 130 | 22 | 163 | | C |
| ATOM | 566 | C | THR | A | 75 | 5.585 | 3.299 | 4.551 | 1.00 | 19.02 | | | C |
| ANISOU | 566 | C | THR | A | 75 | 2319 | 2907 | 2003 | 162 | 4 | 87 | | C |
| ATOM | 567 | O | THR | A | 75 | 5.485 | 4.191 | 5.402 | 1.00 | 21.26 | | | O |
| ANISOU | 567 | O | THR | A | 75 | 2605 | 3216 | 2255 | 208 | −1 | 69 | | O |
| ATOM | 568 | N | LEU | A | 76 | 6.004 | 3.517 | 3.311 | 1.00 | 17.27 | | | N |
| ANISOU | 568 | N | LEU | A | 76 | 2117 | 2639 | 1807 | 134 | −4 | 69 | | N |
| ATOM | 569 | CA | LEU | A | 76 | 6.506 | 4.823 | 2.890 | 1.00 | 16.90 | | | C |
| ANISOU | 569 | CA | LEU | A | 76 | 2096 | 2562 | 1762 | 149 | −17 | 35 | | C |
| ATOM | 570 | CB | LEU | A | 76 | 7.636 | 4.658 | 1.865 | 1.00 | 17.11 | | | C |
| ANISOU | 570 | CB | LEU | A | 76 | 2142 | 2540 | 1820 | 115 | −21 | 25 | | C |
| ATOM | 571 | CG | LEU | A | 76 | 8.823 | 3.796 | 2.294 | 1.00 | 14.29 | | | C |
| ANISOU | 571 | CG | LEU | A | 76 | 1787 | 2166 | 1475 | 98 | −20 | 24 | | C |
| ATOM | 572 | CD1 | LEU | A | 76 | 9.882 | 3.887 | 1.236 | 1.00 | 13.66 | | | C |
| ANISOU | 572 | CD1 | LEU | A | 76 | 1724 | 2047 | 1421 | 74 | −23 | 14 | | C |
| ATOM | 573 | CD2 | LEU | A | 76 | 9.379 | 4.279 | 3.608 | 1.00 | 16.93 | | | C |
| ANISOU | 573 | CD2 | LEU | A | 76 | 2127 | 2510 | 1797 | 128 | −28 | 8 | | C |
| ATOM | 574 | C | LEU | A | 76 | 5.425 | 5.729 | 2.321 | 1.00 | 18.00 | | | C |
| ANISOU | 574 | C | LEU | A | 76 | 2235 | 2714 | 1890 | 167 | −20 | 31 | | C |
| ATOM | 575 | O | LEU | A | 76 | 4.400 | 5.258 | 1.838 | 1.00 | 19.44 | | | O |
| ANISOU | 575 | O | LEU | A | 76 | 2399 | 2919 | 2070 | 156 | −12 | 53 | | O |
| ATOM | 576 | N | LEU | A | 77 | 5.695 | 7.031 | 2.362 | 1.00 | 18.43 | | | N |
| ANISOU | 576 | N | LEU | A | 77 | 2310 | 2749 | 1945 | 193 | −36 | 4 | | N |
| ATOM | 577 | CA | LEU | A | 77 | 4.780 | 8.041 | 1.858 | 1.00 | 18.34 | | | C |
| ANISOU | 577 | CA | LEU | A | 77 | 2301 | 2742 | 1925 | 216 | −42 | −2 | | C |
| ATOM | 578 | CB | LEU | A | 77 | 4.627 | 9.155 | 2.896 | 1.00 | 19.96 | | | C |
| ANISOU | 578 | CB | LEU | A | 77 | 2514 | 2958 | 2112 | 269 | −61 | −32 | | C |
| ATOM | 579 | CG | LEU | A | 77 | 3.775 | 10.387 | 2.585 | 1.00 | 21.93 | | | C |
| ANISOU | 579 | CG | LEU | A | 77 | 2771 | 3207 | 2355 | 304 | −76 | −46 | | C |
| ATOM | 580 | CD1 | LEU | A | 77 | 2.299 | 10.029 | 2.492 | 1.00 | 25.02 | | | C |
| ANISOU | 580 | CD1 | LEU | A | 77 | 3135 | 3656 | 2713 | 317 | −59 | −23 | | C |
| ATOM | 581 | CD2 | LEU | A | 77 | 4.013 | 11.426 | 3.675 | 1.00 | 24.59 | | | C |
| ANISOU | 581 | CD2 | LEU | A | 77 | 3120 | 3540 | 2683 | 358 | −105 | −87 | | C |
| ATOM | 582 | C | LEU | A | 77 | 5.296 | 8.596 | 0.530 | 1.00 | 17.89 | | | C |
| ANISOU | 582 | C | LEU | A | 77 | 2263 | 2637 | 1897 | 193 | −48 | −4 | | C |
| ATOM | 583 | O | LEU | A | 77 | 6.460 | 8.984 | 0.404 | 1.00 | 17.89 | | | O |
| ANISOU | 583 | O | LEU | A | 77 | 2279 | 2595 | 1923 | 182 | −57 | −15 | | O |
| ATOM | 584 | N | LEU | A | 78 | 4.425 | 8.612 | −0.470 | 1.00 | 17.90 | | | N |
| ANISOU | 584 | N | LEU | A | 78 | 2258 | 2649 | 1893 | 187 | −41 | 10 | | N |
| ATOM | 585 | CA | LEU | A | 78 | 4.738 | 9.238 | −1.742 | 1.00 | 18.33 | | | C |
| ANISOU | 585 | CA | LEU | A | 78 | 2326 | 2671 | 1965 | 176 | −44 | 15 | | C |
| ATOM | 586 | CB | LEU | A | 78 | 3.544 | 9.100 | −2.689 | 1.00 | 19.34 | | | C |
| ANISOU | 586 | CB | LEU | A | 78 | 2443 | 2828 | 2077 | 178 | −38 | 29 | | C |
| ATOM | 587 | CG | LEU | A | 78 | 3.729 | 9.627 | −4.106 | 1.00 | 18.92 | | | C |
| ANISOU | 587 | CG | LEU | A | 78 | 2400 | 2755 | 2033 | 172 | −38 | 40 | | C |
| ATOM | 588 | CD1 | LEU | A | 78 | 4.865 | 8.901 | −4.836 | 1.00 | 23.11 | | | C |
| ANISOU | 588 | CD1 | LEU | A | 78 | 2935 | 3268 | 2577 | 142 | −30 | 48 | | C |
| ATOM | 589 | CD2 | LEU | A | 78 | 2.427 | 9.535 | −4.874 | 1.00 | 18.75 | | | C |
| ANISOU | 589 | CD2 | LEU | A | 78 | 2366 | 2769 | 1991 | 183 | −36 | 48 | | C |
| ATOM | 590 | C | LEU | A | 78 | 5.103 | 10.709 | −1.523 | 1.00 | 19.81 | | | C |
| ANISOU | 590 | C | LEU | A | 78 | 2532 | 2823 | 2170 | 202 | −64 | 0 | | C |
| ATOM | 591 | O | LEU | A | 78 | 4.448 | 11.412 | −0.745 | 1.00 | 19.90 | | | O |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 591 | O | LEU | A | 78 | 2545 | 2847 | 2169 | 239 | −77 | −17 | O |
| ATOM | 592 | N | GLU | A | 79 | 6.162 | 11.160 | −2.189 | 1.00 | 22.69 | | N |
| ANISOU | 592 | N | GLU | A | 79 | 2909 | 3144 | 2568 | 183 | −68 | 8 | N |
| ATOM | 593 | CA | GLU | A | 79 | 6.624 | 12.543 | −2.061 | 1.00 | 25.27 | | C |
| ANISOU | 593 | CA | GLU | A | 79 | 3251 | 3424 | 2928 | 200 | −91 | 0 | C |
| ATOM | 594 | CB | GLU | A | 79 | 7.800 | 12.819 | −3.004 | 1.00 | 26.88 | | C |
| ANISOU | 594 | CB | GLU | A | 79 | 3458 | 3585 | 3171 | 170 | −88 | 26 | C |
| ATOM | 595 | CG | GLU | A | 79 | 9.170 | 12.388 | −2.467 | 1.00 | 28.17 | | C |
| ANISOU | 595 | CG | GLU | A | 79 | 3619 | 3726 | 3359 | 146 | −91 | 19 | C |
| ATOM | 596 | CD | GLU | A | 79 | 10.317 | 12.825 | 3.378 | 1.00 | 30.44 | | C |
| ANISOU | 596 | CD | GLU | A | 79 | 3903 | 3975 | 3688 | 120 | −87 | 51 | C |
| ATOM | 597 | OE1 | GLU | A | 79 | 11.449 | 12.328 | −3.205 | 1.00 | 32.69 | | O |
| ANISOU | 597 | OE1 | GLU | A | 79 | 4182 | 4249 | 3989 | 98 | −83 | 53 | O |
| ATOM | 598 | OE2 | GLU | A | 79 | 10.085 | 13.662 | −4.278 | 1.00 | 31.84 | | O |
| ANISOU | 598 | OE2 | GLU | A | 79 | 4080 | 4136 | 3881 | 124 | −87 | 81 | O |
| ATOM | 599 | C | GLU | A | 79 | 5.483 | 13.489 | −2.369 | 1.00 | 26.88 | | C |
| ANISOU | 599 | C | GLU | A | 79 | 3458 | 3632 | 3122 | 232 | −101 | 0 | C |
| ATOM | 600 | O | GLU | A | 79 | 4.725 | 13.263 | −3.314 | 1.00 | 27.90 | | O |
| ANISOU | 600 | O | GLU | A | 79 | 3581 | 3788 | 3232 | 229 | −85 | 21 | O |
| ATOM | 601 | N | ASP | A | 80 | 5.348 | 14.523 | −1.544 | 1.00 | 28.62 | | N |
| ANISOU | 601 | N | ASP | A | 80 | 3689 | 3831 | 3356 | 267 | −131 | −28 | N |
| ATOM | 602 | CA | ASP | A | 80 | 4.355 | 15.581 | −1.757 | 1.00 | 29.53 | | C |
| ANISOU | 602 | CA | ASP | A | 80 | 3810 | 3942 | 3467 | 304 | −147 | −32 | C |
| ATOM | 603 | CB | ASP | A | 80 | 4.554 | 16.235 | −3.135 | 1.00 | 31.58 | | C |
| ANISOU | 603 | CB | ASP | A | 80 | 4075 | 4165 | 3758 | 287 | −143 | 7 | C |
| ATOM | 604 | CG | ASP | A | 80 | 5.963 | 16.774 | −3.322 | 1.00 | 37.49 | | C |
| ANISOU | 604 | CG | ASP | A | 80 | 4829 | 4848 | 4567 | 261 | 157 | 21 | C |
| ATOM | 605 | OD1 | ASP | A | 80 | 6.431 | 17.520 | −2.438 | 1.00 | 44.26 | | O |
| ANISOU | 605 | OD1 | ASP | A | 80 | 5695 | 4661 | 5461 | 277 | −193 | −10 | O |
| ATOM | 606 | OD2 | ASP | A | 80 | 6.608 | 16.446 | −4.343 | 1.00 | 45.72 | | O |
| ANISOU | 606 | OD2 | ASP | A | 80 | 5865 | 5886 | 5622 | 227 | −135 | 62 | O |
| ATOM | 607 | C | ASP | A | 80 | 2.890 | 15.153 | −1.529 | 1.00 | 28.85 | | C |
| ANISOU | 607 | C | ASP | A | 80 | 3711 | 3924 | 3327 | 333 | −133 | −37 | C |
| ATOM | 608 | O | ASP | A | 80 | 1.957 | 15.856 | −1.930 | 1.00 | 29.97 | | O |
| ANISOU | 608 | O | ASP | A | 80 | 3855 | 4074 | 3459 | 361 | −140 | −35 | O |
| ATOM | 609 | N | GLN | A | 81 | 2.697 | 14.004 | −0.886 | 1.00 | 25.62 | | N |
| ANISOU | 609 | N | GLN | A | 81 | 3286 | 3564 | 2886 | 325 | −115 | −40 | N |
| ATOM | 610 | CA | GLN | A | 81 | 1.384 | 13.631 | −0.335 | 1.00 | 27.06 | | C |
| ANISOU | 610 | CA | GLN | A | 81 | 3447 | 3812 | 3021 | 355 | −105 | −43 | C |
| ATOM | 611 | CB | GLN | A | 81 | 1.156 | 12.128 | −0.485 | 1.00 | 27.52 | | C |
| ANISOU | 611 | CB | GLN | A | 81 | 3482 | 3913 | 3062 | 318 | −77 | −17 | C |
| ATOM | 612 | CG | GLN | A | 81 | 0.987 | 11.671 | −1.927 | 1.00 | 31.37 | | C |
| ANISOU | 612 | CG | GLN | A | 81 | 3966 | 4396 | 3559 | 282 | −63 | 8 | C |
| ATOM | 613 | CD | GLN | A | 81 | −0.366 | 12.034 | −2.507 | 1.00 | 40.19 | | C |
| ANISOU | 613 | CD | GLN | A | 81 | 5071 | 5546 | 4654 | 305 | −63 | 16 | C |
| ATOM | 614 | OE1 | GLN | A | 81 | −1.387 | 11.421 | −2.174 | 1.00 | 44.77 | | O |
| ANISOU | 614 | OE1 | GLN | A | 81 | 5623 | 6178 | 5210 | 311 | −53 | 24 | O |
| ATOM | 615 | NE2 | GLN | A | 81 | −0.381 | 13.029 | −3.387 | 1.00 | 42.45 | | N |
| ANISOU | 615 | NE2 | GLN | A | 81 | 5375 | 5803 | 4953 | 317 | −72 | 19 | N |
| ATOM | 616 | C | GLN | A | 81 | 1.320 | 14.051 | 1.148 | 1.00 | 25.07 | | C |
| ANISOU | 616 | C | GLN | A | 81 | 3196 | 3580 | 2750 | 405 | −125 | −79 | C |
| ATOM | 617 | O | GLN | A | 81 | 2.363 | 14.180 | 1.786 | 1.00 | 22.08 | | O |
| ANISOU | 617 | O | GLN | A | 81 | 2830 | 3169 | 2391 | 404 | −141 | −100 | O |
| ATOM | 618 | N | PRO | A | 82 | 0.099 | 14.268 | 1.705 | 1.00 | 25.75 | | N |
| ANISOU | 618 | N | PRO | A | 82 | 3267 | 3724 | 2794 | 453 | −125 | −87 | N |
| ATOM | 619 | CA | PRO | A | 82 | −0.007 | 14.694 | 3.112 | 1.00 | 26.99 | | C |
| ANISOU | 619 | CA | PRO | A | 82 | 3422 | 3911 | 2922 | 514 | −144 | −124 | C |
| ATOM | 620 | CB | PRO | A | 82 | −1.517 | 14.902 | 3.319 | 1.00 | 26.55 | | C |
| ANISOU | 620 | CB | PRO | A | 82 | 3343 | 3925 | 2818 | 563 | −137 | −119 | C |
| ATOM | 621 | CG | PRO | A | 82 | −2.122 | 14.928 | 1.957 | 1.00 | 28.22 | | C |
| ANISOU | 621 | CG | PRO | A | 82 | 3554 | 4124 | 3046 | 531 | −125 | −90 | C |
| ATOM | 622 | CD | PRO | A | 82 | −1.226 | 14.126 | 1.074 | 1.00 | 26.91 | | C |
| ANISOU | 622 | CD | PRO | A | 82 | 3393 | 3916 | 2916 | 459 | −108 | −63 | C |
| ATOM | 623 | C | PRO | A | 82 | 0.511 | 13.641 | 4.099 | 1.00 | 28.47 | | C |
| ANISOU | 623 | C | PRO | A | 82 | 3594 | 4135 | 3089 | 506 | −128 | −118 | C |
| ATOM | 624 | O | PRO | A | 82 | 0.189 | 12.458 | 3.970 | 1.00 | 26.18 | | O |
| ANISOU | 624 | O | PRO | A | 82 | 3278 | 3883 | 2786 | 471 | −95 | −78 | O |
| ATOM | 625 | N | THR | A | 83 | 1.312 | 14.087 | 5.066 | 1.00 | 28.01 | | N |
| ANISOU | 625 | N | THR | A | 83 | 3665 | 4174 | 3148 | 538 | −155 | −158 | N |
| ATOM | 626 | CA | THR | A | 83 | 1.863 | 13.227 | 6.122 | 1.00 | 31.70 | | C |
| ANISOU | 626 | CA | THR | A | 83 | 4005 | 4563 | 3477 | 542 | −145 | −158 | C |
| ATOM | 627 | CB | THR | A | 83 | 2.742 | 14.041 | 7.104 | 1.00 | 32.44 | | C |
| ANISOU | 627 | CB | THR | A | 83 | 4120 | 4630 | 3577 | 589 | −188 | −217 | C |
| ATOM | 628 | OG1 | THR | A | 83 | 3.869 | 14.572 | 6.397 | 1.00 | 35.36 | | O |
| ANISOU | 628 | OG1 | THR | A | 83 | 4516 | 4905 | 4014 | 547 | −213 | −231 | O |
| ATOM | 629 | CG2 | THR | A | 83 | 3.247 | 13.174 | 8.253 | 1.00 | 34.43 | | C |
| ANISOU | 629 | CG2 | THR | A | 83 | 4357 | 4930 | 3795 | 603 | −177 | −216 | C |
| ATOM | 630 | C | THR | A | 83 | 0.759 | 12.506 | 6.895 | 1.00 | 32.33 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 630 | C | THR | A | 83 | 4047 | 4742 | 3495 | 576 | −116 | −129 | C |
| ATOM | 631 | O | THR | A | 83 | −0.283 | 13.092 | 7.196 | 1.00 | 31.77 | | O |
| ANISOU | 631 | O | THR | A | 83 | 3965 | 4721 | 3387 | 632 | −120 | −139 | O |
| ATOM | 632 | N | GLY | A | 84 | 1.001 | 11.229 | 7.194 | 1.00 | 33.10 | | N |
| ANISOU | 632 | N | GLY | A | 84 | 4122 | 4869 | 3584 | 542 | −86 | −89 | N |
| ATOM | 633 | CA | GLY | A | 84 | 0.073 | 10.410 | 7.969 | 1.00 | 34.43 | | C |
| ANISOU | 633 | CA | GLY | A | 84 | 4247 | 5131 | 3703 | 566 | −55 | −47 | C |
| ATOM | 634 | C | GLY | A | 84 | −1.143 | 9.932 | 7.199 | 1.00 | 35.36 | | C |
| ANISOU | 634 | C | GLY | A | 84 | 4335 | 5279 | 3822 | 538 | −29 | 1 | C |
| ATOM | 635 | O | GLY | A | 84 | −1.963 | 9.182 | 7.731 | 1.00 | 36.81 | | O |
| ANISOU | 635 | O | GLY | A | 84 | 4474 | 5537 | 3975 | 547 | −2 | 48 | O |
| ATOM | 636 | N | GLU | A | 85 | −1.261 | 10.354 | 5.942 | 1.00 | 32.61 | | N |
| ANISOU | 636 | N | GLU | A | 85 | 4313 | 5183 | 8817 | 508 | −38 | −7 | N |
| ATOM | 637 | CA | GLU | A | 85 | −2.431 | 10.016 | 5.140 | 1.00 | 34.60 | | C |
| ANISOU | 637 | CA | GLU | A | 85 | 4229 | 5153 | 3762 | 482 | −20 | 29 | C |
| ATOM | 638 | CB | GLU | A | 85 | −2.597 | 10.984 | 3.966 | 1.00 | 35.43 | | C |
| ANISOU | 638 | CB | GLU | A | 85 | 4363 | 5207 | 3891 | 477 | −39 | 5 | C |
| ATOM | 639 | CG | GLU | A | 85 | −4.0.32 | 11.462 | 3.758 | 1.00 | 38.71 | | C |
| ANISOU | 639 | CG | GLU | A | 85 | 4755 | 5675 | 4278 | 513 | −38 | 13 | C |
| ATOM | 640 | CD | GLU | A | 85 | −4378 | 12.733 | 4.544 | 1.00 | 41.24 | | C |
| ANISOU | 640 | CD | GLU | A | 85 | 5088 | 6021 | 4562 | 596 | −59 | −29 | C |
| ATOM | 641 | OE1 | GLU | A | 85 | −5.192 | 13.538 | 4.038 | 1.00 | 41.42 | | O |
| ANISOU | 641 | OE1 | GLU | A | 85 | 5112 | 6048 | 4576 | 624 | −69 | −40 | O |
| ATOM | 642 | OE2 | GLU | A | 85 | −3.848 | 12.932 | 5.659 | 1.00 | 45.75 | | O |
| ANISOU | 642 | OE2 | GLU | A | 85 | 5664 | 6607 | 5110 | 637 | −69 | −55 | O |
| ATOM | 643 | C | GLU | A | 85 | −2.334 | 8.584 | 4.634 | 1.00 | 32.26 | | O |
| ANISOU | 643 | C | GLU | A | 85 | 3910 | 4848 | 3497 | 411 | 2 | 77 | O |
| ATOM | 644 | O | GLU | A | 85 | −1.240 | 8.088 | 4.332 | 1.00 | 32.87 | | O |
| ANISOU | 644 | O | GLU | A | 85 | 4008 | 4872 | 3607 | 368 | −1 | 72 | O |
| ATOM | 645 | N | ASN | A | 86 | −3.462 | 7.918 | 4.572 | 1.00 | 29.04 | | N |
| ANISOU | 645 | N | ASN | A | 86 | 3458 | 4495 | 3082 | 402 | 20 | 121 | N |
| ATOM | 646 | CA | ASN | A | 86 | −3.552 | 6.570 | 4.042 | 1.00 | 26.42 | | C |
| ANISOU | 646 | CA | ASN | A | 86 | 3100 | 4150 | 2789 | 337 | 33 | 164 | C |
| ATOM | 647 | CB | ASN | A | 86 | −4.110 | 5.601 | 5.087 | 1.00 | 26.28 | | C |
| ANISOU | 647 | CB | ASN | A | 86 | 3028 | 4199 | 2756 | 341 | 57 | 222 | C |
| ATOM | 648 | CG | ASN | A | 86 | −3.316 | 5.627 | 6.378 | 1.00 | 28.69 | | C |
| ANISOU | 648 | CG | ASN | A | 86 | 8842 | 4528 | 8081 | 378 | 68 | 218 | C |
| ATOM | 649 | OD1 | ASN | A | 86 | −2.161 | 5.216 | 6.416 | 1.00 | 33.68 | | O |
| ANISOU | 649 | OD1 | ASN | A | 86 | 4000 | 5111 | 3685 | 351 | 57 | 205 | O |
| ATOM | 650 | NDA | ASN | A | 86 | −3.939 | 6.117 | 7.443 | 1.00 | 32.99 | | N |
| ANISOU | 650 | NDA | ASN | A | 86 | 3863 | 5152 | 3519 | 446 | 73 | 226 | N |
| ATOM | 651 | C | ASN | A | 86 | −4.396 | 6.588 | 2.782 | 1.00 | 24.52 | | C |
| ANISOU | 651 | C | ASN | A | 86 | 2850 | 3898 | 2569 | 311 | 27 | 168 | C |
| ATOM | 652 | O | ASN | A | 86 | −5.617 | 6.740 | 2.817 | 1.00 | 24.10 | | O |
| ANISOU | 652 | O | ASN | A | 86 | 2762 | 3898 | 2498 | 332 | 33 | 188 | O |
| ATOM | 653 | N | GLU | A | 87 | −3.725 | 6.453 | 1.654 | 1.00 | 24.12 | | N |
| ANISOU | 653 | N | GLU | A | 87 | 2829 | 3782 | 2553 | 270 | 14 | 148 | N |
| ATOM | 654 | CA | GLU | A | 87 | −4.356 | 5.071 | 0.389 | 1.00 | 25.09 | | C |
| ANISOU | 654 | CA | GLU | A | 87 | 2953 | 3891 | 2688 | 257 | 4 | 140 | C |
| ATOM | 655 | CB | GLU | A | 87 | −4.212 | 8.180 | 0.019 | 1.00 | 26.01 | | C |
| ANISOU | 655 | CB | GLU | A | 87 | 3108 | 3988 | 2785 | 297 | −9 | 102 | C |
| ATOM | 656 | CG | GLU | A | 87 | −5.060 | 8.647 | −1.153 | 1.00 | 32.48 | | C |
| ANISOU | 656 | CG | GLU | A | 87 | 3920 | 4808 | 3599 | 300 | −17 | 97 | C |
| ATOM | 657 | CD | GLU | A | 87 | −6.422 | 9.208 | −0.741 | 1.00 | 35.21 | | C |
| ANISOU | 657 | CD | GLU | A | 87 | 4243 | 5219 | 3918 | 346 | −14 | 106 | C |
| ATOM | 658 | OE1 | GLU | A | 87 | −7.130 | 9.727 | −1.625 | 1.00 | 40.23 | | O |
| ANISOU | 658 | OE1 | GLU | A | 87 | 4878 | 5858 | 4549 | 356 | −23 | 100 | O |
| ATOM | 659 | OE2 | GLU | A | 87 | −6.787 | 9.144 | 0.453 | 1.00 | 38.26 | | O |
| ANISOU | 659 | OE2 | GLU | A | 87 | 4604 | 5655 | 4279 | 375 | −3 | 120 | O |
| ATOM | 660 | C | GLU | A | 87 | −3.646 | 5.844 | −0621 | 1.00 | 25.01 | | C |
| ANISOU | 660 | C | GLU | A | 87 | 2956 | 3828 | 2718 | 203 | 5 | 136 | O |
| ATOM | 661 | O | GLU | A | 87 | −2.415 | 5.757 | −0.625 | 1.00 | 26.89 | | O |
| ANISOU | 661 | O | GLU | A | 87 | 3225 | 4023 | 2969 | 189 | −7 | 120 | O |
| ATOM | 662 | N | MET | A | 88 | −4.427 | 5.196 | −1.468 | 1.00 | 22.55 | | N |
| ANISOU | 662 | N | MET | A | 88 | 2618 | 3523 | 2428 | 176 | −13 | 184 | N |
| ATOM | 663 | CA | MET | A | 88 | −3.857 | 4.465 | −2.578 | 1.00 | 22.85 | | C |
| ANISOU | 663 | CA | MET | A | 88 | 2670 | 3515 | 2499 | 136 | −27 | 134 | C |
| ATOM | 664 | CB | MET | A | 88 | −4.851 | 3.466 | −3.102 | 1.00 | 22.70 | | C |
| ANISOU | 664 | CB | MET | A | 88 | 2606 | 3510 | 2509 | 107 | −41 | 151 | C |
| ATOM | 665 | CG | MET | A | 88 | −5.286 | 2.537 | −1.997 | 1.00 | 28.14 | | C |
| ANISOU | 665 | CG | MET | A | 88 | 3249 | 4224 | 3218 | 90 | −31 | 195 | C |
| ATOM | 666 | SD | MET | A | 88 | −5.718 | 0.950 | −2.619 | 1.00 | 32.35 | | S |
| ANISOU | 666 | SD | MET | A | 88 | 3742 | 4732 | 3817 | 34 | −58 | 213 | S |
| ATOM | 667 | CE | MET | A | 88 | −5.713 | 0.027 | −1.111 | 1.00 | 35.94 | | C |
| ANISOU | 667 | CE | MET | A | 88 | 4155 | 5205 | 4294 | 16 | −39 | 275 | C |
| ATOM | 668 | C | MET | A | 88 | −3.433 | 5.446 | −3.645 | 1.00 | 20.70 | | C |
| ANISOU | 668 | C | MET | A | 88 | 2436 | 3216 | 2212 | 153 | −35 | 102 | C |
| ATOM | 669 | O | MET | A | 88 | −3.957 | 6.557 | −3.727 | 1.00 | 23.43 | | O |

TABLE 9-continued

Atomic coordinates for N-TXNIP(K5A/K6A) protein (SEQ ID NO: 8)

| ANISOU | 669 | O | MET | A | 88 | 2791 | 3581 | 2532 | 189 | −34 | 96 | O |
|---|---|---|---|---|---|---|---|---|---|---|---|---|
| ATOM | 670 | N | VAL | A | 89 | −2.456 | 5.036 | −4.439 | 1.00 | 19.43 | | N |
| ANISOU | 670 | N | VAL | A | 89 | 2300 | 3016 | 2069 | 130 | −43 | 86 | N |
| ATOM | 671 | CA | VAL | A | 89 | −1.871 | 5.907 | −5.444 | 1.00 | 19.75 | | C |
| ANISOU | 671 | CA | VAL | A | 89 | 2375 | 3034 | 2097 | 154 | −46 | 67 | C |
| ATOM | 672 | CB | VAL | A | 89 | −0.328 | 5.958 | −5.251 | 1.00 | 19.88 | | C |
| ANISOU | 672 | CB | VAL | A | 89 | 2421 | 3010 | 2122 | 135 | −39 | 59 | C |
| ATOM | 673 | CG1 | VAL | A | 89 | 0.848 | 6.720 | −6.370 | 1.00 | 24.75 | | C |
| ANISOU | 673 | CG1 | VAL | A | 89 | 3605 | 3605 | 2732 | 146 | −40 | 51 | C |
| ATOM | 674 | CG2 | VAL | A | 89 | 0.007 | 6.587 | −3.890 | 1.00 | 20.68 | | C |
| ANISOU | 674 | CG2 | VAL | A | 89 | 2531 | 3110 | 2217 | 152 | −30 | 62 | C |
| ATOM | 675 | C | VAL | A | 89 | −2.235 | 5.362 | −6.813 | 1.00 | 18.70 | | C |
| ANISOU | 675 | C | VAL | A | 89 | 2233 | 2903 | 1968 | 135 | −62 | 56 | C |
| ATOM | 676 | O | VAL | A | 89 | −2.071 | 4.167 | −7.074 | 1.00 | 18.58 | | O |
| ANISOU | 676 | O | VAL | A | 89 | 2205 | 2878 | 1978 | 107 | −74 | 50 | O |
| ATOM | 677 | N | ILE | A | 90 | −2.751 | 6.230 | −7.680 | 1.00 | 19.11 | | N |
| ANISOU | 677 | N | ILE | A | 90 | 2293 | 2970 | 1999 | 162 | −65 | 51 | N |
| ATOM | 678 | CA | ILE | A | 90 | −2.946 | 5.867 | −9.075 | 1.00 | 19.26 | | C |
| ANISOU | 678 | CA | ILE | A | 90 | 2309 | 2996 | 2013 | 164 | −82 | 36 | C |
| ATOM | 679 | CB | ILE | A | 90 | −4.240 | 6.477 | −9.677 | 1.00 | 20.34 | | C |
| ANISOU | 679 | CB | ILE | A | 90 | 2431 | 3169 | 2129 | 191 | −90 | 36 | C |
| ATOM | 680 | CG1 | ILE | A | 90 | −5.483 | 6.076 | −8.858 | 1.00 | 19.03 | | C |
| ANISOU | 680 | CG1 | ILE | A | 90 | 2224 | 3032 | 1975 | 183 | −95 | 47 | C |
| ATOM | 681 | CD1 | ILE | A | 90 | −5.760 | 4.580 | −8.810 | 1.00 | 25.11 | | C |
| ANISOU | 681 | CD1 | ILE | A | 90 | 2960 | 3798 | 2782 | 145 | −114 | 44 | C |
| ATOM | 682 | CG2 | ILE | A | 90 | −4.385 | 6.097 | −11.149 | 1.00 | 23.08 | | C |
| ANISOU | 682 | CG2 | ILE | A | 90 | 2775 | 3528 | 2465 | 200 | −111 | 16 | C |
| ATOM | 683 | C | ILE | A | 90 | −1.696 | 6.318 | −9.832 | 1.00 | 18.33 | | C |
| ANISOU | 683 | C | ILE | A | 90 | 2225 | 2855 | 1884 | 173 | −74 | 32 | C |
| ATOM | 684 | O | ILE | A | 90 | −1.485 | 7.518 | −1.084 | 1.00 | 21.10 | | O |
| ANISOU | 684 | O | ILE | A | 90 | 2603 | 3210 | 2225 | 197 | −63 | 44 | O |
| ATOM | 685 | N | MET | A | 91 | −0.845 | 5.359 | −10.164 | 1.00 | 17.18 | | N |
| ANISOU | 685 | N | MET | A | 91 | 2121 | 2732 | 1788 | 153 | −80 | 19 | N |
| ATOM | 686 | CA | MET | A | 91 | 0.363 | 5.694 | −10.899 | 1.00 | 16.52 | | C |
| ANISOU | 686 | CA | MET | A | 91 | 2024 | 2598 | 1655 | 163 | −70 | 21 | C |
| ATOM | 687 | CB | MET | A | 91 | 1.474 | 4.705 | −10.575 | 1.00 | 14.54 | | C |
| ANISOU | 687 | CB | MET | A | 91 | 1778 | 2322 | 1424 | 138 | −70 | 11 | C |
| ATOM | 688 | CG | MET | A | 91 | 1.945 | 4.767 | −9.133 | 1.00 | 14.75 | | C |
| ANISOU | 688 | CG | MET | A | 91 | 1808 | 2323 | 1472 | 118 | −58 | 23 | C |
| ATOM | 699 | SD | MET | A | 91 | 3.383 | 3.704 | −8.920 | 1.00 | 17.86 | | S |
| ANISOU | 699 | SD | MET | A | 91 | 2211 | 2689 | 1886 | 94 | −57 | 13 | S |
| ATOM | 690 | CE | MET | A | 91 | 3.743 | 4.005 | −7.179 | 1.00 | 17.65 | | C |
| ANISOU | 690 | CE | MET | A | 91 | 2188 | 2642 | 1877 | 80 | −43 | 28 | C |
| ATOM | 691 | C | MET | A | 91 | 0.092 | 5.742 | −12.391 | 1.00 | 17.90 | | C |
| ANISOU | 691 | C | MET | A | 91 | 2197 | 2802 | 1800 | 191 | −81 | 11 | C |
| ATOM | 692 | O | MET | A | 91 | −0.564 | 4.859 | −12.939 | 1.00 | 17.85 | | O |
| ANISOU | 692 | O | MET | A | 91 | 2173 | 2815 | 1795 | 192 | −106 | −14 | O |
| ATOM | 693 | N | ARG | A | 92 | 0.596 | 6.792 | −13.033 | 1.00 | 18.21 | | N |
| ANISOU | 693 | N | ARG | A | 92 | 2254 | 2847 | 1818 | 216 | −64 | 34 | N |
| ATOM | 694 | CA | ARG | A | 92 | 0.387 | 7.016 | −14.455 | 1.00 | 19.80 | | C |
| ANISOU | 694 | CA | ARG | A | 92 | 2454 | 3085 | 1983 | 252 | −69 | 34 | C |
| ATOM | 695 | CB | ARG | A | 92 | −0.439 | 8.291 | −14.655 | 1.00 | 21.38 | | C |
| ANISOU | 695 | CB | ARG | A | 92 | 2657 | 3299 | 2168 | 279 | −63 | 58 | C |
| ATOM | 696 | CG | ARG | A | 92 | −1.821 | 8.226 | −14.005 | 1.00 | 24.97 | | C |
| ANISOU | 696 | CG | ARG | A | 92 | 3095 | 3761 | 2631 | 273 | −77 | 44 | C |
| ATOM | 697 | CD | ARG | A | 92 | −2.622 | 9.501 | −14.200 | 1.00 | 30.61 | | C |
| ANISOU | 697 | CD | ARG | A | 92 | 3813 | 4489 | 3329 | 305 | −73 | 65 | C |
| ATOM | 698 | NE | ARG | A | 92 | −3.995 | 9.342 | −13.705 | 1.00 | 36.77 | | N |
| ANISOU | 698 | NE | ARG | A | 92 | 4570 | 5289 | 4111 | 805 | −87 | 51 | N |
| ATOM | 699 | CZ | ARG | A | 92 | −4.374 | 9.513 | −12.440 | 1.00 | 40.74 | | C |
| ANISOU | 699 | CZ | ARG | A | 92 | 5068 | 5779 | 4634 | 291 | −83 | 53 | C |
| ATOM | 700 | NH1 | ARG | A | 92 | −3.493 | 9.855 | 11.504 | 1.00 | 42.88 | | N |
| ANISOU | 700 | NH1 | ARG | A | 92 | 5356 | 6013 | 4923 | 278 | −69 | 54 | N |
| ATOM | 701 | NH2 | ARG | A | 92 | −5.647 | 9.335 | −12.109 | 1.00 | 37.52 | | N |
| ANISOU | 701 | NH2 | ARG | A | 92 | 4633 | 5400 | 4225 | 295 | −94 | 46 | N |
| ATOM | 702 | C | ARG | A | 92 | 1.732 | 7.119 | −15.172 | 1.00 | 19.61 | | C |
| ANISOU | 702 | C | ARG | A | 92 | 2443 | 3065 | 1944 | 264 | −53 | 50 | C |
| ATOM | 703 | O | ARG | A | 92 | 2.710 | 7.581 | −14.587 | 1.00 | 19.14 | | O |
| ANISOU | 703 | O | ARG | A | 92 | 2394 | 2973 | 1904 | 248 | −33 | 75 | O |
| ATOM | 704 | N | PRO | A | 93 | 1.795 | 6.681 | −16.444 | 1.00 | 21.00 | | N |
| ANISOU | 704 | N | PRO | A | 93 | 2613 | 3284 | 2084 | 297 | −62 | 37 | N |
| ATOM | 705 | CA | PRO | A | 93 | 3.062 | 6.777 | 17.174 | 1.00 | 21.01 | | C |
| ANISOU | 705 | CA | PRO | A | 93 | 2619 | 3301 | 2062 | 316 | −43 | 58 | C |
| ATOM | 706 | CB | PRO | A | 93 | 2.739 | 6.179 | −18.557 | 1.00 | 22.06 | | C |
| ANISOU | 706 | CB | PRO | A | 93 | 2742 | 3494 | 2146 | 363 | −62 | 30 | C |
| ATOM | 707 | CG | PRO | A | 93 | 1.261 | 6.145 | −18.644 | 1.00 | 23.21 | | C |
| ANISOU | 707 | CG | PRO | A | 93 | 2878 | 3652 | 2289 | 370 | −89 | 4 | C |
| ATOM | 708 | CD | PRO | A | 93 | 0.724 | 6.072 | −17.250 | 1.00 | 20.87 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 708 | CD | PRO | A | 93 | 2581 | 3306 | 2043 | 321 | −93 | −1 | C |
| ATOM | 709 | C | PRO | A | 93 | 3.555 | 8.221 | −17.314 | 1.00 | 22.72 | | C |
| ANISOU | 709 | C | PRO | A | 93 | 2843 | 3511 | 2277 | 326 | 11 | 121 | C |
| ATOM | 710 | O | PRO | A | 93 | 2.753 | 9.164 | −17.270 | 1.00 | 22.99 | | O |
| ANISOU | 710 | O | PRO | A | 93 | 2880 | 3542 | 2313 | 335 | −10 | 142 | O |
| ATOM | 711 | N | GLY | A | 94 | 4.869 | 8.384 | −17.453 | 1.00 | 23.57 | | N |
| ANISOU | 711 | N | GLY | A | 94 | 2953 | 3614 | 2389 | 323 | 11 | 152 | N |
| ATOM | 712 | CA | GLY | A | 94 | 5.476 | 9.701 | −17.654 | 1.00 | 25.16 | | C |
| ANISOU | 712 | CA | GLY | A | 94 | 3155 | 3805 | 2600 | 329 | 38 | 220 | C |
| ATOM | 713 | C | GLY | A | 94 | 5.834 | 10.403 | −16.360 | 1.00 | 27.01 | | C |
| ANISOU | 713 | C | GLY | A | 94 | 3400 | 3970 | 2894 | 288 | 42 | 236 | C |
| ATOM | 714 | O | GLY | A | 94 | 6.253 | 11.564 | −16.368 | 1.00 | 30.27 | | O |
| ANISOU | 714 | O | GLY | A | 94 | 3813 | 4358 | 3331 | 287 | 56 | 288 | O |
| ATOM | 715 | N | ASN | A | 95 | 5.668 | 9.695 | −15.245 | 1.00 | 25.23 | | N |
| ANISOU | 715 | N | ASN | A | 95 | 3181 | 3714 | 2692 | 256 | 27 | 191 | N |
| ATOM | 716 | CA | ASN | A | 95 | 5.942 | 10.234 | −13.921 | 1.00 | 24.92 | | C |
| ANISOU | 716 | CA | ASN | A | 95 | 3151 | 3616 | 2701 | 225 | 25 | 194 | C |
| ATOM | 717 | CB | ASN | A | 95 | 4.636 | 10.401 | −13.136 | 1.00 | 25.15 | | C |
| ANISOU | 717 | CB | ASN | A | 95 | 3185 | 3636 | 2737 | 223 | 8 | 167 | C |
| ATOM | 718 | CG | ASN | A | 95 | 3.600 | 11.223 | −13.883 | 1.00 | 27.91 | | C |
| ANISOU | 718 | CG | ASN | A | 95 | 3534 | 4008 | 3064 | 256 | 6 | 184 | C |
| ATOM | 719 | OD1 | ASN | A | 95 | 3.768 | 12.727 | −14.080 | 1.00 | 33.36 | | O |
| ANISOU | 719 | OD1 | ASN | A | 95 | 4228 | 4678 | 3768 | 268 | 12 | 224 | O |
| ATOM | 720 | ND2 | ASN | A | 95 | 2.515 | 10.577 | −14.291 | 1.00 | 28.10 | | N |
| ANISOU | 720 | ND2 | ASN | A | 95 | 8548 | 4071 | 8057 | 270 | −7 | 155 | N |
| ATOM | 721 | C | ASN | A | 95 | 6.877 | 9.310 | −13.148 | 1.00 | 23.96 | | C |
| ANISOU | 721 | C | ASN | A | 95 | 3029 | 3474 | 2599 | 195 | 25 | 170 | C |
| ATOM | 722 | O | ASN | A | 95 | 6.837 | 8.092 | −13.326 | 1.00 | 25.63 | | O |
| ANISOU | 722 | O | ASN | A | 95 | 3237 | 3709 | 2793 | 193 | 17 | 136 | O |
| ATOM | 723 | N | LYS | A | 96 | 7.722 | 9.894 | −12.302 | 1.00 | 22.92 | | N |
| ANISOU | 723 | N | LYS | A | 96 | 2903 | 3298 | 2508 | 173 | 29 | 186 | N |
| ATOM | 724 | CA | LYS | A | 96 | 8.495 | 9.128 | −11.324 | 1.00 | 22.56 | | C |
| ANISOU | 724 | CA | LYS | A | 96 | 2860 | 3229 | 2484 | 145 | 26 | 161 | C |
| ATOM | 725 | CB | LYS | A | 96 | 9.921 | 9.640 | −11.194 | 1.00 | 23.95 | | C |
| ANISOU | 725 | CB | LYS | A | 96 | 3031 | 3376 | 2691 | 130 | 37 | 192 | C |
| ATOM | 726 | CG | LYS | A | 96 | 10.827 | 9.343 | −12.380 | 1.00 | 28.94 | | C |
| ANISOU | 726 | CG | LYS | A | 96 | 3650 | 4045 | 3303 | 142 | 57 | 222 | C |
| ATOM | 727 | CD | LYS | A | 96 | 12.271 | 9.686 | −12.028 | 1.00 | 31.52 | | C |
| ANISOU | 727 | CD | LYS | A | 96 | 3957 | 4343 | 3668 | 121 | 66 | 250 | C |
| ATOM | 728 | CE | LYS | A | 96 | 13.178 | 9.691 | −13.278 | 1.00 | 36.99 | | C |
| ANISOU | 728 | CE | LYS | A | 96 | 4638 | 5077 | 4341 | 137 | 91 | 297 | C |
| ATOM | 729 | NZ | LYS | A | 96 | 12.947 | 10.865 | −14.142 | 1.00 | 46.39 | | N |
| ANISOU | 729 | NZ | LYS | A | 96 | 5817 | 6276 | 5531 | 156 | 104 | 358 | N |
| ATOM | 730 | C | LYS | A | 96 | 7.794 | 9.246 | −9.974 | 1.00 | 21.48 | | C |
| ANISOU | 730 | C | LYS | A | 96 | 2730 | 3064 | 2365 | 134 | 10 | 134 | C |
| ATOM | 731 | O | LYS | A | 96 | 7.544 | 10.354 | −9.496 | 1.00 | 23.38 | | O |
| ANISOU | 731 | O | LYS | A | 96 | 2978 | 3278 | 2628 | 139 | 4 | 145 | O |
| ATOM | 732 | N | TYR | A | 97 | 7.477 | 8.105 | −9.370 | 1.00 | 17.37 | | N |
| ANISOU | 732 | N | TYR | A | 97 | 2208 | 2553 | 1838 | 122 | 3 | 101 | N |
| ATOM | 733 | CA | TYR | A | 97 | 6.841 | 8.089 | −8.061 | 1.00 | 16.68 | | C |
| ANISOU | 733 | CA | TYR | A | 97 | 2122 | 2453 | 1762 | 115 | −8 | 82 | C |
| ATOM | 734 | CB | TYR | A | 97 | 5.676 | 7.100 | −8.030 | 1.00 | 17.00 | | C |
| ANISOU | 734 | CB | TYR | A | 97 | 2151 | 2524 | 1785 | 115 | −16 | 62 | C |
| ATOM | 735 | CG | TYR | A | 97 | 4.578 | 7.545 | 8.955 | 1.00 | 16.58 | | C |
| ANISOU | 735 | CG | TYR | A | 97 | 2092 | 2496 | 1709 | 137 | −19 | 68 | C |
| ATOM | 736 | CD1 | TYR | A | 97 | 3.585 | 8.405 | −8.502 | 1.00 | 16.91 | | C |
| ANISOU | 736 | CD1 | TYR | A | 97 | 2134 | 2542 | 1748 | 154 | −23 | 71 | C |
| ATOM | 737 | CE1 | TYR | A | 97 | 2.584 | 8.845 | −9.339 | 1.00 | 17.34 | | C |
| ANISOU | 737 | CE1 | TYR | A | 97 | 2185 | 2623 | 1782 | 176 | −27 | 76 | C |
| ATOM | 738 | CZ | TYR | A | 97 | 2.580 | 8.452 | −1.674 | 1.00 | 14.76 | | C |
| ANISOU | 738 | CZ | TYR | A | 97 | 1853 | 3220 | 1434 | 185 | −27 | 78 | C |
| ATOM | 739 | OH | TYR | A | 97 | 1.573 | 8.881 | −11.502 | 1.00 | 19.87 | | O |
| ANISOU | 739 | OH | TYR | A | 97 | 2494 | 2997 | 2059 | 211 | −32 | 82 | O |
| ATOM | 740 | CE2 | TYR | A | 97 | 3.558 | 7.595 | −11.195 | 1.00 | 17.18 | | C |
| ANISOU | 740 | CE2 | TYR | A | 97 | 2159 | 2627 | 1740 | 173 | −24 | 72 | C |
| ATOM | 741 | CD2 | TYR | A | 97 | 4.564 | 7.155 | −10.299 | 1.00 | 14.01 | | C |
| ANISOU | 741 | CD2 | TYR | A | 97 | 1763 | 2198 | 1363 | 148 | −19 | 68 | C |
| ATOM | 742 | C | TYR | A | 97 | 7.901 | 7.750 | −7.040 | 1.00 | 17.79 | | C |
| ANISOU | 742 | C | TYR | A | 97 | 2267 | 2568 | 1926 | 96 | −8 | 73 | C |
| ATOM | 743 | O | TYR | A | 97 | 8.402 | 6.619 | −6.991 | 1.00 | 17.90 | | O |
| ANISOU | 743 | O | TYR | A | 97 | 2276 | 2587 | 1938 | 81 | −6 | 62 | O |
| ATOM | 744 | N | GLU | A | 98 | 8.250 | 8.749 | −6.237 | 1.00 | 17.47 | | N |
| ANISOU | 744 | N | GLU | A | 98 | 2234 | 2496 | 1908 | 99 | −14 | 75 | N |
| ATOM | 745 | CA | GLU | A | 98 | 9.398 | 8.648 | −5.354 | 1.00 | 16.68 | | C |
| ANISOU | 745 | CA | GLU | A | 98 | 2137 | 2369 | 1832 | 85 | −17 | 67 | C |
| ATOM | 746 | CB | GLU | A | 98 | 10.393 | 9.770 | −5.641 | 1.00 | 19.50 | | C |
| ANISOU | 746 | CB | GLU | A | 98 | 2496 | 2689 | 2223 | 82 | −20 | 89 | C |
| ATOM | 747 | CG | GLU | A | 98 | 10.929 | 9.732 | −7.064 | 1.00 | 18.52 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 747 | CG | GLU | A | 98 | 2363 | 2578 | 2094 | 78 | −2 | 123 | C |
| ATOM | 748 | CD | GLU | A | 98 | 11.809 | 10.899 | −7.434 | 1.00 | 29.43 | | C |
| ANISOU | 748 | CD | GLU | A | 98 | 3740 | 3926 | 3515 | 73 | −2 | 160 | C |
| ATOM | 749 | OE1 | GLU | A | 98 | 11.958 | 11.833 | −6.621 | 1.00 | 35.46 | | C |
| ANISOU | 749 | OE1 | GLU | A | 98 | 4509 | 4647 | 4318 | 72 | −23 | 153 | C |
| ATOM | 750 | OE2 | GLU | A | 98 | 12.352 | 10.870 | −8.562 | 1.00 | 32.61 | | C |
| ANISOU | 750 | OE2 | GLU | A | 98 | 4130 | 4347 | 3912 | 73 | 16 | 196 | C |
| ATOM | 751 | C | GLU | A | 98 | 8.961 | 8.660 | −3.897 | 1.00 | 18.05 | | C |
| ANISOU | 751 | C | GLU | A | 98 | 2312 | 2540 | 2004 | 94 | −29 | 43 | C |
| ATOM | 752 | O | GLU | A | 98 | 8.144 | 9.493 | −3.479 | 1.00 | 18.60 | | O |
| ANISOU | 752 | O | GLU | A | 98 | 2386 | 2611 | 2071 | 117 | −40 | 36 | O |
| ATOM | 753 | N | TYR | A | 99 | 9.512 | 7.722 | −3.141 | 1.00 | 15.38 | | N |
| ANISOU | 753 | N | TYR | A | 99 | 1971 | 2205 | 1667 | 82 | −28 | 31 | N |
| ATOM | 754 | CA | TYR | A | 99 | 9.173 | 7.532 | −1.737 | 1.00 | 15.71 | | C |
| ANISOU | 754 | CA | TYR | A | 99 | 2012 | 2258 | 1700 | 94 | −36 | 14 | C |
| ATOM | 755 | CB | TYR | A | 99 | 8.596 | 6.129 | −1.509 | 1.00 | 14.33 | | C |
| ANISOU | 755 | CB | TYR | A | 99 | 1822 | 2114 | 1507 | 84 | −26 | 18 | C |
| ATOM | 756 | CG | TYR | A | 99 | 7.272 | 5.852 | −2.179 | 1.00 | 13.93 | | C |
| ANISOU | 756 | CG | TYR | A | 99 | 1761 | 2092 | 1441 | 86 | −22 | 28 | C |
| ATOM | 757 | CD1 | TYR | A | 99 | 6.089 | 5.824 | −1.433 | 1.00 | 14.41 | | C |
| ANISOU | 757 | CD1 | TYR | A | 99 | 1807 | 2183 | 1483 | 103 | −22 | 31 | C |
| ATOM | 758 | CE1 | TYR | A | 99 | 4.864 | 5.559 | −2.036 | 1.00 | 14.93 | | C |
| ANISOU | 758 | CE1 | TYR | A | 99 | 1857 | 2275 | 1539 | 103 | −21 | 41 | C |
| ATOM | 759 | CZ | TYR | A | 99 | 4.808 | 5.343 | −3.404 | 1.00 | 14.21 | | C |
| ANISOU | 759 | CZ | TYR | A | 99 | 1768 | 2178 | 1452 | 90 | −22 | 42 | C |
| ATOM | 760 | OH | TYR | A | 99 | 3.597 | 5.075 | −4.011 | 1.00 | 17.57 | | O |
| ANISOU | 760 | OH | TYR | A | 99 | 2177 | 2629 | 1869 | 92 | −26 | 47 | O |
| ATOM | 761 | CE2 | TYR | A | 99 | 5.967 | 5.376 | −4.173 | 1.00 | 14.75 | | C |
| ANISOU | 761 | CE2 | TYR | A | 99 | 1852 | 2221 | 1531 | 79 | −21 | 38 | C |
| ATOM | 762 | CD2 | TYR | A | 99 | 7.194 | 5.186 | −3.558 | 1.00 | 12.92 | | C |
| ANISOU | 762 | CD2 | TYR | A | 99 | 1638 | 1964 | 1313 | 75 | −19 | 34 | C |
| ATOM | 763 | C | TYR | A | 99 | 10.447 | 7.638 | −0.930 | 1.00 | 16.54 | | C |
| ANISOU | 763 | C | TYR | A | 99 | 2122 | 2338 | 1826 | 90 | −45 | 1 | C |
| ATOM | 764 | O | TYR | A | 99 | 11.303 | 6.754 | −1.023 | 1.00 | 16.93 | | O |
| ANISOU | 764 | O | TYR | A | 99 | 2168 | 2384 | 1181 | 69 | −37 | 4 | O |
| ATOM | 765 | N | LYS | A | 100 | 10.568 | 8.701 | −0.133 | 1.00 | 17.03 | | N |
| ANISOU | 765 | N | LYS | A | 100 | 2190 | 2380 | 1899 | 112 | −85 | −18 | N |
| ATOM | 766 | CA | LYS | A | 100 | 11.750 | 8.889 | 0.707 | 1.00 | 15.79 | | C |
| ANISOU | 766 | CA | LYS | A | 100 | 2037 | 2198 | 1766 | 112 | −81 | −37 | C |
| ATOM | 767 | CB | LYS | A | 100 | 11.828 | 10.332 | 1.220 | 1.00 | 16.78 | | C |
| ANISOU | 767 | CB | LYS | A | 100 | 2171 | 2290 | 1917 | 137 | −113 | −60 | C |
| ATOM | 768 | CG | LYS | A | 100 | 12.203 | 11.307 | 0.118 | 1.00 | 17.29 | | C |
| ANISOU | 768 | CG | LYS | A | 100 | 2236 | 2310 | 2022 | 121 | −118 | −38 | C |
| ATOM | 769 | CD | LYS | A | 100 | 12.165 | 12.774 | 0.542 | 1.00 | 22.28 | | C |
| ANISOU | 769 | CD | LYS | A | 100 | 2877 | 2898 | 2692 | 146 | −157 | −60 | C |
| ATOM | 770 | CE | LYS | A | 100 | 12.569 | 13.657 | −0.622 | 1.00 | 31.55 | | C |
| ANISOU | 770 | CE | LYS | A | 100 | 4047 | 4026 | 3913 | 124 | −159 | −23 | C |
| ATOM | 771 | NZ | LYS | A | 100 | 12.300 | 15.101 | 0.402 | 1.00 | 34.50 | | N |
| ANISOU | 771 | NZ | LYS | A | 100 | 4428 | 4351 | 4328 | 148 | −198 | −38 | N |
| ATOM | 772 | C | LYS | A | 100 | 11.768 | 7.198 | 1.878 | 1.00 | 16.90 | | C |
| ANISOU | 772 | C | LYS | A | 100 | 2172 | 2369 | 1880 | 121 | −78 | −49 | C |
| ATOM | 773 | O | LYS | A | 100 | 10.715 | 7.572 | 2.428 | 1.00 | 16.97 | | O |
| ANISOU | 773 | O | LYS | A | 100 | 2174 | 2417 | 1855 | 142 | −71 | −48 | O |
| ATOM | 774 | N | PHE | A | 101 | 12.964 | 7.459 | 2.238 | 1.00 | 16.47 | | N |
| ANISOU | 774 | N | PHE | A | 101 | 2117 | 2301 | 1841 | 108 | −81 | −56 | N |
| ATOM | 775 | CA | PHE | A | 101 | 13.143 | 6.686 | 3.459 | 1.00 | 16.24 | | C |
| ANISOU | 775 | CA | PHE | A | 101 | 2083 | 2299 | 1790 | 122 | −81 | −67 | C |
| ATOM | 776 | CB | PHE | A | 101 | 13.199 | 5.169 | 3.186 | 1.00 | 15.68 | | C |
| ANISOU | 776 | CB | PHE | A | 101 | 2003 | 2247 | 1708 | 97 | −58 | −42 | C |
| ATOM | 777 | CG | PHE | A | 101 | 14.400 | 4.732 | 2.370 | 1.00 | 15.68 | | C |
| ANISOU | 777 | CG | PHE | A | 101 | 1924 | 2138 | 1653 | 66 | −53 | −36 | C |
| ATOM | 778 | CD1 | PHE | A | 101 | 15.647 | 4.523 | 2.977 | 1.00 | 14.71 | | C |
| ANISOU | 778 | CD1 | PHE | A | 101 | 1881 | 2083 | 1624 | 63 | −61 | −49 | C |
| ATOM | 779 | CE1 | PHE | A | 101 | 16.758 | 4.122 | 2.222 | 1.00 | 13.56 | | C |
| ANISOU | 779 | CE1 | PHE | A | 101 | 1733 | 1919 | 1500 | 38 | −55 | −42 | C |
| ATOM | 780 | CZ | PHE | A | 101 | 16.628 | 3.910 | 0.844 | 1.00 | 13.38 | | C |
| ANISOU | 780 | CZ | PHE | A | 101 | 1709 | 1895 | 1480 | 20 | −40 | −23 | C |
| ATOM | 781 | CE2 | PHE | A | 101 | 15.391 | 4.096 | 0.232 | 1.00 | 13.22 | | C |
| ANISOU | 781 | CE2 | PHE | A | 101 | 1690 | 1886 | 1445 | 24 | −33 | −13 | C |
| ATOM | 782 | CD2 | PHE | A | 101 | 14.283 | 4.515 | 1.001 | 1.00 | 14.07 | | C |
| ANISOU | 782 | CD2 | PHE | A | 101 | 1801 | 2009 | 1537 | 44 | −40 | −19 | C |
| ATOM | 783 | C | PHE | A | 101 | 14.414 | 7.131 | 4.160 | 1.00 | 16.87 | | C |
| ANISOU | 783 | C | PHE | A | 101 | 2166 | 2351 | 1893 | 128 | −105 | −94 | C |
| ATOM | 784 | O | PHE | A | 101 | 15.822 | 7.713 | 3.544 | 1.00 | 16.54 | | O |
| ANISOU | 784 | O | PHE | A | 101 | 2126 | 2268 | 1892 | 108 | −115 | −94 | O |
| ATOM | 785 | N | GLY | A | 102 | 14.494 | 6.820 | 5.445 | 1.00 | 16.94 | | N |
| ANISOU | 785 | N | GLY | A | 102 | 2172 | 2387 | 1877 | 157 | −114 | −112 | N |
| ATOM | 786 | CA | GLY | A | 102 | 15.667 | 7.169 | 6.223 | 1.00 | 17.72 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 786 | CA | GLY | A | 102 | 2272 | 2465 | 1995 | 169 | −141 | −144 | C |
| ATOM | 787 | C | GLY | A | 102 | 15.610 | 6.437 | 7.533 | 1.00 | 17.63 | | C |
| ANISOU | 787 | C | GLY | A | 102 | 2256 | 2502 | 1942 | 202 | −140 | −153 | C |
| ATOM | 788 | O | GLY | A | 102 | 14.548 | 6.331 | 8.142 | 1.00 | 19.80 | | O |
| ANISOU | 788 | O | GLY | A | 102 | 2526 | 2823 | 2175 | 236 | −133 | −148 | O |
| ATOM | 789 | N | PHE | A | 103 | 16.737 | 5.877 | 7.932 | 1.00 | 17.58 | | N |
| ANISOU | 789 | N | PHE | A | 103 | 2246 | 2489 | 1944 | 194 | −145 | −159 | N |
| ATOM | 790 | CA | PHE | A | 103 | 16.890 | 5.187 | 9.186 | 1.00 | 18.92 | | C |
| ANISOU | 790 | CA | PHE | A | 103 | 2409 | 2703 | 2076 | 227 | −145 | −165 | C |
| ATOM | 791 | CB | PHE | A | 103 | 16.550 | 3.707 | 9.110 | 1.00 | 18.68 | | C |
| ANISOU | 791 | CB | PHE | A | 103 | 2371 | 2703 | 2024 | 209 | 109 | −117 | C |
| ATOM | 792 | CG | PHE | A | 103 | 17.253 | 2.961 | 8.042 | 1.00 | 19.41 | | C |
| ANISOU | 792 | CG | PHE | A | 103 | 2464 | 2761 | 2150 | 158 | −94 | −97 | C |
| ATOM | 793 | CD1 | PHE | A | 103 | 18.396 | 2.269 | 8.311 | 1.00 | 17.41 | | C |
| ANISOU | 793 | CD1 | PHE | A | 103 | 2209 | 2500 | 1905 | 149 | −96 | −99 | C |
| ATOM | 794 | CE1 | PHE | A | 103 | 19.006 | 1.591 | 7.332 | 1.00 | 19.78 | | C |
| ANISOU | 794 | CE1 | PHE | A | 103 | 2509 | 2774 | 2231 | 111 | −83 | −83 | C |
| ATOM | 795 | CZ | PHE | A | 103 | 18.493 | 1.562 | 6.107 | 1.00 | 18.51 | | C |
| ANISOU | 795 | CZ | PHE | A | 103 | 2351 | 2598 | 2084 | 83 | −69 | −66 | C |
| ATOM | 796 | CE2 | PHE | A | 103 | 17.342 | 2.189 | 5.839 | 1.00 | 20.60 | | C |
| ANISOU | 796 | CE2 | PHE | A | 103 | 2617 | 2871 | 2340 | 89 | −66 | −61 | C |
| ATOM | 797 | CD2 | PHE | A | 103 | 16.721 | 2.877 | 6.794 | 1.00 | 16.53 | | C |
| ANISOU | 797 | CD2 | PHE | A | 103 | 2102 | 2379 | 1802 | 125 | −78 | −75 | C |
| ATOM | 798 | C | PHE | A | 103 | 18.312 | 5.375 | 9.085 | 1.00 | 19.74 | | C |
| ANISOU | 798 | C | PHE | A | 103 | 2514 | 2783 | 2204 | 230 | −173 | −198 | C |
| ATOM | 799 | O | PHE | A | 103 | 19.176 | 5.672 | 8.938 | 1.00 | 20.07 | | O |
| ANISOU | 799 | O | PHE | A | 103 | 2556 | 2779 | 2292 | 195 | −181 | −201 | O |
| ATOM | 800 | N | GLU | A | 104 | 18.505 | 5.262 | 10.992 | 1.00 | 21.94 | | N |
| ANISOU | 800 | N | GLU | A | 104 | 2789 | 3099 | 2448 | 278 | −190 | −222 | N |
| ATOM | 801 | CA | GLU | A | 104 | 19.831 | 5.378 | 11.538 | 1.00 | 23.02 | | C |
| ANISOU | 801 | CA | GLU | A | 104 | 2924 | 3219 | 2605 | 285 | −219 | −256 | C |
| ATOM | 802 | C | GLU | A | 104 | 20.390 | 4.036 | 11.902 | 1.00 | 23.12 | | O |
| ANISOU | 802 | C | GLU | A | 104 | 2930 | 3259 | 2597 | 278 | −196 | −229 | C |
| ATOM | 803 | O | GLU | A | 104 | 19.693 | 3.182 | 12.267 | 1.00 | 24.06 | | O |
| ANISOU | 803 | O | GLU | A | 104 | 3044 | 3422 | 2675 | 292 | −169 | −194 | O |
| ATOM | 804 | CB | GLU | A | 104 | 19.882 | 6.423 | 12.651 | 1.00 | 20.96 | | C |
| ANISOU | 804 | CB | GLU | A | 104 | 2885 | 2969 | 2332 | 346 | −268 | −317 | C |
| ATOM | 805 | CG | GLU | A | 104 | 19.537 | 7.760 | 12.018 | 1.00 | 21.09 | | C |
| ANISOU | 805 | CG | GLU | A | 104 | 2688 | 2034 | 3300 | 338 | −295 | −342 | C |
| ATOM | 806 | CD | GLU | A | 104 | 19.609 | 9.000 | 12.860 | 1.00 | 21.63 | | C |
| ANISOU | 806 | CD | GLU | A | 104 | 2760 | 2991 | 2467 | 393 | −355 | −411 | C |
| ATOM | 807 | OE1 | GLU | A | 104 | 20.236 | 9.001 | 13.973 | 1.00 | 21.96 | | O |
| ANISOU | 807 | OE1 | GLU | A | 104 | 2799 | 3055 | 2492 | 436 | −388 | −454 | O |
| ATOM | 808 | OE2 | GLU | A | 104 | 19.051 | 10.013 | 12.382 | 1.00 | 21.75 | | O |
| ANISOU | 808 | OE2 | GLU | A | 104 | 2783 | 2971 | 2511 | 393 | −374 | −424 | O |
| ATOM | 809 | N | LEU | A | 105 | 21.673 | 3.866 | 11.682 | 1.00 | 19.45 | | N |
| ANISOU | 809 | N | LEU | A | 105 | 2461 | 2761 | 2167 | 253 | −207 | −239 | N |
| ATOM | 810 | CA | LEU | A | 105 | 22.328 | 2.614 | 12.033 | 1.00 | 18.82 | | C |
| ANISOU | 810 | CA | LEU | A | 105 | 2376 | 2703 | 2071 | 249 | −190 | −217 | C |
| ATOM | 811 | CB | LEU | A | 105 | 23.613 | 2.458 | 11.215 | 1.00 | 16.36 | | C |
| ANISOU | 811 | CB | LEU | A | 105 | 2062 | 2349 | 1812 | 204 | −192 | −218 | C |
| ATOM | 812 | CG | LEU | A | 105 | 23.368 | 2.240 | 9.175 | 1.00 | 16.08 | | C |
| ANISOU | 812 | CG | LEU | A | 105 | 2027 | 2282 | 1803 | 153 | −164 | −183 | C |
| ATOM | 813 | CD1 | LEU | A | 105 | 24.686 | 2.260 | 8.954 | 1.00 | 15.79 | | C |
| ANISOU | 813 | CD1 | LEU | A | 105 | 1980 | 2210 | 1811 | 118 | −168 | −184 | C |
| ATOM | 814 | CD2 | LEU | A | 105 | 22.619 | 0.933 | 9.471 | 1.00 | 19.84 | | C |
| ANISOU | 814 | CD2 | LEU | A | 105 | 2506 | 2782 | 2250 | 144 | −128 | −139 | C |
| ATOM | 815 | C | LEU | A | 105 | 22.636 | 2.568 | 13.540 | 1.00 | 19.16 | | C |
| ANISOU | 815 | C | LEU | A | 105 | 2414 | 2792 | 2073 | 300 | −213 | −246 | C |
| ATOM | 816 | O | LEU | A | 105 | 22.722 | 3.616 | 14.187 | 1.00 | 20.74 | | O |
| ANISOU | 816 | O | LEU | A | 105 | 2616 | 2994 | 2271 | 348 | −253 | −298 | O |
| ATOM | 817 | N | PRO | A | 106 | 22.785 | 1.356 | 14.105 | 1.00 | 19.87 | | N |
| ANISOU | 817 | N | PRO | A | 106 | 2499 | 2920 | 2129 | 322 | −192 | −214 | N |
| ATOM | 818 | CA | PRO | A | 106 | 23.080 | 1.243 | 15.543 | 1.00 | 21.30 | | C |
| ANISOU | 818 | CA | PRO | A | 106 | 2674 | 3155 | 2264 | 385 | −211 | −236 | C |
| ATOM | 819 | CB | PRO | A | 106 | 23.124 | −0.269 | 15.797 | 1.00 | 23.06 | | C |
| ANISOU | 819 | CB | PRO | A | 106 | 2891 | 3408 | 2463 | 381 | −176 | −178 | C |
| ATOM | 820 | CG | PRO | A | 106 | 23.117 | −0.920 | 14.482 | 1.00 | 21.30 | | C |
| ANISOU | 820 | CG | PRO | A | 106 | 2672 | 3136 | 2284 | 318 | −149 | −141 | C |
| ATOM | 821 | CD | PRO | A | 106 | 22.639 | 0.043 | 13.449 | 1.00 | 19.60 | | C |
| ANISOU | 821 | CD | PRO | A | 106 | 2465 | 2882 | 2102 | 282 | −152 | −157 | C |
| ATOM | 822 | C | PRO | A | 106 | 24.397 | 1.911 | 15.960 | 1.00 | 22.74 | | C |
| ANISOU | 822 | C | PRO | A | 106 | 2854 | 3314 | 2471 | 399 | −258 | −298 | C |
| ATOM | 823 | O | PRO | A | 106 | 25.307 | 2.084 | 15.131 | 1.00 | 20.42 | | O |
| ANISOU | 823 | O | PRO | A | 106 | 2559 | 2965 | 2235 | 351 | −266 | −307 | O |
| ATOM | 824 | N | GLN | A | 107 | 24.465 | 2.300 | 17.233 | 1.00 | 24.40 | | N |
| ANISOU | 824 | N | GLN | A | 107 | 3061 | 3572 | 2638 | 469 | −289 | −339 | N |
| ATOM | 825 | CA | GLN | A | 107 | 25.815 | 3.004 | 17.799 | 1.00 | 27.94 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 825 | CA | GLN | A | 107 | 3504 | 4003 | 3108 | 493 | −345 | −407 | C |
| ATOM | 826 | CB | GLN | A | 107 | 25.243 | 3.638 | 19.144 | 1.00 | 30.16 | | C |
| ANISOU | 826 | CB | GLN | A | 107 | 3784 | 4344 | 3331 | 584 | −383 | −460 | C |
| ATOM | 827 | CG | GLN | A | 107 | 24.231 | 4.774 | 19.045 | 1.00 | 37.77 | | C |
| ANISOU | 827 | CG | GLN | A | 107 | 4755 | 5300 | 4294 | 606 | −4.3 | −491 | C |
| ATOM | 828 | CD | GLN | A | 107 | 24.730 | 5.947 | 18.213 | 1.00 | 42.00 | | C |
| ANISOU | 828 | CD | GLN | A | 107 | 5295 | 5746 | 4917 | 561 | −444 | −535 | C |
| ATOM | 829 | OE1 | GLN | A | 107 | 25.007 | 6.358 | 18.317 | 1.00 | 49.29 | | O |
| ANISOU | 829 | OE1 | GLN | A | 107 | 6210 | 6629 | 5889 | 552 | −489 | −580 | O |
| ATOM | 830 | NE2 | GLN | A | 107 | 23.851 | 6.497 | 17.388 | 1.00 | 46.32 | | N |
| ANISOU | 830 | NE2 | GLN | A | 107 | 5851 | 6262 | 5487 | 533 | −431 | −518 | N |
| ATOM | 831 | C | GLN | A | 107 | 26.845 | 2.121 | 17.985 | 1.00 | 28.68 | | C |
| ANISOU | 831 | C | GLN | A | 107 | 3589 | 4097 | 3210 | 481 | −343 | −399 | C |
| ATOM | 832 | O | GLN | A | 107 | 27.979 | 2.607 | 17.941 | 1.00 | 30.56 | | O |
| ANISOU | 832 | O | GLN | A | 107 | 3819 | 4297 | 3494 | 469 | −381 | −443 | O |
| ATOM | 833 | N | GLY | A | 108 | 26.627 | 0.831 | 18.206 | 1.00 | 27.31 | | N |
| ANISOU | 833 | N | GLY | A | 108 | 3415 | 3965 | 2296 | 485 | −300 | −341 | N |
| ATOM | 834 | CA | GLY | A | 108 | 27.746 | −0.077 | 18.457 | 1.00 | 29.40 | | C |
| ANISOU | 834 | CA | GLY | A | 108 | 3673 | 4234 | 3263 | 482 | −298 | −331 | C |
| ATOM | 835 | C | GLY | A | 108 | 28.441 | −0.504 | 17.173 | 1.00 | 27.68 | | C |
| ANISOU | 835 | C | GLY | A | 108 | 3455 | 3955 | 3108 | 407 | −280 | −308 | C |
| ATOM | 836 | O | GLY | A | 108 | 28.165 | 0.053 | 16.098 | 1.00 | 28.67 | | O |
| ANISOU | 836 | O | GLY | A | 108 | 3584 | 4033 | 3276 | 359 | −274 | −305 | O |
| ATOM | 837 | N | PRO | A | 109 | 29.353 | −1.490 | 17.270 | 1.00 | 26.83 | | N |
| ANISOU | 837 | N | PRO | A | 109 | 3342 | 3852 | 3001 | 404 | −271 | −290 | N |
| ATOM | 838 | CA | PRO | A | 109 | 29.916 | −2.110 | 16.070 | 1.00 | 24.63 | | C |
| ANISOU | 838 | CA | PRO | A | 109 | 3063 | 3527 | 2768 | 340 | −248 | −262 | C |
| ATOM | 839 | CB | PRO | A | 109 | 30.682 | −3.313 | 15.628 | 1.00 | 25.25 | | C |
| ANISOU | 839 | CB | PRO | A | 109 | 3137 | 3631 | 2825 | 360 | −241 | −243 | C |
| ATOM | 840 | CG | PRO | A | 109 | 31.019 | −2.935 | 18.025 | 1.00 | 28.27 | | C |
| ANISOU | 840 | CG | PRO | A | 109 | 3513 | 4061 | 3168 | 425 | −275 | −282 | C |
| ATOM | 841 | CD | PRO | A | 109 | 29.906 | −2.067 | 18.510 | 1.00 | 27.15 | | C |
| ANISOU | 841 | CD | PRO | A | 109 | 3376 | 3945 | 2996 | 457 | −284 | −297 | C |
| ATOM | 842 | C | PRO | A | 109 | 28.796 | −2.575 | 15.130 | 1.00 | 22.07 | | C |
| ANISOU | 842 | C | PRO | A | 109 | 2750 | 3189 | 2448 | 304 | −207 | −211 | C |
| ATOM | 843 | O | PRO | A | 109 | 27.734 | −2.999 | 15.593 | 1.00 | 23.00 | | O |
| ANISOU | 843 | O | PRO | A | 109 | 2873 | 3340 | 2527 | 326 | −188 | −178 | C |
| ATOM | 844 | N | LEU | A | 110 | 29.024 | −2.471 | 13.825 | 1.00 | 19.90 | | N |
| ANISOU | 844 | N | LEU | A | 110 | 2475 | 2867 | 2218 | 252 | −196 | −205 | N |
| ATOM | 845 | CA | LEU | A | 110 | 28.003 | −2.850 | 12.841 | 1.00 | 17.33 | | C |
| ANISOU | 845 | CA | LEU | A | 110 | 2159 | 2526 | 1899 | 219 | −164 | −165 | C |
| ATOM | 846 | CB | LEU | A | 110 | 28.068 | −1.923 | 11.626 | 1.00 | 17.44 | | C |
| ANISOU | 846 | CB | LEU | A | 110 | 2172 | 2500 | 1956 | 178 | −164 | −165 | C |
| ATOM | 847 | CG | LEU | A | 110 | 27.170 | −0.474 | 11.960 | 1.00 | 19.52 | | C |
| ANISOU | 847 | CG | LEU | A | 110 | 2433 | 2757 | 2226 | 191 | −193 | −213 | C |
| ATOM | 848 | CD1 | LEU | A | 110 | 27.724 | 0.370 | 10.702 | 1.00 | 18.51 | | C |
| ANISOU | 848 | CD1 | LEU | A | 110 | 2302 | 2588 | 2144 | 149 | −191 | −212 | C |
| ATOM | 849 | CD2 | LEU | A | 110 | 28.350 | −0.421 | 12.082 | 1.00 | 18.44 | | C |
| ANISOU | 849 | CD2 | LEU | A | 110 | 2307 | 2656 | 2045 | 225 | −186 | −203 | C |
| ATOM | 850 | C | LEU | A | 110 | 28.102 | −4.309 | 12.398 | 1.00 | 18.09 | | C |
| ANISOU | 850 | C | LEU | A | 110 | 2259 | 2817 | 1997 | 202 | −139 | −125 | C |
| ATOM | 851 | O | LEU | A | 110 | 27.283 | −4.795 | 11.613 | 1.00 | 17.74 | | O |
| ANISOU | 851 | O | LEU | A | 110 | 2222 | 2558 | 1960 | 177 | −118 | −94 | O |
| ATOM | 852 | N | GLY | A | 111 | 29.112 | −5.003 | 12.896 | 1.00 | 20.89 | | N |
| ANISOU | 852 | N | GLY | A | 111 | 2609 | 2981 | 2347 | 218 | −147 | −128 | N |
| ATOM | 853 | CA | GLY | A | 111 | 29.279 | −6.408 | 12.586 | 1.00 | 20.77 | | C |
| ANISOU | 853 | CA | GLY | A | 111 | 2599 | 2957 | 2337 | 209 | −130 | −94 | C |
| ATOM | 854 | C | GLY | A | 111 | 30.677 | −6.860 | 12.923 | 1.00 | 22.26 | | C |
| ANISOU | 854 | C | GLY | A | 111 | 2779 | 8150 | 2529 | 224 | −144 | −111 | C |
| ATOM | 855 | O | GLY | A | 111 | 31.461 | −6.113 | 13.527 | 1.00 | 21.40 | | O |
| ANISOU | 855 | O | GLY | A | 111 | 2660 | 3055 | 2416 | 243 | −167 | −148 | O |
| ATOM | 856 | N | THR | A | 112 | 30.985 | −8.090 | 12.531 | 1.00 | 23.58 | | N |
| ANISOU | 856 | N | THR | A | 112 | 2950 | 3302 | 2705 | 217 | −134 | −88 | N |
| ATOM | 857 | CA | THR | A | 112 | 32.319 | −8.630 | 12.737 | 1.00 | 24.53 | | C |
| ANISOU | 857 | CA | THR | A | 112 | 3064 | 3426 | 2830 | 232 | −146 | −102 | C |
| ATOM | 858 | CB | THR | A | 112 | 32.315 | −9.862 | 13.685 | 1.00 | 24.33 | | C |
| ANISOU | 858 | CB | THR | A | 112 | 3043 | 3417 | 2784 | 264 | −144 | −68 | C |
| ATOM | 859 | OG1 | THR | A | 112 | 31.425 | −10.868 | 13.192 | 1.00 | 29.42 | | O |
| ANISOU | 859 | OG1 | THR | A | 112 | 3700 | 4036 | 3444 | 247 | −129 | −25 | O |
| ATOM | 860 | OG2 | THR | A | 112 | 31.872 | −9.465 | 15.080 | 1.00 | 26.35 | | O |
| ANISOU | 860 | OG2 | THR | A | 112 | 3295 | 3717 | 2999 | 303 | −149 | −61 | O |
| ATOM | 861 | C | THR | A | 112 | 32.971 | −8.966 | 11.404 | 1.00 | 25.02 | | C |
| ANISOU | 861 | C | THR | A | 112 | 3124 | 3460 | 2922 | 205 | −140 | −111 | C |
| ATOM | 862 | O | THR | A | 112 | 32.314 | −8.959 | 10.353 | 1.00 | 23.91 | | O |
| ANISOU | 862 | O | THR | A | 112 | 2990 | 3298 | 2797 | 178 | −127 | −102 | O |
| ATOM | 863 | N | SER | A | 113 | 34.274 | −9.222 | 11.453 | 1.00 | 26.50 | | N |
| ANISOU | 863 | N | SER | A | 113 | 3299 | 3653 | 3115 | 217 | −151 | −130 | N |
| ATOM | 864 | CA | SER | A | 113 | 35.017 | −9.675 | 10.287 | 1.00 | 27.90 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 864 | CA | SER | A | 113 | 3470 | 3816 | 3312 | 203 | −146 | −136 | C |
| ATOM | 865 | CB | SER | A | 113 | 35.714 | −8.500 | 9.598 | 1.00 | 29.26 | | C |
| ANISOU | 865 | CB | SER | A | 113 | 3620 | 3993 | 3504 | 182 | −147 | −160 | C |
| ATOM | 866 | OG | SER | A | 113 | 36.674 | −7.902 | 10.455 | 1.00 | 33.63 | | O |
| ANISOU | 866 | OG | SER | A | 113 | 4154 | 4565 | 4061 | 196 | −158 | −188 | O |
| ATOM | 867 | C | SER | A | 113 | 36.030 | −10.735 | 10.704 | 1.00 | 28.35 | | C |
| ANISOU | 867 | C | SER | A | 113 | 3525 | 3881 | 3364 | 231 | −155 | −138 | C |
| ATOM | 868 | O | SER | A | 113 | 36.548 | −10.702 | 11.818 | 1.00 | 26.81 | | O |
| ANISOU | 868 | O | SER | A | 113 | 3324 | 3708 | 3155 | 257 | −168 | −145 | O |
| ATOM | 869 | N | PHE | A | 114 | 36.288 | −11.682 | 9.807 | 1.00 | 29.97 | | N |
| ANISOU | 869 | N | PHE | A | 114 | 3736 | 4070 | 3580 | 232 | −150 | −135 | N |
| ATOM | 870 | CA | PHE | A | 114 | 37.235 | −12.761 | 10.065 | 1.00 | 30.88 | | C |
| ANISOU | 870 | CA | PHE | A | 114 | 3851 | 4189 | 3694 | 261 | −161 | −138 | C |
| ATOM | 871 | CB | PHE | A | 114 | 36.601 | −14.120 | 9.729 | 1.00 | 30.63 | | C |
| ANISOU | 871 | CB | PHE | A | 114 | 3842 | 4123 | 3672 | 268 | −163 | −116 | C |
| ATOM | 872 | CG | PHE | A | 114 | 37.540 | −15.295 | 9.865 | 1.00 | 29.22 | | C |
| ANISOU | 872 | CG | PHE | A | 114 | 3666 | 3939 | 3497 | 300 | −177 | −121 | C |
| ATOM | 873 | CD1 | PHE | A | 114 | 38.157 | −15.585 | 11.077 | 1.00 | 28.78 | | C |
| ANISOU | 873 | CD1 | PHE | A | 114 | 3605 | 3901 | 3427 | 328 | −186 | −112 | C |
| ATOM | 874 | CE1 | PHE | A | 114 | 39.022 | −16.673 | 11.204 | 1.00 | 27.15 | | C |
| ANISOU | 874 | CE1 | PHE | A | 114 | 3402 | 3690 | 3225 | 360 | −200 | −115 | C |
| ATOM | 875 | CZ | PHE | A | 114 | 39.255 | −17.502 | 10.112 | 1.00 | 28.25 | | C |
| ANISOU | 875 | CZ | PHE | A | 114 | 3549 | 3803 | 3382 | 367 | −208 | −130 | C |
| ATOM | 876 | CE2 | PHE | A | 114 | 38.629 | −17.230 | 8.897 | 1.00 | 26.78 | | C |
| ANISOU | 876 | CE2 | PHE | A | 114 | 3367 | 3602 | 3207 | 343 | −200 | −143 | C |
| ATOM | 877 | CD2 | PHE | A | 114 | 37.771 | −16.133 | 8.783 | 1.00 | 29.02 | | C |
| ANISOU | 877 | CD2 | PHE | A | 114 | 3647 | 3892 | 3486 | 308 | 184 | 135 | C |
| ATOM | 878 | C | PHE | A | 114 | 38.497 | −12.526 | 9.246 | 1.00 | 32.98 | | C |
| ANISOU | 878 | C | PHE | A | 114 | 4094 | 4472 | 3968 | 263 | −161 | −164 | C |
| ATOM | 879 | O | PHE | A | 114 | 38.433 | −12.359 | 8.024 | 1.00 | 33.06 | | O |
| ANISOU | 879 | O | PHE | A | 114 | 4099 | 4478 | 3984 | 248 | −150 | −170 | O |
| ATOM | 880 | N | LYS | A | 115 | 39.637 | −12.499 | 9.942 | 1.00 | 36.23 | | N |
| ANISOU | 880 | N | LYS | A | 115 | 4487 | 4907 | 4372 | 284 | −173 | −178 | N |
| ATOM | 881 | CA | LYS | A | 115 | 40.962 | −12.243 | 9.347 | 1.00 | 39.29 | | C |
| ANISOU | 881 | CA | LYS | A | 115 | 4843 | 5319 | 4767 | 289 | −174 | −199 | C |
| ATOM | 882 | CB | LYS | A | 115 | 41.500 | −13.483 | 8.515 | 1.00 | 39.97 | | C |
| ANISOU | 882 | CB | LYS | A | 115 | 4935 | 5404 | 4850 | 315 | −173 | −203 | C |
| ATOM | 883 | CG | LYS | A | 115 | 41.652 | −14.724 | 9.494 | 1.00 | 42.17 | | C |
| ANISOU | 883 | CG | LYS | A | 115 | 5233 | 5670 | 5119 | 350 | −189 | −197 | C |
| ATOM | 884 | CD | LYS | A | 115 | 42.605 | −15.754 | 8.896 | 1.00 | 44.83 | | C |
| ANISOU | 884 | CD | LYS | A | 115 | 5565 | 6013 | 5454 | 384 | −196 | −212 | C |
| ATOM | 885 | CE | LYS | A | 115 | 42.035 | −16.445 | 7.665 | 1.00 | 47.11 | | C |
| ANISOU | 885 | CE | LYS | A | 115 | 5873 | 6277 | 5750 | 387 | −194 | −216 | C |
| ATOM | 886 | NZ | LYS | A | 115 | 42.245 | −15.647 | 6.423 | 1.00 | 52.92 | | N |
| ANISOU | 886 | NZ | LYS | A | 115 | 6585 | 7040 | 6481 | 372 | −175 | −228 | N |
| ATOM | 887 | C | LYS | A | 115 | 41.001 | −11.015 | 8.430 | 1.00 | 40.18 | | C |
| ANISOU | 887 | C | LYS | A | 115 | 4930 | 5439 | 4896 | 255 | −161 | −201 | C |
| ATOM | 888 | O | LYS | A | 115 | 41.734 | −11.002 | 7.436 | 1.00 | 42.29 | | O |
| ANISOU | 888 | O | LYS | A | 115 | 5175 | 5725 | 5169 | 255 | −151 | −204 | O |
| ATOM | 889 | N | GLY | A | 116 | 40.212 | −9.996 | 8.771 | 1.00 | 41.02 | | N |
| ANISOU | 889 | N | GLY | A | 116 | 5041 | 5535 | 5011 | 230 | −162 | −198 | N |
| ATOM | 890 | CA | GLY | A | 116 | 40.135 | −8.747 | 8.000 | 1.00 | 41.75 | | C |
| ANISOU | 890 | CA | GLY | A | 116 | 5111 | 5627 | 5125 | 196 | −152 | −194 | C |
| ATOM | 891 | C | GLY | A | 116 | 39.952 | −8.968 | 6.511 | 1.00 | 41.97 | | C |
| ANISOU | 891 | C | GLY | A | 116 | 5136 | 5658 | 5151 | 187 | −129 | −181 | C |
| ATOM | 892 | O | GLY | A | 116 | 40.610 | −8.320 | 5.696 | 1.00 | 43.05 | | O |
| ANISOU | 892 | O | GLY | A | 116 | 5240 | 5814 | 5303 | 174 | −118 | −173 | O |
| ATOM | 893 | N | LYS | A | 117 | 39.055 | −9.887 | 6.159 | 1.00 | 41.58 | | N |
| ANISOU | 893 | N | LYS | A | 117 | 5121 | 5592 | 5085 | 197 | −123 | −176 | N |
| ATOM | 894 | CA | LYS | A | 117 | 38.894 | −10.341 | 4.780 | 1.00 | 41.03 | | C |
| ANISOU | 894 | CA | LYS | A | 117 | 5053 | 5528 | 5008 | 202 | −107 | −173 | C |
| ATOM | 895 | CB | LYS | A | 117 | 39.888 | −11.476 | 4.495 | 1.00 | 41.75 | | C |
| ANISOU | 895 | CB | LYS | A | 117 | 5141 | 5639 | 5088 | 240 | −113 | −187 | C |
| ATOM | 896 | CG | LYS | A | 117 | 39.938 | −11.971 | 3.056 | 1.00 | 43.68 | | C |
| ANISOU | 896 | CG | LYS | A | 117 | 5382 | 5900 | 5316 | 260 | −102 | −193 | C |
| ATOM | 897 | CD | LYS | A | 117 | 40.841 | −13.196 | 2.951 | 1.00 | 45.10 | | C |
| ANISOU | 897 | CD | LYS | A | 117 | 5561 | 6092 | 5482 | 306 | −115 | −214 | C |
| ATOM | 898 | CE | LYS | A | 117 | 41.033 | −13.645 | 1.514 | 1.00 | 51.12 | | C |
| ANISOU | 898 | CE | LYS | A | 117 | 6317 | 6884 | 6223 | 338 | −107 | −227 | C |
| ATOM | 899 | NZ | LYS | A | 117 | 38.803 | −14.260 | 0.935 | 1.00 | 52.33 | | N |
| ANISOU | 899 | NZ | LYS | A | 117 | 6506 | 7002 | 6374 | 342 | −118 | −240 | N |
| ATOM | 900 | C | LYS | A | 117 | 37.463 | −10.811 | 4.529 | 1.00 | 39.51 | | C |
| ANISOU | 900 | C | LYS | A | 117 | 4896 | 5304 | 4809 | 196 | −107 | −167 | C |
| ATOM | 901 | O | LYS | A | 117 | 36.879 | −10.509 | 3.487 | 1.00 | 40.34 | | O |
| ANISOU | 901 | O | LYS | A | 117 | 5003 | 5411 | 4912 | 186 | −94 | −163 | O |
| ATOM | 902 | N | TYR | A | 118 | 36.905 | −11.546 | 5.489 | 1.00 | 36.68 | | N |
| ANISOU | 902 | N | TYR | A | 118 | 4564 | 4922 | 4452 | 204 | −120 | −164 | N |
| ATOM | 903 | CA | TYR | A | 118 | 35.548 | −12.070 | 5.385 | 1.00 | 34.97 | | C |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 903 | CA | TYR | A | 118 | 4376 | 4673 | 4238 | 196 | −122 | −152 | C |
| ATOM | 904 | CB | TYR | A | 118 | 35.507 | −13.553 | 5.779 | 1.00 | 34.43 | | C |
| ANISOU | 904 | CB | TYR | A | 118 | 4327 | 4580 | 4176 | 220 | −140 | −150 | C |
| ATOM | 905 | CG | TYR | A | 118 | 36.444 | −14.452 | 4.998 | 1.00 | 34.15 | | C |
| ANISOU | 905 | CG | TYR | A | 118 | 4288 | 4549 | 4138 | 251 | −150 | −174 | C |
| ATOM | 906 | CD1 | TYR | A | 118 | 36.087 | −14.941 | 3.738 | 1.00 | 34.12 | | C |
| ANISOU | 906 | CD1 | TYR | A | 118 | 4293 | 4536 | 4136 | 260 | −155 | −191 | C |
| ATOM | 907 | CE1 | TYR | A | 118 | 36.940 | −15.773 | 3.020 | 1.00 | 32.66 | | C |
| ANISOU | 907 | CE1 | TYR | A | 118 | 4105 | 4361 | 3945 | 298 | −167 | −218 | C |
| ATOM | 908 | CZ | TYR | A | 118 | 38.165 | −16.129 | 3.561 | 1.00 | 33.92 | | C |
| ANISOU | 908 | CZ | TYR | A | 118 | 4252 | 4538 | 4097 | 324 | −172 | −225 | C |
| ATOM | 909 | OH | TYR | A | 118 | 39.012 | −16.954 | 2.851 | 1.00 | 37.83 | | O |
| ANISOU | 909 | OH | TYR | A | 118 | 4744 | 5048 | 4583 | 368 | −185 | −255 | O |
| ATOM | 910 | CE2 | TYR | A | 118 | 38.542 | −15.662 | 4.812 | 1.00 | 31.94 | | C |
| ANISOU | 910 | CE2 | TYR | A | 118 | 3992 | 4296 | 3847 | 312 | −167 | −207 | C |
| ATOM | 911 | CD2 | TYR | A | 118 | 37.679 | −14.830 | 5.523 | 1.00 | 31.31 | | C |
| ANISOU | 911 | CD2 | TYR | A | 118 | 3917 | 4207 | 3773 | 277 | −157 | −183 | C |
| ATOM | 912 | C | TYR | A | 118 | 34.628 | −11.278 | 6.305 | 1.00 | 34.20 | | C |
| ANISOU | 912 | C | TYR | A | 118 | 4285 | 4570 | 4141 | 175 | −119 | −135 | C |
| ATOM | 913 | O | TYR | A | 118 | 34.696 | −11.424 | 7.528 | 1.00 | 34.64 | | O |
| ANISOU | 913 | O | TYR | A | 118 | 4343 | 4627 | 4191 | 185 | −127 | −127 | O |
| ATOM | 914 | N | GLY | A | 119 | 33.789 | −10.428 | 5.721 | 1.00 | 33.08 | | N |
| ANISOU | 914 | N | GLY | A | 119 | 4143 | 4424 | 4001 | 150 | −108 | −130 | N |
| ATOM | 915 | CA | GLY | A | 119 | 32.771 | −9.700 | 6.485 | 1.00 | 31.86 | | C |
| ANISOU | 915 | CA | GLY | A | 119 | 3996 | 4265 | 3844 | 136 | −106 | −116 | C |
| ATOM | 916 | C | GLY | A | 119 | 31.666 | −10.641 | 6.931 | 1.00 | 31.26 | | C |
| ANISOU | 916 | C | GLY | A | 119 | 3940 | 4169 | 3769 | 138 | −109 | −94 | C |
| ATOM | 917 | O | GLY | A | 119 | 31.179 | −11.451 | 6.139 | 1.00 | 33.35 | | O |
| ANISOU | 917 | O | GLY | A | 119 | 4215 | 4412 | 4045 | 135 | −112 | −91 | O |
| ATOM | 918 | N | CYS | A | 120 | 31.279 | −10.540 | 8.200 | 1.00 | 27.91 | | N |
| ANISOU | 918 | N | CYS | A | 120 | 3518 | 3753 | 3334 | 147 | −111 | −77 | N |
| ATOM | 919 | CA | CYS | A | 120 | 30.325 | −11.479 | 8.806 | 1.00 | 27.80 | | C |
| ANISOU | 919 | CA | CYS | A | 120 | 3514 | 3725 | 3322 | 151 | −113 | −42 | C |
| ATOM | 920 | CB | CYS | A | 120 | 30.723 | −11.778 | 10.252 | 1.00 | 28.82 | | C |
| ANISOU | 920 | CB | CYS | A | 120 | 3640 | 3876 | 3434 | 179 | −118 | −25 | C |
| ATOM | 921 | SG | CYS | A | 120 | 32.293 | −12.608 | 10.439 | 1.00 | 33.12 | | S |
| ANISOU | 921 | SG | CYS | A | 120 | 4182 | 4422 | 3981 | 205 | −131 | −42 | S |
| ATOM | 922 | C | CYS | A | 120 | 28.905 | −10.954 | 8.813 | 1.00 | 25.26 | | C |
| ANISOU | 922 | C | CYS | A | 120 | 3195 | 3403 | 2998 | 133 | −103 | −21 | C |
| ATOM | 923 | O | CYS | A | 120 | 28.052 | −11.474 | 9.533 | 1.00 | 24.91 | | O |
| ANISOU | 923 | O | CYS | A | 120 | 3152 | 3360 | 2953 | 137 | −100 | 16 | O |
| ATOM | 924 | N | VAL | A | 121 | 28.651 | −9.911 | 8.032 | 1.00 | 24.46 | | N |
| ANISOU | 924 | N | VAL | A | 121 | 3092 | 3305 | 2897 | 115 | −96 | −41 | N |
| ATOM | 925 | CA | VAL | A | 121 | 27.342 | −9.276 | 8.042 | 1.00 | 23.10 | | C |
| ANISOU | 925 | CA | VAL | A | 121 | 2922 | 3137 | 2719 | 102 | −87 | −26 | C |
| ATOM | 926 | CB | VAL | A | 121 | 27.307 | −8.110 | 9.087 | 1.00 | 23.95 | | C |
| ANISOU | 926 | CB | VAL | A | 121 | 3023 | 3274 | 2802 | 117 | −87 | −33 | C |
| ATOM | 927 | CG1 | VAL | A | 121 | 28.159 | −6.915 | 8.636 | 1.00 | 25.86 | | C |
| ANISOU | 927 | CG1 | VAL | A | 121 | 3258 | 3518 | 3050 | 110 | −92 | −70 | C |
| ATOM | 928 | CG2 | VAL | A | 121 | 25.886 | −7.705 | 9.433 | 1.00 | 26.49 | | C |
| ANISOU | 928 | CG2 | VAL | A | 121 | 3346 | 3609 | 3112 | 115 | −78 | −10 | C |
| ATOM | 929 | C | VAL | A | 121 | 26.937 | −8.827 | 6.632 | 1.00 | 21.70 | | C |
| ANISOU | 929 | C | VAL | A | 121 | 2746 | 2944 | 2553 | 79 | −82 | −40 | C |
| ATOM | 930 | O | VAL | A | 121 | 27.792 | −8.468 | 5.808 | 1.00 | 22.78 | | O |
| ANISOU | 930 | O | VAL | A | 121 | 2879 | 3082 | 2604 | 76 | −81 | −63 | O |
| ATOM | 931 | N | ASP | A | 122 | 25.635 | −8.891 | 6.358 | 1.00 | 18.08 | | N |
| ANISOU | 931 | N | ASP | A | 122 | 2419 | 2605 | 2226 | 65 | −77 | −21 | N |
| ATOM | 932 | CA | ASP | A | 122 | 25.061 | −8.367 | 5.115 | 1.00 | 18.63 | | C |
| ANISOU | 932 | CA | ASP | A | 122 | 2364 | 2540 | 2174 | 48 | −72 | −32 | C |
| ATOM | 933 | CB | ASP | A | 122 | 24.420 | −9.487 | 4.301 | 1.00 | 18.92 | | C |
| ANISOU | 933 | CB | ASP | A | 122 | 2405 | 2551 | 2231 | 40 | −82 | −27 | C |
| ATOM | 934 | CG | ASP | A | 122 | 25.442 | −10.339 | 3.564 | 1.00 | 27.60 | | C |
| ANISOU | 934 | CG | ASP | A | 122 | 3508 | 3637 | 3340 | 51 | −94 | −50 | C |
| ATOM | 935 | OD1 | ASP | A | 122 | 26.423 | −9.783 | 3.010 | 1.00 | 35.84 | | O |
| ANISOU | 935 | OD1 | ASP | A | 122 | 4548 | 4698 | 4372 | 59 | −88 | −73 | O |
| ATOM | 936 | OD2 | ASP | A | 122 | 25.253 | −11.572 | 3.524 | 1.00 | 35.31 | | O |
| ANISOU | 936 | OD2 | ASP | A | 122 | 4490 | 4586 | 4340 | 54 | −112 | −45 | O |
| ATOM | 937 | C | ASP | A | 122 | 24.005 | −7.314 | 5.422 | 1.00 | 15.86 | | C |
| ANISOU | 937 | C | ASP | A | 122 | 2010 | 2203 | 1811 | 41 | −64 | −22 | C |
| ATOM | 938 | O | ASP | A | 122 | 23.055 | −7.591 | 6.159 | 1.00 | 18.30 | | O |
| ANISOU | 938 | O | ASP | A | 122 | 2318 | 2519 | 2117 | 44 | −61 | 5 | O |
| ATOM | 939 | N | TYR | A | 123 | 24.185 | −6.109 | 4.874 | 1.00 | 12.94 | | N |
| ANISOU | 939 | N | TYR | A | 123 | 1640 | 1841 | 1438 | 36 | −59 | −39 | N |
| ATOM | 940 | CA | TYR | A | 123 | 23.205 | −5.035 | 4.994 | 1.00 | 12.39 | | C |
| ANISOU | 940 | CA | TYR | A | 123 | 1569 | 1779 | 1358 | 32 | −54 | −35 | C |
| ATOM | 941 | CB | TYR | A | 123 | 23.869 | −3.759 | 5.505 | 1.00 | 13.03 | | C |
| ANISOU | 941 | CB | TYR | A | 123 | 1645 | 1868 | 1436 | 40 | −59 | −54 | C |
| ATOM | 942 | CG | TYR | A | 123 | 24.159 | −3.754 | 6.987 | 1.00 | 13.59 | | C |

TABLE 9-continued

Atomic coordinates for N-TXNIP(K5A/K6A) protein (SEQ ID NO: 8)

| ANISOU | 942 | CG | TYR | A | 123 | 1714 | 1956 | 1493 | 65 | −69 | −58 | C |
|---|---|---|---|---|---|---|---|---|---|---|---|---|
| ATOM | 943 | CD1 | TYR | A | 123 | 25.319 | −4.339 | 7.493 | 1.00 | 17.75 | | C |
| ANISOU | 943 | CD1 | TYR | A | 123 | 2238 | 2486 | 2021 | 76 | −77 | −66 | C |
| ATOM | 944 | CE1 | TYR | A | 123 | 25.595 | −4.315 | 8.860 | 1.00 | 14.98 | | C |
| ANISOU | 944 | CE1 | TYR | A | 123 | 1884 | 2156 | 1651 | 104 | −87 | −72 | C |
| ATOM | 945 | CZ | TYR | A | 123 | 24.697 | −3.708 | 9.731 | 1.00 | 13.73 | | C |
| ANISOU | 945 | CZ | TYR | A | 123 | 1726 | 2022 | 1469 | 126 | −90 | −70 | C |
| ATOM | 946 | OH | TYR | A | 123 | 24.949 | −3.683 | 11.076 | 1.00 | 16.89 | | O |
| ANISOU | 946 | OH | TYR | A | 123 | 2122 | 2453 | 1842 | 164 | −102 | −77 | O |
| ATOM | 947 | CE2 | TYR | A | 123 | 23.546 | −3.110 | 9.249 | 1.00 | 16.43 | | C |
| ANISOU | 947 | CE2 | TYR | A | 123 | 2071 | 2362 | 1810 | 116 | −82 | −62 | C |
| ATOM | 948 | CD2 | TYR | A | 123 | 23.281 | −3.137 | 7.884 | 1.00 | 11.68 | | C |
| ANISOU | 948 | CD2 | TYR | A | 123 | 1473 | 1734 | 1230 | 84 | −72 | −56 | C |
| ATOM | 949 | C | TYR | A | 123 | 22.524 | −4.745 | 3.658 | 1.00 | 13.00 | | C |
| ANISOU | 949 | C | TYR | A | 123 | 1649 | 1849 | 1442 | 16 | −48 | −36 | C |
| ATOM | 950 | O | TYR | A | 123 | 23.171 | −4.681 | 2.604 | 1.00 | 12.65 | | O |
| ANISOU | 950 | O | TYR | A | 123 | 1604 | 1801 | 1403 | 12 | −45 | −47 | O |
| ATOM | 951 | N | TRP | A | 124 | 21.216 | −4.540 | 3.718 | 1.00 | 11.37 | | N |
| ANISOU | 951 | N | TRP | A | 124 | 1443 | 1646 | 1229 | 12 | −44 | −22 | N |
| ATOM | 952 | CA | TRP | A | 124 | 20.440 | −4.295 | 2.510 | 1.00 | 11.56 | | C |
| ANISOU | 952 | CA | TRP | A | 124 | 1469 | 1666 | 1256 | 1 | −40 | −22 | C |
| ATOM | 953 | CB | TRP | A | 124 | 20.224 | −5.589 | 1.712 | 1.00 | 12.88 | | C |
| ANISOU | 953 | CB | TRP | A | 124 | 1638 | 1820 | 1437 | −5 | −48 | −23 | C |
| ATOM | 954 | CG | TRP | A | 124 | 19.828 | −6.824 | 2.500 | 1.00 | 13.33 | | C |
| ANISOU | 954 | CG | TRP | A | 124 | 1692 | 1865 | 1508 | −7 | −58 | −3 | C |
| ATOM | 955 | CD1 | TRP | A | 124 | 20.619 | −7.908 | 2.760 | 1.00 | 15.81 | | C |
| ANISOU | 955 | CD1 | TRP | A | 124 | 2007 | 2163 | 1836 | −2 | −68 | −5 | C |
| ATOM | 956 | NE1 | TRP | A | 124 | 19.914 | −8.856 | 3.456 | 1.00 | 17.07 | | N |
| ANISOU | 956 | NE1 | TRP | A | 124 | 2160 | 2311 | 2015 | −8 | −75 | 26 | N |
| ATOM | 957 | CE2 | TRP | A | 124 | 18.635 | −8.402 | 3.664 | 1.00 | 17.54 | | C |
| ANISOU | 957 | CE2 | TRP | A | 124 | 2210 | 2383 | 2071 | −17 | −68 | 48 | C |
| ATOM | 958 | CD2 | TRP | A | 124 | 18.539 | −7.125 | 3.061 | 1.00 | 16.74 | | C |
| ANISOU | 958 | CD2 | TRP | A | 124 | 2114 | 2299 | 1947 | −15 | −58 | 27 | C |
| ATOM | 959 | CE3 | TRP | A | 124 | 17.322 | −6.435 | 3.132 | 1.00 | 14.75 | | C |
| ANISOU | 959 | CE3 | TRP | A | 124 | 1656 | 2084 | 1686 | −19 | −50 | 41 | C |
| ATOM | 960 | CZ3 | TRP | A | 124 | 16.250 | −7.031 | 3.802 | 1.00 | 15.44 | | C |
| ANISOU | 960 | Cz3 | TRP | A | 124 | 1926 | 2155 | 1784 | −25 | −50 | 79 | C |
| ATOM | 961 | CH2 | TRP | A | 124 | 16.370 | −8.310 | 4.376 | 1.00 | 18.85 | | C |
| ANISOU | 961 | CH2 | TRP | A | 124 | 2350 | 2571 | 2242 | −30 | −58 | 107 | C |
| ATOM | 962 | CZ2 | TRP | A | 124 | 17.555 | −9.003 | 4.334 | 1.00 | 17.24 | | C |
| ANISOU | 962 | CZ2 | TRP | A | 124 | 2157 | 2346 | 2050 | −25 | −68 | 91 | C |
| ATOM | 963 | C | TRP | A | 124 | 19.125 | −3.617 | 2.807 | 1.00 | 12.26 | | C |
| ANISOU | 963 | C | TRP | A | 124 | 1556 | 1766 | 1335 | 1 | −36 | −10 | C |
| ATOM | 964 | O | TRP | A | 124 | 18.673 | −3.579 | 3.962 | 1.00 | 12.08 | | O |
| ANISOU | 964 | O | TRP | A | 124 | 1529 | 1758 | 1302 | 11 | −35 | 4 | O |
| ATOM | 965 | N | VAL | A | 125 | 18.540 | −3.056 | 1.752 | 1.00 | 11.91 | | N |
| ANISOU | 965 | N | VAL | A | 125 | 1514 | 1722 | 1290 | −6 | −33 | −13 | N |
| ATOM | 966 | CA | VAL | A | 125 | 17.182 | −2.539 | 1.781 | 1.00 | 10.71 | | C |
| ANISOU | 966 | CA | VAL | A | 125 | 1359 | 1581 | 1130 | −6 | −30 | −2 | C |
| ATOM | 967 | CB | VAL | A | 125 | 17.146 | −1.022 | 1.488 | 1.00 | 9.25 | | C |
| ANISOU | 967 | CG | VAL | A | 125 | 1177 | 1398 | 938 | −1 | −26 | −10 | C |
| ATOM | 968 | CG1 | VAL | A | 125 | 15.706 | −0.513 | 1.444 | 1.0 | 14.24 | | C |
| ANISOU | 968 | CG1 | VAL | A | 125 | 1807 | 2045 | 1560 | 3 | −24 | 0 | C |
| ATOM | 969 | CG2 | VAL | A | 125 | 17.950 | −0.262 | 2.538 | 1.00 | 13.57 | | C |
| ANISOU | 969 | CG2 | VAL | A | 125 | 1725 | 1945 | 1485 | 12 | −32 | −21 | C |
| ATOM | 970 | C | VAL | A | 125 | 16.377 | −3.275 | 0.725 | 1.00 | 12.42 | | C |
| ANISOU | 970 | C | VAL | A | 125 | 1572 | 1792 | 1354 | −17 | −34 | 2 | C |
| ATOM | 971 | O | VAL | A | 125 | 16.791 | −3.358 | −0.432 | 1.00 | 13.66 | | O |
| ANISOU | 971 | O | VAL | A | 125 | 1733 | 1944 | 1513 | −19 | −36 | −13 | O |
| ATOM | 972 | N | LYS | A | 126 | 15.256 | −3.845 | 1.148 | 1.00 | 12.64 | | N |
| ANISOU | 972 | N | LYS | A | 126 | 1591 | 1825 | 1388 | −23 | −37 | 21 | N |
| ATOM | 973 | CA | LYS | A | 126 | 14.258 | −4.378 | 0.233 | 1.00 | 12.33 | | C |
| ANISOU | 973 | CA | LYS | A | 126 | 1544 | 1779 | 1361 | −34 | −47 | 23 | C |
| ATOM | 974 | CB | LYS | A | 126 | 13.782 | −5.754 | 0.701 | 1.00 | 11.84 | | C |
| ANISOU | 974 | CB | LYS | A | 126 | 1468 | 1702 | 1328 | −47 | −60 | 44 | C |
| ATOM | 975 | CG | LYS | A | 126 | 14.795 | −6.875 | 0.554 | 1.00 | 15.71 | | C |
| ANISOU | 975 | CG | LYS | A | 126 | 1964 | 2164 | 1840 | −49 | −74 | 32 | C |
| ATOM | 976 | CD | LYS | A | 126 | 14.282 | −8.167 | 1.163 | 1.00 | 17.48 | | C |
| ANISOU | 976 | CD | LYS | A | 126 | 2173 | 2367 | 2103 | −63 | −89 | 62 | C |
| ATOM | 977 | CE | LYS | A | 126 | 15.301 | −9.285 | 1.006 | 1.00 | 18.43 | | C |
| ANISOU | 977 | CE | LYS | A | 126 | 2301 | 2455 | 2247 | −62 | −108 | 46 | C |
| ATOM | 978 | NZ | LYS | A | 126 | 14.900 | −10.558 | 1.686 | 1.00 | 26.13 | | N |
| ANISOU | 978 | NZ | LYS | A | 126 | 3259 | 3400 | 3268 | −76 | −125 | 83 | N |
| ATOM | 979 | C | LYS | A | 126 | 13.069 | −3.435 | 0.197 | 1.00 | 12.87 | | C |
| ANISOU | 979 | C | LYS | A | 126 | 1607 | 1869 | 1415 | −30 | −39 | 32 | C |
| ATOM | 980 | O | LYS | A | 126 | 12.720 | −2.832 | 1.210 | 1.00 | 13.54 | | O |
| ANISOU | 980 | O | LYS | A | 126 | 1687 | 1973 | 1485 | −20 | −29 | 47 | O |
| ATOM | 981 | N | ALA | A | 127 | 12.449 | −3.297 | −0.965 | 1.00 | 12.72 | | N |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 981 | N | ALA | A | 127 | 1587 | 1850 | 1396 | −33 | −45 | 22 | N |
| ATOM | 982 | CA | ALA | A | 127 | 11.186 | −2.589 | −1.039 | 1.00 | 14.13 | | C |
| ANISOU | 982 | CA | ALA | A | 127 | 1756 | 2048 | 1563 | −30 | −41 | 32 | C |
| ATOM | 983 | CB | ALA | A | 127 | 11.335 | −1.271 | −1.778 | 1.00 | 13.83 | | C |
| ANISOU | 983 | CB | ALA | A | 127 | 1732 | 2019 | 1504 | −17 | −33 | 19 | C |
| ATOM | 984 | C | ALA | A | 127 | 10.162 | −3.486 | −1.707 | 1.00 | 14.15 | | C |
| ANISOU | 984 | C | ALA | A | 127 | 1744 | 2046 | 1588 | −43 | −59 | 35 | C |
| ATOM | 985 | O | ALA | A | 127 | 10.519 | −4.376 | −2.487 | 1.00 | 14.10 | | O |
| ANISOU | 985 | O | ALA | A | 127 | 1740 | 2019 | 1600 | −49 | −78 | 15 | O |
| ATOM | 986 | N | PHE | A | 128 | 8.895 | −3.246 | −1.375 | 1.00 | 14.70 | | N |
| ANISOU | 986 | N | PHE | A | 128 | 1795 | 2134 | 1656 | −45 | −56 | 56 | N |
| ATOM | 987 | CA | PHE | A | 128 | 7.784 | −4.076 | −1.799 | 1.00 | 14.62 | | C |
| ANISOU | 987 | CA | PHE | A | 128 | 1761 | 2119 | 1675 | −61 | −76 | 65 | C |
| ATOM | 988 | CB | PHE | A | 128 | 7.252 | −4.866 | −0.598 | 1.00 | 15.43 | | C |
| ANISOU | 988 | CB | PHE | A | 128 | 1836 | 2224 | 1803 | −76 | −74 | 109 | C |
| ATOM | 989 | CG | PHE | A | 128 | 8.287 | −5.755 | 0.031 | 1.00 | 17.61 | | C |
| ANISOU | 989 | CG | PHE | A | 128 | 2117 | 2474 | 2098 | −83 | −76 | 117 | C |
| ATOM | 990 | CD1 | PHE | A | 128 | 8.534 | −7.022 | −0.484 | 1.00 | 20.31 | | C |
| ANISOU | 990 | CD1 | PHE | A | 128 | 2457 | 2776 | 2485 | −101 | −105 | 107 | C |
| ATOM | 991 | CE1 | PHE | A | 128 | 9.512 | −7.841 | 0.079 | 1.00 | 21.80 | | C |
| ANISOU | 991 | CE1 | PHE | A | 128 | 2652 | 2940 | 2692 | −104 | −109 | 113 | C |
| ATOM | 992 | CZ | PHE | A | 128 | 10.257 | −7.388 | 1.161 | 1.00 | 18.43 | | C |
| ANISOU | 992 | CZ | PHE | A | 128 | 2234 | 2534 | 2235 | −90 | −83 | 129 | C |
| ATOM | 993 | CE2 | PHE | A | 128 | 10.025 | −6.121 | 1.683 | 1.00 | 19.33 | | C |
| ANISOU | 993 | CE2 | PHE | A | 128 | 2351 | 2689 | 2305 | −71 | −57 | 134 | C |
| ATOM | 994 | CD2 | PHE | A | 128 | 9.046 | −5.307 | 1.111 | 1.00 | 18.45 | | C |
| ANISOU | 994 | CD2 | PHE | A | 128 | 2285 | 2590 | 2178 | −67 | −54 | 128 | O |
| ATOM | 995 | C | PHE | A | 128 | 6.696 | −3.194 | −2.364 | 1.00 | 15.06 | | C |
| ANISOU | 995 | C | PHE | A | 128 | 1810 | 2200 | 1712 | −52 | −73 | 63 | C |
| ATOM | 996 | O | PHE | A | 128 | 6.332 | −2.196 | −1.745 | 1.00 | 16.23 | | O |
| ANISOU | 996 | O | PHE | A | 128 | 1958 | 2375 | 1833 | −37 | −54 | 77 | O |
| ATOM | 997 | N | LEU | A | 129 | 6.204 | −3.565 | −3.544 | 1.00 | 14.75 | | N |
| ANISOU | 997 | N | LEU | A | 129 | 1767 | 2154 | 1685 | −56 | −96 | 41 | N |
| ATOM | 998 | CA | LEU | A | 129 | 5.145 | −2.832 | −4.229 | 1.00 | 14.63 | | C |
| ANISOU | 998 | CA | LEU | A | 129 | 1743 | 2163 | 1652 | −45 | −98 | 36 | C |
| ATOM | 999 | CB | LEU | A | 129 | 5.522 | −2.618 | −5.703 | 1.00 | 13.75 | | C |
| ANISOU | 999 | CB | LEU | A | 129 | 1650 | 2051 | 1528 | −29 | −110 | −2 | C |
| ATOM | 1000 | CG | LEU | A | 129 | 4.580 | −1.804 | −6.593 | 1.00 | 19.23 | | C |
| ANISOU | 1000 | CG | LEU | A | 129 | 2341 | 2772 | 2193 | −11 | −112 | −10 | C |
| ATOM | 1001 | CD1 | LEU | A | 129 | 4.537 | −0.344 | −6.196 | 1.00 | 20.62 | | C |
| ANISOU | 1001 | CD1 | LEU | A | 129 | 2529 | 2970 | 2336 | 6 | −83 | 7 | C |
| ATOM | 1002 | CD2 | LEU | A | 129 | 5.008 | −1.932 | −8.054 | 1.00 | 21.89 | | C |
| ANISOU | 1002 | CD2 | LEU | A | 129 | 2691 | 3114 | 2514 | 9 | −129 | −47 | C |
| ATOM | 1003 | C | LEU | A | 129 | 3.868 | −3.649 | −4.137 | 1.00 | 15.39 | | C |
| ANISOU | 1003 | C | LEU | A | 129 | 1803 | 2259 | 1785 | −66 | −118 | 54 | C |
| ATOM | 1004 | O | LEU | A | 129 | 3.734 | −4.663 | −4.824 | 1.00 | 16.29 | | O |
| ANISOU | 1004 | O | LEU | A | 129 | 1907 | 2347 | 1935 | −79 | −151 | 35 | O |
| ATOM | 1005 | N | ASP | A | 130 | 2.946 | −3.203 | −3.289 | 1.00 | 16.25 | | N |
| ANISOU | 1005 | N | ASP | A | 130 | 1889 | 2397 | 1888 | −65 | −101 | 91 | N |
| ATOM | 1006 | CA | ASP | A | 130 | 1.690 | −3.905 | −3.041 | 1.00 | 18.40 | | C |
| ANISOU | 1006 | CA | ASP | A | 130 | 2117 | 2676 | 2198 | −86 | −116 | 122 | C |
| ATOM | 1007 | CB | ASP | A | 130 | 1.274 | −3.769 | −1.567 | 1.00 | 18.32 | | C |
| ANISOU | 1007 | CB | ASP | A | 130 | 2081 | 2698 | 2180 | −85 | −88 | 177 | C |
| ATOM | 1008 | CG | ASP | A | 130 | 2.230 | −4.467 | −0.614 | 1.00 | 23.83 | | C |
| ANISOU | 1008 | CG | ASP | A | 130 | 2784 | 3377 | 2893 | −94 | −79 | 198 | C |
| ATOM | 1009 | OD1 | ASP | A | 130 | 2.922 | −5.418 | −1.030 | 1.00 | 2553 | | O |
| ANISOU | 1009 | OD1 | ASP | A | 130 | 3009 | 3547 | 3145 | −113 | −102 | 181 | O |
| ATOM | 1010 | OD2 | ASP | A | 130 | 2.281 | −4.067 | 0.566 | 1.00 | 31.21 | | O |
| ANISOU | 1010 | OD2 | ASP | A | 130 | 3713 | 4346 | 3801 | −77 | −51 | 230 | O |
| ATOM | 1011 | C | ASP | A | 130 | 0.589 | −3.334 | −3.921 | 1.00 | 18.50 | | C |
| ANISOU | 1011 | C | ASP | A | 130 | 2118 | 2713 | 2199 | −77 | −126 | 108 | C |
| ATOM | 1012 | O | ASP | A | 130 | 0.412 | −2.119 | −4.001 | 1.00 | 17.91 | | O |
| ANISOU | 1012 | O | ASP | A | 130 | 2059 | 2669 | 2079 | −49 | −106 | 102 | O |
| ATOM | 1013 | N | ARG | A | 131 | −0.140 | −4.221 | −4.583 | 1.00 | 19.24 | | N |
| ANISOU | 1013 | N | ARG | A | 131 | 2183 | 2788 | 2337 | −97 | −162 | 100 | N |
| ATOM | 1014 | CA | ARG | A | 131 | −1.235 | −3.826 | −5.452 | 1.00 | 22.82 | | C |
| ANISOU | 1014 | CA | ARG | A | 131 | 2621 | 3264 | 2785 | −88 | −179 | 84 | C |
| ATOM | 1015 | CB | ARG | A | 131 | 0.775 | −3.797 | −6.919 | 1.00 | 21.56 | | C |
| ANISOU | 1015 | CB | ARG | A | 131 | 2490 | 3091 | 2610 | −70 | −205 | 24 | C |
| ATOM | 1016 | CG | ARG | A | 131 | 0.224 | −2.678 | −7.236 | 1.00 | 20.07 | | C |
| ANISOU | 1016 | CG | ARG | A | 131 | 2347 | 2917 | 2360 | −37 | −175 | 6 | C |
| ATOM | 1017 | CD | ARG | A | 131 | 0.522 | −2.584 | −8.721 | 1.00 | 22.03 | | C |
| ANISOU | 1017 | CD | ARG | A | 131 | 2616 | 3168 | 2586 | −11 | −197 | −42 | C |
| ATOM | 1018 | NE | ARG | A | 131 | 1.133 | −3.803 | −9.236 | 1.00 | 22.36 | | N |
| ANISOU | 1018 | NE | ARG | A | 131 | 2660 | 3175 | 2659 | −19 | −232 | −76 | N |
| ATOM | 1019 | CZ | ARG | A | 131 | 1.175 | −4.133 | −10.522 | 1.00 | 24.26 | | C |
| ANISOU | 1019 | CZ | ARG | A | 131 | 2907 | 3420 | 2891 | 5 | −266 | −124 | C |
| ATOM | 1020 | NH1 | ARG | A | 131 | 0.627 | −3.345 | −11.442 | 1.00 | 26.71 | | N |

TABLE 9-continued

Atomic coordinates for N-TXNIP(K5A/K6A) protein (SEQ ID NO: 8)

| ANISOU | 1020 | NH1 | ARG | A | 131 | 3220 | 3768 | 3161 | 35 | −266 | −139 | N |
|---|---|---|---|---|---|---|---|---|---|---|---|---|
| ATOM | 1021 | NH2 | ARG | A | 131 | 1.748 | −5.271 | −10.887 | 1.00 | 25.46 | | N |
| ANISOU | 1021 | MH2 | ARG | A | 131 | 3062 | 3539 | 3074 | 3 | −302 | −159 | N |
| ATOM | 1022 | C | ARG | A | 131 | −2.386 | −4.803 | −5.260 | 1.00 | 26.15 | | C |
| ANISOU | 1022 | C | ARG | A | 131 | 2988 | 3679 | 3270 | −121 | −206 | 114 | C |
| ATOM | 1023 | O | ARG | A | 131 | −2.154 | −6.009 | −5.142 | 1.00 | 27.17 | | O |
| ANISOU | 1023 | O | ARG | A | 131 | 3101 | 3763 | 3458 | −151 | −234 | 120 | O |
| ATOM | 1024 | N | PRO | A | 132 | −3.630 | −4.285 | −5.202 | 1.00 | 30.69 | | N |
| ANISOU | 1024 | N | PRO | A | 132 | 3530 | 4294 | 3837 | −117 | −201 | 136 | N |
| ATOM | 1025 | CA | PRO | A | 132 | −4.815 | −5.127 | −4.984 | 1.00 | 34.57 | | C |
| ANISOU | 1025 | CA | PRO | A | 132 | 3959 | 4784 | 4393 | −150 | −225 | 174 | C |
| ATOM | 1026 | CB | PRO | A | 132 | −5.977 | −4.131 | −5.102 | 1.00 | 34.75 | | C |
| ANISOU | 1026 | CB | PRO | A | 132 | 3961 | 4865 | 4379 | −128 | −211 | 184 | C |
| ATOM | 1027 | CG | PRO | A | 132 | −5.385 | −2.808 | −4.790 | 1.00 | 34.96 | | C |
| ANISOU | 1027 | CG | PRO | A | 132 | 4033 | 4924 | 4326 | −86 | −167 | 175 | C |
| ATOM | 1028 | CD | PRO | A | 132 | −3.990 | −2.861 | −5.341 | 1.00 | 28.92 | | C |
| ANISOU | 1028 | CD | PRO | A | 132 | 3322 | 4119 | 3547 | −79 | −173 | 129 | C |
| ATOM | 1029 | C | PRO | A | 132 | −4.959 | −6.236 | −6.027 | 1.00 | 37.74 | | C |
| ANISOU | 1029 | C | PRO | A | 132 | 4348 | 5134 | 4860 | −174 | −287 | 133 | C |
| ATOM | 1030 | O | PRO | A | 132 | 4.792 | 5.982 | 7.226 | 1.00 | 38.92 | | O |
| ANISOU | 1030 | O | PRO | A | 132 | 4525 | 5279 | 4985 | −151 | −312 | 71 | O |
| ATOM | 1031 | N | SER | A | 133 | −5.262 | −7.449 | −5.557 | 1.00 | 41.02 | | N |
| ANISOU | 1031 | N | SER | A | 133 | 4719 | 5510 | 5358 | −217 | −314 | 170 | N |
| ATOM | 1032 | CA | SER | A | 133 | −5.409 | −8.654 | −6.398 | 1.00 | 43.53 | | C |
| ANISOU | 1032 | CA | SER | A | 133 | 5018 | 5765 | 5755 | −243 | −384 | 132 | C |
| ATOM | 1033 | CB | SER | A | 133 | −6.802 | −8.707 | −7.057 | 1.00 | 44.85 | | C |
| ANISOU | 1033 | CB | SER | A | 133 | 5137 | 5946 | 5959 | −253 | −422 | 125 | C |
| ATOM | 1034 | OG | SER | A | 133 | −6.938 | −7.735 | −8.084 | 1.00 | 49.30 | | O |
| ANISOU | 1034 | OG | SER | A | 133 | 5733 | 6548 | 6452 | −209 | −422 | 66 | O |
| ATOM | 1035 | C | SER | A | 133 | −4.293 | −8.821 | −7.436 | 1.00 | 42.97 | | C |
| ANISOU | 1035 | C | SER | A | 133 | 5004 | 5662 | 5662 | −216 | −412 | 50 | C |
| ATOM | 1036 | O | SER | A | 133 | −4.542 | −9.118 | −8.605 | 1.00 | 44.85 | | O |
| ANISOU | 1036 | O | SER | A | 133 | 5244 | 5883 | 5915 | −204 | 464 | 12 | O |
| ATOM | 1037 | N | GLN | A | 134 | −3.057 | −8.626 | −6.988 | 1.00 | 4164 | | N |
| ANISOU | 1037 | N | GLN | A | 134 | 4879 | 5489 | 5453 | −202 | −377 | 50 | N |
| ATOM | 1038 | CA | GLN | A | 134 | −1.886 | −8.692 | −7.854 | 1.00 | 39.52 | | C |
| ANISOU | 1038 | CA | GLN | A | 134 | 4662 | 5200 | 5153 | −172 | −392 | −17 | C |
| ATOM | 1039 | CB | GLN | A | 134 | −1.658 | −7.335 | −8.524 | 1.00 | 38.94 | | C |
| ANISOU | 1039 | CB | GLN | A | 134 | 4626 | 5181 | 4987 | −127 | −359 | −47 | C |
| ATOM | 1040 | CG | GLN | A | 134 | −1.023 | −7.413 | −9.902 | 1.00 | 43.42 | | C |
| ANISOU | 1040 | CG | GLN | A | 134 | 5227 | 5745 | 5526 | −89 | −391 | −122 | C |
| ATOM | 1041 | CD | GLN | A | 134 | −1.757 | −6.567 | −10.930 | 1.00 | 46.29 | | C |
| ANISOU | 1041 | CD | GLN | A | 134 | 5591 | 6155 | 5843 | −56 | −396 | −151 | C |
| ATOM | 1042 | OE1 | GLN | A | 134 | −2.140 | −5.425 | −10.658 | 1.00 | 47.98 | | O |
| ANISOU | 1042 | OE1 | GLN | A | 134 | 5808 | 6413 | 6010 | −45 | −354 | −120 | O |
| ATOM | 1043 | NE2 | GLN | A | 134 | −1.956 | −7.125 | −12.120 | 1.00 | 45.50 | | N |
| ANISOU | 1043 | NE2 | GLN | A | 134 | 5488 | 6047 | 5753 | −35 | −452 | −213 | N |
| ATOM | 1044 | C | GLN | A | 134 | −0.678 | −9.088 | −7.009 | 1.00 | 36.72 | | C |
| ANISOU | 1044 | C | GLN | A | 134 | 4331 | 4819 | 4801 | −180 | −369 | 4 | C |
| ATOM | 1045 | O | GLN | A | 134 | −0.592 | −8.692 | −5.848 | 1.00 | 36.44 | | O |
| ANISOU | 1045 | O | GLN | A | 134 | 4291 | 4806 | 4750 | −189 | −322 | 62 | O |
| ATOM | 1046 | N | PRO | A | 135 | 0.239 | −9.904 | −7.571 | 1.00 | 34.71 | | N |
| ANISOU | 1046 | N | PRO | A | 135 | 4100 | 4519 | 4567 | −173 | −405 | −45 | N |
| ATOM | 1047 | CA | PRO | A | 135 | 1.428 | −10.288 | −6.808 | 1.00 | 32.11 | | C |
| ANISOU | 1047 | CA | PRO | A | 135 | 3794 | 4166 | 4240 | −177 | −384 | −27 | C |
| ATOM | 1048 | CB | PRO | A | 135 | 2.183 | −11.209 | −7.771 | 1.00 | 33.47 | | C |
| ANISOU | 1048 | CB | PRO | A | 135 | 3987 | 4293 | 4436 | −160 | −438 | −97 | C |
| ATOM | 1049 | CG | PRO | A | 135 | 1.153 | −11.679 | −8.743 | 1.00 | 35.63 | | C |
| ANISOU | 1049 | CG | PRO | A | 135 | 4234 | 4550 | 4754 | −162 | −500 | −138 | C |
| ATOM | 1050 | CD | PRO | A | 135 | 0.226 | −10.529 | −8.908 | 1.00 | 35.11 | | C |
| ANISOU | 1050 | CD | PRO | A | 135 | 4157 | 4544 | 4639 | −153 | −469 | −121 | C |
| ATOM | 1051 | C | PRO | A | 135 | 2.287 | −9.076 | −6.436 | 1.00 | 28.81 | | C |
| ANISOU | 1051 | C | PRO | A | 135 | 3414 | 3795 | 3737 | −149 | −322 | −18 | C |
| ATOM | 1052 | O | PRO | A | 135 | 2.511 | −8.186 | −7.259 | 1.00 | 26.79 | | O |
| ANISOU | 1052 | O | PRO | A | 135 | 3185 | 3574 | 3421 | −116 | −310 | −55 | O |
| ATOM | 1053 | N | THR | A | 136 | 2.733 | −9.042 | −5.188 | 1.00 | 25.84 | | N |
| ANISOU | 1053 | N | THR | A | 136 | 3038 | 3421 | 3359 | −163 | −286 | 33 | N |
| ATOM | 1054 | CA | THR | A | 136 | 3.658 | 8.010 | −4.717 | 1.00 | 23.33 | | C |
| ANISOU | 1054 | CA | THR | A | 136 | 2754 | 3136 | 2974 | −139 | −235 | 38 | C |
| ATOM | 1055 | CB | THR | A | 136 | 3.875 | −8.135 | −3.188 | 1.00 | 23.10 | | C |
| ANISOU | 1055 | CB | THR | A | 136 | 2713 | 3112 | 2953 | −154 | −203 | 99 | C |
| ATOM | 1056 | OG1 | THR | A | 136 | 2.640 | −7.849 | −2.515 | 1.00 | 26.28 | | O |
| ANISOU | 1056 | OG1 | THR | A | 136 | 3076 | 3546 | 3362 | −166 | −188 | 151 | O |
| ATOM | 1057 | CG2 | THR | A | 136 | 4.961 | −7.177 | −2.674 | 1.00 | 21.17 | | C |
| ANISOU | 1057 | CG2 | THR | A | 136 | 2504 | 2893 | 2647 | −129 | −162 | 96 | C |
| ATOM | 1058 | C | THR | A | 136 | 4.970 | −8.144 | −5.476 | 1.00 | 22.58 | | C |
| ANISOU | 1058 | C | THR | A | 136 | 2697 | 3025 | 2856 | −116 | −245 | −14 | C |
| ATOM | 1059 | O | THR | A | 136 | 5.439 | −9.258 | −5.707 | 1.00 | 24.58 | | O |

TABLE 9-continued

Atomic coordinates for N-TXNIP(K5A/K6A) protein (SEQ ID NO: 8)

| | | | | | | | | | | | |
|---|---|---|---|---|---|---|---|---|---|---|---|
| ANISOU | 1059 | O | THR | A | 136 | 2953 | 3236 | 3152 | −122 | −280 | −36 | O |
| ATOM | 1060 | N | GLN | A | 137 | 5.546 | −7.013 | −5.878 | 1.00 | 18.35 | | N |
| ANISOU | 1060 | N | GLN | A | 137 | 2191 | 2525 | 2258 | −87 | −215 | −32 | N |
| ATOM | 1061 | CA | GLN | A | 137 | 6.844 | −7.004 | −6.546 | 1.00 | 17.69 | | C |
| ANISOU | 1061 | CA | GLN | A | 137 | 2139 | 2437 | 2146 | −62 | −215 | −71 | C |
| ATOM | 1062 | CB | GLN | A | 137 | 6.842 | −6.028 | −7.724 | 1.00 | 15.67 | | C |
| ANISOU | 1062 | CB | GLN | A | 137 | 1897 | 2219 | 1837 | −29 | −207 | −130 | C |
| ATOM | 1063 | CG | GLN | A | 137 | 5.764 | −6.351 | −8.768 | 1.00 | 16.99 | | C |
| ANISOU | 1063 | CG | GLN | A | 137 | 2048 | 2391 | 2016 | −21 | −246 | −130 | C |
| ATOM | 1064 | CD | GLN | A | 137 | 6.043 | −5.804 | −10.155 | 1.00 | 17.94 | | C |
| ANISOU | 1064 | CD | GLN | A | 137 | 2185 | 2546 | 2084 | 21 | −249 | −168 | C |
| ATOM | 1065 | OE1 | GLN | A | 137 | 7.015 | −5.079 | −10.377 | 1.00 | 17.13 | | O |
| ANISOU | 1065 | OE1 | GLN | A | 137 | 2104 | 2467 | 1938 | 43 | −218 | −164 | O |
| ATOM | 1066 | NE2 | GLN | A | 137 | 5.177 | −6.158 | −11.107 | 1.00 | 18.74 | | N |
| ANISOU | 1066 | NE2 | GLN | A | 137 | 2274 | 2655 | 2193 | 35 | −289 | −203 | N |
| ATOM | 1067 | C | GLN | A | 137 | 7.902 | −6.614 | −5.528 | 1.00 | 16.27 | | C |
| ANISOU | 1067 | C | GLN | A | 137 | 1974 | 2260 | 1947 | −63 | −178 | −45 | C |
| ATOM | 1068 | O | GLN | A | 137 | 7.632 | −5.820 | −4.629 | 1.00 | 16.62 | | O |
| ANISOU | 1068 | O | GLN | A | 137 | 2015 | 2324 | 1975 | −68 | −148 | −10 | O |
| ATOM | 1069 | N | GLU | A | 138 | 9.100 | −7.171 | −5.666 | 1.00 | 15.78 | | N |
| ANISOU | 1069 | N | GLU | A | 138 | 1930 | 2180 | 1887 | −54 | −185 | −67 | N |
| ATOM | 1070 | CA | GLU | A | 138 | 10.188 | −6.849 | −4.743 | 1.00 | 15.59 | | C |
| ANISOU | 1070 | CA | GLU | A | 138 | 1920 | 2158 | 1848 | −54 | −155 | −47 | C |
| ATOM | 1071 | CB | GLU | A | 138 | 10.633 | −8.108 | −3.987 | 1.00 | 16.95 | | C |
| ANISOU | 1071 | CB | GLU | A | 138 | 2086 | 2292 | 2063 | −70 | −172 | −37 | C |
| ATOM | 1072 | CG | GLU | A | 138 | 11.790 | −7.875 | −3.019 | 1.00 | 19.80 | | C |
| ANISOU | 1072 | CG | GLU | A | 138 | 2460 | 2655 | 2407 | −66 | −145 | −21 | C |
| ATOM | 1073 | CD | GLU | A | 138 | 12.323 | −9.152 | −2.386 | 1.00 | 26.17 | | C |
| ANISOU | 1073 | CD | GLU | A | 138 | 3264 | 3426 | 3255 | −77 | −163 | −12 | C |
| ATOM | 1074 | OE1 | GLU | A | 138 | 11.552 | −10.124 | −2.226 | 1.00 | 32.76 | | O |
| ANISOU | 1074 | OE1 | GLU | A | 138 | 4078 | 4230 | 4139 | −96 | −189 | 4 | O |
| ATOM | 1075 | OE2 | GLU | A | 138 | 13.524 | −9.171 | −2.035 | 1.00 | 26.52 | | O |
| ANISOU | 1075 | OE2 | GLU | A | 138 | 3322 | 3470 | 3284 | −65 | −151 | −18 | O |
| ATOM | 1076 | C | GLU | A | 138 | 11.390 | −6.245 | −5.469 | 1.00 | 15.40 | | C |
| ANISOU | 1076 | C | GLU | A | 138 | 1918 | 2152 | 1783 | −28 | −140 | −73 | C |
| ATOM | 1077 | O | GLU | A | 138 | 11.664 | −6.583 | −6.614 | 1.00 | 14.67 | | O |
| ANISOU | 1077 | O | GLU | A | 138 | 1831 | 2063 | 1680 | −7 | −159 | −109 | O |
| ATOM | 1078 | N | THR | A | 139 | 12.101 | −5.349 | −4.789 | 1.00 | 14.35 | | N |
| ANISOU | 1078 | N | THR | A | 139 | 1794 | 2031 | 1627 | −26 | −108 | −54 | N |
| ATOM | 1079 | CA | THR | A | 139 | 13.428 | −4.929 | −5.219 | 1.00 | 13.48 | | C |
| ANISOU | 1079 | CA | THR | A | 139 | 1697 | 1932 | 1491 | −8 | −94 | −67 | C |
| ATOM | 1080 | CB | THR | A | 139 | 13.415 | −3.518 | −5.888 | 1.00 | 14.79 | | C |
| ANISOU | 1080 | CB | THR | A | 139 | 1869 | 2129 | 1624 | 6 | −72 | −60 | C |
| ATOM | 1081 | OG1 | THR | A | 139 | 14.709 | −3.210 | −6.419 | 1.00 | 16.20 | | O |
| ANISOU | 1081 | OG1 | THR | A | 139 | 2052 | 2319 | 1783 | 22 | −59 | −65 | O |
| ATOM | 1082 | CG2 | THR | A | 139 | 12.988 | −2.427 | −4.912 | 1.00 | 15.33 | | C |
| ANISOU | 1082 | CG2 | THR | A | 139 | 1936 | 2199 | 1691 | −4 | −53 | −33 | C |
| ATOM | 1083 | C | THR | A | 139 | 14.376 | −5.022 | −4.015 | 1.00 | 14.40 | | C |
| ANISOU | 1083 | C | THR | A | 139 | 1818 | 2036 | 1617 | −17 | −81 | −51 | C |
| ATOM | 1084 | O | THR | A | 139 | 13.943 | −4.928 | −2.873 | 1.00 | 15.71 | | O |
| ANISOU | 1084 | O | THR | A | 139 | 1978 | 2197 | 1793 | −30 | −74 | −27 | O |
| ATOM | 1085 | N | LYS | A | 140 | 15.654 | −5.253 | −4.274 | 1.00 | 13.10 | | N |
| ANISOU | 1085 | N | LYS | A | 140 | 1660 | 1870 | 1445 | −5 | −79 | −66 | N |
| ATOM | 1086 | CA | LYS | A | 140 | 16.635 | −5.351 | −3.195 | 1.00 | 13.58 | | C |
| ANISOU | 1086 | CA | LYS | A | 140 | 1724 | 1921 | 1513 | −10 | −69 | −55 | C |
| ATOM | 1087 | CB | LYS | A | 140 | 16.921 | −6.821 | −2.870 | 1.00 | 14.79 | | C |
| ANISOU | 1087 | CB | LYS | A | 140 | 1877 | 2048 | 1694 | −13 | −92 | −64 | C |
| ATOM | 1088 | CG | LYS | A | 140 | 17.912 | −7.063 | −1.734 | 1.00 | 15.28 | | C |
| ANISOU | 1088 | CG | LYS | A | 140 | 1941 | 2102 | 1762 | −14 | −84 | −53 | C |
| ATOM | 1089 | CD | LYS | A | 140 | 18.314 | −8.544 | −1.653 | 1.00 | 16.37 | | C |
| ANISOU | 1089 | CD | LYS | A | 140 | 2080 | 2211 | 1927 | −12 | −109 | −63 | C |
| ATOM | 1090 | CE | LYS | A | 140 | 19.368 | −8.752 | −0.559 | 1.00 | 18.12 | | C |
| ANISOU | 1090 | CE | LYS | A | 140 | 2305 | 2429 | 2151 | −9 | −100 | −52 | C |
| ATOM | 1091 | NZ | LYS | A | 140 | 19.639 | −10.192 | −0.261 | 1.00 | 22.57 | | N |
| ANISOU | 1091 | NZ | LYS | A | 140 | 2869 | 2961 | 2747 | −8 | −125 | −53 | N |
| ATOM | 1092 | C | LYS | A | 140 | 17.915 | −4.646 | −3.603 | 1.00 | 14.38 | | C |
| ANISOU | 1092 | C | LYS | A | 140 | 1829 | 2040 | 1596 | 3 | 53 | 60 | C |
| ATOM | 1093 | O | LYS | A | 140 | 18.376 | −4.815 | −4.731 | 1.00 | 15.92 | | O |
| ANISOU | 1093 | O | LYS | A | 140 | 2023 | 2250 | 1776 | 21 | −55 | −76 | O |
| ATOM | 1094 | N | LYS | A | 141 | 18.493 | −3.876 | −2.682 | 1.00 | 13.67 | | N |
| ANISOU | 1094 | N | LYS | A | 141 | 1738 | 1949 | 1506 | −3 | −39 | −45 | N |
| ATOM | 1095 | CA | LYS | A | 141 | 19.793 | −3.273 | −2.927 | 1.00 | 14.96 | | C |
| ANISOU | 1095 | CA | LYS | A | 141 | 1898 | 2123 | 1663 | 3 | −26 | −45 | C |
| ATOM | 1096 | CB | LYS | A | 141 | 19.660 | −1.801 | −3.350 | 1.00 | 16.46 | | C |
| ANISOU | 1096 | CB | LYS | A | 141 | 2084 | 2324 | 1848 | 2 | −12 | −29 | C |
| ATOM | 1097 | CG | LYS | A | 141 | 20.969 | −1.196 | −3.914 | 1.00 | 15.49 | | C |
| ANISOU | 1097 | CG | LYS | A | 141 | 1948 | 2213 | 1724 | 7 | 1 | −18 | C |
| ATOM | 1098 | CD | LYS | A | 141 | 20.759 | 0.138 | −4.625 | 1.00 | 22.03 | | C |

TABLE 9-continued

Atomic coordinates for N-TXNIP(K5A/K6A) protein (SEQ ID NO: 8)

| ANISOU | 1098 | CD | LYS | A | 141 | 2769 | 3051 | 2552 | 6 | 14 | 7 | C |
|---|---|---|---|---|---|---|---|---|---|---|---|---|
| ATOM | 1099 | CE | LYS | A | 141 | 20.497 | −0.039 | −6.124 | 1.00 | 25.54 | | C |
| ANISOU | 1099 | CE | LYS | A | 141 | 3209 | 3528 | 2969 | 26 | 23 | 12 | C |
| ATOM | 1100 | NZ | LYS | A | 141 | 20.320 | 1.262 | −6.852 | 1.00 | 24.01 | | N |
| ANISOU | 1100 | NZ | LYS | A | 141 | 3005 | 3345 | 2274 | 27 | 38 | 45 | N |
| ATOM | 1101 | C | LYS | A | 141 | 20.654 | −3.389 | −1.673 | 1.00 | 14.05 | | C |
| ANISOU | 1101 | C | LYS | A | 141 | 1782 | 1996 | 1580 | −1 | −27 | −43 | C |
| ATOM | 1102 | O | LYS | A | 141 | 20.224 | −3.026 | −0.573 | 1.00 | 14.35 | | O |
| ANISOU | 1102 | O | LYS | A | 141 | 1823 | 2028 | 1603 | −7 | −28 | −35 | O |
| ATOM | 1103 | N | ASN | A | 142 | 21.875 | −3.880 | −1.847 | 1.00 | 13.21 | | N |
| ANISOU | 1103 | N | ASN | A | 142 | 1672 | 1893 | 1455 | 7 | −27 | −52 | N |
| ATOM | 1104 | CA | ASN | A | 142 | 22.827 | −3.042 | −0.743 | 1.00 | 14.45 | | C |
| ANISOU | 1104 | CA | ASN | A | 142 | 1826 | 1893 | 1455 | 7 | −27 | −52 | C |
| ATOM | 1105 | CB | ASN | A | 142 | 23.991 | −4.882 | −1.085 | 1.00 | 16.18 | | C |
| ANISOU | 1105 | CB | ASN | A | 142 | 2041 | 2267 | 1840 | 19 | −33 | −66 | C |
| ATOM | 1106 | CG | ASN | A | 142 | 23.546 | −6.295 | −1.109 | 1.00 | 23.25 | | C |
| ANISOU | 1106 | CG | ASN | A | 142 | 2947 | 3151 | 2737 | 28 | −49 | −80 | C |
| ATOM | 1107 | CD1 | ASN | A | 142 | 22.664 | −6.844 | −0.773 | 1.00 | 25.80 | | C |
| ANISOU | 1107 | CD1 | ASN | A | 142 | 3276 | 3455 | 3072 | 19 | −60 | −74 | O |
| ATOM | 1108 | ND2 | ASN | A | 142 | 24.188 | −0.6899 | −2.402 | 1.00 | 34.69 | | C |
| ANISOU | 1108 | ND2 | ASN | A | 142 | 4393 | 4613 | 4177 | 48 | −53 | −98 | N |
| ATOM | 1109 | C | ASN | A | 142 | 23.390 | −2.582 | −0.433 | 1.00 | 14.49 | | C |
| ANISOU | 1109 | C | ASN | A | 142 | 1821 | 2049 | 1034 | −1 | −22 | −44 | C |
| ATOM | 1110 | O | ASN | A | 142 | 23.441 | −1.697 | −1.303 | 1.00 | 14.43 | | O |
| ANISOU | 1110 | O | ASN | A | 142 | 1806 | 2050 | 1827 | −4 | −12 | −33 | O |
| ATOM | 1111 | N | PHE | A | 143 | 23.822 | −2.363 | 0.810 | 1.00 | 14.33 | | N |
| ANISOU | 1111 | N | PHE | A | 143 | 1800 | 2021 | 1822 | −1 | −30 | −48 | N |
| ATOM | 1112 | CA | PHE | A | 143 | 24.876 | −1.220 | 1.140 | 1.00 | 15.17 | | C |
| ANISOU | 1112 | CA | PHE | A | 143 | 1804 | 2122 | 1747 | −6 | −33 | −48 | C |
| ATOM | 1113 | CB | PHE | A | 143 | 23.896 | −0.028 | 1.737 | 1.00 | 16.04 | | C |
| ANISOU | 1113 | CB | PHE | A | 143 | 2009 | 2222 | 1864 | −8 | −41 | −49 | C |
| ATOM | 1114 | CG | PHE | A | 143 | 23.238 | −0.205 | 3.075 | 1.00 | 13.48 | | C |
| ANISOU | 1114 | CG | PHE | A | 143 | 1666 | 1901 | 1528 | 6 | −52 | −60 | C |
| ATOM | 1115 | CD1 | PHE | A | 143 | 23.919 | −0.033 | 4.265 | 1.00 | 12.43 | | C |
| ANISOU | 1115 | CD1 | PHE | A | 143 | 1568 | 1767 | 1397 | 10 | −69 | −78 | C |
| ATOM | 1116 | CC1 | PHE | A | 143 | 20.306 | 0.246 | 5.500 | 1.00 | 14.10 | | C |
| ANISOU | 1116 | CB1 | PHE | A | 143 | 1787 | 2003 | 1597 | 41 | −77 | −84 | C |
| ATOM | 1117 | CZ | PHE | A | 143 | 21.982 | −0.723 | 5.564 | 1.00 | 14.09 | | C |
| ANISOU | 1117 | CZ | PHE | A | 143 | 1783 | 2007 | 1564 | 45 | −66 | −67 | C |
| ATOM | 1118 | CE2 | PHE | A | 143 | 21.284 | −0.983 | 4.379 | 1.00 | 13.05 | | C |
| ANISOU | 1118 | CE2 | PHE | A | 143 | 1654 | 1869 | 1435 | 27 | −52 | −51 | C |
| ATOM | 1119 | CD2 | PHE | A | 143 | 21.914 | −0.759 | 3.138 | 1.00 | 12.47 | | C |
| ANISOU | 1119 | CD2 | PHE | A | 143 | 1578 | 1783 | 1379 | 10 | −46 | −51 | C |
| ATOM | 1120 | C | PHE | A | 143 | 25.873 | −1.662 | 1.968 | 1.00 | 15.77 | | C |
| ANISOU | 1120 | C | PHE | A | 143 | 1963 | 2199 | 1831 | 1 | −42 | −60 | C |
| ATOM | 1121 | O | PHE | A | 143 | 25.840 | −2.733 | 2.577 | 1.00 | 15.91 | | O |
| ANISOU | 1121 | O | PHE | A | 143 | 1990 | 2219 | 1837 | 11 | −45 | −67 | O |
| ATOM | 1122 | N | GLU | A | 144 | 28.938 | −0.862 | 1.936 | 1.00 | 15.50 | | N |
| ANISOU | 1122 | N | GLU | A | 144 | 10000 | 2160 | 1810 | −6 | −46 | −60 | N |
| ATOM | 1123 | CA | GLU | A | 144 | 28.198 | −1.218 | 2.568 | 1.00 | 15.79 | | C |
| ANISOU | 1123 | CA | GLU | A | 144 | 2081 | 2327 | 1992 | 0 | −56 | −71 | C |
| ATOM | 1124 | CB | GLU | A | 144 | 29.377 | −0.859 | 1.662 | 1.00 | 17.59 | | C |
| ANISOU | 1124 | CB | GLU | A | 144 | 2134 | 2437 | 2114 | −10 | −47 | −56 | C |
| ATOM | 1125 | CG | GLU | A | 144 | 29.338 | −1.484 | 0.283 | 1.00 | 22.50 | | C |
| ANISOU | 1125 | CG | GLU | A | 144 | 2752 | 3082 | 2714 | −4 | −24 | −40 | C |
| ATOM | 1126 | CD | GLU | A | 144 | 30.050 | −2.822 | 0.203 | 1.00 | 30.77 | | C |
| ANISOU | 1126 | CD | GLU | A | 144 | 3801 | 4140 | 3743 | 16 | −22 | −53 | C |
| ATOM | 1127 | CE1 | GLU | A | 144 | 30.216 | −3.320 | −0.933 | 1.00 | 34.79 | | O |
| ANISOU | 1127 | CE1 | GLU | A | 144 | 4305 | 4682 | 4234 | 29 | −8 | −46 | O |
| ATOM | 1128 | CE2 | GLU | A | 144 | 30.448 | −3.375 | 1.253 | 1.00 | 35.30 | | O |
| ANISOU | 1128 | CE2 | GLU | A | 144 | 4391 | 4724 | 4328 | 23 | −36 | −70 | O |
| ATOM | 1129 | C | GLU | A | 144 | 28.361 | −0.483 | 3.886 | 1.00 | 16.22 | | C |
| ANISOU | 1129 | C | GLU | A | 144 | 1987 | 2242 | 1934 | 4 | −80 | −90 | C |
| ATOM | 1130 | O | GLU | A | 144 | 27.920 | 0.562 | 4.037 | 1.00 | 14.53 | | O |
| ANISOU | 1130 | O | VAL | A | 144 | 1771 | 2011 | 1737 | −1 | −91 | −93 | O |
| ATOM | 1131 | N | VAL | A | 145 | 26.988 | −1.157 | 4.545 | 1.00 | 17.37 | | N |
| ANISOU | 1131 | N | VAL | A | 145 | 2132 | 2395 | 2071 | 20 | −91 | −106 | N |
| ATOM | 1132 | OA | VAL | A | 145 | 20.270 | −0.558 | 8.138 | 1.00 | 17.41 | | C |
| ANISOU | 1132 | OA | VAL | A | 145 | 2136 | 2397 | 2085 | 34 | −119 | −132 | C |
| ATOM | 1133 | OB | VAL | A | 145 | 28.383 | −1.143 | 7.287 | 1.00 | 17.07 | | C |
| ANISOU | 1133 | OB | VAL | A | 145 | 2112 | 2370 | 2003 | 52 | −133 | −19 | C |
| ATOM | 1134 | CG1 | VAL | A | 145 | 26.898 | −0.907 | 7.026 | 1.00 | 17.27 | | C |
| ANISOU | 1134 | CG1 | VAL | A | 145 | 2152 | 2305 | 2013 | 50 | −111 | −125 | C |
| ATOM | 1135 | CG2 | VAL | A | 145 | 28.563 | −2.639 | 7.521 | 1.00 | 20.41 | | C |
| ANISOU | 1135 | CG2 | VAL | A | 145 | 2541 | 2808 | 2404 | 73 | −112 | −128 | C |
| ATOM | 1136 | C | VAL | A | 145 | 30.743 | −0.688 | 6.527 | 1.00 | 17.77 | | C |
| ANISOU | 1136 | C | VAL | A | 145 | 2159 | 2445 | 2148 | 37 | −133 | −145 | C |
| ATOM | 1137 | O | VAL | A | 145 | 31.464 | −1.571 | 6.042 | 1.00 | 19.13 | | O |

TABLE 9-continued

Atomic coordinates for N-TXNIP(K5A/K6A) protein (SEQ ID NO: 8)

| | | | | | | | | | | | | |
|---|---|---|---|---|---|---|---|---|---|---|---|---|
| ANISOU | 1137 | O | VAL | A | 145 | 2324 | 2628 | 2315 | 35 | −120 | −135 | O |
| ATOM | 1138 | N | VAL | A | 146 | 31.164 | 0.207 | 7.411 | 1.00 | 18.13 | | N |
| ANISOU | 1138 | N | VAL | A | 146 | 2195 | 2480 | 2215 | 45 | −165 | −172 | N |
| ATOM | 1139 | CA | VAL | A | 146 | 32.415 | 0.053 | 8.146 | 1.00 | 20.29 | | C |
| ANISOU | 1139 | CA | VAL | A | 146 | 2449 | 2759 | 2500 | 56 | −188 | −184 | C |
| ATOM | 1140 | CB | VAL | A | 146 | 33.372 | 1.266 | 7.947 | 1.00 | 21.48 | | C |
| ANISOU | 1140 | CB | VAL | A | 146 | 2566 | 2883 | 2713 | 34 | −215 | −203 | C |
| ATOM | 1141 | CG1 | VAL | A | 146 | 33.951 | 1.236 | 6.540 | 1.00 | 24.63 | | C |
| ANISOU | 1141 | CG1 | VAL | A | 146 | 2941 | 3281 | 3137 | 2 | −186 | −163 | C |
| ATOM | 1142 | CG2 | VAL | A | 146 | 32.866 | 2.607 | 8.239 | 1.00 | 23.03 | | C |
| ANISOU | 1142 | CG2 | VAL | A | 146 | 2766 | 3048 | 2936 | 32 | −243 | −221 | C |
| ATOM | 1143 | C | VAL | A | 146 | 32.105 | −0.221 | 9.623 | 1.00 | 21.15 | | C |
| ANISOU | 1143 | C | VAL | A | 146 | 2573 | 2887 | 2574 | 96 | −209 | −223 | C |
| ATOM | 1144 | O | VAL | A | 146 | 30.994 | −0.646 | 9.950 | 1.00 | 21.00 | | O |
| ANISOU | 1144 | O | VAL | A | 146 | 2654 | 2959 | 2593 | 113 | −196 | −214 | O |
| ATOM | 1145 | N | ASP | A | 147 | 33.087 | −0.006 | 10.497 | 1.00 | 22.23 | | N |
| ANISOU | 1145 | N | ASP | A | 147 | 2695 | 3028 | 2724 | 113 | −241 | −255 | N |
| ATOM | 1146 | CA | ASP | A | 147 | 32.919 | −0.244 | 11.937 | 1.00 | 23.94 | | C |
| ANISOU | 1146 | CA | ASP | A | 147 | 2923 | 3273 | 2902 | 151 | −253 | −284 | C |
| ATOM | 1147 | CB | ASP | A | 147 | 31.879 | 0.712 | 12.534 | 1.00 | 24.21 | | C |
| ANISOU | 1147 | CB | ASP | A | 147 | 2969 | 3305 | 3924 | 183 | −284 | −307 | C |
| ATOM | 1148 | CG | ASP | A | 147 | 32.341 | 2.170 | 12.496 | 1.00 | 29.21 | | C |
| ANISOU | 1148 | CG | ASP | A | 147 | 3584 | 3899 | 3616 | 171 | −328 | −344 | C |
| ATOM | 1149 | OD1 | ASP | A | 147 | 33.540 | 2.426 | 12.496 | 1.00 | 29.21 | | O |
| ANISOU | 1149 | OD1 | ASP | A | 147 | 4208 | 4587 | 4301 | 167 | −359 | −569 | O |
| ATOM | 1150 | OD2 | ASP | A | 147 | 31.518 | 3.060 | 12.206 | 1.00 | 28.74 | | O |
| ANISOU | 1150 | OD2 | ASP | A | 147 | 3532 | 3818 | 3571 | 164 | −335 | −347 | O |
| ATOM | 1151 | C | ASP | A | 147 | 82.620 | −1.708 | 12.257 | 1.00 | 23.58 | | C |
| ANISOU | 1151 | C | ASP | A | 147 | 2894 | 3260 | 2805 | 181 | −235 | −257 | C |
| ATOM | 1152 | O | ASP | A | 147 | 31.813 | −2.030 | 13.148 | 1.00 | 22.04 | | O |
| ANISOU | 1152 | O | ASP | A | 147 | 2790 | 3169 | 2642 | 215 | −233 | −254 | O |
| ATOM | 1153 | N | LEU | A | 148 | 33.282 | −2.589 | 11.513 | 1.00 | 24.69 | | N |
| ANISOU | 1153 | N | LEU | A | 148 | 3029 | 3397 | 2955 | 162 | −213 | −234 | N |
| ATOM | 1154 | CA | LEU | A | 148 | 33.304 | −4.006 | 11.826 | 1.00 | 25.04 | | C |
| ANISOU | 1154 | CA | LEU | A | 148 | 3085 | 3463 | 2966 | 181 | −196 | −212 | C |
| ATOM | 1155 | CB | LEU | A | 148 | 33.463 | −4.040 | 10.557 | 1.00 | 24.63 | | C |
| ANISOU | 1155 | CB | LEU | A | 148 | 3035 | 3397 | 2927 | 155 | −168 | −185 | C |
| ATOM | 1156 | CG | LEU | A | 148 | 32.507 | −4.469 | 9.373 | 1.00 | 25.66 | | C |
| ANISOU | 1156 | CG | LEU | A | 148 | 3174 | 3508 | 3065 | 125 | −146 | −163 | C |
| ATOM | 1157 | CD1 | LEU | A | 148 | 32.702 | −5.706 | 8.310 | 1.00 | 27.87 | | C |
| ANISOU | 1157 | CD2 | LEU | A | 148 | 3457 | 3784 | 3348 | 115 | −126 | −146 | C |
| ATOM | 1158 | CD2 | LEU | A | 148 | 31.053 | −4.702 | 9.797 | 1.00 | 25.03 | | C |
| ANISOU | 1158 | CD2 | LEU | A | 148 | 3116 | 3433 | 2962 | 133 | −138 | −148 | C |
| ATOM | 1159 | C | LEU | A | 148 | 34.487 | 4.262 | 12.744 | 1.00 | 25.98 | | C |
| ANISOU | 1159 | C | LEU | A | 148 | 3190 | 3601 | 3079 | 210 | −220 | −236 | C |
| ATOM | 1160 | O | LEU | A | 148 | 35.542 | −3.653 | 12.586 | 1.00 | 27.87 | | O |
| ANISOU | 1160 | O | LEU | A | 148 | 3406 | 3832 | 3353 | 199 | −240 | −260 | O |
| ATOM | 1161 | N | VAL | A | 149 | 34.309 | −5.105 | 13.696 | 1.00 | 26.05 | | N |
| ANISOU | 1161 | N | VAL | A | 149 | 3210 | 3639 | 3049 | 247 | −218 | −225 | N |
| ATOM | 1162 | CA | VAL | A | 149 | 35.383 | −5.519 | 14.623 | 1.00 | 27.02 | | C |
| ANISOU | 1162 | CA | VAL | A | 149 | 3321 | 3786 | 3158 | 281 | −240 | −245 | C |
| ATOM | 1163 | CB | VAL | A | 149 | 34.967 | −5.282 | 16.103 | 1.00 | 27.95 | | C |
| ANISOU | 1163 | CB | VAL | A | 149 | 3445 | 3944 | 3232 | 334 | −260 | −261 | C |
| ATOM | 1164 | CG1 | VAL | A | 149 | 34.751 | −3.783 | 16.361 | 1.00 | 30.33 | | C |
| ANISOU | 1164 | CG1 | VAL | A | 149 | 3738 | 4289 | 3548 | 337 | −292 | −307 | C |
| ATOM | 1165 | CG2 | VAL | A | 149 | 33.720 | −6.079 | 16.459 | 1.00 | 27.05 | | C |
| ANISOU | 1165 | CG2 | VAL | A | 149 | 3349 | 3850 | 3077 | 351 | −231 | −213 | C |
| ATOM | 1166 | C | VAL | A | 149 | 35.796 | −6.970 | 14.376 | 1.00 | 27.59 | | C |
| ANISOU | 1166 | C | VAL | A | 149 | 3400 | 3861 | 3223 | 284 | −220 | −214 | C |
| ATOM | 1167 | O | VAL | A | 149 | 35.008 | −7.752 | 13.858 | 1.00 | 26.43 | | O |
| ANISOU | 1167 | O | VAL | A | 149 | 3269 | 3700 | 3071 | 271 | −184 | −177 | O |
| ATOM | 1168 | N | ASP | A | 150 | 37.032 | −7.325 | 14.721 | 1.00 | 28.28 | | N |
| ANISOU | 1168 | N | ASP | A | 150 | 3473 | 3961 | 3313 | 302 | −235 | −231 | N |
| ATOM | 1169 | CA | ASP | A | 150 | 37.494 | −8.708 | 14.560 | 1.00 | 29.84 | | C |
| ANISOU | 1169 | CA | ASP | A | 150 | 3676 | 4159 | 3503 | 312 | −221 | −206 | C |
| ATOM | 1170 | CB | ASP | A | 150 | 38.954 | −8.851 | 14.990 | 1.00 | 31.10 | | C |
| ANISOU | 1170 | CB | ASP | A | 150 | 3815 | 4337 | 3666 | 334 | −244 | −233 | C |
| ATOM | 1171 | CG | ASP | A | 150 | 39.498 | −10242 | 14.725 | 1.00 | 33.13 | | C |
| ANISOU | 1171 | CG | ASP | A | 150 | 4078 | 4592 | 3920 | 346 | −232 | −210 | C |
| ATOM | 1172 | OD1 | ASP | A | 150 | 39.749 | −10.985 | 15.702 | 1.00 | 37.42 | | O |
| ANISOU | 1172 | OD1 | ASP | A | 150 | 4625 | 5157 | 4435 | 386 | −240 | −201 | O |
| ATOM | 1173 | OD2 | ASP | A | 150 | 39.646 | −10.605 | 13.541 | 1.00 | 36.95 | | O |
| ANISOU | 1173 | OD2 | ASP | A | 150 | 4561 | 5053 | 4425 | 321 | −216 | −202 | O |
| ATOM | 1174 | C | ASP | A | 150 | 36.617 | −9.672 | 15.362 | 1.00 | 31.71 | | C |
| ANISOU | 1174 | C | ASP | A | 150 | 3934 | 4411 | 3705 | 341 | 209 | −165 | C |
| ATOM | 1175 | O | ASP | A | 150 | 35.070 | −9.296 | 16.407 | 1.00 | 31.70 | | O |
| ANISOU | 1175 | O | ASP | A | 150 | 3935 | 4439 | 3672 | 371 | −217 | −165 | O |
| ATOM | 1176 | N | VAL | A | 151 | 36.487 | −10.905 | 14.869 | 1.00 | 32.74 | | N |

TABLE 9-continued

Atomic coordinates for N-TXNIP(K5A/K6A) protein (SEQ ID NO: 8)

| | | | | | | | | | | |
|---|---|---|---|---|---|---|---|---|---|---|
| ANISOU | 1176 | N | VAL | A | 151 | 4077 | 4251 | 3843 | 33 | −193 | −132 | N |
| ATOM | 1177 | CA | VAL | A | 151 | 35.629 | −11.907 | 15.508 | 1.00 | 34.76 | C |
| ANISOU | 1177 | CA | VAL | A | 151 | 4347 | 4780 | 4078 | 355 | −181 | −81 | C |
| ATOM | 1178 | CB | VAL | A | 151 | 35.521 | −13.218 | 14.679 | 1.00 | 35.15 | C |
| ANISOU | 1178 | CB | VAL | A | 151 | 4410 | 4790 | 4157 | 339 | −171 | −51 | C |
| ATOM | 1179 | CG1 | VAL | A | 151 | 34.672 | −12.992 | 13.442 | 1.00 | 33.19 | C |
| ANISOU | 1179 | CG1 | VAL | A | 151 | 4169 | 4506 | 3934 | 296 | −158 | −50 | C |
| ATOM | 1180 | CG2 | VAL | A | 151 | 36.905 | −13.772 | 14.310 | 1.00 | 36.08 | C |
| ANISOU | 1180 | CG2 | VAL | A | 151 | 4522 | 4902 | 4287 | 350 | −183 | −76 | C |
| ATOM | 1181 | C | VAL | A | 151 | 36.038 | −12.221 | 16.951 | 1.00 | 36.97 | C |
| ANISOU | 1181 | C | VAL | A | 151 | 4622 | 5105 | 4321 | 408 | −193 | −72 | C |
| ATOM | 1182 | O | VAL | A | 151 | 35.181 | −12.525 | 17.788 | 1.00 | 37.10 | O |
| ANISOU | 1182 | O | VAL | A | 151 | 4843 | 5145 | 4309 | 431 | −183 | −30 | O |
| ATOM | 1183 | N | ASN | A | 152 | 37.338 | −12.128 | 17.228 | 1.00 | 38.52 | N |
| ANISOU | 1183 | N | ASN | A | 152 | 4805 | 5317 | 4514 | 428 | −213 | −108 | N |
| ATOM | 1184 | CA | ASN | A | 152 | 37.888 | −12.424 | 18.555 | 1.00 | 41.25 | C |
| ANISOU | 1184 | CA | ASN | A | 152 | 5144 | 5707 | 4821 | 483 | −228 | −107 | C |
| ATOM | 1185 | CB | ASN | A | 152 | 39.136 | −13.311 | 18.436 | 1.00 | 41.39 | C |
| ANISOU | 1185 | CB | ASN | A | 152 | 5156 | 5718 | 4850 | 497 | −208 | −112 | C |
| ATOM | 1186 | CG | ASN | A | 152 | 38.850 | −14.637 | 17.740 | 1.00 | 43.11 | C |
| ANISOU | 1186 | CG | ASN | A | 152 | 5391 | 5894 | 5094 | 481 | −220 | −67 | C |
| ATOM | 1187 | OD1 | ASN | A | 152 | 39.647 | −15.113 | 15.038 | 1.00 | 46.22 | O |
| ANISOU | 1187 | OD1 | ASN | A | 152 | 5784 | 6263 | 5514 | 470 | −224 | −84 | O |
| ATOM | 1188 | ND2 | ASN | A | 152 | 37.705 | −15.285 | 18.055 | 1.00 | 45.53 | N |
| ANISOU | 1188 | ND2 | ASN | A | 152 | 5711 | 6193 | 5395 | 483 | −204 | −10 | N |
| ATOM | 1189 | C | ASN | A | 152 | 38.197 | −11.176 | 19.388 | 1.00 | 43.00 | C |
| ANISOU | 1189 | C | ASN | A | 152 | 5350 | 5970 | 5017 | 510 | −255 | −157 | C |
| ATOM | 1190 | O | ASN | A | 152 | 39.061 | −11.207 | 20.273 | 1.00 | 44.17 | O |
| ANISOU | 1190 | O | ASN | A | 152 | 5487 | 6155 | 5141 | 554 | −278 | −180 | O |
| ATOM | 1191 | N | THR | A | 153 | 37.491 | −10.083 | 19.104 | 1.00 | 44.04 | N |
| ANISOU | 1191 | N | THR | A | 153 | 5483 | 6095 | 5157 | 488 | −255 | −176 | N |
| ATOM | 1192 | CA | THR | A | 153 | 37.646 | −8.850 | 19.875 | 1.00 | 45.86 | C |
| ANISOU | 1192 | CA | THR | A | 153 | 5099 | 6355 | 5368 | 510 | −288 | −232 | C |
| ATOM | 1193 | CB | THR | A | 153 | 37.055 | −7.619 | 19.133 | 1.00 | 46.24 | C |
| ANISOU | 1193 | CB | THR | A | 153 | 5747 | 6372 | 5448 | 474 | −292 | −259 | C |
| ATOM | 1194 | OG1 | THR | A | 153 | 37.583 | −6.409 | 19.721 | 1.00 | 49.27 | O |
| ANISOU | 1194 | OG1 | THR | A | 153 | 6115 | 6771 | 5835 | 496 | −336 | −323 | O |
| ATOM | 1195 | OG2 | THR | A | 153 | 35.526 | −7.618 | 19.175 | 1.00 | 47.28 | C |
| ANISOU | 1195 | OG2 | THR | A | 153 | 5897 | 6512 | 5557 | 474 | −266 | −220 | C |
| ATOM | 1196 | C | THR | A | 153 | 37.042 | −0.016 | 21.282 | 1.00 | 47.06 | C |
| ANISOU | 1196 | C | THR | A | 153 | 5855 | 6570 | 5455 | 582 | −291 | −214 | C |
| ATOM | 1197 | O | THR | A | 153 | 35.944 | −9.565 | 21.424 | 1.00 | 47.52 | O |
| ANISOU | 1197 | O | THR | A | 153 | 5926 | 6640 | 5491 | 584 | −261 | −156 | O |
| ATOM | 1198 | N | PRO | A | 154 | 37.776 | −5.580 | 22.324 | 1.00 | 47.90 | N |
| ANISOU | 1198 | N | PRO | A | 154 | 5948 | 6721 | 5530 | 636 | −328 | −260 | N |
| ATOM | 1199 | CA | PRO | A | 154 | 37.306 | −8.607 | 23.708 | 1.00 | 48.84 | C |
| ANISOU | 1199 | CA | PRO | A | 154 | 6066 | 6913 | 5576 | 712 | −333 | −247 | C |
| ATOM | 1200 | CB | PRO | A | 154 | 38.571 | −8.438 | 24.539 | 1.00 | 48.83 | C |
| ANISOU | 1200 | CB | PRO | A | 154 | 6061 | 6960 | 5572 | 761 | −379 | −307 | C |
| ATOM | 1201 | CG | PRO | A | 154 | 39.718 | −8.410 | 23.546 | 1.00 | 49.02 | C |
| ANISOU | 1201 | CG | PRO | A | 154 | 6062 | 6913 | 5851 | 705 | −391 | −336 | C |
| ATOM | 1202 | CD | PRO | A | 154 | 39.113 | −7.968 | 22.263 | 1.00 | 48.60 | C |
| ANISOU | 1202 | CD | PRO | A | 154 | 6017 | 6799 | 5651 | 632 | −369 | −327 | C |
| ATOM | 1203 | C | PRO | A | 154 | 36.227 | −7.672 | 24.059 | 1.00 | 49.62 | C |
| ANISOU | 1203 | C | PRO | A | 154 | 6168 | 7037 | 5848 | 732 | −340 | −267 | C |
| ATOM | 1204 | O | PRO | A | 154 | 36.003 | −6.723 | 23.306 | 1.00 | 50.12 | O |
| ANISOU | 1204 | O | PRO | A | 154 | 6233 | 7056 | 5754 | 688 | −350 | −303 | O |
| TER | 1205 | | PRO | A | 154 | | | | | | |
| ATOM | 1206 | O3 | GOL | B | 801 | −3.025 | −3.577 | −12.710 | 1.00 | 44.54 | O |
| ATOM | 1207 | O3 | GOL | B | 801 | −3.402 | −2.313 | −12.299 | 1.00 | 36.94 | C |
| ATOM | 1208 | O2 | GOL | B | 801 | −4.757 | −2.391 | −11.453 | 1.00 | 41.03 | C |
| ATOM | 1209 | O2 | GOL | B | 801 | −5.084 | −1.082 | −11.035 | 1.00 | 35.83 | O |
| ATOM | 1210 | O1 | GOL | B | 801 | −4.534 | −3.278 | −10.233 | 1.00 | 38.42 | C |
| ATOM | 1211 | O1 | GOL | B | 801 | −3.628 | −2.665 | −9.338 | 1.00 | 39.09 | O |
| ATOM | 1212 | O | HOH | W | 1 | 5.282 | 6.266 | 14.269 | 1.00 | 19.09 | O |
| ATOM | 1213 | O | HOH | W | 2 | 2.523 | −5.418 | −7.260 | 1.00 | 20.15 | O |
| ATOM | 1214 | O | HOH | W | 3 | 2.770 | 3.452 | 0.548 | 1.00 | 18.28 | O |
| ATOM | 1215 | O | HOH | W | 4 | 21.737 | 3.884 | −5.163 | 1.00 | 21.87 | O |
| ATOM | 1216 | O | HOH | W | 5 | 27.077 | 1.545 | 0.429 | 1.00 | 19.29 | O |
| ATOM | 1217 | O | HOH | W | 6 | 25.178 | 4.461 | −0.427 | 1.00 | 19.60 | O |
| ATOM | 1218 | O | HOH | W | 7 | 16.833 | −1.660 | −6.116 | 1.00 | 22.34 | O |
| ATOM | 1219 | O | HOH | W | 8 | 8.395 | 10.707 | 0.394 | 1.00 | 23.36 | O |
| ATOM | 1220 | O | HOH | W | 9 | 0.444 | −6.981 | −3.997 | 1.00 | 25.13 | O |
| ATOM | 1221 | O | HOH | W | 10 | 22.825 | −4.487 | −4.522 | 1.00 | 24.47 | O |
| ATOM | 1222 | O | HOH | W | 11 | 22.558 | 7.831 | 1.186 | 1.00 | 26.19 | O |
| ATOM | 1223 | O | HOH | W | 12 | 26.523 | −5.306 | 3.262 | 1.00 | 29.11 | O |
| ATOM | 1224 | O | HOH | W | 13 | 2.867 | −7.737 | −9.924 | 1.00 | 25.94 | O |
| ATOM | 1225 | O | HOH | W | 14 | 29.339 | −4.145 | 4.033 | 1.00 | 32.73 | O |

TABLE 9-continued

Atomic coordinates for N-TXNIP(K5A/K6A) protein (SEQ ID NO: 8)

| ATOM | 1226 | O | HOH | W | 15 | 11.835 | 5.796 | 6.506 | 1.00 | 27.41 | O |
|---|---|---|---|---|---|---|---|---|---|---|---|
| ATOM | 1227 | O | HOH | W | 16 | 17.832 | 8.912 | −3.663 | 1.00 | 30.12 | O |
| ATOM | 1228 | O | HOH | W | 17 | 8.221 | 8.158 | 3.157 | 1.00 | 26.88 | O |
| ATOM | 1229 | O | HOH | W | 18 | 6.492 | 5.890 | −17.768 | 1.00 | 27.52 | O |
| ATOM | 1230 | O | HOH | W | 19 | 1.834 | 4.347 | −1.858 | 1.00 | 28.73 | O |
| ATOM | 1231 | O | HOH | W | 20 | 21.764 | 5.427 | 16.137 | 1.00 | 36.04 | O |
| ATOM | 1232 | O | HOH | W | 21 | 12.563 | 3.322 | −10.834 | 1.00 | 23.21 | O |
| ATOM | 1233 | O | HOH | W | 22 | 39.315 | −9.182 | 11.298 | 1.00 | 32.44 | O |
| ATOM | 1234 | O | HOH | W | 23 | −3.332 | −1.561 | −15.069 | 1.00 | 29.23 | O |
| ATOM | 1235 | O | HOH | W | 24 | 1.684 | 7.198 | −0.265 | 1.00 | 29.24 | O |
| ATOM | 1236 | O | HOH | W | 25 | 22.140 | 8.922 | 3.745 | 1.00 | 35.91 | O |
| ATOM | 1237 | O | HOH | W | 26 | 35.301 | −2.123 | 9.091 | 1.00 | 38.80 | O |
| ATOM | 1238 | O | HOH | W | 27 | −5.897 | 10.697 | −3.872 | 1.00 | 37.08 | O |
| ATOM | 1239 | O | HOH | W | 28 | 15.726 | −2.204 | −9.921 | 1.00 | 37.83 | O |
| ATOM | 1240 | O | HOH | W | 29 | 14.252 | −0.798 | −12.142 | 1.00 | 34.25 | O |
| ATOM | 1241 | O | HOH | W | 30 | 26.165 | −2.913 | 17.815 | 1.00 | 31.54 | O |
| ATOM | 1242 | O | HOH | W | 31 | 13.649 | −10.827 | 4.194 | 1.00 | 49.90 | O |
| ATOM | 1243 | O | HOH | W | 32 | 23.051 | −8.578 | 16.864 | 1.00 | 47.91 | O |
| ATOM | 1244 | O | HOH | W | 33 | 14.980 | −11.527 | −1.540 | 1.00 | 49.85 | O |
| ATOM | 1245 | O | HOH | W | 34 | 20.845 | 11.511 | −5.172 | 1.00 | 33.12 | O |
| ATOM | 1246 | O | HOH | W | 35 | 24.148 | 2.661 | −4.425 | 1.00 | 35.43 | O |
| ATOM | 1247 | O | HOH | W | 36 | 7.432 | 11.531 | −6.963 | 1.00 | 26.53 | O |
| ATOM | 1248 | O | HOH | W | 37 | −3.496 | 8.931 | −7.061 | 1.00 | 38.42 | O |
| ATOM | 1249 | O | HOH | W | 38 | −0.085 | 10.654 | −10.537 | 1.00 | 34.65 | O |
| ATOM | 1250 | O | HOH | W | 39 | 31.580 | 1.604 | 16.076 | 1.00 | 36.23 | O |
| ATOM | 1251 | O | HOH | W | 40 | 30.657 | 6.889 | 6.765 | 1.00 | 36.33 | O |
| ATOM | 1252 | O | HOH | W | 41 | 30.346 | 6.928 | 12.790 | 1.00 | 35.49 | O |
| ATOM | 1253 | O | HOH | W | 42 | −0.565 | 3.943 | −1.545 | 1.00 | 35.31 | O |
| ATOM | 1254 | O | HOH | W | 43 | 40.272 | −12.895 | 12.525 | 1.00 | 33.00 | O |
| ATOM | 1255 | O | HOH | W | 44 | 17.610 | −11.912 | 1.026 | 1.00 | 53.03 | O |
| ATOM | 1256 | O | HOH | W | 45 | 5.872 | 5.087 | 9.876 | 1.00 | 52.85 | O |
| ATOM | 1257 | O | HOH | W | 46 | 6.775 | 6.757 | 6.106 | 1.00 | 49.76 | O |
| ATOM | 1258 | O | HOH | W | 47 | 18.369 | 12.430 | −7.988 | 1.00 | 35.91 | O |
| ATOM | 1259 | O | HOH | W | 48 | 0.329 | −3.236 | 2.246 | 1.00 | 61.26 | O |
| ATOM | 1260 | O | HOH | W | 49 | 15.688 | 10.724 | 0.987 | 1.00 | 30.14 | O |
| ATOM | 1261 | O | HOH | W | 50 | 24.325 | 10.633 | 9.374 | 1.00 | 40.54 | O |
| ATOM | 1262 | O | HOH | W | 51 | 2.395 | 13.693 | −4.515 | 1.00 | 42.84 | O |
| ATOM | 1263 | O | HOH | W | 52 | 24.486 | −0.589 | 19.373 | 1.00 | 40.89 | O |
| ATOM | 1264 | O | HOH | W | 53 | 12.206 | −11.616 | 0.135 | 1.00 | 46.85 | O |
| ATOM | 1265 | O | HOH | W | 54 | 7.770 | 12.767 | −12.059 | 1.00 | 39.57 | O |
| ATOM | 1266 | O | HOH | W | 55 | −1.050 | −5.024 | −13.767 | 1.00 | 50.16 | O |
| ATOM | 1267 | O | HOH | W | 56 | 40.951 | −9.621 | 17.868 | 1.00 | 48.00 | O |
| ATOM | 1268 | O | HOH | W | 57 | 24.501 | −7.006 | 1.575 | 1.00 | 45.24 | O |
| ATOM | 1269 | O | HOH | W | 58 | 27.096 | −6.859 | 1.290 | 1.00 | 52.29 | O |
| ATOM | 1270 | O | HOH | W | 59 | 24.463 | −2.147 | −3.943 | 1.00 | 40.07 | O |
| ATOM | 1271 | O | HOH | W | 60 | 37.429 | −5.299 | 10.536 | 1.00 | 43.55 | O |
| ATOM | 1272 | O | HOH | W | 61 | 2.222 | −11.298 | −3.480 | 1.00 | 44.19 | O |
| ATOM | 1273 | O | HOH | W | 62 | 32.269 | −23.427 | 16.709 | 1.00 | 39.35 | O |
| ATOM | 1274 | O | HOH | W | 63 | −0.603 | 6.363 | 1.838 | 1.00 | 47.07 | O |
| ATOM | 1275 | O | HOH | W | 64 | 7.926 | −3.723 | 5.420 | 1.00 | 42.42 | O |
| ATOM | 1276 | O | HOH | W | 65 | 21.089 | −11.488 | 3.748 | 1.00 | 45.92 | O |
| ATOM | 1277 | O | HOH | W | 66 | 5.190 | 12.749 | −6.013 | 1.00 | 37.20 | O |
| ATOM | 1278 | O | HOH | W | 67 | 19.987 | −4.154 | −5.672 | 1.00 | 36.45 | O |
| ATOM | 1279 | O | HOH | W | 68 | 6.430 | −11.548 | −6.103 | 1.00 | 43.48 | O |
| ATOM | 1280 | O | HOH | W | 69 | 0.218 | 3.349 | 1.713 | 1.00 | 34.90 | O |
| ATOM | 1281 | O | HOH | W | 70 | 28.714 | −10.578 | 12.494 | 1.00 | 33.16 | O |
| ATOM | 1282 | O | HOH | W | 71 | 16.138 | 5.966 | 12.660 | 1.00 | 45.25 | O |
| ATOM | 1283 | O | HOH | W | 72 | 5.488 | 14.792 | 2.429 | 1.00 | 51.47 | O |
| ATOM | 1284 | O | HOH | W | 73 | 22.654 | −9.761 | 0.607 | 1.00 | 48.15 | O |
| ATOM | 1285 | O | HOH | W | 74 | 10.375 | −1.648 | 12.257 | 1.00 | 37.88 | O |
| ATOM | 1286 | O | HOH | W | 75 | 11.886 | −4.984 | 13.504 | 1.00 | 45.51 | O |
| ATOM | 1287 | O | HOH | W | 76 | 7.476 | 14.681 | 0.873 | 1.00 | 43.55 | O |
| ATOM | 1288 | O | HOH | W | 77 | 30.904 | −13.371 | 14.461 | 1.00 | 34.99 | O |
| ATOM | 1289 | O | HOH | W | 78 | 23.128 | −10.164 | −2.983 | 1.00 | 47.13 | O |
| ATOM | 1290 | O | HOH | W | 79 | 23.260 | −14.586 | 6.223 | 1.00 | 40.31 | O |
| ATOM | 1291 | O | HOH | W | 80 | −6.243 | −6.150 | −1.383 | 1.00 | 53.35 | O |
| ATOM | 1292 | O | HOH | W | 81 | 28.184 | −13.579 | 12.071 | 1.00 | 34.94 | O |
| ATOM | 1293 | O | HOH | W | 82 | 38.811 | −5.248 | 15.485 | 1.00 | 45.36 | O |
| ATOM | 1294 | O | HOH | W | 83 | 35.880 | 0.717 | 10.389 | 1.00 | 39.27 | O |
| ATOM | 1295 | O | HOH | W | 84 | 15.307 | 2.892 | −14.282 | 1.00 | 46.45 | O |
| ATOM | 1296 | O | HOH | W | 85 | −1.301 | 15.504 | −4.876 | 1.00 | 44.97 | O |
| ATOM | 1297 | O | HOH | W | 86 | 33.212 | −0.582 | 15.860 | 1.00 | 43.94 | O |
| ATOM | 1298 | O | HOH | W | 87 | 30.855 | −10.555 | 3.360 | 1.00 | 61.57 | O |
| ATOM | 1299 | O | HOH | W | 88 | 26.757 | 7.112 | −8.957 | 1.00 | 59.41 | O |
| ATOM | 1300 | O | HOH | W | 89 | 9.305 | 13.270 | −7.820 | 1.00 | 58.22 | O |
| ATOM | 1301 | O | HOH | W | 90 | −3.975 | 8.983 | −4.457 | 1.00 | 37.79 | O |
| ATOM | 1302 | O | HOH | W | 91 | 1.412 | −1.103 | 4.568 | 1.00 | 46.52 | O |
| ATOM | 1303 | O | HOH | W | 92 | 28.009 | −2.786 | −3.028 | 1.00 | 55.39 | O |

TABLE 9-continued

| Atomic coordinates for N-TXNIP(K5A/K6A) protein (SEQ ID NO: 8) | | | | | | | | | | |
|---|---|---|---|---|---|---|---|---|---|---|
| ATOM | 1304 | O | HOH | W | 93 | −0.446 | 8.851 | −0.647 | 1.00 | 42.40 | O |
| ATOM | 1305 | O | HOH | W | 94 | 29.160 | −6.863 | 17.337 | 1.00 | 64.08 | O |
| ATOM | 1306 | O | HOH | W | 95 | 10.935 | −2.057 | −18.154 | 1.00 | 46.21 | O |
| ATOM | 1307 | O | HOH | W | 96 | 33.934 | −27.065 | 14.429 | 1.00 | 51.48 | O |
| ATOM | 1308 | O | HOH | W | 97 | −5.99 | 7.578 | −15.180 | 1.00 | 56.75 | O |
| ATOM | 1309 | O | HOH | W | 98 | 27.670 | −17.229 | 5.174 | 1.00 | 42.70 | O |
| ATOM | 1310 | O | HOH | W | 99 | 13.263 | 5.969 | −19.606 | 1.00 | 57.99 | O |
| ATOM | 1311 | O | HOH | W | 100 | −0.403 | −5.370 | −17.536 | 1.00 | 45.51 | O |
| END | | | | | | | | | | | |

TABLE 10

Atomic coordinates for COM1 complex of the modified
TXNIP protein represented by SEQ ID NO: 6 and the modified protein represented by SEQ ID NO: 3

| | | |
|---|---|---|
| HEADER | | XX-XXX-9-xxx |
| COMPND | | |
| REMARK | 3 | |
| REMARK | 3 | REFINEMENT. |
| REMARK | 3 | PROGRAM: REFMAC 5.2.0019 |
| REMARK | 3 | AUTHORS: MURSHUDOV.VAGIN.DODSON |
| REMARK | 3 | |
| REMARK | 3 | REFINEMENT TARGET: MAXIMUM LIKELIHOOD |
| REMARK | 3 | |
| REMARK | 3 | DATA USED IN REFINEMENT. |
| REMARK | 3 | RESOLUTION RANGE HIGH (ANGSTROMS): 2.00 |
| REMARK | 3 | RESOLUTION RANGE LOW (ANGSTROMS): 30.00 |
| REMARK | 3 | DATA CUTOFF (SIGMA(F)): NONE |
| REMARK | 3 | COMPLETENESS FOR RANGE (%): 96.40 |
| REMARK | 3 | NUMBER OF REFLECTIONS: 55014 |
| REMARK | 3 | |
| REMARK | 3 | FIT TO DATA USED IN REFINEMENT. |
| REMARK | 3 | CROSS-VALIDATION METHOD: THROUGHOUT |
| REMARK | 3 | FREE R VALUE TEST SET SELECTION: RANDOM |
| REMARK | 3 | R VALUE (WORKING + TEST SET): 0.22399 |
| REMARK | 3 | R VALUE (WORKING SET): 0.22048 |
| REMARK | 3 | FREE R VALUE: 0.28806 |
| REMARK | 3 | FREE R VALUE TEST SET SIZE (%): 5.1 |
| REMARK | 3 | FREE R VALUE TEST SET COUNT: 2997 |
| REMARK | 3 | |
| REMARK | 3 | FIT IN THE HIGHEST RESOLUTION BIN. |
| REMARK | 3 | TOTAL NUMBER OF BINS USED: 20 |
| REMARK | 3 | BIN RESOLUTION RANGE HIGH: 1.995 |
| REMARK | 3 | BIN RESOLUTION RANGE LOW: 2.047 |
| REMARK | 3 | REFLECTION IN BIN (WORKING SET): 3204 |
| REMARK | 3 | BIN COMPLETENESS (WORKING + TEST) (%): 75.31 |
| REMARK | 3 | BIN R VALUE (WORKING SET): 0.264 |
| REMARK | 3 | BIN FREE R VALUE SET COUNT: 179 |
| REMARK | 3 | BIN FREE R VALUE: 0.340 |
| REMARK | 3 | |
| REMARK | 3 | NUMBER OR NON-HYDROGEN ATOMS USED IN REFINEMENT. |
| REMARK | 3 | ALL ATOMS: 6259 |
| REMARK | 3 | |
| REMARK | 3 | B VALUES. |
| REMARK | 3 | FROM WILSON PLOT (A**2): NULL |
| REMARK | 3 | MEAN B VALUE (OVERALL, A**2): 51.648 |
| REMARK | 3 | OVERALL ANISOTROPIC B VALUE. |
| REMARK | 3 | B11 (A**2): −1.35 |
| REMARK | 3 | B22 (A**2): 1.66 |
| REMARK | 3 | B33 (A**2): −0.33 |
| REMARK | 3 | B12 (A**2): 0.00 |
| REMARK | 3 | B13 (A**2): −0.45 |
| REMARK | 3 | B23 (A**2): 0.00 |

TABLE 10-continued

Atomic coordinates for COM1 complex of the modified
TXNIP protein represented by SEQ ID NO: 6 and the modified protein represented by SEQ ID NO: 3

| REMARK | 3 | | |
|---|---|---|---|
| REMARK | 3 | ESTIMATED OVERALL COORDINATE ERROR. | |
| REMARK | 3 | ESU BASED ON R VALUE | (A): 0.204 |
| REMARK | 3 | ESU BASED ON FREE R VALUE | (A): 0.198 |
| REMARK | 3 | ESU BASED ON MAXIMUM LIKELIHOOD | (A): 0.185 |
| REMARK | 3 | ESU FOR B VALUES BASED ON MAXIMUM LIKELIHOOD (A**2): | 13.619 |
| REMARK | 3 | | |
| REMARK | 3 | CORRELATION COEFFICIENTS. | |
| REMARK | 3 | CORRELATION COEFFICIENT FO-FC:      0.955 | |
| REMARK | 3 | CORRELATION COEFFICIENT FO-FC FREE: 0.923 | |
| REMARK | 3 | | |
| REMARK | 3 | RMS DEVIATIONS FROM IDEAL VALUES    COUNT  RMS    WEIGHT | |
| REMARK | 3 | BOND LENGTHS REFINED ATOMS        (A): 6122; 0.015; 0.022 | |
| REMARK | 3 | BOND ANGLES REFINED ATOMS   (DEGREES): 8246; 1.594; 1.967 | |
| REMARK | 3 | TORSION ANGLES, PERIOD 1   (DEGREES): 760; 7.206; 5.000 | |
| REMARK | 3 | TORSION ANGLES, PERIOD 2   (DEGREES): 258; 32.450; 24.496 | |
| REMARK | 3 | TORSION ANGLES, PERIOD 3   (DEGREES): 1133; 18.895; 15.000 | |
| REMARK | 3 | TORSION ANGLES, PERIOD 4   (DEGREES): 33; 17.581; 15.000 | |
| REMARK | 3 | CHIRAL-CENTER RESTRAINTS (A**3): 925; 0.107; 0.200 | |
| REMARK | 3 | GENERAL PLANES REFINED ATOMS     (A): 4499; 0.006; 0.020 | |
| REMARK | 3 | NON-BONDED CONTACTS REFINED ATOMS     (A): 2355; 0.218; 0.200 | |
| REMARK | 3 | NON-BONDED TORSION REFINED ATOMS  (A): 4082; 0.308; 0.200 | |
| REMARK | 3 | H-BOND (X...Y) REFINED ATOMS (A):  328; 0.152; 0.200 | |
| REMARK | 3 | SYMMETRY VDW REFINED ATOMS (A):   54; 0.245; 0.200 | |
| REMARK | 3 | SYMMETRY H-BOND REFINED ATOMS (A):  12; 0.164; 0.200 | |
| REMARK | 3 | | |
| REMARK | 3 | ISOTROPIC THERMAL FACTOR RESTRAINTS.    COUNT  RMS    WEIGHT | |
| REMARK | 3 | MAIN-CHAIN BOND REFINED ATOMS (A**2): 3914; 2.633; 3.000 | |
| REMARK | 3 | MAIN-CHAIN ANGLE REFINED ATOMS (A**2): 6171; 3.683; 5.000 | |
| REMARK | 3 | SIDE-CHAIN BOND REFINED ATOMS (A**2): 2476; 6.144; 8.000 | |
| REMARK | 3 | SIDE-CHAIN ANGLE REFINED ATOMS (A**2): 2075; 8.258; 11.000 | |
| REMARK | 3 | | |
| REMARK | 3 | NCS RESTRAINTS STATISTICS | |
| REMARK | 3 | NUMBER OF NCS GROUPS: NULL | |
| REMARK | 3 | | |
| REMARK | 3 | TLS DETAILS | |
| REMARK | 3 | NUMBER OF TLS GROUPS: 4 | |
| REMARK | 3 | ATOM RECORD CONTAINS RESIDUAL B FACTORS ONLY | |
| REMARK | 3 | | |
| REMARK | 3 | TLS GROUP:   1 | |
| REMARK | 3 | NUMBER OF COMPONENTS GROUP:  1 | |
| REMARK | 3 | COMPONENTS         C      SSSEQI         TO            C SSSEQI | |
| REMARK | 3 | RESIDUE RANGE:     A        7                            A  298 | |
| REMARK | 3 | ORIGIN FOR THE GROUP (A): -29.3950  -0.5280  41.4110 | |
| REMARK | 3 | T TENSOR | |
| REMARK | 3 | T11:  0.0086 T22:   0.1864 | |
| REMARK | 3 | T33: -0.1294 T12:   0.1721 | |
| REMARK | 3 | T13: -0.0091 T23:  -0.0405 | |
| REMARK | 3 | L TENSOR | |

TABLE 10-continued

Atomic coordinates for COM1 complex of the modified
TXNIP protein represented by SEQ ID NO: 6 and the modified protein represented by SEQ ID NO: 3

| | | | | | | | | |
|---|---|---|---|---|---|---|---|---|
| REMARK | 3 | | L11: 2.1364 | L22: 0.4145 | | | | |
| REMARK | 3 | | L33: 1.8760 | L12: −0.6465 | | | | |
| REMARK | 3 | | L13: 1.9281 | L33: −0.7565 | | | | |
| REMARK | 3 | S TENSOR | | | | | | |
| REMARK | 3 | | S11: −0.2656 | S12: −0.2843 | S13: −0.0318 | | | |
| REMARK | 3 | | S21: 0.0691 | S22: 0.2351 | S23: −0.0044 | | | |
| REMARK | 3 | | S31: −0.3348 | S32: −0.2249 | S33: 0.0306 | | | |
| REMARK | 3 | TLS GROUP: 2 | | | | | | |
| REMARK | 3 | NUMBER OF COMPONENTS GROUP: 1 | | | | | | |
| REMARK | 3 | COMPONENTS | C | SSSCQI | TO | B | SSSCQI | |
| REMARK | 3 | RESIDUE RANGE: | B | 1 | | C | 105 | |
| REMARK | 3 | ORIGIN FOR THE GROUP (A): −68.0280 | | 1.2130 | 6.2330 | | | |
| REMARK | 3 | T TENSOR | | | | | | |
| REMARK | 3 | | T11: −0.0458 | T22: −0.0219 | | | | |
| REMARK | 3 | | T33: −0.0363 | T12: −0.0151 | | | | |
| REMARK | 3 | | T13: −0.1599 | T23: 0.0190 | | | | |
| REMARK | 3 | L TENSOR | | | | | | |
| REMARK | 3 | | L11: 10.4144 | L22: 1.8975 | | | | |
| REMARK | 3 | | L33: 5.5400 | L12: −0.8794 | | | | |
| REMARK | 3 | | L13: 3.0145 | L23: −2.1954 | | | | |
| REMARK | 3 | S TENSOR | | | | | | |
| REMARK | 3 | | S11: 0.5389 | S12: −0.1348 | S13: −1.1150 | | | |
| REMARK | 3 | | S21: −0.4434 | S22: 0.2058 | S23: 0.7639 | | | |
| REMARK | 3 | | S31: 0.7874 | S32: −0.6519 | S33: −0.7447 | | | |
| REMARK | 3 | TLS GROUP 3 | | | | | | |
| REMARK | 3 | NUMBER OF COMPONENTS GROUP: 1 | | | | | | |
| REMARK | 3 | COMPONENTS | C | SSSEQI | TO | C | SSSEQI | |
| REMARK | 3 | RESIDUE RANGE: | C | 8 | | C | 209 | |
| REMARK | 3 | ORIGIN FOR THE GROUP (A): 1.3340 | | 4.6380 | 38.9420 | | | |
| REMARK | 3 | T TENSOR | | | | | | |
| REMARK | 3 | | T11: −0.1543 | T22: 0.0591 | | | | |
| REMARK | 3 | | T33: −0.1018 | T12: −0.0041 | | | | |
| REMARK | 3 | | T13: −0.0518 | T23: −0.0003 | | | | |
| REMARK | 3 | L TENSOR | | | | | | |
| REMARK | 3 | | L11: 1.0062 | L22: 0.2909 | | | | |
| REMARK | 3 | | L33: 1.1938 | L12: −0.0006 | | | | |
| REMARK | 3 | | L13: 0.8690 | L23: −0.0244 | | | | |
| REMARK | 3 | S TENSOR | | | | | | |
| REMARK | 3 | | S11: 0.0059 | S12: 0.0537 | S13: −0.1053 | | | |
| REMARK | 3 | | S21: 0.0770 | S22: −0.0097 | S23: 0.0426 | | | |
| REMARK | 3 | | S31: −0.0280 | S32: 0.0051 | S33: 0.0038 | | | |
| REMARK | 3 | TLS GROUP: 4 | | | | | | |
| REMARK | 3 | NUMBER OF COMPONENTS GROUP: 1 | | | | | | |
| REMARK | 3 | COMPONENTS | C | SSSEQI | TO | D | SSSEQI | |
| REMARK | 3 | RESIDUE RANGE: | D | 1 | | C | 105 | |
| REMARK | 3 | ORIGIN FOR THE GROUP (A): 39.4190 | | 8.8870 | 74.2550 | | | |
| REMARK | 3 | T TENSOR | | | | | | |

TABLE 10-continued

Atomic coordinates for COM1 complex of the modified TXNIP protein represented by SEQ ID NO: 6 and the modified protein represented by SEQ ID NO: 3

| | | | | | | | | | | | | | | |
|---|---|---|---|---|---|---|---|---|---|---|---|---|---|---|
| REMARK | 3 | | T11: −0.0550 | T22: −0.0736 | | | | | | | | | | |
| REMARK | 3 | | T33: −0.0343 | T12: −0.0072 | | | | | | | | | | |
| REMARK | 3 | | T13: −0.2063 | T23: 0.0637 | | | | | | | | | | |
| REMARK | 3 | L TENSOR | | | | | | | | | | | | |
| REMARK | 3 | | L11: 3.9622 | L22: 3.4458 | | | | | | | | | | |
| REMARK | 3 | | L33: 4.6601 | L12: 1.0479 | | | | | | | | | | |
| REMARK | 3 | | L13: 0.5060 | L23: 1.6727 | | | | | | | | | | |
| REMARK | 3 | S TENSOR | | | | | | | | | | | | |
| REMARK | 3 | | S11: 0.3524 | S12: 0.1625 | S13: −0.8176 | | | | | | | | | |
| REMARK | 3 | | S21: 0.5117 | S22: 0.0161 | S23: −0.8845 | | | | | | | | | |
| REMARK | 3 | | S31: 0.4833 | S32: 0.3755 | S33: −0.3685 | | | | | | | | | |
| REMARK | 3 | BULK SOLVENT MODELLING. | | | | | | | | | | | | |
| REMARK | 3 | METHOD USED: MASK | | | | | | | | | | | | |
| REMARK | 3 | PARAMETERS FOR MASK CALCULATION | | | | | | | | | | | | |
| REMARK | 3 | VDW PROBE RADIUS: 1.20 | | | | | | | | | | | | |
| REMARK | 3 | ION PROBE RADIUS: 0.80 | | | | | | | | | | | | |
| REMARK | 3 | SHRINKAGE RADIUS: 0.80 | | | | | | | | | | | | |
| REMARK | 3 | | | | | | | | | | | | | |
| REMARK | 3 | OTHER REFINEMENT REMARKS: NULL | | | | | | | | | | | | |
| LINK | | VAL A 146 | | PRO A 154 | | | | | | | | | | |
| LINK | | ILE A 260 | | ASN A 268 | | | | | | | | | | |
| LINK | | ASP C 147 | | PRO C 154 | | | | | | | | | | |
| LINK | | LYS C 259 | | GLY C 265 | | | | | | | | | | |
| LINK | | ASN A 142 | | PRO A 154 | | | | | | | | | | |
| LINK | | LEU A 105 | | GLY A 116 | | | | | | | | | | |
| LINK | | THR A 220 | | LYS A 228 | | | | | | | | | | |
| LINK | | LYS A 259 | | ARG A 271 | | | | | | | | | | |
| LINK | | GLU A 34 | | VAL A 44 | | | | | | | | | | |
| LINK | | LEU A 129 | | ARG A 131 | | | | | | | | | | |
| LINK | | ALA C 223 | | GLY C 225 | | | | | | | | | | |
| CISPEP | 1 | MET B 74 | PRO B 75 | | | | | | | | 0.00 | | | |
| CISPEP | 2 | ASN C 224 | GLY C 225 | | | | | | | | 0.00 | | | |
| CISPEP | 3 | MET D 74 | PRO D 75 | | | | | | | | 0.00 | | | |
| SSBOND | 1 | CYS C 63 | CYS C 190 | | | | | | | | | | | |
| SSBOND | 2 | CYS A 63 | CYS A 190 | | | | | | | | | | | |
| SSBOND | 3 | CYS C 247 | CYS D 32 | | | | | | | | | | | |
| CRYST1 | 80.135 | 64.022 | 88.295 | 90.00 | 91.28 | 90.00 | P 1 21 1 | | | | | | | |
| SCALE1 | | 0.012478 | 0.000000 | 0.000278 | | | | | | | 0.00000 | | | |
| SCALE2 | | 0.000000 | 0.015620 | 0.000000 | | | | | | | 0.00000 | | | |
| SCALE3 | | 0.000000 | 0.000000 | 0.011328 | | | | | | | 0.00000 | | | |
| ATOM | 1 | N | | ILE | A | 7 | −11.353 | −8.077 | 73.631 | 1.00 | 58.79 | | | N |
| ATOM | 2 | CA | | ILE | A | 7 | −11.103 | −6.775 | 72.926 | 1.00 | 57.02 | | | C |
| ATOM | 3 | CB | | ILE | A | 7 | −11.345 | −6.859 | 71.396 | 1.00 | 54.52 | | | C |
| ATOM | 4 | CG1 | | ILE | A | 7 | −10.312 | −7.774 | 70.728 | 1.00 | 57.32 | | | C |
| ATOM | 5 | CD1 | | ILE | A | 7 | −8.892 | −7.180 | 70.587 | 1.00 | 55.49 | | | C |
| ATOM | 6 | CG2 | | ILE | A | 7 | −11.250 | −5.481 | 70.748 | 1.00 | 48.93 | | | C |
| ATOM | 7 | C | | ILE | A | 7 | −11.933 | −5.666 | 73.544 | 1.00 | 56.60 | | | C |

TABLE 10-continued

Atomic coordinates for COM1 complex of the modified
TXNIP protein represented by SEQ ID NO: 6 and the modified protein represented by SEQ ID NO: 3

| ATOM | 8 | O | ILE | A | 7 | −13.167 | −5.731 | 73.557 | 1.00 | 59.90 | O |
|---|---|---|---|---|---|---|---|---|---|---|---|
| ATOM | 9 | N | LYS | A | 8 | −11.239 | −4.841 | 74.032 | 1.00 | 54.74 | N |
| ATOM | 10 | CA | LYS | A | 8 | −11.836 | −3.567 | 74.832 | 1.00 | 55.14 | C |
| ATOM | 11 | CB | LYS | A | 8 | −10.738 | −2.613 | 75.313 | 1.00 | 55.51 | C |
| ATOM | 12 | CG | LYS | A | 8 | −11.056 | −1.932 | 76.619 | 1.00 | 60.84 | C |
| ATOM | 13 | CD | LYS | A | 8 | −9.897 | −1.092 | 77.111 | 1.00 | 65.45 | C |
| ATOM | 14 | CE | LYS | A | 8 | −9.879 | 0.267 | 76.441 | 1.00 | 62.59 | C |
| ATOM | 15 | NZ | LYS | A | 8 | −8.838 | 1.128 | 77.063 | 1.00 | 79.08 | N |
| ATOM | 16 | C | LYS | A | 8 | −12.931 | −2.791 | 74.103 | 1.00 | 53.36 | C |
| ATOM | 17 | O | LYS | A | 8 | −14.047 | −2.658 | 74.502 | 1.00 | 57.18 | O |
| ATOM | 18 | N | SER | A | 9 | −12.585 | −2.256 | 72.943 | 1.00 | 50.08 | N |
| ATOM | 19 | CA | SER | A | 9 | −13.513 | −1.588 | 72.052 | 1.00 | 46.63 | C |
| ATOM | 20 | CB | SER | A | 9 | −13.592 | −0.097 | 72.355 | 1.00 | 48.20 | C |
| ATOM | 21 | OG | SER | A | 9 | −12.345 | 0.521 | 72.090 | 1.00 | 51.80 | O |
| ATOM | 22 | C | SER | A | 9 | −13.079 | −1.745 | 70.601 | 1.00 | 45.45 | C |
| ATOM | 23 | O | SER | A | 9 | −11.879 | −1.839 | 70.292 | 1.00 | 46.12 | O |
| ATOM | 24 | N | PHE | A | 10 | −14.076 | −1.728 | 69.724 | 1.00 | 45.74 | N |
| ATOM | 25 | CA | PHE | A | 10 | −13.926 | −1.909 | 68.282 | 1.00 | 44.87 | C |
| ATOM | 26 | CB | PHE | A | 10 | −13.812 | −3.403 | 67.941 | 1.00 | 42.94 | C |
| ATOM | 27 | CG | PHE | A | 10 | −13.514 | −3.580 | 66.502 | 1.00 | 43.35 | C |
| ATOM | 28 | CD1 | PHE | A | 10 | −12.469 | −3.053 | 65.864 | 1.00 | 44.11 | C |
| ATOM | 29 | CE1 | PHE | A | 10 | −12.199 | −3.329 | 64.526 | 1.00 | 40.46 | C |
| ATOM | 30 | CZ | PHE | A | 10 | −12.998 | −4.213 | 63.831 | 1.00 | 39.26 | C |
| ATOM | 31 | CE2 | PHE | A | 10 | −14.026 | −4.846 | 64.464 | 1.00 | 42.62 | C |
| ATOM | 32 | CD2 | PHE | A | 10 | −14.288 | −4.581 | 65.783 | 1.00 | 33.66 | C |
| ATOM | 33 | C | PHE | A | 10 | −15.191 | −1.005 | 67.718 | 1.00 | 40.97 | C |
| ATOM | 34 | O | PHE | A | 10 | −16.292 | −1.829 | 67.920 | 1.00 | 44.38 | O |
| ATOM | 35 | N | GLU | A | 11 | −15.039 | −0.157 | 67.056 | 1.00 | 43.07 | N |
| ATOM | 36 | CA | GLU | A | 11 | −16.169 | 0.640 | 66.645 | 1.00 | 43.56 | C |
| ATOM | 37 | CB | GLU | A | 11 | −16.591 | 1.619 | 67.769 | 1.00 | 44.87 | C |
| ATOM | 38 | CG | GLU | A | 11 | −17.170 | 0.992 | 69.078 | 1.00 | 56.04 | C |
| ATOM | 39 | CD | GLU | A | 11 | −18.509 | 0.261 | 68.904 | 1.00 | 65.09 | C |
| ATOM | 40 | OE1 | GLU | A | 11 | −10.303 | 0.626 | 68.006 | 1.00 | 66.87 | O |
| ATOM | 41 | OE2 | GLU | A | 11 | −18.770 | −0.679 | 69.690 | 1.00 | 65.70 | O |
| ATOM | 42 | C | GLU | A | 11 | −15.879 | 1.447 | 65.376 | 1.00 | 41.06 | C |
| ATOM | 43 | O | GLU | A | 11 | −14.760 | 1.920 | 65.174 | 1.00 | 40.89 | O |
| ATOM | 44 | N | VAL | A | 12 | −16.909 | 1.609 | 64.549 | 1.00 | 40.75 | N |
| ATOM | 45 | CA | VAL | A | 12 | −16.891 | 2.527 | 63.396 | 1.00 | 41.71 | C |
| ATOM | 46 | CB | VAL | A | 12 | −17.813 | 1.975 | 62.274 | 1.00 | 43.62 | C |
| ATOM | 47 | CG1 | VAL | A | 12 | −17.854 | 2.901 | 61.027 | 1.00 | 35.75 | C |
| ATOM | 48 | CG2 | VAL | A | 12 | −17.367 | 0.545 | 61.856 | 1.00 | 41.71 | C |
| ATOM | 49 | C | VAL | A | 12 | −17.396 | 3.908 | 63.866 | 1.00 | 44.46 | C |
| ATOM | 50 | O | VAL | A | 12 | −18.530 | 4.013 | 64.326 | 1.00 | 45.11 | O |
| ATOM | 51 | N | VAL | A | 13 | −16.566 | 4.953 | 63.788 | 1.00 | 45.03 | N |
| ATOM | 52 | CA | VAL | A | 13 | −17.013 | 6.302 | 64.151 | 1.00 | 46.58 | C |
| ATOM | 53 | CB | VAL | A | 13 | −16.313 | 6.874 | 65.432 | 1.00 | 47.91 | C |
| ATOM | 54 | CG1 | VAL | A | 13 | −17.005 | 8.186 | 65.927 | 1.00 | 51.51 | C |
| ATOM | 55 | CG2 | VAL | A | 13 | −16.296 | 5.837 | 66.583 | 1.00 | 51.14 | C |
| ATOM | 56 | C | VAL | A | 13 | −16.863 | 7.263 | 62.968 | 1.00 | 46.72 | C |
| ATOM | 57 | O | VAL | A | 13 | −15.756 | 7.692 | 62.636 | 1.00 | 47.56 | O |

TABLE 10-continued

Atomic coordinates for COM1 complex of the modified
TXNIP protein represented by SEQ ID NO: 6 and the modified protein represented by SEQ ID NO: 3

| ATOM | 58 | N | PHE | A | 14 | −17.991 | 7.583 | 62.337 | 1.00 | 45.98 | N |
|---|---|---|---|---|---|---|---|---|---|---|---|
| ATOM | 59 | CA | PHE | A | 14 | −18.049 | 8.552 | 61.227 | 1.00 | 48.87 | C |
| ATOM | 60 | CB | PHE | A | 14 | −19.457 | 8.600 | 60.616 | 1.00 | 46.97 | C |
| ATOM | 61 | CG | PHE | A | 14 | −19.930 | 7.274 | 60.065 | 1.00 | 46.10 | C |
| ATOM | 62 | CD1 | PHE | A | 14 | −19.450 | 6.799 | 58.845 | 1.00 | 44.60 | C |
| ATOM | 63 | CE1 | PHE | A | 14 | −19.871 | 5.573 | 58.339 | 1.00 | 45.53 | C |
| ATOM | 64 | CZ | PHE | A | 14 | −20.789 | 4.810 | 59.047 | 1.00 | 44.93 | C |
| ATOM | 65 | CE2 | PHE | A | 14 | −21.289 | 5.293 | 60.269 | 1.00 | 42.29 | C |
| ATOM | 66 | CD2 | PHE | A | 14 | −20.855 | 6.508 | 60.758 | 1.00 | 41.46 | C |
| ATOM | 67 | C | PHE | A | 14 | −17.662 | 9.929 | 61.736 | 1.00 | 50.79 | C |
| ATOM | 68 | O | PHE | A | 14 | −17.846 | 10.211 | 62.922 | 1.00 | 51.18 | O |
| ATOM | 69 | N | ASN | A | 15 | −17.096 | 10.763 | 60.863 | 1.00 | 53.77 | N |
| ATOM | 70 | CA | ASN | A | 15 | −16.657 | 12.112 | 61.257 | 1.00 | 56.91 | C |
| ATOM | 71 | CB | ASN | A | 15 | −15.792 | 12.755 | 60.168 | 1.00 | 57.71 | C |
| ATOM | 72 | CG | ASN | A | 15 | −14.440 | 12.061 | 59.990 | 1.00 | 61.04 | C |
| ATOM | 73 | OD1 | ASN | A | 15 | −13.847 | 11.540 | 60.945 | 1.00 | 61.86 | O |
| ATOM | 74 | ND2 | ASN | A | 15 | −13.944 | 12.060 | 58.755 | 1.00 | 63.82 | N |
| ATOM | 75 | C | ASN | A | 15 | −17.827 | 13.025 | 61.625 | 1.00 | 59.11 | C |
| ATOM | 76 | O | ASN | A | 15 | −17.717 | 13.850 | 62.538 | 1.00 | 58.71 | O |
| ATOM | 77 | N | ASP | A | 16 | −18.936 | 12.866 | 60.907 | 1.00 | 59.29 | N |
| ATOM | 78 | CA | ASP | A | 16 | −20.215 | 13.489 | 61.250 | 1.00 | 60.67 | C |
| ATOM | 79 | CB | ASP | A | 16 | −20.717 | 14.383 | 60.099 | 1.00 | 63.20 | C |
| ATOM | 80 | CG | ASP | A | 16 | −21.948 | 15.220 | 60.483 | 1.00 | 63.61 | C |
| ATOM | 81 | OD1 | ASP | A | 16 | −22.343 | 15.216 | 61.669 | 1.00 | 65.87 | O |
| ATOM | 82 | OD2 | ASP | A | 16 | −22.523 | 15.889 | 59.591 | 1.00 | 61.86 | O |
| ATOM | 83 | C | ASP | A | 16 | −21.232 | 12.384 | 61.564 | 1.00 | 67.54 | C |
| ATOM | 84 | O | ASP | A | 16 | −21.906 | 11.872 | 60.656 | 1.00 | 64.36 | O |
| ATOM | 85 | N | PRO | A | 17 | −21.332 | 12.000 | 62.850 | 1.00 | 64.42 | N |
| ATOM | 86 | CA | PRO | A | 17 | −22.145 | 10.867 | 63.325 | 1.00 | 65.61 | C |
| ATOM | 87 | CB | PRO | A | 17 | −21.737 | 10.743 | 64.804 | 1.00 | 68.12 | C |
| ATOM | 88 | CG | PRO | A | 17 | −20.425 | 11.471 | 64.905 | 1.00 | 68.42 | C |
| ATOM | 89 | CD | PRO | A | 17 | −20.597 | 12.621 | 63.963 | 1.00 | 68.76 | C |
| ATOM | 90 | C | PRO | A | 17 | −23.666 | 11.024 | 63.192 | 1.00 | 66.47 | C |
| ATOM | 91 | O | PRO | A | 17 | −24.405 | 10.049 | 63.367 | 1.00 | 70.06 | O |
| ATOM | 92 | N | GLU | A | 18 | −24.122 | 12.239 | 62.905 | 1.00 | 69.73 | N |
| ATOM | 93 | CA | GLU | A | 18 | −25.530 | 12.490 | 62.619 | 1.00 | 72.93 | C |
| ATOM | 94 | CB | GLU | A | 18 | −26.185 | 13.339 | 63.724 | 1.00 | 73.98 | C |
| ATOM | 95 | CG | GLU | A | 18 | −26.421 | 12.609 | 65.050 | 1.00 | 74.46 | C |
| ATOM | 96 | CD | GLU | A | 18 | −27.628 | 13.138 | 65.827 | 1.00 | 73.31 | C |
| ATOM | 97 | OE1 | GLU | A | 18 | −28.330 | 14.057 | 65.336 | 1.00 | 75.07 | O |
| ATOM | 98 | OE2 | GLU | A | 18 | −27.879 | 12.619 | 66.938 | 1.00 | 69.85 | O |
| ATOM | 99 | C | GLU | A | 18 | −25.650 | 13.180 | 61.269 | 1.00 | 74.65 | C |
| ATOM | 100 | O | GLU | A | 18 | −25.949 | 14.376 | 61.203 | 1.00 | 75.08 | O |
| ATOM | 101 | N | LYS | A | 19 | −25.400 | 12.431 | 60.197 | 1.00 | 76.88 | N |
| ATOM | 102 | CA | LYS | A | 19 | −25.530 | 12.972 | 58.848 | 1.00 | 75.26 | C |
| ATOM | 103 | CB | LYS | A | 19 | −24.175 | 13.335 | 58.232 | 1.00 | 75.13 | C |
| ATOM | 104 | CG | LYS | A | 19 | −24.330 | 14.156 | 56.950 | 1.00 | 74.85 | C |
| ATOM | 105 | CD | LYS | A | 19 | −23.012 | 14.543 | 56.320 | 1.00 | 71.95 | C |
| ATOM | 106 | CE | LYS | A | 19 | −23.239 | 15.121 | 54.926 | 1.00 | 73.31 | C |
| ATOM | 107 | NZ | LYS | A | 19 | −21.971 | 15.547 | 54.271 | 1.00 | 66.78 | N |

TABLE 10-continued

Atomic coordinates for COM1 complex of the modified
TXNIP protein represented by SEQ ID NO: 6 and the modified protein represented by SEQ ID NO: 3

| ATOM | 108 | C | LYS | A | 19 | −26.271 | 12.064 | 57.890 | 1.00 | 75.83 | C |
|------|-----|------|-----|---|----|---------|--------|--------|------|-------|---|
| ATOM | 109 | O | LYS | A | 19 | −26.099 | 10.843 | 57.910 | 1.00 | 75.57 | O |
| ATOM | 110 | N | VAL | A | 20 | −27.102 | 12.703 | 57.068 | 1.00 | 76.82 | N |
| ATOM | 111 | CA | VAL | A | 20 | −27.692 | 12.129 | 55.872 | 1.00 | 77.57 | C |
| ATOM | 112 | CB | VAL | A | 20 | −28.101 | 12.745 | 55.597 | 1.00 | 77.01 | C |
| ATOM | 113 | CG1 | VAL | A | 20 | −29.579 | 12.468 | 54.175 | 1.00 | 78.18 | C |
| ATOM | 114 | CG2 | VAL | A | 20 | −30.124 | 12.254 | 56.611 | 1.00 | 79.65 | C |
| ATOM | 115 | C | VAL | A | 20 | −26.743 | 12.494 | 54.731 | 1.00 | 78.41 | C |
| ATOM | 116 | O | VAL | A | 20 | −26.622 | 13.670 | 54.364 | 1.00 | 79.09 | O |
| ATOM | 117 | N | TYR | A | 21 | −26.060 | 11.487 | 54.186 | 1.00 | 77.32 | N |
| ATOM | 118 | CA | TYR | A | 21 | −25.133 | 11.696 | 53.079 | 1.00 | 76.53 | C |
| ATOM | 119 | CB | TYR | A | 21 | −24.005 | 10.644 | 53.099 | 1.00 | 76.02 | C |
| ATOM | 120 | CG | TYR | A | 21 | −23.113 | 10.888 | 54.334 | 1.00 | 69.63 | C |
| ATOM | 121 | CD1 | TYR | A | 21 | −21.996 | 11.525 | 54.382 | 1.00 | 68.21 | C |
| ATOM | 122 | CE1 | TYR | A | 21 | −21.167 | 11.571 | 55.529 | 1.00 | 72.93 | C |
| ATOM | 123 | OZ | TYR | A | 21 | −21.450 | 10.772 | 56.643 | 1.00 | 69.78 | O |
| ATOM | 124 | OH | TYR | A | 21 | −20.639 | 10.824 | 57.769 | 1.00 | 65.04 | O |
| ATOM | 125 | CE2 | TYR | A | 21 | −22.566 | 9.924 | 56.611 | 1.00 | 69.84 | C |
| ATOM | 126 | CD2 | TYR | A | 21 | −23.388 | 9.890 | 55.455 | 1.00 | 69.41 | C |
| ATOM | 127 | C | TYR | A | 21 | −25.894 | 11.669 | 51.751 | 1.00 | 77.68 | C |
| ATOM | 128 | O | TYR | A | 21 | −26.881 | 10.935 | 51.610 | 1.00 | 78.42 | O |
| ATOM | 129 | N | GLY | A | 22 | −25.441 | 12.467 | 50.785 | 1.00 | 77.63 | N |
| ATOM | 130 | CA | GLY | A | 22 | −26.093 | 12.536 | 49.472 | 1.00 | 78.10 | C |
| ATOM | 131 | C | GLY | A | 22 | −25.471 | 11.666 | 48.389 | 1.00 | 78.37 | C |
| ATOM | 132 | O | GLY | A | 22 | −24.597 | 10.847 | 48.686 | 1.00 | 78.46 | O |
| ATOM | 133 | N | SER | A | 23 | −25.941 | 11.842 | 47.154 | 1.00 | 78.57 | N |
| ATOM | 134 | CA | SER | A | 23 | −25.328 | 11.228 | 45.970 | 1.00 | 77.19 | C |
| ATOM | 135 | CB | SER | A | 23 | −26.208 | 11.454 | 44.730 | 1.00 | 77.58 | C |
| ATOM | 136 | OG | SER | A | 23 | −25.702 | 10.771 | 43.592 | 1.00 | 75.96 | O |
| ATOM | 137 | C | SER | A | 23 | −23.917 | 11.800 | 45.753 | 1.00 | 75.89 | C |
| ATOM | 138 | O | SER | A | 23 | −23.645 | 12.961 | 46.110 | 1.00 | 74.49 | O |
| ATOM | 139 | N | GLY | A | 24 | −23.025 | 10.974 | 45.199 | 1.00 | 73.52 | N |
| ATOM | 140 | CA | GLY | A | 24 | −21.625 | 11.356 | 44.970 | 1.00 | 72.35 | C |
| ATOM | 141 | C | GLY | A | 24 | −20.938 | 11.972 | 46.177 | 1.00 | 71.89 | C |
| ATOM | 142 | O | GLY | A | 24 | −19.983 | 12.734 | 46.031 | 1.00 | 71.51 | O |
| ATOM | 143 | N | GLU | A | 25 | −21.435 | 11.642 | 47.369 | 1.00 | 71.79 | N |
| ATOM | 144 | CA | GLU | A | 25 | −20.932 | 12.199 | 48.624 | 1.00 | 72.46 | C |
| ATOM | 145 | CB | GLU | A | 25 | −22.105 | 12.477 | 49.578 | 1.00 | 73.68 | C |
| ATOM | 146 | CG | GLU | A | 25 | −21.777 | 13.304 | 50.833 | 1.00 | 76.55 | C |
| ATOM | 147 | CD | GLU | A | 25 | −21.391 | 14.744 | 50.527 | 1.00 | 79.74 | C |
| ATOM | 148 | OE1 | GLU | A | 25 | −20.275 | 14.954 | 50.002 | 1.00 | 79.74 | O |
| ATOM | 149 | OE2 | GLU | A | 25 | −22.195 | 15.659 | 50.830 | 1.00 | 75.09 | O |
| ATOM | 150 | C | GLU | A | 25 | −19.871 | 11.306 | 49.294 | 1.00 | 71.50 | C |
| ATOM | 151 | O | GLU | A | 25 | −19.933 | 10.069 | 49.217 | 1.00 | 71.57 | O |
| ATOM | 152 | N | ARG | A | 26 | −18.897 | 11.954 | 49.927 | 1.00 | 69.34 | N |
| ATOM | 153 | CA | ARG | A | 26 | −17.818 | 11.279 | 50.652 | 1.00 | 68.44 | C |
| ATOM | 154 | CB | ARG | A | 26 | −16.593 | 12.193 | 50.743 | 1.00 | 68.70 | C |
| ATOM | 155 | CG | ARG | A | 26 | −15.277 | 11.483 | 50.996 | 1.00 | 75.43 | C |
| ATOM | 156 | CD | ARG | A | 26 | −14.487 | 11.326 | 49.697 | 1.00 | 88.03 | C |
| ATOM | 157 | NE | ARG | A | 26 | −13.049 | 11.228 | 49.955 | 1.00 | 95.46 | N |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 158 | CZ | ARG | A | 26 | -12.380 | 10.085 | 50.106 | 1.00 | 98.75 | C |
| ATOM | 159 | NH1 | ARG | A | 26 | -13.013 | 8.919 | 50.013 | 1.00 | 98.98 | N |
| ATOM | 160 | NH2 | ARG | A | 26 | -11.071 | 10.106 | 50.347 | 1.00 | 95.74 | N |
| ATOM | 161 | C | ARG | A | 26 | -18.250 | 10.895 | 52.062 | 1.00 | 65.29 | C |
| ATOM | 162 | O | ARG | A | 26 | -18.596 | 11.754 | 52.871 | 1.00 | 67.09 | O |
| ATOM | 163 | N | VAL | A | 27 | -18.230 | 9.598 | 52.343 | 1.00 | 62.43 | N |
| ATOM | 164 | CA | VAL | A | 27 | -18.365 | 9.083 | 53.702 | 1.00 | 56.26 | C |
| ATOM | 165 | CB | VAL | A | 27 | -19.241 | 7.814 | 53.739 | 1.00 | 54.94 | C |
| ATOM | 166 | CG1 | VAL | A | 27 | -19.525 | 7.396 | 55.169 | 1.00 | 49.93 | C |
| ATOM | 167 | CG2 | VAL | A | 27 | -20.540 | 8.039 | 52.985 | 1.00 | 50.38 | C |
| ATOM | 168 | C | VAL | A | 27 | -16.951 | 8.773 | 54.194 | 1.00 | 56.42 | C |
| ATOM | 169 | O | VAL | A | 27 | -16.209 | 8.031 | 53.530 | 1.00 | 50.02 | O |
| ATOM | 170 | N | ALA | A | 28 | -16.583 | 9.356 | 55.338 | 1.00 | 54.67 | N |
| ATOM | 171 | CA | ALA | A | 28 | -15.233 | 9.255 | 55.905 | 1.00 | 53.73 | C |
| ATOM | 172 | CB | ALA | A | 28 | -14.389 | 10.483 | 55.532 | 1.00 | 52.92 | C |
| ATOM | 173 | C | ALA | A | 28 | -15.308 | 9.117 | 57.417 | 1.00 | 52.70 | C |
| ATOM | 174 | O | ALA | A | 28 | -15.206 | 9.676 | 58.069 | 1.00 | 53.26 | O |
| ATOM | 175 | N | GLY | A | 29 | -14.362 | 8.383 | 57.984 | 1.00 | 49.84 | N |
| ATOM | 176 | CA | GLY | A | 29 | -14.381 | 8.154 | 59.417 | 1.00 | 45.72 | C |
| ATOM | 177 | C | GLY | A | 29 | -13.162 | 7.434 | 59.911 | 1.00 | 44.91 | C |
| ATOM | 178 | O | GLY | A | 29 | -12.099 | 7.475 | 59.291 | 1.00 | 43.33 | O |
| ATOM | 179 | N | ARG | A | 30 | -13.329 | 6.788 | 61.057 | 1.00 | 43.93 | N |
| ATOM | 180 | CA | ARG | A | 30 | -12.282 | 5.975 | 61.658 | 1.00 | 40.49 | C |
| ATOM | 181 | CB | ARG | A | 30 | -11.638 | 6.732 | 62.821 | 1.00 | 41.65 | C |
| ATOM | 182 | CG | ARG | A | 30 | -10.485 | 7.632 | 62.425 | 1.00 | 45.86 | C |
| ATOM | 183 | CD | ARG | A | 30 | -10.706 | 9.075 | 62.899 | 1.00 | 51.76 | C |
| ATOM | 184 | NE | ARG | A | 30 | -11.467 | 9.187 | 64.143 | 1.00 | 52.07 | N |
| ATOM | 185 | CZ | ARG | A | 30 | -12.733 | 9.619 | 64.241 | 1.00 | 60.48 | C |
| ATOM | 186 | NH1 | ARG | A | 30 | -13.443 | 9.979 | 63.164 | 1.00 | 50.57 | N |
| ATOM | 187 | NH2 | ARG | A | 30 | -13.305 | 9.676 | 65.436 | 1.00 | 60.28 | N |
| ATOM | 188 | C | ARG | A | 30 | -12.833 | 4.683 | 62.189 | 1.00 | 39.43 | C |
| ATOM | 189 | O | ARG | A | 30 | -13.937 | 4.647 | 62.720 | 1.00 | 39.84 | O |
| ATOM | 190 | N | VAL | A | 31 | -12.040 | 3.622 | 62.073 | 1.00 | 38.20 | N |
| ATOM | 191 | CA | VAL | A | 31 | -12.237 | 2.425 | 62.894 | 1.00 | 37.56 | C |
| ATOM | 192 | CB | VAL | A | 31 | -11.993 | 1.132 | 62.104 | 1.00 | 35.38 | C |
| ATOM | 193 | CG1 | VAL | A | 31 | -12.300 | -0.076 | 62.972 | 1.00 | 38.20 | C |
| ATOM | 194 | CG2 | VAL | A | 31 | -12.839 | 1.132 | 60.886 | 1.00 | 39.08 | C |
| ATOM | 195 | C | VAL | A | 31 | -11.268 | 2.495 | 64.070 | 1.00 | 36.78 | C |
| ATOM | 196 | O | VAL | A | 31 | -10.041 | 2.649 | 63.889 | 1.00 | 36.52 | O |
| ATOM | 197 | N | ILE | A | 32 | -11.821 | 2.390 | 65.279 | 1.00 | 35.84 | N |
| ATOM | 198 | CA | ILE | A | 32 | -11.058 | 2.667 | 66.463 | 1.00 | 37.46 | C |
| ATOM | 199 | CB | ILE | A | 32 | -11.653 | 3.875 | 67.239 | 1.00 | 39.60 | C |
| ATOM | 200 | CG1 | ILE | A | 32 | -11.612 | 5.132 | 66.352 | 1.00 | 40.55 | C |
| ATOM | 201 | CD1 | ILE | A | 32 | -12.428 | 6.309 | 66.890 | 1.00 | 47.57 | C |
| ATOM | 202 | CG2 | ILE | A | 32 | -10.870 | 4.132 | 68.496 | 1.00 | 40.85 | C |
| ATOM | 203 | C | ILE | A | 32 | -10.928 | 1.401 | 67.308 | 1.00 | 38.27 | C |
| ATOM | 204 | O | ILE | A | 32 | -11.936 | 0.782 | 67.694 | 1.00 | 35.35 | O |
| ATOM | 205 | N | VAL | A | 33 | -9.677 | 0.987 | 67.534 | 1.00 | 39.03 | N |
| ATOM | 206 | CA | VAL | A | 33 | -9.399 | -0.217 | 68.321 | 1.00 | 39.18 | C |
| ATOM | 207 | CB | VAL | A | 33 | -8.641 | -1.331 | 67.517 | 1.00 | 38.56 | C |

TABLE 10-continued

Atomic coordinates for COM1 complex of the modified
TXNIP protein represented by SEQ ID NO: 6 and the modified protein represented by SEQ ID NO: 3

| ATOM | 208 | CG1 | VAL | A | 33 | -8.790 | 68.215 | -2.674 | 1.00 | 37.99 | C |
|---|---|---|---|---|---|---|---|---|---|---|---|
| ATOM | 209 | CG2 | VAL | A | 33 | -9.151 | 66.082 | -1.460 | 1.00 | 38.83 | C |
| ATOM | 210 | C | VAL | A | 33 | -8.620 | 69.606 | 0.119 | 1.00 | 40.22 | C |
| ATOM | 211 | O | VAL | A | 33 | -7.650 | 69.592 | 0.888 | 1.00 | 41.17 | O |
| ATOM | 212 | N | GLU | A | 34 | -9.070 | 70.717 | -0.456 | 1.00 | 41.71 | N |
| ATOM | 213 | CA | GLU | A | 34 | -8.362 | 71.982 | -0.391 | 1.00 | 42.21 | C |
| ATOM | 214 | CB | GLU | A | 34 | -9.036 | 72.939 | 0.593 | 1.00 | 43.87 | C |
| ATOM | 215 | CG | GLU | A | 34 | -9.093 | 72.352 | 2.019 | 1.00 | 52.42 | C |
| ATOM | 216 | CD | GLU | A | 34 | -9.910 | 73.174 | 3.017 | 1.00 | 57.15 | C |
| ATOM | 217 | OE1 | GLU | A | 34 | -9.948 | 74.414 | 2.905 | 1.00 | 51.68 | O |
| ATOM | 218 | OE2 | GLU | A | 34 | -10.502 | 72.567 | 3.038 | 1.00 | 62.63 | O |
| ATOM | 219 | C | GLU | A | 34 | -8.369 | 72.545 | -1.801 | 1.00 | 43.65 | C |
| ATOM | 220 | O | GLU | A | 34 | -9.311 | 72.298 | -2.583 | 1.00 | 42.12 | O |
| ATOM | 221 | N | VAL | A | 35 | -7.316 | 73.273 | -2.159 | 1.00 | 43.27 | N |
| ATOM | 222 | CA | VAL | A | 35 | -7.231 | 73.804 | -3.508 | 1.00 | 48.45 | C |
| ATOM | 223 | CB | VAL | A | 35 | -6.289 | 72.962 | -4.382 | 1.00 | 50.50 | C |
| ATOM | 224 | CG1 | VAL | A | 35 | -4.829 | 73.088 | -3.908 | 1.00 | 51.65 | C |
| ATOM | 225 | CG2 | VAL | A | 35 | -6.471 | 73.330 | -5.876 | 1.00 | 58.67 | C |
| ATOM | 226 | C | VAL | A | 35 | -6.837 | 75.280 | -3.502 | 1.00 | 49.60 | C |
| ATOM | 227 | O | VAL | A | 35 | -6.186 | 75.748 | -2.572 | 1.00 | 47.76 | O |
| ATOM | 228 | N | CYS | A | 36 | -7.266 | 75.996 | -4.537 | 1.00 | 52.35 | N |
| ATOM | 229 | CA | CYS | A | 36 | 6.954 | 77.414 | 4.709 | 1.00 | 54.93 | C |
| ATOM | 230 | CB | CYS | A | 36 | -7.915 | 78.027 | -5.726 | 1.00 | 54.34 | C |
| ATOM | 231 | SG | CYS | A | 36 | -9.633 | 77.940 | -5.188 | 1.00 | 69.89 | S |
| ATOM | 232 | C | CYS | A | 36 | -5.518 | 77.624 | -5.162 | 1.00 | 55.26 | C |
| ATOM | 233 | O | CYS | A | 36 | -4.876 | 78.611 | -4.793 | 1.00 | 55.85 | O |
| ATOM | 234 | N | GLU | A | 37 | -5.020 | 76.687 | -5.965 | 1.00 | 55.92 | N |
| ATOM | 235 | CA | GLU | A | 37 | -3.683 | 76.787 | -6.563 | 1.00 | 55.16 | C |
| ATOM | 236 | CB | GLU | A | 37 | -3.792 | 77.283 | -8.005 | 1.00 | 55.66 | C |
| ATOM | 237 | CG | GLU | A | 37 | -4.462 | 76.292 | -8.925 | 1.00 | 60.45 | C |
| ATOM | 238 | CD | GLU | A | 37 | -4.919 | 76.898 | -10.227 | 1.00 | 74.46 | C |
| ATOM | 239 | OE1 | GLU | A | 37 | -5.209 | 78.120 | -10.261 | 1.00 | 76.52 | O |
| ATOM | 240 | OE2 | GLU | A | 37 | 5.001 | 76.134 | 11.216 | 1.00 | 79.00 | O |
| ATOM | 241 | C | GLU | A | 37 | -2.948 | 75.447 | -6.540 | 1.00 | 54.20 | C |
| ATOM | 242 | O | GLU | A | 37 | -3.569 | 74.405 | -6.351 | 1.00 | 53.64 | O |
| ATOM | 243 | N | VAL | A | 38 | -1.632 | 75.483 | -6.767 | 1.00 | 51.60 | N |
| ATOM | 244 | CA | VAL | A | 38 | -0.825 | 74.269 | -6.843 | 1.00 | 50.61 | C |
| ATOM | 245 | CB | VAL | A | 38 | -0.639 | 74.576 | -7.210 | 1.00 | 51.44 | C |
| ATOM | 246 | CG1 | VAL | A | 38 | 1.442 | 73.293 | -7.299 | 1.00 | 48.81 | C |
| ATOM | 247 | CG2 | VAL | A | 38 | 1.245 | 75.497 | -6.171 | 1.00 | 47.23 | C |
| ATOM | 248 | C | VAL | A | 38 | -1.429 | 73.240 | -7.816 | 1.00 | 52.46 | C |
| ATOM | 249 | O | VAL | A | 38 | -1.615 | 73.512 | -9.019 | 1.00 | 52.61 | O |
| ATOM | 250 | N | THR | A | 39 | -1.727 | 72.060 | -7.278 | 1.00 | 47.80 | N |
| ATOM | 251 | CA | THR | A | 39 | -2.528 | 71.074 | -7.978 | 1.00 | 46.47 | C |
| ATOM | 252 | CB | THR | A | 39 | -3.952 | 71.028 | -7.407 | 1.00 | 43.67 | C |
| ATOM | 253 | OG1 | THR | A | 39 | -4.621 | 72.258 | -7.695 | 1.00 | 53.23 | O |
| ATOM | 254 | CG2 | THR | A | 39 | -4.797 | 69.880 | -8.007 | 1.00 | 45.73 | C |
| ATOM | 255 | C | THR | A | 39 | -1.874 | 69.728 | -7.790 | 1.00 | 42.28 | C |
| ATOM | 256 | O | THR | A | 39 | -1.592 | 69.335 | -6.668 | 1.00 | 40.99 | O |
| ATOM | 257 | N | ARG | A | 40 | -1.623 | 69.048 | -8.899 | 1.00 | 41.50 | N |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 258 | CA | ARG | A | 40 | -1.181 | 67.659 | 1.00 | 42.89 | C |
| ATOM | 259 | CB | ARG | A | 40 | -0.124 | 67.401 | 1.00 | 45.11 | C |
| ATOM | 260 | CG | ARG | A | 40 | 1.120 | 68.261 | 1.00 | 51.19 | C |
| ATOM | 261 | CD | ARG | A | 40 | 1.665 | 68.867 | 1.00 | 54.29 | C |
| ATOM | 262 | NE | ARG | A | 40 | 2.048 | 67.868 | 1.00 | 64.77 | N |
| ATOM | 263 | CZ | ARG | A | 40 | 1.304 | 67.521 | 1.00 | 63.43 | C |
| ATOM | 264 | NH1 | ARG | A | 40 | 0.100 | 68.085 | 1.00 | 61.12 | N |
| ATOM | 265 | NH2 | ARG | A | 40 | 1.762 | 66.607 | 1.00 | 53.24 | N |
| ATOM | 266 | C | ARG | A | 40 | -2.364 | 66.737 | 1.00 | 40.73 | C |
| ATOM | 267 | O | ARG | A | 40 | -3.290 | 66.963 | 1.00 | 37.07 | O |
| ATOM | 268 | N | VAL | A | 41 | -2.303 | 65.663 | 1.00 | 38.74 | N |
| ATOM | 269 | CA | VAL | A | 41 | -3.447 | 64.793 | 1.00 | 36.07 | C |
| ATOM | 270 | CB | VAL | A | 41 | -4.013 | 65.049 | 1.00 | 33.74 | C |
| ATOM | 271 | CG1 | VAL | A | 41 | -4.994 | 63.966 | 1.00 | 34.20 | C |
| ATOM | 272 | CG2 | VAL | A | 41 | -4.684 | 66.328 | 1.00 | 32.83 | C |
| ATOM | 273 | C | VAL | A | 41 | -2.952 | 63.386 | 1.00 | 36.16 | C |
| ATOM | 274 | O | VAL | A | 41 | -1.917 | 63.003 | 1.00 | 35.57 | O |
| ATOM | 275 | N | LYS | A | 42 | -3.654 | 62.632 | 1.00 | 35.18 | N |
| ATOM | 276 | CA | LYS | A | 42 | -3.329 | 61.257 | 1.00 | 33.35 | C |
| ATOM | 277 | CB | LYS | A | 42 | -3.942 | 60.812 | 1.00 | 32.75 | C |
| ATOM | 278 | CG | LYS | A | 42 | -3.045 | 60.807 | 1.00 | 46.73 | C |
| ATOM | 279 | CD | LYS | A | 42 | -3.857 | 60.931 | 1.00 | 49.97 | C |
| ATOM | 280 | CE | LYS | A | 42 | -4.294 | 59.595 | 1.00 | 45.77 | C |
| ATOM | 281 | NZ | LYS | A | 42 | -3.076 | 58.944 | 1.00 | 53.24 | N |
| ATOM | 282 | C | LYS | A | 42 | -3.862 | 60.325 | 1.00 | 33.71 | C |
| ATOM | 283 | O | LYS | A | 42 | -3.182 | 59.360 | 1.00 | 34.77 | O |
| ATOM | 284 | N | ALA | A | 43 | -5.114 | 60.521 | 1.00 | 30.14 | N |
| ATOM | 285 | CA | ALA | A | 43 | -5.734 | 59.645 | 1.00 | 30.68 | C |
| ATOM | 286 | CB | ALA | A | 43 | -6.176 | 58.299 | 1.00 | 34.82 | C |
| ATOM | 287 | C | ALA | A | 43 | -6.915 | 60.293 | 1.00 | 32.29 | C |
| ATOM | 288 | O | ALA | A | 43 | -6.676 | 61.187 | 1.00 | 32.12 | O |
| ATOM | 289 | N | VAL | A | 44 | -7.538 | 59.830 | 1.00 | 32.80 | N |
| ATOM | 290 | CA | VAL | A | 44 | -7.222 | 60.046 | 1.00 | 31.57 | C |
| ATOM | 291 | CB | VAL | A | 44 | -8.527 | 60.936 | 1.00 | 35.59 | C |
| ATOM | 292 | CG1 | VAL | A | 44 | -8.433 | 60.841 | 1.00 | 30.20 | C |
| ATOM | 293 | CG2 | VAL | A | 44 | -9.691 | 52.394 | 1.00 | 35.53 | C |
| ATOM | 294 | C | VAL | A | 44 | -8.174 | 58.674 | 1.00 | 32.95 | C |
| ATOM | 295 | O | VAL | A | 44 | -9.031 | 55.440 | 1.00 | 31.59 | O |
| ATOM | 296 | N | ARG | A | 45 | -8.308 | 55.769 | 1.00 | 31.23 | N |
| ATOM | 297 | CA | ARG | A | 45 | -10.240 | 56.680 | 1.00 | 36.06 | C |
| ATOM | 298 | CB | ARG | A | 45 | -10.737 | 56.954 | 1.00 | 35.39 | C |
| ATOM | 299 | CG | ARG | A | 45 | -10.784 | 56.144 | 1.00 | 40.28 | C |
| ATOM | 300 | CD | ARG | A | 45 | -9.689 | 55.518 | 1.00 | 51.80 | C |
| ATOM | 301 | NE | ARG | A | 45 | -9.888 | 55.532 | 1.00 | 51.46 | N |
| ATOM | 302 | CZ | ARG | A | 45 | -10.413 | 55.680 | 1.00 | 51.31 | C |
| ATOM | 303 | NH1 | ARG | A | 45 | -11.585 | 55.518 | 1.00 | 45.29 | N |
| ATOM | 304 | NH2 | ARG | A | 45 | -12.373 | 57.400 | 1.00 | 40.07 | N |
| ATOM | 305 | C | ARG | A | 45 | -11.969 | 57.054 | 1.00 | 36.45 | C |
| ATOM | 306 | O | ARG | A | 45 | -12.127 | 58.120 | 1.00 | 39.20 | O |
| ATOM | 307 | N | ILE | A | 46 | -12.597 | 55.993 | 1.00 | 38.37 | N |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 308 | CA | ILE | A | 46 | −14.000 | −2.516 | 55.950 | 1.00 | 41.80 | C |
| ATOM | 309 | CB | ILE | A | 46 | −14.237 | −0.973 | 56.134 | 1.00 | 42.42 | C |
| ATOM | 310 | CG1 | ILE | A | 46 | −13.572 | −0.140 | 55.037 | 1.00 | 38.23 | C |
| ATOM | 311 | CD1 | ILE | A | 46 | −14.151 | 1.257 | 54.935 | 1.00 | 50.93 | C |
| ATOM | 312 | CG2 | ILE | A | 46 | −13.817 | −0.535 | 57.532 | 1.00 | 42.63 | C |
| ATOM | 313 | C | ILE | A | 46 | −14.743 | −3.019 | 54.718 | 1.00 | 43.03 | C |
| ATOM | 314 | O | ILE | A | 46 | −14.143 | −3.333 | 53.689 | 1.00 | 43.01 | O |
| ATOM | 315 | N | LEU | A | 47 | −15.051 | −3.117 | 54.868 | 1.00 | 41.95 | N |
| ATOM | 316 | CA | LEU | A | 47 | −16.959 | −3.413 | 53.772 | 1.00 | 44.45 | C |
| ATOM | 317 | CB | LEU | A | 47 | −17.477 | −4.850 | 53.864 | 1.00 | 42.37 | C |
| ATOM | 318 | CG | LEU | A | 47 | −18.639 | −5.267 | 52.959 | 1.00 | 45.94 | C |
| ATOM | 319 | CD1 | LEU | A | 47 | −18.190 | −5.376 | 51.504 | 1.00 | 43.80 | C |
| ATOM | 320 | CD2 | LEU | A | 47 | −19.226 | −6.580 | 53.434 | 1.00 | 50.08 | C |
| ATOM | 321 | C | LEU | A | 47 | −18.115 | −2.439 | 53.960 | 1.00 | 44.39 | C |
| ATOM | 322 | O | LEU | A | 47 | −18.762 | −2.436 | 54.992 | 1.00 | 45.41 | O |
| ATOM | 323 | N | ALA | A | 48 | −18.315 | −1.567 | 52.989 | 1.00 | 45.42 | N |
| ATOM | 324 | CA | ALA | A | 48 | −19.406 | −0.648 | 53.035 | 1.00 | 45.31 | C |
| ATOM | 325 | CB | ALA | A | 48 | −18.922 | 0.746 | 52.767 | 1.00 | 45.70 | C |
| ATOM | 326 | C | ALA | A | 48 | −20.411 | −1.113 | 51.982 | 1.00 | 48.06 | C |
| ATOM | 327 | O | ALA | A | 48 | −20.022 | −1.556 | 50.907 | 1.00 | 43.20 | O |
| ATOM | 328 | N | CYS | A | 49 | −21.700 | −1.037 | 52.317 | 1.00 | 50.07 | N |
| ATOM | 329 | CA | CYS | A | 49 | −22.746 | −1.601 | 51.471 | 1.00 | 53.40 | C |
| ATOM | 330 | CB | CYS | A | 49 | −23.089 | −3.011 | 51.923 | 1.00 | 54.24 | C |
| ATOM | 331 | SG | CYS | A | 49 | −21.922 | −4.240 | 51.330 | 1.00 | 74.90 | S |
| ATOM | 332 | C | CYS | A | 49 | −24.022 | −0.787 | 51.471 | 1.00 | 53.02 | C |
| ATOM | 333 | O | CYS | A | 49 | −24.432 | −0.272 | 52.509 | 1.00 | 50.84 | O |
| ATOM | 334 | N | GLY | A | 50 | −24.650 | −0.701 | 50.301 | 1.00 | 51.79 | N |
| ATOM | 335 | CA | GLY | A | 50 | −25.998 | −0.117 | 50.172 | 1.00 | 53.89 | C |
| ATOM | 336 | C | GLY | A | 50 | −26.867 | −1.028 | 49.322 | 1.00 | 54.08 | C |
| ATOM | 337 | O | GLY | A | 50 | −26.540 | −1.308 | 48.171 | 1.00 | 52.36 | O |
| ATOM | 338 | N | VAL | A | 51 | −27.959 | −1.511 | 49.907 | 1.00 | 54.81 | N |
| ATOM | 339 | CA | VAL | A | 51 | −28.828 | −2.497 | 49.271 | 1.00 | 55.19 | C |
| ATOM | 340 | CB | VAL | A | 51 | −28.614 | −3.895 | 49.895 | 1.00 | 58.21 | C |
| ATOM | 341 | CG1 | VAL | A | 51 | −29.533 | −4.928 | 49.265 | 1.00 | 55.70 | C |
| ATOM | 342 | CG2 | VAL | A | 51 | −27.161 | −4.334 | 49.732 | 1.00 | 58.48 | C |
| ATOM | 343 | C | VAL | A | 51 | −30.300 | −2.096 | 49.436 | 1.00 | 57.18 | C |
| ATOM | 344 | O | VAL | A | 51 | −30.778 | −1.899 | 50.573 | 1.00 | 59.11 | O |
| ATOM | 345 | N | ALA | A | 52 | −31.016 | −1.949 | 48.320 | 1.00 | 55.12 | N |
| ATOM | 346 | CA | ALA | A | 52 | −32.474 | −1.833 | 48.398 | 1.00 | 51.69 | C |
| ATOM | 347 | CB | ALA | A | 52 | −32.977 | −0.780 | 47.462 | 1.00 | 51.65 | C |
| ATOM | 348 | C | ALA | A | 52 | −33.136 | −3.180 | 48.123 | 1.00 | 51.73 | C |
| ATOM | 349 | O | ALA | A | 52 | −32.724 | −3.930 | 47.247 | 1.00 | 55.86 | O |
| ATOM | 350 | N | LYS | A | 53 | −34.156 | −3.501 | 48.890 | 1.00 | 55.04 | N |
| ATOM | 351 | CA | LYS | A | 53 | −34.934 | −4.701 | 48.652 | 1.00 | 58.17 | C |
| ATOM | 352 | CB | LYS | A | 53 | −34.839 | −5.631 | 49.865 | 1.00 | 59.44 | C |
| ATOM | 353 | CG | LYS | A | 53 | 35.676 | 6.902 | 49.001 | 1.00 | 63.39 | C |
| ATOM | 354 | CD | LYS | A | 53 | −37.038 | −6.760 | 50.539 | 1.00 | 71.99 | C |
| ATOM | 355 | CE | LYS | A | 53 | −36.945 | −6.868 | 52.084 | 1.00 | 69.04 | C |
| ATOM | 356 | NZ | LYS | A | 53 | −36.521 | −8.215 | 52.594 | 1.00 | 67.47 | N |
| ATOM | 357 | C | LYS | A | 53 | −36.377 | −4.269 | 48.338 | 1.00 | 61.00 | C |

TABLE 10-continued

Atomic coordinates for COM1 complex of the modified
TXNIP protein represented by SEQ ID NO: 6 and the modified protein represented by SEQ ID NO: 3

| | | | | | | | | | | | |
|---|---|---|---|---|---|---|---|---|---|---|---|
| ATOM | 358 | O | LYS | A | 53 | -37.054 | -3.660 | 49.177 | 1.00 | 62.17 | O |
| ATOM | 359 | N | VAL | A | 54 | -36.829 | -4.555 | 47.116 | 1.00 | 62.03 | N |
| ATOM | 360 | CA | VAL | A | 54 | -38.220 | -4.273 | 46.737 | 1.00 | 62.87 | C |
| ATOM | 361 | CB | VAL | A | 54 | -38.330 | -3.547 | 45.378 | 1.00 | 61.47 | C |
| ATOM | 362 | CG1 | VAL | A | 54 | -39.784 | -3.211 | 45.071 | 1.00 | 63.70 | C |
| ATOM | 363 | CG2 | VAL | A | 54 | -37.483 | -2.268 | 45.389 | 1.00 | 53.64 | C |
| ATOM | 364 | C | VAL | A | 54 | -39.021 | -5.567 | 46.744 | 1.00 | 62.17 | C |
| ATOM | 365 | O | VAL | A | 54 | -38.707 | -5.498 | 46.018 | 1.00 | 62.97 | O |
| ATOM | 366 | N | LEU | A | 55 | -40.053 | -5.612 | 47.577 | 1.00 | 62.71 | N |
| ATOM | 367 | CA | LEU | A | 55 | -40.767 | -6.851 | 47.852 | 1.00 | 63.43 | C |
| ATOM | 368 | CB | LEU | A | 55 | -40.133 | -7.542 | 49.076 | 1.00 | 64.87 | C |
| ATOM | 369 | CG | LEU | A | 55 | -40.890 | -8.408 | 50.085 | 1.00 | 64.09 | C |
| ATOM | 370 | CD1 | LEU | A | 55 | -40.178 | -9.741 | 50.324 | 1.00 | 62.05 | C |
| ATOM | 371 | CD2 | LEU | A | 55 | -41.061 | -7.632 | 51.373 | 1.00 | 66.79 | C |
| ATOM | 372 | C | LEU | A | 55 | -42.274 | -5.640 | 48.016 | 1.00 | 63.03 | C |
| ATOM | 373 | O | LEU | A | 55 | -42.721 | -5.608 | 48.514 | 1.00 | 63.11 | O |
| ATOM | 374 | N | TRP | A | 56 | -43.044 | -7.622 | 47.562 | 1.00 | 63.55 | N |
| ATOM | 375 | CA | TRP | A | 56 | -44.500 | -7.603 | 47.648 | 1.00 | 65.15 | C |
| ATOM | 376 | CB | TRP | A | 56 | -45.139 | -6.660 | 46.596 | 1.00 | 64.48 | C |
| ATOM | 377 | CG | TRP | A | 56 | -45.042 | -7.155 | 45.168 | 1.00 | 62.08 | C |
| ATOM | 378 | CD1 | TRP | A | 56 | -46.012 | -7.806 | 44.460 | 1.00 | 58.07 | C |
| ATOM | 379 | NE1 | TRP | A | 56 | -45.557 | -8.113 | 43.200 | 1.00 | 62.30 | N |
| ATOM | 380 | CE2 | TRP | A | 56 | -44.270 | -7.661 | 43.067 | 1.00 | 58.42 | C |
| ATOM | 381 | CD2 | TRP | A | 56 | -43.908 | -7.051 | 44.290 | 1.00 | 62.11 | C |
| ATOM | 382 | CE3 | TRP | A | 56 | -42.623 | -6.500 | 44.416 | 1.00 | 55.21 | C |
| ATOM | 383 | CZ3 | TRP | A | 56 | -41.753 | -6.581 | 43.331 | 1.00 | 57.44 | C |
| ATOM | 384 | CH2 | TRP | A | 56 | -42.145 | -7.197 | 42.130 | 1.00 | 49.50 | C |
| ATOM | 385 | CZ2 | TRP | A | 56 | -43.390 | -7.746 | 41.982 | 1.00 | 56.94 | C |
| ATOM | 386 | C | TRP | A | 56 | -44.963 | -9.039 | 47.467 | 1.00 | 67.87 | C |
| ATOM | 387 | O | TRP | A | 56 | -44.144 | -9.940 | 47.288 | 1.00 | 65.57 | O |
| ATOM | 388 | N | MET | A | 57 | -46.275 | -9.243 | 47.514 | 1.00 | 73.25 | N |
| ATOM | 389 | CA | MET | A | 57 | -46.858 | -10.569 | 47.367 | 1.00 | 77.77 | C |
| ATOM | 390 | CB | MET | A | 57 | -47.339 | -11.084 | 48.724 | 1.00 | 78.22 | C |
| ATOM | 391 | CG | MET | A | 57 | -46.316 | -11.922 | 49.458 | 1.00 | 80.27 | C |
| ATOM | 392 | SD | MET | A | 57 | -47.142 | -13.309 | 50.239 | 1.00 | 84.92 | S |
| ATOM | 393 | CE | MET | A | 57 | -45.885 | -14.577 | 50.171 | 1.00 | 73.51 | C |
| ATOM | 394 | C | MET | A | 57 | -48.002 | -10.572 | 46.358 | 1.00 | 80.34 | C |
| ATOM | 395 | O | MET | A | 57 | -49.058 | -9.995 | 46.617 | 1.00 | 81.58 | O |
| ATOM | 396 | N | GLN | A | 58 | -47.790 | -11.212 | 45.206 | 1.00 | 83.39 | N |
| ATOM | 397 | CA | GLN | A | 58 | -48.800 | -11.243 | 44.132 | 1.00 | 85.13 | C |
| ATOM | 398 | CB | GLN | A | 58 | -48.158 | -11.649 | 42.798 | 1.00 | 85.12 | C |
| ATOM | 399 | CG | GLN | A | 58 | -48.044 | -11.237 | 41.557 | 1.00 | 88.44 | C |
| ATOM | 400 | CD | GLN | A | 58 | -48.759 | -9.763 | 41.183 | 1.00 | 94.95 | C |
| ATOM | 401 | CE1 | GLN | A | 58 | -47.628 | -9.269 | 41.063 | 1.00 | 97.26 | C |
| ATOM | 402 | NE2 | GLN | A | 58 | -49.877 | -9.061 | 40.978 | 1.00 | 88.62 | N |
| ATOM | 403 | C | GLN | A | 58 | -49.907 | -12.224 | 44.524 | 1.00 | 85.89 | C |
| ATOM | 404 | O | GLN | A | 58 | -49.665 | -13.435 | 44.595 | 1.00 | 86.56 | O |
| ATOM | 405 | N | GLY | A | 59 | -51.106 | -11.697 | 44.792 | 1.00 | 86.45 | N |
| ATOM | 406 | CA | GLY | A | 59 | -52.183 | -12.479 | 45.420 | 1.00 | 86.30 | C |
| ATOM | 407 | C | GLY | A | 59 | -51.741 | -12.984 | 46.789 | 1.00 | 86.15 | C |

TABLE 10-continued

Atomic coordinates for COM1 complex of the modified
TXNIP protein represented by SEQ NO: 6 and the modified protein represented by SEQ ID NO: 3

| | | | | | | | | | | |
|---|---|---|---|---|---|---|---|---|---|---|
| ATOM | 408 | O | GLY | A | 59 | -52.084 | -12.396 | 47.818 | 1.00 | 85.66 | O |
| ATOM | 409 | N | SER | A | 60 | -50.967 | -14.074 | 46.781 | 1.00 | 86.54 | N |
| ATOM | 410 | CA | SER | A | 60 | -50.328 | -14.646 | 47.077 | 1.00 | 88.42 | C |
| ATOM | 411 | CB | SER | A | 60 | -51.282 | -15.606 | 48.692 | 1.00 | 86.85 | C |
| ATOM | 412 | CG | SER | A | 60 | -52.384 | -14.912 | 49.250 | 1.00 | 91.06 | O |
| ATOM | 413 | C | SER | A | 60 | -49.003 | -15.361 | 47.652 | 1.00 | 85.94 | C |
| ATOM | 414 | O | SER | A | 60 | -48.595 | -16.302 | 48.356 | 1.00 | 84.79 | O |
| ATOM | 415 | N | GLN | A | 61 | -48.342 | -14.899 | 46.588 | 1.00 | 85.77 | N |
| ATOM | 416 | CA | GLN | A | 61 | -47.046 | -15.432 | 46.142 | 1.00 | 84.80 | C |
| ATOM | 417 | CB | GLN | A | 61 | -47.075 | -15.619 | 44.621 | 1.00 | 85.28 | C |
| ATOM | 418 | CG | GLN | A | 61 | -45.998 | -18.555 | 44.053 | 1.00 | 87.32 | C |
| ATOM | 419 | CD | GLN | A | 61 | -45.834 | -10.433 | 42.534 | 1.00 | 90.33 | C |
| ATOM | 420 | OE1 | GLN | A | 61 | -44.942 | -17.050 | 41.947 | 1.00 | 89.46 | O |
| ATOM | 421 | NE2 | GLN | A | 61 | -46.691 | -15.632 | 41.896 | 1.00 | 89.99 | N |
| ATOM | 422 | C | GLN | A | 61 | -45.916 | -14.471 | 46.551 | 1.00 | 82.57 | C |
| ATOM | 423 | O | GLN | A | 61 | -46.124 | -13.257 | 46.544 | 1.00 | 83.01 | O |
| ATOM | 424 | N | GLN | A | 62 | -44.734 | -15.006 | 46.883 | 1.00 | 79.53 | N |
| ATOM | 425 | CA | GLN | A | 62 | -43.600 | -14.196 | 47.408 | 1.00 | 77.05 | C |
| ATOM | 426 | CB | GLN | A | 62 | -42.821 | -14.953 | 48.503 | 1.00 | 77.18 | C |
| ATOM | 427 | CG | GLN | A | 62 | -42.581 | -19.465 | 48.256 | 1.00 | 79.64 | C |
| ATOM | 428 | CD | GLN | A | 62 | -43.462 | -17.384 | 49.124 | 1.00 | 80.47 | C |
| ATOM | 429 | CE1 | GLN | A | 62 | -43.912 | -17.002 | 50.507 | 1.00 | 80.30 | C |
| ATOM | 430 | NE2 | GLN | A | 62 | -43.687 | -18.607 | 48.650 | 1.00 | 74.33 | N |
| ATOM | 431 | C | GLN | A | 62 | -42.624 | -13.612 | 46.361 | 1.00 | 75.34 | C |
| ATOM | 432 | O | GLN | A | 62 | -41.641 | -14.271 | 45.966 | 1.00 | 74.89 | O |
| ATOM | 433 | N | CYS | A | 63 | -42.891 | -12.364 | 45.947 | 1.00 | 72.09 | N |
| ATOM | 434 | CA | CYS | A | 63 | -42.077 | -11.656 | 44.940 | 1.00 | 68.14 | C |
| ATOM | 435 | CB | CYS | A | 63 | -42.948 | -11.156 | 43.787 | 1.00 | 67.43 | C |
| ATOM | 436 | SG | CYS | A | 63 | -43.102 | -12.439 | 42.561 | 1.00 | 69.81 | S |
| ATOM | 437 | C | CYS | A | 63 | -41.209 | -10.529 | 45.487 | 1.00 | 64.70 | C |
| ATOM | 438 | O | CYS | A | 63 | -41.694 | -9.643 | 46.192 | 1.00 | 63.54 | O |
| ATOM | 439 | N | LYS | A | 64 | -39.925 | -10.571 | 45.140 | 1.00 | 61.11 | N |
| ATOM | 440 | CA | LYS | A | 64 | -38.945 | -9.623 | 45.652 | 1.00 | 60.62 | C |
| ATOM | 441 | CB | LYS | A | 64 | -38.438 | -10.124 | 47.013 | 1.00 | 61.66 | C |
| ATOM | 442 | CG | LYS | A | 64 | -37.121 | -9.546 | 47.502 | 1.00 | 59.89 | C |
| ATOM | 443 | CD | LYS | A | 64 | -36.775 | -10.162 | 48.845 | 1.00 | 66.64 | C |
| ATOM | 444 | CE | LYS | A | 64 | -35.316 | -10.557 | 48.932 | 1.00 | 69.46 | C |
| ATOM | 445 | NZ | LYS | A | 64 | -35.049 | -11.304 | 50.206 | 1.00 | 74.77 | N |
| ATOM | 446 | C | LYS | A | 64 | -37.778 | -9.462 | 44.684 | 1.00 | 58.53 | C |
| ATOM | 447 | O | LYS | A | 64 | -37.321 | -10.449 | 44.123 | 1.00 | 59.50 | O |
| ATOM | 448 | N | GLN | A | 65 | -37.313 | -8.220 | 44.503 | 1.00 | 58.74 | N |
| ATOM | 449 | CA | GLN | A | 65 | -36.104 | -7.871 | 43.728 | 1.00 | 58.09 | C |
| ATOM | 450 | CB | GLN | A | 65 | -36.440 | -6.929 | 42.539 | 1.00 | 60.37 | C |
| ATOM | 451 | CG | GLN | A | 65 | -35.238 | -6.178 | 41.837 | 1.00 | 56.07 | C |
| ATOM | 452 | CD | GLN | A | 65 | -35.650 | -5.276 | 40.629 | 1.00 | 61.51 | C |
| ATOM | 453 | OE1 | GLN | A | 65 | -36.819 | -5.018 | 40.398 | 1.00 | 55.38 | O |
| ATOM | 454 | NE2 | GLN | A | 65 | -34.670 | -4.802 | 39.878 | 1.00 | 48.21 | N |
| ATOM | 455 | C | GLN | A | 65 | -35.171 | -7.164 | 44.683 | 1.00 | 58.95 | C |
| ATOM | 456 | O | GLN | A | 65 | -35.602 | -6.305 | 45.456 | 1.00 | 59.55 | O |
| ATOM | 457 | N | THR | A | 66 | -33.894 | -7.538 | 44.021 | 1.00 | 59.73 | N |

TABLE 10-continued

Atomic coordinates for COM1 complex of the modified
TXNIP protein represented by SEQ ID NO: 6 and the modified protein represented by SEQ ID NO: 3

| ATOM | 458 | CA | THR | A | 66 | −32.816 | −7.001 | 45.473 | 1.00 | 56.02 | C |
|------|-----|-----|-----|---|----|---------|--------|--------|------|-------|---|
| ATOM | 459 | CB | THR | A | 66 | −32.144 | −8.152 | 46.201 | 1.00 | 58.29 | C |
| ATOM | 460 | CG1 | THR | A | 66 | −33.136 | −8.858 | 46.956 | 1.00 | 49.47 | O |
| ATOM | 461 | CG2 | THR | A | 66 | −31.028 | −7.650 | 47.101 | 1.00 | 54.19 | C |
| ATOM | 462 | C | THR | A | 66 | −31.755 | −6.289 | 44.642 | 1.00 | 54.37 | C |
| ATOM | 463 | O | THR | A | 66 | −31.249 | −6.861 | 43.673 | 1.00 | 58.48 | O |
| ATOM | 464 | N | SER | A | 67 | −31.419 | −5.055 | 45.005 | 1.00 | 52.93 | N |
| ATOM | 465 | CA | SER | A | 67 | −30.428 | −4.254 | 44.250 | 1.00 | 52.06 | C |
| ATOM | 466 | CB | SER | A | 67 | −31.129 | −3.184 | 43.416 | 1.00 | 53.41 | C |
| ATOM | 467 | OG | SER | A | 67 | −32.189 | −3.759 | 42.686 | 1.00 | 46.25 | O |
| ATOM | 468 | C | SER | A | 67 | −29.422 | −3.555 | 45.163 | 1.00 | 53.75 | C |
| ATOM | 469 | O | SER | A | 67 | −29.809 | −2.696 | 45.971 | 1.00 | 53.81 | O |
| ATOM | 470 | N | GLU | A | 68 | −28.141 | −3.920 | 45.029 | 1.00 | 51.85 | N |
| ATOM | 471 | CA | GLU | A | 68 | −27.045 | −3.189 | 45.682 | 1.00 | 51.18 | C |
| ATOM | 472 | CB | GLU | A | 68 | −25.757 | −4.023 | 45.729 | 1.00 | 50.13 | C |
| ATOM | 473 | CG | GLU | A | 68 | −25.890 | −5.418 | 46.350 | 1.00 | 57.64 | C |
| ATOM | 474 | CD | GLU | A | 68 | −24.662 | −5.274 | 46.049 | 1.00 | 59.97 | C |
| ATOM | 475 | OE1 | GLU | A | 68 | −23.561 | −5.680 | 45.938 | 1.00 | 55.31 | O |
| ATOM | 476 | OE2 | GLU | A | 68 | −24.801 | −7.516 | 45.889 | 1.00 | 59.73 | O |
| ATOM | 477 | C | GLU | A | 68 | −26.779 | −1.935 | 44.891 | 1.00 | 46.59 | C |
| ATOM | 478 | O | GLU | A | 68 | −26.958 | −1.948 | 43.707 | 1.00 | 49.28 | O |
| ATOM | 479 | N | TYR | A | 69 | −26.361 | −0.853 | 45.557 | 1.00 | 47.22 | N |
| ATOM | 480 | CA | TYR | A | 69 | −25.933 | 0.391 | 44.933 | 1.00 | 45.91 | C |
| ATOM | 481 | CB | TYR | A | 69 | −26.921 | 1.487 | 45.295 | 1.00 | 47.99 | C |
| ATOM | 482 | CG | TYR | A | 69 | −28.268 | 1.282 | 44.622 | 1.00 | 51.11 | C |
| ATOM | 483 | CD1 | TYR | A | 69 | −29.235 | 0.444 | 45.183 | 1.00 | 50.04 | C |
| ATOM | 484 | CE1 | TYR | A | 69 | −30.455 | 0.245 | 44.557 | 1.00 | 55.21 | C |
| ATOM | 485 | CZ | TYR | A | 69 | −30.710 | 0.872 | 43.338 | 1.00 | 52.43 | C |
| ATOM | 486 | OH | TYR | A | 69 | −31.910 | 0.681 | 42.690 | 1.00 | 58.22 | O |
| ATOM | 487 | CE2 | TYR | A | 69 | −29.761 | 1.689 | 42.751 | 1.00 | 50.26 | C |
| ATOM | 488 | CD2 | TYR | A | 69 | −28.547 | 1.886 | 43.395 | 1.00 | 55.81 | C |
| ATOM | 489 | C | TYR | A | 69 | −24.522 | 0.795 | 45.382 | 1.00 | 49.36 | C |
| ATOM | 490 | O | TYR | A | 69 | −23.860 | 1.634 | 44.750 | 1.00 | 48.87 | O |
| ATOM | 491 | N | LEU | A | 70 | −24.083 | 0.202 | 46.492 | 1.00 | 49.78 | N |
| ATOM | 492 | CA | LEU | A | 70 | −22.746 | 0.419 | 47.068 | 1.00 | 50.35 | C |
| ATOM | 493 | CB | LEU | A | 70 | −22.837 | 1.304 | 48.324 | 1.00 | 51.30 | C |
| ATOM | 494 | CG | LEU | A | 70 | −21.568 | 1.882 | 49.083 | 1.00 | 48.16 | C |
| ATOM | 495 | CD1 | LEU | A | 70 | −20.706 | 2.624 | 48.264 | 1.00 | 51.09 | C |
| ATOM | 496 | CD2 | LEU | A | 70 | −21.898 | 2.310 | 50.459 | 1.00 | 46.55 | C |
| ATOM | 497 | C | LEU | A | 70 | −22.190 | −0.921 | 47.473 | 1.00 | 50.36 | C |
| ATOM | 498 | O | LEU | A | 70 | −22.874 | −1.704 | 48.129 | 1.00 | 48.31 | O |
| ATOM | 499 | N | ARG | A | 71 | −20.936 | −1.172 | 47.110 | 1.00 | 53.92 | N |
| ATOM | 500 | CA | ARG | A | 71 | −20.223 | −2.349 | 47.562 | 1.00 | 56.06 | C |
| ATOM | 501 | CB | ARG | A | 71 | −20.506 | −3.547 | 46.658 | 1.00 | 58.71 | C |
| ATOM | 502 | CG | ARG | A | 71 | −19.949 | −4.878 | 47.151 | 1.00 | 62.74 | C |
| ATOM | 503 | CD | ARG | A | 71 | −20.226 | −5.899 | 46.077 | 1.00 | 75.68 | C |
| ATOM | 504 | NE | ARG | A | 71 | −20.713 | −7.175 | 46.592 | 1.00 | 81.75 | N |
| ATOM | 505 | CZ | ARG | A | 71 | −21.447 | −8.033 | 45.886 | 1.00 | 88.02 | C |
| ATOM | 506 | NH1 | ARG | A | 71 | −21.810 | −7.740 | 44.632 | 1.00 | 80.15 | N |
| ATOM | 507 | NH2 | ARG | A | 71 | −21.838 | −0.178 | 48.441 | 1.00 | 91.67 | N |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 508 | C | ARG | A | 71 | -18.750 | -2.011 | 47.511 | 1.00 | 56.15 | C |
| ATOM | 509 | O | ARG | A | 71 | -18.130 | -2.087 | 46.454 | 1.00 | 56.63 | O |
| ATOM | 510 | N | TYR | A | 72 | -18.199 | -1.645 | 48.662 | 1.00 | 54.44 | N |
| ATOM | 511 | CA | TYR | A | 72 | -16.859 | -1.114 | 48.724 | 1.00 | 50.00 | C |
| ATOM | 512 | CB | TYR | A | 72 | -16.922 | 0.380 | 49.016 | 1.00 | 47.16 | C |
| ATOM | 513 | CG | TYR | A | 72 | -15.598 | 0.967 | 49.428 | 1.00 | 52.88 | C |
| ATOM | 514 | CD1 | TYR | A | 72 | -14.674 | 1.368 | 48.471 | 1.00 | 50.97 | C |
| ATOM | 515 | CE1 | TYR | A | 72 | -13.458 | 1.907 | 48.833 | 1.00 | 46.21 | C |
| ATOM | 516 | CZ | TYR | A | 72 | -13.152 | 2.049 | 50.166 | 1.00 | 46.41 | C |
| ATOM | 517 | OH | TYR | A | 72 | -11.934 | 2.577 | 50.524 | 1.00 | 44.54 | O |
| ATOM | 518 | CE2 | TYR | A | 72 | -14.048 | 1.650 | 51.146 | 1.00 | 43.15 | C |
| ATOM | 519 | CD2 | TYR | A | 72 | -15.263 | 1.111 | 50.772 | 1.00 | 47.55 | C |
| ATOM | 520 | C | TYR | A | 72 | -16.090 | -1.846 | 49.811 | 1.00 | 50.40 | C |
| ATOM | 521 | O | TYR | A | 72 | -16.572 | -1.956 | 50.938 | 1.00 | 50.39 | O |
| ATOM | 522 | N | GLU | A | 73 | -14.916 | -2.369 | 49.479 | 1.00 | 50.33 | N |
| ATOM | 523 | CA | GLU | A | 73 | -14.066 | -2.951 | 50.508 | 1.00 | 51.18 | C |
| ATOM | 524 | CB | GLU | A | 73 | -14.106 | -4.474 | 50.480 | 1.00 | 54.38 | C |
| ATOM | 525 | CG | GLU | A | 73 | -13.557 | -5.087 | 49.233 | 1.00 | 53.41 | C |
| ATOM | 526 | CD | GLU | A | 73 | -14.402 | -6.249 | 48.757 | 1.00 | 74.91 | C |
| ATOM | 527 | OC1 | GLU | A | 73 | -14.957 | -6.967 | 49.621 | 1.00 | 72.25 | O |
| ATOM | 528 | OE2 | GLU | A | 73 | -14.514 | -5.433 | 47.521 | 1.00 | 78.38 | O |
| ATOM | 529 | C | GLU | A | 73 | -12.653 | -2.415 | 50.439 | 1.00 | 45.98 | C |
| ATOM | 530 | O | GLU | A | 73 | -12.184 | -2.106 | 49.369 | 1.00 | 43.91 | O |
| ATOM | 531 | N | ASP | A | 74 | -12.021 | -2.254 | 51.609 | 1.00 | 45.84 | N |
| ATOM | 532 | CA | ASP | A | 74 | -10.652 | -1.724 | 51.748 | 1.00 | 44.96 | C |
| ATOM | 533 | CB | ASP | A | 74 | -10.688 | -0.183 | 51.823 | 1.00 | 49.53 | C |
| ATOM | 534 | CG | ASP | A | 74 | -9.309 | 0.474 | 51.566 | 1.00 | 56.87 | C |
| ATOM | 535 | OD1 | ASP | A | 74 | -8.541 | -0.055 | 50.729 | 1.00 | 67.82 | O |
| ATOM | 536 | OD2 | ASP | A | 74 | -9.016 | 1.541 | 52.180 | 1.00 | 56.03 | O |
| ATOM | 537 | C | ASP | A | 74 | -9.964 | -2.291 | 53.002 | 1.00 | 41.01 | C |
| ATOM | 538 | O | ASP | A | 74 | -10.610 | -2.613 | 53.977 | 1.00 | 38.44 | O |
| ATOM | 539 | N | THR | A | 75 | -8.647 | -2.417 | 52.967 | 1.00 | 40.45 | N |
| ATOM | 540 | CA | THR | A | 75 | -7.894 | -2.865 | 54.132 | 1.00 | 37.90 | C |
| ATOM | 541 | CB | THR | A | 75 | -6.846 | -3.914 | 53.695 | 1.00 | 40.57 | C |
| ATOM | 542 | OG1 | THR | A | 75 | -7.525 | -5.138 | 53.385 | 1.00 | 42.88 | O |
| ATOM | 543 | CG2 | THR | A | 75 | -5.892 | -4.218 | 54.791 | 1.00 | 31.51 | C |
| ATOM | 544 | C | THR | A | 75 | -7.263 | -1.603 | 54.738 | 1.00 | 40.02 | C |
| ATOM | 545 | O | THR | A | 75 | -6.594 | -0.856 | 54.038 | 1.00 | 42.70 | O |
| ATOM | 546 | N | LEU | A | 76 | -7.521 | -1.321 | 56.015 | 1.00 | 39.42 | N |
| ATOM | 547 | CA | LEU | A | 76 | -7.096 | -0.066 | 56.542 | 1.00 | 39.12 | C |
| ATOM | 548 | CB | LEU | A | 76 | -8.113 | 0.474 | 57.540 | 1.00 | 42.54 | C |
| ATOM | 549 | CG | LEU | A | 76 | -8.557 | 0.410 | 57.077 | 1.00 | 36.06 | C |
| ATOM | 550 | CD1 | LEU | A | 76 | -10.447 | 0.932 | 58.162 | 1.00 | 40.15 | C |
| ATOM | 551 | CD2 | LEU | A | 76 | -8.779 | 1.173 | 55.729 | 1.00 | 36.92 | C |
| ATOM | 552 | C | LEU | A | 76 | -5.701 | -1.191 | 57.142 | 1.00 | 42.81 | C |
| ATOM | 553 | O | LEU | A | 76 | -5.284 | -1.281 | 57.548 | 1.00 | 40.73 | O |
| ATOM | 554 | N | LEU | A | 77 | -4.977 | 0.928 | 57.165 | 1.00 | 45.19 | N |
| ATOM | 555 | CA | LEU | A | 77 | -3.585 | 0.947 | 57.595 | 1.00 | 48.39 | C |
| ATOM | 556 | CB | LEU | A | 77 | -2.657 | 1.166 | 56.400 | 1.00 | 48.93 | C |
| ATOM | 557 | CG | LEU | A | 77 | -2.926 | 0.401 | 55.110 | 1.00 | 55.02 | C |

TABLE 10-continued

Atomic coordinates for COM1 complex of the modified
TXNIP protein represented by SEQ ID NO: 6 and the modified protein represented by SEQ ID NO: 3

| ATOM | 558 | CD1 | LEU | A | 77 | -1.947 | 54.066 | 0.894 | 1.00 | 53.76 | C |
| ATOM | 559 | CD2 | LEU | A | 77 | -2.803 | 55.328 | -1.125 | 1.00 | 59.53 | C |
| ATOM | 560 | C | LEU | A | 77 | -3.335 | 58.600 | 2.052 | 1.00 | 48.79 | C |
| ATOM | 561 | O | LEU | A | 77 | -3.891 | 58.483 | 3.137 | 1.00 | 51.15 | O |
| ATOM | 562 | N | LEU | A | 78 | -2.479 | 59.569 | 1.757 | 1.00 | 47.74 | N |
| ATOM | 563 | CA | LEU | A | 78 | -2.021 | 60.587 | 2.707 | 1.00 | 47.62 | C |
| ATOM | 564 | CB | LEU | A | 78 | -1.602 | 61.840 | 1.941 | 1.00 | 44.26 | C |
| ATOM | 565 | CG | LEU | A | 78 | -2.638 | 62.723 | 1.267 | 1.00 | 44.18 | C |
| ATOM | 566 | CD1 | LEU | A | 78 | -1.943 | 63.832 | 0.543 | 1.00 | 40.21 | C |
| ATOM | 567 | CD2 | LEU | A | 78 | -3.593 | 63.293 | 2.289 | 1.00 | 48.42 | C |
| ATOM | 568 | C | LEU | A | 78 | -0.798 | 60.084 | 3.475 | 1.00 | 48.70 | C |
| ATOM | 569 | O | LEU | A | 78 | 0.169 | 59.572 | 2.853 | 1.00 | 47.63 | O |
| ATOM | 570 | N | GLU | A | 79 | -0.820 | 60.254 | 4.801 | 1.00 | 47.34 | N |
| ATOM | 571 | CA | GLU | A | 79 | 0.290 | 59.830 | 5.658 | 1.00 | 47.13 | C |
| ATOM | 572 | CB | GLU | A | 79 | -0.069 | 60.033 | 7.127 | 1.00 | 48.90 | C |
| ATOM | 573 | CG | GLU | A | 79 | -1.264 | 59.166 | 7.621 | 1.00 | 56.68 | C |
| ATOM | 574 | CD | GLU | A | 79 | -1.831 | 59.412 | 9.099 | 1.00 | 62.45 | C |
| ATOM | 575 | OE1 | GLU | A | 79 | -2.753 | 59.028 | 9.515 | 1.00 | 65.92 | O |
| ATOM | 576 | OE2 | GLU | A | 79 | -0.803 | 59.997 | 9.041 | 1.00 | 70.57 | O |
| ATOM | 577 | C | GLU | A | 79 | 1.615 | 60.557 | 5.309 | 1.00 | 46.77 | C |
| ATOM | 578 | O | GLU | A | 79 | 2.715 | 60.012 | 5.495 | 1.00 | 44.83 | O |
| ATOM | 579 | N | ASP | A | 80 | 1.516 | 61.770 | 4.778 | 1.00 | 42.42 | N |
| ATOM | 580 | CA | ASP | A | 80 | 2.747 | 62.495 | 4.416 | 1.00 | 43.38 | C |
| ATOM | 581 | CB | ASP | A | 80 | 2.573 | 63.991 | 4.592 | 1.00 | 40.96 | C |
| ATOM | 582 | CG | ASP | A | 80 | 3.926 | 64.742 | 4.594 | 1.00 | 47.92 | C |
| ATOM | 583 | OD1 | ASP | A | 80 | 4.787 | 64.473 | 5.469 | 1.00 | 38.09 | O |
| ATOM | 584 | OD2 | ASP | A | 80 | 4.121 | 65.591 | 3.707 | 1.00 | 45.11 | O |
| ATOM | 585 | C | ASP | A | 80 | 3.005 | 62.164 | 3.005 | 1.00 | 43.58 | C |
| ATOM | 586 | O | ASP | A | 80 | 4.247 | 62.740 | 2.534 | 1.00 | 46.01 | O |
| ATOM | 587 | N | GLN | A | 81 | 2.582 | 61.235 | 2.331 | 1.00 | 40.56 | N |
| ATOM | 588 | CA | GLN | A | 81 | 3.008 | 60.778 | 1.010 | 1.00 | 39.95 | C |
| ATOM | 589 | CB | GLN | A | 81 | 1.998 | 61.182 | -0.062 | 1.00 | 38.95 | C |
| ATOM | 590 | CG | GLN | A | 81 | 1.773 | 62.721 | -0.129 | 1.00 | 44.05 | C |
| ATOM | 591 | CD | GLN | A | 81 | 2.974 | 63.544 | -0.682 | 1.00 | 53.15 | C |
| ATOM | 592 | OE1 | GLN | A | 81 | 3.862 | 63.021 | -1.369 | 1.00 | 48.14 | O |
| ATOM | 593 | NE2 | GLN | A | 81 | 2.964 | 64.849 | -0.402 | 1.00 | 49.52 | N |
| ATOM | 594 | C | GLN | A | 81 | 3.234 | 59.271 | 1.005 | 1.00 | 41.11 | C |
| ATOM | 595 | O | GLN | A | 81 | 2.413 | 58.516 | 0.474 | 1.00 | 41.63 | O |
| ATOM | 596 | N | PRO | A | 82 | 4.389 | 56.823 | 1.536 | 1.00 | 41.29 | N |
| ATOM | 597 | CA | PRO | A | 82 | 4.555 | 57.397 | 1.840 | 1.00 | 40.58 | C |
| ATOM | 598 | CB | PRO | A | 82 | 5.705 | 57.415 | 2.830 | 1.00 | 37.60 | C |
| ATOM | 599 | CG | PRO | A | 82 | 6.584 | 58.583 | 2.360 | 1.00 | 42.53 | C |
| ATOM | 600 | CD | PRO | A | 82 | 5.627 | 59.594 | 1.776 | 1.00 | 39.97 | C |
| ATOM | 601 | C | PRO | A | 82 | 4.970 | 56.557 | 0.622 | 1.00 | 42.08 | C |
| ATOM | 602 | O | PRO | A | 82 | 5.126 | 55.320 | 0.730 | 1.00 | 40.29 | O |
| ATOM | 603 | N | THR | A | 83 | 5.158 | 57.220 | -1.516 | 1.00 | 40.49 | N |
| ATOM | 604 | CA | THR | A | 83 | 5.902 | 56.622 | -1.634 | 1.00 | 43.60 | C |
| ATOM | 605 | CB | THR | A | 83 | 6.615 | 57.704 | -2.465 | 1.00 | 43.28 | C |
| ATOM | 606 | OG1 | THR | A | 83 | 5.779 | 58.851 | -2.553 | 1.00 | 48.15 | O |
| ATOM | 607 | CG2 | THR | A | 83 | 7.915 | 58.094 | -1.759 | 1.00 | 47.93 | C |

TABLE 10-continued

Atomic coordinates for COM1 complex of the modified
TXNIP protein represented by SEQ ID NO: 6 and the modified protein represented by SEQ ID NO: 3

| | | | | | | | | | | | |
|---|---|---|---|---|---|---|---|---|---|---|---|
| ATOM | 608 | C | | THR | A | 83 | 5.114 | -2.529 | 55.661 | 1.00 | 43.45 | C |
| ATOM | 609 | O | | THR | A | 83 | 5.717 | -3.214 | 54.827 | 1.00 | 47.76 | O |
| ATOM | 610 | N | | GLY | A | 84 | 3.788 | -2.522 | 55.766 | 1.00 | 37.71 | N |
| ATOM | 611 | CA | | GLY | A | 84 | 2.971 | -3.368 | 54.914 | 1.00 | 36.96 | C |
| ATOM | 612 | C | | GLY | A | 84 | 2.161 | -4.433 | 55.619 | 1.00 | 36.00 | C |
| ATOM | 613 | O | | GLY | A | 84 | 2.328 | -4.660 | 56.807 | 1.00 | 36.63 | O |
| ATOM | 614 | N | | GLU | A | 85 | 1.288 | -5.085 | 54.861 | 1.00 | 85.31 | N |
| ATOM | 615 | CA | | GLU | A | 85 | 0.293 | -6.034 | 55.370 | 1.00 | 38.29 | C |
| ATOM | 616 | CB | | GLU | A | 85 | -0.771 | -6.229 | 54.299 | 1.00 | 42.86 | C |
| ATOM | 617 | CG | | GLU | A | 85 | -1.690 | -5.057 | 54.130 | 1.00 | 38.03 | C |
| ATOM | 618 | CD | | GLU | A | 85 | -2.438 | -5.157 | 52.809 | 1.00 | 56.88 | C |
| ATOM | 619 | OE1 | | GLU | A | 85 | -3.084 | -6.223 | 52.574 | 1.00 | 40.32 | O |
| ATOM | 620 | OE2 | | GLU | A | 85 | -2.383 | -4.170 | 52.026 | 1.00 | 46.73 | O |
| ATOM | 621 | C | | GLU | A | 85 | 0.821 | -7.418 | 55.729 | 1.00 | 38.31 | C |
| ATOM | 622 | O | | GLU | A | 85 | 0.115 | -8.198 | 56.361 | 1.00 | 41.46 | O |
| ATOM | 623 | N | | ASN | A | 86 | 2.032 | -7.738 | 55.302 | 1.00 | 34.08 | N |
| ATOM | 624 | CA | | ASN | A | 86 | 2.642 | -9.022 | 55.634 | 1.00 | 31.68 | C |
| ATOM | 625 | CB | | ASN | A | 86 | 3.414 | -9.554 | 54.436 | 1.00 | 31.32 | C |
| ATOM | 626 | CG | | ASN | A | 86 | 4.493 | -8.595 | 53.963 | 1.00 | 36.13 | C |
| ATOM | 627 | OD1 | | ASN | A | 86 | 4.349 | -7.370 | 54.087 | 1.00 | 31.16 | O |
| ATOM | 628 | ND2 | | ASN | A | 86 | 5.590 | -9.149 | 53.430 | 1.00 | 28.42 | N |
| ATOM | 629 | C | | ASN | A | 86 | 3.521 | -8.891 | 55.911 | 1.00 | 30.52 | C |
| ATOM | 630 | O | | ASN | A | 86 | 4.409 | -9.689 | 57.175 | 1.00 | 31.81 | O |
| ATOM | 631 | N | | GLU | A | 87 | 3.244 | 7.857 | 57.700 | 1.00 | 34.00 | N |
| ATOM | 632 | CA | | GLU | A | 87 | 3.829 | -7.677 | 59.030 | 1.00 | 36.36 | C |
| ATOM | 633 | CB | | GLU | A | 87 | 4.898 | -6.583 | 58.999 | 1.00 | 38.96 | C |
| ATOM | 634 | CG | | GLU | A | 87 | 5.567 | -6.340 | 60.307 | 1.00 | 46.65 | C |
| ATOM | 635 | CD | | GLU | A | 87 | 7.011 | -6.812 | 60.352 | 1.00 | 50.83 | C |
| ATOM | 636 | OE1 | | GLU | A | 87 | 7.786 | -6.029 | 60.956 | 1.00 | 60.51 | O |
| ATOM | 637 | OE2 | | GLU | A | 87 | 7.373 | -7.913 | 59.810 | 1.00 | 61.73 | O |
| ATOM | 638 | C | | GLU | A | 87 | 2.674 | -7.291 | 59.937 | 1.00 | 36.27 | C |
| ATOM | 639 | O | | GLU | A | 87 | 1.932 | -6.334 | 59.663 | 1.00 | 35.82 | O |
| ATOM | 640 | N | | MET | A | 88 | 2.440 | -8.081 | 60.971 | 1.00 | 33.78 | N |
| ATOM | 641 | CA | | MET | A | 88 | 1.327 | -7.788 | 61.871 | 1.00 | 35.63 | C |
| ATOM | 642 | CB | | MET | A | 88 | 0.964 | -9.006 | 62.710 | 1.00 | 33.08 | C |
| ATOM | 643 | CG | | MET | A | 88 | 0.562 | -10.208 | 61.841 | 1.00 | 41.93 | C |
| ATOM | 644 | SD | | MET | A | 88 | -0.080 | -11.557 | 62.845 | 1.00 | 40.90 | S |
| ATOM | 645 | CE | | MET | A | 88 | 1.407 | -12.350 | 63.378 | 1.00 | 41.38 | C |
| ATOM | 646 | C | | MET | A | 88 | 1.704 | -6.657 | 62.793 | 1.00 | 35.10 | C |
| ATOM | 647 | O | | MET | A | 88 | 2.880 | -6.430 | 63.034 | 1.00 | 36.73 | O |
| ATOM | 648 | N | | VAL | A | 89 | 0.688 | -5.991 | 63.320 | 1.00 | 32.63 | N |
| ATOM | 649 | CA | | VAL | A | 89 | 0.808 | -4.861 | 64.238 | 1.00 | 36.86 | C |
| ATOM | 650 | CB | | VAL | A | 89 | -0.288 | -3.854 | 63.913 | 1.00 | 34.27 | C |
| ATOM | 651 | CG1 | | VAL | A | 89 | -0.500 | -2.849 | 65.058 | 1.00 | 42.87 | C |
| ATOM | 652 | CG2 | | VAL | A | 89 | 0.075 | -3.141 | 62.641 | 1.00 | 39.71 | C |
| ATOM | 653 | C | | VAL | A | 89 | 0.615 | -5.342 | 65.675 | 1.00 | 38.29 | C |
| ATOM | 654 | O | | VAL | A | 89 | -0.250 | -6.170 | 65.930 | 1.00 | 34.53 | O |
| ATOM | 655 | N | | ILE | A | 90 | 1.438 | -4.841 | 66.598 | 1.00 | 39.52 | N |
| ATOM | 656 | CA | | ILE | A | 90 | 1.300 | -5.158 | 68.029 | 1.00 | 38.49 | C |
| ATOM | 657 | CB | | ILE | A | 90 | 2.653 | -5.426 | 68.724 | 1.00 | 41.87 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 658 | CG1 | ILE | A | 90 | 3.468 | -6.463 | 67.944 | 1.00 | 40.23 | C |
| ATOM | 659 | CD1 | ILE | A | 90 | 4.927 | -5.480 | 68.352 | 1.00 | 47.34 | C |
| ATOM | 660 | CG2 | ILE | A | 90 | 2.421 | -5.915 | 70.167 | 1.00 | 43.28 | C |
| ATOM | 661 | C | ILE | A | 90 | 0.612 | -3.997 | 68.687 | 1.00 | 37.39 | C |
| ATOM | 662 | O | ILE | A | 90 | 1.080 | -2.862 | 68.604 | 1.00 | 37.39 | O |
| ATOM | 663 | N | MET | A | 91 | -0.530 | -4.288 | 69.297 | 1.00 | 35.28 | N |
| ATOM | 664 | CA | MET | A | 91 | -1.364 | -3.288 | 69.913 | 1.00 | 37.51 | C |
| ATOM | 665 | CB | MET | A | 91 | -2.825 | -3.511 | 69.519 | 1.00 | 35.03 | C |
| ATOM | 666 | CG | MET | A | 91 | -3.223 | -3.095 | 68.087 | 1.00 | 37.44 | C |
| ATOM | 667 | SD | MET | A | 91 | -5.038 | -3.020 | 67.937 | 1.00 | 42.12 | S |
| ATOM | 668 | CE | MET | A | 91 | -5.302 | -2.355 | 66.287 | 1.00 | 34.91 | C |
| ATOM | 669 | C | MET | A | 91 | -1.207 | -3.458 | 71.430 | 1.00 | 39.53 | C |
| ATOM | 670 | O | MET | A | 91 | -1.114 | -4.583 | 71.921 | 1.00 | 38.75 | O |
| ATOM | 671 | N | ARG | A | 92 | -1.166 | -2.349 | 72.155 | 1.00 | 41.91 | N |
| ATOM | 672 | CA | ARG | A | 92 | -0.945 | -2.386 | 73.622 | 1.00 | 44.30 | C |
| ATOM | 673 | CB | ARG | A | 92 | 0.477 | -1.901 | 73.957 | 1.00 | 43.70 | C |
| ATOM | 674 | CG | ARG | A | 92 | 1.531 | -2.890 | 73.549 | 1.00 | 52.63 | C |
| ATOM | 675 | CD | ARG | A | 92 | 2.821 | -2.252 | 73.135 | 1.00 | 61.18 | C |
| ATOM | 676 | NE | ARG | A | 92 | 3.595 | -3.209 | 72.348 | 1.00 | 71.89 | N |
| ATOM | 677 | CZ | ARG | A | 92 | 4.888 | -3.095 | 72.054 | 1.00 | 75.40 | C |
| ATOM | 678 | NH1 | ARG | A | 92 | 5.503 | -2.055 | 72.494 | 1.00 | 80.30 | N |
| ATOM | 679 | NH2 | ARG | A | 92 | 5.479 | -4.034 | 71.321 | 1.00 | 69.26 | N |
| ATOM | 680 | C | ARG | A | 92 | -1.996 | -1.544 | 74.358 | 1.00 | 45.88 | C |
| ATOM | 681 | O | ARG | A | 92 | -2.490 | -0.563 | 73.788 | 1.00 | 44.78 | O |
| ATOM | 682 | N | PRO | A | 93 | -2.347 | -1.920 | 75.624 | 1.00 | 48.00 | N |
| ATOM | 683 | CA | PRO | A | 93 | -3.340 | -1.126 | 76.369 | 1.00 | 51.33 | C |
| ATOM | 684 | CB | PRO | A | 93 | -3.477 | -1.880 | 77.698 | 1.00 | 50.10 | C |
| ATOM | 685 | CG | PRO | A | 93 | -2.261 | -2.701 | 77.800 | 1.00 | 48.34 | C |
| ATOM | 686 | CD | PRO | A | 93 | -1.883 | -3.075 | 76.414 | 1.00 | 47.04 | C |
| ATOM | 687 | C | PRO | A | 93 | -2.885 | 0.313 | 76.608 | 1.00 | 53.79 | C |
| ATOM | 688 | O | PRO | A | 93 | -1.682 | 0.575 | 76.660 | 1.00 | 45.61 | O |
| ATOM | 689 | N | GLY | A | 94 | 3.842 | 1.232 | 76.729 | 1.00 | 55.57 | N |
| ATOM | 690 | CA | GLY | A | 94 | -3.559 | 2.652 | 76.941 | 1.00 | 56.73 | C |
| ATOM | 691 | C | GLY | A | 94 | -3.528 | 3.494 | 75.670 | 1.00 | 59.14 | C |
| ATOM | 692 | O | GLY | A | 94 | -3.513 | 4.732 | 75.736 | 1.00 | 60.44 | O |
| ATOM | 693 | N | ASN | A | 95 | -3.549 | 2.824 | 74.515 | 1.00 | 58.63 | N |
| ATOM | 694 | CA | ASN | A | 95 | -3.504 | 3.486 | 73.222 | 1.00 | 56.90 | C |
| ATOM | 695 | CB | ASN | A | 95 | -2.379 | 2.915 | 72.351 | 1.00 | 58.47 | C |
| ATOM | 696 | CG | ASN | A | 95 | -1.060 | 2.796 | 73.086 | 1.00 | 58.13 | C |
| ATOM | 697 | OD1 | ASN | A | 95 | -0.398 | 3.794 | 73.362 | 1.00 | 63.55 | O |
| ATOM | 698 | ND2 | ASN | A | 95 | -0.553 | 1.566 | 73.385 | 1.00 | 56.04 | N |
| ATOM | 699 | C | ASN | A | 95 | -4.803 | 3.309 | 72.470 | 1.00 | 56.08 | C |
| ATOM | 700 | O | ASN | A | 95 | -5.478 | 2.284 | 72.612 | 1.00 | 54.70 | O |
| ATOM | 701 | N | LYS | A | 96 | -5.132 | 4.325 | 71.671 | 1.00 | 54.48 | N |
| ATOM | 702 | CA | LYS | A | 96 | -6.247 | 4.301 | 70.731 | 1.00 | 53.29 | C |
| ATOM | 703 | CB | LYS | A | 96 | -7.072 | 5.582 | 70.842 | 1.00 | 54.05 | C |
| ATOM | 704 | CG | LYS | A | 96 | -7.718 | 5.809 | 72.200 | 1.00 | 61.90 | C |
| ATOM | 705 | CD | LYS | A | 96 | -8.767 | 6.934 | 72.131 | 1.00 | 65.14 | C |
| ATOM | 706 | CE | LYS | A | 96 | -8.147 | 8.320 | 72.341 | 1.00 | 71.01 | C |
| ATOM | 707 | NZ | LYS | A | 96 | -9.193 | 9.387 | 72.459 | 1.00 | 72.08 | N |

TABLE 10-continued

Atomic coordinates for COM1 complex of the modified
TXNIP protein represented by SEQ ID NO: 6 and the modified protein represented by SEQ ID NO: 3

| ATOM | 708 | C | LYS | A | 96 | −5.694 | 4.193 | 69.316 | 1.00 | 50.39 | C |
|---|---|---|---|---|---|---|---|---|---|---|---|
| ATOM | 709 | O | LYS | A | 96 | −5.046 | 5.119 | 68.820 | 1.00 | 51.44 | O |
| ATOM | 710 | N | TYR | A | 97 | −5.941 | 3.055 | 68.675 | 1.00 | 46.86 | N |
| ATOM | 711 | CA | TYR | A | 97 | −5.465 | 2.821 | 67.323 | 1.00 | 44.01 | C |
| ATOM | 712 | CB | TYR | A | 97 | −5.006 | 1.370 | 67.140 | 1.00 | 43.81 | C |
| ATOM | 713 | CG | TYR | A | 97 | −3.915 | 0.991 | 68.112 | 1.00 | 39.41 | C |
| ATOM | 714 | CD1 | TYR | A | 97 | −2.571 | 1.087 | 67.756 | 1.00 | 41.11 | C |
| ATOM | 715 | CE1 | TYR | A | 97 | −1.564 | 0.772 | 58.671 | 1.00 | 34.77 | C |
| ATOM | 716 | CZ | TYR | A | 97 | −1.810 | 0.341 | 59.942 | 1.00 | 38.97 | C |
| ATOM | 717 | OH | TYR | A | 97 | −0.924 | 0.000 | 70.847 | 1.00 | 38.09 | O |
| ATOM | 718 | CE2 | TYR | A | 97 | −3.238 | 0.245 | 70.313 | 1.00 | 33.23 | C |
| ATOM | 719 | CD2 | TYR | A | 97 | −4.226 | 0.569 | 69.409 | 1.00 | 36.44 | C |
| ATOM | 720 | C | TYR | A | 97 | −6.608 | 3.180 | 66.396 | 1.00 | 44.77 | C |
| ATOM | 721 | O | TYR | A | 97 | −7.687 | 2.577 | 66.462 | 1.00 | 44.28 | O |
| ATOM | 722 | N | GLU | A | 98 | −6.375 | 4.212 | 65.585 | 1.00 | 43.81 | N |
| ATOM | 723 | CA | GLU | A | 98 | −7.399 | 4.790 | 64.718 | 1.00 | 46.46 | C |
| ATOM | 724 | CB | GLU | A | 98 | −7.605 | 6.295 | 65.002 | 1.00 | 47.30 | C |
| ATOM | 725 | CG | GLU | A | 98 | −7.604 | 6.649 | 66.493 | 1.00 | 49.79 | C |
| ATOM | 726 | CD | GLU | A | 98 | −7.980 | 8.105 | 66.790 | 1.00 | 58.90 | C |
| ATOM | 727 | OE1 | GLU | A | 98 | −7.852 | 8.981 | 65.903 | 1.00 | 55.83 | O |
| ATOM | 728 | OE2 | GLU | A | 98 | −8.397 | 8.370 | 67.937 | 1.00 | 64.93 | O |
| ATOM | 729 | C | GLU | A | 98 | −6.983 | 4.576 | 63.289 | 1.00 | 44.45 | C |
| ATOM | 730 | O | GLU | A | 98 | −5.941 | 5.071 | 62.845 | 1.00 | 43.75 | O |
| ATOM | 731 | N | TYR | A | 99 | −7.816 | 3.813 | 82.586 | 1.00 | 44.30 | N |
| ATOM | 732 | CA | TYR | A | 99 | −7.653 | 3.519 | 61.172 | 1.00 | 41.40 | C |
| ATOM | 733 | CB | TYR | A | 99 | −8.060 | 2.071 | 60.909 | 1.00 | 39.58 | C |
| ATOM | 734 | CG | TYR | A | 99 | −7.176 | 1.002 | 61.518 | 1.00 | 34.37 | C |
| ATOM | 735 | CD1 | TYR | A | 99 | −6.224 | 0.371 | 60.735 | 1.00 | 36.00 | C |
| ATOM | 736 | CE1 | TYR | A | 99 | −5.421 | −0.617 | 61.222 | 1.00 | 39.51 | C |
| ATOM | 737 | CZ | TYR | A | 99 | −5.526 | −1.020 | 62.520 | 1.00 | 39.71 | C |
| ATOM | 738 | OH | TYR | A | 99 | −4.659 | −2.031 | 62.904 | 1.00 | 32.47 | O |
| ATOM | 739 | CE2 | TYR | A | 99 | −6.465 | −0.429 | 63.364 | 1.00 | 35.31 | C |
| ATOM | 740 | CD2 | TYR | A | 99 | −7.326 | 0.581 | 62.841 | 1.00 | 32.04 | C |
| ATOM | 741 | C | TYR | A | 99 | −8.581 | 4.415 | 60.358 | 1.00 | 44.84 | C |
| ATOM | 742 | O | TYR | A | 99 | −9.792 | 4.368 | 60.528 | 1.00 | 46.39 | O |
| ATOM | 743 | N | LYS | A | 100 | −8.013 | 5.231 | 59.481 | 1.00 | 48.94 | N |
| ATOM | 744 | CA | LYS | A | 100 | −8.817 | 6.094 | 58.604 | 1.00 | 48.73 | C |
| ATOM | 745 | CB | LYS | A | 100 | −7.927 | 7.139 | 57.933 | 1.00 | 50.38 | C |
| ATOM | 746 | CG | LYS | A | 100 | −7.381 | 8.217 | 58.820 | 1.00 | 63.06 | C |
| ATOM | 747 | CD | LYS | A | 100 | −6.728 | 9.277 | 57.940 | 1.00 | 64.22 | C |
| ATOM | 748 | CE | LYS | A | 100 | −6.681 | 10.632 | 58.615 | 1.00 | 69.28 | C |
| ATOM | 749 | NZ | LYS | A | 100 | −6.672 | 11.719 | 57.595 | 1.00 | 48.75 | N |
| ATOM | 750 | C | LYS | A | 100 | −9.506 | 5.287 | 57.494 | 1.00 | 48.86 | C |
| ATOM | 751 | O | LYS | A | 100 | −8.868 | 4.456 | 56.845 | 1.00 | 50.23 | O |
| ATOM | 752 | N | PHE | A | 101 | −10.802 | 5.532 | 57.294 | 1.00 | 52.22 | N |
| ATOM | 753 | CA | PHE | A | 101 | −11.522 | 5.083 | 56.086 | 1.00 | 51.76 | C |
| ATOM | 754 | CB | PHE | A | 101 | −12.480 | 3.922 | 56.373 | 1.00 | 51.29 | C |
| ATOM | 755 | CG | PHE | A | 101 | −13.731 | 4.304 | 57.103 | 1.00 | 48.87 | C |
| ATOM | 756 | CD1 | PHE | A | 101 | −14.839 | 4.774 | 56.411 | 1.00 | 49.84 | C |
| ATOM | 757 | CE1 | PHE | A | 101 | −16.019 | 5.122 | 57.087 | 1.00 | 49.84 | C |

TABLE 10-continued

Atomic coordinates for COM1 complex of the modified
TXNIP protein represented by SEQ ID NO: 6 and the modified protein represented by SEQ ID NO: 3

| ATOM | 758 | CZ | PHE | A | 101 | −16.104 | 4.950 | 58.474 | 1.00 | 51.47 | C |
|---|---|---|---|---|---|---|---|---|---|---|---|
| ATOM | 759 | CE2 | PHE | A | 101 | −15.002 | 4.457 | 59.179 | 1.00 | 56.33 | C |
| ATOM | 760 | CD2 | PHE | A | 101 | −13.824 | 4.128 | 58.485 | 1.00 | 51.95 | C |
| ATOM | 761 | C | PHE | A | 101 | −12.228 | 6.214 | 55.331 | 1.00 | 52.66 | C |
| ATOM | 762 | O | PHE | A | 101 | −12.476 | 7.287 | 55.871 | 1.00 | 54.30 | O |
| ATOM | 763 | N | GLY | A | 102 | −12.541 | 5.965 | 54.067 | 1.00 | 53.72 | N |
| ATOM | 764 | CA | GLY | A | 102 | −13.197 | 6.962 | 53.235 | 1.00 | 51.75 | C |
| ATOM | 765 | C | GLY | A | 102 | −13.583 | 6.368 | 51.903 | 1.00 | 51.33 | C |
| ATOM | 766 | O | GLY | A | 102 | −12.762 | 5.746 | 51.236 | 1.00 | 52.31 | O |
| ATOM | 767 | N | PHE | A | 103 | −14.847 | 6.528 | 51.534 | 1.00 | 50.77 | N |
| ATOM | 768 | CA | PHE | A | 103 | −15.329 | 8.094 | 50.224 | 1.00 | 52.26 | C |
| ATOM | 769 | CB | PHE | A | 103 | −15.889 | 4.666 | 50.289 | 1.00 | 49.56 | C |
| ATOM | 770 | CG | PHE | A | 103 | −17.013 | 4.496 | 51.290 | 1.00 | 51.52 | C |
| ATOM | 771 | CD1 | PHE | A | 103 | −18.338 | 4.615 | 50.897 | 1.00 | 45.80 | C |
| ATOM | 772 | CE1 | PHE | A | 103 | −19.363 | 4.485 | 51.821 | 1.00 | 43.96 | C |
| ATOM | 773 | CZ | PHE | A | 103 | −19.075 | 4.218 | 53.161 | 1.00 | 47.77 | C |
| ATOM | 774 | CE2 | PHE | A | 103 | −17.755 | 4.088 | 53.569 | 1.00 | 39.23 | C |
| ATOM | 775 | CD2 | PHE | A | 103 | −16.734 | 4.234 | 52.633 | 1.00 | 49.51 | C |
| ATOM | 776 | C | PHE | A | 103 | −16.395 | 7.082 | 49.723 | 1.00 | 55.81 | C |
| ATOM | 777 | O | PHE | A | 103 | −17.118 | 7.685 | 50.516 | 1.00 | 55.38 | O |
| ATOM | 778 | N | GLU | A | 104 | −16.465 | 7.242 | 48.402 | 1.00 | 59.28 | N |
| ATOM | 779 | CA | GLU | A | 104 | −17.434 | 8.120 | 47.751 | 1.00 | 62.14 | C |
| ATOM | 780 | CB | GLU | A | 104 | −16.787 | 8.777 | 46.525 | 1.00 | 61.30 | C |
| ATOM | 781 | CG | GLU | A | 104 | −17.206 | 10.210 | 46.297 | 1.00 | 68.34 | C |
| ATOM | 782 | CD | GLU | A | 104 | −16.127 | 11.056 | 45.636 | 1.00 | 77.56 | C |
| ATOM | 783 | OE1 | GLU | A | 104 | −15.995 | 12.241 | 46.020 | 1.00 | 77.02 | O |
| ATOM | 784 | OE2 | GLU | A | 104 | −15.409 | 10.548 | 44.743 | 1.00 | 78.57 | O |
| ATOM | 785 | C | GLU | A | 104 | −18.654 | 7.296 | 47.337 | 1.00 | 62.30 | C |
| ATOM | 786 | O | GLU | A | 104 | −18.503 | 6.232 | 46.711 | 1.00 | 60.48 | O |
| ATOM | 787 | N | LEU | A | 105 | −19.847 | 7.772 | 47.710 | 1.00 | 62.06 | N |
| ATOM | 788 | CA | LEU | A | 105 | −21.105 | 7.141 | 47.294 | 1.00 | 63.01 | C |
| ATOM | 789 | CB | LEU | A | 105 | −22.281 | 7.688 | 48.117 | 1.00 | 62.52 | C |
| ATOM | 790 | CG | LEU | A | 105 | −22.470 | 7.338 | 49.602 | 1.00 | 59.69 | C |
| ATOM | 791 | CD1 | LEU | A | 105 | −23.369 | 8.387 | 50.245 | 1.00 | 56.22 | C |
| ATOM | 792 | CD2 | LEU | A | 105 | −23.037 | 5.932 | 49.840 | 1.00 | 44.46 | C |
| ATOM | 793 | C | LEU | A | 105 | −21.333 | 7.372 | 45.779 | 1.00 | 64.76 | C |
| ATOM | 794 | O | LEU | A | 105 | −20.725 | 8.280 | 45.204 | 1.00 | 65.38 | O |
| ATOM | 795 | N | PRO | A | 106 | −22.178 | 6.540 | 45.124 | 1.00 | 65.41 | N |
| ATOM | 796 | CA | PRO | A | 106 | −22.394 | 6.699 | 43.675 | 1.00 | 68.25 | C |
| ATOM | 797 | CB | PRO | A | 106 | −23.214 | 6.458 | 43.298 | 1.00 | 67.60 | C |
| ATOM | 798 | CG | PRO | A | 106 | −23.139 | 4.540 | 44.477 | 1.00 | 66.25 | C |
| ATOM | 799 | CD | PRO | A | 106 | −22.958 | 5.411 | 45.661 | 1.00 | 64.87 | C |
| ATOM | 800 | C | PRO | A | 106 | −28.185 | 7.954 | 43.284 | 1.00 | 70.34 | C |
| ATOM | 801 | O | PRO | A | 106 | −23.939 | 8.495 | 44.103 | 1.00 | 69.70 | O |
| ATOM | 802 | N | GLN | A | 107 | −22.982 | 8.403 | 42.042 | 1.00 | 73.01 | N |
| ATOM | 803 | CA | GLN | A | 107 | −23.863 | 9.373 | 41.374 | 1.00 | 75.06 | C |
| ATOM | 804 | CB | GLN | A | 107 | −23.161 | 10.020 | 40.178 | 1.00 | 74.56 | C |
| ATOM | 805 | CG | GLN | A | 107 | −22.902 | 11.510 | 40.324 | 1.00 | 79.53 | C |
| ATOM | 806 | CD | GLN | A | 107 | −21.621 | 11.828 | 41.074 | 1.00 | 85.01 | C |
| ATOM | 807 | OE1 | GLN | A | 107 | −21.133 | 11.027 | 41.872 | 1.00 | 91.44 | O |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 808 | NE2 | GLN | A | 107 | −21.071 | 13.011 | 40.822 | 1.00 | 87.28 | N |
| ATOM | 809 | C | GLN | A | 107 | −25.130 | 8.686 | 40.886 | 1.00 | 76.17 | C |
| ATOM | 810 | O | GLN | A | 107 | −25.067 | 7.591 | 40.314 | 1.00 | 78.58 | O |
| ATOM | 811 | N | GLY | A | 108 | −26.276 | 9.325 | 41.102 | 1.00 | 75.22 | N |
| ATOM | 812 | CA | GLY | A | 108 | −27.542 | 8.766 | 40.647 | 1.00 | 73.94 | C |
| ATOM | 813 | C | GLY | A | 108 | −28.294 | 7.959 | 41.695 | 1.00 | 73.32 | C |
| ATOM | 814 | O | GLY | A | 108 | −28.259 | 8.295 | 42.888 | 1.00 | 72.45 | O |
| ATOM | 815 | N | PRO | A | 109 | −28.978 | 6.877 | 41.262 | 1.00 | 73.10 | N |
| ATOM | 816 | CA | PRO | A | 109 | −29.936 | 6.239 | 42.170 | 1.00 | 72.89 | C |
| ATOM | 817 | CB | PRO | A | 109 | −30.608 | 5.167 | 41.294 | 1.00 | 72.33 | C |
| ATOM | 818 | CG | PRO | A | 109 | −29.608 | 4.860 | 40.233 | 1.00 | 71.89 | C |
| ATOM | 819 | CD | PRO | A | 109 | −28.882 | 6.165 | 39.972 | 1.00 | 73.82 | C |
| ATOM | 820 | C | PRO | A | 109 | −29.224 | 5.627 | 43.379 | 1.00 | 71.83 | C |
| ATOM | 821 | O | PRO | A | 109 | −28.201 | 4.944 | 43.219 | 1.00 | 70.07 | O |
| ATOM | 822 | N | LEU | A | 109 | −29.741 | 5.915 | 44.573 | 1.00 | 70.62 | N |
| ATOM | 823 | CA | LEU | A | 110 | −29.172 | 5.371 | 45.795 | 1.00 | 69.97 | C |
| ATOM | 824 | CB | LEU | A | 110 | −28.857 | 6.480 | 46.810 | 1.00 | 69.60 | C |
| ATOM | 825 | CG | LEU | A | 110 | −27.762 | 7.479 | 46.389 | 1.00 | 72.16 | C |
| ATOM | 826 | CD1 | LEU | A | 110 | −27.726 | 8.689 | 47.300 | 1.00 | 75.23 | C |
| ATOM | 827 | CD2 | LEU | A | 110 | −26.366 | 6.851 | 46.275 | 1.00 | 68.21 | C |
| ATOM | 828 | C | LEU | A | 110 | −30.075 | 4.284 | 46.366 | 1.00 | 70.53 | C |
| ATOM | 829 | O | LEU | A | 110 | −29.809 | 3.736 | 47.443 | 1.00 | 69.90 | O |
| ATOM | 830 | N | GLY | A | 111 | −31.130 | 3.961 | 45.620 | 1.00 | 70.97 | N |
| ATOM | 831 | CA | GLY | A | 111 | −32.045 | 2.882 | 45.994 | 1.00 | 73.80 | C |
| ATOM | 832 | C | GLY | A | 111 | −33.151 | 3.333 | 46.920 | 1.00 | 76.84 | C |
| ATOM | 833 | O | GLY | A | 111 | −33.915 | 2.516 | 47.448 | 1.00 | 77.20 | O |
| ATOM | 834 | N | THR | A | 112 | −33.238 | 4.646 | 47.103 | 1.00 | 79.00 | N |
| ATOM | 835 | CA | THR | A | 112 | −34.171 | 5.257 | 48.037 | 1.00 | 81.08 | C |
| ATOM | 836 | CB | THR | A | 112 | −33.539 | 6.576 | 48.642 | 1.00 | 81.45 | C |
| ATOM | 837 | OG1 | THR | A | 112 | −34.199 | 6.958 | 49.857 | 1.00 | 76.66 | O |
| ATOM | 838 | CG2 | THR | A | 112 | −33.520 | 7.734 | 47.627 | 1.00 | 80.97 | C |
| ATOM | 839 | C | THR | A | 112 | −35.533 | 5.437 | 47.330 | 1.00 | 83.15 | C |
| ATOM | 840 | O | THR | A | 112 | −36.466 | 6.030 | 47.881 | 1.00 | 83.29 | O |
| ATOM | 841 | N | SER | A | 113 | −35.630 | 4.862 | 46.123 | 1.00 | 84.97 | N |
| ATOM | 842 | CA | SER | A | 113 | −36.783 | 5.006 | 45.212 | 1.00 | 86.24 | C |
| ATOM | 843 | CB | SER | A | 113 | −36.508 | 4.322 | 43.858 | 1.00 | 85.72 | C |
| ATOM | 844 | OG | SER | A | 113 | −35.984 | 3.010 | 44.016 | 1.00 | 85.21 | O |
| ATOM | 845 | C | SER | A | 113 | −38.112 | 4.530 | 45.801 | 1.00 | 87.57 | C |
| ATOM | 846 | O | SER | A | 113 | −39.057 | 5.321 | 45.924 | 1.00 | 88.79 | O |
| ATOM | 847 | N | PHE | A | 114 | −38.181 | 3.247 | 46.158 | 1.00 | 88.74 | N |
| ATOM | 848 | CA | PHE | A | 114 | −39.373 | 2.679 | 46.794 | 1.00 | 89.16 | C |
| ATOM | 849 | CB | PHE | A | 114 | −39.990 | 1.554 | 45.948 | 1.00 | 89.42 | C |
| ATOM | 850 | CG | PHE | A | 114 | −40.243 | 1.954 | 44.528 | 1.00 | 91.03 | C |
| ATOM | 851 | CD1 | PHE | A | 114 | −41.250 | 2.874 | 44.221 | 1.00 | 93.20 | C |
| ATOM | 852 | CE1 | PHE | A | 114 | −41.477 | 3.273 | 42.915 | 1.00 | 93.51 | C |
| ATOM | 853 | CZ | PHE | A | 114 | −40.689 | 2.757 | 41.894 | 1.00 | 95.40 | C |
| ATOM | 854 | CE2 | PHE | A | 114 | −39.676 | 1.837 | 42.188 | 1.00 | 94.28 | C |
| ATOM | 855 | CD2 | PHE | A | 114 | −39.458 | 1.445 | 43.501 | 1.00 | 88.88 | C |
| ATOM | 856 | C | PHE | A | 114 | −39.067 | 2.213 | 48.208 | 1.00 | 89.19 | C |
| ATOM | 857 | O | PHE | A | 114 | −38.158 | 1.411 | 48.438 | 1.00 | 89.75 | O |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 858 | N | LYS | A | 115 | −39.839 | 2.749 | 49.145 | 1.00 | 88.65 | N |
| ATOM | 859 | CA | LYS | A | 115 | −39.657 | 2.503 | 50.564 | 1.00 | 87.10 | C |
| ATOM | 860 | CB | LYS | A | 115 | −38.869 | 3.656 | 51.216 | 1.00 | 87.74 | C |
| ATOM | 861 | CG | LYS | A | 115 | −39.597 | 5.015 | 51.263 | 1.00 | 90.46 | C |
| ATOM | 862 | CD | LYS | A | 115 | −39.462 | 5.813 | 49.959 | 1.00 | 91.70 | C |
| ATOM | 863 | CE | LYS | A | 115 | −40.120 | 7.184 | 50.066 | 1.00 | 94.09 | C |
| ATOM | 864 | NZ | LYS | A | 115 | −39.616 | 8.119 | 49.021 | 1.00 | 94.84 | N |
| ATOM | 865 | C | LYS | A | 115 | −41.011 | 2.298 | 51.248 | 1.00 | 84.59 | C |
| ATOM | 866 | O | LYS | A | 115 | −42.070 | 2.589 | 50.680 | 1.00 | 85.36 | O |
| ATOM | 867 | N | GLY | A | 116 | −40.960 | 1.780 | 52.468 | 1.00 | 82.60 | N |
| ATOM | 868 | CA | GLY | A | 116 | −42.141 | 1.597 | 53.290 | 1.00 | 79.47 | C |
| ATOM | 869 | C | GLY | A | 116 | −42.967 | 0.417 | 52.837 | 1.00 | 76.29 | C |
| ATOM | 870 | O | GLY | A | 116 | −42.626 | −0.733 | 53.120 | 1.00 | 76.28 | O |
| ATOM | 871 | N | LYS | A | 117 | −44.053 | 0.714 | 52.127 | 1.00 | 73.18 | N |
| ATOM | 872 | CA | LYS | A | 117 | −45.019 | −0.290 | 51.704 | 1.00 | 70.39 | C |
| ATOM | 873 | CB | LYS | A | 117 | −46.009 | 0.328 | 50.701 | 1.00 | 69.60 | C |
| ATOM | 874 | CG | LYS | A | 117 | −47.481 | −0.018 | 50.916 | 1.00 | 71.45 | C |
| ATOM | 875 | CD | LYS | A | 117 | −47.816 | −1.480 | 50.620 | 1.00 | 72.53 | C |
| ATOM | 876 | CE | LYS | A | 117 | −49.325 | −1.714 | 50.689 | 1.00 | 73.52 | C |
| ATOM | 877 | NZ | LYS | A | 117 | −49.649 | −3.160 | 50.821 | 1.00 | 72.76 | N |
| ATOM | 878 | C | LYS | A | 117 | −44.302 | −1.488 | 51.075 | 1.00 | 68.43 | C |
| ATOM | 879 | O | LYS | A | 117 | −44.440 | −2.624 | 51.539 | 1.00 | 66.06 | O |
| ATOM | 880 | N | TYR | A | 118 | −43.515 | −1.214 | 50.035 | 1.00 | 66.25 | N |
| ATOM | 881 | CA | TYR | A | 118 | −42.945 | −2.271 | 49.213 | 1.00 | 65.84 | C |
| ATOM | 882 | CB | TYR | A | 118 | −43.337 | −2.075 | 47.748 | 1.00 | 64.20 | C |
| ATOM | 883 | CG | TYR | A | 118 | −44.828 | −2.015 | 47.502 | 1.00 | 62.07 | C |
| ATOM | 884 | CD1 | TYR | A | 118 | −45.623 | −3.163 | 47.565 | 1.00 | 62.51 | C |
| ATOM | 885 | CE1 | TYR | A | 118 | −47.012 | −3.097 | 47.320 | 1.00 | 62.85 | C |
| ATOM | 886 | CZ | TYR | A | 118 | −47.589 | −1.874 | 47.011 | 1.00 | 60.79 | C |
| ATOM | 887 | OH | TYR | A | 118 | −48.942 | −1.768 | 46.771 | 1.00 | 67.58 | O |
| ATOM | 888 | CE2 | TYR | A | 118 | −46.813 | −0.766 | 46.941 | 1.00 | 60.89 | C |
| ATOM | 889 | CD2 | TYR | A | 118 | −45.443 | −0.808 | 47.183 | 1.00 | 59.80 | C |
| ATOM | 890 | C | TYR | A | 118 | −41.434 | −2.343 | 49.336 | 1.00 | 66.42 | C |
| ATOM | 891 | O | TYR | A | 118 | −40.849 | −3.419 | 49.197 | 1.00 | 67.00 | O |
| ATOM | 892 | N | GLY | A | 119 | −40.816 | −1.195 | 49.604 | 1.00 | 66.77 | N |
| ATOM | 893 | CA | GLY | A | 119 | −39.365 | −1.099 | 49.664 | 1.00 | 68.12 | C |
| ATOM | 894 | C | GLY | A | 119 | −38.706 | −0.940 | 51.029 | 1.00 | 67.38 | C |
| ATOM | 895 | O | GLY | A | 119 | −39.315 | −0.467 | 51.994 | 1.00 | 66.48 | O |
| ATOM | 896 | N | SER | A | 120 | −37.440 | −1.351 | 51.081 | 1.00 | 66.86 | N |
| ATOM | 897 | CA | SER | A | 120 | −36.532 | −1.046 | 52.179 | 1.00 | 67.25 | C |
| ATOM | 898 | CB | SER | A | 120 | −36.513 | −2.189 | 53.200 | 1.00 | 68.19 | C |
| ATOM | 899 | OG | SER | A | 120 | −36.959 | −3.398 | 52.616 | 1.00 | 69.17 | O |
| ATOM | 900 | C | SER | A | 120 | −35.114 | −0.739 | 51.645 | 1.00 | 66.65 | C |
| ATOM | 901 | O | SER | A | 120 | −34.714 | −1.255 | 50.599 | 1.00 | 66.84 | O |
| ATOM | 902 | N | VAL | A | 121 | −34.394 | 0.138 | 52.343 | 1.00 | 64.79 | N |
| ATOM | 903 | CA | VAL | A | 121 | −33.029 | 0.531 | 51.983 | 1.00 | 64.40 | C |
| ATOM | 904 | CB | VAL | A | 121 | −32.967 | 1.993 | 51.407 | 1.00 | 63.41 | C |
| ATOM | 905 | CG1 | VAL | A | 121 | −33.077 | 3.046 | 52.515 | 1.00 | 68.20 | C |
| ATOM | 906 | CG2 | VAL | A | 121 | −31.707 | 2.216 | 50.594 | 1.00 | 61.86 | C |
| ATOM | 907 | C | VAL | A | 121 | −32.090 | 0.296 | 53.197 | 1.00 | 65.82 | C |

TABLE 10-continued

Atomic coordinates for COM1 complex of the modified
TXNIP protein represented by SEQ ID NO: 6 and the modified protein represented by SEQ ID NO: 3

| | | | | | | | | | | | |
|---|---|---|---|---|---|---|---|---|---|---|---|
| ATOM | 908 | O | VAL | A | 121 | -32.525 | 0.323 | 54.362 | 1.00 | 65.00 | O |
| ATOM | 909 | N | ASP | A | 122 | -30.811 | 0.056 | 52.921 | 1.00 | 63.29 | N |
| ATOM | 910 | CA | ASP | A | 122 | -29.888 | -0.415 | 53.045 | 1.00 | 62.93 | C |
| ATOM | 911 | CB | ASP | A | 122 | -29.837 | -1.947 | 53.877 | 1.00 | 65.88 | C |
| ATOM | 912 | CG | ASP | A | 122 | -30.083 | -2.617 | 55.208 | 1.00 | 69.29 | C |
| ATOM | 913 | OD1 | ASP | A | 122 | -30.740 | -3.678 | 55.183 | 1.00 | 72.24 | O |
| ATOM | 914 | OD2 | ASP | A | 122 | -29.622 | -2.112 | 56.258 | 1.00 | 78.15 | O |
| ATOM | 915 | C | ASP | A | 122 | -28.509 | 0.114 | 53.591 | 1.00 | 59.30 | C |
| ATOM | 916 | O | ASP | A | 122 | -27.969 | -0.254 | 52.557 | 1.00 | 61.08 | O |
| ATOM | 917 | N | TYR | A | 123 | -27.946 | 0.986 | 54.411 | 1.00 | 54.43 | N |
| ATOM | 918 | CA | TYR | A | 123 | -26.569 | 1.431 | 54.193 | 1.00 | 52.16 | C |
| ATOM | 919 | CB | TYR | A | 123 | -26.511 | 2.888 | 53.714 | 1.00 | 50.69 | C |
| ATOM | 920 | CG | TYR | A | 123 | -26.692 | 3.018 | 52.222 | 1.00 | 54.39 | C |
| ATOM | 921 | CD1 | TYR | A | 123 | -25.637 | 3.412 | 51.404 | 1.00 | 51.51 | C |
| ATOM | 922 | CE1 | TYR | A | 123 | -25.793 | 3.515 | 50.041 | 1.00 | 53.14 | C |
| ATOM | 923 | CZ | TYR | A | 123 | -27.035 | 3.239 | 49.479 | 1.00 | 57.49 | C |
| ATOM | 924 | OH | TYR | A | 123 | -27.222 | 3.348 | 48.128 | 1.00 | 54.97 | O |
| ATOM | 925 | CE2 | TYR | A | 123 | -28.103 | 2.856 | 50.272 | 1.00 | 58.01 | C |
| ATOM | 926 | CD2 | TYR | A | 123 | -27.925 | 2.745 | 51.629 | 1.00 | 55.57 | C |
| ATOM | 927 | C | TYR | A | 123 | -25.709 | 1.230 | 55.431 | 1.00 | 50.15 | C |
| ATOM | 928 | O | TYR | A | 123 | -26.008 | 1.770 | 56.482 | 1.00 | 50.81 | O |
| ATOM | 929 | N | TRP | A | 124 | -24.651 | 0.435 | 55.316 | 1.00 | 45.83 | N |
| ATOM | 930 | CA | TRP | A | 124 | -23.796 | 0.235 | 56.459 | 1.00 | 42.79 | C |
| ATOM | 931 | CB | TRP | A | 124 | -24.267 | -0.938 | 57.312 | 1.00 | 43.66 | C |
| ATOM | 932 | CG | TRP | A | 124 | -24.079 | -2.154 | 50.501 | 1.00 | 55.20 | C |
| ATOM | 933 | CD1 | TRP | A | 124 | -25.957 | -2.559 | 56.316 | 1.00 | 57.11 | C |
| ATOM | 934 | NE1 | TRP | A | 124 | -25.949 | -3.744 | 55.614 | 1.00 | 61.06 | N |
| ATOM | 935 | CE1 | TRP | A | 124 | -24.651 | -4.135 | 55.394 | 1.00 | 56.97 | C |
| ATOM | 936 | CD2 | TRP | A | 124 | -23.815 | -3.160 | 55.982 | 1.00 | 53.47 | C |
| ATOM | 937 | CE3 | TRP | A | 124 | -22.424 | -3.320 | 55.898 | 1.00 | 58.79 | C |
| ATOM | 938 | CZ3 | TRP | A | 124 | -21.913 | -4.449 | 55.226 | 1.00 | 55.58 | C |
| ATOM | 939 | CH2 | TRP | A | 124 | -22.778 | -5.400 | 54.648 | 1.00 | 60.46 | C |
| ATOM | 940 | CZ2 | TRP | A | 124 | -24.148 | -5.257 | 54.720 | 1.00 | 56.58 | C |
| ATOM | 941 | C | TRP | A | 124 | -22.349 | 0.032 | 56.112 | 1.00 | 43.48 | C |
| ATOM | 942 | O | TRP | A | 124 | -21.999 | -0.236 | 54.948 | 1.00 | 40.97 | O |
| ATOM | 943 | N | VAL | A | 125 | -21.532 | 0.130 | 57.160 | 1.00 | 43.05 | N |
| ATOM | 944 | CA | VAL | A | 125 | -20.106 | -0.267 | 57.163 | 1.00 | 41.04 | C |
| ATOM | 945 | CB | VAL | A | 125 | -19.199 | 0.891 | 57.636 | 1.00 | 40.47 | C |
| ATOM | 946 | CG1 | VAL | A | 125 | -17.767 | 0.462 | 57.613 | 1.00 | 35.29 | C |
| ATOM | 947 | CG2 | VAL | A | 125 | -19.403 | 2.141 | 56.787 | 1.00 | 35.68 | C |
| ATOM | 948 | C | VAL | A | 125 | -19.907 | -1.357 | 58.204 | 1.00 | 42.26 | C |
| ATOM | 949 | O | VAL | A | 125 | -20.310 | -1.161 | 59.364 | 1.00 | 41.97 | O |
| ATOM | 950 | N | LYS | A | 126 | -19.329 | -2.496 | 57.796 | 1.00 | 41.47 | N |
| ATOM | 951 | CA | LYS | A | 126 | -18.754 | -3.457 | 58.739 | 1.00 | 41.75 | C |
| ATOM | 952 | CB | LYS | A | 126 | -19.083 | -4.905 | 58.397 | 1.00 | 42.33 | C |
| ATOM | 953 | CG | LYS | A | 126 | -20.536 | -5.263 | 58.348 | 1.00 | 51.05 | C |
| ATOM | 954 | CD | LYS | A | 126 | -20.662 | -6.760 | 58.515 | 1.00 | 60.53 | C |
| ATOM | 955 | CE | LYS | A | 126 | -22.095 | -7.245 | 58.354 | 1.00 | 71.62 | C |
| ATOM | 956 | NZ | LYS | A | 126 | -22.416 | -7.492 | 56.922 | 1.00 | 70.53 | N |
| ATOM | 957 | C | LYS | A | 126 | -17.247 | -3.311 | 58.671 | 1.00 | 36.91 | C |

TABLE 10-continued

Atomic coordinates for COM1 complex of the modified
TXNIP protein represented by SEQ ID NO: 6 and the modified protein represented by SEQ ID NO: 3

| ATOM | 958 | O | LYS | A | 126 | -16.677 | 57.573 | 1.00 | 33.74 | O |
|------|-----|-----|-----|---|-----|---------|--------|------|-------|---|
| ATOM | 959 | N | ALA | A | 127 | -16.640 | 59.849 | 1.00 | 34.82 | N |
| ATOM | 960 | CA | ALA | A | 127 | -15.203 | 60.069 | 1.00 | 35.81 | C |
| ATOM | 961 | CB | ALA | A | 127 | -14.750 | 61.144 | 1.00 | 32.00 | C |
| ATOM | 962 | C | ALA | A | 127 | -14.981 | 60.555 | 1.00 | 38.14 | C |
| ATOM | 963 | O | ALA | A | 127 | -15.708 | 61.312 | 1.00 | 39.96 | O |
| ATOM | 964 | N | PHE | A | 128 | -13.867 | 60.140 | 1.00 | 39.59 | N |
| ATOM | 965 | CA | PHE | A | 128 | -13.479 | 60.589 | 1.00 | 39.10 | C |
| ATOM | 966 | CB | PHE | A | 128 | -13.430 | 59.392 | 1.00 | 40.84 | C |
| ATOM | 967 | CG | PHE | A | 128 | -14.669 | 58.516 | 1.00 | 38.61 | C |
| ATOM | 968 | CD1 | PHE | A | 128 | -15.741 | 58.760 | 1.00 | 47.46 | C |
| ATOM | 969 | CE1 | PHE | A | 128 | -16.876 | 57.951 | 1.00 | 53.91 | C |
| ATOM | 970 | CZ | PHE | A | 128 | -16.949 | 56.860 | 1.00 | 51.80 | C |
| ATOM | 971 | CC2 | PHE | A | 128 | -15.890 | 56.601 | 1.00 | 47.84 | C |
| ATOM | 972 | CD2 | PHE | A | 128 | -14.747 | 57.418 | 1.00 | 33.57 | C |
| ATOM | 973 | C | PHE | A | 128 | -12.121 | 61.216 | 1.00 | 39.50 | C |
| ATOM | 974 | O | PHE | A | 128 | -11.239 | 60.640 | 1.00 | 36.00 | O |
| ATOM | 975 | N | LEU | A | 129 | -11.954 | 62.397 | 1.00 | 38.52 | N |
| ATOM | 976 | CA | LEU | A | 129 | -10.644 | 63.017 | 1.00 | 40.53 | C |
| ATOM | 977 | CB | LEU | A | 129 | -7.380 | 64.514 | 1.00 | 38.33 | C |
| ATOM | 978 | CG | LEU | A | 129 | -10.761 | 65.434 | 1.00 | 40.74 | C |
| ATOM | 979 | CD1 | LEU | A | 129 | -9.549 | 64.985 | 1.00 | 38.85 | C |
| ATOM | 980 | CD2 | LEU | A | 129 | -8.514 | 66.885 | 1.00 | 39.81 | C |
| ATOM | 981 | C | LEU | A | 129 | -10.019 | 62.850 | 1.00 | 40.43 | C |
| ATOM | 982 | O | LEU | A | 129 | -10.116 | 63.359 | 1.00 | 39.86 | O |
| ATOM | 983 | N | ASP | A | 130 | -10.724 | 62.179 | 1.00 | 38.61 | N |
| ATOM | 984 | CA | ASP | A | 130 | -8.975 | 61.983 | 1.00 | 37.75 | C |
| ATOM | 985 | CB | ASP | A | 130 | -8.416 | 60.547 | 1.00 | 39.82 | C |
| ATOM | 986 | CG | ASP | A | 130 | -7.945 | 59.525 | 1.00 | 47.12 | C |
| ATOM | 987 | OD1 | ASP | A | 130 | -9.065 | 59.859 | 1.00 | 46.32 | O |
| ATOM | 988 | OD2 | ASP | A | 130 | -10.227 | 58.369 | 1.00 | 47.89 | O |
| ATOM | 989 | C | ASP | A | 130 | -8.784 | 62.930 | 1.00 | 37.56 | C |
| ATOM | 990 | O | ASP | A | 130 | -7.246 | 63.075 | 1.00 | 38.05 | O |
| ATOM | 991 | N | ARG | A | 131 | -7.154 | 63.565 | 1.00 | 36.39 | N |
| ATOM | 992 | CA | ARG | A | 131 | -6.098 | 64.534 | 1.00 | 37.40 | C |
| ATOM | 993 | CB | ARG | A | 131 | -6.642 | 65.945 | 1.00 | 37.07 | C |
| ATOM | 994 | CG | ARG | A | 131 | -6.943 | 66.410 | 1.00 | 37.63 | C |
| ATOM | 995 | CD | ARG | A | 131 | -7.788 | 67.689 | 1.00 | 85.47 | C |
| ATOM | 996 | NE | ARG | A | 131 | -7.067 | 68.841 | 1.00 | 48.48 | N |
| ATOM | 997 | CZ | ARG | A | 131 | -7.636 | 69.935 | 1.00 | 54.97 | C |
| ATOM | 998 | NH1 | ARG | A | 131 | -8.955 | 70.022 | 1.00 | 43.84 | N |
| ATOM | 999 | NH2 | ARG | A | 131 | -11.687 | 70.945 | 1.00 | 53.63 | N |
| ATOM | 1000 | C | ARG | A | 131 | -5.613 | 64.282 | 1.00 | 41.85 | C |
| ATOM | 1001 | O | ARG | A | 131 | -6.391 | 63.795 | 1.00 | 40.64 | O |
| ATOM | 1002 | N | PRO | A | 132 | -4.326 | 64.592 | 1.00 | 43.97 | N |
| ATOM | 1003 | CA | PRO | A | 132 | -3.758 | 64.497 | 1.00 | 46.47 | C |
| ATOM | 1004 | CB | PRO | A | 132 | -2.353 | 65.062 | 1.00 | 47.87 | C |
| ATOM | 1005 | CG | PRO | A | 132 | -2.072 | 64.974 | 1.00 | 47.28 | C |
| ATOM | 1006 | CD | PRO | A | 132 | -3.367 | 65.133 | 1.00 | 42.02 | C |
| ATOM | 1007 | C | PRO | A | 132 | -4.533 | 65.404 | 1.00 | 49.16 | C |

TABLE 10-continued

Atomic coordinates for COM1 complex of the modified
TXNIP protein represented by SEQ ID NO: 6 and the modified protein represented by SEQ ID NO: 3

| ATOM | 1008 | O   | PRO | A | 132 | -4.762  | 66.566 | 1.00 | 49.59 | O |
|------|------|-----|-----|---|-----|---------|--------|------|-------|---|
| ATOM | 1009 | N   | SER | A | 133 | -4.944  | 64.870 | 1.00 | 51.11 | N |
| ATOM | 1010 | CA  | SER | A | 133 | -5.562  | 65.659 | 1.00 | 52.93 | C |
| ATOM | 1011 | CB  | SER | A | 133 | -4.612  | 66.754 | 1.00 | 54.41 | C |
| ATOM | 1012 | OG  | SER | A | 133 | -3.339  | 66.230 | 1.00 | 61.05 | O |
| ATOM | 1013 | C   | SER | A | 133 | -6.914  | 66.259 | 1.00 | 55.73 | C |
| ATOM | 1014 | O   | SER | A | 133 | -7.491  | 67.030 | 1.00 | 59.49 | O |
| ATOM | 1015 | N   | GLN | A | 134 | -7.446  | 65.889 | 1.00 | 54.57 | N |
| ATOM | 1016 | CA  | GLN | A | 134 | -8.779  | 66.318 | 1.00 | 54.27 | C |
| ATOM | 1017 | CB  | GLN | A | 134 | -8.745  | 67.068 | 1.00 | 51.77 | C |
| ATOM | 1018 | CG  | GLN | A | 134 | -7.805  | 68.261 | 1.00 | 53.74 | C |
| ATOM | 1019 | CD  | GLN | A | 134 | -8.112  | 69.280 | 1.00 | 62.65 | C |
| ATOM | 1020 | OE1 | GLN | A | 134 | -9.250  | 59.380 | 1.00 | 62.66 | O |
| ATOM | 1021 | NE2 | GLN | A | 134 | -7.087  | 70.043 | 1.00 | 55.21 | N |
| ATOM | 1022 | C   | GLN | A | 134 | -9.755  | 65.155 | 1.00 | 55.07 | C |
| ATOM | 1023 | O   | GLN | A | 134 | -9.340  | 64.013 | 1.00 | 57.20 | O |
| ATOM | 1024 | N   | PRO | A | 135 | -11.055 | 65.430 | 1.00 | 56.03 | N |
| ATOM | 1025 | CA  | PRO | A | 135 | -12.080 | 64.466 | 1.00 | 53.75 | C |
| ATOM | 1026 | CB  | PRO | A | 135 | -13.377 | 65.119 | 1.00 | 53.57 | C |
| ATOM | 1027 | CG  | PRO | A | 135 | -12.942 | 66.113 | 1.00 | 59.20 | C |
| ATOM | 1028 | CD  | PRO | A | 135 | -11.642 | 66.629 | 1.00 | 58.17 | C |
| ATOM | 1029 | C   | PRO | A | 135 | -12.120 | 64.317 | 1.00 | 52.18 | C |
| ATOM | 1030 | O   | PRO | A | 135 | -11.809 | 65.255 | 1.00 | 51.75 | O |
| ATOM | 1031 | N   | THR | A | 136 | -12.468 | 63.136 | 1.00 | 52.15 | N |
| ATOM | 1032 | CA  | THR | A | 136 | -12.447 | 62.917 | 1.00 | 53.80 | C |
| ATOM | 1033 | CB  | THR | A | 136 | -12.453 | 61.418 | 1.00 | 53.97 | C |
| ATOM | 1034 | OG1 | THR | A | 136 | -13.778 | 60.898 | 1.00 | 56.43 | O |
| ATOM | 1035 | CG2 | THR | A | 136 | -11.548 | 60.595 | 1.00 | 59.83 | C |
| ATOM | 1036 | C   | THR | A | 136 | -13.620 | 63.708 | 1.00 | 52.34 | C |
| ATOM | 1037 | O   | THR | A | 136 | -12.001 | 63.825 | 1.00 | 51.77 | O |
| ATOM | 1038 | N   | GLN | A | 137 | -12.613 | 64.309 | 1.00 | 50.62 | N |
| ATOM | 1039 | CA  | GLN | A | 137 | -13.395 | 65.036 | 1.00 | 48.70 | C |
| ATOM | 1040 | CB  | GLN | A | 137 | -14.435 | 66.280 | 1.00 | 45.74 | C |
| ATOM | 1041 | CG  | GLN | A | 137 | -13.845 | 66.967 | 1.00 | 52.84 | C |
| ATOM | 1042 | CD  | GLN | A | 137 | -14.719 | 68.340 | 1.00 | 46.47 | C |
| ATOM | 1043 | OE1 | GLN | A | 137 | -14.198 | 68.825 | 1.00 | 51.26 | O |
| ATOM | 1044 | NE2 | GLN | A | 137 | -13.259 | 68.973 | 1.00 | 45.98 | N |
| ATOM | 1045 | C   | GLN | A | 137 | -14.809 | 64.122 | 1.00 | 49.45 | C |
| ATOM | 1046 | O   | GLN | A | 137 | -14.967 | 63.383 | 1.00 | 47.77 | O |
| ATOM | 1047 | N   | GLU | A | 138 | -14.192 | 64.171 | 1.00 | 50.34 | N |
| ATOM | 1048 | CA  | GLU | A | 138 | -16.280 | 63.387 | 1.00 | 51.36 | C |
| ATOM | 1049 | CB  | GLU | A | 138 | -16.866 | 62.163 | 1.00 | 55.31 | C |
| ATOM | 1050 | CG  | GLU | A | 138 | -17.607 | 62.388 | 1.00 | 60.28 | C |
| ATOM | 1051 | CD  | GLU | A | 138 | -19.018 | 61.158 | 1.00 | 60.92 | C |
| ATOM | 1052 | OE1 | GLU | A | 138 | -19.550 | 61.207 | 1.00 | 65.95 | O |
| ATOM | 1053 | OE2 | GLU | A | 138 | -19.714 | 60.128 | 1.00 | 67.16 | O |
| ATOM | 1054 | C   | GLU | A | 138 | -19.775 | 64.163 | 1.00 | 50.39 | C |
| ATOM | 1055 | O   | GLU | A | 138 | -17.724 | 65.173 | 1.00 | 47.67 | O |
| ATOM | 1056 | N   | THR | A | 139 | -18.344 | 63.675 | 1.00 | 49.58 | N |
| ATOM | 1057 | CA  | THR | A | 139 | -18.673 | 64.114 | 1.00 | 46.88 | C |

TABLE 10-continued

Atomic coordinates for COM1 complex of the modified TXNIP protein represented by SEQ ID NO: 6 and the modified protein represented by SEQ ID NO: 3

| | | | | | | | | | |
|---|---|---|---|---|---|---|---|---|---|
| ATOM | 1058 | CB | THR | A | 139 | -17.980 | -3.422 | 64.941 | 1.00 | 46.50 | C |
| ATOM | 1059 | OG1 | THR | A | 139 | -18.971 | -2.543 | 65.480 | 1.00 | 44.51 | O |
| ATOM | 1060 | CG2 | THR | A | 139 | -17.012 | -2.617 | 64.067 | 1.00 | 42.13 | C |
| ATOM | 1061 | C | THR | A | 139 | -19.360 | -3.843 | 62.905 | 1.00 | 46.28 | C |
| ATOM | 1062 | O | THR | A | 139 | -18.730 | 3.686 | 61.858 | 1.00 | 43.02 | O |
| ATOM | 1063 | N | THR | A | 139 | -20.626 | -3.433 | 63.067 | 1.00 | 45.35 | N |
| ATOM | 1064 | CA | LYS | A | 140 | -21.456 | -2.889 | 61.986 | 1.00 | 48.02 | C |
| ATOM | 1065 | CB | LYS | A | 140 | -22.521 | -3.930 | 61.619 | 1.00 | 49.53 | C |
| ATOM | 1066 | CG | LYS | A | 140 | -23.586 | -3.482 | 60.605 | 1.00 | 54.13 | C |
| ATOM | 1067 | CD | LYS | A | 140 | -24.434 | -4.679 | 60.223 | 1.00 | 60.07 | C |
| ATOM | 1068 | CE | LYS | A | 140 | -25.562 | -4.316 | 59.283 | 1.00 | 66.14 | C |
| ATOM | 1069 | NZ | LYS | A | 140 | -26.682 | -5.297 | 59.401 | 1.00 | 66.25 | N |
| ATOM | 1070 | C | LYS | A | 140 | -22.132 | -1.569 | 62.393 | 1.00 | 46.56 | C |
| ATOM | 1071 | O | LYS | A | 140 | -22.785 | -1.529 | 63.415 | 1.00 | 48.52 | O |
| ATOM | 1072 | N | LYS | A | 140 | -21.948 | -0.506 | 61.609 | 1.00 | 46.60 | N |
| ATOM | 1073 | CA | LYS | A | 141 | -22.659 | 0.779 | 61.810 | 1.00 | 47.55 | C |
| ATOM | 1074 | CB | LYS | A | 141 | -21.715 | 1.889 | 62.267 | 1.00 | 48.50 | C |
| ATOM | 1075 | CG | LYS | A | 141 | -21.759 | 2.169 | 63.754 | 1.00 | 49.77 | C |
| ATOM | 1076 | CD | LYS | A | 141 | -22.685 | 3.340 | 64.083 | 1.00 | 50.21 | C |
| ATOM | 1077 | CE | LYS | A | 141 | -22.613 | 3.643 | 65.571 | 1.00 | 58.70 | C |
| ATOM | 1078 | NZ | LYS | A | 141 | -21.226 | 3.922 | 66.075 | 1.00 | 51.89 | N |
| ATOM | 1079 | C | LYS | A | 141 | -23.425 | 1.275 | 60.582 | 1.00 | 48.14 | C |
| ATOM | 1080 | O | LYS | A | 141 | -22.814 | 1.597 | 59.535 | 1.00 | 43.25 | O |
| ATOM | 1081 | N | ASN | A | 142 | -24.751 | 1.378 | 60.729 | 1.00 | 46.45 | N |
| ATOM | 1082 | CA | ASN | A | 142 | -25.594 | 1.901 | 59.659 | 1.00 | 48.93 | C |
| ATOM | 1083 | CB | ASN | A | 142 | -27.074 | 1.604 | 59.920 | 1.00 | 51.70 | C |
| ATOM | 1084 | CG | ASN | A | 142 | -27.410 | 0.138 | 59.767 | 1.00 | 56.34 | C |
| ATOM | 1085 | OD1 | ASN | A | 142 | -27.254 | -0.643 | 60.703 | 1.00 | 62.81 | O |
| ATOM | 1086 | ND2 | ASN | A | 142 | -27.898 | -0.243 | 58.583 | 1.00 | 67.81 | N |
| ATOM | 1087 | C | ASN | A | 142 | -25.380 | 3.399 | 59.463 | 1.00 | 50.51 | C |
| ATOM | 1088 | O | ASN | A | 142 | -25.023 | 4.100 | 60.411 | 1.00 | 52.26 | O |
| ATOM | 1089 | N | PHE | A | 143 | -25.570 | 3.883 | 58.234 | 1.00 | 47.97 | N |
| ATOM | 1090 | CA | PHE | A | 143 | -25.611 | 5.323 | 57.978 | 1.00 | 50.89 | C |
| ATOM | 1091 | CB | PHE | A | 143 | -24.291 | 5.909 | 57.416 | 1.00 | 49.41 | C |
| ATOM | 1092 | CG | PHE | A | 143 | -23.881 | 5.341 | 56.080 | 1.00 | 49.21 | C |
| ATOM | 1093 | CD1 | PHE | A | 143 | -24.309 | 5.932 | 54.894 | 1.00 | 47.65 | C |
| ATOM | 1094 | CE1 | PHE | A | 143 | -23.947 | 5.392 | 53.645 | 1.00 | 36.53 | C |
| ATOM | 1095 | CZ | PHE | A | 143 | -23.118 | 4.258 | 53.594 | 1.00 | 45.83 | C |
| ATOM | 1096 | CE2 | PHE | A | 143 | -22.679 | 3.674 | 54.781 | 1.00 | 47.00 | C |
| ATOM | 1097 | CD2 | PHE | A | 143 | -23.046 | 4.215 | 56.007 | 1.00 | 47.24 | C |
| ATOM | 1098 | C | PHE | A | 143 | -26.811 | 5.684 | 57.101 | 1.00 | 54.82 | C |
| ATOM | 1099 | O | PHE | A | 143 | -27.484 | 4.803 | 56.494 | 1.00 | 53.86 | O |
| ATOM | 1100 | N | GLU | A | 144 | -27.067 | 6.987 | 57.037 | 1.00 | 58.48 | N |
| ATOM | 1101 | CA | GLU | A | 144 | -28.277 | 7.498 | 56.409 | 1.00 | 60.86 | C |
| ATOM | 1102 | CB | GLU | A | 144 | -28.938 | 8.574 | 57.281 | 1.00 | 59.77 | C |
| ATOM | 1103 | CG | GLU | A | 144 | -30.390 | 8.839 | 56.908 | 1.00 | 65.80 | C |
| ATOM | 1104 | CD | GLU | A | 144 | -31.376 | 7.812 | 57.480 | 1.00 | 73.18 | C |
| ATOM | 1105 | OE1 | GLU | A | 144 | -30.936 | 6.826 | 58.137 | 1.00 | 61.74 | O |
| ATOM | 1106 | OE2 | GLU | A | 144 | -32.803 | 8.010 | 57.270 | 1.00 | 70.20 | O |
| ATOM | 1107 | C | GLU | A | 144 | -27.996 | 8.053 | 55.042 | 1.00 | 62.05 | C |

TABLE 10-continued

Atomic coordinates for COM1 complex of the modified
TXNIP protein represented by SEQ ID NO: 6 and the modified protein represented by SEQ ID NO: 3

| ATOM | 1108 | O   | GLU | A | 144 | −27.111 | 8.899  | 54.861 | 1.00 | 61.53 | O |
|------|------|-----|-----|---|-----|---------|--------|--------|------|-------|---|
| ATOM | 1109 | N   | VAL | A | 145 | −28.778 | 7.577  | 54.084 | 1.00 | 65.73 | N |
| ATOM | 1110 | CA  | VAL | A | 145 | −28.732 | 8.100  | 52.742 | 1.00 | 69.13 | C |
| ATOM | 1111 | CB  | VAL | A | 145 | −28.390 | 7.000  | 51.726 | 1.00 | 68.27 | C |
| ATOM | 1112 | CG1 | VAL | A | 145 | −29.650 | 6.326  | 51.179 | 1.00 | 69.10 | C |
| ATOM | 1113 | CG2 | VAL | A | 145 | −27.536 | 7.575  | 50.620 | 1.00 | 72.08 | C |
| ATOM | 1114 | C   | VAL | A | 145 | −30.047 | 8.836  | 52.447 | 1.00 | 71.28 | C |
| ATOM | 1115 | O   | VAL | A | 145 | −31.051 | 8.643  | 53.153 | 1.00 | 70.40 | O |
| ATOM | 1116 | N   | VAL | A | 146 | −30.018 | 9.675  | 51.412 | 1.00 | 73.07 | N |
| ATOM | 1117 | CA  | VAL | A | 146 | −31.051 | 10.674 | 51.162 | 1.00 | 75.08 | C |
| ATOM | 1118 | CB  | VAL | A | 146 | −30.464 | 11.853 | 50.358 | 1.00 | 75.37 | C |
| ATOM | 1119 | CG1 | VAL | A | 146 | −30.563 | 11.600 | 48.834 | 1.00 | 76.53 | C |
| ATOM | 1120 | CG2 | VAL | A | 146 | −31.124 | 13.157 | 50.761 | 1.00 | 78.50 | C |
| ATOM | 1121 | C   | VAL | A | 146 | −32.281 | 10.096 | 50.457 | 1.00 | 76.35 | C |
| ATOM | 1122 | O   | VAL | A | 146 | −33.385 | 10.646 | 50.561 | 1.00 | 77.77 | O |
| ATOM | 1123 | N   | PRO | A | 154 | −43.962 | 7.099  | 43.320 | 1.00 | 76.71 | N |
| ATOM | 1124 | CA  | PRO | A | 154 | −45.231 | 6.623  | 42.748 | 1.00 | 76.56 | C |
| ATOM | 1125 | CB  | PRO | A | 154 | −44.998 | 6.751  | 41.239 | 1.00 | 76.85 | C |
| ATOM | 1126 | CG  | PRO | A | 154 | −43.504 | 6.547  | 41.075 | 1.00 | 76.49 | C |
| ATOM | 1127 | CD  | PRO | A | 154 | −42.858 | 7.087  | 42.337 | 1.00 | 76.20 | C |
| ATOM | 1128 | C   | PRO | A | 154 | −45.514 | 5.162  | 43.137 | 1.00 | 74.29 | C |
| ATOM | 1129 | O   | PRO | A | 154 | −44.560 | 4.388  | 43.330 | 1.00 | 74.99 | O |
| ATOM | 1130 | N   | ASP | A | 155 | −46.794 | 4.783  | 43.244 | 1.00 | 69.42 | N |
| ATOM | 1131 | CA  | ASP | A | 155 | −47.117 | 3.442  | 43.741 | 1.00 | 64.24 | C |
| ATOM | 1132 | CB  | ASP | A | 155 | −48.577 | 3.291  | 44.153 | 1.00 | 65.85 | C |
| ATOM | 1133 | CG  | ASP | A | 155 | −48.801 | 2.060  | 45.030 | 1.00 | 67.37 | C |
| ATOM | 1134 | CD1 | ASP | A | 155 | −49.339 | 1.052  | 44.529 | 1.00 | 69.06 | C |
| ATOM | 1135 | CD2 | ASP | A | 155 | −48.421 | 2.088  | 46.222 | 1.00 | 73.69 | C |
| ATOM | 1136 | C   | ASP | A | 155 | −46.714 | 2.313  | 42.798 | 1.00 | 59.56 | C |
| ATOM | 1137 | O   | ASP | A | 155 | −47.016 | 2.327  | 41.610 | 1.00 | 59.13 | O |
| ATOM | 1138 | N   | LEU | A | 156 | −46.031 | 1.332  | 43.366 | 1.00 | 53.24 | N |
| ATOM | 1139 | CA  | LEU | A | 156 | −45.515 | 0.189  | 42.630 | 1.00 | 51.27 | C |
| ATOM | 1140 | CB  | LEU | A | 156 | −44.767 | −0.719 | 43.610 | 1.00 | 50.25 | C |
| ATOM | 1141 | CG  | LEU | A | 156 | −44.051 | −1.917 | 43.009 | 1.00 | 54.72 | C |
| ATOM | 1142 | CD1 | LEU | A | 156 | −42.802 | −1.444 | 42.271 | 1.00 | 52.41 | C |
| ATOM | 1143 | CD2 | LEU | A | 156 | −43.721 | −2.920 | 44.097 | 1.00 | 56.24 | C |
| ATOM | 1144 | C   | LEU | A | 156 | −46.608 | −0.604 | 41.911 | 1.00 | 46.19 | C |
| ATOM | 1145 | O   | LEU | A | 156 | −46.392 | −1.155 | 40.834 | 1.00 | 45.76 | O |
| ATOM | 1146 | N   | MET | A | 157 | −47.784 | −0.659 | 42.514 | 1.00 | 42.93 | N |
| ATOM | 1147 | CA  | MET | A | 157 | −48.853 | −1.480 | 41.985 | 1.00 | 42.56 | C |
| ATOM | 1148 | CB  | MET | A | 157 | −49.503 | −2.237 | 43.136 | 1.00 | 43.19 | C |
| ATOM | 1149 | CG  | MET | A | 157 | −48.601 | −3.252 | 43.772 | 1.00 | 43.90 | C |
| ATOM | 1150 | SD  | MET | A | 157 | −48.344 | −4.638 | 42.657 | 1.00 | 55.30 | S |
| ATOM | 1151 | CE  | MET | A | 157 | −46.606 | −4.552 | 42.235 | 1.00 | 47.84 | C |
| ATOM | 1152 | C   | MET | A | 157 | −49.888 | −0.710 | 41.131 | 1.00 | 42.93 | C |
| ATOM | 1153 | O   | MET | A | 157 | −50.874 | −1.292 | 40.655 | 1.00 | 39.35 | O |
| ATOM | 1154 | N   | ALA | A | 158 | −49.667 | 0.597  | 40.963 | 1.00 | 41.04 | N |
| ATOM | 1155 | CA  | ALA | A | 158 | −50.575 | 1.459  | 40.236 | 1.00 | 36.27 | C |
| ATOM | 1156 | CB  | ALA | A | 158 | −50.389 | 2.915  | 40.619 | 1.00 | 37.74 | C |
| ATOM | 1157 | C   | ALA | A | 158 | −50.254 | 1.301  | 38.774 | 1.00 | 38.85 | C |
|      |      |     |     |   |     |         |        |        |      | 39.37 | C |

TABLE 10-continued

Atomic coordinates for COM1 complex of the modified
TXNIP protein represented by SEQ ID NO: 6 and the modified protein represented by SEQ ID NO: 3

| ATOM | 1158 | O | ALA | A | 158 | −49.072 | 1.150 | 38.432 | 1.00 | 40.53 | O |
|---|---|---|---|---|---|---|---|---|---|---|---|
| ATOM | 1159 | N | PRO | A | 159 | −51.299 | 1.341 | 37.917 | 1.00 | 39.57 | N |
| ATOM | 1160 | CA | PRO | A | 159 | −51.126 | 1.361 | 35.471 | 1.00 | 40.81 | C |
| ATOM | 1161 | CB | PRO | A | 159 | −52.532 | 1.649 | 35.955 | 1.00 | 39.57 | C |
| ATOM | 1162 | CG | PRO | A | 159 | −53.419 | 1.052 | 38.986 | 1.00 | 33.96 | C |
| ATOM | 1163 | CD | PRO | A | 159 | −52.728 | 1.385 | 38.281 | 1.00 | 35.90 | C |
| ATOM | 1164 | C | PRO | A | 159 | −50.178 | 2.454 | 36.013 | 1.00 | 44.82 | C |
| ATOM | 1165 | O | PRO | A | 159 | −50.012 | 3.468 | 36.692 | 1.00 | 42.89 | O |
| ATOM | 1166 | N | VAL | A | 160 | −49.562 | 2.227 | 34.854 | 1.00 | 45.39 | N |
| ATOM | 1167 | CA | VAL | A | 160 | −48.654 | 3.182 | 34.253 | 1.00 | 47.51 | C |
| ATOM | 1168 | CB | VAL | A | 160 | −47.232 | 2.628 | 34.120 | 1.00 | 46.21 | C |
| ATOM | 1169 | CG1 | VAL | A | 160 | −46.282 | 3.724 | 33.612 | 1.00 | 49.09 | C |
| ATOM | 1170 | CG2 | VAL | A | 160 | −46.733 | 2.039 | 35.425 | 1.00 | 49.97 | C |
| ATOM | 1171 | C | VAL | A | 160 | −49.182 | 3.438 | 32.846 | 1.00 | 45.24 | C |
| ATOM | 1172 | O | VAL | A | 160 | −49.551 | 2.502 | 32.154 | 1.00 | 45.04 | O |
| ATOM | 1173 | N | SER | A | 161 | −49.282 | 4.710 | 32.474 | 1.00 | 46.73 | N |
| ATOM | 1174 | CA | SER | A | 161 | −49.624 | 5.107 | 31.118 | 1.00 | 46.18 | C |
| ATOM | 1175 | CB | SER | A | 161 | −51.051 | 5.605 | 31.045 | 1.00 | 47.99 | C |
| ATOM | 1176 | CG | SER | A | 161 | −51.152 | 6.976 | 31.365 | 1.00 | 56.18 | C |
| ATOM | 1177 | C | SER | A | 161 | −48.598 | 6.154 | 30.657 | 1.00 | 48.91 | C |
| ATOM | 1178 | O | SER | A | 161 | −48.133 | 6.967 | 31.483 | 1.00 | 49.24 | O |
| ATOM | 1179 | N | ALA | A | 162 | −48.190 | 6.060 | 29.375 | 1.00 | 43.77 | N |
| ATOM | 1180 | CA | ALA | A | 162 | −47.232 | 6.972 | 28.721 | 1.00 | 37.78 | C |
| ATOM | 1181 | CB | ALA | A | 162 | −45.805 | 6.460 | 28.806 | 1.00 | 34.57 | C |
| ATOM | 1182 | C | ALA | A | 162 | −47.636 | 7.141 | 27.242 | 1.00 | 36.65 | C |
| ATOM | 1183 | O | ALA | A | 162 | −48.271 | 6.245 | 26.678 | 1.00 | 32.92 | O |
| ATOM | 1184 | N | LYS | A | 163 | −47.278 | 8.302 | 26.674 | 1.00 | 32.66 | N |
| ATOM | 1185 | CA | LYS | A | 163 | −47.545 | 8.663 | 25.286 | 1.00 | 36.13 | C |
| ATOM | 1186 | CB | LYS | A | 163 | −48.815 | 9.510 | 25.191 | 1.00 | 36.70 | C |
| ATOM | 1187 | CG | LYS | A | 163 | −48.657 | 10.965 | 25.634 | 1.00 | 51.47 | C |
| ATOM | 1188 | CD | LYS | A | 163 | −49.467 | 11.935 | 24.758 | 1.00 | 60.24 | C |
| ATOM | 1189 | CE | LYS | A | 163 | −48.641 | 12.404 | 23.525 | 1.00 | 70.84 | C |
| ATOM | 1190 | NZ | LYS | A | 163 | −49.478 | 12.848 | 22.850 | 1.00 | 69.38 | N |
| ATOM | 1191 | C | LYS | A | 163 | −46.348 | 9.434 | 24.744 | 1.00 | 37.51 | C |
| ATOM | 1192 | O | LYS | A | 163 | −45.642 | 10.106 | 25.513 | 1.00 | 37.21 | O |
| ATOM | 1193 | N | LYS | A | 164 | −46.104 | 9.312 | 23.435 | 1.00 | 35.50 | N |
| ATOM | 1194 | CA | LYS | A | 164 | −45.040 | 10.079 | 22.726 | 1.00 | 36.08 | C |
| ATOM | 1195 | CB | LYS | A | 164 | −43.710 | 9.336 | 22.710 | 1.00 | 31.83 | C |
| ATOM | 1196 | CG | LYS | A | 164 | −42.497 | 10.131 | 22.218 | 1.00 | 41.74 | C |
| ATOM | 1197 | CD | LYS | A | 164 | −41.570 | 10.442 | 23.363 | 1.00 | 53.88 | C |
| ATOM | 1198 | CE | LYS | A | 164 | −40.116 | 10.426 | 22.921 | 1.00 | 62.09 | C |
| ATOM | 1199 | NZ | LYS | A | 164 | −39.297 | 9.588 | 23.853 | 1.00 | 43.94 | N |
| ATOM | 1200 | C | LYS | A | 164 | −45.478 | 0.216 | 21.283 | 1.00 | 37.34 | C |
| ATOM | 1201 | O | LYS | A | 164 | −45.924 | 9.242 | 20.680 | 1.00 | 37.06 | O |
| ATOM | 1202 | N | GLU | A | 165 | −45.332 | 11.423 | 20.753 | 1.00 | 38.13 | N |
| ATOM | 1203 | CA | GLU | A | 165 | −45.603 | 11.744 | 19.351 | 1.00 | 39.64 | C |
| ATOM | 1204 | CB | GLU | A | 165 | −46.716 | 12.770 | 19.308 | 1.00 | 39.43 | C |
| ATOM | 1205 | CG | GLU | A | 165 | −47.235 | 13.075 | 17.946 | 1.00 | 53.37 | C |
| ATOM | 1206 | CD | GLU | A | 165 | −47.916 | 14.410 | 17.931 | 1.00 | 68.12 | C |
| ATOM | 1207 | OE1 | GLU | A | 165 | −47.252 | 15.402 | 18.330 | 1.00 | 71.57 | O |

TABLE 10-continued

Atomic coordinates for COM1 complex of the modified
TXNIP protein represented by SEQ ID NO: 6 and the modified protein represented by SEQ ID NO: 3

| ATOM | 1208 | OE2 | GLU | A | 165 | −49.102 | 14.462 | 17.530 | 1.00 | 72.76 | O |
|---|---|---|---|---|---|---|---|---|---|---|---|
| ATOM | 1209 | C | GLU | A | 165 | −44.356 | 12.381 | 18.757 | 1.00 | 39.97 | C |
| ATOM | 1210 | O | GLU | A | 165 | −43.610 | 13.102 | 19.451 | 1.00 | 38.36 | O |
| ATOM | 1211 | N | LYS | A | 166 | −44.102 | 12.107 | 17.480 | 1.00 | 38.95 | N |
| ATOM | 1212 | CA | LYS | A | 166 | −42.939 | 12.628 | 16.762 | 1.00 | 35.86 | C |
| ATOM | 1213 | CB | LYS | A | 166 | −41.904 | 11.526 | 16.560 | 1.00 | 38.04 | C |
| ATOM | 1214 | CG | LYS | A | 166 | −40.470 | 12.050 | 16.459 | 1.00 | 48.89 | C |
| ATOM | 1215 | CD | LYS | A | 166 | −39.449 | 10.929 | 16.398 | 1.00 | 60.15 | C |
| ATOM | 1216 | CE | LYS | A | 166 | −39.434 | 10.281 | 15.016 | 1.00 | 57.97 | C |
| ATOM | 1217 | NZ | LYS | A | 166 | −38.060 | 10.062 | 14.513 | 1.00 | 46.08 | N |
| ATOM | 1218 | C | LYS | A | 166 | −43.385 | 13.063 | 15.393 | 1.00 | 35.83 | C |
| ATOM | 1219 | O | LYS | A | 166 | −44.201 | 12.395 | 14.765 | 1.00 | 28.34 | O |
| ATOM | 1220 | N | LYS | A | 167 | −42.840 | 14.196 | 14.952 | 1.00 | 35.22 | N |
| ATOM | 1221 | CA | LYS | A | 167 | −43.004 | 14.751 | 13.645 | 1.00 | 36.49 | C |
| ATOM | 1222 | CB | LYS | A | 167 | −42.721 | 16.248 | 13.641 | 1.00 | 38.04 | C |
| ATOM | 1223 | CG | LYS | A | 167 | −43.069 | 16.956 | 12.343 | 1.00 | 49.97 | C |
| ATOM | 1224 | CD | LYS | A | 167 | −42.480 | 18.367 | 12.288 | 1.00 | 57.31 | C |
| ATOM | 1225 | CE | LYS | A | 167 | −43.002 | 19.170 | 11.098 | 1.00 | 61.20 | C |
| ATOM | 1226 | NZ | LYS | A | 167 | −42.126 | 20.352 | 10.792 | 1.00 | 63.11 | N |
| ATOM | 1227 | C | LYS | A | 167 | −42.232 | 13.964 | 12.659 | 1.00 | 35.68 | C |
| ATOM | 1228 | O | LYS | A | 167 | −41.007 | 13.829 | 12.839 | 1.00 | 31.50 | O |
| ATOM | 1229 | N | VAL | A | 168 | −42.885 | 13.431 | 11.617 | 1.00 | 33.61 | N |
| ATOM | 1230 | CA | VAL | A | 168 | −42.195 | 12.752 | 10.544 | 1.00 | 30.12 | C |
| ATOM | 1231 | CB | VAL | A | 168 | −42.448 | 11.206 | 10.574 | 1.00 | 28.95 | C |
| ATOM | 1232 | CG1 | VAL | A | 168 | −41.735 | 10.522 | 9.400 | 1.00 | 34.10 | C |
| ATOM | 1233 | CG2 | VAL | A | 168 | −42.008 | 10.576 | 11.888 | 1.00 | 31.88 | C |
| ATOM | 1234 | C | VAL | A | 168 | −42.689 | 13.361 | 9.223 | 1.00 | 33.21 | C |
| ATOM | 1235 | O | VAL | A | 168 | −43.664 | 12.855 | 8.632 | 1.00 | 31.25 | O |
| ATOM | 1236 | N | SER | A | 169 | −42.046 | 14.442 | 8.754 | 1.00 | 34.18 | N |
| ATOM | 1237 | CA | SER | A | 169 | −42.576 | 15.213 | 7.754 | 1.00 | 31.66 | C |
| ATOM | 1238 | CB | SER | A | 169 | −42.092 | 16.664 | 7.605 | 1.00 | 33.84 | C |
| ATOM | 1239 | OG | SER | A | 169 | −40.680 | 16.681 | 7.646 | 1.00 | 36.61 | O |
| ATOM | 1240 | C | SER | A | 169 | −42.148 | 14.657 | 6.244 | 1.00 | 31.16 | C |
| ATOM | 1241 | O | SER | A | 169 | −41.222 | 13.877 | 6.175 | 1.00 | 27.62 | O |
| ATOM | 1242 | N | SER | A | 170 | −42.855 | 15.108 | 5.194 | 1.00 | 30.81 | N |
| ATOM | 1243 | CA | SER | A | 170 | −42.672 | 14.762 | 3.797 | 1.00 | 32.96 | C |
| ATOM | 1244 | CB | SER | A | 170 | −43.848 | 13.883 | 3.308 | 1.00 | 32.64 | C |
| ATOM | 1245 | OG | SER | A | 170 | −43.236 | 12.586 | 3.804 | 1.00 | 47.94 | O |
| ATOM | 1246 | C | SER | A | 170 | −42.885 | 16.075 | 3.102 | 1.00 | 32.54 | C |
| ATOM | 1247 | O | SER | A | 170 | −43.454 | 16.987 | 3.690 | 1.00 | 32.32 | O |
| ATOM | 1248 | N | MET | A | 171 | −42.521 | 16.167 | 1.826 | 1.00 | 34.70 | N |
| ATOM | 1249 | CA | MET | A | 171 | −42.899 | 17.345 | 1.037 | 1.00 | 35.17 | C |
| ATOM | 1250 | CB | MET | A | 171 | −42.346 | 17.224 | −0.390 | 1.00 | 35.32 | C |
| ATOM | 1251 | CG | MET | A | 171 | −41.820 | 18.523 | −0.957 | 1.00 | 42.28 | C |
| ATOM | 1252 | SD | MET | A | 171 | −41.620 | 18.471 | 2.749 | 1.00 | 42.63 | S |
| ATOM | 1253 | CE | MET | A | 171 | −43.236 | 19.076 | −3.205 | 1.00 | 46.53 | C |
| ATOM | 1254 | C | MET | A | 171 | −44.421 | 17.515 | 0.981 | 1.00 | 35.72 | C |
| ATOM | 1255 | O | MET | A | 171 | −44.955 | 18.642 | 1.080 | 1.00 | 35.81 | O |
| ATOM | 1256 | N | PHE | A | 172 | −45.119 | 16.390 | 0.827 | 1.00 | 36.93 | N |
| ATOM | 1257 | CA | PHE | A | 172 | −46.580 | 16.389 | 0.573 | 1.00 | 38.17 | C |

TABLE 10-continued

Atomic coordinates for COM1 complex of the modified
TXNIP protein represented by SEQ ID NO: 6 and the modified protein represented by SEQ ID NO: 3

| | | | | | | | | | |
|---|---|---|---|---|---|---|---|---|---|
| ATOM | 1258 | CB | PHE | A | 172 | −46.951 | 15.384 | −0.534 | 1.00 | 35.31 | C |
| ATOM | 1259 | CG | PHE | A | 172 | −46.429 | 15.796 | −1.890 | 1.00 | 48.02 | C |
| ATOM | 1260 | CD1 | PHE | A | 172 | −46.831 | 17.004 | −2.462 | 1.00 | 46.86 | C |
| ATOM | 1261 | CE1 | PHE | A | 172 | −46.313 | 17.415 | −3.693 | 1.00 | 47.10 | C |
| ATOM | 1262 | CZ | PHE | A | 172 | −45.385 | 16.610 | −4.367 | 1.00 | 44.37 | C |
| ATOM | 1263 | CE2 | PHE | A | 172 | −44.984 | 15.414 | −3.817 | 1.00 | 45.58 | C |
| ATOM | 1264 | CD2 | PHE | A | 172 | −45.495 | 15.013 | −2.573 | 1.00 | 50.25 | C |
| ATOM | 1265 | C | PHE | A | 172 | −48.618 | 16.157 | 1.810 | 1.00 | 39.10 | C |
| ATOM | 1266 | O | PHE | A | 172 | −46.732 | 16.343 | 1.815 | 1.00 | 37.25 | O |
| ATOM | 1267 | N | ILE | A | 173 | −47.321 | 15.734 | 2.875 | 1.00 | 37.34 | N |
| ATOM | 1268 | CA | ILE | A | 173 | −47.610 | 15.663 | 4.217 | 1.00 | 37.32 | C |
| ATOM | 1269 | CB | ILE | A | 173 | −48.164 | 14.182 | 4.643 | 1.00 | 35.15 | C |
| ATOM | 1270 | CG1 | ILE | A | 173 | −48.296 | 13.366 | 3.460 | 1.00 | 39.43 | C |
| ATOM | 1271 | CD1 | ILE | A | 173 | −48.534 | 11.859 | 3.746 | 1.00 | 39.82 | C |
| ATOM | 1272 | CG2 | ILE | A | 173 | −46.362 | 14.125 | 5.880 | 1.00 | 38.05 | C |
| ATOM | 1273 | C | ILE | A | 173 | −45.690 | 16.367 | 5.193 | 1.00 | 37.33 | C |
| ATOM | 1274 | O | ILE | A | 173 | −46.310 | 15.715 | 5.992 | 1.00 | 38.89 | O |
| ATOM | 1275 | N | PRO | A | 174 | −45.348 | 17.709 | 5.142 | 1.00 | 36.67 | N |
| ATOM | 1276 | CA | PRO | A | 174 | −45.566 | 18.458 | 5.961 | 1.00 | 37.91 | C |
| ATOM | 1277 | CB | PRO | A | 174 | −46.334 | 19.913 | 5.585 | 1.00 | 37.26 | C |
| ATOM | 1278 | CG | PRO | A | 174 | −47.159 | 19.825 | 4.208 | 1.00 | 41.88 | C |
| ATOM | 1279 | CD | PRO | A | 174 | −45.580 | 18.599 | 4.318 | 1.00 | 39.18 | C |
| ATOM | 1280 | C | PRO | A | 174 | −44.632 | 18.286 | 7.477 | 1.00 | 39.15 | C |
| ATOM | 1281 | O | PRO | A | 174 | −46.822 | 18.382 | 8.255 | 1.00 | 38.20 | O |
| ATOM | 1282 | N | ASP | A | 175 | −47.128 | 18.028 | 7.885 | 1.00 | 42.28 | N |
| ATOM | 1283 | CA | ASP | A | 175 | −48.283 | 17.838 | 8.310 | 1.00 | 43.92 | C |
| ATOM | 1284 | CB | ASP | A | 175 | −48.335 | 18.750 | 9.774 | 1.00 | 48.31 | C |
| ATOM | 1285 | CG | ASP | A | 175 | −47.291 | 18.886 | 11.301 | 1.00 | 58.14 | C |
| ATOM | 1286 | OD1 | ASP | A | 175 | −49.404 | 19.244 | 11.905 | 1.00 | 69.70 | O |
| ATOM | 1287 | OD2 | ASP | A | 175 | −47.429 | 18.610 | 11.899 | 1.00 | 71.32 | O |
| ATOM | 1288 | C | ASP | A | 175 | −48.240 | 16.381 | 9.674 | 1.00 | 39.79 | C |
| ATOM | 1289 | O | ASP | A | 175 | −46.761 | 16.121 | 10.558 | 1.00 | 38.90 | O |
| ATOM | 1290 | N | GLY | A | 176 | −46.962 | 15.440 | 9.008 | 1.00 | 36.27 | N |
| ATOM | 1291 | CA | GLY | A | 176 | −46.466 | 14.019 | 9.276 | 1.00 | 33.05 | C |
| ATOM | 1292 | C | GLY | A | 176 | −45.587 | 13.736 | 10.681 | 1.00 | 31.38 | C |
| ATOM | 1293 | O | GLY | A | 176 | −47.040 | 14.434 | 11.199 | 1.00 | 32.18 | O |
| ATOM | 1294 | N | ARG | A | 177 | −46.729 | 12.720 | 11.316 | 1.00 | 32.42 | N |
| ATOM | 1295 | CA | ARG | A | 177 | −47.678 | 12.403 | 12.681 | 1.00 | 31.96 | C |
| ATOM | 1296 | CB | ARG | A | 177 | −47.207 | 13.124 | 13.628 | 1.00 | 39.35 | C |
| ATOM | 1297 | CG | ARG | A | 177 | −48.325 | 14.522 | 13.911 | 1.00 | 49.57 | C |
| ATOM | 1298 | CD | ARG | A | 177 | −47.805 | 15.533 | 14.149 | 1.00 | 65.20 | C |
| ATOM | 1299 | NE | ARG | A | 177 | −46.941 | 16.904 | 14.060 | 1.00 | 68.37 | N |
| ATOM | 1300 | CZ | ARG | A | 177 | −46.478 | 17.451 | 14.920 | 1.00 | 76.70 | C |
| ATOM | 1301 | NH1 | ARG | A | 177 | −46.533 | 16.754 | 15.958 | 1.00 | 71.28 | N |
| ATOM | 1302 | NH2 | ARG | A | 177 | −46.836 | 18.706 | 14.745 | 1.00 | 77.07 | N |
| ATOM | 1303 | C | ARG | A | 177 | −47.646 | 10.933 | 12.947 | 1.00 | 31.25 | C |
| ATOM | 1304 | O | ARG | A | 177 | −46.010 | 10.251 | 12.357 | 1.00 | 29.27 | O |
| ATOM | 1305 | N | VAL | A | 178 | −46.166 | 10.448 | 13.863 | 1.00 | 30.94 | N |
| ATOM | 1306 | CA | VAL | A | 178 | −46.929 | 9.091 | 14.349 | 1.00 | 25.98 | C |
| ATOM | 1307 | CB | VAL | A | 178 | −44.929 | 8.254 | 14.006 | 1.00 | 24.25 | C |

TABLE 10-continued

Atomic coordinates for COM1 complex of the modified
TXNIP protein represented by SEQ ID NO: 6 and the modified protein represented by SEQ ID NO: 3

| ATOM | 1308 | CG1 | VAL | A | 178 | −45.031 | 6.882 | 14.632 | 1.00 | 32.45 | C |
|---|---|---|---|---|---|---|---|---|---|---|---|
| ATOM | 1309 | CG2 | VAL | A | 178 | −44.771 | 8.107 | 12.474 | 1.00 | 23.95 | C |
| ATOM | 1310 | C | VAL | A | 178 | −46.332 | 0.174 | 15.850 | 1.00 | 30.78 | C |
| ATOM | 1311 | O | VAL | A | 178 | −45.543 | 9.888 | 16.524 | 1.00 | 27.05 | O |
| ATOM | 1312 | N | SER | A | 179 | −47.336 | 8.485 | 16.421 | 1.00 | 27.53 | N |
| ATOM | 1313 | CA | SER | A | 179 | −47.476 | 8.546 | 17.882 | 1.00 | 28.15 | C |
| ATOM | 1314 | CB | SER | A | 179 | −48.637 | 9.462 | 18.270 | 1.00 | 33.64 | C |
| ATOM | 1315 | OG | SER | A | 179 | −49.877 | 8.820 | 18.023 | 1.00 | 43.26 | O |
| ATOM | 1316 | C | SER | A | 179 | −47.711 | 7.174 | 18.476 | 1.00 | 32.44 | C |
| ATOM | 1317 | O | SER | A | 179 | −48.128 | 6.232 | 17.781 | 1.00 | 32.12 | O |
| ATOM | 1318 | N | VAL | A | 180 | −47.398 | 7.053 | 19.773 | 1.00 | 33.91 | N |
| ATOM | 1319 | CA | VAL | A | 180 | −47.675 | 5.834 | 20.520 | 1.00 | 32.79 | C |
| ATOM | 1320 | CB | VAL | A | 180 | −46.478 | 4.831 | 20.590 | 1.00 | 37.23 | C |
| ATOM | 1321 | CG1 | VAL | A | 180 | −45.146 | 5.501 | 20.925 | 1.00 | 38.48 | C |
| ATOM | 1322 | CG2 | VAL | A | 180 | 46.786 | 3.695 | 21.578 | 1.00 | 37.13 | C |
| ATOM | 1323 | C | VAL | A | 180 | −48.097 | 6.273 | 21.872 | 1.00 | 32.87 | C |
| ATOM | 1324 | O | VAL | A | 180 | −47.497 | 7.171 | 22.440 | 1.00 | 30.47 | O |
| ATOM | 1325 | N | SER | A | 181 | −49.134 | 5.620 | 22.368 | 1.00 | 34.04 | N |
| ATOM | 1326 | CA | SER | A | 181 | −49.660 | 5.818 | 23.688 | 1.00 | 33.68 | C |
| ATOM | 1327 | CB | SER | A | 181 | −50.971 | 6.591 | 23.581 | 1.00 | 35.96 | C |
| ATOM | 1328 | OG | SER | A | 181 | −51.482 | 5.832 | 24.865 | 1.00 | 50.10 | O |
| ATOM | 1329 | C | SER | A | 181 | −49.872 | 4.402 | 24.232 | 1.00 | 35.39 | C |
| ATOM | 1330 | O | SER | A | 181 | −50.473 | 3.565 | 23.557 | 1.00 | 38.37 | O |
| ATOM | 1331 | N | ALA | A | 182 | −49.364 | 4.122 | 25.435 | 1.00 | 32.10 | N |
| ATOM | 1332 | CA | ALA | A | 182 | −49.388 | 2.752 | 25.974 | 1.00 | 30.28 | C |
| ATOM | 1333 | CB | ALA | A | 182 | −48.035 | 2.127 | 25.834 | 1.00 | 28.02 | C |
| ATOM | 1334 | C | ALA | A | 182 | −49.810 | 2.759 | 27.430 | 1.00 | 33.17 | C |
| ATOM | 1335 | O | ALA | A | 182 | −49.685 | 3.791 | 28.090 | 1.00 | 31.63 | O |
| ATOM | 1336 | N | ARG | A | 183 | −50.343 | 1.618 | 27.907 | 1.00 | 30.05 | N |
| ATOM | 1337 | CA | ARG | A | 183 | −50.776 | 1.463 | 29.273 | 1.00 | 30.01 | C |
| ATOM | 1338 | CB | ARG | A | 183 | −52.312 | 1.683 | 29.435 | 1.00 | 29.73 | C |
| ATOM | 1339 | CG | ARG | A | 183 | −52.933 | 2.741 | 28.572 | 1.00 | 42.79 | C |
| ATOM | 1340 | CD | ARG | A | 183 | −54.461 | 2.766 | 28.750 | 1.00 | 42.63 | C |
| ATOM | 1341 | NE | ARG | A | 183 | −54.722 | 3.168 | 30.106 | 1.00 | 44.90 | N |
| ATOM | 1342 | CZ | ARG | A | 183 | −55.068 | 4.397 | 30.461 | 1.00 | 49.59 | C |
| ATOM | 1343 | NH1 | ARG | A | 183 | −55.263 | 5.353 | 29.554 | 1.00 | 57.02 | N |
| ATOM | 1344 | NH2 | ARG | A | 183 | −55.220 | 4.658 | 31.725 | 1.00 | 35.21 | N |
| ATOM | 1345 | C | ARG | A | 183 | −50.452 | 0.086 | 29.715 | 1.00 | 28.67 | C |
| ATOM | 1346 | O | ARG | A | 183 | −50.664 | −0.873 | 28.970 | 1.00 | 29.24 | O |
| ATOM | 1347 | N | ILE | A | 184 | −49.906 | −0.024 | 30.926 | 1.00 | 32.41 | N |
| ATOM | 1348 | CA | ILE | A | 184 | −49.752 | −1.294 | 31.614 | 1.00 | 30.09 | C |
| ATOM | 1349 | CB | ILE | A | 184 | −48.253 | −1.743 | 31.692 | 1.00 | 26.95 | C |
| ATOM | 1350 | CG1 | ILE | A | 184 | −47.375 | −0.670 | 32.334 | 1.00 | 27.08 | C |
| ATOM | 1351 | CD1 | ILE | A | 184 | −45.926 | −1.130 | 32.700 | 1.00 | 32.85 | C |
| ATOM | 1352 | CG2 | ILE | A | 184 | −47.765 | −2.083 | 30.295 | 1.00 | 29.79 | C |
| ATOM | 1353 | C | ILE | A | 184 | −50.375 | −1.269 | 33.027 | 1.00 | 34.15 | C |
| ATOM | 1354 | O | ILE | A | 184 | −50.610 | −0.194 | 33.584 | 1.00 | 36.08 | O |
| ATOM | 1355 | N | ASP | A | 185 | −50.537 | −2.454 | 33.619 | 1.00 | 33.90 | N |
| ATOM | 1356 | CA | ASP | A | 185 | −51.325 | −2.631 | 34.854 | 1.00 | 33.79 | C |
| ATOM | 1357 | CG | ASP | A | 185 | −51.735 | −4.100 | 35.007 | 1.00 | 33.79 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 1358 | CG | ASP | A | 185 | -52.648 | 33.895 | -4.593 | 1.00 | 41.25 | C |
| ATOM | 1359 | OD1 | ASP | A | 185 | -52.974 | 33.883 | -5.790 | 1.00 | 50.62 | O |
| ATOM | 1360 | OD2 | ASP | A | 185 | -53.055 | 33.027 | -3.804 | 1.00 | 44.32 | O |
| ATOM | 1361 | C | ASP | A | 185 | -50.629 | 36.142 | -2.184 | 1.00 | 33.44 | C |
| ATOM | 1362 | O | ASP | A | 185 | -51.264 | 37.166 | -1.961 | 1.00 | 37.78 | O |
| ATOM | 1363 | N | ARG | A | 186 | -49.322 | 36.104 | -2.071 | 1.00 | 31.96 | N |
| ATOM | 1364 | CA | ARG | A | 186 | -48.531 | 37.304 | -1.805 | 1.00 | 35.93 | C |
| ATOM | 1365 | CB | ARG | A | 186 | -48.748 | 38.361 | -2.881 | 1.00 | 38.32 | C |
| ATOM | 1366 | CG | ARG | A | 186 | -48.211 | 38.010 | -4.248 | 1.00 | 38.19 | C |
| ATOM | 1367 | CD | ARG | A | 186 | -48.781 | 38.981 | -5.263 | 1.00 | 44.58 | C |
| ATOM | 1368 | NE | ARG | A | 186 | -48.354 | 38.627 | -6.610 | 1.00 | 43.20 | N |
| ATOM | 1369 | CZ | ARG | A | 186 | -49.098 | 37.927 | -7.462 | 1.00 | 46.85 | C |
| ATOM | 1370 | NH1 | ARG | A | 186 | -50.301 | 37.502 | -7.094 | 1.00 | 42.38 | N |
| ATOM | 1371 | NH2 | ARG | A | 186 | -48.628 | 37.687 | -8.670 | 1.00 | 41.07 | N |
| ATOM | 1372 | C | ARG | A | 186 | -47.074 | 36.917 | -1.759 | 1.00 | 33.63 | C |
| ATOM | 1373 | O | ARG | A | 186 | -46.750 | 35.776 | -2.063 | 1.00 | 36.18 | O |
| ATOM | 1374 | N | LYS | A | 187 | -46.208 | 37.857 | -1.374 | 1.00 | 34.39 | N |
| ATOM | 1375 | CA | LYS | A | 187 | -44.757 | 37.641 | -1.329 | 1.00 | 38.75 | C |
| ATOM | 1376 | CB | LYS | A | 187 | -44.160 | 38.547 | -0.262 | 1.00 | 42.51 | C |
| ATOM | 1377 | CG | LYS | A | 187 | -43.075 | 37.933 | 0.574 | 1.00 | 52.57 | C |
| ATOM | 1378 | CD | LYS | A | 187 | -42.430 | 38.949 | 1.531 | 1.00 | 55.20 | C |
| ATOM | 1379 | CE | LYS | A | 187 | -40.957 | 38.552 | 1.812 | 1.00 | 57.73 | C |
| ATOM | 1380 | NZ | LYS | A | 187 | -40.580 | 38.615 | 3.268 | 1.00 | 59.31 | N |
| ATOM | 1381 | C | LYS | A | 187 | -44.099 | 38.016 | -2.657 | 1.00 | 38.93 | C |
| ATOM | 1382 | O | LYS | A | 187 | -43.145 | 37.388 | -3.083 | 1.00 | 39.65 | O |
| ATOM | 1383 | N | GLY | A | 188 | -44.608 | 39.049 | -3.329 | 1.00 | 40.95 | N |
| ATOM | 1384 | CA | GLY | A | 188 | -43.907 | 39.574 | -4.517 | 1.00 | 36.72 | C |
| ATOM | 1385 | C | GLY | A | 188 | -44.511 | 39.109 | -5.819 | 1.00 | 40.75 | C |
| ATOM | 1386 | O | GLY | A | 188 | -45.701 | 39.295 | -6.036 | 1.00 | 37.42 | O |
| ATOM | 1387 | N | PHE | A | 189 | -43.685 | 38.520 | -6.697 | 1.00 | 43.53 | N |
| ATOM | 1388 | CA | PHE | A | 189 | -44.139 | 37.976 | -7.998 | 1.00 | 42.67 | C |
| ATOM | 1389 | CB | PHE | A | 189 | -44.104 | 36.435 | -8.023 | 1.00 | 41.98 | C |
| ATOM | 1390 | CG | PHE | A | 189 | -45.075 | 35.783 | -7.076 | 1.00 | 37.02 | C |
| ATOM | 1391 | CD1 | PHE | A | 189 | -46.355 | 35.454 | -7.492 | 1.00 | 40.86 | C |
| ATOM | 1392 | CE1 | PHE | A | 189 | -47.267 | 34.844 | -6.609 | 1.00 | 34.96 | C |
| ATOM | 1393 | CZ | PHE | A | 189 | -46.877 | 34.584 | -5.301 | 1.00 | 36.32 | C |
| ATOM | 1394 | CE2 | PHE | A | 189 | -45.592 | 34.911 | -4.889 | 1.00 | 33.96 | C |
| ATOM | 1395 | CD2 | PHE | A | 189 | -44.698 | 35.502 | -5.777 | 1.00 | 31.96 | C |
| ATOM | 1396 | C | PHE | A | 189 | -43.207 | 38.487 | -9.082 | 1.00 | 44.82 | C |
| ATOM | 1397 | O | PHE | A | 189 | -42.059 | 38.777 | -8.802 | 1.00 | 41.58 | O |
| ATOM | 1398 | N | CYS | A | 190 | -43.725 | 38.578 | -10.308 | 1.00 | 47.34 | N |
| ATOM | 1399 | CA | CYS | A | 190 | -42.970 | 39.014 | -11.477 | 1.00 | 50.83 | C |
| ATOM | 1400 | CB | CYS | A | 190 | -43.937 | 39.716 | -12.439 | 1.00 | 54.28 | C |
| ATOM | 1401 | SG | CYS | A | 190 | -44.590 | 41.316 | -11.860 | 1.00 | 71.45 | S |
| ATOM | 1402 | C | CYS | A | 190 | -42.392 | 37.812 | -12.199 | 1.00 | 48.11 | C |
| ATOM | 1403 | O | CYS | A | 190 | -43.079 | 36.796 | -12.322 | 1.00 | 45.85 | O |
| ATOM | 1404 | N | GLU | A | 191 | -41.167 | 37.924 | -12.722 | 1.00 | 49.55 | N |
| ATOM | 1405 | CA | GLU | A | 191 | -40.643 | 36.885 | -13.613 | 1.00 | 51.42 | C |
| ATOM | 1406 | CB | GLU | A | 191 | -39.351 | 37.338 | -14.302 | 1.00 | 53.26 | C |
| ATOM | 1407 | CG | GLU | A | 191 | -38.170 | 37.509 | -13.335 | 1.00 | 55.25 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 1408 | CD | GLU | A | 191 | -36.844 | 37.788 | 1.00 | 59.39 | C |
| ATOM | 1409 | OE1 | GLU | A | 191 | -35.804 | 37.472 | 1.00 | 60.66 | O |
| ATOM | 1410 | OE2 | GLU | A | 191 | -36.840 | 38.311 | 1.00 | 53.55 | O |
| ATOM | 1411 | C | GLU | A | 191 | -41.707 | 36.532 | 1.00 | 52.19 | C |
| ATOM | 1412 | O | GLU | A | 191 | -42.363 | 37.419 | 1.00 | 55.07 | O |
| ATOM | 1413 | N | GLY | A | 192 | -41.923 | 35.245 | 1.00 | 52.31 | N |
| ATOM | 1414 | CA | GLY | A | 192 | -42.935 | 34.812 | 1.00 | 52.20 | C |
| ATOM | 1415 | C | GLY | A | 192 | -44.278 | 34.491 | 1.00 | 52.75 | C |
| ATOM | 1416 | O | GLY | A | 192 | -45.091 | 33.800 | 1.00 | 53.26 | O |
| ATOM | 1417 | N | ASP | A | 193 | -44.517 | 34.978 | 1.00 | 53.35 | N |
| ATOM | 1418 | CA | ASP | A | 193 | -45.709 | 34.596 | 1.00 | 52.02 | C |
| ATOM | 1419 | CB | ASP | A | 193 | -45.779 | 35.379 | 1.00 | 52.54 | C |
| ATOM | 1420 | CG | ASP | A | 193 | -46.366 | 36.769 | 1.00 | 58.00 | C |
| ATOM | 1421 | OD1 | ASP | A | 193 | -46.806 | 37.114 | 1.00 | 65.03 | O |
| ATOM | 1422 | OD2 | ASP | A | 193 | -46.386 | 37.525 | 1.00 | 60.67 | O |
| ATOM | 1423 | C | ASP | A | 193 | -45.790 | 33.094 | 1.00 | 52.60 | C |
| ATOM | 1424 | O | ASP | A | 193 | -44.904 | 32.302 | 1.00 | 53.74 | O |
| ATOM | 1425 | N | GLU | A | 194 | -46.886 | 32.720 | 1.00 | 49.80 | N |
| ATOM | 1426 | CA | GLU | A | 194 | -46.997 | 31.445 | 1.00 | 49.57 | C |
| ATOM | 1427 | CB | GLU | A | 194 | -48.107 | 30.624 | 1.00 | 51.11 | C |
| ATOM | 1428 | CG | GLU | A | 194 | -47.567 | 29.582 | 1.00 | 60.50 | C |
| ATOM | 1429 | CD | GLU | A | 194 | -48.510 | 29.308 | 1.00 | 71.14 | C |
| ATOM | 1430 | OE1 | GLU | A | 194 | -49.713 | 29.064 | 1.00 | 76.91 | O |
| ATOM | 1431 | OE2 | GLU | A | 194 | -48.039 | 29.337 | 1.00 | 76.27 | O |
| ATOM | 1432 | C | GLU | A | 194 | -47.311 | 31.713 | 1.00 | 47.29 | C |
| ATOM | 1433 | O | GLU | A | 194 | -48.127 | 32.583 | 1.00 | 46.40 | O |
| ATOM | 1434 | N | ILE | A | 195 | -46.635 | 30.989 | 1.00 | 43.53 | N |
| ATOM | 1435 | CA | ILE | A | 195 | -47.019 | 30.945 | 1.00 | 38.53 | C |
| ATOM | 1436 | CB | ILE | A | 195 | -45.797 | 30.783 | 1.00 | 38.34 | C |
| ATOM | 1437 | CG1 | ILE | A | 195 | -44.720 | 31.828 | 1.00 | 42.85 | C |
| ATOM | 1438 | CD1 | ILE | A | 195 | -43.462 | 31.702 | 1.00 | 40.67 | C |
| ATOM | 1439 | CG2 | ILE | A | 195 | -46.217 | 30.853 | 1.00 | 35.89 | C |
| ATOM | 1440 | C | ILE | A | 195 | -47.987 | 29.779 | 1.00 | 39.54 | C |
| ATOM | 1441 | O | ILE | A | 195 | -47.637 | 28.650 | 1.00 | 38.03 | O |
| ATOM | 1442 | N | SER | A | 196 | -49.227 | 30.104 | 1.00 | 39.67 | N |
| ATOM | 1443 | CA | SER | A | 196 | -50.283 | 29.155 | 1.00 | 38.61 | C |
| ATOM | 1444 | CB | SER | A | 196 | -51.607 | 29.830 | 1.00 | 42.28 | C |
| ATOM | 1445 | OG | SER | A | 196 | -52.708 | 28.953 | 1.00 | 44.84 | O |
| ATOM | 1446 | C | SER | A | 196 | -50.239 | 28.767 | 1.00 | 36.69 | C |
| ATOM | 1447 | O | SER | A | 196 | -50.121 | 29.631 | 1.00 | 35.36 | O |
| ATOM | 1448 | N | ILE | A | 197 | -50.299 | 27.466 | 1.00 | 33.53 | N |
| ATOM | 1449 | CA | ILE | A | 197 | -50.103 | 26.946 | 1.00 | 33.75 | C |
| ATOM | 1450 | CB | ILE | A | 197 | -48.809 | 26.034 | 1.00 | 33.86 | C |
| ATOM | 1451 | CG1 | ILE | A | 197 | -47.525 | 26.760 | 1.00 | 36.65 | C |
| ATOM | 1452 | CD1 | ILE | A | 197 | -46.358 | 25.800 | 1.00 | 38.48 | C |
| ATOM | 1453 | CG2 | ILE | A | 197 | -48.657 | 25.636 | 1.00 | 28.41 | C |
| ATOM | 1454 | C | ILE | A | 197 | -51.280 | 26.126 | 1.00 | 34.16 | C |
| ATOM | 1455 | O | ILE | A | 197 | -51.701 | 25.188 | 1.00 | 35.97 | O |
| ATOM | 1456 | N | HIS | A | 198 | -51.748 | 26.467 | 1.00 | 29.05 | N |
| ATOM | 1457 | CA | HIS | A | 198 | -52.774 | 25.748 | 1.00 | 29.16 | C |

TABLE 10-continued

Atomic coordinates for COM1 complex of the modified
TXNIP protein represented by SEQ ID NO: 6 and the modified protein represented by SEQ ID NO: 3

| ATOM | 1458 | CB | HIS | A | 198 | −53.736 | 26.766 | −1.155 | 1.00 | 28.61 | C |
|------|------|------|-----|---|-----|---------|--------|--------|------|-------|---|
| ATOM | 1459 | CG | HIS | A | 198 | −54.892 | 26.179 | −0.406 | 1.00 | 36.86 | C |
| ATOM | 1460 | ND1 | HIS | A | 198 | −54.848 | 25.917 | 0.951 | 1.00 | 45.40 | N |
| ATOM | 1461 | CE1 | HIS | A | 198 | −56.013 | 25.428 | 1.341 | 1.00 | 38.83 | C |
| ATOM | 1462 | NE2 | HIS | A | 198 | −56.809 | 25.363 | 0.287 | 1.00 | 38.75 | N |
| ATOM | 1463 | CD2 | HIS | A | 198 | −56.133 | 25.829 | −0.817 | 1.00 | 35.94 | C |
| ATOM | 1464 | C | HIS | A | 198 | −52.042 | 25.088 | −0.582 | 1.00 | 31.81 | C |
| ATOM | 1465 | O | HIS | A | 198 | −51.443 | 25.786 | 0.234 | 1.00 | 31.76 | O |
| ATOM | 1466 | N | ALA | A | 199 | −52.059 | 23.755 | −0.520 | 1.00 | 31.21 | N |
| ATOM | 1467 | CA | ALA | A | 199 | −51.423 | 23.067 | 0.597 | 1.00 | 30.88 | C |
| ATOM | 1468 | CB | ALA | A | 199 | −49.992 | 22.753 | 0.294 | 1.00 | 27.56 | C |
| ATOM | 1469 | C | ALA | A | 199 | −52.170 | 21.815 | 1.020 | 1.00 | 31.60 | C |
| ATOM | 1470 | O | ALA | A | 199 | −52.883 | 21.195 | 0.240 | 1.00 | 31.93 | O |
| ATOM | 1471 | N | ASP | A | 200 | −52.000 | 21.465 | 2.280 | 1.00 | 30.50 | N |
| ATOM | 1472 | CA | ASP | A | 200 | −52.618 | 20.272 | 2.828 | 1.00 | 30.24 | C |
| ATOM | 1473 | CB | ASP | A | 200 | −53.669 | 20.657 | 3.888 | 1.00 | 29.38 | C |
| ATOM | 1474 | CG | ASP | A | 200 | −54.856 | 21.398 | 3.302 | 1.00 | 38.29 | C |
| ATOM | 1475 | OD1 | ASP | A | 200 | −55.192 | 21.280 | 2.086 | 1.00 | 36.70 | O |
| ATOM | 1476 | OD2 | ASP | A | 200 | −55.466 | 22.128 | 4.077 | 1.00 | 26.61 | O |
| ATOM | 1477 | C | ASP | A | 200 | −51.504 | 19.532 | 3.515 | 1.00 | 31.54 | C |
| ATOM | 1478 | O | ASP | A | 200 | −50.681 | 20.153 | 4.211 | 1.00 | 30.53 | O |
| ATOM | 1479 | N | PHE | A | 201 | −51.503 | 18.205 | 3.363 | 1.00 | 29.95 | N |
| ATOM | 1480 | CA | PHE | A | 201 | −50.400 | 17.398 | 3.838 | 1.00 | 29.52 | C |
| ATOM | 1481 | CB | PHE | A | 201 | −49.706 | 16.785 | 2.612 | 1.00 | 29.10 | C |
| ATOM | 1482 | CG | PHE | A | 201 | −49.059 | 17.821 | 1.699 | 1.00 | 28.51 | C |
| ATOM | 1483 | CD1 | PHE | A | 201 | −47.839 | 18.362 | 2.027 | 1.00 | 28.10 | C |
| ATOM | 1484 | CE1 | PHE | A | 201 | −47.222 | 19.297 | 1.196 | 1.00 | 32.08 | C |
| ATOM | 1485 | CZ | PHE | A | 201 | −47.854 | 19.719 | 0.074 | 1.00 | 33.12 | C |
| ATOM | 1486 | CE2 | PHE | A | 201 | −49.074 | 19.196 | −0.286 | 1.00 | 27.14 | C |
| ATOM | 1487 | CD2 | PHE | A | 201 | −49.668 | 18.223 | 0.516 | 1.00 | 35.38 | C |
| ATOM | 1488 | C | PHE | A | 201 | −51.034 | 16.293 | 4.670 | 1.00 | 33.05 | C |
| ATOM | 1489 | O | PHE | A | 201 | −51.954 | 15.699 | 4.200 | 1.00 | 34.17 | O |
| ATOM | 1490 | N | GLU | A | 202 | −50.553 | 16.021 | 5.881 | 1.00 | 31.39 | N |
| ATOM | 1491 | CA | GLU | A | 202 | −51.060 | 14.879 | 6.643 | 1.00 | 31.79 | C |
| ATOM | 1492 | CB | GLU | A | 202 | −51.441 | 15.247 | 8.076 | 1.00 | 31.62 | C |
| ATOM | 1493 | CG | GLU | A | 202 | −52.628 | 16.126 | 8.323 | 1.00 | 45.42 | C |
| ATOM | 1494 | CD | GLU | A | 202 | −53.353 | 15.707 | 9.615 | 1.00 | 48.40 | C |
| ATOM | 1495 | OE1 | GLU | A | 202 | −52.861 | 14.835 | 10.410 | 1.00 | 52.68 | O |
| ATOM | 1496 | OE2 | GLU | A | 202 | −54.435 | 16.240 | 9.823 | 1.00 | 51.41 | O |
| ATOM | 1497 | C | GLU | A | 202 | −49.958 | 13.865 | 6.828 | 1.00 | 31.34 | C |
| ATOM | 1498 | O | GLU | A | 202 | −48.822 | 14.252 | 7.110 | 1.00 | 31.04 | O |
| ATOM | 1499 | N | ASN | A | 203 | −50.295 | 12.588 | 6.754 | 1.00 | 28.41 | N |
| ATOM | 1500 | CA | ASN | A | 203 | −49.320 | 11.497 | 7.047 | 1.00 | 28.26 | C |
| ATOM | 1501 | CB | ASN | A | 203 | −48.771 | 10.910 | 5.783 | 1.00 | 29.36 | C |
| ATOM | 1502 | CG | ASN | A | 203 | −47.738 | 9.845 | 5.966 | 1.00 | 31.84 | C |
| ATOM | 1503 | OD1 | ASN | A | 203 | −47.143 | 9.798 | 7.045 | 1.00 | 28.05 | O |
| ATOM | 1504 | ND2 | ASN | A | 203 | −47.536 | 8.950 | 4.982 | 1.00 | 26.51 | N |
| ATOM | 1505 | C | ASN | A | 203 | −49.903 | 10.401 | 7.918 | 1.00 | 31.34 | C |
| ATOM | 1506 | O | ASN | A | 203 | −50.532 | 9.471 | 7.418 | 1.00 | 28.67 | O |
| ATOM | 1507 | N | THR | A | 204 | −49.734 | 10.504 | 9.237 | 1.00 | 28.19 | N |

TABLE 10-continued

Atomic coordinates for COM1 complex of the modified
TXNIP protein represented by SEQ ID NO: 6 and the modified protein represented by SEQ ID NO: 3

| | | | | | | | | | | | |
|---|---|---|---|---|---|---|---|---|---|---|---|
| ATOM | 1508 | CA  | THR | A | 204 | −50.159 | 10.139 | 9.441  | 1.00 | 28.81 | C |
| ATOM | 1509 | CB  | THR | A | 204 | −50.771 | 11.491 | 9.992  | 1.00 | 32.00 | C |
| ATOM | 1510 | OG1 | THR | A | 204 | −49.826 | 12.128 | 10.842 | 1.00 | 30.76 | O |
| ATOM | 1511 | CG2 | THR | A | 204 | −52.002 | 11.236 | 10.853 | 1.00 | 32.22 | C |
| ATOM | 1512 | C   | THR | A | 204 | −48.947 | 10.461 | 8.564  | 1.00 | 30.81 | C |
| ATOM | 1513 | O   | THR | A | 204 | −49.057 | 11.212 | 7.583  | 1.00 | 33.85 | O |
| ATOM | 1514 | N   | SER | A | 205 | −47.784 | 9.877  | 8.875  | 1.00 | 28.80 | N |
| ATOM | 1515 | CA  | SER | A | 205 | −46.569 | 10.082 | 8.040  | 1.00 | 26.52 | C |
| ATOM | 1516 | CB  | SER | A | 205 | −45.349 | 9.502  | 8.758  | 1.00 | 26.46 | C |
| ATOM | 1517 | OG  | SER | A | 205 | −45.133 | 8.169  | 8.319  | 1.00 | 32.23 | O |
| ATOM | 1518 | C   | SER | A | 205 | −46.736 | 9.420  | 6.656  | 1.00 | 29.80 | C |
| ATOM | 1519 | O   | SER | A | 205 | −47.684 | 8.625  | 6.463  | 1.00 | 29.01 | O |
| ATOM | 1520 | N   | SER | A | 206 | −45.841 | 9.754  | 5.687  | 1.00 | 26.21 | N |
| ATOM | 1521 | CA  | SER | A | 206 | −45.773 | 9.070  | 4.422  | 1.00 | 29.85 | C |
| ATOM | 1522 | CB  | SER | A | 206 | −44.973 | 9.904  | 3.402  | 1.00 | 30.13 | C |
| ATOM | 1523 | OG  | SER | A | 206 | −43.635 | 10.009 | 3.882  | 1.00 | 31.92 | O |
| ATOM | 1524 | C   | SER | A | 206 | −45.164 | 7.665  | 4.482  | 1.00 | 31.00 | C |
| ATOM | 1525 | O   | SER | A | 206 | −45.253 | 6.940  | 3.510  | 1.00 | 31.18 | O |
| ATOM | 1526 | N   | ARG | A | 207 | −44.618 | 7.266  | 5.633  | 1.00 | 30.74 | N |
| ATOM | 1527 | CA  | ARG | A | 207 | −43.874 | 6.002  | 5.804  | 1.00 | 30.75 | C |
| ATOM | 1528 | CB  | ARG | A | 207 | −42.862 | 6.206  | 6.944  | 1.00 | 26.21 | C |
| ATOM | 1529 | CG  | ARG | A | 207 | −41.488 | 6.726  | 6.556  | 1.00 | 37.96 | C |
| ATOM | 1530 | CD  | ARG | A | 207 | −41.546 | 7.810  | 5.484  | 1.00 | 40.57 | C |
| ATOM | 1531 | NE  | ARG | A | 207 | −40.400 | 8.723  | 5.519  | 1.00 | 40.24 | N |
| ATOM | 1532 | CZ  | ARG | A | 207 | −40.516 | 10.042 | 5.694  | 1.00 | 50.03 | C |
| ATOM | 1533 | NH1 | ARG | A | 207 | −41.714 | 10.000 | 5.840  | 1.00 | 37.20 | N |
| ATOM | 1534 | NH2 | ARG | A | 207 | −39.435 | 10.806 | 5.720  | 1.00 | 49.55 | N |
| ATOM | 1535 | C   | ARG | A | 207 | −44.760 | 4.843  | 6.234  | 1.00 | 32.07 | C |
| ATOM | 1536 | O   | ARG | A | 207 | −45.807 | 5.068  | 6.800  | 1.00 | 28.17 | O |
| ATOM | 1537 | N   | ILE | A | 208 | −44.287 | 3.606  | 6.066  | 1.00 | 30.02 | N |
| ATOM | 1538 | CA  | ILE | A | 208 | −44.945 | 2.456  | 6.676  | 1.00 | 30.53 | C |
| ATOM | 1539 | CB  | ILE | A | 208 | −44.874 | 1.203  | 5.770  | 1.00 | 28.72 | C |
| ATOM | 1540 | CG1 | ILE | A | 208 | −45.691 | 1.400  | 4.484  | 1.00 | 30.42 | C |
| ATOM | 1541 | CD1 | ILE | A | 208 | −45.222 | 0.507  | 3.273  | 1.00 | 35.42 | C |
| ATOM | 1542 | CG2 | ILE | A | 208 | −45.385 | 0.014  | 6.510  | 1.00 | 34.68 | C |
| ATOM | 1543 | C   | ILE | A | 208 | −44.124 | 2.192  | 7.924  | 1.00 | 32.38 | C |
| ATOM | 1544 | O   | ILE | A | 208 | −42.890 | 2.005  | 7.813  | 1.00 | 31.77 | O |
| ATOM | 1545 | N   | VAL | A | 209 | −44.779 | 2.207  | 9.096  | 1.00 | 30.42 | N |
| ATOM | 1546 | CA  | VAL | A | 209 | −44.071 | 2.122  | 10.400 | 1.00 | 25.51 | C |
| ATOM | 1547 | CB  | VAL | A | 209 | −44.334 | 3.381  | 11.261 | 1.00 | 26.77 | C |
| ATOM | 1548 | CG1 | VAL | A | 209 | −44.135 | 4.659  | 10.416 | 1.00 | 20.25 | C |
| ATOM | 1549 | CG2 | VAL | A | 209 | −45.730 | 3.356  | 11.876 | 1.00 | 20.82 | C |
| ATOM | 1550 | C   | VAL | A | 209 | −44.407 | 0.792  | 11.099 | 1.00 | 29.61 | C |
| ATOM | 1551 | O   | VAL | A | 209 | −45.364 | 0.126  | 10.701 | 1.00 | 29.55 | O |
| ATOM | 1552 | N   | VAL | A | 210 | −43.595 | 0.366  | 12.065 | 1.00 | 29.88 | N |
| ATOM | 1553 | CA  | VAL | A | 210 | −43.755 | −0.934 | 12.693 | 1.00 | 30.46 | C |
| ATOM | 1554 | CB  | VAL | A | 210 | −42.711 | −1.997 | 12.225 | 1.00 | 30.02 | C |
| ATOM | 1555 | CG1 | VAL | A | 210 | −42.980 | −3.334 | 12.946 | 1.00 | 28.24 | C |
| ATOM | 1556 | CG2 | VAL | A | 210 | −42.764 | −2.208 | 10.765 | 1.00 | 36.36 | C |
| ATOM | 1557 | C   | VAL | A | 210 | −43.619 | −0.793 | 14.197 | 1.00 | 31.20 | C |

TABLE 10-continued

Atomic coordinates for COM1 complex of the modified
TXNIP protein represented by SEQ ID NO: 6 and the modified protein represented by SEQ ID NO: 3

| ATOM | 1558 | O | VAL | A | 210 | -42.534 | -0.429 | 14.700 | 1.00 | 31.02 | O |
|---|---|---|---|---|---|---|---|---|---|---|---|
| ATOM | 1559 | N | PRO | A | 211 | -44.717 | -1.078 | 14.939 | 1.00 | 33.59 | N |
| ATOM | 1560 | CA | PRO | A | 211 | -44.692 | -1.064 | 16.409 | 1.00 | 27.00 | C |
| ATOM | 1561 | CB | PRO | A | 211 | -46.158 | -1.036 | 16.769 | 1.00 | 28.45 | C |
| ATOM | 1562 | CG | PRO | A | 211 | -46.800 | -1.826 | 15.692 | 1.00 | 28.64 | C |
| ATOM | 1563 | CD | PRO | A | 211 | 46.062 | 1.427 | 14.415 | 1.00 | 31.62 | C |
| ATOM | 1564 | C | PRO | A | 211 | -44.047 | -2.332 | 16.978 | 1.00 | 31.20 | C |
| ATOM | 1565 | O | PRO | A | 211 | -44.237 | -3.450 | 16.442 | 1.00 | 26.53 | O |
| ATOM | 1566 | N | LYS | A | 211 | -43.232 | -2.150 | 18.004 | 1.00 | 29.31 | N |
| ATOM | 1567 | CA | LYS | A | 212 | -42.472 | -3.251 | 18.605 | 1.00 | 28.91 | C |
| ATOM | 1568 | CB | LYS | A | 212 | -41.033 | -3.361 | 18.016 | 1.00 | 27.41 | C |
| ATOM | 1569 | CG | LYS | A | 212 | -40.984 | -3.339 | 16.507 | 1.00 | 26.22 | C |
| ATOM | 1570 | CD | LYS | A | 212 | -39.544 | -3.526 | 15.987 | 1.00 | 29.31 | C |
| ATOM | 1571 | CE | LYS | A | 212 | -39.514 | -3.519 | 14.472 | 1.00 | 32.98 | C |
| ATOM | 1572 | NZ | LYS | A | 212 | -38.081 | -3.498 | 14.046 | 1.00 | 37.36 | N |
| ATOM | 1573 | C | LYS | A | 212 | -42.420 | -2.989 | 20.079 | 1.00 | 32.10 | C |
| ATOM | 1574 | O | LYS | A | 212 | -42.680 | -1.872 | 20.530 | 1.00 | 31.68 | O |
| ATOM | 1575 | N | ALA | A | 213 | -42.157 | -4.038 | 20.851 | 1.00 | 32.57 | N |
| ATOM | 1576 | CA | ALA | A | 213 | -41.960 | -3.846 | 22.274 | 1.00 | 30.64 | C |
| ATOM | 1577 | CB | ALA | A | 213 | -43.265 | -3.938 | 23.014 | 1.00 | 27.65 | C |
| ATOM | 1578 | C | ALA | A | 213 | -40.978 | -4.898 | 22.796 | 1.00 | 27.62 | C |
| ATOM | 1579 | O | ALA | A | 213 | -40.823 | -5.962 | 22.221 | 1.00 | 31.26 | O |
| ATOM | 1580 | N | ALA | A | 214 | -40.291 | -4.586 | 23.872 | 1.00 | 30.11 | N |
| ATOM | 1581 | CA | ALA | A | 214 | -39.256 | -5.473 | 24.339 | 1.00 | 27.81 | C |
| ATOM | 1582 | CB | ALA | A | 214 | -37.935 | -5.327 | 23.528 | 1.00 | 29.87 | C |
| ATOM | 1583 | C | ALA | A | 214 | -39.034 | -5.166 | 25.768 | 1.00 | 31.78 | C |
| ATOM | 1584 | O | ALA | A | 214 | -39.120 | -3.995 | 26.210 | 1.00 | 30.05 | O |
| ATOM | 1585 | N | ILE | A | 215 | -38.768 | -6.226 | 26.515 | 1.00 | 31.28 | N |
| ATOM | 1586 | CA | ILE | A | 215 | -38.279 | -6.068 | 27.869 | 1.00 | 30.48 | C |
| ATOM | 1587 | CB | ILE | A | 215 | -38.751 | -7.192 | 28.805 | 1.00 | 30.28 | C |
| ATOM | 1588 | CG1 | ILE | A | 215 | -40.254 | -7.088 | 29.057 | 1.00 | 38.42 | C |
| ATOM | 1589 | CD1 | ILE | A | 215 | -40.888 | -8.440 | 29.399 | 1.00 | 45.27 | C |
| ATOM | 1590 | CG2 | ILE | A | 215 | -38.044 | -7.082 | 30.166 | 1.00 | 37.32 | C |
| ATOM | 1591 | C | ILE | A | 215 | -36.755 | -6.040 | 27.755 | 1.00 | 31.63 | C |
| ATOM | 1592 | O | ILE | A | 215 | -36.140 | -6.843 | 27.030 | 1.00 | 30.47 | O |
| ATOM | 1593 | N | VAL | A | 216 | -36.134 | -5.089 | 28.431 | 1.00 | 31.91 | N |
| ATOM | 1594 | CA | VAL | A | 216 | -34.660 | -4.964 | 28.414 | 1.00 | 37.11 | C |
| ATOM | 1595 | CB | VAL | A | 216 | -34.189 | -3.697 | 27.633 | 1.00 | 39.95 | C |
| ATOM | 1596 | CG1 | VAL | A | 216 | -34.646 | -3.748 | 26.172 | 1.00 | 37.88 | C |
| ATOM | 1597 | CG2 | VAL | A | 216 | -34.734 | -2.432 | 28.297 | 1.00 | 43.04 | C |
| ATOM | 1598 | C | VAL | A | 216 | -34.128 | -4.917 | 29.858 | 1.00 | 36.61 | C |
| ATOM | 1599 | O | VAL | A | 216 | -34.767 | -4.320 | 30.751 | 1.00 | 36.35 | O |
| ATOM | 1600 | N | ALA | A | 217 | -32.987 | -5.580 | 30.061 | 1.00 | 38.81 | N |
| ATOM | 1601 | CA | ALA | A | 217 | -32.326 | -5.780 | 31.368 | 1.00 | 39.39 | C |
| ATOM | 1602 | CB | ALA | A | 217 | -32.038 | -7.258 | 31.597 | 1.00 | 37.63 | C |
| ATOM | 1603 | C | ALA | A | 217 | -31.024 | -5.031 | 31.306 | 1.00 | 42.80 | C |
| ATOM | 1604 | O | ALA | A | 217 | -30.175 | -5.316 | 30.456 | 1.00 | 45.03 | O |
| ATOM | 1605 | N | ARG | A | 218 | -30.860 | -4.042 | 32.165 | 1.00 | 43.59 | N |
| ATOM | 1606 | CA | ARG | A | 218 | -29.634 | -3.280 | 32.160 | 1.00 | 45.58 | C |
| ATOM | 1607 | CB | ARG | A | 218 | -29.945 | -1.791 | 32.119 | 1.00 | 45.69 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 1608 | CG | ARG | A | 218 | −30.720 | −1.370 | 30.873 | 1.00 | 42.92 | C |
| ATOM | 1609 | CD | ARG | A | 218 | −30.867 | 0.142 | 30.843 | 1.00 | 46.13 | C |
| ATOM | 1610 | NE | ARG | A | 218 | −31.785 | 0.574 | 29.778 | 1.00 | 53.31 | N |
| ATOM | 1611 | CZ | ARG | A | 218 | −33.072 | 0.847 | 29.982 | 1.00 | 52.24 | C |
| ATOM | 1612 | NH1 | ARG | A | 218 | −33.592 | 0.720 | 31.211 | 1.00 | 43.90 | N |
| ATOM | 1613 | NH2 | ARG | A | 218 | −33.838 | 1.228 | 28.958 | 1.00 | 40.23 | N |
| ATOM | 1614 | C | ARG | A | 218 | −28.760 | −3.660 | 33.375 | 1.00 | 47.52 | C |
| ATOM | 1615 | O | ARG | A | 218 | −29.011 | −3.229 | 34.486 | 1.00 | 46.08 | O |
| ATOM | 1616 | N | HIS | A | 219 | −27.752 | −4.492 | 33.125 | 1.00 | 49.89 | N |
| ATOM | 1617 | CA | HIS | A | 219 | −26.904 | −5.036 | 34.188 | 1.00 | 51.47 | C |
| ATOM | 1618 | CB | HIS | A | 219 | −26.228 | −6.321 | 33.754 | 1.00 | 50.86 | C |
| ATOM | 1619 | CG | HIS | A | 219 | −27.178 | −7.449 | 33.518 | 1.00 | 56.13 | C |
| ATOM | 1620 | ND1 | HIS | A | 219 | −27.868 | −7.606 | 32.333 | 1.00 | 62.38 | N |
| ATOM | 1621 | CE1 | HIS | A | 219 | −28.621 | −8.690 | 32.405 | 1.00 | 59.02 | C |
| ATOM | 1622 | NE2 | HIS | A | 219 | −28.446 | −9.241 | 33.593 | 1.00 | 65.49 | N |
| ATOM | 1623 | CD2 | HIS | A | 219 | −27.548 | −8.485 | 34.309 | 1.00 | 63.66 | C |
| ATOM | 1624 | C | HIS | A | 219 | −25.859 | −4.037 | 34.611 | 1.00 | 50.60 | C |
| ATOM | 1625 | O | HIS | A | 219 | −25.101 | −3.513 | 33.808 | 1.00 | 50.02 | O |
| ATOM | 1626 | N | THR | A | 220 | −25.868 | −3.750 | 35.897 | 1.00 | 52.69 | N |
| ATOM | 1627 | CA | THR | A | 220 | −24.852 | −2.945 | 36.518 | 1.00 | 52.85 | C |
| ATOM | 1628 | CB | THR | A | 220 | −25.481 | −1.843 | 37.429 | 1.00 | 52.60 | C |
| ATOM | 1629 | OG1 | THR | A | 220 | −25.940 | −0.756 | 36.617 | 1.00 | 57.42 | O |
| ATOM | 1630 | CG2 | THR | A | 220 | −24.449 | −1.281 | 38.371 | 1.00 | 54.63 | C |
| ATOM | 1631 | C | THR | A | 220 | −24.030 | −3.988 | 37.283 | 1.00 | 50.84 | C |
| ATOM | 1632 | O | THR | A | 220 | −24.549 | −4.750 | 38.105 | 1.00 | 51.99 | O |
| ATOM | 1633 | N | TYR | A | 221 | −22.768 | −4.083 | 36.931 | 1.00 | 54.40 | N |
| ATOM | 1634 | CA | TYR | A | 221 | −21.943 | −5.223 | 37.370 | 1.00 | 55.25 | C |
| ATOM | 1635 | CB | TYR | A | 221 | −21.901 | −6.378 | 36.332 | 1.00 | 56.42 | C |
| ATOM | 1636 | CG | TYR | A | 221 | −21.248 | −6.064 | 34.994 | 1.00 | 60.00 | C |
| ATOM | 1637 | CD1 | TYR | A | 221 | −19.954 | −6.499 | 34.701 | 1.00 | 62.67 | C |
| ATOM | 1638 | CE1 | TYR | A | 221 | −19.355 | −6.217 | 33.452 | 1.00 | 63.42 | C |
| ATOM | 1639 | CZ | TYR | A | 221 | −20.062 | −5.500 | 32.484 | 1.00 | 65.06 | C |
| ATOM | 1640 | OH | TYR | A | 221 | −19.490 | −5.217 | 31.260 | 1.00 | 56.98 | O |
| ATOM | 1641 | CE2 | TYR | A | 221 | −21.346 | −5.069 | 32.750 | 1.00 | 61.84 | C |
| ATOM | 1642 | CD2 | TYR | A | 221 | −21.939 | −5.359 | 34.002 | 1.00 | 65.91 | C |
| ATOM | 1643 | C | TYR | A | 221 | −20.564 | −4.710 | 37.677 | 1.00 | 55.47 | C |
| ATOM | 1644 | O | TYR | A | 221 | −20.136 | −3.686 | 37.102 | 1.00 | 53.78 | O |
| ATOM | 1645 | N | LEU | A | 222 | −19.892 | −5.408 | 38.600 | 1.00 | 52.35 | N |
| ATOM | 1646 | CA | LEU | A | 222 | −18.534 | −5.050 | 38.975 | 1.00 | 56.13 | C |
| ATOM | 1647 | CB | LEU | A | 222 | −18.260 | −5.372 | 40.456 | 1.00 | 57.21 | C |
| ATOM | 1648 | CG | LEU | A | 222 | −19.207 | −4.773 | 41.494 | 1.00 | 54.83 | C |
| ATOM | 1649 | CD1 | LEU | A | 222 | −19.169 | −5.593 | 42.788 | 1.00 | 56.70 | C |
| ATOM | 1650 | CD2 | LEU | A | 222 | −18.897 | −3.305 | 41.733 | 1.00 | 67.28 | C |
| ATOM | 1651 | C | LEU | A | 222 | −17.586 | −5.833 | 38.095 | 1.00 | 56.26 | C |
| ATOM | 1652 | O | LEU | A | 222 | −17.585 | −7.082 | 38.145 | 1.00 | 52.71 | O |
| ATOM | 1653 | N | ALA | A | 223 | −16.817 | −5.098 | 37.275 | 1.00 | 55.71 | N |
| ATOM | 1654 | CA | ALA | A | 223 | −15.825 | −5.688 | 36.381 | 1.00 | 56.86 | C |
| ATOM | 1655 | CB | ALA | A | 223 | −16.442 | −6.126 | 35.070 | 1.00 | 57.95 | C |
| ATOM | 1656 | C | ALA | A | 223 | −14.680 | −4.706 | 36.134 | 1.00 | 58.20 | C |
| ATOM | 1657 | O | ALA | A | 223 | −14.913 | −3.530 | 35.779 | 1.00 | 57.95 | O |

TABLE 10-continued

Atomic coordinates for COM1 complex of the modified
TXNIP protein represented by SEQ ID NO: 6 and the modified protein represented by SEQ ID NO: 3

| ATOM | 1658 | N | ASN | A | 224 | −13.473 | −5.229 | 36.327 | 1.00 | 59.16 | N |
|---|---|---|---|---|---|---|---|---|---|---|---|
| ATOM | 1659 | CA | ASN | A | 224 | −12.240 | −4.438 | 36.475 | 1.00 | 57.55 | C |
| ATOM | 1660 | CB | ASN | A | 224 | −11.867 | −3.745 | 35.152 | 1.00 | 56.17 | C |
| ATOM | 1661 | CG | ASN | A | 224 | −11.163 | −4.690 | 34.182 | 1.00 | 68.62 | C |
| ATOM | 1662 | OD1 | ASN | A | 224 | −10.472 | −4.249 | 33.242 | 1.00 | 67.36 | O |
| ATOM | 1663 | ND2 | ASN | A | 224 | −11.312 | −6.004 | 34.423 | 1.00 | 64.61 | N |
| ATOM | 1664 | C | ASN | A | 224 | −12.278 | −3.449 | 37.645 | 1.00 | 54.05 | C |
| ATOM | 1665 | O | ASN | A | 224 | −12.690 | −3.787 | 38.772 | 1.00 | 53.18 | O |
| ATOM | 1666 | N | GLY | A | 225 | −11.859 | −2.223 | 37.365 | 1.00 | 54.25 | N |
| ATOM | 1667 | CA | GLY | A | 225 | −11.072 | −1.185 | 38.307 | 1.00 | 55.09 | C |
| ATOM | 1668 | C | GLY | A | 225 | −13.149 | −0.399 | 38.294 | 1.00 | 58.27 | C |
| ATOM | 1669 | O | GLY | A | 225 | −13.205 | 0.725 | 38.791 | 1.00 | 60.25 | O |
| ATOM | 1670 | N | GLN | A | 226 | −14.178 | −0.998 | 37.585 | 1.00 | 59.36 | N |
| ATOM | 1671 | CA | GLN | A | 226 | −15.404 | 0.273 | 37.334 | 1.00 | 60.75 | C |
| ATOM | 1672 | CB | GLN | A | 226 | −15.409 | 0.121 | 35.372 | 1.00 | 58.01 | C |
| ATOM | 1673 | CG | GLN | A | 226 | −14.197 | 0.959 | 35.372 | 1.00 | 66.38 | C |
| ATOM | 1674 | CD | GLN | A | 226 | −14.221 | 2.421 | 35.841 | 1.00 | 78.13 | C |
| ATOM | 1675 | OE1 | GLN | A | 226 | −14.285 | 2.708 | 37.047 | 1.00 | 77.44 | O |
| ATOM | 1676 | NE2 | GLN | A | 226 | −14.137 | 3.355 | 34.883 | 1.00 | 77.38 | N |
| ATOM | 1677 | C | GLN | A | 226 | −16.730 | 0.965 | 37.657 | 1.00 | 50.37 | C |
| ATOM | 1678 | O | GLN | A | 226 | −16.831 | −2.184 | 37.867 | 1.00 | 58.82 | O |
| ATOM | 1679 | N | THR | A | 227 | −17.741 | −0.115 | 37.740 | 1.00 | 62.71 | N |
| ATOM | 1680 | CA | THR | A | 227 | −19.117 | −0.505 | 37.579 | 1.00 | 63.58 | C |
| ATOM | 1681 | CB | THR | A | 227 | −20.012 | 0.274 | 38.551 | 1.00 | 64.44 | C |
| ATOM | 1682 | OG1 | THR | A | 227 | −19.653 | −0.071 | 39.900 | 1.00 | 65.66 | O |
| ATOM | 1683 | CG2 | THR | A | 227 | −21.497 | −0.036 | 38.304 | 1.00 | 61.90 | C |
| ATOM | 1684 | C | THR | A | 227 | −19.443 | −0.182 | 36.119 | 1.00 | 61.90 | C |
| ATOM | 1685 | O | THR | A | 227 | −19.384 | 0.983 | 35.704 | 1.00 | 84.46 | O |
| ATOM | 1686 | N | LYS | A | 228 | −19.702 | −1.220 | 35.329 | 1.00 | 57.90 | N |
| ATOM | 1687 | CA | LYS | A | 228 | −20.197 | −1.029 | 33.941 | 1.00 | 57.35 | C |
| ATOM | 1688 | CB | LYS | A | 228 | −19.284 | −1.718 | 32.905 | 1.00 | 58.00 | C |
| ATOM | 1689 | CG | LYS | A | 228 | −17.995 | −0.926 | 32.550 | 1.00 | 62.03 | C |
| ATOM | 1690 | CD | LYS | A | 228 | −17.305 | −1.406 | 31.280 | 1.00 | 57.11 | C |
| ATOM | 1691 | CE | LYS | A | 228 | −16.527 | −2.706 | 31.462 | 1.00 | 57.06 | C |
| ATOM | 1692 | NZ | LYS | A | 228 | −15.752 | −3.101 | 30.233 | 1.00 | 58.21 | N |
| ATOM | 1693 | C | LYS | A | 228 | −21.650 | −1.517 | 33.804 | 1.00 | 53.24 | C |
| ATOM | 1694 | O | LYS | A | 228 | −22.198 | −2.129 | 34.747 | 1.00 | 52.17 | O |
| ATOM | 1695 | N | VAL | A | 229 | −22.244 | −1.271 | 32.531 | 1.00 | 55.15 | N |
| ATOM | 1696 | CA | VAL | A | 229 | −23.638 | −1.057 | 32.533 | 1.00 | 52.12 | C |
| ATOM | 1697 | CB | VAL | A | 229 | −24.657 | −0.447 | 31.773 | 1.00 | 56.62 | C |
| ATOM | 1698 | CG1 | VAL | A | 229 | −24.205 | 0.804 | 32.159 | 1.00 | 55.71 | C |
| ATOM | 1699 | CG2 | VAL | A | 229 | −26.114 | −0.836 | 30.993 | 1.00 | 48.84 | C |
| ATOM | 1700 | C | VAL | A | 229 | −23.792 | −2.374 | 30.932 | 1.00 | 50.09 | C |
| ATOM | 1701 | O | VAL | A | 229 | −23.416 | −1.860 | 29.932 | 1.00 | 48.60 | O |
| ATOM | 1702 | N | LEU | A | 230 | −24.321 | −3.592 | 31.046 | 1.00 | 45.32 | N |
| ATOM | 1703 | CA | LEU | A | 230 | −24.666 | −4.318 | 29.826 | 1.00 | 46.51 | C |
| ATOM | 1704 | CB | LEU | A | 230 | −24.302 | −5.788 | 30.038 | 1.00 | 46.36 | C |
| ATOM | 1705 | CG | LEU | A | 230 | −24.359 | −5.900 | 29.001 | 1.00 | 52.20 | C |
| ATOM | 1706 | CD1 | LEU | A | 230 | −23.736 | −6.482 | 27.682 | 1.00 | 53.05 | C |
| ATOM | 1707 | CD2 | LEU | A | 230 | −23.532 | −8.116 | 29.552 | 1.00 | 57.32 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 1708 | C | LEU | A | 230 | -26.190 | 29.651 | -4.161 | 1.00 | 43.65 | C |
| ATOM | 1709 | O | LEU | A | 230 | -26.936 | 30.587 | 4.398 | 1.00 | 41.16 | O |
| ATOM | 1710 | N | THR | A | 231 | -26.638 | 28.478 | -3.746 | 1.00 | 45.55 | N |
| ATOM | 1711 | CA | THR | A | 231 | -28.069 | 28.107 | -3.796 | 1.00 | 42.80 | C |
| ATOM | 1712 | CB | THR | A | 231 | -28.480 | 27.298 | -2.555 | 1.00 | 46.87 | C |
| ATOM | 1713 | OG1 | THR | A | 231 | -28.016 | 27.975 | -1.371 | 1.00 | 50.03 | O |
| ATOM | 1714 | OG2 | THR | A | 231 | -30.001 | 27.136 | -2.487 | 1.00 | 39.89 | O |
| ATOM | 1715 | C | THR | A | 231 | -28.415 | 27.355 | -5.068 | 1.00 | 41.35 | C |
| ATOM | 1716 | O | THR | A | 231 | -27.893 | 26.273 | -5.356 | 1.00 | 42.16 | O |
| ATOM | 1717 | N | GLN | A | 232 | -29.290 | 27.951 | -5.857 | 1.00 | 40.57 | N |
| ATOM | 1718 | CA | GLN | A | 232 | -29.722 | 27.354 | -7.106 | 1.00 | 40.70 | C |
| ATOM | 1719 | CB | GLN | A | 232 | -29.565 | 28.370 | -8.217 | 1.00 | 42.29 | C |
| ATOM | 1720 | CG | GLN | A | 232 | -30.007 | 27.874 | -9.567 | 1.00 | 49.94 | C |
| ATOM | 1721 | CD | GLN | A | 232 | -29.911 | 28.924 | -10.676 | 1.00 | 55.50 | C |
| ATOM | 1722 | OE1 | GLN | A | 232 | -29.658 | 30.095 | -10.424 | 1.00 | 55.41 | O |
| ATOM | 1723 | NE2 | GLN | A | 232 | -30.127 | 28.490 | -11.920 | 1.00 | 62.04 | N |
| ATOM | 1724 | C | GLN | A | 232 | -31.212 | 25.949 | -7.005 | 1.00 | 40.92 | C |
| ATOM | 1725 | O | GLN | A | 232 | -32.020 | 27.698 | -6.489 | 1.00 | 42.29 | O |
| ATOM | 1727 | N | LYS | A | 233 | -31.553 | 25.789 | -7.533 | 1.00 | 38.31 | N |
| ATOM | 1728 | CA | LYS | A | 233 | -32.939 | 25.295 | -7.591 | 1.00 | 37.89 | C |
| ATOM | 1729 | CB | LYS | A | 233 | -32.944 | 23.781 | -7.383 | 1.00 | 35.83 | C |
| ATOM | 1730 | CG | LYS | A | 233 | -34.319 | 23.130 | -7.294 | 1.00 | 36.47 | C |
| ATOM | 1731 | CD | LYS | A | 233 | -34.116 | 21.640 | -7.447 | 1.00 | 44.08 | C |
| ATOM | 1732 | CE | LYS | A | 233 | -35.417 | 26.920 | -7.549 | 1.00 | 48.94 | C |
| ATOM | 1733 | NZ | LYS | A | 233 | -35.168 | 19.461 | -7.712 | 1.00 | 38.90 | N |
| ATOM | 1734 | C | LYS | A | 233 | -33.489 | 25.658 | -8.969 | 1.00 | 34.81 | C |
| ATOM | 1735 | O | LYS | A | 233 | -32.914 | 25.319 | -10.004 | 1.00 | 30.50 | O |
| ATOM | 1736 | N | LEU | A | 234 | -34.579 | 26.399 | -8.974 | 1.00 | 34.45 | N |
| ATOM | 1737 | CA | LEU | A | 234 | -35.238 | 26.763 | -10.206 | 1.00 | 35.01 | C |
| ATOM | 1738 | CB | LEU | A | 234 | -35.704 | 28.216 | -10.138 | 1.00 | 32.75 | C |
| ATOM | 1739 | CG | LEU | A | 234 | -34.620 | 29.243 | -9.772 | 1.00 | 33.13 | C |
| ATOM | 1740 | CD1 | LEU | A | 234 | -35.128 | 30.654 | -9.903 | 1.00 | 33.00 | C |
| ATOM | 1741 | CD2 | LEU | A | 234 | -33.440 | 29.055 | -10.706 | 1.00 | 41.19 | C |
| ATOM | 1742 | C | LEU | A | 234 | -36.390 | 25.793 | -10.435 | 1.00 | 38.17 | C |
| ATOM | 1743 | O | LEU | A | 234 | -36.191 | 24.575 | -10.404 | 1.00 | 34.11 | O |
| ATOM | 1744 | N | SER | A | 235 | -37.586 | 26.310 | -10.692 | 1.00 | 32.50 | N |
| ATOM | 1745 | CA | SER | A | 235 | -38.653 | 25.416 | -11.079 | 1.00 | 39.39 | C |
| ATOM | 1746 | CB | SER | A | 235 | 39.813 | 26.223 | 11.677 | 1.00 | 39.31 | C |
| ATOM | 1747 | OG | SER | A | 235 | -40.096 | 27.330 | -10.843 | 1.00 | 48.89 | O |
| ATOM | 1748 | C | SER | A | 235 | -39.052 | 24.567 | -9.859 | 1.00 | 33.95 | C |
| ATOM | 1749 | O | SER | A | 235 | -38.881 | 24.994 | -8.707 | 1.00 | 32.62 | O |
| ATOM | 1750 | N | SER | A | 236 | -39.507 | 23.350 | -10.118 | 1.00 | 34.4 | N |
| ATOM | 1751 | CA | SER | A | 236 | -39.884 | 22.444 | -9.044 | 1.00 | 33.55 | C |
| ATOM | 1752 | CB | SER | A | 236 | -38.739 | 21.490 | -8.707 | 1.00 | 28.26 | C |
| ATOM | 1753 | OG | SER | A | 236 | -38.378 | 20.694 | -9.818 | 1.00 | 35.56 | O |
| ATOM | 1754 | C | SER | A | 236 | -41.090 | 21.630 | -9.421 | 1.00 | 36.80 | C |
| ATOM | 1755 | O | SER | A | 236 | -41.342 | 21.425 | -10.607 | 1.00 | 33.40 | O |
| ATOM | 1756 | N | VAL | A | 237 | -41.821 | 21.156 | -8.407 | 1.00 | 38.48 | N |
| ATOM | 1757 | CA | VAL | A | 237 | -42.893 | 20.171 | -8.615 | 1.00 | 40.14 | C |
| ATOM | 1757 | CB | VAL | A | 237 | -44.340 | 20.772 | -8.561 | 1.00 | 40.79 | C |

TABLE 10-continued

Atomic coordinates for COM1 complex of the modified
TXNIP protein represented by SEQ ID NO: 6 and the modified protein represented by SEQ ID NO: 3

| ATOM | 1758 | CG1 | VAL | A | 237 | -44.674 | -9.808 | 21.538 | 1.00 | 46.97 | C |
|---|---|---|---|---|---|---|---|---|---|---|---|
| ATOM | 1759 | CG2 | VAL | A | 237 | -44.557 | -7.385 | 21.651 | 1.00 | 37.25 | C |
| ATOM | 1760 | C | VAL | A | 237 | -42.784 | -7.631 | 19.005 | 1.00 | 41.55 | C |
| ATOM | 1761 | O | VAL | A | 237 | -42.298 | -6.514 | 19.153 | 1.00 | 36.36 | O |
| ATOM | 1762 | N | ARG | A | 238 | -43.213 | -8.082 | 17.832 | 1.00 | 42.99 | N |
| ATOM | 1763 | CA | ARG | A | 238 | -43.387 | -7.227 | 16.671 | 1.00 | 42.49 | C |
| ATOM | 1764 | CB | ARG | A | 238 | -42.679 | -7.888 | 15.505 | 1.00 | 41.92 | C |
| ATOM | 1765 | CG | ARG | A | 238 | -42.240 | -0.951 | 14.470 | 1.00 | 45.36 | C |
| ATOM | 1766 | CD | ARG | A | 238 | -41.665 | -7.705 | 13.309 | 1.00 | 45.73 | C |
| ATOM | 1767 | NE | ARG | A | 238 | -41.936 | -6.987 | 12.055 | 1.00 | 44.15 | N |
| ATOM | 1768 | CZ | ARG | A | 238 | -41.008 | -5.371 | 11.324 | 1.00 | 44.20 | C |
| ATOM | 1769 | NH1 | ARG | A | 238 | -41.352 | -5.754 | 10.197 | 1.00 | 38.23 | N |
| ATOM | 1770 | NH2 | ARG | A | 238 | -39.731 | -6.386 | 11.706 | 1.00 | 52.42 | N |
| ATOM | 1771 | C | ARG | A | 238 | -44.890 | -7.102 | 16.361 | 1.00 | 43.98 | C |
| ATOM | 1772 | O | ARG | A | 238 | -45.653 | -8.071 | 16.505 | 1.00 | 42.89 | O |
| ATOM | 1773 | N | GLY | A | 239 | -45.329 | -5.920 | 15.947 | 1.00 | 41.30 | N |
| ATOM | 1774 | CA | GLY | A | 239 | -46.728 | -5.768 | 15.535 | 1.00 | 38.77 | C |
| ATOM | 1775 | C | GLY | A | 239 | -46.833 | -5.736 | 14.023 | 1.00 | 38.13 | C |
| ATOM | 1776 | O | GLY | A | 239 | -45.800 | -5.705 | 13.320 | 1.00 | 36.20 | O |
| ATOM | 1777 | N | ASN | A | 240 | -48.062 | -5.736 | 13.498 | 1.00 | 37.43 | N |
| ATOM | 1778 | CA | ASN | A | 240 | -48.247 | -5.599 | 12.044 | 1.00 | 40.33 | C |
| ATOM | 1779 | CB | ASN | A | 240 | -49.718 | -5.710 | 11.665 | 1.00 | 42.01 | C |
| ATOM | 1780 | CG | ASN | A | 240 | -50.272 | -7.042 | 11.981 | 1.00 | 51.93 | C |
| ATOM | 1781 | OD1 | ASN | A | 240 | -49.881 | -8.049 | 11.383 | 1.00 | 45.29 | O |
| ATOM | 1782 | ND2 | ASN | A | 240 | -51.165 | -7.081 | 12.957 | 1.00 | 58.32 | N |
| ATOM | 1783 | C | ASN | A | 240 | -47.780 | -4.225 | 11.643 | 1.00 | 38.95 | C |
| ATOM | 1784 | O | ASN | A | 240 | -47.933 | -3.283 | 12.423 | 1.00 | 42.67 | O |
| ATOM | 1785 | N | HIS | A | 241 | -47.216 | -4.105 | 10.449 | 1.00 | 35.19 | N |
| ATOM | 1786 | CA | HIS | A | 241 | 46.833 | 2.799 | 9.964 | 1.00 | 37.82 | C |
| ATOM | 1787 | CB | HIS | A | 241 | -46.125 | -2.909 | 8.624 | 1.00 | 39.35 | C |
| ATOM | 1788 | CG | HIS | A | 241 | -46.964 | -3.504 | 7.534 | 1.00 | 52.04 | C |
| ATOM | 1789 | ND1 | HIS | A | 241 | -47.126 | -4.867 | 7.373 | 1.00 | 64.85 | N |
| ATOM | 1790 | CE1 | HIS | A | 241 | -47.904 | -5.096 | 6.327 | 1.00 | 66.06 | C |
| ATOM | 1791 | NE2 | HIS | A | 241 | -48.252 | -3.933 | 5.803 | 1.00 | 62.74 | N |
| ATOM | 1792 | CD2 | HIS | A | 241 | -47.681 | -2.920 | 6.540 | 1.00 | 58.21 | C |
| ATOM | 1793 | C | HIS | A | 241 | -48.068 | -1.917 | 9.867 | 1.00 | 39.52 | C |
| ATOM | 1794 | O | HIS | A | 241 | -49.199 | -2.422 | 9.721 | 1.00 | 40.33 | O |
| ATOM | 1795 | N | ILE | A | 242 | -47.860 | -0.607 | 9.933 | 1.00 | 33.93 | N |
| ATOM | 1796 | CA | ILE | A | 242 | -48.958 | 0.337 | 9.910 | 1.00 | 28.85 | C |
| ATOM | 1797 | CB | ILE | A | 242 | -49.011 | 1.138 | 11.264 | 1.00 | 25.31 | C |
| ATOM | 1798 | CG1 | ILE | A | 242 | -49.225 | 0.190 | 12.462 | 1.00 | 29.88 | C |
| ATOM | 1799 | CD1 | ILE | A | 242 | -49.009 | 0.867 | 13.846 | 1.00 | 36.05 | C |
| ATOM | 1800 | CG2 | ILE | A | 242 | -50.101 | 2.139 | 11.230 | 1.00 | 29.36 | C |
| ATOM | 1801 | C | ILE | A | 242 | -48.728 | 1.261 | 8.717 | 1.00 | 32.52 | C |
| ATOM | 1802 | O | ILE | A | 242 | -47.753 | 2.010 | 8.722 | 1.00 | 28.43 | O |
| ATOM | 1803 | N | ILE | A | 243 | -49.604 | 1.213 | 7.695 | 1.00 | 31.49 | N |
| ATOM | 1804 | CA | ILE | A | 243 | -49.406 | 2.036 | 6.505 | 1.00 | 28.40 | C |
| ATOM | 1805 | CB | ILE | A | 243 | -50.242 | 1.517 | 5.258 | 1.00 | 28.60 | C |
| ATOM | 1806 | CG1 | ILE | A | 243 | -51.763 | 1.771 | 5.458 | 1.00 | 33.05 | C |
| ATOM | 1807 | CD1 | ILE | A | 243 | -52.660 | 1.415 | 4.238 | 1.00 | 32.32 | C |

TABLE 10-continued

Atomic coordinates for COM1 complex of the modified
TXNIP protein represented by SEQ NO: 6 and the modified protein represented by SEQ ID NO: 3

| | | | | | | | | | | |
|---|---|---|---|---|---|---|---|---|---|---|
| ATOM | 1808 | CG2 | ILE | A | 243 | −49.965 | 0.055 | 5.004 | 1.00 | 34.23 | C |
| ATOM | 1809 | C | ILE | A | 243 | −49.775 | 3.483 | 6.792 | 1.00 | 30.77 | C |
| ATOM | 1810 | O | ILE | A | 243 | −50.462 | 3.795 | 7.795 | 1.00 | 27.66 | O |
| ATOM | 1811 | N | SER | A | 244 | −49.341 | 4.363 | 5.891 | 1.00 | 28.68 | N |
| ATOM | 1812 | CA | SER | A | 244 | −49.630 | 5.780 | 5.963 | 1.00 | 31.99 | C |
| ATOM | 1813 | CB | SER | A | 244 | −49.112 | 6.497 | 4.704 | 1.00 | 26.52 | C |
| ATOM | 1814 | OG | SER | A | 244 | −49.306 | 7.889 | 4.845 | 1.00 | 37.69 | O |
| ATOM | 1815 | C | SER | A | 244 | −51.134 | 6.017 | 6.064 | 1.00 | 33.67 | C |
| ATOM | 1816 | O | SER | A | 244 | −51.928 | 5.429 | 5.298 | 1.00 | 30.41 | O |
| ATOM | 1817 | N | GLY | A | 245 | −51.537 | 6.853 | 7.013 | 1.00 | 30.05 | N |
| ATOM | 1818 | CA | GLY | A | 245 | −52.955 | 7.234 | 7.084 | 1.00 | 27.99 | C |
| ATOM | 1819 | C | GLY | A | 245 | −53.821 | 6.214 | 7.797 | 1.00 | 32.85 | C |
| ATOM | 1820 | O | GLY | A | 245 | −55.018 | 6.162 | 7.557 | 1.00 | 30.79 | O |
| ATOM | 1821 | N | THR | A | 246 | −53.229 | 5.429 | 8.710 | 1.00 | 33.33 | N |
| ATOM | 1822 | CA | THR | A | 246 | −53.982 | 4.465 | 9.535 | 1.00 | 28.36 | C |
| ATOM | 1823 | CB | THR | A | 246 | −53.912 | 3.024 | 8.999 | 1.00 | 32.63 | C |
| ATOM | 1824 | OG1 | THR | A | 246 | −52.544 | 2.557 | 8.991 | 1.00 | 28.73 | O |
| ATOM | 1825 | CG2 | THR | A | 246 | −54.488 | 2.925 | 7.564 | 1.00 | 28.25 | C |
| ATOM | 1826 | C | THR | A | 246 | −53.448 | 4.490 | 10.951 | 1.00 | 29.99 | C |
| ATOM | 1827 | O | THR | A | 246 | −52.366 | 5.053 | 11.214 | 1.00 | 30.29 | O |
| ATOM | 1828 | N | CYS | A | 247 | −54.232 | 3.927 | 11.869 | 1.00 | 29.87 | N |
| ATOM | 1829 | CA | CYS | A | 247 | −53.822 | 3.695 | 13.241 | 1.00 | 29.70 | C |
| ATOM | 1830 | CB | CYS | A | 247 | −54.740 | 4.437 | 14.172 | 1.00 | 30.31 | C |
| ATOM | 1831 | SG | CYS | A | 247 | −54.713 | 6.227 | 13.962 | 1.00 | 36.59 | S |
| ATOM | 1832 | C | CYS | A | 247 | −54.023 | 2.210 | 13.497 | 1.00 | 32.77 | C |
| ATOM | 1833 | O | CYS | A | 247 | −54.795 | 1.547 | 12.787 | 1.00 | 34.00 | O |
| ATOM | 1834 | N | ALA | A | 248 | −53.374 | 1.712 | 14.541 | 1.00 | 32.37 | N |
| ATOM | 1835 | CA | ALA | A | 248 | −53.646 | 0.370 | 15.035 | 1.00 | 31.36 | C |
| ATOM | 1836 | CB | ALA | A | 248 | −52.742 | −0.657 | 14.362 | 1.00 | 34.69 | C |
| ATOM | 1837 | C | ALA | A | 248 | −53.504 | 0.304 | 16.539 | 1.00 | 34.95 | C |
| ATOM | 1838 | O | ALA | A | 248 | −52.898 | 1.176 | 17.147 | 1.00 | 33.98 | O |
| ATOM | 1839 | N | SER | A | 249 | −54.032 | −0.775 | 17.110 | 1.00 | 33.68 | N |
| ATOM | 1840 | CA | SER | A | 249 | −54.201 | −0.944 | 18.548 | 1.00 | 33.56 | C |
| ATOM | 1841 | CB | SER | A | 249 | −55.691 | −0.921 | 18.875 | 1.00 | 32.70 | C |
| ATOM | 1842 | OG | SER | A | 249 | −56.134 | 0.421 | 18.828 | 1.00 | 37.50 | O |
| ATOM | 1843 | C | SER | A | 249 | −53.657 | −2.277 | 18.951 | 1.00 | 33.34 | C |
| ATOM | 1844 | O | SER | A | 249 | −53.645 | −3.243 | 18.149 | 1.00 | 29.97 | O |
| ATOM | 1845 | N | TRP | A | 250 | −53.138 | −2.315 | 20.175 | 1.00 | 32.96 | N |
| ATOM | 1846 | CA | TRP | A | 250 | −52.848 | −3.571 | 20.829 | 1.00 | 32.52 | C |
| ATOM | 1847 | CB | TRP | A | 250 | −51.414 | −3.631 | 21.344 | 1.00 | 33.65 | C |
| ATOM | 1848 | CG | TRP | A | 250 | −50.323 | −3.782 | 20.297 | 1.00 | 31.27 | C |
| ATOM | 1849 | CD1 | TRP | A | 250 | −50.460 | −3.995 | 18.930 | 1.00 | 33.69 | C |
| ATOM | 1850 | NE1 | TRP | A | 250 | −49.217 | −4.097 | 18.350 | 1.00 | 34.35 | N |
| ATOM | 1851 | CE2 | TRP | A | 250 | −48.263 | −3.961 | 19.336 | 1.00 | 37.33 | C |
| ATOM | 1852 | CD2 | TRP | A | 250 | −48.935 | −3.772 | 20.565 | 1.00 | 32.66 | C |
| ATOM | 1853 | CE3 | TRP | A | 250 | −48.170 | −3.505 | 21.742 | 1.00 | 32.72 | C |
| ATOM | 1854 | CZ3 | TRP | A | 250 | −46.783 | −3.617 | 21.653 | 1.00 | 26.81 | C |
| ATOM | 1855 | CH2 | TRP | A | 250 | −46.138 | −3.819 | 20.395 | 1.00 | 25.30 | C |
| ATOM | 1856 | CZ2 | TRP | A | 250 | −46.858 | −4.001 | 19.249 | 1.00 | 24.26 | C |
| ATOM | 1857 | C | TRP | A | 250 | −53.785 | −3.575 | 22.007 | 1.00 | 34.51 | C |

TABLE 10-continued

Atomic coordinates for COM1 complex of the modified
TXNIP protein represented by SEQ ID NO: 6 and the modified protein represented by SE TABLE 10-continued Atomic coordinates for COM1 complex of the modified
TXNIP protein represented by SEQ ID NO: 6 and the modified protein represented by SEQ ID NO: 3

| | | | | | | | | | | | |
|---|---|---|---|---|---|---|---|---|---|---|---|
| ATOM | 1908 | N | VAL | A | 257 | -12.274 | -42.353 | 31.142 | 1.00 | 41.79 | N |
| ATOM | 1909 | CA | VAL | A | 257 | -11.897 | -41.219 | 31.946 | 1.00 | 43.71 | C |
| ATOM | 1910 | CB | VAL | A | 257 | -11.312 | -41.608 | 33.323 | 1.00 | 44.71 | C |
| ATOM | 1911 | CG1 | VAL | A | 257 | -10.893 | -40.345 | 34.044 | 1.00 | 42.42 | C |
| ATOM | 1912 | CG2 | VAL | A | 257 | -10.124 | -42.533 | 33.144 | 1.00 | 41.86 | C |
| ATOM | 1913 | C | VAL | A | 257 | -13.109 | -40.342 | 32.153 | 1.00 | 47.64 | C |
| ATOM | 1914 | O | VAL | A | 257 | -14.003 | -40.655 | 32.934 | 1.00 | 49.91 | O |
| ATOM | 1915 | N | GLN | A | 258 | -13.141 | -39.221 | 31.450 | 1.00 | 51.14 | N |
| ATOM | 1916 | CA | GLN | A | 258 | -14.281 | -38.320 | 31.543 | 1.00 | 52.21 | C |
| ATOM | 1917 | CB | GLN | A | 258 | -14.367 | -37.484 | 30.284 | 1.00 | 52.41 | C |
| ATOM | 1918 | CG | GLN | A | 258 | -14.663 | -36.340 | 29.054 | 1.00 | 48.71 | C |
| ATOM | 1919 | CD | GLN | A | 258 | -14.696 | -37.534 | 27.790 | 1.00 | 47.38 | C |
| ATOM | 1920 | OE1 | GLN | A | 258 | -13.910 | -36.603 | 27.607 | 1.00 | 56.66 | O |
| ATOM | 1921 | NE2 | GLN | A | 258 | -15.617 | -37.874 | 26.908 | 1.00 | 56.98 | N |
| ATOM | 1922 | C | GLN | A | 258 | -14.227 | -37.444 | 32.794 | 1.00 | 56.46 | C |
| ATOM | 1923 | O | GLN | A | 258 | -13.142 | -37.115 | 33.314 | 1.00 | 54.71 | O |
| ATOM | 1924 | N | LYS | A | 259 | -15.425 | -37.101 | 33.257 | 1.00 | 60.21 | N |
| ATOM | 1925 | CA | LYS | A | 259 | -15.642 | -36.186 | 34.381 | 1.00 | 62.09 | C |
| ATOM | 1926 | CB | LYS | A | 259 | -14.227 | -36.379 | 34.919 | 1.00 | 61.97 | C |
| ATOM | 1927 | CG | LYS | A | 259 | -17.057 | -37.800 | 35.408 | 1.00 | 66.19 | C |
| ATOM | 1928 | CD | LYS | A | 259 | -17.359 | -38.114 | 35.355 | 1.00 | 71.63 | C |
| ATOM | 1929 | CE | LYS | A | 259 | -18.854 | -37.194 | 35.262 | 1.00 | 77.87 | C |
| ATOM | 1930 | NZ | LYS | A | 259 | -19.674 | -37.390 | 36.056 | 1.00 | 75.68 | N |
| ATOM | 1931 | C | LYS | A | 259 | -21.141 | -34.771 | 33.860 | 1.00 | 64.32 | C |
| ATOM | 1932 | O | LYS | A | 259 | -15.483 | -34.369 | 32.929 | 1.00 | 64.07 | O |
| ATOM | 1933 | N | ILE | A | 260 | -16.181 | -34.004 | 34.449 | 1.00 | 68.17 | N |
| ATOM | 1934 | CA | ILE | A | 260 | -14.571 | -32.637 | 33.957 | 1.00 | 69.45 | C |
| ATOM | 1935 | CB | ILE | A | 260 | -14.334 | -32.197 | 34.125 | 1.00 | 71.02 | C |
| ATOM | 1936 | CG1 | ILE | A | 260 | -12.848 | -31.517 | 32.842 | 1.00 | 70.85 | C |
| ATOM | 1937 | CD1 | ILE | A | 260 | -12.361 | -31.782 | 32.546 | 1.00 | 62.10 | C |
| ATOM | 1938 | CG2 | ILE | A | 260 | -10.928 | -31.332 | 35.400 | 1.00 | 69.34 | C |
| ATOM | 1939 | C | ILE | A | 260 | -12.641 | -31.624 | 34.562 | 1.00 | 68.85 | C |
| ATOM | 1940 | O | ILE | A | 260 | -15.311 | -31.846 | 34.563 | 1.00 | 67.35 | O |
| ATOM | 1941 | N | ASN | A | 268 | -10.948 | -20.557 | 40.812 | 1.00 | 58.90 | N |
| ATOM | 1942 | CA | ASN | A | 268 | -9.562 | -20.145 | 40.558 | 1.00 | 61.80 | C |
| ATOM | 1943 | CB | ASN | A | 268 | -9.508 | -18.871 | 39.716 | 1.00 | 59.44 | C |
| ATOM | 1944 | CG | ASN | A | 268 | -9.183 | -17.620 | 40.553 | 1.00 | 70.38 | C |
| ATOM | 1945 | OD1 | ASN | A | 268 | -9.094 | -16.507 | 40.011 | 1.00 | 67.15 | O |
| ATOM | 1946 | ND2 | ASN | A | 268 | -8.994 | -17.803 | 41.874 | 1.00 | 62.41 | N |
| ATOM | 1947 | C | ASN | A | 268 | -8.596 | -21.194 | 39.956 | 1.00 | 61.49 | C |
| ATOM | 1948 | O | ASN | A | 268 | 7.442 | 20.860 | 39.617 | 1.00 | 60.36 | O |
| ATOM | 1949 | N | ILE | A | 269 | -9.029 | -22.444 | 39.857 | 1.00 | 62.11 | N |
| ATOM | 1950 | CA | ILE | A | 269 | -8.041 | -23.451 | 39.454 | 1.00 | 63.15 | C |
| ATOM | 1951 | CB | ILE | A | 269 | -8.589 | -24.541 | 38.495 | 1.00 | 63.13 | C |
| ATOM | 1952 | CG1 | ILE | A | 269 | -9.463 | -25.553 | 39.225 | 1.00 | 63.92 | C |
| ATOM | 1953 | OD1 | ILE | A | 269 | -9.144 | -26.985 | 38.803 | 1.00 | 51.18 | O |
| ATOM | 1954 | CG2 | ILE | A | 269 | -9.326 | -23.931 | 37.297 | 1.00 | 58.09 | C |
| ATOM | 1955 | C | ILE | A | 269 | -7.360 | -24.051 | 40.685 | 1.00 | 61.43 | C |
| ATOM | 1956 | O | ILE | A | 269 | -8.039 | -24.470 | 41.635 | 1.00 | 65.16 | O |
| ATOM | 1957 | N | LEU | A | 270 | -6.026 | -24.060 | 40.689 | 1.00 | 58.33 | N |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 1958 | CA | SER | A | 270 | -24.774 | 41.730 | -5.246 | 1.00 | 53.63 | C |
| ATOM | 1959 | CB | SER | A | 270 | -24.417 | 41.594 | -3.761 | 1.00 | 53.39 | C |
| ATOM | 1960 | CG | SER | A | 270 | -22.966 | 41.874 | -3.330 | 1.00 | 54.46 | C |
| ATOM | 1961 | CD1 | SER | A | 270 | -22.525 | 40.980 | -2.264 | 1.00 | 49.15 | C |
| ATOM | 1962 | CD2 | SER | A | 270 | -22.795 | 43.299 | -2.838 | 1.00 | 47.31 | C |
| ATOM | 1963 | C | SER | A | 270 | -26.287 | 41.585 | -5.410 | 1.00 | 53.70 | C |
| ATOM | 1964 | O | SER | A | 270 | -27.013 | 42.455 | -5.997 | 1.00 | 48.46 | O |
| ATOM | 1965 | N | SER | A | 270 | -26.766 | 40.451 | -4.893 | 1.00 | 50.32 | N |
| ATOM | 1966 | CA | SER | A | 271 | -28.197 | 40.203 | -4.840 | 1.00 | 50.48 | C |
| ATOM | 1967 | CB | SER | A | 271 | -28.751 | 40.758 | -3.534 | 1.00 | 49.09 | C |
| ATOM | 1968 | CG | SER | A | 271 | -28.035 | 40.246 | -2.318 | 1.00 | 48.83 | C |
| ATOM | 1969 | CD | SER | A | 271 | -28.684 | 40.848 | -1.127 | 1.00 | 48.09 | C |
| ATOM | 1970 | NE | SER | A | 271 | -28.326 | 40.140 | 0.087 | 1.00 | 44.38 | N |
| ATOM | 1971 | CZ | SER | A | 271 | -27.211 | 40.336 | 0.774 | 1.00 | 52.70 | C |
| ATOM | 1972 | NH1 | SER | A | 271 | -26.304 | 41.218 | 0.353 | 1.00 | 53.10 | N |
| ATOM | 1973 | NH2 | SER | A | 271 | -27.003 | 39.033 | 1.885 | 1.00 | 48.80 | N |
| ATOM | 1974 | C | SER | A | 271 | -28.531 | 38.711 | -4.967 | 1.00 | 48.66 | C |
| ATOM | 1975 | O | SER | A | 271 | -27.709 | 37.849 | -4.645 | 1.00 | 47.72 | O |
| ATOM | 1976 | N | SER | A | 271 | -29.719 | 38.441 | -5.495 | 1.00 | 50.63 | N |
| ATOM | 1977 | CA | SER | A | 272 | -30.309 | 37.104 | -5.469 | 1.00 | 52.26 | C |
| ATOM | 1978 | CB | SER | A | 272 | -30.836 | 36.660 | -6.844 | 1.00 | 52.69 | C |
| ATOM | 1979 | CG1 | SER | A | 272 | -31.227 | 35.173 | -6.826 | 1.00 | 53.36 | C |
| ATOM | 1980 | CG2 | SER | A | 272 | -29.815 | 36.888 | -7.913 | 1.00 | 55.21 | C |
| ATOM | 1981 | C | SER | A | 272 | -31.486 | 37.152 | -4.513 | 1.00 | 52.93 | C |
| ATOM | 1982 | O | SER | A | 272 | -32.311 | 38.069 | -4.582 | 1.00 | 55.12 | O |
| ATOM | 1983 | N | SER | A | 273 | -31.564 | 36.208 | -3.599 | 1.00 | 52.32 | N |
| ATOM | 1984 | CA | SER | A | 273 | 32.748 | 36.122 | 2.776 | 1.00 | 50.63 | C |
| ATOM | 1985 | CB | SER | A | 273 | -32.460 | 36.404 | -1.308 | 1.00 | 54.10 | C |
| ATOM | 1986 | CG | SER | A | 273 | -31.343 | 35.603 | -0.694 | 1.00 | 56.12 | C |
| ATOM | 1987 | CD | SER | A | 273 | -30.933 | 36.151 | 0.676 | 1.00 | 63.29 | C |
| ATOM | 1988 | OE1 | SER | A | 273 | -30.872 | 35.325 | 1.619 | 1.00 | 69.24 | O |
| ATOM | 1989 | OE2 | SER | A | 273 | -30.684 | 37.390 | 0.801 | 1.00 | 57.27 | O |
| ATOM | 1990 | C | SER | A | 273 | -33.441 | 34.794 | -2.996 | 1.00 | 45.95 | C |
| ATOM | 1991 | O | SER | A | 273 | -32.797 | 33.741 | -3.126 | 1.00 | 41.02 | O |
| ATOM | 1992 | N | SER | A | 274 | -34.760 | 34.871 | -3.077 | 1.00 | 45.23 | N |
| ATOM | 1993 | CA | SER | A | 274 | -35.585 | 33.745 | -3.470 | 1.00 | 40.25 | C |
| ATOM | 1994 | CB | SER | A | 274 | -36.516 | 34.1863 | -4.574 | 1.00 | 41.42 | C |
| ATOM | 1995 | CG | SER | A | 274 | -35.814 | 34.635 | -5.822 | 1.00 | 36.03 | C |
| ATOM | 1996 | CD1 | SER | A | 274 | -35.542 | 33.735 | -5.860 | 1.00 | 40.54 | C |
| ATOM | 1997 | CE1 | SER | A | 274 | -34.873 | 34.170 | -8.036 | 1.00 | 38.96 | C |
| ATOM | 1998 | CZ | SER | A | 274 | -34.509 | 35.514 | -8.163 | 1.00 | 50.23 | C |
| ATOM | 1999 | OH | SER | A | 274 | -33.881 | 35.953 | -9.310 | 1.00 | 52.37 | O |
| ATOM | 2000 | CE2 | SER | A | 274 | -34.777 | 36.412 | -7.142 | 1.00 | 40.87 | C |
| ATOM | 2001 | CD2 | SER | A | 274 | -35.437 | 35.972 | -5.980 | 1.00 | 37.00 | C |
| ATOM | 2002 | C | SER | A | 274 | -36.437 | 33.216 | -2.336 | 1.00 | 39.63 | C |
| ATOM | 2003 | O | SER | A | 274 | -36.730 | 33.928 | -1.372 | 1.00 | 35.87 | O |
| ATOM | 2004 | N | SER | A | 275 | -36.835 | 31.951 | -2.476 | 1.00 | 36.38 | N |
| ATOM | 2005 | CA | SER | A | 275 | -37.712 | 31.308 | -1.536 | 1.00 | 34.72 | C |
| ATOM | 2006 | CB | SER | A | 275 | -36.896 | 30.613 | -0.456 | 1.00 | 37.54 | C |
| ATOM | 2007 | OG | SER | A | 275 | -36.638 | 31.499 | 0.625 | 1.00 | 37.95 | O |

TABLE 10-continued

Atomic coordinates for COM1 complex of the modified
TXNIP protein represented by SEQ ID NO: 6 and the modified protein represented by SEQ ID NO: 3

| ATOM | 2008 | C | SER | A | 275 | −38.491 | −2.308 | 30.283 | 1.00 | 30.66 | C |
|---|---|---|---|---|---|---|---|---|---|---|---|
| ATOM | 2009 | O | SER | A | 275 | −37.993 | −3.270 | 29.706 | 1.00 | 30.79 | O |
| ATOM | 2010 | N | SER | A | 276 | −39.737 | −1.900 | 30.112 | 1.00 | 33.10 | N |
| ATOM | 2011 | CA | SER | A | 276 | −40.512 | −2.209 | 28.960 | 1.00 | 31.63 | C |
| ATOM | 2012 | CB | SER | A | 276 | −41.993 | −2.125 | 29.343 | 1.00 | 27.98 | C |
| ATOM | 2013 | CG | SER | A | 276 | −42.988 | −2.540 | 28.262 | 1.00 | 31.93 | C |
| ATOM | 2014 | CD1 | LEU | A | 276 | −42.659 | −3.805 | 27.508 | 1.00 | 31.84 | C |
| ATOM | 2015 | CD2 | LEU | A | 276 | −44.375 | −2.664 | 28.910 | 1.00 | 30.44 | C |
| ATOM | 2016 | C | LEU | A | 276 | −40.259 | −1.146 | 27.913 | 1.00 | 32.75 | C |
| ATOM | 2017 | O | LEU | A | 276 | −40.592 | 0.020 | 28.110 | 1.00 | 28.76 | O |
| ATOM | 2018 | N | LEU | A | 277 | −39.746 | −1.529 | 26.749 | 1.00 | 27.18 | N |
| ATOM | 2019 | CA | LEU | A | 277 | −39.699 | −0.551 | 25.697 | 1.00 | 32.86 | C |
| ATOM | 2020 | CB | LEU | A | 277 | −38.392 | −0.689 | 24.909 | 1.00 | 33.33 | C |
| ATOM | 2021 | CG | LEU | A | 277 | −37.096 | −0.560 | 25.693 | 1.00 | 39.77 | C |
| ATOM | 2022 | CD1 | LEU | A | 277 | −35.931 | −0.613 | 24.740 | 1.00 | 44.75 | C |
| ATOM | 2023 | CD2 | LEU | A | 277 | −37.043 | 0.673 | 26.539 | 1.00 | 38.03 | C |
| ATOM | 2024 | C | LEU | A | 277 | −40.836 | −0.783 | 24.733 | 1.00 | 32.62 | C |
| ATOM | 2025 | O | LEU | A | 277 | −41.014 | −1.913 | 24.232 | 1.00 | 31.95 | O |
| ATOM | 2026 | N | ILE | A | 278 | −41.527 | 0.294 | 24.392 | 1.00 | 32.59 | N |
| ATOM | 2027 | CA | ILE | A | 278 | −42.595 | 0.263 | 23.383 | 1.00 | 33.09 | C |
| ATOM | 2028 | CB | ILE | A | 278 | −43.994 | 0.560 | 23.982 | 1.00 | 31.86 | C |
| ATOM | 2029 | CG1 | ILE | A | 278 | −44.336 | −0.490 | 25.039 | 1.00 | 36.21 | C |
| ATOM | 2030 | CD1 | ILE | A | 278 | −45.227 | 0.010 | 26.165 | 1.00 | 41.10 | C |
| ATOM | 2031 | CG2 | ILE | A | 278 | −45.086 | 0.481 | 22.883 | 1.00 | 32.86 | C |
| ATOM | 2032 | C | ILE | A | 278 | −42.247 | 1.309 | 22.358 | 1.00 | 34.26 | C |
| ATOM | 2033 | O | ILE | A | 278 | −42.166 | 2.486 | 22.700 | 1.00 | 34.88 | O |
| ATOM | 2034 | N | TYR | A | 279 | −42.002 | 0.890 | 21.126 | 1.00 | 31.22 | N |
| ATOM | 2035 | CA | TYR | A | 279 | −41.494 | 1.838 | 20.169 | 1.00 | 33.54 | C |
| ATOM | 2036 | CB | TYR | A | 279 | −39.946 | 1.848 | 20.177 | 1.00 | 33.14 | C |
| ATOM | 2037 | CG | TYR | A | 279 | −39.259 | 0.528 | 19.914 | 1.00 | 32.62 | C |
| ATOM | 2038 | CD1 | TYR | A | 279 | −39.164 | −0.459 | 20.905 | 1.00 | 36.25 | C |
| ATOM | 2039 | CE1 | TYR | A | 279 | −38.522 | −1.671 | 20.654 | 1.00 | 29.08 | C |
| ATOM | 2040 | CZ | TYR | A | 279 | −37.921 | −1.861 | 19.426 | 1.00 | 37.85 | C |
| ATOM | 2041 | OH | TYR | A | 279 | −37.266 | −3.025 | 19.120 | 1.00 | 38.32 | O |
| ATOM | 2042 | CE2 | TYR | A | 279 | −37.088 | −0.802 | 18.443 | 1.00 | 43.44 | C |
| ATOM | 2043 | CD2 | TYR | A | 279 | −38.655 | 0.295 | 18.705 | 1.00 | 33.76 | C |
| ATOM | 2044 | C | TYR | A | 279 | −42.011 | 1.584 | 18.789 | 1.00 | 32.72 | C |
| ATOM | 2045 | O | TYR | A | 279 | −42.583 | 0.521 | 18.507 | 1.00 | 27.72 | O |
| ATOM | 2046 | N | VAL | A | 280 | −41.770 | 2.557 | 17.923 | 1.00 | 32.35 | N |
| ATOM | 2047 | CA | VAL | A | 280 | −42.218 | 2.487 | 18.542 | 1.00 | 28.68 | C |
| ATOM | 2048 | CB | VAL | A | 280 | −43.331 | 3.528 | 16.208 | 1.00 | 27.03 | C |
| ATOM | 2049 | CG1 | VAL | A | 280 | −43.739 | 3.400 | 14.738 | 1.00 | 25.57 | C |
| ATOM | 2050 | CG2 | VAL | A | 280 | −44.583 | 3.331 | 17.071 | 1.00 | 31.19 | C |
| ATOM | 2051 | C | VAL | A | 280 | −41.015 | 2.725 | 15.682 | 1.00 | 28.06 | C |
| ATOM | 2052 | O | VAL | A | 280 | −40.354 | 3.757 | 15.770 | 1.00 | 30.94 | O |
| ATOM | 2053 | N | SER | A | 281 | −40.677 | 1.735 | 14.882 | 1.00 | 27.78 | N |
| ATOM | 2054 | CA | SER | A | 281 | −39.506 | 1.886 | 13.930 | 1.00 | 29.69 | C |
| ATOM | 2055 | CB | SER | A | 281 | −39.052 | 0.487 | 13.624 | 1.00 | 32.60 | C |
| ATOM | 2056 | OG | SER | A | 281 | −38.298 | 0.478 | 12.429 | 1.00 | 45.11 | O |
| ATOM | 2057 | C | SER | A | 281 | −40.111 | 2.658 | 12.693 | 1.00 | 32.31 | C |

TABLE 10-continued

Atomic coordinates for COM1 complex of the modified
TXNIP protein represented by SEQ ID NO: 6 and the modified protein represented by SEQ ID NO: 3

| ATOM | 2058 | O   | SER | A | 281 | -41.137 | 2.313  | 12.097 | 1.00 | 29.51  | O |
|------|------|-----|-----|---|-----|---------|--------|--------|------|--------|---|
| ATOM | 2059 | N   | VAL | A | 282 | -39.393 | 3.728  | 12.337 | 1.00 | 32.67  | N |
| ATOM | 2060 | CA  | VAL | A | 282 | -39.778 | 4.629  | 11.256 | 1.00 | 34.74  | C |
| ATOM | 2061 | CB  | VAL | A | 282 | -39.994 | 6.099  | 11.773 | 1.00 | 30.93  | C |
| ATOM | 2062 | CG1 | VAL | A | 282 | -40.424 | 7.002  | 10.625 | 1.00 | 35.02  | C |
| ATOM | 2063 | CG2 | VAL | A | 282 | -41.014 | 6.124  | 12.883 | 1.00 | 27.90  | C |
| ATOM | 2064 | C   | VAL | A | 282 | -38.637 | 4.625  | 10.246 | 1.00 | 36.36  | C |
| ATOM | 2065 | O   | VAL | A | 282 | -37.567 | 5.160  | 10.580 | 1.00 | 36.22  | O |
| ATOM | 2066 | N   | PRO | A | 283 | -38.820 | 3.956  | 9.073  | 1.00 | 36.37  | N |
| ATOM | 2067 | CA  | PRO | A | 283 | -37.757 | 3.840  | 8.063  | 1.00 | 40.51  | C |
| ATOM | 2068 | CB  | PRO | A | 283 | -38.441 | 3.128  | 6.882  | 1.00 | 38.03  | C |
| ATOM | 2069 | CG  | PRO | A | 283 | -39.527 | 2.355  | 7.514  | 1.00 | 41.22  | C |
| ATOM | 2070 | CG  | PRO | A | 283 | -40.038 | 3.245  | 8.626  | 1.00 | 34.96  | C |
| ATOM | 2071 | C   | PRO | A | 283 | -37.274 | 5.206  | 7.604  | 1.00 | 42.96  | C |
| ATOM | 2072 | O   | PRO | A | 283 | -38.102 | 6.088  | 7.341  | 1.00 | 39.419 | O |
| ATOM | 2073 | N   | GLY | A | 284 | -35.944 | 5.361  | 7.532  | 1.00 | 45.44  | N |
| ATOM | 2074 | CA  | GLY | A | 284 | -35.304 | 6.638  | 7.209  | 1.00 | 45.37  | C |
| ATOM | 2075 | C   | GLY | A | 284 | -35.218 | 7.635  | 8.350  | 1.00 | 47.47  | C |
| ATOM | 2076 | O   | GLY | A | 284 | -34.572 | 8.667  | 8.194  | 1.00 | 52.08  | O |
| ATOM | 2077 | N   | SER | A | 285 | -35.867 | 7.350  | 9.492  | 1.00 | 45.01  | N |
| ATOM | 2078 | CA  | SER | A | 285 | -35.822 | 0.225  | 10.665 | 1.00 | 42.70  | C |
| ATOM | 2079 | CB  | SER | A | 285 | -37.138 | 8.984  | 10.876 | 1.00 | 43.57  | C |
| ATOM | 2080 | OG  | SER | A | 285 | -37.557 | 9.707  | 9.713  | 1.00 | 59.75  | O |
| ATOM | 2081 | C   | SER | A | 285 | -35.470 | 7.451  | 11.951 | 1.00 | 40.44  | C |
| ATOM | 2082 | O   | SER | A | 285 | -35.257 | 6.241  | 11.925 | 1.00 | 40.37  | O |
| ATOM | 2083 | N   | LYS | A | 286 | -35.389 | 8.169  | 13.061 | 1.00 | 38.32  | N |
| ATOM | 2084 | CA  | LYS | A | 286 | -35.139 | 7.547  | 14.330 | 1.00 | 38.86  | C |
| ATOM | 2085 | CB  | LYS | A | 286 | -34.464 | 8.552  | 15.267 | 1.00 | 42.97  | C |
| ATOM | 2086 | CG  | LYS | A | 286 | -33.013 | 8.833  | 14.879 | 1.00 | 46.65  | C |
| ATOM | 2087 | CD  | LYS | A | 286 | -32.198 | 9.140  | 16.114 | 1.00 | 53.59  | C |
| ATOM | 2088 | CE  | LYS | A | 286 | -31.915 | 10.611 | 16.259 | 1.00 | 58.02  | C |
| ATOM | 2089 | NZ  | LYS | A | 286 | 33.153  | 11.424 | 16.331 | 1.00 | 70.69  | N |
| ATOM | 2090 | C   | LYS | A | 286 | -36.435 | 7.007  | 14.924 | 1.00 | 38.71  | C |
| ATOM | 2091 | O   | LYS | A | 286 | -37.521 | 7.518  | 14.599 | 1.00 | 38.91  | O |
| ATOM | 2092 | N   | LYS | A | 287 | -36.332 | 5.977  | 15.780 | 1.00 | 36.60  | N |
| ATOM | 2093 | CA  | LYS | A | 287 | -37.507 | 5.361  | 16.426 | 1.00 | 34.35  | C |
| ATOM | 2094 | CB  | LYS | A | 287 | -37.092 | 4.169  | 17.301 | 1.00 | 29.63  | C |
| ATOM | 2095 | CG  | LYS | A | 287 | -36.365 | 3.015  | 16.525 | 1.00 | 29.198 | C |
| ATOM | 2096 | CD  | LYS | A | 287 | -36.597 | 2.202  | 17.612 | 1.00 | 23.66  | C |
| ATOM | 2097 | CE  | LYS | A | 287 | -34.782 | 1.009  | 17.071 | 1.00 | 28.22  | C |
| ATOM | 2098 | NZ  | LYS | A | 287 | -33.712 | 1.411  | 16.083 | 1.00 | 34.17  | N |
| ATOM | 2099 | C   | LYS | A | 287 | -38.223 | 6.375  | 17.301 | 1.00 | 34.59  | C |
| ATOM | 2100 | O   | LYS | A | 287 | -37.607 | 7.338  | 17.776 | 1.00 | 38.11  | O |
| ATOM | 2101 | N   | VAL | A | 288 | -39.513 | 6.166  | 17.534 | 1.00 | 32.67  | N |
| ATOM | 2102 | CA  | VAL | A | 288 | -40.247 | 6.935  | 18.539 | 1.00 | 32.60  | C |
| ATOM | 2103 | CB  | VAL | A | 288 | -41.689 | 7.221  | 18.092 | 1.00 | 32.09  | C |
| ATOM | 2104 | CG1 | VAL | A | 288 | -42.412 | 8.067  | 19.125 | 1.00 | 38.55  | C |
| ATOM | 2105 | CG2 | VAL | A | 288 | -41.726 | 7.881  | 16.697 | 1.00 | 37.25  | C |
| ATOM | 2106 | C   | VAL | A | 288 | -40.362 | 5.953  | 19.710 | 1.00 | 34.80  | C |
| ATOM | 2107 | O   | VAL | A | 288 | -40.993 | 4.891  | 19.545 | 1.00 | 34.76  | O |

TABLE 10-continued

Atomic coordinates for COM1 complex of the modified TXNIP protein represented by SEQ ID NO: 6 and the modified protein represented by SEQ ID NO: 3

| | | | | | | | | | | |
|---|---|---|---|---|---|---|---|---|---|---|
| ATOM | 2108 | N | ILE | A | 289 | -39.820 | 20.880 | 6.315 | 1.00 | 31.94 | N |
| ATOM | 2109 | CA | ILE | A | 289 | -39.611 | 21.958 | 5.322 | 1.00 | 34.04 | C |
| ATOM | 2110 | CB | ILE | A | 289 | -38.056 | 22.186 | 5.077 | 1.00 | 34.57 | C |
| ATOM | 2111 | CG1 | ILE | A | 289 | -37.393 | 20.945 | 4.461 | 1.00 | 33.36 | C |
| ATOM | 2112 | CD1 | ILE | A | 289 | -35.862 | 20.757 | 4.883 | 1.00 | 34.42 | C |
| ATOM | 2113 | CG2 | ILE | A | 289 | -37.738 | 23.440 | 4.223 | 1.00 | 35.75 | C |
| ATOM | 2114 | C | ILE | A | 289 | -40.308 | 23.252 | 5.714 | 1.00 | 36.26 | C |
| ATOM | 2115 | O | ILE | A | 289 | -40.146 | 23.717 | 8.870 | 1.00 | 37.02 | O |
| ATOM | 2116 | N | LEU | A | 290 | -41.106 | 23.812 | 4.783 | 1.00 | 31.28 | N |
| ATOM | 2117 | CA | LEU | A | 290 | -41.461 | 25.247 | 4.813 | 1.00 | 33.64 | C |
| ATOM | 2118 | CB | LEU | A | 290 | -42.922 | 25.495 | 4.425 | 1.00 | 31.12 | C |
| ATOM | 2119 | CG | LEU | A | 290 | -43.991 | 24.780 | 5.260 | 1.00 | 38.23 | C |
| ATOM | 2120 | CD1 | LEU | A | 290 | -45.411 | 25.007 | 4.693 | 1.00 | 25.98 | C |
| ATOM | 2121 | CD2 | LEU | A | 290 | -43.928 | 25.236 | 5.661 | 1.00 | 36.71 | C |
| ATOM | 2122 | C | LEU | A | 290 | -40.554 | 26.028 | 3.856 | 1.00 | 34.03 | C |
| ATOM | 2123 | O | LEU | A | 290 | -40.315 | 25.616 | 2.723 | 1.00 | 35.11 | O |
| ATOM | 2124 | N | ASP | A | 291 | -40.030 | 27.134 | 4.341 | 1.00 | 33.69 | N |
| ATOM | 2125 | CA | ASP | A | 291 | -39.300 | 28.083 | 3.520 | 1.00 | 33.02 | C |
| ATOM | 2126 | CB | ASP | A | 291 | -37.920 | 28.308 | 4.141 | 1.00 | 36.19 | C |
| ATOM | 2127 | CG | ASP | A | 291 | -37.042 | 29.284 | 3.342 | 1.00 | 36.82 | C |
| ATOM | 2128 | OD1 | ASP | A | 291 | -37.540 | 30.293 | 2.806 | 1.00 | 46.80 | O |
| ATOM | 2129 | OD2 | ASP | A | 291 | -35.834 | 29.010 | 3.250 | 1.00 | 38.36 | O |
| ATOM | 2130 | C | ASP | A | 291 | -40.096 | 29.380 | 3.527 | 1.00 | 36.15 | C |
| ATOM | 2131 | O | ASP | A | 291 | -40.190 | 30.030 | 4.561 | 1.00 | 33.52 | O |
| ATOM | 2132 | N | LEU | A | 292 | -40.686 | 29.760 | 2.388 | 1.00 | 32.87 | N |
| ATOM | 2133 | CA | LEU | A | 292 | -41.409 | 31.050 | 2.344 | 1.00 | 34.92 | C |
| ATOM | 2134 | CB | LEU | A | 292 | -42.826 | 30.868 | 1.756 | 1.00 | 33.77 | C |
| ATOM | 2135 | CG | LEU | A | 292 | -43.805 | 29.834 | 2.322 | 1.00 | 33.06 | C |
| ATOM | 2136 | CD1 | LEU | A | 292 | -45.108 | 29.966 | 1.577 | 1.00 | 37.65 | C |
| ATOM | 2137 | CD2 | LEU | A | 292 | -44.054 | 30.074 | 3.810 | 1.00 | 47.98 | C |
| ATOM | 2138 | C | LEU | A | 292 | -40.640 | 32.059 | 1.466 | 1.00 | 35.09 | C |
| ATOM | 2139 | O | LEU | A | 292 | -40.573 | 31.898 | 0.249 | 1.00 | 38.34 | O |
| ATOM | 2140 | N | PRO | A | 293 | -40.058 | 33.109 | 2.077 | 1.00 | 41.81 | N |
| ATOM | 2141 | CA | PRO | A | 293 | -39.341 | 34.128 | 1.276 | 1.00 | 39.12 | C |
| ATOM | 2142 | CB | PRO | A | 293 | -38.831 | 35.126 | 2.324 | 1.00 | 40.28 | C |
| ATOM | 2143 | CG | PRO | A | 293 | -38.861 | 34.383 | 3.629 | 1.00 | 47.77 | C |
| ATOM | 2144 | CD | PRO | A | 293 | -40.041 | 33.432 | 3.523 | 1.00 | 41.19 | C |
| ATOM | 2145 | C | PRO | A | 293 | -40.197 | 34.863 | 0.247 | 1.00 | 40.14 | C |
| ATOM | 2146 | O | PRO | A | 293 | -41.347 | 35.237 | 0.508 | 1.00 | 36.50 | O |
| ATOM | 2147 | N | LEU | A | 294 | -39.599 | 35.107 | -0.911 | 1.00 | 34.60 | N |
| ATOM | 2148 | CA | LEU | A | 294 | -40.268 | 35.735 | -2.035 | 1.00 | 33.41 | C |
| ATOM | 2149 | CB | LEU | A | 294 | -40.339 | 34.750 | -3.221 | 1.00 | 34.72 | C |
| ATOM | 2150 | CG | LEU | A | 294 | -41.067 | 33.414 | -2.976 | 1.00 | 29.25 | C |
| ATOM | 2151 | CD1 | LEU | A | 294 | -40.882 | 32.565 | -4.219 | 1.00 | 56.01 | C |
| ATOM | 2152 | CD2 | LEU | A | 294 | -42.532 | 33.671 | -2.718 | 1.00 | 37.85 | C |
| ATOM | 2153 | C | LEU | A | 294 | -39.437 | 36.932 | -2.442 | 1.00 | 37.53 | C |
| ATOM | 2154 | O | LEU | A | 294 | -38.256 | 37.022 | -2.133 | 1.00 | 35.78 | O |
| ATOM | 2155 | N | LEU | A | 294 | -40.090 | 37.865 | -3.106 | 1.00 | 38.51 | N |
| ATOM | 2156 | CA | VAL | A | 295 | -39.420 | 38.927 | -3.770 | 1.00 | 41.12 | C |
| ATOM | 2157 | CB | VAL | A | 295 | -39.948 | 40.287 | -3.246 | 1.00 | 41.86 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2158 | CG1 | VAL | A | 295 | −39.397 | −4.087 | 41.409 | 1.00 | 39.99 | C |
| ATOM | 2159 | CG2 | VAL | A | 295 | −39.565 | −1.766 | 40.455 | 1.00 | 44.40 | C |
| ATOM | 2160 | C | VAL | A | 295 | −39.755 | −5.237 | 38.759 | 1.00 | 42.11 | C |
| ATOM | 2161 | O | VAL | A | 295 | −40.298 | −5.599 | 37.731 | 1.00 | 41.62 | O |
| ATOM | 2162 | N | ILE | A | 296 | −38.738 | −60.86 | 38.632 | 1.00 | 42.12 | N |
| ATOM | 2163 | CA | ILE | A | 296 | −39.004 | −7.496 | 38.360 | 1.00 | 44.43 | C |
| ATOM | 2164 | CB | ILE | A | 296 | −38.465 | −7.929 | 36.945 | 1.00 | 43.81 | C |
| ATOM | 2165 | CG1 | ILE | A | 296 | −39.375 | −7.367 | 35.857 | 1.00 | 43.46 | C |
| ATOM | 2166 | CD1 | ILE | A | 296 | −38.940 | −6.079 | 35.379 | 1.00 | 55.38 | C |
| ATOM | 2167 | OG2 | ILE | A | 296 | −38.454 | −9.436 | 36.772 | 1.00 | 36.08 | O |
| ATOM | 2168 | C | ILE | A | 296 | −38.407 | −8.338 | 39.459 | 1.00 | 45.16 | C |
| ATOM | 2169 | O | ILE | A | 296 | −37.227 | −8.275 | 39.080 | 1.00 | 46.41 | O |
| ATOM | 2170 | N | GLY | A | 297 | −39.236 | −9.119 | 40.154 | 1.00 | 50.29 | N |
| ATOM | 2171 | CA | GLY | A | 297 | −38.782 | −9.905 | 41.292 | 1.00 | 53.84 | C |
| ATOM | 2172 | C | GLY | A | 297 | −38.869 | −11.412 | 41.135 | 1.00 | 56.04 | C |
| ATOM | 2173 | O | GLY | A | 297 | −39.666 | −11.936 | 40.352 | 1.00 | 56.39 | O |
| ATOM | 2174 | N | SER | A | 298 | −38.061 | −12.102 | 41.934 | 1.00 | 58.12 | N |
| ATOM | 2175 | CA | SER | A | 298 | −37.863 | −13.546 | 41.843 | 1.00 | 59.02 | C |
| ATOM | 2176 | CB | SER | A | 298 | −36.491 | −13.882 | 42.405 | 1.00 | 59.98 | C |
| ATOM | 2177 | OG | SER | A | 298 | −35.519 | −12.922 | 41.983 | 1.00 | 61.45 | O |
| ATOM | 2178 | C | SER | A | 298 | −38.937 | −14.398 | 42.539 | 1.00 | 58.45 | C |
| ATOM | 2179 | O | SER | A | 298 | −39.765 | −13.895 | 43.297 | 1.00 | 55.67 | O |
| TER | | | | | | | | | | | |
| ATOM | 2180 | N | MET | B | 1 | −77.136 | 9.876 | 4.933 | 1.00 | 65.94 | N |
| ATOM | 2181 | CA | MET | B | 1 | −76.863 | 9.605 | 6.370 | 1.00 | 65.76 | C |
| ATOM | 2182 | CB | MET | B | 1 | −78.141 | 9.696 | 7.225 | 1.00 | 66.86 | C |
| ATOM | 2183 | CG | MET | B | 1 | −78.383 | 11.045 | 7.914 | 1.00 | 70.50 | C |
| ATOM | 2184 | SD | MET | B | 1 | −79.386 | 12.186 | 6.930 | 1.00 | 83.85 | S |
| ATOM | 2185 | CE | MET | B | 1 | −81.061 | 11.559 | 7.188 | 1.00 | 82.25 | C |
| ATOM | 2186 | C | MET | B | 1 | −76.193 | 8.253 | 6.618 | 1.00 | 65.44 | C |
| ATOM | 2187 | O | MET | B | 1 | −76.439 | 7.276 | 5.896 | 1.00 | 55.05 | O |
| ATOM | 2188 | N | VAL | B | 2 | −75.361 | 8.228 | 7.661 | 1.00 | 64.33 | N |
| ATOM | 2189 | CA | VAL | B | 2 | −74.624 | 7.040 | 8.112 | 1.00 | 62.08 | C |
| ATOM | 2190 | CB | VAL | B | 2 | −73.117 | 7.352 | 8.345 | 1.00 | 62.50 | C |
| ATOM | 2191 | CG1 | VAL | B | 2 | −72.379 | 6.125 | 8.849 | 1.00 | 55.96 | C |
| ATOM | 2192 | CG2 | VAL | B | 2 | −72.484 | 7.867 | 7.072 | 1.00 | 51.74 | C |
| ATOM | 2193 | C | VAL | B | 2 | −75.223 | 6.488 | 9.401 | 1.00 | 62.07 | C |
| ATOM | 2194 | O | VAL | B | 2 | −75.384 | 7.204 | 10.393 | 1.00 | 59.72 | O |
| ATOM | 2195 | N | LYS | B | 3 | −75.541 | 5.200 | 9.353 | 1.00 | 62.90 | N |
| ATOM | 2196 | CA | LYS | B | 3 | −76.120 | 4.497 | 10.495 | 1.00 | 66.17 | C |
| ATOM | 2197 | CB | LYS | B | 3 | −76.815 | 3.226 | 9.992 | 1.00 | 65.30 | C |
| ATOM | 2198 | CG | LYS | B | 3 | −78.090 | 2.811 | 10.724 | 1.00 | 68.78 | C |
| ATOM | 2199 | CD | LYS | B | 3 | −78.887 | 1.824 | 9.449 | 1.00 | 76.01 | C |
| ATOM | 2200 | CE | LYS | B | 3 | −79.287 | 2.458 | 8.495 | 1.00 | 76.01 | C |
| ATOM | 2201 | NZ | LYS | B | 3 | −79.422 | 1.466 | 7.392 | 1.00 | 78.86 | N |
| ATOM | 2202 | C | LYS | B | 3 | −75.013 | 4.128 | 11.487 | 1.00 | 66.32 | C |
| ATOM | 2203 | O | LYS | B | 3 | −74.213 | 3.233 | 11.210 | 1.00 | 67.13 | O |
| ATOM | 2204 | N | GLN | B | 4 | −74.061 | 4.825 | 12.623 | 1.00 | 67.16 | N |
| ATOM | 2205 | CA | GLN | B | 4 | −74.128 | 4.391 | 13.761 | 1.00 | 67.29 | C |
| ATOM | 2206 | CB | GLN | B | 4 | −74.240 | 5.353 | 14.952 | 1.00 | 67.26 | C |

TABLE 10-continued

Atomic coordinates for COM1 complex of the modified
TXNIP protein represented by SEQ ID NO: 6 and the modified protein represented by SEQ ID NO: 3

| | | | | | | | | | |
|---|---|---|---|---|---|---|---|---|---|
| ATOM | 2207 | CG | GLN | B | 4 | -73.593 | 6.726 | 14.725 | 1.00 | 69.66 | C |
| ATOM | 2208 | CD | GLN | B | 4 | -74.481 | 7.915 | 15.139 | 1.00 | 75.14 | C |
| ATOM | 2209 | OE1 | GLN | B | 4 | -75.516 | 7.755 | 15.802 | 1.00 | 71.83 | O |
| ATOM | 2210 | NE2 | GLN | B | 4 | -74.073 | 9.117 | 14.733 | 1.00 | 69.50 | N |
| ATOM | 2211 | C | GLN | B | 4 | -75.577 | 2.993 | 14.160 | 1.00 | 66.55 | C |
| ATOM | 2212 | O | GLN | B | 4 | -75.778 | 2.729 | 14.258 | 1.00 | 67.79 | O |
| ATOM | 2213 | N | ILE | B | 5 | -73.620 | 2.094 | 14.358 | 1.00 | 66.08 | N |
| ATOM | 2214 | CA | ILE | B | 5 | -79.944 | 0.689 | 14.577 | 1.00 | 67.39 | C |
| ATOM | 2215 | CB | ILE | B | 5 | -73.705 | -0.173 | 13.297 | 1.00 | 66.31 | C |
| ATOM | 2216 | CG1 | ILE | B | 5 | -74.845 | -0.053 | 12.312 | 1.00 | 65.78 | C |
| ATOM | 2217 | CD1 | ILE | B | 5 | -74.729 | -0.733 | 11.040 | 1.00 | 62.90 | C |
| ATOM | 2218 | CG2 | ILE | B | 5 | -73.584 | -1.680 | 13.625 | 1.00 | 69.24 | C |
| ATOM | 2219 | C | ILE | B | 5 | -73.251 | 0.152 | 15.828 | 1.00 | 67.92 | C |
| ATOM | 2220 | O | ILE | B | 5 | -72.024 | 0.013 | 15.872 | 1.00 | 68.85 | O |
| ATOM | 2221 | N | GLU | B | 6 | -74.068 | -0.514 | 16.836 | 1.00 | 68.44 | N |
| ATOM | 2222 | CA | GLU | B | 6 | -73.591 | -0.358 | 18.197 | 1.00 | 68.25 | C |
| ATOM | 2223 | CB | GLU | B | 6 | -74.194 | 0.713 | 19.110 | 1.00 | 67.59 | C |
| ATOM | 2224 | CG | GLU | B | 6 | -73.380 | 2.006 | 19.103 | 1.00 | 71.66 | C |
| ATOM | 2225 | CD | GLU | B | 6 | -74.247 | 3.259 | 19.063 | 1.00 | 77.36 | C |
| ATOM | 2226 | OE1 | GLU | B | 6 | -75.356 | 3.258 | 19.642 | 1.00 | 80.15 | O |
| ATOM | 2227 | OE2 | GLU | B | 6 | -73.803 | 4.252 | 18.446 | 1.00 | 78.54 | O |
| ATOM | 2228 | C | GLU | B | 6 | -73.821 | -1.758 | 18.756 | 1.00 | 68.30 | C |
| ATOM | 2229 | O | GLU | B | 6 | -73.699 | -1.978 | 19.956 | 1.00 | 68.49 | O |
| ATOM | 2230 | N | SER | B | 7 | -74.133 | -2.703 | 17.872 | 1.00 | 68.34 | N |
| ATOM | 2231 | CA | SER | B | 7 | -74.379 | -4.091 | 18.274 | 1.00 | 69.57 | C |
| ATOM | 2232 | CB | SER | B | 7 | -75.871 | -4.342 | 18.556 | 1.00 | 69.04 | C |
| ATOM | 2233 | CG | SER | B | 7 | -76.270 | -3.789 | 19.798 | 1.00 | 68.63 | C |
| ATOM | 2234 | O | SER | B | 7 | -73.866 | -5.085 | 17.235 | 1.00 | 69.90 | O |
| ATOM | 2235 | C | SER | B | 7 | -73.595 | 4.724 | 16.091 | 1.00 | 70.23 | C |
| ATOM | 2236 | N | LYS | B | 8 | -73.822 | -6.343 | 17.654 | 1.00 | 70.39 | N |
| ATOM | 2237 | CA | LYS | B | 8 | -73.384 | -7.441 | 18.808 | 1.00 | 70.43 | C |
| ATOM | 2238 | CB | LYS | B | 8 | -72.897 | -8.616 | 17.670 | 1.00 | 70.49 | C |
| ATOM | 2239 | CG | LYS | B | 8 | -72.399 | -8.206 | 19.053 | 1.00 | 69.22 | C |
| ATOM | 2240 | CD | LYS | B | 8 | -72.101 | -9.419 | 19.933 | 1.00 | 71.52 | C |
| ATOM | 2241 | OE | LYS | B | 8 | -72.608 | -9.228 | 21.365 | 1.00 | 69.15 | O |
| ATOM | 2242 | NZ | LYS | B | 8 | -72.044 | -8.024 | 22.044 | 1.00 | 67.50 | N |
| ATOM | 2243 | C | LYS | B | 8 | -74.536 | -7.881 | 15.916 | 1.00 | 70.41 | C |
| ATOM | 2244 | O | LYS | B | 8 | -74.358 | -8.045 | 14.709 | 1.00 | 70.45 | O |
| ATOM | 2245 | N | THR | B | 9 | -75.716 | -8.063 | 16.513 | 1.00 | 70.84 | N |
| ATOM | 2246 | CA | THR | B | 9 | -76.905 | -8.480 | 15.758 | 1.00 | 71.03 | C |
| ATOM | 2247 | CB | THR | B | 9 | -77.999 | -9.152 | 16.640 | 1.00 | 70.60 | C |
| ATOM | 2248 | OG1 | THR | B | 9 | -78.226 | -8.403 | 17.833 | 1.00 | 68.94 | O |
| ATOM | 2249 | CG2 | THR | B | 9 | -77.589 | -10.579 | 17.007 | 1.00 | 68.13 | C |
| ATOM | 2250 | C | THR | B | 9 | -77.506 | -7.339 | 14.933 | 1.00 | 71.86 | C |
| ATOM | 2251 | O | THR | B | 9 | -78.235 | -7.595 | 13.969 | 1.00 | 71.60 | O |
| ATOM | 2252 | N | ALA | B | 10 | -77.188 | -6.093 | 15.308 | 1.00 | 72.80 | N |
| ATOM | 2253 | CA | ALA | B | 10 | -77.569 | -4.903 | 14.521 | 1.00 | 72.95 | C |
| ATOM | 2254 | CB | ALA | B | 10 | -77.567 | -3.636 | 15.391 | 1.00 | 72.83 | C |
| ATOM | 2255 | C | ALA | B | 10 | -75.679 | -4.716 | 13.286 | 1.00 | 73.00 | C |
| ATOM | 2256 | O | ALA | B | 10 | -76.956 | -3.869 | 12.435 | 1.00 | 74.12 | O |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2257 | N | ALA | B | 10 | -75.610 | 13.198 | -5.506 | 1.00 | 72.13 | N |
| ATOM | 2258 | CA | PHE | B | 11 | -74.788 | 11.992 | -5.567 | 1.00 | 71.47 | C |
| ATOM | 2259 | CB | PHE | B | 11 | -73.334 | 12.335 | -5.948 | 1.00 | 71.43 | C |
| ATOM | 2260 | CG | PHE | B | 11 | -72.378 | 11.173 | -5.825 | 1.00 | 69.76 | C |
| ATOM | 2261 | CD1 | PHE | B | 11 | -72.064 | 10.636 | -4.574 | 1.00 | 66.42 | C |
| ATOM | 2262 | CE1 | PHE | B | 11 | -71.189 | 9.554 | -4.463 | 1.00 | 67.45 | C |
| ATOM | 2263 | CZ | PHE | B | 11 | -70.611 | 9.005 | -5.614 | 1.00 | 63.93 | C |
| ATOM | 2264 | CE2 | PHE | B | 11 | -70.914 | 9.535 | -6.862 | 1.00 | 60.71 | C |
| ATOM | 2265 | CD2 | PHE | B | 11 | -70.790 | 10.615 | -6.962 | 1.00 | 65.56 | C |
| ATOM | 2266 | C | PHE | B | 11 | -75.422 | 10.984 | -6.534 | 1.00 | 70.42 | C |
| ATOM | 2267 | O | PHE | B | 11 | -75.210 | 9.770 | -6.425 | 1.00 | 68.81 | O |
| ATOM | 2268 | N | GLN | B | 12 | -76.212 | 11.505 | -7.468 | 1.00 | 71.52 | N |
| ATOM | 2269 | CA | GLN | B | 12 | -77.054 | 10.083 | -8.338 | 1.00 | 72.00 | C |
| ATOM | 2270 | CB | GLN | B | 12 | -77.383 | 11.425 | -9.637 | 1.00 | 72.03 | C |
| ATOM | 2271 | CG | GLN | B | 12 | -77.071 | 10.624 | -10.902 | 1.00 | 73.12 | C |
| ATOM | 2272 | CD | GLN | B | 12 | -75.575 | 10.524 | -11.193 | 1.00 | 74.34 | C |
| ATOM | 2273 | OE1 | GLN | B | 12 | -74.982 | 9.447 | -11.102 | 1.00 | 74.59 | O |
| ATOM | 2274 | NE2 | GLN | B | 12 | -74.961 | 11.654 | -11.537 | 1.00 | 75.62 | N |
| ATOM | 2275 | C | GLN | B | 12 | -78.330 | 10.273 | -7.590 | 1.00 | 72.32 | C |
| ATOM | 2276 | O | GLN | B | 12 | -78.831 | 9.159 | -7.776 | 1.00 | 71.75 | O |
| ATOM | 2277 | N | GLN | B | 12 | -78.843 | 11.174 | -6.747 | 1.00 | 73.09 | N |
| ATOM | 2278 | CA | GLU | B | 13 | -79.870 | 10.823 | -5.755 | 1.00 | 73.91 | C |
| ATOM | 2279 | CB | GLU | B | 13 | -80.659 | 12.053 | -5.282 | 1.00 | 73.69 | C |
| ATOM | 2280 | CG | GLU | B | 13 | -81.795 | 12.492 | -6.816 | 1.00 | 70.58 | C |
| ATOM | 2281 | CD | GLU | B | 13 | -81.517 | 13.795 | -6.917 | 1.00 | 70.60 | C |
| ATOM | 2282 | OE1 | GLU | B | 13 | -80.587 | 14.529 | -6.523 | 1.00 | 70.21 | O |
| ATOM | 2283 | OE2 | GLU | B | 13 | -82.246 | 14.100 | -7.885 | 1.00 | 67.24 | O |
| ATOM | 2284 | C | GLU | B | 13 | -79.243 | 10.105 | -4.548 | 1.00 | 74.57 | C |
| ATOM | 2285 | O | GLU | B | 13 | -78.995 | 10.716 | -3.503 | 1.00 | 73.64 | O |
| ATOM | 2286 | N | ALA | B | 14 | -78.977 | 8.810 | -4.732 | 1.00 | 75.53 | N |
| ATOM | 2287 | CA | ALA | B | 14 | -78.527 | 7.857 | -3.696 | 1.00 | 75.16 | C |
| ATOM | 2288 | CB | ALA | B | 14 | -77.449 | 8.441 | -2.813 | 1.00 | 75.00 | C |
| ATOM | 2289 | C | ALA | B | 14 | -78.010 | 6.623 | -4.424 | 1.00 | 75.53 | C |
| ATOM | 2290 | O | ALA | B | 14 | -78.332 | 5.484 | -4.061 | 1.00 | 75.56 | O |
| ATOM | 2291 | N | LEU | B | 15 | -77.225 | 6.884 | -5.472 | 1.00 | 75.70 | N |
| ATOM | 2292 | CA | LEU | B | 15 | -76.730 | 5.880 | -6.145 | 1.00 | 76.31 | C |
| ATOM | 2293 | CB | LEU | B | 15 | -75.777 | 6.556 | -7.414 | 1.00 | 76.70 | C |
| ATOM | 2294 | CG | LEU | B | 15 | -74.530 | 5.850 | -7.966 | 1.00 | 77.61 | C |
| ATOM | 2295 | CD1 | LEU | B | 15 | -73.343 | 6.030 | -7.027 | 1.00 | 67.85 | C |
| ATOM | 2296 | CD2 | LEU | B | 15 | -74.187 | 6.384 | -9.354 | 1.00 | 77.62 | C |
| ATOM | 2297 | C | LEU | B | 15 | -77.894 | 5.223 | -7.174 | 1.00 | 76.41 | C |
| ATOM | 2298 | O | LEU | B | 15 | -77.760 | 4.103 | -7.684 | 1.00 | 75.30 | O |
| ATOM | 2299 | N | ASP | B | 16 | -79.015 | 5.943 | -7.241 | 1.00 | 76.76 | N |
| ATOM | 2300 | CA | ASP | B | 16 | -80.260 | 5.455 | -7.839 | 1.00 | 77.09 | C |
| ATOM | 2301 | CB | ASP | B | 16 | -81.054 | 6.622 | -8.456 | 1.00 | 77.14 | C |
| ATOM | 2302 | CG | ASP | B | 16 | -81.583 | 7.612 | -7.409 | 1.00 | 77.17 | C |
| ATOM | 2303 | OD1 | ASP | B | 16 | -80.956 | 7.774 | -6.336 | 1.00 | 75.87 | O |
| ATOM | 2304 | OD2 | ASP | B | 16 | -82.635 | 8.235 | -7.670 | 1.00 | 78.89 | O |
| ATOM | 2305 | C | ASP | B | 16 | -81.129 | 4.665 | -6.845 | 1.00 | 76.73 | C |
| ATOM | 2306 | O | ASP | B | 16 | -81.666 | 3.611 | -7.191 | 1.00 | 76.77 | O |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2307 | N | ALA | B | 17 | −81.247 | −5.616 | 5.101 | 1.00 | 76.64 | N |
| ATOM | 2308 | CA | ALA | B | 17 | −82.073 | −4.558 | 4.581 | 1.00 | 76.63 | C |
| ATOM | 2309 | CB | ALA | B | 17 | −82.101 | −3.321 | 5.485 | 1.00 | 76.45 | C |
| ATOM | 2310 | C | ALA | B | 17 | −81.618 | −4.178 | 3.173 | 1.00 | 76.70 | C |
| ATOM | 2311 | O | ALA | B | 17 | −82.426 | −3.755 | 2.350 | 1.00 | 76.25 | O |
| ATOM | 2312 | N | ALA | B | 18 | −83.319 | −4.325 | 2.917 | 1.00 | 77.48 | N |
| ATOM | 2313 | CA | ALA | B | 18 | −79.740 | −4.092 | 1.593 | 1.00 | 77.46 | C |
| ATOM | 2314 | CB | ALA | B | 18 | −78.207 | −3.973 | 1.694 | 1.00 | 77.60 | C |
| ATOM | 2315 | C | ALA | B | 18 | −80.137 | −5.223 | 0.648 | 1.00 | 76.62 | C |
| ATOM | 2316 | O | ALA | B | 18 | −80.085 | −6.395 | 1.017 | 1.00 | 76.55 | O |
| ATOM | 2317 | N | GLY | B | 19 | −80.548 | −4.865 | −0.563 | 1.00 | 76.42 | N |
| ATOM | 2318 | CA | GLY | B | 19 | −80.084 | −5.856 | −1.547 | 1.00 | 76.13 | C |
| ATOM | 2319 | C | GLY | B | 19 | −79.795 | −6.344 | −2.347 | 1.00 | 75.62 | C |
| ATOM | 2320 | O | GLY | B | 19 | −78.839 | −6.890 | −1.782 | 1.00 | 75.96 | O |
| ATOM | 2321 | N | ASP | B | 20 | −79.857 | −6.143 | −3.663 | 1.00 | 74.43 | N |
| ATOM | 2322 | CA | ASP | B | 20 | −78.694 | −6.298 | −4.540 | 1.00 | 73.28 | C |
| ATOM | 2323 | CB | ASP | B | 20 | −79.131 | −6.296 | −6.013 | 1.00 | 73.39 | C |
| ATOM | 2324 | CG | ASP | B | 20 | −79.788 | −7.601 | −6.446 | 1.00 | 42.88 | C |
| ATOM | 2325 | OD1 | ASP | B | 20 | −79.875 | −8.545 | −5.631 | 1.00 | 72.80 | O |
| ATOM | 2326 | OD2 | ASP | B | 20 | −80.212 | −7.080 | −7.622 | 1.00 | 68.15 | O |
| ATOM | 2327 | C | ASP | B | 20 | −77.689 | −5.156 | −4.306 | 1.00 | 72.59 | C |
| ATOM | 2328 | O | ASP | B | 20 | −76.624 | −5.114 | −4.934 | 1.00 | 72.03 | O |
| ATOM | 2329 | N | LYS | B | 21 | −79.034 | −4.243 | −3.395 | 1.00 | 71.13 | N |
| ATOM | 2330 | CA | LYS | B | 21 | −77.298 | −2.994 | −3.235 | 1.00 | 70.28 | C |
| ATOM | 2331 | CB | LYS | B | 21 | −78.225 | −1.831 | −2.837 | 1.00 | 70.24 | C |
| ATOM | 2332 | CG | LYS | B | 21 | −78.964 | −1.976 | −1.516 | 1.00 | 71.60 | C |
| ATOM | 2333 | CD | LYS | B | 21 | −79.919 | −0.799 | −1.343 | 1.00 | 76.88 | C |
| ATOM | 2334 | CE | LYS | B | 21 | −80.328 | −0.603 | 0.112 | 1.00 | 78.80 | C |
| ATOM | 2335 | NZ | LYS | B | 21 | −81.912 | −0.618 | 0.263 | 1.00 | 78.28 | N |
| ATOM | 2336 | C | LYS | B | 21 | −76.050 | −3.075 | −2.339 | 1.00 | 69.59 | C |
| ATOM | 2337 | O | LYS | B | 21 | −75.973 | −3.860 | −1.374 | 1.00 | 69.66 | O |
| ATOM | 2338 | N | LEU | B | 22 | −75.077 | −2.245 | −2.701 | 1.00 | 66.82 | N |
| ATOM | 2339 | CA | LEU | B | 22 | −73.778 | −2.199 | −2.064 | 1.00 | 62.29 | C |
| ATOM | 2340 | CB | LEU | B | 22 | −72.794 | −1.476 | −2.986 | 1.00 | 61.94 | C |
| ATOM | 2341 | CG | LEU | B | 22 | −71.352 | −1.239 | −2.544 | 1.00 | 53.13 | C |
| ATOM | 2342 | CD1 | LEU | B | 22 | −70.444 | −2.231 | −3.242 | 1.00 | 48.78 | C |
| ATOM | 2343 | CD2 | LEU | B | 22 | −70.982 | −0.178 | −2.895 | 1.00 | 46.47 | C |
| ATOM | 2344 | C | LEU | B | 22 | −73.847 | −1.513 | −0.703 | 1.00 | 60.87 | C |
| ATOM | 2345 | O | LEU | B | 22 | −74.461 | −0.443 | 0.542 | 1.00 | 58.39 | O |
| ATOM | 2346 | N | VAL | B | 23 | −73.221 | −2.155 | 0.277 | 1.00 | 60.20 | N |
| ATOM | 2347 | CA | VAL | B | 23 | −73.030 | −1.543 | 1.593 | 1.00 | 59.91 | C |
| ATOM | 2348 | CB | VAL | B | 23 | −73.604 | −2.427 | 2.754 | 1.00 | 59.66 | C |
| ATOM | 2349 | CG1 | VAL | B | 23 | −73.054 | −3.843 | 2.710 | 1.00 | 59.73 | C |
| ATOM | 2350 | CG2 | VAL | B | 23 | −73.354 | −1.787 | 4.106 | 1.00 | 59.98 | C |
| ATOM | 2351 | C | VAL | B | 23 | −71.550 | −1.174 | 1.704 | 1.00 | 58.50 | C |
| ATOM | 2352 | O | VAL | B | 23 | −70.982 | −1.831 | 1.235 | 1.00 | 55.59 | O |
| ATOM | 2353 | N | VAL | B | 24 | −71.313 | −0.102 | 2.355 | 1.00 | 57.41 | N |
| ATOM | 2354 | CA | VAL | B | 24 | −69.973 | 0.338 | 2.931 | 1.00 | 57.68 | C |
| ATOM | 2355 | CB | VAL | B | 24 | −69.500 | 1.561 | 2.070 | 1.00 | 55.87 | C |
| ATOM | 2356 | CG1 | VAL | B | 24 | −70.445 | 2.717 | 2.183 | 1.00 | 58.08 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2357 | CG2 | VAL | B | 24 | -68.053 | 1.978 | 2.407 | 1.00 | 57.15 | C |
| ATOM | 2358 | C | VAL | B | 24 | -69.878 | 0.587 | 4.450 | 1.00 | 58.55 | C |
| ATOM | 2359 | O | VAL | B | 24 | -70.673 | 1.332 | 5.017 | 1.00 | 59.52 | O |
| ATOM | 2360 | N | VAL | B | 25 | -68.924 | -0.772 | 5.108 | 1.00 | 58.72 | N |
| ATOM | 2361 | CA | VAL | B | 25 | -68.731 | 0.078 | 6.556 | 1.00 | 59.01 | C |
| ATOM | 2362 | CB | VAL | B | 25 | -68.716 | -1.282 | 7.268 | 1.00 | 59.37 | C |
| ATOM | 2363 | CG1 | VAL | B | 25 | -68.950 | -1.106 | 8.768 | 1.00 | 55.50 | C |
| ATOM | 2364 | CG2 | VAL | B | 25 | -69.756 | -2.221 | 6.663 | 1.00 | 60.72 | C |
| ATOM | 2365 | C | VAL | B | 25 | -67.412 | 0.806 | 6.857 | 1.00 | 59.49 | C |
| ATOM | 2366 | O | VAL | B | 25 | -66.356 | 0.416 | 6.357 | 1.00 | 60.60 | O |
| ATOM | 2367 | N | ASP | B | 26 | -67.493 | 1.878 | 7.638 | 1.00 | 58.68 | N |
| ATOM | 2368 | CA | ASP | B | 26 | -66.339 | 2.584 | 8.165 | 1.00 | 59.28 | C |
| ATOM | 2369 | CB | ASP | B | 26 | -66.621 | 4.110 | 8.223 | 1.00 | 56.36 | C |
| ATOM | 2370 | CG | ASP | B | 26 | -65.489 | 4.924 | 8.859 | 1.00 | 59.37 | C |
| ATOM | 2371 | OD1 | ASP | B | 26 | -64.492 | 4.339 | 9.316 | 1.00 | 66.74 | O |
| ATOM | 2372 | OD2 | ASP | B | 26 | -65.596 | 6.173 | 8.935 | 1.00 | 57.96 | O |
| ATOM | 2373 | C | ASP | B | 26 | -66.015 | 2.029 | 9.565 | 1.00 | 57.78 | C |
| ATOM | 2374 | O | ASP | B | 26 | -66.618 | 2.443 | 10.551 | 1.00 | 57.98 | O |
| ATOM | 2375 | N | PHE | B | 27 | -65.069 | 1.087 | 9.634 | 1.00 | 57.51 | N |
| ATOM | 2376 | CA | PHE | B | 27 | -64.490 | 0.607 | 10.915 | 1.00 | 55.59 | C |
| ATOM | 2377 | CB | PHE | B | 27 | -63.802 | -0.673 | 10.796 | 1.00 | 57.36 | C |
| ATOM | 2378 | CG | PHE | B | 27 | -64.740 | -1.796 | 10.553 | 1.00 | 62.63 | C |
| ATOM | 2379 | CD1 | PHE | B | 27 | -65.310 | -2.471 | 11.620 | 1.00 | 66.31 | C |
| ATOM | 2380 | CE1 | PHE | B | 27 | -66.192 | -3.507 | 11.400 | 1.00 | 70.86 | C |
| ATOM | 2381 | CZ | PHE | B | 27 | -66.530 | -3.868 | 10.093 | 1.00 | 72.58 | C |
| ATOM | 2382 | CE2 | PHE | B | 27 | -65.968 | -3.196 | 9.023 | 1.00 | 70.88 | C |
| ATOM | 2383 | CD2 | PHE | B | 27 | -65.079 | -2.164 | 9.256 | 1.00 | 67.65 | C |
| ATOM | 2384 | C | PHE | B | 27 | -63.519 | 1.716 | 11.401 | 1.00 | 56.15 | C |
| ATOM | 2385 | O | PHE | B | 27 | -62.410 | 1.856 | 10.878 | 1.00 | 57.20 | O |
| ATOM | 2386 | N | SER | B | 28 | -63.954 | 2.449 | 12.404 | 1.00 | 55.00 | N |
| ATOM | 2387 | CA | SER | B | 28 | -63.301 | 3.655 | 12.844 | 1.00 | 53.41 | C |
| ATOM | 2388 | CB | SER | B | 28 | -64.281 | 4.796 | 12.667 | 1.00 | 51.21 | C |
| ATOM | 2389 | OG | SER | B | 28 | -63.708 | 6.000 | 13.117 | 1.00 | 63.55 | O |
| ATOM | 2390 | C | SER | B | 28 | -62.980 | 3.529 | 14.311 | 1.00 | 53.51 | C |
| ATOM | 2391 | O | SER | B | 28 | -63.309 | 2.527 | 14.926 | 1.00 | 56.91 | O |
| ATOM | 2392 | N | ALA | B | 29 | -62.329 | 4.548 | 14.866 | 1.00 | 51.76 | N |
| ATOM | 2393 | CA | ALA | B | 29 | -62.090 | 4.650 | 16.285 | 1.00 | 54.98 | C |
| ATOM | 2394 | CB | ALA | B | 29 | -60.808 | 3.902 | 16.705 | 1.00 | 55.91 | C |
| ATOM | 2395 | C | ALA | B | 29 | -61.970 | 6.134 | 16.579 | 1.00 | 57.32 | C |
| ATOM | 2396 | O | ALA | B | 29 | -61.534 | 6.992 | 15.727 | 1.00 | 58.03 | O |
| ATOM | 2397 | N | THR | B | 30 | -62.362 | 6.489 | 17.791 | 1.00 | 61.45 | N |
| ATOM | 2398 | CA | THR | B | 30 | -62.544 | 7.866 | 18.200 | 1.00 | 63.79 | C |
| ATOM | 2399 | CB | THR | B | 30 | -63.504 | 7.946 | 19.460 | 1.00 | 65.77 | C |
| ATOM | 2400 | CG1 | THR | B | 30 | -63.834 | 9.310 | 19.736 | 1.00 | 75.71 | C |
| ATOM | 2401 | CG2 | THR | B | 30 | -62.899 | 7.302 | 20.745 | 1.00 | 66.04 | C |
| ATOM | 2402 | C | THR | B | 30 | -61.241 | 8.625 | 18.445 | 1.00 | 61.29 | C |
| ATOM | 2403 | O | THR | B | 30 | -61.206 | 9.841 | 18.315 | 1.00 | 63.53 | O |
| ATOM | 2404 | N | TRP | B | 31 | -60.175 | 7.901 | 18.794 | 1.00 | 60.42 | N |
| ATOM | 2405 | CA | TRP | B | 31 | -58.875 | 8.494 | 19.134 | 1.00 | 55.48 | C |
| ATOM | 2406 | CB | TRP | B | 31 | -58.182 | 7.656 | 20.233 | 1.00 | 58.08 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2407 | CG | TRP | B | 31 | −58.139 | 6.193 | 19.878 | 1.00 | 48.39 | C |
| ATOM | 2408 | CD1 | TRP | B | 31 | −59.040 | 5.248 | 20.251 | 1.00 | 48.78 | O |
| ATOM | 2409 | NE1 | TRP | B | 31 | −58.711 | 4.037 | 19.709 | 1.00 | 51.23 | N |
| ATOM | 2410 | CE2 | TRP | B | 31 | −57.570 | 4.182 | 18.958 | 1.00 | 46.82 | C |
| ATOM | 2411 | CD2 | TRP | B | 31 | −57.175 | 5.529 | 19.047 | 1.00 | 44.17 | C |
| ATOM | 2412 | CE3 | TRP | B | 31 | −56.034 | 5.947 | 18.343 | 1.00 | 41.18 | C |
| ATOM | 2413 | CZ3 | TRP | B | 31 | −55.315 | 5.006 | 17.624 | 1.00 | 45.20 | C |
| ATOM | 2414 | CH2 | TRP | B | 31 | −55.732 | 3.665 | 17.570 | 1.00 | 48.67 | C |
| ATOM | 2415 | CZ2 | TRP | B | 31 | −56.845 | 3.237 | 18.238 | 1.00 | 45.01 | C |
| ATOM | 2416 | C | TRP | B | 31 | −57.962 | 8.509 | 17.907 | 1.00 | 54.70 | C |
| ATOM | 2417 | O | TRP | B | 31 | −56.923 | 9.264 | 17.952 | 1.00 | 56.22 | O |
| ATOM | 2418 | N | CYS | B | 32 | −58.380 | 7.999 | 16.803 | 1.00 | 54.15 | N |
| ATOM | 2419 | CA | CYS | B | 32 | −57.596 | 7.880 | 15.596 | 1.00 | 53.88 | C |
| ATOM | 2420 | CB | CYS | B | 32 | −58.077 | 6.636 | 14.878 | 1.00 | 53.14 | C |
| ATOM | 2421 | SG | CYS | B | 32 | −57.345 | 6.336 | 13.307 | 1.00 | 60.44 | S |
| ATOM | 2422 | C | CYS | B | 32 | −57.696 | 9.122 | 14.677 | 1.00 | 55.89 | C |
| ATOM | 2423 | O | CYS | B | 32 | −58.755 | 9.401 | 14.1218 | 1.00 | 52.24 | O |
| ATOM | 2424 | N | GLY | B | 33 | −56.595 | 9.871 | 14.550 | 1.00 | 54.34 | N |
| ATOM | 2425 | CA | GLY | B | 33 | −56.514 | 11.063 | 13.717 | 1.00 | 54.25 | C |
| ATOM | 2426 | C | GLY | B | 33 | −56.989 | 10.832 | 12.283 | 1.00 | 55.00 | C |
| ATOM | 2427 | O | GLY | B | 33 | −57.036 | 11.470 | 11.851 | 1.00 | 57.12 | O |
| ATOM | 2428 | N | PRO | B | 34 | −56.341 | 9.918 | 11.523 | 1.00 | 49.90 | N |
| ATOM | 2429 | CA | PRO | B | 34 | −56.891 | 9.649 | 10.178 | 1.00 | 51.78 | C |
| ATOM | 2430 | CB | PRO | B | 34 | −56.004 | 8.518 | 9.650 | 1.00 | 53.27 | C |
| ATOM | 2431 | CG | PRO | B | 34 | −54.724 | 8.623 | 10.430 | 1.00 | 48.37 | C |
| ATOM | 2432 | CD | PRO | B | 34 | −55.107 | 9.140 | 11.783 | 1.00 | 52.33 | C |
| ATOM | 2433 | C | PRO | B | 34 | −58.380 | 9.235 | 10.127 | 1.00 | 54.14 | C |
| ATOM | 2434 | O | PRO | B | 34 | −59.046 | 9.630 | 9.203 | 1.00 | 54.51 | O |
| ATOM | 2435 | N | ALA | B | 35 | −58.906 | 8.481 | 11.107 | 1.00 | 55.16 | N |
| ATOM | 2436 | CA | ALA | B | 35 | −60.345 | 8.111 | 11.096 | 1.00 | 54.83 | C |
| ATOM | 2437 | CB | ALA | B | 35 | −60.644 | 6.982 | 12.049 | 1.00 | 52.09 | C |
| ATOM | 2438 | C | ALA | B | 35 | −61.304 | 9.284 | 11.350 | 1.00 | 68.51 | C |
| ATOM | 2439 | O | ALA | B | 35 | −62.388 | 9.354 | 10.741 | 1.00 | 60.20 | O |
| ATOM | 2440 | N | LYS | B | 36 | −60.919 | 10.185 | 12.245 | 1.00 | 56.14 | N |
| ATOM | 2441 | CA | LYS | B | 36 | −61.603 | 11.460 | 12.455 | 1.00 | 57.13 | C |
| ATOM | 2442 | CB | LYS | B | 36 | −61.024 | 12.158 | 13.648 | 1.00 | 59.26 | C |
| ATOM | 2443 | CG | LYS | B | 36 | −61.328 | 11.482 | 14.978 | 1.00 | 67.88 | C |
| ATOM | 2444 | CD | LYS | B | 36 | −61.050 | 12.425 | 16.162 | 1.00 | 69.96 | C |
| ATOM | 2445 | CE | LYS | B | 36 | −62.215 | 13.423 | 16.371 | 1.00 | 81.45 | C |
| ATOM | 2446 | NZ | LYS | B | 36 | −62.535 | 13.721 | 17.814 | 1.00 | 78.84 | N |
| ATOM | 2447 | C | LYS | B | 36 | −61.531 | 12.440 | 11.242 | 1.00 | 50.01 | C |
| ATOM | 2448 | O | LYS | B | 36 | −62.469 | 13.209 | 10.980 | 1.00 | 54.61 | O |
| ATOM | 2449 | N | MET | B | 37 | −60.400 | 12.466 | 10.553 | 1.00 | 55.20 | N |
| ATOM | 2450 | CA | MET | B | 37 | −60.281 | 13.267 | 9.344 | 1.00 | 56.71 | C |
| ATOM | 2451 | CB | MET | B | 37 | −58.822 | 13.336 | 8.876 | 1.00 | 57.55 | C |
| ATOM | 2452 | CG | MET | B | 37 | −58.598 | 14.040 | 7.522 | 1.00 | 68.05 | C |
| ATOM | 2453 | SD | MET | B | 37 | −58.898 | 12.990 | 6.060 | 1.00 | 65.29 | S |
| ATOM | 2454 | CE | MET | B | 37 | −57.306 | 12.187 | 5.890 | 1.00 | 66.73 | C |
| ATOM | 2455 | C | MET | B | 37 | −61.243 | 12.744 | 8.240 | 1.00 | 55.63 | C |
| ATOM | 2456 | O | MET | B | 37 | −61.882 | 13.529 | 7.574 | 1.00 | 55.93 | O |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2457 | N | ILE | B | 38 | -61.362 | 11.431 | 8.060 | 1.00 | 54.10 | N |
| ATOM | 2458 | CA | ILE | B | 38 | -62.137 | 10.903 | 6.940 | 1.00 | 54.83 | C |
| ATOM | 2459 | CB | ILE | B | 38 | -61.696 | 9.460 | 6.612 | 1.00 | 54.80 | C |
| ATOM | 2460 | CG1 | ILE | B | 38 | -62.105 | 9.074 | 5.192 | 1.00 | 61.72 | C |
| ATOM | 2461 | CD1 | ILE | B | 38 | -61.389 | 9.832 | 4.164 | 1.00 | 55.76 | C |
| ATOM | 2462 | CG2 | ILE | B | 38 | -62.228 | 8.468 | 7.608 | 1.00 | 56.29 | C |
| ATOM | 2463 | C | ILE | B | 38 | -63.649 | 11.004 | 7.217 | 1.00 | 55.47 | C |
| ATOM | 2464 | O | ILE | B | 38 | -64.488 | 10.999 | 6.313 | 1.00 | 55.38 | O |
| ATOM | 2465 | N | LYS | B | 39 | -63.969 | 11.117 | 8.491 | 1.00 | 51.91 | N |
| ATOM | 2466 | CA | LYS | B | 39 | -65.327 | 10.999 | 8.995 | 1.00 | 52.56 | C |
| ATOM | 2467 | CB | LYS | B | 39 | -65.330 | 11.262 | 10.491 | 1.00 | 53.41 | C |
| ATOM | 2468 | CG | LYS | B | 39 | -66.613 | 11.068 | 11.221 | 1.00 | 59.42 | C |
| ATOM | 2469 | CD | LYS | B | 39 | -66.536 | 11.816 | 12.565 | 1.00 | 68.26 | C |
| ATOM | 2470 | CE | LYS | B | 39 | -66.540 | 13.354 | 12.404 | 1.00 | 73.39 | C |
| ATOM | 2471 | NZ | LYS | B | 39 | -67.872 | 13.905 | 11.926 | 1.00 | 67.87 | N |
| ATOM | 2472 | C | LYS | B | 39 | -66.316 | 11.892 | 8.264 | 1.00 | 51.93 | C |
| ATOM | 2473 | O | LYS | B | 39 | -67.308 | 11.371 | 7.771 | 1.00 | 53.09 | O |
| ATOM | 2474 | N | PRO | B | 40 | -66.058 | 13.221 | 8.156 | 1.00 | 49.67 | N |
| ATOM | 2475 | CA | PRO | B | 40 | -67.090 | 13.995 | 7.471 | 1.00 | 50.72 | C |
| ATOM | 2476 | CB | PRO | B | 40 | -66.550 | 15.435 | 7.477 | 1.00 | 51.13 | C |
| ATOM | 2477 | CG | PRO | B | 40 | -65.361 | 15.448 | 8.323 | 1.00 | 48.47 | C |
| ATOM | 2478 | CD | PRO | B | 40 | -64.919 | 14.046 | 8.562 | 1.00 | 47.30 | C |
| ATOM | 2479 | C | PRO | B | 40 | -67.278 | 13.567 | 6.013 | 1.00 | 54.09 | C |
| ATOM | 2480 | O | PRO | B | 40 | -68.421 | 13.623 | 5.497 | 1.00 | 53.51 | O |
| ATOM | 2481 | N | PHE | B | 41 | -66.174 | 13.164 | 5.631 | 1.00 | 49.95 | N |
| ATOM | 2482 | CA | PHE | B | 41 | -66.160 | 12.850 | 3.921 | 1.00 | 50.55 | C |
| ATOM | 2483 | CB | PHE | B | 41 | -64.729 | 12.648 | 3.417 | 1.00 | 50.07 | C |
| ATOM | 2484 | CG | PHE | B | 41 | -63.885 | 13.888 | 3.496 | 1.00 | 55.50 | C |
| ATOM | 2485 | CD1 | PHE | B | 41 | -62.736 | 13.920 | 4.300 | 1.00 | 63.07 | C |
| ATOM | 2486 | CD2 | PHE | B | 41 | -61.949 | 15.078 | 4.380 | 1.00 | 62.78 | C |
| ATOM | 2487 | CZ | PHE | B | 41 | -62.310 | 16.222 | 3.669 | 1.00 | 61.97 | C |
| ATOM | 2488 | CE2 | PHE | B | 41 | -63.474 | 16.212 | 2.863 | 1.00 | 59.36 | C |
| ATOM | 2489 | CD2 | PHE | B | 41 | -64.250 | 15.045 | 2.793 | 1.00 | 59.63 | C |
| ATOM | 2490 | C | PHE | B | 41 | -67.002 | 11.636 | 3.655 | 1.00 | 50.15 | C |
| ATOM | 2491 | O | PHE | B | 41 | -67.742 | 11.574 | 2.670 | 1.00 | 49.98 | O |
| ATOM | 2492 | N | PHE | B | 42 | -66.926 | 10.698 | 4.581 | 1.00 | 49.30 | N |
| ATOM | 2493 | CA | PHE | B | 42 | -67.724 | 9.491 | 4.538 | 1.00 | 51.33 | C |
| ATOM | 2494 | CB | PHE | B | 42 | -66.252 | 5.576 | 5.653 | 1.00 | 47.38 | C |
| ATOM | 2495 | CG | PHE | B | 42 | -67.884 | 7.225 | 5.632 | 1.00 | 53.81 | C |
| ATOM | 2496 | CD1 | PHE | B | 42 | -67.562 | 6.311 | 4.650 | 1.00 | 43.57 | C |
| ATOM | 2497 | CE1 | PHE | B | 42 | -68.119 | 5.062 | 4.642 | 1.00 | 49.34 | C |
| ATOM | 2498 | CZ | PHE | B | 42 | -69.026 | 4.711 | 5.612 | 1.00 | 49.69 | C |
| ATOM | 2499 | CE2 | PHE | B | 42 | -69.397 | 5.613 | 6.593 | 1.00 | 55.31 | C |
| ATOM | 2500 | CD2 | PHE | B | 42 | -68.799 | 6.861 | 6.609 | 1.00 | 53.23 | C |
| ATOM | 2501 | C | PHE | B | 42 | -69.240 | 9.796 | 4.681 | 1.00 | 53.77 | C |
| ATOM | 2502 | O | PHE | B | 42 | -70.096 | 9.119 | 4.079 | 1.00 | 52.55 | O |
| ATOM | 2503 | N | HIS | B | 43 | -69.559 | 10.810 | 5.480 | 1.00 | 54.93 | N |
| ATOM | 2504 | CA | HIS | B | 43 | -70.941 | 11.285 | 5.606 | 1.00 | 57.23 | C |
| ATOM | 2505 | CB | HIS | B | 43 | -71.083 | 12.123 | 6.892 | 1.00 | 56.17 | C |
| ATOM | 2506 | CG | HIS | B | 43 | -72.462 | 12.678 | 7.111 | 1.00 | 64.27 | O |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2507 | ND1 | HIS | B | 43 | -72.816 | 13.959 | 6.740 | 1.00 | 65.07 | N |
| ATOM | 2508 | CE1 | HIS | B | 43 | -74.084 | 14.167 | 7.047 | 1.00 | 62.50 | C |
| ATOM | 2509 | NE2 | HIS | B | 43 | -74.562 | 13.074 | 7.617 | 1.00 | 65.00 | N |
| ATOM | 2510 | CD2 | HIS | B | 43 | -73.569 | 12.128 | 7.674 | 1.00 | 60.03 | C |
| ATOM | 2511 | C | HIS | B | 43 | -71.425 | 12.052 | 4.334 | 1.00 | 57.04 | C |
| ATOM | 2512 | O | HIS | B | 43 | -72.525 | 11.802 | 3.810 | 1.00 | 57.41 | O |
| ATOM | 2513 | N | SER | B | 44 | -70.620 | 12.993 | 3.851 | 1.00 | 57.89 | N |
| ATOM | 2514 | CA | SER | B | 44 | -70.908 | 12.655 | 2.581 | 1.00 | 58.73 | C |
| ATOM | 2515 | CB | SER | B | 44 | -69.791 | 14.619 | 2.214 | 1.00 | 59.08 | C |
| ATOM | 2516 | OG | SER | B | 44 | -69.725 | 15.664 | 3.153 | 1.00 | 62.40 | O |
| ATOM | 2517 | C | SER | B | 44 | -71.105 | 12.663 | 1.433 | 1.00 | 59.01 | C |
| ATOM | 2518 | O | SER | B | 44 | -71.918 | 12.917 | 0.556 | 1.00 | 62.70 | O |
| ATOM | 2519 | N | LEU | B | 45 | -70.350 | 11.561 | 1.412 | 1.00 | 56.05 | N |
| ATOM | 2520 | CA | LEU | B | 45 | -70.538 | 10.495 | 0.409 | 1.00 | 55.15 | C |
| ATOM | 2521 | CB | LEU | B | 45 | -69.388 | 9.482 | 0.433 | 1.00 | 55.68 | C |
| ATOM | 2522 | CG | LEU | B | 45 | -68.044 | 9.836 | -0.230 | 1.00 | 50.95 | C |
| ATOM | 2523 | CD1 | LEU | B | 45 | -66.911 | 8.930 | 0.197 | 1.00 | 52.59 | C |
| ATOM | 2524 | CD2 | LEU | B | 45 | -68.158 | 9.848 | -1.753 | 1.00 | 45.10 | C |
| ATOM | 2525 | C | LEU | B | 45 | -71.878 | 9.778 | 0.571 | 1.00 | 57.81 | C |
| ATOM | 2526 | O | LEU | B | 45 | -72.470 | 9.325 | -0.412 | 1.00 | 57.57 | O |
| ATOM | 2527 | N | SER | B | 46 | -72.366 | 9.693 | 1.809 | 1.00 | 57.56 | N |
| ATOM | 2528 | CA | SER | B | 46 | -73.624 | 9.012 | 2.080 | 1.00 | 56.39 | C |
| ATOM | 2529 | CB | SER | B | 46 | -73.779 | 8.693 | 3.568 | 1.00 | 56.81 | C |
| ATOM | 2530 | OG | SER | B | 46 | -73.792 | 9.878 | 4.333 | 1.00 | 53.03 | O |
| ATOM | 2531 | C | SER | B | 46 | -74.832 | 9.796 | 1.601 | 1.00 | 55.98 | C |
| ATOM | 2532 | O | SER | B | 46 | -74.866 | 9.192 | 1.271 | 1.00 | 55.04 | O |
| ATOM | 2533 | N | GLU | B | 47 | -74.710 | 11.127 | 1.599 | 1.00 | 54.89 | N |
| ATOM | 2534 | CA | GLU | B | 47 | -75.749 | 12.001 | 1.068 | 1.00 | 56.15 | C |
| ATOM | 2535 | CB | GLU | B | 47 | -75.538 | 13.466 | 1.474 | 1.00 | 57.93 | C |
| ATOM | 2536 | CG | GLU | B | 47 | -75.075 | 13.702 | 2.905 | 1.00 | 64.07 | C |
| ATOM | 2537 | CD | GLU | B | 47 | -76.182 | 13.611 | 3.940 | 1.00 | 67.13 | C |
| ATOM | 2538 | OE1 | GLU | B | 47 | -76.491 | 14.663 | 4.541 | 1.00 | 71.01 | O |
| ATOM | 2539 | OE2 | GLU | B | 47 | -76.738 | 12.505 | 4.165 | 1.00 | 70.04 | O |
| ATOM | 2540 | C | GLU | B | 47 | -75.718 | 11.910 | -0.448 | 1.00 | 54.94 | C |
| ATOM | 2541 | O | GLU | B | 47 | -76.774 | 11.802 | -1.099 | 1.00 | 50.25 | O |
| ATOM | 2542 | N | LYS | B | 48 | -74.505 | 11.960 | -1.013 | 1.00 | 50.68 | N |
| ATOM | 2543 | CA | LYS | B | 48 | -74.364 | 11.906 | -2.460 | 1.00 | 52.36 | C |
| ATOM | 2544 | CB | LYS | B | 48 | -72.928 | 12.151 | -2.935 | 1.00 | 48.56 | C |
| ATOM | 2545 | CG | LYS | B | 48 | -72.867 | 12.743 | -4.339 | 1.00 | 46.19 | C |
| ATOM | 2546 | CD | LYS | B | 48 | -71.640 | 12.340 | -5.105 | 1.00 | 47.88 | C |
| ATOM | 2547 | CE | LYS | B | 48 | -71.529 | 13.079 | -6.428 | 1.00 | 41.47 | C |
| ATOM | 2548 | NZ | LYS | B | 48 | -72.456 | 12.571 | -7.473 | 1.00 | 53.95 | N |
| ATOM | 2549 | C | LYS | B | 48 | -74.895 | 10.592 | -3.029 | 1.00 | 54.58 | C |
| ATOM | 2550 | O | LYS | B | 48 | -75.798 | 10.585 | -3.886 | 1.00 | 57.75 | O |
| ATOM | 2551 | N | TYR | B | 49 | -74.375 | 9.491 | -2.508 | 1.00 | 53.74 | N |
| ATOM | 2552 | CA | TYR | B | 49 | -74.646 | 8.168 | -3.058 | 1.00 | 55.98 | C |
| ATOM | 2553 | CB | TYR | B | 49 | -73.348 | 7.318 | -3.081 | 1.00 | 56.33 | C |
| ATOM | 2554 | CG | TYR | B | 49 | -72.263 | 7.851 | -4.026 | 1.00 | 59.28 | C |
| ATOM | 2555 | CD1 | TYR | B | 49 | -72.265 | 7.511 | -5.379 | 1.00 | 56.67 | C |
| ATOM | 2556 | CE1 | TYR | B | 49 | -71.287 | 8.001 | -6.256 | 1.00 | 61.89 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2557 | CZ | TYR | B | 49 | −70.278 | 8.839 | −5.788 | 1.00 | 63.01 | C |
| ATOM | 2558 | OH | TYR | B | 49 | −69.310 | 9.303 | −6.675 | 1.00 | 52.60 | O |
| ATOM | 2559 | CE2 | TYR | B | 49 | −70.253 | 9.199 | −4.442 | 1.00 | 57.35 | C |
| ATOM | 2560 | CD2 | TYR | B | 49 | −71.246 | 8.701 | −3.566 | 1.00 | 59.15 | C |
| ATOM | 2561 | C | TYR | B | 49 | −79.793 | 7.492 | −2.293 | 1.00 | 55.11 | C |
| ATOM | 2562 | O | TYR | B | 49 | −75.589 | 6.517 | −1.579 | 1.00 | 53.87 | O |
| ATOM | 2563 | N | SER | B | 50 | −77.011 | 8.021 | −2.467 | 1.00 | 56.81 | N |
| ATOM | 2564 | CA | SER | B | 50 | −78.208 | 7.515 | −1.760 | 1.00 | 57.36 | C |
| ATOM | 2565 | CB | SER | B | 50 | −79.378 | 8.485 | −1.936 | 1.00 | 57.43 | C |
| ATOM | 2566 | OG | SER | B | 50 | −79.769 | 8.544 | −3.299 | 1.00 | 57.14 | O |
| ATOM | 2567 | C | SER | B | 50 | −78.626 | 6.082 | −2.160 | 1.00 | 59.00 | C |
| ATOM | 2568 | O | SER | B | 50 | −79.366 | 5.404 | −1.433 | 1.00 | 59.70 | O |
| ATOM | 2569 | N | ASN | B | 51 | −78.143 | 5.635 | −3.317 | 1.00 | 60.79 | N |
| ATOM | 2570 | CA | ASN | B | 51 | −78.294 | 4.252 | −3.784 | 1.00 | 62.06 | C |
| ATOM | 2571 | CB | ASN | B | 51 | −77.968 | 4.174 | −5.288 | 1.00 | 64.24 | C |
| ATOM | 2572 | CG | ASN | B | 51 | −76.599 | 4.812 | −5.648 | 1.00 | 68.96 | C |
| ATOM | 2573 | OD1 | ASN | B | 51 | −76.233 | 5.888 | −5.148 | 1.00 | 59.81 | O |
| ATOM | 2574 | ND2 | ASN | B | 51 | −75.856 | 4.147 | −6.543 | 1.00 | 67.94 | N |
| ATOM | 2575 | C | ASN | B | 51 | −77.435 | 3.240 | −3.001 | 1.00 | 61.43 | C |
| ATOM | 2576 | O | ASN | B | 51 | −77.637 | 2.024 | −3.105 | 1.00 | 61.19 | O |
| ATOM | 2577 | N | VAL | B | 52 | −76.476 | 3.752 | −2.227 | 1.00 | 60.48 | N |
| ATOM | 2578 | CA | VAL | B | 52 | −75.559 | 2.918 | −1.427 | 1.00 | 59.08 | C |
| ATOM | 2579 | CB | VAL | B | 52 | −74.075 | 3.216 | −1.773 | 1.00 | 59.13 | C |
| ATOM | 2580 | CG1 | VAL | B | 52 | −73.095 | 2.500 | −0.801 | 1.00 | 59.98 | C |
| ATOM | 2581 | CG2 | VAL | B | 52 | −73.781 | 2.830 | −3.209 | 1.00 | 56.79 | C |
| ATOM | 2582 | C | VAL | B | 52 | −75.824 | 3.109 | 0.067 | 1.00 | 58.02 | C |
| ATOM | 2583 | O | VAL | B | 52 | −76.135 | 4.222 | 0.512 | 1.00 | 55.61 | O |
| ATOM | 2584 | N | ILE | B | 53 | −75.712 | 2.023 | 0.834 | 1.00 | 59.06 | N |
| ATOM | 2585 | CA | ILE | B | 53 | −75.948 | 2.088 | 2.279 | 1.00 | 60.35 | C |
| ATOM | 2586 | CB | ILE | B | 53 | −76.903 | 0.941 | 2.763 | 1.00 | 62.15 | C |
| ATOM | 2587 | CG1 | ILE | B | 53 | −77.998 | 1.473 | 3.709 | 1.00 | 69.19 | C |
| ATOM | 2588 | CD1 | ILE | B | 53 | −79.341 | 0.706 | 3.599 | 1.00 | 62.15 | C |
| ATOM | 2589 | CG2 | ILE | B | 53 | −76.173 | −0.240 | 3.352 | 1.00 | 56.76 | C |
| ATOM | 2590 | C | ILE | B | 53 | −74.622 | 2.211 | 3.069 | 1.00 | 62.56 | C |
| ATOM | 2591 | O | ILE | B | 53 | −73.711 | 1.377 | 2.943 | 1.00 | 61.03 | O |
| ATOM | 2592 | N | PHE | B | 54 | −74.525 | 3.290 | 3.843 | 1.00 | 62.45 | N |
| ATOM | 2593 | CA | PHE | B | 54 | −73.340 | 3.586 | 4.638 | 1.00 | 64.58 | C |
| ATOM | 2594 | CB | PHE | B | 54 | −73.017 | 5.075 | 4.557 | 1.00 | 63.25 | C |
| ATOM | 2595 | CG | PHE | B | 54 | −72.518 | 5.498 | 3.227 | 1.00 | 68.83 | C |
| ATOM | 2596 | CD1 | PHE | B | 54 | −73.357 | 5.440 | 2.098 | 1.00 | 67.13 | C |
| ATOM | 2597 | CE1 | PHE | B | 54 | −72.892 | 5.831 | 0.850 | 1.00 | 68.02 | C |
| ATOM | 2598 | CZ | PHE | B | 54 | −71.578 | 6.300 | 0.718 | 1.00 | 67.07 | C |
| ATOM | 2599 | CE2 | PHE | B | 54 | −70.737 | 6.361 | 1.842 | 1.00 | 64.34 | C |
| ATOM | 2600 | CD2 | PHE | B | 54 | −71.212 | 5.959 | 3.084 | 1.00 | 57.25 | C |
| ATOM | 2601 | C | PHE | B | 54 | −73.543 | 3.179 | 6.078 | 1.00 | 63.06 | C |
| ATOM | 2602 | O | PHE | B | 54 | −74.607 | 3.417 | 6.640 | 1.00 | 64.11 | O |
| ATOM | 2603 | N | LEU | B | 55 | −72.515 | 2.564 | 6.659 | 1.00 | 63.22 | N |
| ATOM | 2604 | CA | LEU | B | 55 | −72.515 | 2.108 | 8.051 | 1.00 | 62.80 | C |
| ATOM | 2605 | CB | LEU | B | 55 | −72.686 | 0.582 | 8.142 | 1.00 | 62.48 | C |
| ATOM | 2606 | CG | LEU | B | 55 | −73.862 | −0.124 | 7.454 | 1.00 | 62.42 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2607 | CD1 | LEU | B | 55 | −73.820 | −1.645 | 7.694 | 1.00 | 59.97 | C |
| ATOM | 2608 | CD2 | LEU | B | 55 | −75.196 | 0.462 | 7.891 | 1.00 | 57.51 | C |
| ATOM | 2609 | C | LEU | B | 55 | −71.198 | 2.487 | 8.747 | 1.00 | 63.37 | C |
| ATOM | 2610 | O | LEU | B | 55 | −70.142 | 2.505 | 8.101 | 1.00 | 62.04 | O |
| ATOM | 2611 | N | GLU | B | 56 | −71.273 | 2.779 | 10.048 | 1.00 | 63.37 | N |
| ATOM | 2612 | CA | GLU | B | 56 | −70.101 | 3.058 | 10.872 | 1.00 | 63.56 | C |
| ATOM | 2613 | CB | GLU | B | 56 | −70.076 | 4.518 | 11.350 | 1.00 | 63.69 | C |
| ATOM | 2614 | CG | GLU | B | 56 | −68.906 | 4.831 | 12.805 | 1.00 | 67.73 | C |
| ATOM | 2615 | CD | GLU | B | 56 | −68.420 | 6.278 | 12.250 | 1.00 | 69.84 | C |
| ATOM | 2616 | OE1 | GLU | B | 56 | −69.003 | 7.097 | 11.512 | 1.00 | 75.90 | O |
| ATOM | 2617 | OE2 | GLU | B | 56 | −67.440 | 6.598 | 12.952 | 1.00 | 70.61 | O |
| ATOM | 2618 | C | GLU | B | 56 | −70.033 | 2.100 | 12.073 | 1.00 | 63.88 | C |
| ATOM | 2619 | O | GLU | B | 56 | −71.000 | 1.948 | 12.814 | 1.00 | 62.95 | O |
| ATOM | 2620 | N | VAL | B | 57 | −68.879 | 1.462 | 12.247 | 1.00 | 64.15 | N |
| ATOM | 2621 | CA | VAL | B | 57 | −68.591 | 0.619 | 13.413 | 1.00 | 62.52 | C |
| ATOM | 2622 | CB | VAL | B | 57 | −68.354 | −0.849 | 12.995 | 1.00 | 62.67 | C |
| ATOM | 2623 | CG1 | VAL | B | 57 | −67.864 | −1.694 | 14.191 | 1.00 | 61.42 | C |
| ATOM | 2624 | CG2 | VAL | B | 57 | −69.647 | −1.439 | 12.382 | 1.00 | 63.80 | C |
| ATOM | 2625 | C | VAL | B | 57 | −67.356 | −1.147 | 14.162 | 1.00 | 63.82 | C |
| ATOM | 2626 | O | VAL | B | 57 | −66.249 | 1.228 | 13.606 | 1.00 | 61.91 | O |
| ATOM | 2627 | N | ASP | B | 58 | −67.548 | 1.512 | 15.424 | 1.00 | 64.22 | N |
| ATOM | 2628 | CA | ASP | B | 58 | −66.442 | 1.932 | 16.252 | 1.00 | 62.38 | C |
| ATOM | 2629 | CB | ASP | B | 58 | −66.914 | 2.861 | 17.380 | 1.00 | 61.21 | C |
| ATOM | 2630 | CG | ASP | B | 58 | −65.777 | 3.332 | 18.268 | 1.00 | 62.92 | C |
| ATOM | 2631 | OD1 | ASP | B | 58 | −65.028 | 2.486 | 18.792 | 1.00 | 69.56 | O |
| ATOM | 2632 | OD2 | ASP | B | 58 | −65.633 | 4.557 | 18.460 | 1.00 | 66.92 | O |
| ATOM | 2633 | C | ASP | B | 58 | −65.748 | 0.697 | 16.818 | 1.00 | 62.29 | C |
| ATOM | 2634 | O | ASP | B | 58 | −66.299 | −0.025 | 17.661 | 1.00 | 60.41 | O |
| ATOM | 2635 | N | VAL | B | 59 | −64.522 | 0.476 | 16.352 | 1.00 | 58.73 | N |
| ATOM | 2636 | CA | VAL | B | 59 | −63.778 | −0.737 | 16.677 | 1.00 | 56.64 | C |
| ATOM | 2637 | CB | VAL | B | 59 | −62.377 | −0.753 | 15.994 | 1.00 | 57.33 | C |
| ATOM | 2638 | CG1 | VAL | B | 59 | −62.510 | −0.641 | 14.476 | 1.00 | 54.19 | C |
| ATOM | 2639 | CG2 | VAL | B | 59 | −61.472 | 0.316 | 16.547 | 1.00 | 53.05 | C |
| ATOM | 2640 | C | VAL | B | 59 | −63.629 | −0.997 | 18.179 | 1.00 | 54.13 | C |
| ATOM | 2641 | O | VAL | B | 59 | −63.484 | −2.148 | 18.585 | 1.00 | 52.98 | O |
| ATOM | 2642 | N | ASP | B | 60 | −63.650 | 0.065 | 18.988 | 1.00 | 53.49 | N |
| ATOM | 2643 | CA | ASP | B | 60 | −63.419 | −0.054 | 20.443 | 1.00 | 56.58 | C |
| ATOM | 2644 | CB | ASP | B | 60 | −62.726 | 1.191 | 20.987 | 1.00 | 54.67 | C |
| ATOM | 2645 | CG | ASP | B | 60 | −61.319 | 1.345 | 20.467 | 1.00 | 61.90 | C |
| ATOM | 2646 | OD1 | ASP | B | 60 | −60.950 | 2.481 | 20.080 | 1.00 | 67.77 | O |
| ATOM | 2647 | OD2 | ASP | B | 60 | −60.594 | 0.326 | 20.431 | 1.00 | 49.09 | O |
| ATOM | 2648 | C | ASP | B | 60 | −64.702 | −0.291 | 21.246 | 1.00 | 58.77 | C |
| ATOM | 2649 | O | ASP | B | 60 | −64.674 | −0.398 | 22.464 | 1.00 | 58.02 | O |
| ATOM | 2650 | N | ASP | B | 61 | −65.830 | −0.342 | 20.562 | 1.00 | 61.71 | N |
| ATOM | 2651 | CA | ASP | B | 61 | −67.092 | −0.516 | 21.246 | 1.00 | 65.81 | C |
| ATOM | 2652 | CB | ASP | B | 61 | −68.032 | 0.654 | 20.958 | 1.00 | 66.59 | C |
| ATOM | 2653 | CG | ASP | B | 61 | −67.621 | 1.924 | 21.692 | 1.00 | 69.89 | C |
| ATOM | 2654 | OD1 | ASP | B | 61 | −66.694 | 1.858 | 22.544 | 1.00 | 75.28 | O |
| ATOM | 2655 | OD2 | ASP | B | 61 | −68.223 | 2.988 | 21.411 | 1.00 | 72.04 | O |
| ATOM | 2656 | C | ASP | B | 61 | −67.669 | −1.828 | 20.783 | 1.00 | 67.66 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2657 | O | ASP | B | 61 | −68.110 | −2.643 | 21.598 | 1.00 | 69.38 | O |
| ATOM | 2658 | N | CYS | B | 62 | −67.623 | −2.031 | 19.471 | 1.00 | 66.83 | N |
| ATOM | 2659 | CA | CYS | B | 62 | −68.007 | −3.288 | 18.875 | 1.00 | 68.21 | C |
| ATOM | 2660 | CB | CYS | B | 62 | −68.784 | −3.024 | 17.589 | 1.00 | 70.54 | C |
| ATOM | 2661 | SG | CYS | B | 62 | −70.146 | −1.877 | 17.748 | 1.00 | 74.64 | S |
| ATOM | 2662 | C | CYS | B | 62 | −66.781 | −4.133 | 18.570 | 1.00 | 68.13 | C |
| ATOM | 2663 | O | CYS | B | 62 | −66.658 | −4.653 | 17.465 | 1.00 | 67.74 | O |
| ATOM | 2664 | N | GLN | B | 63 | −65.885 | −4.280 | 19.551 | 1.00 | 69.60 | N |
| ATOM | 2665 | CA | GLN | B | 63 | −64.721 | −5.173 | 19.428 | 1.00 | 70.93 | C |
| ATOM | 2666 | CB | GLN | B | 63 | −63.991 | −5.350 | 20.774 | 1.00 | 70.77 | C |
| ATOM | 2667 | CG | GLN | B | 63 | −63.381 | −4.065 | 21.351 | 1.00 | 74.80 | C |
| ATOM | 2668 | CD | GLN | B | 63 | −61.897 | −4.198 | 21.727 | 1.00 | 79.35 | C |
| ATOM | 2669 | OE1 | GLN | B | 63 | −61.490 | −5.158 | 22.387 | 1.00 | 76.60 | O |
| ATOM | 2670 | NE2 | GLN | B | 63 | −61.086 | −3.218 | 21.304 | 1.00 | 74.47 | N |
| ATOM | 2671 | C | GLN | B | 63 | −65.108 | −6.540 | 18.848 | 1.00 | 70.88 | C |
| ATOM | 2672 | O | GLN | B | 63 | −64.278 | −7.221 | 18.232 | 1.00 | 71.46 | O |
| ATOM | 2673 | N | ASP | B | 64 | −66.375 | −6.913 | 19.041 | 1.00 | 69.95 | N |
| ATOM | 2674 | CA | ASP | B | 64 | −66.942 | −8.168 | 18.554 | 1.00 | 69.29 | C |
| ATOM | 2675 | CB | ASP | B | 64 | −68.373 | −8.376 | 19.098 | 1.00 | 70.92 | C |
| ATOM | 2676 | CG | ASP | B | 64 | −68.734 | −7.414 | 20.231 | 1.00 | 73.43 | C |
| ATOM | 2677 | OD1 | ASP | B | 64 | −67.956 | −7.311 | 21.205 | 1.00 | 76.86 | O |
| ATOM | 2678 | OD2 | ASP | B | 64 | −69.804 | −6.766 | 20.147 | 1.00 | 72.28 | O |
| ATOM | 2679 | C | ASP | B | 64 | −66.963 | −8.232 | 17.022 | 1.00 | 87.08 | C |
| ATOM | 2680 | O | ASP | B | 64 | −66.361 | −9.129 | 16.427 | 1.00 | 66.64 | O |
| ATOM | 2681 | N | VAL | B | 65 | −67.669 | −7.292 | 16.395 | 1.00 | 64.88 | N |
| ATOM | 2682 | CA | VAL | B | 65 | −67.791 | −7.278 | 14.930 | 1.00 | 64.96 | C |
| ATOM | 2683 | CB | VAL | B | 65 | −68.989 | −6.391 | 14.409 | 1.00 | 64.22 | C |
| ATOM | 2684 | CG1 | VAL | B | 65 | −68.962 | −5.002 | 14.990 | 1.00 | 61.40 | C |
| ATOM | 2685 | OG2 | VAL | B | 65 | −69.017 | −6.338 | 12.889 | 1.00 | 62.68 | O |
| ATOM | 2686 | C | VAL | B | 65 | −66.438 | −6.991 | 14.245 | 1.00 | 64.72 | C |
| ATOM | 2687 | O | VAL | B | 65 | −66.099 | −7.618 | 13.231 | 1.00 | 63.79 | O |
| ATOM | 2688 | N | ALA | B | 66 | −65.671 | −6.070 | 14.835 | 1.00 | 55.33 | N |
| ATOM | 2689 | CA | ALA | B | 66 | −64.274 | −5.823 | 14.474 | 1.00 | 63.44 | C |
| ATOM | 2690 | CB | ALA | B | 66 | −63.613 | −4.948 | 15.529 | 1.00 | 63.30 | C |
| ATOM | 2691 | C | ALA | B | 66 | −63.502 | −7.128 | 14.307 | 1.00 | 62.90 | C |
| ATOM | 2692 | O | ALA | B | 66 | −62.990 | −7.419 | 13.227 | 1.00 | 62.60 | O |
| ATOM | 2693 | N | SER | B | 67 | −63.445 | −7.918 | 15.375 | 1.00 | 62.98 | N |
| ATOM | 2694 | CA | SER | B | 67 | −62.736 | −9.199 | 15.378 | 1.00 | 64.25 | C |
| ATOM | 2695 | CB | SER | B | 67 | −62.908 | −9.875 | 16.738 | 1.00 | 64.15 | C |
| ATOM | 2696 | OG | SER | B | 67 | −62.982 | −11.291 | 16.634 | 1.00 | 70.98 | O |
| ATOM | 2697 | C | SER | B | 67 | −63.164 | −10.147 | 14.248 | 1.00 | 64.73 | C |
| ATOM | 2698 | O | SER | B | 67 | −62.316 | −10.784 | 13.606 | 1.00 | 65.04 | O |
| ATOM | 2699 | N | GLU | B | 68 | −64.477 | −11.221 | 14.020 | 1.00 | 63.80 | N |
| ATOM | 2700 | CA | GLU | B | 68 | −65.090 | −11.151 | 13.070 | 1.00 | 62.75 | C |
| ATOM | 2701 | CB | GLU | B | 68 | −66.584 | −11.276 | 13.304 | 1.00 | 62.49 | C |
| ATOM | 2702 | CG | GLU | B | 68 | −67.196 | −12.612 | 12.955 | 1.00 | 63.78 | C |
| ATOM | 2703 | CD | GLU | B | 68 | −68.708 | −12.552 | 12.853 | 1.00 | 63.54 | C |
| ATOM | 2704 | OE1 | GLU | B | 68 | −69.237 | −11.525 | 12.360 | 1.00 | 64.98 | O |
| ATOM | 2705 | OE2 | GLU | B | 68 | −69.363 | −13.533 | 13.261 | 1.00 | 56.63 | O |
| ATOM | 2706 | C | GLU | B | 68 | −64.888 | −10.728 | 11.616 | 1.00 | 62.65 | C |

TABLE 10-continued

Atomic coordinates for COM1 complex of the modified TXNIP protein represented by SEQ ID NO: 6 and the modified protein represented by SEQ ID NO: 3

| | | | | | | | | | | |
|---|---|---|---|---|---|---|---|---|---|---|
| ATOM | 2707 | O | GLU | B | 68 | −64.887 | −11.573 | 10.713 | 1.00 | 62.51 | O |
| ATOM | 2708 | N | CYS | B | 69 | −64.756 | −9.416 | 11.400 | 1.00 | 61.15 | N |
| ATOM | 2709 | CA | CYS | B | 69 | −64.431 | −8.843 | 10.090 | 1.00 | 59.86 | C |
| ATOM | 2710 | CB | CYS | B | 69 | −65.032 | −7.441 | 9.958 | 1.00 | 60.35 | C |
| ATOM | 2711 | SG | CYS | B | 69 | −66.844 | −7.400 | 10.076 | 1.00 | 64.87 | S |
| ATOM | 2712 | C | CYS | B | 69 | −62.916 | −8.784 | 9.876 | 1.00 | 57.62 | C |
| ATOM | 2713 | O | CYS | B | 69 | −62.437 | −8.446 | 8.785 | 1.00 | 55.42 | O |
| ATOM | 2714 | N | GLU | B | 70 | −62.180 | −9.135 | 10.933 | 1.00 | 55.82 | N |
| ATOM | 2715 | CA | GLU | B | 70 | −60.714 | −9.117 | 10.947 | 1.00 | 55.45 | C |
| ATOM | 2716 | CB | GLU | B | 70 | −60.135 | −10.265 | 10.114 | 1.00 | 56.06 | C |
| ATOM | 2717 | CG | GLU | B | 70 | −60.513 | −11.645 | 10.628 | 1.00 | 57.67 | C |
| ATOM | 2718 | CD | GLU | B | 70 | −60.289 | −12.718 | 9.596 | 1.00 | 61.02 | C |
| ATOM | 2719 | OE1 | GLU | B | 70 | −59.548 | −12.452 | 8.625 | 1.00 | 60.26 | O |
| ATOM | 2720 | OE2 | GLU | B | 70 | −60.851 | −13.823 | 9.754 | 1.00 | 64.93 | O |
| ATOM | 2721 | C | GLU | B | 70 | −60.160 | −7.763 | 10.504 | 1.00 | 54.32 | C |
| ATOM | 2722 | O | GLU | B | 70 | −59.322 | −7.683 | 9.601 | 1.00 | 54.63 | O |
| ATOM | 2723 | N | VAL | B | 71 | −60.684 | −6.716 | 11.138 | 1.00 | 52.28 | N |
| ATOM | 2724 | CA | VAL | B | 71 | −60.175 | −5.358 | 11.043 | 1.00 | 53.40 | C |
| ATOM | 2725 | CB | VAL | B | 71 | −61.260 | −4.348 | 11.459 | 1.00 | 50.63 | C |
| ATOM | 2726 | CG1 | VAL | B | 71 | −60.695 | −2.958 | 11.578 | 1.00 | 50.15 | C |
| ATOM | 2727 | CG2 | VAL | B | 71 | −62.349 | −4.325 | 10.426 | 1.00 | 55.05 | C |
| ATOM | 2728 | C | VAL | B | 71 | −58.920 | −5.248 | 11.937 | 1.00 | 56.03 | C |
| ATOM | 2729 | O | VAL | B | 71 | −58.908 | −5.714 | 13.076 | 1.00 | 57.50 | O |
| ATOM | 2730 | N | LYS | B | 72 | −57.859 | −4.660 | 11.399 | 1.00 | 56.14 | N |
| ATOM | 2731 | CA | LYS | B | 72 | −55.574 | −4.659 | 12.070 | 1.00 | 55.82 | C |
| ATOM | 2732 | CB | LYS | B | 72 | −55.596 | −5.577 | 11.335 | 1.00 | 53.53 | C |
| ATOM | 2733 | CG | LYS | B | 72 | −55.901 | −7.061 | 11.553 | 1.00 | 61.39 | C |
| ATOM | 2734 | CD | LYS | B | 72 | −55.155 | −7.982 | 10.581 | 1.00 | 68.22 | C |
| ATOM | 2735 | CE | LYS | B | 72 | −55.028 | −8.435 | 9.394 | 1.00 | 68.77 | C |
| ATOM | 2736 | NZ | LYS | B | 72 | −55.497 | −9.710 | 8.820 | 1.00 | 64.65 | N |
| ATOM | 2737 | C | LYS | B | 72 | −56.053 | −3.238 | 12.162 | 1.00 | 55.61 | C |
| ATOM | 2738 | O | LYS | B | 72 | −55.067 | −2.985 | 12.847 | 1.00 | 57.72 | O |
| ATOM | 2739 | N | CYS | B | 73 | −56.737 | −2.319 | 11.478 | 1.00 | 52.46 | N |
| ATOM | 2740 | CA | CYS | B | 73 | −56.362 | −0.921 | 11.480 | 1.00 | 51.52 | C |
| ATOM | 2741 | CB | CYS | B | 73 | −55.188 | −0.675 | 10.517 | 1.00 | 47.10 | C |
| ATOM | 2742 | SG | CYS | B | 73 | −55.545 | −0.945 | 8.776 | 1.00 | 52.97 | S |
| ATOM | 2743 | C | CYS | B | 73 | −57.554 | −0.041 | 11.151 | 1.00 | 52.77 | C |
| ATOM | 2744 | O | CYS | B | 73 | −58.610 | −0.523 | 10.750 | 1.00 | 56.47 | O |
| ATOM | 2745 | N | MET | B | 74 | −57.378 | 1.257 | 11.304 | 1.00 | 50.58 | N |
| ATOM | 2746 | CA | MET | B | 74 | −58.480 | 2.207 | 11.194 | 1.00 | 54.73 | C |
| ATOM | 2747 | CB | MET | B | 74 | −58.968 | 2.645 | 12.583 | 1.00 | 56.45 | C |
| ATOM | 2748 | CG | MET | B | 74 | −59.615 | 1.567 | 13.449 | 1.00 | 57.78 | C |
| ATOM | 2749 | SD | MET | B | 74 | −58.525 | 0.294 | 14.119 | 1.00 | 58.44 | S |
| ATOM | 2750 | CE | MET | B | 74 | −57.632 | 1.204 | 15.395 | 1.00 | 59.05 | C |
| ATOM | 2751 | C | MET | B | 74 | −57.949 | 3.438 | 10.488 | 1.00 | 54.83 | C |
| ATOM | 2752 | O | MET | B | 74 | −56.783 | 3.807 | 10.722 | 1.00 | 53.75 | O |
| ATOM | 2753 | N | PRO | B | 75 | −58.772 | 4.087 | 9.635 | 1.00 | 53.71 | N |
| ATOM | 2754 | CA | PRO | B | 75 | −60.087 | 3.601 | 9.168 | 1.00 | 55.53 | C |
| ATOM | 2755 | CB | PRO | B | 75 | −60.687 | 4.794 | 8.368 | 1.00 | 55.24 | C |
| ATOM | 2756 | CG | PRO | B | 75 | −59.576 | 5.727 | 8.101 | 1.00 | 57.47 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2757 | CD  | PRO | B | 75 | -58.391 | 5.377  | 9.031  | 1.00 | 50.85 | C |
| ATOM | 2758 | C   | PRO | B | 75 | -59.873 | 2.428  | 8.254  | 1.00 | 55.41 | C |
| ATOM | 2759 | O   | PRO | B | 75 | -58.973 | 2.482  | 7.411  | 1.00 | 55.92 | O |
| ATOM | 2760 | N   | THR | B | 76 | -60.646 | 1.358  | 8.448  | 1.00 | 53.09 | N |
| ATOM | 2761 | CA  | THR | B | 76 | -60.785 | -0.339 | 7.422  | 1.00 | 53.93 | C |
| ATOM | 2762 | CB  | THR | B | 76 | -60.494 | -1.073 | 7.956  | 1.00 | 54.95 | C |
| ATOM | 2763 | OG1 | THR | B | 76 | -59.092 | -1.237 | 8.190  | 1.00 | 56.63 | O |
| ATOM | 2764 | OG2 | THR | B | 76 | -60.960 | -2.133 | 6.977  | 1.00 | 58.21 | O |
| ATOM | 2765 | C   | THR | B | 76 | -62.210 | 0.387  | 6.848  | 1.00 | 53.87 | C |
| ATOM | 2766 | O   | THR | B | 76 | -63.177 | 0.537  | 7.591  | 1.00 | 54.59 | O |
| ATOM | 2767 | N   | PHE | B | 77 | -62.314 | 0.265  | 5.527  | 1.00 | 54.55 | N |
| ATOM | 2768 | CA  | PHE | B | 77 | -63.600 | 0.234  | 4.818  | 1.00 | 53.54 | C |
| ATOM | 2769 | CB  | PHE | B | 77 | -63.643 | 1.332  | 3.777  | 1.00 | 54.27 | C |
| ATOM | 2770 | CG  | PHE | B | 77 | -63.479 | 2.699  | 4.338  | 1.00 | 50.94 | C |
| ATOM | 2771 | CD1 | PHE | B | 77 | -64.569 | 3.375  | 4.854  | 1.00 | 55.22 | C |
| ATOM | 2772 | CE1 | PHE | B | 77 | -64.422 | 4.663  | 5.385  | 1.00 | 56.15 | C |
| ATOM | 2773 | CZ  | PHE | B | 77 | -63.166 | 5.277  | 5.384  | 1.00 | 60.00 | C |
| ATOM | 2774 | CE2 | PHE | B | 77 | -62.075 | 4.612  | 4.864  | 1.00 | 46.71 | C |
| ATOM | 2775 | CD2 | PHE | B | 77 | -62.281 | 3.322  | 4.337  | 1.00 | 47.02 | C |
| ATOM | 2776 | C   | PHE | B | 77 | -63.841 | -1.123 | 4.151  | 1.00 | 53.42 | C |
| ATOM | 2777 | O   | PHE | B | 77 | -63.022 | -1.607 | 3.372  | 1.00 | 53.57 | O |
| ATOM | 2778 | N   | GLN | B | 78 | -64.963 | -1.749 | 4.481  | 1.00 | 55.54 | N |
| ATOM | 2779 | CA  | GLN | B | 78 | -65.333 | -3.041 | 3.887  | 1.00 | 53.74 | C |
| ATOM | 2780 | CB  | GLN | B | 78 | -65.583 | -4.070 | 4.982  | 1.00 | 53.85 | C |
| ATOM | 2781 | CG  | GLN | B | 78 | -64.484 | -4.191 | 6.008  | 1.00 | 55.91 | C |
| ATOM | 2782 | CD  | GLN | B | 78 | -64.381 | -5.600 | 6.554  | 1.00 | 65.25 | C |
| ATOM | 2783 | OE1 | GLN | B | 78 | -65.382 | -6.320 | 6.631  | 1.00 | 72.09 | O |
| ATOM | 2784 | NE2 | GLN | B | 78 | -63.168 | -6.012 | 6.927  | 1.00 | 65.38 | N |
| ATOM | 2785 | C   | GLN | B | 78 | -66.582 | -2.912 | 3.012  | 1.00 | 51.63 | C |
| ATOM | 2786 | O   | GLN | B | 78 | -67.548 | -2.275 | 3.407  | 1.00 | 50.05 | O |
| ATOM | 2787 | N   | PHE | B | 79 | -66.560 | -3.519 | 1.831  | 1.00 | 52.28 | N |
| ATOM | 2788 | CA  | PHE | B | 79 | -67.668 | -3.352 | 0.887  | 1.00 | 54.23 | C |
| ATOM | 2789 | CB  | PHE | B | 79 | -67.165 | -2.751 | -0.424 | 1.00 | 55.23 | C |
| ATOM | 2790 | CG  | PHE | B | 79 | -66.570 | -1.369 | -0.288 | 1.00 | 55.15 | C |
| ATOM | 2791 | CD1 | PHE | B | 79 | -65.337 | -1.172 | 0.351  | 1.00 | 58.99 | C |
| ATOM | 2792 | CE1 | PHE | B | 79 | -64.776 | -0.105 | 0.465  | 1.00 | 59.25 | C |
| ATOM | 2793 | CZ  | PHE | B | 79 | -65.445 | -1.205 | -0.074 | 1.00 | 53.35 | C |
| ATOM | 2794 | CE2 | PHE | B | 79 | -65.673 | -1.012 | -0.723 | 1.00 | 56.61 | C |
| ATOM | 2795 | CD2 | PHE | B | 79 | -67.215 | -0.270 | -0.839 | 1.00 | 50.52 | C |
| ATOM | 2796 | C   | PHE | B | 79 | -68.346 | -4.685 | 0.609  | 1.00 | 55.82 | C |
| ATOM | 2797 | O   | PHE | B | 79 | -67.671 | -5.680 | 0.300  | 1.00 | 54.37 | O |
| ATOM | 2798 | N   | PHE | B | 80 | -69.678 | -4.697 | 0.712  | 1.00 | 57.98 | N |
| ATOM | 2799 | CA  | PHE | B | 80 | -70.487 | -5.904 | 0.491  | 1.00 | 58.52 | C |
| ATOM | 2800 | CB  | PHE | B | 80 | -71.151 | -6.385 | 1.700  | 1.00 | 57.28 | C |
| ATOM | 2801 | CG  | PHE | B | 80 | -70.237 | -6.420 | 2.985  | 1.00 | 60.59 | C |
| ATOM | 2802 | CD1 | PHE | B | 80 | -69.933 | -5.249 | 3.690  | 1.00 | 58.00 | C |
| ATOM | 2803 | CE1 | PHE | B | 80 | -69.106 | -5.279 | 4.810  | 1.00 | 61.48 | C |
| ATOM | 2804 | CZ  | PHE | B | 80 | -68.567 | -6.496 | 5.241  | 1.00 | 59.77 | C |
| ATOM | 2805 | CE2 | PHE | B | 80 | -68.871 | -7.671 | 4.552  | 1.00 | 65.00 | C |
| ATOM | 2806 | CD2 | PHE | B | 80 | -69.712 | -7.628 | 3.433  | 1.00 | 58.70 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2807 | C | PHE | B | 80 | -71.598 | -5.671 | -0.552 | 1.00 | 60.53 | C |
| ATOM | 2808 | O | PHE | B | 80 | -72.253 | -4.614 | -0.565 | 1.00 | 59.79 | O |
| ATOM | 2809 | N | LYS | B | 81 | -71.883 | -6.636 | -1.417 | 1.00 | 61.07 | N |
| ATOM | 2810 | CA | LYS | B | 81 | -73.050 | -6.460 | -2.294 | 1.00 | 62.73 | C |
| ATOM | 2811 | CB | LYS | B | 81 | -72.770 | -6.859 | -3.746 | 1.00 | 61.66 | C |
| ATOM | 2812 | CG | LYS | B | 81 | -73.294 | -5.840 | -4.731 | 1.00 | 62.19 | C |
| ATOM | 2813 | CD | LYS | B | 81 | -72.215 | -5.219 | -5.571 | 1.00 | 63.16 | C |
| ATOM | 2814 | CE | LYS | B | 81 | -71.584 | -6.231 | -6.482 | 1.00 | 65.83 | C |
| ATOM | 2815 | NZ | LYS | B | 81 | -70.524 | -5.662 | -7.353 | 1.00 | 65.65 | N |
| ATOM | 2816 | C | LYS | B | 81 | -74.389 | -7.055 | -1.764 | 1.00 | 63.93 | C |
| ATOM | 2817 | O | LYS | B | 81 | -75.308 | -6.311 | -1.427 | 1.00 | 62.88 | O |
| ATOM | 2818 | N | LYS | B | 82 | -74.516 | -8.367 | -1.684 | 1.00 | 65.97 | N |
| ATOM | 2819 | CA | LYS | B | 82 | -75.776 | -8.909 | -1.189 | 1.00 | 67.29 | C |
| ATOM | 2820 | CB | LYS | B | 82 | -76.132 | -10.205 | -1.915 | 1.00 | 66.34 | C |
| ATOM | 2821 | CG | LYS | B | 82 | -75.669 | -10.268 | -3.367 | 1.00 | 64.42 | C |
| ATOM | 2822 | CD | LYS | B | 82 | -76.792 | -9.935 | -4.342 | 1.00 | 66.25 | C |
| ATOM | 2823 | CE | LYS | B | 82 | -76.890 | -10.959 | -5.475 | 1.00 | 62.13 | C |
| ATOM | 2824 | NZ | LYS | B | 82 | -78.184 | -11.694 | -5.510 | 1.00 | 58.80 | N |
| ATOM | 2825 | C | LYS | B | 82 | -75.624 | -9.169 | 0.290 | 1.00 | 68.33 | C |
| ATOM | 2826 | O | LYS | B | 82 | -76.582 | -9.289 | 1.053 | 1.00 | 68.46 | O |
| ATOM | 2827 | N | GLY | B | 83 | -74.368 | -9.244 | 0.666 | 1.00 | 68.58 | N |
| ATOM | 2828 | CA | LYS | B | 83 | -73.931 | -9.752 | 1.970 | 1.00 | 69.41 | C |
| ATOM | 2829 | CB | LYS | B | 83 | -72.564 | -10.420 | 1.918 | 1.00 | 59.75 | C |
| ATOM | 2830 | C | LYS | B | 83 | -71.959 | -10.695 | 2.961 | 1.00 | 70.94 | C |
| ATOM | 2831 | N | GLN | B | 84 | -72.082 | -10.684 | 0.700 | 1.00 | 68.93 | N |
| ATOM | 2832 | CA | GLN | B | 84 | -70.722 | -11.182 | 0.469 | 1.00 | 68.08 | C |
| ATOM | 2833 | CB | GLN | B | 84 | -70.681 | -12.107 | -0.755 | 1.00 | 68.19 | C |
| ATOM | 2834 | CG | GLN | B | 84 | -71.979 | -12.861 | -1.064 | 1.00 | 70.82 | C |
| ATOM | 2835 | CD | GLN | B | 84 | -72.148 | -14.137 | -0.252 | 1.00 | 73.97 | C |
| ATOM | 2836 | OE1 | GLN | B | 84 | -71.564 | -14.292 | 0.826 | 1.00 | 74.62 | O |
| ATOM | 2837 | NE2 | GLN | B | 84 | -72.957 | -15.060 | -0.771 | 1.00 | 71.67 | N |
| ATOM | 2838 | C | GLN | B | 84 | -69.756 | -10.007 | 0.253 | 1.00 | 67.67 | C |
| ATOM | 2839 | O | GLN | B | 84 | -69.968 | -9.175 | -0.645 | 1.00 | 67.60 | O |
| ATOM | 2840 | N | LYS | B | 85 | -68.703 | -9.939 | 1.070 | 1.00 | 65.93 | N |
| ATOM | 2841 | CA | LYS | B | 85 | -67.684 | -8.897 | 0.930 | 1.00 | 64.61 | C |
| ATOM | 2842 | CB | LYS | B | 85 | -66.613 | -9.018 | 2.026 | 1.00 | 64.48 | C |
| ATOM | 2843 | CG | LYS | B | 85 | -65.399 | -8.094 | 1.853 | 1.00 | 59.40 | C |
| ATOM | 2844 | CD | LYS | B | 85 | -64.932 | -7.483 | 3.181 | 1.00 | 59.93 | C |
| ATOM | 2845 | CE | LYS | B | 85 | -64.587 | -8.525 | 4.242 | 1.00 | 54.50 | C |
| ATOM | 2846 | NZ | LYS | B | 85 | -63.272 | -9.187 | 4.015 | 1.00 | 56.77 | N |
| ATOM | 2847 | C | LYS | B | 85 | -67.062 | -8.929 | -0.463 | 1.00 | 63.98 | C |
| ATOM | 2848 | O | LYS | B | 85 | -66.585 | -9.971 | -0.920 | 1.00 | 63.09 | O |
| ATOM | 2849 | N | VAL | B | 86 | -67.092 | -7.783 | -1.138 | 1.00 | 63.08 | N |
| ATOM | 2850 | CA | VAL | B | 86 | -66.586 | -7.690 | -2.509 | 1.00 | 63.91 | C |
| ATOM | 2851 | CB | VAL | B | 86 | -67.726 | -7.334 | -3.543 | 1.00 | 63.83 | C |
| ATOM | 2852 | CG1 | VAL | B | 86 | -68.264 | -5.912 | -3.340 | 1.00 | 51.70 | C |
| ATOM | 2853 | CG2 | VAL | B | 86 | -67.256 | -7.559 | -4.978 | 1.00 | 63.51 | C |
| ATOM | 2854 | C | VAL | B | 86 | -65.368 | -6.756 | -2.606 | 1.00 | 63.78 | C |
| ATOM | 2855 | O | VAL | B | 86 | -64.564 | -6.850 | -3.539 | 1.00 | 61.92 | O |
| ATOM | 2856 | N | GLY | B | 87 | -65.226 | -5.875 | -1.625 | 1.00 | 62.60 | N |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2857 | CA | GLY | B | 87 | −64.108 | −4.954 | −1.598 | 1.00 | 61.12 | C |
| ATOM | 2858 | C | GLY | B | 87 | −63.606 | −4.749 | −0.184 | 1.00 | 60.72 | C |
| ATOM | 2859 | O | GLY | B | 87 | −64.213 | −5.217 | 0.800 | 1.00 | 59.15 | O |
| ATOM | 2860 | N | GLU | B | 88 | −62.482 | −4.049 | −0.090 | 1.00 | 60.55 | N |
| ATOM | 2861 | CA | GLU | B | 88 | −61.910 | −3.682 | 1.195 | 1.00 | 59.10 | C |
| ATOM | 2862 | CB | GLU | B | 88 | −61.664 | −4.922 | 2.035 | 1.00 | 58.53 | C |
| ATOM | 2863 | CG | GLU | B | 88 | −61.644 | −4.622 | 3.510 | 1.00 | 62.62 | C |
| ATOM | 2864 | CD | GLU | B | 88 | −60.973 | −5.721 | 4.302 | 1.00 | 73.50 | C |
| ATOM | 2865 | OE1 | GLU | B | 88 | −60.894 | −6.869 | 3.783 | 1.00 | 69.51 | O |
| ATOM | 2866 | OE2 | GLU | B | 88 | −60.526 | −5.429 | 5.440 | 1.00 | 75.80 | O |
| ATOM | 2867 | C | GLU | B | 88 | −60.610 | −2.944 | 1.005 | 1.00 | 57.02 | C |
| ATOM | 2868 | O | GLU | B | 88 | −59.771 | −3.336 | 0.181 | 1.00 | 54.56 | O |
| ATOM | 2869 | N | PHE | B | 89 | −60.466 | −1.865 | 1.768 | 1.00 | 56.20 | N |
| ATOM | 2870 | CA | PHE | B | 89 | −59.199 | −1.171 | 1.900 | 1.00 | 54.23 | C |
| ATOM | 2871 | CB | PHE | B | 89 | −58.948 | −0.228 | 0.709 | 1.00 | 55.10 | C |
| ATOM | 2872 | CG | PHE | B | 89 | −59.646 | 1.104 | 0.815 | 1.00 | 56.25 | C |
| ATOM | 2873 | CD1 | PHE | B | 89 | −58.954 | 2.226 | 1.260 | 1.00 | 51.18 | C |
| ATOM | 2874 | CE1 | PHE | B | 89 | −59.588 | 3.466 | 1.372 | 1.00 | 45.19 | C |
| ATOM | 2875 | CZ | PHE | B | 89 | −60.940 | 3.597 | 0.980 | 1.00 | 55.21 | C |
| ATOM | 2876 | CE2 | PHE | B | 89 | −61.643 | 2.476 | 0.523 | 1.00 | 49.41 | C |
| ATOM | 2877 | CD2 | PHE | B | 89 | −60.987 | 1.241 | 0.434 | 1.00 | 54.94 | C |
| ATOM | 2878 | C | PHE | B | 89 | −59.094 | −0.436 | 3.232 | 1.00 | 53.55 | C |
| ATOM | 2879 | O | PHE | B | 89 | −60.111 | −0.049 | 3.831 | 1.00 | 54.40 | O |
| ATOM | 2880 | N | SER | B | 90 | −57.853 | −0.221 | 3.673 | 1.00 | 51.34 | N |
| ATOM | 2881 | CA | SER | B | 90 | −57.563 | 0.596 | 4.857 | 1.00 | 50.45 | C |
| ATOM | 2882 | CB | SER | B | 90 | −56.669 | −0.189 | 5.796 | 1.00 | 50.37 | C |
| ATOM | 2883 | OG | SER | B | 90 | −57.329 | −1.362 | 6.262 | 1.00 | 53.18 | O |
| ATOM | 2884 | C | SER | B | 90 | −56.901 | 1.924 | 4.501 | 1.00 | 48.30 | C |
| ATOM | 2885 | O | SER | B | 90 | −56.165 | 2.006 | 3.545 | 1.00 | 48.47 | O |
| ATOM | 2886 | N | GLY | B | 91 | −57.178 | 2.966 | 5.270 | 1.00 | 50.82 | N |
| ATOM | 2887 | CA | GLY | B | 91 | −56.556 | 4.269 | 5.054 | 1.00 | 53.78 | C |
| ATOM | 2888 | C | GLY | B | 91 | −57.520 | 5.428 | 4.838 | 1.00 | 55.33 | C |
| ATOM | 2889 | O | GLY | B | 91 | −58.506 | 5.315 | 4.132 | 1.00 | 56.28 | O |
| ATOM | 2890 | N | ALA | B | 92 | −57.204 | 6.575 | 5.413 | 1.00 | 57.76 | N |
| ATOM | 2891 | CA | ALA | B | 92 | −58.074 | 7.751 | 5.274 | 1.00 | 55.48 | C |
| ATOM | 2892 | CB | ALA | B | 92 | −57.780 | 8.732 | 6.389 | 1.00 | 55.96 | C |
| ATOM | 2893 | C | ALA | B | 92 | −57.858 | 8.384 | 3.907 | 1.00 | 56.47 | C |
| ATOM | 2894 | O | ALA | B | 92 | −57.383 | 9.509 | 3.794 | 1.00 | 59.61 | O |
| ATOM | 2895 | N | ASN | B | 93 | −58.206 | 7.642 | 2.863 | 1.00 | 55.91 | N |
| ATOM | 2896 | CA | ASN | B | 93 | −58.029 | 8.073 | 1.471 | 1.00 | 56.43 | C |
| ATOM | 2897 | CB | ASN | B | 93 | −57.284 | 6.956 | 0.726 | 1.00 | 56.22 | C |
| ATOM | 2898 | CG | ASN | B | 93 | −56.825 | 7.353 | −0.671 | 1.00 | 61.49 | C |
| ATOM | 2899 | OD1 | ASN | B | 93 | −57.348 | 8.279 | −1.301 | 1.00 | 51.25 | O |
| ATOM | 2900 | ND2 | ASN | B | 93 | −55.841 | 6.616 | −1.175 | 1.00 | 66.19 | N |
| ATOM | 2901 | C | ASN | B | 93 | −59.389 | 8.321 | 0.842 | 1.00 | 55.42 | C |
| ATOM | 2902 | O | ASN | B | 93 | −60.087 | 7.372 | 0.535 | 1.00 | 55.78 | O |
| ATOM | 2903 | N | LYS | B | 94 | −59.774 | 9.592 | 0.683 | 1.00 | 57.54 | N |
| ATOM | 2904 | CA | LYS | B | 94 | −61.124 | 9.969 | 0.234 | 1.00 | 57.17 | C |
| ATOM | 2905 | CB | LYS | B | 94 | −61.324 | 11.487 | 0.280 | 1.00 | 56.46 | C |
| ATOM | 2906 | CG | LYS | B | 94 | −60.939 | 12.197 | 1.537 | 1.00 | 64.88 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2907 | CD  | LYS | B | 94  | −60.973 | 13.705 | 1.312  | 1.00 | 69.02 | C |
| ATOM | 2908 | CE  | LYS | B | 94  | −60.254 | 14.068 | 0.023  | 1.00 | 74.45 | C |
| ATOM | 2909 | NZ  | LYS | B | 94  | −59.595 | 15.405 | 0.061  | 1.00 | 75.54 | N |
| ATOM | 2910 | C   | LYS | B | 94  | −61.370 | 9.547  | −1.213 | 1.00 | 57.53 | C |
| ATOM | 2911 | O   | LYS | B | 94  | −62.473 | 9.105  | −1.385 | 1.00 | 58.78 | O |
| ATOM | 2912 | N   | GLU | B | 95  | −60.332 | 9.730  | −2.022 | 1.00 | 56.40 | N |
| ATOM | 2913 | CA  | GLU | B | 95  | −60.414 | 9.509  | −3.465 | 1.00 | 51.79 | C |
| ATOM | 2914 | CB  | GLU | B | 95  | −59.219 | 10.150 | −4.186 | 1.00 | 51.43 | C |
| ATOM | 2915 | CG  | GLU | B | 95  | −59.197 | 11.692 | −4.168 | 1.00 | 54.73 | C |
| ATOM | 2916 | CD  | GLU | B | 95  | −58.670 | 12.315 | −2.849 | 1.00 | 66.69 | C |
| ATOM | 2917 | OE1 | GLU | B | 95  | −58.049 | 11.612 | −1.983 | 1.00 | 58.98 | O |
| ATOM | 2918 | OE2 | GLU | B | 95  | −58.897 | 13.537 | −2.689 | 1.00 | 67.58 | O |
| ATOM | 2919 | C   | GLU | B | 95  | −60.469 | 8.006  | −3.676 | 1.00 | 49.68 | C |
| ATOM | 2920 | O   | GLU | B | 95  | −61.215 | 7.561  | −4.513 | 1.00 | 47.24 | O |
| ATOM | 2921 | N   | LYS | B | 96  | −59.733 | 7.212  | −2.895 | 1.00 | 44.28 | N |
| ATOM | 2922 | CA  | LYS | B | 96  | −59.830 | 5.754  | −3.021 | 1.00 | 47.73 | C |
| ATOM | 2923 | CB  | LYS | B | 96  | −58.747 | 5.003  | −2.233 | 1.00 | 52.83 | C |
| ATOM | 2924 | CG  | LYS | B | 96  | −58.721 | 3.482  | −2.512 | 1.00 | 55.89 | C |
| ATOM | 2925 | CD  | LYS | B | 96  | −57.445 | 2.839  | −1.963 | 1.00 | 66.63 | C |
| ATOM | 2926 | CE  | LYS | B | 96  | −57.186 | 1.447  | −2.579 | 1.00 | 74.92 | C |
| ATOM | 2927 | NZ  | LYS | B | 96  | −56.220 | 0.662  | −1.732 | 1.00 | 74.14 | N |
| ATOM | 2928 | C   | LYS | B | 96  | −61.189 | 5.274  | −2.539 | 1.00 | 50.55 | C |
| ATOM | 2929 | O   | LYS | B | 96  | −61.743 | 4.336  | −3.108 | 1.00 | 53.20 | O |
| ATOM | 2930 | N   | LEU | B | 97  | −61.729 | 5.904  | −1.493 | 1.00 | 50.24 | N |
| ATOM | 2931 | CA  | LEU | B | 97  | −63.024 | 5.501  | −0.953 | 1.00 | 48.23 | C |
| ATOM | 2932 | CB  | LEU | B | 97  | −63.299 | 6.209  | 0.372  | 1.00 | 50.30 | C |
| ATOM | 2933 | CG  | LEU | B | 97  | −64.692 | 6.165  | 1.026  | 1.00 | 47.86 | C |
| ATOM | 2934 | CD1 | LEU | B | 97  | −65.096 | 4.785  | 1.490  | 1.00 | 50.25 | C |
| ATOM | 2935 | CD2 | LEU | B | 97  | −64.699 | 7.157  | 2.173  | 1.00 | 51.86 | C |
| ATOM | 2936 | C   | LEU | B | 97  | −64.152 | 5.749  | −1.971 | 1.00 | 49.77 | C |
| ATOM | 2937 | O   | LEU | B | 97  | −64.971 | 4.861  | −2.213 | 1.00 | 47.51 | O |
| ATOM | 2938 | N   | GLU | B | 98  | −64.196 | 6.947  | −2.560 | 1.00 | 49.47 | N |
| ATOM | 2939 | CA  | GLU | B | 98  | −65.217 | 7.235  | −3.569 | 1.00 | 48.25 | C |
| ATOM | 2940 | CB  | GLU | B | 98  | −65.286 | 8.729  | −3.937 | 1.00 | 46.21 | C |
| ATOM | 2941 | CG  | GLU | B | 98  | −66.495 | 9.084  | −4.867 | 1.00 | 50.37 | C |
| ATOM | 2942 | CD  | GLU | B | 98  | −66.640 | 10.590 | −5.139 | 1.00 | 48.78 | C |
| ATOM | 2943 | OE1 | GLU | B | 98  | −65.651 | 11.348 | −4.928 | 1.00 | 45.69 | O |
| ATOM | 2944 | OE2 | GLU | B | 98  | −67.754 | 11.009 | −5.554 | 1.00 | 44.48 | O |
| ATOM | 2945 | C   | GLU | B | 98  | −64.901 | 0.393  | −4.804 | 1.00 | 52.85 | C |
| ATOM | 2946 | O   | GLU | B | 98  | −65.890 | 5.831  | −5.377 | 1.00 | 58.28 | O |
| ATOM | 2947 | N   | ALA | B | 99  | −63.706 | 6.315  | −5.226 | 1.00 | 51.45 | N |
| ATOM | 2948 | CA  | ALA | B | 99  | −63.375 | 5.551  | −6.407 | 1.00 | 53.38 | C |
| ATOM | 2949 | CB  | ALA | B | 99  | −61.905 | 5.669  | −6.742 | 1.00 | 51.87 | C |
| ATOM | 2950 | C   | ALA | B | 99  | −63.815 | 4.093  | −6.261 | 1.00 | 54.87 | C |
| ATOM | 2951 | O   | ALA | B | 99  | −64.298 | 3.518  | −7.224 | 1.00 | 51.88 | O |
| ATOM | 2952 | N   | THR | B | 100 | −63.698 | 3.526  | −5.054 | 1.00 | 54.05 | N |
| ATOM | 2953 | CA  | THR | B | 100 | −64.053 | 2.110  | −4.804 | 1.00 | 55.42 | C |
| ATOM | 2954 | CB  | THR | B | 100 | −63.517 | 1.574  | −3.439 | 1.00 | 54.99 | C |
| ATOM | 2955 | OG1 | THR | B | 100 | −62.101 | 1.766  | −3.365 | 1.00 | 56.92 | O |
| ATOM | 2956 | OG2 | THR | B | 100 | −68.811 | 0.081  | −3.267 | 1.00 | 54.35 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 2957 | C | THR | B | 100 | -65.558 | 1.920 | -4.842 | 1.00 | 56.95 | C |
| ATOM | 2958 | O | THR | B | 100 | -66.043 | 0.872 | -5.264 | 1.00 | 57.28 | O |
| ATOM | 2959 | N | ILE | B | 101 | -66.290 | 2.927 | -4.379 | 1.00 | 58.02 | N |
| ATOM | 2960 | CA | ILE | B | 101 | -67.757 | 2.911 | -4.442 | 1.00 | 58.94 | C |
| ATOM | 2961 | CB | ILE | B | 101 | -68.353 | 4.136 | -3.679 | 1.00 | 59.95 | C |
| ATOM | 2962 | CG1 | ILE | B | 101 | -68.138 | 3.962 | -2.161 | 1.00 | 55.20 | C |
| ATOM | 2963 | CD1 | ILE | B | 101 | -68.489 | 5.194 | -1.317 | 1.00 | 46.14 | C |
| ATOM | 2964 | CG2 | ILE | B | 101 | -69.841 | 4.395 | -4.093 | 1.00 | 51.51 | C |
| ATOM | 2965 | C | ILE | B | 101 | -68.232 | 2.859 | -5.901 | 1.00 | 59.49 | C |
| ATOM | 2966 | O | ILE | B | 101 | -68.929 | 1.923 | -6.316 | 1.00 | 60.92 | O |
| ATOM | 2967 | N | ASN | B | 102 | -67.819 | 3.851 | -6.686 | 1.00 | 60.21 | N |
| ATOM | 2968 | CA | ASN | B | 102 | -68.130 | 3.903 | -8.111 | 1.00 | 58.70 | C |
| ATOM | 2969 | CB | ASN | B | 102 | -67.326 | 5.009 | -8.811 | 1.00 | 58.18 | C |
| ATOM | 2970 | CG | ASN | B | 102 | -67.577 | 6.399 | -8.233 | 1.00 | 52.84 | C |
| ATOM | 2971 | OD1 | ASN | B | 102 | -68.676 | 6.630 | -7.656 | 1.00 | 51.82 | O |
| ATOM | 2972 | ND2 | ASN | B | 102 | -66.546 | 7.357 | -8.420 | 1.00 | 51.93 | N |
| ATOM | 2973 | C | ASN | B | 102 | -67.778 | 2.579 | -8.774 | 1.00 | 60.60 | C |
| ATOM | 2974 | O | ASN | B | 102 | -68.476 | 2.120 | -9.695 | 1.00 | 61.04 | O |
| ATOM | 2975 | N | GLU | B | 103 | -66.671 | 1.986 | -8.319 | 1.00 | 59.41 | N |
| ATOM | 2976 | CA | GLU | B | 103 | -66.145 | 0.744 | -8.894 | 1.00 | 61.24 | C |
| ATOM | 2977 | CB | GLU | B | 103 | -64.661 | 0.573 | -8.542 | 1.00 | 61.83 | C |
| ATOM | 2978 | CG | GLU | B | 103 | -64.060 | -0.810 | -8.758 | 1.00 | 65.26 | C |
| ATOM | 2979 | CD | GLU | B | 103 | -62.749 | -0.980 | -7.998 | 1.00 | 69.40 | C |
| ATOM | 2980 | OE1 | GLU | B | 103 | -61.748 | -0.338 | -8.387 | 1.00 | 73.24 | O |
| ATOM | 2981 | OE2 | GLU | B | 103 | -62.719 | -1.760 | -7.018 | 1.00 | 64.96 | O |
| ATOM | 2982 | C | GLU | B | 103 | -66.978 | -0.492 | -8.520 | 1.00 | 62.07 | C |
| ATOM | 2983 | O | GLU | B | 103 | -67.15 | -1.465 | -9.289 | 1.00 | 63.47 | O |
| ATOM | 2984 | N | LEU | B | 104 | -67.692 | -0.431 | -7.393 | 1.00 | 60.81 | N |
| ATOM | 2985 | CA | LEU | B | 104 | -68.407 | -1.607 | -6.881 | 1.00 | 61.45 | C |
| ATOM | 2986 | CB | LEU | B | 104 | -67.968 | -1.919 | -5.447 | 1.00 | 61.55 | C |
| ATOM | 2987 | CG | LEU | B | 104 | -66.610 | -2.580 | -5.216 | 1.00 | 58.94 | C |
| ATOM | 2988 | CD1 | LEU | B | 104 | -66.404 | -2.708 | -3.728 | 1.00 | 64.88 | C |
| ATOM | 2989 | CD2 | LEU | B | 104 | -66.494 | -3.943 | 5.894 | 1.00 | 62.15 | C |
| ATOM | 2990 | C | LEU | B | 104 | -69.945 | -1.607 | -6.982 | 1.00 | 62.13 | C |
| ATOM | 2991 | O | LEU | B | 104 | -70.540 | -2.670 | -7.163 | 1.00 | 62.31 | O |
| ATOM | 2992 | N | VAL | B | 105 | -70.567 | -0.429 | -6.856 | 1.00 | 63.35 | N |
| ATOM | 2993 | CA | VAL | B | 105 | -72.044 | -0.239 | -6.853 | 1.00 | 61.88 | C |
| ATOM | 2994 | CB | VAL | B | 105 | -72.433 | 1.165 | -7.402 | 1.00 | 60.97 | C |
| ATOM | 2995 | CG1 | VAL | B | 105 | -73.849 | 1.173 | -8.027 | 1.00 | 62.19 | C |
| ATOM | 2996 | CG2 | VAL | B | 105 | -72.303 | 2.229 | -6.379 | 1.00 | 53.51 | C |
| ATOM | 2997 | C | VAL | B | 105 | -72.874 | -1.355 | -7.528 | 1.00 | 64.06 | C |
| ATOM | 2998 | O | VAL | B | 105 | -73.781 | -1.938 | -6.919 | 1.00 | 64.40 | O |
| ATOM | 2999 | OXT | VAL | B | 105 | -72.664 | -1.696 | -8.698 | 1.00 | 63.15 | O |
| TER | 3001 | | VAL | B | 105 | | | | | | |
| ATOM | 3001 | N | LYS | C | 8 | -16.361 | 6.444 | 5.932 | 1.00 | 58.47 | N |
| ATOM | 3001 | CA | LYS | C | 8 | -15.932 | 7.843 | 5.588 | 1.00 | 60.05 | C |
| ATOM | 3002 | CB | LYS | C | 8 | -17.129 | 0.730 | 5.002 | 1.00 | 59.08 | C |
| ATOM | 3003 | CG | LYS | C | 8 | -16.711 | 10.140 | 4.965 | 1.00 | 56.23 | C |
| ATOM | 3004 | CD | LYS | C | 8 | -17.857 | 11.097 | 4.994 | 1.00 | 56.69 | C |
| ATOM | 3005 | CE | LYS | C | 8 | -17.365 | 12.502 | 4.694 | 1.00 | 69.90 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 3006 | NZ | LYS | C | 8 | −18.497 | 13.411 | 4.332 | 1.00 | 78.67 | N |
| ATOM | 3007 | C | LYS | C | 8 | −15.093 | 8.553 | 6.658 | 1.00 | 62.35 | C |
| ATOM | 3008 | O | LYS | C | 8 | −13.946 | 8.928 | 6.403 | 1.00 | 63.39 | O |
| ATOM | 3009 | N | SER | C | 9 | −15.701 | 8.799 | 7.824 | 1.00 | 61.32 | N |
| ATOM | 3010 | CA | SER | C | 9 | −15.016 | 9.449 | 8.953 | 1.00 | 59.32 | C |
| ATOM | 3011 | CB | SER | C | 9 | −15.571 | 10.853 | 9.280 | 1.00 | 59.08 | C |
| ATOM | 3012 | OG | SER | C | 9 | −16.361 | 11.336 | 8.156 | 1.00 | 65.30 | O |
| ATOM | 3013 | C | SER | C | 9 | −15.180 | 8.584 | 10.107 | 1.00 | 57.00 | C |
| ATOM | 3014 | O | SER | C | 9 | −16.201 | 7.884 | 10.374 | 1.00 | 57.04 | O |
| ATOM | 3015 | N | PHE | C | 10 | −14.202 | 8.655 | 11.073 | 1.00 | 54.21 | N |
| ATOM | 3016 | CA | PHE | C | 10 | −14.216 | 7.868 | 12.274 | 1.00 | 50.34 | C |
| ATOM | 3017 | CB | PHE | C | 10 | −13.716 | 6.478 | 11.952 | 1.00 | 48.51 | C |
| ATOM | 3018 | CG | PHE | C | 10 | −13.813 | 5.532 | 13.089 | 1.00 | 51.98 | C |
| ATOM | 3019 | CD1 | PHE | C | 10 | −14.944 | 5.506 | 13.891 | 1.00 | 51.05 | C |
| ATOM | 3020 | CE1 | PHE | C | 10 | −15.25 | 4.632 | 14.942 | 1.00 | 49.84 | C |
| ATOM | 3021 | CZ | PHE | C | 10 | −14.020 | 3.758 | 15.179 | 1.00 | 47.81 | C |
| ATOM | 3022 | CE2 | PHE | C | 10 | −12.893 | 3.759 | 14.381 | 1.00 | 55.05 | C |
| ATOM | 3023 | CD2 | PHE | C | 10 | −12.791 | 4.650 | 13.344 | 1.00 | 40.44 | C |
| ATOM | 3024 | C | PHE | C | 10 | −13.265 | 8.552 | 13.223 | 1.00 | 50.76 | C |
| ATOM | 3025 | O | PHE | C | 10 | −12.063 | 8.455 | 13.038 | 1.00 | 45.73 | O |
| ATOM | 3026 | N | GLU | C | 11 | −18.790 | 9.272 | 14.209 | 1.00 | 48.40 | N |
| ATOM | 3027 | CA | GLU | C | 11 | −12.905 | 10.112 | 15.009 | 1.00 | 51.21 | C |
| ATOM | 3028 | CB | GLU | C | 11 | −12.907 | 11.548 | 14.463 | 1.00 | 54.19 | C |
| ATOM | 3029 | CG | GLU | C | 11 | −11.626 | 12.348 | 14.817 | 1.00 | 60.97 | C |
| ATOM | 3030 | CD | GLU | C | 11 | −11.836 | 13.856 | 14.778 | 1.00 | 60.47 | C |
| ATOM | 3031 | OE1 | GLU | C | 11 | −12.777 | 14.290 | 14.101 | 1.00 | 51.05 | O |
| ATOM | 3032 | OE2 | GLU | C | 11 | −11.070 | 14.612 | 15.428 | 1.00 | 57.81 | O |
| ATOM | 3033 | C | GLU | C | 11 | −13.304 | 10.137 | 16.473 | 1.00 | 47.85 | C |
| ATOM | 3034 | O | GLU | C | 11 | −14.502 | 10.154 | 16.784 | 1.00 | 45.20 | O |
| ATOM | 3035 | N | VAL | C | 12 | −12.302 | 10.165 | 17.361 | 1.00 | 47.39 | N |
| ATOM | 3036 | CA | VAL | C | 12 | −12.566 | 10.423 | 18.764 | 1.00 | 44.83 | C |
| ATOM | 3037 | CB | VAL | C | 12 | −11.505 | 9.765 | 19.671 | 1.00 | 49.05 | C |
| ATOM | 3038 | CG1 | VAL | C | 12 | −11.689 | 10.216 | 21.113 | 1.00 | 41.09 | C |
| ATOM | 3039 | CG2 | VAL | C | 12 | −11.596 | 8.227 | 19.583 | 1.00 | 42.11 | C |
| ATOM | 3040 | C | VAL | C | 12 | −12.602 | 11.945 | 18.933 | 1.00 | 45.57 | C |
| ATOM | 3041 | O | VAL | C | 12 | −11.678 | 12.644 | 18.515 | 1.00 | 46.86 | O |
| ATOM | 3042 | N | VAL | C | 13 | −13.664 | 12.464 | 19.544 | 1.00 | 45.91 | N |
| ATOM | 3043 | CA | VAL | C | 13 | −13.793 | 13.909 | 19.788 | 1.00 | 40.64 | C |
| ATOM | 3044 | CB | VAL | C | 13 | −14.908 | 14.533 | 18.884 | 1.00 | 42.84 | C |
| ATOM | 3045 | CG1 | VAL | C | 13 | −15.051 | 16.034 | 19.114 | 1.00 | 45.23 | C |
| ATOM | 3046 | CG2 | VAL | C | 13 | −14.571 | 14.304 | 17.442 | 1.00 | 41.89 | C |
| ATOM | 3047 | C | VAL | C | 13 | −13.974 | 14.175 | 21.289 | 1.00 | 38.95 | C |
| ATOM | 3048 | O | VAL | C | 13 | −13.035 | 13.935 | 21.861 | 1.00 | 39.74 | O |
| ATOM | 3049 | N | PHE | C | 14 | −12.926 | 14.687 | 21.936 | 1.00 | 40.83 | N |
| ATOM | 3050 | CA | PHE | C | 14 | −13.029 | 15.064 | 23.331 | 1.00 | 40.78 | C |
| ATOM | 3051 | CB | PHE | C | 14 | −11.647 | 15.233 | 23.859 | 1.00 | 39.50 | C |
| ATOM | 3052 | CG | PHE | C | 14 | −10.827 | 13.964 | 23.998 | 1.00 | 41.09 | C |
| ATOM | 3053 | CD1 | PHE | C | 14 | −11.082 | 12.976 | 24.952 | 1.00 | 31.95 | C |
| ATOM | 3054 | CE1 | PHE | C | 14 | −10.311 | 11.796 | 24.985 | 1.00 | 32.98 | C |
| ATOM | 3055 | CZ | PHE | C | 14 | −9.273 | 11.621 | 24.083 | 1.00 | 38.46 | C |

TABLE 10-continued

Atomic coordinates for COM1 complex of the modified
TXNIP protein represented by SEQ ID NO: 6 and the modified protein represented by SEQ ID NO: 3

| | | | | | | | | | |
|---|---|---|---|---|---|---|---|---|---|
| ATOM | 3056 | CE2 | C | PHE | 14 | −9.011 | 12.593 | 23.125 | 1.00 | 35.33 | C |
| ATOM | 3057 | CD2 | C | PHE | 14 | −9.801 | 13.756 | 23.070 | 1.00 | 38.94 | C |
| ATOM | 3058 | C | C | PHE | 14 | −13.826 | 16.345 | 23.493 | 1.00 | 42.40 | C |
| ATOM | 3059 | O | C | PHE | 14 | −13.711 | 17.255 | 22.683 | 1.00 | 44.03 | O |
| ATOM | 3060 | N | C | ASN | 15 | −14.622 | 16.400 | 24.560 | 1.00 | 43.13 | N |
| ATOM | 3061 | CA | C | ASN | 15 | −15.455 | 17.537 | 24.905 | 1.00 | 43.25 | C |
| ATOM | 3062 | CB | C | ASN | 15 | −16.318 | 17.183 | 26.113 | 1.00 | 43.22 | C |
| ATOM | 3063 | CG | C | ASN | 15 | −17.526 | 16.322 | 25.745 | 1.00 | 39.96 | C |
| ATOM | 3064 | OD1 | C | ASN | 15 | −17.771 | 16.027 | 24.570 | 1.00 | 44.03 | O |
| ATOM | 3065 | ND2 | C | ASN | 15 | −18.277 | 15.911 | 26.755 | 1.00 | 46.15 | N |
| ATOM | 3066 | C | C | ASN | 15 | −14.664 | 18.807 | 25.215 | 1.00 | 46.16 | C |
| ATOM | 3067 | O | C | ASN | 15 | −15.106 | 19.908 | 24.866 | 1.00 | 48.49 | O |
| ATOM | 3068 | N | C | ASP | 16 | −13.522 | 18.640 | 25.897 | 1.00 | 42.46 | N |
| ATOM | 3069 | CA | C | ASP | 16 | −12.515 | 19.698 | 26.161 | 1.00 | 41.60 | C |
| ATOM | 3070 | CB | C | ASP | 16 | −12.218 | 19.772 | 27.677 | 1.00 | 43.28 | C |
| ATOM | 3071 | CG | C | ASP | 16 | −13.488 | 19.810 | 28.535 | 1.00 | 59.34 | C |
| ATOM | 3072 | OD1 | C | ASP | 16 | −13.659 | 18.932 | 29.435 | 1.00 | 63.27 | O |
| ATOM | 3073 | OD2 | C | ASP | 16 | −14.327 | 20.698 | 28.279 | 1.00 | 59.36 | O |
| ATOM | 3074 | C | C | ASP | 16 | −11.208 | 19.309 | 25.445 | 1.00 | 38.79 | C |
| ATOM | 3075 | O | C | ASP | 16 | −10.325 | 18.701 | 26.055 | 1.00 | 40.61 | O |
| ATOM | 3076 | N | C | PRO | 17 | −11.079 | 19.605 | 24.150 | 1.00 | 39.29 | N |
| ATOM | 3077 | CA | C | PRO | 17 | −9.897 | 19.065 | 23.470 | 1.00 | 41.43 | C |
| ATOM | 3078 | CB | C | PRO | 17 | −10.187 | 19.338 | 21.987 | 1.00 | 44.18 | C |
| ATOM | 3079 | CG | C | PRO | 17 | −11.271 | 20.262 | 21.939 | 1.00 | 38.38 | C |
| ATOM | 3080 | CD | C | PRO | 17 | −11.962 | 20.351 | 23.239 | 1.00 | 40.65 | C |
| ATOM | 3081 | C | C | PRO | 17 | −8.514 | 19.632 | 23.893 | 1.00 | 43.71 | C |
| ATOM | 3082 | O | C | PRO | 17 | −7.499 | 19.008 | 23.641 | 1.00 | 42.48 | O |
| ATOM | 3083 | N | C | GLU | 18 | −8.537 | 20.780 | 24.577 | 1.00 | 42.73 | N |
| ATOM | 3084 | CA | C | GLU | 18 | −7.276 | 21.370 | 25.070 | 1.00 | 36.57 | C |
| ATOM | 3085 | CB | C | GLU | 18 | −7.219 | 22.848 | 24.671 | 1.00 | 38.53 | C |
| ATOM | 3086 | CG | C | GLU | 18 | −6.608 | 23.086 | 23.300 | 1.00 | 42.71 | C |
| ATOM | 3087 | CD | C | GLU | 18 | −7.460 | 22.533 | 22.181 | 1.00 | 44.89 | C |
| ATOM | 3088 | OE1 | C | GLU | 18 | −8.603 | 21.002 | 22.008 | 1.00 | 56.07 | O |
| ATOM | 3089 | OE2 | C | GLU | 18 | −6.988 | 21.632 | 21.467 | 1.00 | 47.92 | O |
| ATOM | 3090 | C | C | GLU | 18 | −7.023 | 21.183 | 26.567 | 1.00 | 37.56 | C |
| ATOM | 3091 | O | C | GLU | 18 | −6.011 | 21.633 | 27.113 | 1.00 | 34.75 | O |
| ATOM | 3092 | N | C | LYS | 19 | −7.918 | 20.477 | 27.246 | 1.00 | 33.99 | N |
| ATOM | 3093 | CA | C | LYS | 19 | −7.729 | 20.296 | 28.657 | 1.00 | 34.73 | C |
| ATOM | 3094 | CB | C | LYS | 19 | −8.996 | 19.797 | 29.311 | 1.00 | 35.81 | C |
| ATOM | 3095 | CG | C | LYS | 19 | −8.863 | 19.715 | 30.852 | 1.00 | 39.17 | C |
| ATOM | 3096 | CD | C | LYS | 19 | −10.208 | 19.377 | 31.433 | 1.00 | 43.21 | C |
| ATOM | 3097 | CE | C | LYS | 19 | −10.050 | 19.163 | 32.018 | 1.00 | 50.88 | C |
| ATOM | 3098 | NZ | C | LYS | 19 | −11.410 | 18.958 | 33.458 | 1.00 | 57.21 | N |
| ATOM | 3099 | C | C | LYS | 19 | −6.582 | 19.338 | 28.946 | 1.00 | 38.52 | C |
| ATOM | 3100 | O | C | LYS | 19 | −6.384 | 18.359 | 28.236 | 1.00 | 39.00 | O |
| ATOM | 3101 | N | C | VAL | 20 | −5.853 | 19.632 | 30.017 | 1.00 | 38.57 | N |
| ATOM | 3102 | CA | C | VAL | 20 | −4.814 | 18.709 | 30.581 | 1.00 | 37.17 | C |
| ATOM | 3103 | CB | C | VAL | 20 | −3.545 | 19.604 | 30.894 | 1.00 | 36.84 | C |
| ATOM | 3104 | CG1 | C | VAL | 20 | −2.435 | 18.780 | 31.383 | 1.00 | 39.57 | C |
| ATOM | 3105 | CG2 | C | VAL | 20 | −3.066 | 20.386 | 29.610 | 1.00 | 29.68 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 3106 | C | VAL | C | 20 | -5.449 | 18.262 | 31.879 | 1.00 | 40.74 | O |
| ATOM | 3107 | O | VAL | C | 20 | -5.757 | 19.072 | 32.768 | 1.00 | 39.40 | O |
| ATOM | 3108 | N | TYR | C | 21 | -5.681 | 16.947 | 31.968 | 1.00 | 39.40 | N |
| ATOM | 3109 | CA | TYR | C | 21 | -6.521 | 16.384 | 33.030 | 1.00 | 39.38 | C |
| ATOM | 3110 | CB | TYR | C | 21 | -7.259 | 15.135 | 32.549 | 1.00 | 43.52 | C |
| ATOM | 3111 | CG | TYR | C | 21 | -8.201 | 15.356 | 31.406 | 1.00 | 39.37 | C |
| ATOM | 3112 | CD1 | TYR | C | 21 | -9.552 | 15.593 | 31.612 | 1.00 | 39.19 | C |
| ATOM | 3113 | CE1 | TYR | C | 21 | -9.814 | 15.814 | 30.533 | 1.00 | 39.92 | C |
| ATOM | 3114 | CZ | TYR | C | 21 | -9.863 | 15.789 | 29.276 | 1.00 | 46.74 | C |
| ATOM | 3115 | OH | TYR | C | 21 | -10.634 | 15.990 | 28.184 | 1.00 | 49.20 | O |
| ATOM | 3116 | CE2 | TYR | C | 21 | -8.509 | 15.555 | 29.085 | 1.00 | 32.22 | C |
| ATOM | 3117 | CD2 | TYR | C | 21 | -7.718 | 15.345 | 30.118 | 1.00 | 41.71 | C |
| ATOM | 3118 | C | TYR | C | 21 | -5.723 | 15.994 | 34.265 | 1.00 | 39.21 | C |
| ATOM | 3119 | O | TYR | C | 21 | -4.588 | 15.539 | 34.166 | 1.00 | 35.48 | O |
| ATOM | 3120 | N | GLY | C | 22 | -6.365 | 16.804 | 35.428 | 1.00 | 39.20 | N |
| ATOM | 3121 | CA | GLY | C | 22 | -5.676 | 15.775 | 36.684 | 1.00 | 42.02 | C |
| ATOM | 3122 | C | GLY | C | 22 | -6.310 | 14.556 | 37.298 | 1.00 | 43.24 | C |
| ATOM | 3123 | O | GLY | C | 22 | -7.337 | 14.085 | 36.850 | 1.00 | 39.50 | O |
| ATOM | 3124 | N | SER | C | 23 | -5.673 | 14.038 | 38.332 | 1.00 | 46.02 | N |
| ATOM | 3125 | CA | SER | C | 23 | -6.111 | 12.837 | 38.997 | 1.00 | 46.07 | C |
| ATOM | 3126 | CB | SER | C | 23 | -5.206 | 12.642 | 40.222 | 1.00 | 50.25 | C |
| ATOM | 3127 | OG | SER | C | 23 | -5.498 | 11.418 | 40.815 | 1.00 | 61.04 | O |
| ATOM | 3128 | C | SER | C | 23 | -7.573 | 12.972 | 39.397 | 1.00 | 45.06 | C |
| ATOM | 3129 | O | SER | C | 23 | -8.032 | 14.043 | 39.806 | 1.00 | 44.98 | O |
| ATOM | 3130 | N | GLY | C | 24 | -8.337 | 11.905 | 39.217 | 1.00 | 44.75 | N |
| ATOM | 3131 | CA | GLY | C | 24 | -9.754 | 11.954 | 39.557 | 1.00 | 46.55 | C |
| ATOM | 3132 | C | GLY | C | 24 | -10.729 | 12.623 | 38.598 | 1.00 | 48.61 | C |
| ATOM | 3133 | O | GLY | C | 24 | -11.933 | 12.482 | 38.706 | 1.00 | 49.00 | O |
| ATOM | 3134 | N | GLU | C | 25 | -10.243 | 13.328 | 37.579 | 1.00 | 44.97 | N |
| ATOM | 3135 | CA | GLU | C | 25 | -11.141 | 14.012 | 36.635 | 1.00 | 43.32 | C |
| ATOM | 3136 | CB | GLU | C | 25 | -10.437 | 15.189 | 35.934 | 1.00 | 42.44 | C |
| ATOM | 3137 | CG | GLU | C | 25 | -9.862 | 16.213 | 36.920 | 1.00 | 46.34 | C |
| ATOM | 3138 | CD | GLU | C | 25 | -9.525 | 17.543 | 36.261 | 1.00 | 53.56 | C |
| ATOM | 3139 | OE1 | GLU | C | 25 | -8.501 | 17.631 | 35.558 | 1.00 | 43.27 | O |
| ATOM | 3140 | OE2 | GLU | C | 25 | -10.271 | 18.522 | 36.463 | 1.00 | 61.83 | O |
| ATOM | 3141 | C | GLU | C | 25 | -11.814 | 13.113 | 35.618 | 1.00 | 42.99 | C |
| ATOM | 3142 | O | GLU | C | 25 | -11.325 | 12.041 | 35.281 | 1.00 | 42.31 | O |
| ATOM | 3143 | N | ARG | C | 26 | -12.953 | 13.578 | 35.109 | 1.00 | 43.37 | N |
| ATOM | 3144 | CA | ARG | C | 26 | -13.706 | 12.023 | 34.132 | 1.00 | 44.05 | C |
| ATOM | 3145 | CB | ARG | C | 26 | -15.225 | 13.034 | 34.319 | 1.00 | 44.08 | C |
| ATOM | 3146 | CG | ARG | C | 26 | -16.086 | 12.246 | 33.333 | 1.00 | 59.36 | C |
| ATOM | 3147 | CD | ARG | C | 26 | -17.377 | 11.764 | 33.969 | 1.00 | 76.13 | C |
| ATOM | 3148 | NE | ARG | C | 26 | -18.033 | 10.732 | 33.162 | 1.00 | 88.55 | N |
| ATOM | 3149 | CZ | ARG | C | 26 | -18.050 | 9.426 | 33.448 | 1.00 | 92.94 | C |
| ATOM | 3150 | NH1 | ARG | C | 26 | -17.446 | 8.947 | 34.531 | 1.00 | 86.27 | N |
| ATOM | 3151 | NH2 | ARG | C | 26 | -18.692 | 8.587 | 32.643 | 1.00 | 98.62 | N |
| ATOM | 3152 | C | ARG | C | 26 | -13.223 | 13.185 | 32.724 | 1.00 | 41.71 | C |
| ATOM | 3153 | O | ARG | C | 26 | -13.013 | 14.349 | 32.400 | 1.00 | 42.10 | O |
| ATOM | 3154 | N | VAL | C | 27 | -13.042 | 12.169 | 31.890 | 1.00 | 41.32 | N |
| ATOM | 3155 | CA | VAL | C | 27 | -12.670 | 12.404 | 30.505 | 1.00 | 39.54 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 3156 | CB | VAL | C | 27 | −11.405 | 11.634 | 30.110 | 1.00 | 37.84 | C |
| ATOM | 3157 | CG1 | VAL | C | 27 | −11.021 | 11.989 | 28.737 | 1.00 | 32.46 | C |
| ATOM | 3158 | CG2 | VAL | C | 27 | −10.238 | 11.957 | 31.093 | 1.00 | 36.44 | C |
| ATOM | 3159 | C | VAL | C | 27 | −13.852 | 11.980 | 29.680 | 1.00 | 39.79 | C |
| ATOM | 3160 | O | VAL | C | 27 | −14.259 | 10.814 | 29.740 | 1.00 | 43.34 | O |
| ATOM | 3161 | N | ALA | C | 28 | −14.446 | 12.940 | 28.965 | 1.00 | 39.95 | N |
| ATOM | 3162 | CA | ALA | C | 28 | −15.662 | 12.683 | 28.208 | 1.00 | 38.82 | C |
| ATOM | 3163 | CB | ALA | C | 28 | −16.892 | 13.312 | 28.945 | 1.00 | 40.51 | C |
| ATOM | 3164 | C | ALA | C | 28 | −15.580 | 13.170 | 26.768 | 1.00 | 38.84 | C |
| ATOM | 3165 | O | ALA | C | 28 | −14.921 | 14.150 | 26.459 | 1.00 | 36.76 | O |
| ATOM | 3166 | N | GLY | C | 29 | −16.265 | 12.476 | 25.869 | 1.00 | 37.58 | N |
| ATOM | 3167 | CA | GLY | C | 29 | −16.310 | 12.920 | 24.499 | 1.00 | 37.35 | C |
| ATOM | 3168 | C | GLY | C | 29 | −17.299 | 12.113 | 23.720 | 1.00 | 39.23 | C |
| ATOM | 3169 | O | GLY | C | 29 | −18.238 | 11.536 | 24.291 | 1.00 | 35.21 | O |
| ATOM | 3170 | N | ARG | C | 30 | −17.077 | 12.092 | 22.409 | 1.00 | 35.56 | N |
| ATOM | 3171 | CA | ARG | C | 30 | −17.937 | 11.396 | 21.509 | 1.00 | 39.01 | C |
| ATOM | 3172 | CB | ARG | C | 30 | −18.854 | 12.393 | 20.755 | 1.00 | 39.68 | C |
| ATOM | 3173 | CG | ARG | C | 30 | −20.023 | 12.937 | 21.568 | 1.00 | 40.31 | C |
| ATOM | 3174 | CD | ARG | C | 30 | −20.544 | 14.270 | 20.999 | 1.00 | 48.25 | C |
| ATOM | 3175 | NE | ARG | C | 30 | −19.439 | 15.220 | 20.782 | 1.00 | 52.75 | N |
| ATOM | 3176 | CZ | ARG | C | 30 | −19.400 | 16.150 | 19.821 | 1.00 | 62.04 | C |
| ATOM | 3177 | NH1 | ARG | C | 30 | −20.403 | 16.287 | 18.948 | 1.00 | 62.34 | N |
| ATOM | 3178 | NH2 | ARG | C | 30 | −18.353 | 16.955 | 19.725 | 1.00 | 55.14 | N |
| ATOM | 3179 | C | ARG | C | 30 | −17.046 | 10.651 | 20.550 | 1.00 | 40.68 | C |
| ATOM | 3180 | O | ARG | C | 30 | −15.918 | 11.062 | 20.289 | 1.00 | 41.03 | O |
| ATOM | 3181 | N | VAL | C | 31 | −17.507 | 9.405 | 20.089 | 1.00 | 42.77 | N |
| ATOM | 3182 | CA | VAL | C | 31 | −16.915 | 8.862 | 18.909 | 1.00 | 41.50 | C |
| ATOM | 3183 | CB | VAL | C | 31 | −16.710 | 7.344 | 19.097 | 1.00 | 40.75 | C |
| ATOM | 3184 | CG1 | VAL | C | 31 | −16.164 | 6.715 | 17.816 | 1.00 | 42.20 | C |
| ATOM | 3185 | CG2 | VAL | C | 31 | −15.782 | 7.064 | 20.273 | 1.00 | 40.18 | C |
| ATOM | 3186 | C | VAL | C | 31 | −17.910 | 9.134 | 17.766 | 1.00 | 43.48 | C |
| ATOM | 3187 | O | VAL | C | 31 | −19.975 | 8.747 | 17.615 | 1.00 | 43.27 | O |
| ATOM | 3188 | N | ILE | C | 32 | −17.453 | 9.840 | 16.749 | 1.00 | 46.43 | N |
| ATOM | 3189 | CA | ILE | C | 32 | −18.345 | 10.323 | 15.715 | 1.00 | 48.26 | C |
| ATOM | 3190 | CB | ILE | C | 32 | −18.251 | 11.866 | 15.545 | 1.00 | 49.24 | C |
| ATOM | 3191 | CG1 | ILE | C | 32 | −18.403 | 12.560 | 16.919 | 1.00 | 47.09 | C |
| ATOM | 3192 | CD1 | ILE | C | 32 | −18.057 | 14.053 | 10.893 | 1.00 | 45.10 | C |
| ATOM | 3193 | CG2 | ILE | C | 32 | −19.269 | 12.355 | 14.492 | 1.00 | 52.56 | C |
| ATOM | 3194 | C | ILE | C | 32 | −18.037 | 9.559 | 14.417 | 1.00 | 51.45 | C |
| ATOM | 3195 | O | ILE | C | 32 | −16.888 | 9.517 | 13.958 | 1.00 | 47.68 | O |
| ATOM | 3196 | N | VAL | C | 33 | −19.084 | 8.947 | 13.851 | 1.00 | 52.85 | N |
| ATOM | 3197 | CA | VAL | C | 33 | −18.933 | 7.007 | 12.756 | 1.00 | 55.77 | C |
| ATOM | 3198 | CB | VAL | C | 33 | −19.371 | 6.548 | 13.135 | 1.00 | 55.11 | C |
| ATOM | 3199 | CG1 | VAL | C | 33 | −18.875 | 5.549 | 12.089 | 1.00 | 64.13 | C |
| ATOM | 3200 | CG2 | VAL | C | 33 | −18.844 | 6.130 | 14.489 | 1.00 | 58.09 | C |
| ATOM | 3201 | C | VAL | C | 33 | −19.773 | 8.490 | 12.355 | 1.00 | 56.73 | C |
| ATOM | 3202 | O | VAL | C | 33 | −18.037 | 8.874 | 11.786 | 1.00 | 56.06 | O |
| ATOM | 3203 | N | GLU | C | 34 | −20.937 | 9.517 | 10.416 | 1.00 | 60.64 | N |
| ATOM | 3204 | CA | GLU | C | 34 | −19.172 | 8.513 | 9.186 | 1.00 | 65.76 | C |
| ATOM | 3205 | CB | GLU | C | 34 | −19.503 | 10.299 | 8.737 | 1.00 | 65.14 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 3206 | CG | GLU | C | 34 | −19.708 | 11.365 | 9.793 | 1.00 | 69.08 | C |
| ATOM | 3207 | CD | GLU | C | 34 | −20.073 | 12.715 | 9.202 | 1.00 | 73.94 | C |
| ATOM | 3208 | OE1 | GLU | C | 34 | −19.828 | 12.031 | 7.992 | 1.00 | 75.08 | O |
| ATOM | 3209 | OE2 | GLU | C | 34 | −20.610 | 13.562 | 9.951 | 1.00 | 74.55 | O |
| ATOM | 3210 | C | GLU | C | 34 | −19.620 | 7.903 | 8.058 | 1.00 | 68.45 | C |
| ATOM | 3211 | O | GLU | C | 34 | −18.510 | 7.349 | 7.948 | 1.00 | 67.95 | O |
| ATOM | 3212 | N | VAL | C | 34 | −20.660 | 7.673 | 7.245 | 1.00 | 70.92 | N |
| ATOM | 3213 | CA | VAL | C | 35 | −21.298 | 6.823 | 6.060 | 1.00 | 72.44 | C |
| ATOM | 3214 | CB | VAL | C | 35 | −20.562 | 5.450 | 6.221 | 1.00 | 72.89 | C |
| ATOM | 3215 | CG1 | VAL | C | 35 | −20.578 | 4.592 | 7.258 | 1.00 | 73.36 | C |
| ATOM | 3216 | CG2 | VAL | C | 35 | −22.776 | 5.620 | 6.568 | 1.00 | 71.53 | C |
| ATOM | 3217 | C | VAL | C | 35 | −20.985 | 7.546 | 4.770 | 1.00 | 73.19 | C |
| ATOM | 3218 | O | VAL | C | 35 | −21.804 | 6.470 | 4.797 | 1.00 | 67.87 | O |
| ATOM | 3219 | N | CYS | C | 36 | −20.356 | 7.117 | 3.670 | 1.00 | 77.54 | N |
| ATOM | 3220 | CA | CYS | C | 36 | −20.646 | 7.564 | 2.297 | 1.00 | 82.50 | C |
| ATOM | 3221 | CB | CYS | C | 36 | −19.341 | 7.728 | 1.500 | 1.00 | 84.15 | C |
| ATOM | 3222 | SG | CYS | C | 36 | −18.748 | 9.441 | 1.353 | 1.00 | 89.38 | S |
| ATOM | 3223 | C | CYS | C | 36 | −21.560 | 9.579 | 1.564 | 1.00 | 83.15 | C |
| ATOM | 3224 | O | CYS | C | 36 | −22.096 | 6.896 | 0.502 | 1.00 | 83.77 | O |
| ATOM | 3225 | N | GLU | C | 37 | −21.715 | 5.388 | 2.143 | 1.00 | 84.05 | N |
| ATOM | 3226 | CA | GLU | C | 37 | −22.529 | 4.305 | 1.596 | 1.00 | 84.45 | C |
| ATOM | 3227 | CB | GLU | C | 37 | −21.682 | 3.463 | 0.643 | 1.00 | 84.99 | C |
| ATOM | 3228 | CG | GLU | C | 37 | −21.938 | 1.953 | 0.639 | 1.00 | 87.14 | C |
| ATOM | 3229 | CD | GLU | C | 37 | −20.696 | 1.180 | 0.237 | 1.00 | 91.73 | C |
| ATOM | 3230 | OE1 | GLU | C | 37 | −19.818 | 1.756 | −0.450 | 1.00 | 91.53 | O |
| ATOM | 3231 | OE2 | GLU | C | 37 | −20.589 | −0.008 | 0.616 | 1.00 | 92.16 | O |
| ATOM | 3232 | C | GLU | C | 37 | −23.126 | 3.465 | 2.737 | 1.00 | 85.77 | C |
| ATOM | 3233 | O | GLU | C | 37 | −22.456 | 3.205 | 3.749 | 1.00 | 86.67 | O |
| ATOM | 3234 | N | VAL | C | 38 | −24.393 | 3.081 | 2.572 | 1.00 | 84.92 | N |
| ATOM | 3235 | CA | VAL | C | 38 | −25.146 | 2.262 | 3.532 | 1.00 | 84.76 | C |
| ATOM | 3236 | CB | VAL | C | 38 | −26.456 | 1.691 | 2.890 | 1.00 | 85.58 | C |
| ATOM | 3237 | CG1 | VAL | C | 38 | −27.365 | 1.055 | 3.950 | 1.00 | 84.47 | C |
| ATOM | 3238 | CG2 | VAL | C | 38 | −27.215 | 2.778 | 2.104 | 1.00 | 86.14 | C |
| ATOM | 3239 | C | VAL | C | 38 | −24.301 | 1.112 | 4.100 | 1.00 | 85.03 | C |
| ATOM | 3240 | O | VAL | C | 38 | −23.655 | 0.367 | 3.345 | 1.00 | 85.04 | O |
| ATOM | 3241 | N | THR | C | 39 | −24.295 | 0.988 | 5.431 | 1.00 | 83.61 | N |
| ATOM | 3242 | CA | THR | C | 39 | −23.494 | −0.033 | 6.124 | 1.00 | 82.26 | C |
| ATOM | 3243 | CB | THR | C | 39 | −22.036 | 0.452 | 6.365 | 1.00 | 82.40 | C |
| ATOM | 3244 | OG1 | THR | C | 39 | −21.510 | −0.139 | 7.562 | 1.00 | 81.21 | O |
| ATOM | 3245 | OG2 | THR | C | 39 | −21.994 | 1.944 | 6.521 | 1.00 | 82.12 | O |
| ATOM | 3246 | C | THR | C | 39 | −24.115 | −0.509 | 7.443 | 1.00 | 81.51 | C |
| ATOM | 3247 | O | THR | C | 39 | −24.803 | 0.254 | 8.121 | 1.00 | 82.81 | O |
| ATOM | 3248 | N | ARG | C | 40 | −23.872 | −1.773 | 7.787 | 1.00 | 79.72 | N |
| ATOM | 3249 | CA | ARG | C | 40 | −24.233 | −2.323 | 9.102 | 1.00 | 78.85 | C |
| ATOM | 3250 | CB | ARG | C | 40 | −24.523 | −3.800 | 8.976 | 1.00 | 78.59 | C |
| ATOM | 3251 | CG | ARG | C | 40 | −25.594 | −4.277 | 10.042 | 1.00 | 82.55 | C |
| ATOM | 3252 | CD | ARG | C | 40 | −26.200 | −5.599 | 9.637 | 1.00 | 91.79 | C |
| ATOM | 3253 | NE | ARG | C | 40 | −27.537 | −5.780 | 10.215 | 1.00 | 97.19 | N |
| ATOM | 3254 | CZ | ARG | C | 40 | −28.184 | −6.944 | 10.275 | 1.00 | 97.18 | C |
| ATOM | 3255 | NH1 | ARG | C | 40 | −27.628 | −8.057 | 9.804 | 1.00 | 96.07 | N |

TABLE 10-continued

Atomic coordinates for COM1 complex of the modified
TXNIP protein represented by SEQ ID NO: 6 and the modified protein represented by SEQ ID NO: 3

| | | | | | | | | | |
|---|---|---|---|---|---|---|---|---|---|
| ATOM | 3256 | NH2 | ARG | C | 40 | −29.389 | 10.820 | 1.00 | 95.35 | N |
| ATOM | 3257 | C | ARG | C | 40 | −23.066 | 10.095 | 1.00 | 76.10 | C |
| ATOM | 3258 | O | ARG | C | 40 | −21.906 | 9.680 | 1.00 | 77.78 | O |
| ATOM | 3259 | N | VAL | C | 41 | −23.363 | 11.939 | 1.00 | 71.83 | N |
| ATOM | 3260 | CA | VAL | C | 41 | −22.309 | 12.396 | 1.00 | 67.96 | C |
| ATOM | 3261 | CB | VAL | C | 41 | −22.165 | 12.823 | 1.00 | 60.29 | C |
| ATOM | 3262 | CG1 | VAL | C | 41 | −21.184 | 13.980 | 1.00 | 61.98 | C |
| ATOM | 3263 | CG2 | VAL | C | 41 | −21.750 | 11.633 | 1.00 | 66.02 | C |
| ATOM | 3264 | C | VAL | C | 41 | −22.514 | 13.620 | 1.00 | 67.68 | C |
| ATOM | 3265 | O | VAL | C | 41 | −23.452 | 14.390 | 1.00 | 67.18 | O |
| ATOM | 3266 | N | LYS | C | 42 | −21.634 | 13.792 | 1.00 | 66.59 | N |
| ATOM | 3267 | CA | LYS | C | 42 | −21.730 | 14.926 | 1.00 | 66.79 | C |
| ATOM | 3268 | CB | LYS | C | 42 | −20.754 | 14.758 | 1.00 | 66.86 | C |
| ATOM | 3269 | CG | LYS | C | 42 | −20.640 | 15.995 | 1.00 | 72.12 | C |
| ATOM | 3270 | CD | LYS | C | 42 | −19.690 | 15.761 | 1.00 | 78.71 | C |
| ATOM | 3271 | CC | LYS | C | 42 | −20.345 | 14.889 | 1.00 | 87.05 | C |
| ATOM | 3272 | NZ | LYS | C | 42 | −19.469 | 14.687 | 1.00 | 91.82 | N |
| ATOM | 3273 | C | LYS | C | 42 | −21.525 | 16.278 | 1.00 | 66.12 | C |
| ATOM | 3274 | O | LYS | C | 42 | −22.190 | 17.277 | 1.00 | 63.50 | O |
| ATOM | 3275 | N | ALA | C | 43 | −20.597 | 16.295 | 1.00 | 65.30 | N |
| ATOM | 3276 | CA | ALA | C | 43 | −20.229 | 17.499 | 1.00 | 62.84 | C |
| ATOM | 3277 | CB | ALA | C | 43 | −19.461 | 18.471 | 1.00 | 64.37 | C |
| ATOM | 3278 | C | ALA | C | 43 | −19.408 | 17.232 | 1.00 | 62.32 | C |
| ATOM | 3279 | O | ALA | C | 43 | −18.838 | 16.146 | 1.00 | 61.69 | O |
| ATOM | 3280 | N | VAL | C | 44 | −19.416 | 18.240 | 1.00 | 60.62 | N |
| ATOM | 3281 | CA | VAL | C | 44 | −18.365 | 18.486 | 1.00 | 55.42 | C |
| ATOM | 3282 | CB | VAL | C | 44 | −18.812 | 18.216 | 1.00 | 55.10 | C |
| ATOM | 3283 | CG1 | VAL | C | 44 | −17.767 | 18.656 | 1.00 | 51.27 | C |
| ATOM | 3284 | CG2 | VAL | C | 44 | −19.023 | 16.750 | 1.00 | 40.57 | C |
| ATOM | 3285 | C | VAL | C | 44 | −17.899 | 19.907 | 1.00 | 56.64 | C |
| ATOM | 3286 | O | VAL | C | 44 | −18.699 | 20.850 | 1.00 | 56.85 | O |
| ATOM | 3287 | N | ARG | C | 45 | −16.601 | 20.044 | 1.00 | 54.60 | N |
| ATOM | 3288 | CA | ARG | C | 45 | −15.962 | 21.347 | 1.00 | 56.03 | C |
| ATOM | 3289 | CB | ARG | C | 45 | −15.359 | 21.528 | 1.00 | 56.29 | C |
| ATOM | 3290 | CG | ARG | C | 45 | −16.387 | 21.528 | 1.00 | 59.71 | C |
| ATOM | 3291 | CD | ARG | C | 45 | −15.754 | 21.290 | 1.00 | 60.98 | C |
| ATOM | 3292 | NE | ARG | C | 45 | −15.003 | 20.030 | 1.00 | 65.00 | N |
| ATOM | 3293 | CZ | ARG | C | 45 | −13.707 | 19.919 | 1.00 | 64.04 | C |
| ATOM | 3294 | NH1 | ARG | C | 45 | −12.984 | 20.995 | 1.00 | 58.19 | N |
| ATOM | 3295 | NH2 | ARG | C | 45 | −13.136 | 18.714 | 1.00 | 62.31 | N |
| ATOM | 3296 | C | ARG | C | 45 | −14.870 | 21.470 | 1.00 | 53.46 | C |
| ATOM | 3297 | O | ARG | C | 45 | −14.375 | 20.467 | 1.00 | 49.10 | O |
| ATOM | 3298 | N | ILE | C | 46 | −14.562 | 22.711 | 1.00 | 52.79 | N |
| ATOM | 3299 | CA | ILE | C | 46 | −13.364 | 23.028 | 1.00 | 52.71 | C |
| ATOM | 3300 | CB | ILE | C | 46 | −13.663 | 23.691 | 1.00 | 49.34 | C |
| ATOM | 3301 | CG1 | ILE | C | 46 | −14.570 | 24.913 | 1.00 | 45.97 | C |
| ATOM | 3302 | CD1 | ILE | C | 46 | −14.436 | 25.906 | 1.00 | 53.75 | C |
| ATOM | 3303 | CG2 | ILE | C | 46 | −14.228 | 22.659 | 1.00 | 42.09 | C |
| ATOM | 3304 | C | ILE | C | 46 | −12.468 | 23.962 | 1.00 | 52.51 | C |
| ATOM | 3305 | O | ILE | C | 46 | −12.900 | 24.780 | 1.00 | 54.82 | O |

TABLE 10-continued

Atomic coordinates for COM1 complex of the modified
TXNIP protein represented by SEQ ID NO: 6 and the modified protein represented by SEQ ID NO: 3

| | | | | | | | | | |
|---|---|---|---|---|---|---|---|---|---|
| ATOM | 3306 | N | LEU | C | 47 | −11.174 | 1.745 | 23.869 | 1.00 | 51.57 | N |
| ATOM | 3307 | CA | LEU | C | 47 | −10.226 | 1.434 | 24.949 | 1.00 | 46.35 | C |
| ATOM | 3308 | CB | LEU | C | 47 | −9.239 | 0.377 | 24.464 | 1.00 | 49.67 | C |
| ATOM | 3309 | CG | LEU | C | 47 | −8.012 | 0.091 | 25.293 | 1.00 | 51.79 | C |
| ATOM | 3310 | CD1 | LEU | C | 47 | −8.321 | −0.728 | 26.566 | 1.00 | 56.90 | C |
| ATOM | 3311 | CD2 | LEU | C | 47 | −6.978 | −0.605 | 24.394 | 1.00 | 62.20 | C |
| ATOM | 3312 | C | LEU | C | 47 | −9.485 | 2.714 | 25.388 | 1.00 | 44.94 | C |
| ATOM | 3313 | O | LEU | C | 47 | −9.011 | 3.475 | 24.551 | 1.00 | 44.59 | O |
| ATOM | 3314 | N | ALA | C | 48 | −9.422 | 2.973 | 26.688 | 1.00 | 45.90 | N |
| ATOM | 3315 | CA | ALA | C | 48 | −8.664 | 4.110 | 27.181 | 1.00 | 46.82 | C |
| ATOM | 3316 | CB | ALA | C | 48 | −9.512 | 5.060 | 27.964 | 1.00 | 41.84 | C |
| ATOM | 3317 | C | ALA | C | 48 | −7.540 | 3.621 | 28.057 | 1.00 | 48.88 | C |
| ATOM | 3318 | O | ALA | C | 48 | −7.766 | 2.949 | 29.054 | 1.00 | 52.48 | O |
| ATOM | 3319 | N | CYS | C | 49 | −6.337 | 4.040 | 27.760 | 1.00 | 48.32 | N |
| ATOM | 3320 | CA | CYS | C | 49 | −5.157 | 3.557 | 28.452 | 1.00 | 46.25 | C |
| ATOM | 3321 | CB | CYS | C | 49 | −4.328 | 2.638 | 27.554 | 1.00 | 49.58 | C |
| ATOM | 3322 | SG | CYS | C | 49 | −5.025 | 0.979 | 27.279 | 1.00 | 66.18 | S |
| ATOM | 3323 | C | CYS | C | 49 | −4.281 | 4.689 | 28.874 | 1.00 | 43.09 | C |
| ATOM | 3324 | O | CYS | C | 49 | −4.221 | 5.735 | 28.226 | 1.00 | 40.87 | O |
| ATOM | 3325 | N | GLY | C | 50 | −3.528 | 4.445 | 29.933 | 1.00 | 39.81 | N |
| ATOM | 3326 | CA | GLY | C | 50 | −2.595 | 5.401 | 30.434 | 1.00 | 38.52 | C |
| ATOM | 3327 | C | GLY | C | 50 | −1.460 | 4.527 | 30.870 | 1.00 | 41.98 | C |
| ATOM | 3328 | O | GLY | C | 50 | −1.618 | 3.712 | 31.783 | 1.00 | 39.07 | O |
| ATOM | 3329 | N | VAL | C | 51 | −0.325 | 4.667 | 30.221 | 1.00 | 43.24 | N |
| ATOM | 3330 | CA | VAL | C | 51 | 0.848 | 3.865 | 30.611 | 1.00 | 43.18 | C |
| ATOM | 3331 | CB | VAL | C | 51 | 0.981 | 2.594 | 29.760 | 1.00 | 45.10 | C |
| ATOM | 3332 | CG1 | VAL | C | 51 | 1.107 | 2.951 | 28.271 | 1.00 | 18.12 | C |
| ATOM | 3333 | CG2 | VAL | C | 51 | 2.198 | 1.713 | 30.250 | 1.00 | 45.26 | C |
| ATOM | 3334 | C | VAL | C | 51 | 2.137 | 4.666 | 30.637 | 1.00 | 42.07 | C |
| ATOM | 3335 | O | VAL | C | 51 | 2.387 | 5.499 | 29.758 | 1.00 | 42.65 | O |
| ATOM | 3336 | N | ALA | C | 52 | 2.945 | 4.413 | 31.670 | 1.00 | 42.49 | N |
| ATOM | 3337 | CA | ALA | C | 52 | 4.292 | 4.986 | 31.817 | 1.00 | 42.70 | C |
| ATOM | 3338 | CB | ALA | C | 52 | 4.449 | 5.673 | 33.151 | 1.00 | 44.67 | C |
| ATOM | 3339 | C | ALA | C | 52 | 5.328 | 3.882 | 31.678 | 1.00 | 46.52 | C |
| ATOM | 3340 | O | ALA | C | 52 | 5.094 | 2.744 | 32.100 | 1.00 | 42.47 | O |
| ATOM | 3341 | N | LYS | C | 53 | 6.440 | 4.205 | 31.021 | 1.00 | 47.16 | N |
| ATOM | 3342 | CA | LYS | C | 53 | 7.590 | 3.300 | 30.924 | 1.00 | 51.46 | C |
| ATOM | 3343 | CB | LYS | C | 53 | 7.734 | 2.770 | 29.513 | 1.00 | 49.07 | C |
| ATOM | 3344 | CG | LYS | C | 53 | 6.458 | 2.250 | 28.959 | 1.00 | 56.95 | C |
| ATOM | 3345 | CD | LYS | C | 53 | 6.668 | 1.390 | 27.732 | 1.00 | 66.19 | C |
| ATOM | 3346 | CE | LYS | C | 53 | 5.385 | 0.671 | 27.347 | 1.00 | 68.42 | C |
| ATOM | 3347 | NZ | LYS | C | 53 | 4.468 | 1.538 | 26.537 | 1.00 | 75.62 | N |
| ATOM | 3348 | C | LYS | C | 53 | 8.811 | 4.103 | 31.270 | 1.00 | 54.40 | C |
| ATOM | 3349 | O | LYS | C | 53 | 9.060 | 5.143 | 30.652 | 1.00 | 58.74 | O |
| ATOM | 3350 | N | VAL | C | 54 | 9.540 | 3.656 | 32.282 | 1.00 | 51.83 | N |
| ATOM | 3351 | CA | VAL | C | 54 | 10.798 | 4.271 | 32.681 | 1.00 | 52.63 | C |
| ATOM | 3352 | CB | VAL | C | 54 | 10.834 | 4.549 | 34.207 | 1.00 | 49.38 | C |
| ATOM | 3353 | CG1 | VAL | C | 54 | 12.011 | 5.414 | 34.608 | 1.00 | 62.21 | C |
| ATOM | 3354 | CG2 | VAL | C | 54 | 9.543 | 5.243 | 34.044 | 1.00 | 84.77 | C |
| ATOM | 3355 | C | VAL | C | 54 | 11.858 | 3.263 | 32.208 | 1.00 | 50.79 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 3356 | O | VAL | 54 | 11.706 | 2.061 | 32.397 | 1.00 | 49.46 | O |
| ATOM | 3357 | N | LEU | 55 | 12.874 | 3.755 | 31.507 | 1.00 | 50.50 | N |
| ATOM | 3358 | CA | LEU | 55 | 13.875 | 2.917 | 30.889 | 1.00 | 48.88 | C |
| ATOM | 3359 | CB | LEU | 55 | 13.622 | 2.923 | 29.381 | 1.00 | 54.01 | C |
| ATOM | 3360 | CG | LEU | 55 | 13.985 | 1.722 | 28.500 | 1.00 | 61.51 | C |
| ATOM | 3361 | CD1 | LEU | 55 | 13.160 | 0.503 | 28.913 | 1.00 | 65.62 | C |
| ATOM | 3362 | CD2 | LEU | 55 | 13.696 | 2.047 | 27.036 | 1.00 | 58.27 | C |
| ATOM | 3363 | C | LEU | 55 | 15.176 | 3.641 | 31.190 | 1.00 | 48.34 | C |
| ATOM | 3364 | O | LEU | 55 | 15.204 | 4.870 | 31.088 | 1.00 | 48.58 | O |
| ATOM | 3365 | N | TRP | 56 | 16.215 | 2.914 | 31.620 | 1.00 | 48.74 | N |
| ATOM | 3366 | CA | TRP | 56 | 17.577 | 3.473 | 31.848 | 1.00 | 42.84 | C |
| ATOM | 3367 | CB | TRP | 56 | 17.745 | 4.202 | 33.222 | 1.00 | 42.65 | C |
| ATOM | 3368 | CG | TRP | 56 | 17.714 | 3.321 | 34.476 | 1.00 | 44.11 | C |
| ATOM | 3369 | CD1 | TRP | 56 | 18.796 | 2.938 | 35.261 | 1.00 | 42.20 | C |
| ATOM | 3370 | NE1 | TRP | 56 | 18.358 | 2.136 | 36.288 | 1.00 | 41.34 | N |
| ATOM | 3371 | CE2 | TRP | 56 | 16.996 | 2.017 | 36.229 | 1.00 | 46.73 | C |
| ATOM | 3372 | CD2 | TRP | 56 | 16.549 | 2.756 | 35.110 | 1.00 | 42.65 | C |
| ATOM | 3373 | CE3 | TRP | 56 | 15.181 | 2.777 | 34.820 | 1.00 | 42.73 | C |
| ATOM | 3374 | CZ3 | TRP | 56 | 14.313 | 2.075 | 35.649 | 1.00 | 53.89 | C |
| ATOM | 3375 | CH2 | TRP | 56 | 14.798 | 1.357 | 36.761 | 1.00 | 45.08 | C |
| ATOM | 3376 | CZ2 | TRP | 56 | 16.118 | 1.337 | 37.075 | 1.00 | 44.62 | C |
| ATOM | 3377 | C | TRP | 56 | 18.620 | 2.365 | 31.721 | 1.00 | 43.99 | C |
| ATOM | 3378 | O | TRP | 56 | 18.275 | 1.191 | 31.773 | 1.00 | 40.68 | O |
| ATOM | 3379 | N | MET | 57 | 19.884 | 2.755 | 31.578 | 1.00 | 44.19 | N |
| ATOM | 3380 | CA | MET | 57 | 21.011 | 1.813 | 31.496 | 1.00 | 46.31 | C |
| ATOM | 3381 | CB | MET | 57 | 22.012 | 2.213 | 30.384 | 1.00 | 48.75 | C |
| ATOM | 3382 | CG | MET | 57 | 21.487 | 2.181 | 28.963 | 1.00 | 39.57 | C |
| ATOM | 3383 | SD | MET | 57 | 20.873 | 0.576 | 28.472 | 1.00 | 48.86 | S |
| ATOM | 3384 | CE | MET | 57 | 22.358 | -0.379 | 28.720 | 1.00 | 38.91 | C |
| ATOM | 3385 | C | MET | 57 | 21.740 | 1.826 | 32.826 | 1.00 | 45.43 | C |
| ATOM | 3386 | O | MET | 57 | 22.091 | 2.893 | 33.327 | 1.00 | 48.81 | O |
| ATOM | 3387 | N | GLN | 58 | 21.928 | 0.654 | 33.424 | 1.00 | 43.43 | N |
| ATOM | 3388 | CA | GLN | 58 | 22.818 | 0.534 | 34.581 | 1.00 | 47.14 | C |
| ATOM | 3389 | CB | GLN | 58 | 22.135 | -0.246 | 35.722 | 1.00 | 50.35 | C |
| ATOM | 3390 | CG | GLN | 58 | 22.534 | 0.176 | 37.163 | 1.00 | 49.39 | C |
| ATOM | 3391 | CD | GLN | 58 | 21.854 | 1.496 | 37.609 | 1.00 | 69.33 | C |
| ATOM | 3392 | OE1 | GLN | 58 | 20.595 | 1.623 | 37.678 | 1.00 | 61.66 | O |
| ATOM | 3393 | NE2 | GLN | 58 | 22.691 | 2.475 | 37.938 | 1.00 | 34.58 | N |
| ATOM | 3394 | C | GLN | 58 | 24.048 | -0.188 | 34.053 | 1.00 | 43.45 | C |
| ATOM | 3395 | O | GLN | 58 | 24.023 | -1.396 | 33.816 | 1.00 | 44.53 | O |
| ATOM | 3396 | N | GLY | 59 | 25.102 | 0.566 | 33.783 | 1.00 | 44.93 | N |
| ATOM | 3397 | CA | GLY | 59 | 26.254 | 0.010 | 33.076 | 1.00 | 42.33 | C |
| ATOM | 3398 | C | GLY | 59 | 25.806 | -0.465 | 31.723 | 1.00 | 42.76 | C |
| ATOM | 3399 | O | GLY | 59 | 25.148 | 0.281 | 30.981 | 1.00 | 45.21 | O |
| ATOM | 3400 | N | SER | 60 | 26.104 | -1.718 | 31.394 | 1.00 | 43.76 | N |
| ATOM | 3401 | CA | SER | 60 | 25.664 | -2.272 | 30.110 | 1.00 | 46.44 | C |
| ATOM | 3402 | CB | SER | 60 | 26.603 | -3.371 | 29.676 | 1.00 | 46.96 | C |
| ATOM | 3403 | CG | SER | 60 | 26.536 | -4.449 | 30.579 | 1.00 | 46.38 | O |
| ATOM | 3404 | C | SER | 60 | 24.274 | -2.874 | 30.112 | 1.00 | 46.95 | C |
| ATOM | 3405 | O | SER | 60 | 23.844 | -3.446 | 29.091 | 1.00 | 43.75 | O |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 3406 | N | GLN | C | 61 | 23.584 | −2.786 | 31.250 | 1.00 | 44.80 | N |
| ATOM | 3407 | CA | GLN | C | 61 | 22.290 | −3.458 | 31.429 | 1.00 | 45.07 | C |
| ATOM | 3408 | CB | GLN | C | 61 | 22.299 | −4.207 | 32.765 | 1.00 | 49.30 | C |
| ATOM | 3409 | CG | GLN | C | 61 | 21.020 | −5.015 | 33.046 | 1.00 | 54.65 | C |
| ATOM | 3410 | CD | GLN | C | 61 | 21.184 | −6.490 | 32.720 | 1.00 | 63.33 | C |
| ATOM | 3411 | OE1 | GLN | C | 61 | 20.330 | −7.099 | 32.074 | 1.00 | 70.56 | O |
| ATOM | 3412 | NE2 | GLN | C | 61 | 22.295 | −7.068 | 33.165 | 1.00 | 74.58 | N |
| ATOM | 3413 | C | GLN | C | 61 | 21.129 | −2.451 | 31.439 | 1.00 | 43.21 | C |
| ATOM | 3414 | O | GLN | C | 61 | 21.156 | −1.483 | 32.239 | 1.00 | 41.38 | O |
| ATOM | 3415 | N | GLN | C | 62 | 20.124 | −2.700 | 30.503 | 1.00 | 30.73 | N |
| ATOM | 3416 | CA | GLN | C | 62 | 18.903 | −1.872 | 30.535 | 1.00 | 43.63 | C |
| ATOM | 3417 | CB | GLN | C | 62 | 18.187 | −2.006 | 29.184 | 1.00 | 43.61 | C |
| ATOM | 3418 | CG | GLN | C | 62 | 17.085 | −0.958 | 29.003 | 1.00 | 44.69 | C |
| ATOM | 3419 | CD | GLN | C | 62 | 16.425 | −1.003 | 27.648 | 1.00 | 58.40 | C |
| ATOM | 3420 | OE1 | GLN | C | 62 | 16.563 | −1.967 | 26.896 | 1.00 | 68.10 | O |
| ATOM | 3421 | NE2 | GLN | C | 62 | 15.706 | 0.048 | 27.324 | 1.00 | 57.71 | N |
| ATOM | 3422 | C | GLN | C | 62 | 17.955 | −2.318 | 31.625 | 1.00 | 43.58 | C |
| ATOM | 3423 | O | GLN | C | 62 | 17.813 | −3.522 | 31.860 | 1.00 | 45.75 | O |
| ATOM | 3424 | N | CYS | C | 63 | 17.318 | −1.363 | 32.303 | 1.00 | 42.05 | N |
| ATOM | 3425 | CA | CYS | C | 63 | 16.350 | −1.696 | 33.354 | 1.00 | 40.83 | C |
| ATOM | 3426 | CB | CYS | C | 63 | 16.877 | −1.330 | 34.759 | 1.00 | 43.32 | C |
| ATOM | 3427 | SG | CYS | C | 63 | 18.352 | −2.344 | 35.088 | 1.00 | 53.55 | S |
| ATOM | 3428 | C | CYS | C | 63 | 15.079 | −0.970 | 32.992 | 1.00 | 43.09 | C |
| ATOM | 3429 | O | CYS | C | 63 | 15.147 | 0.113 | 32.403 | 1.00 | 41.15 | O |
| ATOM | 3430 | N | LYS | C | 64 | 13.943 | −1.599 | 33.279 | 1.00 | 38.94 | N |
| ATOM | 3431 | CA | LYS | C | 64 | 12.636 | −1.098 | 32.817 | 1.00 | 40.22 | C |
| ATOM | 3432 | CB | LYS | C | 64 | 12.266 | −1.817 | 31.513 | 1.00 | 43.20 | C |
| ATOM | 3433 | CG | LYS | C | 64 | 10.928 | −1.367 | 30.871 | 1.00 | 57.55 | C |
| ATOM | 3434 | CD | LYS | C | 64 | 10.551 | −2.367 | 29.776 | 1.00 | 61.10 | C |
| ATOM | 3435 | CE | LYS | C | 64 | 9.741 | −1.718 | 28.645 | 1.00 | 73.07 | C |
| ATOM | 3436 | NZ | LYS | C | 64 | 9.498 | −2.716 | 27.573 | 1.00 | 72.63 | N |
| ATOM | 3437 | C | LYS | C | 64 | 11.550 | −1.295 | 33.881 | 1.00 | 39.04 | C |
| ATOM | 3438 | O | LYS | C | 64 | 11.443 | −2.380 | 34.472 | 1.00 | 33.86 | O |
| ATOM | 3439 | N | GLN | C | 65 | 10.785 | −0.233 | 34.174 | 1.00 | 40.81 | N |
| ATOM | 3440 | CA | GLN | C | 65 | 9.550 | −0.321 | 34.992 | 1.00 | 42.27 | C |
| ATOM | 3441 | CB | GLN | C | 65 | 9.628 | 0.498 | 36.288 | 1.00 | 42.00 | C |
| ATOM | 3442 | CG | GLN | C | 65 | 8.310 | 0.488 | 37.137 | 1.00 | 42.32 | C |
| ATOM | 3443 | CD | GLN | C | 65 | 8.445 | 1.022 | 38.580 | 1.00 | 47.37 | C |
| ATOM | 3444 | OE1 | GLN | C | 65 | 9.418 | 1.691 | 38.933 | 1.00 | 53.21 | O |
| ATOM | 3445 | NE2 | GLN | C | 65 | 7.453 | 0.708 | 39.424 | 1.00 | 48.30 | N |
| ATOM | 3446 | C | GLN | C | 65 | 8.394 | 0.192 | 34.133 | 1.00 | 44.49 | C |
| ATOM | 3447 | O | GLN | C | 65 | 8.407 | 1.341 | 33.706 | 1.00 | 45.68 | O |
| ATOM | 3448 | N | THR | C | 66 | 7.438 | −0.688 | 33.848 | 1.00 | 42.48 | N |
| ATOM | 3449 | CA | THR | C | 66 | 6.207 | −0.317 | 33.151 | 1.00 | 43.06 | C |
| ATOM | 3450 | CB | THR | C | 66 | 5.854 | −1.357 | 32.102 | 1.00 | 44.16 | C |
| ATOM | 3451 | OG1 | THR | C | 66 | 6.931 | −1.440 | 31.149 | 1.00 | 53.19 | O |
| ATOM | 3452 | CG2 | THR | C | 66 | 4.577 | −0.965 | 31.379 | 1.00 | 52.34 | C |
| ATOM | 3453 | C | THR | C | 66 | 5.089 | −0.170 | 34.193 | 1.00 | 42.53 | C |
| ATOM | 3454 | O | THR | C | 66 | 4.942 | −1.025 | 35.078 | 1.00 | 43.10 | O |
| ATOM | 3455 | N | SER | C | 67 | 4.333 | 0.922 | 34.104 | 1.00 | 41.20 | N |

TABLE 10-continued

Atomic coordinates for COM1 complex of the modified
TXNIP protein represented by SEQ ID NO: 6 and the modified protein represented by SEQ ID NO: 3

| ATOM | 3456 | CA  | SER | 67 | 3.257   | 35.068 | 1.242  | 1.00 | 38.37 | C |
|------|------|-----|-----|----|---------|--------|--------|------|-------|---|
| ATOM | 3457 | CB  | SER | 67 | 3.674   | 35.966 | 2.384  | 1.00 | 41.02 | C |
| ATOM | 3458 | OG  | SER | 67 | 4.775   | 36.771 | 2.043  | 1.00 | 44.84 | O |
| ATOM | 3459 | C   | SER | 67 | 1.985   | 34.321 | 1.686  | 1.00 | 43.68 | C |
| ATOM | 3460 | O   | SER | 67 | 1.977   | 33.696 | 2.750  | 1.00 | 44.95 | O |
| ATOM | 3461 | N   | GLU | 68 | 0.926   | 34.411 | 0.880  | 1.00 | 39.06 | N |
| ATOM | 3462 | CA  | GLU | 68 | -0.407  | 33.953 | 1.226  | 1.00 | 44.87 | C |
| ATOM | 3463 | CB  | GLU | 68 | -1.196  | 33.791 | -0.046 | 1.00 | 43.72 | C |
| ATOM | 3464 | CG  | GLU | 68 | -1.099  | 32.454 | -0.618 | 1.00 | 47.90 | C |
| ATOM | 3465 | CD  | GLU | 68 | -1.923  | 32.345 | -1.862 | 1.00 | 58.91 | C |
| ATOM | 3466 | OE1 | GLU | 68 | -3.058  | 31.821 | -1.799 | 1.00 | 49.46 | O |
| ATOM | 3467 | OE2 | GLU | 68 | -1.431  | 32.810 | -2.907 | 1.00 | 46.88 | O |
| ATOM | 3468 | C   | GLU | 68 | -1.121  | 34.957 | 2.126  | 1.00 | 45.44 | C |
| ATOM | 3469 | O   | GLU | 68 | -1.139  | 35.147 | 1.857  | 1.00 | 46.96 | O |
| ATOM | 3470 | N   | TYR | 69 | -1.717  | 34.473 | 3.205  | 1.00 | 48.88 | N |
| ATOM | 3471 | CA  | TYR | 69 | -2.383  | 35.349 | 4.145  | 1.00 | 46.49 | C |
| ATOM | 3472 | CB  | TYR | 69 | -1.817  | 35.192 | 5.551  | 1.00 | 47.13 | C |
| ATOM | 3473 | CG  | TYR | 69 | -0.489  | 35.806 | 5.700  | 1.00 | 50.59 | C |
| ATOM | 3474 | CD1 | TYR | 69 | 0.662   | 35.010 | 5.747  | 1.00 | 41.95 | C |
| ATOM | 3475 | CE1 | TYR | 69 | 1.862   | 35.555 | 5.867  | 1.00 | 49.55 | C |
| ATOM | 3476 | CZ  | TYR | 69 | 1.981   | 36.927 | 5.946  | 1.00 | 49.94 | C |
| ATOM | 3477 | OH  | TYR | 69 | 3.206   | 37.442 | 6.078  | 1.00 | 49.08 | O |
| ATOM | 3478 | CE2 | TYR | 69 | 0.891   | 37.756 | 5.924  | 1.00 | 52.96 | C |
| ATOM | 3479 | CD2 | TYR | 69 | -0.353  | 37.183 | 5.785  | 1.00 | 47.86 | C |
| ATOM | 3480 | C   | TYR | 69 | -3.856  | 35.082 | 4.177  | 1.00 | 46.11 | C |
| ATOM | 3481 | O   | TYR | 69 | -4.622  | 35.954 | 4.580  | 1.00 | 47.93 | O |
| ATOM | 3482 | N   | LEU | 70 | -4.236  | 33.887 | 3.737  | 1.00 | 45.21 | N |
| ATOM | 3483 | CA  | LEU | 70 | -5.598  | 33.420 | 3.770  | 1.00 | 46.93 | C |
| ATOM | 3484 | CB  | LEU | 70 | -5.849  | 32.585 | 5.023  | 1.00 | 42.41 | C |
| ATOM | 3485 | CG  | LEU | 70 | -7.176  | 31.832 | 5.116  | 1.00 | 46.43 | C |
| ATOM | 3486 | CD1 | LEU | 70 | -8.385  | 32.838 | 5.207  | 1.00 | 46.88 | C |
| ATOM | 3487 | CD2 | LEU | 70 | -7.173  | 30.853 | 6.303  | 1.00 | 38.47 | C |
| ATOM | 3488 | C   | LEU | 70 | -5.841  | 32.520 | 2.586  | 1.00 | 48.45 | C |
| ATOM | 3489 | O   | LEU | 70 | -5.165  | 31.500 | 2.402  | 1.00 | 48.54 | O |
| ATOM | 3490 | N   | ARG | 71 | -6.843  | 32.857 | 1.791  | 1.00 | 47.95 | N |
| ATOM | 3491 | CA  | ARG | 71 | -7.221  | 31.988 | 0.719  | 1.00 | 50.31 | C |
| ATOM | 3492 | CB  | ARG | 71 | -6.499  | 32.287 | -0.584 | 1.00 | 53.53 | C |
| ATOM | 3493 | CG  | ARG | 71 | -6.740  | 31.241 | -1.686 | 1.00 | 50.79 | C |
| ATOM | 3494 | CD  | ARG | 71 | -6.548  | 31.869 | -3.062 | 1.00 | 56.47 | C |
| ATOM | 3495 | NE  | ARG | 71 | -5.197  | 32.407 | -3.260 | 1.00 | 54.31 | N |
| ATOM | 3496 | CZ  | ARG | 71 | -4.846  | 33.216 | -4.252 | 1.00 | 48.96 | C |
| ATOM | 3497 | NH1 | ARG | 71 | -5.740  | 33.637 | -5.125 | 1.00 | 49.28 | N |
| ATOM | 3498 | NH2 | ARG | 71 | -3.590  | 33.635 | -4.357 | 1.00 | 50.71 | N |
| ATOM | 3499 | C   | ARG | 71 | -8.719  | 32.110 | 0.578  | 1.00 | 56.67 | C |
| ATOM | 3500 | O   | ARG | 71 | -9.220  | 33.135 | 0.103  | 1.00 | 55.62 | O |
| ATOM | 3501 | N   | TYR | 72 | -9.392  | 31.058 | 1.041  | 1.00 | 54.65 | N |
| ATOM | 3502 | CA  | TYR | 72 | -10.814 | 31.014 | 1.270  | 1.00 | 56.86 | C |
| ATOM | 3503 | CB  | TYR | 72 | -11.142 | 31.208 | 2.774  | 1.00 | 54.24 | C |
| ATOM | 3504 | CG  | TYR | 72 | -12.595 | 30.923 | 3.104  | 1.00 | 60.53 | C |
| ATOM | 3505 | CD1 | TYR | 72 | -13.547 | 31.950 | 3.082  | 1.00 | 55.41 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 3506 | CE1 | TYR | C | 72 | −14.911 | 3.637 | 31.689 | 1.00 | 68.10 | C |
| ATOM | 3507 | CZ | TYR | C | 72 | −15.312 | 3.664 | 30.393 | 1.00 | 61.64 | C |
| ATOM | 3508 | OH | TYR | C | 72 | −16.640 | 3.948 | 30.135 | 1.00 | 71.73 | O |
| ATOM | 3509 | CE2 | TYR | C | 72 | −14.379 | 3.685 | 29.356 | 1.00 | 63.24 | C |
| ATOM | 3510 | CD2 | TYR | C | 72 | −13.029 | 3.393 | 29.619 | 1.00 | 51.09 | C |
| ATOM | 3511 | C | TYR | C | 72 | −11.260 | 0.820 | 29.643 | 1.00 | 55.68 | C |
| ATOM | 3512 | O | TYR | C | 72 | −10.721 | 1.238 | 28.631 | 1.00 | 57.62 | O |
| ATOM | 3513 | N | GLU | C | 73 | −12.267 | −0.037 | 29.605 | 1.00 | 58.82 | N |
| ATOM | 3514 | CA | GLU | C | 73 | −12.822 | −0.467 | 28.341 | 1.00 | 57.79 | C |
| ATOM | 3515 | CB | GLU | C | 73 | −12.324 | −1.873 | 27.999 | 1.00 | 58.95 | C |
| ATOM | 3516 | CG | GLU | C | 73 | −12.148 | −2.122 | 26.499 | 1.00 | 68.83 | C |
| ATOM | 3517 | CD | GLU | C | 73 | −11.610 | −3.515 | 26.164 | 1.00 | 78.62 | C |
| ATOM | 3518 | OE1 | GLU | C | 73 | −11.269 | −4.276 | 27.103 | 1.00 | 82.31 | O |
| ATOM | 3519 | OE2 | GLU | C | 73 | −11.529 | −3.846 | 24.951 | 1.00 | 81.65 | O |
| ATOM | 3520 | C | GLU | C | 73 | −14.356 | −0.395 | 28.440 | 1.00 | 58.34 | C |
| ATOM | 3521 | O | GLU | C | 73 | −14.914 | −0.325 | 29.545 | 1.00 | 58.89 | O |
| ATOM | 3522 | N | ASP | C | 74 | −15.028 | −0.373 | 27.293 | 1.00 | 53.97 | N |
| ATOM | 3523 | CA | ASP | C | 74 | −15.479 | −0.118 | 27.251 | 1.00 | 56.74 | C |
| ATOM | 3524 | CB | ASP | C | 74 | −16.786 | 1.298 | 27.734 | 1.00 | 57.21 | C |
| ATOM | 3525 | CG | ASP | C | 74 | −18.143 | 1.411 | 28.369 | 1.00 | 51.87 | C |
| ATOM | 3526 | OD1 | ASP | C | 74 | −18.621 | 0.410 | 28.936 | 1.00 | 57.95 | O |
| ATOM | 3527 | OD2 | ASP | C | 74 | −18.725 | 2.512 | 28.313 | 1.00 | 72.14 | O |
| ATOM | 3528 | C | ASP | C | 74 | −16.995 | −0.275 | 25.839 | 1.00 | 54.36 | C |
| ATOM | 3529 | O | ASP | C | 74 | −15.268 | −0.046 | 24.890 | 1.00 | 55.77 | O |
| ATOM | 3530 | N | THR | C | 75 | −19.240 | −0.716 | 25.699 | 1.00 | 56.77 | N |
| ATOM | 3531 | CA | THR | C | 75 | −18.894 | −0.754 | 24.385 | 1.00 | 53.10 | C |
| ATOM | 3532 | CB | THR | C | 75 | −19.567 | −2.115 | 24.149 | 1.00 | 56.86 | C |
| ATOM | 3533 | CG1 | THR | C | 75 | −18.606 | −3.157 | 24.421 | 1.00 | 55.05 | C |
| ATOM | 3534 | CG2 | THR | C | 75 | −20.115 | −2.233 | 22.697 | 1.00 | 56.75 | C |
| ATOM | 3535 | C | THR | C | 75 | −19.926 | 0.358 | 24.369 | 1.00 | 51.17 | C |
| ATOM | 3536 | O | THR | C | 75 | −20.676 | 0.530 | 25.340 | 1.00 | 47.93 | O |
| ATOM | 3537 | N | LEU | C | 76 | −19.963 | 1.112 | 23.267 | 1.00 | 51.59 | N |
| ATOM | 3538 | CA | LEU | C | 76 | −20.769 | 2.341 | 23.168 | 1.00 | 47.02 | C |
| ATOM | 3539 | CG | LEU | C | 76 | −19.950 | 3.471 | 22.499 | 1.00 | 46.11 | C |
| ATOM | 3540 | CG | LEU | C | 76 | −18.558 | 3.816 | 23.082 | 1.00 | 37.59 | C |
| ATOM | 3541 | CD1 | LEU | C | 76 | −17.999 | 5.020 | 22.382 | 1.00 | 37.62 | C |
| ATOM | 3542 | CD2 | LEU | C | 76 | −18.589 | 4.011 | 25.596 | 1.00 | 47.57 | C |
| ATOM | 3543 | C | LEU | C | 76 | −22.116 | 2.160 | 22.430 | 1.00 | 47.06 | C |
| ATOM | 3544 | O | LEU | C | 76 | −22.219 | 1.832 | 21.483 | 1.00 | 45.16 | O |
| ATOM | 3545 | N | LEU | C | 77 | −23.108 | 2.948 | 22.839 | 1.00 | 47.83 | N |
| ATOM | 3546 | CA | LEU | C | 77 | −24.464 | 2.891 | 22.241 | 1.00 | 49.50 | C |
| ATOM | 3547 | CB | LEU | C | 77 | −25.448 | 2.400 | 23.292 | 1.00 | 51.51 | C |
| ATOM | 3548 | CG | LEU | C | 77 | −25.308 | 1.021 | 23.939 | 1.00 | 55.20 | C |
| ATOM | 3549 | CD1 | LEU | C | 77 | −26.503 | 0.833 | 24.855 | 1.00 | 57.67 | C |
| ATOM | 3550 | CD2 | LEU | C | 77 | −25.243 | −0.128 | 22.890 | 1.00 | 00.19 | C |
| ATOM | 3551 | C | LEU | C | 77 | −24.986 | 4.230 | 21.732 | 1.00 | 00.19 | C |
| ATOM | 3552 | O | LEU | C | 77 | −24.725 | 5.262 | 22.338 | 1.00 | 46.32 | O |
| ATOM | 3553 | N | LEU | C | 78 | −25.785 | 4.205 | 20.549 | 1.00 | 47.97 | N |
| ATOM | 3554 | CA | LEU | C | 78 | −26.576 | 5.356 | 20.284 | 1.00 | 47.78 | C |
| ATOM | 3555 | CB | LEU | C | 78 | −26.870 | 5.379 | 18.777 | 1.00 | 47.87 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 3556 | CG | LEU | C | 78 | −25.855 | 5.597 | 17.855 | 1.00 | 49.56 | C |
| ATOM | 3557 | CD1 | LEU | C | 78 | −26.015 | 5.181 | 16.482 | 1.00 | 55.90 | C |
| ATOM | 3558 | CD2 | LEU | C | 78 | −25.505 | 7.038 | 17.800 | 1.00 | 5.60 | C |
| ATOM | 3559 | C | LEU | C | 78 | −27.875 | 5.330 | 21.065 | 1.00 | 49.50 | C |
| ATOM | 3560 | O | LEU | C | 78 | −28.356 | 4.250 | 21.455 | 1.00 | 50.41 | O |
| ATOM | 3561 | N | GLU | C | 79 | −20.459 | 0.510 | 21.275 | 1.00 | 50.71 | N |
| ATOM | 3562 | CA | GLU | C | 79 | −29.802 | 6.632 | 21.815 | 1.00 | 50.64 | C |
| ATOM | 3563 | CB | GLU | C | 79 | −30.253 | 8.097 | 21.874 | 1.00 | 54.43 | C |
| ATOM | 3564 | CG | GLU | C | 79 | −29.955 | 8.839 | 23.171 | 1.00 | 61.45 | C |
| ATOM | 3565 | CD | GLU | C | 79 | −30.748 | 10.152 | 23.282 | 1.00 | 69.89 | C |
| ATOM | 3566 | OE1 | GLU | C | 79 | −30.385 | 11.144 | 22.595 | 1.00 | 69.48 | O |
| ATOM | 3567 | OE2 | GLU | C | 79 | −31.738 | 10.186 | 24.054 | 1.00 | 73.51 | O |
| ATOM | 3568 | C | GLU | C | 79 | −30.792 | 5.844 | 20.947 | 1.00 | 45.05 | C |
| ATOM | 3569 | O | GLU | C | 79 | −31.740 | 5.285 | 21.547 | 1.00 | 43.61 | O |
| ATOM | 3570 | N | ASP | C | 80 | −30.555 | 5.790 | 19.542 | 1.00 | 43.88 | N |
| ATOM | 3571 | CA | ASP | C | 80 | −31.465 | 5.100 | 18.701 | 1.00 | 44.98 | C |
| ATOM | 3572 | CB | ASP | C | 80 | −31.308 | 5.683 | 17.204 | 1.00 | 45.23 | C |
| ATOM | 3573 | CG | ASP | C | 80 | −32.489 | 5.371 | 16.407 | 1.00 | 39.05 | C |
| ATOM | 3574 | OD1 | ASP | C | 80 | −33.626 | 5.537 | 16.878 | 1.00 | 30.82 | O |
| ATOM | 3575 | OD2 | ASP | C | 80 | −32.280 | 4.950 | 15.248 | 1.00 | 42.86 | O |
| ATOM | 3576 | C | ASP | C | 80 | −31.327 | 3.562 | 18.564 | 1.00 | 43.23 | C |
| ATOM | 3577 | O | ASP | C | 80 | −31.915 | 2.886 | 17.822 | 1.00 | 42.99 | O |
| ATOM | 3578 | N | GLN | C | 81 | −30.584 | 3.028 | 19.620 | 1.00 | 45.64 | N |
| ATOM | 3579 | CA | GLN | C | 81 | −30.343 | 1.599 | 19.783 | 1.00 | 45.09 | C |
| ATOM | 3580 | CB | GLN | C | 81 | −28.839 | 1.337 | 19.810 | 1.00 | 43.40 | C |
| ATOM | 3581 | CG | GLN | C | 81 | −28.110 | 1.229 | 18.499 | 1.00 | 45.37 | C |
| ATOM | 3582 | CD | GLN | C | 81 | −26.663 | 0.755 | 18.732 | 1.00 | 59.05 | C |
| ATOM | 3583 | OE1 | GLN | C | 81 | −25.779 | 1.534 | 19.132 | 1.00 | 60.50 | O |
| ATOM | 3584 | ND2 | GLN | C | 81 | −26.423 | 0.535 | 10.495 | 1.00 | 61.20 | N |
| ATOM | 3585 | C | GLN | C | 81 | −30.883 | 1.169 | 21.148 | 1.00 | 41.23 | C |
| ATOM | 3586 | O | GLN | C | 81 | −30.121 | 0.171 | 21.980 | 1.00 | 44.05 | O |
| ATOM | 3587 | N | PRO | C | 82 | −32.186 | 1.286 | 21.378 | 1.00 | 40.02 | N |
| ATOM | 3588 | CA | PRO | C | 82 | −32.652 | 1.096 | 22.758 | 1.00 | 41.45 | C |
| ATOM | 3589 | CB | PRO | C | 82 | −34.052 | 1.670 | 22.715 | 1.00 | 37.82 | C |
| ATOM | 3590 | CG | PRO | C | 82 | −34.564 | 1.307 | 21.302 | 1.00 | 40.01 | C |
| ATOM | 3591 | CD | PRO | C | 82 | −33.289 | 1.574 | 20.454 | 1.00 | 42.31 | C |
| ATOM | 3592 | C | PRO | C | 82 | −32.654 | −0.341 | 23.341 | 1.00 | 42.43 | C |
| ATOM | 3593 | O | PRO | C | 82 | −32.750 | −0.507 | 24.565 | 1.00 | 43.25 | O |
| ATOM | 3594 | N | THR | C | 83 | −32.546 | −1.368 | 22.497 | 1.00 | 40.37 | N |
| ATOM | 3595 | CA | THR | C | 83 | −32.519 | −2.752 | 23.000 | 1.00 | 38.94 | C |
| ATOM | 3596 | CB | THR | C | 83 | −33.255 | −3.711 | 22.062 | 1.00 | 39.93 | C |
| ATOM | 3597 | OG1 | THR | C | 83 | −32.652 | −3.784 | 20.836 | 1.00 | 39.55 | O |
| ATOM | 3598 | OG2 | THR | C | 83 | −34.699 | −3.216 | 21.790 | 1.00 | 30.47 | O |
| ATOM | 3599 | C | THR | C | 83 | −31.062 | −3.198 | 23.274 | 1.00 | 43.97 | C |
| ATOM | 3600 | O | THR | C | 83 | −31.785 | −4.336 | 23.677 | 1.00 | 44.14 | O |
| ATOM | 3601 | N | GLY | C | 84 | −30.138 | −2.280 | 23.045 | 1.00 | 45.65 | N |
| ATOM | 3602 | CA | GLY | C | 84 | −28.822 | −2.415 | 23.562 | 1.00 | 49.92 | C |
| ATOM | 3603 | C | GLY | C | 84 | −27.754 | −2.951 | 22.659 | 1.00 | 53.51 | C |
| ATOM | 3604 | O | GLY | C | 84 | −27.856 | −2.881 | 21.445 | 1.00 | 50.82 | O |
| ATOM | 3605 | N | GLU | C | 85 | −26.851 | −3.542 | 23.326 | 1.00 | 59.49 | N |

TABLE 10-continued

Atomic coordinates for COM1 complex of the modified
TXNIP protein represented by SEQ ID NO: 6 and the modified protein represented by SEQ ID NO: 3

| ATOM | 3606 | CA  | GLU | C | 85 | -25.425 | -3.804 | 22.798 | 1.00 | 65.68 | C |
|------|------|-----|-----|---|----|---------|--------|--------|------|-------|---|
| ATOM | 3607 | CB  | GLU | C | 85 | -24.554 | -4.436 | 23.944 | 1.00 | 67.95 | C |
| ATOM | 3608 | CG  | GLU | C | 85 | -25.024 | -4.043 | 25.354 | 1.00 | 70.37 | C |
| ATOM | 3609 | CD  | GLU | C | 85 | -24.365 | -2.789 | 25.844 | 1.00 | 69.76 | C |
| ATOM | 3610 | OE1 | GLU | C | 85 | -23.126 | -2.682 | 25.708 | 1.00 | 75.52 | O |
| ATOM | 3611 | OE2 | GLU | C | 85 | -25.079 | -1.916 | 26.369 | 1.00 | 67.88 | O |
| ATOM | 3612 | C   | GLU | C | 85 | -25.399 | -4.914 | 21.069 | 1.00 | 66.82 | C |
| ATOM | 3613 | O   | GLU | C | 85 | -24.398 | -5.021 | 20.964 | 1.00 | 64.26 | O |
| ATOM | 3614 | N   | ASN | C | 86 | -26.475 | -5.686 | 21.532 | 1.00 | 70.57 | N |
| ATOM | 3615 | CA  | ASN | C | 86 | -25.610 | -5.606 | 20.402 | 1.00 | 73.50 | C |
| ATOM | 3616 | CB  | ASN | C | 86 | -27.295 | -7.904 | 20.806 | 1.00 | 73.68 | C |
| ATOM | 3617 | CG  | ASN | C | 86 | -26.520 | -9.112 | 20.354 | 1.00 | 74.29 | C |
| ATOM | 3618 | OD1 | ASN | C | 86 | -25.588 | -9.542 | 21.033 | 1.00 | 77.00 | O |
| ATOM | 3619 | ND2 | ASN | C | 86 | -26.885 | -9.664 | 19.202 | 1.00 | 74.10 | N |
| ATOM | 3620 | C   | ASN | C | 86 | -27.330 | -6.000 | 19.210 | 1.00 | 73.76 | C |
| ATOM | 3621 | O   | ASN | C | 86 | -26.938 | -5.239 | 18.067 | 1.00 | 75.63 | O |
| ATOM | 3622 | N   | GLU | C | 87 | -28.388 | -5.235 | 19.464 | 1.00 | 74.55 | N |
| ATOM | 3623 | CA  | GLU | C | 87 | -29.053 | -4.504 | 18.385 | 1.00 | 73.73 | C |
| ATOM | 3624 | CB  | GLU | C | 87 | -29.892 | -3.338 | 18.942 | 1.00 | 75.01 | C |
| ATOM | 3625 | CG  | GLU | C | 87 | -30.595 | -2.488 | 17.872 | 1.00 | 70.62 | C |
| ATOM | 3626 | CD  | GLU | C | 87 | -31.088 | -1.554 | 18.426 | 1.00 | 75.83 | C |
| ATOM | 3627 | OE1 | GLU | C | 87 | -32.095 | -1.699 | 19.599 | 1.00 | 75.83 | O |
| ATOM | 3628 | OE2 | GLU | C | 87 | -32.141 | -0.673 | 17.664 | 1.00 | 72.00 | O |
| ATOM | 3629 | C   | GLU | C | 87 | -27.995 | -3.986 | 17.409 | 1.00 | 73.29 | C |
| ATOM | 3630 | O   | GLU | C | 87 | -27.211 | -3.093 | 17.750 | 1.00 | 73.65 | O |
| ATOM | 3631 | N   | MET | C | 88 | -27.940 | -4.587 | 16.222 | 1.00 | 72.26 | N |
| ATOM | 3632 | CA  | MET | C | 88 | -27.110 | -4.075 | 15.133 | 1.00 | 72.39 | C |
| ATOM | 3633 | CB  | MET | C | 88 | -27.288 | -4.911 | 13.858 | 1.00 | 74.50 | C |
| ATOM | 3634 | CG  | MET | C | 88 | -26.562 | -6.254 | 13.857 | 1.00 | 78.17 | C |
| ATOM | 3635 | SD  | MET | C | 88 | -24.864 | -6.114 | 13.267 | 1.00 | 79.56 | S |
| ATOM | 3636 | CE  | MET | C | 88 | -24.350 | -7.839 | 13.226 | 1.00 | 77.50 | C |
| ATOM | 3637 | C   | MET | C | 88 | -27.533 | -2.551 | 14.852 | 1.00 | 71.05 | C |
| ATOM | 3638 | O   | MET | C | 88 | -28.634 | -2.243 | 15.218 | 1.00 | 72.12 | O |
| ATOM | 3639 | N   | VAL | C | 89 | -26.668 | -1.892 | 14.197 | 1.00 | 69.29 | N |
| ATOM | 3640 | CA  | VAL | C | 89 | -26.996 | -0.508 | 13.858 | 1.00 | 67.49 | C |
| ATOM | 3641 | CB  | VAL | C | 89 | -26.198 | -0.521 | 14.721 | 1.00 | 65.84 | C |
| ATOM | 3642 | CG1 | VAL | C | 89 | -24.820 | -0.040 | 15.081 | 1.00 | 65.56 | C |
| ATOM | 3643 | CG2 | VAL | C | 89 | -26.118 | 1.907  | 14.048 | 1.00 | 60.21 | C |
| ATOM | 3644 | C   | VAL | C | 89 | -26.806 | -0.302 | 12.369 | 1.00 | 66.65 | C |
| ATOM | 3645 | O   | VAL | C | 89 | -25.781 | -0.664 | 11.809 | 1.00 | 66.06 | O |
| ATOM | 3646 | N   | ILE | C | 90 | -27.826 | 0.258  | 11.738 | 1.00 | 68.26 | N |
| ATOM | 3647 | CA  | ILE | C | 90 | -27.830 | 0.456  | 10.294 | 1.00 | 67.32 | C |
| ATOM | 3648 | CB  | ILE | C | 90 | -29.234 | 0.131  | 9.666  | 1.00 | 67.46 | C |
| ATOM | 3649 | CG1 | ILE | C | 90 | -29.436 | -1.392 | 9.590  | 1.00 | 67.42 | C |
| ATOM | 3650 | CD1 | ILE | C | 90 | -28.482 | -2.137 | 8.635  | 1.00 | 68.09 | C |
| ATOM | 3651 | CG2 | ILE | C | 90 | -29.416 | 0.798  | 8.302  | 1.00 | 65.65 | C |
| ATOM | 3652 | C   | ILE | C | 90 | -27.386 | 1.890  | 10.019 | 1.00 | 66.04 | C |
| ATOM | 3653 | O   | ILE | C | 90 | -28.157 | 2.844  | 10.173 | 1.00 | 64.13 | O |
| ATOM | 3654 | N   | MET | C | 91 | -26.119 | 2.028  | 9.652  | 1.00 | 66.32 | N |
| ATOM | 3655 | CA  | MET | C | 91 | -25.564 | 3.345  | 9.368  | 1.00 | 67.84 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 3656 | CB | MET | C | 91 | −24.084 | 3.442 | 9.754 | 1.00 | 65.45 | C |
| ATOM | 3657 | CG | MET | C | 91 | −23.812 | 3.407 | 11.249 | 1.00 | 62.80 | C |
| ATOM | 3658 | SD | MET | C | 91 | −22.143 | 3.972 | 11.567 | 1.00 | 60.87 | S |
| ATOM | 3659 | CE | MET | C | 91 | −22.189 | 5.588 | 10.767 | 1.00 | 44.66 | C |
| ATOM | 3660 | C | MET | C | 91 | −25.735 | 3.678 | 7.903 | 1.00 | 69.75 | C |
| ATOM | 3661 | O | MET | C | 91 | −25.165 | 3.002 | 7.030 | 1.00 | 69.68 | O |
| ATOM | 3662 | N | ARG | C | 92 | −26.512 | 4.731 | 7.653 | 1.00 | 71.43 | N |
| ATOM | 3663 | CA | ARG | C | 92 | −26.802 | 5.201 | 6.301 | 1.00 | 72.19 | C |
| ATOM | 3664 | CB | ARG | C | 92 | −28.331 | 5.284 | 6.066 | 1.00 | 72.43 | C |
| ATOM | 3665 | CG | ARG | C | 92 | −28.981 | 6.687 | 6.166 | 1.00 | 75.69 | C |
| ATOM | 3666 | CD | ARG | C | 92 | −30.522 | 6.622 | 6.301 | 1.00 | 83.60 | C |
| ATOM | 3667 | NE | ARG | C | 92 | −31.065 | 5.400 | 5.702 | 1.00 | 90.23 | N |
| ATOM | 3668 | CZ | ARG | C | 92 | −31.374 | 4.299 | 6.387 | 1.00 | 89.09 | C |
| ATOM | 3669 | NH1 | ARG | C | 92 | −31.218 | 4.270 | 7.708 | 1.00 | 86.37 | N |
| ATOM | 3670 | NH2 | ARG | C | 92 | −31.843 | 3.231 | 5.751 | 1.00 | 83.05 | N |
| ATOM | 3671 | C | ARG | C | 92 | −26.139 | 6.552 | 6.074 | 1.00 | 71.22 | C |
| ATOM | 3672 | O | ARG | C | 92 | −26.038 | 7.352 | 7.010 | 1.00 | 70.94 | O |
| ATOM | 3673 | N | PRO | C | 93 | −25.697 | 6.816 | 4.828 | 1.00 | 72.22 | N |
| ATOM | 3674 | CA | PRO | C | 93 | −24.992 | 8.064 | 4.480 | 1.00 | 73.49 | C |
| ATOM | 3675 | CB | PRO | C | 93 | −24.741 | 7.921 | 2.973 | 1.00 | 72.95 | C |
| ATOM | 3676 | CG | PRO | C | 93 | −24.837 | 6.472 | 2.695 | 1.00 | 68.28 | C |
| ATOM | 3677 | CD | PRO | C | 93 | −25.829 | 5.923 | 3.662 | 1.00 | 71.30 | C |
| ATOM | 3678 | C | PRO | C | 93 | −25.784 | 9.343 | 4.776 | 1.00 | 73.88 | C |
| ATOM | 3679 | O | PRO | C | 93 | −26.992 | 9.281 | 4.934 | 1.00 | 74.29 | O |
| ATOM | 3680 | N | GLY | C | 94 | −25.142 | 10.461 | 4.730 | 1.00 | 74.77 | N |
| ATOM | 3681 | CA | GLY | C | 94 | −25.984 | 11.579 | 4.749 | 1.00 | 75.40 | C |
| ATOM | 3682 | C | GLY | C | 94 | −25.912 | 12.366 | 5.987 | 1.00 | 76.26 | C |
| ATOM | 3683 | O | GLY | C | 94 | −25.849 | 13.552 | 5.745 | 1.00 | 76.45 | O |
| ATOM | 3684 | N | ASN | C | 95 | −25.930 | 11.723 | 7.184 | 1.00 | 75.63 | N |
| ATOM | 3685 | CA | ASN | C | 95 | −25.984 | 12.317 | 8.554 | 1.00 | 75.71 | C |
| ATOM | 3686 | CB | ASN | C | 95 | −27.281 | 12.113 | 9.246 | 1.00 | 76.88 | C |
| ATOM | 3687 | CG | ASN | C | 95 | −28.218 | 11.180 | 8.490 | 1.00 | 77.97 | C |
| ATOM | 3688 | CD1 | ASN | C | 95 | −29.062 | 11.644 | 7.750 | 1.00 | 73.11 | O |
| ATOM | 3689 | ND2 | ASN | C | 95 | −28.097 | 9.574 | 8.710 | 1.00 | 71.70 | N |
| ATOM | 3690 | C | ASN | C | 95 | −24.850 | 11.855 | 9.587 | 1.00 | 75.60 | C |
| ATOM | 3691 | O | ASN | C | 95 | −24.217 | 10.289 | 9.396 | 1.00 | 75.29 | O |
| ATOM | 3692 | N | LYS | C | 96 | −24.697 | 12.588 | 10.698 | 1.00 | 72.19 | N |
| ATOM | 3693 | CA | LYS | C | 96 | −23.658 | 12.348 | 11.741 | 1.00 | 68.57 | C |
| ATOM | 3694 | CB | LYS | C | 96 | −23.363 | 13.682 | 12.402 | 1.00 | 70.33 | C |
| ATOM | 3695 | CG | LYS | C | 96 | −22.039 | 14.297 | 12.097 | 1.00 | 72.45 | C |
| ATOM | 3696 | CD | LYS | C | 96 | −22.143 | 15.807 | 12.214 | 1.00 | 78.98 | C |
| ATOM | 3697 | CE | LYS | C | 96 | −20.934 | 16.417 | 12.886 | 1.00 | 81.93 | C |
| ATOM | 3698 | NZ | LYS | C | 96 | −20.328 | 17.508 | 12.088 | 1.00 | 80.79 | N |
| ATOM | 3699 | O | LYS | C | 96 | −23.948 | 11.394 | 12.919 | 1.00 | 63.62 | O |
| ATOM | 3700 | C | LYS | C | 96 | −24.799 | 11.693 | 13.722 | 1.00 | 62.79 | C |
| ATOM | 3701 | N | TYR | C | 97 | −23.193 | 10.311 | 13.068 | 1.00 | 57.59 | N |
| ATOM | 3702 | CA | TYR | C | 97 | −23.318 | 9.422 | 14.231 | 1.00 | 53.20 | C |
| ATOM | 3703 | CB | TYR | C | 97 | −23.381 | 7.694 | 13.810 | 1.00 | 58.29 | C |
| ATOM | 3704 | CG | TYR | C | 97 | −24.388 | 7.620 | 12.715 | 1.00 | 58.47 | C |
| ATOM | 3705 | CD1 | TYR | C | 97 | −25.621 | 7.110 | 13.024 | 1.00 | 60.04 | C |

TABLE 10-continued

Atomic coordinates for COM1 complex of the modified
TXNIP protein represented by SEQ ID NO: 6 and the modified protein represented by SEQ ID NO: 3

| ATOM | 3706 | CE1 | TYR | C | 97 | −26.510 | 6.774 | 12.055 | 1.00 | 68.57 | C |
|---|---|---|---|---|---|---|---|---|---|---|---|
| ATOM | 3707 | CZ | TYR | C | 97 | −26.182 | 6.935 | 10.751 | 1.00 | 68.85 | C |
| ATOM | 3708 | OH | TYR | C | 97 | −27.084 | 6.587 | 9.784 | 1.00 | 69.10 | O |
| ATOM | 3709 | CE2 | TYR | C | 97 | −24.952 | 7.417 | 10.414 | 1.00 | 66.07 | C |
| ATOM | 3710 | CD2 | TYR | C | 97 | −24.065 | 7.743 | 11.390 | 1.00 | 56.14 | C |
| ATOM | 3711 | C | TYR | C | 97 | −22.388 | 9.627 | 15.501 | 1.00 | 48.07 | C |
| ATOM | 3712 | O | TYR | C | 97 | −21.060 | 9.522 | 15.527 | 1.00 | 44.79 | O |
| ATOM | 3713 | N | GLU | C | 98 | −23.110 | 9.944 | 15.581 | 1.00 | 46.66 | N |
| ATOM | 3714 | CA | GLU | C | 98 | −22.319 | 10.330 | 17.768 | 1.00 | 48.12 | C |
| ATOM | 3715 | CB | GLU | C | 98 | −22.757 | 11.720 | 18.222 | 1.00 | 47.74 | C |
| ATOM | 3716 | CG | GLU | C | 98 | −22.396 | 12.864 | 17.284 | 1.00 | 46.02 | C |
| ATOM | 3717 | CD | GLU | C | 98 | −22.952 | 14.206 | 17.772 | 1.00 | 59.93 | C |
| ATOM | 3718 | OE1 | GLU | C | 98 | −23.308 | 14.343 | 18.970 | 1.00 | 64.64 | O |
| ATOM | 3719 | OE2 | GLU | C | 98 | −23.031 | 15.149 | 16.959 | 1.00 | 70.23 | O |
| ATOM | 3720 | C | GLU | C | 98 | −22.521 | 0.343 | 18.041 | 1.00 | 40.07 | C |
| ATOM | 3721 | O | GLU | C | 98 | −23.627 | 9.250 | 19.504 | 1.00 | 48.69 | O |
| ATOM | 3722 | N | TYR | C | 99 | −21.473 | 8.506 | 19.296 | 1.00 | 46.18 | N |
| ATOM | 3723 | CA | TYR | C | 99 | −21.515 | 7.719 | 20.467 | 1.00 | 46.18 | C |
| ATOM | 3724 | CB | TYR | C | 99 | −20.749 | 6.444 | 20.159 | 1.00 | 45.27 | C |
| ATOM | 3725 | CG | TYR | C | 99 | −21.360 | 5.523 | 19.145 | 1.00 | 53.41 | C |
| ATOM | 3726 | CD | TYR | C | 99 | −21.833 | 4.273 | 19.533 | 1.00 | 57.23 | C |
| ATOM | 3727 | CE1 | TYR | C | 99 | −22.376 | 3.390 | 18.610 | 1.00 | 54.80 | C |
| ATOM | 3728 | CZ | TYR | C | 99 | −22.450 | 3.744 | 17.298 | 1.00 | 53.09 | C |
| ATOM | 3729 | OH | TYR | C | 99 | −22.975 | 2.831 | 16.417 | 1.00 | 63.00 | O |
| ATOM | 3730 | CE2 | TYR | C | 99 | −21.980 | 4.982 | 16.863 | 1.00 | 62.74 | C |
| ATOM | 3731 | CD2 | TYR | C | 99 | −21.423 | 5.863 | 17.793 | 1.00 | 55.28 | C |
| ATOM | 3732 | C | TYR | C | 99 | −20.810 | 8.391 | 21.651 | 1.00 | 42.71 | C |
| ATOM | 3733 | O | TYR | C | 99 | −19.592 | 8.531 | 21.630 | 1.00 | 39.72 | O |
| ATOM | 3734 | N | LYS | C | 100 | −21.544 | 8.777 | 22.688 | 1.00 | 40.01 | N |
| ATOM | 3735 | CA | LYS | C | 100 | −20.907 | 9.372 | 23.866 | 1.00 | 36.59 | C |
| ATOM | 3736 | CB | LYS | C | 100 | −21.947 | 9.993 | 24.770 | 1.00 | 38.44 | C |
| ATOM | 3737 | CG | LYS | C | 100 | −22.654 | 11.197 | 24.193 | 1.00 | 43.20 | C |
| ATOM | 3738 | CD | LYS | C | 100 | −23.808 | 11.613 | 25.099 | 1.00 | 56.75 | C |
| ATOM | 3739 | CE | LYS | C | 100 | −24.632 | 12.738 | 24.470 | 1.00 | 70.94 | C |
| ATOM | 3740 | NZ | LYS | C | 100 | −26.099 | 12.620 | 24.766 | 1.00 | 70.94 | N |
| ATOM | 3741 | C | LYS | C | 100 | −20.078 | 8.359 | 24.583 | 1.00 | 39.07 | C |
| ATOM | 3742 | O | LYS | C | 100 | −20.465 | 7.219 | 24.804 | 1.00 | 39.66 | O |
| ATOM | 3743 | N | PHE | C | 101 | −18.961 | 8.813 | 25.253 | 1.00 | 35.71 | N |
| ATOM | 3744 | CA | PHE | C | 101 | −18.166 | 8.024 | 26.207 | 1.00 | 39.01 | C |
| ATOM | 3745 | CB | PHE | C | 101 | −16.946 | 7.351 | 25.541 | 1.00 | 36.69 | C |
| ATOM | 3746 | CG | PHE | C | 101 | −15.888 | 8.316 | 25.068 | 1.00 | 37.39 | C |
| ATOM | 3747 | CD1 | PHE | C | 101 | −14.914 | 8.812 | 25.950 | 1.00 | 40.50 | C |
| ATOM | 3748 | CE1 | PHE | C | 101 | −13.941 | 9.704 | 25.518 | 1.00 | 34.71 | C |
| ATOM | 3749 | CZ | PHE | C | 101 | −13.910 | 10.100 | 24.181 | 1.00 | 31.04 | C |
| ATOM | 3750 | CE2 | PHE | C | 101 | −14.846 | 9.599 | 23.301 | 1.00 | 32.20 | C |
| ATOM | 3751 | CD2 | PHE | C | 101 | −15.837 | 8.713 | 23.740 | 1.00 | 41.47 | C |
| ATOM | 3752 | C | PHE | C | 101 | −17.714 | 8.898 | 27.353 | 1.00 | 36.64 | C |
| ATOM | 3753 | O | PHE | C | 101 | −17.619 | 10.121 | 27.221 | 1.00 | 37.88 | O |
| ATOM | 3754 | N | GLY | C | 102 | −17.397 | 8.268 | 28.490 | 1.00 | 40.53 | N |
| ATOM | 3755 | CA | GLY | C | 102 | −16.912 | 9.029 | 29.615 | 1.00 | 35.18 | C |

TABLE 10-continued

Atomic coordinates for COM1 complex of the modified
TXNIP protein represented by SEQ ID NO: 6 and the modified protein represented by SEQ ID NO: 3

| | | | | | | | | | |
|---|---|---|---|---|---|---|---|---|---|
| ATOM | 3756 | C | GLY | 102 | -16.250 | 8.077 | 30.580 | 1.00 | 44.92 | C |
| ATOM | 3757 | O | GLY | 102 | -16.686 | 6.932 | 30.764 | 1.00 | 45.83 | O |
| ATOM | 3758 | N | PHE | 103 | -15.170 | 8.528 | 31.187 | 1.00 | 45.05 | N |
| ATOM | 3759 | CA | PHE | 103 | -14.551 | 7.698 | 32.212 | 1.00 | 44.11 | C |
| ATOM | 3760 | CB | PHE | 103 | -13.668 | 6.647 | 31.551 | 1.00 | 39.85 | C |
| ATOM | 3761 | CG | PHE | 103 | -12.610 | 7.226 | 30.649 | 1.00 | 38.84 | C |
| ATOM | 3762 | CD1 | PHE | 103 | -11.410 | 7.706 | 31.186 | 1.00 | 39.86 | C |
| ATOM | 3763 | CE1 | PHE | 103 | -10.453 | 8.238 | 30.361 | 1.00 | 40.16 | C |
| ATOM | 3764 | CZ | PHE | 103 | -10.689 | 8.805 | 29.002 | 1.00 | 32.49 | C |
| ATOM | 3765 | CE2 | PHE | 103 | -11.872 | 7.842 | 28.453 | 1.00 | 37.43 | C |
| ATOM | 3766 | CD2 | PHE | 103 | -12.817 | 7.306 | 29.283 | 1.00 | 38.74 | C |
| ATOM | 3767 | C | PHE | 103 | -13.792 | 8.583 | 33.161 | 1.00 | 47.12 | C |
| ATOM | 3768 | O | PHE | 103 | -13.525 | 9.757 | 32.885 | 1.00 | 45.82 | O |
| ATOM | 3769 | N | GLU | 104 | -13.461 | 8.025 | 34.310 | 1.00 | 51.98 | N |
| ATOM | 3770 | CA | GLU | 104 | -12.811 | 8.788 | 35.319 | 1.00 | 50.08 | C |
| ATOM | 3771 | CB | GLU | 104 | -13.564 | 8.709 | 36.644 | 1.00 | 54.53 | C |
| ATOM | 3772 | CG | GLU | 104 | -14.352 | 9.978 | 36.930 | 1.00 | 61.71 | C |
| ATOM | 3773 | CD | GLU | 104 | -15.844 | 9.746 | 37.239 | 1.00 | 82.59 | C |
| ATOM | 3774 | OE1 | GLU | 104 | -16.517 | 10.715 | 37.676 | 1.00 | 86.12 | O |
| ATOM | 3775 | OE2 | GLU | 104 | -16.354 | 8.616 | 37.035 | 1.00 | 85.87 | O |
| ATOM | 3776 | C | GLU | 104 | -11.383 | 8.308 | 35.408 | 1.00 | 50.62 | C |
| ATOM | 3777 | O | GLU | 104 | -11.070 | 7.111 | 35.230 | 1.00 | 51.19 | O |
| ATOM | 3778 | N | LEU | 105 | -10.497 | 9.272 | 35.586 | 1.00 | 47.23 | N |
| ATOM | 3779 | CA | LEU | 105 | -9.131 | 8.946 | 35.827 | 1.00 | 43.60 | C |
| ATOM | 3780 | CB | LEU | 105 | -8.246 | 10.143 | 35.540 | 1.00 | 44.09 | C |
| ATOM | 3781 | CG | LEU | 105 | -8.190 | 10.574 | 34.081 | 1.00 | 37.23 | C |
| ATOM | 3782 | CD1 | LEU | 105 | -7.328 | 11.773 | 34.081 | 1.00 | 37.23 | C |
| ATOM | 3783 | CD2 | LEU | 105 | -7.648 | 9.490 | 33.199 | 1.00 | 37.86 | C |
| ATOM | 3784 | C | LEU | 105 | -9.052 | 8.536 | 37.298 | 1.00 | 46.39 | C |
| ATOM | 3785 | O | LEU | 105 | -9.704 | 9.160 | 38.150 | 1.00 | 41.41 | O |
| ATOM | 3786 | N | PRO | 106 | -8.248 | 7.499 | 37.588 | 1.00 | 50.11 | N |
| ATOM | 3787 | CA | PRO | 106 | -8.111 | 6.919 | 38.936 | 1.00 | 53.07 | C |
| ATOM | 3788 | CB | PRO | 106 | -7.116 | 5.778 | 38.736 | 1.00 | 52.52 | C |
| ATOM | 3789 | CG | PRO | 106 | -6.379 | 6.142 | 37.488 | 1.00 | 57.74 | C |
| ATOM | 3790 | CD | PRO | 106 | -7.332 | 6.872 | 36.617 | 1.00 | 50.83 | C |
| ATOM | 3791 | C | PRO | 106 | -7.521 | 7.950 | 39.899 | 1.00 | 53.47 | C |
| ATOM | 3792 | O | PRO | 106 | -6.877 | 8.904 | 39.469 | 1.00 | 51.90 | O |
| ATOM | 3793 | N | GLN | 107 | -7.758 | 7.749 | 41.192 | 1.00 | 58.52 | N |
| ATOM | 3794 | CA | GLN | 107 | -7.388 | 8.725 | 42.220 | 1.00 | 60.66 | C |
| ATOM | 3795 | CB | GLN | 107 | -7.960 | 8.289 | 43.580 | 1.00 | 63.31 | C |
| ATOM | 3796 | CG | GLN | 107 | -9.447 | 8.603 | 43.777 | 1.00 | 65.07 | C |
| ATOM | 3797 | CD | GLN | 107 | -9.800 | 10.043 | 43.424 | 1.00 | 65.28 | C |
| ATOM | 3798 | OE1 | GLN | 107 | -9.088 | 10.980 | 43.795 | 1.00 | 73.67 | O |
| ATOM | 3799 | NE2 | GLN | 107 | -10.900 | 10.222 | 42.701 | 1.00 | 61.89 | N |
| ATOM | 3800 | C | GLN | 107 | -5.893 | 8.912 | 42.388 | 1.00 | 61.28 | C |
| ATOM | 3801 | O | GLN | 107 | -5.435 | 9.994 | 42.757 | 1.00 | 62.00 | O |
| ATOM | 3802 | N | GLY | 108 | -5.136 | 7.857 | 42.141 | 1.00 | 62.18 | N |
| ATOM | 3803 | CA | GLY | 108 | -3.807 | 7.757 | 42.741 | 1.00 | 67.63 | C |
| ATOM | 3804 | C | GLY | 108 | -2.937 | 8.932 | 42.373 | 1.00 | 66.87 | C |
| ATOM | 3805 | O | GLY | 108 | -3.447 | 9.946 | 41.888 | 1.00 | 64.90 | O |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 3806 | N | PRO | C | 109 | −1.620 | 8.818 | 42.627 | 1.00 | 66.47 | N |
| ATOM | 3807 | CA | PRO | C | 109 | −0.764 | 9.634 | 41.805 | 1.00 | 63.66 | C |
| ATOM | 3808 | CB | PRO | C | 109 | 0.569 | 9.665 | 42.574 | 1.00 | 65.42 | C |
| ATOM | 3809 | CG | PRO | C | 109 | 0.565 | 8.459 | 43.451 | 1.00 | 64.64 | C |
| ATOM | 3810 | CD | PRO | C | 109 | −0.878 | 8.014 | 43.622 | 1.00 | 68.90 | C |
| ATOM | 3811 | C | PRO | C | 109 | −0.645 | 8.911 | 40.476 | 1.00 | 63.34 | C |
| ATOM | 3812 | O | PRO | C | 109 | −0.214 | 7.750 | 40.447 | 1.00 | 66.44 | O |
| ATOM | 3813 | N | LEU | C | 110 | −1.095 | 9.568 | 39.408 | 1.00 | 58.93 | N |
| ATOM | 3814 | CA | LEU | C | 110 | −0.902 | 9.122 | 38.033 | 1.00 | 57.19 | C |
| ATOM | 3815 | CB | LEU | C | 110 | −1.896 | 9.778 | 37.084 | 1.00 | 56.26 | C |
| ATOM | 3816 | CG | LEU | C | 110 | −3.267 | 10.304 | 37.471 | 1.00 | 59.72 | C |
| ATOM | 3817 | CD1 | LEU | C | 110 | −3.551 | 11.537 | 36.505 | 1.00 | 52.01 | C |
| ATOM | 3818 | CD2 | LEU | C | 110 | 4.310 | 9.238 | 37.271 | 1.00 | 54.00 | C |
| ATOM | 3819 | C | LEU | C | 110 | 0.434 | 9.642 | 37.569 | 1.00 | 55.23 | C |
| ATOM | 3820 | O | LEU | C | 110 | 0.901 | 10.658 | 38.083 | 1.00 | 56.73 | O |
| ATOM | 3821 | N | GLY | C | 111 | 1.029 | 8.996 | 36.563 | 1.00 | 52.28 | N |
| ATOM | 3822 | CA | GLY | C | 111 | 2.290 | 9.473 | 36.028 | 1.00 | 46.84 | C |
| ATOM | 3823 | C | GLY | C | 111 | 1.903 | 10.673 | 35.189 | 1.00 | 51.77 | C |
| ATOM | 3824 | O | GLY | C | 111 | 0.770 | 10.731 | 34.648 | 1.00 | 52.29 | O |
| ATOM | 3825 | N | THR | C | 112 | 2.809 | 11.633 | 35.044 | 1.00 | 49.97 | N |
| ATOM | 3826 | CA | THR | C | 112 | 3.267 | 12.787 | 34.167 | 1.00 | 53.97 | C |
| ATOM | 3827 | CB | THR | C | 112 | 3.267 | 14.031 | 34.636 | 1.00 | 52.16 | C |
| ATOM | 3828 | OG1 | THR | C | 112 | 2.993 | 14.234 | 36.016 | 1.00 | 56.58 | O |
| ATOM | 3829 | CG2 | THR | C | 112 | 2.835 | 15.282 | 33.868 | 1.00 | 50.46 | C |
| ATOM | 3830 | C | THR | C | 112 | 2.871 | 12.465 | 32.707 | 1.00 | 55.13 | C |
| ATOM | 3831 | O | THR | C | 112 | 3.854 | 11.755 | 32.454 | 1.00 | 56.86 | O |
| ATOM | 3832 | N | SER | C | 113 | 2.071 | 12.973 | 31.766 | 1.00 | 53.54 | N |
| ATOM | 3833 | CA | SER | C | 113 | 2.316 | 12.860 | 30.331 | 1.00 | 52.55 | C |
| ATOM | 3834 | CB | SER | C | 113 | 1.277 | 13.692 | 29.552 | 1.00 | 50.49 | C |
| ATOM | 3835 | OG | SER | C | 113 | 0.017 | 13.063 | 29.470 | 1.00 | 43.62 | O |
| ATOM | 3836 | C | SER | C | 113 | 3.721 | 13.380 | 29.987 | 1.00 | 51.42 | C |
| ATOM | 3837 | O | SER | C | 113 | 3.989 | 14.540 | 30.217 | 1.00 | 53.10 | O |
| ATOM | 3838 | N | PHE | C | 114 | 4.580 | 12.516 | 29.393 | 1.00 | 54.24 | N |
| ATOM | 3839 | CA | PHE | C | 114 | 6.001 | 14.742 | 29.155 | 1.00 | 55.99 | C |
| ATOM | 3840 | CB | PHE | C | 114 | 6.770 | 12.221 | 30.394 | 1.00 | 60.16 | C |
| ATOM | 3841 | CG | PHE | C | 114 | 8.179 | 12.738 | 30.560 | 1.00 | 68.71 | C |
| ATOM | 3842 | CD1 | PHE | C | 114 | 8.473 | 14.103 | 30.504 | 1.00 | 81.11 | C |
| ATOM | 3843 | CE1 | PHE | C | 114 | 9.798 | 14.567 | 30.704 | 1.00 | 88.56 | C |
| ATOM | 3844 | CZ | PHE | C | 114 | 10.824 | 13.656 | 31.006 | 1.00 | 86.95 | C |
| ATOM | 3845 | CE2 | PHE | C | 114 | 10.532 | 12.298 | 31.097 | 1.00 | 85.46 | C |
| ATOM | 3846 | CD2 | PHE | C | 114 | 9.211 | 11.847 | 30.885 | 1.00 | 81.16 | C |
| ATOM | 3847 | C | PHE | C | 114 | 6.511 | 11.990 | 27.914 | 1.00 | 57.58 | C |
| ATOM | 3848 | O | PHE | C | 114 | 6.055 | 10.890 | 27.599 | 1.00 | 51.51 | O |
| ATOM | 3849 | N | LYS | C | 115 | 7.452 | 12.618 | 27.209 | 1.00 | 62.41 | N |
| ATOM | 3850 | CA | LYS | C | 115 | 6.376 | 11.966 | 26.277 | 1.00 | 66.46 | C |
| ATOM | 3851 | CB | LYS | C | 115 | 8.004 | 12.213 | 24.811 | 1.00 | 68.81 | C |
| ATOM | 3852 | CG | LYS | C | 115 | 7.275 | 11.064 | 24.161 | 1.00 | 69.71 | C |
| ATOM | 3853 | CD | LYS | C | 115 | 5.774 | 11.260 | 24.216 | 1.00 | 76.03 | C |
| ATOM | 3854 | CE | LYS | C | 115 | 5.045 | 9.931 | 24.364 | 1.00 | 71.82 | C |
| ATOM | 3855 | NZ | LYS | C | 115 | 5.606 | 8.825 | 23.515 | 1.00 | 73.50 | N |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 3856 | C | | LYS | C | 115 | 9.688 | 12.644 | 26.599 | 1.00 | 68.48 | C |
| ATOM | 3857 | O | | LYS | C | 115 | 9.825 | 13.858 | 26.447 | 1.00 | 69.24 | O |
| ATOM | 3858 | N | | GLY | C | 116 | 10.640 | 11.883 | 27.114 | 1.00 | 70.07 | N |
| ATOM | 3859 | CA | | GLY | C | 116 | 11.823 | 12.507 | 27.653 | 1.00 | 71.00 | C |
| ATOM | 3860 | C | | GLY | C | 116 | 12.927 | 11.539 | 27.990 | 1.00 | 72.07 | C |
| ATOM | 3861 | O | | GLY | C | 116 | 13.116 | 10.512 | 27.313 | 1.00 | 71.55 | O |
| ATOM | 3862 | N | | LYS | C | 117 | 13.633 | 11.888 | 29.059 | 1.00 | 71.24 | N |
| ATOM | 3863 | CA | | LYS | C | 117 | 14.922 | 11.314 | 29.416 | 1.00 | 70.74 | C |
| ATOM | 3864 | CB | | LYS | C | 117 | 15.414 | 12.020 | 30.682 | 1.00 | 73.68 | C |
| ATOM | 3865 | CG | | LYS | C | 117 | 14.291 | 12.290 | 31.720 | 1.00 | 77.27 | C |
| ATOM | 3866 | CD | | LYS | C | 117 | 14.519 | 13.284 | 32.502 | 1.00 | 78.70 | C |
| ATOM | 3867 | CE | | LYS | C | 117 | 14.168 | 14.808 | 31.656 | 1.00 | 82.04 | C |
| ATOM | 3868 | NZ | | LYS | C | 117 | 13.725 | 15.966 | 32.486 | 1.00 | 82.76 | N |
| ATOM | 3869 | C | | LYS | C | 117 | 14.880 | 9.793 | 29.610 | 1.00 | 68.11 | C |
| ATOM | 3870 | O | | LYS | C | 117 | 15.202 | 9.014 | 28.701 | 1.00 | 66.37 | O |
| ATOM | 3871 | N | | TYR | C | 118 | 14.464 | 9.384 | 30.798 | 1.00 | 66.14 | N |
| ATOM | 3872 | CA | | TYR | C | 118 | 14.352 | 7.984 | 31.116 | 1.00 | 65.00 | C |
| ATOM | 3873 | CB | | TYR | C | 118 | 14.838 | 7.738 | 32.567 | 1.00 | 61.92 | C |
| ATOM | 3874 | CG | | TYR | C | 118 | 10.246 | 8.253 | 32.885 | 1.00 | 61.12 | C |
| ATOM | 3875 | CD1 | | TYR | C | 118 | 17.378 | 7.548 | 32.481 | 1.00 | 55.78 | C |
| ATOM | 3876 | CE1 | | TYR | C | 118 | 18.676 | 8.022 | 32.772 | 1.00 | 64.27 | C |
| ATOM | 3877 | CZ | | TYR | C | 118 | 18.834 | 9.211 | 33.474 | 1.00 | 57.11 | C |
| ATOM | 3878 | OH | | TYR | C | 118 | 20.092 | 9.684 | 33.749 | 1.00 | 64.39 | O |
| ATOM | 3879 | CE2 | | TYR | C | 118 | 17.724 | 9.925 | 33.894 | 1.00 | 53.52 | C |
| ATOM | 3880 | CD2 | | TYR | C | 118 | 16.444 | 9.444 | 33.606 | 1.00 | 46.26 | C |
| ATOM | 3881 | C | | TYR | C | 118 | 12.897 | 7.498 | 30.838 | 1.00 | 63.75 | C |
| ATOM | 3882 | O | | TYR | C | 118 | 12.200 | 7.058 | 31.739 | 1.00 | 66.15 | O |
| ATOM | 3883 | N | | GLY | C | 119 | 12.443 | 7.634 | 29.588 | 1.00 | 64.78 | N |
| ATOM | 3884 | CA | | GLY | C | 119 | 11.148 | 7.092 | 29.110 | 1.00 | 63.16 | C |
| ATOM | 3885 | C | | GLY | C | 119 | 9.906 | 7.980 | 28.968 | 1.00 | 63.16 | C |
| ATOM | 3886 | O | | GLY | C | 119 | 9.970 | 9.215 | 29.164 | 1.00 | 62.47 | O |
| ATOM | 3887 | N | | SER | C | 120 | 8.761 | 7.343 | 28.688 | 1.00 | 59.76 | N |
| ATOM | 3888 | CA | | SER | C | 120 | 7.500 | 8.018 | 28.307 | 1.00 | 54.00 | C |
| ATOM | 3889 | CB | | SER | C | 120 | 7.156 | 7.601 | 26.889 | 1.00 | 54.13 | C |
| ATOM | 3890 | OG | | SER | C | 120 | 6.678 | 6.270 | 26.861 | 1.00 | 60.12 | O |
| ATOM | 3891 | C | | SER | C | 120 | 6.265 | 7.676 | 29.212 | 1.00 | 51.77 | C |
| ATOM | 3892 | O | | SER | C | 120 | 6.187 | 6.752 | 29.904 | 1.00 | 49.33 | O |
| ATOM | 3893 | N | | VAL | C | 121 | 5.304 | 8.697 | 29.187 | 1.00 | 49.70 | N |
| ATOM | 3894 | CA | | VAL | C | 121 | 3.958 | 8.467 | 29.757 | 1.00 | 44.03 | C |
| ATOM | 3895 | CB | | VAL | C | 121 | 3.736 | 9.248 | 31.103 | 1.00 | 45.02 | C |
| ATOM | 3896 | CG1 | | VAL | C | 121 | 2.394 | 8.926 | 31.704 | 1.00 | 40.64 | C |
| ATOM | 3897 | CG2 | | VAL | C | 121 | 4.802 | 8.888 | 32.120 | 1.00 | 49.74 | C |
| ATOM | 3898 | C | | VAL | C | 121 | 2.966 | 8.874 | 28.695 | 1.00 | 40.16 | C |
| ATOM | 3899 | O | | VAL | C | 121 | 3.120 | 9.945 | 28.117 | 1.00 | 39.83 | O |
| ATOM | 3900 | N | | ASP | C | 122 | 2.017 | 7.998 | 28.360 | 1.00 | 44.03 | N |
| ATOM | 3901 | CA | | ASP | C | 122 | 1.030 | 8.275 | 27.292 | 1.00 | 35.02 | C |
| ATOM | 3902 | CB | | ASP | C | 122 | 1.291 | 7.403 | 26.057 | 1.00 | 39.55 | C |
| ATOM | 3903 | CG | | ASP | C | 122 | 2.691 | 7.508 | 25.560 | 1.00 | 42.15 | C |
| ATOM | 3904 | OD1 | | ASP | C | 122 | 3.309 | 6.444 | 25.304 | 1.00 | 56.83 | O |
| ATOM | 3905 | OD2 | | ASP | C | 122 | 3.169 | 8.656 | 25.440 | 1.00 | 67.40 | O |
| | | | | | | | | | | 71.86 | O |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 3906 | C | ASP | C | 122 | −0.354 | 7.890 | 27.724 | 1.00 | 38.97 | C |
| ATOM | 3907 | O | ASP | C | 122 | −0.534 | 6.750 | 28.188 | 1.00 | 36.60 | O |
| ATOM | 3908 | N | TYR | C | 123 | −1.315 | 8.813 | 27.546 | 1.00 | 37.76 | N |
| ATOM | 3909 | CA | TYR | C | 123 | −2.753 | 8.510 | 27.693 | 1.00 | 35.79 | C |
| ATOM | 3910 | CB | TYR | C | 123 | −3.392 | 9.418 | 28.740 | 1.00 | 35.27 | C |
| ATOM | 3911 | CG | TYR | C | 123 | −2.949 | 9.176 | 30.162 | 1.00 | 33.53 | C |
| ATOM | 3912 | CD1 | TYR | C | 123 | −3.778 | 8.559 | 31.065 | 1.00 | 31.23 | C |
| ATOM | 3913 | CE1 | TYR | C | 123 | −3.383 | 8.383 | 32.385 | 1.00 | 30.54 | C |
| ATOM | 3914 | CZ | TYR | C | 123 | −2.152 | 8.739 | 32.792 | 1.00 | 39.01 | C |
| ATOM | 3915 | OH | TYR | C | 123 | −1.845 | 8.544 | 34.110 | 1.00 | 42.33 | O |
| ATOM | 3916 | CE2 | TYR | C | 123 | −1.261 | 9.365 | 31.912 | 1.00 | 36.50 | C |
| ATOM | 3917 | CD2 | TYR | C | 123 | −1.697 | 9.596 | 30.602 | 1.00 | 33.02 | C |
| ATOM | 3918 | C | TYR | C | 123 | −3.448 | 8.694 | 26.375 | 1.00 | 35.44 | C |
| ATOM | 3919 | O | TYR | C | 123 | −3.181 | 9.635 | 25.618 | 1.00 | 36.76 | O |
| ATOM | 3920 | N | TRP | C | 124 | −4.382 | 7.821 | 26.072 | 1.00 | 33.44 | N |
| ATOM | 3921 | CA | TRP | C | 124 | −5.033 | 7.906 | 24.792 | 1.00 | 33.01 | C |
| ATOM | 3922 | CB | TRP | C | 124 | −4.140 | 7.354 | 23.647 | 1.00 | 39.56 | C |
| ATOM | 3923 | CG | TRP | C | 124 | −3.384 | 6.054 | 23.933 | 1.00 | 48.05 | C |
| ATOM | 3924 | CD1 | TRP | C | 124 | −2.047 | 5.926 | 24.203 | 1.00 | 47.66 | C |
| ATOM | 3925 | NE1 | TRP | C | 124 | −1.716 | 4.603 | 27.374 | 1.00 | 43.71 | N |
| ATOM | 3926 | CE2 | TRP | C | 124 | −2.838 | 3.832 | 24.200 | 1.00 | 52.46 | C |
| ATOM | 3927 | CD2 | TRP | C | 124 | −8.912 | 4.707 | 23.906 | 1.00 | 48.92 | C |
| ATOM | 3928 | CE3 | TRP | C | 124 | −5.191 | 4.166 | 23.708 | 1.00 | 50.92 | C |
| ATOM | 3929 | CZ3 | TRP | C | 124 | −5.359 | 2.787 | 23.781 | 1.00 | 50.22 | C |
| ATOM | 3930 | CH2 | TRP | C | 124 | −4.263 | 1.936 | 24.051 | 1.00 | 52.82 | C |
| ATOM | 3931 | CZ2 | TRP | C | 124 | −2.995 | 2.440 | 24.258 | 1.00 | 50.32 | C |
| ATOM | 3932 | C | TRP | C | 124 | −6.343 | 7.168 | 24.851 | 1.00 | 38.75 | C |
| ATOM | 3933 | O | TRP | C | 124 | −6.567 | 6.358 | 25.768 | 1.00 | 39.84 | O |
| ATOM | 3934 | N | VAL | C | 125 | −7.234 | 7.498 | 23.911 | 1.00 | 37.68 | N |
| ATOM | 3935 | CA | VAL | C | 125 | −8.466 | 6.739 | 23.724 | 1.00 | 41.43 | C |
| ATOM | 3936 | CB | VAL | C | 125 | −9.755 | 7.600 | 23.838 | 1.00 | 42.81 | C |
| ATOM | 3937 | CG1 | VAL | C | 125 | −11.036 | 6.767 | 23.483 | 1.00 | 35.12 | C |
| ATOM | 3938 | CG2 | VAL | C | 125 | −9.877 | 8.190 | 25.237 | 1.00 | 34.40 | C |
| ATOM | 3939 | C | VAL | C | 125 | −8.379 | 6.185 | 22.316 | 1.00 | 43.20 | C |
| ATOM | 3940 | O | VAL | C | 125 | −8.048 | 6.909 | 21.385 | 1.00 | 43.84 | O |
| ATOM | 3941 | N | LYS | C | 126 | −8.668 | 4.893 | 22.199 | 1.00 | 42.30 | N |
| ATOM | 3942 | CA | LYS | C | 126 | −8.699 | 4.175 | 20.951 | 1.00 | 43.27 | C |
| ATOM | 3943 | CB | LYS | C | 126 | −7.865 | 2.904 | 21.134 | 1.00 | 44.77 | C |
| ATOM | 3944 | CG | LYS | C | 126 | −7.179 | 2.381 | 19.888 | 1.00 | 57.40 | C |
| ATOM | 3945 | CD | LYS | C | 126 | 5.681 | 2.688 | 19.883 | 1.00 | 66.87 | C |
| ATOM | 3946 | CE | LYS | C | 126 | −4.866 | 1.513 | 20.426 | 1.00 | 73.77 | C |
| ATOM | 3947 | NZ | LYS | C | 126 | −3.498 | 1.428 | 19.825 | 1.00 | 64.15 | N |
| ATOM | 3948 | C | LYS | C | 126 | −10.161 | 3.723 | 20.740 | 1.00 | 43.83 | C |
| ATOM | 3949 | O | LYS | C | 126 | −10.745 | 3.120 | 21.655 | 1.00 | 44.39 | O |
| ATOM | 3950 | N | ALA | C | 127 | −10.736 | 4.049 | 19.590 | 1.00 | 45.12 | N |
| ATOM | 3951 | CA | ALA | C | 127 | −12.074 | 3.572 | 19.196 | 1.00 | 48.03 | C |
| ATOM | 3952 | CB | ALA | C | 127 | −12.918 | 4.696 | 18.592 | 1.00 | 45.24 | C |
| ATOM | 3953 | C | ALA | C | 127 | −11.920 | 2.478 | 18.176 | 1.00 | 52.69 | C |
| ATOM | 3954 | O | ALA | C | 127 | −11.087 | 2.599 | 17.275 | 1.00 | 54.84 | O |
| ATOM | 3955 | N | PHE | C | 128 | −12.726 | 1.424 | 18.325 | 1.00 | 55.40 | N |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 3956 | CA | | PHE | C | 128 | -12.803 | 0.306 | 17.378 | 1.00 | 58.97 | C |
| ATOM | 3957 | CB | | PHE | C | 128 | -12.559 | -1.003 | 18.111 | 1.00 | 57.90 | C |
| ATOM | 3958 | CG | | PHE | C | 128 | -11.402 | -0.957 | 19.047 | 1.00 | 58.86 | C |
| ATOM | 3959 | CD1 | | PHE | C | 128 | -10.137 | -1.314 | 18.615 | 1.00 | 64.77 | C |
| ATOM | 3960 | CE1 | | PHE | C | 128 | -9.056 | -1.268 | 19.478 | 1.00 | 59.89 | C |
| ATOM | 3961 | CZ | | PHE | C | 128 | -9.240 | -0.886 | 20.794 | 1.00 | 59.18 | C |
| ATOM | 3962 | CE2 | | PHE | C | 128 | -10.489 | -0.520 | 21.237 | 1.00 | 60.32 | C |
| ATOM | 3963 | CD2 | | PHE | C | 128 | -11.574 | -0.567 | 20.365 | 1.00 | 61.85 | C |
| ATOM | 3964 | C | | PHE | C | 128 | -14.189 | 0.225 | 16.762 | 1.00 | 60.82 | C |
| ATOM | 3965 | O | | PHE | C | 128 | -15.203 | 0.248 | 17.469 | 1.00 | 63.15 | O |
| ATOM | 3966 | N | | LEU | C | 129 | -14.228 | 0.148 | 15.447 | 1.00 | 63.79 | N |
| ATOM | 3967 | CA | | LEU | C | 129 | -15.465 | -0.052 | 14.711 | 1.00 | 65.95 | C |
| ATOM | 3968 | CB | | LEU | C | 129 | -15.469 | 0.868 | 13.486 | 1.00 | 63.07 | C |
| ATOM | 3969 | CG | | LEU | C | 129 | -16.693 | 0.978 | 12.587 | 1.00 | 69.19 | C |
| ATOM | 3970 | CD1 | | LEU | C | 129 | -17.970 | 1.213 | 13.401 | 1.00 | 59.70 | C |
| ATOM | 3971 | CD2 | | LEU | C | 129 | -16.482 | 2.083 | 11.541 | 1.00 | 63.82 | C |
| ATOM | 3972 | C | | LEU | C | 129 | -15.577 | -1.540 | 14.318 | 1.00 | 68.44 | C |
| ATOM | 3973 | O | | LEU | C | 129 | -14.821 | -2.023 | 13.483 | 1.00 | 69.13 | O |
| ATOM | 3974 | N | | ASP | C | 130 | -16.482 | -2.276 | 14.962 | 1.00 | 70.37 | N |
| ATOM | 3975 | CA | | ASP | C | 130 | -16.692 | -3.679 | 14.626 | 1.00 | 71.74 | C |
| ATOM | 3976 | CB | | ASP | C | 130 | -17.232 | -4.462 | 15.823 | 1.00 | 70.66 | C |
| ATOM | 3977 | CG | | ASP | C | 130 | -16.217 | -4.618 | 16.943 | 1.00 | 78.23 | C |
| ATOM | 3978 | OD1 | | ASP | C | 130 | -16.652 | -4.858 | 18.098 | 1.00 | 82.70 | O |
| ATOM | 3979 | OD2 | | ASP | C | 130 | -14.996 | -4.505 | 16.680 | 1.00 | 79.50 | O |
| ATOM | 3980 | C | | ASP | C | 130 | -17.693 | -3.762 | 13.486 | 1.00 | 74.20 | C |
| ATOM | 3981 | O | | ASP | C | 130 | -18.684 | -3.021 | 13.469 | 1.00 | 75.30 | O |
| ATOM | 3982 | N | | ARG | C | 131 | -17.449 | -4.669 | 12.540 | 1.00 | 76.17 | N |
| ATOM | 3983 | CA | | ARG | C | 131 | -18.380 | -4.886 | 11.420 | 1.00 | 76.30 | C |
| ATOM | 3984 | CB | | ARG | C | 131 | -17.945 | -4.066 | 10.200 | 1.00 | 75.80 | C |
| ATOM | 3985 | CG | | ARG | C | 131 | -18.191 | -2.584 | 10.340 | 1.00 | 70.29 | C |
| ATOM | 3986 | CD | | ARG | C | 131 | -17.360 | -1.820 | 9.351 | 1.00 | 76.40 | C |
| ATOM | 3987 | NE | | ARG | C | 131 | -18.011 | -1.639 | 8.052 | 1.00 | 78.25 | N |
| ATOM | 3988 | CZ | | ARG | C | 131 | -17.391 | -1.211 | 6.947 | 1.00 | 80.59 | C |
| ATOM | 3989 | NH1 | | ARG | C | 131 | -16.094 | -0.930 | 6.964 | 1.00 | 70.89 | N |
| ATOM | 3990 | NH2 | | ARG | C | 131 | -18.068 | -1.073 | 5.811 | 1.00 | 80.56 | N |
| ATOM | 3991 | C | | ARG | C | 131 | -18.533 | -6.379 | 11.054 | 1.00 | 78.00 | C |
| ATOM | 3992 | O | | ARG | C | 131 | -17.607 | -7.170 | 11.290 | 1.00 | 78.21 | O |
| ATOM | 3993 | N | | PRO | C | 132 | -19.710 | -6.772 | 10.490 | 1.00 | 79.28 | N |
| ATOM | 3994 | CA | | PRO | C | 132 | -19.876 | -8.154 | 10.007 | 1.00 | 78.24 | C |
| ATOM | 3995 | CB | | PRO | C | 132 | -21.340 | -8.212 | 8.564 | 1.00 | 77.47 | C |
| ATOM | 3996 | CG | | PRO | C | 132 | -21.993 | -7.025 | 10.192 | 1.00 | 79.55 | C |
| ATOM | 3997 | CD | | PRO | C | 132 | -20.933 | -5.976 | 10.275 | 1.00 | 78.50 | C |
| ATOM | 3998 | C | | PRO | C | 132 | -18.944 | -8.477 | 8.834 | 1.00 | 78.36 | C |
| ATOM | 3999 | O | | PRO | C | 132 | -18.946 | -7.788 | 7.787 | 1.00 | 76.51 | O |
| ATOM | 4000 | N | | SER | C | 133 | -18.126 | -9.504 | 9.058 | 1.00 | 79.26 | N |
| ATOM | 4001 | CA | | SER | C | 133 | -17.239 | -10.086 | 8.043 | 1.00 | 79.35 | C |
| ATOM | 4002 | CB | | SER | C | 133 | -18.039 | -10.493 | 6.797 | 1.00 | 79.85 | C |
| ATOM | 4003 | OG | | SER | C | 133 | -19.109 | -11.356 | 7.159 | 1.00 | 80.94 | O |
| ATOM | 4004 | C | | SER | C | 133 | -16.025 | -9.222 | 7.684 | 1.00 | 77.80 | C |
| ATOM | 4005 | O | | SER | C | 133 | -15.148 | -9.660 | 6.934 | 1.00 | 76.73 | O |

TABLE 10-continued

Atomic coordinates for COM1 complex of the modified
TXNIP protein represented by SEQ ID NO: 6 and the modified protein represented by SEQ ID NO: 3

| ATOM | 4006 | N | GLN | C | 134 | -15.974 | -8.013 | 8.246 | 1.00 | 76.61 | N |
|------|------|-----|-----|---|-----|---------|--------|-------|------|-------|---|
| ATOM | 4007 | CA | GLN | C | 134 | -14.885 | -7.078 | 7.996 | 1.00 | 76.16 | C |
| ATOM | 4008 | CB | GLN | C | 134 | -15.429 | -5.662 | 7.823 | 1.00 | 76.33 | C |
| ATOM | 4009 | CC | GLN | C | 134 | -16.152 | -5.428 | 6.511 | 1.00 | 79.07 | C |
| ATOM | 4010 | CD | GLN | C | 134 | -15.203 | -5.267 | 5.344 | 1.00 | 81.24 | C |
| ATOM | 4011 | OE1 | GLN | C | 134 | -15.376 | -5.899 | 4.295 | 1.00 | 79.63 | O |
| ATOM | 4012 | NE2 | GLN | C | 134 | -14.191 | -4.420 | 5.517 | 1.00 | 78.26 | N |
| ATOM | 4013 | C | GLN | C | 134 | -13.859 | -7.094 | 9.123 | 1.00 | 76.26 | C |
| ATOM | 4014 | O | GLN | C | 134 | -14.221 | -7.303 | 10.288 | 1.00 | 75.71 | O |
| ATOM | 4015 | N | PRO | C | 135 | -12.567 | -6.863 | 8.791 | 1.00 | 76.09 | N |
| ATOM | 4016 | CA | PRO | C | 135 | -11.618 | -6.648 | 9.879 | 1.00 | 74.38 | C |
| ATOM | 4017 | CB | PRO | C | 135 | -10.285 | -6.574 | 9.162 | 1.00 | 74.68 | C |
| ATOM | 4018 | CG | PRO | C | 135 | -10.593 | -6.130 | 7.777 | 1.00 | 75.69 | C |
| ATOM | 4019 | CD | PRO | C | 135 | -11.922 | -6.763 | 7.456 | 1.00 | 76.57 | C |
| ATOM | 4020 | C | PRO | C | 135 | -11.975 | -5.322 | 10.565 | 1.00 | 73.60 | C |
| ATOM | 4021 | O | PRO | C | 135 | -12.457 | -4.385 | 9.902 | 1.00 | 69.83 | O |
| ATOM | 4022 | N | THR | C | 136 | -11.774 | -5.261 | 11.881 | 1.00 | 73.11 | N |
| ATOM | 4023 | CA | THR | C | 136 | -12.251 | -4.120 | 12.699 | 1.00 | 71.79 | C |
| ATOM | 4024 | CB | THR | C | 136 | -12.450 | -4.478 | 14.161 | 1.00 | 71.46 | C |
| ATOM | 4025 | OG1 | THR | C | 136 | -11.213 | -4.940 | 14.712 | 1.00 | 78.00 | O |
| ATOM | 4026 | CG2 | THR | C | 136 | -13.485 | -5.589 | 14.323 | 1.00 | 74.15 | C |
| ATOM | 4027 | C | THR | C | 136 | -11.296 | -2.946 | 12.513 | 1.00 | 69.65 | C |
| ATOM | 4028 | O | THR | C | 136 | -10.079 | -3.116 | 12.576 | 1.00 | 69.99 | O |
| ATOM | 4029 | N | GLN | C | 137 | -11.856 | -1.762 | 12.292 | 1.00 | 65.70 | N |
| ATOM | 4030 | CA | GLN | C | 137 | -11.062 | -0.557 | 12.086 | 1.00 | 62.81 | C |
| ATOM | 4031 | CB | GLN | C | 137 | -11.821 | 0.365 | 11.145 | 1.00 | 60.78 | C |
| ATOM | 4032 | CG | GLN | C | 137 | -11.109 | 1.633 | 10.730 | 1.00 | 60.56 | C |
| ATOM | 4033 | CD | GLN | C | 137 | -11.943 | 2.390 | 9.738 | 1.00 | 58.48 | C |
| ATOM | 4034 | OE1 | GLN | C | 137 | -12.949 | 1.876 | 9.277 | 1.00 | 61.61 | O |
| ATOM | 4035 | NE2 | GLN | C | 137 | -11.543 | 3.609 | 9.399 | 1.00 | 54.50 | N |
| ATOM | 4036 | C | GLN | C | 137 | -10.740 | 0.140 | 13.421 | 1.00 | 61.52 | C |
| ATOM | 4037 | O | GLN | C | 137 | -11.538 | 0.107 | 14.360 | 1.00 | 61.34 | O |
| ATOM | 4038 | N | GLU | C | 138 | -9.575 | 0.798 | 13.479 | 1.00 | 59.66 | N |
| ATOM | 4039 | CA | GLU | C | 138 | -9.123 | 1.566 | 14.648 | 1.00 | 57.00 | C |
| ATOM | 4040 | CB | GLU | C | 138 | -7.767 | 1.045 | 15.095 | 1.00 | 59.68 | C |
| ATOM | 4041 | CG | GLU | C | 138 | -7.795 | -0.207 | 15.931 | 1.00 | 65.06 | C |
| ATOM | 4042 | CD | GLU | C | 138 | -6.439 | -0.490 | 16.520 | 1.00 | 67.77 | C |
| ATOM | 4043 | OE1 | GLU | C | 138 | -6.133 | -1.683 | 16.74 | 1.00 | 69.71 | O |
| ATOM | 4044 | OE2 | GLU | C | 138 | -5.685 | 0.490 | 16.750 | 1.00 | 64.71 | O |
| ATOM | 4045 | C | GLU | C | 138 | -8.948 | 3.068 | 14.409 | 1.00 | 56.06 | C |
| ATOM | 4046 | O | GLU | C | 138 | -8.605 | 3.505 | 13.3.8 | 1.00 | 54.56 | O |
| ATOM | 4047 | N | THR | C | 139 | -9.174 | 3.854 | 15.467 | 1.00 | 53.97 | N |
| ATOM | 4048 | CA | THR | C | 139 | -8.722 | 5.252 | 15.513 | 1.00 | 49.82 | C |
| ATOM | 4049 | CB | THR | C | 139 | -9.786 | 6.257 | 14.984 | 1.00 | 46.22 | C |
| ATOM | 4050 | OG1 | THR | C | 139 | -9.221 | 7.573 | 14.913 | 1.00 | 50.89 | O |
| ATOM | 4051 | CG2 | THR | C | 139 | -10.994 | 6.345 | 15.884 | 1.00 | 40.35 | C |
| ATOM | 4052 | C | THR | C | 139 | -8.229 | 5.571 | 16.042 | 1.00 | 48.03 | C |
| ATOM | 4053 | O | THR | C | 139 | -8.771 | 5.069 | 17.915 | 1.00 | 51.28 | O |
| ATOM | 4054 | N | LYS | C | 140 | -7.198 | 6.401 | 17.053 | 1.00 | 47.20 | N |
| ATOM | 4055 | CA | LYS | C | 140 | -6.576 | 6.715 | 18.349 | 1.00 | 74.91 | C |

TABLE 10-continued

Atomic coordinates for COM1 complex of the modified
TXNIP protein represented by SEQ ID NO: 6 and the modified protein represented by SEQ ID NO: 3

| ATOM | 4056 | CB  | LYS | C | 140 | -5.236 | 5.996  | 18.459 | 1.00 | 48.26 | C |
|------|------|-----|-----|---|-----|--------|--------|--------|------|-------|---|
| ATOM | 4057 | CG  | LYS | C | 140 | -4.366 | 6.402  | 19.623 | 1.00 | 50.60 | C |
| ATOM | 4058 | CD  | LYS | C | 140 | -3.201 | 5.484  | 19.693 | 1.00 | 57.68 | C |
| ATOM | 4059 | CE  | LYS | C | 140 | -2.037 | 6.149  | 20.377 | 1.00 | 58.00 | C |
| ATOM | 4060 | NZ  | LYS | C | 140 | -0.854 | 5.302  | 20.131 | 1.00 | 57.29 | N |
| ATOM | 4061 | C   | LYS | C | 140 | -6.370 | 8.212  | 18.491 | 1.00 | 47.40 | C |
| ATOM | 4062 | O   | LYS | C | 140 | -5.932 | 8.859  | 17.537 | 1.00 | 44.30 | O |
| ATOM | 4063 | N   | LYS | C | 141 | -6.736 | 8.755  | 19.658 | 1.00 | 44.30 | N |
| ATOM | 4064 | CA  | LYS | C | 141 | -6.420 | 10.134 | 20.007 | 1.00 | 39.71 | C |
| ATOM | 4065 | CB  | LYS | C | 141 | -7.547 | 11.028 | 19.840 | 1.00 | 4.028 | C |
| ATOM | 4066 | CG  | LYS | C | 141 | -7.258 | 12.452 | 19.511 | 1.00 | 39.99 | C |
| ATOM | 4067 | CD  | LYS | C | 141 | -8.460 | 13.305 | 19.292 | 1.00 | 42.55 | C |
| ATOM | 4068 | CE  | LYS | C | 141 | -8.529 | 13.740 | 17.861 | 1.00 | 48.24 | C |
| ATOM | 4069 | NZ  | LYS | C | 141 | -9.694 | 14.625 | 17.679 | 1.00 | 49.51 | N |
| ATOM | 4070 | C   | LYS | C | 141 | -5.867 | 10.246 | 21.446 | 1.00 | 37.50 | C |
| ATOM | 4071 | O   | LYS | C | 141 | -6.441 | 9.707  | 22.395 | 1.00 | 39.70 | O |
| ATOM | 4072 | N   | ASN | C | 142 | -4.737 | 10.925 | 21.587 | 1.00 | 37.96 | N |
| ATOM | 4073 | CA  | ASN | C | 142 | -4.067 | 11.110 | 22.873 | 1.00 | 36.57 | C |
| ATOM | 4074 | CB  | ASN | C | 142 | -2.656 | 11.641 | 22.671 | 1.00 | 39.03 | C |
| ATOM | 4075 | CG  | ASN | C | 142 | -1.788 | 10.691 | 21.867 | 1.00 | 52.39 | C |
| ATOM | 4076 | OD1 | ASN | C | 142 | -1.232 | 11.072 | 20.835 | 1.00 | 64.20 | O |
| ATOM | 4077 | ND2 | ASN | C | 142 | -1.687 | 9.444  | 22.321 | 1.00 | 51.39 | N |
| ATOM | 4078 | C   | ASN | C | 142 | -4.807 | 12.151 | 23.659 | 1.00 | 35.87 | C |
| ATOM | 4079 | O   | ASN | C | 142 | -5.518 | 12.949 | 23.179 | 1.00 | 34.11 | O |
| ATOM | 4080 | N   | PHE | C | 143 | -4.585 | 12.168 | 24.964 | 1.00 | 35.27 | N |
| ATOM | 4081 | CA  | PHE | C | 143 | -5.053 | 13.253 | 25.797 | 1.00 | 35.15 | C |
| ATOM | 4082 | CB  | PHE | C | 143 | -6.465 | 13.026 | 26.364 | 1.00 | 30.91 | C |
| ATOM | 4083 | CG  | PHE | C | 143 | -6.594 | 11.881 | 27.311 | 1.00 | 34.75 | C |
| ATOM | 4084 | CD1 | PHE | C | 143 | -7.008 | 10.642 | 26.857 | 1.00 | 34.51 | C |
| ATOM | 4085 | CE1 | PHE | C | 143 | -7.116 | 9.584  | 27.717 | 1.00 | 29.82 | C |
| ATOM | 4086 | CZ  | PHE | C | 143 | -6.896 | 9.765  | 29.065 | 1.00 | 29.86 | C |
| ATOM | 4087 | CE2 | PHE | C | 143 | -6.487 | 11.019 | 29.549 | 1.00 | 35.51 | C |
| ATOM | 4088 | CD2 | PHE | C | 143 | -6.359 | 12.050 | 28.665 | 1.00 | 33.66 | C |
| ATOM | 4089 | C   | PHE | C | 143 | -4.001 | 13.498 | 26.838 | 1.00 | 35.09 | C |
| ATOM | 4090 | O   | PHE | C | 143 | -3.194 | 12.586 | 27.138 | 1.00 | 36.21 | O |
| ATOM | 4091 | N   | GLU | C | 144 | -3.958 | 14.727 | 27.366 | 1.00 | 32.31 | N |
| ATOM | 4092 | CA  | GLU | C | 144 | -2.878 | 15.080 | 28.296 | 1.00 | 30.96 | C |
| ATOM | 4093 | CB  | GLU | C | 144 | -2.298 | 16.465 | 27.984 | 1.00 | 37.97 | C |
| ATOM | 4094 | CG  | GLU | C | 144 | -1.737 | 16.563 | 26.585 | 1.00 | 44.95 | C |
| ATOM | 4095 | CD  | GLU | C | 144 | -0.526 | 15.647 | 26.363 | 1.00 | 32.23 | C |
| ATOM | 4096 | OE1 | GLU | C | 144 | -0.406 | 15.655 | 27.187 | 1.00 | 43.14 | O |
| ATOM | 4097 | OE2 | GLU | C | 144 | -0.559 | 14.912 | 25.353 | 1.00 | 51.24 | O |
| ATOM | 4098 | C   | GLU | C | 144 | -3.278 | 15.014 | 29.739 | 1.00 | 34.51 | C |
| ATOM | 4099 | O   | GLU | C | 144 | -4.409 | 15.394 | 30.087 | 1.00 | 32.08 | O |
| ATOM | 4100 | N   | VAL | C | 145 | -2.329 | 14.566 | 30.565 | 1.00 | 31.91 | N |
| ATOM | 4101 | CA  | VAL | C | 145 | -2.538 | 14.420 | 32.017 | 1.00 | 38.33 | C |
| ATOM | 4102 | CB  | VAL | C | 145 | -2.536 | 12.932 | 32.408 | 1.00 | 38.53 | C |
| ATOM | 4103 | CG1 | VAL | C | 145 | -2.525 | 12.716 | 33.907 | 1.00 | 48.12 | C |
| ATOM | 4104 | CG2 | VAL | C | 145 | -3.794 | 12.260 | 31.796 | 1.00 | 37.21 | C |
| ATOM | 4105 | C   | VAL | C | 145 | -1.434 | 15.153 | 32.760 | 1.00 | 41.65 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 4106 | O   | VAL | C | 145 | -0.314 | 15.195 | 32.284 | 1.00 | 43.03 | O |
| ATOM | 4107 | N   | VAL | C | 146 | -1.766 | 15.742 | 33.907 | 1.00 | 44.76 | N |
| ATOM | 4108 | CA  | VAL | C | 146 | -0.738 | 16.247 | 34.828 | 1.00 | 48.21 | C |
| ATOM | 4109 | CB  | VAL | C | 146 | -0.588 | 17.786 | 34.763 | 1.00 | 50.85 | C |
| ATOM | 4110 | CG1 | VAL | C | 146 | -1.945 | 18.529 | 35.040 | 1.00 | 56.24 | C |
| ATOM | 4111 | CG2 | VAL | C | 146 | -0.536 | 18.277 | 35.728 | 1.00 | 55.26 | C |
| ATOM | 4112 | C   | VAL | C | 146 | -1.079 | 15.801 | 36.252 | 1.00 | 50.72 | C |
| ATOM | 4113 | O   | VAL | C | 146 | -2.204 | 15.931 | 35.679 | 1.00 | 45.98 | O |
| ATOM | 4114 | N   | ASP | C | 147 | -0.100 | 15.263 | 36.974 | 1.00 | 54.68 | N |
| ATOM | 4115 | CA  | ASP | C | 147 | -0.262 | 15.021 | 38.401 | 1.00 | 60.02 | C |
| ATOM | 4116 | CB  | ASP | C | 147 | -0.312 | 13.663 | 38.806 | 1.00 | 60.32 | C |
| ATOM | 4117 | CG  | ASP | C | 147 | -0.471 | 13.018 | 39.983 | 1.00 | 60.32 | C |
| ATOM | 4118 | OD1 | ASP | C | 147 | -1.738 | 13.081 | 40.023 | 1.00 | 62.61 | O |
| ATOM | 4119 | OD2 | ASP | C | 147 | 0.192  | 12.444 | 40.870 | 1.00 | 75.85 | O |
| ATOM | 4120 | C   | ASP | C | 147 | 0.358  | 16.142 | 39.248 | 1.00 | 61.55 | C |
| ATOM | 4121 | O   | ASP | C | 147 | 1.464  | 16.610 | 38.962 | 1.00 | 62.55 | O |
| ATOM | 4122 | N   | PRO | C | 154 | 12.324 | 14.890 | 39.787 | 1.00 | 75.53 | N |
| ATOM | 4123 | CA  | PRO | C | 154 | 1.780  | 15.046 | 39.734 | 1.00 | 47.48 | C |
| ATOM | 4124 | CB  | PRO | C | 154 | 14.174 | 15.150 | 41.207 | 1.00 | 74.68 | C |
| ATOM | 4125 | CG  | PRO | C | 154 | 13.123 | 14.364 | 41.930 | 1.00 | 76.84 | C |
| ATOM | 4126 | CD  | PRO | C | 154 | 11.855 | 14.415 | 41.013 | 1.00 | 76.47 | C |
| ATOM | 4127 | C   | PRO | C | 154 | 14.487 | 13.859 | 39.059 | 1.00 | 73.39 | C |
| ATOM | 4128 | O   | PRO | C | 154 | 13.915 | 12.765 | 39.004 | 1.00 | 73.46 | O |
| ATOM | 4129 | N   | ASP | C | 155 | 15.711 | 14.105 | 38.563 | 1.00 | 71.26 | N |
| ATOM | 4130 | CA  | ASP | C | 155 | 16.539 | 13.153 | 37.795 | 1.00 | 68.33 | C |
| ATOM | 4131 | CB  | ASP | C | 155 | 17.956 | 13.734 | 37.564 | 1.00 | 68.56 | C |
| ATOM | 4132 | CG  | ASP | C | 155 | 18.944 | 12.733 | 36.910 | 1.00 | 65.20 | C |
| ATOM | 4133 | OD1 | ASP | C | 155 | 18.523 | 11.782 | 36.239 | 1.00 | 61.46 | O |
| ATOM | 4134 | OD2 | ASP | C | 155 | 20.175 | 12.926 | 37.047 | 1.00 | 73.54 | O |
| ATOM | 4135 | C   | ASP | C | 155 | 16.634 | 11.822 | 38.518 | 1.00 | 66.07 | C |
| ATOM | 4136 | O   | ASP | C | 155 | 16.914 | 11.785 | 39.712 | 1.00 | 66.30 | O |
| ATOM | 4137 | N   | LEU | C | 156 | 16.411 | 10.746 | 37.767 | 1.00 | 61.01 | N |
| ATOM | 4138 | CA  | LEU | C | 156 | 16.351 | 9.390  | 38.290 | 1.00 | 58.71 | C |
| ATOM | 4139 | CB  | LEU | C | 156 | 15.823 | 8.483  | 37.192 | 1.00 | 61.03 | C |
| ATOM | 4140 | CG  | LEU | C | 156 | 15.351 | 7.058  | 37.414 | 1.00 | 50.15 | C |
| ATOM | 4141 | CD1 | LEU | C | 156 | 14.355 | 6.773  | 36.344 | 1.00 | 65.43 | C |
| ATOM | 4142 | CD2 | LEU | C | 156 | 16.526 | 6.161  | 37.227 | 1.00 | 61.37 | C |
| ATOM | 4143 | C   | LEU | C | 156 | 17.697 | 8.871  | 38.816 | 1.00 | 55.67 | C |
| ATOM | 4144 | O   | LEU | C | 156 | 17.735 | 7.995  | 39.671 | 1.00 | 51.96 | O |
| ATOM | 4145 | N   | MET | C | 157 | 18.791 | 9.402  | 38.279 | 1.00 | 51.07 | N |
| ATOM | 4146 | CA  | MET | C | 157 | 20.128 | 9.044  | 38.698 | 1.00 | 46.00 | C |
| ATOM | 4147 | CB  | MET | C | 157 | 21.085 | 9.052  | 37.497 | 1.00 | 51.13 | C |
| ATOM | 4148 | CG  | MET | C | 157 | 20.733 | 80.62  | 36.393 | 1.00 | 56.38 | C |
| ATOM | 4149 | SD  | MET | C | 157 | 20.191 | 6.323  | 36.880 | 1.00 | 71.11 | S |
| ATOM | 4150 | CE  | MET | C | 157 | 19.428 | 5.977  | 37.737 | 1.00 | 59.50 | C |
| ATOM | 4151 | C   | MET | C | 157 | 16.526 | 10.007 | 39.759 | 1.00 | 43.06 | C |
| ATOM | 4152 | O   | MET | C | 157 | 20.657 | 9.845  | 40.216 | 1.00 | 42.02 | O |
| ATOM | 4153 | N   | ALA | C | 158 | 21.777 | 11.022 | 40.142 | 1.00 | 51.07 | N |
| ATOM | 4154 | CA  | ALA | C | 158 | 19.879 | 11.980 | 41.168 | 1.00 | 43.62 | C |
| ATOM | 4155 | CB  | ALA | C | 158 | 19.624 | 13.304 | 41.029 | 1.00 | 48.36 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 4156 | C | ALA | 158 | 20.174 | 11.417 | 42.593 | 1.00 | 47.15 | C |
| ATOM | 4157 | O | ALA | 158 | 19.207 | 10.695 | 42.849 | 1.00 | 46.65 | O |
| ATOM | 4158 | N | PRO | 159 | 21.073 | 11.770 | 43.535 | 1.00 | 50.24 | N |
| ATOM | 4159 | CA | PRO | 159 | 21.019 | 11.203 | 44.879 | 1.00 | 50.08 | C |
| ATOM | 4160 | CB | PRO | 159 | 22.254 | 11.790 | 45.551 | 1.00 | 51.66 | C |
| ATOM | 4161 | CG | PRO | 159 | 22.530 | 13.062 | 44.824 | 1.00 | 55.70 | C |
| ATOM | 4162 | CD | PRO | 159 | 22.150 | 12.760 | 43.308 | 1.00 | 50.61 | C |
| ATOM | 4163 | C | PRO | 159 | 19.763 | 11.633 | 45.606 | 1.00 | 53.82 | C |
| ATOM | 4164 | O | PRO | 159 | 19.253 | 12.726 | 45.358 | 1.00 | 56.90 | O |
| ATOM | 4165 | N | VAL | 160 | 19.237 | 10.770 | 64.470 | 1.00 | 54.29 | N |
| ATOM | 4166 | CA | VAL | 160 | 17.959 | 11.035 | 47.154 | 1.00 | 53.86 | C |
| ATOM | 4167 | CB | VAL | 160 | 16.889 | 9.964 | 46.814 | 1.00 | 54.03 | C |
| ATOM | 4168 | CG1 | VAL | 160 | 15.564 | 10.280 | 47.506 | 1.00 | 62.18 | C |
| ATOM | 4169 | CG2 | VAL | 160 | 16.638 | 9.877 | 45.321 | 1.00 | 58.58 | C |
| ATOM | 4170 | C | VAL | 160 | 18.246 | 11.063 | 48.657 | 1.00 | 54.00 | C |
| ATOM | 4171 | O | VAL | 160 | 18.982 | 10.216 | 49.164 | 1.00 | 48.82 | O |
| ATOM | 4172 | N | SER | 161 | 17.667 | 12.026 | 49.363 | 1.00 | 52.17 | N |
| ATOM | 4173 | CA | SER | 161 | 17.995 | 12.200 | 50.771 | 1.00 | 54.64 | C |
| ATOM | 4174 | CB | SER | 161 | 19.275 | 13.027 | 50.901 | 1.00 | 51.49 | C |
| ATOM | 4175 | OG | SER | 161 | 18.985 | 14.393 | 50.689 | 1.00 | 65.11 | O |
| ATOM | 4176 | C | SER | 161 | 16.849 | 12.867 | 51.518 | 1.00 | 53.83 | C |
| ATOM | 4177 | O | SER | 161 | 15.944 | 13.440 | 50.894 | 1.00 | 51.19 | O |
| ATOM | 4178 | N | ALA | 162 | 16.895 | 12.790 | 52.850 | 1.00 | 50.26 | N |
| ATOM | 4179 | CA | ALA | 162 | 15.873 | 13.374 | 53.689 | 1.00 | 44.91 | C |
| ATOM | 4180 | CB | ALA | 162 | 14.636 | 12.545 | 53.640 | 1.00 | 45.43 | C |
| ATOM | 4181 | C | ALA | 162 | 16.415 | 13.416 | 55.128 | 1.00 | 45.14 | C |
| ATOM | 4182 | O | ALA | 162 | 17.365 | 12.714 | 55.440 | 1.00 | 44.02 | O |
| ATOM | 4183 | N | LYS | 163 | 15.788 | 14.224 | 55.978 | 1.00 | 45.14 | N |
| ATOM | 4184 | CA | LYS | 163 | 16.008 | 14.250 | 57.411 | 1.00 | 44.33 | C |
| ATOM | 4185 | CB | LYS | 163 | 17.229 | 15.238 | 57.729 | 1.00 | 50.87 | C |
| ATOM | 4186 | CG | LYS | 163 | 17.008 | 16.673 | 57.246 | 1.00 | 56.98 | C |
| ATOM | 4187 | CD | LYS | 163 | 18.346 | 17.347 | 57.013 | 1.00 | 71.75 | C |
| ATOM | 4188 | CE | LYS | 163 | 18.254 | 18.867 | 57.103 | 1.00 | 81.02 | C |
| ATOM | 4189 | NZ | LYS | 163 | 19.619 | 19.456 | 57.306 | 1.00 | 80.65 | N |
| ATOM | 4190 | C | LYS | 163 | 14.852 | 14.535 | 58.192 | 1.00 | 45.54 | C |
| ATOM | 4191 | O | LYS | 163 | 13.961 | 15.237 | 57.696 | 1.00 | 44.93 | O |
| ATOM | 4192 | N | LYS | 164 | 14.756 | 13.944 | 59.387 | 1.00 | 42.53 | N |
| ATOM | 4193 | CA | LYS | 164 | 13.630 | 14.131 | 60.266 | 1.00 | 42.47 | C |
| ATOM | 4194 | CB | LYS | 164 | 12.636 | 13.000 | 60.075 | 1.00 | 42.83 | C |
| ATOM | 4195 | CG | LYS | 164 | 11.244 | 13.241 | 60.614 | 1.00 | 47.76 | C |
| ATOM | 4196 | CD | LYS | 164 | 10.283 | 13.403 | 59.471 | 1.00 | 50.57 | C |
| ATOM | 4197 | CE | LYS | 164 | 80.991 | 12.791 | 59.800 | 1.00 | 62.87 | C |
| ATOM | 4198 | NZ | LYS | 164 | 8.285 | 12.271 | 58.579 | 1.00 | 66.43 | N |
| ATOM | 4199 | C | LYS | 164 | 14.156 | 14.133 | 61.076 | 1.00 | 45.53 | C |
| ATOM | 4200 | O | LYS | 164 | 15.045 | 13.367 | 62.054 | 1.00 | 41.03 | O |
| ATOM | 4201 | N | GLU | 165 | 13.623 | 15.033 | 62.516 | 1.00 | 48.05 | N |
| ATOM | 4202 | CA | GLU | 165 | 13.978 | 15.114 | 63.927 | 1.00 | 48.85 | C |
| ATOM | 4203 | CB | GLU | 165 | 14.848 | 16.344 | 64.205 | 1.00 | 48.33 | C |
| ATOM | 4204 | CG | GLU | 165 | 15.094 | 16.595 | 65.692 | 1.00 | 56.66 | C |
| ATOM | 4205 | CD | GLU | 165 | 16.474 | 17.137 | 65.988 | 1.00 | 68.08 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 4206 | OE1 | GLU | C | 165 | 16.857 | 18.147 | 65.354 | 1.00 | 71.86 | O |
| ATOM | 4207 | OE2 | GLU | C | 165 | 17.165 | 16.577 | 66.864 | 1.00 | 72.73 | O |
| ATOM | 4208 | C | GLU | C | 165 | 12.688 | 15.152 | 64.470 | 1.00 | 50.64 | C |
| ATOM | 4209 | O | GLU | C | 165 | 11.763 | 15.885 | 64.389 | 1.00 | 51.25 | O |
| ATOM | 4210 | N | LYS | C | 166 | 12.615 | 14.325 | 65.760 | 1.00 | 51.20 | N |
| ATOM | 4211 | CA | LYS | C | 166 | 11.431 | 14.263 | 66.595 | 1.00 | 46.99 | C |
| ATOM | 4212 | CB | LYS | C | 166 | 10.745 | 12.911 | 66.466 | 1.00 | 45.11 | C |
| ATOM | 4213 | CG | LYS | C | 166 | 9.246 | 12.974 | 66.795 | 1.00 | 56.92 | C |
| ATOM | 4214 | CD | LYS | C | 166 | 8.582 | 11.610 | 66.708 | 1.00 | 60.23 | C |
| ATOM | 4215 | CE | LYS | C | 166 | 8.433 | 10.986 | 68.079 | 1.00 | 66.15 | C |
| ATOM | 4216 | NZ | LYS | C | 166 | 8.402 | 9.519 | 67.930 | 1.00 | 55.25 | N |
| ATOM | 4217 | C | LYS | C | 166 | 11.816 | 14.499 | 68.059 | 1.00 | 44.59 | C |
| ATOM | 4218 | O | LYS | C | 166 | 12.816 | 13.969 | 68.548 | 1.00 | 38.32 | O |
| ATOM | 4219 | N | LYS | C | 167 | 10.997 | 15.295 | 68.727 | 1.00 | 42.88 | N |
| ATOM | 4220 | CA | LYS | C | 167 | 11.077 | 15.528 | 70.154 | 1.00 | 44.74 | C |
| ATOM | 4221 | CB | LYS | C | 167 | 1.243 | 16.762 | 70.499 | 1.00 | 45.46 | C |
| ATOM | 4222 | CG | LYS | C | 167 | 10.325 | 17.200 | 71.941 | 1.00 | 49.83 | C |
| ATOM | 4223 | CD | LYS | C | 167 | 9.300 | 18.290 | 72.311 | 1.00 | 61.14 | C |
| ATOM | 4224 | CE | LYS | C | 167 | 7.999 | 17.707 | 72.906 | 1.00 | 63.78 | C |
| ATOM | 4225 | NZ | LYS | C | 167 | 7.410 | 18.581 | 73.976 | 1.00 | 59.86 | N |
| ATOM | 4226 | C | LYS | C | 167 | 10.564 | 14.263 | 70.855 | 1.00 | 43.60 | C |
| ATOM | 4227 | O | LYS | C | 167 | 9.463 | 13.794 | 70.578 | 1.00 | 41.018 | O |
| ATOM | 4228 | N | VAL | C | 168 | 11.388 | 13.697 | 71.741 | 1.00 | 43.90 | N |
| ATOM | 4229 | CA | VAL | C | 168 | 11.021 | 12.531 | 72.522 | 1.00 | 38.55 | C |
| ATOM | 4230 | CB | VAL | C | 168 | 11.739 | 11.256 | 72.035 | 1.00 | 37.19 | C |
| ATOM | 4231 | CG1 | VAL | C | 168 | 11.259 | 10.057 | 72.845 | 1.00 | 38.16 | C |
| ATOM | 4232 | CG2 | VAL | C | 168 | 11.502 | 11.018 | 70.552 | 1.00 | 63.01 | C |
| ATOM | 4233 | C | VAL | C | 168 | 11.419 | 12.854 | 73.952 | 1.00 | 38.73 | C |
| ATOM | 4234 | O | VAL | C | 168 | 12.555 | 13.495 | 74.396 | 1.00 | 37.87 | O |
| ATOM | 4235 | N | SER | C | 169 | 10.407 | 14.099 | 74.650 | 1.00 | 40.35 | N |
| ATOM | 4236 | CA | SER | C | 169 | 10.803 | 15.401 | 75.934 | 1.00 | 36.05 | C |
| ATOM | 4237 | CB | SER | C | 169 | 10.023 | 15.125 | 76.103 | 1.00 | 41.30 | C |
| ATOM | 4238 | OG | SER | C | 169 | 8.647 | 13.165 | 76.188 | 1.00 | 40.70 | O |
| ATOM | 4239 | C | SER | C | 169 | 10.509 | 12.171 | 77.090 | 1.00 | 42.49 | C |
| ATOM | 4240 | O | SER | C | 169 | 9.771 | 13.559 | 76.950 | 1.00 | 45.71 | O |
| ATOM | 4241 | N | SER | C | 170 | 11.074 | 12.793 | 78.237 | 1.00 | 39.91 | N |
| ATOM | 4242 | CA | SER | C | 170 | 11.261 | 12.438 | 79.438 | 1.00 | 38.13 | C |
| ATOM | 4243 | CB | SER | C | 170 | 12.762 | 11.216 | 79.501 | 1.00 | 38.73 | C |
| ATOM | 4244 | OG | SER | C | 170 | 13.015 | 13.853 | 80.107 | 1.00 | 37.87 | O |
| ATOM | 4245 | C | SER | C | 170 | 11.029 | 15.041 | 80.519 | 1.00 | 38.81 | C |
| ATOM | 4246 | O | SER | C | 170 | 11.202 | 13.460 | 80.253 | 1.00 | 42.88 | O |
| ATOM | 4247 | N | MET | C | 171 | 10.693 | 14.451 | 81.742 | 1.00 | 39.16 | N |
| ATOM | 4248 | CA | MET | C | 171 | 10.722 | 13.899 | 82.824 | 1.00 | 41.28 | C |
| ATOM | 4249 | CB | MET | C | 171 | 10.150 | 14.955 | 84.130 | 1.00 | 40.48 | C |
| ATOM | 4250 | CG | MET | C | 171 | 10.155 | 14.191 | 85.218 | 1.00 | 40.93 | C |
| ATOM | 4251 | SD | MET | C | 171 | 9.361 | 12.836 | 86.774 | 1.00 | 42.40 | S |
| ATOM | 4252 | CE | MET | C | 171 | 9.920 | 15.025 | 86.998 | 1.00 | 37.78 | C |
| ATOM | 4253 | C | MET | C | 171 | 12.141 | 16.243 | 83.061 | 1.00 | 49.34 | C |
| ATOM | 4254 | O | MET | C | 171 | 12.299 | 14.156 | 83.251 | 1.00 | 44.72 | O |
| ATOM | 4255 | N | PHE | C | 172 | 13.159 | | 83.013 | 1.00 | 41.02 | N |

TABLE 10-continued

Atomic coordinates for COM1 complex of the modified
TXNIP protein represented by SEQ ID NO: 6 and the modified protein represented by SEQ ID NO: 3

| ATOM | 4256 | CA  | PHE | C | 172 | 14.542 | 14.591 | 83.270 | 1.00 | 43.56 | C |
|------|------|-----|-----|---|-----|--------|--------|--------|------|-------|---|
| ATOM | 4257 | CB  | PHE | C | 172 | 15.282 | 13.571 | 84.147 | 1.00 | 42.50 | C |
| ATOM | 4258 | CG  | PHE | C | 172 | 14.661 | 13.405 | 85.501 | 1.00 | 42.81 | C |
| ATOM | 4259 | CD1 | PHE | C | 172 | 14.622 | 14.476 | 86.399 | 1.00 | 48.42 | C |
| ATOM | 4260 | CE1 | PHE | C | 172 | 14.012 | 14.343 | 87.653 | 1.00 | 52.89 | C |
| ATOM | 4261 | CZ  | PHE | C | 172 | 13.437 | 13.121 | 88.022 | 1.00 | 50.60 | C |
| ATOM | 4262 | CE2 | PHE | C | 172 | 13.454 | 12.049 | 87.117 | 1.00 | 43.95 | C |
| ATOM | 4263 | CD2 | PHE | C | 172 | 14.059 | 12.207 | 85.861 | 1.00 | 41.73 | C |
| ATOM | 4264 | C   | PHE | C | 172 | 15.344 | 14.976 | 82.023 | 1.00 | 44.01 | C |
| ATOM | 4265 | O   | PHE | C | 172 | 16.406 | 15.602 | 82.129 | 1.00 | 41.30 | O |
| ATOM | 4266 | N   | ILE | C | 173 | 14.830 | 14.609 | 80.848 | 1.00 | 42.56 | N |
| ATOM | 4267 | CA  | ILE | C | 173 | 15.391 | 15.104 | 79.590 | 1.00 | 42.62 | C |
| ATOM | 4268 | CB  | ILE | C | 173 | 16.105 | 14.004 | 78.736 | 1.00 | 41.56 | C |
| ATOM | 4269 | CG1 | ILE | C | 173 | 16.996 | 13.105 | 79.596 | 1.00 | 40.93 | C |
| ATOM | 4270 | CD1 | ILE | C | 173 | 17.447 | 11.849 | 78.870 | 1.00 | 43.24 | C |
| ATOM | 4271 | CG2 | ILE | C | 173 | 16.915 | 14.654 | 77.597 | 1.00 | 44.37 | C |
| ATOM | 4272 | C   | ILE | C | 173 | 14.255 | 15.691 | 78.793 | 1.00 | 43.85 | C |
| ATOM | 4273 | O   | ILE | C | 173 | 13.798 | 15.097 | 77.804 | 1.00 | 44.56 | O |
| ATOM | 4274 | N   | PRO | C | 174 | 13.725 | 16.872 | 79.210 | 1.00 | 43.29 | N |
| ATOM | 4275 | CA  | PRO | C | 174 | 12.584 | 17.44  | 78.517 | 1.00 | 44.87 | C |
| ATOM | 4276 | CB  | PRO | C | 174 | 12.327 | 18.748 | 79.281 | 1.00 | 46.23 | C |
| ATOM | 4277 | CG  | PRO | C | 174 | 13.012 | 18.564 | 80.591 | 1.00 | 46.70 | C |
| ATOM | 4278 | CD  | PRO | C | 174 | 14.196 | 17.741 | 80.303 | 1.00 | 42.95 | C |
| ATOM | 4279 | C   | PRO | C | 174 | 12.888 | 17.743 | 77.054 | 1.00 | 46.77 | C |
| ATOM | 4280 | O   | PRO | C | 174 | 11.961 | 17.809 | 76.250 | 1.00 | 49.83 | O |
| ATOM | 4281 | N   | ASP | C | 175 | 14.164 | 17.939 | 76.717 | 1.00 | 48.21 | N |
| ATOM | 4282 | CA  | ASP | C | 175 | 14.559 | 18.323 | 75.351 | 1.00 | 49.61 | C |
| ATOM | 4283 | CB  | ASP | C | 175 | 15.584 | 19.459 | 75.381 | 1.00 | 51.49 | C |
| ATOM | 4284 | CG  | ASP | C | 175 | 15.101 | 20.679 | 76.146 | 1.00 | 63.46 | C |
| ATOM | 4285 | OD1 | ASP | C | 175 | 15.972 | 21.444 | 76.627 | 1.00 | 65.97 | O |
| ATOM | 4286 | OD2 | ASP | C | 175 | 13.865 | 20.890 | 76.261 | 1.00 | 70.34 | O |
| ATOM | 4287 | C   | ASP | C | 175 | 15.139 | 17.142 | 74.570 | 1.00 | 45.24 | C |
| ATOM | 4288 | O   | ASP | C | 175 | 15.877 | 17.326 | 73.593 | 1.00 | 44.77 | O |
| ATOM | 4289 | N   | GLY | C | 176 | 14.836 | 15.936 | 75.029 | 1.00 | 42.19 | N |
| ATOM | 4290 | CA  | GLY | C | 176 | 15.233 | 14.737 | 74.331 | 1.00 | 40.01 | C |
| ATOM | 4291 | C   | GLY | C | 176 | 14.729 | 14.734 | 72.694 | 1.00 | 38.84 | C |
| ATOM | 4292 | O   | GLY | C | 176 | 13.653 | 15.263 | 72.591 | 1.00 | 39.98 | O |
| ATOM | 4293 | N   | ARG | C | 177 | 15.516 | 14.132 | 72.004 | 1.00 | 39.16 | N |
| ATOM | 4294 | CA  | ARG | C | 177 | 15.234 | 14.159 | 70.570 | 1.00 | 38.63 | C |
| ATOM | 4295 | CB  | ARG | C | 177 | 15.809 | 15.422 | 69.915 | 1.00 | 41.42 | C |
| ATOM | 4296 | CG  | ARG | C | 177 | 15.023 | 16.667 | 70.276 | 1.00 | 47.85 | C |
| ATOM | 4297 | CD  | ARG | C | 177 | 15.596 | 17.948 | 69.716 | 1.00 | 66.67 | C |
| ATOM | 4298 | NE  | ARG | C | 177 | 14.650 | 19.059 | 69.885 | 1.00 | 69.69 | N |
| ATOM | 4299 | CZ  | ARG | C | 177 | 13.583 | 19.273 | 69.112 | 1.00 | 76.69 | C |
| ATOM | 4300 | NH1 | ARG | C | 177 | 13.293 | 18.456 | 68.096 | 1.00 | 71.54 | N |
| ATOM | 4301 | NH2 | ARG | C | 177 | 12.795 | 20.313 | 69.355 | 1.00 | 07.75 | N |
| ATOM | 4302 | C   | ARG | C | 177 | 15.849 | 12.595 | 69.915 | 1.00 | 77.27 | C |
| ATOM | 4303 | O   | ARG | C | 177 | 16.897 | 12.469 | 70.365 | 1.00 | 36.23 | O |
| ATOM | 4304 | N   | VAL | C | 178 | 15.208 | 12.519 | 68.830 | 1.00 | 40.18 | N |
| ATOM | 4305 | CA  | VAL | C | 178 | 15.712 | 11.449 | 67.987 | 1.00 | 35.92 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 4306 | CB | VAL | C | 178 | 14.875 | 10.168 | 68.135 | 1.00 | 36.42 | C |
| ATOM | 4307 | CG1 | VAL | C | 178 | 15.269 | 9.111 | 67.073 | 1.00 | 34.93 | C |
| ATOM | 4308 | CG2 | VAL | C | 178 | 15.013 | 9.604 | 69.558 | 1.00 | 29.01 | C |
| ATOM | 4309 | C | VAL | C | 178 | 15.685 | 11.963 | 66.563 | 1.00 | 37.59 | C |
| ATOM | 4310 | O | VAL | C | 178 | 14.672 | 12.472 | 66.131 | 1.00 | 35.35 | O |
| ATOM | 4311 | N | SER | C | 179 | 16.805 | 11.837 | 65.852 | 1.00 | 38.43 | N |
| ATOM | 4312 | CA | SER | C | 179 | 16.921 | 12.363 | 64.480 | 1.00 | 40.42 | C |
| ATOM | 4313 | CB | SER | C | 179 | 17.841 | 13.590 | 64.474 | 1.00 | 42.23 | C |
| ATOM | 4314 | OG | SER | C | 179 | 19.188 | 13.200 | 64.288 | 1.00 | 55.87 | O |
| ATOM | 4315 | C | SER | C | 179 | 17.495 | 11.286 | 63.575 | 1.00 | 39.65 | C |
| ATOM | 4316 | O | SER | C | 179 | 18.180 | 10.365 | 64.057 | 1.00 | 34.43 | O |
| ATOM | 4317 | N | VAL | C | 180 | 17.175 | 11.377 | 62.272 | 1.00 | 40.21 | N |
| ATOM | 4318 | CA | VAL | C | 180 | 17.773 | 10.538 | 61.236 | 1.00 | 63.42 | C |
| ATOM | 4319 | CB | VAL | C | 180 | 17.000 | 9.214 | 61.019 | 1.00 | 40.84 | C |
| ATOM | 4320 | CG1 | VAL | C | 180 | 15.488 | 9.446 | 60.789 | 1.00 | 42.88 | C |
| ATOM | 4321 | CG2 | VAL | C | 180 | 17.608 | 8.389 | 59.880 | 1.00 | 39.59 | C |
| ATOM | 4322 | C | VAL | C | 180 | 17.833 | 11.357 | 59.975 | 1.00 | 38.63 | C |
| ATOM | 4323 | O | VAL | C | 180 | 16.893 | 12.107 | 59.665 | 1.00 | 38.90 | O |
| ATOM | 4324 | N | SER | C | 181 | 18.060 | 11.267 | 50.205 | 1.00 | 30.32 | N |
| ATOM | 4325 | CA | SER | C | 181 | 19.139 | 11.822 | 57.961 | 1.00 | 41.71 | C |
| ATOM | 4326 | CB | SER | C | 181 | 20.053 | 13.043 | 57.955 | 1.00 | 43.10 | C |
| ATOM | 4327 | OG | SER | C | 181 | 21.389 | 12.659 | 58.153 | 1.00 | 51.55 | O |
| ATOM | 4328 | C | SER | C | 181 | 19.813 | 10.724 | 57.204 | 1.00 | 42.38 | C |
| ATOM | 4329 | O | SER | C | 181 | 20.688 | 10.070 | 57.736 | 1.00 | 41.14 | O |
| ATOM | 4330 | N | ALA | C | 182 | 19.409 | 10.531 | 55.950 | 1.00 | 38.80 | N |
| ATOM | 4331 | CA | ALA | C | 182 | 19.889 | 9.411 | 55.174 | 1.00 | 40.66 | C |
| ATOM | 4332 | CB | ALA | C | 182 | 18.952 | 8.246 | 55.287 | 1.00 | 40.62 | C |
| ATOM | 4333 | C | ALA | C | 182 | 19.956 | 9.849 | 53.744 | 1.00 | 43.09 | C |
| ATOM | 4334 | O | ALA | C | 182 | 19.259 | 10.785 | 53.357 | 1.00 | 42.67 | O |
| ATOM | 4335 | N | ARG | C | 183 | 20.800 | 9.179 | 52.971 | 1.00 | 42.67 | N |
| ATOM | 4336 | CA | ARG | C | 183 | 20.988 | 9.533 | 51.583 | 1.00 | 47.12 | C |
| ATOM | 4337 | CB | ARG | C | 183 | 22.167 | 10.495 | 51.434 | 1.00 | 50.69 | C |
| ATOM | 4338 | CG | ARG | C | 183 | 22.295 | 11.123 | 50.036 | 1.00 | 58.39 | C |
| ATOM | 4339 | CD | ARG | C | 183 | 23.693 | 11.725 | 79.795 | 1.00 | 60.41 | C |
| ATOM | 4340 | NE | ARG | C | 183 | 24.169 | 11.433 | 48.429 | 1.00 | 81.41 | N |
| ATOM | 4341 | CZ | ARG | C | 183 | 25.120 | 12.108 | 47.780 | 1.00 | 82.71 | C |
| ATOM | 4342 | NH1 | ARG | C | 183 | 25.740 | 13.140 | 48.349 | 1.00 | 86.54 | N |
| ATOM | 4343 | NH2 | ARG | C | 183 | 25.475 | 11.751 | 46.548 | 1.00 | 78.98 | N |
| ATOM | 4344 | C | ARG | C | 183 | 21.299 | 8.263 | 50.832 | 1.00 | 44.21 | C |
| ATOM | 4345 | O | ARG | C | 183 | 22.045 | 7.446 | 51.317 | 1.00 | 40.15 | O |
| ATOM | 4346 | N | ILE | C | 184 | 20.714 | 8.121 | 49.643 | 1.00 | 43.86 | N |
| ATOM | 4347 | CA | ILE | C | 184 | 21.083 | 7.078 | 48.705 | 1.00 | 42.93 | C |
| ATOM | 4348 | CB | ILE | C | 184 | 19.913 | 6.131 | 48.429 | 1.00 | 41.64 | C |
| ATOM | 4349 | CG1 | ILE | C | 184 | 18.678 | 6.915 | 47.976 | 1.00 | 40.83 | C |
| ATOM | 4350 | CD1 | ILE | C | 184 | 19.667 | 5.261 | 49.689 | 1.00 | 37.57 | C |
| ATOM | 4351 | CG2 | ILE | C | 184 | 19.667 | 5.261 | 49.689 | 1.00 | 42.97 | C |
| ATOM | 4352 | C | ILE | C | 184 | 21.559 | 7.724 | 47.414 | 1.00 | 40.63 | C |
| ATOM | 4353 | O | ILE | C | 184 | 21.193 | 8.872 | 47.115 | 1.00 | 39.14 | O |
| ATOM | 4354 | N | ASP | C | 185 | 22.361 | 6.995 | 46.645 | 1.00 | 42.53 | N |
| ATOM | 4355 | CA | ASP | C | 185 | 2.023 | 7.623 | 45.515 | 1.00 | 46.57 | C |

TABLE 10-continued

Atomic coordinates for COM1 complex of the modified
TXNIP protein represented by SEQ ID NO: 6 and the modified protein represented by SEQ ID NO: 3

| ATOM | 4356 | CB | ASP | C | 185 | 24.316 | 45.144 | 6.900 | 1.00 | 51.28 | C |
|---|---|---|---|---|---|---|---|---|---|---|---|
| ATOM | 4357 | CG | ASP | C | 185 | 24.078 | 44.591 | 5.521 | 1.00 | 65.39 | C |
| ATOM | 4358 | OD1 | ASP | C | 185 | 23.636 | 43.422 | 5.416 | 1.00 | 77.25 | O |
| ATOM | 4359 | OD2 | ASP | C | 185 | 24.383 | 45.310 | 4.539 | 1.00 | 73.72 | O |
| ATOM | 4360 | C | ASP | C | 185 | 22.158 | 44.294 | 7.875 | 1.00 | 46.42 | C |
| ATOM | 4361 | O | ASP | C | 185 | 22.507 | 43.450 | 8.693 | 1.00 | 43.03 | O |
| ATOM | 4362 | N | ARG | C | 186 | 21.016 | 44.202 | 7.185 | 1.00 | 42.57 | N |
| ATOM | 4363 | CA | ARG | C | 186 | 20.114 | 43.038 | 7.351 | 1.00 | 41.01 | C |
| ATOM | 4364 | CB | ARG | C | 186 | 20.652 | 41.829 | 6.585 | 1.00 | 39.23 | C |
| ATOM | 4365 | CG | ARG | C | 186 | 20.921 | 42.087 | 5.146 | 1.00 | 41.74 | C |
| ATOM | 4366 | CD | ARG | C | 186 | 21.648 | 40.975 | 4.508 | 1.00 | 42.93 | C |
| ATOM | 4367 | NE | ARG | C | 186 | 21.492 | 40.999 | 3.047 | 1.00 | 43.21 | N |
| ATOM | 4368 | CZ | ARG | C | 186 | 22.340 | 41.591 | 2.216 | 1.00 | 45.66 | C |
| ATOM | 4369 | NH1 | ARG | C | 186 | 23.386 | 42.234 | 2.707 | 1.00 | 46.96 | N |
| ATOM | 4370 | NH2 | ARG | C | 186 | 22.140 | 41.557 | 0.903 | 1.00 | 43.09 | N |
| ATOM | 4371 | C | ARG | C | 186 | 18.710 | 42.586 | 7.171 | 1.00 | 42.18 | C |
| ATOM | 4372 | O | ARG | C | 186 | 18.548 | 44.502 | 6.357 | 1.00 | 41.33 | O |
| ATOM | 4373 | N | LYS | C | 187 | 17.710 | 42.586 | 7.171 | 1.00 | 41.25 | N |
| ATOM | 4374 | CA | LYS | C | 187 | 16.357 | 42.856 | 6.729 | 1.00 | 42.70 | C |
| ATOM | 4375 | CB | LYS | C | 187 | 15.400 | 42.481 | 7.859 | 1.00 | 43.75 | C |
| ATOM | 4376 | CG | LYS | C | 187 | 13.938 | 42.498 | 7.528 | 1.00 | 50.54 | C |
| ATOM | 4377 | CD | LYS | C | 187 | 13.112 | 42.080 | 8.751 | 1.00 | 49.94 | C |
| ATOM | 4378 | CE | LYS | C | 187 | 11.711 | 42.585 | 8.668 | 1.00 | 60.91 | C |
| ATOM | 4379 | NZ | LYS | C | 187 | 11.021 | 42.535 | 9.985 | 1.00 | 69.90 | N |
| ATOM | 4380 | C | LYS | C | 187 | 16.002 | 42.095 | 5.423 | 1.00 | 44.46 | C |
| ATOM | 4381 | O | LYS | C | 187 | 15.150 | 42.536 | 4.648 | 1.00 | 41.20 | O |
| ATOM | 4382 | N | GLY | C | 188 | 16.650 | 40.591 | 5.182 | 1.00 | 44.17 | N |
| ATOM | 4383 | CA | GLY | C | 188 | 16.264 | 40.090 | 4.058 | 1.00 | 40.19 | C |
| ATOM | 4384 | C | GLY | C | 188 | 17.253 | 40.311 | 2.938 | 1.00 | 38.67 | C |
| ATOM | 4385 | O | GLY | C | 188 | 18.459 | 40.234 | 3.146 | 1.00 | 37.97 | O |
| ATOM | 4386 | N | PHE | C | 189 | 16.735 | 40.629 | 1.749 | 1.00 | 39.38 | N |
| ATOM | 4387 | CA | PHE | C | 189 | 17.570 | 40.870 | 0.579 | 1.00 | 38.58 | C |
| ATOM | 4388 | CB | PHE | C | 189 | 17.541 | 42.370 | 0.184 | 1.00 | 37.74 | C |
| ATOM | 4389 | CG | PHE | C | 189 | 18.231 | 43.254 | 1.170 | 1.00 | 38.28 | C |
| ATOM | 4390 | CD1 | PHE | C | 189 | 19.581 | 43.513 | 1.066 | 1.00 | 34.88 | C |
| ATOM | 4391 | CE1 | PHE | C | 189 | 20.240 | 44.325 | 2.004 | 1.00 | 36.61 | C |
| ATOM | 4392 | CZ | PHE | C | 189 | 19.523 | 44.830 | 3.064 | 1.00 | 28.63 | C |
| ATOM | 4393 | CE2 | PHE | C | 189 | 18.183 | 44.545 | 3.182 | 1.00 | 30.63 | C |
| ATOM | 4394 | CD2 | PHE | C | 189 | 17.538 | 43.779 | 2.231 | 1.00 | 39.21 | C |
| ATOM | 4395 | C | PHE | C | 189 | 17.019 | 40.075 | -0.565 | 1.00 | 38.52 | C |
| ATOM | 4396 | O | PHE | C | 189 | 15.826 | 39.815 | -0.612 | 1.00 | 41.69 | O |
| ATOM | 4397 | N | CYS | C | 190 | 17.887 | 39.701 | -1.492 | 1.00 | 36.36 | N |
| ATOM | 4398 | CA | CYS | C | 190 | 17.491 | 39.000 | -2.700 | 1.00 | 42.33 | C |
| ATOM | 4399 | CB | CYS | C | 190 | 18.611 | 38.044 | -3.117 | 1.00 | 46.04 | C |
| ATOM | 4400 | SG | CYS | C | 190 | 19.126 | 36.877 | -1.784 | 1.00 | 63.16 | S |
| ATOM | 4401 | C | CYS | C | 190 | 17.729 | 39.989 | -3.828 | 1.00 | 38.57 | C |
| ATOM | 4402 | O | CYS | C | 190 | 18.022 | 40.972 | -3.941 | 1.00 | 34.16 | O |
| ATOM | 4403 | N | GLU | C | 191 | 16.307 | 39.713 | -4.685 | 1.00 | 38.41 | N |
| ATOM | 4404 | CA | GLU | C | 191 | 16.073 | 40.600 | -5.799 | 1.00 | 43.33 | C |
| ATOM | 4405 | CB | GLU | C | 191 | 14.891 | 40.086 | -6.648 | 1.00 | 4.77 | C |

TABLE 10-continued

Atomic coordinates for COM1 complex of the modified
TXNIP protein represented by SEQ ID NO: 6 and the modified protein represented by SEQ ID NO: 3

| | | | | | | | | | | | |
|---|---|---|---|---|---|---|---|---|---|---|---|
| ATOM | 4406 | CG | GLU | C | 191 | 15.307 | -7.828 | 39.279 | 1.00 | 52.42 | C |
| ATOM | 4407 | CD | GLU | C | 191 | 14.227 | -8.309 | 38.354 | 1.00 | 66.05 | C |
| ATOM | 4408 | OE1 | GLU | C | 191 | 14.499 | -8.416 | 37.122 | 1.00 | 62.02 | O |
| ATOM | 4409 | OE2 | GLU | C | 191 | 13.117 | -8.578 | 38.861 | 1.00 | 65.58 | O |
| ATOM | 4410 | C | GLU | C | 191 | 17.338 | -6.580 | 40.751 | 1.00 | 45.51 | C |
| ATOM | 4411 | O | GLU | C | 191 | 18.017 | -6.841 | 39.765 | 1.00 | 47.58 | O |
| ATOM | 4412 | N | GLY | C | 192 | 17.735 | -6.849 | 41.996 | 1.00 | 46.83 | N |
| ATOM | 4413 | CA | GLY | C | 192 | 18.939 | -7.630 | 42.278 | 1.00 | 46.07 | C |
| ATOM | 4414 | C | GLY | C | 192 | 20.131 | -6.796 | 42.698 | 1.00 | 46.94 | C |
| ATOM | 4415 | O | GLY | C | 192 | 21.124 | -7.335 | 43.203 | 1.00 | 49.28 | O |
| ATOM | 4416 | N | ASP | C | 193 | 20.049 | -5.486 | 42.467 | 1.00 | 45.08 | N |
| ATOM | 4417 | CA | ASP | C | 193 | 21.098 | -4.553 | 42.838 | 1.00 | 42.51 | C |
| ATOM | 4418 | CB | ASP | C | 193 | 20.936 | -3.249 | 42.041 | 1.00 | 45.42 | C |
| ATOM | 4419 | CG | ASP | C | 193 | 21.493 | -3.340 | 40.604 | 1.00 | 54.28 | C |
| ATOM | 4420 | OD1 | ASP | C | 193 | 21.715 | -4.461 | 40.085 | 1.00 | 54.17 | O |
| ATOM | 4421 | OD2 | ASP | C | 193 | 21.722 | -2.270 | 39.991 | 1.00 | 61.91 | O |
| ATOM | 4422 | C | ASP | C | 193 | 20.978 | -4.305 | 44.341 | 1.00 | 42.86 | C |
| ATOM | 4423 | O | ASP | C | 193 | 19.978 | -4.669 | 44.947 | 1.00 | 40.07 | O |
| ATOM | 4424 | N | GLU | C | 194 | 22.022 | -3.768 | 44.964 | 1.00 | 42.08 | N |
| ATOM | 4425 | CA | GLU | C | 194 | 21.912 | -3.386 | 46.371 | 1.00 | 46.01 | C |
| ATOM | 4426 | CB | GLU | C | 194 | 23.164 | -3.814 | 47.141 | 1.00 | 49.67 | C |
| ATOM | 4427 | CG | GLU | C | 194 | 24.353 | -2.906 | 46.965 | 1.00 | 58.56 | C |
| ATOM | 4428 | CD | GLU | C | 194 | 25.492 | -3.250 | 47.925 | 1.00 | 68.89 | C |
| ATOM | 4429 | OE1 | GLU | C | 194 | 25.836 | -4.450 | 48.022 | 1.00 | 80.45 | O |
| ATOM | 4430 | OE2 | GLU | C | 194 | 26.028 | -2.322 | 48.582 | 1.00 | 79.45 | O |
| ATOM | 4431 | C | GLU | C | 194 | 21.663 | -1.892 | 45.493 | 1.00 | 43.96 | C |
| ATOM | 4432 | O | GLU | C | 194 | 22.228 | -1.112 | 45.738 | 1.00 | 46.05 | O |
| ATOM | 4433 | N | ILE | C | 195 | 20.769 | -1.474 | 47.376 | 1.00 | 43.70 | N |
| ATOM | 4434 | CA | ILE | C | 195 | 20.738 | -0.044 | 47.752 | 1.00 | 43.44 | C |
| ATOM | 4435 | CB | ILE | C | 195 | 19.338 | 0.449 | 48.198 | 1.00 | 42.78 | C |
| ATOM | 4436 | CG1 | ILE | C | 195 | 18.277 | 0.077 | 47.169 | 1.00 | 46.42 | C |
| ATOM | 4437 | CD1 | ILE | C | 195 | 16.842 | 0.481 | 47.559 | 1.00 | 38.66 | C |
| ATOM | 4438 | CG2 | ILE | C | 195 | 19.367 | 1.974 | 48.511 | 1.00 | 44.43 | C |
| ATOM | 4439 | C | ILE | C | 195 | 21.712 | 0.118 | 48.923 | 1.00 | 46.42 | C |
| ATOM | 4440 | O | ILE | C | 195 | 21.520 | -0.490 | 49.969 | 1.00 | 47.79 | O |
| ATOM | 4441 | N | SER | C | 196 | 22.738 | 0.948 | 48.758 | 1.00 | 41.98 | N |
| ATOM | 4442 | CA | SER | C | 196 | 23.716 | 1.181 | 49.813 | 1.00 | 44.17 | C |
| ATOM | 4443 | CB | SER | C | 196 | 25.109 | 1.246 | 49.173 | 1.00 | 47.48 | C |
| ATOM | 4444 | OG | SER | C | 196 | 26.025 | 2.071 | 49.877 | 1.00 | 58.92 | O |
| ATOM | 4445 | C | SER | C | 196 | 23.295 | 2.472 | 50.499 | 1.00 | 42.47 | C |
| ATOM | 4446 | O | SER | C | 196 | 23.186 | 3.511 | 49.857 | 1.00 | 41.67 | O |
| ATOM | 4447 | N | ILE | C | 197 | 22.946 | 2.378 | 51.780 | 1.00 | 41.41 | N |
| ATOM | 4448 | CA | ILE | C | 197 | 22.349 | 3.512 | 52.508 | 1.00 | 41.41 | C |
| ATOM | 4449 | CB | ILE | C | 197 | 21.175 | 3.057 | 53.432 | 1.00 | 42.50 | C |
| ATOM | 4450 | CG1 | ILE | C | 197 | 20.111 | 2.275 | 52.623 | 1.00 | 40.88 | C |
| ATOM | 4451 | CD1 | ILE | C | 197 | 19.119 | 1.564 | 53.470 | 1.00 | 41.55 | C |
| ATOM | 4452 | CG2 | ILE | C | 197 | 20.533 | 4.286 | 54.111 | 1.00 | 86.85 | C |
| ATOM | 4453 | C | ILE | C | 197 | 23.381 | 4.195 | 53.401 | 1.00 | 44.41 | C |
| ATOM | 4454 | O | ILE | C | 197 | 23.976 | 3.537 | 54.230 | 1.00 | 40.87 | O |
| ATOM | 4455 | N | HIS | C | 198 | 23.533 | 5.515 | 53.260 | 1.00 | 43.18 | N |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 4456 | CA | HIS | C | 198 | 24.305 | 6.304 | 54.215 | 1.00 | 44.50 | C |
| ATOM | 4457 | CB | HIS | C | 198 | 25.235 | 7.256 | 53.452 | 1.00 | 48.01 | C |
| ATOM | 4458 | CG | HIS | C | 198 | 26.201 | 6.544 | 52.540 | 1.00 | 53.63 | C |
| ATOM | 4459 | ND1 | HIS | C | 198 | 27.525 | 5.339 | 52.884 | 1.00 | 59.11 | N |
| ATOM | 4460 | CE1 | HIS | C | 198 | 28.125 | 5.682 | 51.909 | 1.00 | 84.40 | C |
| ATOM | 4461 | NE2 | HIS | C | 198 | 27.238 | 5.445 | 50.956 | 1.00 | 70.37 | N |
| ATOM | 4462 | CD2 | HIS | C | 198 | 26.028 | 5.977 | 51.329 | 1.00 | 65.33 | C |
| ATOM | 4463 | C | HIS | C | 198 | 23.305 | 7.075 | 55.141 | 1.00 | 41.56 | C |
| ATOM | 4464 | O | HIS | C | 198 | 22.502 | 7.809 | 54.675 | 1.00 | 41.88 | O |
| ATOM | 4465 | N | ALA | C | 199 | 23.525 | 6.910 | 56.451 | 1.00 | 39.55 | N |
| ATOM | 4466 | CA | ALA | C | 199 | 22.575 | 7.480 | 57.405 | 1.00 | 37.50 | C |
| ATOM | 4467 | CB | ALA | C | 199 | 21.457 | 6.439 | 57.682 | 1.00 | 34.49 | C |
| ATOM | 4468 | C | ALA | C | 199 | 23.270 | 7.818 | 58.696 | 1.00 | 36.43 | C |
| ATOM | 4469 | O | ALA | C | 199 | 24.161 | 7.083 | 59.118 | 1.00 | 32.75 | O |
| ATOM | 4470 | N | ASP | C | 200 | 22.802 | 8.803 | 59.377 | 1.00 | 35.38 | N |
| ATOM | 4471 | CA | ASP | C | 200 | 23.349 | 9.238 | 50.679 | 1.00 | 36.79 | C |
| ATOM | 4472 | CB | ASP | C | 200 | 24.075 | 10.580 | 60.506 | 1.00 | 36.28 | C |
| ATOM | 4473 | CG | ASP | C | 200 | 25.348 | 10.525 | 59.794 | 1.00 | 45.55 | C |
| ATOM | 4474 | OD1 | ASP | C | 200 | 26.073 | 9.491 | 59.781 | 1.00 | 39.84 | O |
| ATOM | 4475 | OD2 | ASP | C | 200 | 25.049 | 11.570 | 59.188 | 1.00 | 40.63 | O |
| ATOM | 4476 | C | ASP | C | 200 | 22.154 | 9.388 | 61.618 | 1.00 | 36.49 | C |
| ATOM | 4477 | O | ASP | C | 200 | 21.206 | 10.089 | 61.285 | 1.00 | 32.64 | O |
| ATOM | 4478 | N | PHE | C | 200 | 22.387 | 8.755 | 62.787 | 1.00 | 32.78 | N |
| ATOM | 4479 | CA | PHE | C | 201 | 21.202 | 8.752 | 63.794 | 1.00 | 33.69 | C |
| ATOM | 4480 | CB | PHE | C | 201 | 20.802 | 7.311 | 64.124 | 1.00 | 34.25 | C |
| ATOM | 4481 | CG | PHE | C | 201 | 20.477 | 6.485 | 62.939 | 1.00 | 42.78 | C |
| ATOM | 4482 | CD1 | PHE | C | 201 | 19.180 | 6.469 | 62.421 | 1.00 | 33.52 | C |
| ATOM | 4483 | CE1 | PHE | C | 201 | 18.885 | 5.693 | 61.299 | 1.00 | 41.79 | C |
| ATOM | 4484 | CZ | PHE | C | 201 | 19.891 | 4.981 | 60.690 | 1.00 | 33.28 | C |
| ATOM | 4485 | CE2 | PHE | C | 201 | 21.168 | 4.990 | 61.206 | 1.00 | 37.68 | C |
| ATOM | 4486 | CD2 | PHE | C | 201 | 21.459 | 5.717 | 62.329 | 1.00 | 38.95 | C |
| ATOM | 4487 | C | PHE | C | 201 | 21.693 | 9.388 | 65.081 | 1.00 | 35.66 | C |
| ATOM | 4488 | O | PHE | C | 201 | 22.787 | 9.075 | 65.508 | 1.00 | 32.85 | O |
| ATOM | 4489 | N | GLU | C | 202 | 20.898 | 10.295 | 65.672 | 1.00 | 36.02 | N |
| ATOM | 4490 | CA | GLU | C | 202 | 21.192 | 10.934 | 66.970 | 1.00 | 39.75 | C |
| ATOM | 4491 | CB | GLU | C | 202 | 21.193 | 12.473 | 66.850 | 1.00 | 40.75 | C |
| ATOM | 4492 | CG | GLU | C | 202 | 22.524 | 13.173 | 66.983 | 1.00 | 55.45 | C |
| ATOM | 4493 | CD | GLU | C | 202 | 22.441 | 14.612 | 67.527 | 1.00 | 48.70 | C |
| ATOM | 4494 | CE1 | GLU | C | 202 | 21.644 | 14.903 | 68.459 | 1.00 | 47.68 | C |
| ATOM | 4495 | CE2 | GLU | C | 202 | 23.200 | 15.450 | 67.008 | 1.00 | 51.55 | C |
| ATOM | 4496 | C | GLU | C | 202 | 20.080 | 10.552 | 67.960 | 1.00 | 37.45 | C |
| ATOM | 4497 | O | GLU | C | 202 | 18.889 | 10.662 | 67.632 | 1.00 | 34.68 | O |
| ATOM | 4498 | N | ASN | C | 203 | 20.475 | 10.141 | 69.182 | 1.00 | 32.70 | N |
| ATOM | 4499 | CA | ASN | C | 203 | 19.554 | 9.824 | 70.252 | 1.00 | 32.69 | C |
| ATOM | 4500 | CB | ASN | C | 203 | 19.486 | 8.292 | 70.529 | 1.00 | 32.80 | C |
| ATOM | 4501 | CG | ASN | C | 203 | 18.485 | 7.957 | 71.364 | 1.00 | 30.41 | C |
| ATOM | 4502 | OD1 | ASN | C | 203 | 17.670 | 8.811 | 72.005 | 1.00 | 32.87 | O |
| ATOM | 4503 | ND2 | ASN | C | 2037 | 18.593 | 6.767 | 72.229 | 1.00 | 28.58 | N |
| ATOM | 4504 | C | ASN | C | 203 | 19.954 | 10.541 | 71.552 | 1.00 | 32.12 | C |
| ATOM | 4505 | O | ASN | C | 203 | 20.806 | 10.053 | 72.203 | 1.00 | 31.66 | O |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 4506 | N | THR | 204 | 19.328 | 11.676 | 71.862 | 1.00 | 34.42 | N |
| ATOM | 4507 | CA | THR | 204 | 19.508 | 12.840 | 73.175 | 1.00 | 37.68 | C |
| ATOM | 4508 | CB | THR | 204 | 19.682 | 13.861 | 72.999 | 1.00 | 40.02 | C |
| ATOM | 4509 | OG1 | THR | 204 | 18.557 | 14.360 | 72.299 | 1.00 | 35.94 | O |
| ATOM | 4510 | OG2 | THR | 204 | 20.932 | 14.215 | 72.171 | 1.00 | 44.34 | C |
| ATOM | 4511 | C | THR | 204 | 18.299 | 12.089 | 74.102 | 1.00 | 37.53 | C |
| ATOM | 4512 | O | THR | 204 | 18.109 | 12.703 | 75.100 | 1.00 | 37.02 | O |
| ATOM | 4513 | N | SER | 205 | 17.378 | 11.221 | 73.889 | 1.00 | 37.86 | N |
| ATOM | 4514 | CA | SER | 205 | 16.211 | 10.928 | 74.533 | 1.00 | 37.04 | C |
| ATOM | 4515 | CB | SER | 205 | 15.073 | 10.367 | 73.687 | 1.00 | 37.12 | C |
| ATOM | 4516 | OG | SER | 205 | 15.347 | 9.019 | 73.365 | 1.00 | 37.11 | O |
| ATOM | 4517 | C | SER | 205 | 16.587 | 9.888 | 75.581 | 1.00 | 37.59 | C |
| ATOM | 4518 | O | SER | 205 | 17.682 | 9.315 | 75.513 | 1.00 | 35.76 | O |
| ATOM | 4519 | N | SER | 206 | 15.654 | 9.580 | 76.494 | 1.00 | 35.06 | N |
| ATOM | 4520 | CA | SER | 206 | 15.898 | 8.592 | 77.547 | 1.00 | 38.04 | C |
| ATOM | 4521 | CB | SER | 206 | 14.959 | 8.834 | 78.735 | 1.00 | 38.73 | C |
| ATOM | 4522 | OG | SER | 206 | 13.618 | 8.647 | 78.315 | 1.00 | 37.10 | O |
| ATOM | 4523 | C | SER | 206 | 15.749 | 7.140 | 77.106 | 1.00 | 37.76 | C |
| ATOM | 4524 | O | SER | 206 | 15.972 | 6.216 | 77.912 | 1.00 | 38.18 | O |
| ATOM | 4525 | N | ARG | 207 | 15.877 | 8.930 | 75.850 | 1.00 | 37.17 | N |
| ATOM | 4526 | CA | ARG | 207 | 15.010 | 5.596 | 75.351 | 1.00 | 37.33 | C |
| ATOM | 4527 | CB | ARG | 207 | 13.795 | 5.659 | 74.382 | 1.00 | 38.85 | C |
| ATOM | 4528 | CG | ARG | 207 | 12.426 | 5.750 | 75.050 | 1.00 | 44.03 | C |
| ATOM | 4529 | CD | ARG | 207 | 12.104 | 7.164 | 75.478 | 1.00 | 51.73 | C |
| ATOM | 4530 | NE | ARG | 207 | 10.850 | 7.352 | 76.800 | 1.00 | 54.46 | N |
| ATOM | 4531 | CZ | ARG | 207 | 10.410 | 8.520 | 76.546 | 1.00 | 55.81 | C |
| ATOM | 4532 | NH1 | ARG | 207 | 11.193 | 9.594 | 76.512 | 1.00 | 43.05 | N |
| ATOM | 4533 | NH2 | ARG | 207 | 9.187 | 8.611 | 77.059 | 1.00 | 59.23 | N |
| ATOM | 4534 | C | ARG | 207 | 16.102 | 5.021 | 74.600 | 1.00 | 35.76 | C |
| ATOM | 4535 | O | ARG | 207 | 17.057 | 5.765 | 74.165 | 1.00 | 34.96 | O |
| ATOM | 4536 | N | ILE | 208 | 16.214 | 3.698 | 74.473 | 1.00 | 34.83 | N |
| ATOM | 4537 | CA | ILE | 208 | 17.100 | 2.999 | 73.585 | 1.00 | 34.87 | C |
| ATOM | 4538 | CB | ILE | 208 | 17.449 | 1.612 | 74.125 | 1.00 | 33.21 | C |
| ATOM | 4539 | CG1 | ILE | 208 | 18.142 | 1.721 | 75.508 | 1.00 | 37.95 | C |
| ATOM | 4540 | CD1 | ILE | 208 | 18.248 | 0.394 | 76.238 | 1.00 | 43.29 | C |
| ATOM | 4541 | CG2 | ILE | 208 | 18.391 | 0.891 | 73.194 | 1.00 | 34.69 | C |
| ATOM | 4542 | C | ILE | 208 | 15.253 | 2.853 | 72.315 | 1.00 | 36.94 | C |
| ATOM | 4543 | O | ILE | 208 | 15.133 | 2.295 | 72.371 | 1.00 | 36.60 | O |
| ATOM | 4544 | N | VAL | 209 | 16.781 | 3.385 | 71.213 | 1.00 | 37.18 | N |
| ATOM | 4545 | CA | VAL | 209 | 16.111 | 3.450 | 60.884 | 1.00 | 33.21 | C |
| ATOM | 4546 | CB | VAL | 209 | 15.945 | 4.926 | 69.366 | 1.00 | 34.07 | C |
| ATOM | 4547 | CG1 | VAL | 209 | 15.324 | 5.837 | 70.480 | 1.00 | 30.26 | C |
| ATOM | 4548 | CG2 | VAL | 209 | 17.257 | 5.540 | 68.854 | 1.00 | 26.82 | C |
| ATOM | 4549 | C | VAL | 209 | 16.830 | 2.517 | 68.886 | 1.00 | 34.74 | C |
| ATOM | 4550 | O | VAL | 209 | 17.974 | 2.089 | 69.112 | 1.00 | 36.97 | O |
| ATOM | 4551 | N | VAL | 210 | 16.141 | 2.139 | 67.814 | 1.00 | 34.17 | N |
| ATOM | 4552 | CA | VAL | 210 | 16.638 | 1.103 | 66.937 | 1.00 | 36.52 | C |
| ATOM | 4553 | CB | VAL | 210 | 15.900 | -0.240 | 87.147 | 1.00 | 35.95 | C |
| ATOM | 4554 | CG1 | VAL | 210 | 16.494 | -1.321 | 66.212 | 1.00 | 33.01 | C |
| ATOM | 4555 | CG2 | VAL | 210 | 15.971 | -0.680 | 67.619 | 1.00 | 41.86 | C |

TABLE 10-continued

Atomic coordinates for COM1 complex of the modified
TXNIP protein represented by SEQ ID NO: 6 and the modified protein represented by SEQ ID NO: 3

| | | | | | | | | | | | |
|---|---|---|---|---|---|---|---|---|---|---|---|
| ATOM | 4556 | C | VAL | C | 210 | 16.433 | 1.538 | 65.510 | 1.00 | 37.90 | C |
| ATOM | 4557 | O | VAL | C | 210 | 15.281 | 1.679 | 65.073 | 1.00 | 38.65 | O |
| ATOM | 4558 | N | PRO | C | 211 | 17.535 | 1.751 | 64.777 | 1.00 | 38.74 | N |
| ATOM | 4559 | CA | PRO | C | 211 | 17.439 | 2.163 | 63.395 | 1.00 | 36.34 | C |
| ATOM | 4560 | CB | PRO | C | 211 | 18.799 | 2.770 | 63.131 | 1.00 | 38.03 | C |
| ATOM | 4561 | CG | PRO | C | 211 | 18.749 | 2.018 | 64.046 | 1.00 | 38.02 | C |
| ATOM | 4562 | CD | PRO | C | 211 | 18.931 | 1.553 | 65.211 | 1.00 | 39.58 | C |
| ATOM | 4563 | C | PRO | C | 211 | 17.149 | 0.962 | 62.491 | 1.00 | 39.74 | C |
| ATOM | 4564 | O | PRO | C | 211 | 17.674 | -0.127 | 62.721 | 1.00 | 34.62 | O |
| ATOM | 4565 | N | LYS | C | 212 | 16.285 | 1.155 | 61.481 | 1.00 | 38.87 | N |
| ATOM | 4566 | CA | LYS | C | 212 | 15.868 | 0.064 | 60.604 | 1.00 | 37.51 | C |
| ATOM | 4567 | CB | LYS | C | 212 | 14.557 | -0.538 | 61.102 | 1.00 | 32.75 | C |
| ATOM | 4568 | CG | LYS | C | 212 | 14.684 | -1.254 | 62.401 | 1.00 | 37.11 | C |
| ATOM | 4569 | CD | LYS | C | 212 | 13.368 | -1.563 | 63.025 | 1.00 | 38.33 | C |
| ATOM | 4570 | CE | LYS | C | 212 | 13.540 | -2.223 | 64.347 | 1.00 | 38.38 | C |
| ATOM | 4571 | NZ | LYS | C | 212 | 12.210 | -2.566 | 64.898 | 1.00 | 46.63 | N |
| ATOM | 4572 | C | LYS | C | 212 | 15.616 | 0.661 | 59.250 | 1.00 | 36.89 | C |
| ATOM | 4573 | O | LYS | C | 212 | 15.295 | 1.825 | 59.162 | 1.00 | 36.20 | O |
| ATOM | 4574 | N | ALA | C | 213 | 15.733 | -0.143 | 58.202 | 1.00 | 37.38 | N |
| ATOM | 4575 | CA | ALA | C | 213 | 15.263 | 0.261 | 56.887 | 1.00 | 36.59 | C |
| ATOM | 4576 | CB | ALA | C | 213 | 16.399 | 0.757 | 56.012 | 1.00 | 35.84 | C |
| ATOM | 4577 | C | ALA | C | 213 | 14.517 | -0.884 | 56.210 | 1.00 | 39.01 | C |
| ATOM | 4578 | O | ALA | C | 213 | 14.734 | -2.058 | 56.512 | 1.00 | 39.62 | O |
| ATOM | 4579 | N | ALA | C | 214 | 13.641 | -0.528 | 55.280 | 1.00 | 35.54 | N |
| ATOM | 4580 | CA | ALA | C | 214 | 12.838 | -1.521 | 54.579 | 1.00 | 35.21 | C |
| ATOM | 4581 | CB | ALA | C | 214 | 11.582 | -1.872 | 55.409 | 1.00 | 31.33 | C |
| ATOM | 4582 | C | ALA | C | 214 | 12.422 | -0.976 | 53.106 | 1.00 | 36.27 | C |
| ATOM | 4583 | O | ALA | C | 214 | 12.103 | 0.222 | 53.106 | 1.00 | 35.63 | O |
| ATOM | 4584 | N | ILE | C | 215 | 12.433 | -1.850 | 52.197 | 1.00 | 36.96 | N |
| ATOM | 4585 | CA | ILE | C | 215 | 11.745 | -1.580 | 50.923 | 1.00 | 39.38 | C |
| ATOM | 4586 | CB | ILE | C | 215 | 12.409 | -2.227 | 49.661 | 1.00 | 40.89 | C |
| ATOM | 4587 | CG1 | ILE | C | 215 | 13.865 | -1.765 | 49.501 | 1.00 | 40.76 | C |
| ATOM | 4588 | CD1 | ILE | C | 215 | 14.785 | 2.759 | 40.666 | 1.00 | 45.59 | C |
| ATOM | 4589 | CG2 | ILE | C | 215 | 11.559 | -1.834 | 48.419 | 1.00 | 38.65 | C |
| ATOM | 4590 | C | ILE | C | 215 | 10.289 | -1.985 | 51.002 | 1.00 | 38.57 | C |
| ATOM | 4591 | O | ILE | C | 215 | 9.951 | -3.098 | 51.396 | 1.00 | 36.54 | O |
| ATOM | 4592 | N | VAL | C | 216 | 9.418 | -1.048 | 50.683 | 1.00 | 38.30 | N |
| ATOM | 4593 | CA | VAL | C | 216 | 7.994 | -1.299 | 50.757 | 1.00 | 36.91 | C |
| ATOM | 4594 | CB | VAL | C | 216 | 7.383 | -0.447 | 51.854 | 1.00 | 37.62 | C |
| ATOM | 4595 | CG1 | VAL | C | 216 | 5.892 | -0.712 | 51.968 | 1.00 | 44.94 | C |
| ATOM | 4596 | CG2 | VAL | C | 216 | 8.121 | -0.803 | 53.250 | 1.00 | 33.61 | C |
| ATOM | 4597 | C | VAL | C | 216 | 7.353 | -1.097 | 49.361 | 1.00 | 37.22 | C |
| ATOM | 4598 | O | VAL | C | 216 | 7.651 | -0.135 | 48.693 | 1.00 | 39.21 | O |
| ATOM | 4599 | N | ALA | C | 217 | 6.564 | -2.090 | 48.927 | 1.00 | 39.41 | N |
| ATOM | 4600 | CA | ALA | C | 217 | 5.910 | -2.134 | 47.596 | 1.00 | 36.58 | C |
| ATOM | 4601 | CB | ALA | C | 217 | 6.141 | -3.488 | 46.968 | 1.00 | 31.33 | C |
| ATOM | 4602 | C | ALA | C | 217 | 4.442 | -1.945 | 47.788 | 1.00 | 35.05 | C |
| ATOM | 4603 | O | ALA | C | 217 | 3.850 | -2.596 | 48.659 | 1.00 | 33.58 | O |
| ATOM | 4604 | N | ARG | C | 218 | 3.848 | -1.056 | 47.003 | 1.00 | 32.43 | N |
| ATOM | 4605 | CA | ARG | C | 218 | 2.406 | -0.878 | 46.990 | 1.00 | 35.05 | C |

TABLE 10-continued

Atomic coordinates for COM1 complex of the modified
TXNIP protein represented by SEQ ID NO: 6 and the modified protein represented by SEQ ID NO: 3

| | | | | | | | | | |
|---|---|---|---|---|---|---|---|---|---|
| ATOM | 4606 | CB  | ARG | C | 218 | 2.055   | 0.599   | 47.181 | 1.00 | 34.39 | C |
| ATOM | 4607 | CG  | ARG | C | 218 | 2.464   | 1.133   | 48.514 | 1.00 | 54.39 | C |
| ATOM | 4608 | CD  | ARG | C | 218 | 2.295   | 2.630   | 48.527 | 1.00 | 60.96 | C |
| ATOM | 4609 | NE  | ARG | C | 218 | 3.532   | 3.305   | 48.151 | 1.00 | 68.85 | N |
| ATOM | 4610 | CZ  | ARG | C | 218 | 4.572   | 3.421   | 48.971 | 1.00 | 64.90 | C |
| ATOM | 4611 | NH1 | ARG | C | 218 | 4.534   | 2.910   | 50.202 | 1.00 | 61.40 | N |
| ATOM | 4612 | NH2 | ARG | C | 218 | 5.637   | 4.057   | 48.556 | 1.00 | 55.42 | N |
| ATOM | 4613 | C   | ARG | C | 218 | 2.001   | -1.283  | 45.617 | 1.00 | 33.67 | C |
| ATOM | 4614 | O   | ARG | C | 218 | 2.313   | -0.573  | 44.661 | 1.00 | 33.47 | O |
| ATOM | 4615 | N   | HIS | C | 219 | 1.353   | -2.437  | 45.510 | 1.00 | 32.42 | N |
| ATOM | 4616 | CA  | HIS | C | 219 | 0.897   | -2.940  | 44.228 | 1.00 | 31.89 | C |
| ATOM | 4617 | CB  | HIS | C | 219 | 0.849   | -4.492  | 44.289 | 1.00 | 28.88 | C |
| ATOM | 4618 | CG  | HIS | C | 219 | 2.096   | -5.089  | 44.859 | 1.00 | 33.23 | C |
| ATOM | 4619 | ND1 | HIS | C | 219 | 3.145   | -5.50   | 44.065 | 1.00 | 39.87 | N |
| ATOM | 4620 | CE1 | HIS | C | 219 | 4.128   | -5.949  | 44.838 | 1.00 | 42.99 | C |
| ATOM | 4621 | NE2 | HIS | C | 219 | 3.751   | -5.838  | 46.102 | 1.00 | 41.38 | N |
| ATOM | 4622 | CD2 | HIS | C | 219 | 2.489   | -5.291  | 46.143 | 1.00 | 26.43 | C |
| ATOM | 4623 | C   | HIS | C | 219 | -0.493  | -2.455  | 43.983 | 1.00 | 32.97 | C |
| ATOM | 4624 | O   | HIS | C | 219 | -1.378  | -2.775  | 44.784 | 1.00 | 32.79 | O |
| ATOM | 4625 | N   | THR | C | 220 | -0.722  | -1.749  | 42.864 | 1.00 | 35.88 | N |
| ATOM | 4626 | CA  | THR | C | 220 | -2.101  | -1.314  | 42.497 | 1.00 | 36.79 | C |
| ATOM | 4627 | CB  | THR | C | 220 | -2.133  | 0.051   | 41.865 | 1.00 | 36.68 | C |
| ATOM | 4628 | OG1 | THR | C | 220 | -1.641  | 1.006   | 42.805 | 1.00 | 39.72 | O |
| ATOM | 4629 | CG2 | THR | C | 220 | -3.503  | 0.435   | 41.44  | 1.00 | 47.52 | C |
| ATOM | 4630 | C   | THR | C | 220 | -2.652  | -2.355  | 41.576 | 1.00 | 38.36 | C |
| ATOM | 4631 | O   | THR | C | 220 | -1.987  | -2.782  | 40.608 | 1.00 | 35.05 | O |
| ATOM | 4632 | N   | TYR | C | 221 | -3.847  | -2.834  | 41.935 | 1.00 | 37.95 | N |
| ATOM | 4633 | CA  | TYR | C | 221 | -4.491  | -3.870  | 41.170 | 1.00 | 41.27 | C |
| ATOM | 4634 | CB  | TYR | C | 221 | -4.143  | -5.221  | 41.760 | 1.00 | 43.64 | C |
| ATOM | 4635 | CG  | TYR | C | 221 | -4.792  | -5.499  | 43.097 | 1.00 | 47.78 | C |
| ATOM | 4636 | CD1 | TYR | C | 221 | -4.331  | -4.892  | 44.271 | 1.00 | 48.68 | C |
| ATOM | 4637 | CE1 | TYR | C | 221 | -4.929  | -5.168  | 45.503 | 1.00 | 46.09 | C |
| ATOM | 4638 | CZ  | TYR | C | 221 | -6.000  | -6.061  | 45.546 | 1.00 | 52.54 | C |
| ATOM | 4639 | OH  | TYR | C | 221 | -6.612  | 6.345   | 46.742 | 1.00 | 49.42 | O |
| ATOM | 4640 | CE2 | TYR | C | 221 | -6.468  | -6.680  | 44.386 | 1.00 | 44.26 | C |
| ATOM | 4641 | CD2 | TYR | C | 221 | -5.854  | -6.403  | 43.184 | 1.00 | 54.30 | C |
| ATOM | 4642 | C   | TYR | C | 221 | -5.986  | -3.580  | 41.118 | 1.00 | 42.79 | C |
| ATOM | 4643 | O   | TYR | C | 221 | -6.485  | -2.730  | 41.874 | 1.00 | 43.59 | O |
| ATOM | 4644 | N   | LEU | C | 222 | -6.674  | -4.220  | 40.169 | 1.00 | 44.82 | N |
| ATOM | 4645 | CA  | LEU | C | 222 | -8.122  | -4.018  | 39.911 | 1.00 | 43.26 | C |
| ATOM | 4646 | CB  | LEU | C | 222 | -8.408  | -3.956  | 38.393 | 1.00 | 43.03 | C |
| ATOM | 4647 | CG  | LEU | C | 222 | -7.843  | -2.775  | 37.575 | 1.00 | 49.28 | C |
| ATOM | 4648 | CD1 | LEU | C | 222 | -8.137  | -2.836  | 36.052 | 1.00 | 48.56 | C |
| ATOM | 4649 | CD2 | LEU | C | 222 | -8.197  | -1.354  | 38.125 | 1.00 | 47.51 | C |
| ATOM | 4650 | C   | LEU | C | 222 | -8.829  | -5.199  | 40.519 | 1.00 | 45.31 | C |
| ATOM | 4651 | O   | LEU | C | 222 | -8.446  | -8.338  | 40.261 | 1.00 | 45.76 | O |
| ATOM | 4652 | N   | ALA | C | 223 | -9.833  | -4.976  | 41.365 | 1.00 | 49.63 | N |
| ATOM | 4653 | CA  | ALA | C | 223 | -10.408 | -6.158  | 42.054 | 1.00 | 57.50 | C |
| ATOM | 4654 | CB  | ALA | C | 223 | -9.790  | -6.353  | 43.440 | 1.00 | 57.79 | C |
| ATOM | 4655 | C   | ALA | C | 223 | -11.934 | -6.230  | 42.120 | 1.00 | 61.34 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 4656 | O | ALA | C | 223 | −12.500 | −7.173 | 42.672 | 1.00 | 64.73 | O |
| ATOM | 4657 | N | ASN | C | 224 | −12.590 | −5.237 | 41.537 | 1.00 | 67.84 | N |
| ATOM | 4658 | CA | ASN | C | 224 | −14.040 | −5.301 | 41.273 | 1.00 | 68.65 | C |
| ATOM | 4659 | CB | ASN | C | 224 | −14.494 | −6.702 | 40.825 | 1.00 | 70.16 | C |
| ATOM | 4660 | CG | ASN | C | 224 | −13.648 | −7.264 | 39.677 | 1.00 | 76.47 | C |
| ATOM | 4661 | OD1 | ASN | C | 224 | −12.704 | −6.621 | 39.195 | 1.00 | 79.81 | O |
| ATOM | 4662 | ND2 | ASN | C | 224 | −13.981 | −8.480 | 39.244 | 1.00 | 80.93 | N |
| ATOM | 4663 | C | ASN | C | 224 | −14.873 | −4.786 | 42.442 | 1.00 | 68.64 | C |
| ATOM | 4664 | O | ASN | C | 224 | −15.000 | −5.432 | 43.498 | 1.00 | 70.17 | O |
| ATOM | 4665 | N | GLY | C | 225 | −15.416 | −3.594 | 42.238 | 1.00 | 65.8 | N |
| ATOM | 4666 | CA | GLY | C | 225 | −15.160 | −2.858 | 40.997 | 1.00 | 59.93 | C |
| ATOM | 4667 | C | GLY | C | 225 | −14.311 | −1.671 | 41.368 | 1.00 | 57.94 | C |
| ATOM | 4668 | O | GLY | C | 225 | −14.696 | −0.500 | 41.157 | 1.00 | 56.59 | O |
| ATOM | 4669 | N | GLN | C | 226 | −13.151 | −1.975 | 41.948 | 1.00 | 52.85 | N |
| ATOM | 4670 | CA | GLN | C | 226 | −12.268 | −0.940 | 42.427 | 1.00 | 51.26 | C |
| ATOM | 4671 | CB | GLN | C | 226 | −12.269 | −0.889 | 43.967 | 1.00 | 50.42 | C |
| ATOM | 4672 | CG | GLN | C | 226 | −13.643 | −0.826 | 44.706 | 1.00 | 49.93 | C |
| ATOM | 4673 | CD | GLN | C | 226 | −13.496 | −1.231 | 45.184 | 1.00 | 50.98 | C |
| ATOM | 4674 | OE1 | GLN | C | 226 | −14.148 | −2.176 | 46.651 | 1.00 | 40.66 | O |
| ATOM | 4675 | NE2 | GLN | C | 226 | −12.583 | −0.560 | 46.902 | 1.00 | 42.90 | N |
| ATOM | 4676 | C | GLN | C | 226 | −10.825 | −1.141 | 41.970 | 1.00 | 48.37 | C |
| ATOM | 4677 | O | GLN | C | 226 | −10.370 | −2.251 | 41.632 | 1.00 | 42.38 | O |
| ATOM | 4678 | N | THR | C | 227 | −10.113 | −0.022 | 41.992 | 1.00 | 49.57 | N |
| ATOM | 4679 | CA | THR | C | 227 | −8.686 | −0.022 | 42.095 | 1.00 | 49.74 | C |
| ATOM | 4680 | CB | THR | C | 227 | −8.136 | 1.289 | 41.532 | 1.00 | 52.39 | C |
| ATOM | 4681 | OG1 | THR | C | 227 | −8.584 | 1.430 | 40.168 | 1.00 | 51.22 | O |
| ATOM | 4682 | CG2 | THR | C | 227 | −6.620 | 1.277 | 41.546 | 1.00 | 48.72 | C |
| ATOM | 4683 | C | THR | C | 227 | −8.359 | −0.139 | 43.601 | 1.00 | 49.81 | C |
| ATOM | 4684 | O | THR | C | 227 | −8.858 | 0.662 | 44.425 | 1.00 | 47.56 | O |
| ATOM | 4685 | N | LYS | C | 228 | −7.563 | −1.150 | 43.953 | 1.00 | 47.41 | N |
| ATOM | 4686 | CA | LYS | C | 228 | −7.057 | −1.329 | 45.333 | 1.00 | 44.57 | C |
| ATOM | 4687 | CB | LYS | C | 228 | −7.601 | −2.633 | 45.931 | 1.00 | 46.20 | C |
| ATOM | 4688 | CG | LYS | C | 228 | −9.127 | −2.778 | 45.856 | 1.00 | 48.24 | C |
| ATOM | 4689 | CD | LYS | C | 228 | −9.524 | −4.187 | 46.230 | 1.00 | 50.79 | C |
| ATOM | 4690 | CE | LYS | C | 228 | −10.997 | −4.293 | 46.587 | 1.00 | 58.30 | C |
| ATOM | 4691 | NZ | LYS | C | 228 | −11.171 | −5.443 | 47.540 | 1.00 | 49.57 | N |
| ATOM | 4692 | C | LYS | C | 228 | −5.518 | −1.327 | 45.385 | 1.00 | 46.92 | C |
| ATOM | 4693 | O | LYS | C | 228 | −4.860 | −1.422 | 44.345 | 1.00 | 43.91 | O |
| ATOM | 4694 | N | VAL | C | 229 | −4.959 | −1.233 | 46.594 | 1.00 | 42.56 | N |
| ATOM | 4695 | CA | VAL | C | 229 | −3.512 | −1.184 | 46.788 | 1.00 | 42.54 | C |
| ATOM | 4696 | CB | VAL | C | 229 | −3.048 | 0.188 | 47.322 | 1.00 | 44.84 | C |
| ATOM | 4697 | CG1 | VAL | C | 229 | −1.523 | 0.212 | 47.559 | 1.00 | 42.80 | C |
| ATOM | 4698 | CG2 | VAL | C | 229 | −3.456 | 1.344 | 46.380 | 1.00 | 42.73 | C |
| ATOM | 4699 | C | VAL | C | 229 | −3.169 | −2.251 | 47.823 | 1.00 | 44.28 | C |
| ATOM | 4700 | O | VAL | C | 229 | −3.783 | −1.327 | 48.899 | 1.00 | 42.01 | O |
| ATOM | 4701 | N | LEU | C | 230 | −2.265 | −3.104 | 47.472 | 1.00 | 43.72 | N |
| ATOM | 4702 | CA | LEU | C | 230 | −1.707 | −4.135 | 48.442 | 1.00 | 38.55 | C |
| ATOM | 4703 | CB | LEU | C | 230 | −1.667 | −5.577 | 47.904 | 1.00 | 39.26 | C |
| ATOM | 4704 | CG | LEU | C | 230 | −0.734 | −6.441 | 48.765 | 1.00 | 37.31 | C |
| ATOM | 4705 | CD1 | LEU | C | 230 | −1.511 | −7.056 | 49.902 | 1.00 | 47.09 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 4706 | CD2 | LEU | 230 | 0.015 | 48.014 | 45.45 | 1.00 | | C |
| ATOM | 4707 | C | LEU | 230 | -0.318 | 48.775 | 35.18 | 1.00 | | C |
| ATOM | 4708 | O | LEU | 230 | 0.505 | 47.872 | 36.27 | 1.00 | | O |
| ATOM | 4709 | N | THR | 230 | -3.534 | 50.060 | 30.95 | 1.00 | | N |
| ATOM | 4710 | CA | THR | 231 | -3.404 | 50.543 | 35.53 | 1.00 | | C |
| ATOM | 4711 | CB | THR | 231 | -0.066 | 51.543 | 37.99 | 1.00 | | C |
| ATOM | 4712 | OG1 | THR | 231 | 1.214 | 50.933 | 43.83 | 1.00 | | O |
| ATOM | 4713 | CG2 | THR | 231 | 1.028 | 81.104 | 43.50 | 1.00 | | C |
| ATOM | 4714 | C | THR | 231 | 0.199 | 81.844 | 33.53 | 1.00 | | C |
| ATOM | 4715 | O | THR | 231 | 2.339 | 51.838 | 33.56 | 1.00 | | O |
| ATOM | 4716 | N | GLN | 231 | 1.988 | 50.721 | 34.20 | 1.00 | | N |
| ATOM | 4717 | CA | GLN | 232 | -4.991 | 51.040 | 34.20 | 1.00 | | C |
| ATOM | 4718 | CB | GLN | 232 | -4.244 | 49.821 | 39.01 | 1.00 | | C |
| ATOM | 4719 | CG | GLN | 232 | 4.046 | 49.875 | 39.07 | 1.00 | | C |
| ATOM | 4720 | CD | GLN | 232 | 5.038 | 48.616 | 48.70 | 1.00 | | C |
| ATOM | 4721 | OE1 | GLN | 232 | 5.045 | 47.484 | 45.93 | 1.00 | | O |
| ATOM | 4722 | NE2 | GLN | 232 | 4.936 | 48.815 | 50.92 | 1.00 | | N |
| ATOM | 4723 | C | GLN | 232 | 5.229 | 51.442 | 35.83 | 1.00 | | C |
| ATOM | 4724 | O | GLN | 232 | 5.453 | 50.678 | 35.88 | 1.00 | | O |
| ATOM | 4725 | N | LYS | 232 | 6.137 | 52.639 | 36.14 | 1.00 | | N |
| ATOM | 4726 | CA | LYS | 233 | 5.904 | 51.495 | 35.84 | 1.00 | | C |
| ATOM | 4727 | CB | LYS | 233 | 7.315 | 53.046 | 38.79 | 1.00 | | C |
| ATOM | 4728 | CG | LYS | 233 | 7.454 | 54.531 | 45.70 | 1.00 | | C |
| ATOM | 4729 | CD | LYS | 233 | 8.838 | 55.131 | 46.86 | 1.00 | | C |
| ATOM | 4730 | CE | LYS | 233 | 8.585 | 56.558 | 46.33 | 1.00 | | C |
| ATOM | 4731 | NZ | LYS | 233 | 9.914 | 57.376 | 55.45 | 1.00 | | N |
| ATOM | 4732 | C | LYS | 233 | 9.677 | 58.864 | 39.85 | 1.00 | | C |
| ATOM | 4733 | O | LYS | 233 | 8.197 | 52.588 | 33.24 | 1.00 | | O |
| ATOM | 4734 | N | LEU | 233 | 7.997 | 52.396 | 36.44 | 1.00 | | N |
| ATOM | 4735 | CA | LEU | 234 | 9.144 | 50.853 | 41.99 | 1.00 | | C |
| ATOM | 4736 | CB | LEU | 234 | 10.108 | 49.485 | 36.98 | 1.00 | | C |
| ATOM | 4737 | CG | LEU | 234 | 10.498 | 48.588 | 44.00 | 1.00 | | C |
| ATOM | 4738 | CD1 | LEU | 234 | 9.266 | 47.233 | 36.36 | 1.00 | | C |
| ATOM | 4739 | CD2 | LEU | 234 | 9.627 | 48.416 | 39.03 | 1.00 | | C |
| ATOM | 4740 | C | LEU | 234 | 8.487 | 51.804 | 45.54 | 1.00 | | C |
| ATOM | 4741 | O | LEU | 234 | 11.329 | 52.975 | 47.52 | 1.00 | | O |
| ATOM | 4742 | N | LEU | 234 | 11.203 | 51.324 | 44.33 | 1.00 | | N |
| ATOM | 4743 | CA | SER | 235 | 12.506 | 52.131 | 43.72 | 1.00 | | C |
| ATOM | 4744 | CB | SER | 235 | 13.685 | 51.254 | 46.14 | 1.00 | | C |
| ATOM | 4745 | OG | SER | 235 | 14.917 | 50.205 | 53.56 | 1.00 | | O |
| ATOM | 4746 | C | SER | 235 | 14.656 | 48.588 | 43.84 | 1.00 | | C |
| ATOM | 4747 | O | SER | 235 | 13.732 | 53.232 | 43.50 | 1.00 | | O |
| ATOM | 4748 | N | SER | 235 | 13.234 | 53.050 | 43.56 | 1.00 | | N |
| ATOM | 4749 | CA | SER | 236 | 14.313 | 54.367 | 40.15 | 1.00 | | C |
| ATOM | 4750 | CB | SER | 236 | 14.580 | 55.444 | 41.23 | 1.00 | | C |
| ATOM | 4751 | OG | SER | 236 | 13.457 | 56.480 | 44.66 | 1.00 | | O |
| ATOM | 4752 | C | SER | 236 | 13.258 | 57.004 | 44.83 | 1.00 | | C |
| ATOM | 4753 | O | SER | 236 | 15.927 | 56.106 | 38.46 | 1.00 | | O |
| ATOM | 4754 | N | VAL | 237 | 16.465 | 55.946 | 42.09 | 1.00 | | N |
| ATOM | 4755 | CA | VAL | 237 | 17.617 | 57.898 | 44.19 | 1.00 | | C |

TABLE 10-continued

Atomic coordinates for COM1 complex of the modified
TXNIP protein represented by SEQ ID NO: 6 and the modified protein represented by SEQ ID NO: 3

| | | | | | | | | | | | |
|---|---|---|---|---|---|---|---|---|---|---|---|
| ATOM | 4756 | CB | VAL | C | 237 | 18.933 | -3.914 | 57.099 | 1.00 | 42.81 | C |
| ATOM | 4757 | CG1 | VAL | C | 237 | 19.467 | -4.809 | 55.954 | 1.00 | 52.21 | C |
| ATOM | 4758 | CG2 | VAL | C | 237 | 18.750 | -2.496 | 56.647 | 1.00 | 43.52 | C |
| ATOM | 4759 | C | VAL | C | 237 | 17.364 | -3.819 | 59.052 | 1.00 | 44.04 | C |
| ATOM | 4760 | O | VAL | C | 237 | 16.510 | -2.943 | 59.179 | 1.00 | 39.24 | O |
| ATOM | 4761 | N | ARG | C | 238 | 18.156 | -4.231 | 60.036 | 1.00 | 45.59 | N |
| ATOM | 4762 | CA | ARG | C | 238 | 18.136 | -3.718 | 61.400 | 1.00 | 49.43 | C |
| ATOM | 4763 | CB | ARG | C | 238 | 17.725 | -4.862 | 62.305 | 1.00 | 49.57 | C |
| ATOM | 4764 | CG | ARG | C | 238 | 17.236 | -4.481 | 63.666 | 1.00 | 59.15 | C |
| ATOM | 4765 | CD | ARG | C | 238 | 17.023 | -5.742 | 64.484 | 1.00 | 62.64 | C |
| ATOM | 4766 | NE | ARG | C | 238 | 16.059 | -5.531 | 65.558 | 1.00 | 72.25 | N |
| ATOM | 4767 | CZ | ARG | C | 238 | 16.387 | -5.206 | 66.806 | 1.00 | 79.94 | C |
| ATOM | 4768 | NH1 | ARG | C | 238 | 17.667 | 5.055 | 67.153 | 1.00 | 80.50 | N |
| ATOM | 4769 | NH2 | ARG | C | 238 | 15.431 | -5.027 | 67.713 | 1.00 | 83.68 | N |
| ATOM | 4770 | C | ARG | C | 238 | 19.565 | -3.281 | 61.775 | 1.00 | 49.72 | C |
| ATOM | 4771 | O | ARG | C | 238 | 20.512 | -4.007 | 61.510 | 1.00 | 47.62 | O |
| ATOM | 4772 | N | GLY | C | 239 | 19.731 | -2.112 | 62.385 | 1.00 | 47.12 | N |
| ATOM | 4773 | CA | GLY | C | 239 | 21.046 | -1.724 | 62.906 | 1.00 | 42.75 | C |
| ATOM | 4774 | C | GLY | C | 239 | 21.167 | -2.038 | 64.394 | 1.00 | 42.67 | C |
| ATOM | 4775 | O | GLY | C | 239 | 20.216 | -2.503 | 65.012 | 1.00 | 41.52 | O |
| ATOM | 4776 | N | ASN | C | 240 | 22.322 | -1.765 | 64.991 | 1.00 | 42.07 | N |
| ATOM | 4777 | CA | ASN | C | 240 | 22.484 | -1.942 | 66.440 | 1.00 | 42.50 | C |
| ATOM | 4778 | CB | ASN | C | 240 | 23.931 | -1.656 | 66.844 | 1.00 | 42.48 | C |
| ATOM | 4779 | CG | ASN | C | 240 | 24.929 | -2.432 | 66.032 | 1.00 | 54.77 | C |
| ATOM | 4780 | OD1 | ASN | C | 240 | 25.860 | -1.847 | 65.459 | 1.00 | 51.83 | O |
| ATOM | 4781 | ND2 | ASN | C | 240 | 24.772 | -3.764 | 65.999 | 1.00 | 49.18 | N |
| ATOM | 4782 | C | ASN | C | 240 | 21.570 | -0.963 | 67.171 | 1.00 | 39.38 | C |
| ATOM | 4783 | O | ASN | C | 240 | 21.226 | 0.091 | 66.612 | 1.00 | 39.76 | O |
| ATOM | 4784 | N | HIS | C | 241 | 21.141 | -1.324 | 68.369 | 1.00 | 41.52 | N |
| ATOM | 4785 | CA | HIS | C | 241 | 20.437 | -0.398 | 69.277 | 1.00 | 44.87 | C |
| ATOM | 4786 | CB | HIS | C | 241 | 20.811 | -1.065 | 70.633 | 1.00 | 48.81 | C |
| ATOM | 4787 | CG | HIS | C | 241 | 19.087 | -2.095 | 70.629 | 1.00 | 65.93 | C |
| ATOM | 4788 | ND1 | HIS | C | 241 | 19.172 | -3.278 | 69.924 | 1.00 | 80.90 | N |
| ATOM | 4789 | CE1 | HIS | C | 241 | 18.077 | -3.993 | 70.127 | 1.00 | 76.16 | C |
| ATOM | 4790 | NE2 | HIS | C | 241 | 17.295 | -3.329 | 70.959 | 1.00 | 73.70 | N |
| ATOM | 4791 | CD2 | HIS | C | 241 | 17.905 | -2.142 | 71.294 | 1.00 | 74.91 | C |
| ATOM | 4792 | C | HIS | C | 241 | 21.305 | 0.864 | 69.526 | 1.00 | 44.06 | C |
| ATOM | 4793 | O | HIS | C | 241 | 22.541 | 0.800 | 69.530 | 1.00 | 42.54 | O |
| ATOM | 4794 | N | ILE | C | 242 | 20.654 | 1.998 | 69.755 | 1.00 | 41.47 | N |
| ATOM | 4795 | CA | ILE | C | 242 | 21.354 | 3.251 | 69.981 | 1.00 | 35.75 | C |
| ATOM | 4796 | CB | ILE | C | 242 | 21.001 | 4.263 | 68.880 | 1.00 | 35.25 | C |
| ATOM | 4797 | CG1 | ILE | C | 242 | 21.468 | 3.738 | 67.517 | 1.00 | 38.48 | C |
| ATOM | 4798 | CD1 | ILE | C | 242 | 21.182 | 4.714 | 66.298 | 1.00 | 36.60 | C |
| ATOM | 4799 | CG2 | ILE | C | 242 | 21.693 | 5.665 | 69.186 | 1.00 | 32.94 | C |
| ATOM | 4800 | C | ILE | C | 242 | 20.937 | 3.775 | 71.348 | 1.00 | 37.25 | C |
| ATOM | 4801 | O | ILE | C | 242 | 19.782 | 4.167 | 71.549 | 1.00 | 36.32 | O |
| ATOM | 4802 | N | ILE | C | 243 | 21.870 | 3.774 | 72.304 | 1.00 | 37.37 | N |
| ATOM | 4803 | CA | ILE | C | 243 | 21.525 | 4.041 | 73.680 | 1.00 | 33.86 | C |
| ATOM | 4804 | CB | ILE | C | 243 | 22.549 | 3.445 | 74.653 | 1.00 | 38.64 | C |
| ATOM | 4805 | CG1 | ILE | C | 243 | 23.923 | 4.170 | 74.567 | 1.00 | 30.38 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 4806 | CD1 | ILE | C | 243 | 24.947 | 3.786 | 75.781 | 1.00 | 30.14 | C |
| ATOM | 4807 | CG2 | ILE | C | 243 | 22.662 | 1.926 | 74.437 | 1.00 | 35.90 | C |
| ATOM | 4808 | C | ILE | C | 243 | 21.404 | 5.550 | 73.865 | 1.00 | 34.76 | C |
| ATOM | 4809 | O | ILE | C | 243 | 21.877 | 5.311 | 73.030 | 1.00 | 32.83 | O |
| ATOM | 4810 | N | SER | C | 244 | 20.753 | 5.965 | 74.942 | 1.00 | 30.46 | N |
| ATOM | 4811 | CA | SER | C | 244 | 20.592 | 7.373 | 75.265 | 1.00 | 34.12 | C |
| ATOM | 4812 | CB | SER | C | 244 | 19.947 | 7.491 | 76.633 | 1.00 | 35.34 | C |
| ATOM | 4813 | CG | SER | C | 244 | 19.771 | 8.846 | 76.994 | 1.00 | 35.67 | C |
| ATOM | 4814 | C | SER | C | 244 | 21.940 | 8.075 | 75.274 | 1.00 | 35.39 | C |
| ATOM | 4815 | O | SER | C | 244 | 22.894 | 7.583 | 75.895 | 1.00 | 36.41 | O |
| ATOM | 4816 | N | GLY | C | 245 | 22.038 | 9.197 | 74.565 | 1.00 | 33.64 | N |
| ATOM | 4817 | CA | GLY | C | 245 | 23.250 | 10.021 | 74.597 | 1.00 | 37.32 | C |
| ATOM | 4818 | C | GLY | C | 245 | 24.354 | 9.572 | 73.649 | 1.00 | 37.52 | C |
| ATOM | 4819 | O | GLY | C | 245 | 25.542 | 9.765 | 73.940 | 1.00 | 38.32 | O |
| ATOM | 4820 | N | THR | C | 246 | 23.983 | 8.955 | 72.527 | 1.00 | 36.46 | N |
| ATOM | 4821 | CA | THR | C | 246 | 24.959 | 8.596 | 71.494 | 1.00 | 32.98 | C |
| ATOM | 4822 | CB | THR | C | 246 | 25.387 | 7.139 | 71.583 | 1.00 | 32.24 | C |
| ATOM | 4823 | OG1 | THR | C | 246 | 24.257 | 6.287 | 71.318 | 1.00 | 33.41 | O |
| ATOM | 4824 | CG2 | THR | C | 246 | 26.045 | 6.788 | 72.981 | 1.00 | 31.32 | C |
| ATOM | 4825 | C | THR | C | 246 | 24.373 | 8.787 | 70.113 | 1.00 | 36.77 | C |
| ATOM | 4826 | O | THR | C | 246 | 23.164 | 8.944 | 69.969 | 1.00 | 40.15 | O |
| ATOM | 4827 | N | CYS | C | 247 | 25.254 | 8.762 | 69.106 | 1.00 | 37.47 | N |
| ATOM | 4828 | CA | CYS | C | 247 | 24.929 | 8.803 | 67.705 | 1.00 | 36.65 | C |
| ATOM | 4829 | CB | CYS | C | 247 | 25.584 | 10.001 | 67.041 | 1.00 | 39.82 | C |
| ATOM | 4830 | SG | CYS | C | 247 | 25.143 | 11.616 | 67.656 | 1.00 | 44.36 | S |
| ATOM | 4831 | C | CYS | C | 247 | 25.509 | 7.574 | 67.044 | 1.00 | 36.26 | C |
| ATOM | 4832 | O | CYS | C | 247 | 26.406 | 6.948 | 67.588 | 1.00 | 37.29 | O |
| ATOM | 4833 | N | ALA | C | 248 | 24.985 | 7.204 | 65.881 | 1.00 | 36.31 | N |
| ATOM | 4834 | CA | ALA | C | 248 | 25.587 | 6.137 | 65.091 | 1.00 | 37.10 | C |
| ATOM | 4835 | CB | ALA | C | 248 | 24.973 | 4.797 | 65.401 | 1.00 | 37.38 | C |
| ATOM | 4836 | C | ALA | C | 248 | 25.350 | 6.457 | 63.673 | 1.00 | 36.33 | C |
| ATOM | 4837 | O | ALA | C | 248 | 24.537 | 7.315 | 63.370 | 1.00 | 38.78 | O |
| ATOM | 4838 | N | SER | C | 249 | 26.056 | 5.758 | 62.805 | 1.00 | 35.49 | N |
| ATOM | 4839 | CA | SER | C | 249 | 26.097 | 6.089 | 61.398 | 1.00 | 36.24 | C |
| ATOM | 4840 | CB | SER | C | 249 | 27.441 | 6.711 | 61.083 | 1.00 | 37.76 | C |
| ATOM | 4841 | CG | SER | C | 249 | 27.461 | 8.082 | 61.363 | 1.00 | 47.04 | C |
| ATOM | 4842 | C | SER | C | 249 | 26.043 | 4.788 | 60.641 | 1.00 | 38.10 | C |
| ATOM | 4843 | O | SER | C | 249 | 26.660 | 3.807 | 61.043 | 1.00 | 36.50 | O |
| ATOM | 4844 | N | TRP | C | 250 | 25.350 | 4.769 | 59.517 | 1.00 | 37.60 | N |
| ATOM | 4845 | CA | TRP | C | 250 | 25.553 | 3.629 | 58.601 | 1.00 | 38.70 | C |
| ATOM | 4846 | CB | TRP | C | 250 | 24.217 | 3.093 | 58.070 | 1.00 | 41.73 | C |
| ATOM | 4847 | CG | TRP | C | 250 | 23.269 | 2.417 | 59.077 | 1.00 | 30.20 | C |
| ATOM | 4848 | CD1 | TRP | C | 250 | 23.550 | 1.933 | 60.330 | 1.00 | 37.79 | C |
| ATOM | 4849 | NE1 | TRP | C | 250 | 22.399 | 1.365 | 60.892 | 1.00 | 32.46 | N |
| ATOM | 4850 | CE2 | TRP | C | 250 | 21.390 | 1.499 | 59.958 | 1.00 | 32.27 | C |
| ATOM | 4851 | CD2 | TRP | C | 250 | 21.903 | 2.103 | 58.826 | 1.00 | 36.81 | C |
| ATOM | 4852 | CE3 | TRP | C | 250 | 21.042 | 2.351 | 57.743 | 1.00 | 40.13 | C |
| ATOM | 4853 | CZ3 | TRP | C | 250 | 19.738 | 1.940 | 57.827 | 1.00 | 32.23 | C |
| ATOM | 4854 | CH2 | TRP | C | 250 | 19.250 | 1.296 | 59.970 | 1.00 | 32.10 | C |
| ATOM | 4855 | CZ2 | TRP | C | 250 | 20.065 | 1.044 | 60.055 | 1.00 | 39.52 | C |

TABLE 10-continued

Atomic coordinates for COM1 complex of the modified
TXNIP protein represented by SEQ ID NO: 6 and the modified protein represented by SEQ ID NO: 3

| | | | | | | | | | |
|---|---|---|---|---|---|---|---|---|---|
| ATOM | 4856 | C | TRP | C | 250 | 26.388 | 4.172 | 57.445 | 1.00 | 37.50 | C |
| ATOM | 4857 | O | TRP | C | 250 | 26.138 | 5.257 | 56.947 | 1.00 | 37.67 | O |
| ATOM | 4858 | N | ARG | C | 251 | 27.382 | 3.419 | 57.012 | 1.00 | 40.41 | N |
| ATOM | 4859 | CA | ARG | C | 251 | 28.263 | 3.892 | 55.949 | 1.00 | 46.77 | C |
| ATOM | 4860 | CB | ARG | C | 251 | 29.706 | 3.960 | 56.434 | 1.00 | 46.07 | C |
| ATOM | 4861 | CG | ARG | C | 251 | 29.905 | 4.894 | 57.598 | 1.00 | 51.69 | C |
| ATOM | 4862 | CD | ARG | C | 251 | 31.324 | 4.759 | 58.185 | 1.00 | 70.97 | C |
| ATOM | 4863 | NE | ARG | C | 251 | 31.394 | 5.446 | 59.473 | 1.00 | 68.51 | N |
| ATOM | 4864 | CZ | ARG | C | 251 | 31.588 | 6.734 | 59.614 | 1.00 | 73.16 | C |
| ATOM | 4865 | NH1 | ARG | C | 251 | 31.070 | 7.474 | 58.543 | 1.00 | 62.07 | N |
| ATOM | 4866 | NH2 | ARG | C | 251 | 31.697 | 7.279 | 60.829 | 1.00 | 71.70 | N |
| ATOM | 4867 | C | ARG | C | 251 | 28.158 | 2.957 | 54.756 | 1.00 | 48.34 | C |
| ATOM | 4868 | O | ARG | C | 251 | 29.077 | 2.168 | 54.468 | 1.00 | 50.92 | O |
| ATOM | 4869 | N | GLY | C | 252 | 27.051 | 3.050 | 54.066 | 1.00 | 48.56 | N |
| ATOM | 4870 | CA | GLY | C | 252 | 26.833 | 2.207 | 52.915 | 1.00 | 49.48 | C |
| ATOM | 4871 | C | GLY | C | 252 | 26.304 | 0.869 | 53.380 | 1.00 | 51.07 | C |
| ATOM | 4872 | O | GLY | C | 252 | 25.792 | -0.174 | 52.973 | 1.00 | 54.27 | O |
| ATOM | 4873 | N | LYS | C | 253 | 25.302 | 0.894 | 54.247 | 1.00 | 48.86 | N |
| ATOM | 4874 | CA | LYS | C | 253 | 24.676 | -0.348 | 54.549 | 1.00 | 47.18 | C |
| ATOM | 4875 | CB | LYS | C | 253 | 23.891 | -0.081 | 55.915 | 1.00 | 48.02 | C |
| ATOM | 4876 | CG | LYS | C | 253 | 22.638 | -0.841 | 58.045 | 1.00 | 53.90 | C |
| ATOM | 4877 | CD | LYS | C | 253 | 22.833 | -1.984 | 56.914 | 1.00 | 48.29 | C |
| ATOM | 4878 | CE | LYS | C | 253 | 22.391 | -1.636 | 58.284 | 1.00 | 35.72 | C |
| ATOM | 4879 | NZ | LYS | C | 253 | 23.497 | -2.141 | 59.156 | 1.00 | 47.37 | N |
| ATOM | 4880 | C | LYS | C | 253 | 23.779 | -0.765 | 53.478 | 1.00 | 47.57 | C |
| ATOM | 4881 | O | LYS | C | 253 | 23.084 | 0.088 | 52.940 | 1.00 | 46.14 | O |
| ATOM | 4882 | N | SER | C | 254 | 23.801 | -2.042 | 53.087 | 1.00 | 48.43 | N |
| ATOM | 4883 | CA | SER | C | 254 | 23.112 | -2.491 | 51.863 | 1.00 | 50.36 | C |
| ATOM | 4884 | CB | SER | C | 254 | 24.009 | -3.376 | 51.004 | 1.00 | 51.10 | C |
| ATOM | 4885 | OG | SER | C | 254 | 25.129 | -3.837 | 51.732 | 1.00 | 61.92 | O |
| ATOM | 4886 | C | SER | C | 254 | 21.783 | -3.187 | 52.067 | 1.00 | 50.94 | C |
| ATOM | 4887 | O | SER | C | 254 | 21.603 | -3.999 | 52.981 | 1.00 | 48.79 | O |
| ATOM | 4888 | N | LEU | C | 255 | 20.845 | -2.872 | 51.188 | 1.00 | 48.58 | N |
| ATOM | 4889 | CA | LEU | C | 255 | 19.589 | -3.572 | 51.161 | 1.00 | 48.25 | C |
| ATOM | 4890 | CB | LEU | C | 255 | 18.497 | -2.583 | 51.556 | 1.00 | 51.07 | C |
| ATOM | 4891 | CG | LEU | C | 255 | 17.135 | -3.032 | 52.079 | 1.00 | 45.94 | C |
| ATOM | 4892 | CD1 | LEU | C | 255 | 17.206 | -4.380 | 52.730 | 1.00 | 52.46 | C |
| ATOM | 4893 | CD2 | LEU | C | 255 | 16.719 | -2.032 | 53.074 | 1.00 | 47.65 | C |
| ATOM | 4894 | C | LEU | C | 255 | 19.378 | -4.152 | 49.743 | 1.00 | 49.28 | C |
| ATOM | 4895 | O | LEU | C | 255 | 19.602 | -3.461 | 48.758 | 1.00 | 44.11 | O |
| ATOM | 4896 | N | ARG | C | 256 | 18.939 | -5.404 | 49.639 | 1.00 | 52.39 | N |
| ATOM | 4897 | CA | ARG | C | 256 | 18.775 | -6.031 | 48.327 | 1.00 | 55.06 | C |
| ATOM | 4898 | CB | ARG | C | 256 | 19.119 | -7.523 | 48.351 | 1.00 | 58.10 | C |
| ATOM | 4899 | CG | ARG | C | 256 | 19.670 | -8.034 | 46.999 | 1.00 | 61.83 | C |
| ATOM | 4900 | CD | ARG | C | 256 | 20.936 | -8.877 | 47.158 | 1.00 | 75.52 | C |
| ATOM | 4901 | NE | ARG | C | 256 | 22.003 | -8.128 | 47.831 | 1.00 | 83.33 | N |
| ATOM | 4902 | CZ | ARG | C | 256 | 23.027 | -7.530 | 47.219 | 1.00 | 87.02 | C |
| ATOM | 4903 | NH1 | ARG | C | 256 | 23.933 | -6.868 | 47.936 | 1.00 | 85.75 | N |
| ATOM | 4904 | NH2 | ARG | C | 256 | 23.159 | -7.598 | 45.896 | 1.00 | 87.16 | N |
| ATOM | 4905 | C | ARG | C | 256 | 17.416 | -5.770 | 47.671 | 1.00 | 55.54 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 4906 | O | ARG | C | 256 | 16.341 | -5.951 | 48.283 | 1.00 | 54.28 | O |
| ATOM | 4907 | N | VAL | C | 257 | 17.471 | -5.356 | 46.416 | 1.00 | 55.93 | N |
| ATOM | 4908 | CA | VAL | C | 257 | 16.265 | -5.227 | 45.604 | 1.00 | 55.80 | C |
| ATOM | 4909 | CB | VAL | C | 257 | 16.469 | -4.227 | 44.453 | 1.00 | 55.58 | C |
| ATOM | 4910 | CG1 | VAL | C | 257 | 15.134 | -3.958 | 43.779 | 1.00 | 82.07 | C |
| ATOM | 4911 | CG2 | VAL | C | 257 | 17.083 | -2.922 | 44.930 | 1.00 | 48.30 | C |
| ATOM | 4912 | C | VAL | C | 257 | 16.014 | -6.595 | 44.998 | 1.00 | 59.25 | C |
| ATOM | 4913 | O | VAL | C | 257 | 16.752 | -7.000 | 44.115 | 1.00 | 58.87 | O |
| ATOM | 4914 | N | GLN | C | 258 | 15.014 | -7.344 | 45.457 | 1.00 | 64.55 | N |
| ATOM | 4915 | CA | GLN | C | 258 | 14.793 | -8.675 | 44.832 | 1.00 | 69.85 | C |
| ATOM | 4916 | CB | GLN | C | 258 | 14.621 | -9.798 | 45.873 | 1.00 | 69.71 | C |
| ATOM | 4917 | CG | GLN | C | 258 | 14.437 | -9.328 | 47.315 | 1.00 | 74.75 | C |
| ATOM | 4918 | CD | GLN | C | 258 | 12.982 | -9.127 | 47.696 | 1.00 | 82.97 | C |
| ATOM | 4919 | OE1 | GLN | C | 258 | 12.602 | -9.315 | 48.860 | 1.00 | 88.00 | O |
| ATOM | 4920 | NE2 | GLN | C | 258 | 12.153 | -8.756 | 46.722 | 1.00 | 82.24 | N |
| ATOM | 4921 | C | GLN | C | 258 | 13.716 | -8.699 | 43.717 | 1.00 | 72.73 | C |
| ATOM | 4922 | O | GLN | C | 258 | 12.980 | -7.724 | 43.542 | 1.00 | 74.44 | O |
| ATOM | 4923 | N | LYS | C | 259 | 13.661 | -9.804 | 42.965 | 1.00 | 75.60 | N |
| ATOM | 4924 | CA | LYS | C | 259 | 12.692 | -10.025 | 41.866 | 1.00 | 78.62 | C |
| ATOM | 4925 | CB | LYS | C | 259 | 11.982 | -11.372 | 42.040 | 1.00 | 79.25 | C |
| ATOM | 4926 | CG | LYS | C | 259 | 11.277 | -11.866 | 40.781 | 1.00 | 81.82 | C |
| ATOM | 4927 | CD | LYS | C | 259 | 12.116 | -12.885 | 40.022 | 1.00 | 82.89 | C |
| ATOM | 4928 | CE | LYS | C | 259 | 11.989 | -14.269 | 40.649 | 1.00 | 86.09 | C |
| ATOM | 4929 | NZ | LYS | C | 259 | 12.101 | -15.351 | 39.636 | 1.00 | 89.95 | N |
| ATOM | 4930 | C | LYS | C | 259 | 11.653 | -8.904 | 41.619 | 1.00 | 80.21 | C |
| ATOM | 4931 | O | LYS | C | 259 | 10.505 | -8.946 | 42.098 | 1.00 | 80.25 | O |
| ATOM | 4932 | N | GLY | C | 266 | -2.541 | -11.067 | 39.299 | 1.00 | 69.19 | N |
| ATOM | 4933 | CA | GLY | C | 266 | -1.591 | -11.066 | 38.180 | 1.00 | 68.54 | C |
| ATOM | 4934 | C | GLY | C | 266 | -1.968 | -10.071 | 37.090 | 1.00 | 67.69 | C |
| ATOM | 4935 | O | GLY | C | 266 | -1.510 | -8.923 | 37.104 | 1.00 | 67.88 | O |
| ATOM | 4936 | N | SER | C | 267 | -2.807 | -10.509 | 36.148 | 1.00 | 65.35 | N |
| ATOM | 4937 | CA | SER | C | 267 | -3.254 | -9.666 | 35.016 | 1.00 | 64.51 | C |
| ATOM | 4938 | CB | SER | C | 267 | -4.184 | -10.453 | 34.076 | 1.00 | 63.61 | C |
| ATOM | 4939 | OG | SER | C | 267 | -3.433 | -11.244 | 33.138 | 1.00 | 70.77 | O |
| ATOM | 4940 | C | SER | C | 267 | -3.946 | -8.359 | 35.433 | 1.00 | 61.17 | C |
| ATOM | 4941 | O | SER | C | 267 | -3.950 | -7.372 | 34.685 | 1.00 | 60.45 | O |
| ATOM | 4942 | N | ASN | C | 268 | -4.551 | -8.365 | 36.615 | 1.00 | 57.88 | N |
| ATOM | 4943 | CA | ASN | C | 268 | -5.171 | -7.169 | 37.125 | 1.00 | 55.97 | C |
| ATOM | 4944 | CB | ASN | C | 268 | -6.455 | -7.492 | 37.913 | 1.00 | 60.83 | C |
| ATOM | 4945 | CG | ASN | C | 268 | -6.228 | -8.524 | 39.021 | 1.00 | 67.37 | C |
| ATOM | 4946 | OD1 | ASN | C | 268 | -5.341 | -9.378 | 38.922 | 1.00 | 74.04 | O |
| ATOM | 4947 | ND2 | ASN | C | 268 | -7.044 | -8.453 | 40.080 | 1.00 | 73.89 | N |
| ATOM | 4948 | C | ASN | C | 268 | -4.205 | -6.291 | 37.920 | 1.00 | 54.59 | C |
| ATOM | 4949 | O | ASN | C | 268 | -4.627 | -5.255 | 38.407 | 1.00 | 53.91 | O |
| ATOM | 4950 | N | ILE | C | 269 | -2.922 | -6.689 | 38.020 | 1.00 | 49.11 | N |
| ATOM | 4951 | CA | ILE | C | 269 | 1.876 | 5.791 | 38.531 | 1.00 | 51.82 | C |
| ATOM | 4952 | CB | ILE | C | 269 | -0.653 | -6.588 | 39.151 | 1.00 | 46.96 | C |
| ATOM | 4953 | CG1 | ILE | C | 269 | 0.130 | -5.575 | 40.050 | 1.00 | 52.22 | C |
| ATOM | 4954 | CD1 | ILE | C | 269 | 1.579 | -5.439 | 39.731 | 1.00 | 52.19 | C |
| ATOM | 4955 | CG2 | ILE | C | 269 | 0.202 | -7.188 | 38.089 | 1.00 | 59.13 | C |

TABLE 10-continued

Atomic coordinates for COM1 complex of the modified TXNIP protein represented by SEQ ID NO: 6 and the modified protein represented by SEQ ID NO: 3

| ATOM | 4956 | C | ILE | 269 | -1.429 | -4.707 | 37.520 | 1.00 | 51.18 | C |
|------|------|---|-----|-----|--------|--------|--------|------|-------|---|
| ATOM | 4957 | O | ILE | 269 | -0.910 | -5.001 | 36.441 | 1.00 | 54.23 | O |
| ATOM | 4958 | N | LEU | 270 | -1.622 | -3.452 | 37.897 | 1.00 | 44.94 | N |
| ATOM | 4959 | CA | LEU | 270 | -1.409 | -2.353 | 36.995 | 1.00 | 39.26 | C |
| ATOM | 4960 | CB | LEU | 270 | -2.474 | -1.274 | 37.240 | 1.00 | 40.84 | C |
| ATOM | 4961 | CG | LEU | 270 | -3.728 | -1.366 | 36.350 | 1.00 | 48.90 | C |
| ATOM | 4962 | CD1 | LEU | 270 | -4.374 | -2.704 | 36.496 | 1.00 | 54.52 | C |
| ATOM | 4963 | CD2 | LEU | 270 | -4.690 | -0.275 | 36.720 | 1.00 | 50.65 | C |
| ATOM | 4964 | C | LEU | 270 | -0.057 | -1.768 | 37.162 | 1.00 | 35.25 | C |
| ATOM | 4965 | O | LEU | 270 | 0.616 | -1.453 | 36.183 | 1.00 | 31.42 | O |
| ATOM | 4966 | N | ARG | 271 | 0.331 | -1.559 | 38.423 | 1.00 | 32.56 | N |
| ATOM | 4967 | CA | ARG | 271 | 1.651 | -1.002 | 38.680 | 1.00 | 34.32 | C |
| ATOM | 4968 | CB | ARG | 271 | 1.663 | 0.503 | 38.452 | 1.00 | 37.45 | C |
| ATOM | 4969 | CG | ARG | 271 | 0.549 | 1.254 | 39.090 | 1.00 | 44.05 | C |
| ATOM | 4970 | CD | ARG | 271 | 0.829 | 2.716 | 38.988 | 1.00 | 51.20 | C |
| ATOM | 4971 | NE | ARG | 271 | 0.067 | 3.516 | 39.950 | 1.00 | 58.24 | N |
| ATOM | 4972 | CZ | ARG | 271 | -1.254 | 3.650 | 39.956 | 1.00 | 56.14 | C |
| ATOM | 4973 | NH1 | ARG | 271 | -2.038 | 2.987 | 39.076 | 1.00 | 40.54 | N |
| ATOM | 4974 | NH2 | ARG | 271 | -1.798 | 4.434 | 40.887 | 1.00 | 65.11 | N |
| ATOM | 4975 | C | ARG | 271 | 2.093 | -1.265 | 40.093 | 1.00 | 31.60 | C |
| ATOM | 4976 | O | ARG | 271 | 1.324 | -1.720 | 40.914 | 1.00 | 31.58 | O |
| ATOM | 4977 | N | VAL | 272 | 3.360 | -0.999 | 40.363 | 1.00 | 35.94 | N |
| ATOM | 4978 | CA | VAL | 272 | 3.875 | 1.142 | 41.741 | 1.00 | 38.70 | C |
| ATOM | 4979 | CB | VAL | 272 | 4.774 | -2.351 | 41.926 | 1.00 | 36.15 | C |
| ATOM | 4980 | CG1 | VAL | 272 | 5.093 | -2.601 | 43.462 | 1.00 | 33.38 | C |
| ATOM | 4981 | CG2 | VAL | 272 | 4.190 | -3.574 | 41.292 | 1.00 | 41.84 | C |
| ATOM | 4982 | C | VAL | 272 | 4.719 | 0.065 | 42.013 | 1.00 | 42.43 | C |
| ATOM | 4983 | O | VAL | 272 | 5.569 | 0.387 | 41.188 | 1.00 | 42.97 | O |
| ATOM | 4984 | N | GLU | 273 | 4.461 | 0.728 | 43.150 | 1.00 | 41.13 | N |
| ATOM | 4985 | CA | GLU | 273 | 5.237 | 1.878 | 43.618 | 1.00 | 42.70 | C |
| ATOM | 4986 | CB | GLU | 273 | 4.339 | 3.041 | 43.977 | 1.00 | 43.75 | C |
| ATOM | 4987 | CG | GLU | 273 | 3.510 | 3.515 | 42.774 | 1.00 | 56.69 | C |
| ATOM | 4988 | CD | GLU | 273 | 2.520 | 4.575 | 43.130 | 1.00 | 67.61 | C |
| ATOM | 4989 | OE1 | GLU | 273 | 2.365 | 4.861 | 44.342 | 1.00 | 73.56 | O |
| ATOM | 4990 | OE2 | GLU | 273 | 1.893 | 5.124 | 42.194 | 1.00 | 79.18 | O |
| ATOM | 4991 | C | GLU | 273 | 6.043 | 1.470 | 44.842 | 1.00 | 41.44 | C |
| ATOM | 4992 | O | GLU | 273 | 5.538 | 0.800 | 45.733 | 1.00 | 37.23 | O |
| ATOM | 4993 | N | TYR | 274 | 7.306 | 1.867 | 44.840 | 1.00 | 40.66 | N |
| ATOM | 4994 | CA | TYR | 274 | 8.279 | 1.383 | 45.788 | 1.00 | 40.35 | C |
| ATOM | 4995 | CB | TYR | 274 | 9.438 | 0.747 | 45.051 | 1.00 | 40.23 | C |
| ATOM | 4996 | CG | TYR | 274 | 9.120 | -0.532 | 44.260 | 1.00 | 42.18 | C |
| ATOM | 4997 | CD1 | TYR | 274 | 9.282 | -1.769 | 44.850 | 1.00 | 38.02 | C |
| ATOM | 4998 | CE1 | TYR | 274 | 9.058 | -2.920 | 44.171 | 1.00 | 39.41 | C |
| ATOM | 4999 | CZ | TYR | 274 | 8.684 | -2.876 | 42.864 | 1.00 | 43.84 | C |
| ATOM | 5000 | OH | TYR | 274 | 8.471 | -4.078 | 42.279 | 1.00 | 42.68 | O |
| ATOM | 5001 | CE2 | TYR | 274 | 8.492 | -1.671 | 42.211 | 1.00 | 36.15 | C |
| ATOM | 5002 | CD2 | TYR | 274 | 8.764 | -0.493 | 42.916 | 1.00 | 42.60 | C |
| ATOM | 5003 | C | TYR | 274 | 8.795 | 2.563 | 46.852 | 1.00 | 40.71 | C |
| ATOM | 5004 | O | TYR | 274 | 8.963 | 3.657 | 46.058 | 1.00 | 39.78 | O |
| ATOM | 5005 | N | SER | 275 | 9.023 | 2.346 | 47.868 | 1.00 | 40.93 | N |

TABLE 10-continued

Atomic coordinates for COM1 complex of the modified
TXNIP protein represented by SEQ ID NO: 6 and the modified protein represented by SEQ ID NO: 3

| ATOM | 5006 | CA  | SER | C | 275 | 9.672  | 48.718 | 3.329  | 1.00 | 35.16 | O |
|------|------|-----|-----|---|-----|--------|--------|--------|------|-------|---|
| ATOM | 5007 | CB  | SER | C | 275 | 8.614  | 49.650 | 3.894  | 1.00 | 40.78 | O |
| ATOM | 5008 | OG  | SER | C | 275 | 7.866  | 48.980 | 4.880  | 1.00 | 51.47 | O |
| ATOM | 5009 | C   | SER | C | 275 | 10.696 | 49.568 | 2.617  | 1.00 | 36.34 | O |
| ATOM | 5010 | O   | SER | C | 275 | 10.504 | 49.956 | 1.456  | 1.00 | 33.96 | O |
| ATOM | 5011 | N   | LEU | C | 276 | 11.779 | 49.886 | 3.308  | 1.00 | 35.35 | N |
| ATOM | 5012 | CA  | LEU | C | 276 | 12.694 | 50.910 | 2.838  | 1.00 | 35.10 | C |
| ATOM | 5013 | CB  | LEU | C | 276 | 14.087 | 50.517 | 3.209  | 1.00 | 36.90 | C |
| ATOM | 5014 | CG  | LEU | C | 276 | 15.206 | 51.552 | 3.092  | 1.00 | 36.11 | C |
| ATOM | 5015 | CD1 | LEU | C | 276 | 15.457 | 51.922 | 1.657  | 1.00 | 39.58 | C |
| ATOM | 5016 | CD2 | LEU | C | 276 | 16.464 | 50.959 | 3.698  | 1.00 | 37.39 | C |
| ATOM | 5017 | C   | LEU | C | 276 | 12.367 | 52.200 | 3.564  | 1.00 | 34.23 | C |
| ATOM | 5018 | O   | LEU | C | 276 | 12.411 | 52.240 | 4.794  | 1.00 | 36.85 | O |
| ATOM | 5019 | N   | LEU | C | 277 | 12.007 | 53.241 | 2.818  | 1.00 | 34.57 | N |
| ATOM | 5020 | CA  | LEU | C | 277 | 11.730 | 54.550 | 3.400  | 1.00 | 35.87 | C |
| ATOM | 5021 | CB  | LEU | C | 277 | 10.607 | 55.298 | 2.668  | 1.00 | 35.81 | C |
| ATOM | 5022 | CG  | LEU | C | 277 | 9.308  | 54.497 | 2.702  | 1.00 | 41.46 | C |
| ATOM | 5023 | CD1 | LEU | C | 277 | 8.284  | 55.297 | 2.039  | 1.00 | 48.51 | C |
| ATOM | 5024 | CD2 | LEU | C | 277 | 8.926  | 54.213 | 4.133  | 1.00 | 40.03 | C |
| ATOM | 5025 | C   | LEU | C | 277 | 12.993 | 55.337 | 3.318  | 1.00 | 37.44 | C |
| ATOM | 5026 | O   | LEU | C | 277 | 13.550 | 55.433 | 2.224  | 1.00 | 42.07 | O |
| ATOM | 5027 | N   | ILE | C | 278 | 13.467 | 55.846 | 4.460  | 1.00 | 35.51 | N |
| ATOM | 5028 | CA  | ILE | C | 278 | 14.553 | 56.865 | 4.490  | 1.00 | 37.42 | C |
| ATOM | 5029 | CB  | ILE | C | 278 | 15.774 | 56.435 | 5.266  | 1.00 | 39.21 | C |
| ATOM | 5030 | CG1 | ILE | C | 278 | 16.222 | 55.061 | 4.776  | 1.00 | 36.81 | C |
| ATOM | 5031 | CD1 | ILE | C | 278 | 16.871 | 54.175 | 5.801  | 1.00 | 42.78 | C |
| ATOM | 5032 | CG2 | ILE | C | 278 | 16.904 | 57.544 | 5.145  | 1.00 | 38.30 | C |
| ATOM | 5033 | C   | ILE | C | 278 | 13.952 | 58.082 | 5.094  | 1.00 | 38.06 | C |
| ATOM | 5034 | O   | ILE | C | 278 | 13.470 | 58.064 | 6.283  | 1.00 | 39.48 | O |
| ATOM | 5035 | N   | TYR | C | 279 | 13.878 | 59.139 | 4.309  | 1.00 | 37.10 | N |
| ATOM | 5036 | CA  | TYR | C | 279 | 13.215 | 60.318 | 4.799  | 1.00 | 38.94 | C |
| ATOM | 5037 | CB  | TYR | C | 279 | 11.732 | 60.324 | 4.390  | 1.00 | 38.60 | C |
| ATOM | 5038 | CG  | TYR | C | 279 | 11.492 | 60.294 | 2.903  | 1.00 | 40.71 | C |
| ATOM | 5039 | CD1 | TYR | C | 279 | 11.620 | 59.087 | 2.158  | 1.00 | 38.72 | C |
| ATOM | 5040 | CE1 | TYR | C | 279 | 11.390 | 59.064 | 0.774  | 1.00 | 31.42 | C |
| ATOM | 5041 | CZ  | TYR | C | 279 | 11.023 | 60.259 | 0.142  | 1.00 | 33.46 | C |
| ATOM | 5042 | OH  | TYR | C | 279 | 10.787 | 60.334 | -1.215 | 1.00 | 47.42 | O |
| ATOM | 5043 | CE2 | TYR | C | 279 | 10.892 | 61.445 | 0.860  | 1.00 | 37.14 | C |
| ATOM | 5044 | CD2 | TYR | C | 279 | 11.124 | 61.449 | 2.234  | 1.00 | 40.75 | C |
| ATOM | 5045 | C   | TYR | C | 279 | 13.884 | 61.640 | 4.398  | 1.00 | 38.25 | C |
| ATOM | 5046 | O   | TYR | C | 279 | 14.777 | 61.899 | 3.524  | 1.00 | 36.89 | O |
| ATOM | 5047 | N   | VAL | C | 280 | 13.451 | 62.697 | 5.071  | 1.00 | 36.12 | N |
| ATOM | 5048 | CA  | VAL | C | 280 | 13.969 | 64.039 | 4.735  | 1.00 | 37.19 | C |
| ATOM | 5049 | CB  | VAL | C | 280 | 14.774 | 34.647 | 5.897  | 1.00 | 37.92 | C |
| ATOM | 5050 | CG1 | VAL | C | 280 | 15.239 | 66.048 | 5.543  | 1.00 | 34.25 | C |
| ATOM | 5051 | CG2 | VAL | C | 280 | 15.972 | 63.794 | 6.215  | 1.00 | 35.19 | C |
| ATOM | 5052 | C   | VAL | C | 280 | 12.774 | 64.895 | 4.336  | 1.00 | 37.90 | C |
| ATOM | 5053 | O   | VAL | C | 280 | 11.820 | 65.035 | 5.104  | 1.00 | 35.23 | O |
| ATOM | 5054 | N   | SER | C | 281 | 12.817 | 65.425 | 3.123  | 1.00 | 41.33 | N |
| ATOM | 5055 | CA  | SER | C | 281 | 11.828 | 66.407 | 2.695  | 1.00 | 42.63 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 5056 | CB | SER | C | 281 | 11.783 | 66.473 | 1.164 | 1.00 | 46.34 | C |
| ATOM | 5057 | OG | SER | C | 281 | 11.463 | 65.200 | 0.649 | 1.00 | 52.19 | O |
| ATOM | 5058 | C | SER | C | 281 | 12.162 | 67.791 | 3.261 | 1.00 | 41.25 | C |
| ATOM | 5059 | O | SER | C | 281 | 13.245 | 68.319 | 3.007 | 1.00 | 39.31 | O |
| ATOM | 5060 | N | VAL | C | 282 | 11.218 | 68.368 | 4.002 | 1.00 | 40.25 | N |
| ATOM | 5061 | CA | VAL | C | 282 | 11.357 | 69.675 | 4.626 | 1.00 | 39.33 | C |
| ATOM | 5062 | CB | VAL | C | 282 | 11.057 | 69.587 | 6.159 | 1.00 | 40.63 | C |
| ATOM | 5063 | CG1 | VAL | C | 282 | 11.233 | 70.946 | 6.841 | 1.00 | 37.79 | C |
| ATOM | 5064 | CG2 | VAL | C | 282 | 11.928 | 68.550 | 6.822 | 1.00 | 41.31 | C |
| ATOM | 5065 | C | VAL | C | 282 | 10.324 | 70.583 | 3.951 | 1.00 | 41.88 | C |
| ATOM | 5066 | O | VAL | C | 282 | 9.139 | 70.423 | 4.210 | 1.00 | 44.25 | O |
| ATOM | 5067 | N | PRO | C | 283 | 10.757 | 71.517 | 3.065 | 1.00 | 45.03 | N |
| ATOM | 5068 | CA | PRO | C | 283 | 9.845 | 72.433 | 2.338 | 1.00 | 45.32 | C |
| ATOM | 5069 | CB | PRO | C | 283 | 10.796 | 73.362 | 1.587 | 1.00 | 47.86 | C |
| ATOM | 5070 | CG | PRO | C | 283 | 11.999 | 72.528 | 1.370 | 1.00 | 47.27 | C |
| ATOM | 5071 | CD | PRO | C | 283 | 12.153 | 71.729 | 2.850 | 1.00 | 44.19 | C |
| ATOM | 5072 | C | PRO | C | 283 | 8.907 | 73.229 | 3.229 | 1.00 | 47.69 | C |
| ATOM | 5073 | O | PRO | C | 283 | 9.334 | 73.835 | 4.203 | 1.00 | 47.64 | O |
| ATOM | 5074 | N | GLY | C | 284 | 7.611 | 73.179 | 2.907 | 1.00 | 52.28 | N |
| ATOM | 5075 | CA | GLY | C | 284 | 6.568 | 73.792 | 3.736 | 1.00 | 53.26 | C |
| ATOM | 5076 | C | GLY | C | 284 | 6.329 | 73.114 | 5.076 | 1.00 | 54.93 | C |
| ATOM | 5077 | O | GLY | C | 284 | 5.735 | 73.692 | 5.975 | 1.00 | 57.13 | O |
| ATOM | 5078 | N | SER | C | 285 | 6.778 | 71.874 | 5.220 | 1.00 | 55.71 | N |
| ATOM | 5079 | CA | SER | C | 285 | 6.520 | 71.123 | 6.437 | 1.00 | 54.73 | C |
| ATOM | 5080 | CB | SER | C | 285 | 7.646 | 71.358 | 7.447 | 1.00 | 54.98 | C |
| ATOM | 5081 | OG | SER | C | 285 | 7.347 | 70.800 | 8.708 | 1.00 | 61.65 | O |
| ATOM | 5082 | C | SER | C | 285 | 6.345 | 69.641 | 6.103 | 1.00 | 52.47 | C |
| ATOM | 5083 | O | SER | C | 285 | 6.555 | 69.224 | 4.962 | 1.00 | 52.14 | O |
| ATOM | 5084 | N | LYS | C | 286 | 5.944 | 68.844 | 7.084 | 1.00 | 51.58 | N |
| ATOM | 5085 | CA | LYS | C | 286 | 5.799 | 67.407 | 6.843 | 1.00 | 51.97 | C |
| ATOM | 5086 | CB | LYS | C | 286 | 4.964 | 66.735 | 7.932 | 1.00 | 50.90 | C |
| ATOM | 5087 | CG | LYS | C | 286 | 3.476 | 67.132 | 7.889 | 1.00 | 54.13 | C |
| ATOM | 5088 | CD | LYS | C | 286 | 2.577 | 66.189 | 8.715 | 1.00 | 60.67 | C |
| ATOM | 5089 | CE | LYS | C | 286 | 2.954 | 66.168 | 10.202 | 1.00 | 67.48 | C |
| ATOM | 5090 | NZ | LYS | C | 286 | 1.919 | 65.495 | 11.045 | 1.00 | 66.53 | N |
| ATOM | 5091 | C | LYS | C | 286 | 7.171 | 66.758 | 6.719 | 1.00 | 50.50 | C |
| ATOM | 5092 | O | LYS | C | 286 | 8.157 | 67.201 | 7.225 | 1.00 | 52.08 | O |
| ATOM | 5093 | N | LYS | C | 287 | 7.231 | 65.615 | 6.039 | 1.00 | 47.43 | N |
| ATOM | 5094 | CA | LYS | C | 287 | 8.448 | 64.826 | 5.937 | 1.00 | 43.48 | C |
| ATOM | 5095 | CB | LYS | C | 287 | 8.243 | 63.675 | 4.956 | 1.00 | 42.83 | C |
| ATOM | 5096 | CG | LYS | C | 287 | 8.052 | 64.127 | 3.492 | 1.00 | 38.08 | C |
| ATOM | 5097 | CD | LYS | C | 287 | 7.782 | 62.903 | 2.607 | 1.00 | 41.26 | C |
| ATOM | 5098 | CE | LYS | C | 287 | 7.573 | 63.350 | 1.177 | 1.00 | 49.40 | C |
| ATOM | 5099 | NZ | LYS | C | 287 | 6.339 | 64.205 | 1.032 | 1.00 | 56.77 | N |
| ATOM | 5100 | C | LYS | C | 287 | 8.834 | 64.276 | 7.288 | 1.00 | 43.46 | C |
| ATOM | 5101 | O | LYS | C | 287 | 7.983 | 64.030 | 8.128 | 1.00 | 42.62 | O |
| ATOM | 5102 | N | VAL | C | 288 | 10.123 | 64.086 | 7.506 | 1.00 | 43.68 | N |
| ATOM | 5103 | CA | VAL | C | 288 | 10.557 | 63.229 | 8.586 | 1.00 | 41.18 | C |
| ATOM | 5104 | CB | VAL | C | 288 | 11.519 | 63.886 | 9.623 | 1.00 | 41.73 | C |
| ATOM | 5105 | CG1 | VAL | C | 288 | 12.023 | 65.253 | 9.161 | 1.00 | 40.65 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 5106 | CG2 | VAL | C | 288 | 12.616 | 10.068 | 62.961 | 1.00 | 43.65 | C |
| ATOM | 5107 | C | VAL | C | 288 | 10.981 | 8.005 | 61.883 | 1.00 | 40.95 | C |
| ATOM | 5108 | O | VAL | C | 288 | 11.874 | 7.158 | 61.800 | 1.00 | 37.66 | O |
| ATOM | 5109 | N | ILE | C | 289 | 10.265 | 8.438 | 60.850 | 1.00 | 39.34 | N |
| ATOM | 5110 | CA | ILE | C | 289 | 10.266 | 7.723 | 59.557 | 1.00 | 38.85 | C |
| ATOM | 5111 | CB | ILE | C | 289 | 8.868 | 7.183 | 59.225 | 1.00 | 42.67 | C |
| ATOM | 5112 | CG1 | ILE | C | 289 | 8.361 | 6.256 | 60.299 | 1.00 | 42.73 | C |
| ATOM | 5113 | CD1 | ILE | C | 289 | 6.857 | 6.003 | 60.175 | 1.00 | 41.29 | C |
| ATOM | 5114 | CG2 | ILE | C | 289 | 8.853 | 6.420 | 57.851 | 1.00 | 38.45 | C |
| ATOM | 5115 | C | ILE | C | 289 | 10.690 | 8.615 | 58.417 | 1.00 | 40.98 | C |
| ATOM | 5116 | O | ILE | C | 289 | 10.140 | 9.711 | 58.259 | 1.00 | 42.86 | O |
| ATOM | 5117 | N | LEU | C | 290 | 11.644 | 8.147 | 57.614 | 1.00 | 40.65 | N |
| ATOM | 5118 | CA | LEU | C | 290 | 11.945 | 8.750 | 56.303 | 1.00 | 40.95 | C |
| ATOM | 5119 | CB | LEU | C | 290 | 13.445 | 8.939 | 56.082 | 1.00 | 42.61 | C |
| ATOM | 5120 | CG | LEU | C | 290 | 14.243 | 9.700 | 57.158 | 1.00 | 44.58 | C |
| ATOM | 5121 | CD1 | LEU | C | 290 | 15.665 | 9.707 | 56.787 | 1.00 | 33.77 | C |
| ATOM | 5122 | CD2 | LEU | C | 290 | 13.701 | 11.119 | 57.222 | 1.00 | 33.64 | C |
| ATOM | 5123 | C | LEU | C | 290 | 11.430 | 7.807 | 55.231 | 1.00 | 43.14 | C |
| ATOM | 5124 | O | LEU | C | 290 | 11.650 | 6.619 | 55.808 | 1.00 | 45.00 | O |
| ATOM | 5125 | N | ASP | C | 291 | 10.750 | 8.366 | 54.241 | 1.00 | 42.57 | N |
| ATOM | 5126 | CA | ASP | C | 291 | 10.259 | 7.632 | 53.076 | 1.00 | 43.06 | C |
| ATOM | 5127 | CB | ASP | C | 291 | 8.739 | 7.808 | 53.021 | 1.00 | 46.60 | C |
| ATOM | 5128 | CG | ASP | C | 291 | 8.073 | 6.992 | 51.918 | 1.00 | 49.32 | C |
| ATOM | 5129 | OD1 | ASP | C | 291 | 8.718 | 6.628 | 50.914 | 1.00 | 48.00 | O |
| ATOM | 5130 | OD2 | ASP | C | 291 | 6.887 | 6.727 | 52.072 | 1.00 | 50.61 | O |
| ATOM | 5131 | C | ASP | C | 291 | 10.902 | 8.237 | 51.822 | 1.00 | 42.10 | C |
| ATOM | 5132 | O | ASP | C | 291 | 10.602 | 9.370 | 51.440 | 1.00 | 38.78 | O |
| ATOM | 5133 | N | LEU | C | 292 | 11.798 | 7.477 | 51.197 | 1.00 | 40.80 | N |
| ATOM | 5134 | CA | LEU | C | 292 | 12.411 | 7.884 | 49.961 | 1.00 | 41.59 | C |
| ATOM | 5135 | CB | LEU | C | 292 | 13.914 | 7.591 | 49.996 | 1.00 | 39.23 | C |
| ATOM | 5136 | CG | LEU | C | 292 | 14.719 | 8.031 | 51.232 | 1.00 | 44.76 | C |
| ATOM | 5137 | CD1 | LEU | C | 292 | 16.174 | 7.842 | 50.941 | 1.00 | 42.21 | C |
| ATOM | 5138 | CD2 | LEU | C | 292 | 14.396 | 9.488 | 51.485 | 1.00 | 49.46 | C |
| ATOM | 5139 | C | LEU | C | 292 | 11.798 | 7.087 | 48.805 | 1.00 | 43.71 | C |
| ATOM | 5140 | O | LEU | C | 292 | 11.953 | 5.880 | 48.771 | 1.00 | 41.15 | O |
| ATOM | 5141 | N | PRO | C | 293 | 11.102 | 7.752 | 47.876 | 1.00 | 44.74 | N |
| ATOM | 5142 | CA | PRO | C | 293 | 10.557 | 7.080 | 46.699 | 1.00 | 45.01 | C |
| ATOM | 5143 | CB | PRO | C | 293 | 9.877 | 8.213 | 45.940 | 1.00 | 48.38 | C |
| ATOM | 5144 | CG | PRO | C | 293 | 9.535 | 9.206 | 47.027 | 1.00 | 50.74 | C |
| ATOM | 5145 | CD | PRO | C | 293 | 10.781 | 9.187 | 47.849 | 1.00 | 47.40 | C |
| ATOM | 5146 | C | PRO | C | 293 | 11.636 | 6.504 | 45.815 | 1.00 | 41.60 | C |
| ATOM | 5147 | O | PRO | C | 293 | 12.698 | 7.109 | 45.640 | 1.00 | 46.40 | O |
| ATOM | 5148 | N | LEU | C | 294 | 11.356 | 5.317 | 45.288 | 1.00 | 36.70 | N |
| ATOM | 5149 | CA | LEU | C | 294 | 12.250 | 4.590 | 44.441 | 1.00 | 35.95 | C |
| ATOM | 5150 | CB | LEU | C | 294 | 12.649 | 3.288 | 45.123 | 1.00 | 34.62 | C |
| ATOM | 5151 | CG | LEU | C | 294 | 13.431 | 3.305 | 46.450 | 1.00 | 42.19 | C |
| ATOM | 5152 | CD1 | LEU | C | 294 | 13.601 | 1.893 | 46.854 | 1.00 | 39.10 | C |
| ATOM | 5153 | CD2 | LEU | C | 294 | 14.800 | 4.017 | 46.382 | 1.00 | 38.21 | C |
| ATOM | 5154 | C | LEU | C | 294 | 11.591 | 4.254 | 48.088 | 1.00 | 37.90 | C |
| ATOM | 5155 | O | LEU | C | 294 | 10.363 | 4.243 | 42.957 | 1.00 | 38.01 | O |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 5156 | N | VAL | C | 295 | 12.430 | 3.944 | 42.107 | 1.00 | 39.44 | N |
| ATOM | 5157 | CA | VAL | C | 295 | 11.972 | 3.385 | 40.848 | 1.00 | 38.24 | C |
| ATOM | 5158 | CB | VAL | C | 295 | 12.397 | 4.288 | 39.667 | 1.00 | 39.21 | C |
| ATOM | 5159 | CG1 | VAL | C | 295 | 12.273 | 3.558 | 38.325 | 1.00 | 37.25 | C |
| ATOM | 5160 | CG2 | VAL | C | 295 | 11.567 | 5.538 | 39.659 | 1.00 | 39.57 | C |
| ATOM | 5161 | C | VAL | C | 295 | 12.655 | 2.034 | 40.811 | 1.00 | 36.03 | C |
| ATOM | 5162 | O | VAL | C | 295 | 13.857 | 1.933 | 41.065 | 1.00 | 38.28 | O |
| ATOM | 5163 | N | ILE | C | 296 | 11.915 | 0.955 | 40.583 | 1.00 | 35.39 | N |
| ATOM | 5164 | CA | ILE | C | 296 | 12.602 | -0.349 | 40.536 | 1.00 | 36.00 | C |
| ATOM | 5165 | CB | ILE | C | 296 | 12.280 | -1.206 | 41.791 | 1.00 | 38.78 | C |
| ATOM | 5166 | CG1 | ILE | C | 296 | 13.035 | -0.602 | 42.995 | 1.00 | 41.33 | C |
| ATOM | 5167 | CD1 | ILE | C | 296 | 12.778 | -1.276 | 44.300 | 1.00 | 56.82 | C |
| ATOM | 5168 | CG2 | ILE | C | 296 | 12.700 | -2.662 | 41.625 | 1.00 | 35.52 | C |
| ATOM | 5169 | C | ILE | C | 296 | 12.259 | -0.994 | 39.218 | 1.00 | 36.51 | C |
| ATOM | 5170 | O | ILE | C | 296 | 11.120 | -1.117 | 38.913 | 1.00 | 33.85 | O |
| ATOM | 5171 | N | GLY | C | 297 | 13.272 | -1.369 | 38.440 | 1.00 | 38.51 | N |
| ATOM | 5172 | CA | GLY | C | 297 | 13.069 | -1.910 | 37.121 | 1.00 | 40.48 | C |
| ATOM | 5173 | C | GLY | C | 297 | 13.609 | -3.310 | 37.006 | 1.00 | 43.56 | C |
| ATOM | 5174 | O | GLY | C | 297 | 14.509 | -3.684 | 37.745 | 1.00 | 41.93 | O |
| ATOM | 5175 | N | SER | C | 298 | 13.028 | -4.100 | 36.103 | 1.00 | 44.76 | N |
| ATOM | 5176 | CA | SER | C | 298 | 13.570 | -5.428 | 35.822 | 1.00 | 47.24 | C |
| ATOM | 5177 | CB | SER | C | 298 | 12.423 | -6.364 | 35.455 | 1.00 | 48.75 | C |
| ATOM | 5178 | CG | SER | C | 298 | 11.871 | -5.921 | 34.243 | 1.00 | 48.43 | O |
| ATOM | 5179 | C | SER | C | 298 | 14.620 | -5.361 | 34.683 | 1.00 | 47.97 | C |
| ATOM | 5180 | O | SER | C | 298 | 14.636 | -4.398 | 33.895 | 1.00 | 45.55 | O |
| ATOM | 5181 | N | ARG | C | 299 | 15.473 | -6.390 | 34.609 | 1.00 | 49.56 | N |
| ATOM | 5182 | CA | ARG | C | 299 | 16.579 | -6.480 | 33.658 | 1.00 | 51.87 | C |
| ATOM | 5183 | CB | ARG | C | 299 | 17.723 | -7.284 | 34.278 | 1.00 | 55.02 | C |
| ATOM | 5184 | CG | ARG | C | 299 | 17.918 | -7.027 | 35.771 | 1.00 | 56.10 | C |
| ATOM | 5185 | CD | ARG | C | 299 | 19.302 | -7.419 | 36.264 | 1.00 | 72.04 | C |
| ATOM | 5186 | NE | ARG | C | 299 | 20.222 | -6.273 | 36.319 | 1.00 | 74.07 | N |
| ATOM | 5187 | CZ | ARG | C | 299 | 20.849 | -5.846 | 37.416 | 1.00 | 71.18 | C |
| ATOM | 5188 | NH1 | ARG | C | 299 | 20.676 | -6.469 | 38.580 | 1.00 | 58.63 | N |
| ATOM | 5189 | NH2 | ARG | C | 299 | 21.676 | -4.800 | 37.347 | 1.00 | 69.87 | N |
| ATOM | 5190 | C | ARG | C | 299 | 16.155 | -7.135 | 32.351 | 1.00 | 54.78 | C |
| ATOM | 5191 | O | ARG | C | 299 | 15.232 | -6.663 | 31.375 | 1.00 | 57.45 | O |
| TER | 5192 | | | | | | | | | | |
| ATOM | 5192 | N | MET | D | 1 | 44.907 | 19.389 | 78.423 | 1.00 | 51.78 | N |
| ATOM | 5193 | CA | MET | D | 1 | 44.688 | 19.473 | 76.955 | 1.00 | 49.37 | C |
| ATOM | 5194 | CB | MET | D | 1 | 45.924 | 20.021 | 76.265 | 1.00 | 48.94 | C |
| ATOM | 5195 | CG | MET | D | 1 | 46.275 | 21.434 | 76.676 | 1.00 | 58.21 | C |
| ATOM | 5196 | SD | MET | D | 1 | 44.876 | 22.584 | 76.595 | 1.00 | 60.23 | S |
| ATOM | 5197 | CE | MET | D | 1 | 44.512 | 22.503 | 74.838 | 1.00 | 52.19 | C |
| ATOM | 5198 | C | MET | D | 1 | 44.406 | 18.112 | 76.384 | 1.00 | 48.95 | C |
| ATOM | 5199 | O | MET | D | 1 | 44.830 | 17.112 | 76.943 | 1.00 | 50.02 | O |
| ATOM | 5200 | N | VAL | D | 2 | 43.738 | 18.103 | 75.237 | 1.00 | 49.94 | N |
| ATOM | 5201 | CA | VAL | D | 2 | 43.389 | 16.885 | 74.492 | 1.00 | 48.31 | C |
| ATOM | 5202 | CB | VAL | D | 2 | 41.882 | 16.843 | 74.268 | 1.00 | 48.82 | C |
| ATOM | 5203 | CG1 | VAL | D | 2 | 41.498 | 15.717 | 73.306 | 1.00 | 40.17 | C |
| ATOM | 5204 | CG2 | VAL | D | 2 | 41.168 | 16.683 | 75.614 | 1.00 | 43.10 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 5205 | C | VAL | D | 2 | 44.093 | 16.868 | 73.122 | 1.00 | 49.55 | C |
| ATOM | 5206 | O | VAL | D | 2 | 43.974 | 17.832 | 72.362 | 1.00 | 45.15 | O |
| ATOM | 5207 | N | LYS | D | 3 | 44.831 | 15.794 | 72.809 | 1.00 | 47.32 | N |
| ATOM | 5208 | CA | LYS | D | 3 | 45.503 | 15.716 | 71.510 | 1.00 | 47.30 | C |
| ATOM | 5209 | CB | LYS | D | 3 | 46.802 | 14.919 | 71.624 | 1.00 | 50.16 | C |
| ATOM | 5210 | CG | LYS | D | 3 | 47.522 | 14.686 | 70.293 | 1.00 | 52.67 | C |
| ATOM | 5211 | CD | LYS | D | 3 | 48.531 | 13.550 | 70.407 | 1.00 | 52.71 | C |
| ATOM | 5212 | CE | LYS | D | 3 | 49.745 | 13.798 | 69.531 | 1.00 | 51.20 | C |
| ATOM | 5213 | NZ | LYS | D | 3 | 49.440 | 14.649 | 68.360 | 1.00 | 50.45 | N |
| ATOM | 5214 | C | LYS | D | 3 | 44.622 | 15.073 | 70.445 | 1.00 | 47.37 | C |
| ATOM | 5215 | O | LYS | D | 3 | 44.067 | 14.010 | 70.573 | 1.00 | 47.35 | O |
| ATOM | 5216 | N | GLN | D | 4 | 44.522 | 15.721 | 69.285 | 1.00 | 47.62 | N |
| ATOM | 5217 | CA | GLN | D | 4 | 43.809 | 15.198 | 68.136 | 1.00 | 49.63 | C |
| ATOM | 5218 | CB | GLN | D | 4 | 43.381 | 16.332 | 67.213 | 1.00 | 48.70 | C |
| ATOM | 5219 | CG | GLN | D | 4 | 42.354 | 15.862 | 66.172 | 1.00 | 55.81 | C |
| ATOM | 5220 | CD | GLN | D | 4 | 40.922 | 15.879 | 66.710 | 1.00 | 61.65 | C |
| ATOM | 5221 | OE1 | GLN | D | 4 | 40.550 | 16.787 | 67.449 | 1.00 | 61.90 | O |
| ATOM | 5222 | NE2 | GLN | D | 4 | 40.117 | 14.885 | 66.328 | 1.00 | 51.21 | N |
| ATOM | 5223 | C | GLN | D | 4 | 44.626 | 14.216 | 67.316 | 1.00 | 49.25 | C |
| ATOM | 5224 | O | GLN | D | 4 | 45.685 | 14.565 | 66.823 | 1.00 | 49.73 | O |
| ATOM | 5225 | N | ILE | D | 5 | 44.098 | 13.007 | 67.144 | 1.00 | 49.95 | N |
| ATOM | 5226 | CA | ILE | D | 5 | 44.735 | 11.978 | 66.337 | 1.00 | 50.73 | C |
| ATOM | 5227 | CB | ILE | D | 5 | 44.557 | 10.601 | 66.966 | 1.00 | 50.89 | C |
| ATOM | 5228 | CG1 | ILE | D | 5 | 45.129 | 10.568 | 68.388 | 1.00 | 41.77 | C |
| ATOM | 5229 | CD1 | ILE | D | 5 | 46.634 | 10.904 | 68.495 | 1.00 | 43.61 | C |
| ATOM | 5230 | CG2 | ILE | D | 5 | 45.110 | 9.533 | 66.058 | 1.00 | 48.14 | C |
| ATOM | 5231 | C | ILE | D | 5 | 44.178 | 11.959 | 64.910 | 1.00 | 53.14 | C |
| ATOM | 5232 | O | ILE | D | 5 | 43.011 | 11.652 | 64.703 | 1.00 | 50.20 | O |
| ATOM | 5233 | N | GLU | D | 6 | 45.035 | 12.273 | 63.935 | 1.00 | 54.75 | N |
| ATOM | 5234 | CA | GLU | D | 6 | 44.607 | 12.464 | 62.543 | 1.00 | 55.57 | C |
| ATOM | 5235 | CB | GLU | D | 6 | 45.295 | 13.684 | 61.912 | 1.00 | 55.36 | C |
| ATOM | 5236 | CG | GLU | D | 6 | 44.964 | 15.043 | 62.551 | 1.00 | 59.50 | C |
| ATOM | 5237 | CD | GLU | D | 6 | 43.509 | 15.512 | 62.339 | 1.00 | 69.55 | C |
| ATOM | 5238 | OE1 | GLU | D | 6 | 42.654 | 14.744 | 61.834 | 1.00 | 64.65 | O |
| ATOM | 5239 | OE2 | GLU | D | 6 | 43.217 | 16.673 | 62.697 | 1.00 | 69.71 | O |
| ATOM | 5240 | C | GLU | D | 6 | 44.855 | 11.227 | 61.698 | 1.00 | 55.94 | C |
| ATOM | 5241 | O | GLU | D | 6 | 44.439 | 11.165 | 60.535 | 1.00 | 57.73 | O |
| ATOM | 5242 | N | SER | D | 7 | 45.486 | 10.226 | 62.309 | 1.00 | 54.64 | N |
| ATOM | 5243 | CA | SER | D | 7 | 45.985 | 9.082 | 61.579 | 1.00 | 53.64 | C |
| ATOM | 5244 | CB | SER | D | 7 | 47.339 | 9.468 | 60.985 | 1.00 | 54.56 | C |
| ATOM | 5245 | OG | SER | D | 7 | 48.278 | 8.431 | 61.113 | 1.00 | 54.50 | O |
| ATOM | 5246 | C | SER | D | 7 | 46.118 | 7.815 | 62.427 | 1.00 | 54.71 | C |
| ATOM | 5247 | O | SER | D | 7 | 46.073 | 7.863 | 63.650 | 1.00 | 56.16 | O |
| ATOM | 5248 | N | LYS | D | 8 | 46.311 | 6.683 | 61.762 | 1.00 | 54.34 | N |
| ATOM | 5249 | CA | LYS | D | 8 | 46.538 | 5.407 | 62.440 | 1.00 | 55.71 | C |
| ATOM | 5250 | CB | LYS | D | 8 | 46.155 | 4.268 | 61.502 | 1.00 | 55.55 | C |
| ATOM | 5251 | CG | LYS | D | 8 | 45.706 | 3.009 | 62.211 | 1.00 | 59.79 | C |
| ATOM | 5252 | CD | LYS | D | 8 | 44.953 | 2.085 | 61.258 | 1.00 | 49.93 | C |
| ATOM | 5253 | CE | LYS | D | 8 | 45.913 | 1.233 | 60.458 | 1.00 | 57.96 | C |
| ATOM | 5254 | NZ | LYS | D | 8 | 46.658 | 0.265 | 61.325 | 1.00 | 62.12 | N |

TABLE 10-continued

Atomic coordinates for COM1 complex of the modified TXNIP protein represented by SEQ ID NO: 6 and the modified protein represented by SEQ ID NO: 3

| ATOM | 5255 | C | LYS | D | 8 | 48.004 | 5.221 | 62.891 | 1.00 | 55.46 | C |
|---|---|---|---|---|---|---|---|---|---|---|---|
| ATOM | 5256 | O | LYS | D | 8 | 48.305 | 4.416 | 63.783 | 1.00 | 52.52 | O |
| ATOM | 5257 | N | THR | D | 9 | 48.894 | 5.945 | 62.217 | 1.00 | 55.16 | N |
| ATOM | 5258 | CA | THR | D | 9 | 50.304 | 6.002 | 62.540 | 1.00 | 55.07 | C |
| ATOM | 5259 | CB | THR | D | 9 | 51.124 | 6.489 | 61.311 | 1.00 | 55.22 | C |
| ATOM | 5260 | OG1 | THR | D | 9 | 51.142 | 5.455 | 60.319 | 1.00 | 51.42 | O |
| ATOM | 5261 | CG2 | THR | D | 9 | 52.576 | 6.858 | 61.690 | 1.00 | 56.15 | C |
| ATOM | 5262 | C | THR | D | 9 | 50.494 | 6.909 | 63.760 | 1.00 | 56.17 | C |
| ATOM | 5263 | O | THR | D | 9 | 51.276 | 6.586 | 64.655 | 1.00 | 57.37 | O |
| ATOM | 5264 | N | ALA | D | 10 | 49.758 | 8.025 | 63.801 | 1.00 | 54.53 | N |
| ATOM | 5265 | CA | ALA | D | 10 | 49.812 | 8.957 | 64.923 | 1.00 | 51.49 | C |
| ATOM | 5266 | CB | ALA | D | 10 | 49.151 | 10.275 | 64.571 | 1.00 | 52.83 | C |
| ATOM | 5267 | C | ALA | D | 10 | 49.151 | 8.331 | 66.130 | 1.00 | 49.60 | C |
| ATOM | 5268 | O | ALA | D | 10 | 49.541 | 8.577 | 67.263 | 1.00 | 47.72 | O |
| ATOM | 5269 | N | PHE | D | 11 | 48.154 | 7.497 | 65.882 | 1.00 | 49.19 | N |
| ATOM | 5270 | CA | PHE | D | 11 | 47.542 | 6.765 | 60.962 | 1.00 | 47.89 | C |
| ATOM | 5271 | CB | PHE | D | 11 | 46.329 | 5.977 | 66.497 | 1.00 | 48.18 | C |
| ATOM | 5272 | CG | PHE | D | 11 | 45.454 | 5.539 | 67.619 | 1.00 | 45.97 | C |
| ATOM | 5273 | CD1 | PHE | D | 11 | 44.935 | 6.469 | 68.507 | 1.00 | 49.11 | C |
| ATOM | 5274 | CE1 | PHE | D | 11 | 44.132 | 6.065 | 69.559 | 1.00 | 56.20 | C |
| ATOM | 5275 | CZ | PHE | D | 11 | 43.843 | 4.716 | 69.738 | 1.00 | 52.89 | C |
| ATOM | 5276 | CE2 | PHE | D | 11 | 44.365 | 3.786 | 68.871 | 1.00 | 50.74 | C |
| ATOM | 5277 | CD2 | PHE | D | 11 | 45.172 | 4.198 | 67.815 | 1.00 | 51.98 | C |
| ATOM | 5278 | C | PHE | D | 11 | 48.547 | 5.847 | 67.623 | 1.00 | 48.39 | C |
| ATOM | 5279 | O | PHE | D | 11 | 48.707 | 5.895 | 68.833 | 1.00 | 49.55 | O |
| ATOM | 5280 | N | GLN | D | 12 | 49.225 | 5.022 | 66.828 | 1.00 | 48.61 | N |
| ATOM | 5281 | CA | GLN | D | 12 | 50.258 | 4.104 | 67.340 | 1.00 | 47.24 | C |
| ATOM | 5282 | CB | GLN | D | 12 | 50.904 | 3.354 | 66.174 | 1.00 | 47.25 | C |
| ATOM | 5283 | CG | GLN | D | 12 | 51.490 | 1.989 | 66.525 | 1.00 | 51.90 | C |
| ATOM | 5284 | CD | GLN | D | 12 | 50.547 | 1.128 | 67.353 | 1.00 | 57.68 | C |
| ATOM | 5285 | OE1 | GLN | D | 12 | 50.406 | 1.324 | 68.563 | 1.00 | 55.77 | O |
| ATOM | 5286 | NE2 | GLN | D | 12 | 49.910 | 0.155 | 66.704 | 1.00 | 58.15 | N |
| ATOM | 5287 | C | GLN | D | 12 | 51.324 | 4.837 | 68.155 | 1.00 | 47.96 | C |
| ATOM | 5288 | O | GLN | D | 12 | 51.630 | 4.472 | 69.300 | 1.00 | 49.88 | O |
| ATOM | 5289 | N | GLU | D | 13 | 51.882 | 5.874 | 67.540 | 1.00 | 47.03 | N |
| ATOM | 5290 | CA | GLU | D | 13 | 52.856 | 6.757 | 68.154 | 1.00 | 47.70 | C |
| ATOM | 5291 | CB | GLU | D | 13 | 53.221 | 7.866 | 67.157 | 1.00 | 47.65 | C |
| ATOM | 5292 | CG | GLU | D | 13 | 54.359 | 8.798 | 67.600 | 1.00 | 55.47 | C |
| ATOM | 5293 | CD | GLU | D | 13 | 55.642 | 8.082 | 68.006 | 1.00 | 58.56 | C |
| ATOM | 5294 | OE1 | GLU | D | 13 | 56.411 | 8.636 | 68.808 | 1.00 | 59.53 | O |
| ATOM | 5295 | OE2 | GLU | D | 13 | 55.881 | 6.923 | 67.534 | 1.00 | 59.58 | O |
| ATOM | 5296 | C | GLU | D | 13 | 52.422 | 7.358 | 69.498 | 1.00 | 48.93 | C |
| ATOM | 5297 | O | GLU | D | 13 | 53.254 | 7.637 | 70.340 | 1.00 | 50.29 | O |
| ATOM | 5298 | N | ALA | D | 14 | 51.127 | 7.560 | 69.702 | 1.00 | 49.22 | N |
| ATOM | 5299 | CA | ALA | D | 14 | 50.644 | 8.134 | 70.955 | 1.00 | 49.85 | C |
| ATOM | 5300 | CB | ALA | D | 14 | 49.280 | 8.702 | 70.753 | 1.00 | 48.21 | C |
| ATOM | 5301 | C | ALA | D | 14 | 50.595 | 7.105 | 72.080 | 1.00 | 49.74 | C |
| ATOM | 5302 | O | ALA | D | 14 | 50.931 | 7.414 | 73.222 | 1.00 | 51.59 | O |
| ATOM | 5303 | N | LEU | D | 15 | 50.175 | 5.884 | 71.746 | 1.00 | 49.82 | N |
| ATOM | 5304 | CA | LEU | D | 15 | 50.026 | 4.786 | 72.712 | 1.00 | 51.00 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 5305 | CB | LEU | D | 15 | 49.355 | 3.579 | 72.042 | 1.00 | 49.44 | C |
| ATOM | 5306 | CG | LEU | D | 15 | 47.841 | 3.322 | 72.072 | 1.00 | 53.90 | C |
| ATOM | 5307 | CD1 | LEU | D | 15 | 46.999 | 4.562 | 72.418 | 1.00 | 48.37 | C |
| ATOM | 5308 | CD2 | LEU | D | 15 | 47.443 | 2.736 | 70.737 | 1.00 | 40.25 | C |
| ATOM | 5309 | C | LEU | D | 15 | 51.365 | 4.333 | 73.273 | 1.00 | 52.27 | C |
| ATOM | 5310 | O | LEU | D | 15 | 51.456 | 3.930 | 74.433 | 1.00 | 52.62 | O |
| ATOM | 5311 | N | ASP | D | 16 | 52.385 | 4.377 | 72.418 | 1.00 | 52.37 | N |
| ATOM | 5312 | CA | ASP | D | 16 | 53.723 | 3.926 | 72.759 | 1.00 | 52.32 | C |
| ATOM | 5313 | CB | ASP | D | 16 | 54.464 | 3.412 | 71.510 | 1.00 | 51.30 | C |
| ATOM | 5314 | CG | ASP | D | 16 | 53.733 | 2.243 | 70.811 | 1.00 | 53.32 | C |
| ATOM | 5315 | OD1 | ASP | D | 16 | 52.846 | 1.559 | 71.440 | 1.00 | 51.77 | O |
| ATOM | 5316 | OD2 | ASP | D | 16 | 54.062 | 2.013 | 69.613 | 1.00 | 46.51 | O |
| ATOM | 5317 | C | ASP | D | 16 | 54.529 | 5.037 | 73.441 | 1.00 | 53.27 | C |
| ATOM | 5318 | O | ASP | D | 16 | 55.318 | 4.756 | 74.330 | 1.00 | 53.75 | O |
| ATOM | 5319 | N | ALA | D | 17 | 54.335 | 6.288 | 73.024 | 1.00 | 53.52 | N |
| ATOM | 5320 | CA | ALA | D | 17 | 54.988 | 7.426 | 73.678 | 1.00 | 52.90 | C |
| ATOM | 5321 | CB | ALA | D | 17 | 54.765 | 8.726 | 72.906 | 1.00 | 53.07 | C |
| ATOM | 5322 | C | ALA | D | 17 | 54.490 | 7.570 | 75.101 | 1.00 | 53.36 | C |
| ATOM | 5323 | O | ALA | D | 17 | 55.210 | 8.064 | 75.960 | 1.00 | 53.20 | O |
| ATOM | 5324 | N | ALA | D | 18 | 53.247 | 7.169 | 75.347 | 1.00 | 53.82 | N |
| ATOM | 5325 | CA | ALA | D | 18 | 52.758 | 7.051 | 76.712 | 1.00 | 53.57 | C |
| ATOM | 5326 | CB | ALA | D | 18 | 51.248 | 6.862 | 76.736 | 1.00 | 58.86 | C |
| ATOM | 5327 | C | ALA | D | 18 | 53.474 | 5.845 | 77.307 | 1.00 | 53.21 | C |
| ATOM | 5328 | O | ALA | D | 18 | 53.781 | 4.880 | 76.603 | 1.00 | 55.09 | O |
| ATOM | 5329 | N | GLY | D | 19 | 53.769 | 5.900 | 78.592 | 1.00 | 53.15 | N |
| ATOM | 5330 | CA | GLY | D | 19 | 54.570 | 4.838 | 79.209 | 1.00 | 51.52 | C |
| ATOM | 5331 | C | GLY | D | 19 | 53.613 | 3.783 | 79.712 | 1.00 | 51.88 | C |
| ATOM | 5332 | O | GLY | D | 19 | 52.995 | 3.037 | 78.912 | 1.00 | 50.08 | O |
| ATOM | 5333 | N | ASP | D | 20 | 53.489 | 3.746 | 81.047 | 1.00 | 51.45 | N |
| ATOM | 5334 | CA | ASP | D | 20 | 52.466 | 2.938 | 81.714 | 1.00 | 51.91 | C |
| ATOM | 5335 | CB | ASP | D | 20 | 53.098 | 2.204 | 82.907 | 1.00 | 53.09 | C |
| ATOM | 5336 | CG | ASP | D | 20 | 54.097 | 3.082 | 83.659 | 1.00 | 57.21 | C |
| ATOM | 5337 | OD1 | ASP | D | 20 | 54.849 | 2.537 | 84.508 | 1.00 | 67.20 | O |
| ATOM | 5338 | OD2 | ASP | D | 20 | 54.143 | 4.311 | 83.399 | 1.00 | 60.45 | O |
| ATOM | 5339 | C | ASP | D | 20 | 51.314 | 3.834 | 82.188 | 1.00 | 50.66 | C |
| ATOM | 5340 | O | ASP | D | 20 | 50.527 | 3.443 | 83.143 | 1.00 | 51.50 | O |
| ATOM | 5341 | N | LYS | D | 21 | 51.233 | 5.058 | 81.512 | 1.00 | 48.88 | N |
| ATOM | 5342 | CA | LYS | D | 21 | 50.176 | 5.987 | 81.904 | 1.00 | 48.96 | C |
| ATOM | 5343 | CB | LYS | D | 21 | 50.539 | 7.442 | 81.516 | 1.00 | 49.43 | C |
| ATOM | 5344 | CG | LYS | D | 21 | 51.746 | 7.513 | 80.538 | 1.00 | 48.53 | C |
| ATOM | 5345 | CD | LYS | D | 21 | 53.006 | 8.064 | 81.259 | 1.00 | 54.17 | C |
| ATOM | 5346 | CE | LYS | D | 21 | 52.952 | 9.610 | 81.362 | 1.00 | 49.22 | C |
| ATOM | 5347 | NZ | LYS | D | 21 | 52.869 | 10.296 | 79.970 | 1.00 | 51.62 | N |
| ATOM | 5348 | C | LYS | D | 21 | 48.848 | 5.592 | 81.240 | 1.00 | 48.67 | C |
| ATOM | 5349 | O | LYS | D | 21 | 48.822 | 5.023 | 80.132 | 1.00 | 47.56 | O |
| ATOM | 5350 | N | LEU | D | 22 | 47.764 | 5.871 | 81.958 | 1.00 | 48.21 | N |
| ATOM | 5351 | CA | LEU | D | 22 | 46.419 | 5.792 | 81.418 | 1.00 | 48.62 | C |
| ATOM | 5352 | CB | LEU | D | 22 | 45.381 | 6.140 | 82.498 | 1.00 | 48.77 | C |
| ATOM | 5353 | CG | LEU | D | 22 | 43.899 | 5.903 | 82.138 | 1.00 | 51.92 | C |
| ATOM | 5354 | CD1 | LEU | D | 22 | 43.606 | 4.401 | 82.010 | 1.00 | 46.50 | C |

TABLE 10-continued

Atomic coordinates for COM1 complex of the modified
TXNIP protein represented by SEQ ID NO: 6 and the modified protein represented by SEQ ID NO: 3

| | | | | | | | | | |
|---|---|---|---|---|---|---|---|---|---|
| ATOM | 5355 | CD2 | LEU | D | 22 | 42.963 | 6.539 | 83.172 | 1.00 | 44.99 | C |
| ATOM | 5356 | C | LEU | D | 22 | 46.271 | 6.717 | 80.197 | 1.00 | 47.43 | C |
| ATOM | 5357 | O | LEU | D | 22 | 46.726 | 7.866 | 80.190 | 1.00 | 44.03 | O |
| ATOM | 5358 | N | VAL | D | 23 | 45.358 | 6.177 | 79.146 | 1.00 | 49.03 | N |
| ATOM | 5359 | CA | VAL | D | 23 | 45.656 | 6.925 | 77.923 | 1.00 | 47.78 | C |
| ATOM | 5360 | CB | VAL | D | 23 | 46.141 | 6.344 | 76.704 | 1.00 | 48.40 | C |
| ATOM | 5361 | CG1 | VAL | D | 23 | 45.805 | 7.089 | 75.402 | 1.00 | 43.30 | C |
| ATOM | 5362 | CG2 | VAL | D | 23 | 47.637 | 6.339 | 76.968 | 1.00 | 51.95 | C |
| ATOM | 5363 | C | VAL | D | 23 | 43.867 | 6.713 | 77.728 | 1.00 | 48.23 | C |
| ATOM | 5364 | O | VAL | D | 23 | 43.404 | 5.566 | 77.708 | 1.00 | 45.05 | O |
| ATOM | 5365 | N | VAL | D | 24 | 43.114 | 7.809 | 77.564 | 1.00 | 48.82 | N |
| ATOM | 5366 | CA | VAL | D | 24 | 41.691 | 7.742 | 77.366 | 1.00 | 47.45 | C |
| ATOM | 5367 | CB | VAL | D | 24 | 40.829 | 8.338 | 78.501 | 1.00 | 48.55 | C |
| ATOM | 5368 | CG1 | VAL | D | 24 | 41.182 | 9.758 | 78.733 | 1.00 | 51.52 | C |
| ATOM | 5369 | CG2 | VAL | D | 24 | 39.325 | 8.216 | 78.178 | 1.00 | 45.20 | C |
| ATOM | 5370 | C | VAL | D | 24 | 41.435 | 8.403 | 76.000 | 1.00 | 48.54 | C |
| ATOM | 5371 | O | VAL | D | 24 | 41.982 | 9.484 | 75.707 | 1.00 | 43.75 | O |
| ATOM | 5372 | N | VAL | D | 25 | 40.653 | 7.729 | 75.150 | 1.00 | 45.38 | N |
| ATOM | 5373 | CA | VAL | D | 25 | 40.380 | 8.260 | 73.814 | 1.00 | 45.33 | C |
| ATOM | 5374 | CB | VAL | D | 25 | 40.796 | 7.260 | 72.703 | 1.00 | 44.41 | C |
| ATOM | 5375 | CG1 | VAL | D | 25 | 40.580 | 7.885 | 71.320 | 1.00 | 45.35 | C |
| ATOM | 5376 | CG2 | VAL | D | 25 | 42.245 | 6.844 | 72.858 | 1.00 | 45.67 | C |
| ATOM | 5377 | C | VAL | D | 25 | 38.914 | 8.617 | 73.680 | 1.00 | 45.72 | C |
| ATOM | 5378 | O | VAL | D | 25 | 38.062 | 7.783 | 73.916 | 1.00 | 48.31 | O |
| ATOM | 5379 | N | ASP | D | 26 | 38.625 | 9.859 | 73.297 | 1.00 | 48.51 | N |
| ATOM | 5380 | CA | ASP | D | 26 | 37.278 | 10.267 | 72.932 | 1.00 | 43.05 | C |
| ATOM | 5381 | CB | ASP | D | 26 | 37.105 | 11.758 | 73.195 | 1.00 | 46.80 | C |
| ATOM | 5382 | CG | ASP | D | 26 | 35.746 | 12.252 | 72.917 | 1.00 | 45.29 | C |
| ATOM | 5383 | OD1 | ASP | D | 26 | 34.904 | 11.416 | 72.495 | 1.00 | 47.77 | O |
| ATOM | 5384 | OD2 | ASP | D | 26 | 35.527 | 13.493 | 73.053 | 1.00 | 47.16 | O |
| ATOM | 5385 | C | ASP | D | 26 | 37.085 | 9.958 | 71.453 | 1.00 | 44.97 | C |
| ATOM | 5386 | O | ASP | D | 26 | 37.643 | 10.653 | 70.597 | 1.00 | 41.74 | O |
| ATOM | 5387 | N | PHE | D | 27 | 36.346 | 8.876 | 71.149 | 1.00 | 42.52 | N |
| ATOM | 5388 | CA | PHE | D | 27 | 35.900 | 8.609 | 69.760 | 1.00 | 47.15 | C |
| ATOM | 5389 | CB | PHE | D | 27 | 35.683 | 7.121 | 69.492 | 1.00 | 45.67 | C |
| ATOM | 5390 | CG | PHE | D | 27 | 36.957 | 6.314 | 69.435 | 1.00 | 48.38 | C |
| ATOM | 5391 | CD1 | PHE | D | 27 | 37.644 | 6.143 | 68.220 | 1.00 | 41.44 | C |
| ATOM | 5392 | CE1 | PHE | D | 27 | 38.772 | 5.389 | 68.136 | 1.00 | 43.70 | C |
| ATOM | 5393 | CZ | PHE | D | 27 | 39.269 | 4.755 | 69.277 | 1.00 | 52.13 | C |
| ATOM | 5394 | CE2 | PHE | D | 27 | 38.615 | 4.910 | 70.501 | 1.00 | 48.56 | C |
| ATOM | 5395 | CD2 | PHE | D | 27 | 37.448 | 5.689 | 70.566 | 1.00 | 51.11 | C |
| ATOM | 5396 | C | PHE | D | 27 | 34.615 | 9.371 | 69.489 | 1.00 | 43.23 | C |
| ATOM | 5397 | O | PHE | D | 27 | 33.529 | 9.006 | 69.943 | 1.00 | 45.00 | O |
| ATOM | 5398 | N | SER | D | 28 | 34.772 | 10.415 | 68.703 | 1.00 | 44.56 | N |
| ATOM | 5399 | CA | SER | D | 28 | 33.836 | 11.501 | 68.540 | 1.00 | 44.58 | C |
| ATOM | 5400 | CB | SER | D | 28 | 34.533 | 12.753 | 69.087 | 1.00 | 48.08 | C |
| ATOM | 5401 | CG | SER | D | 28 | 33.629 | 13.829 | 69.262 | 1.00 | 53.05 | C |
| ATOM | 5402 | CO | SER | D | 28 | 33.484 | 11.739 | 67.037 | 1.00 | 44.23 | O |
| ATOM | 5403 | O | SER | D | 28 | 34.111 | 11.187 | 66.116 | 1.00 | 44.71 | O |
| ATOM | 5404 | N | ALA | D | 29 | 32.469 | 12.569 | 66.820 | 1.00 | 44.58 | N |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 5405 | CA  | ALA | D | 29 | 32.056 | 13.001 | 65.507 | 1.00 | 47.54 | C |
| ATOM | 5406 | CB  | ALA | D | 29 | 30.860 | 12.195 | 65.062 | 1.00 | 43.39 | C |
| ATOM | 5407 | C   | ALA | D | 29 | 31.693 | 14.459 | 65.648 | 1.00 | 47.85 | C |
| ATOM | 5408 | O   | ALA | D | 29 | 31.110 | 14.832 | 66.639 | 1.00 | 49.41 | O |
| ATOM | 5409 | N   | THR | D | 30 | 32.042 | 15.253 | 64.652 | 1.00 | 45.91 | N |
| ATOM | 5410 | CA  | THR | D | 30 | 31.779 | 16.681 | 64.645 | 1.00 | 48.34 | C |
| ATOM | 5411 | CB  | THR | D | 30 | 32.547 | 17.273 | 63.430 | 1.00 | 50.49 | C |
| ATOM | 5412 | OG1 | THR | D | 30 | 33.932 | 17.427 | 63.781 | 1.00 | 54.94 | O |
| ATOM | 5413 | CG2 | THR | D | 30 | 32.015 | 18.540 | 63.050 | 1.00 | 50.33 | C |
| ATOM | 5414 | C   | THR | D | 30 | 30.275 | 17.100 | 64.580 | 1.00 | 50.32 | C |
| ATOM | 5415 | O   | THR | D | 30 | 29.895 | 18.176 | 65.083 | 1.00 | 47.25 | O |
| ATOM | 5416 | N   | TRP | D | 30 | 29.450 | 16.265 | 63.929 | 1.00 | 49.20 | N |
| ATOM | 5417 | CA  | TRP | D | 31 | 28.006 | 16.485 | 63.732 | 1.00 | 50.26 | C |
| ATOM | 5418 | CB  | TRP | D | 31 | 27.578 | 15.850 | 62.397 | 1.00 | 47.26 | C |
| ATOM | 5419 | CG  | TRP | D | 31 | 28.002 | 14.416 | 62.304 | 1.00 | 46.07 | C |
| ATOM | 5420 | CD1 | TRP | D | 31 | 29.129 | 13.941 | 61.718 | 1.00 | 41.62 | C |
| ATOM | 5421 | NE1 | TRP | D | 31 | 29.187 | 12.568 | 61.841 | 1.00 | 42.04 | N |
| ATOM | 5422 | CE2 | TRP | D | 31 | 28.071 | 12.132 | 62.501 | 1.00 | 39.40 | C |
| ATOM | 5423 | CD2 | TRP | D | 31 | 27.293 | 13.267 | 62.807 | 1.00 | 37.29 | C |
| ATOM | 5424 | CE3 | TRP | D | 31 | 26.069 | 13.090 | 63.484 | 1.00 | 46.65 | C |
| ATOM | 5425 | CZ3 | TRP | D | 31 | 25.679 | 11.787 | 63.855 | 1.00 | 37.74 | C |
| ATOM | 5426 | CH2 | TRP | D | 31 | 26.485 | 10.683 | 63.533 | 1.00 | 33.39 | C |
| ATOM | 5427 | CZ2 | TRP | D | 31 | 27.671 | 10.830 | 62.846 | 1.00 | 41.82 | C |
| ATOM | 5428 | C   | TRP | D | 31 | 27.112 | 15.931 | 64.851 | 1.00 | 50.47 | C |
| ATOM | 5429 | O   | TRP | D | 31 | 25.026 | 16.225 | 64.001 | 1.00 | 49.26 | O |
| ATOM | 5430 | N   | CYS | D | 32 | 27.698 | 15.156 | 65.761 | 1.00 | 51.33 | N |
| ATOM | 5431 | CA  | CYS | D | 32 | 26.964 | 14.392 | 66.795 | 1.00 | 50.78 | C |
| ATOM | 5432 | CB  | CYS | D | 32 | 27.777 | 13.144 | 67.163 | 1.00 | 51.86 | C |
| ATOM | 5433 | SG  | CYS | D | 32 | 27.047 | 12.161 | 68.525 | 1.00 | 53.52 | S |
| ATOM | 5434 | C   | CYS | D | 32 | 26.692 | 15.196 | 68.070 | 1.00 | 49.39 | C |
| ATOM | 5435 | O   | CYS | D | 32 | 27.628 | 15.559 | 68.798 | 1.00 | 49.12 | O |
| ATOM | 5436 | N   | GLY | D | 33 | 25.423 | 15.436 | 68.366 | 1.00 | 44.53 | N |
| ATOM | 5437 | CA  | GLY | D | 33 | 25.002 | 16.226 | 69.525 | 1.00 | 43.18 | C |
| ATOM | 5438 | C   | GLY | D | 33 | 25.687 | 15.791 | 70.828 | 1.00 | 46.15 | C |
| ATOM | 5439 | O   | GLY | D | 33 | 26.449 | 16.562 | 71.418 | 1.00 | 47.94 | O |
| ATOM | 5440 | N   | PRO | D | 34 | 25.407 | 14.563 | 71.299 | 1.00 | 45.21 | N |
| ATOM | 5441 | CA  | PRO | D | 34 | 26.050 | 14.084 | 72.539 | 1.00 | 44.98 | C |
| ATOM | 5442 | CB  | PRO | D | 34 | 25.649 | 12.610 | 72.601 | 1.00 | 42.70 | C |
| ATOM | 5443 | CG  | PRO | D | 34 | 24.344 | 12.565 | 71.882 | 1.00 | 41.84 | C |
| ATOM | 5444 | CD  | PRO | D | 34 | 24.457 | 13.572 | 70.750 | 1.00 | 45.09 | C |
| ATOM | 5445 | C   | PRO | D | 34 | 27.568 | 14.250 | 72.540 | 1.00 | 46.40 | C |
| ATOM | 5446 | O   | PRO | D | 34 | 28.119 | 14.649 | 73.558 | 1.00 | 45.29 | O |
| ATOM | 5447 | N   | ALA | D | 35 | 28.223 | 13.992 | 71.397 | 1.00 | 46.49 | N |
| ATOM | 5448 | CA  | ALA | D | 35 | 29.684 | 14.116 | 71.274 | 1.00 | 44.50 | C |
| ATOM | 5449 | CB  | ALA | D | 35 | 30.175 | 13.543 | 69.939 | 1.00 | 41.27 | C |
| ATOM | 5450 | C   | ALA | D | 35 | 30.166 | 15.562 | 71.483 | 1.00 | 47.17 | C |
| ATOM | 5451 | O   | ALA | D | 35 | 31.074 | 15.803 | 72.263 | 1.00 | 46.21 | O |
| ATOM | 5452 | N   | LYS | D | 36 | 29.547 | 16.523 | 70.809 | 1.00 | 42.77 | N |
| ATOM | 5453 | CA  | LYS | D | 36 | 29.842 | 17.948 | 71.045 | 1.00 | 47.82 | C |
| ATOM | 5454 | CB  | LYS | D | 36 | 28.928 | 18.868 | 70.219 | 1.00 | 45.80 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 5455 | CG | LYS | D | 36 | 29.005 | 18.766 | 68.728 | 1.00 | 53.51 | C |
| ATOM | 5456 | CD | LYS | D | 36 | 27.812 | 19.611 | 68.101 | 1.00 | 50.69 | C |
| ATOM | 5457 | CE | LYS | D | 36 | 27.348 | 19.016 | 66.773 | 1.00 | 56.79 | C |
| ATOM | 5458 | NZ | LYS | D | 36 | 26.405 | 19.886 | 65.948 | 1.00 | 64.71 | N |
| ATOM | 5459 | C | LYS | D | 36 | 29.605 | 18.340 | 72.510 | 1.00 | 46.31 | C |
| ATOM | 5460 | O | LYS | D | 36 | 30.313 | 19.171 | 73.054 | 1.00 | 49.45 | O |
| ATOM | 5461 | N | MET | D | 37 | 28.554 | 17.812 | 73.117 | 1.00 | 46.90 | N |
| ATOM | 5462 | CA | MET | D | 37 | 28.190 | 18.221 | 74.459 | 1.00 | 45.95 | C |
| ATOM | 5463 | CB | MET | D | 37 | 26.855 | 17.581 | 74.862 | 1.00 | 45.98 | C |
| ATOM | 5464 | CG | MET | D | 37 | 26.384 | 17.859 | 76.312 | 1.00 | 44.48 | C |
| ATOM | 5465 | CD | MET | D | 37 | 27.016 | 16.731 | 77.578 | 1.00 | 56.23 | C |
| ATOM | 5466 | CE | MET | D | 37 | 25.816 | 15.410 | 77.409 | 1.00 | 57.05 | S |
| ATOM | 5467 | C | MET | D | 37 | 29.314 | 17.845 | 75.451 | 1.00 | 47.19 | C |
| ATOM | 5468 | O | MET | D | 37 | 29.654 | 18.627 | 76.364 | 1.00 | 46.47 | O |
| ATOM | 5469 | N | ILE | D | 38 | 29.862 | 16.642 | 75.299 | 1.00 | 45.62 | N |
| ATOM | 5470 | CA | ILE | D | 38 | 30.790 | 16.146 | 76.320 | 1.00 | 44.40 | C |
| ATOM | 5471 | CB | ILE | D | 38 | 30.689 | 14.609 | 76.520 | 1.00 | 46.04 | C |
| ATOM | 5472 | CG1 | ILE | D | 38 | 31.338 | 14.214 | 77.873 | 1.00 | 43.45 | C |
| ATOM | 5473 | CD1 | ILE | D | 38 | 30.629 | 13.066 | 78.553 | 1.00 | 46.20 | C |
| ATOM | 5474 | CG2 | ILE | D | 38 | 31.233 | 13.834 | 75.300 | 1.00 | 49.82 | C |
| ATOM | 5475 | C | ILE | D | 38 | 32.218 | 16.641 | 76.112 | 1.00 | 46.85 | C |
| ATOM | 5476 | O | ILE | D | 38 | 33.068 | 16.478 | 77.001 | 1.00 | 46.74 | O |
| ATOM | 5477 | N | LYS | D | 39 | 32.482 | 17.257 | 74.941 | 1.00 | 42.87 | N |
| ATOM | 5478 | CA | LYS | D | 39 | 33.844 | 17.653 | 74.563 | 1.00 | 43.76 | C |
| ATOM | 5479 | CB | LYS | D | 39 | 33.856 | 18.362 | 73.185 | 1.00 | 43.06 | C |
| ATOM | 5480 | CG | LYS | D | 39 | 34.254 | 17.506 | 72.048 | 1.00 | 55.75 | C |
| ATOM | 5481 | CD | LYS | D | 39 | 34.447 | 18.387 | 70.802 | 1.00 | 54.62 | C |
| ATOM | 5482 | CE | LYS | D | 39 | 35.879 | 18.820 | 70.663 | 1.00 | 54.46 | C |
| ATOM | 5483 | NZ | LYS | D | 39 | 36.124 | 19.557 | 69.381 | 1.00 | 69.55 | N |
| ATOM | 5484 | C | LYS | D | 39 | 34.550 | 18.583 | 75.541 | 1.00 | 44.99 | C |
| ATOM | 5485 | O | LYS | D | 39 | 35.741 | 18.363 | 75.830 | 1.00 | 43.77 | O |
| ATOM | 5486 | N | PRO | D | 40 | 33.872 | 19.696 | 75.959 | 1.00 | 46.48 | N |
| ATOM | 5487 | CA | PRO | D | 40 | 34.428 | 20.647 | 76.967 | 1.00 | 43.02 | C |
| ATOM | 5488 | CB | PRO | D | 40 | 33.271 | 21.628 | 77.216 | 1.00 | 42.37 | C |
| ATOM | 5489 | CG | PRO | D | 40 | 32.404 | 21.531 | 76.039 | 1.00 | 46.26 | C |
| ATOM | 5490 | CD | PRO | D | 40 | 32.535 | 20.125 | 75.504 | 1.00 | 42.96 | C |
| ATOM | 5491 | C | PRO | D | 40 | 37.719 | 19.937 | 78.267 | 1.00 | 47.39 | C |
| ATOM | 5492 | O | PRO | D | 40 | 35.691 | 20.280 | 78.988 | 1.00 | 46.05 | O |
| ATOM | 5493 | N | PHE | D | 41 | 33.882 | 18.956 | 78.594 | 1.00 | 45.83 | N |
| ATOM | 5494 | CA | PHE | D | 41 | 34.065 | 18.268 | 79.871 | 1.00 | 45.07 | C |
| ATOM | 5495 | CB | PHE | D | 41 | 32.819 | 17.477 | 80.294 | 1.00 | 48.72 | C |
| ATOM | 5496 | CG | PHE | D | 41 | 31.632 | 18.342 | 80.619 | 1.00 | 55.21 | C |
| ATOM | 5497 | CD1 | PHE | D | 41 | 31.650 | 10.101 | 81.716 | 1.00 | 58.16 | C |
| ATOM | 5498 | CE1 | PHE | D | 41 | 30.558 | 20.004 | 82.010 | 1.00 | 53.76 | C |
| ATOM | 5499 | CZ | PHE | D | 41 | 29.431 | 19.975 | 81.191 | 1.00 | 68.19 | C |
| ATOM | 5500 | CE2 | PHE | D | 41 | 29.404 | 19.136 | 80.070 | 1.00 | 66.14 | C |
| ATOM | 5501 | CD2 | PHE | D | 41 | 30.505 | 18.334 | 79.790 | 1.00 | 61.88 | C |
| ATOM | 5502 | C | PHE | D | 41 | 35.247 | 17.335 | 79.779 | 1.00 | 44.06 | C |
| ATOM | 5503 | O | PHE | D | 41 | 35.985 | 17.177 | 80.738 | 1.00 | 43.91 | O |
| ATOM | 5504 | N | PHE | D | 42 | 35.419 | 16.688 | 78.639 | 1.00 | 42.08 | N |

TABLE 10-continued

Atomic coordinates for COM1 complex of the modified
TXNIP protein represented by SEQ ID NO: 6 and the modified protein represented by SEQ ID NO: 3

| | | | | | | | | | | | |
|---|---|---|---|---|---|---|---|---|---|---|---|
| ATOM | 5505 | CA | PHE | D | 42 | 36.608 | 15.827 | 78.422 | 1.00 | 43.12 | C |
| ATOM | 5506 | CB | PHE | D | 42 | 36.460 | 15.210 | 77.014 | 1.00 | 46.32 | C |
| ATOM | 5507 | CG | PHE | D | 42 | 37.429 | 14.119 | 76.715 | 1.00 | 37.47 | C |
| ATOM | 5508 | CD1 | PHE | D | 42 | 37.356 | 12.897 | 77.366 | 1.00 | 41.83 | C |
| ATOM | 5509 | CE1 | PHE | D | 42 | 38.269 | 11.894 | 77.065 | 1.00 | 38.69 | C |
| ATOM | 5510 | CZ | PHE | D | 42 | 39.247 | 12.099 | 76.113 | 1.00 | 42.03 | C |
| ATOM | 5511 | CE2 | PHE | D | 42 | 39.342 | 13.317 | 75.480 | 1.00 | 34.01 | C |
| ATOM | 5512 | CD2 | PHE | D | 42 | 38.431 | 14.315 | 75.778 | 1.00 | 46.46 | C |
| ATOM | 5513 | C | PHE | D | 42 | 37.859 | 16.679 | 78.491 | 1.00 | 43.31 | C |
| ATOM | 5514 | O | PHE | D | 42 | 38.882 | 16.266 | 79.012 | 1.00 | 42.73 | O |
| ATOM | 5515 | N | HIS | D | 43 | 37.780 | 17.910 | 77.969 | 1.00 | 42.42 | N |
| ATOM | 5516 | CA | HIS | D | 43 | 38.886 | 18.848 | 78.095 | 1.00 | 40.30 | C |
| ATOM | 5517 | CB | HIS | D | 43 | 38.667 | 20.079 | 77.234 | 1.00 | 40.12 | C |
| ATOM | 5518 | CG | HIS | D | 43 | 39.723 | 21.110 | 77.448 | 1.00 | 51.79 | C |
| ATOM | 5519 | ND1 | HIS | D | 43 | 40.895 | 21.126 | 76.728 | 1.00 | 50.68 | N |
| ATOM | 5520 | CE1 | HIS | D | 43 | 41.650 | 22.111 | 77.164 | 1.00 | 57.00 | C |
| ATOM | 5521 | NE2 | HIS | D | 43 | 41.037 | 22.714 | 78.164 | 1.00 | 56.39 | N |
| ATOM | 5522 | CD2 | HIS | D | 43 | 39.824 | 22.105 | 78.352 | 1.00 | 57.44 | C |
| ATOM | 5523 | C | HIS | D | 43 | 39.205 | 19.312 | 79.525 | 1.00 | 42.96 | C |
| ATOM | 5524 | O | HIS | D | 43 | 40.385 | 19.354 | 70.050 | 1.00 | 30.30 | O |
| ATOM | 5525 | N | SER | D | 44 | 38.176 | 19.735 | 80.240 | 1.00 | 41.90 | N |
| ATOM | 5526 | CA | SER | D | 44 | 38.329 | 20.128 | 81.615 | 1.00 | 43.75 | C |
| ATOM | 5527 | CB | SER | D | 44 | 36.951 | 20.470 | 82.164 | 1.00 | 44.71 | C |
| ATOM | 5528 | OG | SER | D | 44 | 36.481 | 21.589 | 81.454 | 1.00 | 46.63 | O |
| ATOM | 5529 | C | SER | D | 44 | 38.965 | 19.014 | 82.418 | 1.00 | 45.90 | C |
| ATOM | 5530 | O | SER | D | 44 | 39.792 | 19.266 | 83.302 | 1.00 | 49.23 | O |
| ATOM | 5531 | N | LEU | D | 45 | 38.575 | 17.772 | 82.129 | 1.00 | 42.89 | N |
| ATOM | 5532 | CA | LEU | D | 45 | 39.146 | 16.637 | 82.861 | 1.00 | 41.30 | C |
| ATOM | 5533 | CB | LEU | D | 45 | 38.365 | 15.367 | 82.562 | 1.00 | 44.40 | C |
| ATOM | 5534 | CG | LEU | D | 45 | 37.012 | 15.039 | 83.222 | 1.00 | 49.55 | C |
| ATOM | 5535 | CD1 | LEU | D | 45 | 36.476 | 13.788 | 82.567 | 1.00 | 36.67 | C |
| ATOM | 5536 | CD2 | LEU | D | 45 | 37.140 | 14.815 | 84.708 | 1.00 | 46.27 | C |
| ATOM | 5537 | C | LEU | D | 45 | 40.615 | 16.424 | 82.514 | 1.00 | 42.26 | C |
| ATOM | 5538 | O | LEU | D | 45 | 41.431 | 16.068 | 83.384 | 1.00 | 43.84 | O |
| ATOM | 5539 | N | SER | D | 46 | 40.968 | 16.651 | 81.254 | 1.00 | 42.85 | N |
| ATOM | 5540 | CA | SER | D | 46 | 42.363 | 16.543 | 80.801 | 1.00 | 43.29 | C |
| ATOM | 5541 | CB | SER | D | 46 | 42.451 | 16.726 | 79.275 | 1.00 | 41.55 | C |
| ATOM | 5542 | OG | SER | D | 46 | 42.528 | 18.086 | 78.928 | 1.00 | 41.79 | O |
| ATOM | 5543 | C | SER | D | 46 | 43.280 | 17.541 | 81.502 | 1.00 | 42.45 | C |
| ATOM | 5544 | O | SER | D | 46 | 44.488 | 17.290 | 81.657 | 1.00 | 42.93 | O |
| ATOM | 5545 | N | GLU | D | 47 | 42.706 | 18.674 | 81.901 | 1.00 | 41.68 | N |
| ATOM | 5546 | CA | GLU | D | 47 | 43.424 | 19.690 | 82.697 | 1.00 | 44.72 | C |
| ATOM | 5547 | CB | GLU | D | 47 | 42.770 | 21.054 | 82.499 | 1.00 | 47.26 | C |
| ATOM | 5548 | CG | GLU | D | 47 | 43.025 | 21.679 | 81.112 | 1.00 | 52.73 | C |
| ATOM | 5549 | CD | GLU | D | 47 | 44.509 | 21.929 | 80.829 | 1.00 | 58.37 | C |
| ATOM | 5550 | OE1 | GLU | D | 47 | 45.241 | 22.328 | 81.762 | 1.00 | 63.82 | O |
| ATOM | 5551 | OE2 | GLU | D | 47 | 44.957 | 21.721 | 79.878 | 1.00 | 57.61 | O |
| ATOM | 5552 | C | GLU | D | 47 | 43.507 | 19.356 | 84.190 | 1.00 | 45.31 | C |
| ATOM | 5553 | O | GLU | D | 47 | 44.503 | 19.883 | 84.863 | 1.00 | 42.93 | O |
| ATOM | 5554 | N | LYS | D | 48 | 42.473 | 18.705 | 84.726 | 1.00 | 45.81 | N |

TABLE 10-continued

Atomic coordinates for COM1 complex of the modified
TXNIP prot

TABLE 10-continued

Atomic coordinates for COM1 complex of the modified
TXNIP protein represented by SEQ ID NO: 6 and the modified protein represented by SEQ ID NO: 3

| ATOM | 5605 | CA  | PHE | D | 54 | 43.754 | 12.445 | 78.652 | 1.00 | 41.98 | C |
|------|------|-----|-----|---|----|--------|--------|--------|------|-------|---|
| ATOM | 5606 | CB  | PHE | D | 54 | 42.965 | 13.613 | 77.284 | 1.00 | 40.32 | C |
| ATOM | 5607 | CG  | PHE | D | 54 | 42.496 | 13.353 | 78.701 | 1.00 | 42.19 | C |
| ATOM | 5608 | CD1 | PHE | D | 54 | 43.387 | 13.415 | 79.782 | 1.00 | 47.65 | C |
| ATOM | 5609 | CE1 | PHE | D | 54 | 42.950 | 13.173 | 81.090 | 1.00 | 46.34 | C |
| ATOM | 5610 | CZ  | PHE | D | 54 | 41.618 | 12.886 | 81.335 | 1.00 | 46.86 | C |
| ATOM | 5611 | CE2 | PHE | D | 54 | 40.726 | 12.840 | 80.271 | 1.00 | 54.23 | C |
| ATOM | 5612 | CD2 | PHE | D | 54 | 41.170 | 13.072 | 78.966 | 1.00 | 53.58 | C |
| ATOM | 5613 | C   | PHE | D | 54 | 43.848 | 12.637 | 75.144 | 1.00 | 45.83 | C |
| ATOM | 5614 | O   | PHE | D | 54 | 44.492 | 13.580 | 74.662 | 1.00 | 43.60 | O |
| ATOM | 5615 | N   | LEU | D | 55 | 43.196 | 11.746 | 74.398 | 1.00 | 43.62 | N |
| ATOM | 5616 | CA  | LEU | D | 55 | 43.222 | 11.810 | 72.943 | 1.00 | 44.07 | C |
| ATOM | 5617 | CB  | LEU | D | 55 | 43.914 | 10.576 | 72.370 | 1.00 | 46.54 | C |
| ATOM | 5618 | CG  | LEU | D | 55 | 45.308 | 10.162 | 72.840 | 1.00 | 45.20 | C |
| ATOM | 5619 | CD1 | LEU | D | 55 | 45.680 | 8.855  | 72.193 | 1.00 | 42.63 | C |
| ATOM | 5620 | CD2 | LEU | D | 55 | 46.314 | 11.256 | 72.496 | 1.00 | 42.54 | C |
| ATOM | 5621 | C   | LEU | D | 55 | 41.821 | 11.893 | 72.370 | 1.00 | 43.71 | C |
| ATOM | 5622 | O   | LEU | D | 55 | 40.882 | 11.424 | 72.985 | 1.00 | 42.73 | O |
| ATOM | 5623 | N   | GLU | D | 56 | 41.688 | 12.503 | 71.198 | 1.00 | 43.76 | N |
| ATOM | 5624 | CA  | GLU | D | 56 | 40.415 | 12.440 | 70.454 | 1.00 | 48.04 | C |
| ATOM | 5625 | CB  | GLU | D | 56 | 39.689 | 13.782 | 70.377 | 1.00 | 49.64 | C |
| ATOM | 5626 | CG  | GLU | D | 56 | 38.318 | 13.614 | 69.644 | 1.00 | 44.97 | C |
| ATOM | 5627 | CD  | GLU | D | 56 | 37.712 | 14.922 | 69.204 | 1.00 | 62.32 | C |
| ATOM | 5628 | OE1 | GLU | D | 56 | 37.512 | 15.795 | 70.084 | 1.00 | 57.12 | O |
| ATOM | 5629 | OE2 | GLU | D | 56 | 37.435 | 15.067 | 67.973 | 1.00 | 56.35 | O |
| ATOM | 5630 | C   | GLU | D | 56 | 40.623 | 11.914 | 69.028 | 1.00 | 47.39 | C |
| ATOM | 5631 | O   | GLU | D | 56 | 41.536 | 12.349 | 68.323 | 1.00 | 48.54 | O |
| ATOM | 5632 | N   | VAL | D | 57 | 39.772 | 10.973 | 68.640 | 1.00 | 46.90 | N |
| ATOM | 5633 | CA  | VAL | D | 57 | 39.714 | 10.482 | 67.260 | 1.00 | 45.81 | C |
| ATOM | 5634 | CB  | VAL | D | 57 | 39.984 | 8.972  | 67.209 | 1.00 | 46.22 | C |
| ATOM | 5635 | CG1 | VAL | D | 57 | 39.960 | 8.465  | 65.775 | 1.00 | 48.02 | C |
| ATOM | 5636 | CG2 | VAL | D | 57 | 41.342 | 8.672  | 67.869 | 1.00 | 39.46 | C |
| ATOM | 5637 | C   | VAL | D | 57 | 38.364 | 10.802 | 66.666 | 1.00 | 45.88 | C |
| ATOM | 5638 | O   | VAL | D | 57 | 37.337 | 10.400 | 67.203 | 1.00 | 43.24 | O |
| ATOM | 5639 | N   | ASP | D | 58 | 38.367 | 11.538 | 65.557 | 1.00 | 45.37 | N |
| ATOM | 5640 | CA  | ASP | D | 58 | 37.134 | 11.823 | 64.849 | 1.00 | 47.62 | C |
| ATOM | 5641 | CB  | ASP | D | 58 | 37.232 | 13.136 | 64.081 | 1.00 | 47.86 | C |
| ATOM | 5642 | CG  | ASP | D | 58 | 35.936 | 13.497 | 63.398 | 1.00 | 50.72 | C |
| ATOM | 5643 | OD1 | ASP | D | 58 | 35.506 | 12.754 | 62.501 | 1.00 | 50.92 | O |
| ATOM | 5644 | OD2 | ASP | D | 58 | 35.344 | 14.522 | 63.763 | 1.00 | 46.12 | O |
| ATOM | 5645 | C   | ASP | D | 58 | 36.872 | 10.665 | 63.920 | 1.00 | 44.92 | C |
| ATOM | 5646 | O   | ASP | D | 58 | 37.675 | 10.367 | 63.019 | 1.00 | 46.96 | O |
| ATOM | 5647 | N   | VAL | D | 59 | 35.761 | 9.990  | 64.164 | 1.00 | 43.94 | N |
| ATOM | 5648 | CA  | VAL | D | 59 | 35.507 | 8.701  | 63.514 | 1.00 | 45.77 | C |
| ATOM | 5649 | CB  | VAL | D | 59 | 34.311 | 7.947  | 64.164 | 1.00 | 43.94 | C |
| ATOM | 5650 | CG1 | VAL | D | 59 | 34.495 | 7.811  | 65.650 | 1.00 | 44.95 | C |
| ATOM | 5651 | CG2 | VAL | D | 59 | 32.980 | 8.640  | 63.836 | 1.00 | 49.96 | C |
| ATOM | 5652 | C   | VAL | D | 59 | 35.215 | 8.871  | 62.015 | 1.00 | 45.76 | C |
| ATOM | 5653 | O   | VAL | D | 59 | 35.247 | 7.881  | 61.259 | 1.00 | 47.33 | O |
| ATOM | 5654 | N   | ASP | D | 60 | 34.917 | 10.108 | 61.598 | 1.00 | 44.34 | N |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 5655 | CA  | ASP | D | 60 | 34.674 | 10.387 | 60.176 | 1.00 | 45.36 | C |
| ATOM | 5656 | CB  | ASP | D | 60 | 33.736 | 11.580 | 59.975 | 1.00 | 45.74 | C |
| ATOM | 5657 | CG  | ASP | D | 60 | 32.381 | 11.287 | 60.475 | 1.00 | 53.12 | C |
| ATOM | 5658 | OD1 | ASP | D | 60 | 31.772 | 12.082 | 61.255 | 1.00 | 58.89 | O |
| ATOM | 5659 | OD2 | ASP | D | 60 | 31.804 | 10.230 | 60.116 | 1.00 | 50.52 | O |
| ATOM | 5660 | C   | ASP | D | 60 | 35.978 | 10.592 | 59.442 | 1.00 | 46.33 | C |
| ATOM | 5661 | O   | ASP | D | 60 | 36.126 | 10.153 | 58.312 | 1.00 | 47.56 | O |
| ATOM | 5662 | N   | ASP | D | 61 | 36.924 | 11.256 | 60.092 | 1.00 | 47.04 | N |
| ATOM | 5663 | CA  | ASP | D | 61 | 38.221 | 11.520 | 59.505 | 1.00 | 48.99 | C |
| ATOM | 5664 | CB  | ASP | D | 61 | 38.933 | 12.658 | 60.230 | 1.00 | 49.34 | C |
| ATOM | 5665 | CG  | ASP | D | 61 | 38.171 | 13.975 | 60.182 | 1.00 | 52.23 | C |
| ATOM | 5666 | OD1 | ASP | D | 61 | 37.610 | 14.340 | 59.126 | 1.00 | 55.41 | O |
| ATOM | 5667 | OD2 | ASP | D | 61 | 38.199 | 14.686 | 61.209 | 1.00 | 52.09 | O |
| ATOM | 5668 | C   | ASP | D | 61 | 39.108 | 10.281 | 59.533 | 1.00 | 52.51 | C |
| ATOM | 5669 | O   | ASP | D | 61 | 39.838 | 10.012 | 58.558 | 1.00 | 52.35 | O |
| ATOM | 5670 | N   | CYS | D | 62 | 39.049 | 9.544  | 60.643 | 1.00 | 52.76 | N |
| ATOM | 5671 | CA  | CYS | D | 62 | 39.869 | 8.350  | 60.837 | 1.00 | 55.28 | C |
| ATOM | 5672 | CB  | CYS | D | 62 | 40.729 | 8.505  | 62.081 | 1.00 | 55.72 | C |
| ATOM | 5673 | SG  | CYS | D | 62 | 41.784 | 9.941  | 62.015 | 1.00 | 64.64 | S |
| ATOM | 5674 | C   | CYS | D | 62 | 39.014 | 7.099  | 60.946 | 1.00 | 54.12 | C |
| ATOM | 5675 | O   | CYS | D | 62 | 38.967 | 6.458  | 61.991 | 1.00 | 53.96 | O |
| ATOM | 5676 | N   | GLN | D | 63 | 38.339 | 6.745  | 59.860 | 1.00 | 56.00 | N |
| ATOM | 5677 | CA  | GLN | D | 63 | 37.417 | 5.598  | 59.876 | 1.00 | 59.33 | C |
| ATOM | 5678 | CB  | GLN | D | 63 | 36.637 | 5.468  | 58.554 | 1.00 | 61.29 | C |
| ATOM | 5679 | CG  | GLN | D | 63 | 36.006 | 6.753  | 58.035 | 1.00 | 68.11 | C |
| ATOM | 5680 | CD  | GLN | D | 63 | 35.515 | 6.653  | 56.577 | 1.00 | 77.29 | C |
| ATOM | 5681 | OE1 | GLN | D | 63 | 35.398 | 7.760  | 55.879 | 1.00 | 79.98 | O |
| ATOM | 5682 | NE2 | GLN | D | 63 | 35.231 | 5.430  | 56.118 | 1.00 | 81.11 | N |
| ATOM | 5683 | C   | GLN | D | 63 | 38.127 | 4.281  | 60.215 | 1.00 | 58.06 | C |
| ATOM | 5684 | O   | GLN | D | 63 | 37.544 | 3.415  | 60.861 | 1.00 | 57.77 | O |
| ATOM | 5685 | N   | ASP | D | 64 | 39.381 | 4.143  | 59.769 | 1.00 | 59.03 | N |
| ATOM | 5686 | CA  | ASP | D | 64 | 40.181 | 2.927  | 59.993 | 1.00 | 59.42 | C |
| ATOM | 5687 | CB  | ASP | D | 64 | 41.378 | 2.864  | 59.027 | 1.00 | 60.23 | C |
| ATOM | 5688 | CG  | ASP | D | 64 | 42.345 | 4.040  | 59.189 | 1.00 | 65.06 | C |
| ATOM | 5689 | OD1 | ASP | D | 64 | 41.928 | 5.132  | 59.643 | 1.00 | 70.36 | O |
| ATOM | 5690 | OD2 | ASP | D | 64 | 43.540 | 3.870  | 58.843 | 1.00 | 75.99 | O |
| ATOM | 5691 | C   | ASP | D | 64 | 40.630 | 2.729  | 61.452 | 1.00 | 58.41 | C |
| ATOM | 5692 | O   | ASP | D | 64 | 40.646 | 1.602  | 61.955 | 1.00 | 60.95 | O |
| ATOM | 5693 | N   | VAL | D | 65 | 41.001 | 3.818  | 62.124 | 1.00 | 55.77 | N |
| ATOM | 5694 | CA  | VAL | D | 65 | 41.302 | 3.776  | 63.558 | 1.00 | 54.61 | C |
| ATOM | 5695 | CB  | VAL | D | 65 | 41.854 | 5.139  | 64.102 | 1.00 | 55.00 | C |
| ATOM | 5696 | CG1 | VAL | D | 65 | 42.094 | 5.093  | 65.607 | 1.00 | 45.71 | C |
| ATOM | 5697 | CG2 | VAL | D | 65 | 43.135 | 5.505  | 63.400 | 1.00 | 56.28 | C |
| ATOM | 5698 | C   | VAL | D | 65 | 40.019 | 3.349  | 64.269 | 1.00 | 53.37 | C |
| ATOM | 5699 | O   | VAL | D | 65 | 40.026 | 2.384  | 65.044 | 1.00 | 53.41 | O |
| ATOM | 5700 | N   | ALA | D | 66 | 38.912 | 4.029  | 63.955 | 1.00 | 51.42 | N |
| ATOM | 5701 | CA  | ALA | D | 66 | 37.608 | 3.691  | 64.527 | 1.00 | 47.51 | C |
| ATOM | 5702 | CB  | ALA | D | 66 | 36.559 | 4.617  | 64.006 | 1.00 | 47.07 | C |
| ATOM | 5703 | C   | ALA | D | 66 | 37.185 | 2.238  | 64.319 | 1.00 | 47.52 | C |
| ATOM | 5704 | O   | ALA | D | 66 | 36.644 | 1.613  | 65.234 | 1.00 | 46.36 | O |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 5705 | N | SER | D | 67 | 37.419 | 1.697 | 63.123 | 1.00 | 47.29 | N |
| ATOM | 5706 | CA | SER | D | 67 | 36.989 | 0.335 | 62.835 | 1.00 | 48.46 | C |
| ATOM | 5707 | CB | SER | D | 67 | 36.775 | 0.102 | 61.326 | 1.00 | 50.07 | C |
| ATOM | 5708 | OG | SER | D | 67 | 37.899 | 0.493 | 60.563 | 1.00 | 57.77 | O |
| ATOM | 5709 | C | SER | D | 67 | 37.903 | -0.713 | 63.465 | 1.00 | 47.72 | C |
| ATOM | 5710 | O | SER | D | 67 | 37.442 | -1.780 | 63.880 | 1.00 | 45.78 | O |
| ATOM | 5711 | N | GLU | D | 68 | 39.194 | -0.410 | 63.541 | 1.00 | 50.89 | N |
| ATOM | 5712 | CA | GLU | D | 68 | 40.130 | -1.295 | 64.238 | 1.00 | 53.07 | C |
| ATOM | 5713 | CB | GLU | D | 68 | 41.572 | -0.011 | 63.934 | 1.00 | 54.20 | C |
| ATOM | 5714 | CG | GLU | D | 68 | 41.990 | -1.311 | 62.533 | 1.00 | 62.12 | C |
| ATOM | 5715 | CD | GLU | D | 68 | 43.436 | -0.978 | 62.216 | 1.00 | 70.69 | C |
| ATOM | 5716 | OE1 | GLU | D | 68 | 43.832 | -1.167 | 61.044 | 1.00 | 70.10 | O |
| ATOM | 5717 | OE2 | GLU | D | 68 | 44.175 | -0.530 | 63.128 | 1.00 | 72.37 | O |
| ATOM | 5718 | C | GLU | D | 68 | 39.866 | -1.301 | 65.745 | 1.00 | 51.98 | C |
| ATOM | 5719 | O | GLU | D | 68 | 39.976 | -2.329 | 66.408 | 1.00 | 52.75 | O |
| ATOM | 5720 | N | CYS | D | 69 | 39.483 | -0.147 | 66.275 | 1.00 | 53.22 | N |
| ATOM | 5721 | CA | CYS | D | 69 | 39.069 | -0.062 | 67.666 | 1.00 | 50.32 | C |
| ATOM | 5722 | CB | CYS | D | 69 | 39.317 | 1.349 | 68.192 | 1.00 | 50.25 | C |
| ATOM | 5723 | SG | CYS | D | 69 | 41.095 | 1.799 | 68.095 | 1.00 | 46.98 | S |
| ATOM | 5724 | C | CYS | D | 69 | 37.617 | -0.536 | 57.847 | 1.00 | 50.70 | C |
| ATOM | 5725 | O | CYS | D | 69 | 37.136 | -0.659 | 58.974 | 1.00 | 52.29 | O |
| ATOM | 5726 | N | GLU | D | 70 | 36.939 | -0.816 | 66.730 | 1.00 | 49.00 | N |
| ATOM | 5727 | CA | GLU | D | 70 | 35.578 | -1.353 | 66.727 | 1.00 | 49.15 | C |
| ATOM | 5728 | CB | GLU | D | 70 | 35.524 | -2.751 | 67.343 | 1.00 | 50.78 | C |
| ATOM | 5729 | CG | GLU | D | 70 | 36.157 | 3.845 | 68.500 | 1.00 | 51.38 | C |
| ATOM | 5730 | OD | GLU | D | 70 | 36.127 | -5.184 | 67.207 | 1.00 | 54.24 | O |
| ATOM | 5731 | OE1 | GLU | D | 70 | 36.537 | -5.246 | 68.390 | 1.00 | 58.44 | O |
| ATOM | 5732 | OE2 | GLU | D | 70 | 35.695 | -6.172 | 66.583 | 1.00 | 59.17 | O |
| ATOM | 5733 | C | GLU | D | 70 | 34.573 | -0.424 | 67.402 | 1.00 | 48.64 | C |
| ATOM | 5734 | O | GLU | D | 70 | 33.725 | -0.836 | 68.211 | 1.00 | 48.98 | O |
| ATOM | 5735 | N | VAL | D | 71 | 34.655 | 0.839 | 67.035 | 1.00 | 46.55 | N |
| ATOM | 5736 | CA | VAL | D | 71 | 33.754 | 1.825 | 67.571 | 1.00 | 46.03 | C |
| ATOM | 5737 | CB | VAL | D | 71 | 34.484 | 3.167 | 67.654 | 1.00 | 44.01 | C |
| ATOM | 5738 | CG1 | VAL | D | 71 | 33.540 | 4.293 | 57.956 | 1.00 | 47.00 | C |
| ATOM | 5739 | CG2 | VAL | D | 71 | 35.497 | 3.052 | 68.775 | 1.00 | 45.26 | C |
| ATOM | 5740 | C | VAL | D | 71 | 32.470 | 1.836 | 66.718 | 1.00 | 46.80 | C |
| ATOM | 5741 | O | VAL | D | 71 | 32.540 | 1.779 | 65.491 | 1.00 | 48.20 | O |
| ATOM | 5742 | N | LYS | D | 72 | 31.328 | 1.885 | 67.370 | 1.00 | 47.15 | N |
| ATOM | 5743 | CA | LYS | D | 72 | 30.063 | 1.695 | 66.675 | 1.00 | 49.17 | C |
| ATOM | 5744 | CB | LYS | D | 72 | 29.453 | 0.340 | 67.052 | 1.00 | 51.51 | C |
| ATOM | 5745 | CG | LYS | D | 72 | 30.068 | -0.830 | 66.272 | 1.00 | 52.29 | C |
| ATOM | 5746 | CD | LYS | D | 72 | 30.154 | -2.075 | 67.118 | 1.00 | 54.88 | C |
| ATOM | 5747 | CE | LYS | D | 72 | 31.270 | -2.984 | 66.608 | 1.00 | 62.14 | C |
| ATOM | 5748 | NZ | LYS | D | 72 | 31.467 | -4.187 | 67.469 | 1.00 | 64.72 | N |
| ATOM | 5749 | C | LYS | D | 72 | 29.088 | 2.836 | 66.919 | 1.00 | 48.56 | C |
| ATOM | 5750 | O | LYS | D | 72 | 28.075 | 2.980 | 66.233 | 1.00 | 45.15 | O |
| ATOM | 5751 | N | CYS | D | 73 | 29.406 | 3.637 | 67.024 | 1.00 | 46.47 | N |
| ATOM | 5752 | CA | CYS | D | 73 | 28.539 | 4.821 | 68.235 | 1.00 | 44.60 | C |
| ATOM | 5753 | CB | CYS | D | 73 | 27.489 | 4.499 | 69.189 | 1.00 | 45.53 | C |
| ATOM | 5754 | SG | CYS | D | 73 | 28.024 | 3.815 | 70.786 | 1.00 | 48.68 | S |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 5755 | C | CYS | D | 73 | 29.560 | 5.838 | 68.868 | 1.00 | 43.52 | C |
| ATOM | 5756 | O | CYS | D | 73 | 30.719 | 5.512 | 69.252 | 1.00 | 42.06 | O |
| ATOM | 5757 | N | MET | D | 74 | 29.024 | 7.042 | 69.010 | 1.00 | 40.25 | N |
| ATOM | 5758 | CA | MET | D | 74 | 29.780 | 8.202 | 69.471 | 1.00 | 41.42 | C |
| ATOM | 5759 | CB | MET | D | 74 | 30.074 | 9.108 | 68.291 | 1.00 | 40.05 | C |
| ATOM | 5760 | CG | MET | D | 74 | 31.039 | 8.508 | 67.251 | 1.00 | 42.13 | C |
| ATOM | 5761 | SD | MET | D | 74 | 30.322 | 7.298 | 65.131 | 1.00 | 52.41 | S |
| ATOM | 5762 | CE | MET | D | 74 | 29.208 | 8.333 | 65.212 | 1.00 | 45.39 | C |
| ATOM | 5763 | C | MET | D | 74 | 28.937 | 8.983 | 70.488 | 1.00 | 41.12 | C |
| ATOM | 5764 | O | MET | D | 74 | 27.732 | 9.066 | 70.302 | 1.00 | 41.93 | O |
| ATOM | 5765 | N | PRO | D | 75 | 29.549 | 9.536 | 71.562 | 1.00 | 41.62 | N |
| ATOM | 5766 | CA | PRO | D | 75 | 30.954 | 9.357 | 71.973 | 1.00 | 39.94 | C |
| ATOM | 5767 | CB | PRO | D | 75 | 31.148 | 10.411 | 73.048 | 1.00 | 39.90 | C |
| ATOM | 5768 | CG | PRO | D | 75 | 29.848 | 10.572 | 73.670 | 1.00 | 41.91 | C |
| ATOM | 5769 | CD | PRO | D | 75 | 28.834 | 10.423 | 72.505 | 1.00 | 39.59 | C |
| ATOM | 5770 | C | PRO | D | 75 | 31.153 | 8.000 | 72.560 | 1.00 | 41.35 | C |
| ATOM | 5771 | O | PRO | D | 75 | 30.279 | 7.529 | 73.274 | 1.00 | 39.98 | O |
| ATOM | 5772 | N | THR | D | 76 | 32.257 | 7.356 | 72.197 | 1.00 | 41.47 | N |
| ATOM | 5773 | CA | THR | D | 76 | 32.717 | 6.121 | 72.856 | 1.00 | 42.77 | C |
| ATOM | 5774 | CB | THR | D | 76 | 32.857 | 4.952 | 71.880 | 1.00 | 46.66 | C |
| ATOM | 5775 | OG1 | THR | D | 76 | 31.554 | 4.569 | 71.448 | 1.00 | 47.85 | O |
| ATOM | 5776 | CG2 | THR | D | 76 | 33.512 | 3.693 | 72.523 | 1.00 | 49.70 | C |
| ATOM | 5777 | C | THR | D | 76 | 34.069 | 6.468 | 73.485 | 1.00 | 45.14 | C |
| ATOM | 5778 | O | THR | D | 76 | 34.901 | 7.111 | 72.844 | 1.00 | 42.52 | O |
| ATOM | 5779 | N | PHE | D | 77 | 34.265 | 6.037 | 74.733 | 1.00 | 43.22 | N |
| ATOM | 5780 | CA | PHE | D | 77 | 35.497 | 6.309 | 75.452 | 1.00 | 43.11 | C |
| ATOM | 5781 | CB | PHE | D | 77 | 35.161 | 6.996 | 76.752 | 1.00 | 37.90 | C |
| ATOM | 5782 | CG | PHE | D | 77 | 34.595 | 8.396 | 76.555 | 1.00 | 44.57 | C |
| ATOM | 5783 | CD1 | PHE | D | 77 | 35.440 | 9.442 | 76.319 | 1.00 | 38.57 | C |
| ATOM | 5784 | CE1 | PHE | D | 77 | 34.897 | 10.702 | 76.104 | 1.00 | 49.55 | C |
| ATOM | 5785 | CZ | PHE | D | 77 | 33.520 | 10.876 | 76.159 | 1.00 | 35.01 | C |
| ATOM | 5786 | CE2 | PHE | D | 77 | 32.692 | 9.823 | 76.434 | 1.00 | 44.99 | C |
| ATOM | 5787 | CD2 | PHE | D | 77 | 33.230 | 8.570 | 76.614 | 1.00 | 43.54 | C |
| ATOM | 5788 | C | PHE | D | 77 | 36.227 | 5.006 | 75.710 | 1.00 | 42.39 | C |
| ATOM | 5789 | O | PHE | D | 77 | 35.693 | 4.118 | 76.318 | 1.00 | 44.58 | O |
| ATOM | 5790 | N | GLN | D | 78 | 37.425 | 4.898 | 75.169 | 1.00 | 41.07 | N |
| ATOM | 5791 | CA | GLN | D | 78 | 38.234 | 3.730 | 75.373 | 1.00 | 41.75 | C |
| ATOM | 5792 | CB | GLN | D | 78 | 38.660 | 3.168 | 74.039 | 1.00 | 42.17 | C |
| ATOM | 5793 | CG | GLN | D | 78 | 37.463 | 2.613 | 73.226 | 1.00 | 48.56 | C |
| ATOM | 5794 | CD | GLN | D | 78 | 37.905 | 1.714 | 72.102 | 1.00 | 48.56 | C |
| ATOM | 5795 | OE1 | GLN | D | 78 | 39.068 | 1.728 | 71.727 | 1.00 | 51.64 | O |
| ATOM | 5796 | NE2 | GLN | D | 78 | 36.971 | 0.941 | 71.537 | 1.00 | 45.64 | N |
| ATOM | 5797 | C | GLN | D | 78 | 39.440 | 4.115 | 76.233 | 1.00 | 41.66 | C |
| ATOM | 5798 | O | GLN | D | 78 | 39.934 | 5.219 | 76.111 | 1.00 | 38.37 | O |
| ATOM | 5799 | N | PHE | D | 79 | 39.892 | 3.168 | 77.062 | 1.00 | 40.93 | N |
| ATOM | 5800 | CA | PHE | D | 79 | 40.915 | 3.360 | 78.088 | 1.00 | 43.25 | C |
| ATOM | 5801 | CB | PHE | D | 79 | 40.271 | 3.149 | 79.488 | 1.00 | 38.73 | C |
| ATOM | 5802 | CG | PHE | D | 79 | 39.215 | 4.192 | 79.822 | 1.00 | 46.94 | C |
| ATOM | 5803 | CD1 | PHE | D | 79 | 37.894 | 4.073 | 79.327 | 1.00 | 34.03 | C |
| ATOM | 5804 | CE1 | PHE | D | 79 | 36.915 | 5.095 | 79.577 | 1.00 | 51.64 | C |

TABLE 10-continued

Atomic coordinates for COM1 complex of the modified
TXNIP protein represented by SEQ ID NO: 6 and the modified protein represented by SEQ ID NO: 3

| ATOM | 5805 | CZ  | PHE | D | 79 | 37.255 | 6.243  | 80.308 | 1.00 | 29.87 | C |
|------|------|-----|-----|---|----|--------|--------|--------|------|-------|---|
| ATOM | 5806 | CE2 | PHE | D | 79 | 38.566 | 6.335  | 80.853 | 1.00 | 37.51 | C |
| ATOM | 5807 | CD2 | PHE | D | 79 | 39.544 | 5.327  | 80.577 | 1.00 | 34.48 | C |
| ATOM | 5808 | C   | PHE | D | 79 | 42.118 | 2.429  | 77.808 | 1.00 | 43.61 | C |
| ATOM | 5809 | O   | PHE | D | 79 | 41.933 | 1.215  | 77.665 | 1.00 | 45.42 | O |
| ATOM | 5810 | N   | PHE | D | 80 | 43.326 | 2.994  | 77.665 | 1.00 | 42.07 | N |
| ATOM | 5811 | CA  | PHE | D | 80 | 44.545 | 2.177  | 77.402 | 1.00 | 44.50 | C |
| ATOM | 5812 | CB  | PHE | D | 80 | 45.119 | 2.435  | 76.012 | 1.00 | 41.60 | C |
| ATOM | 5813 | CG  | PHE | D | 80 | 44.149 | 2.141  | 74.903 | 1.00 | 49.76 | C |
| ATOM | 5814 | CD1 | PHE | D | 80 | 43.170 | 3.069  | 74.558 | 1.00 | 44.21 | C |
| ATOM | 5815 | CE1 | PHE | D | 80 | 42.251 | 2.796  | 73.539 | 1.00 | 46.25 | C |
| ATOM | 5816 | CZ  | PHE | D | 80 | 42.307 | 1.602  | 72.856 | 1.00 | 46.03 | C |
| ATOM | 5817 | CE2 | PHE | D | 80 | 43.264 | 0.675  | 73.176 | 1.00 | 42.57 | C |
| ATOM | 5818 | CD2 | PHE | D | 80 | 44.196 | 0.934  | 74.211 | 1.00 | 35.89 | C |
| ATOM | 5819 | C   | PHE | D | 80 | 45.691 | 2.306  | 78.422 | 1.00 | 46.58 | C |
| ATOM | 5820 | O   | PHE | D | 80 | 45.859 | 3.347  | 79.057 | 1.00 | 47.91 | O |
| ATOM | 5821 | N   | LYS | D | 81 | 46.480 | 1.122  | 78.531 | 1.00 | 47.01 | N |
| ATOM | 5822 | CA  | LYS | D | 81 | 47.704 | 1.134  | 79.306 | 1.00 | 49.17 | C |
| ATOM | 5823 | CB  | LYS | D | 81 | 47.450 | 0.449  | 80.652 | 1.00 | 49.03 | C |
| ATOM | 5824 | CG  | LYS | D | 81 | 47.072 | 1.374  | 81.813 | 1.00 | 51.56 | C |
| ATOM | 5825 | CD  | LYS | D | 81 | 46.612 | 0.528  | 83.002 | 1.00 | 57.72 | C |
| ATOM | 5826 | CE  | LYS | D | 81 | 47.158 | 1.064  | 84.317 | 1.00 | 64.84 | C |
| ATOM | 5827 | NZ  | LYS | D | 81 | 46.277 | 2.140  | 84.859 | 1.00 | 68.03 | N |
| ATOM | 5828 | C   | LYS | D | 81 | 48.709 | 0.302  | 78.502 | 1.00 | 48.75 | C |
| ATOM | 5829 | O   | LYS | D | 81 | 48.419 | -0.846 | 78.131 | 1.00 | 47.96 | O |
| ATOM | 5830 | N   | LYS | D | 82 | 49.880 | 0.879  | 78.218 | 1.00 | 49.71 | N |
| ATOM | 5831 | CA  | LYS | D | 82 | 50.932 | 0.162  | 77.483 | 1.00 | 49.93 | C |
| ATOM | 5832 | CB  | LYS | D | 82 | 51.616 | -0.872 | 78.399 | 1.00 | 48.69 | C |
| ATOM | 5833 | CG  | LYS | D | 82 | 52.832 | -0.327 | 79.143 | 1.00 | 50.64 | C |
| ATOM | 5834 | CD  | LYS | D | 82 | 54.140 | -0.772 | 78.454 | 1.00 | 58.64 | C |
| ATOM | 5835 | CE  | LYS | D | 82 | 55.310 | 0.212  | 78.778 | 1.00 | 52.29 | C |
| ATOM | 5836 | NZ  | LYS | D | 82 | 55.845 | 0.037  | 80.303 | 1.00 | 44.60 | N |
| ATOM | 5837 | C   | LYS | D | 82 | 50.421 | -0.495 | 76.191 | 1.00 | 50.39 | C |
| ATOM | 5838 | O   | LYS | D | 82 | 50.857 | -1.592 | 75.824 | 1.00 | 49.69 | O |
| ATOM | 5839 | N   | GLY | D | 83 | 49.491 | 0.185  | 75.515 | 1.00 | 51.13 | N |
| ATOM | 5840 | CA  | GLY | D | 83 | 48.962 | -0.246 | 74.215 | 1.00 | 52.28 | C |
| ATOM | 5841 | C   | GLY | D | 83 | 47.853 | -1.286 | 74.272 | 1.00 | 52.92 | C |
| ATOM | 5842 | O   | GLY | D | 83 | 47.455 | -1.822 | 73.239 | 1.00 | 52.01 | O |
| ATOM | 5843 | N   | GLN | D | 84 | 47.367 | -1.560 | 75.485 | 1.00 | 53.60 | N |
| ATOM | 5844 | CA  | GLN | D | 84 | 46.365 | -2.596 | 75.775 | 1.00 | 54.17 | C |
| ATOM | 5845 | CB  | GLN | D | 84 | 46.951 | -3.630 | 76.097 | 1.00 | 53.63 | C |
| ATOM | 5846 | CG  | GLN | D | 84 | 47.751 | -4.762 | 75.561 | 1.00 | 53.69 | C |
| ATOM | 5847 | CD  | GLN | D | 84 | 40.850 | -5.085 | 74.541 | 1.00 | 49.73 | C |
| ATOM | 5848 | OE1 | GLN | D | 84 | 46.179 | -5.700 | 76.256 | 1.00 | 47.78 | O |
| ATOM | 5849 | NE2 | GLN | D | 84 | 48.825 | -6.995 | 76.413 | 1.00 | 53.65 | N |
| ATOM | 5850 | C   | GLN | D | 84 | 45.127 | -1.969 | 77.321 | 1.00 | 53.73 | C |
| ATOM | 5851 | O   | GLN | D | 84 | 45.257 | -1.143 | 75.956 | 1.00 | 53.77 | O |
| ATOM | 5852 | N   | LYS | D | 85 | 43.939 | -2.380 | 76.376 | 1.00 | 52.49 | N |
| ATOM | 5853 | CA  | LYS | D | 85 | 42.671 | -1.754 | 76.376 | 1.00 | 51.03 | C |
| ATOM | 5854 | CB  | LYS | D | 85 | 41.583 | -1.887 | 75.286 | 1.00 | 51.03 | C |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 5855 | CG  | LYS | D | 85 | 40.223 | −1.279 | 75.688 | 1.00 | 50.56 | C |
| ATOM | 5856 | CD  | LYS | D | 85 | 39.195 | −1.285 | 74.545 | 1.00 | 49.76 | C |
| ATOM | 5857 | CE  | LYS | D | 85 | 38.959 | −2.690 | 73.996 | 1.00 | 56.91 | C |
| ATOM | 5858 | NZ  | LYS | D | 85 | 38.453 | −2.664 | 72.586 | 1.00 | 60.05 | N |
| ATOM | 5859 | C   | LYS | D | 85 | 42.160 | −2.297 | 77.710 | 1.00 | 51.03 | C |
| ATOM | 5860 | O   | LYS | D | 85 | 42.008 | −3.506 | 77.878 | 1.00 | 51.51 | O |
| ATOM | 5861 | N   | VAL | D | 86 | 41.881 | −1.393 | 78.650 | 1.00 | 50.29 | N |
| ATOM | 5862 | CA  | VAL | D | 86 | 41.455 | −1.801 | 79.999 | 1.00 | 46.71 | C |
| ATOM | 5863 | CB  | VAL | D | 86 | 42.499 | −1.438 | 81.108 | 1.00 | 48.99 | C |
| ATOM | 5864 | CG1 | VAL | D | 86 | 43.745 | −2.278 | 80.949 | 1.00 | 46.59 | C |
| ATOM | 5865 | CG2 | VAL | D | 86 | 42.842 | 0.043  | 81.105 | 1.00 | 46.37 | C |
| ATOM | 5866 | C   | VAL | D | 86 | 40.053 | −1.323 | 80.371 | 1.00 | 45.03 | C |
| ATOM | 5867 | O   | VAL | D | 86 | 39.561 | −1.569 | 81.476 | 1.00 | 40.11 | O |
| ATOM | 5868 | N   | GLY | D | 87 | 39.389 | −0.654 | 79.433 | 1.00 | 42.78 | N |
| ATOM | 5869 | CA  | GLY | D | 87 | 38.028 | −0.241 | 70.697 | 1.00 | 44.23 | C |
| ATOM | 5870 | C   | GLY | D | 87 | 37.407 | 0.423  | 78.498 | 1.00 | 44.80 | C |
| ATOM | 5871 | O   | GLY | D | 87 | 37.111 | 0.856  | 77.577 | 1.00 | 44.43 | O |
| ATOM | 5872 | N   | GLU | D | 88 | 36.084 | 0.510  | 78.531 | 1.00 | 44.53 | N |
| ATOM | 5873 | CA  | GLU | D | 88 | 35.329 | 1.125  | 77.450 | 1.00 | 47.91 | C |
| ATOM | 5874 | CB  | GLU | D | 88 | 35.439 | 0.254  | 76.194 | 1.00 | 47.01 | C |
| ATOM | 5875 | CG  | GLU | D | 88 | 34.605 | 0.717  | 75.011 | 1.00 | 58.56 | C |
| ATOM | 5876 | CD  | GLU | D | 88 | 34.725 | −0.214 | 73.813 | 1.00 | 54.89 | C |
| ATOM | 5877 | OE1 | GLU | D | 88 | 35.327 | −1.318 | 73.932 | 1.00 | 57.37 | O |
| ATOM | 5878 | OE2 | GLU | D | 88 | 34.216 | 0.177  | 72.753 | 1.00 | 61.90 | O |
| ATOM | 5879 | C   | GLU | D | 88 | 33.885 | 1.262  | 77.879 | 1.00 | 47.82 | C |
| ATOM | 5880 | O   | GLU | D | 88 | 33.344 | 0.384  | 78.533 | 1.00 | 50.48 | O |
| ATOM | 5881 | N   | PHE | D | 89 | 33.283 | 2.390  | 77.549 | 1.00 | 45.41 | N |
| ATOM | 5882 | CA  | PHE | D | 89 | 31.848 | 2.552  | 77.645 | 1.00 | 45.13 | C |
| ATOM | 5883 | CB  | PHE | D | 89 | 31.391 | 3.069  | 79.013 | 1.00 | 45.32 | C |
| ATOM | 5884 | CG  | PHE | D | 89 | 31.776 | 4.512  | 79.271 | 1.00 | 47.89 | C |
| ATOM | 5885 | CD1 | PHE | D | 89 | 30.902 | 5.550  | 78.967 | 1.00 | 38.93 | C |
| ATOM | 5886 | CE1 | PHE | D | 89 | 31.265 | 5.871  | 79.193 | 1.00 | 43.48 | C |
| ATOM | 5887 | CZ  | PHE | D | 89 | 32.265 | 7.143  | 79.748 | 1.00 | 43.11 | C |
| ATOM | 5888 | CE2 | PHE | D | 89 | 33.363 | 6.094  | 80.069 | 1.00 | 46.89 | C |
| ATOM | 5889 | CD2 | PHE | D | 89 | 33.000 | 4.809  | 79.839 | 1.00 | 39.62 | C |
| ATOM | 5890 | C   | PHE | D | 89 | 31.488 | 3.540  | 76.547 | 1.00 | 46.76 | C |
| ATOM | 5891 | O   | PHE | D | 89 | 32.359 | 4.177  | 75.968 | 1.00 | 47.29 | O |
| ATOM | 5892 | N   | SER | D | 90 | 30.203 | 3.638  | 76.256 | 1.00 | 48.04 | N |
| ATOM | 5893 | CA  | SER | D | 90 | 29.722 | 4.529  | 75.237 | 1.00 | 46.62 | C |
| ATOM | 5894 | CB  | SER | D | 90 | 29.052 | 3.706  | 74.143 | 1.00 | 47.11 | C |
| ATOM | 5895 | OG  | SER | D | 90 | 30.023 | 3.279  | 73.190 | 1.00 | 41.80 | O |
| ATOM | 5896 | C   | SER | D | 90 | 28.767 | 5.536  | 75.878 | 1.00 | 47.56 | C |
| ATOM | 5897 | O   | SER | D | 90 | 28.086 | 5.204  | 76.842 | 1.00 | 44.33 | O |
| ATOM | 5898 | N   | GLY | D | 91 | 28.741 | 6.778  | 75.386 | 1.00 | 42.37 | N |
| ATOM | 5899 | CA  | GLY | D | 91 | 27.710 | 7.702  | 75.849 | 1.00 | 41.92 | C |
| ATOM | 5900 | C   | GLY | D | 91 | 28.235 | 8.979  | 76.431 | 1.00 | 44.68 | C |
| ATOM | 5901 | O   | GLY | D | 91 | 29.238 | 8.961  | 77.117 | 1.00 | 47.54 | O |
| ATOM | 5902 | N   | ALA | D | 92 | 27.562 | 10.099 | 76.165 | 1.00 | 48.01 | N |
| ATOM | 5903 | CA  | ALA | D | 92 | 27.938 | 11.376 | 76.807 | 1.00 | 48.71 | C |
| ATOM | 5904 | CB  | ALA | D | 92 | 27.355 | 12.544 | 76.048 | 1.00 | 46.03 | C |

TABLE 10-continued

Atomic coordinates for COM1 complex of the modified
TXNIP protein represented by SEQ ID NO: 6 and the modified protein represented by SEQ ID NO: 3

| | | | | | | | | | | | |
|---|---|---|---|---|---|---|---|---|---|---|---|
| ATOM | 5905 | C | ALA | D | 92 | 27.566 | 11.441 | 78.313 | 1.00 | 50.93 | C |
| ATOM | 5906 | O | ALA | D | 92 | 26.711 | 12.245 | 78.722 | 1.00 | 49.60 | O |
| ATOM | 5907 | N | ASN | D | 93 | 28.214 | 10.583 | 79.109 | 1.00 | 50.62 | N |
| ATOM | 5908 | CA | ASN | D | 93 | 27.978 | 0.415 | 80.567 | 1.00 | 48.89 | C |
| ATOM | 5909 | CB | ASN | D | 93 | 27.610 | 8.965 | 80.865 | 1.00 | 45.10 | C |
| ATOM | 5910 | CG | ASN | D | 93 | 27.089 | 8.752 | 82.275 | 1.00 | 51.20 | C |
| ATOM | 5911 | OD1 | ASN | D | 93 | 27.244 | 9.598 | 83.160 | 1.00 | 49.42 | O |
| ATOM | 5912 | ND2 | ASN | D | 93 | 26.487 | 7.585 | 82.496 | 1.00 | 51.09 | N |
| ATOM | 5913 | C | ASN | D | 93 | 29.243 | 10.804 | 81.336 | 1.00 | 49.01 | C |
| ATOM | 5914 | O | ASN | D | 93 | 30.138 | 9.969 | 81.553 | 1.00 | 50.36 | O |
| ATOM | 5915 | N | LYS | D | 94 | 29.291 | 12.065 | 81.752 | 1.00 | 48.68 | N |
| ATOM | 5916 | CA | LYS | D | 94 | 30.483 | 12.674 | 82.330 | 1.00 | 52.09 | C |
| ATOM | 5917 | CB | LYS | D | 94 | 30.341 | 14.198 | 82.409 | 1.00 | 54.01 | C |
| ATOM | 5918 | CG | LYS | D | 94 | 29.233 | 14.681 | 83.312 | 1.00 | 60.55 | C |
| ATOM | 5919 | CD | LYS | D | 94 | 28.849 | 16.128 | 83.022 | 1.00 | 72.15 | C |
| ATOM | 5920 | CE | LYS | D | 94 | 28.059 | 16.698 | 84.199 | 1.00 | 85.75 | C |
| ATOM | 5921 | NZ | LYS | D | 94 | 27.311 | 17.941 | 83.858 | 1.00 | 85.75 | N |
| ATOM | 5922 | C | LYS | D | 94 | 30.878 | 12.091 | 83.669 | 1.00 | 51.57 | C |
| ATOM | 5923 | O | LYS | D | 94 | 32.064 | 11.959 | 83.960 | 1.00 | 52.81 | O |
| ATOM | 5924 | N | GLU | D | 95 | 29.882 | 11.699 | 84.456 | 1.00 | 52.02 | N |
| ATOM | 5925 | CA | GLU | D | 95 | 30.123 | 11.127 | 85.772 | 1.00 | 51.67 | C |
| ATOM | 5926 | CB | GLU | D | 95 | 28.843 | 11.124 | 86.604 | 1.00 | 53.69 | C |
| ATOM | 5927 | CG | GLU | D | 95 | 28.407 | 12.523 | 87.085 | 1.00 | 55.20 | C |
| ATOM | 5928 | CD | GLU | D | 95 | 27.697 | 13.344 | 86.010 | 1.00 | 64.34 | C |
| ATOM | 5929 | OE1 | GLU | D | 95 | 27.353 | 12.779 | 84.944 | 1.00 | 69.83 | O |
| ATOM | 5930 | OE2 | GLU | D | 95 | 27.466 | 14.556 | 86.235 | 1.00 | 68.04 | O |
| ATOM | 5931 | C | GLU | D | 95 | 30.667 | 9.723 | 85.568 | 1.00 | 51.89 | C |
| ATOM | 5932 | O | GLU | D | 95 | 31.630 | 9.345 | 86.193 | 1.00 | 50.04 | O |
| ATOM | 5933 | N | LYS | D | 96 | 30.094 | 8.961 | 84.642 | 1.00 | 47.45 | N |
| ATOM | 5934 | CA | LYS | D | 96 | 30.709 | 7.690 | 84.279 | 1.00 | 45.44 | C |
| ATOM | 5935 | CB | LYS | D | 96 | 29.877 | 6.901 | 83.261 | 1.00 | 44.89 | C |
| ATOM | 5936 | CG | LYS | D | 96 | 30.142 | 5.395 | 83.304 | 1.00 | 39.47 | C |
| ATOM | 5937 | CD | LYS | D | 96 | 29.421 | 4.689 | 82.125 | 1.00 | 34.30 | C |
| ATOM | 5938 | CE | LYS | D | 96 | 28.997 | 3.285 | 82.558 | 1.00 | 52.08 | C |
| ATOM | 5939 | NZ | LYS | D | 96 | 28.392 | 2.553 | 81.402 | 1.00 | 44.16 | N |
| ATOM | 5940 | C | LYS | D | 96 | 32.118 | 7.917 | 83.762 | 1.00 | 46.06 | C |
| ATOM | 5941 | O | LYS | D | 96 | 33.024 | 7.186 | 84.158 | 1.00 | 47.16 | O |
| ATOM | 5942 | N | LEU | D | 97 | 32.305 | 8.942 | 82.910 | 1.00 | 45.22 | N |
| ATOM | 5943 | CA | LEU | D | 97 | 33.618 | 9.332 | 82.399 | 1.00 | 39.81 | C |
| ATOM | 5944 | CB | LEU | D | 97 | 33.552 | 10.648 | 81.565 | 1.00 | 41.01 | C |
| ATOM | 5945 | CG | LEU | D | 97 | 34.766 | 11.196 | 80.785 | 1.00 | 48.61 | C |
| ATOM | 5946 | CD1 | LEU | D | 97 | 35.495 | 10.121 | 80.060 | 1.00 | 33.39 | C |
| ATOM | 5947 | CD2 | LEU | D | 97 | 34.484 | 12.433 | 79.800 | 1.00 | 37.91 | C |
| ATOM | 5948 | C | LEU | D | 97 | 34.641 | 9.480 | 83.541 | 1.00 | 43.19 | C |
| ATOM | 5949 | O | LEU | D | 97 | 35.670 | 8.805 | 83.549 | 1.00 | 45.72 | O |
| ATOM | 5950 | N | GLU | D | 98 | 34.359 | 10.363 | 84.488 | 1.00 | 42.83 | N |
| ATOM | 5951 | CA | GLU | D | 98 | 35.322 | 10.635 | 85.562 | 1.00 | 40.40 | C |
| ATOM | 5952 | CB | GLU | D | 98 | 34.936 | 11.869 | 86.393 | 1.00 | 41.24 | C |
| ATOM | 5953 | CG | GLU | D | 98 | 36.004 | 12.278 | 87.468 | 1.00 | 37.77 | C |
| ATOM | 5954 | CD | GLU | D | 98 | 35.703 | 13.609 | 88.121 | 1.00 | 42.72 | C |

TABLE 10-continued

Atomic coordinates for COM1 complex of the modified
TXNIP protein represented by SEQ ID NO: 6 and the modified protein represented by SEQ ID NO: 3

| ATOM | 5955 | OE1 | GLU | D | 98 | 34.552 | 88.069 | 14.075 | 1.00 | 46.65 | O |
|---|---|---|---|---|---|---|---|---|---|---|---|
| ATOM | 5956 | OE2 | GLU | D | 98 | 36.623 | 88.721 | 14.205 | 1.00 | 43.90 | O |
| ATOM | 5957 | C | GLU | D | 98 | 35.548 | 86.467 | 9.451 | 1.00 | 44.20 | C |
| ATOM | 5958 | O | GLU | D | 98 | 36.664 | 86.949 | 9.264 | 1.00 | 49.54 | O |
| ATOM | 5959 | N | ALA | D | 99 | 34.490 | 86.721 | 8.685 | 1.00 | 44.20 | N |
| ATOM | 5960 | CA | ALA | D | 99 | 34.530 | 87.630 | 7.533 | 1.00 | 44.95 | C |
| ATOM | 5961 | CB | ALA | D | 99 | 33.126 | 87.965 | 7.098 | 1.00 | 44.32 | C |
| ATOM | 5962 | C | ALA | D | 99 | 35.324 | 87.011 | 6.377 | 1.00 | 45.62 | C |
| ATOM | 5963 | O | ALA | D | 99 | 36.071 | 87.680 | 5.706 | 1.00 | 40.12 | O |
| ATOM | 5964 | N | THR | D | 100 | 35.190 | 85.713 | 6.170 | 1.00 | 41.94 | N |
| ATOM | 5965 | CA | THR | D | 100 | 36.039 | 85.004 | 5.199 | 1.00 | 43.92 | C |
| ATOM | 5966 | CB | THR | D | 100 | 35.559 | 83.548 | 4.950 | 1.00 | 44.13 | C |
| ATOM | 5967 | OG1 | THR | D | 100 | 34.119 | 83.514 | 4.913 | 1.00 | 42.05 | O |
| ATOM | 5968 | CG2 | THR | D | 100 | 36.142 | 83.008 | 3.639 | 1.00 | 43.59 | C |
| ATOM | 5969 | C | THR | D | 100 | 37.521 | 84.997 | 5.607 | 1.00 | 46.46 | C |
| ATOM | 5970 | O | THR | D | 100 | 38.396 | 85.192 | 4.771 | 1.00 | 46.36 | O |
| ATOM | 5971 | N | ILE | D | 101 | 37.799 | 84.760 | 5.884 | 1.00 | 49.34 | N |
| ATOM | 5972 | CA | ILE | D | 101 | 39.181 | 84.831 | 7.387 | 1.00 | 50.71 | C |
| ATOM | 5973 | CB | ILE | D | 101 | 39.275 | 84.486 | 8.894 | 1.00 | 50.54 | C |
| ATOM | 5974 | CG1 | ILE | D | 101 | 39.370 | 82.980 | 9.077 | 1.00 | 46.39 | C |
| ATOM | 5975 | CD1 | ILE | D | 101 | 38.934 | 82.551 | 10.466 | 1.00 | 50.63 | C |
| ATOM | 5976 | CG2 | ILE | D | 101 | 40.519 | 85.134 | 9.539 | 1.00 | 45.50 | C |
| ATOM | 5977 | C | ILE | D | 101 | 39.792 | 86.199 | 7.133 | 1.00 | 52.36 | C |
| ATOM | 5978 | O | ILE | D | 101 | 40.888 | 86.299 | 6.577 | 1.00 | 54.84 | O |
| ATOM | 5979 | N | ASN | D | 102 | 39.068 | 87.244 | 7.524 | 1.00 | 51.83 | N |
| ATOM | 5980 | CA | ASN | D | 102 | 39.519 | 88.617 | 7.334 | 1.00 | 47.43 | C |
| ATOM | 5981 | CB | ASN | D | 102 | 38.471 | 89.608 | 7.841 | 1.00 | 46.78 | C |
| ATOM | 5982 | CG | ASN | D | 102 | 38.406 | 89.678 | 9.359 | 1.00 | 48.96 | C |
| ATOM | 5983 | OD1 | ASN | D | 102 | 39.390 | 89.390 | 10.037 | 1.00 | 49.35 | O |
| ATOM | 5984 | ND2 | ASN | D | 102 | 37.222 | 90.077 | 9.909 | 1.00 | 47.85 | N |
| ATOM | 5985 | C | ASN | D | 102 | 39.755 | 88.911 | 5.859 | 1.00 | 50.27 | C |
| ATOM | 5986 | O | ASN | D | 102 | 40.576 | 89.767 | 5.509 | 1.00 | 48.67 | O |
| ATOM | 5987 | N | GLU | D | 103 | 39.010 | 88.223 | 5.006 | 1.00 | 45.69 | N |
| ATOM | 5988 | CA | GLU | D | 103 | 38.986 | 88.494 | 3.590 | 1.00 | 45.18 | C |
| ATOM | 5989 | CB | GLU | D | 103 | 37.610 | 88.071 | 3.028 | 1.00 | 43.70 | C |
| ATOM | 5990 | CG | GLU | D | 103 | 37.340 | 88.252 | 1.544 | 1.00 | 42.86 | C |
| ATOM | 5991 | CD | GLU | D | 103 | 35.996 | 87.630 | 1.084 | 1.00 | 50.57 | C |
| ATOM | 5992 | OE1 | GLU | D | 103 | 35.649 | 86.488 | 1.516 | 1.00 | 46.31 | O |
| ATOM | 5993 | OE2 | GLU | D | 103 | 35.293 | 88.273 | 0.256 | 1.00 | 56.72 | O |
| ATOM | 5994 | C | GLU | D | 103 | 40.139 | 87.781 | 2.896 | 1.00 | 44.65 | C |
| ATOM | 5995 | O | GLU | D | 103 | 40.481 | 88.110 | 1.776 | 1.00 | 45.78 | O |
| ATOM | 5996 | N | LEU | D | 104 | 40.745 | 86.806 | 3.553 | 1.00 | 45.35 | N |
| ATOM | 5997 | CA | LEU | D | 104 | 41.739 | 85.971 | 2.896 | 1.00 | 48.78 | C |
| ATOM | 5998 | CB | LEU | D | 104 | 41.239 | 84.522 | 2.719 | 1.00 | 46.64 | C |
| ATOM | 5999 | CG | LEU | D | 104 | 40.162 | 84.173 | 1.686 | 1.00 | 48.17 | C |
| ATOM | 6000 | CD1 | LEU | D | 104 | 39.563 | 82.792 | 1.941 | 1.00 | 49.98 | C |
| ATOM | 6001 | CD2 | LEU | D | 104 | 40.593 | 84.260 | 0.256 | 1.00 | 38.14 | C |
| ATOM | 6002 | C | LEU | D | 104 | 43.149 | 85.970 | 3.462 | 1.00 | 51.91 | C |
| ATOM | 6003 | O | LEU | D | 104 | 44.049 | 85.323 | 2.908 | 1.00 | 52.03 | O |
| ATOM | 6004 | N | VAL | D | 105 | 43.334 | 86.671 | 4.589 | 1.00 | 53.74 | N |

TABLE 10-continued

Atomic coordinates for COM1 complex of the modified
TXNIP protein represented by SEQ ID NO: 6 and the modified protein represented by SEQ ID NO: 3

| | | | | | | | | | | |
|---|---|---|---|---|---|---|---|---|---|---|
| ATOM | 6005 | CA | VAL | D | 105 | 44.639 | 5.234 | 86.766 | 1.00 | 55.55 | C |
| ATOM | 6006 | CB | VAL | D | 105 | 44.569 | 6.654 | 87.393 | 1.00 | 56.32 | C |
| ATOM | 6007 | CG1 | VAL | D | 105 | 44.683 | 7.701 | 86.332 | 1.00 | 55.25 | C |
| ATOM | 6008 | CG2 | VAL | D | 105 | 43.299 | 6.857 | 88.217 | 1.00 | 55.55 | C |
| ATOM | 6009 | C | VAL | D | 105 | 45.624 | 4.358 | 87.556 | 1.00 | 58.70 | C |
| ATOM | 6010 | O | VAL | D | 105 | 45.281 | 3.783 | 88.605 | 1.00 | 59.69 | O |
| ATOM | 6011 | OXT | VAL | D | 105 | 46.782 | 4.196 | 87.145 | 1.00 | 60.38 | O |
| TER | 6015 | | VAL | D | 105 | | | | | | |
| ATOM | 6012 | O | HOH | W | 1 | 28.722 | 12.428 | 58.402 | 1.00 | 57.39 | O |
| ATOM | 6013 | O | HOH | W | 2 | 46.553 | 19.157 | 87.344 | 1.00 | 60.58 | O |
| ATOM | 6014 | O | HOH | W | 3 | -0.567 | 11.558 | 27.281 | 1.00 | 30.04 | O |
| ATOM | 6015 | O | HOH | W | 4 | -39.432 | 15.484 | 10.180 | 1.00 | 48.06 | O |
| ATOM | 6016 | O | HOH | W | 5 | 26.018 | 5.872 | 79.190 | 1.00 | 55.96 | O |
| ATOM | 6017 | O | HOH | W | 6 | 2.948 | 14.441 | 26.402 | 1.00 | 44.67 | O |
| ATOM | 6018 | O | HOH | W | 7 | 23.150 | 18.046 | 66.697 | 1.00 | 59.99 | O |
| ATOM | 6019 | O | HOH | W | 8 | -35.599 | 0.963 | 34.424 | 1.00 | 58.99 | O |
| ATOM | 6020 | O | HOH | W | 9 | 25.967 | -3.464 | 54.873 | 1.00 | 58.78 | O |
| ATOM | 6021 | O | HOH | W | 10 | -33.980 | 3.312 | 13.855 | 1.00 | 38.31 | O |
| ATOM | 6022 | O | HOH | W | 11 | 34.794 | -0.030 | 81.481 | 1.00 | 57.32 | O |
| ATOM | 6023 | O | HOH | W | 12 | 14.997 | -7.259 | 59.551 | 1.00 | 47.59 | O |
| ATOM | 6024 | O | HOH | W | 13 | -13.183 | -7.071 | 3.174 | 1.00 | 65.27 | O |
| ATOM | 6025 | O | HOH | W | 14 | -36.072 | -2.268 | 15.444 | 1.00 | 50.64 | O |
| ATOM | 6026 | O | HOH | W | 15 | -10.395 | -11.497 | 65.407 | 1.00 | 44.07 | O |
| ATOM | 6027 | O | HOH | W | 16 | 37.740 | 17.611 | 74.257 | 1.00 | 34.60 | O |
| ATOM | 6028 | O | HOH | W | 17 | 5.092 | 9.687 | 69.671 | 1.00 | 61.79 | O |
| ATOM | 6029 | O | HOH | W | 18 | 13.931 | 2.194 | 75.916 | 1.00 | 42.79 | O |
| ATOM | 6030 | O | HOH | W | 19 | 24.536 | 3.346 | 71.228 | 1.00 | 40.01 | O |
| ATOM | 6031 | O | HOH | W | 20 | 7.540 | 15.296 | 27.203 | 1.00 | 42.09 | O |
| ATOM | 6032 | O | HOH | W | 21 | 8.016 | 3.301 | 42.314 | 1.00 | 30.48 | O |
| ATOM | 6033 | O | HOH | W | 22 | -37.916 | -5.571 | 19.597 | 1.00 | 44.61 | O |
| ATOM | 6034 | O | HOH | W | 23 | -44.947 | 13.554 | 22.697 | 1.00 | 49.98 | O |
| ATOM | 6035 | O | HOH | W | 24 | 28.674 | 0.985 | 77.132 | 1.00 | 60.10 | O |
| ATOM | 6036 | O | HOH | W | 25 | -3.523 | -3.333 | 01.071 | 1.00 | 30.30 | O |
| ATOM | 6037 | O | HOH | W | 26 | 25.351 | 12.628 | 83.179 | 1.00 | 57.61 | O |
| ATOM | 6038 | O | HOH | W | 27 | -4.814 | -3.689 | 58.546 | 1.00 | 35.36 | O |
| ATOM | 6039 | O | HOH | W | 28 | -14.527 | -12.202 | 57.434 | 1.00 | 62.62 | O |
| ATOM | 6040 | O | HOH | W | 29 | -3.172 | -5.464 | 57.180 | 1.00 | 41.39 | O |
| ATOM | 6041 | O | HOH | W | 30 | -10.20 | -3.507 | 22.982 | 1.00 | 63.87 | O |
| ATOM | 6042 | O | HOH | W | 31 | 7.652 | 11.358 | 75.806 | 1.00 | 53.92 | O |
| ATOM | 6043 | O | HOH | W | 32 | 6.556 | 10.826 | 71.956 | 1.00 | 74.08 | O |
| ATOM | 6044 | O | HOH | W | 33 | -14.233 | -1.751 | 24.770 | 1.00 | 69.95 | O |
| ATOM | 6045 | O | HOH | W | 34 | 3.350 | 6.328 | 57.665 | 1.00 | 58.46 | O |
| ATOM | 6046 | O | HOH | W | 35 | 31.584 | 21.271 | 72.228 | 1.00 | 38.42 | O |
| ATOM | 6047 | O | HOH | W | 36 | 20.657 | 12.579 | 62.054 | 1.00 | 43.11 | O |
| ATOM | 6048 | O | HOH | W | 37 | 4.191 | -4.054 | 34.851 | 1.00 | 55.72 | O |
| ATOM | 6049 | O | HOH | W | 38 | -13.052 | 15.736 | 27.252 | 1.00 | 37.23 | O |
| ATOM | 6050 | O | HOH | W | 39 | 15.951 | 17.137 | 37.678 | 1.00 | 59.72 | O |
| ATOM | 6051 | O | HOH | W | 40 | -14.275 | 15.922 | 29.833 | 1.00 | 43.19 | O |
| ATOM | 6052 | O | HOH | W | 41 | -17.908 | 5.337 | 28.050 | 1.00 | 41.70 | O |
| ATOM | 6053 | O | HOH | W | 42 | -12.705 | -2.370 | 8.462 | 1.00 | 49.15 | O |

TABLE 10-continued

Atomic coordinates for COM1 complex of the modified
TXNIP protein represented by SEQ ID NO: 6 and the modified protein represented by SEQ ID NO: 3

| ATOM | 6054 | HOH | W | 43 | −29.359 | −8.785 | 23.861 | 1.00 | 43.19 | O |
|---|---|---|---|---|---|---|---|---|---|---|
| ATOM | 6055 | HOH | W | 44 | 28.896 | 21.126 | 77.151 | 1.00 | 50.62 | O |
| ATOM | 6056 | HOH | W | 45 | 11.427 | 14.341 | 55.968 | 1.00 | 62.24 | O |
| ATOM | 6057 | HOH | W | 46 | 20.251 | 3.822 | 77.261 | 1.00 | 48.67 | O |
| ATOM | 6058 | HOH | W | 47 | −30.314 | 5.963 | 13.821 | 1.00 | 49.27 | O |
| ATOM | 6059 | HOH | W | 48 | −51.803 | −2.21 | 10.857 | 1.00 | 47.47 | O |
| ATOM | 6060 | HOH | W | 49 | −31.844 | −12.539 | 26.306 | 1.00 | 45.34 | O |
| ATOM | 6061 | HOH | W | 50 | −68.353 | −6.161 | −7.735 | 1.00 | 60.07 | O |
| ATOM | 6062 | HOH | W | 51 | −54.737 | 10.048 | 4.904 | 1.00 | 45.82 | O |
| ATOM | 6063 | HOH | W | 52 | −52.173 | −0.071 | 8.680 | 1.00 | 36.96 | O |
| ATOM | 6064 | HOH | W | 53 | −32.595 | 4.997 | 23.999 | 1.00 | 53.07 | O |
| ATOM | 6065 | HOH | W | 54 | −5.855 | 16.652 | 26.524 | 1.00 | 31.36 | O |
| ATOM | 6066 | HOH | W | 55 | −10.505 | 0.690 | 46.676 | 1.00 | 54.98 | O |
| ATOM | 6067 | HOH | W | 56 | −3.235 | 12.080 | 19.043 | 1.00 | 47.60 | O |
| ATOM | 6068 | HOH | W | 57 | −7.305 | 19.721 | 34.840 | 1.00 | 45.63 | O |
| ATOM | 6069 | HOH | W | 58 | 7.763 | 13.784 | 73.252 | 1.00 | 55.91 | O |
| ATOM | 6070 | HOH | W | 59 | −38.358 | 8.569 | 20.849 | 1.00 | 42.85 | O |
| ATOM | 6071 | HOH | W | 60 | −53.439 | 3.854 | 25.255 | 1.00 | 39.98 | O |
| ATOM | 6072 | HOH | W | 61 | −4.023 | −7.196 | 55.053 | 1.00 | 46.78 | O |
| ATOM | 6073 | HOH | W | 62 | −19.305 | −0.079 | 65.354 | 1.00 | 48.13 | O |
| ATOM | 6074 | HOH | W | 63 | 28.697 | 4.302 | 64.033 | 1.00 | 46.30 | O |
| ATOM | 6075 | HOH | W | 64 | 7.932 | 10.340 | 61.241 | 1.00 | 39.71 | O |
| ATOM | 6076 | HOH | W | 65 | −24.250 | 7.794 | 22.734 | 1.00 | 39.79 | O |
| ATOM | 6077 | HOH | W | 66 | −63.495 | 11.377 | −6.444 | 1.00 | 44.40 | O |
| ATOM | 6078 | HOH | W | 67 | −49.903 | 10.321 | 21.276 | 1.00 | 54.56 | O |
| ATOM | 6079 | HOH | W | 68 | −6.575 | 2.413 | 53.073 | 1.00 | 61.73 | O |
| ATOM | 6080 | HOH | W | 69 | −58.913 | −0.583 | 18.487 | 1.00 | 46.38 | O |
| ATOM | 6081 | HOH | W | 70 | −8.767 | 16.306 | 25.658 | 1.00 | 42.42 | O |
| ATOM | 6082 | HOH | W | 71 | −38.316 | 7.012 | 4.502 | 1.00 | 45.57 | O |
| ATOM | 6083 | HOH | W | 72 | −9.608 | 10.007 | 16.443 | 1.00 | 37.15 | O |
| ATOM | 6084 | HOH | W | 73 | −46.557 | 2.743 | 39.007 | 1.00 | 50.81 | O |
| ATOM | 6085 | HOH | W | 74 | 13.854 | 11.879 | 76.597 | 1.00 | 38.68 | O |
| ATOM | 6086 | HOH | W | 75 | −70.216 | 3.009 | 17.017 | 1.00 | 63.84 | O |
| ATOM | 6087 | HOH | W | 76 | 0.801 | 1.297 | 43.250 | 1.00 | 56.42 | O |
| ATOM | 6088 | HOH | W | 77 | −54.036 | −9.095 | 21.709 | 1.00 | 56.42 | O |
| ATOM | 6089 | HOH | W | 78 | −4.194 | −11.813 | 68.894 | 1.00 | 44.10 | O |
| ATOM | 6090 | HOH | W | 79 | 5.162 | −0.908 | 38.110 | 1.00 | 37.40 | O |
| ATOM | 6091 | HOH | W | 80 | 22.633 | 4.143 | 47.318 | 1.00 | 59.56 | O |
| ATOM | 6092 | HOH | W | 81 | −19.752 | 13.159 | 26.090 | 1.00 | 47.31 | O |
| ATOM | 6093 | HOH | W | 82 | −17.529 | −4.244 | 68.635 | 1.00 | 49.89 | O |
| ATOM | 6094 | HOH | W | 83 | −4.994 | 4.745 | 41.410 | 1.00 | 52.36 | O |
| ATOM | 6095 | HOH | W | 84 | −36.723 | 4.098 | 12.987 | 1.00 | 39.29 | O |
| ATOM | 6096 | HOH | W | 85 | −1.963 | −5.432 | 61.059 | 1.00 | 42.25 | O |
| ATOM | 6097 | HOH | W | 86 | 53.791 | −0.857 | 68.564 | 1.00 | 61.34 | O |
| ATOM | 6098 | HOH | W | 87 | −11.428 | 9.824 | 9.789 | 1.00 | 63.01 | O |
| ATOM | 6099 | HOH | W | 88 | −25.667 | −7.692 | 58.549 | 1.00 | 61.79 | O |
| ATOM | 6100 | HOH | W | 89 | 10.683 | 11.851 | 54.520 | 1.00 | 48.54 | O |
| ATOM | 6101 | HOH | W | 90 | 7.658 | −3.114 | 35.352 | 1.00 | 40.74 | O |
| ATOM | 6102 | HOH | W | 91 | 7.062 | −9.060 | 56.725 | 1.00 | 42.22 | O |
| ATOM | 6103 | HOH | W | 92 | 40.254 | 14.724 | 62.498 | 1.00 | 57.56 | O |

TABLE 10-continued

Atomic coordinates for COM1 complex of the modified
TXNIP protein represented by SEQ ID NO: 6 and the modified protein represented by SEQ ID NO: 3

| ATOM | 6104 | HOH | W | 93 | 47.073 | 14.493 | 75.316 | 1.00 | 55.16 | O |
|------|------|-----|---|-----|---------|---------|---------|------|-------|---|
| ATOM | 6105 | HOH | W | 94 | -6.837 | -0.540 | 48.629 | 1.00 | 42.66 | O |
| ATOM | 6106 | HOH | W | 95 | -0.491 | -5.196 | 58.882 | 1.00 | 41.75 | O |
| ATOM | 6107 | HOH | W | 96 | -50.225 | -7.775 | 33.030 | 1.00 | 59.66 | O |
| ATOM | 6108 | HOH | W | 97 | 47.973 | 13.316 | 64.599 | 1.00 | 59.66 | O |
| ATOM | 6109 | HOH | W | 98 | 42.975 | 7.524 | 59.195 | 1.00 | 56.95 | O |
| ATOM | 6110 | HOH | W | 99 | -15.105 | 19.278 | 21.238 | 1.00 | 55.46 | O |
| ATOM | 6111 | HOH | W | 100 | 33.587 | 10.496 | 56.006 | 1.00 | 58.51 | O |
| ATOM | 6112 | HOH | W | 101 | -5.577 | 13.728 | 56.173 | 1.00 | 59.97 | O |
| ATOM | 6113 | HOH | W | 102 | 46.103 | 15.363 | 80.651 | 1.00 | 42.76 | O |
| ATOM | 6114 | HOH | W | 103 | -9.888 | 22.807 | 19.500 | 1.00 | 59.25 | O |
| ATOM | 6115 | HOH | W | 104 | -52.657 | 2.635 | 32.666 | 1.00 | 51.32 | O |
| ATOM | 6116 | HOH | W | 105 | -1.010 | 2.802 | 19.751 | 1.00 | 58.19 | O |
| ATOM | 6117 | HOH | W | 106 | 14.028 | 16.044 | 54.468 | 1.00 | 54.91 | O |
| ATOM | 6118 | HOH | W | 107 | 8.920 | 7.177 | 42.548 | 1.00 | 60.97 | O |
| ATOM | 6119 | HOH | W | 108 | -16.180 | 11.874 | 12.350 | 1.00 | 50.09 | O |
| ATOM | 6120 | HOH | W | 109 | 40.560 | 12.975 | 64.642 | 1.00 | 46.53 | O |
| ATOM | 6121 | HOH | W | 110 | 46.208 | 14.914 | 77.838 | 1.00 | 42.41 | O |
| ATOM | 6122 | HOH | W | 111 | 4.262 | 5.121 | 27.418 | 1.00 | 51.20 | O |
| ATOM | 6123 | HOH | W | 112 | -22.324 | 5.242 | 24.780 | 1.00 | 46.21 | O |
| ATOM | 6124 | HOH | W | 113 | 47.502 | 20.870 | 82.958 | 1.00 | 58.84 | O |
| ATOM | 6125 | HOH | W | 114 | -15.610 | 23.149 | 24.928 | 1.00 | 65.26 | O |
| ATOM | 6126 | HOH | W | 115 | -8.106 | -4.516 | 12.532 | 1.00 | 60.90 | O |
| ATOM | 6127 | HOH | W | 116 | 30.362 | 20.814 | 65.291 | 1.00 | 45.53 | O |
| ATOM | 6128 | HOH | W | 117 | 8.372 | 3.534 | 67.595 | 1.00 | 40.01 | O |
| ATOM | 6129 | HOH | W | 118 | 12.248 | 17.381 | 61.359 | 1.00 | 47.33 | O |
| ATOM | 6130 | HOH | W | 119 | -61.741 | 16.108 | 7.788 | 1.00 | 47.48 | O |
| ATOM | 6131 | HOH | W | 120 | -13.004 | 14.272 | 62.476 | 1.00 | 65.34 | O |
| ATOM | 6132 | HOH | W | 121 | -34.544 | 7.046 | 18.572 | 1.00 | 38.78 | O |
| ATOM | 6133 | HOH | W | 122 | -55.779 | -2.575 | 15.236 | 1.00 | 43.88 | O |
| ATOM | 6134 | HOH | W | 123 | -8.243 | 16.780 | 21.598 | 1.00 | 40.43 | O |
| ATOM | 6135 | HOH | W | 124 | -12.966 | -6.269 | 53.309 | 1.00 | 50.84 | O |
| ATOM | 6136 | HOH | W | 125 | -10.483 | 22.752 | 25.617 | 1.00 | 49.66 | O |
| ATOM | 6137 | HOH | W | 126 | 5.210 | 7.453 | 62.909 | 1.00 | 48.61 | O |
| ATOM | 6138 | HOH | W | 127 | -2.454 | -10.572 | 63.242 | 1.00 | 53.17 | O |
| ATOM | 6139 | HOH | W | 128 | -5.113 | -0.038 | 73.500 | 1.00 | 53.90 | O |
| ATOM | 6140 | HOH | W | 129 | -41.549 | -0.265 | 8.153 | 1.00 | 46.70 | O |
| ATOM | 6141 | HOH | W | 130 | -44.649 | 12.269 | 6.308 | 1.00 | 38.48 | O |
| ATOM | 6142 | HOH | W | 131 | 7.550 | 5.574 | 44.580 | 1.00 | 59.15 | O |
| ATOM | 6143 | HOH | W | 132 | 37.573 | 24.292 | 82.060 | 1.00 | 70.23 | O |
| ATOM | 6144 | HOH | W | 133 | 2.715 | -3.378 | 59.487 | 1.00 | 57.23 | O |
| ATOM | 6145 | HOH | W | 134 | 49.771 | -4.017 | 73.375 | 1.00 | 59.05 | O |
| ATOM | 6146 | HOH | W | 135 | 16.600 | 11.173 | 42.200 | 1.00 | 49.70 | O |
| ATOM | 6147 | HOH | W | 136 | -44.308 | -6.366 | 10.961 | 1.00 | 42.11 | O |
| ATOM | 6148 | HOH | W | 137 | 2.667 | 11.836 | 26.234 | 1.00 | 46.51 | O |
| ATOM | 6149 | HOH | W | 138 | 16.223 | 14.617 | 48.000 | 1.00 | 56.05 | O |
| ATOM | 6150 | HOH | W | 139 | 37.044 | -5.429 | 71.106 | 1.00 | 63.29 | O |
| ATOM | 6151 | HOH | W | 140 | -8.114 | 2.334 | 35.643 | 1.00 | 35.94 | O |
| ATOM | 6152 | HOH | W | 141 | 23.191 | -5.045 | 54.900 | 1.00 | 55.77 | O |
| ATOM | 6153 | HOH | W | 142 | -51.552 | 9.537 | 4.065 | 1.00 | 39.59 | O |

TABLE 10-continued

Atomic coordinates for COM1 complex of the modified
TXNIP protein represented by SEQ ID NO: 6 and the modified protein represented by SEQ ID NO: 3

| | | | | | | | | | |
|---|---|---|---|---|---|---|---|---|---|
| ATOM | 6154 | O | HOH | W | 143 | −54.118 | 5.925 | 3.632 | 1.00 | 47.02 | O |
| ATOM | 6155 | O | HOH | W | 144 | 23.695 | 8.296 | 40.047 | 1.00 | 46.81 | O |
| ATOM | 6156 | O | HOH | W | 145 | −32.824 | −8.697 | 38.939 | 1.00 | 58.59 | O |
| ATOM | 6157 | O | HOH | W | 146 | −17.096 | −4.116 | 27.680 | 1.00 | 62.14 | O |
| ATOM | 6158 | O | HOH | W | 147 | −51.335 | 11.506 | 6.300 | 1.00 | 36.20 | O |
| ATOM | 6159 | O | HOH | W | 148 | 24.878 | 2.142 | 68.070 | 1.00 | 51.40 | O |
| ATOM | 6160 | O | HOH | W | 149 | −11.337 | 3.580 | 52.990 | 1.00 | 49.90 | O |
| ATOM | 6161 | O | HOH | W | 150 | −3.530 | −0.885 | 51.174 | 1.00 | 62.00 | O |
| ATOM | 6162 | O | HOH | W | 151 | 37.287 | 15.251 | 72.953 | 1.00 | 33.85 | O |
| ATOM | 6163 | O | HOH | W | 152 | 4.457 | 3.022 | 39.368 | 1.00 | 37.87 | O |
| ATOM | 6164 | O | HOH | W | 153 | −20.987 | −4.460 | 67.129 | 1.00 | 65.75 | O |
| ATOM | 6165 | O | HOH | W | 154 | −48.360 | 3.585 | 3.288 | 1.00 | 39.85 | O |
| ATOM | 6166 | O | HOH | W | 155 | −10.920 | −0.462 | 35.135 | 1.00 | 52.07 | O |
| ATOM | 6167 | O | HOH | W | 156 | 11.788 | −3.135 | 59.137 | 1.00 | 48.40 | O |
| ATOM | 6168 | O | HOH | W | 157 | −49.753 | −5.418 | 32.216 | 1.00 | 41.28 | O |
| ATOM | 6169 | O | HOH | W | 158 | 54.729 | 4.697 | 1.479 | 1.00 | 54.31 | O |
| ATOM | 6170 | O | HOH | W | 159 | 6.879 | 3.016 | 35.472 | 1.00 | 42.86 | O |
| ATOM | 6171 | O | HOH | W | 160 | 33.298 | 14.571 | 72.095 | 1.00 | 58.88 | O |
| ATOM | 6172 | O | HOH | W | 161 | 41.249 | 18.427 | 63.260 | 1.00 | 54.69 | O |
| ATOM | 6173 | O | HOH | W | 162 | 47.399 | 18.938 | 79.018 | 1.00 | 55.42 | O |
| ATOM | 6174 | O | HOH | W | 163 | 38.114 | 14.55 | 56.160 | 1.00 | 67.26 | O |
| ATOM | 6175 | O | HOH | W | 164 | −12.201 | −13.229 | 68.504 | 1.00 | 57.18 | O |
| ATOM | 6176 | O | HOH | W | 165 | −4.472 | 3.460 | 38.764 | 1.00 | 50.15 | O |
| ATOM | 6177 | O | HOH | W | 166 | 24.622 | 8.189 | 77.968 | 1.00 | 54.21 | O |
| ATOM | 6178 | O | HOH | W | 167 | −2.456 | 15.388 | 23.450 | 1.00 | 38.58 | O |
| ATOM | 6179 | O | HOH | W | 168 | −28.829 | −6.491 | 23.424 | 1.00 | 60.16 | O |
| ATOM | 6180 | O | HOH | W | 169 | −4.716 | 14.778 | 20.756 | 1.00 | 58.41 | O |
| ATOM | 6181 | O | HOH | W | 170 | −28.533 | −1.430 | 36.129 | 1.00 | 48.87 | O |
| ATOM | 6182 | O | HOH | W | 171 | 51.138 | 10.772 | 68.228 | 1.00 | 65.98 | O |
| ATOM | 6183 | O | HOH | W | 172 | 27.473 | 0.689 | 57.998 | 1.00 | 59.26 | O |
| ATOM | 6184 | O | HOH | W | 173 | −36.058 | 1.629 | 11.106 | 1.00 | 48.89 | O |
| ATOM | 6185 | O | HOH | W | 174 | 40.382 | −0.790 | 70.690 | 1.00 | 60.04 | O |
| ATOM | 6186 | O | HOH | W | 175 | 23.511 | 11.615 | 55.994 | 1.00 | 58.28 | O |
| ATOM | 6187 | O | HOH | W | 176 | −27.893 | −8.727 | 43.417 | 1.00 | 64.51 | O |
| ATOM | 6188 | O | HOH | W | 177 | −25.818 | 5.196 | 41.304 | 1.00 | 57.75 | O |
| ATOM | 6189 | O | HOH | W | 178 | 14.904 | −4.333 | 30.202 | 1.00 | 55.03 | O |
| ATOM | 6190 | O | HOH | W | 179 | −76.708 | 15.409 | 6.925 | 1.00 | 62.92 | O |
| ATOM | 6191 | O | HOH | W | 180 | −51.178 | 6.996 | 19.843 | 1.00 | 45.76 | O |
| ATOM | 6192 | O | HOH | W | 181 | −43.066 | −16.209 | 40.357 | 1.00 | 59.36 | O |
| ATOM | 6193 | O | HOH | W | 182 | −18.246 | 20.266 | 24.873 | 1.00 | 56.40 | O |
| ATOM | 6194 | O | HOH | W | 183 | −58.127 | 11.649 | 2.297 | 1.00 | 52.06 | O |
| ATOM | 6195 | O | HOH | W | 184 | −43.529 | −5.272 | 7.994 | 1.00 | 63.60 | O |
| ATOM | 6196 | O | HOH | W | 185 | −54.623 | 7.080 | −3.678 | 1.00 | 64.59 | O |
| ATOM | 6197 | O | HOH | W | 186 | 28.406 | 10.047 | 58.665 | 1.00 | 49.59 | O |
| ATOM | 6198 | O | HOH | W | 187 | −33.728 | 4.825 | 10.295 | 1.00 | 57.73 | O |
| ATOM | 6199 | O | HOH | W | 188 | 45.194 | 10.596 | 89.089 | 1.00 | 55.86 | O |
| ATOM | 6200 | O | HOH | W | 189 | 49.422 | −0.975 | 69.803 | 1.00 | 50.89 | O |
| ATOM | 6201 | O | HOH | W | 190 | 12.222 | 19.123 | 65.693 | 1.00 | 61.30 | O |
| ATOM | 6202 | O | HOH | W | 191 | −14.619 | −0.758 | 9.251 | 1.00 | 43.87 | O |
| ATOM | 6203 | O | HOH | W | 192 | 36.219 | 22.925 | 78.924 | 1.00 | 51.23 | O |

TABLE 10-continued

Atomic coordinates for COM1 complex of the modified
TXNIP protein represented by SEQ ID NO: 6 and the modified protein represented by SEQ ID NO: 3

| | | | | | | | | | |
|---|---|---|---|---|---|---|---|---|---|
| ATOM | 6204 | O | HOH | W | 193 | −46.533 | 10.567 | 28.651 | 1.00 | 50.19 | O |
| ATOM | 6205 | O | HOH | W | 194 | −76.438 | 6.750 | 0.972 | 1.00 | 60.95 | O |
| ATOM | 6206 | O | HOH | W | 195 | −11.710 | 8.498 | 40.315 | 1.00 | 68.08 | O |
| ATOM | 6207 | O | HOH | W | 196 | 23.362 | 1.563 | 46.099 | 1.00 | 43.66 | O |
| ATOM | 6208 | O | HOH | W | 197 | −38.725 | −2.507 | 11.281 | 1.00 | 52.23 | O |
| ATOM | 6209 | O | HOH | W | 198 | −52.479 | −8.958 | 44.427 | 1.00 | 53.82 | O |
| ATOM | 6210 | O | HOH | W | 199 | 4.868 | 9.316 | 20.974 | 1.00 | 55.37 | O |
| ATOM | 6211 | O | HOH | W | 200 | 27.394 | 3.846 | 47.878 | 1.00 | 56.95 | O |
| ATOM | 6212 | O | HOH | W | 201 | −37.336 | −11.895 | 52.095 | 1.00 | 61.10 | O |
| ATOM | 6213 | O | HOH | W | 202 | −11.138 | −10.783 | 68.300 | 1.00 | 51.55 | O |
| ATOM | 6214 | O | HOH | W | 203 | 39.808 | 13.693 | 92.054 | 1.00 | 52.22 | O |
| ATOM | 6215 | O | HOH | W | 204 | −50.604 | 14.875 | 11.049 | 1.00 | 47.71 | O |
| ATOM | 6216 | O | HOH | W | 205 | −42.021 | 3.419 | 4.323 | 1.00 | 36.15 | O |
| ATOM | 6217 | O | HOH | W | 206 | −10.857 | 16.104 | 20.648 | 1.00 | 39.22 | O |
| ATOM | 6218 | O | HOH | W | 207 | −15.039 | −2.968 | 2.476 | 1.00 | 67.99 | O |
| ATOM | 6219 | O | HOH | W | 208 | −34.954 | 2.819 | 4.764 | 1.00 | 57.86 | O |
| ATOM | 6220 | O | HOH | W | 209 | −61.818 | 3.799 | 22.967 | 1.00 | 55.88 | O |
| ATOM | 6221 | O | HOH | W | 210 | −43.504 | 15.933 | 20.824 | 1.00 | 59.71 | O |
| ATOM | 6222 | O | HOH | W | 211 | −72.820 | −11.999 | 4.970 | 1.00 | 58.71 | O |
| ATOM | 6223 | O | HOH | W | 212 | −9.021 | 3.248 | 49.077 | 1.00 | 61.19 | O |
| ATOM | 6224 | O | HOH | W | 213 | −71.648 | −3.000 | 20.745 | 1.00 | 70.27 | O |
| ATOM | 6225 | O | HOH | W | 214 | 25.776 | 10.185 | 56.254 | 1.00 | 56.02 | O |
| ATOM | 6226 | O | HOH | W | 215 | −55.896 | 11.746 | 0.060 | 1.00 | 66.45 | O |
| ATOM | 6227 | O | HOH | W | 216 | −73.036 | −5.374 | 22.820 | 1.00 | 68.23 | O |
| ATOM | 6228 | O | HOH | W | 217 | −28.563 | 1.809 | 33.654 | 1.00 | 64.75 | O |
| ATOM | 6229 | O | HOH | W | 218 | 42.658 | 9.737 | 57.756 | 1.00 | 64.44 | O |
| ATOM | 6230 | O | HOH | W | 219 | −58.131 | −3.652 | 8.717 | 1.00 | 48.34 | O |
| ATOM | 6231 | O | HOH | W | 220 | −17.348 | 5.572 | 34.109 | 1.00 | 55.12 | O |
| ATOM | 6232 | O | HOH | W | 221 | −4.780 | −15.030 | 71.597 | 1.00 | 63.65 | O |
| ATOM | 6233 | O | HOH | W | 222 | −14.718 | −11.096 | 41.952 | 1.00 | 66.17 | O |
| ATOM | 6234 | O | HOH | W | 223 | −49.678 | −3.835 | 15.521 | 1.00 | 58.21 | O |
| ATOM | 6235 | O | HOH | W | 224 | −21.987 | 1.741 | 26.766 | 1.00 | 63.98 | O |
| ATOM | 6236 | O | HOH | W | 225 | −11.261 | 10.696 | 73.552 | 1.00 | 63.71 | O |
| ATOM | 6237 | O | HOH | W | 226 | −17.246 | 15.779 | 22.439 | 1.00 | 50.54 | O |
| ATOM | 6238 | O | HOH | W | 227 | −20.989 | −2.826 | 28.157 | 1.00 | 68.70 | O |
| ATOM | 6239 | O | HOH | W | 228 | −40.465 | 17.719 | 6.735 | 1.00 | 57.61 | O |
| ATOM | 6240 | O | HOH | W | 229 | −17.203 | 6.101 | 37.478 | 1.00 | 68.83 | O |
| ATOM | 6241 | O | HOH | W | 230 | 26.371 | 13.747 | 81.067 | 1.00 | 51.51 | O |
| ATOM | 6242 | O | HOH | W | 231 | −20.145 | 7.663 | 30.810 | 1.00 | 65.17 | O |
| ATOM | 6243 | O | HOH | W | 232 | −41.086 | 15.969 | 16.883 | 1.00 | 51.10 | O |
| ATOM | 6244 | O | HOH | W | 233 | −35.526 | 11.732 | 13.365 | 1.00 | 51.83 | O |
| ATOM | 6245 | O | HOH | W | 234 | −34.643 | −3.851 | 44.163 | 1.00 | 58.92 | O |
| ATOM | 6246 | O | HOH | W | 235 | −42.001 | −17.097 | 52.481 | 1.00 | 69.56 | O |
| ATOM | 6247 | O | HOH | W | 236 | 10.136 | −9.671 | 44.981 | 1.00 | 60.86 | O |
| ATOM | 6248 | O | HOH | W | 237 | 23.784 | −4.824 | 63.327 | 1.00 | 59.63 | O |
| ATOM | 6249 | O | HOH | W | 238 | 12.368 | 14.380 | 36.712 | 1.00 | 69.40 | O |
| ATOM | 6250 | O | HOH | W | 239 | 33.051 | 14.011 | 62.291 | 1.00 | 38.89 | O |
| ATOM | 6251 | O | HOH | W | 240 | −50.562 | −8.588 | 47.923 | 1.00 | 58.78 | O |
| ATOM | 6252 | O | HOH | W | 241 | −13.893 | 9.889 | 39.916 | 1.00 | 58.04 | O |
| ATOM | 6253 | O | HOH | W | 242 | −29.250 | 8.127 | 18.289 | 1.00 | 53.27 | O |

TABLE 10-continued

Atomic coordinates for COM1 complex of the modified
TXNIP protein represented by SEQ ID NO: 6 and the modified protein represented by SEQ ID NO: 3

| | | | | | | | | | |
|---|---|---|---|---|---|---|---|---|---|
| ATOM | 6254 | O | HOH | W | 243 | 19.922 | -5.211 | 28.964 | 1.00 | 53.44 | O |
| ATOM | 6255 | O | HOH | W | 244 | 23.616 | -3.632 | 26.615 | 1.00 | 48.58 | O |
| ATOM | 6256 | O | HOH | W | 245 | -22.987 | 0.285 | 18.065 | 1.00 | 56.93 | O |
| ATOM | 6257 | O | HOH | W | 246 | -30.022 | 2.824 | 14.706 | 1.00 | 58.13 | O |
| ATOM | 6258 | O | HOH | W | 247 | -2.107 | 4.429 | 44.195 | 1.00 | 67.13 | O |
| ATOM | 6259 | O | HOH | W | 248 | -13.070 | -0.700 | 32.583 | 1.00 | 44.92 | O |
| END | | | | | | | | | | |

TABLE 11

| | | |
|---|---|---|
| HEADER | ---- | XX-XXX-XX XXXX |
| COMPND | --- | |
| REMARK | 3 | |
| REMARK | 3 | REFINEMENT. |
| REMARK | 3 | PROGRAM: REFMAC 5.2.0019 |
| REMARK | 3 | AUTHORS: MURSHUDOV. VAGIN, DODSON |
| REMARK | 3 | |
| REMARK | 3 | REFINEMENT TARGET: MAXIMUM LIKELIHOOD |
| REMARK | 3 | |
| REMARK | 3 | DATA USED IN REFINEMENT |
| REMARK | 3 | RESOLUTION RANGE HIGH (ANGSTROMS): 2.70 |
| REMARK | 3 | REGOLUTION RANGE LOW (ANGSTROMS): 40.00 |
| REMARK | 3 | DATA CUTOFF (SIGMA(F)): NONE |
| REMARK | 3 | COMPLETENESS FOR RANGE (%): 99.49 |
| REMARK | 3 | NUMBER OF REFLECTIONS: 22957 |
| REMARK | 3 | |
| REMARK | 3 | FIT TO DATA USED IN REFINEMENT. |
| REMARK | 3 | CROSS-VALIDATION METHOD: THROUGHOUT |
| REMARK | 3 | FREE R VALUE TEST SET SELECTION: RANDOM |
| REMARK | 3 | R VALUE (WORKING + TEST SET): 0.20130 |
| REMARK | 3 | R VALUE (WORKING SET): 0.19589 |
| REMARK | 3 | FREE R VALUE: 0.26401 |
| REMARK | 3 | FREE R VALUE TEST SET SIZE (%): 7.8 |
| REMARK | 3 | FREE R VALUE TEST SET COUNT: 1942 |
| REMARK | 3 | |
| REMARK | 3 | FIT IN THE HIGHEST RESOLUTION BIN |
| REMARK | 3 | TOTAL NUMBER OF BINS USED: 20 |
| REMARK | 3 | BIN RESOLUTION RANGE HIGH: 2.704 |
| REMARK | 3 | BIN RESOLUTION RANGE LOW: 2.774 |
| REMARK | 3 | REFLECTION IN BIN (WORKING SET): 1568 |
| REMARK | 3 | BIN COMPLETENESS (WORKING + TEST) (%): 93.89 |
| REMARK | 3 | BIN R VALUE (WORKING SET): 0.253 |
| REMARK | 3 | BIN FREE R VALUE SET COUNT: 139 |
| REMARK | 3 | BIN FREE R VALUE: 0.348 |
| REMARK | 3 | |
| REMARK | 3 | NUMBER IF NON-HYDROGEN ATOMS USED IN REFINEMENT. |
| REMARK | 3 | ALL ATOMS: 6074 |
| REMARK | 3 | |
| REMARK | 3 | B VALUES |
| REMARK | 3 | FROM WILSON PLOT (A**2): NULL |
| REMARK | 3 | MEAN B VALUE (OVERALL. A**2): 55.593 |
| REMARK | 3 | OVERALL ANISOTROPIC B VALUE. |
| REMARK | 3 | B11 (A**2):       −1.63 |
| REMARK | 3 | B22 (A**2):        3.94 |
| REMARK | 3 | B33 (A**2):       −2.37 |
| REMARK | 3 | B12 (A**2):        0.00 |
| REMARK | 3 | B13 (A**2):       −1.91 |
| REMARK | 3 | B23 (A**2):        0.00 |
| REMARK | 3 | |
| REMARK | 3 | ESTIMATED OVERALL COORDINATE ERROR. |
| REMARK | 3 | ESU BASED ON R VALUE (A): NULL |
| REMARK | 3 | ESU BASED ON FREE R VALUE (A): 0:378 |
| REMARK | 3 | ESU BASED ON MAXIMUM LIKELIHOOD (A): 0.275 |
| REMARK | 3 | ESU FOR B VALUES BASED ON MAXIMUM LIKELIHOOD (A**2): 28.731 |
| REMARK | 3 | |
| REMARK | 3 | CORRELATION COEFFICIENTS. |
| REMARK | 3 | CORRELATION COEFFICIENT FO-FC: 0.946 |
| REMARK | 3 | CORRELATION COEFFICIENT FO-FC FREE: 0.905 |
| REMARK | 3 | |
| REMARK | 3 | RMS DEVIATIONS FROM IDEAL VALUES COUNT RMS WEIGHT |
| REMARK | 3 | BOND LENGTHS REFINED ATOMS (A): 6125: 0.022: 0.022 |
| REMARK | 3 | BOND ANGLES REFINED ATOMS (DEGREES): 8250: 2.148: 1.967 |
| REMARK | 3 | TORSION ANGLES. PERIOD 1 (DEGREES): 760: 8.426: 5.000 |
| REMARK | 3 | TORSION ANGLES. PERIOD 2 (DEGREES): 259: 37.838: 24.440 |
| REMARK | 3 | TORSION ANGLES. PERIOD 3 (DEGREES): 1135: 22.704: 15.000 |
| REMARK | 3 | TORSION ANGLES, PERIOD 4 (DEGREES): 34: 19.359: 15.000 |
| REMARK | 3 | CHIRAL-CENTER RESTRAINTS (A**3): 926: 0.134: 0.200 |
| REMARK | 3 | GENERAL PLANES REFINED ATOMS (A): 4504: 0.007: 0.020 |
| REMARK | 3 | NON-BONDED CONTACTS REFINED ATOMS (A): 2664: 0.268: 0.200 |
| REMARK | 3 | NON-BONDED TORSION REFINED ATOMS (A): 4090: 0.331: 0.200 |
| REMARK | 3 | H-BOND (X . . .Y) REFINED ATOMS (A): 243: 0 189: 0.200 |
| REMARK | 3 | SYMMETRY VDW REFINED ATOMS (A): 69: 0.274: 0.200 |
| REMARK | 3 | SYMMETRY H-BOND REFINED ATOMS (A): 8: 0.155: 0.200 |
| REMARK | 3 | |
| REMARK | 3 | ISOTROPIC THERMAL FACTOR RESTRAINTS. COUNT RMS WEIGHT |
| REMARK | 3 | MAIN-CHAIN BOND REFINED ATOMS (A**2): 3896: 1.252: 1.500 |
| REMARK | 3 | MAIN-CHAIN ANGLE REFINED ATOMS (A**2): 6168: 1.865: 2.000 |
| REMARK | 3 | SIDE-CHAIN BOND REFINED ATOMS (A**2): 2498: 2:866: 3.000 |
| REMARK | 3 | SIDE-CHAIN ANGLE REFINED ATOMS (A**2): 2082: 4.375: 4.550 |
| REMARK | 3 | |

TABLE 11-continued

| REMARK | 3 | NCS RESTRAINTS STATISTICS | | |
|---|---|---|---|---|
| REMARK | 3 | NUMBER OF NCS GROUPS : NULL | | |
| REMARK | 3 | | | |
| REMARK | 3 | | | |
| REMARK | 3 | TLS DETAILS | | |
| REMARK | 3 | NUMBER OF TLS GROUPS: 4 | | |
| REMARK | 3 | ATOM RECORD CONTAINS RESIDUAL B FACTORS ONLY | | |
| REMARK | 3 | | | |
| REMARK | 3 | TLS GROUP: 1 | | |
| REMARK | 3 | NUMBER OF COMPONENTS GROUP: 1 | | |
| REMARK | 3 | COMPONENTS C SSSEQI TO C SSSEQI | | |
| REMARK | 3 | RESIDUE RANGE : A 7 A 298 | | |
| REMARK | 3 | ORIGIN FOR THE GROUP (A): 10.8635 −3.8251 41.4633 | | |
| REMARK | 3 | T TENSOR | | |
| REMARK | 3 | T11: 0.0355 | T22: 0.0077 | |
| REMARK | 3 | T33: −0.0196 | T12: 0.0766 | |
| REMARK | 3 | T13: 0.0353 | T23: −0.0359 | |
| REMARK | 3 | L TENSOR | | |
| REMARK | 3 | L11: 1.3745 | L22: 0.1970 | |
| REMARK | 3 | L33: 1.6361 | L12: −0.3932 | |
| REMARK | 3 | L13: 1.4967 | L23: −0.4512 | |
| REMARK | 3 | S TENSOR | | |
| REMARK | 3 | S11: −0.1291 | S12: −0.1393 | S13: 0.0051 |
| REMARK | 3 | S21: 0.0486 | S22: 0.0761 | S23: −0.0456 |
| REMARK | 3 | S31: 0.1720 | S32: 0.0707 | S33: 0.0530 |
| REMARK | 3 | | | |
| REMARK | 3 | TLS GROUP: 2 | | |
| REMARK | 3 | NUMBER OF COMPONENTS GROUP: 1 | | |
| REMARK | 3 | COMPONENTS C SSSEQI TO C SSSEQI | | |
| REMARK | 3 | RESIDUE RANGE: B 1 B 105 | | |
| REMARK | 3 | ORIGIN FOR THE GROUP (A): −27.8363 −1.6952 6.4891 | | |
| REMARK | 3 | T TENSOR | | |
| REMARK | 3 | T11: −0 1467 | T22: 0.0588 | |
| REMARK | 3 | T33: −0.0493 | T12: 0.0086 | |
| REMARK | 3 | T13: −0.0224 | T23: 0.0007 | |
| REMARK | 3 | L TENSOR | | |
| REMARK | 3 | L11: 3.8654 | L22: 1.5744 | |
| REMARK | 3 | L33: 3.4605 | L12: 0.1427 | |
| REMARK | 3 | L13: 1.8856 | L23: 0.0410 | |
| REMARK | 3 | S TENSOR | | |
| REMARK | 3 | S11: 0.2820 | S12: −0.0791 | S13: −0.5409 |
| REMARK | 3 | S21: 0.0235 | S22: −0.0300 | S23: 0.6027 |
| REMARK | 3 | S31: 0.2906 | S32: −0.6732 | S33: −0.2520 |
| REMARK | 3 | | | |
| REMARK | 3 | TLS GROUP: 3 | | |
| REMARK | 3 | NUMBER OF COMPONENTS GROUP: 1 | | |
| REMARK | 3 | COMPONENTS C SSSEQI TO C SSSEQI | | |
| REMARK | 3 | RESIDUE RANGE: C 8 C 299 | | |
| REMARK | 3 | ORIGIN FOR THE GROUP (A): 41.5119 1.9937 39.1443 | | |
| REMARK | 5 | T TENSOR | | |
| REMARK | 3 | T11: −0.1103 | T22: −0.0627 | |
| REMARK | 3 | T33: −0.0482 | T12: −0.0175 | |
| REMARK | 3 | T13: 0.0258 | T23: −0.0014 | |
| REMARK | 3 | L TENSOR | | |
| REMARK | 3 | L11: 1.1742 | L22: 0.3796 | |
| REMARK | 3 | L33: 1.6991 | L12: −0.0203 | |
| REMARK | 3 | L13: 1.1790 | L23: −0.0245 | |
| REMARK | 3 | S TENSOR | | |
| REMARK | 3 | S11: 0.0059 | S12: 0.0063 | S13: −0.0837 |
| REMARK | 3 | S21: −0.0027 | S22: 0.0025 | S23: 0.0418 |
| REMARK | 3 | S31: 0.0416 | S32: −0.0839 | S33: −0.0084 |
| REMARK | 3 | | | |
| REMARK | 3 | TLS GROUP: 4 | | |
| REMARK | 3 | NUMBER OF COMPONENTS GROUP: 1 | | |
| REMARK | 3 | COMPONENTS C SSSEQI TO C SSSEQI | | |
| REMARK | 3 | RESIDUE RANGE: D 1 D 105 | | |
| REMARK | 3 | ORIGIN FOR THE GROUP (A): 79.4923 6.3122 74.6094 | | |
| REMARK | 3 | T TENSOR | | |
| REMARK | 3 | T11: −0.1313 | T22: −0.1975 | |
| REMARK | 3 | T33: 0.1389 | T12: 0 0102 | |
| REMARK | 3 | T13: −0.1147 | T23: 0.0346 | |
| REMARK | 3 | L TENSOR | | |
| REMARK | 3 | L11: 3.6496 | L22: 3.6691 | |
| REMARK | 3 | L33: 3.1340 | L12: 0.3087 | |
| REMARK | 3 | L13: −0.2725 | L23: −0.0221 | |
| REMARK | 3 | S TENSOR | | |
| REMARK | 3 | S11: 0.1266 | S12: 0.1999 | S13: −0.2359 |
| REMARK | 3 | S21: 0.1508 | S22: −0.0870 | S23: −0.2931 |
| REMARK | 3 | S31: 0:1397 | S32: 0.3250 | S33: −0 0397 |
| REMARK | 3 | | | |

TABLE 11-continued

| REMARK | 3 | | | | | | | | | |
|---|---|---|---|---|---|---|---|---|---|---|
| REMARK | 3 | BULK SOLVENT MODELLING. | | | | | | | | |
| REMARK | 3 | METHOD USED: MASK | | | | | | | | |
| REMARK | 3 | PARAMETERS FOR MASK CALCULATION | | | | | | | | |
| REMARK | 3 | VDW PROBE RADIUS: 1.20 | | | | | | | | |
| REMARK | 3 | ION PROBE RADIUS: 0.80 | | | | | | | | |
| REMARK | 3 | SHRINKAGE RADIUS: 0.80 | | | | | | | | |
| REMARK | 3 | | | | | | | | | |
| REMARK | 3 | OTHER REFINEMENT REMARKS: NULL | | | | | | | | |
| REMARK | 3 | | | | | | | | | |
| SSSBOND | 1 | CYS A | 63 | CYS A | 190 | | | | | |
| SSBOND | 2 | CYS C | 63 | CYS C | 190 | | | | | |
| SSOND | 3 | CYS C | 247 | CYS D | 32 | | | | | |
| LINK | | VAL A | 145 | ASP A | 155 | gap | | | | |
| CISPEP | 1 | GLN A | 226 | THR A | 227 | 0.00 | | | | |
| LINK | | ARG A | 261 | ASN A | 268 | gap | | | | |
| CISPEP | 2 | MET B | 74 | PRO B | 75 | 0.00 | | | | |
| LINK | | LEU C | 148 | PRO C | 154 | gap | | | | |
| CISPEP | 3 | ASN C | 224 | GLY C | 225 | 0.00 | | | | |
| LINK | | GLN C | 258 | LEU C | 265 | gap | | | | |
| LINK | | ILE A | 260 | ASN A | 268 | gap | | | | |
| CISPEP | 4 | MET D | 74 | PRO D | 75 | 0.00 | | | | |
| CRYST1 | | 79.826 | | 64.990 | | 88.416 | 90.00 | 90.88 | 90.00 | P 1 21 1 |
| SCALE1 | | 0.012527 | | 0.000000 | | 0.000192 | 0.00000 | | | |
| SCALE2 | | 0.000000 | | 0.015387 | | 0.000000 | 0.00000 | | | |
| SCALE3 | | 0.000000 | | 0.000000 | | 0.011312 | 0.00000 | | | |
| ATOM | 1 | N | ILE A | 7 | 29.005 | −11.559 | 73.910 | 1.00 | 54.24 | N |
| ATOM | 2 | CA | ILE A | 7 | 29.311 | −10.223 | 73.301 | 1.00 | 53.88 | C |
| ATOM | 3 | CB | ILE A | 7 | 28.895 | −10.129 | 71.823 | 1.00 | 53.42 | C |
| ATOM | 4 | CG1 | ILE A | 7 | 29.763 | −11.010 | 70.939 | 1.00 | 51.90 | C |
| ATOM | 5 | CD1 | ILE A | 7 | 31.179 | −10.517 | 70.774 | 1.00 | 50.66 | C |
| ATOM | 6 | CG2 | ILE A | 7 | 29.039 | −8.710 | 71.335 | 1.00 | 53.67 | O |
| ATOM | 7 | C | ILE A | 7 | 28.456 | −9.244 | 74.025 | 1.00 | 53.93 | C |
| ATOM | 8 | O | ILE A | 7 | 27.313 | −9.533 | 74.280 | 1.00 | 53.98 | O |
| ATOM | 9 | N | LYS A | 8 | 29.010 | −8.075 | 74.312 | 1.00 | 54.59 | N |
| ATOM | 10 | CA | LYS A | 8 | 28.400 | −7.083 | 75.213 | 1.00 | 54.86 | C |
| ATOM | 11 | CB | LYS A | 8 | 29.473 | −6.158 | 75.782 | 1.00 | 55.06 | C |
| ATOM | 12 | CG | LYS A | 8 | 29.041 | −5.333 | 76.934 | 1.00 | 56.50 | C |
| ATOM | 13 | CD | LYS A | 8 | 30.125 | −4.325 | 77.304 | 1.00 | 58.63 | C |
| ATOM | 14 | CE | LYS A | 8 | 29.528 | −3.212 | 78.158 | 1.00 | 57.43 | C |
| ATOM | 15 | NZ | LYS A | 8 | 29.573 | −1.968 | 77.352 | 1.00 | 57.30 | N |
| ATOM | 16 | C | LYS A | 8 | 27.358 | −6.211 | 74.551 | 1.00 | 54.83 | C |
| ATOM | 17 | O | LYS A | 8 | 26.444 | −5.724 | 75.235 | 1.00 | 55.11 | O |
| ATOM | 18 | N | SER A | 9 | 27.529 | −5.978 | 73.245 | 1.00 | 54.33 | N |
| ATOM | 19 | CA | SER A | 9 | 26.678 | −5.075 | 72.451 | 1.00 | 53.56 | C |
| ATOM | 20 | CB | SER A | 9 | 26.976 | −3.637 | 72.976 | 1.00 | 53.24 | C |
| ATOM | 21 | CG | SER A | 9 | 26.693 | −2.738 | 71.878 | 1.00 | 53.32 | O |
| ATOM | 22 | C | SER A | 9 | 27.099 | −5.049 | 70.981 | 1.00 | 53 75 | C |
| ATOM | 23 | C | SER A | 9 | 28.275 | −4.818 | 70.674 | 1.00 | 54.14 | O |
| ATOM | 24 | N | PHE A | 10 | 26.107 | −5.234 | 70.099 | 1.00 | 53.55 | N |
| ATOM | 25 | CA | PHE A | 10 | 26.254 | −5.286 | 68.648 | 1.00 | 52.88 | C |
| ATOM | 26 | CB | PHE A | 10 | 26.227 | −6.758 | 68.236 | 1.00 | 52 84 | C |
| ATOM | 27 | CG | PHE A | 10 | 26.580 | −6.991 | 68.816 | 1.00 | 49.89 | C |
| ATOM | 28 | CD1 | PHE A | 10 | 27.624 | −6.325 | 66.237 | 1.00 | 46.97 | C |
| ATOM | 29 | CE1 | PHE A | 10 | 27.952 | −6.542 | 64.946 | 1.00 | 47.71 | C |
| ATOM | 30 | CZ | PHE A | 10 | 27.250 | −7.436 | 64.185 | 1.00 | 46.90 | C |
| ATOM | 31 | CE2 | PHE A | 10 | 26.235 | −8.121 | 64.746 | 1.00 | 49.27 | O |
| ATOM | 32 | CD2 | PHE A | 10 | 25.887 | −7.892 | 66.074 | 1.00 | 49.44 | C |
| ATOM | 33 | C | PHE A | 10 | 25.088 | −4.568 | 67.971 | 1.00 | 53.36 | C |
| ATOM | 34 | C | PHE A | 10 | 23.977 | −5.117 | 67.894 | 1.00 | 53.21 | O |
| ATOM | 35 | N | GLU A | 11 | 25.296 | −3.346 | 67.486 | 1.00 | 53.35 | N |
| ATOM | 36 | CA | GLU A | 11 | 24.127 | −2.576 | 67.024 | 1.00 | 53.81 | C |
| ATOM | 37 | CB | GLU A | 11 | 23.632 | −1.592 | 68.116 | 1.00 | 53.97 | C |
| ATOM | 38 | CG | GLU A | 11 | 23.187 | −2.256 | 69.456 | 1.00 | 56.51 | C |
| ATOM | 39 | CD | GLU A | 11 | 21.869 | −3.051 | 69.340 | 1.00 | 58.19 | C |
| ATOM | 40 | OE1 | GLU A | 11 | 20.986 | −2.629 | 68.566 | 1.00 | 59.05 | O |
| ATOM | 41 | OE2 | GLU A | 11 | 21.710 | −4.099 | 70.012 | 1.00 | 58.41 | O |
| ATOM | 42 | C | GLU A | 11 | 24.331 | −1.848 | 65.701 | 1.00 | 53.47 | C |
| ATOM | 43 | C | GLU A | 11 | 25.452 | −1.467 | 65.856 | 1.00 | 53.30 | O |
| ATOM | 44 | N | VAL A | 12 | 23.234 | −1.648 | 64.974 | 1.00 | 53.12 | N |
| ATOM | 45 | CA | VAL A | 12 | 23.268 | −0.924 | 63.734 | 1.00 | 52.63 | C |
| ATOM | 46 | CB | VAL A | 12 | 22.400 | −1.645 | 62.665 | 1.00 | 53.26 | C |
| ATOM | 47 | CG1 | VAL A | 12 | 22.041 | −0.733 | 61.403 | 1.00 | 52.49 | C |
| ATOM | 48 | CG2 | VAL A | 12 | 23.053 | −2.987 | 62.231 | 1.00 | 51.76 | C |
| ATOM | 49 | C | VAL A | 12 | 22.714 | 0.425 | 64.073 | 1.00 | 53.22 | C |
| ATOM | 50 | O | VAL A | 12 | 21.613 | 0.507 | 64.576 | 1.00 | 53.73 | O |
| ATOM | 51 | N | VAL A | 13 | 23.461 | 1.498 | 63.844 | 1.00 | 53.51 | N |
| ATOM | 52 | CA | VAL A | 13 | 22.901 | 2.810 | 64.157 | 1.00 | 54.21 | C |
| ATOM | 53 | CB | VAL A | 13 | 23.462 | 3.349 | 65.448 | 1.00 | 54.93 | C |
| ATOM | 54 | CG1 | VAL A | 13 | 22.466 | 4.386 | 66.129 | 1.00 | 54.06 | C |

TABLE 11-continued

| | | | | | | | | | |
|---|---|---|---|---|---|---|---|---|---|
| ATOM | 55 | CG2 | VAL A | 13 | 23.786 | 2.175 | 66.367 | 1.00 | 55.93 | C |
| ATOM | 56 | C | VAL A | 13 | 23.071 | 3.837 | 63.048 | 1.00 | 54.38 | C |
| ATOM | 57 | O | VAL A | 13 | 24.190 | 4.048 | 62.539 | 1.00 | 54.66 | O |
| ATOM | 58 | N | PHE A | 14 | 21.945 | 4.461 | 62.676 | 1.00 | 53.88 | N |
| ATOM | 59 | CA | PHF A | 14 | 21.911 | 5.330 | 61.505 | 1.00 | 53.25 | C |
| ATOM | 60 | CB | PHE A | 14 | 20.541 | 5.318 | 60.801 | 1.00 | 53.25 | C |
| ATOM | 61 | CG | PHE A | 14 | 20.123 | 3.959 | 60.274 | 1.00 | 51.25 | C |
| ATOM | 62 | CD1 | PHE A | 14 | 20.616 | 3.481 | 59.073 | 1.00 | 50.92 | C |
| ATOM | 63 | CE1 | PHE A | 14 | 20.248 | 2.222 | 58.589 | 1.00 | 51.17 | C |
| ATOM | 64 | CZ | PHE A | 14 | 19.352 | 1.428 | 59.302 | 1.00 | 51.95 | C |
| ATOM | 65 | CE2 | PHE A | 14 | 18.829 | 1.905 | 60.512 | 1.00 | 51.68 | C |
| ATOM | 66 | CD2 | PHE A | 14 | 19.231 | 3.164 | 60.989 | 1.00 | 51.06 | C |
| ATOM | 67 | C | PHE A | 14 | 22.214 | 6.678 | 62.031 | 1.00 | 53.27 | C |
| ATOM | 68 | O | PHE A | 14 | 21.925 | 6.950 | 63.185 | 1.00 | 53.72 | O |
| ATOM | 69 | N | ASN A | 15 | 22.784 | 7.531 | 61.196 | 1.00 | 53.56 | N |
| ATOM | 70 | CA | ASN A | 15 | 23.081 | 8.893 | 61.631 | 1.00 | 53.80 | C |
| ATOM | 71 | CB | ASN A | 15 | 23.923 | 9.564 | 60.588 | 1.00 | 52.82 | C |
| ATOM | 72 | CG | ASN A | 15 | 25.106 | 8.704 | 60.239 | 1.00 | 50.93 | C |
| ATOM | 73 | OD1 | ASN A | 15 | 25.569 | 8.000 | 61.145 | 1.00 | 45.58 | O |
| ATOM | 74 | ND2 | ASN A | 15 | 25.477 | 8.680 | 58.937 | 1.00 | 49.17 | N |
| ATOM | 75 | C | ASN A | 15 | 21.919 | 9.746 | 62.070 | 1.00 | 54.44 | C |
| ATOM | 76 | O | ASN A | 15 | 22.045 | 10.441 | 63.063 | 1.00 | 55.06 | O |
| ATOM | 77 | N | ASP A | 16 | 20.810 | 9.683 | 61.340 | 1.00 | 55.53 | N |
| ATOM | 78 | CA | ASP A | 16 | 19.526 | 10.175 | 61.830 | 1.00 | 57.30 | C |
| ATOM | 79 | CB | ASP A | 16 | 18.826 | 11.116 | 60.824 | 1.00 | 57.94 | C |
| ATOM | 80 | CG | ASP A | 16 | 17.414 | 11.608 | 61.310 | 1.00 | 58.66 | C |
| ATOM | 81 | OD1 | ASP A | 16 | 16.827 | 11.072 | 62.297 | 1.00 | 60.79 | O |
| ATOM | 82 | OD2 | ASP A | 16 | 16.877 | 12.545 | 60.671 | 1.00 | 58.42 | C |
| ATOM | 83 | C | ASP A | 16 | 18.643 | 8.974 | 62.109 | 1.00 | 58.00 | C |
| ATOM | 84 | O | ASP A | 16 | 17.982 | 8.465 | 61.194 | 1.00 | 57.51 | O |
| ATOM | 85 | N | PRO A | 17 | 18.634 | 8.519 | 63.379 | 1.00 | 59.10 | N |
| ATOM | 86 | CA | PRO A | 17 | 17.874 | 7.329 | 63.787 | 1.00 | 59.49 | C |
| ATOM | 87 | CB | PRO A | 17 | 18.249 | 7.175 | 65.279 | 1.00 | 59.82 | C |
| ATOM | 88 | CG | PRO A | 17 | 19.628 | 7.897 | 65.401 | 1.00 | 59.44 | C |
| ATOM | 89 | CD | PRO A | 17 | 19.390 | 9.101 | 64.516 | 1.00 | 59.19 | C |
| ATOM | 90 | C | PRO A | 17 | 16.359 | 7.479 | 63.585 | 1.00 | 59.88 | C |
| ATOM | 91 | O | PRO A | 17 | 15.631 | 6.471 | 63.529 | 1.00 | 60.31 | O |
| ATOM | 92 | N | GLU A | 18 | 15.903 | 8.722 | 63.430 | 1.00 | 60.15 | N |
| ATOM | 93 | CA | GLU A | 18 | 14.479 | 9.034 | 63.260 | 1.00 | 60 15 | C |
| ATOM | 94 | CB | GLU A | 18 | 14.078 | 10.223 | 64.167 | 1.00 | 60.23 | C |
| ATOM | 95 | CG | GLU A | 18 | 13.975 | 9.873 | 65.074 | 1.00 | 59.51 | C |
| ATOM | 96 | CD | GLU A | 18 | 12.565 | 10.080 | 66.254 | 1.00 | 58.28 | C |
| ATOM | 97 | OE1 | GLU A | 18 | 11.603 | 10.288 | 65.463 | 1.00 | 57.70 | O |
| ATOM | 98 | OE2 | GLU A | 18 | 12.415 | 10.016 | 67.503 | 1.00 | 56.59 | O |
| ATOM | 99 | C | GLU A | 18 | 14.034 | 9.276 | 61.793 | 1.00 | 60.42 | C |
| ATOM | 100 | O | GLU A | 18 | 12.859 | 9.621 | 61.533 | 1.00 | 60.73 | O |
| ATOM | 101 | N | LYS A | 19 | 14.958 | 9.077 | 60.848 | 1.00 | 60.29 | N |
| ATOM | 102 | CA | LYS A | 19 | 14.722 | 9.367 | 59.442 | 1.00 | 60.03 | C |
| ATOM | 103 | CB | LYS A | 19 | 16.028 | 9.646 | 58.721 | 1.00 | 60.05 | C |
| ATOM | 104 | CG | LYS A | 19 | 15.922 | 9.768 | 57.214 | 1.00 | 59.85 | C |
| ATOM | 105 | CD | LYS A | 19 | 15.495 | 11.173 | 56.722 | 1.00 | 51.40 | C |
| ATOM | 106 | CE | LYS A | 19 | 15.601 | 11.319 | 65.238 | 1.00 | 61.81 | O |
| ATOM | 107 | NZ | LYS A | 19 | 17.024 | 11.494 | 54.828 | 1.00 | 62.83 | N |
| ATOM | 108 | C | LYS A | 10 | 14.047 | 8.238 | 58.741 | 1.00 | 60.73 | C |
| ATOM | 109 | O | LYS A | 19 | 14.340 | 7.069 | 58.993 | 1.00 | 60.52 | O |
| ATOM | 110 | N | VAL A | 20 | 13.136 | 8.525 | 57.855 | 1.00 | 62.14 | N |
| ATOM | 111 | CA | VAL A | 20 | 12.550 | 7.773 | 56.835 | 1.00 | 53.14 | C |
| ATOM | 112 | CB | VAL A | 20 | 11.006 | 7.812 | 56.916 | 1.00 | 63.08 | C |
| ATOM | 113 | CG1 | VAL A | 90 | 10.338 | 7.360 | 55.513 | 1.00 | 63.43 | C |
| ATOM | 114 | CG2 | VAL A | 20 | 10.525 | 8.981 | 58.091 | 1.00 | 62.40 | C |
| ATOM | 115 | C | VAL A | 20 | 13.079 | 8.340 | 55.527 | 1.00 | 64.09 | C |
| ATOM | 116 | O | VAL A | 20 | 13.136 | 9.561 | 55.346 | 1.00 | 63.88 | O |
| ATOM | 117 | N | TYR A | 21 | 13.467 | 7.445 | 54.623 | 1.00 | 65.64 | N |
| ATOM | 118 | CA | TYR A | 21 | 14.332 | 7.817 | 53.503 | 1.00 | 67.22 | C |
| ATOM | 119 | CB | TYR A | 21 | 15.580 | 6.897 | 53.469 | 1.00 | 67.39 | C |
| ATOM | 120 | CG | TYR A | 21 | 16.407 | 6.823 | 54.766 | 1.00 | 67.24 | C |
| ATOM | 121 | CD1 | TYR A | 21 | 17.689 | 7.373 | 54.837 | 1.00 | 66.14 | C |
| ATOM | 122 | CE1 | TYR A | 21 | 18.442 | 7.285 | 56.005 | 1.00 | 67.24 | C |
| ATOM | 123 | CZ | TYR A | 21 | 17.917 | 6.640 | 57.124 | 1.00 | 68.74 | C |
| ATOM | 124 | OH | TYR A | 21 | 18.630 | 6.568 | 58.299 | 1.00 | 69.30 | O |
| ATOM | 125 | CE2 | TYR A | 21 | 16.661 | 6.060 | 57.075 | 1.00 | 69.83 | C |
| ATOM | 126 | CD2 | TYR A | 21 | 15.916 | 6.146 | 55.897 | 1.00 | 69.28 | C |
| ATOM | 127 | C | TYR A | 21 | 13.619 | 7.844 | 52.130 | 1.00 | 67.98 | C |
| ATOM | 128 | O | TYR A | 21 | 12.544 | 7.219 | 51.954 | 1.00 | 67.26 | O |
| ATOM | 129 | N | GLY A | 22 | 14.230 | 8.561 | 51.170 | 1.00 | 69.08 | N |
| ATOM | 130 | CA | GLY A | 22 | 13.669 | 8.674 | 49.803 | 1.00 | 71.02 | C |
| ATOM | 131 | C | GLY A | 22 | 14.484 | 8.303 | 48.559 | 1.00 | 71.91 | C |
| ATOM | 132 | O | GLY A | 22 | 15.715 | 8.234 | 48.615 | 1.00 | 72.57 | O |
| ATOM | 133 | N | SER A | 23 | 13.780 | 8.090 | 47.435 | 1.00 | 72.56 | N |
| ATOM | 134 | CA | SER A | 23 | 14.358 | 7.594 | 46.168 | 1.00 | 73.49 | C |

TABLE 11-continued

| | | | | | | | | | |
|---|---|---|---|---|---|---|---|---|---|
| ATOM | 135 | CB | SER A | 23 | 13.322 | 7.646 | 45.028 | 1.00 | 73.30 | C |
| ATOM | 136 | OG | SER A | 23 | 13.938 | 7.523 | 43.748 | 1.00 | 74.01 | O |
| ATOM | 137 | C | SER A | 23 | 15.629 | 8.345 | 45.784 | 1.00 | 73.77 | C |
| ATOM | 138 | O | SER A | 23 | 15.693 | 9.574 | 45.901 | 1.00 | 74.23 | O |
| ATOM | 139 | N | GLY A | 24 | 16.649 | 7.601 | 45.363 | 1.00 | 74.18 | N |
| ATOM | 140 | CA | GLY A | 24 | 17.969 | 8.199 | 45.149 | 1.00 | 74.77 | C |
| ATOM | 141 | C | GLY A | 24 | 18.749 | 8.663 | 46.383 | 1.00 | 74.94 | C |
| ATOM | 142 | O | GLY A | 24 | 19.916 | 9.044 | 46.242 | 1.00 | 75.22 | O |
| ATOM | 143 | N | GLU A | 25 | 18.148 | 8.610 | 47.592 | 1.00 | 75.00 | N |
| ATOM | 144 | CA | GLU A | 25 | 18.825 | 9.106 | 48.821 | 1.00 | 74.77 | O |
| ATOM | 145 | CB | GLU A | 25 | 17.792 | 9.643 | 49.839 | 1.00 | 74.88 | C |
| ATOM | 145 | CG | GLU A | 25 | 18.432 | 10.279 | 51.069 | 1.00 | 77.41 | C |
| ATOM | 147 | CD | GLU A | 25 | 18.394 | 11.793 | 50.990 | 1.00 | 80.80 | C |
| ATOM | 148 | OE1 | GLU A | 25 | 17.335 | 12.355 | 51.362 | 1.00 | 82.13 | O |
| ATOM | 149 | OE2 | GLU A | 25 | 19.406 | 12.424 | 50.576 | 1.00 | 82.58 | O |
| ATOM | 150 | C | GLU A | 25 | 19.825 | 8.140 | 49.531 | 1.00 | 73.94 | C |
| ATOM | 151 | O | GLU A | 25 | 19.799 | 6.901 | 49.328 | 1.00 | 73.62 | O |
| ATOM | 152 | N | ARG A | 25 | 20.663 | 8.735 | 50.391 | 1.00 | 72.53 | N |
| ATOM | 153 | CA | ARG A | 26 | 21.857 | 8.091 | 50.943 | 1.00 | 71.72 | C |
| ATOM | 154 | CB | ARG A | 26 | 23.066 | 8.997 | 50.640 | 1.00 | 72.41 | C |
| ATOM | 155 | CG | ARG A | 26 | 24.286 | 8.911 | 51.566 | 1.00 | 75.08 | C |
| ATOM | 156 | CD | ARG A | 26 | 25.080 | 7.655 | 51.296 | 1.00 | 81.96 | C |
| ATOM | 157 | NE | ARG A | 26 | 26.101 | 7.810 | 50.242 | 1.00 | 85.66 | N |
| ATOM | 158 | CZ | ARG A | 26 | 27.191 | 7.037 | 50.123 | 1.00 | 86.75 | C |
| ATOM | 159 | NH1 | ARG A | 26 | 27.424 | 6.050 | 50.992 | 1.00 | 86.90 | N |
| ATOM | 160 | NH2 | ARG A | 26 | 28.057 | 7.251 | 49.133 | 1.00 | 87.35 | N |
| ATOM | 161 | C | ARG A | 26 | 21.777 | 7.681 | 52.437 | 1.00 | 70.11 | C |
| ATOM | 162 | O | ARG A | 26 | 21.898 | 8.521 | 53.324 | 1.00 | 69.54 | O |
| ATOM | 163 | N | VAL A | 27 | 21.598 | 6.378 | 52.684 | 1.00 | 68.60 | N |
| ATOM | 164 | CA | VAL A | 27 | 25.530 | 5.784 | 54.035 | 1.00 | 66.93 | C |
| ATOM | 165 | CB | VAL A | 27 | 20.753 | 4.473 | 54.023 | 1.00 | 66.96 | C |
| ATOM | 166 | CG1 | VAL A | 27 | 20.346 | 4.098 | 55.467 | 1.00 | 66.57 | C |
| ATOM | 167 | CG2 | VAL A | 27 | 19.556 | 4.548 | 53.089 | 1.00 | 66.64 | C |
| ATOM | 168 | C | VAL A | 27 | 22.901 | 5.400 | 54.614 | 1.00 | 65.96 | C |
| ATOM | 169 | O | VAL A | 27 | 23.612 | 4.574 | 54.019 | 1.00 | 66.75 | O |
| ATOM | 170 | N | ALA A | 28 | 23.244 | 5.937 | 55.788 | 1.00 | 63.80 | N |
| ATOM | 171 | CA | ALA A | 28 | 24.592 | 5.784 | 56.368 | 1.00 | 62.20 | C |
| ATOM | 172 | CB | ALA A | 28 | 25.546 | 6.894 | 55.882 | 1.00 | 61.81 | C |
| ATOM | 173 | C | ALA A | 28 | 24.593 | 5.744 | 57.888 | 1.00 | 61.17 | C |
| ATOM | 174 | O | ALA A | 28 | 23.616 | 6.141 | 58.555 | 1.00 | 61.37 | O |
| ATOM | 175 | N | GLY A | 29 | 25.712 | 5.279 | 58.437 | 1.00 | 59.85 | N |
| ATOM | 176 | CA | GLY A | 29 | 25.866 | 5.211 | 59.886 | 1.00 | 57.23 | C |
| ATOM | 177 | C | GLY A | 29 | 26.892 | 4.194 | 60.290 | 1.00 | 55.33 | C |
| ATOM | 178 | O | GLY A | 29 | 27.964 | 4.079 | 59.699 | 1.00 | 55.52 | O |
| ATOM | 179 | N | ARG A | 30 | 26.594 | 3.428 | 61.305 | 1.00 | 53.60 | N |
| ATOM | 180 | CA | ARG A | 30 | 27.611 | 2.495 | 61.683 | 1.00 | 52.99 | C |
| ATOM | 181 | CB | ARG A | 30 | 28.772 | 3.207 | 62.357 | 1.00 | 52.94 | C |
| ATOM | 182 | CG | ARG A | 30 | 28.371 | 3.995 | 63.520 | 1.00 | 54.25 | C |
| ATOM | 183 | CD | ARG A | 30 | 29.212 | 5.278 | 63.707 | 1.00 | 50.31 | C |
| AT OM | 184 | NE | ARG A | 30 | 28.750 | 5.892 | 64.954 | 1.00 | 59.23 | N |
| ATOM | 185 | CZ | ARG A | 30 | 27.505 | 6.349 | 65.133 | 1.00 | 61.58 | C |
| ATOM | 186 | NH1 | ARG A | 30 | 26.610 | 6.276 | 64.120 | 1.00 | 62.69 | N |
| ATOM | 187 | NH2 | ARG A | 30 | 27.148 | 6.872 | 66.313 | 1.00 | 58.57 | N |
| ATOM | 188 | C | ARG A | 30 | 27.141 | 1.321 | 62.490 | 1.00 | 52.11 | C |
| ATOM | 189 | O | ARG A | 30 | 26.045 | 1.297 | 63.052 | 1.00 | 52.92 | O |
| ATOM | 190 | N | VAL A | 31 | 27.971 | 0.308 | 62.472 | 1.00 | 50.65 | N |
| ATOM | 191 | CA | VAL A | 31 | 27.750 | −0.845 | 63.266 | 1.00 | 49.32 | C |
| ATOM | 192 | CB | VAL A | 31 | 28.106 | −2.039 | 52.444 | 1.00 | 49.32 | C |
| ATOM | 193 | CG1 | VAL A | 31 | 27.961 | −3.327 | 63.259 | 1.00 | 48.33 | C |
| ATOM | 194 | CG2 | VAL A | 31 | 27.259 | −2.032 | 61.183 | 1.00 | 48.18 | C |
| ATOM | 195 | C | VAL A | 31 | 28.716 | −0.675 | 64.432 | 1.00 | 48.96 | C |
| ATOM | 196 | O | VAL A | 31 | 29.897 | −0.315 | 64.249 | 1.00 | 49.54 | O |
| ATOM | 197 | N | ILE A | 32 | 28.227 | −0.885 | 65.636 | 1.00 | 47.99 | N |
| ATOM | 198 | CA | ILE A | 32 | 29.069 | −0.639 | 66.774 | 1.00 | 47.85 | C |
| ATOM | 199 | CB | ILE A | 32 | 28.591 | 0.607 | 67.557 | 1.00 | 46.95 | C |
| ATOM | 200 | CG1 | ILE A | 32 | 28.650 | 1.822 | 66.661 | 1.00 | 45.98 | C |
| ATOM | 201 | CD1 | ILE A | 32 | 27.558 | 2.767 | 66.984 | 1.00 | 46.32 | C |
| ATOM | 202 | CG2 | ILE A | 32 | 29.577 | 1.014 | 68.611 | 1.00 | 45.60 | C |
| ATOM | 203 | C | ILE A | 32 | 29.101 | −1.908 | 67.606 | 1.00 | 48.58 | C |
| ATOM | 204 | O | ILE A | 32 | 28.057 | −2.544 | 67.840 | 1.00 | 48.54 | O |
| ATOM | 205 | N | VAL A | 33 | 30.325 | −2.272 | 68.005 | 1.00 | 49.82 | N |
| ATOM | 206 | CA | VAL A | 33 | 30.640 | −3.521 | 68.726 | 1.00 | 51.00 | C |
| ATOM | 207 | CB | VAL A | 33 | 31.407 | −4.563 | 67.792 | 1.00 | 50.75 | C |
| ATOM | 208 | CG1 | VAL A | 33 | 31.386 | −5.967 | 68.345 | 1.00 | 48.30 | C |
| ATOM | 209 | CG2 | VAL A | 33 | 30.790 | −4.589 | 66.418 | 1.00 | 51.27 | C |
| ATOM | 210 | C | VAL A | 33 | 31.455 | −3.194 | 69.991 | 1.00 | 51.91 | C |
| ATOM | 211 | O | VAL A | 33 | 32.427 | −2.414 | 69.943 | 1.00 | 50.68 | O |
| ATOM | 212 | N | GLU A | 34 | 31.004 | −3.792 | 71.097 | 1.00 | 54.17 | N |
| ATOM | 213 | CA | GLU A | 34 | 31.687 | −3.822 | 72.405 | 1.00 | 57.44 | C |
| ATOM | 214 | CB | GLU A | 34 | 31.004 | −2.887 | 73.405 | 1.00 | 57.39 | C |

TABLE 11-continued

| | | | | | | | | | | |
|---|---|---|---|---|---|---|---|---|---|---|
| ATOM | 215 | CG | GLU A | 34 | 31.687 | −1.399 | 73.279 | 1.00 | 61.75 | C |
| ATOM | 216 | CD | GLU A | 34 | 30.421 | −0.457 | 74.057 | 1.00 | 67.03 | C |
| ATOM | 217 | OE1 | GLU A | 34 | 29.632 | −0.936 | 74.912 | 1.00 | 68.25 | O |
| ATOM | 218 | OE2 | GLU A | 34 | 30.437 | 0.771 | 73.815 | 1.00 | 68.21 | O |
| ATOM | 219 | C | GLU A | 34 | 31.669 | −5.259 | 72.972 | 1.00 | 58.41 | C |
| ATOM | 220 | O | GLU A | 34 | 30.628 | −5.944 | 72.909 | 1.00 | 58.27 | O |
| ATOM | 221 | N | VAL A | 35 | 32.805 | −5.724 | 73.499 | 1.00 | 59.75 | N |
| ATOM | 222 | CA | VAL A | 35 | 32.833 | −7.045 | 74.113 | 1.00 | 61.53 | C |
| ATOM | 223 | CB | VAL A | 35 | 33.870 | −8.014 | 73.512 | 1.00 | 61.75 | C |
| ATOM | 224 | CG1 | VAL A | 35 | 33.305 | −9.482 | 73.577 | 1.00 | 63.01 | C |
| ATOM | 225 | CG2 | VAL A | 35 | 34.310 | −7.601 | 72.124 | 1.00 | 60.56 | C |
| ATOM | 226 | C | VAL A | 35 | 33.209 | −6.948 | 75.563 | 1.00 | 62.82 | C |
| ATOM | 227 | O | VAL A | 35 | 33.910 | −6.007 | 75.982 | 1.00 | 63.09 | O |
| ATOM | 228 | N | CYS A | 36 | 32.785 | −7.960 | 76.321 | 1.00 | 64.01 | N |
| ATOM | 229 | CA | CYS A | 36 | 33.228 | −8.120 | 77.729 | 1.00 | 65.37 | C |
| ATOM | 230 | CB | CYS A | 36 | 32.397 | 9.193 | 78.453 | 1.00 | 64.76 | C |
| ATOM | 231 | SG | CYS A | 36 | 30.656 | −9.017 | 78.065 | 1.00 | 69.83 | S |
| ATOM | 232 | C | CYS A | 36 | 34.735 | −8.434 | 77.797 | 1.00 | 64.95 | C |
| ATOM | 233 | O | CYS A | 36 | 35.537 | −7.568 | 78.199 | 1.00 | 65.29 | C |
| ATOM | 234 | N | GLU A | 37 | 35.097 | −9.646 | 77.384 | 1.00 | 64.59 | N |
| ATOM | 235 | CA | GLU A | 37 | 36.479 | −10.082 | 77.330 | 1.00 | 63.88 | C |
| ATOM | 236 | CB | GLU A | 37 | 36.570 | −11.517 | 77.834 | 1.00 | 64.37 | C |
| ATOM | 237 | CG | GLU A | 37 | 35.284 | −12.274 | 77.654 | 1.00 | 67.60 | C |
| ATOM | 238 | CD | GLU A | 37 | 33.519 | −13.533 | 76.869 | 1.00 | 73.16 | C |
| ATOM | 239 | OE1 | GLU A | 37 | 35.591 | −14.615 | 77.515 | 1.00 | 74.44 | O |
| ATOM | 240 | OE2 | GLU A | 37 | 35.684 | −13.431 | 75.615 | 1.00 | 74.70 | O |
| ATOM | 241 | C | GLU A | 37 | 37.026 | −9.971 | 75.907 | 1.00 | 62.40 | C |
| ATOM | 242 | O | GLU A | 37 | 36.251 | −9.978 | 74.937 | 1.00 | 61.67 | O |
| ATOM | 243 | N | VAL A | 38 | 38.359 | −9.867 | 75.798 | 1.00 | 60.90 | N |
| ATOM | 244 | CA | VAL A | 38 | 39.041 | −9.835 | 74.502 | 1.00 | 58.93 | C |
| ATOM | 245 | CB | VAL A | 38 | 40.563 | −10.130 | 74.565 | 1.00 | 58.27 | C |
| ATOM | 246 | CG1 | VAL A | 38 | 41.147 | −9.756 | 75.898 | 1.00 | 57.81 | C |
| ATOM | 247 | CG2 | VAL A | 38 | 40.839 | −11.571 | 74.215 | 1.00 | 57.03 | O |
| ATOM | 248 | C | VAL A | 38 | 38.408 | −10.806 | 73.497 | 1.00 | 58.59 | C |
| ATOM | 249 | O | VAL A | 38 | 37.948 | −11.924 | 73.852 | 1.00 | 58.08 | O |
| ATOM | 250 | N | THR A | 39 | 38.371 | −10.349 | 72.241 | 1.00 | 57.19 | N |
| ATOM | 251 | CA | THR A | 39 | 37.801 | −11.142 | 71.190 | 1.00 | 55.61 | C |
| ATOM | 252 | CB | THR A | 39 | 36.290 | −10.891 | 71.078 | 1.00 | 55.90 | O |
| ATOM | 253 | OG1 | THR A | 39 | 35.673 | −11.068 | 72.371 | 1.00 | 56.11 | O |
| ATOM | 254 | OG2 | THR A | 39 | 35.653 | −11.880 | 70.085 | 1.00 | 56.77 | C |
| ATOM | 255 | C | THR A | 39 | 38.511 | −10.984 | 69.852 | 1.00 | 53.99 | C |
| ATOM | 256 | O | THR A | 39 | 38.723 | −9.889 | 69.345 | 1.00 | 53.80 | C |
| ATOM | 257 | N | ARG A | 40 | 30.919 | −12.114 | 69.324 | 1.00 | 51.89 | N |
| ATOM | 258 | CA | ARG A | 40 | 39.311 | −12.183 | 67.964 | 1.00 | 50.84 | C |
| ATOM | 259 | CB | ARG A | 40 | 43.163 | −13.449 | 67.703 | 1.00 | 51.09 | C |
| ATOM | 260 | CG | ARG A | 40 | 41.610 | −13.351 | 68.235 | 1.00 | 53.34 | C |
| ATOM | 261 | CD | ARG A | 40 | 42.120 | −14.663 | 68.891 | 1.00 | 59.31 | C |
| ATOM | 262 | NE | ARG A | 40 | 41.644 | −15 871 | 68.189 | 1.00 | 62.71 | N |
| ATOM | 263 | CZ | ARG A | 40 | 42.216 | −16.376 | 67.095 | 1.00 | 61.66 | C |
| ATOM | 264 | NH1 | ARG A | 40 | 43.296 | −15.791 | 66.571 | 1.00 | 62.91 | N |
| ATOM | 265 | NH2 | ARG A | 40 | 41.697 | −17.446 | 68.511 | 1.00 | 61.39 | N |
| ATOM | 266 | C | ARG A | 40 | 38.006 | −12.179 | 67.161 | 1.00 | 49.16 | C |
| ATOM | 267 | O | ARG A | 40 | 37.085 | −12.970 | 67.413 | 1.00 | 49.42 | O |
| ATOM | 268 | N | VAL A | 41 | 37.948 | −11.252 | 66.209 | 1.00 | 46.85 | N |
| ATOM | 269 | CA | VAL A | 41 | 36.833 | −11.031 | 65.326 | 1.00 | 43.89 | C |
| ATOM | 270 | CB | VAL A | 41 | 36.374 | −9.572 | 65.430 | 1.00 | 43.78 | C |
| ATOM | 271 | CG1 | VAL A | 41 | 35.434 | −9.215 | 64.278 | 1.00 | 42.28 | C |
| ATOM | 272 | CG2 | VAL A | 41 | 35.705 | −9.326 | 66.784 | 1.00 | 42.15 | C |
| ATOM | 273 | C | VAL A | 41 | 37.231 | −11.301 | 63.890 | 1.00 | 43.29 | C |
| ATOM | 274 | O | VAL A | 41 | 38.327 | −10.850 | 63.443 | 1.00 | 43.00 | O |
| ATOM | 275 | N | LYS A | 42 | 36.453 | −12.016 | 63.151 | 1.00 | 41.59 | N |
| ATOM | 276 | CA | LYS A | 42 | 36.850 | −12.423 | 61.840 | 1.00 | 41.39 | C |
| ATOM | 277 | CB | LYS A | 42 | 36.378 | −13.869 | 61.610 | 1.00 | 42.13 | C |
| ATOM | 278 | CG | LYS A | 42 | 36.968 | −14.580 | 60.403 | 1.00 | 43.01 | C |
| ATOM | 279 | CD | LYS A | 42 | 36.901 | −16 095 | 60.557 | 1.00 | 40.95 | O |
| ATOM | 280 | CE | LYS A | 42 | 35.796 | −16.657 | 59.753 | 1.00 | 42.51 | C |
| ATOM | 281 | NZ | LYS A | 42 | 36.315 | −17.146 | 58.459 | 1.00 | 46.66 | N |
| ATOM | 282 | C | LYS A | 42 | 36.330 | −11.449 | 60.778 | 1.00 | 40.33 | O |
| ATOM | 283 | O | LYS A | 42 | 36.936 | −11.318 | 59.740 | 1.00 | 40.80 | O |
| ATOM | 284 | N | ALA A | 43 | 35.220 | −10.760 | 61.016 | 1.00 | 39.26 | N |
| ATOM | 285 | CA | ALA A | 43 | 34.670 | −9.807 | 60.027 | 1.00 | 37.20 | C |
| ATOM | 286 | CB | ALA A | 43 | 34.367 | −10.500 | 58.708 | 1.00 | 36.36 | C |
| ATOM | 287 | C | ALA A | 43 | 33.428 | −9.115 | 60.553 | 1.00 | 36.90 | C |
| ATOM | 288 | O | ALA A | 43 | 32.794 | −9 591 | 61.490 | 1.00 | 35 42 | O |
| ATOM | 289 | N | VAL A | 44 | 33.071 | −7.975 | 59.989 | 1.00 | 37.71 | N |
| ATOM | 290 | CA | VAL A | 44 | 31.748 | −7.404 | 60.270 | 1.00 | 38.06 | C |
| ATOM | 291 | CB | VAL A | 44 | 31.870 | −6.109 | 61.069 | 1.00 | 38.48 | C |
| ATOM | 292 | CG1 | VAL A | 44 | 30.518 | −5.428 | 61.225 | 1.00 | 38.22 | C |
| ATOM | 293 | CG2 | VAL A | 44 | 32.438 | −6.426 | 62.458 | 1.00 | 38.69 | C |
| ATOM | 294 | O | VAL A | 44 | 31.184 | −7.159 | 58.931 | 1.00 | 37.60 | O |

TABLE 11-continued

| ATOM | 295 | O | VAL A | 44 | 31.877 | −6.631 | 58.116 | 1.00 | 37.58 | O |
|---|---|---|---|---|---|---|---|---|---|---|
| ATOM | 296 | N | ARG A | 45 | 29.979 | 7.638 | 58.641 | 1.00 | 38.54 | N |
| ATOM | 297 | CA | ARG A | 45 | 29.447 | −7.463 | 57.241 | 1.00 | 40.04 | C |
| ATOM | 298 | CB | ARG A | 45 | 29.683 | −8.660 | 56.280 | 1.00 | 38.91 | C |
| ATOM | 299 | CG | ARG A | 45 | 30.230 | −9.885 | 56.918 | 1.00 | 39.55 | C |
| ATOM | 300 | CD | ARG A | 45 | 30.157 | −11.133 | 56.040 | 1.00 | 41.20 | C |
| ATOM | 301 | NE | ARG A | 45 | 29.795 | −12.224 | 56.927 | 1.00 | 41.64 | N |
| ATOM | 302 | CZ | ARG A | 45 | 28.623 | −12.846 | 56.899 | 1.00 | 40.64 | C |
| ATOM | 303 | NH1 | ARG A | 45 | 27.738 | −12.538 | 55.963 | 1.00 | 40.68 | N |
| ATOM | 304 | NH2 | ARG A | 45 | 28.353 | −13.788 | 57.796 | 1.00 | 36.45 | N |
| ATOM | 305 | C | ARG A | 45 | 28.022 | −6.982 | 57.206 | 1.00 | 40.69 | C |
| ATOM | 306 | O | ARG A | 45 | 27.314 | −7.172 | 58.175 | 1.00 | 40.94 | O |
| ATOM | 307 | N | ILE A | 46 | 27.619 | −6.305 | 56.132 | 1.00 | 42.15 | N |
| ATOM | 308 | CA | ILE A | 46 | 26.230 | −5.793 | 56.081 | 1.00 | 44.21 | C |
| ATOM | 309 | CB | ILE A | 46 | 26.074 | −4.214 | 56.158 | 1.00 | 43.85 | C |
| ATOM | 310 | CG1 | ILE A | 46 | 26.685 | −3.549 | 54.941 | 1.00 | 44.78 | C |
| ATOM | 311 | CD1 | ILE A | 46 | 26.503 | −2.060 | 54.956 | 1.00 | 47.95 | O |
| ATOM | 312 | CG2 | ILE A | 46 | 26.714 | −3.635 | 57.415 | 1.00 | 44.43 | C |
| ATOM | 313 | C | ILE A | 46 | 25.496 | −6.286 | 54.864 | 1.00 | 44.69 | C |
| ATOM | 314 | O | ILE A | 46 | 26.112 | −6.471 | 53.792 | 1.00 | 44.49 | O |
| ATOM | 315 | N | LEU A | 47 | 24.192 | −6.495 | 55.062 | 1.00 | 45.04 | N |
| ATOM | 316 | CA | LEU A | 47 | 23.240 | −6.678 | 53.988 | 1.00 | 45.78 | C |
| ATOM | 317 | CB | LEU A | 47 | 22.731 | −8.094 | 54.044 | 1.00 | 45.36 | C |
| ATOM | 318 | CG | LEU A | 47 | 21.836 | −8.563 | 52.903 | 1.00 | 45.74 | C |
| ATOM | 319 | CD1 | LEU A | 47 | 22.473 | −8.427 | 51.504 | 1.00 | 47.93 | C |
| ATOM | 320 | CD2 | LEU A | 47 | 21.382 | −9.980 | 53.139 | 1.00 | 45.58 | C |
| ATOM | 321 | C | LEU A | 47 | 22.095 | −5.652 | 54.162 | 1.00 | 47.25 | C |
| ATOM | 322 | O | LEU A | 47 | 21.545 | −5.443 | 55.258 | 1.00 | 47.49 | O |
| ATOM | 323 | N | ALA A | 48 | 21.765 | −4.950 | 53.103 | 1.00 | 48.45 | N |
| ATOM | 324 | CA | ALA A | 48 | 20.635 | −4.045 | 53.178 | 1.00 | 50.17 | C |
| ATOM | 325 | CB | ALA A | 48 | 21.083 | −2.630 | 52.941 | 1.00 | 49.92 | C |
| ATOM | 326 | C | ALA A | 48 | 19.667 | −4.478 | 52.121 | 1.00 | 51.67 | C |
| ATOM | 327 | O | ALA A | 48 | 20.073 | −4.700 | 50.994 | 1.00 | 51.13 | O |
| ATOM | 328 | N | CYS A | 49 | 18.398 | −4.623 | 52.476 | 1.00 | 54.51 | N |
| ATOM | 329 | CA | CYS A | 49 | 17.390 | −5.039 | 51.492 | 1.00 | 58.59 | C |
| ATOM | 330 | CB | CYS A | 49 | 16.847 | −6.413 | 51.828 | 1.00 | 58.88 | C |
| ATOM | 331 | SG | CYS A | 49 | 18.150 | −7.646 | 51.999 | 1.00 | 68.20 | S |
| ATOM | 332 | C | CYS A | 49 | 16.204 | −4.138 | 51.458 | 1.00 | 59.45 | C |
| ATOM | 333 | O | CYS A | 49 | 15.880 | −3.496 | 52.459 | 1.00 | 61.22 | O |
| ATOM | 334 | N | GLY A | 50 | 15.530 | −4.125 | 50.316 | 1.00 | 60.35 | N |
| ATOM | 335 | CA | GLY A | 50 | 14.181 | −3.556 | 50.200 | 1.00 | 60.14 | C |
| ATOM | 336 | C | GLY A | 50 | 13.314 | −4.595 | 49.518 | 1.00 | 59.73 | C |
| ATOM | 337 | O | GLY A | 50 | 13.670 | −5.080 | 48.473 | 1.00 | 60.18 | O |
| ATOM | 338 | N | VAL A | 51 | 12.203 | −4.999 | 50.107 | 1.00 | 59.64 | N |
| ATOM | 339 | CA | VAL A | 51 | 11.359 | −5.976 | 49.412 | 1.00 | 59.32 | C |
| ATOM | 340 | CB | VAL A | 51 | 11.522 | −7.433 | 49.968 | 1.00 | 58.76 | C |
| ATOM | 341 | CG1 | VAL A | 51 | 10.475 | −8.334 | 49.357 | 1.00 | 57.25 | C |
| ATOM | 342 | CG2 | VAL A | 51 | 12.860 | −7.992 | 49.667 | 1.00 | 57.70 | C |
| ATOM | 343 | C | VAL A | 51 | 9.882 | −5.618 | 49.526 | 1.00 | 59.44 | C |
| ATOM | 244 | O | VAL A | 51 | 9.306 | −5.776 | 50. 610 | 1.00 | 59.43 | O |
| ATOM | 345 | N | ALA A | 52 | 9.255 | −5.153 | 48.443 | 1.00 | 59.00 | N |
| ATOM | 346 | CA | ALA A | 52 | 7.784 | −5.132 | 48.455 | 1.00 | 58.91 | C |
| ATOM | 347 | CB | ALA A | 52 | 7.223 | −4 038 | 47.620 | 1.00 | 58.32 | C |
| ATOM | 348 | C | ALA A | 52 | 7.168 | −6.500 | 48.116 | 1.00 | 58.83 | C |
| ATOM | 349 | O | ALA A | 52 | 7.701 | −7.313 | 47.346 | 1.00 | 59.07 | O |
| ATOM | 350 | N | LYS A | 53 | 6.052 | −6.772 | 48.743 | 1.00 | 58.67 | N |
| ATOM | 351 | CA | LYS A | 53 | 5.442 | −8.061 | 48.603 | 1.00 | 59.17 | C |
| ATOM | 352 | CB | LYS A | 53 | 5.779 | −8.885 | 49.853 | 1.00 | 59.21 | C |
| ATOM | 353 | CG | LYS A | 53 | 5.012 | −10.161 | 50.047 | 1.00 | 62.57 | C |
| ATOM | 354 | CD | LYS A | 53 | 5.653 | −11.046 | 51.146 | 1.00 | 69.69 | C |
| ATOM | 355 | CE | LYS A | 53 | 4.582 | −11.990 | 51.837 | 1.00 | 73.65 | C |
| ATOM | 356 | NZ | LYS A | 53 | 5.166 | −13.166 | 52.616 | 1.00 | 74.51 | N |
| ATOM | 357 | C | LYS A | 53 | 3.937 | −7.758 | 48.401 | 1.00 | 59.28 | C |
| ATOM | 358 | O | LYS A | 53 | 3.272 | −7.127 | 49.267 | 1.00 | 58.98 | O |
| ATOM | 359 | N | VAL A | 54 | 3.425 | −8.127 | 47.225 | 1.00 | 58.40 | N |
| ATOM | 360 | CA | VAL A | 54 | 2.037 | −7.837 | 46.893 | 1.00 | 58.45 | C |
| ATOM | 360 | CB | VAL A | 54 | 1.929 | −7.075 | 45.528 | 1.00 | 58.20 | C |
| ATOM | 362 | CG1 | VAL A | 54 | 0.478 | −6.793 | 45.156 | 1.00 | 55.93 | C |
| ATOM | 363 | CG2 | VAL A | 54 | 2.746 | −5.749 | 45.581 | 1.00 | 57.36 | C |
| ATOM | 364 | C | VAL A | 54 | 1.257 | −9.145 | 46.918 | 1.00 | 59.21 | C |
| ATOM | 365 | O | VAL A | 54 | 1.682 | −10.121 | 46.296 | 1.00 | 58.73 | O |
| ATOM | 366 | N | LEU A | 55 | 0.153 | −9.190 | 47.674 | 1.00 | 60.61 | N |
| ATOM | 367 | CA | LEU A | 55 | −0.635 | −10.454 | 47.802 | 1.00 | 62.05 | C |
| ATOM | 368 | CB | LEU A | 55 | −0.044 | −11.375 | 48.880 | 1.00 | 62.58 | C |
| ATOM | 369 | CG | LEU A | 55 | −0.263 | −11.234 | 50.393 | 1.00 | 63.31 | C |
| ATOM | 370 | CD1 | LEU A | 55 | 0.919 | −11.972 | 51.027 | 1.00 | 64.71 | C |
| ATOM | 371 | CD2 | LEU A | 55 | −0.336 | −9.788 | 50.901 | 1.00 | 62.74 | C |
| ATOM | 372 | C | LEU A | 55 | −2.153 | −10.338 | 47.369 | 1.00 | 62.38 | C |
| ATOM | 373 | O | LEU A | 55 | −2.654 | −9.399 | 48.562 | 1.00 | 62.62 | O |
| ATOM | 374 | N | TRP A | 55 | −2.890 | −11.293 | 47.431 | 1.00 | 63.36 | N |

TABLE 11-continued

| | | | | | | | | | |
|---|---|---|---|---|---|---|---|---|---|
| ATOM | 375 | CA | TRP A | 56 | -4.337 | -11.165 | 47.446 | 1.00 | 65.00 | C |
| ATOM | 376 | CB | TRP A | 56 | -4.831 | 10.188 | 46.356 | 1.00 | 64.21 | C |
| ATOM | 377 | CG | TRP A | 56 | -4.698 | -10.705 | 44.895 | 1.00 | 62.48 | C |
| ATOM | 378 | CD1 | TRP A | 56 | -5.652 | -11.372 | 44.169 | 1.00 | 60.94 | C |
| ATOM | 379 | NE1 | TRP A | 56 | -5.190 | -11.661 | 42.911 | 1.00 | 59.49 | N |
| ATOM | 380 | CE2 | TRP A | 56 | -3.913 | -11.183 | 42.789 | 1.00 | 61.29 | C |
| ATOM | 381 | CD2 | TRP A | 56 | -3.568 | -10.566 | 44.022 | 1.00 | 60.02 | C |
| ATOM | 382 | CE3 | TRP A | 56 | -2.293 | -9.993 | 44.162 | 1.00 | 57.05 | C |
| ATOM | 383 | CZ3 | TRP A | 56 | -1.409 | -10.046 | 43.087 | 1.00 | 56.02 | C |
| ATOM | 384 | CH2 | TRP A | 56 | -1.768 | -10.667 | 41.870 | 1.00 | 58.31 | C |
| ATOM | 385 | CZ2 | TRP A | 56 | -3.017 | -11.246 | 41.597 | 1.00 | 60.49 | C |
| ATOM | 386 | C | TRP A | 56 | -4.921 | -12.544 | 47.278 | 1.00 | 66.99 | C |
| ATOM | 387 | O | TRP A | 56 | -4.172 | -13.483 | 47.008 | 1.00 | 66.86 | O |
| ATOM | 388 | N | MET A | 57 | -6.244 | -12.646 | 47.460 | 1.00 | 69.86 | N |
| ATOM | 389 | CA | MET A | 57 | -7.007 | -13.904 | 47.359 | 1.00 | 72.88 | C |
| ATOM | 390 | CB | MET A | 57 | -7.653 | -14.293 | 48.715 | 1.00 | 73.43 | C |
| ATOM | 391 | CG | MET A | 57 | -6.683 | -14.451 | 49.904 | 1.00 | 76.48 | C |
| ATOM | 392 | SD | MET A | 57 | -5.923 | -16.103 | 50.074 | 1.00 | 84.81 | S |
| ATOM | 393 | CE | MET A | 57 | -4.191 | -15.697 | 50.487 | 1.00 | 81.82 | C |
| ATOM | 394 | C | MET A | 57 | -8.093 | -13.771 | 46.293 | 1.00 | 74.08 | C |
| ATOM | 395 | O | MET A | 57 | -9.079 | -13.048 | 46.483 | 1.00 | 74.27 | O |
| ATOM | 396 | N | GLN A | 58 | -7.903 | -14.454 | 45.167 | 1.00 | 76.15 | N |
| ATOM | 397 | CA | GLN A | 58 | -8.866 | -14.404 | 44.044 | 1.00 | 77.84 | C |
| ATOM | 398 | CB | GLN A | 58 | -8.190 | -14.866 | 42.746 | 1.00 | 78.26 | C |
| ATOM | 399 | CG | GLN A | 58 | -8.849 | -14.394 | 41.475 | 1.00 | 80.90 | C |
| ATOM | 400 | CD | GLN A | 58 | -8.179 | -13.134 | 40.887 | 1.00 | 84.93 | C |
| ATOM | 401 | OE1 | GLN A | 58 | -7.113 | -13.208 | 40.246 | 1.00 | 85.33 | O |
| ATOM | 402 | NE2 | GLN A | 58 | -8.830 | -11.973 | 41.072 | 1.00 | 86.19 | N |
| ATOM | 403 | C | GLN A | 58 | -9.976 | -15.383 | 44.410 | 1.00 | 78.32 | C |
| ATOM | 404 | O | GLN A | 58 | -9.662 | -16.544 | 44.765 | 1.00 | 76.82 | O |
| ATOM | 405 | N | GLY A | 59 | -11.243 | -14.939 | 44.334 | 1.00 | 78.40 | N |
| ATOM | 406 | CA | GLY A | 59 | 12.363 | 15.695 | 44.902 | 1.00 | 78.31 | C |
| ATOM | 407 | C | GLY A | 59 | -12.048 | -16.026 | 46.371 | 1.00 | 78.26 | C |
| ATOM | 408 | O | GLY A | 59 | -12.606 | -15.413 | 47.278 | 1.00 | 78.80 | O |
| ATOM | 409 | N | SER A | 60 | 11.160 | -17.002 | 46.593 | 1.00 | 77.47 | N |
| ATOM | 410 | CA | SER A | 60 | -10.500 | -17.231 | 47.879 | 1.00 | 76.74 | C |
| ATOM | 411 | CB | SER A | 60 | -11.450 | -17.943 | 48.856 | 1.00 | 77.29 | C |
| ATOM | 412 | OG | SER A | 60 | -11.013 | -17.878 | 50.212 | 1.00 | 77.62 | O |
| ATOM | 413 | C | SER A | 60 | -9.231 | -18.066 | 47.609 | 1.00 | 76.28 | C |
| ATOM | 414 | O | SER A | 60 | -9.119 | -19.221 | 48.061 | 1.00 | 75.87 | O |
| ATOM | 415 | N | GLN A | 61 | -8.280 | -17.483 | 46.059 | 1.00 | 75.41 | N |
| ATOM | 416 | CA | GLN A | 61 | -7.083 | -18.213 | 46.411 | 1.00 | 74.09 | C |
| ATOM | 417 | CB | GLN A | 61 | -7.199 | -18.497 | 44.920 | 1.00 | 73.74 | C |
| ATOM | 418 | CG | GLN A | 61 | -6.819 | -19.926 | 44.580 | 1.00 | 74.69 | C |
| ATOM | 419 | CD | GLN A | 61 | -5.527 | 20.051 | 43.746 | 1.00 | 75.64 | C |
| ATOM | 420 | OE1 | GLN A | 61 | -4.538 | -20.678 | 44.176 | 1.00 | 73.80 | O |
| ATOM | 421 | NE2 | GLN A | 61 | -5.549 | -19.471 | 42.534 | 1.00 | 75.00 | N |
| ATOM | 422 | C | GLN A | 61 | -5.753 | -17.507 | 46.750 | 1.00 | 73.23 | C |
| ATOM | 423 | O | GLN A | 61 | -5.710 | -16.286 | 46.815 | 1.00 | 73.42 | O |
| ATOM | 424 | N | GLN A | 62 | -4.677 | -18.274 | 46.957 | 1.00 | 72.02 | N |
| ATOM | 425 | CA | GLN A | 62 | -3.354 | -17.726 | 47.373 | 1.00 | 70.51 | C |
| ATOM | 426 | CB | GLN A | 62 | -2.534 | -18.781 | 48.141 | 1.00 | 70.64 | C |
| ATOM | 427 | CG | GLN A | 62 | -2.721 | -18.697 | 49.662 | 1.00 | 72.27 | C |
| ATOM | 428 | CD | GLN A | 62 | -3.023 | -20.058 | 50.351 | 1.00 | 73.01 | C |
| ATOM | 429 | OE1 | GLN A | 62 | -3.666 | -20.954 | 49.765 | 1.00 | 73.06 | O |
| ATOM | 430 | NE2 | GLN A | 62 | -2.560 | -20.201 | 51.603 | 1.00 | 69.51 | N |
| ATOM | 431 | C | GLN A | 62 | -2.527 | -17.138 | 46.229 | 1.00 | 68.80 | C |
| ATOM | 432 | O | GLN A | 62 | -1.817 | -17.860 | 45.498 | 1.00 | 69.20 | O |
| ATOM | 433 | N | CYS A | 63 | -2.588 | -15.823 | 46.095 | 1.00 | 66.08 | N |
| ATOM | 434 | CA | CYS A | 63 | -1.964 | -15.203 | 44.959 | 1.00 | 64.18 | C |
| ATOM | 435 | CB | CYS A | 63 | -3.035 | -14.706 | 44.012 | 1.00 | 63.92 | C |
| ATOM | 436 | SG | CYS A | 63 | -2.491 | -15.049 | 42.395 | 1.00 | 63.91 | S |
| ATOM | 437 | C | CYS A | 63 | -0.985 | -14.095 | 45.304 | 1.00 | 62.87 | C |
| ATOM | 438 | O | CYS A | 63 | -1.388 | -13.085 | 45.872 | 1.00 | 62.85 | O |
| ATOM | 439 | N | LYS A | 64 | 0.289 | -14.277 | 44.940 | 1.00 | 61.36 | N |
| ATOM | 440 | CA | LYS A | 64 | 1.349 | -13.408 | 45.436 | 1.00 | 60.44 | C |
| ATOM | 441 | CB | LYS A | 64 | 1.816 | -13.945 | 46.763 | 1.00 | 60.78 | C |
| ATOM | 442 | CG | LYS A | 64 | 2.762 | -12.995 | 47.425 | 1.00 | 63.58 | C |
| ATOM | 443 | CD | LYS A | 64 | 3.399 | -13.575 | 48.640 | 1.00 | 67.23 | C |
| ATOM | 444 | CE | LYS A | 64 | 4.430 | -14.616 | 48.299 | 1.00 | 67.11 | C |
| ATOM | 445 | NZ | LYS A | 64 | 5.402 | -14.483 | 49.404 | 1.00 | 69.76 | N |
| ATOM | 446 | C | LYS A | 64 | 2.592 | -13.152 | 44.559 | 1.00 | 59.84 | C |
| ATOM | 447 | O | LYS A | 64 | 3.159 | -14.079 | 43.989 | 1.00 | 59.44 | O |
| ATOM | 448 | N | GLN A | 65 | 3.012 | -11.881 | 44.473 | 1.00 | 59.37 | N |
| ATOM | 449 | CA | GLN A | 65 | 4.290 | -11.482 | 43.833 | 1.00 | 58.93 | C |
| ATOM | 450 | CB | GLN A | 65 | 4.061 | -10.671 | 42.533 | 1.00 | 59.59 | C |
| ATOM | 451 | CG | GLN A | 65 | 4.935 | -9.336 | 42.364 | 1.00 | 60.27 | C |
| ATOM | 452 | CD | GLN A | 65 | 4.757 | -8.634 | 40.981 | 1.00 | 60.93 | C |
| ATOM | 453 | OE1 | GLN A | 65 | 3.970 | -7.684 | 40.845 | 1.00 | 59.11 | O |
| ATOM | 454 | NE2 | GLN A | 65 | 5.485 | -9.116 | 39.960 | 1.00 | 59.60 | N |

TABLE 11-continued

| ATOM | 455 | C | GLN A | 65 | 5.245 | −10.719 | 44.767 | 1.00 | 57.93 | C |
|---|---|---|---|---|---|---|---|---|---|---|
| ATOM | 456 | O | GLN A | 65 | 4.837 | −9.820 | 45.498 | 1.00 | 58.13 | O |
| ATOM | 457 | N | THR A | 66 | 6.530 | −11.054 | 44.679 | 1.00 | 56.75 | N |
| ATOM | 458 | CA | THR A | 66 | 7.589 | −10.493 | 45.537 | 1.00 | 54.86 | C |
| ATOM | 459 | CB | THR A | 66 | 8.321 | −11.672 | 46.171 | 1.00 | 54.83 | C |
| ATOM | 469 | OG1 | THR A | 66 | 7.349 | −12.517 | 46.798 | 1.00 | 54.92 | O |
| ATOM | 461 | OG2 | THR A | 65 | 9.360 | −11.227 | 47.167 | 1.00 | 54.17 | C |
| ATOM | 462 | C | THR A | 66 | 8.555 | −9.709 | 44.657 | 1.00 | 53.60 | C |
| ATOM | 463 | O | THR A | 66 | 8.915 | −10.199 | 43.611 | 1.00 | 53.05 | O |
| ATOM | 464 | N | SER A | 67 | 8.969 | −8.502 | 45.027 | 1.00 | 53.05 | N |
| ATOM | 465 | CA | SER A | 67 | 9.855 | −7.728 | 44.126 | 1.00 | 52.95 | C |
| ATOM | 466 | CB | SER A | 67 | 9.085 | −6.747 | 43.228 | 1.00 | 52.59 | C |
| ATOM | 467 | OG | SER A | 67 | 7.832 | −7.234 | 42.768 | 1.00 | 50.91 | O |
| ATOM | 468 | C | SER A | 67 | 10.885 | −6.938 | 44.923 | 1.00 | 53.94 | C |
| ATOM | 469 | O | SER A | 67 | 10.508 | −6.143 | 45.802 | 1.00 | 55.21 | O |
| ATOM | 470 | N | GLU A | 68 | 12.170 | −7.117 | 44.621 | 1.00 | 53.61 | N |
| ATOM | 471 | CA | GLU A | 68 | 13.211 | −6.402 | 45.362 | 1.00 | 53.72 | C |
| ATOM | 472 | CB | GLU A | 68 | 14.472 | −7.248 | 45.516 | 1.00 | 54.45 | C |
| ATOM | 473 | CG | GLU A | 68 | 14.201 | −8.729 | 45.965 | 1.00 | 56.01 | C |
| ATOM | 474 | CD | GLU A | 68 | 15.459 | −9.561 | 45.985 | 1.00 | 57.56 | C |
| ATOM | 475 | OE1 | GLU A | 68 | 16.486 | −9.144 | 45.379 | 1.00 | 56.37 | O |
| ATOM | 476 | OE2 | GLU A | 68 | 15.416 | −10.620 | 46.632 | 1.00 | 60.71 | O |
| ATOM | 477 | C | GLU A | 68 | 13.554 | −5.080 | 44.732 | 1.00 | 53.20 | C |
| ATOM | 478 | O | GLU A | 68 | 13.207 | −4.844 | 43.586 | 1.00 | 53.30 | O |
| ATOM | 479 | N | TYR A | 69 | 14.232 | −4.221 | 45.498 | 1.00 | 52.82 | N |
| ATOM | 480 | CA | TYR A | 69 | 14.577 | −2.865 | 45.084 | 1.00 | 52.32 | C |
| ATOM | 481 | CB | TYR A | 69 | 13.530 | −1.893 | 45.558 | 1.00 | 51.84 | C |
| ATOM | 482 | CG | TYR A | 69 | 12.247 | −2.068 | 44.820 | 1.00 | 52.73 | C |
| ATOM | 483 | CD1 | TYR A | 69 | 11.353 | −3.107 | 45.147 | 1.00 | 51.31 | C |
| ATOM | 484 | CF1 | TYR A | 69 | 10.168 | −3.283 | 44.444 | 1.00 | 50.62 | C |
| ATOM | 485 | CZ | TYR A | 69 | 9.876 | −2.401 | 43.413 | 1.00 | 52.03 | C |
| ATOM | 486 | OH | TYR A | 69 | 8.708 | −2.515 | 42.698 | 1.00 | 53.65 | O |
| ATOM | 487 | CE2 | TYR A | 69 | 10.743 | −1.378 | 43.077 | 1.00 | 52.01 | C |
| ATOM | 488 | CD2 | TYR A | 69 | 11.922 | −1.218 | 43.772 | 1.00 | 52.11 | C |
| ATOM | 489 | C | TYR A | 69 | 15.912 | −2.746 | 45.654 | 1.00 | 52.33 | C |
| ATOM | 490 | O | TYR A | 69 | 16.505 | −1.434 | 45.529 | 1.00 | 51.54 | O |
| ATOM | 491 | N | LEU A | 70 | 16.378 | −3.313 | 46.588 | 1.00 | 51.79 | N |
| ATOM | 492 | CA | LEU A | 70 | 17.714 | −3.162 | 47.146 | 1.00 | 51.63 | C |
| ATOM | 493 | CB | LEU A | 70 | 17.625 | −2.336 | 48.413 | 1.00 | 50.85 | C |
| ATOM | 494 | CG | LEU A | 70 | 18.907 | −1.615 | 48.840 | 1.00 | 46.79 | C |
| ATOM | 495 | CD1 | LEU A | 70 | 19.474 | −0.730 | 47.754 | 1.00 | 47.46 | C |
| ATOM | 496 | CD2 | LEU A | 70 | 18.556 | −0.775 | 50.020 | 1.00 | 45.00 | C |
| ATOM | 497 | C | LEU A | 70 | 18.317 | −4.506 | 47.481 | 1.00 | 52.94 | C |
| ATOM | 498 | O | LEU A | 70 | 17.652 | −5.346 | 48.083 | 1.00 | 54.45 | O |
| ATOM | 499 | N | ARG A | 71 | 19.557 | −4.730 | 47.063 | 1.00 | 53.79 | N |
| ATOM | 500 | CA | ARG A | 71 | 20.277 | −5.887 | 47.521 | 1.00 | 54.65 | C |
| ATOM | 501 | CB | ARG A | 71 | 20.459 | −7.046 | 46.534 | 1.00 | 54.83 | C |
| ATOM | 502 | CG | ARG A | 71 | 19.597 | −8.265 | 46.898 | 1.00 | 60.66 | C |
| ATOM | 503 | CD | ARG A | 71 | 19.813 | −9.414 | 45.858 | 1.00 | 67.56 | C |
| ATOM | 504 | NE | ARG A | 71 | 18.763 | −10.447 | 45.874 | 1.00 | 71.85 | N |
| ATOM | 505 | CZ | ARG A | 71 | 18.681 | −11.475 | 45.021 | 1.00 | 73.30 | C |
| ATOM | 506 | NH1 | ARG A | 71 | 19.568 | −11.642 | 44.054 | 1.00 | 74.20 | N |
| ATOM | 507 | NH2 | ARG A | 71 | 17.696 | −12.353 | 45.141 | 1.00 | 75.58 | N |
| ATOM | 508 | C | ARG A | 71 | 21.728 | −5.269 | 47.605 | 1.00 | 53.66 | C |
| ATOM | 509 | O | ARG A | 71 | 22.297 | 4.891 | 46.591 | 1.00 | 54.32 | O |
| ATOM | 510 | N | TYR A | 72 | 22.216 | −5.077 | 48.815 | 1.00 | 52.55 | N |
| ATOM | 511 | CA | TYR A | 72 | 23.461 | −4.386 | 48.967 | 1.00 | 50.91 | C |
| ATOM | 512 | CB | TYR A | 72 | 23.223 | −2.882 | 49.213 | 1.00 | 50.94 | C |
| ATOM | 513 | CG | TYR A | 72 | 24.483 | −2.157 | 49.535 | 1.00 | 50.60 | C |
| ATOM | 514 | CD1 | TYR A | 72 | 25.195 | −1.471 | 48.538 | 1.00 | 50.85 | C |
| ATOM | 515 | CE1 | TYR A | 72 | 26.386 | −0.836 | 48.835 | 1.00 | 51.21 | C |
| ATOM | 516 | CZ | TYR A | 72 | 26.866 | −0.915 | 50.148 | 1.00 | 51.23 | C |
| ATOM | 517 | OH | TYR A | 72 | 28.025 | −0.320 | 50.501 | 1.00 | 52.21 | O |
| ATOM | 518 | CE2 | TYR A | 72 | 26.190 | −1.606 | 51.128 | 1.00 | 49.94 | C |
| ATOM | 519 | CD2 | TYR A | 72 | 25.009 | −2.211 | 50.925 | 1.00 | 48.25 | C |
| ATOM | 520 | C | TYR A | 72 | 24.226 | −5.097 | 50.065 | 1.00 | 50.35 | C |
| ATOM | 521 | O | TYR A | 72 | 23.692 | −5.419 | 51.126 | 1.00 | 49.15 | O |
| ATOM | 522 | N | GLU A | 73 | 25.476 | −5.408 | 49.772 | 1.00 | 50.92 | N |
| ATOM | 523 | CA | GLU A | 73 | 26.294 | −6.124 | 50.735 | 1.00 | 51.68 | C |
| ATOM | 524 | CB | GLU A | 73 | 26.202 | −7.649 | 50.610 | 1.00 | 51.78 | C |
| ATOM | 525 | CG | GLU A | 73 | 26.047 | −8.149 | 49.212 | 1.00 | 54.54 | C |
| ATOM | 526 | CD | GLU A | 73 | 25.656 | −9.609 | 49.166 | 1.00 | 57.83 | C |
| ATOM | 527 | OE1 | GLU A | 73 | 25.712 | −10.295 | 50.206 | 1.00 | 59.23 | O |
| ATOM | 528 | OE2 | GLU A | 73 | 25.286 | −10.088 | 48.081 | 1.00 | 59.33 | O |
| ATOM | 529 | C | GLU A | 73 | 27.686 | −5.643 | 50.641 | 1.00 | 51.33 | C |
| ATOM | 530 | O | GLU A | 73 | 28.156 | −5.308 | 49.554 | 1.00 | 51.83 | O |
| ATOM | 531 | N | ASP A | 74 | 28.307 | −5.553 | 51.814 | 1.00 | 51.35 | N |
| ATOM | 532 | CA | ASP A | 74 | 29.634 | −4.993 | 51.979 | 1.00 | 51.00 | C |
| ATOM | 533 | CB | ASP A | 74 | 29.548 | −3.455 | 52.047 | 1.00 | 52.43 | C |
| ATOM | 534 | CG | ASP A | 74 | 30.885 | −2.723 | 51.651 | 1.00 | 56.57 | C |

TABLE 11-continued

| | | | | | | | | | |
|---|---|---|---|---|---|---|---|---|---|
| ATOM | 535 | OD1 | ASP A | 74 | 31.576 | −3.140 | 50.673 | 1.00 | 61.45 | O |
| ATOM | 536 | OD2 | ASP A | 74 | 31.218 | −1.685 | 52.306 | 1.00 | 60.30 | O |
| ATOM | 537 | C | ASP A | 74 | 30.242 | −5.547 | 53.254 | 1.00 | 49.70 | C |
| ATOM | 538 | O | ASP A | 74 | 29.556 | −5.909 | 54.220 | 1.00 | 49.00 | O |
| ATOM | 539 | N | THR A | 75 | 31.551 | −5.267 | 53.233 | 1.00 | 48.63 | N |
| ATOM | 540 | CA | THR A | 75 | 32.280 | −6.009 | 54.380 | 1.00 | 47.78 | C |
| ATOM | 541 | CB | THR A | 75 | 33.285 | −7.051 | 53.985 | 1.00 | 47.38 | C |
| ATOM | 542 | OG1 | THR A | 75 | 32.551 | −8.140 | 53.444 | 1.00 | 46.44 | O |
| ATOM | 543 | CG2 | THR A | 75 | 34.021 | −7.559 | 55.175 | 1.00 | 46.68 | C |
| ATOM | 544 | C | THR A | 75 | 32.907 | −4.710 | 54.829 | 1.00 | 47.76 | C |
| ATOM | 545 | O | THR A | 75 | 33.461 | −4.006 | 53.989 | 1.00 | 47.29 | O |
| ATOM | 546 | N | LEU A | 76 | 32.781 | −4.412 | 56.130 | 1.00 | 46.61 | N |
| ATOM | 547 | CA | LEU A | 76 | 33.199 | −3.158 | 56.717 | 1.00 | 47.00 | C |
| ATOM | 548 | CB | LEU A | 76 | 32.125 | −2.637 | 57.667 | 1.00 | 45.65 | C |
| ATOM | 549 | CG | LEU A | 76 | 30.732 | −2.549 | 57.058 | 1.00 | 45.50 | C |
| ATOM | 550 | CD1 | LEU A | 76 | 29.784 | −1.861 | 58.021 | 1.00 | 43.80 | C |
| ATOM | 551 | CD2 | LEU A | 76 | 30.720 | −1.890 | 55.655 | 1.00 | 40.35 | C |
| ATOM | 552 | C | LEU A | 76 | 34.541 | −3.241 | 57.452 | 1.00 | 48.49 | C |
| ATOM | 553 | O | LEU A | 76 | 34.969 | −4.330 | 57.840 | 1.00 | 48.38 | O |
| ATOM | 554 | N | LEU A | 77 | 35.178 | −2.081 | 57.690 | 1.00 | 49.89 | N |
| ATOM | 555 | CA | LEU A | 77 | 36.596 | −2.034 | 58.079 | 1.00 | 51.00 | C |
| ATOM | 556 | CB | LEU A | 77 | 37.440 | −1.723 | 56.858 | 1.00 | 50.42 | C |
| ATOM | 557 | CG | LEU A | 77 | 37.241 | −2.625 | 55.651 | 1.00 | 50.72 | C |
| ATOM | 558 | CD1 | LEU A | 77 | 38.070 | −2.029 | 54.525 | 1.00 | 49.78 | C |
| ATOM | 559 | CD2 | LEU A | 77 | 37.644 | −4.111 | 55.958 | 1.00 | 49.33 | C |
| ATOM | 560 | C | LEU A | 77 | 36.882 | −0.940 | 59.042 | 1.00 | 51.90 | C |
| ATOM | 561 | O | LEU A | 77 | 36.603 | 0.211 | 58.763 | 1.00 | 52.15 | O |
| ATOM | 562 | N | LEU A | 78 | 37.501 | −1.272 | 60.166 | 1.00 | 53.85 | N |
| ATOM | 563 | CA | LEU A | 78 | 37.856 | −0.245 | 61.142 | 1.00 | 54.73 | C |
| ATOM | 564 | CB | LEU A | 78 | 38.473 | −0.853 | 62.376 | 1.00 | 53.86 | C |
| ATOM | 565 | CG | LEU A | 78 | 37.776 | −1.883 | 63.212 | 1.00 | 53.29 | C |
| ATOM | 566 | CD1 | LEU A | 78 | 38.806 | −2.310 | 64.159 | 1.00 | 53.68 | C |
| ATOM | 567 | CD2 | LEU A | 78 | 36.592 | −1.295 | 63.962 | 1.00 | 56.05 | C |
| ATOM | 568 | C | LEU A | 78 | 38.901 | 0.629 | 60.501 | 1.00 | 56.57 | C |
| ATOM | 569 | O | LEU A | 78 | 39.802 | 0.120 | 59.792 | 1.00 | 56.48 | O |
| ATOM | 570 | N | GLU A | 79 | 38.802 | 1.934 | 60.758 | 1.00 | 58.76 | N |
| ATOM | 571 | CA | GLU A | 79 | 39.795 | 2.901 | 60.271 | 1.00 | 60.35 | C |
| ATOM | 572 | CB | GLU A | 79 | 39.306 | 4.308 | 60.568 | 1.00 | 60.97 | C |
| ATOM | 573 | CG | GLU A | 79 | 37.951 | 4.605 | 59.888 | 1.00 | 64.52 | C |
| ATOM | 574 | CD | GLU A | 79 | 37.333 | 5.961 | 60.273 | 1.00 | 69.49 | C |
| ATOM | 575 | OE1 | GLU A | 79 | 36.260 | 5.951 | 60.943 | 1.00 | 71.01 | O |
| ATOM | 576 | OE2 | GLU A | 79 | 37.921 | 7.028 | 59.930 | 1.00 | 68.77 | O |
| ATOM | 577 | C | GLU A | 79 | 41.228 | 2.626 | 60.789 | 1.00 | 60.65 | C |
| ATOM | 578 | O | GLU A | 79 | 42.170 | 2.525 | 59.988 | 1.00 | 60.84 | O |
| ATOM | 579 | N | ASP A | 80 | 41.395 | 2.425 | 62.096 | 1.00 | 61.09 | N |
| ATOM | 580 | CA | ASP A | 80 | 42.735 | 2.080 | 62.623 | 1.00 | 62.27 | C |
| ATOM | 581 | CB | ASP A | 80 | 42.837 | 2.393 | 64.120 | 1.00 | 62.36 | C |
| ATOM | 582 | CG | ASP A | 80 | 44.230 | 2.070 | 64.689 | 1.00 | 63.93 | C |
| ATOM | 583 | OD1 | ASP A | 80 | 45.187 | 2.832 | 64.377 | 1.00 | 64.01 | O |
| ATOM | 584 | OD2 | ASP A | 80 | 44.367 | 1.051 | 65.430 | 1.00 | 63.72 | O |
| ATOM | 585 | C | ASP A | 80 | 43.206 | 0.623 | 62.402 | 1.00 | 62.57 | C |
| ATOM | 586 | O | ASP A | 80 | 44.053 | 0.107 | 63.144 | 1.00 | 62.93 | C |
| ATOM | 587 | N | GLN A | 81 | 42.670 | −0.057 | 61.404 | 1.00 | 62.52 | N |
| ATOM | 588 | CA | GLN A | 81 | 43.006 | −1.468 | 61.222 | 1.00 | 62.82 | C |
| ATOM | 589 | CB | GLN A | 81 | 41.884 | −2.346 | 61.780 | 1.00 | 63.20 | C |
| ATOM | 590 | CG | GLN A | 81 | 41.920 | −3.814 | 61.351 | 1.00 | 65.72 | C |
| ATOM | 591 | CD | GLN A | 81 | 43.003 | −4.660 | 62.065 | 1.00 | 71.57 | C |
| ATOM | 592 | OE1 | GLN A | 81 | 42.955 | −5.906 | 61.999 | 1.00 | 73.29 | O |
| ATOM | 593 | NE2 | GLN A | 81 | 43.974 | −3.997 | 62.760 | 1.00 | 71.63 | N |
| ATOM | 594 | C | GLN A | 81 | 43.311 | −1.778 | 59.742 | 1.00 | 62.64 | C |
| ATOM | 595 | O | GLN A | 81 | 42.760 | −2.748 | 59.164 | 1.00 | 62.60 | O |
| ATOM | 596 | N | PRO A | 82 | 44.219 | −0.978 | 59.131 | 1.00 | 61.65 | N |
| ATOM | 597 | CA | PRO A | 82 | 44.266 | −0.928 | 57.689 | 1.00 | 60.94 | C |
| ATOM | 598 | CB | PRO A | 87 | 44.318 | 0.151 | 57.431 | 1.00 | 60.79 | C |
| ATOM | 599 | CG | PRO A | 82 | 46.231 | 0.000 | 58.586 | 1.00 | 61.06 | C |
| ATOM | 600 | CD | PRO A | 82 | 45.284 | −0.151 | 59.723 | 1.00 | 61.54 | C |
| ATOM | 601 | C | PRO A | 82 | 44.651 | −2.256 | 57.005 | 1.00 | 60.15 | C |
| ATOM | 602 | O | PRO A | 82 | 44.469 | −2.389 | 55.792 | 1.00 | 60.69 | O |
| ATOM | 603 | N | THR A | 83 | 45.130 | −3.260 | 57.751 | 1.00 | 58.67 | N |
| ATOM | 604 | CA | THR A | 83 | 45.745 | −4.452 | 57.118 | 1.00 | 57.42 | C |
| ATOM | 605 | CB | THR A | 83 | 46.532 | −5.286 | 58.133 | 1.00 | 57.19 | C |
| ATOM | 606 | OG1 | THR A | 83 | 45.723 | −5.484 | 59.298 | 1.00 | 58.15 | O |
| ATOM | 607 | CG2 | THR A | 83 | 47.772 | −4.521 | 58.552 | 1.00 | 56.89 | C |
| ATOM | 608 | C | THR A | 83 | 44.900 | −5.301 | 56.093 | 1.00 | 50.22 | C |
| ATOM | 609 | O | THR A | 83 | 45.404 | −5.615 | 55.013 | 1.00 | 56.95 | O |
| ATOM | 610 | N | GLY A | 84 | 43.647 | −5.651 | 56.376 | 1.00 | 54.52 | N |
| ATOM | 611 | CA | GLY A | 84 | 42.883 | −6.444 | 55.410 | 1.00 | 51.80 | C |
| ATOM | 612 | C | GLY A | 84 | 42.117 | −7.618 | 55.960 | 1.00 | 50.22 | C |
| ATOM | 613 | O | GLY A | 84 | 42.301 | −8.012 | 57.089 | 1.00 | 51.04 | O |
| ATOM | 614 | N | GLU A | 85 | 41.242 | −8.188 | 55.151 | 1.00 | 48.73 | N |

TABLE 11-continued

| | | | | | | | | | | |
|---|---|---|---|---|---|---|---|---|---|---|
| ATOM | 615 | CA | GLU A | 85 | 40.313 | −9.198 | 55.615 | 1.00 | 46.86 | C |
| ATOM | 616 | CB | GLU A | 85 | 39.197 | −9.331 | 54.618 | 1.00 | 46.67 | C |
| ATOM | 617 | CG | GLU A | 85 | 38.498 | −8.047 | 54.265 | 1.00 | 49.21 | C |
| ATOM | 618 | CD | GLU A | 85 | 37.654 | −8.217 | 52.998 | 1.00 | 49.21 | C |
| ATOM | 619 | OF1 | GLU A | 85 | 37.099 | −9.323 | 52.826 | 1.00 | 49.64 | O |
| ATOM | 620 | OE2 | GLU A | 85 | 37.560 | −7.269 | 52.184 | 1.00 | 47.94 | O |
| ATOM | 621 | C | GLU A | 85 | 40.944 | −10.573 | 55.772 | 1.00 | 45.54 | C |
| ATOM | 622 | O | GLU A | 85 | 40.242 | −11.560 | 55.935 | 1.00 | 45.78 | O |
| ATOM | 623 | N | ASN A | 86 | 42.256 | −10.668 | 55.684 | 1.00 | 43.46 | N |
| ATOM | 624 | CA | ASN A | 86 | 42.879 | −11.943 | 55.928 | 1.00 | 41.43 | C |
| ATOM | 625 | CB | ASN A | 86 | 43.666 | −12.401 | 54.706 | 1.00 | 40.58 | C |
| ATOM | 626 | CG | ASN A | 86 | 44.744 | −11.403 | 54.290 | 1.00 | 37.58 | C |
| ATOM | 627 | OD1 | ASN A | 86 | 44.645 | −10.184 | 54.528 | 1.00 | 34.23 | O |
| ATOM | 628 | ND2 | ASN A | 86 | 45.774 | −11.913 | 53.656 | 1.00 | 31.96 | N |
| ATOM | 629 | C | ASN A | 86 | 43.763 | −11.848 | 57.154 | 1.00 | 41.64 | C |
| ATOM | 630 | O | ASN A | 86 | 44.703 | −12.616 | 57.303 | 1.00 | 40 56 | O |
| ATOM | 631 | N | GLU A | 87 | 43.432 | −10.879 | 58.006 | 1.00 | 41.82 | N |
| ATOM | 632 | CA | GLU A | 87 | 44.030 | −10.684 | 59.305 | 1.00 | 43.52 | C |
| ATOM | 633 | CB | GLU A | 87 | 44.940 | −9.490 | 59.268 | 1.00 | 44.17 | C |
| ATOM | 634 | CG | GLU A | 87 | 45.039 | −9.230 | 60.584 | 1.00 | 49.24 | C |
| ATOM | 635 | CD | GLU A | 87 | 47.139 | −9.532 | 60.482 | 1.00 | 58.40 | C |
| ATOM | 636 | OE1 | GLU A | 87 | 47.530 | −10.687 | 60.045 | 1.00 | 58.89 | O |
| ATOM | 637 | OE2 | GLU A | 87 | 47.908 | −8.575 | 60.812 | 1.00 | 5.28 | O |
| ATOM | 638 | C | GLU A | 87 | 42.909 | −10.330 | 60.272 | 1.00 | 43.94 | C |
| ATOM | 639 | O | GLU A | 87 | 42.234 | −9.308 | 60.102 | 1.00 | 44.06 | O |
| ATOM | 640 | N | MET A | 88 | 42.692 | −11.157 | 61.288 | 1.00 | 44.11 | N |
| ATOM | 641 | CA | MET A | 88 | 41.621 | −10.880 | 62.225 | 1.00 | 44.01 | C |
| ATOM | 642 | CB | MET A | 88 | 41.287 | −12.132 | 63.024 | 1.00 | 43.97 | C |
| ATOM | 643 | CG | MET A | 88 | 40.293 | −13.008 | 62.322 | 1.00 | 44.97 | C |
| ATOM | 644 | SD | MET A | 88 | 40.286 | −14.627 | 63.044 | 1.00 | 42.61 | S |
| ATOM | 645 | CE | MET A | 88 | 41.932 | −15.100 | 62.737 | 1.00 | 39.89 | C |
| ATOM | 646 | C | MET A | 88 | 41.997 | −9.755 | 63.175 | 1.00 | 43.75 | C |
| ATOM | 647 | O | MET A | 88 | 43.175 | −9.463 | 63.422 | 1.00 | 44.08 | O |
| ATOM | 648 | N | VAL A | 89 | 40.976 | −9.174 | 63.753 | 1.00 | 43.51 | N |
| ATOM | 649 | CA | VAL A | 89 | 41.116 | −8.041 | 64.631 | 1.00 | 43.35 | C |
| ATOM | 650 | CB | VAL A | 89 | 40.040 | −7.057 | 64.299 | 1.00 | 42.39 | C |
| ATOM | 651 | CG1 | VAL A | 89 | 39.984 | −5.293 | 65.299 | 1.00 | 40.37 | C |
| ATOM | 652 | CG2 | VAL A | 89 | 40.291 | −6.568 | 62.891 | 1.00 | 42.54 | C |
| ATOM | 653 | C | VAL A | 89 | 40.980 | −8.437 | 66.086 | 1.00 | 44.34 | C |
| ATOM | 654 | O | VAL A | 89 | 40.187 | −9.335 | 55.430 | 1.00 | 44.14 | O |
| ATOM | 655 | N | ILE A | 90 | 41.768 | −7.97 | 66.948 | 1.00 | 44.79 | N |
| ATOM | 656 | CA | ILE A | 90 | 41.619 | −8.108 | 68.360 | 1.00 | 46.01 | C |
| ATOM | 657 | CB | ILE A | 90 | 42.987 | −8.397 | 69.052 | 1.00 | 46.31 | C |
| ATOM | 658 | CG1 | ILE A | 90 | 43.780 | −9.356 | 68.188 | 1.00 | 45.79 | C |
| ATOM | 659 | CD1 | ILE A | 90 | 44.769 | −10.170 | 68.921 | 1.00 | 45.28 | C |
| ATOM | 660 | CG2 | ILE A | 90 | 42.777 | −8.968 | 70.480 | 1.00 | 45.51 | C |
| ATOM | 661 | C | ILE A | 90 | 40.602 | −7.035 | 09.015 | 1.00 | 45.61 | C |
| ATOM | 662 | O | ILE A | 90 | 41.188 | −5.889 | 69.002 | 1.00 | 45.26 | O |
| ATOM | 663 | N | MET A | 91 | 39.644 | −7.405 | 69.539 | 1.00 | 46.65 | N |
| ATOM | 664 | CA | MET A | 91 | 38.795 | −6.417 | 70.184 | 1.00 | 48.35 | C |
| ATOM | 665 | CB | MET A | 91 | 37.323 | −6.599 | 69.800 | 1.00 | 47.66 | C |
| ATOM | 666 | CG | MET A | 91 | 36.983 | −6.059 | 68.394 | 1.00 | 48.12 | C |
| ATOM | 667 | SD | MET A | 91 | 35.183 | −5.985 | 68.057 | 1.00 | 49.56 | S |
| ATOM | 668 | CE | MET A | 91 | 35.358 | −5.358 | 66.392 | 1.00 | 46.96 | C |
| ATOM | 669 | C | MET A | 91 | 38.993 | −6.495 | 71.668 | 1.00 | 49.48 | C |
| ATOM | 670 | O | MET A | 91 | 39.302 | −7.560 | 72.203 | 1.00 | 49.66 | O |
| ATOM | 671 | N | ARG A | 92 | 38.801 | −5.382 | 72.346 | 1.00 | 51.49 | N |
| ATOM | 672 | CA | ARG A | 92 | 38.933 | −5.375 | 73.819 | 1.00 | 53.87 | C |
| ATOM | 673 | CB | ARG A | 92 | 40.286 | −4.812 | 74.238 | 1.00 | 53.77 | C |
| ATOM | 674 | CG | ARG A | 92 | 41.329 | −5.845 | 74.376 | 1.00 | 55.46 | C |
| ATOM | 675 | CD | ARG A | 92 | 42.604 | −5.258 | 73.912 | 1.00 | 59.88 | C |
| ATOM | 676 | NE | ARG A | 92 | 43.425 | −6.275 | 73.268 | 1.00 | 63.47 | N |
| ATOM | 677 | CZ | ARG A | 92 | 44.655 | −6.034 | 72.846 | 1.00 | 64.27 | C |
| ATOM | 678 | NH1 | ARG A | 92 | 45.137 | −4.808 | 73.019 | 1.00 | 64.78 | N |
| ATOM | 679 | NH2 | ARG A | 92 | 45.390 | −6.992 | 72.270 | 1.00 | 62.95 | N |
| ATOM | 680 | C | ARG A | 92 | 37.861 | −4.646 | 74.628 | 1.00 | 54.74 | C |
| ATOM | 681 | O | ARG A | 92 | 37.326 | −3.578 | 74.209 | 1.00 | 54.97 | O |
| ATOM | 682 | N | PRO A | 93 | 37.586 | −5.178 | 75.833 | 1.00 | 55.69 | N |
| ATOM | 683 | CA | PRO A | 93 | 36.682 | −4.464 | 76.747 | 1.00 | 56.18 | C |
| ATOM | 684 | CB | PRO A | 93 | 37.024 | −5.065 | 78.110 | 1.00 | 56.31 | C |
| ATOM | 685 | CG | PRO A | 93 | 38.120 | −6.142 | 77.849 | 1.00 | 55.28 | C |
| ATOM | 686 | CD | PRO A | 93 | 38.097 | −6.439 | 76.411 | 1.00 | 55.16 | C |
| ATOM | 687 | C | PRO A | 93 | 37.063 | −2.990 | 76.742 | 1.00 | 56.94 | C |
| ATOM | 688 | O | PRO A | 93 | 38.227 | −2.084 | 70.544 | 1.00 | 57.39 | O |
| ATOM | 689 | N | GLY A | 94 | 36.113 | −2.081 | 76.927 | 1.00 | 57.84 | N |
| ATOM | 690 | CA | GLY A | 94 | 36.467 | −0.687 | 77.183 | 1.00 | 58.45 | C |
| ATOM | 691 | C | GLY A | 94 | 36.203 | 0.193 | 75.992 | 1.00 | 59.46 | C |
| ATOM | 692 | O | GLY A | 94 | 35.192 | 0.915 | 75.955 | 1.00 | 59.77 | O |
| ATOM | 693 | N | ASN A | 95 | 37.099 | 0.146 | 75.009 | 1.00 | 59 48 | N |
| ATOM | 694 | CA | ASN A | 95 | 36.829 | 0.842 | 73.768 | 1.00 | 59.46 | C |

TABLE 11-continued

| | | | | | | | | | | |
|---|---|---|---|---|---|---|---|---|---|---|
| ATOM | 695 | CB | ASN A | 95 | 38.064 | 0.914 | 72.875 | 1.00 | 60.28 | C |
| ATOM | 696 | CG | ASN A | 95 | 39.092 | −0.171 | 73.206 | 1.00 | 62.12 | C |
| ATOM | 697 | OD1 | ASN A | 95 | 38.755 | −1.341 | 73.447 | 1.00 | 62.51 | O |
| ATOM | 698 | ND2 | ASN A | 95 | 40.359 | 0.223 | 73.210 | 1.00 | 65.35 | N |
| ATOM | 699 | O | ASN A | 95 | 35.629 | 0.237 | 73.060 | 1.00 | 58.96 | O |
| ATOM | 700 | O | ASN A | 95 | 35.146 | −0.838 | 73.435 | 1.00 | 59 19 | O |
| ATOM | 701 | N | LYS A | 96 | 35.182 | 0.943 | 72.023 | 1.00 | 58.29 | N |
| ATOM | 702 | CA | LYS A | 96 | 33.848 | 0.848 | 71.436 | 1.00 | 56.76 | C |
| ATOM | 703 | CG | LYS A | 96 | 33.048 | 2.094 | 71.898 | 1.00 | 57.72 | C |
| ATOM | 704 | CG | LYS A | 96 | 31.491 | 2.155 | 71.704 | 1.00 | 58.59 | C |
| ATOM | 705 | CD | LYS A | 96 | 30.854 | 3.383 | 72.454 | 1.00 | 60.30 | C |
| ATOM | 706 | CE | LYS A | 96 | 29.307 | 3.570 | 72.208 | 1.00 | 62.06 | C |
| ATOM | 707 | NZ | LYS A | 96 | 28.872 | 4.451 | 71.016 | 1.00 | 61.04 | N |
| ATOM | 708 | C | LYS A | 96 | 34.169 | 0.932 | 69.965 | 1.00 | 55.34 | C |
| ATOM | 709 | O | LYS A | 96 | 34.589 | 1.981 | 69.490 | 1.00 | 54.32 | O |
| ATOM | 710 | N | TYR A | 97 | 34.010 | −0.191 | 69.257 | 1.00 | 54.64 | N |
| ATOM | 711 | CA | TYR A | 97 | 34.571 | −0.377 | 67.906 | 1.00 | 53.27 | C |
| ATOM | 712 | CB | TYR A | 97 | 35.068 | −1.816 | 67.741 | 1.00 | 53.26 | C |
| ATOM | 713 | CG | TYR A | 97 | 36.253 | −2.191 | 68.622 | 1.00 | 52.42 | C |
| ATOM | 714 | CD1 | TYR A | 97 | 37.562 | −1.923 | 68.219 | 1.00 | 51.64 | C |
| ATOM | 715 | CE1 | TYR A | 97 | 38.638 | −2.236 | 68.999 | 1.00 | 48.12 | C |
| ATOM | 716 | CZ | TYR A | 97 | 38.442 | −2.836 | 70.214 | 1.00 | 50.93 | C |
| ATOM | 717 | OH | TYR A | 97 | 39.553 | −3.194 | 70.999 | 1.00 | 54.00 | O |
| ATOM | 718 | CE2 | TYR A | 97 | 37.153 | −3.110 | 70.650 | 1.00 | 51.03 | C |
| ATOM | 719 | CD2 | TYR A | 97 | 36.068 | −2.798 | 69.852 | 1.00 | 51.49 | C |
| ATOM | 720 | C | TYR A | 97 | 33.526 | −0.042 | 66.850 | 1.00 | 53.09 | C |
| ATOM | 721 | O | TYR A | 97 | 32.424 | −0.599 | 66.857 | 1.00 | 52.42 | O |
| ATOM | 722 | N | GLU A | 98 | 33.879 | 0.875 | 65.591 | 1.00 | 53.17 | N |
| ATOM | 723 | CA | GLU A | 98 | 32.885 | 1.568 | 65.098 | 1.00 | 53.59 | C |
| ATOM | 724 | CB | GLU A | 98 | 32.805 | 3.064 | 65.427 | 1.00 | 53.54 | C |
| ATOM | 725 | CG | GLU A | 98 | 32.101 | 3.314 | 66.760 | 1.00 | 57.79 | C |
| ATOM | 726 | CD | GLU A | 98 | 32.035 | 4.772 | 67.143 | 1.00 | 64.85 | C |
| ATOM | 727 | OE1 | GLU A | 98 | 33.075 | 5.480 | 67.051 | 1.00 | 66.67 | O |
| ATOM | 728 | OE2 | GLU A | 98 | 30.933 | 5.215 | 67.549 | 1.00 | 67.69 | O |
| ATOM | 729 | C | GLU A | 98 | 33.163 | 1.358 | 63.633 | 1.00 | 53.08 | C |
| ATOM | 730 | O | GLU A | 98 | 34.269 | 1.672 | 63.132 | 1.00 | 53.17 | O |
| ATOM | 731 | N | TYR A | 99 | 32.165 | 0.793 | 62.955 | 1.00 | 51.47 | C |
| ATOM | 732 | CA | TYR A | 99 | 32.331 | 0.411 | 61.560 | 1.00 | 51.47 | C |
| ATOM | 733 | CB | TYR A | 99 | 31.964 | −1.064 | 61.357 | 1.00 | 50.77 | C |
| ATOM | 734 | CG | TYR A | 99 | 32.913 | −2.108 | 61.912 | 1.00 | 48.96 | C |
| ATOM | 735 | CD1 | TYR A | 99 | 33.801 | −2.756 | 61.088 | 1.00 | 48.94 | C |
| ATOM | 736 | CE1 | TYR A | 99 | 34.648 | −3.703 | 61.561 | 1.00 | 44.83 | C |
| ATOM | 737 | CZ | TYR A | 99 | 34.624 | −4.034 | 62.869 | 1.00 | 42.94 | C |
| ATOM | 738 | OH | TYR A | 99 | 35.489 | −5.017 | 63.303 | 1.00 | 42.01 | O |
| ATOM | 739 | CE2 | TYR A | 99 | 33.744 | −3.420 | 63.718 | 1.00 | 43.83 | C |
| ATOM | 740 | CD2 | TYR A | 99 | 32.893 | −2.477 | 63.243 | 1.00 | 46.66 | C |
| ATOM | 741 | C | TYR A | 99 | 31.374 | 1.276 | 60.756 | 1.00 | 51.78 | C |
| ATOM | 742 | O | TYR A | 99 | 30.164 | 1.224 | 60.991 | 1.00 | 51.80 | O |
| ATOM | 743 | N | LYS A | 100 | 31.890 | 2.062 | 59.815 | 1.00 | 51.71 | N |
| ATOM | 744 | CA | LYS A | 100 | 31.014 | 2.859 | 58.952 | 1.00 | 52.50 | C |
| ATOM | 745 | CB | LYS A | 100 | 31.786 | 4.025 | 58.351 | 1.00 | 52.43 | C |
| ATOM | 746 | CG | LYS A | 100 | 32.296 | 5.042 | 59.328 | 1.00 | 54.03 | C |
| ATOM | 247 | CD | LYS A | 100 | 33.325 | 5.873 | 58.587 | 1.00 | 56.76 | C |
| ATOM | 748 | CE | LYS A | 100 | 33.151 | 7.372 | 58.847 | 1.00 | 57.66 | C |
| ATOM | 749 | NZ | LYS A | 100 | 34.186 | 8.123 | 58.057 | 1.00 | 57.52 | N |
| ATOM | 750 | C | LYS A | 100 | 30.422 | 2.069 | 57.772 | 1.00 | 52.63 | C |
| ATOM | 751 | O | LYS A | 100 | 31.122 | 1.327 | 57.079 | 1.00 | 53.07 | C |
| ATOM | 752 | N | PHE A | 101 | 29.149 | 2.272 | 57.492 | 1.00 | 52.42 | N |
| ATOM | 753 | CA | PHE A | 101 | 28.639 | 1.852 | 56.200 | 1.00 | 52.16 | C |
| ATOM | 754 | CB | PHE A | 101 | 27.697 | 0.681 | 56.354 | 1.00 | 51.64 | C |
| ATOM | 755 | CG | PHE A | 101 | 26.475 | 1.004 | 57.120 | 1.00 | 50.64 | C |
| ATOM | 756 | CD1 | PHE A | 101 | 25.364 | 1.537 | 56.479 | 1.00 | 51.12 | C |
| ATOM | 757 | CE1 | PHE A | 101 | 24.207 | 1.845 | 57.182 | 1.00 | 49.52 | C |
| ATOM | 758 | CZ | PHE A | 101 | 24.140 | 1.599 | 58.537 | 1.00 | 49.04 | C |
| ATOM | 759 | CE2 | PHE A | 101 | 25.266 | 1.052 | 59.203 | 1.00 | 50.02 | C |
| ATOM | 760 | CD2 | PHE A | 101 | 26.425 | 0.788 | 58.490 | 1.00 | 48.81 | C |
| ATOM | 761 | C | PHE A | 101 | 27.876 | 2.974 | 55.523 | 1.00 | 52.77 | C |
| ATOM | 762 | O | PHE A | 101 | 27.346 | 3.895 | 56.201 | 1.00 | 52.73 | O |
| ATOM | 763 | N | GLY A | 102 | 27.798 | 2.859 | 54.194 | 1.00 | 52.52 | N |
| ATOM | 764 | CA | GLY A | 102 | 27.037 | 3.795 | 53.367 | 1.00 | 52.44 | C |
| ATOM | 765 | C | GLY A | 102 | 26.524 | 3.246 | 52.046 | 1.00 | 51.53 | C |
| ATOM | 765 | O | GLY A | 102 | 27.275 | 2.828 | 51.177 | 1.00 | 51.25 | O |
| ATOM | 767 | N | PHE A | 103 | 25.227 | 3.244 | 51.902 | 1.00 | 51.44 | N |
| ATOM | 768 | CA | PHE A | 103 | 24.656 | 2.891 | 50.640 | 1.00 | 52.46 | C |
| ATOM | 769 | CB | PHE A | 103 | 24.154 | 1.453 | 50.658 | 1.00 | 51.37 | C |
| ATOM | 770 | CG | PHE A | 103 | 23.070 | 1.223 | 51.642 | 1.00 | 49 43 | C |
| ATOM | 771 | CD1 | PHE A | 103 | 21.746 | 1.439 | 51.291 | 1.00 | 45.71 | C |
| ATOM | 772 | CE1 | PHE A | 103 | 20.742 | 1.237 | 52.224 | 1.00 | 47.34 | C |
| ATOM | 773 | CZ | PHE A | 103 | 21.062 | 0.809 | 53.637 | 1.00 | 47.02 | C |
| ATOM | 774 | CE2 | PHE A | 103 | 22.374 | 0.600 | 53.887 | 1.00 | 47.04 | C |

TABLE 11-continued

| ATOM | 775 | CD2 | PHE A | 103 | 23.373 | 0.816 | 52.946 | 1.00 | 48.15 | C |
|------|-----|-----|-------|-----|--------|-------|--------|------|-------|---|
| ATOM | 776 | C | PHE A | 103 | 23.541 | 3.885 | 50.307 | 1.00 | 53.73 | C |
| ATOM | 777 | O | PHE A | 103 | 23.039 | 4.617 | 51.171 | 1.00 | 52.89 | O |
| ATOM | 778 | N | GLU A | 104 | 23.184 | 3.919 | 49.034 | 1.00 | 55.94 | N |
| ATOM | 779 | CA | GLU A | 104 | 22.304 | 4.970 | 48.539 | 1.00 | 58.52 | C |
| ATOM | 780 | CB | GLU A | 104 | 23.094 | 6.114 | 47.864 | 1.00 | 58.36 | C |
| ATOM | 781 | CG | GLU A | 104 | 23.233 | 6.020 | 46.355 | 1.00 | 61.22 | C |
| ATOM | 782 | CD | GLU A | 104 | 24.171 | 7.085 | 45.833 | 1.00 | 67.42 | C |
| ATOM | 783 | OE1 | GLU A | 104 | 23.735 | 7.980 | 45.059 | 1.00 | 67.59 | O |
| ATOM | 784 | OE2 | GLU A | 104 | 25.359 | 7.055 | 46.237 | 1.00 | 70.55 | O |
| ATOM | 785 | C | GLU A | 104 | 21.289 | 4.345 | 47.606 | 1.00 | 58.79 | C |
| ATOM | 786 | O | GLU A | 104 | 21.657 | 3.728 | 46.593 | 1.00 | 59.15 | O |
| ATOM | 787 | N | LEU A | 105 | 20.021 | 4.503 | 47.979 | 1.00 | 59.21 | N |
| ATOM | 788 | CA | LEU A | 105 | 18.921 | 3.833 | 47.306 | 1.00 | 59.60 | C |
| ATOM | 789 | CB | LEU A | 105 | 17.602 | 4.214 | 47.986 | 1.00 | 59.45 | C |
| ATOM | 790 | CG | LEU A | 105 | 17.604 | 3.915 | 49.498 | 1.00 | 59.15 | C |
| ATOM | 791 | CD1 | LEU A | 105 | 17.030 | 5.069 | 50.308 | 1.00 | 56.99 | C |
| ATOM | 792 | CD2 | LEU A | 105 | 16.889 | 2.582 | 49.813 | 1.00 | 58.28 | C |
| ATOM | 793 | C | LEU A | 105 | 18.884 | 4.148 | 45.807 | 1.00 | 00.25 | C |
| ATOM | 794 | O | LEU A | 105 | 19.446 | 5.184 | 45.356 | 1.00 | 59.78 | O |
| ATOM | 795 | N | PRO A | 106 | 18.243 | 3.245 | 45.021 | 1.00 | 60.72 | N |
| ATOM | 796 | CA | PRO A | 106 | 18.004 | 3.537 | 43.621 | 1.00 | 60.95 | C |
| ATOM | 797 | CB | PRO A | 106 | 17.475 | 2.217 | 43.085 | 1.00 | 61.01 | C |
| ATOM | 798 | CG | PRO A | 106 | 16.755 | 1.651 | 44.228 | 1.00 | 60.35 | C |
| ATOM | 799 | CD | PRO A | 106 | 17.681 | 1.933 | 45.382 | 1.00 | 60.80 | C |
| ATOM | 800 | C | PRO A | 106 | 16.912 | 4.581 | 43.522 | 1.00 | 60.92 | C |
| ATOM | 801 | O | PRO A | 105 | 15.948 | 4.581 | 44.274 | 1.00 | 60.87 | O |
| ATOM | 802 | N | GLN A | 107 | 17.089 | 5.495 | 42.599 | 1.00 | 61.40 | N |
| ATOM | 803 | CA | GLN A | 107 | 16.022 | 6.363 | 42.175 | 1.00 | 61.20 | C |
| ATOM | 804 | CB | GLN A | 107 | 16.617 | 7.297 | 41.160 | 1.00 | 58.91 | C |
| ATOM | 805 | CG | GLN A | 107 | 18.110 | 7.396 | 41.452 | 1.00 | 54.81 | C |
| ATOM | 806 | CD | GLN A | 107 | 18.524 | 8.811 | 41.297 | 1.00 | 51.93 | C |
| ATOM | 807 | OE1 | GLN A | 107 | 18.547 | 9.507 | 42.288 | 1.00 | 47.12 | O |
| ATOM | 808 | NE2 | GLN A | 107 | 18.799 | 9.206 | 40.029 | 1.00 | 51.92 | N |
| ATOM | 809 | C | GLN A | 107 | 14.987 | 5.505 | 41.476 | 1.00 | 62.96 | C |
| ATOM | 810 | O | GLN A | 107 | 15.276 | 4.355 | 41.055 | 1.00 | 63.61 | O |
| ATOM | 811 | N | GLY A | 108 | 13.794 | 6.059 | 41.306 | 1.00 | 63.90 | N |
| ATOM | 812 | CA | GLY A | 108 | 12.728 | 5.259 | 40.746 | 1.00 | 65.37 | C |
| ATOM | 813 | C | GLY A | 108 | 11.926 | 4.701 | 41.908 | 1.00 | 66.40 | C |
| ATOM | 814 | O | GLY A | 108 | 12.025 | 5.207 | 43.037 | 1.00 | 65.66 | O |
| ATOM | 815 | N | PRO A | 109 | 11.128 | 3.645 | 41.643 | 1.00 | 67.35 | N |
| ATOM | 816 | CA | PRO A | 109 | 10.190 | 3.241 | 42.696 | 1.00 | 67.64 | C |
| ATOM | 817 | CB | PRO A | 109 | 9.232 | 2.233 | 41.994 | 1.00 | 67.75 | C |
| ATOM | 818 | CG | PRO A | 109 | 10.017 | 1.686 | 40.811 | 1.00 | 67.56 | C |
| ATOM | 819 | CD | PRO A | 109 | 11.096 | 2.741 | 40.463 | 1.00 | 67.58 | C |
| ATOM | 820 | C | PRO A | 109 | 10.979 | 2.549 | 43.785 | 1.00 | 67.25 | C |
| ATOM | 821 | O | PRO A | 109 | 12.051 | 1.978 | 43.524 | 1.00 | 67.61 | O |
| ATOM | 822 | N | LEU A | 110 | 10.410 | 2.635 | 45.001 | 1.00 | 66.61 | N |
| ATOM | 823 | CA | LEU A | 110 | 10.984 | 1.822 | 46.076 | 1.00 | 65.64 | C |
| ATOM | 824 | CB | LEU A | 110 | 11.402 | 2.716 | 47.244 | 1.00 | 65.62 | C |
| ATOM | 825 | CG | LEU A | 110 | 12.481 | 3.674 | 46.673 | 1.00 | 66.33 | C |
| ATOM | 826 | CD1 | LEU A | 110 | 12.698 | 4.943 | 47.482 | 1.00 | 64.63 | C |
| ATOM | 827 | CD2 | LEU A | 110 | 13.828 | 2.964 | 46.369 | 1.00 | 66.00 | C |
| ATOM | 828 | C | LEU A | 110 | 9.895 | 0.789 | 46.356 | 1.00 | 64.73 | C |
| ATOM | 829 | O | LEU A | 110 | 10.011 | −0.093 | 47.211 | 1.00 | 63.24 | O |
| ATOM | 830 | N | GLY A | 111 | 8.845 | 0.900 | 45.552 | 1.00 | 64.65 | N |
| ATOM | 831 | CA | GLY A | 111 | 7.781 | −0.087 | 45.548 | 1.00 | 65.28 | C |
| ATOM | 832 | C | GLY A | 111 | 6.866 | −0.109 | 46.770 | 1.00 | 64.79 | C |
| ATOM | 833 | O | GLY A | 111 | 6.410 | −1.190 | 47.180 | 1.00 | 54.93 | O |
| ATOM | 834 | N | THR A | 112 | 6.610 | 1.073 | 47.344 | 1.00 | 63.87 | N |
| ATOM | 835 | CA | THR A | 112 | 5.570 | 1.280 | 48.357 | 1.00 | 51.96 | C |
| ATOM | 836 | CB | THR A | 112 | 5.535 | 2.779 | 48.824 | 1.00 | 59.68 | C |
| ATOM | 837 | OG1 | THR A | 112 | 5.376 | 3.597 | 47.651 | 1.00 | 50.69 | O |
| ATOM | 838 | OG2 | THR A | 112 | 6.849 | 3.212 | 49.587 | 1.00 | 57.65 | O |
| ATOM | 839 | C | THR A | 112 | 4.222 | 1.042 | 47.684 | 1.00 | 64.74 | C |
| ATOM | 840 | O | THR A | 112 | 3.259 | 0.600 | 48.314 | 1.00 | 63.81 | O |
| ATOM | 841 | N | SER A | 113 | 4.193 | 1.367 | 46.377 | 1.00 | 67.42 | N |
| ATOM | 842 | CA | SER A | 113 | 2.977 | 1.627 | 45.584 | 1.00 | 69.82 | C |
| ATOM | 843 | CB | SER A | 113 | 3.162 | 1.184 | 44.121 | 1.00 | 69.58 | C |
| ATOM | 844 | OG | SER A | 113 | 3.722 | −0.115 | 44.037 | 1.00 | 70.30 | O |
| ATOM | 845 | C | SER A | 113 | 1.692 | 1.068 | 46.196 | 1.00 | 71.57 | C |
| ATOM | 846 | O | SER A | 113 | 0.761 | 1.841 | 46.507 | 1.00 | 72.45 | O |
| ATOM | 847 | N | PHE A | 114 | 1.665 | −0.257 | 45.395 | 1.00 | 73.39 | N |
| ATOM | 848 | CA | PHE A | 114 | 0.537 | −1.948 | 47.048 | 1.00 | 74.48 | C |
| ATOM | 849 | CB | PHE A | 114 | 0.130 | −2.208 | 46.290 | 1.00 | 74.58 | C |
| ATOM | 850 | CG | PHE A | 114 | −0.187 | −1.975 | 44.853 | 1.00 | 74.32 | C |
| ATOM | 851 | CD1 | PHE A | 114 | −1.504 | −1.960 | 44.426 | 1.00 | 74.70 | C |
| ATOM | 852 | CE1 | PHE A | 114 | −1.807 | −1.750 | 43.104 | 1.00 | 75.28 | C |
| ATOM | 853 | CZ | PHE A | 114 | −0.778 | −1.565 | 42.177 | 1.00 | 76.10 | C |
| ATOM | 854 | CE2 | PHE A | 114 | 0.546 | −1.569 | 42.597 | 1.00 | 75.94 | C |

TABLE 11-continued

| | | | | | | | | | | |
|---|---|---|---|---|---|---|---|---|---|---|
| ATOM | 855 | CD2 | PHE A | 114 | 0.832 | −1.778 | 43.928 | 1.00 | 74.60 | C |
| ATOM | 856 | C | PHE A | 114 | 0.824 | −1.350 | 48.480 | 1.00 | 75.19 | C |
| ATOM | 857 | O | PHE A | 114 | 0.248 | −2.341 | 48.952 | 1.00 | 75.75 | O |
| ATOM | 858 | N | LYS A | 115 | 1.701 | −0.603 | 49.167 | 1.00 | 75.53 | N |
| ATOM | 859 | CA | LYS A | 155 | 1.748 | −0.651 | 50.644 | 1.00 | 75.71 | C |
| ATOM | 860 | CB | LYS A | 115 | 2.878 | 0.213 | 51.267 | 1.00 | 75.72 | C |
| ATOM | 861 | CG | LYS A | 115 | 2.756 | 1.743 | 51.064 | 1.00 | 76.11 | C |
| ATOM | 862 | CD | LYS A | 115 | 3.375 | 2.567 | 52.203 | 1.00 | 77.59 | C |
| ATOM | 863 | CE | LYS A | 115 | 3.474 | 4.064 | 51.789 | 1.00 | 77.69 | C |
| ATOM | 864 | NZ | LYS A | 115 | 2.950 | 4.950 | 52.897 | 1.00 | 75.93 | N |
| ATOM | 865 | C | LYS A | 115 | 0.368 | 0.165 | 51.091 | 1.00 | 75.19 | C |
| ATOM | 866 | O | LYS A | 115 | 0.196 | 0.985 | 51.548 | 1.00 | 75.82 | O |
| ATOM | 867 | N | GLY A | 116 | −0.617 | −1.037 | 50.911 | 1.00 | 73.75 | N |
| ATOM | 868 | CA | GLY A | 116 | −1.983 | −0.699 | 51.202 | 1.00 | 72.25 | C |
| ATOM | 869 | C | GLY A | 116 | −2.593 | −1.944 | 51.761 | 1.00 | 71.20 | C |
| ATOM | 870 | O | GLY A | 116 | −1.906 | −2.788 | 52.338 | 1.00 | 71.14 | O |
| ATOM | 871 | N | LYS A | 117 | −3.895 | −2.056 | 51.558 | 1.00 | 70.18 | N |
| ATOM | 872 | CA | LYS A | 117 | −4.661 | −3.244 | 51.898 | 1.00 | 69.03 | C |
| ATOM | 873 | CB | LYS A | 117 | −6.128 | −2.981 | 51.495 | 1.00 | 68.43 | C |
| ATOM | 874 | CG | LYS A | 117 | −6.912 | −4.148 | 50.956 | 1.00 | 67.86 | C |
| ATOM | 875 | CD | LYS A | 117 | −7.977 | −3.658 | 49.968 | 1.00 | 66.92 | C |
| ATOM | 876 | CE | LYS A | 117 | −9.275 | −4.443 | 50.122 | 1.00 | 67.26 | C |
| ATOM | 877 | NZ | LYS A | 117 | −9.044 | −5.849 | 50.623 | 1.00 | 65.60 | N |
| ATOM | 878 | C | LYS A | 117 | −4.059 | −4.517 | 51.239 | 1.00 | 68.43 | C |
| ATOM | 879 | O | LYS A | 117 | −4.273 | −5.636 | 51.716 | 1.00 | 68.02 | O |
| ATOM | 880 | N | TYR A | 118 | −3.292 | −4.336 | 50.163 | 1.00 | 67.71 | N |
| ATOM | 881 | CA | TYR A | 118 | −2.911 | −5.457 | 49.320 | 1.00 | 67.60 | C |
| ATOM | 882 | CB | TYR A | 118 | −3.291 | −5.192 | 47.857 | 1.00 | 67.03 | C |
| ATOM | 883 | CG | TYR A | 118 | −4.769 | −5.353 | 47.566 | 1.00 | 64.39 | C |
| ATOM | 884 | CD1 | TYR A | 118 | −5.374 | −6.611 | 47.639 | 1.00 | 62.66 | C |
| ATOM | 885 | CE1 | TYR A | 118 | −6.176 | −6.782 | 47.396 | 1.00 | 60.65 | C |
| ATOM | 886 | CA | TYR A | 118 | −7.477 | −5.692 | 47.039 | 1.00 | 62.47 | C |
| ATOM | 887 | OH | TYR A | 118 | −8.812 | −5.898 | 46.783 | 1.00 | 64.33 | O |
| ATOM | 888 | CE2 | TYR A | 118 | −6.913 | −4.422 | 46.919 | 1.00 | 61.50 | C |
| ATOM | 889 | CD2 | TYR A | 118 | −5.559 | −4.257 | 47.194 | 1.00 | 62.33 | C |
| ATOM | 890 | C | TYR A | 118 | 1.441 | 5.823 | 49.440 | 1.00 | 68.32 | C |
| ATOM | 891 | O | TYR A | 118 | −1.077 | −6.980 | 49.323 | 1.00 | 68.02 | O |
| ATOM | 892 | N | GLY A | 119 | −0.597 | −4.826 | 49.671 | 1.00 | 69.18 | N |
| ATOM | 893 | CA | GLY A | 119 | 0.831 | −5.076 | 49.792 | 1.00 | 9.91 | C |
| ATOM | 894 | C | GLY A | 119 | 1.479 | −4.448 | 51.015 | 1.00 | 70.31 | C |
| ATOM | 895 | O | GLY A | 119 | 0.801 | −3.833 | 51.850 | 1.00 | 70.04 | O |
| ATOM | 896 | N | CYS A | 120 | 2.805 | −4.621 | 51.093 | 1.00 | 70.59 | N |
| ATOM | 897 | CA | CYS A | 120 | 3.662 | −4.027 | 52.129 | 1.00 | 70.68 | C |
| ATOM | 898 | CB | CYS A | 120 | 3.491 | −4.738 | 53.462 | 1.00 | 70.59 | C |
| ATOM | 899 | SG | CYS A | 120 | 3.938 | −6.451 | 53.304 | 1.00 | 75.20 | S |
| ATOM | 900 | C | CYS A | 120 | 5.134 | −4.089 | 51.693 | 1.00 | 69.71 | C |
| ATOM | 901 | O | CYS A | 120 | 5.492 | −4.989 | 50.835 | 1.00 | 69.81 | O |
| ATOM | 902 | N | VAL A | 121 | 5.958 | −3.238 | 52.313 | 1.00 | 68.66 | N |
| ATOM | 903 | CA | VAL A | 121 | 7.322 | −2.939 | 51.889 | 1.00 | 67.86 | C |
| ATOM | 904 | CB | VAL A | 121 | 7.375 | −1.541 | 51.195 | 1.00 | 67.45 | C |
| ATOM | 905 | CG1 | VAL A | 121 | 6.990 | −0.427 | 52.171 | 1.00 | 68.07 | C |
| ATOM | 906 | CG2 | VAL A | 121 | 8.723 | −1.264 | 50.588 | 1.00 | 65.97 | C |
| ATOM | 907 | C | VAL A | 121 | 8.354 | −3.058 | 53.067 | 1.00 | 67.75 | C |
| ATOM | 908 | O | VAL A | 121 | 8.260 | −2.353 | 54.090 | 1.00 | 68.27 | O |
| ATOM | 909 | N | ASP A | 122 | 9.334 | −3.953 | 52.918 | 1.00 | 66.60 | N |
| ATOM | 910 | CA | ASP A | 122 | 10.304 | −4.220 | 53.990 | 1.00 | 65.13 | C |
| ATOM | 911 | CB | ASP A | 122 | 10.401 | −5.725 | 54.297 | 1.00 | 65.76 | C |
| ATOM | 912 | CG | ASP A | 122 | 9.319 | −6.212 | 55.252 | 1.00 | 67.89 | C |
| ATOM | 913 | OD1 | ASP A | 122 | 9.287 | −7.446 | 55.501 | 1.00 | 70.93 | O |
| ATOM | 914 | OD2 | ASP A | 122 | 8.509 | −5.379 | 55.750 | 1.00 | 70.15 | O |
| ATOM | 915 | C | ASP A | 122 | 11.892 | −3.683 | 53.686 | 1.00 | 63.01 | C |
| ATOM | 916 | O | ASP A | 122 | 12.355 | −4.138 | 57.752 | 1.00 | 63.45 | O |
| ATOM | 917 | N | TYR A | 123 | 12.127 | −2.718 | 54.475 | 1.00 | 60.10 | N |
| ATOM | 918 | CA | TYR A | 123 | 13.509 | −2.343 | 54.458 | 1.00 | 58.02 | C |
| ATOM | 919 | CB | TYR A | 123 | 13.660 | −0.876 | 54.084 | 1.00 | 57.79 | C |
| ATOM | 920 | CG | TYR A | 123 | 13.480 | −0.623 | 52.624 | 1.00 | 58.06 | C |
| ATOM | 921 | CD1 | TYR A | 123 | 14.458 | 0.008 | 51.889 | 1.00 | 60.74 | C |
| ATOM | 922 | CE1 | TYR A | 123 | 14.302 | 0.257 | 50.529 | 1.00 | 61.47 | C |
| ATOM | 923 | CZ | TYR A | 123 | 13.147 | −0.149 | 49.894 | 1.00 | 62.57 | C |
| ATOM | 924 | OH | TYR A | 123 | 12.959 | 0.999 | 48.540 | 1.00 | 61.73 | O |
| ATOM | 925 | CE2 | TYR A | 123 | 12.163 | −0.794 | 50.618 | 1.00 | 61.81 | C |
| ATOM | 926 | CD2 | TYR A | 123 | 12.337 | −1.019 | 51.972 | 1.00 | 60 22 | C |
| ATOM | 927 | C | TYR A | 123 | 14.175 | −2.673 | −55.781 | 1.00 | 56.49 | C |
| ATOM | 928 | O | TYR A | 123 | 13.521 | −2.746 | 56.289 | 1.00 | 56.57 | O |
| ATOM | 929 | N | TRP A | 124 | 15.472 | −2.924 | 55.703 | 1.00 | 54.41 | N |
| ATOM | 930 | CA | TRP A | 124 | 16.321 | −3.085 | 56.868 | 1.00 | 52.86 | C |
| ATOM | 931 | CB | TRP A | 124 | 15.908 | −4.252 | 57.717 | 1.00 | 53.40 | C |
| ATOM | 932 | CG | TRP A | 124 | 15.496 | −5.421 | 56.963 | 1.00 | 55.74 | C |
| ATOM | 933 | CD1 | TRP A | 124 | 14.223 | −5.807 | 56.735 | 1.00 | 58.43 | C |
| ATOM | 934 | NE1 | TRP A | 124 | 14.202 | −6.960 | 55.984 | 1.00 | 59.55 | N |

TABLE 11-continued

| | | | | | | | | | | |
|---|---|---|---|---|---|---|---|---|---|---|
| ATOM | 935 | CE2 | TRP A | 124 | 15.486 | −7.353 | 55.732 | 1.00 | 57.45 | C |
| ATOM | 936 | CD2 | TRP A | 124 | 16.338 | −6.388 | 56.316 | 1.00 | 57.72 | C |
| ATOM | 937 | CE3 | TRP A | 124 | 17.724 | −6.550 | 56.191 | 1.00 | 59.54 | C |
| ATOM | 938 | CZ3 | TRP A | 124 | 18.202 | −7.667 | 55.476 | 1.00 | 58.58 | C |
| ATOM | 939 | CH2 | TRP A | 124 | 17.312 | −8.589 | 54.903 | 1.00 | 56.56 | C |
| ATOM | 940 | CZ2 | TRP A | 124 | 15.963 | −8.449 | 55.019 | 1.00 | 54.96 | C |
| ATOM | 941 | C | TRP A | 124 | 17.747 | −3.306 | 56.462 | 1.00 | 51.27 | C |
| ATOM | 942 | O | TRP A | 124 | 18.078 | −3.376 | 55.266 | 1.00 | 51.33 | O |
| ATOM | 943 | N | VAL A | 125 | 18.579 | −3.422 | 57.486 | 1.00 | 49.31 | N |
| ATOM | 944 | CA | VAL A | 125 | 19.999 | −3.676 | 57.352 | 1.00 | 47.39 | C |
| ATOM | 945 | CB | VAL A | 125 | 20.783 | −2.419 | 57.745 | 1.00 | 46.41 | C |
| ATOM | 946 | CG1 | VAL A | 125 | 22.216 | −2.694 | 57.839 | 1.00 | 45.15 | C |
| ATOM | 947 | CG2 | VAL A | 125 | 20.515 | −1.289 | 56.781 | 1.00 | 45.18 | C |
| ATOM | 948 | C | VAL A | 125 | 20.280 | −4.783 | 58.347 | 1.00 | 47.30 | C |
| ATOM | 949 | O | VAL A | 125 | 19.973 | −4.638 | 59.522 | 1.00 | 47.36 | O |
| ATOM | 950 | N | LYS A | 126 | 20.824 | −5.912 | 57.895 | 1.00 | 47.28 | N |
| ATOM | 951 | CA | LYS A | 126 | 21.467 | −6.480 | 58.832 | 1.00 | 46.83 | C |
| ATOM | 952 | CB | LYS A | 126 | 21.238 | −8.262 | 58.428 | 1.00 | 46.63 | C |
| ATOM | 953 | CG | LYS A | 126 | 19.797 | 8.666 | 58.521 | 1.00 | 51.37 | C |
| ATOM | 954 | CD | LYS A | 126 | 19.736 | −10.189 | 58.480 | 1.00 | 59.34 | C |
| ATOM | 955 | CE | LYS A | 126 | 18.284 | −10.739 | 58.441 | 1.00 | 63.41 | C |
| ATOM | 956 | NZ | LYS A | 126 | 17.689 | −10.623 | 57.051 | 1.00 | 64.68 | N |
| ATOM | 957 | C | LYS A | 126 | 22.947 | −6.555 | 58.814 | 1.00 | 45.95 | C |
| ATOM | 958 | O | LYS A | 126 | 23.486 | −6.215 | 57.754 | 1.00 | 46.16 | O |
| ATOM | 959 | N | ALA A | 127 | 23.586 | −6.628 | 59.987 | 1.00 | 45.15 | N |
| ATOM | 960 | CA | ALA A | 127 | 20.058 | −6.663 | 60.114 | 1.00 | 43.96 | C |
| ATOM | 961 | CB | ALA A | 127 | 25.543 | −5.654 | 61.060 | 1.00 | 43.16 | C |
| ATOM | 962 | C | ALA A | 127 | 25.395 | −8.008 | 60.645 | 1.00 | 43.28 | C |
| ATOM | 963 | O | ALA A | 127 | 24.597 | −8.585 | 61.356 | 1.00 | 42.75 | O |
| ATOM | 964 | N | PHE A | 128 | 26.577 | −8.511 | 60.316 | 1.00 | 43.39 | N |
| ATOM | 965 | CA | PHE A | 128 | 26.982 | −9.833 | 60.783 | 1.00 | 43.64 | C |
| ATOM | 966 | CB | PHE A | 128 | 27.012 | −10.815 | 59.652 | 1.00 | 43.26 | C |
| ATOM | 967 | CG | PHE A | 128 | 25.730 | −10.893 | 58.870 | 1.00 | 45.36 | C |
| ATOM | 968 | CD1 | PHE A | 128 | 24.807 | −11.892 | 59.127 | 1.00 | 46.34 | C |
| ATOM | 969 | CE1 | PHE A | 128 | 23.629 | −12.002 | 58.353 | 1.00 | 45.83 | C |
| ATOM | 970 | CZ | PHE A | 128 | 23.373 | −11.108 | 57.323 | 1.00 | 45.94 | C |
| ATOM | 971 | CE2 | PHE A | 128 | 24.275 | −10.069 | 57.062 | 1.00 | 45.74 | C |
| ATOM | 972 | CD2 | PHE A | 128 | 25.451 | −9.971 | 57.838 | 1.00 | 47.03 | C |
| ATOM | 973 | C | PHE A | 128 | 28.337 | −9.784 | 61.435 | 1.00 | 43.80 | C |
| ATOM | 974 | O | PHE A | 128 | 29.248 | −9.117 | 60.921 | 1.00 | 44.70 | O |
| ATOM | 975 | N | LEU A | 129 | 28.445 | −10.443 | 62.58 | 1.00 | 43.27 | N |
| ATOM | 976 | CA | LEU A | 129 | 29.719 | −10.630 | 63.275 | 1.00 | 43.61 | C |
| ATOM | 977 | CB | LEU A | 129 | 29.565 | −10.323 | 64.738 | 1.00 | 43.32 | C |
| ATOM | 978 | CG | LEU A | 129 | 30.855 | −10.323 | 65.532 | 1.00 | 45.38 | C |
| ATOM | 979 | CD1 | LEU A | 129 | 31.740 | −9.131 | 65.158 | 1.00 | 47.40 | C |
| ATOM | 980 | CD2 | LEU A | 129 | 30.556 | −10.284 | 67.026 | 1.00 | 47.28 | C |
| ATOM | 981 | C | LEU A | 129 | 30.233 | −12.069 | 63.116 | 1.00 | 44.59 | C |
| ATOM | 982 | O | LEU A | 129 | 29.595 | −13.077 | 63.578 | 1.00 | 44.88 | O |
| ATOM | 983 | N | ASP A | 130 | 31.373 | −12.169 | 62.444 | 1.00 | 44.56 | N |
| ATOM | 984 | CA | ASP A | 130 | 31.926 | −13.444 | 62.116 | 1.00 | 45.48 | C |
| ATOM | 985 | CB | ASP A | 130 | 32.482 | −13.409 | 60.691 | 1.00 | 45.46 | C |
| ATOM | 986 | CG | ASP A | 130 | 31.386 | −13.409 | 59.608 | 1.00 | 46.91 | C |
| ATOM | 987 | OD1 | ASP A | 130 | 30.295 | −13.297 | 59.906 | 1.00 | 47.29 | O |
| ATOM | 988 | OD2 | ASP A | 130 | 31.624 | −12.902 | 58.454 | 1.00 | 46.55 | O |
| ATOM | 989 | C | ASP A | 130 | 33.035 | −13.567 | 63.139 | 1.00 | 46.74 | C |
| ATOM | 990 | O | ASP A | 130 | 33.789 | −12.629 | 63.305 | 1.00 | 46.78 | O |
| ATOM | 991 | N | ARG A | 131 | 33.108 | −14.684 | 63.863 | 1.00 | 48.38 | N |
| ATOM | 992 | CA | ARG A | 131 | 34.154 | −14.896 | 64.882 | 1.00 | 50.35 | C |
| ATOM | 993 | CB | ARG A | 131 | 33.600 | −14.727 | 66.285 | 1.00 | 50.63 | C |
| ATOM | 994 | CG | ARG A | 131 | 33.682 | −13.326 | 66.873 | 1.00 | 52.90 | C |
| ATOM | 995 | CD | ARG A | 131 | 32.606 | −13.196 | 67.940 | 1.00 | 53.29 | C |
| ATOM | 996 | NE | ARG A | 131 | 32.836 | −14.214 | 68.939 | 1.00 | 53.15 | N |
| ATOM | 997 | CZ | ARG A | 131 | 31.978 | −14.553 | 59.888 | 1.00 | 55.32 | C |
| ATOM | 998 | NH1 | ARG A | 131 | 30.801 | −13.944 | 69.985 | 1.00 | 52.60 | N |
| ATOM | 999 | NH2 | ARG A | 131 | 32.314 | −15.520 | 70.741 | 1.00 | 56.01 | N |
| ATOM | 1000 | C | ARG A | 131 | 34.627 | −16.323 | 64.809 | 1.00 | 51.56 | C |
| ATOM | 1001 | O | ARG A | 131 | 33.782 | −17.223 | 64.716 | 1.00 | 52.89 | O |
| ATOM | 1002 | N | PRO A | 132 | 35.952 | −16.559 | 64.938 | 1.00 | 51.90 | N |
| ATOM | 1003 | CA | PRO A | 132 | 36.495 | −17.887 | 64.686 | 1.00 | 52.18 | C |
| ATOM | 1004 | CB | PRO A | 132 | 37.976 | −17.723 | 65.083 | 1.00 | 52.08 | C |
| ATOM | 1005 | CG | PRO A | 132 | 38.041 | −16.528 | 65.928 | 1.00 | 51.15 | C |
| ATOM | 1006 | CD | PRO A | 132 | 37.011 | −15.623 | 65.373 | 1.00 | 51.97 | C |
| ATOM | 1007 | C | PRO A | 132 | 35.796 | −18.998 | 65.510 | 1.00 | 53.09 | C |
| ATOM | 1008 | O | PRO A | 132 | 35.544 | −18.810 | 66.705 | 1.00 | 53.11 | O |
| ATOM | 1009 | N | SER A | 133 | 35.748 | −20.126 | 64.868 | 1.00 | 53.87 | N |
| ATOM | 1010 | CA | SER A | 133 | 34.775 | −21.238 | 65.522 | 1.00 | 55.66 | C |
| ATOM | 1011 | CB | SER A | 133 | 35.649 | −21.932 | 66.561 | 1.00 | 55.54 | C |
| ATOM | 1012 | OG | SER A | 133 | 36.963 | −22.210 | 66.089 | 1.00 | 58.47 | O |
| ATOM | 1013 | C | SER A | 133 | 33.477 | −20.826 | 66.223 | 1.00 | 56.70 | C |
| ATOM | 1014 | O | SER A | 133 | 33.103 | −21.424 | 67.249 | 1.00 | 57.46 | O |

TABLE 11-continued

| | | | | | | | | | |
|---|---|---|---|---|---|---|---|---|---|
| ATOM | 1015 | N | GLN A | 134 | 32.791 | −19.814 | 65.692 | 1.00 | 56.44 | N |
| ATOM | 1016 | CA | GLN A | 134 | 31.506 | −19.419 | 66.243 | 1.00 | 56.38 | C |
| ATOM | 1017 | CB | GLN A | 134 | 31.629 | −18.053 | 66.856 | 1.00 | 56.51 | C |
| ATOM | 1018 | CG | GLN A | 134 | 32.567 | −18.049 | 68.033 | 1.00 | 60.38 | C |
| ATOM | 1019 | CD | GLN A | 134 | 31.959 | −18.676 | 69.725 | 1.00 | 64.16 | C |
| ATOM | 1020 | OE1 | GLN A | 134 | 30.744 | −19.081 | 69.309 | 1.00 | 63.10 | O |
| ATOM | 1021 | NE2 | GLN A | 134 | 32.773 | −18.754 | 70.319 | 1.00 | 66.11 | N |
| ATOM | 1022 | C | GLN A | 134 | 30.44 | −19.734 | 65.173 | 1.00 | 55.50 | C |
| ATOM | 1023 | O | GLN A | 134 | 30.773 | −10.201 | 64.006 | 1.00 | 65.61 | O |
| ATOM | 1024 | N | PRO A | 135 | 29.170 | −19.555 | 65.545 | 1.00 | 55.19 | N |
| ATOM | 1025 | CA | PRO A | 135 | 28.236 | −19.716 | 64.476 | 1.00 | 54.67 | C |
| ATOM | 1026 | CB | PRO A | 135 | 26.893 | −19.819 | 64.899 | 1.00 | 54.25 | C |
| ATOM | 1027 | CG | PRO A | 135 | 27.233 | −20.664 | 66.161 | 1.00 | 55.45 | C |
| ATOM | 1028 | CD | PRO A | 135 | 28.480 | −20.063 | 66.745 | 1.00 | 54.68 | C |
| ATOM | 1029 | C | PRO A | 135 | 28.173 | −17.644 | 64.382 | 1.00 | 54.16 | C |
| ATOM | 1030 | O | PRO A | 135 | 28.271 | −16.898 | 65.378 | 1.00 | 53.02 | O |
| ATOM | 1031 | N | THR A | 136 | 28.065 | −17.157 | 63.173 | 1.00 | 54.06 | N |
| ATOM | 1032 | CA | THR A | 136 | 28.037 | −15.731 | 63.080 | 1.00 | 54.77 | C |
| ATOM | 1033 | CB | THR A | 136 | 27.955 | −15.235 | 61.615 | 1.00 | 55.05 | C |
| ATOM | 1034 | OG1 | THR A | 136 | 26.632 | −14.762 | 61.238 | 1.00 | 52.88 | O |
| ATOM | 1035 | OG2 | THR A | 136 | 28.433 | −16.358 | 60.588 | 1.00 | 55.12 | O |
| ATOM | 1036 | C | THR A | 136 | 26.825 | −15.305 | 63.897 | 1.00 | 54.83 | C |
| ATOM | 1037 | O | THR A | 136 | 25.764 | −15.938 | 63.845 | 1.00 | 54.23 | O |
| ATOM | 1038 | N | GLN A | 137 | 27.003 | 14.247 | 64.672 | 1.00 | 55.01 | N |
| ATOM | 1039 | CA | GLN A | 137 | 25.903 | −13.616 | 65.362 | 1.00 | 54.54 | C |
| ATOM | 1040 | CB | GLN A | 137 | 26.454 | −12.871 | 66.551 | 1.00 | 54.59 | C |
| ATOM | 1041 | CG | GLN A | 137 | 25.372 | −12.340 | 67.492 | 1.00 | 56.77 | C |
| ATOM | 1042 | CD | GLN A | 137 | 25.951 | −11.511 | 68.611 | 1.00 | 57.13 | C |
| ATOM | 1043 | OE1 | GLN A | 137 | 27.134 | −11.666 | 68.971 | 1.00 | 58.01 | O |
| ATOM | 1044 | NR2 | GLN A | 137 | 25.143 | −10.612 | 69.154 | 1.00 | 56.33 | N |
| ATOM | 1045 | C | GLN A | 137 | 25.281 | −12.633 | 64.390 | 1.00 | 54.33 | C |
| ATOM | 1046 | O | GLN A | 137 | 25.984 | −12.157 | 63.513 | 1.00 | 55.02 | O |
| ATOM | 1047 | N | GLU A | 138 | 23.994 | −12.316 | 64.514 | 1.00 | 53.90 | N |
| ATOM | 1048 | CA | GLU A | 138 | 23.468 | −11.238 | 63.682 | 1.00 | 54.24 | C |
| ATOM | 1049 | CB | GLU A | 138 | 22.905 | −11.784 | 62.362 | 1.00 | 54.62 | C |
| ATOM | 1050 | CG | GLU A | 138 | 21.401 | −11.889 | 62.268 | 1.00 | 57.47 | C |
| ATOM | 1051 | CD | GLU A | 138 | 20.946 | −13.016 | 61.324 | 1.00 | 64.03 | C |
| ATOM | 1052 | OE1 | GLU A | 138 | 21.134 | −14.231 | 61.654 | 1.00 | 65.38 | O |
| ATOM | 1053 | OE2 | GLU A | 138 | 20.391 | −12.687 | 60.244 | 1.00 | 67.38 | O |
| ATOM | 1054 | C | GLU A | 138 | 22.516 | −10.217 | 64.367 | 1.00 | 53.87 | C |
| ATOM | 1055 | O | GLU A | 138 | 21.853 | −10.530 | 65.334 | 1.00 | 54.04 | O |
| ATOM | 1056 | N | THR A | 139 | 22.490 | −8.993 | 63.840 | 1.00 | 53.03 | N |
| ATOM | 1057 | CA | THR A | 139 | 21.601 | −7.933 | 64.282 | 1.00 | 51.77 | C |
| ATOM | 1058 | CB | THR A | 139 | 22.368 | −6.849 | 65.032 | 1.00 | 51.29 | C |
| ATOM | 1059 | OG1 | THR A | 139 | 21.441 | −6.012 | 65.706 | 1.00 | 49.02 | O |
| ATOM | 1060 | CG2 | THR A | 139 | 23.136 | −5.989 | 64.101 | 1.00 | 50.58 | C |
| AOTM | 1061 | C | THR A | 139 | 20.836 | −7.305 | 63.095 | 1.00 | 52.35 | C |
| ATOM | 1062 | O | THR A | 139 | 21.433 | −6.848 | 62.112 | 1.00 | 52.83 | O |
| ATOM | 1063 | N | LYS A | 140 | 19.513 | −7.266 | 63.192 | 1.00 | 52.24 | N |
| ATOM | 1064 | CA | LYS A | 140 | 18.677 | −6.840 | 52.071 | 1.00 | 52.40 | C |
| ATOM | 1065 | CB | LYS A | 140 | 17.623 | −7.947 | 61.744 | 1.00 | 52.77 | C |
| ATOM | 1066 | CG | LYS A | 140 | 16.680 | −7.636 | 80.577 | 1.00 | 52.31 | C |
| ATOM | 1067 | CD | LYS A | 140 | 15.453 | −8.553 | 60.492 | 1.00 | 53.71 | C |
| ATOM | 1068 | CE | LYS A | 140 | 14.692 | −8.232 | 59.179 | 1.00 | 54.03 | C |
| ATOM | 1069 | NZ | LYS A | 140 | 13.239 | −8.544 | 59.225 | 1.00 | 55.01 | N |
| ATOM | 1070 | C | LYS A | 140 | 18.009 | −5.525 | 62.455 | 1.00 | 51.70 | C |
| ATOM | 1071 | O | LYS A | 140 | 17.394 | −5.452 | 63.510 | 1.00 | 52.08 | O |
| ATOM | 1072 | N | LYS A | 141 | 18.115 | −4.503 | 61.613 | 1.00 | 51.15 | N |
| ATOM | 1073 | CA | LYS A | 141 | 17.495 | −3.196 | 61.920 | 1.00 | 51.64 | C |
| ATOM | 1074 | CB | LYS A | 141 | 18.542 | −2.211 | 62.429 | 1.00 | 50.31 | C |
| ATOM | 1075 | CG | LYS A | 141 | 18.004 | −0.841 | 62.704 | 1.00 | 48.62 | C |
| ATOM | 1076 | CD | LYS A | 141 | 17.408 | −0.798 | 64.085 | 1.00 | 46.35 | C |
| ATOM | 1077 | CE | LYS A | 141 | 17.747 | 0.486 | 64.737 | 1.00 | 42.30 | C |
| ATOM | 1078 | NZ | LYS A | 141 | 17.928 | 0.180 | 66.146 | 1.00 | 42.43 | N |
| ATOM | 1079 | C | LYS A | 141 | 16.670 | −2.537 | 60.775 | 1.00 | 52.59 | C |
| ATOM | 1080 | O | LYS A | 141 | 17.239 | −2.120 | 59.723 | 1.00 | 53.26 | O |
| ATOM | 1081 | N | ASN A | 142 | 15.358 | −2.358 | 61.007 | 1.00 | 52.58 | N |
| ATOM | 1082 | CA | ASN A | 142 | 14.449 | −1.921 | 59.970 | 1.00 | 52.75 | C |
| ATOM | 1083 | CB | ASN A | 142 | 13.029 | −2.012 | 60.404 | 1.00 | 52.03 | C |
| ATOM | 1084 | CG | ASN A | 142 | 12.623 | −3.524 | 60.329 | 1.00 | 53.18 | C |
| ATOM | 1085 | OD1 | ASN A | 142 | 12.633 | −4.134 | 59.238 | 1.00 | 57.06 | O |
| ATOM | 1086 | ND2 | ASN A | 142 | 12.302 | −4.106 | 61.483 | 1.00 | 52.20 | N |
| ATOM | 1087 | C | ASN A | 142 | 14.674 | −0.513 | 59.576 | 1.00 | 53.52 | C |
| ATOM | 1088 | O | ASN A | 142 | 15.365 | 0.214 | 60.271 | 1.00 | 54.39 | O |
| ATOM | 1089 | N | PHE A | 143 | 14.144 | −0.316 | 58.424 | 1.00 | 54.80 | N |
| ATOM | 1090 | CA | PHE A | 143 | 14.072 | 1.207 | 58.053 | 1.00 | 56.00 | C |
| ATOM | 1091 | CB | PHE A | 143 | 15.435 | 1.893 | 57.598 | 1.00 | 56.01 | C |
| ATOM | 1092 | CG | PHE A | 143 | 15.938 | 1.393 | 56.255 | 1.00 | 57.00 | C |
| ATOM | 1093 | CD1 | PHE A | 143 | 15.876 | 2.220 | 55.121 | 1.00 | 58.89 | C |
| ATOM | 1094 | CE1 | PHE A | 143 | 16.349 | 1.769 | 53.880 | 1.00 | 57.80 | C |

TABLE 11-continued

| ATOM | 1095 | CZ  | PHE A | 143 | 16.916  | 0.469  | 53.774 | 1.00 | 57.44 | C |
| ATOM | 1096 | CE2 | PHE A | 143 | 16.990  | −0.346 | 54.897 | 1.00 | 56.24 | C |
| ATOM | 1097 | CD2 | PHE A | 143 | 16.498  | 0.116  | 56.124 | 1.00 | 55.92 | C |
| ATOM | 1098 | C   | PHE A | 143 | 12.895  | 1.595  | 57.109 | 1.00 | 56.59 | C |
| ATOM | 1099 | O   | PHE A | 143 | 12.192  | 0.692  | 56.625 | 1.00 | 55.75 | O |
| ATOM | 1100 | N   | GLN A | 144 | 12.637  | 2.879  | 56.924 | 1.00 | 58.09 | N |
| ATOM | 1101 | CA  | GLN A | 144 | 11.493  | 3.272  | 56.126 | 1.00 | 60.03 | C |
| ATOM | 1102 | CB  | GLN A | 144 | 10.361  | 3.941  | 56.959 | 1.00 | 59.59 | C |
| ATOM | 1103 | CG  | GLN A | 144 | 10.116  | 3.412  | 58.364 | 1.00 | 59.44 | C |
| ATOM | 1104 | CD  | GLN A | 144 | 8.885   | 2.536  | 58.526 | 1.00 | 58.92 | C |
| ATOM | 1105 | OE1 | GLN A | 144 | 8.924   | 1.352  | 58.224 | 1.00 | 59.15 | O |
| ATOM | 1106 | NE2 | GLN A | 144 | 7.811   | 3.100  | 59.086 | 1.00 | 61.18 | N |
| ATOM | 1107 | C   | GLN A | 144 | 11.890  | 4.199  | 54.999 | 1.00 | 60.94 | C |
| ATOM | 1108 | O   | GLN A | 144 | 12.926  | 4.879  | 55.019 | 1.00 | 60.23 | O |
| ATOM | 1109 | N   | VAL A | 145 | 10.969  | 4.245  | 54.055 | 1.00 | 62.71 | N |
| ATOM | 1110 | CA  | VAL A | 145 | 11.120  | 4.985  | 52.845 | 1.00 | 64.72 | C |
| ATOM | 1111 | CB  | VAL A | 145 | 11.507  | 3.971  | 51.841 | 1.00 | 65.38 | C |
| ATOM | 1112 | CG1 | VAL A | 145 | 10.617  | 2.738  | 51.819 | 1.00 | 67.82 | C |
| ATOM | 1113 | CG2 | VAL A | 145 | 11.740  | 4.633  | 50.494 | 1.00 | 67.93 | C |
| ATOM | 1114 | C   | VAL A | 145 | 9.731   | 5.448  | 52.449 | 1.00 | 64.72 | C |
| ATOM | 1115 | O   | VAL A | 145 | 8.741   | 4.880  | 52.939 | 1.00 | 65.42 | O |
| ATOM | 1116 | N   | ASP A | 155 | −7.628  | 1.661  | 43.091 | 1.00 | 59.40 | N |
| ATOM | 1117 | CA  | ASP A | 155 | −7.388  | 0.510  | 43.990 | 1.00 | 58.92 | C |
| ATOM | 1118 | CB  | ASP A | 155 | −8.676  | −0.317 | 44.255 | 1.00 | 59.48 | C |
| ATOM | 1119 | CG  | ASP A | 155 | −8.648  | −1.454 | 45.293 | 1.00 | 61.20 | C |
| ATOM | 1120 | OD1 | ASP A | 155 | −8.690  | −2.654 | 44.969 | 1.00 | 60.94 | O |
| ATOM | 1121 | OD2 | ASP A | 155 | −8.100  | −1.148 | 46.460 | 1.00 | 65.24 | O |
| ATOM | 1122 | C   | ASP A | 55  | −6.316  | −0.366 | 43.381 | 1.00 | 57.62 | C |
| ATOM | 1123 | O   | ASP A | 155 | −5.145  | −0.079 | 43.539 | 1.00 | 59.13 | O |
| ATOM | 1124 | N   | LEU A | 156 | −6.699  | −1.417 | 42.660 | 1.00 | 55.17 | N |
| ATOM | 1125 | CA  | LEU A | 156 | −5.751  | −2.482 | 42.311 | 1.00 | 53.32 | C |
| ATOM | 1126 | CB  | LEU A | 156 | −4.897  | −2.910 | 43.501 | 1.00 | 52.53 | C |
| ATOM | 1127 | CG  | LEU A | 156 | −4.473  | −4.369 | 43.195 | 1.00 | 51.95 | C |
| ATOM | 1128 | CD1 | LEU A | 156 | −3.368  | −4.503 | 42.148 | 1.00 | 50.19 | C |
| ATOM | 1129 | CD2 | LEU A | 156 | −4.062  | −5.068 | 44.426 | 1.00 | 53.76 | C |
| ATOM | 1130 | C   | LEU A | 156 | −6.518  | −3.706 | 41.802 | 1.00 | 51.71 | C |
| ATOM | 1131 | O   | LEU A | 156 | −6.067  | −4.476 | 40.898 | 1.00 | 50.22 | O |
| ATOM | 1132 | N   | MET A | 157 | −7.675  | −3.885 | 42.422 | 1.00 | 49.87 | N |
| ATOM | 1133 | CA  | MET A | 157 | −8.678  | −4.749 | 41.879 | 1.00 | 49.09 | C |
| ATOM | 1134 | CB  | MET A | 157 | −9.294  | −5.582 | 42.972 | 1.00 | 48.74 | C |
| ATOM | 1135 | CG  | MET A | 157 | −8.231  | −6.355 | 43.703 | 1.00 | 52.48 | C |
| ATOM | 1136 | SD  | MET A | 157 | −7.860  | −7.924 | 42.873 | 1.00 | 59.19 | S |
| ATOM | 1137 | CE  | MET A | 157 | −6.311  | −7.666 | 42.066 | 1.00 | 57.45 | C |
| ATOM | 1138 | C   | MET A | 157 | −9.692  | −3.927 | 41.104 | 1.00 | 48.22 | C |
| ATOM | 1139 | O   | MET A | 157 | −10.618 | −4.500 | 40.522 | 1.00 | 48.38 | O |
| ATOM | 1140 | N   | ALA A | 158 | −9.461  | −2.599 | 41.084 | 1.00 | 47.80 | N |
| ATOM | 1141 | CA  | ALA A | 158 | −10.226 | −1.651 | 40.225 | 1.00 | 48.09 | C |
| ATOM | 1142 | CB  | ALA A | 158 | −9.903  | −0.235 | 40.594 | 1.00 | 47.28 | C |
| ATOM | 1143 | C   | ALA A | 158 | −9.918  | −1.865 | 38.748 | 1.00 | 48.84 | C |
| ATOM | 1144 | O   | ALA A | 158 | −8.757  | −2.194 | 38.367 | 1.00 | 49.05 | O |
| ATOM | 1145 | N   | PRO A | 159 | −10.944 | −1.732 | 37.904 | 1.00 | 48.44 | N |
| ATOM | 1146 | CA  | PRO A | 159 | −10.733 | −1.703 | 36.471 | 1.00 | 48.41 | C |
| ATOM | 1147 | CB  | PRO A | 159 | −12.119 | −1.378 | 35.926 | 1.00 | 47.82 | C |
| ATOM | 1148 | CG  | PRO A | 159 | −12.983 | −2.009 | 36.849 | 1.00 | 48.52 | C |
| ATOM | 1149 | CD  | PRO A | 159 | −12.369 | −1.736 | 38.207 | 1.00 | 48.63 | C |
| ATOM | 1150 | C   | PRO A | 159 | −9.733  | −0.656 | 36.029 | 1.00 | 48.59 | C |
| ATOM | 1151 | O   | PRO A | 159 | −9.615  | 0.430  | 36.634 | 1.00 | 47.74 | O |
| ATOM | 1152 | N   | VAL A | 160 | −9.023  | −1.030 | 34.971 | 1.00 | 49.01 | N |
| ATOM | 1153 | CA  | VAL A | 160 | −8.142  | −0.145 | 34.256 | 1.00 | 49.37 | C |
| ATOM | 1154 | CB  | VAL A | 160 | −6.779  | −0.731 | 34.037 | 1.00 | 49.87 | C |
| ATOM | 1155 | CG1 | VAL A | 160 | −5.788  | 0.411  | 33.739 | 1.00 | 51.02 | C |
| ATOM | 1156 | CG2 | VAL A | 160 | 6.340   | −1.592 | 35.260 | 1.00 | 48.82 | C |
| ATOM | 1157 | C   | VAL A | 160 | −8.724  | 0.045  | 32.899 | 1.00 | 49.57 | C |
| ATOM | 1158 | O   | VAL A | 160 | −9.312  | −0.868 | 32.318 | 1.00 | 50.30 | O |
| ATOM | 1159 | N   | SER A | 161 | −8.566  | 1.259  | 32.201 | 1.00 | 49.18 | N |
| ATOM | 1160 | CA  | SER A | 161 | −9.042  | 1.632  | 31.096 | 1.00 | 48.04 | C |
| ATOM | 1161 | CB  | SER A | 161 | −10.415 | 2.189  | 31.218 | 1.00 | 47.96 | C |
| ATOM | 1162 | OG  | SER A | 161 | −10.208 | 3.532  | 31.535 | 1.00 | 49.21 | O |
| ATOM | 1163 | C   | SER A | 161 | −8.120  | 2.768  | 30.665 | 1.00 | 47.41 | C |
| ATOM | 1164 | O   | SER A | 161 | −7.627  | 3.517  | 31.523 | 1.00 | 46.55 | O |
| ATOM | 1165 | N   | ALA A | 162 | −7.872  | 2.877  | 29.349 | 1.00 | 46.08 | N |
| ATOM | 1166 | CA  | ALA A | 162 | −6.943  | 3.869  | 28.807 | 1.00 | 44.11 | C |
| ATOM | 1167 | CB  | ALA A | 162 | −5.531  | 3.380  | 28.918 | 1.00 | 42.91 | C |
| ATOM | 1168 | C   | ALA A | 162 | −7.309  | 4.164  | 27.363 | 1.00 | 44.12 | C |
| ATOM | 1169 | O   | ALA A | 162 | −7.917  | 3.327  | 26.673 | 1.00 | 43.80 | O |
| ATOM | 1170 | N   | LYS A | 163 | −6.497  | 5.356  | 26.890 | 1.00 | 43.83 | N |
| ATOM | 1171 | CA  | LYS A | 163 | −7.161  | 5.673  | 25.496 | 1.00 | 43.62 | C |
| ATOM | 1172 | CB  | LYS A | 163 | −8.557  | 6.265  | 25.305 | 1.00 | 44.12 | C |
| ATOM | 1173 | CG  | LYS A | 163 | −8.625  | 7.735  | 25.019 | 1.00 | 51.27 | C |
| ATOM | 1174 | CD  | LYS A | 163 | −8.944  | 8.617  | 26.230 | 1.00 | 59.18 | C |

TABLE 11-continued

| | | | | | | | | | |
|---|---|---|---|---|---|---|---|---|---|
| ATOM | 1175 | CE | LYS A | 163 | −8.880 | 10.121 | 25.844 | 1.00 | 64.28 | C |
| ATOM | 1176 | NZ | LYS A | 163 | −9.379 | 10.375 | 24.420 | 1.00 | 66.41 | N |
| ATOM | 1177 | C | LYS A | 163 | −6.021 | 6.439 | 24.841 | 1.00 | 42.11 | C |
| ATOM | 1178 | O | LYS A | 163 | −5.299 | 7.135 | 25.488 | 1.00 | 41.71 | O |
| ATOM | 1179 | N | LYS A | 164 | −5.816 | 6.271 | 23.546 | 1.00 | 42.54 | N |
| ATOM | 1180 | CA | LYS A | 164 | −4.972 | 7.055 | 22.811 | 1.00 | 42.36 | C |
| ATOM | 1181 | CB | LYS A | 164 | −3.432 | 6.403 | 22.806 | 1.00 | 41.43 | C |
| ATOM | 1182 | CG | LYS A | 164 | −2.281 | 7.357 | 22.589 | 1.00 | 44.25 | C |
| ATOM | 1183 | CD | LYS A | 164 | −1.455 | 4.503 | 23.896 | 1.00 | 51.77 | C |
| ATOM | 1184 | CE | LYS A | 164 | 0.104 | 7.570 | 23.687 | 1.00 | 53.80 | C |
| ATOM | 1185 | NZ | LYS A | 164 | 0.723 | 6.200 | 23.487 | 1.00 | 54.32 | N |
| ATOM | 1186 | C | LYS A | 164 | −5.211 | 7.289 | 21.375 | 1.00 | 42.89 | C |
| ATOM | 1187 | O | LYS A | 164 | −5.750 | 6.379 | 20.716 | 1.00 | 42.52 | O |
| ATOM | 1188 | N | GLU A | 165 | −4.977 | 8.531 | 20.923 | 1.00 | 43.44 | N |
| ATOM | 1189 | CA | GLU A | 165 | −5.198 | 8.963 | 19.554 | 1.00 | 43.48 | C |
| ATOM | 1190 | CB | GLU A | 165 | −6.255 | 10.014 | 19.481 | 1.00 | 44.07 | C |
| ATOM | 1191 | CG | GLU A | 165 | −7.071 | 9.817 | 18.424 | 1.00 | 49.74 | C |
| ATOM | 1192 | CD | GLU A | 165 | −8.161 | 10.814 | 18.126 | 1.00 | 56.98 | C |
| ATOM | 1193 | OE1 | GLU A | 165 | −8.067 | 11.789 | 18.908 | 1.00 | 62.45 | O |
| ATOM | 1194 | OE2 | GLU A | 165 | −9.075 | 10.638 | 17.269 | 1.00 | 57.43 | O |
| ATOM | 1195 | C | GLU A | 165 | −3.959 | 9.529 | 18.946 | 1.00 | 42.69 | C |
| ATOM | 1196 | O | GLU A | 165 | −3.168 | 10.153 | 19.625 | 1.00 | 42.94 | O |
| ATOM | 1197 | N | LYS A | 166 | −3.780 | 9.297 | 17.655 | 1.00 | 43.23 | N |
| ATOM | 1198 | CA | LYS A | 166 | −2.612 | 9.803 | 16.927 | 1.00 | 43.74 | C |
| ATOM | 1199 | CB | LYS A | 166 | −1.515 | 8.733 | 16.754 | 1.00 | 44.24 | C |
| ATOM | 1200 | CG | LYS A | 166 | −0.330 | 9.187 | 15.917 | 1.00 | 47.92 | C |
| ATOM | 1201 | CD | LYS A | 166 | 0.973 | 9.414 | 16.701 | 1.00 | 54.62 | C |
| ATOM | 1202 | CE | LYS A | 166 | 1.842 | 8.089 | 16.816 | 1.00 | 59.14 | C |
| ATOM | 1203 | NZ | LYS A | 166 | 2.193 | 7.424 | 15.481 | 1.00 | 59.27 | N |
| ATOM | 1204 | C | LYS A | 166 | −3.089 | 10.260 | 15.585 | 1.00 | 42.58 | C |
| ATOM | 1205 | O | LYS A | 166 | −3.800 | 9.540 | 14.904 | 1.00 | 48.08 | O |
| ATOM | 1206 | N | LYS A | 167 | −2.178 | 11.480 | 15.246 | 1.00 | 41.54 | N |
| ATOM | 1207 | CA | LYS A | 167 | −2.961 | 12.057 | 13.960 | 1.00 | 40.53 | C |
| ATOM | 1208 | CB | LYS A | 167 | −2.508 | 13.507 | 14.006 | 1.00 | 40.08 | C |
| ATOM | 1209 | CG | LYS A | 167 | −2.493 | 14.174 | 12.670 | 1.00 | 44.48 | C |
| ATOM | 1210 | CD | LYS A | 167 | −1.823 | 15.570 | 12.746 | 1.00 | 49.40 | C |
| ATOM | 1211 | CE | LYS A | 167 | −2.354 | 16.544 | 11.648 | 1.00 | 49.58 | C |
| ATOM | 1212 | NZ | LYS A | 167 | −1.332 | 17.624 | 11.469 | 1.00 | 51.18 | N |
| ATOM | 1213 | C | LYS A | 167 | −2.155 | 11.273 | 12.939 | 1.00 | 39.29 | C |
| ATOM | 1214 | O | LYS A | 167 | −0.987 | 11.003 | 13.130 | 1.00 | 39.46 | O |
| ATOM | 1215 | N | VAL A | 168 | −2.783 | 10.882 | 11.853 | 1.00 | 38.36 | N |
| ATOM | 1216 | CA | VAL A | 168 | −2.086 | 10.139 | 10.830 | 1.00 | 37.55 | C |
| ATOM | 1217 | CB | VAL A | 168 | −2.282 | 8.619 | 10.992 | 1.00 | 37.74 | C |
| ATOM | 1218 | CG1 | VAL A | 168 | −1.928 | 7.868 | 9.689 | 1.00 | 35.78 | C |
| ATOM | 1219 | CG2 | VAL A | 168 | −1.537 | 8.104 | 12.207 | 1.00 | 31.50 | C |
| ATOM | 1220 | C | VAL A | 168 | −2.660 | 10.646 | 9.522 | 1.00 | 38.61 | C |
| ATOM | 1221 | O | VAL A | 168 | −3.698 | 10.194 | 9.050 | 1.00 | 38.39 | O |
| ATOM | 1222 | N | SER A | 169 | −1.957 | 11.633 | 8.967 | 1.00 | 39.91 | N |
| ATOM | 1223 | CA | SER A | 169 | −2.497 | 12.462 | 7.910 | 1.00 | 40.32 | C |
| ATOM | 1224 | CB | SER A | 169 | −2.041 | 13.874 | 8.124 | 1.00 | 40.53 | C |
| ATOM | 1225 | CG | SER A | 169 | −0.771 | 13.991 | 7.534 | 1.00 | 39.86 | O |
| ATOM | 1226 | C | SER A | 169 | −2.047 | 12.031 | 6.529 | 1.00 | 40.77 | C |
| ATOM | 1227 | O | SER A | 169 | −1.117 | 11.205 | 6.351 | 1.00 | 41.24 | O |
| ATOM | 1228 | N | SER A | 170 | −2.701 | 12.655 | 5.559 | 1.00 | 40.68 | N |
| ATOM | 1229 | CA | SER A | 170 | −2.693 | 12.234 | 4.182 | 1.00 | 40.96 | C |
| ATOM | 1230 | CB | SER A | 170 | −3.845 | 11.276 | 3.973 | 1.00 | 40.70 | C |
| ATOM | 1231 | CG | SER A | 170 | −3.340 | 10.166 | 3.298 | 1.00 | 43.77 | C |
| ATOM | 1232 | C | SER A | 170 | −2.965 | 13.492 | 3.379 | 1.00 | 40.87 | C |
| ATOM | 1233 | O | SER A | 170 | −3.586 | 14.437 | 3.893 | 1.00 | 40.97 | O |
| ATOM | 1234 | N | MET A | 171 | −2.558 | 13.528 | 2.124 | 1.00 | 40.48 | N |
| ATOM | 1235 | CA | MET A | 171 | −2.890 | 14.707 | 1.325 | 1.00 | 41.02 | C |
| ATOM | 1236 | CB | MET A | 171 | −2.146 | 14.678 | −0.033 | 1.00 | 41.18 | C |
| ATOM | 1237 | CG | MET A | 171 | −2.524 | 15.754 | −1.046 | 1.00 | 42.06 | C |
| ATOM | 1238 | SD | MET A | 171 | −1.283 | 16.061 | −2.352 | 1.00 | 41.25 | S |
| ATOM | 1239 | CE | MET A | 171 | −2.492 | 16.308 | −3.669 | 1.00 | 42.13 | C |
| ATOM | 1240 | C | MET A | 171 | −4.427 | 14.834 | 1.228 | 1.00 | 1.25 | C |
| ATOM | 1241 | O | MET A | 171 | −4.988 | 15.882 | 1.500 | 1.00 | 40.81 | O |
| ATOM | 1242 | N | PHE A | 172 | −5.109 | 13.742 | 0.909 | 1.00 | 42.23 | N |
| ATOM | 1243 | CA | PHE A | 172 | −6.566 | 13.768 | 0.880 | 1.00 | 43.73 | C |
| ATOM | 1244 | CB | PHE A | 172 | −7.091 | 12.851 | −0.227 | 1.00 | 44.66 | C |
| ATOM | 1245 | CG | PHE A | 172 | −6.518 | 13.195 | −1.604 | 1.00 | 47.63 | C |
| ATOM | 1246 | CD1 | PHE A | 172 | −6.988 | 14.204 | −2.323 | 1.00 | 49.30 | C |
| ATOM | 1247 | CE1 | PHE A | 172 | −6.438 | 14.616 | −3.585 | 1.00 | 52.65 | C |
| ATOM | 1248 | CZ | PHE A | 172 | −5.422 | 13.841 | −4.146 | 1.00 | 52.30 | C |
| ATOM | 1249 | CE2 | PHE A | 172 | −4.942 | 12.757 | −3.437 | 1.00 | 52.18 | C |
| ATOM | 1250 | CD2 | PHE A | 172 | −5.487 | 12.436 | −2.165 | 1.00 | 49.95 | C |
| ATOM | 1251 | C | PHE A | 172 | −7.280 | 13.567 | 2.221 | 1.00 | 43.96 | C |
| ATOM | 1252 | O | PHE A | 172 | −8.459 | 13.818 | 2.305 | 1.00 | 43.90 | O |
| ATOM | 1253 | N | ILE A | 173 | −6.559 | 13.163 | 3.276 | 1.00 | 44.92 | N |
| ATOM | 1254 | CA | ILE A | 173 | −7.122 | 13.062 | 4.631 | 1.00 | 44.08 | C |

TABLE 11-continued

| ATOM | 1255 | CB | ILE A | 173 | −7.400 | 11.585 | 5.056 | 1.00 | 43.48 | C |
| --- | --- | --- | --- | --- | --- | --- | --- | --- | --- | --- |
| ATOM | 1256 | CG1 | ILE A | 173 | −8.151 | 10.824 | 3.963 | 1.00 | 43.24 | C |
| ATOM | 1257 | CD1 | ILE A | 173 | −8.048 | 9.311 | 4.061 | 1.00 | 41.24 | C |
| ATOM | 1258 | CG2 | ILE A | 173 | −8.244 | 11.557 | 6.245 | 1.00 | 40.72 | C |
| ATOM | 1259 | C | ILE A | 173 | −6.216 | 13.762 | 5.640 | 1.00 | 44.66 | C |
| ATOM | 1260 | O | ILE A | 173 | −5.713 | 13.142 | 6.568 | 1.00 | 44.35 | O |
| ATOM | 1261 | N | PRO A | 174 | −6.050 | 15.091 | 5.508 | 1.00 | 45.55 | N |
| ATOM | 1262 | CA | PRO A | 174 | −5.083 | 15.797 | 6.369 | 1.00 | 45.91 | C |
| ATOM | 1263 | CB | PRO A | 174 | −5.177 | 17.240 | 5.875 | 1.00 | 45.21 | C |
| ATOM | 1264 | CG | PRO A | 174 | −6.490 | 17.349 | 5.294 | 1.00 | 44.79 | C |
| ATOM | 1265 | CD | PRO A | 174 | −6.777 | 16.035 | 4.841 | 1.00 | 45.80 | C |
| ATOM | 1266 | C | PRO A | 174 | −5.440 | 15.712 | 7.863 | 1.00 | 46.58 | C |
| ATOM | 1267 | O | PRO A | 174 | −4.611 | 15.982 | 8.721 | 1.00 | 47.07 | O |
| ATOM | 1268 | N | ASP A | 175 | −6.666 | 15.311 | 8.173 | 1.00 | 47.83 | N |
| ATOM | 1269 | CA | ASP A | 175 | −7.087 | 15.143 | 9.579 | 1.00 | 47.42 | C |
| ATOM | 1270 | CB | ASP A | 175 | −8.390 | 15.889 | 9.808 | 1.00 | 48.71 | C |
| ATOM | 1271 | CG | ASP A | 175 | −8.432 | 16.741 | 11.055 | 1.00 | 55.18 | C |
| ATOM | 1272 | OD1 | ASP A | 175 | −8.446 | 16.173 | 12.193 | 1.00 | 61.22 | O |
| ATOM | 1273 | OD2 | ASP A | 175 | −8.206 | 17.987 | 10.691 | 1.00 | 60.98 | O |
| ATOM | 1274 | C | ASP A | 175 | −7.293 | 13.699 | 10.010 | 1.00 | 45.29 | C |
| ATOM | 1275 | O | ASP A | 175 | −8.089 | 13.462 | 10.901 | 1.00 | 43.54 | O |
| ATOM | 1276 | N | GLY A | 176 | −6.609 | 12.755 | 9.343 | 1.00 | 44.44 | N |
| ATOM | 1277 | CA | GLY A | 176 | −6.723 | 11.305 | 9.606 | 1.00 | 42.74 | C |
| ATOM | 1278 | C | GLY A | 176 | −6.222 | 10.947 | 10.993 | 1.00 | 42.63 | C |
| ATOM | 1279 | O | GLY A | 176 | −5.226 | 11.510 | 11.50 | 1.00 | 43.18 | O |
| ATOM | 1280 | N | ARG A | 177 | −6.953 | 10.059 | 11.653 | 1.00 | 41.73 | N |
| ATOM | 1281 | CA | ARG A | 177 | −6.657 | 9.752 | 13.034 | 1.00 | 41.60 | C |
| ATOM | 1282 | CB | ARG A | 177 | −7.684 | 10.400 | 13.086 | 1.00 | 42.38 | C |
| ATOM | 1283 | CG | ARG A | 177 | −7.733 | 11.910 | 13.782 | 1.00 | 49.29 | C |
| ATOM | 1284 | CD | ARG A | 177 | −7.730 | 12.768 | 15.096 | 1.00 | 60.55 | C |
| ATOM | 1285 | NE | ARG A | 177 | −7.703 | 14.231 | 14.872 | 1.00 | 64.85 | N |
| ATOM | 1286 | CZ | ARG A | 177 | −8.244 | 15.118 | 15.719 | 1.00 | 70.82 | C |
| ATOM | 1287 | NH1 | ARG A | 177 | −8.856 | 14.685 | 16.821 | 1.00 | 72.14 | N |
| ATOM | 1288 | NH2 | ARG A | 177 | −8.192 | 16.440 | 15.482 | 1.00 | 72.12 | N |
| ATOM | 1289 | C | ARG A | 177 | −6.595 | 8.275 | 13.191 | 1.00 | 39.31 | C |
| ATOM | 1290 | O | ARG A | 177 | −7.162 | 7.555 | 12.426 | 1.00 | 38.67 | O |
| ATOM | 1291 | N | VAL A | 178 | −5.872 | 7.817 | 14.182 | 1.00 | 38.30 | N |
| ATOM | 1292 | CA | VAL A | 178 | −6.006 | 6.432 | 14.604 | 1.00 | 37.56 | C |
| ATOM | 1293 | CB | VAL A | 178 | −4.810 | 5.810 | 14.207 | 1.00 | 36.70 | C |
| ATOM | 1294 | CG1 | VAL A | 178 | −4.862 | 4.320 | 14.926 | 1.00 | 37.12 | C |
| ATOM | 1295 | CG2 | VAL A | 178 | −4.857 | 5.376 | 12.731 | 1.00 | 37.21 | C |
| ATOM | 1296 | C | VAL A | 178 | −6.152 | 6.343 | 16.108 | 1.00 | 37.56 | C |
| ATOM | 1297 | O | VAL A | 178 | −5.397 | 6.951 | 16.834 | 1.00 | 37.27 | O |
| ATOM | 1298 | N | SER A | 179 | −7.124 | 5.606 | 16.593 | 1.00 | 37.92 | N |
| ATOM | 1299 | CA | SER A | 179 | −7.164 | 5.470 | 17.999 | 1.00 | 39.08 | C |
| ATOM | 1300 | CB | SER A | 179 | −8.114 | 6.482 | 18.603 | 1.00 | 39.33 | C |
| ATOM | 1301 | OG | SER A | 179 | −9.389 | 6.226 | 18.078 | 1.00 | 44.69 | O |
| ATOM | 1302 | C | SER A | 179 | −7.490 | 4.100 | 18.510 | 1.00 | 39.15 | C |
| ATOM | 1303 | O | SER A | 179 | −7.992 | 3.206 | 17.481 | 1.00 | 37.94 | O |
| ATOM | 1304 | N | VAL A | 180 | −7.158 | 3.979 | 19.784 | 1.00 | 39.56 | N |
| ATOM | 1305 | CA | VAL A | 180 | −7.314 | 2.722 | 20.514 | 1.00 | 39.27 | C |
| ATOM | 1306 | CB | VAL A | 180 | −5.993 | 1.991 | 20.541 | 1.00 | 39.48 | C |
| ATOM | 1307 | CG1 | VAL A | 180 | −4.820 | 2.928 | 20.918 | 1.00 | 39.75 | C |
| ATOM | 1308 | CG2 | VAL A | 180 | −6.105 | 0.802 | 21.493 | 1.00 | 39.09 | C |
| ATOM | 1309 | C | VAL A | 180 | −7.711 | 3.211 | 21.906 | 1.00 | 38.39 | C |
| ATOM | 1310 | O | VAL A | 180 | −7.089 | 4.075 | 22.497 | 1.00 | 37.53 | O |
| ATOM | 1311 | N | SER A | 181 | −8.768 | 2.581 | 22.390 | 1.00 | 38.41 | N |
| ATOM | 1312 | CA | SER A | 181 | −9.312 | 2.775 | 23.713 | 1.00 | 37.85 | C |
| ATOM | 1313 | CB | SER A | 181 | −10.617 | 3.466 | 23.547 | 1.00 | 36.56 | C |
| ATOM | 1314 | OG | SER A | 181 | −11.236 | 3.491 | 24.770 | 1.00 | 40.11 | O |
| ATOM | 1315 | C | SER A | 181 | −9.505 | 1.359 | 24.280 | 1.00 | 37.67 | C |
| ATOM | 1316 | O | SER A | 181 | −10.062 | 0.511 | 23.618 | 1.00 | 37.86 | O |
| ATOM | 1317 | N | ALA A | 182 | −9.034 | 1.107 | 25.490 | 1.00 | 37.88 | N |
| ATOM | 1318 | CA | ALA A | 182 | −8.887 | −0.267 | 26.012 | 1.00 | 37.90 | C |
| ATOM | 1319 | CB | ALA A | 182 | −7.438 | −0.665 | 26.016 | 1.00 | 36.81 | C |
| ATOM | 1320 | C | ALA A | 182 | −9.395 | −0.351 | 27.412 | 1.00 | 37.81 | C |
| ATOM | 1321 | O | ALA A | 182 | −9.210 | 0.618 | 28.146 | 1.00 | 37.63 | O |
| ATOM | 1322 | N | ARG A | 183 | −9.995 | −1.493 | 27.800 | 1.00 | 38.15 | N |
| ATOM | 1323 | CA | ARG A | 183 | −10.296 | −1.780 | 29.238 | 1.00 | 38.46 | C |
| ATOM | 1324 | CB | ARG A | 183 | −11.676 | −1.406 | 29.655 | 1.00 | 37.11 | C |
| ATOM | 1325 | CG | ARG A | 183 | −12.322 | −0.479 | 28.820 | 1.00 | 40.22 | C |
| ATOM | 1326 | CD | ARG A | 183 | −13.825 | −0.564 | 29.049 | 1.00 | 44.76 | C |
| ATOM | 1327 | NE | ARG A | 183 | −14.174 | 0.192 | 30.241 | 1.00 | 51.70 | N |
| ATOM | 1328 | CZ | ARG A | 183 | −14.591 | 1.450 | 30.214 | 1.00 | 52.35 | C |
| ATOM | 1329 | NH1 | ARG A | 183 | −14.730 | 2.077 | 23.036 | 1.00 | 50.67 | N |
| ATOM | 1330 | NH2 | ARG A | 183 | −14.890 | 2.082 | 31.351 | 1.00 | 48.42 | N |
| ATOM | 1331 | C | ARG A | 183 | −10.167 | −3.219 | 29.649 | 1.00 | 38.97 | C |
| ATOM | 1332 | O | ARG A | 183 | −10.445 | −4.168 | 28.867 | 1.00 | 39.94 | O |
| ATOM | 1333 | N | ILE A | 184 | −9.734 | −3.368 | 30.903 | 1.00 | 39.15 | N |
| ATOM | 1334 | CA | ILE A | 184 | −9.552 | −4.669 | 31.578 | 1.00 | 37.76 | C |

TABLE 11-continued

| | | | | | | | | | |
|---|---|---|---|---|---|---|---|---|---|
| ATOM | 1335 | CB | ILE A | 184 | −8.122 | −5.117 | 31.572 | 1.00 | 36.59 | C |
| ATOM | 1336 | CG1 | ILE A | 184 | −7.285 | −4.085 | 32.307 | 1.00 | 35.88 | C |
| ATOM | 1337 | CD1 | ILE A | 184 | −5.843 | −4.523 | 32.644 | 1.00 | 38.14 | C |
| ATOM | 1338 | CG2 | ILE A | 184 | −7.668 | −5.292 | 30.154 | 1.00 | 33.83 | C |
| ATOM | 1339 | C | ILE A | 184 | −9.997 | −4.568 | 33.009 | 1.00 | 37.91 | C |
| ATOM | 1340 | O | ILE A | 184 | −10.208 | −3.496 | 33.542 | 1.00 | 37.72 | O |
| ATOM | 1341 | N | ASP A | 185 | −10.113 | −5.713 | 33.637 | 1.00 | 39.44 | N |
| ATOM | 1342 | CA | ASP A | 185 | −10.922 | −5.841 | 34.867 | 1.00 | 40.40 | C |
| ATOM | 1343 | CB | ASP A | 185 | −11.314 | −7.298 | 35.088 | 1.00 | 40.25 | C |
| ATOM | 1344 | CG | ASP A | 185 | −12.203 | −7.826 | 34.009 | 1.00 | 41.96 | C |
| ATOM | 1345 | OD1 | ASP A | 185 | −12.521 | −9.029 | 34.00 | 1.00 | 45.32 | O |
| ATOM | 1346 | OD2 | ASP A | 185 | −12.639 | −7.043 | 33.168 | 1.00 | 47.91 | O |
| ATOM | 1347 | C | ASP A | 185 | −10.246 | −5.363 | 36.122 | 1.00 | 40.30 | C |
| ATOM | 1348 | O | ASP A | 185 | −10.912 | −5.137 | 37.111 | 1.00 | 41.04 | O |
| ATOM | 1349 | N | ARG A | 186 | −8.935 | −5.251 | 36.087 | 1.00 | 40.34 | N |
| ATOM | 1350 | CA | ARG A | 186 | −8.184 | −4.996 | 37.279 | 1.00 | 41.66 | C |
| ATOM | 1351 | CB | ARG A | 186 | −8.477 | −3.047 | 38.329 | 1.00 | 42.15 | C |
| ATOM | 1352 | CG | ARG A | 186 | −8.062 | −7.508 | 37.937 | 1.00 | 42.07 | C |
| ATOM | 1353 | CD | ARG A | 186 | −8.565 | −8.421 | 38.967 | 1.00 | 39.99 | C |
| ATOM | 1354 | NE | ARG A | 186 | −8.242 | −9.777 | 38.747 | 1.00 | 44.64 | N |
| ATOM | 1355 | CZ | ARG A | 186 | −8.855 | −10.613 | 37.910 | 1.00 | 47.09 | C |
| ATOM | 1356 | NH1 | ARG A | 186 | −9.919 | −10.183 | 37.225 | 1.00 | 45.49 | N |
| ATOM | 1357 | NH2 | ARG A | 186 | −8.411 | −11.876 | 37.769 | 1.00 | 46.09 | N |
| ATOM | 1358 | C | ARG A | 186 | −6.745 | −5.110 | 36.920 | 1.00 | 42.30 | C |
| ATOM | 1359 | O | ARG A | 186 | −6.400 | −5.611 | 35.867 | 1.00 | 42.33 | O |
| ATOM | 1360 | N | LYS A | 187 | −5.908 | −4.663 | 37.826 | 1.00 | 43.37 | N |
| ATOM | 1361 | CA | LYS A | 187 | −4.514 | −4.527 | 37.557 | 1.00 | 44.34 | C |
| ATOM | 1362 | CB | LYS A | 187 | −4.037 | −3.328 | 38.348 | 1.00 | 44.99 | C |
| ATOM | 1363 | CG | LYS A | 187 | −2.700 | −2.816 | 37.939 | 1.00 | 49.48 | C |
| ATOM | 1364 | CD | LYS A | 187 | −2.299 | −1.477 | 38.639 | 1.00 | 54.26 | C |
| ATOM | 1365 | CE | LYS A | 187 | −0.750 | −1.323 | 38.488 | 1.00 | 58.80 | C |
| ATOM | 1366 | NZ | LYS A | 187 | −0.063 | −0.270 | 39.330 | 1.00 | 61.87 | N |
| ATOM | 1367 | C | LYS A | 187 | −3.763 | −5.782 | 37.997 | 1.00 | 44.51 | C |
| ATOM | 1368 | O | LYS A | 187 | −2.590 | −5.935 | 37.654 | 1.00 | 45.10 | O |
| ATOM | 1369 | N | GLY A | 188 | −4.427 | −6.677 | 38.753 | 1.00 | 44.25 | N |
| ATOM | 1370 | CA | GLY A | 188 | −3.727 | −7.746 | 39.474 | 1.00 | 43.89 | C |
| ATOM | 1371 | C | GLY A | 188 | −4.129 | −9.127 | 39.028 | 1.00 | 44.64 | C |
| ATOM | 1372 | O | GLY A | 188 | −5.238 | −9.464 | 39.184 | 1.00 | 45.82 | O |
| ATOM | 1373 | N | PHE A | 189 | −3.206 | −9.936 | 38.476 | 1.00 | 44.66 | N |
| ATOM | 1374 | CA | PHE A | 189 | −3.577 | −11.261 | 37.948 | 1.00 | 45.07 | C |
| ATOM | 1375 | CB | PHE A | 189 | −3.625 | −11.272 | 36.391 | 1.00 | 45.07 | C |
| ATOM | 1376 | CG | PHE A | 189 | −4.642 | −10.314 | 35.773 | 1.00 | 41.56 | C |
| ATOM | 1377 | CD1 | PHE A | 189 | −5.947 | −10.471 | 35.502 | 1.00 | 40.88 | C |
| ATOM | 1378 | CE1 | PHE A | 189 | −6.893 | −9.866 | 34.929 | 1.00 | 41.86 | C |
| ATOM | 1379 | CZ | PHE A | 189 | −6.507 | −8.535 | 34.595 | 1.00 | 41.81 | C |
| ATOM | 1380 | CE2 | PHE A | 189 | −5.195 | −8.109 | 34.858 | 1.00 | 39.07 | C |
| ATOM | 1381 | CD2 | PHE A | 189 | −4.280 | −9.000 | 35.453 | 1.00 | 38.73 | C |
| ATOM | 1382 | C | PHE A | 189 | −2.707 | −12.435 | 38.412 | 1.00 | 46.16 | C |
| ATOM | 1383 | O | PHE A | 189 | −1.514 | −12.296 | 38.640 | 1.00 | 45.12 | O |
| ATOM | 1384 | N | CYS A | 190 | −3.322 | −13.609 | 38.517 | 1.00 | 47.93 | N |
| ATOM | 1385 | CA | CYS A | 190 | −2.617 | −14.798 | 38.921 | 1.00 | 50.00 | C |
| ATOM | 1386 | CB | CYS A | 190 | −3.596 | −15.759 | 39.589 | 1.00 | 51.18 | C |
| ATOM | 1387 | SG | CYS A | 190 | −4.177 | −15.488 | 41.235 | 1.00 | 59.02 | S |
| ATOM | 1388 | C | CYS A | 190 | −2.117 | −15.465 | 37.657 | 1.00 | 49.69 | C |
| ATOM | 1389 | O | CYS A | 190 | −2.984 | −15.587 | 36.723 | 1.00 | 49.66 | O |
| AOTM | 1390 | N | GLU A | 191 | −0.924 | −15.932 | 37.623 | 1.00 | 49.34 | N |
| ATOM | 1391 | CA | GLU A | 191 | −0.492 | −16.920 | 36.624 | 1.00 | 49.96 | C |
| ATOM | 1392 | CB | GLU A | 191 | 0.676 | −17.713 | 37.177 | 1.00 | 50.51 | C |
| ATOM | 1393 | CG | GLU A | 191 | 1.975 | −17.041 | 36.847 | 1.00 | 54.61 | C |
| ATOM | 1394 | CD | GLU A | 191 | 3.133 | −17.531 | 37.658 | 1.00 | 57.68 | C |
| ATOM | 1395 | OE1 | GLU A | 191 | 4.211 | −16.872 | 37.518 | 1.00 | 55.39 | O |
| ATOM | 1396 | OE2 | GLU A | 191 | 2.946 | −18.543 | 38.412 | 1.00 | 59.83 | O |
| ATOM | 1397 | C | GLU A | 191 | −1.568 | −17.932 | 36.229 | 1.00 | 49.90 | C |
| ATOM | 1398 | O | GLU A | 191 | −2.261 | −18.489 | 37.115 | 1.00 | 51.13 | O |
| ATOM | 1399 | N | GLY A | 192 | −1.700 | −18.213 | 34.933 | 1.00 | 48.74 | N |
| ATOM | 1400 | CA | GLY A | 192 | −2.791 | −19.074 | 34.454 | 1.00 | 47.83 | C |
| ATOM | 1401 | C | GLY A | 192 | −4.078 | −18.333 | 34.061 | 1.00 | 48.35 | C |
| ATOM | 1402 | O | GLY A | 192 | −4.912 | −18.873 | 33.298 | 1.00 | 47.74 | O |
| AOTM | 1403 | N | ASP A | 193 | −4.259 | −17.095 | 34.537 | 1.00 | 47.16 | N |
| ATOM | 1404 | CA | ASP A | 193 | −5.467 | −16.413 | 34.204 | 1.00 | 46.93 | C |
| ATOM | 1405 | CB | ASP A | 193 | −5.573 | −15.175 | 35.020 | 1.00 | 48.27 | C |
| ATOM | 1406 | CG | ASP A | 193 | −5.997 | −15.461 | 36.406 | 1.00 | 48.03 | C |
| ATOM | 1407 | OD1 | ASP A | 193 | −6.145 | −16.654 | 36.691 | 1.00 | 51.21 | O |
| ATOM | 1408 | OD2 | ASP A | 193 | −6.173 | −14.518 | 37.191 | 1.00 | 45.94 | O |
| ATOM | 1409 | C | ASP A | 193 | −5.553 | −16.000 | 32.79 | 1.00 | 47.25 | C |
| ATOM | 1410 | O | ASP A | 193 | −4.576 | −16.007 | 32.034 | 1.00 | 48.79 | O |
| ATOM | 1411 | N | GLU A | 194 | −6.479 | −15.643 | 32.389 | 1.00 | 46.78 | N |
| ATOM | 1412 | CA | GLU A | 194 | −6.958 | −14.995 | 31.146 | 1.00 | 47.04 | C |
| ATOM | 1413 | CB | GLU A | 194 | −8.280 | −15.462 | 30.557 | 1.00 | 47.57 | C |
| ATOM | 1414 | CG | GLU A | 194 | −8.165 | −16.040 | 29.155 | 1.00 | 52.56 | C |

TABLE 11-continued

| ATOM | 1415 | CD | GLU A | 194 | −8.223 | −17.576 | 29.149 | 1.00 | 60.99 | C |
|---|---|---|---|---|---|---|---|---|---|---|
| ATOM | 1416 | OE1 | GLU A | 194 | −9.315 | −18.123 | 28.837 | 1.00 | 52.81 | O |
| ATOM' | 1417 | OE2 | GLU A | 194 | −7.188 | −18.244 | 29.475 | 1.00 | 64.55 | O |
| ATOM | 1418 | C | GLU A | 194 | −7.068 | −13.506 | 31.496 | 1.00 | 46.31 | C |
| ATOM | 1419 | O | GLU A | 194 | −7.787 | −13.138 | 32.398 | 1.00 | 46.27 | O |
| ATOM | 1420 | N | ILE A | 195 | −6.349 | −12.628 | 30.814 | 1.00 | 45.52 | N |
| ATOM | 1421 | CA | ILE A | 195 | −6.742 | −11.238 | 30.847 | 1.00 | 44.67 | C |
| ATOM | 1422 | CB | ILE A | 195 | −5.574 | −10.328 | 30.677 | 1.00 | 44.53 | C |
| ATOM | 1423 | CG1 | ILE A | 195 | −4.583 | −10.519 | 31.832 | 1.00 | 44.52 | C |
| ATOM | 1424 | CD1 | ILE A | 195 | −3.293 | −9.708 | 31.674 | 1.00 | 44.44 | C |
| ATOM | 1425 | CG2 | ILE A | 195 | −6.060 | −8.902 | 30.588 | 1.00 | 44.93 | C |
| ATOM | 1426 | C | ILE A | 195 | −7.745 | −11.005 | 29.717 | 1.00 | 44.57 | C |
| ATOM | 1427 | O | ILE A | 195 | −7.538 | −11.400 | 28.542 | 1.00 | 44.75 | O |
| ATOM | 1428 | N | SER A | 196 | −8.834 | −10.365 | 30.070 | 1.00 | 43.77 | N |
| ATOM | 1429 | CA | SER A | 196 | −9.926 | −10.220 | 29.130 | 1.00 | 43.80 | C |
| ATOM | 1430 | CB | SER A | 196 | −11.252 | −10.615 | 29.763 | 1.00 | 43.05 | C |
| ATOM | 1431 | OG | SER A | 196 | −12.153 | −10.873 | 28.713 | 1.00 | 45.00 | O |
| ATOM | 1432 | C | SER A | 196 | −9.994 | −8.777 | 28.680 | 1.00 | 43.00 | C |
| ATOM | 1433 | O | SER A | 196 | −9.962 | −7.883 | 29.526 | 1.00 | 43.32 | O |
| ATOM | 1434 | N | ILE A | 197 | −10.094 | −8.561 | 27.384 | 1.00 | 41.74 | N |
| ATOM | 1435 | CA | ILE A | 197 | −9.926 | −7.239 | 26.812 | 1.00 | 41.07 | C |
| ATOM | 1436 | CB | ILE A | 197 | −8.702 | −7.119 | 25.900 | 1.00 | 40.44 | C |
| ATOM | 1437 | CG1 | ILE A | 197 | −7.452 | −7.699 | 26.569 | 1.00 | 41.18 | C |
| ATOM | 1438 | CD1 | ILE A | 197 | −6.168 | −7.699 | 25.706 | 1.00 | 36.78 | C |
| ATOM | 1439 | CG2 | ILE A | 197 | −8.467 | −5.660 | 25.584 | 1.00 | 38.00 | C |
| ATOM | 1440 | C | ILE A | 197 | −11.117 | −6.695 | 26.045 | 1.00 | 41.83 | C |
| ATOM | 1441 | O | ILE A | 197 | −11.672 | −7.353 | 25.144 | 1.00 | 40.77 | O |
| ATOM | 1442 | N | HIS A | 198 | −11.446 | −5.457 | 26.409 | 1.00 | 41.94 | N |
| ATOM | 1443 | CA | HIS A | 198 | −12.462 | −4.667 | 25.789 | 1.00 | 42.53 | C |
| ATOM | 1444 | CB | HIS A | 198 | −13.392 | −4.120 | 26.868 | 1.00 | 42.72 | C |
| ATOM | 1445 | CG | HIS A | 198 | −14.625 | −3.474 | 26.316 | 1.00 | 46.04 | C |
| ATOM | 1446 | ND1 | HIS A | 198 | −14.762 | −2.104 | 26.197 | 1.00 | 48.64 | N |
| ATOM | 1447 | CE1 | HIS A | 198 | −15.942 | −1.825 | 25.667 | 1.00 | 47.14 | C |
| ATOM | 1448 | NE2 | HIS A | 198 | −16.552 | −2.965 | 25.393 | 1.00 | 46.11 | N |
| ATOM | 1449 | CD2 | HIS A | 198 | −15.762 | −4.012 | 25.804 | 1.00 | 46.09 | C |
| ATOM | 1450 | C | HIS A | 198 | −11.740 | −3.504 | 25.150 | 1.00 | 43.35 | C |
| ATOM | 1451 | O | HIS A | 198 | −11.042 | −2.722 | 25.838 | 1.00 | 45.09 | O |
| ATOM | 1452 | N | ALA A | 199 | −11.860 | −3.380 | 23.837 | 1.00 | 42.68 | N |
| ATOM | 1453 | CA | ALA A | 199 | −11.133 | −2.327 | 23.122 | 1.00 | 41.62 | C |
| ATOM | 1454 | CB | ALA A | 199 | −9.704 | −2.733 | 22.851 | 1.00 | 40.87 | C |
| ATOM | 1455 | C | ALA A | 199 | −11.849 | −1.863 | 21.838 | 1.00 | 41.36 | C |
| ATOM | 1456 | O | ALA A | 199 | −12.521 | −2.657 | 21.150 | 1.00 | 41.14 | O |
| ATOM | 1457 | N | ASP A | 200 | −11.764 | −0.561 | 21.593 | 1.00 | 40.12 | N |
| ATOM | 1458 | CA | ASP A | 200 | −12.321 | 0.003 | 20.424 | 1.00 | 40.56 | C |
| ATOM | 1459 | CB | ASP A | 200 | −13.388 | 1.055 | 20.752 | 1.00 | 40.65 | C |
| ATOM | 1460 | CG | ASP A | 200 | −14.569 | 0.542 | 21.648 | 1.00 | 41.23 | C |
| ATOM | 1461 | OD1 | ASP A | 200 | −15.019 | −0.620 | 21.581 | 1.00 | 40.37 | O |
| ATOM | 1462 | OD2 | ASP A | 200 | −15.093 | 1.393 | 22.418 | 1.00 | 44.10 | O |
| ATOM | 1463 | C | ASP A | 200 | −11.168 | 0.648 | 19.621 | 1.00 | 41.30 | C |
| ATOM | 1464 | O | ASP A | 200 | −10.282 | 1.336 | 20.187 | 1.00 | 41.72 | O |
| ATOM | 1465 | N | PHE A | 201 | −11.172 | 0.424 | 18.309 | 1.00 | 40.57 | N |
| ATOM | 1466 | CA | PHE A | 201 | −10.168 | 0.998 | 17.456 | 1.00 | 40.67 | C |
| ATOM | 1467 | CB | PHE A | 201 | −9.392 | −0.141 | 16.809 | 1.00 | 40.93 | C |
| ATOM | 1468 | CG | PHE A | 201 | −8.767 | −1.090 | 17.793 | 1.00 | 39.58 | C |
| ATOM | 1469 | CD1 | PHE A | 201 | −7.538 | −0.836 | 18.317 | 1.00 | 37.01 | C |
| ATOM | 1470 | CE1 | PHE A | 201 | −6.963 | −1.725 | 19.197 | 1.00 | 37.09 | C |
| ATOM | 1471 | CZ | PHE A | 201 | −7.635 | −2.889 | 19.544 | 1.00 | 39.00 | C |
| ATOM | 1472 | CE2 | PHE A | 201 | −8.872 | −3.166 | 19.002 | 1.00 | 37.48 | C |
| ATOM | 1473 | CD2 | PHE A | 201 | −9.418 | −2.271 | 18.147 | 1.00 | 40.20 | C |
| ATOM | 1474 | C | PHE A | 201 | −10.809 | 1.840 | 16.372 | 1.00 | 40.58 | C |
| ATOM | 1475 | O | PHE A | 201 | −11.666 | 1.353 | 15.713 | 1.00 | 41.94 | O |
| ATOM | 1476 | N | GLU A | 202 | −10.408 | 3.083 | 16.173 | 1.00 | 40.74 | N |
| ATOM | 1477 | CA | GLU A | 202 | −10.854 | 3.837 | 14.980 | 1.00 | 41.73 | C |
| ATOM | 1478 | CB | GLU A | 202 | −11.236 | 5.265 | 15.305 | 1.00 | 43.10 | C |
| ATOM | 1479 | CG | GLU A | 202 | −12.192 | 5.586 | 16.442 | 1.00 | 48.59 | C |
| ATOM | 1480 | CD | GLU A | 202 | −13.039 | 6.828 | 16.059 | 1.00 | 55.27 | C |
| ATOM | 1481 | OE1 | GLU A | 202 | −12.719 | 7.512 | 15.037 | 1.00 | 53.75 | O |
| ATOM | 1482 | OE2 | GLU A | 202 | −14.049 | 7.090 | 16.758 | 1.00 | 59.21 | O |
| ATOM | 1483 | C | GLU A | 202 | −9.750 | 4.035 | 13.966 | 1.00 | 40.03 | C |
| ATOM | 1484 | O | GLU A | 202 | −8.618 | 4.194 | 14.437 | 1.00 | 39.85 | O |
| ATOM | 1485 | N | ASN A | 203 | −10.086 | 4.110 | 12.684 | 1.00 | 38.71 | N |
| ATOM | 1486 | CA | ASN A | 203 | −9.107 | 4.419 | 11.659 | 1.00 | 37.33 | C |
| ATOM | 1487 | CB | ASN A | 203 | −8.486 | 3.155 | 11.127 | 1.00 | 35.93 | C |
| ATOM | 1488 | CG | ASN A | 203 | −7.559 | 3.396 | 9.974 | 1.00 | 34.61 | C |
| ATOM | 1489 | OD1 | ASN A | 203 | | 7.054 | 4.504 | 9.732 | 1.00 | 32.58 | O |
| ATOM | 1490 | ND2 | ASN A | 203 | −7.318 | 2.341 | 9.242 | 1.00 | 30.37 | N |
| ATOM | 1491 | C | ASN A | 203 | −9.718 | 5.218 | 10.518 | 1.00 | 38.49 | C |
| ATOM | 1492 | O | ASN A | 203 | −10.335 | 4.656 | 9.591 | 1.00 | 39.45 | O |
| ATOM | 1493 | N | THR A | 204 | −9.516 | 6.531 | 10.595 | 1.00 | 38.37 | N |
| ATOM | 1494 | CA | THR A | 204 | −9.954 | 7.475 | 9.591 | 1.00 | 38.40 | C |

TABLE 11-continued

| | | | | | | | | | |
|---|---|---|---|---|---|---|---|---|---|
| ATOM | 1495 | CB | THR A | 204 | −10.645 | 8.697 | 10.205 | 1.00 | 38.12 | C |
| ATOM | 1496 | OG1 | THR A | 204 | −9.753 | 9.333 | 11.110 | 1.00 | 40.16 | O |
| ATOM | 1497 | CG2 | THR A | 204 | −11.892 | 8.277 | 10.987 | 1.00 | 39.56 | C |
| ATOM | 1498 | C | THR A | 204 | −8.806 | 7.972 | 8.743 | 1.00 | 38.33 | C |
| ATOM | 1499 | O | THR A | 204 | −9.029 | 8.822 | 7.889 | 1.00 | 39.41 | O |
| ATOM | 1500 | N | SER A | 205 | −7.608 | 7.435 | 8.974 | 1.00 | 37.86 | N |
| ATOM | 1501 | CA | SER A | 205 | −6.437 | 7.637 | 8.156 | 1.00 | 37.94 | C |
| ATOM | 1502 | CB | SER A | 205 | −5.226 | 7.078 | 8.880 | 1.00 | 37.81 | C |
| ATOM | 1503 | OG | SER A | 205 | −5.065 | 5.694 | 8.536 | 1.00 | 37.80 | O |
| ATOM | 1504 | C | SER A | 205 | −6.565 | 6.793 | 6.885 | 1.00 | 38.90 | C |
| ATOM | 1505 | O | SER A | 205 | 7.379 | 5.870 | 6.814 | 1.00 | 39.05 | O |
| ATOM | 1506 | N | SER A | 206 | −5.706 | 7.084 | 5.907 | 1.00 | 39.84 | N |
| ATOM | 1507 | CA | SER A | 206 | −5.654 | 6.355 | 4.641 | 1.00 | 39.44 | C |
| ATOM | 1508 | CB | SER A | 206 | −4.985 | 7.237 | 3.582 | 1.00 | 38.26 | C |
| ATOM | 1509 | OG | SER A | 206 | −3.636 | 7.502 | 3.894 | 1.00 | 37.52 | O |
| ATOM | 1510 | C | SER A | 206 | −4.921 | 5.007 | 4.729 | 1.00 | 40.39 | C |
| ATOM | 1511 | O | SER A | 206 | −4.792 | 4.319 | 3.743 | 1.00 | 40.90 | O |
| ATOM | 1512 | N | ARG A | 207 | −4.397 | 4.621 | 5.881 | 1.00 | 41.46 | N |
| ATOM | 1513 | CA | ARG A | 207 | −3.652 | 3.352 | 5.916 | 1.00 | 42.20 | C |
| ATOM | 1514 | CB | ARG A | 207 | −2.394 | 3.433 | 6.800 | 1.00 | 42.15 | C |
| ATOM | 1515 | CG | ARG A | 207 | −1.716 | 4.785 | 6.847 | 1.00 | 45.22 | C |
| ATOM | 1516 | CD | ARG A | 207 | −0.774 | 4.082 | 5.676 | 1.00 | 52.23 | C |
| ATOM | 1517 | NE | ARG A | 207 | 0.107 | 6.145 | 5.884 | 1.00 | 56.51 | N |
| ATOM | 1518 | CZ | ARG A | 207 | −0.307 | 7.424 | 5.908 | 1.00 | 57.48 | C |
| ATOM | 1519 | NH1 | ARG A | 207 | −1.607 | 7.759 | 5.730 | 1.00 | 52.69 | N |
| ATOM | 1520 | NH2 | ARG A | 207 | 0.589 | 8.386 | 6.127 | 1.00 | 60.24 | N |
| ATOM | 1521 | C | ARG A | 207 | −4.534 | 2.207 | 6.389 | 1.00 | 40.85 | C |
| ATOM | 1522 | O | ARG A | 207 | −5.459 | 2.433 | 7.132 | 1.00 | 42.73 | O |
| ATOM | 1523 | N | ILE A | 208 | −4.249 | 0.992 | 5.947 | 1.00 | 39.27 | N |
| ATOM | 1524 | CA | ILE A | 208 | −4.744 | −0.198 | 6.601 | 1.00 | 37.95 | C |
| ATOM | 1525 | CB | ILE A | 208 | −4.575 | −1.400 | 5.690 | 1.00 | 37.37 | C |
| ATOM | 1526 | CG1 | ILE A | 208 | −5.599 | −1.346 | 4.557 | 1.00 | 34.46 | C |
| ATOM | 1527 | CD1 | ILE A | 208 | −5.241 | −2.231 | 2.337 | 1.00 | 25.20 | C |
| ATOM | 1528 | CG2 | ILE A | 208 | −4.741 | −2.733 | 6.505 | 1.00 | 39.80 | C |
| ATOM | 1529 | C | ILE A | 208 | −3.896 | −0.418 | 7.856 | 1.00 | 38.73 | C |
| ATOM | 1530 | O | ILE A | 208 | −2.628 | −0.457 | 7.752 | 1.00 | 39.37 | O |
| ATOM | 1531 | N | VAL A | 209 | −4.542 | −0.584 | 9.024 | 1.00 | 37.68 | N |
| ATOM | 1532 | CA | VAL A | 209 | −3.799 | −0.664 | 10.312 | 1.00 | 37.05 | C |
| ATOM | 1533 | CB | VAL A | 209 | −4.090 | 0.560 | 11.229 | 1.00 | 37.18 | C |
| ATOM | 1534 | CG1 | VAL A | 209 | −3.726 | 1.877 | 10.550 | 1.00 | 35.19 | C |
| ATOM | 1535 | CG2 | VAL A | 209 | −5.557 | 0.566 | 11.772 | 1.00 | 34.25 | C |
| ATOM | 1536 | C | VAL A | 209 | −4.137 | −1.965 | 11.054 | 1.00 | 38.38 | C |
| ATOM | 1537 | O | VAL A | 209 | −5.203 | −2.521 | 10.826 | 1.00 | 39.67 | O |
| ATOM | 1538 | N | VAL A | 210 | −3.270 | −2.454 | 11.939 | 1.00 | 38.27 | N |
| ATOM | 1539 | CA | VAL A | 210 | −3.516 | 3.727 | 12.572 | 1.00 | 38.08 | C |
| ATOM | 1540 | CB | VAL A | 210 | −2.473 | −4.692 | 12.126 | 1.00 | 38.78 | C |
| ATOM | 1541 | CG1 | VAL A | 210 | −2.726 | −6.118 | 12.695 | 1.00 | 38.41 | C |
| ATOM | 1542 | CG2 | VAL A | 210 | −2.471 | −4.707 | 10.664 | 1.00 | 40.02 | C |
| ATOM | 1543 | C | VAL A | 210 | −3.417 | −3.579 | 14.082 | 1.00 | 38.18 | C |
| ATOM | 1544 | O | VAL A | 210 | −2.442 | −3.060 | 14.569 | 1.00 | 38.69 | O |
| ATOM | 1545 | N | PRO A | 211 | −4.445 | −4.012 | 14.827 | 1.00 | 38.19 | N |
| ATOM | 1546 | CA | PRO A | 211 | −4.358 | −3.865 | 16.277 | 1.00 | 37.39 | C |
| ATOM | 1547 | CB | PRO A | 211 | −5.819 | −3.764 | 16.681 | 1.00 | 37.19 | C |
| ATOM | 1548 | CG | PRO A | 211 | −6.625 | −4.534 | 15.590 | 1.00 | 36.16 | C |
| ATOM | 1549 | CD | PRO A | 211 | −5.736 | −4.624 | 14.388 | 1.00 | 38.07 | C |
| ATOM | 1550 | C | PRO A | 211 | −3.727 | −5.116 | 16.880 | 1.00 | 37.45 | C |
| ATOM | 1551 | O | PRO A | 211 | −3.938 | −6.229 | 16.365 | 1.00 | 37.80 | O |
| ATOM | 1552 | N | LYS A | 212 | −2.957 | −4.946 | 17.958 | 1.00 | 36.98 | N |
| ATOM | 1553 | CA | LYS A | 212 | −2.231 | −6.066 | 18.601 | 1.00 | 36.15 | C |
| ATOM | 1554 | CB | LYS A | 212 | −0.817 | −6.231 | 18.029 | 1.00 | 35.86 | C |
| ATOM | 1555 | OG | LYS A | 212 | −0.717 | −6.406 | 16.507 | 1.00 | 34.14 | O |
| ATOM | 1556 | CD | LYS A | 212 | 0.724 | −6.360 | 16.079 | 1.00 | 35.23 | C |
| ATOM | 1557 | CE | LYS A | 212 | 0.882 | −6.128 | 14.583 | 1.00 | 37.11 | C |
| ATOM | 1558 | NZ | LYS A | 212 | 2.233 | −6.488 | 14.003 | 1.00 | 40.36 | N |
| ATOM | 1559 | C | LYS A | 212 | −2.164 | −5.900 | 20.122 | 1.00 | 37.12 | C |
| ATOM | 1560 | O | LYS A | 212 | −2.416 | −4.782 | 20.703 | 1.00 | 36.71 | O |
| ATOM | 1561 | N | ALA A | 213 | −1.857 | −7.008 | 20.800 | 1.00 | 36.16 | N |
| ATOM | 1562 | CA | ALA A | 213 | −1.653 | −6.882 | 22.256 | 1.00 | 35.01 | C |
| ATOM | 1563 | CB | ALA A | 213 | −2.919 | −7.179 | 22.994 | 1.00 | 34.18 | C |
| ATOM | 1564 | C | ALA A | 213 | −0.582 | −7.846 | 22.691 | 1.00 | 35.59 | C |
| ATOM | 1565 | O | ALA A | 213 | −0.386 | −8.947 | 22.068 | 1.00 | 34.75 | O |
| ATOM | 1566 | N | ALA A | 214 | 0.132 | −7.461 | 23.745 | 1.00 | 34.71 | N |
| ATOM | 1567 | CA | ALA A | 214 | 1.103 | −8.406 | 24.295 | 1.00 | 35.44 | C |
| ATOM | 1568 | CB | ALA A | 214 | 2.462 | −8.383 | 25.695 | 1.00 | 34.85 | C |
| ATOM | 1569 | C | ALA A | 214 | 1.292 | −8.105 | 25.695 | 1.00 | 35.42 | C |
| ATOM | 1570 | O | ALA A | 214 | 1.118 | −6.935 | 26.104 | 1.00 | 35.25 | O |
| ATOM | 1571 | N | ILE A | 215 | 1.593 | −9.176 | 26.439 | 1.00 | 35.71 | N |
| ATOM | 1572 | CA | ILE A | 215 | 1.997 | −9.049 | 27.831 | 1.00 | 36.56 | C |
| ATOM | 1573 | CB | ILE A | 215 | 1.444 | −10.236 | 28.722 | 1.00 | 37.25 | C |
| ATOM | 1574 | CG1 | ILE A | 215 | −0.015 | −10.018 | 29.116 | 1.00 | 36.37 | C |

TABLE 11-continued

| ATOM | 1575 | CD1 | ILE A | 215 | −0.703 | −11.290 | 29.663 | 1.00 | 33.01 | C |
|---|---|---|---|---|---|---|---|---|---|---|
| ATOM | 1576 | CG2 | ILE A | 215 | 2.277 | −10.420 | 29.976 | 1.00 | 35.78 | C |
| ATOM | 1577 | C | ILE A | 215 | 3.518 | −9.034 | 27.772 | 1.00 | 36.51 | C |
| ATOM | 1578 | O | ILE A | 215 | 4.153 | −9.917 | 27.193 | 1.00 | 35.67 | O |
| ATOM | 1579 | N | VAL A | 216 | 4.109 | −8.028 | 28.360 | 1.00 | 36.82 | N |
| ATOM | 1580 | CA | VAL A | 216 | 5.555 | −7.997 | 28.361 | 1.00 | 38.55 | C |
| ATOM | 1581 | CB | VAL A | 216 | 6.091 | −6.812 | 27.545 | 1.00 | 39.52 | C |
| ATOM | 1582 | CG1 | VAL A | 216 | 5.814 | −7.044 | 26.027 | 1.00 | 40.74 | C |
| ATOM | 1583 | CG2 | VAL A | 216 | 5.462 | −5.510 | 27.984 | 1.00 | 38.25 | C |
| ATOM | 1584 | C | VAL A | 216 | 6.135 | −8.047 | 29.785 | 1.00 | 39.34 | C |
| ATOM | 1585 | O | VAL A | 216 | 5.491 | −7.676 | 30.770 | 1.00 | 38.26 | O |
| ATOM | 1586 | N | ALA A | 217 | 7.338 | −8.578 | 29.892 | 1.00 | 41.21 | N |
| ATOM | 1587 | CA | ALA A | 217 | 7.962 | −8.795 | 31.201 | 1.00 | 42.64 | C |
| ATOM | 1588 | CB | ALA A | 217 | 8.243 | −10.268 | 31.393 | 1.00 | 41.94 | C |
| ATOM | 1589 | C | ALA A | 217 | 9.247 | −8.004 | 31.147 | 1.00 | 43.60 | C |
| ATOM | 1590 | O | ALA A | 217 | 10.050 | −8.198 | 30.190 | 1.00 | 44.43 | O |
| ATOM | 1591 | N | ARG A | 218 | 9.415 | −7.076 | 32.089 | 1.00 | 44.02 | N |
| ATOM | 1592 | CA | ARG A | 218 | 10.703 | −6.374 | 32.256 | 1.00 | 45.78 | C |
| ATOM | 1593 | CB | ARG A | 218 | 10.474 | −4.892 | 32.328 | 1.00 | 44.86 | C |
| ATOM | 1594 | CG | ARG A | 218 | 9.627 | −4.460 | 31.205 | 1.00 | 47.70 | C |
| ATOM | 1595 | CD | ARG A | 218 | 9.335 | −2.983 | 31.284 | 1.00 | 53.52 | C |
| ATOM | 1596 | NE | ARG A | 218 | 8.587 | −2.541 | 30.108 | 1.00 | 55.19 | N |
| ATOM | 1597 | CZ | ARG A | 218 | 7.260 | −2.417 | 30.076 | 1.00 | 56.21 | C |
| ATOM | 1598 | NH1 | ARG A | 218 | 6.509 | −2.710 | 31.163 | 1.00 | 53.32 | N |
| ATOM | 1599 | NH2 | ARG A | 218 | 6.689 | −2.004 | 28.946 | 1.00 | 52.45 | N |
| ATOM | 1600 | C | ARG A | 218 | 11.518 | −6.852 | 33.466 | 1.00 | 46.60 | C |
| ATOM | 1601 | O | ARG A | 218 | 11.220 | −6.486 | 34.586 | 1.00 | 46.51 | O |
| ATOM | 1602 | N | HIS A | 219 | 12.514 | −7.707 | 33.243 | 1.00 | 48.08 | N |
| ATOM | 1603 | CA | HIS A | 219 | 13.331 | −8.189 | 34.363 | 1.00 | 49.51 | C |
| ATOM | 1604 | CB | HIS A | 219 | 14.052 | −9.450 | 34.023 | 1.00 | 49.60 | C |
| ATOM | 1605 | CG | HIS A | 219 | 13.216 | −10.401 | 33.266 | 1.00 | 51.80 | C |
| ATOM | 1606 | ND1 | HIS A | 219 | 12.502 | −11.447 | 33.870 | 1.00 | 53.38 | N |
| ATOM | 1607 | CE1 | HIS A | 219 | 11.873 | −12.113 | 32.964 | 1.00 | 54.92 | C |
| ATOM | 1608 | NE2 | HIS A | 219 | 12.050 | −11.523 | 31.795 | 1.00 | 58.11 | N |
| ATOM | 1609 | CD2 | HIS A | 219 | 12.891 | −10.449 | 31.957 | 1.00 | 54.98 | C |
| ATOM | 1610 | C | HIS A | 219 | 14.384 | −7.183 | 34.647 | 1.00 | 50.50 | C |
| ATOM | 1611 | O | HIS A | 219 | 15.153 | −6.809 | 33.754 | 1.00 | 50.28 | O |
| ATOM | 1612 | N | THR A | 220 | 14.400 | 6.738 | 35.892 | 1.00 | 52.36 | N |
| ATOM | 1613 | CA | THR A | 220 | 15.468 | −5.910 | 38.400 | 1.00 | 53.85 | C |
| ATOM | 1614 | CB | THR A | 220 | 14.928 | −4.879 | 37.391 | 1.00 | 53.45 | C |
| ATOM | 1615 | OG1 | THR A | 220 | 13.540 | −4.670 | 37.102 | 1.00 | 53.47 | O |
| ATOM | 1616 | CG2 | THR A | 220 | 15.717 | −3.577 | 37.302 | 1.00 | 52.40 | C |
| ATOM | 1617 | C | THR A | 220 | 16.359 | −6.940 | 37.090 | 1.00 | 55.36 | C |
| ATOM | 1618 | O | THR A | 220 | 15.889 | −7.757 | 37.946 | 1.00 | 55.15 | O |
| ATOM | 1619 | N | TYR A | 221 | 17.628 | −6.943 | 36.685 | 1.00 | 56.71 | N |
| ATOM | 1620 | CA | TYR A | 221 | 18.535 | −7.995 | 37.153 | 1.00 | 59.10 | C |
| ATOM | 1621 | CB | TYR A | 221 | 18.655 | −9.213 | 36.181 | 1.00 | 58.62 | C |
| ATOM | 1622 | CG | TYR A | 221 | 19.299 | −8.891 | 34.846 | 1.00 | 59.07 | C |
| ATOM | 1623 | CD1 | TYR A | 221 | 20.610 | −9.251 | 34.565 | 1.00 | 61.92 | C |
| ATOM | 1624 | CE1 | TYR A | 221 | 21.194 | −8.952 | 33.324 | 1.00 | 83.18 | C |
| ATOM | 1625 | CZ | TYR A | 221 | 20.435 | −8.729 | 32.380 | 1.00 | 64.99 | C |
| ATOM | 1626 | OH | TYR A | 221 | 20.938 | −7.945 | 31.145 | 1.00 | 66.96 | O |
| ATOM | 1627 | CE2 | TYR A | 221 | 19.142 | −7.909 | 32.657 | 1.00 | 62.42 | C |
| ATOM | 1628 | CD2 | TYR A | 221 | 18.595 | −8.213 | 33.871 | 1.00 | 60.09 | C |
| ATOM | 1629 | C | TYR A | 221 | 19.884 | −7.432 | 37.487 | 1.00 | 59.98 | C |
| ATOM | 1630 | O | TYR A | 221 | 20.325 | −6.368 | 36.942 | 1.00 | 59.83 | O |
| ATOM | 1631 | N | LEU A | 222 | 20.509 | −8.178 | 38.397 | 1.00 | 61.39 | N |
| ATOM | 1632 | CA | LEU A | 222 | 21.871 | −7.910 | 38.847 | 1.00 | 63.61 | C |
| ATOM | 1633 | CB | LEU A | 222 | 22.028 | −8.341 | 40.309 | 1.00 | 62.98 | C |
| ATOM | 1634 | CG | LEU A | 222 | 21.282 | −7.473 | 41.325 | 1.00 | 63.02 | C |
| ATOM | 1635 | CD1 | LEU A | 222 | 21.463 | −8.070 | 42.756 | 1.00 | 61.49 | C |
| ATOM | 1636 | CD2 | LEU A | 222 | 21.629 | −5.923 | 41.201 | 1.00 | 60.77 | C |
| ATOM | 1637 | C | LEU A | 222 | 22.940 | −8.569 | 37.953 | 1.00 | 64.69 | C |
| ATOM | 1638 | O | LEU A | 222 | 23.067 | −9.826 | 37.951 | 1.00 | 64.81 | O |
| ATOM | 1639 | N | ALA A | 223 | 23.675 | −7.738 | 37.191 | 1.00 | 65.52 | N |
| ATOM | 1640 | CA | ALA A | 223 | 24.806 | −8.256 | 36.397 | 1.00 | 67.79 | C |
| ATOM | 1641 | CB | ALA A | 223 | 24.325 | −8.974 | 35.082 | 1.00 | 67.44 | C |
| ATOM | 1642 | C | ALA A | 223 | 25.945 | −7.268 | 36.082 | 1.00 | 69.31 | C |
| ATOM | 1643 | O | ALA A | 223 | 25.702 | −6.130 | 35.604 | 1.00 | 69.36 | O |
| ATOM | 1644 | N | ASN A | 224 | 27.180 | −7.743 | 36.334 | 1.00 | 70.36 | N |
| ATOM | 1645 | CA | ASN A | 224 | 28.422 | −7.067 | 35.924 | 1.00 | 71.15 | C |
| ATOM | 1646 | CB | ASN A | 224 | 28.609 | −7.127 | 34.394 | 1.00 | 71.97 | C |
| ATOM | 1647 | CG | ASN A | 224 | 28.792 | −8.579 | 33.863 | 1.00 | 73.02 | C |
| ATOM | 1648 | OD1 | ASN A | 224 | 29.156 | −9.501 | 34.610 | 1.00 | 72.47 | O |
| ATOM | 1649 | ND2 | ASN A | 224 | 28.545 | −8.766 | 32.563 | 1.00 | 72.69 | N |
| ATOM | 1650 | C | ASN A | 224 | 28.523 | −5.627 | 36.432 | 1.00 | 71.70 | C |
| ATOM | 1651 | O | ASN A | 224 | 28.812 | −4.686 | 35.644 | 1.00 | 71.63 | O |
| ATOM | 1652 | N | GLY A | 225 | 28.281 | −5.487 | 37.750 | 1.00 | 71.80 | N |
| ATOM | 1653 | CA | GLY A | 225 | 28.253 | −4.201 | 38.458 | 1.00 | 71.58 | C |
| ATOM | 1654 | C | GLY A | 225 | 26.932 | 3.433 | 38.426 | 1.00 | 71.90 | C |

TABLE 11-continued

| ATOM | 1655 | O | GLY A | 225 | 26.842 | −2.307 | 38.961 | 1.00 | 71.41 | O |
|------|------|------|-------|-----|--------|--------|--------|------|-------|---|
| ATOM | 1656 | N | GLN A | 226 | 25.907 | −4.061 | 37.829 | 1.00 | 72.24 | N |
| ATOM | 1657 | CA | GLN A | 226 | 24.671 | −3.394 | 37.362 | 1.00 | 72.31 | C |
| ATOM | 1658 | CB | GLN A | 226 | 24.744 | −3.359 | 35.829 | 1.00 | 72.54 | C |
| ATOM | 1659 | CG | GLN A | 226 | 25.667 | −2.273 | 35.182 | 1.00 | 73.97 | C |
| ATOM | 1660 | CD | GLN A | 226 | 26.768 | −1.728 | 36.106 | 1.00 | 76.68 | C |
| ATOM | 1661 | OE1 | GLN A | 226 | 27.884 | −2.262 | 36.129 | 1.00 | 78.84 | O |
| ATOM | 1662 | NE2 | GLN A | 226 | 26.456 | −0.665 | 35.873 | 1.00 | 75.15 | N |
| ATOM | 1663 | C | GLN A | 226 | 23.371 | −4.095 | 37.873 | 1.00 | 71.90 | C |
| ATOM | 1664 | O | GLN A | 226 | 23.447 | −5.282 | 38.244 | 1.00 | 72.77 | O |
| ATOM | 1665 | N | THR A | 227 | 22.165 | −3.495 | 37.855 | 1.00 | 71.08 | N |
| ATOM | 1666 | CA | THR A | 227 | 21.636 | −2.335 | 37.069 | 1.00 | 69.43 | C |
| ATOM | 1667 | CB | THR A | 227 | 22.551 | −1.053 | 37.047 | 1.00 | 69.27 | C |
| ATOM | 1668 | OG1 | THR A | 227 | 21.757 | 0.075 | 36.628 | 1.00 | 71.33 | O |
| ATOM | 1669 | CG2 | THR A | 227 | 23.570 | −1.146 | 36.006 | 1.00 | 68.61 | C |
| ATOM | 1670 | C | THR A | 227 | 21.082 | −2.624 | 35.639 | 1.00 | 67.58 | C |
| ATOM | 1671 | O | THR A | 227 | 21.101 | −1.717 | 34.782 | 1.00 | 68.22 | O |
| ATOM | 1672 | N | LYS A | 228 | 20.589 | −3.826 | 35.347 | 1.00 | 64.53 | N |
| ATOM | 1673 | CA | LYS A | 228 | 19.964 | −3.975 | 34.00 | 1.00 | 62.00 | C |
| ATOM | 1674 | CB | LYS A | 228 | 20.804 | −4.844 | 33.050 | 1.00 | 62.49 | C |
| ATOM | 1675 | CG | LYS A | 228 | 22.098 | −4.230 | 32.467 | 1.00 | 60.48 | C |
| ATOM | 1676 | CD | LYS A | 228 | 22.955 | −5.411 | 31.970 | 1.00 | 55.92 | C |
| ATOM | 1677 | CE | LYS A | 228 | 24.170 | −4.976 | 31.177 | 1.00 | 53.23 | C |
| ATOM | 1678 | NZ | LYS A | 228 | 24.423 | −5.872 | 30.016 | 1.00 | 49.66 | N |
| ATOM | 1679 | C | LYS A | 228 | 18.507 | −4.445 | 33.954 | 1.00 | 60.33 | C |
| ATOM | 1680 | O | LYS A | 228 | 17.979 | −5.094 | 34.887 | 1.00 | 60.10 | O |
| ATOM | 1681 | N | VAL A | 229 | 17.860 | −4.115 | 32.847 | 1.00 | 58.16 | N |
| ATOM | 1682 | CA | VAL A | 229 | 16.484 | −4.554 | 32.597 | 1.00 | 55.57 | C |
| ATOM | 1683 | CB | VAL A | 229 | 15.409 | −3.428 | −32.784 | 1.00 | 55.31 | C |
| ATOM | 1684 | CG1 | VAL A | 229 | 15.824 | −2.102 | 32.190 | 1.00 | 52.04 | C |
| ATOM | 1685 | CG2 | VAL A | 229 | 14.101 | −3.892 | 32.190 | 1.00 | 56.29 | C |
| ATOM | 1686 | C | VAL A | 229 | 15.396 | −5.168 | 31.226 | 1.00 | 54.39 | C |
| ATOM | 1687 | O | VAL A | 229 | 16.830 | −4.559 | 30.251 | 1.00 | 54.71 | O |
| ATOM | 1688 | N | LEU A | 230 | −15.890 | −6.395 | 31.166 | 1.00 | 52.77 | N |
| ATOM | 1689 | CA | LEU A | 230 | 15.632 | −7.094 | 29.908 | 1.00 | 51.35 | C |
| ATOM | 1690 | CB | LEU A | 230 | 16.228 | −8.483 | 29.994 | 1.00 | 51.38 | C |
| ATOM | 1691 | CG | LEU A | 230 | 15.756 | −9.453 | 28.929 | 1.00 | 52.81 | C |
| ATOM | 1692 | CD1 | LEU A | 230 | 16.859 | −9.730 | 27.918 | 1.00 | 54.72 | C |
| ATOM | 1693 | CD2 | LEU A | 230 | 15.323 | −10.714 | 29.589 | 1.00 | 54.75 | C |
| ATOM | 1694 | C | LEU A | 230 | 14.110 | −7.204 | 29.647 | 1.00 | 50.72 | C |
| ATOM | 1695 | O | LEU A | 230 | 13.334 | −7.569 | 30.563 | 1.00 | 50.68 | O |
| ATOM | 1696 | N | TRH A | 231 | 13.682 | −6.891 | 28.423 | 1.00 | 49.15 | N |
| ATOM | 1697 | CA | THR A | 231 | 12.282 | −7.056 | 28.023 | 1.00 | 48.64 | C |
| ATOM | 1698 | CB | THR A | 231 | 11.853 | −5.884 | 27.196 | 1.00 | 48.63 | C |
| ATOM | 1699 | OG1 | THR A | 231 | 12.403 | 4.718 | 27.795 | 1.00 | 51.80 | O |
| ATOM | 1700 | CG2 | THR A | 231 | 10.366 | −5.733 | 27.201 | 1.00 | 48.82 | C |
| ATOM | 1701 | C | THR A | 231 | 11.983 | −8.359 | 27.252 | 1.00 | 48.12 | C |
| ATOM | 1702 | O | THR A | 231 | 12.531 | −8.636 | 26.171 | 1.00 | 47.90 | O |
| ATOM | 1703 | N | GLN A | 232 | 11.087 | −9.135 | 27.834 | 1.00 | 47.22 | N |
| ATOM | 1704 | CA | GLN A | 232 | 10.631 | −10.390 | 27.291 | 1.00 | 46.95 | C |
| ATOM | 1705 | CB | GLN A | 232 | 10.701 | −11.442 | 28.386 | 1.00 | 47.47 | C |
| ATOM | 1706 | CG | GLN A | 232 | 10.869 | −12.865 | 27.933 | 1.00 | 51.53 | C |
| ATOM | 1707 | CD | GLN A | 232 | 10.427 | −13.591 | 28.989 | 1.00 | 56.04 | C |
| ATOM | 1708 | OE1 | GLN A | 232 | 10.582 | −13.797 | 30.211 | 1.00 | 57.31 | O |
| ATOM | 1709 | NE2 | GLN A | 232 | 9.888 | −15.060 | 28.481 | 1.00 | 56.94 | N |
| ATOM | 1710 | C | GLN A | 232 | 9.165 | −10.185 | 26.855 | 1.00 | 46.13 | C |
| ATOM | 1711 | O | GLN A | 232 | 8.414 | −9.466 | 27.551 | 1.00 | 46.70 | O |
| ATOM | 1712 | N | LYS A | 233 | 8.796 | −10.779 | 25.737 | 1.00 | 44.93 | N |
| ATOM | 1713 | CA | LYS A | 233 | 7.449 | −10.802 | 25.209 | 1.00 | 42.67 | C |
| ATOM | 1714 | CB | LYS A | 233 | 7.541 | −10.650 | 23.694 | 1.00 | 41.94 | C |
| ATOM | 1715 | CG | LYS A | 233 | 6.201 | −10.465 | 22.986 | 1.00 | 39.94 | C |
| ATOM | 1716 | CD | LYS A | 233 | 6.449 | −10.779 | 21.540 | 1.00 | 36.59 | C |
| ATOM | 1717 | CE | LYS A | 233 | 5.343 | −10.304 | 20.659 | 1.00 | 40.62 | C |
| ATOM | 1718 | NZ | LYS A | 233 | 5.263 | −11.016 | 19.331 | 1.00 | 41.44 | N |
| ATOM | 1719 | C | LYS A | 233 | 6.836 | 12.160 | 25.553 | 1.00 | 42.38 | C |
| ATOM | 1720 | O | LYS A | 233 | 7.376 | −13.217 | 25.135 | 1.00 | 41.36 | O |
| ATOM | 1721 | N | LEU A | 234 | 5.742 | −12.147 | 26.321 | 1.00 | 41.80 | N |
| ATOM | 1722 | CA | LEU A | 234 | 5.030 | −13.395 | 26.657 | 1.00 | 41.96 | C |
| ATOM | 1723 | CB | LEU A | 234 | 4.645 | −13.464 | 28.141 | 1.00 | 42.08 | C |
| ATOM | 1724 | CG | LEU A | 234 | 5.768 | −13.215 | 29.184 | 1.00 | 40.86 | C |
| ATOM | 1725 | CD1 | LEU A | 234 | 5.254 | −13.223 | 30.626 | 1.00 | 37.60 | C |
| ATOM | 1726 | CD2 | LEU A | 234 | 6.801 | −14.237 | 29.047 | 1.00 | 40.68 | C |
| ATOM | 1727 | C | LEU A | 234 | 3.845 | −13.625 | 25.682 | 1.00 | 42.3.4 | C |
| ATOM | 1728 | O | LEU A | 234 | 4.059 | −13.609 | 24.493 | 1.00 | 42.96 | O |
| ATOM | 1729 | N | SER A | 235 | 2.610 | −13.821 | 26.126 | 1.00 | 42.23 | N |
| ATOM | 1730 | CA | SER A | 235 | 1.548 | −14.123 | 25.150 | 1.00 | 41.75 | C |
| ATOM | 1731 | CB | SER A | 235 | 0.333 | −14.860 | 25.770 | 1.00 | 42.61 | C |
| ATOM | 1732 | OG | SER A | 235 | 0.133 | −14.594 | 27.159 | 1.00 | 46.55 | O |
| ATOM | 1733 | C | SER A | 235 | 1.173 | −12.933 | 24.287 | 1.00 | 40.13 | C |
| ATOM | 1734 | O | SER A | 235 | 1.436 | −11.830 | 24.633 | 1.00 | 39.80 | O |

TABLE 11-continued

| ATOM | 1735 | N | SER A | 236 | 0.622 | −13.175 | 23.117 | 1.00 | 39.94 | N |
|---|---|---|---|---|---|---|---|---|---|---|
| ATOM | 1736 | CA | SER A | 236 | 0.203 | −12.081 | 22.260 | 1.00 | 39.98 | C |
| ATOM | 1737 | CB | SER A | 236 | 1.374 | −11.454 | 21.501 | 1.00 | 39.98 | C |
| ATOM | 1738 | OG | SER A | 236 | 1.886 | −12.270 | 20.483 | 1.00 | 36.77 | O |
| ATOM | 1739 | C | SER A | 236 | −0.837 | −12.538 | 21.290 | 1.00 | 40.67 | C |
| ATOM | 1740 | O | SER A | 236 | −0.903 | −13.715 | 20.993 | 1.00 | 41.90 | O |
| ATOM | 1741 | N | VAL A | 237 | −1.677 | −11.603 | 20.853 | 1.00 | 41.64 | N |
| ATOM | 1742 | CA | VAL A | 237 | −2.679 | −11.784 | 19.827 | 1.00 | 41.71 | C |
| ATOM | 1743 | CB | VAL A | 237 | −4.070 | −11.634 | 20.379 | 1.00 | 41.76 | C |
| ATOM | 1744 | CG1 | VAL A | 237 | −4.531 | −12.905 | 21.083 | 1.00 | 44.54 | C |
| ATOM | 1745 | CG2 | VAL A | 237 | −4.148 | −10.468 | 21.321 | 1.00 | 38.31 | C |
| ATOM | 1746 | C | VAL A | 237 | −2.552 | −10.616 | 18.877 | 1.00 | 43.58 | C |
| ATOM | 1747 | O | VAL A | 237 | −1.937 | −9.550 | 19.217 | 1.00 | 45.02 | O |
| ATOM | 1748 | N | ARG A | 238 | −3.247 | −10.788 | 17.748 | 1.00 | 44.01 | N |
| ATOM | 1749 | CA | ARG A | 238 | −3.229 | −9.952 | 16.563 | 1.00 | 43.77 | C |
| ATOM | 1750 | CB | ARG A | 238 | −2.466 | −10.727 | 15.519 | 1.00 | 43.96 | C |
| ATOM | 1751 | CG | ARG A | 238 | −2.163 | −9.977 | 14.340 | 1.00 | 46.38 | C |
| ATOM | 1752 | CD | ARG A | 238 | −1.646 | −10.830 | 13.162 | 1.00 | 48.56 | C |
| ATOM | 1753 | NE | ARG A | 238 | −1.739 | −9.916 | 12.012 | 1.00 | 50.91 | N |
| ATOM | 1754 | CZ | ARG A | 238 | −0.716 | −9.408 | 11.316 | 1.00 | 49.36 | C |
| ATOM | 1755 | NH1 | ARG A | 238 | −0.978 | −8.533 | 10.353 | 1.00 | 47.57 | N |
| ATOM | 1756 | NH2 | ARG A | 238 | 0.548 | −9.793 | 11.544 | 1.00 | 48.90 | N |
| ATOM | 1757 | C | ARG A | 238 | 4.697 | 9.892 | 16.139 | 1.00 | 44.20 | C |
| ATOM | 1758 | O | ARG A | 238 | −5.389 | −10.925 | 16.131 | 1.00 | 43.52 | O |
| ATOM | 1759 | N | GLY A | 239 | −5.217 | −8.697 | 15.829 | 1.00 | 43.51 | N |
| ATOM | 1760 | CA | GLY A | 239 | −6.610 | −8.621 | 15.380 | 1.00 | 42.07 | C |
| ATOM | 1761 | C | GLY A | 239 | −6.658 | −8.596 | 13.882 | 1.00 | 42.44 | C |
| ATOM | 1762 | O | GLY A | 239 | −5.264 | −8.536 | 13.243 | 1.00 | 42.12 | O |
| ATOM | 1763 | N | ASN A | 240 | −7.856 | −8.629 | 13.304 | 1.00 | 43.46 | N |
| ATOM | 1764 | CA | ASN A | 240 | −8.018 | −8.416 | 11.851 | 1.00 | 44.87 | C |
| ATOM | 1765 | CB | ASN A | 240 | −9.477 | −8.539 | 11.493 | 1.00 | 44.96 | C |
| ATOM | 1766 | CG | ASN A | 240 | −9.971 | −9.863 | 11.778 | 1.00 | 48.65 | C |
| ATOM | 1767 | OD1 | ASN A | 240 | −9.413 | −10.825 | 11.262 | 1.00 | 52.52 | O |
| ATOM | 1768 | ND2 | ASN A | 240 | −10.969 | −9.978 | 12.660 | 1.00 | 50.19 | N |
| ATOM | 1769 | C | ASN A | 240 | −7.571 | −7.053 | 11.396 | 1.00 | 45.24 | C |
| ATOM | 1770 | O | ASN A | 240 | −7.832 | −6.040 | 12.103 | 1.00 | 45.75 | O |
| ATOM | 1771 | N | HIS A | 241 | −6.930 | −6.986 | 10.230 | 1.00 | 45.51 | N |
| ATOM | 1772 | CA | HIS A | 241 | −6.515 | −5.670 | 9.738 | 1.00 | 46.35 | C |
| ATOM | 1773 | CB | HIS A | 241 | −5.860 | −5.787 | 8.381 | 1.00 | 47.40 | C |
| ATOM | 1774 | CG | HIS A | 241 | −6.769 | −6.323 | 7.319 | 1.00 | 55.30 | C |
| ATOM | 1775 | ND1 | HIS A | 241 | −6.670 | −7.616 | 6.832 | 1.00 | 57.08 | N |
| ATOM | 1776 | CE1 | HIS A | 241 | −7.598 | −7.800 | 5.907 | 1.00 | 59.02 | C |
| ATOM | 1777 | NE2 | HIS A | 241 | −8.303 | −6.682 | 6.783 | 1.00 | 60.98 | N |
| ATOM | 1778 | CD2 | HIS A | 241 | −7.807 | −5.740 | 6.653 | 1.00 | 59.09 | C |
| ATOM | 1779 | C | HIS A | 241 | −7.745 | −4.748 | 9.734 | 1.00 | 44.85 | C |
| ATOM | 1780 | O | HIS A | 241 | −8.850 | −5.242 | 9.645 | 1.00 | 45.67 | O |
| ATOM | 1781 | N | ILE A | 242 | −7.581 | −3.441 | 9.920 | 1.00 | 43.66 | N |
| ATOM | 1782 | CA | ILE A | 242 | −8.720 | −2.486 | 9.890 | 1.00 | 41.89 | C |
| ATOM | 1783 | CB | ILE A | 242 | −8.793 | −1.665 | 11.180 | 1.00 | 41.97 | C |
| ATOM | 1784 | CG1 | ILE A | 242 | −9.162 | −2.558 | 12.350 | 1.00 | 41.43 | C |
| ATOM | 1785 | CD1 | ILE A | 242 | −8.308 | −2.363 | 13.538 | 1.00 | 42.10 | C |
| ATOM | 1786 | CG2 | ILE A | 242 | −9.808 | −0.563 | 11.077 | 1.00 | 40.89 | C |
| ATOM | 1787 | C | ILE A | 242 | −8.529 | −1.536 | 8.731 | 1.00 | 41.37 | C |
| ATOM | 1788 | O | ILE A | 242 | −7.591 | −0.739 | 8.706 | 1.00 | 40.96 | O |
| ATOM | 1789 | N | ILE A | 243 | −9.401 | −1.631 | 7.742 | 1.00 | 40.70 | N |
| ATOM | 1790 | CA | ILE A | 243 | −9.269 | −0.774 | 6.584 | 1.00 | 39.46 | C |
| ATOM | 1791 | CB | ILE A | 243 | −10.127 | −1.290 | 5.454 | 1.00 | 38.93 | C |
| ATOM | 1792 | CG1 | ILE A | 243 | −11.611 | −1.229 | 5.775 | 1.00 | 38.76 | C |
| ATOM | 1793 | CD1 | ILE A | 243 | −12.510 | −1.520 | 4.495 | 1.00 | 36.76 | C |
| ATOM | 1794 | CG2 | ILE A | 243 | −9.765 | −2.640 | 5.146 | 1.00 | 35.37 | C |
| ATOM | 1795 | C | ILE A | 243 | −9.615 | 0.693 | 6.877 | 1.00 | 40.78 | C |
| ATOM | 1796 | O | ILE A | 243 | −10.311 | 1.014 | 7.882 | 1.00 | 40.62 | O |
| ATOM | 1797 | N | SER A | 244 | −9.132 | 1.584 | 5.998 | 1.00 | 41.15 | N |
| ATOM | 1798 | CA | SER A | 244 | −9.387 | 3.018 | 6.137 | 1.00 | 42.54 | C |
| ATOM | 1799 | CB | SER A | 244 | −8.761 | 3.802 | 4.978 | 1.00 | 43.09 | C |
| ATOM | 1800 | OG | SER A | 244 | −9.345 | 5.118 | 4.840 | 1.00 | 45.81 | O |
| ATOM | 1801 | C | SER A | 244 | −10.892 | 3.301 | 6.235 | 1.00 | 42.36 | C |
| ATOM | 1802 | O | SER A | 244 | −11.687 | 2.593 | 5.628 | 1.00 | 43.36 | O |
| ATOM | 1803 | N | GLY A | 245 | −11.283 | 4.318 | 6.996 | 1.00 | 42.11 | N |
| ATOM | 1804 | CA | GLY A | 245 | −12.669 | 4.646 | 7.155 | 1.00 | 41.60 | C |
| ATOM | 1805 | C | GLY A | 245 | −13.456 | 3.560 | 7.867 | 1.00 | 43.12 | C |
| ATOM | 1806 | O | GLY A | 245 | −14.634 | 3.445 | 7.616 | 1.00 | 44.17 | O |
| ATOM | 1807 | N | THR A | 246 | −12.844 | 2.747 | 8.750 | 1.00 | 43.49 | N |
| ATOM | 1808 | CA | THR A | 246 | −13.628 | 1.841 | 9.614 | 1.00 | 43.41 | C |
| ATOM | 1809 | CB | THR A | 246 | −13.665 | 0.404 | 9.115 | 1.00 | 43.94 | C |
| ATOM | 1810 | OG1 | THR A | 246 | −12.327 | −0.033 | 8.893 | 1.00 | 45.42 | O |
| ATOM | 1811 | CG2 | THR A | 246 | −14.449 | 0.296 | 7.838 | 1.00 | 43.65 | C |
| ATOM | 1812 | C | THR A | 246 | −13.109 | 1.785 | 11.033 | 1.00 | 43.54 | C |
| ATOM | 1813 | O | THR A | 246 | −12.081 | 2.370 | 11.332 | 1.00 | 43.23 | O |
| ATOM | 1814 | N | CYS A | 247 | −13.872 | 1.102 | 11.897 | 1.00 | 44.45 | N |

TABLE 11-continued

| ATOM | 1815 | CA | CYS A | 247 | −13.503 | 0.759 | 13.288 | 1.00 | 45.13 | C |
|---|---|---|---|---|---|---|---|---|---|---|
| ATOM | 1816 | CB | CYS A | 247 | −14.357 | 1.494 | 14.321 | 1.00 | 44.68 | C |
| ATOM | 1817 | SG | CYS A | 247 | −14.498 | 3.261 | 14.158 | 1.00 | 48.61 | S |
| ATOM | 1818 | C | CYS A | 247 | −13.824 | −0.695 | 13.506 | 1.00 | 45.05 | C |
| ATOM | 1819 | O | CYS A | 247 | −14.743 | −1.231 | 12.866 | 1.00 | 45.24 | O |
| ATOM | 1820 | N | ALA A | 248 | 13.111 | −1.308 | 14.447 | 1.00 | 44.48 | N |
| ATOM | 1821 | CA | ALA A | 248 | −13.432 | −2.653 | 14.912 | 1.00 | 43.85 | C |
| ATOM | 1822 | CB | ALA A | 248 | −12.570 | −3.700 | 14.227 | 1.00 | 43.79 | C |
| ATOM | 1823 | C | ALA A | 248 | −13.214 | −2.684 | 16.403 | 1.00 | 43.50 | C |
| ATOM | 1824 | O | ALA A | 248 | −12.684 | −1.717 | 16.971 | 1.00 | 43.41 | O |
| ATOM | 1825 | N | SER A | 249 | −13.592 | −3.827 | 16.998 | 1.00 | 43.05 | N |
| ATOM | 1826 | CA | SER A | 249 | −13.785 | −4.035 | 18.443 | 1.00 | 41.27 | C |
| ATOM | 1827 | CB | SER A | 249 | −15.255 | −4.071 | 18.719 | 1.00 | 40.45 | C |
| ATOM | 1828 | OG | SER A | 249 | −15.639 | −2.776 | 18.970 | 1.00 | 42.33 | O |
| ATOM | 1829 | C | SER A | 249 | −13.245 | −5.351 | 18.972 | 1.00 | 40.58 | C |
| ATOM | 1830 | O | SER A | 249 | −13.285 | −6.361 | 18.268 | 1.00 | 38.98 | O |
| ATOM | 1831 | N | TRP A | 250 | −12.738 | −5.319 | 20.211 | 1.00 | 40.32 | N |
| ATOM | 1832 | CA | TRP A | 250 | −12.508 | −6.551 | 20.948 | 1.00 | 40.82 | C |
| ATOM | 1833 | CB | TRP A | 250 | −11.057 | −6.689 | 21.483 | 1.00 | 40.67 | C |
| ATOM | 1834 | CG | TRP A | 250 | −10.047 | −6.794 | 20.429 | 1.00 | 39.94 | C |
| ATOM | 1835 | CD1 | TRP A | 250 | −10.281 | −6.986 | 19.075 | 1.00 | 39.55 | C |
| ATOM | 1836 | NE1 | TRP A | 250 | −9.090 | −7.008 | 18.383 | 1.00 | 40.18 | N |
| ATOM | 1837 | CE2 | TRP | 250 | −8.059 | −6.836 | 19.278 | 1.00 | 40.11 | C |
| ATOM | 1838 | CD2 | TRP A | 250 | −8.634 | −6.684 | 20.578 | 1.00 | 39.41 | C |
| ATOM | 1839 | CE3 | TRP A | 250 | −7.785 | −6.526 | 21.668 | 1.00 | 38.75 | C |
| ATOM | 1840 | CZ3 | TRP A | 250 | −6.379 | −6.544 | 21.430 | 1.00 | 36.16 | C |
| ATOM | 1841 | CH2 | TRP A | 250 | −5.862 | −6.659 | 20.143 | 1.00 | 34.07 | C |
| ATOM | 1842 | CZ2 | TRP A | 250 | −6.670 | −6.818 | 19.060 | 1.00 | 36.63 | C |
| ATOM | 1843 | C | TRP A | 250 | −13.504 | −6.587 | 22.076 | 1.00 | 40.86 | C |
| ATOM | 1844 | O | TRP A | 250 | −13.761 | −5.587 | 22.727 | 1.00 | 40.92 | O |
| ATOM | 1845 | N | ARG A | 251 | −14.077 | −7.750 | 22.305 | 1.00 | 41.84 | N |
| ATOM | 1846 | CA | ARG A | 251 | −15.141 | −7.882 | 23.311 | 1.00 | 42.37 | C |
| ATOM | 1847 | CB | ARG A | 251 | −16.511 | −7.966 | 22.633 | 1.00 | 41.29 | C |
| ATOM | 1848 | CG | ARG A | 251 | −16.900 | −6.675 | 22.014 | 1.00 | 38.27 | C |
| ATOM | 1849 | CD | ARG A | 251 | −17.206 | −5.717 | 23.066 | 1.00 | 38.21 | C |
| ATOM | 1850 | NE | ARG A | 251 | −17.660 | −4.464 | 22.521 | 1.00 | 43.40 | N |
| ATOM | 1851 | CZ | ARG A | 251 | −16.867 | −3.428 | 22.289 | 1.00 | 44.50 | C |
| ATOM | 1852 | NH1 | ARG A | 251 | −15.577 | −3.515 | 22.538 | 1.00 | 50.06 | N |
| ATOM | 1853 | NH2 | ARG A | 251 | −17.348 | −2.305 | 21.814 | 1.00 | 44.99 | N |
| ATOM | 1854 | C | ARG A | 251 | −14.872 | −9.144 | 24.023 | 1.00 | 43.01 | C |
| ATOM | 1855 | O | ARG A | 251 | −15.343 | −10.185 | 23.616 | 1.00 | 43.90 | O |
| ATOM | 1856 | N | GLY A | 252 | −14.016 | −9.075 | 25.020 | 1.00 | 44.32 | N |
| ATOM | 1857 | CA | GLY A | 252 | −13.658 | −10.279 | 25.771 | 1.00 | 45.70 | C/ |
| ATOM | 1858 | C | GLY A | 252 | −12.513 | −11.075 | 25.172 | 1.00 | 45.94 | C |
| ATOM | 1859 | O | GLY A | 252 | −12.158 | −12.135 | 25.691 | 1.00 | 47.33 | O |
| ATOM | 1860 | N | LYS A | 253 | −11.954 | −10.576 | 24.086 | 1.00 | 44.79 | N |
| ATOM | 1861 | CA | LYS A | 253 | −10.784 | −11.153 | 23.526 | 1.00 | 45.35 | C |
| ATOM | 1862 | CB | LYS A | 253 | −10.260 | −10.270 | 22.410 | 1.00 | 45.65 | C |
| ATOM | 1863 | CG | LYS A | 253 | −8.828 | −10.527 | 22.084 | 1.00 | 46.48 | C |
| ATOM | 1864 | CD | LYS A | 253 | −8.687 | −11.222 | 20.765 | 1.00 | 48.09 | C |
| ATOM | 1865 | CE | LYS A | 253 | −8.865 | −10.251 | 19.621 | 1.00 | 47.17 | C |
| AOTM | 1866 | NZ | LYS A | 253 | −8.980 | −11.072 | 18.436 | 1.00 | 50.58 | N |
| ATOM | 1867 | C | LYS A | 253 | −9.765 | −11.206 | 24.642 | 1.00 | 45.78 | C |
| ATOM | 1868 | O | LYS A | 253 | −9.634 | −10.263 | 25.423 | 1.00 | 46.65 | O |
| ATOM | 1869 | N | SER A | 254 | −9.045 | −12.319 | 24.721 | 1.00 | 45.73 | N |
| ATOM | 1870 | CA | SER A | 254 | −8.394 | −12.692 | 25.973 | 1.00 | 45.16 | C |
| ATOM | 1871 | CB | SER A | 254 | −9.280 | −13.722 | 26.725 | 1.00 | 45.35 | C |
| ATOM | 1872 | OG | SER A | 254 | −8.917 | −15.077 | 26.487 | 1.00 | 47.55 | O |
| ATOM | 1873 | C | SER A | 254 | −6.907 | −13.145 | 25.809 | 1.00 | 43.70 | C |
| ATOM | 1874 | O | SER A | 254 | −6.579 | −13.813 | 24.847 | 1.00 | 42.32 | O |
| ATOM | 1875 | N | LEU A | 255 | −6.031 | −12.741 | 26.736 | 1.00 | 42.45 | N |
| ATOM | 1876 | CA | LEU A | 255 | −4.649 | −13.184 | 26.722 | 1.00 | 41.63 | C |
| ATOM | 1877 | CB | LEU A | 255 | −3.716 | −11.998 | 26.771 | 1.00 | 41.01 | C |
| ATOM | 1878 | CG | LEU A | 255 | −3.293 | −11.348 | 25.513 | 1.00 | 37.95 | C |
| ATOM | 1879 | CD1 | LEU A | 255 | −2.474 | −10.226 | 25.949 | 1.00 | 37.80 | C |
| ATOM | 1880 | CD2 | LEU A | 255 | −2.475 | −12.332 | 24.818 | 1.00 | 39.33 | C |
| ATOM | 1881 | C | LEU A | 255 | −4.390 | −13.950 | 27.982 | 1.00 | 42.36 | C |
| ATOM | 1882 | O | LEU A | 255 | −4.828 | −13.514 | 29.050 | 1.00 | 41.87 | O |
| ATOM | 1883 | N | ARG A | 256 | −3.625 | −15.031 | 27.844 | 1.00 | 42.04 | N |
| ATOM | 1884 | CA | ARG A | 256 | −3.276 | −15.947 | 28.911 | 1.00 | 44.20 | C |
| ATOM | 1885 | CB | ARG A | 256 | −2.830 | −17.297 | 28.258 | 1.00 | 44.46 | C |
| ATOM | 1886 | CG | ARG A | 256 | −2.176 | −18.358 | 29.165 | 1.00 | 44.03 | C |
| ATOM | 1887 | CD | ARG A | 256 | −3.105 | −18.740 | 30.328 | 1.00 | 52.30 | C |
| ATOM | 1888 | NE | ARG A | 256 | −4.314 | −19.480 | 29.927 | 1.00 | 55.85 | N |
| ATOM | 1889 | CZ | ARG A | 256 | −4.358 | −20.799 | 29.664 | 1.00 | 58.59 | C |
| ATOM | 1890 | NH1 | ARG A | 256 | −3.254 | −21.544 | 29.710 | 1.00 | 55.50 | N |
| ATOM | 1891 | NH2 | ARG A | 256 | −5.516 | −21.377 | 29.303 | 1.00 | 60.80 | N |
| ATOM | 1892 | C | ARG A | 256 | −2.134 | −15.357 | 29.727 | 1.00 | 44.86 | C |
| ATOM | 1893 | O | ARG A | 256 | −1.203 | −14.780 | 29.157 | 1.00 | 44.39 | O |
| ATOM | 1894 | N | VAL A | 257 | −2.141 | −15.565 | 31.041 | 1.00 | 45.98 | N |

TABLE 11-continued

| | | | | | | | | | |
|---|---|---|---|---|---|---|---|---|---|
| ATOM | 1895 | CA | VAL A | 257 | −0.953 | −15.190 | 31.825 | 1.00 | 47.59 | C |
| ATOM | 1896 | CB | VAL A | 257 | −1.338 | −14.528 | 33.140 | 1.00 | 46.66 | C |
| ATOM | 1897 | CG1 | VAL A | 257 | −0.137 | −13.858 | 33.744 | 1.00 | 45.37 | C |
| ATOM | 1898 | CG2 | VAL A | 257 | −2.417 | −13.523 | 32.887 | 1.00 | 45.29 | C |
| ATOM | 1899 | C | VAL A | 257 | −0.074 | −16.388 | 32.111 | 1.00 | 49.86 | C |
| ATOM | 1900 | O | VAL A | 257 | −0.395 | −17.204 | 32.982 | 1.00 | 50.96 | O |
| ATOM | 1901 | N | GLN A | 258 | 1.034 | −16.513 | 31.392 | 1.00 | 52.45 | N |
| ATOM | 1902 | CA | GLN A | 258 | 1.902 | −17.698 | 31.557 | 1.00 | 54.37 | C |
| ATOM | 1903 | CB | GLN A | 258 | 2.561 | −18.081 | 30.242 | 1.00 | 53.91 | C |
| ATOM | 1904 | CG | GLN A | 258 | 2.391 | −17.033 | 29.162 | 1.00 | 56.91 | C |
| ATOM | 1905 | CD | GLN A | 258 | 3.068 | −17.378 | 27.849 | 1.00 | 57.90 | C |
| ATOM | 1906 | OE1 | GLN A | 258 | 2.630 | −18.265 | 27.101 | 1.00 | 59.70 | O |
| ATOM | 1907 | NE2 | GLN A | 258 | 4.124 | −16.650 | 27.545 | 1.00 | 57.19 | N |
| ATOM | 1908 | C | GLN A | 258 | 2.940 | −17.512 | 32.678 | 1.00 | 55.95 | C |
| ATOM | 1909 | O | GLN A | 258 | 3.409 | −16.366 | 32.922 | 1.00 | 55.04 | O |
| ATOM | 1910 | N | LYS A | 259 | 3.230 | −18.625 | 33.390 | 1.00 | 57.95 | N |
| ATOM | 1911 | CA | LYS A | 259 | 4.351 | −18.717 | 34.355 | 1.00 | 60.10 | C |
| ATOM | 1912 | CB | LYS A | 259 | 4.489 | −20.133 | 34.927 | 1.00 | 60.43 | C |
| ATOM | 1913 | CG | LYS A | 259 | 3.181 | −20.858 | 35.292 | 1.00 | 63.67 | C |
| ATOM | 1914 | CD | LYS A | 259 | 3.209 | −22.414 | 34.966 | 1.00 | 66.34 | C |
| ATOM | 1915 | CE | LYS A | 259 | 2.865 | −22.696 | 33.437 | 1.00 | 66.97 | C |
| ATOM | 1916 | NZ | LYS A | 259 | 2.104 | −23.982 | 33.228 | 1.00 | 65.53 | N |
| ATOM | 1917 | C | LYS A | 259 | 5.639 | −18.417 | 33.608 | 1.00 | 61.14 | C |
| ATOM | 1918 | O | LYS A | 259 | 5.760 | −18.741 | 32.441 | 1.00 | 60.48 | O |
| ATOM | 1919 | N | ILE A | 260 | 6.623 | −17.815 | 34.256 | 1.00 | 63.51 | N |
| ATOM | 1920 | CA | ILE A | 260 | 7.957 | −17.731 | 33.615 | 1.00 | 65.22 | C |
| ATOM | 1921 | CB | ILE A | 260 | 8.680 | −16.412 | 33.929 | 1.00 | 65.30 | C |
| ATOM | 1922 | CG1 | ILE A | 260 | 7.735 | −15.232 | 33.603 | 1.00 | 64.89 | C |
| ATOM | 1923 | CD1 | ILE A | 260 | 8.311 | −14.169 | 32.710 | 1.00 | 63.98 | C |
| ATOM | 1924 | CG2 | ILE A | 260 | 10.098 | −16.391 | 33.249 | 1.00 | 64.71 | C |
| ATOM | 1925 | C | ILE A | 260 | 8.797 | −18.928 | 34.078 | 1.00 | 65.58 | C |
| ATOM | 1926 | O | ILE A | 260 | 8.321 | −19.714 | 34.917 | 1.00 | 66.90 | O |
| ATOM | 1927 | N | ARG A | 261 | 10.020 | −19.073 | 33.546 | 1.00 | 67.89 | N |
| ATOM | 1928 | CA | ARG A | 261 | 10.980 | −20.095 | 34.029 | 1.00 | 68.69 | C |
| ATOM | 1929 | CB | ARG A | 261 | 11.797 | −20.668 | 32.873 | 1.00 | 68.73 | C |
| ATOM | 1930 | CG | ARG A | 261 | 11.626 | −22.188 | 32.693 | 1.00 | 71.95 | C |
| ATOM | 1931 | CD | ARG A | 261 | 12.576 | −23.014 | 33.637 | 1.00 | 75.42 | C |
| ATOM | 1932 | NE | ARG A | 261 | 13.753 | −22.226 | 34.056 | 1.00 | 76.35 | N |
| ATOM | 1933 | CZ | ARG A | 261 | 14.934 | −22.218 | 33.429 | 1.00 | 76.13 | C |
| ATOM | 1934 | NH1 | ARG A | 261 | 15.127 | −22.978 | 32.351 | 1.00 | 75.58 | N |
| ATOM | 1935 | NH2 | ARG A | 261 | 15.930 | −21.448 | 33.878 | 1.00 | 74.58 | N |
| ATOM | 1936 | C | ARG A | 261 | 11.887 | −19.595 | 35.164 | 1.00 | 68.51 | C |
| ATOM | 1937 | O | ARG A | 261 | 11.736 | −20.010 | 36.324 | 1.00 | 68.18 | O |
| ATOM | 1938 | N | ASN A | 268 | 19.389 | −13.865 | 40.743 | 1.00 | 65.44 | N |
| ATOM | 1939 | CA | ASN A | 268 | 19.999 | −12.556 | 40.441 | 1.00 | 65.39 | C |
| ATOM | 1940 | CB | ASN A | 268 | 21.240 | −12.719 | 39.665 | 1.00 | 65.21 | C |
| ATOM | 1941 | CG | ASN A | 268 | 22.543 | −12.273 | 40.502 | 1.00 | 66.25 | C |
| ATOM | 1942 | OD1 | ASN A | 268 | 22.425 | 12.044 | 41.713 | 1.00 | 62.39 | C |
| ATOM | 1943 | ND2 | ASN A | 268 | 23.714 | −12.125 | 39.849 | 1.00 | 67.53 | N |
| ATOM | 1944 | C | ASN A | 268 | 19.090 | −11.465 | 39.800 | 1.00 | 64.95 | C |
| ATOM | 1945 | O | ASN A | 268 | 19.542 | −10.370 | 39.410 | 1.00 | 65.09 | O |
| ATOM | 1946 | N | ILE A | 269 | 17.810 | −11.758 | 39.696 | 1.00 | 63.89 | N |
| ATOM | 1947 | CA | ILE A | 269 | 16.891 | −10.737 | 39.232 | 1.00 | 63.44 | C |
| ATOM | 1948 | CB | ILE A | 269 | 15.777 | −11.347 | 38.329 | 1.00 | 64.00 | C |
| ATOM | 1949 | CG1 | ILE A | 269 | 15.199 | −12.604 | 38.978 | 1.00 | 64.25 | C |
| ATOM | 1950 | CD1 | ILE A | 269 | 13.722 | −12.739 | 38.713 | 1.00 | 68.77 | C |
| ATOM | 1951 | CG2 | ILE A | 269 | 16.335 | −11.704 | 35.916 | 1.00 | 64.48 | C |
| ATOM | 1952 | C | ILE A | 269 | 16.302 | −10.116 | 40.493 | 1.00 | 61.67 | C |
| ATOM | 1953 | O | ILE A | 269 | 16.033 | −10.875 | 41.436 | 1.00 | 62.18 | O |
| ATOM | 1954 | N | LEU A | 270 | 16.116 | −8.781 | 40.531 | 1.00 | 58.75 | N |
| ATOM | 1955 | CA | LEU A | 270 | 15.429 | −8.125 | 41.682 | 1.00 | 55.54 | C |
| ATOM | 1956 | CB | LEU A | 270 | 15.749 | −6.642 | 41.782 | 1.00 | 54.79 | C |
| ATOM | 1957 | CG | LEU A | 270 | 17.256 | −6.393 | 41.727 | 1.00 | 53.81 | C |
| ATOM | 1958 | CD1 | LEU A | 270 | 17.613 | −5.326 | 40.779 | 1.00 | 48.96 | C |
| ATOM | 1959 | CD2 | LEU A | 270 | 17.757 | −6.037 | 43.050 | 1.00 | 49.73 | C |
| ATOM | 1960 | C | LEU A | 270 | 13.952 | −8.319 | 41.523 | 1.00 | 54.43 | C |
| ATOM | 1961 | O | LEU A | 270 | 13.319 | −8.941 | 42.362 | 1.00 | 53.41 | O |
| ATOM | 1962 | N | ARG A | 271 | 13.419 | −7.847 | 40.400 | 1.00 | 53.65 | N |
| ATOM | 1963 | CA | ARG A | 271 | 11.988 | −7.963 | 40.119 | 1.00 | 53.06 | C |
| ATOM | 1964 | CB | ARG A | 271 | 11.320 | −6.685 | 40.553 | 1.00 | 52.89 | C |
| ATOM | 1965 | CG | ARG A | 271 | 11.990 | −5.508 | 39.894 | 1.00 | 51.87 | C |
| ATOM | 1966 | CD | ARG A | 271 | 11.430 | −4.269 | 40.478 | 1.00 | 49.59 | C |
| ATOM | 1967 | NE | ARG A | 271 | 12.615 | −3.546 | 40.882 | 1.00 | 53.41 | N |
| ATOM | 1968 | CZ | ARG A | 271 | 13.045 | −2.419 | 40.343 | 1.00 | 52.77 | C |
| ATOM | 1969 | NH1 | ARG A | 271 | 12.361 | −1.823 | 39.386 | 1.00 | 53.39 | N |
| ATOM | 1970 | NH2 | ARG A | 271 | 14.160 | −1.867 | 40.799 | 1.00 | 55.05 | N |
| ATOM | 1971 | C | ARG A | 271 | 11.668 | −8.167 | 38.641 | 1.00 | 53.57 | C |
| ATOM | 1972 | O | ARG A | 271 | 12.533 | −7.961 | 37.752 | 1.00 | 54.29 | O |
| ATOM | 1973 | N | VAL A | 272 | 10.422 | −8.550 | 38.372 | 1.00 | 52.65 | N |
| ATOM | 1974 | CA | VAL A | 272 | 9.910 | −8.525 | 37.003 | 1.00 | 52.83 | C |

TABLE 11-continued

| | | | | | | | | | |
|---|---|---|---|---|---|---|---|---|---|
| ATOM | 1975 | CB | VAL A | 272 | 9.376 | −9.891 | 36.558 | 1.00 | 52.33 | C |
| ATOM | 1976 | CG1 | VAL A | 272 | 9.044 | −9.972 | 35.001 | 1.00 | 51.74 | C |
| ATOM | 1977 | CG2 | VAL A | 272 | 10.214 | −10.962 | 37.088 | 1.00 | 52.37 | C |
| ATOM | 1978 | C | VAL A | 272 | 8.732 | −7.561 | 38.966 | 1.00 | 52.65 | C |
| ATOM | 1979 | O | VAL A | 272 | 7.758 | −7.794 | 37.617 | 1.00 | 54.26 | O |
| ATOM | 1980 | N | GLU A | 273 | 8.806 | −6.484 | 36.221 | 1.00 | 51.92 | N |
| ATOM | 1981 | CA | GLU A | 273 | 7.632 | −5.675 | 35.993 | 1.00 | 51.18 | C |
| ATOM | 1982 | CB | GLU A | 273 | 8.023 | −4.215 | 35.875 | 1.00 | 52.40 | C |
| ATOM | 1983 | CG | GLU A | 273 | 8.561 | −3.585 | 37.162 | 1.00 | 55.83 | C |
| ATOM | 1984 | CD | GLU A | 273 | 9.350 | −2.319 | 36.861 | 1.00 | 61.55 | C |
| ATOM | 1985 | OE1 | GLU A | 273 | 9.164 | −1.723 | 35.712 | 1.00 | 65.47 | O |
| ATOM | 1986 | OE2 | GLU A | 273 | 10.144 | −1.941 | 37.770 | 1.00 | 56.53 | O |
| ATOM | 1987 | C | GLU A | 273 | 6.912 | 6.091 | 34.704 | 1.00 | 49.53 | C |
| ATOM | 1988 | O | GLU A | 273 | 7.523 | −6.298 | 33.674 | 1.00 | 48.98 | O |
| ATOM | 1989 | N | TYR A | 274 | 5.595 | −6.154 | 34.784 | 1.00 | 48.17 | N |
| ATOM | 1990 | CA | TYR A | 274 | 4.713 | −6.653 | 33.743 | 1.00 | 45.83 | C |
| ATOM | 1991 | CB | TYR A | 274 | 3.842 | −7.655 | 34.388 | 1.00 | 45.71 | C |
| ATOM | 1992 | CG | TYR A | 274 | 4.557 | −8.878 | 34.791 | 1.00 | 45.71 | C |
| ATOM | 1993 | CD1 | TYR A | 274 | 4.716 | −9.930 | 33.887 | 1.00 | 45.97 | C |
| ATOM | 1994 | CE1 | TYR A | 274 | 5.360 | −11.106 | 34.260 | 1.00 | 45.17 | C |
| ATOM | 1995 | CZ | TYR A | 274 | 5.833 | −11.238 | 35.549 | 1.00 | 44.97 | C |
| ATOM | 1996 | OH | TYR A | 274 | 6.433 | −12.393 | 35.896 | 1.00 | 9.54 | O |
| ATOM | 1997 | CE2 | TYR A | 274 | 5.686 | −10.231 | 36.479 | 1.00 | 47.15 | C |
| ATOM | 1998 | CD2 | TYR A | 274 | 5.025 | −9.037 | 36.091 | 1.00 | 48.15 | C |
| ATOM | 1999 | C | TYR A | 274 | 3.795 | −5.606 | 33.142 | 1.00 | 44.20 | C |
| ATOM | 2000 | O | TYR A | 274 | 3.422 | −4.661 | 33.814 | 1.00 | 45.17 | O |
| ATOM | 2001 | N | SER A | 275 | 3.444 | −5.744 | 31.877 | 1.00 | 41.99 | N |
| ATOM | 2002 | CA | SER A | 275 | 2.585 | −4.750 | 31.263 | 1.00 | 41.57 | C |
| ATOM | 2003 | CB | SER A | 275 | 3.388 | −3.650 | 30.532 | 1.00 | 42.58 | C |
| ATOM | 2004 | OG | SER A | 275 | 3.662 | −2.507 | 31.341 | 1.00 | 44.08 | O |
| ATOM | 2005 | C | SER A | 275 | 1.752 | −5.414 | 30.256 | 1.00 | 39.91 | C |
| ATOM | 2006 | O | SER A | 275 | 2.181 | −6.387 | 29.631 | 1.00 | 40.86 | O |
| ATOM | 2007 | N | LEU A | 276 | 0.560 | −4.885 | 30.079 | 1.00 | 38.14 | N |
| ATOM | 2008 | CA | LEU A | 276 | −0.228 | −5.198 | 28.937 | 1.00 | 37.09 | C |
| ATOM | 2009 | CB | LEU A | 276 | −1.650 | −5.396 | 29.355 | 1.00 | 36.78 | C |
| ATOM | 2010 | CG | LEU A | 276 | −2.694 | −5.653 | 28.256 | 1.00 | 35.00 | C |
| ATOM | 2011 | CD1 | LEU A | 276 | −2.365 | −6.856 | 27.323 | 1.00 | 30.33 | C |
| ATOM | 2012 | CD2 | LEU A | 276 | −3.866 | −5.920 | 29.039 | 1.00 | 28.95 | C |
| ATOM | 2013 | C | LEU A | 276 | −0.120 | −4.043 | 27.951 | 1.00 | 37.82 | C |
| ATOM | 2014 | O | LEU A | 276 | −0.392 | −2.887 | 28.277 | 1.00 | 37.39 | O |
| ATOM | 2015 | N | LEU A | 277 | 0.330 | −4.388 | 26.755 | 1.00 | 38.11 | N |
| ATOM | 2016 | CA | LEU A | 277 | 0.483 | −3.476 | 25.671 | 1.00 | 38.38 | C |
| ATOM | 2017 | CB | LEU A | 277 | 1.837 | −3.720 | 24.982 | 1.00 | 38.74 | C |
| ATOM | 2018 | CG | LEU A | 277 | 3.067 | −2.851 | 25.387 | 1.00 | 39.05 | C |
| ATOM | 2019 | CD1 | LEU A | 277 | 3.094 | −2.412 | 26.844 | 1.00 | 34.62 | C |
| ATOM | 2020 | CD2 | LEU A | 277 | 4.318 | −3.616 | 25.078 | 1.00 | 41.16 | C |
| ATOM | 2021 | C | LEU A | 277 | −0.631 | 3.716 | 24.704 | 1.00 | 38.57 | C |
| ATOM | 2022 | O | LEU A | 277 | −0.812 | −4.813 | 24.223 | 1.00 | 39.80 | O |
| ATOM | 2023 | N | ILE A | 278 | −1.400 | −2.675 | 24.493 | 1.00 | 39.62 | N |
| ATOM | 2024 | CA | ILE A | 278 | −2.403 | −2.687 | 23.370 | 1.00 | 39.22 | C |
| ATOM | 2025 | CB | ILE A | 278 | −3.815 | −2.408 | 32.911 | 1.00 | 39.39 | C |
| ATOM | 2026 | CG1 | ILE A | 278 | −4.271 | −3.546 | 24.806 | 1.00 | 41.53 | C |
| ATOM | 2027 | CD1 | ILE A | 278 | −5.018 | −3.045 | 26.038 | 1.00 | 41.68 | C |
| ATOM | 2028 | CG2 | ILE A | 278 | −4.804 | −2.498 | 22.808 | 1.00 | 40.95 | C |
| ATOM | 2029 | C | ILE A | 278 | −1.949 | −1.600 | 22.385 | 1.00 | 38.52 | C |
| ATOM | 2030 | O | ILE A | 278 | −1.775 | −0.441 | 22.764 | 1.00 | 38.49 | O |
| ATOM | 2031 | N | TYR A | 279 | −1.713 | −1.988 | 21.139 | 1.00 | 37.38 | N |
| ATOM | 2032 | CA | TYR A | 279 | 1.108 | 1.083 | 20.191 | 1.00 | 37.10 | C |
| ATOM | 2033 | CB | TYR A | 279 | 0.457 | −1.129 | 20.229 | 1.00 | 36.90 | C |
| ATOM | 2034 | CG | TYR A | 279 | 1.147 | −2.493 | 19.924 | 1.00 | 40.58 | C |
| ATOM | 2035 | CD1 | TYR A | 279 | 1.082 | −3.585 | 20.843 | 1.00 | 39.98 | C |
| ATOM | 2036 | CE1 | TYR A | 279 | 1.703 | −4.842 | 20.525 | 1.00 | 40.30 | C |
| ATOM | 2037 | CZ | TYR A | 279 | 2.402 | −4.974 | 19.315 | 1.00 | 39.02 | C |
| ATOM | 2038 | OH | TYR A | 279 | 2.991 | −6.175 | 18.994 | 1.00 | 39.60 | O |
| ATOM | 2039 | CE2 | TYR A | 279 | 2.492 | −3.900 | 18.417 | 1.00 | 36.52 | C |
| ATOM | 2040 | CD2 | TYR A | 279 | 1.874 | −2.694 | 18.704 | 1.00 | 37.00 | C |
| ATOM | 2041 | C | TYR A | 279 | −1.745 | −1.247 | 18.820 | 1.00 | 36.61 | C |
| ATOM | 2042 | O | TYR A | 279 | −2.409 | −2.215 | 18.526 | 1.00 | 36.79 | O |
| ATOM | 2043 | N | VAL A | 280 | −1.660 | −0.238 | 18.00 | 1.00 | 36.12 | N |
| ATOM | 2044 | CA | VAL A | 280 | −2.184 | −0.394 | 16.681 | 1.00 | 35.05 | C |
| ATOM | 2045 | CB | VAL A | 280 | −3.213 | 0.704 | 16.265 | 1.00 | 35.30 | C |
| ATOM | 2046 | CG1 | VAL A | 280 | −3.640 | 0.486 | 14.804 | 1.00 | 34.26 | C |
| ATOM | 2047 | CG2 | VAL A | 280 | −4.381 | 0.690 | 17.135 | 1.00 | 33.18 | C |
| ATOM | 2048 | C | VAL A | 280 | −0.975 | −0.107 | 15.901 | 1.00 | 34.49 | C |
| ATOM | 2049 | O | VAL A | 280 | −0.380 | 0.959 | 16.002 | 1.00 | 34.98 | O |
| ATOM | 2050 | N | SER A | 281 | −0.601 | −1.041 | 15.089 | 1.00 | 34.02 | N |
| ATOM | 2051 | CA | SER A | 281 | 0.550 | −0.806 | 14.270 | 1.00 | 35.18 | C |
| ATOM | 2052 | CB | SER A | 281 | 1.280 | −2.126 | 14.138 | 1.00 | 34.38 | C |
| ATOM | 2053 | OG | SER A | 281 | 1.525 | −2.327 | 12.821 | 1.00 | 35.73 | O |
| ATOM | 2054 | C | SER A | 281 | 0.163 | −0.118 | 12.933 | 1.00 | 35.69 | C |

TABLE 11-continued

| | | | | | | | | | |
|---|---|---|---|---|---|---|---|---|---|
| ATOM | 2055 | O | SER A | 281 | −0.828 | −0.457 | 12.301 | 1.00 | 33.97 | O |
| ATOM | 2056 | N | VAL A | 282 | 0.933 | 0.890 | 12.532 | 1.00 | 38.71 | N |
| ATOM | 2057 | CA | VAL A | 282 | 0.544 | 1.795 | 11.376 | 1.00 | 40.25 | C |
| ATOM | 2058 | CB | VAL A | 282 | 0.241 | 3.234 | 11.852 | 1.00 | 39.18 | C |
| ATOM | 2059 | CG1 | VAL A | 282 | −0.140 | 4.060 | 10.706 | 1.00 | 40.09 | C |
| ATOM | 2060 | CG2 | VAL A | 282 | −0.888 | 3.240 | 12.853 | 1.00 | 39.62 | C |
| ATOM | 2061 | C | VAL A | 282 | 1.618 | 1.865 | 10.281 | 1.00 | 41.19 | C |
| ATOM | 2062 | O | VAL A | 282 | 2.672 | 2.428 | 10.502 | 1.00 | 41.14 | O |
| ATOM | 2063 | N | PRO A | 283 | 1.359 | 1.273 | 9.107 | 1.00 | 42.67 | N |
| ATOM | 2064 | CA | PRO A | 283 | 2.446 | 1.188 | 8.125 | 1.00 | 44.35 | C |
| ATOM | 2065 | CB | PRO A | 283 | 1.808 | 0.426 | 6.497 | 1.00 | 43.22 | C |
| ATOM | 2066 | CG | PRO A | 283 | 0.691 | −0.318 | 7.537 | 1.00 | 43.02 | C |
| ATOM | 2067 | CD | PRO A | 283 | 0.143 | 0.614 | 8.610 | 1.00 | 42.87 | C |
| ATOM | 2068 | C | PRO A | 283 | 2.923 | 2.572 | 7.706 | 1.00 | 45.51 | C |
| ATOM | 2069 | O | PRO A | 283 | 2.080 | 3.413 | 7.429 | 1.00 | 46.40 | O |
| ATOM | 2070 | N | GLY A | 284 | 4.251 | 2.790 | 7.681 | 1.00 | 46.60 | N |
| ATOM | 2071 | CA | GLY A | 284 | 4.847 | 4.106 | 7.456 | 1.00 | 47.28 | C |
| ATOM | 2072 | C | GLY A | 284 | 4.948 | 5.028 | 8.682 | 1.00 | 48.87 | C |
| ATOM | 2073 | O | GLY A | 284 | 5.427 | 6.172 | 8.549 | 1.00 | 49.34 | O |
| ATOM | 2074 | N | SER A | 285 | 4.532 | 4.567 | 9.874 | 1.00 | 48.33 | N |
| ATOM | 2075 | CA | SER A | 285 | 4.489 | 5.441 | 11.050 | 1.00 | 49.03 | C |
| ATOM | 2076 | CB | SER A | 285 | 3.147 | 6.189 | 11.143 | 1.00 | 49.89 | C |
| ATOM | 2077 | OG | SER A | 285 | 2.951 | 7.040 | 10.023 | 1.00 | 54.03 | O |
| ATOM | 2078 | C | SER A | 285 | 4.760 | 4.727 | 12.388 | 1.00 | 48.99 | C |
| ATOM | 2079 | O | SER A | 285 | 4.842 | 3.493 | 12.446 | 1.00 | 50.09 | O |
| ATOM | 2080 | N | LYS A | 286 | 4.903 | 5.494 | 13.470 | 1.00 | 47.51 | N |
| ATOM | 2081 | CA | LYS A | 286 | 5.153 | 4.880 | 14.675 | 1.00 | 46.39 | C |
| ATOM | 2082 | CB | LYS A | 286 | 5.716 | 5.932 | 15.748 | 1.00 | 46.87 | C |
| ATOM | 2083 | CG | LYS A | 286 | 7.166 | 6.329 | 15.515 | 1.00 | 48.40 | C |
| ATOM | 2084 | CD | LYS A | 286 | 7.328 | 7.832 | 15.650 | 1.00 | 52.11 | C |
| ATOM | 2085 | CE | LYS A | 286 | 8.794 | 8.193 | 15.763 | 1.00 | 54.41 | C |
| ATOM | 2086 | NZ | LYS A | 286 | 9.293 | 7.856 | 17.152 | 1.00 | 59.34 | N |
| ATOM | 2087 | C | LYS A | 286 | 3.864 | 4.210 | 15.306 | 1.00 | 44.71 | C |
| ATOM | 2088 | O | LYS A | 286 | 2.792 | 4.685 | 15.044 | 1.00 | 44.20 | O |
| ATOM | 2089 | N | LYS A | 287 | 3.976 | 3.117 | 16.049 | 1.00 | 43.36 | N |
| ATOM | 2090 | CA | LYS A | 287 | 2.820 | 2.518 | 16.704 | 1.00 | 42.67 | C |
| ATOM | 2091 | CB | LYS A | 287 | 3.261 | 1.366 | 17.608 | 1.00 | 41.54 | C |
| ATOM | 2092 | CG | LYS A | 287 | 3.917 | 0.244 | 16.828 | 1.00 | 43.83 | C |
| ATOM | 2093 | CD | LYS A | 287 | 4.637 | −0.754 | 17.738 | 1.00 | 43.93 | C |
| ATOM | 2094 | CE | LYS A | 287 | 5.183 | −1.900 | 16.921 | 1.00 | 44.16 | C |
| ATOM | 2095 | NZ | LYS A | 287 | 6.625 | −1.768 | 16.445 | 1.00 | 49.47 | N |
| ATOM | 2096 | C | LYS A | 287 | 2.030 | 3.552 | 17.527 | 1.00 | 42.74 | C |
| ATOM | 2097 | O | LYS A | 287 | 2.588 | 4.623 | 17.903 | 1.00 | 43.55 | O |
| ATOM | 2098 | N | VAL A | 288 | 0.742 | 3.252 | 17.763 | 1.00 | 40.87 | N |
| ATOM | 2099 | CA | VAL A | 288 | −0.073 | 3.947 | 18.772 | 1.00 | 39.55 | C |
| ATOM | 2100 | CB | VAL A | 288 | −1.494 | 4.375 | 18.245 | 1.00 | 39.44 | C |
| ATOM | 2101 | CG1 | VAL A | 288 | −2.272 | 5.199 | 19.261 | 1.00 | 35.69 | C |
| ATOM | 2102 | CG2 | VAL A | 288 | −1.384 | 5.101 | 16.937 | 1.00 | 39.30 | C |
| ATOM | 2103 | C | VAL A | 288 | −0.233 | 2.857 | 19.803 | 1.00 | 39.46 | C |
| ATOM | 2104 | O | VAL A | 288 | −0.896 | 1.826 | 19.539 | 1.00 | 39.13 | O |
| ATOM | 2105 | N | ILE A | 289 | 0.366 | 3.107 | 20.965 | 1.00 | 39.04 | N |
| ATOM | 2106 | CA | ILE A | 289 | 0.675 | 2.116 | 22.012 | 1.00 | 38.13 | C |
| ATOM | 2107 | CB | ILE A | 289 | 2.240 | 2.119 | 22.333 | 1.00 | 37.39 | C |
| ATOM | 2108 | CG1 | ILE A | 289 | 3.115 | 1.540 | 21.249 | 1.00 | 36.08 | C |
| ATOM | 2109 | CD1 | ILE A | 289 | 4.489 | 2.180 | 21.267 | 1.00 | 33.34 | C |
| ATOM | 2110 | CG2 | ILE A | 289 | 2.549 | 1.342 | 23.543 | 1.00 | 37.64 | C |
| ATOM | 2111 | C | ILE A | 289 | 0.015 | 2.603 | 23.308 | 1.00 | 39.08 | C |
| ATOM | 2112 | O | ILE A | 289 | 0.338 | 3.740 | 23.784 | 1.00 | 40.12 | O |
| ATOM | 2113 | N | LEU A | 290 | −0.894 | 1.792 | 23.871 | 1.00 | 38.76 | N |
| ATOM | 2114 | CA | LEU A | 290 | −1.181 | 1.803 | 25.323 | 1.00 | 38.52 | C |
| ATOM | 2115 | CB | LEU A | 290 | −2.623 | 1.455 | 25.547 | 1.00 | 38.30 | C |
| ATOM | 2116 | CG | LEU A | 290 | −3.716 | 2.126 | 24.774 | 1.00 | 39.48 | C |
| ATOM | 2117 | CD1 | LEU A | 290 | −5.004 | 1.384 | 25.096 | 1.00 | 37.18 | C |
| ATOM | 2118 | CD2 | LEU A | 290 | −3.881 | 3.687 | 25.045 | 1.00 | 38.51 | C |
| ATOM | 2119 | C | LEU A | 290 | −0.337 | 0.775 | 26.106 | 1.00 | 38.76 | C |
| ATOM | 2120 | O | LEU A | 290 | −0.247 | −0.423 | 25.742 | 1.00 | 38.07 | O |
| ATOM | 2121 | N | ASP A | 291 | 0.259 | 1.234 | 27.201 | 1.00 | 39.30 | N |
| ATOM | 2122 | CA | ASP A | 291 | 1.023 | 0.386 | 28.126 | 1.00 | 38.65 | C |
| ATOM | 2123 | CB | ASP A | 291 | 2.358 | 1.021 | 28.341 | 1.00 | 37.93 | C |
| ATOM | 2124 | CG | ASP A | 291 | 3.238 | 0.242 | 29.272 | 1.00 | 43.23 | C |
| ATOM | 2125 | OD1 | ASP A | 291 | 2.740 | −0.328 | 30.299 | 1.00 | 48.52 | O |
| ATOM | 2126 | OD2 | ASP A | 291 | 4.472 | 0.209 | 28.988 | 1.00 | 44.65 | O |
| ATOM | 2127 | C | ASP A | 291 | 0.285 | 0.378 | 29.440 | 1.00 | 38.48 | C |
| ATOM | 2128 | O | ASP A | 291 | 0.286 | 1.370 | 30.140 | 1.00 | 38.87 | O |
| ATOM | 2129 | N | LEU A | 292 | −0.325 | −0.745 | 29.794 | 1.00 | 38.88 | N |
| ATOM | 2130 | CA | LEU A | 292 | −1.106 | −0.858 | 31.013 | 1.00 | 38.69 | C |
| ATOM | 2131 | CB | LEU A | 292 | −2.366 | −1.600 | 30.679 | 1.00 | 37.44 | C |
| ATOM | 2132 | CG | LEU A | 292 | −3.609 | −0.781 | 30.457 | 1.00 | 34.22 | C |
| ATOM | 2133 | CD1 | LEU A | 292 | −3.184 | 0.571 | 30.078 | 1.00 | 35.26 | C |
| ATOM | 2134 | CD2 | LEU A | 292 | −4.455 | −1.412 | 29.379 | 1.00 | 29.48 | C |

TABLE 11-continued

| ATOM | 2135 | C | LEU A | 292 | −0.434 | −1.676 | 32.062 | 1.00 | 40.54 | C |
|---|---|---|---|---|---|---|---|---|---|---|
| ATOM | 2136 | O | LEU A | 292 | −0.395 | −2.870 | 31.951 | 1.00 | 41.57 | O |
| ATOM | 2137 | N | PRO A | 293 | 0.074 | −1.056 | 33.127 | 1.00 | 42.41 | N |
| ATOM | 2138 | CA | PRO A | 293 | 0.837 | −1.879 | 34.121 | 1.00 | 42.28 | C |
| ATOM | 2139 | CB | PRO A | 293 | 1.274 | −0.842 | 35.153 | 1.00 | 42.21 | C |
| ATOM | 2140 | CG | PRO A | 293 | 1.242 | 0.497 | 34.386 | 1.00 | 43.55 | C |
| ATOM | 2141 | CD | PRO A | 293 | 0.028 | 0.370 | −33.508 | 1.00 | 42.97 | C |
| ATOM | 2142 | C | PRO A | 293 | 0.057 | −2.998 | 34.821 | 1.00 | 41.99 | C |
| ATOM | 2143 | O | PRO A | 293 | −1.062 | −2.812 | 35.293 | 1.00 | 41.88 | O |
| ATOM | 2144 | N | LEU A | 294 | 0.674 | −4.154 | 34.920 | 1.00 | 41.62 | N |
| ATOM | 2145 | CA | LEU A | 294 | 0.121 | −5.218 | 35.727 | 1.00 | 41.16 | C |
| ATOM | 2146 | CB | LEU A | 294 | −0.087 | −6.490 | 34.905 | 1.00 | 40.09 | C |
| ATOM | 2147 | CG | LEU A | 294 | −0.595 | −6.278 | 33.490 | 1.00 | 40.78 | C |
| ATOM | 2148 | CD1 | LEU A | 294 | −0.246 | −7.378 | 32.512 | 1.00 | 41.23 | C |
| ATOM | 2149 | CD2 | LEU A | 294 | −2.071 | −5.972 | 33.462 | 1.00 | 42.14 | C |
| ATOM | 2150 | C | LEU A | 294 | 1.014 | −5.550 | 36.915 | 1.00 | 41.76 | C |
| ATOM | 2151 | O | LEU A | 294 | 2.198 | −5.178 | 36.994 | 1.00 | 41.41 | O |
| ATOM | 2152 | N | VAL A | 295 | 0.380 | −6.249 | 37.843 | 1.00 | 42.13 | N |
| ATOM | 2153 | CA | VAL A | 295 | 1.000 | −6.984 | 38.890 | 1.00 | 42.23 | C |
| ATOM | 2154 | CB | VAL A | 295 | 0.398 | −6.573 | 40.210 | 1.00 | 41.95 | C |
| ATOM | 2155 | CG1 | VAL A | 295 | 0.703 | −7.638 | 41.259 | 1.00 | 41.18 | C |
| ATOM | 2156 | CG2 | VAL A | 295 | 0.902 | −5.220 | 40.616 | 1.00 | 40.30 | C |
| ATOM | 2157 | C | VAL A | 295 | 0.590 | −8.446 | 38.693 | 1.00 | 43.30 | C |
| ATOM | 2158 | O | VAL A | 295 | −0.617 | −8.772 | 38.626 | 1.00 | 41.83 | O |
| ATOM | 2159 | N | ILE A | 296 | 1.588 | −9.327 | 38.653 | 1.00 | 45.30 | N |
| ATOM | 2160 | CA | ILE A | 296 | 1.339 | −10.769 | 38.388 | 1.00 | 47.01 | C |
| ATOM | 2161 | CB | ILE A | 296 | 1.685 | −11.109 | 36.916 | 1.00 | 47.68 | C |
| ATOM | 2162 | CG1 | ILE A | 296 | 0.525 | −10.592 | 36.039 | 1.00 | 47.24 | C |
| ATOM | 2163 | CD1 | ILE A | 296 | 1.004 | −9.989 | 34.822 | 1.00 | 49.75 | C |
| ATOM | 2164 | CG2 | ILE A | 296 | 1.887 | −12.647 | 36.701 | 1.00 | 46.34 | C |
| ATOM | 2165 | C | ILE A | 296 | 1.955 | −11.741 | 39.377 | 1.00 | 47.27 | C |
| ATOM | 2166 | O | ILE A | 296 | 3.166 | −11.888 | 39.436 | 1.00 | 48.42 | C |
| ATOM | 2167 | N | GLY A | 297 | 1.130 | −12.381 | 40.183 | 1.00 | 48.20 | N |
| ATOM | 2168 | CA | GLY A | 297 | 1.651 | −13.292 | 41.212 | 1.00 | 49.82 | C |
| ATOM | 2169 | C | GLY A | 297 | 1.351 | −14.764 | 40.995 | 1.00 | 50.92 | C |
| ATOM | 2170 | O | GLY A | 297 | 0.695 | −15.155 | 40.020 | 1.00 | 51.27 | O |
| ATOM | 2171 | N | SER A | 298 | 1.804 | −15.590 | 41.391 | 1.00 | 52.54 | N |
| ATOM | 2172 | CA | SER A | 298 | 1.527 | −17.035 | 41.884 | 1.00 | 53.17 | C |
| ATOM | 2173 | CB | SER A | 298 | 2.813 | −17.753 | 41.619 | 1.00 | 52.67 | C |
| ATOM | 2174 | OG | SER A | 298 | 3.833 | −17.040 | 42.274 | 1.00 | 51.24 | O |
| ATOM | 2175 | C | SER A | 298 | 0.872 | −17.590 | 43.154 | 1.00 | 54.28 | C |
| ATOM | 2176 | O | SER A | 298 | 0.408 | −18.767 | 43.172 | 1.00 | 56.27 | O |
| TER | | | | | | | | | | |
| ATOM | 2177 | N | MET B | 1 | −36.842 | 6.337 | 4.770 | 1.00 | 75.64 | N |
| ATOM | 2178 | CA | MET B | 1 | −36.659 | 6.309 | 6.262 | 1.00 | 75.04 | C |
| ATOM | 2179 | CB | MET B | 1 | −37.961 | 6.677 | 6.950 | 1.00 | 76.52 | C |
| ATOM | 2180 | CG | MET B | 1 | −38.025 | 8.129 | 7.316 | 1.00 | 79.99 | C |
| ATOM | 2181 | SD | MET B | 1 | −38.639 | 8.229 | 9.014 | 1.00 | 88.81 | S |
| ATOM | 2182 | CE | MET B | 1 | 37.197 | 7.632 | 9.954 | 1.00 | 86.49 | C |
| ATOM | 2183 | C | MET B | 1 | −36.073 | 5.007 | 6.852 | 1.00 | 74.83 | C |
| ATOM | 2184 | O | MET B | 1 | −36.260 | 3.917 | 6.292 | 1.00 | 75.02 | O |
| ATOM | 2185 | N | VAL B | 2 | −35.377 | 5.132 | 7.989 | 1.00 | 73.47 | N |
| ATOM | 2186 | CA | VAL B | 2 | −34.536 | 4.047 | 8.532 | 1.00 | 72.05 | C |
| ATOM | 2187 | CB | VAL B | 2 | −33.067 | 4.509 | 8.752 | 1.00 | 72.12 | C |
| ATOM | 2188 | CG1 | VAL B | 2 | −32.161 | 3.314 | 9.003 | 1.00 | 72.17 | C |
| ATOM | 2189 | CG2 | VAL B | 2 | −32.551 | 5.323 | 7.568 | 1.00 | 72.91 | C |
| ATOM | 2190 | C | VAL B | 2 | −35.029 | 3.516 | 9.867 | 1.00 | 71.00 | C |
| ATOM | 2191 | O | VAL B | 2 | −34.995 | 4.228 | 10.869 | 1.00 | 70.30 | O |
| ATOM | 2192 | N | LYS B | 3 | −35.453 | 2.254 | 9.874 | 1.00 | 70.37 | N |
| ATOM | 2193 | CA | LYS B | 3 | −35.959 | 1.610 | 11.087 | 1.00 | 70.01 | C |
| ATOM | 2194 | CB | LYS B | 3 | −36.805 | 0.364 | 10.765 | 1.00 | 69.98 | C |
| ATOM | 2195 | CG | LYS B | 3 | −38.148 | 0.670 | 10.092 | 1.00 | 71.89 | C |
| ATOM | 2196 | CD | LYS B | 3 | −38.471 | −0.304 | 8.927 | 1.00 | 73.41 | C |
| ATOM | 2197 | CE | LYS B | 3 | −39.869 | −0.055 | 8.386 | 1.00 | 74.86 | C |
| ATOM | 2108 | NZ | LYS B | 3 | −39.927 | −0.208 | 6.805 | 1.00 | 77.33 | N |
| ATOM | 2199 | C | LYS B | 3 | −34.768 | 1.237 | 1.955 | 1.00 | 68.70 | C |
| ATOM | 2200 | O | LYS B | 3 | −33.981 | 0.373 | 11.568 | 1.00 | 68.83 | O |
| ATOM | 2201 | N | GLN B | 4 | −34.625 | 1.917 | 13.097 | 1.00 | 67.11 | N |
| ATOM | 2202 | CA | GLN B | 4 | −33.734 | 1.465 | 14.161 | 1.00 | 65.57 | C |
| ATOM | 2203 | CB | GLN B | 4 | −33.839 | 2.390 | 15.382 | 1.00 | 60.50 | C |
| ATOM | 2204 | CG | GLN B | 4 | −33.088 | 3.743 | 15.107 | 1.00 | 59.07 | C |
| ATOM | 2205 | CD | GLN B | 4 | −33.937 | 5.010 | 15.369 | 1.00 | 54.09 | C |
| ATOM | 2206 | OE1 | GLN B | 4 | −34.916 | 4.985 | 16.183 | 1.00 | 51.74 | O |
| ATOM | 2207 | NE2 | GLN B | 4 | −33.574 | 6.143 | 14.683 | 1.00 | 52.18 | N |
| ATOM | 2208 | C | GLN B | 4 | −34.163 | 0.040 | 14.454 | 1.00 | 66.34 | C |
| ATOM | 2209 | O | GLN B | 4 | −35.245 | −0.362 | 14.023 | 1.00 | 66.35 | O |
| ATOM | 2210 | N | ILE B | 5 | −33.309 | −0.750 | 15.096 | 1.00 | 67.27 | N |
| ATOM | 2211 | CA | ILE B | 5 | −33.603 | −2.184 | 15.257 | 1.00 | 68.59 | C |
| ATOM | 2212 | CB | ILE B | 5 | −33.240 | −2.991 | 13.978 | 1.00 | 68.11 | C |

TABLE 11-continued

| | | | | | | | | | | |
|---|---|---|---|---|---|---|---|---|---|---|
| ATOM | 2213 | CG1 | ILE B | 5 | −34.417 | −2.975 | 12.994 | 1.00 | 66.67 | C |
| ATOM | 2214 | CD1 | ILE B | 5 | −34.309 | −4.032 | 11.901 | 1.00 | 66.76 | C |
| ATOM | 2215 | CG2 | ILE B | 5 | −32.755 | −4.426 | 14.335 | 1.00 | 67.22 | C |
| ATOM | 2216 | C | ILE B | 5 | −32.909 | −2.765 | 16.499 | 1.00 | 70.10 | C |
| ATOM | 2217 | O | ILE B | 5 | −31.721 | −2.468 | 16.710 | 1.00 | 71.00 | O |
| ATOM | 2218 | N | GLU B | 6 | −33.627 | −3.588 | 17.294 | 1.00 | 71.12 | N |
| ATOM | 2219 | CA | GLU B | 6 | −33.110 | −4.073 | 18.597 | 1.00 | 72.31 | C |
| ATOM | 2220 | CB | GLU B | 6 | −33.721 | −3.280 | 19.767 | 1.00 | 73.00 | C |
| ATOM | 2221 | CG | GLU B | 6 | −33.250 | −1.837 | 19.867 | 1.00 | 75.86 | C |
| ATOM | 2222 | CD | GLU B | 6 | −34.204 | −0.883 | 19.153 | 1.00 | 79.62 | C |
| ATOM | 2223 | OE1 | GLU B | 6 | −35.445 | −1.230 | 19.099 | 1.00 | 80.30 | O |
| ATOM | 2224 | OE2 | GLU B | 6 | −33.717 | 0.210 | 18.659 | 1.00 | 81.05 | O |
| ATOM | 2225 | C | GLU B | 6 | −33.151 | −5.566 | 18.962 | 1.00 | 72.16 | C |
| ATOM | 2226 | O | GLU B | 6 | −32.664 | −5.932 | 20.041 | 1.00 | 72.14 | O |
| ATOM | 2227 | N | SER B | 7 | −33.715 | −6.432 | 18.124 | 1.00 | 72.05 | N |
| ATOM | 2228 | CA | SER B | 7 | −33.684 | −7.873 | 18.452 | 1.00 | 72.30 | C |
| ATOM | 2229 | CB | SER B | 7 | −34.987 | −8.338 | 19.161 | 1.00 | 72.24 | C |
| ATOM | 2230 | OG | SER B | 7 | −35.991 | −8.785 | 18.263 | 1.00 | 70.50 | O |
| ATOM | 2231 | C | SER B | 7 | −33.402 | −8.703 | 17.216 | 1.00 | 72.62 | C |
| ATOM | 2232 | O | SER B | 7 | −33.599 | −8.206 | 16.110 | 1.00 | 72.67 | O |
| ATOM | 2233 | N | LYS B | 8 | −32.954 | −9.949 | 17.378 | 1.00 | 73.05 | N |
| ATOM | 2234 | CA | LYS B | 8 | −32.902 | −10.835 | 16.215 | 1.00 | 73.77 | C |
| ATOM | 2235 | CB | LYS B | 8 | −32.116 | −12.123 | 16.464 | 1.00 | 73.84 | C |
| ATOM | 2236 | CG | LYS B | 8 | −32.020 | −13.021 | 15.209 | 1.00 | 74.56 | C |
| ATOM | 2237 | CD | LYS B | 8 | −31.465 | −14.383 | 15.533 | 1.00 | 76.03 | C |
| ATOM | 2238 | CE | LYS B | 8 | −30.047 | −14.265 | 16.073 | 1.00 | 77.12 | C |
| ATOM | 2239 | NZ | LYS B | 8 | −29.569 | −15.559 | 16.614 | 1.00 | 77.80 | N |
| ATOM | 2240 | C | LYS B | 8 | 34.315 | −11.139 | 15.691 | 1.00 | 74.50 | C |
| ATOM | 2241 | O | LYS B | 8 | −34.496 | −11.274 | 14.471 | 1.00 | 74.80 | O |
| ATOM | 2242 | N | THR B | 9 | −35.308 | −11.247 | 16.592 | 1.00 | 74.96 | N |
| ATOM | 2243 | CA | THR B | 9 | −36.704 | −11.459 | 16.143 | 1.00 | 75.25 | C |
| ATOM | 2244 | CB | THR B | 9 | −37.705 | −12.048 | 17.233 | 1.00 | 74.89 | C |
| ATOM | 2245 | OG1 | THR B | 9 | −37.654 | −11.297 | 18.454 | 1.00 | 74 19 | O |
| ATOM | 2246 | CG2 | THR B | 9 | −37.395 | −13.498 | 17.525 | 1.00 | 73 89 | C |
| ATOM | 2247 | C | THR B | 9 | −37.268 | −10.209 | 15.436 | 1.00 | 75.87 | C |
| ATOM | 2248 | O | THR B | 9 | −38.019 | −10.337 | 14.446 | 1.00 | 75.83 | O |
| ATOM | 2249 | N | ALA B | 10 | −36.888 | −9.018 | 15.927 | 1.00 | 76.19 | N |
| ATOM | 2250 | CA | ALA B | 10 | −37.198 | −7.755 | 15.226 | 1.00 | 76.61 | C |
| ATOM | 2251 | CB | ALA B | 10 | −36.817 | −6.518 | 16.076 | 1.00 | 76.28 | C |
| ATOM | 2252 | C | ALA B | 10 | −36.543 | −7.726 | 13.822 | 1.00 | 76.90 | C |
| ATOM | 2253 | O | ALA B | 10 | −37.153 | −7.260 | 12.833 | 1.00 | 77.00 | O |
| ATOM | 2254 | N | PHE B | 11 | −35.332 | −8.279 | 13.740 | 1.00 | 77.04 | N |
| ATOM | 2255 | CA | PHE B | 11 | −34.617 | −8.455 | 12.469 | 1.00 | 77.34 | C |
| ATOM | 2256 | CB | PHE B | 11 | −33.205 | −8.967 | 12.718 | 1.00 | 77.47 | C |
| ATOM | 2257 | CG | PHE B | 11 | −32.281 | −8.769 | 11.561 | 1.00 | 76.96 | C |
| ATOM | 2258 | CD1 | PHE B | 11 | −32.109 | −7.505 | 11.000 | 1.00 | 76.03 | C |
| ATOM | 2259 | CE1 | PHE B | 11 | −31.233 | −7.317 | 9.932 | 1.00 | 75.84 | C |
| ATOM | 2260 | CZ | PHE B | 11 | −30.518 | −8.402 | 9.408 | 1.00 | 74.73 | C |
| ATOM | 2261 | CE2 | PHE B | 11 | −30.683 | −9.668 | 9.966 | 1.00 | 75.58 | C |
| ATOM | 2262 | CD2 | PHE B | 11 | −31.562 | −9.485 | 11.040 | 1.00 | 76.84 | C |
| ATOM | 2263 | C | PHE B | 11 | −35.307 | −9.402 | 11.513 | 1.00 | 77.49 | C |
| ATOM | 2264 | O | PHE B | 11 | −35.538 | −9.039 | 10.364 | 1.00 | 77.26 | O |
| ATOM | 2265 | N | GLN B | 12 | −35.616 | −10.612 | 11.990 | 1.00 | 78.31 | N |
| ATOM | 2266 | CA | GLN B | 12 | −36.420 | −11.581 | 11.218 | 1.00 | 79.00 | C |
| ATOM | 2267 | CB | GLN B | 12 | −36.862 | −12.798 | 12.053 | 1.00 | 78.80 | C |
| ATOM | 2268 | CG | GLN B | 12 | −35.762 | −13.833 | 12.416 | 1.00 | 79.31 | C |
| ATOM | 2269 | CD | GLN B | 12 | −34.857 | −14.317 | 11.248 | 1.00 | 79.34 | C |
| ATOM | 2270 | OE1 | GLN B | 12 | −35.208 | −14.241 | 10.063 | 1.00 | 77.15 | O |
| ATOM | 2271 | NE2 | GLN B | 12 | −33.676 | −14.830 | 11.612 | 1.00 | 79.83 | N |
| ATOM | 2272 | C | GLN B | 12 | −37.625 | −10.898 | 10.579 | 1.00 | 79.25 | C |
| ATOM | 2273 | O | GLN B | 12 | −37.847 | −11.040 | 9.370 | 1.00 | 78.96 | O |
| ATOM | 2274 | N | GLU B | 13 | −38.366 | −10.135 | 11.389 | 1.00 | 79.96 | N |
| ATOM | 2275 | CA | GLU B | 13 | −39.495 | −9.350 | 10.898 | 1.00 | 80.91 | C |
| ATOM | 2276 | CB | GLU B | 13 | −39.950 | −8.282 | 11.883 | 1.00 | 81.24 | C |
| ATOM | 2277 | CG | GLU B | 13 | −41.255 | −8.594 | 12.571 | 1.00 | 81.20 | C |
| ATOM | 2278 | CD | GLU B | 13 | −41.037 | −8.978 | 14.022 | 1.00 | 82.02 | C |
| ATOM | 2279 | OE1 | GLU B | 13 | −40.250 | −8.292 | 14.726 | 1.00 | 83.46 | O |
| ATOM | 2280 | OE2 | GLU B | 13 | −41.656 | −9.960 | 14.475 | 1.00 | 82.29 | O |
| ATOM | 2281 | C | GLU B | 13 | −39.202 | −8.651 | 9.387 | 1.00 | 81.42 | C |
| ATOM | 2282 | O | GLU B | 13 | −39.853 | −8.973 | 8.593 | 1.00 | 82.01 | O |
| ATOM | 2283 | N | ALA B | 14 | −38.251 | −7.723 | 9.569 | 1.00 | 81.46 | N |
| ATOM | 2284 | CA | ALA B | 14 | −38.038 | −6.936 | 8.338 | 1.00 | 81.89 | C |
| ATOM | 2285 | CB | ALA B | 14 | −36.962 | −5.886 | 8.540 | 1.00 | 82.04 | C |
| ATOM | 2286 | C | ALA B | 14 | −37.757 | −7.796 | 7.083 | 1.00 | 81.92 | C |
| ATOM | 2287 | O | ALA B | 14 | −38.258 | −7.506 | 5.974 | 1.00 | 81.42 | O |
| ATOM | 2288 | N | LEU B | 15 | −36.980 | −8.861 | 7.292 | 1.00 | 82.20 | N |
| ATOM | 2289 | CA | LEU B | 15 | −36.656 | −9.859 | 6.267 | 1.00 | 82.65 | C |
| ATOM | 2290 | CB | LEU B | 15 | −35.852 | −10.998 | 6.905 | 1.00 | 82.86 | C |
| ATOM | 2291 | CG | LEU B | 15 | −34.544 | −10.508 | 7.556 | 1.00 | 82.98 | C |
| ATOM | 2292 | CD1 | LEU B | 15 | −34.107 | −11.372 | 8.749 | 1.00 | 82.62 | C |

TABLE 11-continued

| | | | | | | | | | | |
|---|---|---|---|---|---|---|---|---|---|---|
| ATOM | 2293 | CD2 | LEU B | 15 | −33.392 | −10.320 | 6.541 | 1.00 | 82.67 | C |
| ATOM | 2294 | C | LEU B | 15 | −37.923 | −10.377 | 5.603 | 1.00 | 82.76 | C |
| ATOM | 2295 | O | LEU B | 15 | −37.920 | −10.770 | 4.431 | 1.00 | 82.58 | O |
| ATOM | 2296 | N | ASP B | 16 | −39.005 | −10.346 | 6.379 | 1.00 | 82.98 | N |
| ATOM | 2297 | CA | ASP B | 16 | −40.365 | −10.550 | 5.885 | 1.00 | 83.08 | C |
| ATOM | 2298 | CB | ASP B | 16 | −41.245 | −11.147 | 6.992 | 1.00 | 83.31 | C |
| ATOM | 2299 | CG | ASP B | 16 | −40.544 | −12.285 | 7.736 | 1.00 | 84.25 | C |
| ATOM | 2300 | OD1 | ASP B | 16 | −39.286 | −12.731 | 7.646 | 1.00 | 84.25 | O |
| ATOM | 2301 | OD2 | ASP B | 16 | −41.253 | −13.091 | 8.396 | 1.00 | 85.05 | O |
| ATOM | 2302 | C | ASP B | 16 | −40.976 | −9.246 | 5.363 | 1.00 | 82.84 | C |
| ATOM | 2303 | O | ASP B | 16 | −41.431 | −9.201 | 4.219 | 1.00 | 82.58 | O |
| ATOM | 2304 | N | ALA B | 17 | −40.967 | −8.202 | 6.207 | 1.00 | 82.89 | N |
| ATOM | 2305 | CA | ALA B | 17 | −41.568 | −6.874 | 5.922 | 1.00 | 82.72 | C |
| ATOM | 2306 | CB | ALA B | 17 | −41.005 | −5.789 | 6.880 | 1.00 | 82.85 | C |
| ATOM | 2307 | C | ALA B | 17 | −41.409 | −6.445 | 4.465 | 1.00 | 82.51 | C |
| ATOM | 2308 | O | ALA B | 17 | −42.406 | −6.260 | 3.762 | 1.00 | 82.44 | O |
| ATOM | 2309 | N | ALA B | 18 | −40.154 | −6.294. | 4.028 | 1.00 | 82.32 | N |
| ATOM | 2310 | CA | ALA B | 18 | −39.821 | −6.099 | 2.608 | 1.00 | 81.71 | C |
| ATOM | 2311 | CB | ALA B | 18 | −38.328 | −5.779 | 2.443 | 1.00 | 81.72 | C |
| ATOM | 2312 | C | ALA B | 18 | −40.165 | −7.334 | 1.787 | 1.00 | 81.07 | C |
| ATOM | 2313 | O | ALA B | 18 | −39.877 | −8.485 | 2.167 | 1.00 | 81.21 | O |
| ATOM | 2314 | N | GLY B | 19 | −40.850 | −7.124 | 0.664 | 1.00 | 80.21 | N |
| ATOM | 2315 | CA | GLY B | 19 | −41.193 | −8.230 | −0.214 | 1.00 | 78.83 | C |
| ATOM | 2316 | C | GLY B | 19 | −39.953 | −8.593 | −1.004 | 1.00 | 77.59 | C |
| ATOM | 2317 | O | GLY B | 19 | −38.878 | −8.792 | −0.441 | 1.00 | 76.84 | O |
| ATOM | 2318 | N | ASP B | 20 | −40.120 | −8.666 | −2.320 | 1.00 | 76.73 | N |
| ATOM | 2319 | CA | ASP B | 20 | −39.006 | −8.827 | −3.233 | 1.00 | 75.99 | C |
| ATOM | 2320 | CB | ASP B | 20 | −39.515 | −8.936 | −4.675 | 1.00 | 76.18 | C |
| ATOM | 2321 | CG | ASP B | 20 | −39.942 | −10.352 | −5.049 | 1.00 | 76.57 | C |
| ATOM | 2322 | OD1 | ASP B | 20 | −41.062 | −10.486 | −5.593 | 1.00 | 76.28 | O |
| ATOM | 2323 | OD2 | ASP B | 20 | −39.165 | −11.320 | −4.827 | 1.00 | 76.33 | O |
| ATOM | 2324 | C | ASP B | 20 | −37.992 | −7.667 | −3.125 | 1.00 | 75.32 | C |
| ATOM | 2325 | O | ASP B | 20 | −36.908 | −7.739 | −3.740 | 1.00 | 75.30 | O |
| ATOM | 2326 | N | LYS B | 21 | −38.328 | −6.622 | −2.349 | 1.00 | 73.78 | N |
| ATOM | 2327 | CA | LYS B | 21 | −37.454 | −5.438 | −2.230 | 1.00 | 72.44 | C |
| ATOM | 2328 | CB | LYS B | 21 | −38.231 | −4.174 | −1.772 | 1.00 | 72.47 | C |
| ATOM | 2329 | CG | LYS B | 21 | −39.541 | −4.404 | −0.995 | 1.00 | 72.15 | C |
| ATOM | 2330 | CD | LYS B | 21 | −40.266 | −2.979 | −0.728 | 1.00 | 73.22 | C |
| ATOM | 2331 | CE | LYS B | 21 | −41.765 | −3.390 | 0.034 | 1.00 | 74.40 | C |
| ATOM | 2332 | NZ | LYS B | 21 | 42.144 | 2.153 | 1.016 | 1.00 | 74.19 | N |
| ATOM | 2333 | C | LYS B | 21 | −36.074 | −5.641 | −1.488 | 1.00 | 71.44 | C |
| ATOM | 2334 | O | LYS B | 21 | −35.994 | −6.220 | −0.392 | 1.00 | 71.08 | O |
| ATOM | 2335 | N | LEU B | 22 | −34.998 | −5.183 | −2.143 | 1.00 | 70.08 | N |
| ATOM | 2336 | CA | LEU B | 22 | −33.651 | 5.204 | 1.598 | 1.00 | 68.37 | C |
| ATOM | 2337 | CB | LEU B | 22 | −32.604 | −4.667 | −2.590 | 1.00 | 68.13 | C |
| ATOM | 2338 | CG | LEU B | 22 | −31.218 | −4.091 | −2.188 | 1.00 | 65.64 | C |
| ATOM | 2339 | CD1 | LEU B | 22 | −30.061 | −4.705 | −2.969 | 1.00 | 64.37 | C |
| ATOM | 2340 | CD2 | LEU B | 22 | −31.168 | −2.589 | −2.354 | 1.00 | 63.48 | C |
| ATOM | 2341 | C | LEU B | 22 | −33.660 | −4.401 | −0.338 | 1.00 | 68.20 | C |
| ATOM | 2342 | O | LEU B | 22 | −34.374 | −3.397 | −0.184 | 1.00 | 67.95 | O |
| ATOM | 2343 | N | VAL B | 23 | −32.873 | −4.692 | 0.592 | 1.00 | 68.04 | N |
| ATOM | 2344 | CA | VAL B | 23 | −32.826 | −4.293 | 1.913 | 1.00 | 67.56 | C |
| ATOM | 2345 | CB | VAL B | 23 | −33.774 | −5.071 | 2.929 | 1.00 | 67.46 | C |
| ATOM | 2346 | CG1 | VAL B | 23 | −33.534 | −6.570 | 2.862 | 1.00 | 67.77 | C |
| ATOM | 2347 | CG2 | VAL B | 23 | −33.634 | −4.572 | 4.320 | 1.00 | 67.17 | C |
| ATOM | 2348 | C | VAL B | 23 | −31.340 | −4.129 | 2.297 | 1.00 | 66.19 | C |
| ATOM | 2349 | O | VAL B | 23 | −30.533 | −5.043 | 2.141 | 1.00 | 65.57 | O |
| ATOM | 2350 | N | VAL B | 24 | −31.002 | −2.907 | 2.689 | 1.00 | 64.87 | N |
| ATOM | 2351 | CA | VAL B | 24 | −29.658 | −2.516 | 3.027 | 1.00 | 63.27 | C |
| ATOM | 2352 | CB | VAL B | 24 | −29.306 | −1.176 | 2.328 | 1.00 | 62.93 | C |
| ATOM | 2353 | CG1 | VAL B | 24 | −30.238 | −0.096 | 2.768 | 1.00 | 61.63 | C |
| ATOM | 2354 | CG2 | VAL B | 24 | −27.823 | −0.760 | 2.547 | 1.00 | 63.02 | C |
| ATOM | 2355 | C | VAL B | 24 | −29.633 | −2.411 | 4.545 | 1.00 | 62.70 | C |
| ATOM | 2356 | O | VAL B | 24 | −30.602 | −2.008 | 5.183 | 1.00 | 63.13 | O |
| ATOM | 2357 | N | VAL B | 25 | −28.544 | −2.841 | 5.139 | 1.00 | 61.97 | N |
| ATOM | 2358 | CA | VAL B | 25 | −28.430 | −2.763 | 6.579 | 1.00 | 61.49 | C |
| ATOM | 2359 | CB | VAL B | 25 | −28.444 | −4.156 | 7.222 | 1.00 | 61.37 | C |
| ATOM | 2360 | CG1 | VAL B | 25 | −28.436 | −4.050 | 8.573 | 1.00 | 59.05 | C |
| ATOM | 2361 | CG2 | VAL B | 25 | −29.633 | −4.964 | 6.702 | 1.00 | 60.63 | C |
| ATOM | 2362 | C | VAL B | 25 | −27.119 | −2.109 | 6.924 | 1.00 | 61.42 | C |
| ATOM | 2363 | O | VAL B | 25 | −26.053 | −2.542 | 6.482 | 1.00 | 62.12 | O |
| ATOM | 2364 | N | ASP B | 26 | −27.216 | −1.058 | 7.700 | 1.00 | 60.57 | N |
| ATOM | 2365 | CA | ASP B | 26 | −26.077 | −0.443 | 8.294 | 1.00 | 60.33 | C |
| ATOM | 2366 | CB | ASP B | 26 | −26.377 | 1.065 | 8.385 | 1.00 | 60.25 | C |
| ATOM | 2367 | CG | ASP B | 26 | −25.223 | 1.882 | 8.934 | 1.00 | 61.47 | C |
| ATOM | 2368 | OD1 | ASP B | 26 | −24.403 | 1.342 | 9.720 | 1.00 | 61.10 | O |
| ATOM | 2369 | OD2 | ASP B | 26 | −25.155 | 3.088 | 8.592 | 1.00 | 63.03 | O |
| ATOM | 2370 | C | ASP B | 26 | −25.863 | −1.104 | 9.697 | 1.00 | 60.34 | C |
| ATOM | 2371 | O | ASP B | 26 | −26.680 | −0.923 | 10.631 | 1.00 | 60.06 | O |
| ATOM | 2372 | N | PHE B | 27 | −24.788 | −1.883 | 9.837 | 1.00 | 59.27 | N |

TABLE 11-continued

| | | | | | | | | | | |
|---|---|---|---|---|---|---|---|---|---|---|
| ATOM | 2373 | CA | PHE B | 27 | −24.309 | −2.263 | 11.150 | 1.00 | 58.41 | C |
| ATOM | 2374 | CB | PHE B | 27 | −23.561 | −3.565 | 11.101 | 1.00 | 59.17 | C |
| ATOM | 2375 | CG | PHE B | 27 | −24.420 | −4.722 | 10.699 | 1.00 | 60.54 | C |
| ATOM | 2376 | CD1 | PHE B | 27 | −25.017 | −5.535 | 11.671 | 1.00 | 59.16 | C |
| ATOM | 2377 | CE1 | PHE B | 27 | −25.787 | −8.613 | 11.314 | 1.00 | 57.84 | C |
| ATOM | 2378 | CZ | PHE B | 27 | −26.013 | −6.878 | 9.986 | 1.00 | 59.48 | C |
| ATOM | 2379 | CE2 | PHE B | 27 | −25.439 | −6.060 | 8.989 | 1.00 | 60.31 | C |
| ATOM | 2380 | CD2 | PHE B | 27 | −24.653 | −4.990 | 9.348 | 1.00 | 59.46 | C |
| ATOM | 2381 | C | PHE B | 27 | −23.380 | −1.212 | 11.579 | 1.00 | 58.00 | C |
| ATOM | 2382 | O | PHE B | 27 | −22.249 | −1.140 | 11.138 | 1.00 | 58.10 | O |
| ATOM | 2383 | N | SER B | 28 | −23.895 | −0.390 | 12.458 | 1.00 | 58.15 | N |
| ATOM | 2384 | CA | SER B | 28 | −23.291 | 0.831 | 12.874 | 1.00 | 58.08 | C |
| ATOM | 2385 | CB | SER B | 28 | −24.446 | 1.812 | 12.871 | 1.00 | 58.17 | C |
| ATOM | 2386 | OG | SER B | 28 | −24.078 | 3.081 | 13.361 | 1.00 | 62.55 | O |
| ATOM | 2387 | C | SER B | 28 | −22.722 | 0.709 | 14.300 | 1.00 | 57.91 | C |
| ATOM | 2388 | O | SER B | 28 | −22.823 | −0.342 | 14.962 | 1.00 | 57.23 | O |
| ATOM | 2389 | N | ALA B | 29 | −22.156 | 1.811 | 14.789 | 1.00 | 57.80 | N |
| ATOM | 2390 | CA | ALA B | 29 | −21.822 | 1.949 | 16.216 | 1.00 | 57.23 | C |
| ATOM | 2391 | CB | ALA B | 29 | −20.570 | 1.105 | 16.589 | 1.00 | 57.17 | C |
| ATOM | 2392 | C | ALA B | 29 | −21.636 | 3.406 | 16.663 | 1.00 | 56.77 | C |
| ATOM | 2393 | O | ALA B | 29 | −20.955 | 4.197 | 16.022 | 1.00 | 57.45 | O |
| ATOM | 2394 | N | THR B | 30 | 22.272 | 3.706 | 17.774 | 1.00 | 55.83 | N |
| ATOM | 2395 | CA | THR B | 30 | −22.214 | 4.929 | 18.546 | 1.00 | 55.48 | C |
| ATOM | 2396 | CB | THR B | 30 | −22.559 | 4.482 | 20.003 | 1.00 | 56.74 | C |
| ATOM | 2397 | OG1 | THR B | 30 | −23.962 | 4.219 | 20.053 | 1.00 | 54.50 | O |
| ATOM | 2398 | CG2 | THR B | 30 | −21.990 | 5.429 | 21.209 | 1.00 | 54.17 | C |
| ATOM | 2399 | C | THR B | 30 | −20.921 | 5.732 | 18.590 | 1.00 | 55.16 | C |
| ATOM | 2400 | O | THR B | 30 | −20.940 | 6.967 | 18.413 | 1.00 | 54.72 | O |
| ATOM | 2401 | N | TRP B | 31 | −19.832 | 5.028 | 18.915 | 1.00 | 53.87 | N |
| ATOM | 2402 | CA | TRP B | 31 | −18.532 | 5.638 | 19.253 | 1.00 | 52.72 | C |
| ATOM | 2403 | CB | TRP B | 31 | −17.854 | 4.841 | 20.394 | 1.00 | 52.16 | C |
| ATOM | 2404 | CG | TRP B | 31 | −17.861 | 3.320 | 20.135 | 1.00 | 52.12 | C |
| ATOM | 2405 | CD1 | TRP B | 31 | −18.817 | 2.424 | 20.580 | 1.00 | 51.80 | C |
| ATOM | 2406 | NE1 | TRP B | 31 | −18.543 | 1.151 | 20.118 | 1.00 | 51.17 | N |
| ATOM | 2407 | CE2 | TRP B | 31 | −17.436 | 1.210 | 19.303 | 1.00 | 54.36 | C |
| ATOM | 2408 | CD2 | TRP B | 31 | −16.997 | 2.570 | 19.276 | 1.00 | 49.88 | C |
| ATOM | 2409 | CE3 | TRP B | 31 | −15.880 | 2.899 | 18.513 | 1.00 | 45.43 | C |
| ATOM | 2410 | CZ3 | TRP B | 31 | −15.210 | 1.896 | 17.831 | 1.00 | 50.13 | C |
| ATOM | 2411 | CH2 | TRP B | 31 | −15.651 | 0.545 | 17.852 | 1.00 | 49.94 | C |
| ATOM | 2412 | CZ2 | TRP B | 31 | −16.758 | 0.176 | 18.584 | 1.00 | 53.05 | C |
| ATOM | 2413 | C | TRP B | 31 | −17.635 | 5.723 | 18.013 | 1.00 | 52.28 | C |
| ATOM | 2414 | O | TRP B | 31 | −16.547 | 6.260 | 18.082 | 1.00 | 50.83 | O |
| ATOM | 2415 | N | CYS B | 32 | −18.124 | 5.193 | 16.891 | 1.00 | 53.19 | N |
| ATOM | 2416 | CA | CYS B | 32 | −17.386 | 5.118 | 15.654 | 1.00 | 54.95 | C |
| ATOM | 2417 | CB | CYS B | 32 | −17.862 | 3.907 | 14.880 | 1.00 | 55.50 | C |
| ATOM | 2418 | SG | CYS B | 32 | −17.001 | 3.580 | 13.268 | 1.00 | 59.30 | S |
| ATOM | 2419 | C | CYS B | 32 | −17.506 | 6.384 | 14.784 | 1.00 | 56.07 | C |
| ATOM | 2420 | O | CYS B | 32 | −18.544 | 6.655 | 14.188 | 1.00 | 56.72 | O |
| ATOM | 2421 | N | GLY B | 33 | −16.413 | 7.137 | 14.690 | 1.00 | 57.13 | N |
| ATOM | 2422 | CA | GLY B | 33 | −16.335 | 8.340 | 13.860 | 1.00 | 57.80 | C |
| ATOM | 2423 | C | GLY B | 33 | −16.904 | 8.099 | 12.483 | 1.00 | 58.64 | C |
| ATOM | 2424 | O | GLY B | 33 | −17.879 | 8.756 | 12.119 | 1.00 | 59.79 | O |
| ATOM | 2425 | N | PRO B | 34 | −16.327 | 7.133 | 11.726 | 1.00 | 58.05 | N |
| ATOM | 2426 | CA | PRO B | 34 | −16.801 | 6.893 | 10.365 | 1.00 | 57.72 | C |
| ATOM | 2427 | CB | PRO B | 34 | −15.830 | 5.816 | 9.804 | 1.00 | 57.59 | C |
| ATOM | 2428 | CG | PRO B | 34 | −14.658 | 5.844 | 10.750 | 1.00 | 57.32 | C |
| ATOM | 2429 | CD | PRO B | 34 | −15.189 | 6.264 | 12.074 | 1.00 | 57.45 | C |
| ATOM | 2430 | C | PRO B | 34 | −18.429 | 6.440 | 10.253 | 1.00 | 57.20 | C |
| ATOM | 2431 | O | PRO B | 34 | −18.845 | 6.658 | 9.208 | 1.00 | 58.06 | O |
| ATOM | 2432 | N | ALA B | 35 | −18.830 | 5.819 | 11.269 | 1.00 | 56.09 | N |
| ATOM | 2433 | CA | ALA B | 35 | −20.198 | 5.373 | 11.075 | 1.00 | 55.20 | C |
| ATOM | 2434 | CB | ALA B | 35 | −20.511 | 4.200 | 11.900 | 1.00 | 55.33 | C |
| ATOM | 2435 | C | ALA B | 35 | −21.125 | 6.514 | 11.397 | 1.00 | 55.29 | C |
| ATOM | 2436 | O | ALA B | 35 | −22.213 | 6.604 | 10.841 | 1.00 | 55.71 | O |
| ATOM | 2437 | N | LYS B | 36 | −20.684 | 7.376 | 12.304 | 1.00 | 54.99 | N |
| ATOM | 2438 | CA | LYS B | 36 | −21.390 | 8.593 | 12.617 | 1.00 | 55.29 | C |
| ATOM | 2439 | CB | LYS B | 36 | −20.760 | 9.298 | 13.820 | 1.00 | 55.47 | C |
| ATOM | 2440 | CG | LYS B | 36 | −21.262 | 8.746 | 15.141 | 1.00 | 57.18 | C |
| ATOM | 2441 | CD | LYS B | 36 | −29.754 | 9.525 | 16.354 | 1.00 | 60.60 | C |
| ATOM | 2442 | CE | LYS B | 36 | −19.301 | 9.154 | 16.715 | 1.00 | 59.91 | C |
| ATOM | 2443 | NZ | LYS B | 36 | −18.990 | 9.623 | 18.087 | 1.00 | 61.48 | N |
| ATOM | 2444 | C | LYS B | 36 | −21.418 | 9.531 | 11.432 | 1.00 | 55.61 | C |
| ATOM | 2445 | O | LYS B | 36 | −22.446 | 10.130 | 11.140 | 1.00 | 55.21 | O |
| ATOM | 2446 | N | MET B | 37 | −20.292 | 9.673 | 10.749 | 1.00 | 56.30 | N |
| ATOM | 2447 | CA | MET B | 37 | −20.273 | 10.476 | 9.551 | 1.00 | 58.06 | C |
| ATOM | 2448 | CB | MET B | 37 | −18.838 | 10.641 | 9.055 | 1.00 | 58.17 | C |
| ATOM | 2449 | CG | MET B | 37 | −18.669 | 11.258 | 7.662 | 1.00 | 60.88 | C |
| ATOM | 2450 | SD | MET B | 37 | −18.840 | 10.183 | 6.149 | 1.00 | 70.27 | S |
| ATOM | 2451 | CE | MET B | 37 | −17.180 | 9.476 | 5.998 | 1.00 | 61.48 | C |
| ATOM | 2452 | O | MET B | 37 | −21.237 | 9.950 | 8.442 | 1.00 | 58.60 | O |

TABLE 11-continued

| | | | | | | | | | | |
|---|---|---|---|---|---|---|---|---|---|---|
| ATOM | 2453 | O | MET B | 37 | −21.752 | 10.723 | 7.662 | 1.00 | 59.98 | O |
| ATOM | 2454 | N | ILE B | 38 | −21.509 | 8.658 | 8.379 | 1.00 | 58.64 | N |
| ATOM | 2455 | CA | ILE B | 38 | −22.183 | 8.126 | 7.221 | 1.00 | 58.31 | C |
| ATOM | 2456 | CB | ILE B | 38 | −21.586 | 6.767 | 6.832 | 1.00 | 58.06 | C |
| ATOM | 2457 | CG1 | ILE B | 38 | −22.024 | 6.350 | 5.431 | 1.00 | 57.53 | C |
| ATOM | 2458 | CD1 | ILE B | 38 | −21.112 | 6.726 | 4.325 | 1.00 | 56.36 | C |
| ATOM | 2459 | CG2 | ILE B | 38 | −22.030 | 5.704 | 7.814 | 1.00 | 57.35 | C |
| ATOM | 2460 | C | ILE B | 38 | −23.692 | 8.021 | 7.474 | 1.00 | 59.53 | C |
| ATOM | 2461 | O | ILE B | 38 | −24.495 | 8.070 | 6.505 | 1.00 | 59.20 | O |
| ATOM | 2462 | N | LYS B | 39 | −24.076 | 7.861 | 8.759 | 1.00 | 59.89 | N |
| ATOM | 2463 | CA | LYS B | 39 | −25.505 | 7.927 | 9.205 | 1.00 | 59.95 | C |
| ATOM | 2464 | CB | LYS B | 39 | −25.659 | 8.220 | 10.701 | 1.00 | 59.99 | C |
| ATOM | 2465 | CG | LYS B | 39 | −25.798 | 6.995 | 11.603 | 1.00 | 63.49 | C |
| ATOM | 2466 | CD | LYS B | 39 | −26.731 | 7.237 | 12.848 | 1.00 | 67.72 | C |
| ATOM | 2467 | CE | LYS B | 39 | −26.896 | 8.757 | 13.268 | 1.00 | 70.40 | C |
| ATOM | 2468 | NZ | LYS B | 39 | −25.670 | 9.547 | 13.683 | 1.00 | 68.95 | N |
| ATOM | 2469 | C | LYS B | 39 | −26.326 | 8.966 | 8.464 | 1.00 | 59.49 | C |
| ATOM | 2470 | O | LYS B | 39 | −27.318 | 8.615 | 7.831 | 1.00 | 60.53 | O |
| ATOM | 2471 | N | PRO B | 40 | −25.935 | 10.257 | 8.525 | 1.00 | 58.90 | N |
| ATOM | 2472 | CA | PRO B | 40 | −26.607 | 11.154 | 7.721 | 1.00 | 58.30 | C |
| ATOM | 2473 | CB | PRO B | 40 | −26.105 | 12.521 | 7.786 | 1.00 | 57.95 | C |
| ATOM | 2474 | CG | PRO B | 40 | −25.115 | 12.402 | 8.929 | 1.00 | 58.70 | C |
| ATOM | 2475 | CD | PRO B | 40 | −24.834 | 10.963 | 9.212 | 1.00 | 57.83 | C |
| ATOM | 2476 | C | PRO B | 40 | −27.001 | 10.685 | 6.261 | 1.00 | 57.88 | C |
| ATOM | 2477 | O | PRO B | 40 | −28.141 | 10.645 | 5.787 | 1.00 | 57.01 | O |
| ATOM | 2478 | N | PHE B | 41 | −25.914 | 10.308 | 5.570 | 1.00 | 57.26 | N |
| ATOM | 2479 | CA | PHE B | 41 | −26.026 | 9.990 | 4.142 | 1.00 | 57.05 | C |
| ATOM | 2480 | CB | PHE B | 41 | −24.663 | 9.896 | 3.448 | 1.00 | 57.73 | C |
| ATOM | 2481 | CG | PHE B | 41 | −28.827 | 11.142 | 3.609 | 1.00 | 60.03 | C |
| ATOM | 2482 | CD1 | PHE B | 41 | −22.791 | 11.188 | 4.558 | 1.00 | 61.03 | C |
| ATOM | 2483 | CE1 | PHE B | 41 | −22.054 | 12.367 | 4.743 | 1.00 | 62.83 | C |
| ATOM | 2484 | CZ | PHE B | 41 | −22.351 | 13.520 | 3.956 | 1.00 | 61.31 | C |
| ATOM | 2485 | CE2 | PHE B | 41 | −23.374 | 13.465 | 3.013 | 1.00 | 58.51 | C |
| ATOM | 2486 | CD2 | PHE B | 41 | −24.112 | 12.292 | 2.854 | 1.00 | 59.45 | C |
| ATOM | 2487 | C | PHE B | 41 | −26.850 | 8.738 | 3.963 | 1.00 | 56.78 | C |
| ATOM | 2488 | O | PHE B | 41 | −27.591 | 8.595 | 2.970 | 1.00 | 57.39 | O |
| ATOM | 2489 | N | PHE B | 42 | −26.758 | 7.849 | 4.940 | 1.00 | 55.65 | N |
| ATOM | 2490 | CA | PHE B | 42 | −27.584 | 6.697 | 4.954 | 1.00 | 55.20 | C |
| ATOM | 2491 | CB | PHE B | 42 | −27.159 | 5.761 | 6.081 | 1.00 | 55.17 | C |
| ATOM | 2492 | CG | PHE B | 42 | −27.799 | 4.401 | 6.007 | 1.00 | 53.94 | C |
| ATOM | 2493 | CD1 | PHE B | 42 | −27.535 | 3.550 | 4.950 | 1.00 | 53.17 | C |
| ATOM | 2494 | CE1 | PHE B | 42 | −28.128 | 2.300 | 4.868 | 1.00 | 54.20 | C |
| ATOM | 2495 | CZ | PHE B | 42 | −29.003 | 1.879 | 5.851 | 1.00 | 56.42 | C |
| ATOM | 2496 | CE2 | PHE B | 42 | −29.726 | 2.719 | 6.927 | 1.00 | 56.71 | C |
| ATOM | 2497 | CD2 | PHE B | 42 | −28.683 | 3.988 | 6.981 | 1.00 | 55.03 | C |
| ATOM | 2498 | C | PHE B | 42 | −29.055 | 7.088 | 5.069 | 1.00 | 56.48 | C |
| ATOM | 2499 | O | PHE B | 42 | −29.924 | 6.456 | 4.421 | 1.00 | 56.01 | O |
| ATOM | 2500 | N | HIS B | 43 | −29.345 | 8.138 | 5.852 | 1.00 | 57.71 | N |
| ATOM | 2501 | CA | HIS B | 43 | −30.751 | 8.619 | 6.039 | 1.00 | 58.68 | C |
| ATOM | 2502 | CB | HIS B | 43 | −30.919 | 9.596 | 7.236 | 1.00 | 59.30 | C |
| ATOM | 2503 | CG | HIS B | 43 | −32.361 | 9.841 | 7.641 | 1.00 | 62.89 | C |
| ATOM | 2504 | ND1 | HIS B | 43 | −33.196 | 10.728 | 6.976 | 1.00 | 64.76 | N |
| ATOM | 2505 | CE1 | HIS B | 43 | −34.395 | 10.712 | 7.535 | 1.00 | 64.75 | C |
| ATOM | 2506 | NE2 | HIS B | 43 | −34.367 | 9.868 | 8.555 | 1.00 | 65.51 | N |
| ATOM | 2507 | CD2 | HIS B | 43 | −33.110 | 9.311 | 8.467 | 1.00 | 63.96 | C |
| ATOM | 2508 | C | HIS B | 43 | −31.366 | 9.207 | 4.752 | 1.00 | 58.34 | C |
| ATOM | 2509 | O | HIS B | 43 | −32.470 | 8.809 | 4.369 | 1.00 | 58.62 | O |
| ATOM | 2510 | N | SER B | 44 | −30.676 | 10.144 | 4.099 | 1.00 | 57.79 | N |
| ATOM | 2511 | CA | SER B | 44 | −31.204 | 10.737 | 2.877 | 1.00 | 57.96 | C |
| ATOM | 2512 | CB | SER B | 44 | −30.274 | 11.807 | 2.346 | 1.00 | 57.32 | C |
| ATOM | 2513 | OG | SER B | 44 | 29.452 | 12.290 | 3.368 | 1.00 | 57.20 | O |
| ATOM | 2514 | C | SER B | 44 | −31.454 | 9.659 | 1.797 | 1.00 | 58.68 | C |
| ATOM | 2515 | O | SER B | 44 | −32.538 | 9.590 | 1.224 | 1.00 | 57.96 | O |
| ATOM | 2516 | N | LEU B | 45 | −30.465 | 8.796 | 1.548 | 1.00 | 59.43 | N |
| ATOM | 2517 | CA | LEU B | 45 | −30.669 | 7.704 | 0.598 | 1.00 | 59.73 | C |
| ATOM | 2518 | CB | LEU B | 45 | −29.470 | 8.737 | 0.537 | 1.00 | 59.77 | C |
| ATOM | 2519 | CG | LEU B | 45 | −28.119 | 7.271 | −0.016 | 1.00 | 60.96 | C |
| ATOM | 2520 | CD1 | LEU B | 45 | −26.876 | 6.335 | 0.130 | 1.00 | 60.30 | C |
| ATOM | 2521 | CD2 | LEU B | 45 | −28.238 | 7.731 | −1.464 | 1.00 | 61.37 | C |
| ATOM | 2522 | C | LEU B | 45 | −31.953 | 6.950 | 0.899 | 1.00 | 50.04 | C |
| ATOM | 2523 | O | LEU B | 45 | −32.579 | 5.466 | −0.027 | 1.00 | 60.97 | O |
| ATOM | 2524 | N | SER B | 46 | −32.367 | 6.851 | 2.167 | 1.00 | 59.82 | N |
| ATOM | 2525 | CA | SER B | 46 | −33.639 | 6.191 | 2.473 | 1.00 | 59.56 | C |
| ATOM | 2526 | CB | SER B | 46 | −33.744 | 5.809 | 3.947 | 1.00 | 59.49 | C |
| ATOM | 2527 | OG | SER B | 46 | −33.978 | 6.938 | 4.790 | 1.00 | 58.64 | O |
| ATOM | 2528 | C | SER B | 46 | −34.846 | 7.015 | 2.020 | 1.00 | 59.99 | C |
| ATOM | 2529 | O | SER B | 46 | −35.901 | 6.459 | 1.711 | 1.00 | 59.43 | O |
| ATOM | 2530 | N | GLU B | 47 | −34.680 | 8.336 | 1.991 | 1.00 | 60.78 | N |
| ATOM | 2531 | CA | GLU B | 47 | −35.706 | 9.231 | 1.429 | 1.00 | 62.09 | C |
| ATOM | 2532 | CB | GLU B | 47 | −35.494 | 10.727 | 1.786 | 1.00 | 62.27 | C |

TABLE 11-continued

| | | | | | | | | | | |
|---|---|---|---|---|---|---|---|---|---|---|
| ATOM | 2533 | CB | GLU B | 47 | −35.195 | 11.052 | 3.266 | 1.00 | 54.92 | C |
| ATOM | 2534 | CD | GLU B | 47 | −36.432 | 11.068 | 4.206 | 1.00 | 70.48 | C |
| ATOM | 2535 | OE1 | GLU B | 47 | −36.708 | 12.169 | 4.776 | 1.00 | 73.77 | O |
| ATOM | 2536 | OE2 | GLU B | 47 | −37.105 | 10.010 | 4.406 | 1.00 | 69.27 | O |
| ATOM | 2537 | C | GLU B | 47 | −35.773 | 9.012 | −0.086 | 1.00 | 62.11 | C |
| ATOM | 2538 | O | GLU B | 47 | −36.836 | 8.700 | −0.601 | 1.00 | 62.69 | O |
| ATOM | 2539 | N | LYS B | 48 | −34.652 | 9.134 | −0.797 | 1.00 | 62.19 | N |
| ATOM | 2540 | CA | LYS B | 48 | −34.618 | 8.758 | −2.230 | 1.00 | 62.33 | C |
| ATOM | 2541 | CB | LYS B | 48 | −33.221 | 8.888 | −2.819 | 1.00 | 61.78 | C |
| ATOM | 2542 | CG | LYSB | 48 | −33.025 | 10.026 | −3.796 | 1.00 | 60.77 | C |
| ATOM | 2543 | CD | LYS B | 48 | −32.010 | 9.564 | −4.889 | 1.00 | 60.21 | C |
| ATOM | 2544 | CE | LYS B | 48 | 31.772 | 10.597 | −5.991 | 1.00 | 57.15 | C |
| ATOM | 2545 | NZ | LYS B | 48 | −32.767 | 10.496 | −7.104 | 1.00 | 56.87 | N |
| ATOM | 2546 | C | LYS B | 48 | −35.179 | 7.362 | −2.564 | 1.00 | 63.02 | C |
| ATOM | 2547 | O | LYS B | 48 | −36.132 | 7.256 | −3.327 | 1.00 | 62.87 | O |
| ATOM | 2548 | N | TYR B | 49 | −34.607 | 6.301 | −1.987 | 1.00 | 64.15 | N |
| ATOM | 2549 | CA | TYR B | 49 | −34.877 | 4.295 | −2.456 | 1.00 | 65.01 | C |
| ATOM | 2550 | CB | TYR B | 49 | −33.571 | 4.109 | −2.566 | 1.00 | 65.12 | C |
| ATOM | 2251 | CG | TYR B | 49 | −32.556 | 4.728 | −3.523 | 1.00 | 67.05 | C |
| ATOM | 2252 | CD1 | TYR B | 49 | −32.650 | 4.532 | −4.915 | 1.00 | 67.78 | C |
| ATOM | 2253 | CE1 | TYR B | 49 | −31.734 | 5.104 | −5.804 | 1.00 | 67.51 | C |
| ATOM | 2554 | CZ | TYR B | 49 | −30.704 | 5.903 | −5.314 | 1.00 | 71.70 | C |
| ATOM | 2555 | OH | TYR B | 49 | −29.779 | 6.481 | −6.180 | 1.00 | 72.28 | O |
| ATOM | 2356 | CE2 | TYR B | 49 | −30.582 | 6.123 | −3.930 | 1.00 | 71.37 | C |
| ATOM | 2557 | CD2 | TYR B | 49 | −31.512 | 5.521 | −3.044 | 1.00 | 70.31 | C |
| ATOM | 2558 | C | TYR B | 49 | −35.962 | 4.199 | 1.670 | 1.00 | 65.09 | C |
| ATOM | 2259 | O | TYR B | 49 | −35.717 | 3.209 | −0.997 | 1.00 | 65.42 | O |
| ATOM | 2260 | N | SER B | 50 | −37.181 | 4.694 | −1.766 | 1.00 | 65.47 | N |
| ATOM | 2261 | CA | SER B | 50 | −38.263 | 4.139 | −0.956 | 1.00 | 66.58 | C |
| ATOM | 2262 | CB | SER B | 50 | −39.321 | 5.200 | −0.701 | 1.00 | 66.45 | C |
| ATOM | 2263 | OG | SER B | 50 | −39.237 | 6.171 | −1.732 | 1.00 | 68.05 | O |
| ATOM | 2264 | C | SER B | 50 | −38.845 | 2.878 | −1.584 | 1.00 | 66.74 | C |
| ATOM | 2265 | O | SER B | 50 | −39.784 | 2.263 | −1.061 | 1.00 | 66.29 | O |
| ATOM | 2266 | N | ASN B | 51 | −38.249 | 2.489 | −2.696 | 1.00 | 67.11 | N |
| ATOM | 2267 | CA | ASN B | 51 | −38.489 | 1.186 | −3.257 | 1.00 | 68.25 | C |
| ATOM | 2268 | CB | ASN B | 51 | −38.230 | 1.212 | −4.771 | 1.00 | 69.32 | C |
| ATOM | 2269 | CG | ASN B | 51 | −36.854 | 1.831 | −5.159 | 1.00 | 71.87 | C |
| ATOM | 2270 | OD1 | ASN B | 51 | −36.435 | 2.900 | −4.647 | 1.00 | 72.68 | O |
| ATOM | 2271 | ND2 | ASN B | 51 | −36.166 | 1.160 | −6.112 | 1.00 | 72.93 | N |
| ATOM | 2272 | C | ASN B | 51 | −37.623 | 0.153 | −2.557 | 1.00 | 67.90 | C |
| ATOM | 2273 | O | ASN B | 51 | −37.733 | −1.050 | −2.807 | 1.00 | 67.58 | O |
| ATOM | 2274 | N | VAL B | 52 | −36.776 | 0.665 | −1.660 | 1.00 | 68.24 | N |
| ATOM | 2275 | CA | VAL B | 52 | −35.756 | −0.095 | −0.904 | 1.00 | 67.91 | C |
| ATOM | 2276 | CB | VAL B | 52 | −34.338 | 0.419 | −1.225 | 1.00 | 67.71 | C |
| ATOM | 2277 | CG1 | VAL B | 52 | −33.293 | −0.507 | −0.664 | 1.00 | 66.91 | C |
| ATOM | 2278 | CG2 | VAL B | 52 | −34.163 | 0.623 | −2.732 | 1.00 | 67.98 | C |
| ATOM | 2279 | C | VAL B | 52 | −35.956 | 0.087 | 0.602 | 1.00 | 68.03 | C |
| ATOM | 2280 | O | VAL B | 52 | −36.334 | 1.185 | 1.078 | 1.00 | 67.42 | O |
| ATOM | 2281 | N | ILE B | 53 | −35.682 | −0.966 | 1.341 | 1.00 | 68.43 | N |
| ATOM | 2282 | CA | ILE B | 53 | −35.809 | −0.975 | 2.803 | 1.00 | 69.01 | C |
| ATOM | 2283 | CB | ILE B | 53 | −36.425 | −2.282 | 3.375 | 1.00 | 68.93 | C |
| ATOM | 2284 | CG1 | ILE B | 53 | −37.854 | −2.495 | 2.838 | 1.00 | 69.28 | C |
| ATOM | 2285 | CD1 | ILE B | 53 | −38.729 | −1.211 | 2.711 | 1.00 | 69.22 | C |
| ATOM | 2286 | CG2 | ILE B | 53 | −36.375 | −2.266 | 4.898 | 1.00 | 67.78 | C |
| ATOM | 2287 | C | ILE B | 53 | −34.469 | −0.785 | 3.447 | 1.00 | 69.33 | C |
| ATOM | 2288 | O | ILE B | 53 | −33.647 | −1.567 | 3.199 | 1.00 | 69.13 | O |
| ATOM | 2289 | N | PHE B | 54 | −34.370 | 0.258 | 4.268 | 1.00 | 69.77 | N |
| ATOM | 2290 | CA | PHE B | 54 | −33.781 | 0.510 | 5.039 | 1.00 | 70.15 | C |
| ATOM | 2291 | CB | PHE B | 54 | −32.781 | 1.984 | 5.007 | 1.00 | 70.60 | C |
| ATOM | 2292 | CG | PHE B | 54 | −32.589 | 2.525 | 3.645 | 1.00 | 71.93 | C |
| ATOM | 2293 | CD1 | PHE B | 54 | −33.639 | 2.526 | 2.731 | 1.00 | 73.48 | C |
| ATOM | 2294 | CE1 | PHE B | 54 | −33.469 | 3.049 | 1.446 | 1.00 | 74.58 | C |
| ATOM | 2295 | CZ | PHE B | 54 | −32.232 | 3.592 | 1.077 | 1.00 | 74.75 | C |
| ATOM | 2596 | CE2 | PHE B | 54 | −31.165 | 3.607 | 1.997 | 1.00 | 73.84 | C |
| ATOM | 2597 | CD2 | PHE B | 54 | −31.357 | 3.074 | 3.278 | 1.00 | 73.14 | C |
| ATOM | 2598 | C | PHE B | 54 | −33.374 | 0.127 | 6.479 | 1.00 | 69.59 | C |
| ATOM | 2599 | O | PHE B | 54 | −34.457 | 0.329 | 7.031 | 1.00 | 69.83 | O |
| ATOM | 2600 | N | LEU B | 55 | −32.323 | −0.395 | 7.089 | 1.00 | 68.97 | N |
| ATOM | 2601 | CA | LEU B | 55 | −32.340 | −0.711 | 8.500 | 1.00 | 68.41 | C |
| ATOM | 2602 | CB | LEU B | 55 | −32.665 | −2.193 | 8.690 | 1.00 | 68.29 | C |
| ATOM | 2603 | CG | LEU B | 55 | −33.850 | −2.846 | 7.960 | 1.00 | 67.42 | C |
| ATOM | 2604 | CD1 | LEU B | 55 | −33.675 | −4.384 | 7.959 | 1.00 | 65.18 | C |
| ATOM | 2605 | CD2 | LEU B | 55 | −35.215 | −2.431 | 8.552 | 1.00 | 66.06 | C |
| ATOM | 2606 | C | LEU B | 55 | −30.976 | −0.375 | 9.131 | 1.00 | 68.19 | C |
| ATOM | 2607 | O | LEU B | 55 | −29.946 | −0.645 | 8.427 | 1.00 | 68.50 | O |
| ATOM | 2608 | N | GLU B | 56 | 31.001 | −0.102 | 10.441 | 1.00 | 67.22 | N |
| ATOM | 2609 | CA | GLU B | 56 | −29.821 | 0.066 | 11.272 | 1.00 | 66.56 | C |
| ATOM | 2610 | CB | GLU B | 56 | −29.856 | 1.404 | 12.005 | 1.00 | 87.03 | C |
| ATOM | 2611 | CG | GLU B | 56 | −28.481 | 1.803 | 12.634 | 1.00 | 68.20 | C |
| ATOM | 2612 | CD | GLU B | 56 | −28.281 | 3.314 | 12.612 | 1.00 | 71.39 | C |

TABLE 11-continued

| ATOM | 2613 | OE1 | GLU B | 56 | −29.332 | 3.985 | 12.510 | 1.00 | 76.48 | O |
|---|---|---|---|---|---|---|---|---|---|---|
| ATOM | 2614 | OE2 | GLU B | 56 | −27.130 | 3.837 | 12.671 | 1.00 | 69.97 | O |
| ATOM | 2615 | C | GLU B | 56 | −29.763 | −1.018 | 12.321 | 1.00 | 65.94 | C |
| ATOM | 2616 | O | GLU B | 56 | −30.781 | −1.412 | 12.850 | 1.00 | 66.33 | O |
| ATOM | 2617 | N | VAL B | 57 | −28.557 | −1.487 | 12.617 | 1.00 | 62.25 | N |
| ATOM | 2618 | CA | VAL B | 57 | −28.265 | −2.325 | 13.776 | 1.00 | 63.79 | C |
| ATOM | 2619 | CB | VAL B | 57 | −27.964 | −3.768 | 13.373 | 1.00 | 63.05 | C |
| ATOM | 2620 | CG1 | VAL B | 57 | −27.641 | −4.605 | 14.636 | 1.00 | 63.31 | C |
| ATOM | 2621 | CG2 | VAL B | 57 | −29.116 | −4.364 | 12.542 | 1.00 | 63.01 | C |
| ATOM | 2622 | C | VAL B | 57 | −27.015 | −1.813 | 14.493 | 1.00 | 63.43 | C |
| ATOM | 2623 | O | VAL B | 57 | −25.944 | −1.676 | 13.898 | 1.00 | 62.01 | O |
| ATOM | 2624 | N | ASP B | 58 | −27.164 | −1.544 | 15.782 | 1.00 | 63.60 | N |
| ATOM | 2625 | CA | ASP B | 58 | −26.040 | −1.191 | 16.613 | 1.00 | 63.55 | C |
| ATOM | 2626 | CB | ASP B | 58 | −26.477 | −0.319 | 17.767 | 1.00 | 62.70 | C |
| ATOM | 2627 | CG | ASP B | 58 | −25.317 | 0.271 | 18.489 | 1.00 | 64.17 | C |
| ATOM | 2628 | OD1 | ASP B | 58 | −24.505 | −0.492 | 19.057 | 1.00 | 67.81 | O |
| ATOM | 2629 | OD2 | ASP B | 58 | −25.187 | 1.505 | 18.502 | 1.00 | 65.01 | O |
| ATOM | 2630 | C | ASP B | 58 | −25.340 | −2.462 | 17.109 | 1.00 | 64.10 | C |
| ATOM | 2631 | O | ASP B | 58 | −25.886 | −3.204 | 17.291 | 1.00 | 64.02 | O |
| ATOM | 2632 | N | VAL B | 59 | −24.120 | −2.682 | 16.608 | 1.00 | 64.27 | N |
| ATOM | 2633 | CA | VAL B | 59 | −23.305 | −3.851 | 16.930 | 1.00 | 64.46 | C |
| ATOM | 2634 | CB | VAL B | 59 | −21.883 | −3.763 | 16.278 | 1.00 | 64.19 | C |
| ATOM | 2635 | CG1 | VAL B | 59 | −21.980 | −3.760 | 14.792 | 1.00 | 62.66 | C |
| ATOM | 2636 | CG2 | VAL B | 59 | −21.116 | −2.540 | 16.733 | 1.00 | 63.50 | C |
| ATOM | 2637 | C | VAL B | 59 | −23.122 | −4.064 | 18.426 | 1.00 | 65.36 | C |
| ATOM | 2638 | O | VAL B | 59 | −22.917 | −5.192 | 18.894 | 1.00 | 64.77 | O |
| ATOM | 2639 | N | ASP B | 60 | −23.154 | −2.970 | 19.171 | 1.00 | 66.86 | N |
| ATOM | 2640 | CA | ASP B | 60 | −23.072 | −3.066 | 20.614 | 1.00 | 68.24 | C |
| ATOM | 2641 | CB | ASP B | 60 | −22.497 | −1.770 | 21.199 | 1.00 | 68.43 | C |
| ATOM | 2642 | CG | ASP B | 60 | −20.985 | −1.643 | 20.971 | 1.00 | 69.30 | C |
| ATOM | 2643 | OD1 | ASP B | 60 | −20.517 | −0.541 | 20.618 | 1.00 | 69.99 | O |
| ATOM | 2644 | OD2 | ASP B | 60 | −20.262 | −2.647 | 21.143 | 1.00 | 70.16 | O |
| ATOM | 2645 | C | ASP B | 60 | −24.426 | −3.430 | 21.231 | 1.00 | 68.81 | C |
| ATOM | 2646 | O | ASP B | 60 | −24.474 | −4.026 | 22.303 | 1.00 | 68.99 | O |
| ATOM | 2647 | N | ASP B | 61 | −25.521 | −3.080 | 20.558 | 1.00 | 69.62 | N |
| ATOM | 2648 | CA | ASP B | 61 | −28.845 | −3.310 | 21.138 | 1.00 | 70.96 | C |
| ATOM | 2649 | CB | ASP B | 61 | −27.904 | −2.361 | 20.593 | 1.00 | 71.34 | C |
| ATOM | 2650 | CG | ASP B | 61 | 27.932 | 1.044 | 21.323 | 1.00 | 72.99 | C |
| ATOM | 2651 | OD1 | ASP B | 61 | −27.386 | −0.984 | 22.461 | 1.00 | 73.20 | O |
| ATOM | 2652 | OD2 | ASP B | 61 | −28.504 | −0.081 | 20.744 | 1.00 | 74.12 | O |
| ATOM | 2653 | C | ASP B | 61 | −27.289 | −4.693 | 20.830 | 1.00 | 71.34 | C |
| ATOM | 2654 | O | ASP B | 61 | −27.979 | −5.310 | 21.627 | 1.00 | 72.08 | O |
| ATOM | 2655 | N | CYS B | 61 | −26.903 | −5.175 | 19.659 | 1.00 | 71.51 | N |
| ATOM | 2656 | CA | CYS B | 62 | −27.287 | −6.490 | 19.220 | 1.00 | 71.67 | C |
| ATOM | 2657 | CB | CYS B | 62 | −28.075 | −6.302 | 17.026 | 1.00 | 71.71 | C |
| ATOM | 2658 | SG | CYS B | 62 | −29.471 | −5.242 | 18.014 | 1.00 | 57.01 | S |
| ATOM | 2659 | C | CYS B | 62 | −26.036 | −7.280 | 18.987 | 1.00 | 71.43 | C |
| ATOM | 2660 | O | CYS B | 62 | −25.817 | −7.776 | 17.876 | 1.00 | 71.58 | O |
| ATOM | 2661 | N | GLN B | 63 | −25.201 | −7.391 | 20.023 | 1.00 | 71.17 | N |
| ATOM | 2662 | CA | GLN B | 63 | −23.995 | −8.197 | 19.907 | 1.00 | 70.77 | C |
| ATOM | 2663 | CB | GLN B | 63 | −23.371 | −8.485 | 21.289 | 1.00 | 70.39 | C |
| ATOM | 2664 | CG | GLN B | 63 | −21.834 | −8.279 | 21.379 | 1.00 | 72.03 | C |
| ATOM | 2665 | CD | GLN B | 63 | −21.369 | −6.951 | 22.090 | 1.00 | 75.42 | C |
| ATOM | 2666 | OE1 | GLN B | 63 | −21.420 | −6.844 | 23.319 | 1.00 | 75.50 | O |
| ATOM | 2667 | NE2 | GLN B | 63 | −20.882 | −5.958 | 21.301 | 1.00 | 75.33 | N |
| ATOM | 2668 | C | GLN B | 63 | −24.440 | −.460 | 19.121 | 1.00 | 70.44 | C |
| ATOM | 2669 | O | GLN B | 63 | −23.789 | −9.855 | 18.137 | 1.00 | 70.48 | O |
| ATOM | 2670 | N | ASP B | 64 | −25.611 | −10.006 | 19.477 | 1.00 | 69.82 | N |
| ATOM | 2671 | CA | ASP B | 64 | −26.112 | −11.252 | 18.854 | 1.00 | 69.48 | C |
| ATOM | 2672 | CB | ASP B | 64 | −27.288 | −11.888 | 19.655 | 1.00 | 69.46 | C |
| ATOM | 2673 | CG | ASP B | 64 | −28.585 | −11.080 | 19.581 | 1.00 | 70.35 | C |
| ATOM | 2674 | OD1 | ASP B | 64 | −28.543 | −9.834 | 19.497 | 1.00 | 70.83 | O |
| ATOM | 2675 | OD2 | ASP B | 64 | −29.675 | −11.699 | 19.618 | 1.00 | 72.78 | O |
| ATOM | 2676 | C | ASP B | 64 | −26.345 | −11.239 | 17.319 | 1.00 | 68.89 | C |
| ATOM | 2677 | O | ASP B | 64 | −25.922 | −12.169 | 16.620 | 1.00 | 68.93 | O |
| ATOM | 2678 | N | VAL B | 65 | −26.956 | −10.200 | 16.767 | 1.00 | 68.24 | N |
| ATOM | 2679 | CA | VAL B | 65 | −27.155 | −10.223 | 15.312 | 1.00 | 68.57 | C |
| ATOM | 2680 | CB | VAL B | 65 | −28.330 | −9.316 | 14.828 | 1.00 | 68.57 | C |
| ATOM | 2681 | CG1 | VAL B | 65 | −27.902 | −7.888 | 14.661 | 1.00 | 69.22 | C |
| ATOM | 2682 | CG2 | VAL B | 65 | −28.867 | −9.824 | 13.519 | 1.00 | 68.71 | C |
| ATOM | 2683 | C | VAL B | 65 | −25.849 | −9.956 | 14.555 | 1.00 | 68.95 | C |
| ATOM | 2684 | O | VAL B | 65 | −25.561 | −10.580 | 13.507 | 1.00 | 68.66 | O |
| ATOM | 2685 | N | ALA B | 66 | −25.055 | −9.037 | 15.112 | 1.00 | 69.27 | N |
| ATOM | 2686 | CA | ALA B | 66 | −23.712 | −8.759 | 14.622 | 1.00 | 69.64 | C |
| ATOM | 2687 | CB | ALA B | 66 | −22.934 | −7.863 | 15.597 | 1.00 | 69.82 | C |
| ATOM | 2688 | C | ALA B | 66 | 22.990 | 10.085 | 14.407 | 1.00 | 69.55 | C |
| ATOM | 2689 | O | ALA B | 66 | −22.378 | −10.300 | 13.355 | 1.00 | 69.63 | O |
| ATOM | 2690 | N | SER B | 67 | −23.097 | −10.983 | 15.380 | 1.00 | 69.74 | N |
| ATOM | 2691 | CA | SER B | 67 | −22.426 | −12.255 | 15.234 | 1.00 | 70.43 | C |
| ATOM | 2692 | CB | SER B | 67 | −22.171 | −12.908 | 16.570 | 1.00 | 70.99 | C |

TABLE 11-continued

| | | | | | | | | | | |
|---|---|---|---|---|---|---|---|---|---|---|
| ATOM | 2693 | OG | SER B | 67 | −20.953 | −13.635 | 16.464 | 1.00 | 73.34 | O |
| ATOM | 2694 | C | SER B | 67 | −23.063 | −13.224 | 14.247 | 1.00 | 70.17 | C |
| ATOM | 2695 | O | SER B | 67 | −22.359 | −13.740 | 13.362 | 1.00 | 69.89 | O |
| ATOM | 2696 | N | GLU B | 68 | −24.375 | −13.454 | 14.380 | 1.00 | 70.14 | N |
| ATOM | 2697 | CA | GLU B | 68 | −25.128 | −14.209 | 13.361 | 1.00 | 70.36 | C |
| ATOM | 2698 | CB | GLU B | 68 | −26.650 | −14.094 | 13.569 | 1.00 | 70.30 | C |
| ATOM | 2699 | CG | GLU B | 68 | −27.361 | −15.416 | 13.985 | 1.00 | 70.62 | C |
| ATOM | 2700 | CD | GLU B | 68 | −28.141 | −16.118 | 12.829 | 1.00 | 70.84 | C |
| ATOM | 2701 | OE1 | GLU B | 68 | −28.527 | −15.446 | 11.833 | 1.00 | 68.91 | O |
| ATOM | 2702 | OE2 | GLU B | 68 | −28.378 | −17.355 | 12.932 | 1.00 | 70.34 | O |
| ATOM | 2703 | C | GLU B | 68 | −24.749 | −13.970 | 11.927 | 1.00 | 70.59 | C |
| ATOM | 2704 | O | GLUB | 68 | −24.884 | −14.591 | 10.985 | 1.00 | 70.69 | O |
| ATOM | 2705 | N | CYS B | 69 | −24.265 | −12.544 | 11.780 | 1.00 | 70.46 | N |
| ATOM | 2706 | CA | CYS B | 69 | −23.932 | −11.961 | 10.471 | 1.00 | 70.00 | C |
| ATOM | 2707 | CB | CYS B | 69 | −24.591 | −10.595 | 10.331 | 1.00 | 70.71 | C |
| ATOM | 2708 | SG | CYS B | 69 | −26.364 | −10.564 | 10.066 | 1.00 | 70.82 | S |
| ATOM | 2709 | C | CYS B | 69 | −22.452 | −11.722 | 10.216 | 1.00 | 69.35 | C |
| ATOM | 2710 | O | CYS B | 69 | −22.124 | −10.895 | 9.366 | 1.00 | 68.55 | O |
| ATOM | 2711 | N | GLU B | 70 | −21.579 | −12.415 | 10.951 | 1.00 | 68.70 | N |
| ATOM | 2712 | CA | GLU B | 70 | −20.119 | −12.186 | 10.896 | 1.00 | 67.94 | C |
| ATOM | 2713 | CB | GLU B | 70 | −19.463 | −13.105 | 9.871 | 1.00 | 68.09 | C |
| ATOM | 2714 | CG | GLU B | 70 | −19.260 | −14.488 | 10.369 | 1.00 | 70.05 | C |
| ATOM | 2715 | CD | GLU B | 70 | −19.743 | −15.480 | 9.362 | 1.00 | 71.86 | C |
| ATOM | 2716 | OE1 | GLU B | 70 | −19.163 | −15.481 | 8.256 | 1.00 | 72.67 | O |
| ATOM | 2717 | OE2 | GLU B | 70 | −20.711 | −16.225 | 9.663 | 1.00 | 71.30 | O |
| ATOM | 2718 | C | GLU B | 70 | −19.684 | −10.746 | 10.609 | 1.00 | 66.65 | C |
| ATOM | 2719 | O | GLU B | 70 | −18.937 | −10.487 | 9.660 | 1.00 | 85.94 | O |
| ATOM | 2720 | N | VAL B | 71 | −20.121 | −9.811 | 11.420 | 1.00 | 65.27 | N |
| ATOM | 2721 | CA | VAL B | 71 | −19.679 | −8.472 | 11.143 | 1.00 | 65.18 | C |
| ATOM | 2722 | CB | VAL B | 71 | −20.756 | −7.428 | 11.457 | 1.00 | 66.13 | C |
| ATOM | 2723 | CG1 | VAL B | 71 | −20.148 | −6.019 | 11.449 | 1.00 | 67.88 | C |
| ATOM | 2724 | CG2 | VAL B | 71 | −21.894 | −7.531 | 10.440 | 1.00 | 65.98 | C |
| ATOM | 2725 | C | VAL B | 71 | −18.381 | −8.187 | 11.865 | 1.00 | 63.85 | C |
| ATOM | 2726 | O | VAL B | 71 | −18.254 | −8.459 | 13.039 | 1.00 | 63.48 | O |
| ATOM | 2727 | N | LYS B | 72 | −17.413 | −7.624 | 11.157 | 1.00 | 62.90 | N |
| ATOM | 2728 | CA | LYS B | 72 | −16.097 | −7.473 | 11.739 | 1.00 | 61.61 | C |
| ATOM | 2729 | CB | LYS B | 72 | −15.056 | −8.031 | 10.808 | 1.00 | 61.68 | C |
| ATOM | 2730 | CG | LYS B | 72 | −15.140 | −9.547 | 10.779 | 1.00 | 64.97 | C |
| ATOM | 2731 | CD | LYS B | 72 | −14.221 | −10.194 | 11.835 | 1.00 | 68.85 | C |
| ATOM | 2732 | CE | LYS B | 72 | −14.852 | −11.403 | 12.531 | 1.00 | 69.69 | C |
| ATOM | 2733 | NZ | LYS B | 72 | −13.816 | −11.950 | 13.470 | 1.00 | 69.74 | N |
| ATOM | 2734 | C | LYS B | 72 | −15.816 | −6.049 | 12.079 | 1.00 | 60.55 | C |
| ATOM | 2735 | O | LYS B | 72 | −15.094 | −5.760 | 13.024 | 1.00 | 60.77 | O |
| ATOM | 2736 | N | CYS B | 73 | −16.430 | −5.143 | 11.349 | 1.00 | 59.36 | N |
| ATOM | 2737 | CA | CYS B | 73 | −16.122 | −3.754 | 11.539 | 1.00 | 58.77 | C |
| ATOM | 2738 | CB | CYS B | 73 | −14.848 | −3.396 | 10.752 | 1.00 | 59.74 | C |
| ATOM | 2739 | SG | CYS B | 73 | −15.116 | −3.521 | 8.946 | 1.00 | 64.15 | S |
| ATOM | 2740 | C | CYS B | 73 | −17.281 | −2.890 | 11.131 | 1.00 | 56.84 | C |
| ATOM | 2741 | O | CYS B | 73 | −18.2387 | −3.352 | 10.557 | 1.00 | 56.99 | O |
| ATOM | 2742 | N | MET B | 74 | −17.419 | −1.612 | 11.419 | 1.00 | 55.89 | N |
| ATOM | 2743 | CA | MET B | 74 | −18.315 | −0.691 | 11.308 | 1.00 | 55.23 | C |
| ATOM | 2744 | CB | MET B | 74 | −18.796 | −0.181 | 12.698 | 1.00 | 54.63 | C |
| ATOM | 2745 | CG | MET B | 74 | −19.350 | −1.180 | 13.650 | 1.00 | 53.08 | C |
| ATOM | 2746 | SD | MET B | 74 | −18.161 | −2.425 | 14.244 | 1.00 | 60.31 | S |
| ATOM | 2747 | CE | MET B | 74 | −17.188 | −1.695 | 15.580 | 1.00 | 51.46 | C |
| ATOM | 2748 | C | MET B | 74 | −17.728 | 0.477 | 10.593 | 1.00 | 54.65 | C |
| ATOM | 2749 | O | MET B | 74 | −16.555 | 0.751 | 10.792 | 1.00 | 54.85 | O |
| ATOM | 2750 | N | PRO B | 75 | −18.511 | 1.156 | 9.754 | 1.00 | 54.54 | N |
| ATOM | 2751 | CA | PRO B | 75 | −19.793 | 0.723 | 9.219 | 1.00 | 54.40 | C |
| ATOM | 2752 | CB | PRO B | 75 | 20.271 | 1.926 | 8.394 | 1.00 | 54.50 | C |
| ATOM | 2753 | CG | PRO B | 75 | −19.283 | 2.994 | 8.551 | 1.00 | 55.89 | C |
| ATOM | 2754 | CD | PRO B | 75 | −18.103 | 2.495 | 9.286 | 1.00 | 54.66 | C |
| ATOM | 2755 | C | PRO B | 75 | −19.558 | −0.409 | 8.250 | 1.00 | 54.29 | C |
| ATOM | 2756 | O | PRO B | 75 | −18.608 | −0.32 | 7.449 | 1.00 | 54.50 | O |
| ATOM | 2757 | N | THR B | 76 | −20.367 | −1.469 | 8.344 | 1.00 | 53.70 | N |
| ATOM | 2758 | CA | THR B | 76 | −20.468 | −2.492 | 7.284 | 1.00 | 52.82 | C |
| ATOM | 2759 | CB | THR B | 76 | −20.219 | −3.937 | 7.802 | 1.00 | 53.28 | C |
| ATOM | 2760 | OG1 | THR B | 76 | −18.842 | −4.144 | 8.065 | 1.00 | 49.94 | O |
| ATOM | 2761 | CG2 | THR B | 76 | −20.702 | 5.020 | 6.752 | 1.00 | 52.99 | C |
| ATOM | 2762 | C | THR B | 76 | −21.890 | −2.506 | 6.777 | 1.00 | 52.76 | C |
| ATOM | 2763 | O | THR B | 76 | −22.838 | −2.499 | 7.544 | 1.00 | 52.47 | O |
| ATOM | 2764 | N | PHE B | 77 | −22.053 | −2.587 | 5.480 | 1.00 | 52.91 | N |
| ATOM | 2765 | CA | PHE B | 77 | −23.386 | −2.600 | 4.938 | 1.00 | 53.04 | C |
| ATOM | 2766 | CB | PHE B | 77 | −23.501 | −1.507 | 3.920 | 1.00 | 51.58 | C |
| ATOM | 2767 | CG | PHE B | 77 | −23.389 | −0.158 | 4.471 | 1.00 | 49.15 | C |
| ATOM | 2768 | CD1 | PHE B | 77 | −24.498 | 0.476 | 4.999 | 1.00 | 50.76 | C |
| ATOM | 2769 | CE1 | PHE B | 77 | −24.418 | 1.777 | 5.506 | 1.00 | 51.92 | C |
| ATOM | 2770 | CZ | PHE B | 77 | −23.207 | 2.463 | 5.449 | 1.00 | 52.36 | C |
| ATOM | 2771 | CE2 | PHE B | 77 | −22.085 | 1.825 | 4.885 | 1.00 | 51.01 | C |
| ATOM | 2772 | CD2 | PHE B | 77 | −22.192 | 0.522 | 4.409 | 1.00 | 48.39 | C |

TABLE 11-continued

| | | | | | | | | | |
|---|---|---|---|---|---|---|---|---|---|
| ATOM | 2773 | C | PHE B | 77 | −23.690 | −3.495 | 4.285 | 1.00 | 54.71 | C |
| ATOM | 2774 | O | PHE B | 77 | −22.889 | −4.490 | 3.523 | 1.00 | 55.14 | O |
| ATOM | 2775 | N | GLN B | 78 | −24.850 | −4.500 | 4.570 | 1.00 | 56.34 | N |
| ATOM | 2776 | CA | GLN B | 78 | −25.184 | −5.760 | 3.909 | 1.00 | 58.44 | C |
| ATOM | 2777 | CB | GLN B | 78 | −25.242 | −6.886 | 4.930 | 1.00 | 58.59 | C |
| ATOM | 2778 | CG | GLN B | 78 | −23.957 | −7.128 | 5.602 | 1.00 | 60.01 | C |
| ATOM | 2779 | CD | GLN B | 78 | −23.946 | −8.461 | 6.428 | 1.00 | 61.40 | C |
| ATOM | 2780 | OE1 | GLN B | 78 | −22.893 | −8.490 | 6.847 | 1.00 | 63.37 | O |
| ATOM | 2781 | NE2 | GLN B | 78 | −25.119 | −9.068 | 6.590 | 1.00 | 63.17 | N |
| ATOM | 2782 | C | GLN B | 78 | −26.493 | −5.683 | 3.117 | 1.00 | 59.32 | C |
| ATOM | 2783 | O | GLN B | 78 | −27.476 | −5.088 | 3.586 | 1.00 | 59.18 | O |
| ATOM | 2784 | N | PHE B | 79 | −26.497 | −6.288 | 1.926 | 1.00 | 60.88 | N |
| ATOM | 2785 | CA | PHE B | 79 | −27.261 | −6.250 | 1.038 | 1.00 | 62.27 | C |
| ATOM | 2786 | CB | PHE B | 79 | −27.331 | −5.608 | −0.304 | 1.00 | 62.26 | C |
| ATOM | 2787 | CG | PHE B | 79 | −26.751 | −4.213 | −0.187 | 1.00 | 63.28 | C |
| ATOM | 2788 | CD1 | PHE B | 79 | −25.607 | −3.976 | 0.543 | 1.00 | 63.73 | C |
| ATOM | 2789 | CE1 | PHE B | 79 | −25.074 | −2.703 | 0.644 | 1.00 | 65.78 | C |
| ATOM | 2790 | CZ | PHE B | 79 | −25.696 | −1.631 | 0.009 | 1.00 | 67.81 | C |
| ATOM | 2791 | CE2 | PHE B | 79 | −26.840 | −1.849 | −0.738 | 1.00 | 65.78 | C |
| ATOM | 2792 | CD2 | PHE B | 79 | −27.356 | −3.135 | −0.831 | 1.00 | 65.88 | C |
| ATOM | 2793 | C | PHE B | 79 | −28.238 | −7.618 | 0.809 | 1.00 | 63.05 | C |
| ATOM | 2794 | O | PHE B | 79 | −27.512 | −8.573 | 0.513 | 1.00 | 62.85 | O |
| ATOM | 2795 | N | PHE B | 80 | −29.557 | −7.669 | 0.941 | 1.00 | 65.00 | N |
| ATOM | 2796 | CA | PHE B | 80 | −30.404 | −8.852 | 0.695 | 1.00 | 66.65 | C |
| ATOM | 2797 | CB | PHE B | 80 | −31.012 | −9.358 | 2.005 | 1.00 | 66.12 | C |
| ATOM | 2798 | CG | PHE B | 80 | −30.055 | −9.352 | 3.125 | 1.00 | 67.46 | C |
| ATOM | 2799 | CD1 | PHE B | 80 | −29.756 | −8.168 | 3.790 | 1.00 | 67.44 | C |
| ATOM | 2800 | CE1 | PHE B | 80 | −28.837 | −8.146 | 4.831 | 1.00 | 66.84 | C |
| ATOM | 2801 | CZ | PHE B | 80 | −28.193 | −9.333 | 5.226 | 1.00 | 67.00 | C |
| ATOM | 2802 | CE2 | PHE B | 80 | −28.463 | −10.524 | 4.554 | 1.00 | 67.48 | C |
| ATOM | 2803 | CE2 | PHE B | 80 | −29.401 | −10.521 | 3.498 | 1.00 | 68.95 | C |
| ATOM | 2804 | C | PHE B | 80 | −31.551 | −8.562 | −0.292 | 1.00 | 67.92 | C |
| ATOM | 2805 | O | PHE B | 80 | 32.139 | 7.457 | 0.324 | 1.00 | 67.65 | O |
| ATOM | 2806 | N | LYS B | 81 | −31.849 | −9.590 | −1.090 | 1.00 | 69.67 | N |
| ATOM | 2807 | CA | LYS B | 81 | −33.074 | −9.701 | −1.883 | 1.00 | 70.31 | C |
| ATOM | 2808 | CB | LYS B | 81 | −32.754 | −9.634 | −3.384 | 1.00 | 70.36 | C |
| ATOM | 2809 | CG | LYS B | 81 | −33.752 | −8.796 | −4.242 | 1.00 | 70.16 | C |
| ATOM | 2810 | CD | LYS B | 81 | −32.973 | −7.934 | −5.291 | 1.00 | 70.55 | C |
| ATOM | 2811 | CE | LYS B | 81 | −31.767 | −8.728 | −8.007 | 1.00 | 70.37 | C |
| ATOM | 2812 | NZ | LYS B | 81 | −31.275 | −7.975 | −7.313 | 1.00 | 69.33 | N |
| ATOM | 2813 | C | LYS B | 81 | −33.652 | −11.068 | −1.521 | 1.00 | 70.79 | C |
| ATOM | 2814 | O | LYS B | 81 | −32.928 | −12.066 | −1.457 | 1.00 | 70.84 | O |
| ATOM | 2815 | N | LYS B | 82 | −34.956 | −11.106 | −1.723 | 1.00 | 71.86 | N |
| ATOM | 2816 | CA | LYS B | 82 | −35.670 | −12.358 | −0.924 | 1.00 | 72.11 | C |
| ATOM | 2817 | CB | LYS B | 82 | −35.403 | −13.512 | −1.930 | 1.00 | 71.81 | C |
| ATOM | 2818 | CG | LYS B | 82 | −35.953 | −13.289 | −3.366 | 1.00 | 70.88 | C |
| ATOM | 2819 | CD | LYS B | 82 | −37.164 | −14.175 | −3.720 | 1.00 | 69.21 | C |
| ATOM | 2820 | CE | LYS B | 82 | −37.475 | −14.176 | −5.254 | 1.00 | 66.83 | C |
| ATOM | 2821 | NZ | LYS B | 82 | −38.782 | −14.787 | −5.616 | 1.00 | 63.29 | N |
| ATOM | 2822 | C | LYS B | 82 | −35.375 | −12.807 | 0.507 | 1.00 | 72.32 | C |
| ATOM | 2823 | O | LYS B | 82 | −36.164 | −13.541 | 1.092 | 1.00 | 72.93 | O |
| ATOM | 2824 | N | GLY B | 83 | −34.263 | −12.356 | 1.075 | 1.00 | 72.41 | N |
| ATOM | 2825 | CA | GLY B | 83 | −33.868 | −12.795 | 2.410 | 1.00 | 72.45 | C |
| ATOM | 2826 | C | GLY B | 83 | −32.394 | −13.137 | 2.442 | 1.00 | 72.55 | C |
| ATOM | 2827 | O | GLY B | 83 | −31.772 | −13.187 | 3.504 | 1.00 | 72.50 | O |
| ATOM | 2828 | N | GLN B | 84 | −31.820 | −13.356 | 1.269 | 1.00 | 72.52 | N |
| ATOM | 2829 | CA | GLN B | 84 | −30.454 | −13.844 | 1.206 | 1.00 | 72.67 | C |
| ATOM | 2830 | CB | GLN B | 84 | −30.416 | −15.100 | 0.326 | 1.00 | 72.92 | C |
| ATOM | 2831 | CG | GLN B | 84 | −31.399 | −16.197 | 0.813 | 1.00 | 73.92 | C |
| ATOM | 2832 | CD | GLN B | 84 | −31.110 | −16.716 | 2.259 | 1.00 | 75.23 | C |
| ATOM | 2833 | OE1 | GLN B | 84 | −31.011 | −17.390 | 2.478 | 1.00 | 74.42 | O |
| ATOM | 2834 | NE2 | GLN B | 84 | −30.984 | −15.793 | 3.237 | 1.00 | 74.74 | N |
| ATOM | 2835 | C | GLN B | 84 | −29.482 | −12.758 | 0.748 | 1.00 | 72.24 | C |
| ATOM | 2836 | O | GLN B | 84 | −29.710 | −12.112 | −0.283 | 1.00 | 72.63 | O |
| ATOM | 2837 | N | LYS B | 85 | −28.422 | −12.534 | 1.525 | 1.00 | 71.28 | N |
| ATOM | 2838 | CA | LYS B | 85 | −27.433 | −11.511 | 1.177 | 1.00 | 0.34 | C |
| ATOM | 2839 | CB | LYS B | 85 | −26.146 | −11.680 | 2.001 | 1.00 | 70.46 | C |
| ATOM | 2840 | CG | LYS B | 85 | 25.200 | −10.451 | 1.941 | 1.00 | 70.19 | C |
| ATOM | 2841 | CD | LYS B | 85 | −23.856 | −10.675 | 2.610 | 1.00 | 69.56 | C |
| ATOM | 2842 | CE | LYS B | 85 | −24.039 | −11.096 | 4.073 | 1.00 | 69.26 | C |
| ATOM | 2843 | NZ | LYS B | 85 | −22.812 | −11.737 | 4.611 | 1.00 | 67.15 | N |
| ATOM | 2844 | C | LYS B | 85 | −27.090 | −11.605 | −0.299 | 1.00 | 69.72 | C |
| ATOM | 2845 | O | LYS B | 85 | −27.008 | −12.698 | −0.857 | 1.00 | 70.04 | O |
| ATOM | 2846 | N | VAL B | 86 | −26.916 | −10.473 | −0.953 | 1.00 | 68.72 | N |
| ATOM | 2847 | CA | VAL B | 86 | −26.347 | −10.525 | −2.295 | 1.00 | 68.14 | C |
| ATOM | 2848 | CB | VAL B | 86 | −27.390 | −10.347 | −3.482 | 1.00 | 67.73 | C |
| ATOM | 2849 | CG1 | VAL B | 86 | −28.824 | −10.607 | −3.029 | 1.00 | 67.53 | C |
| ATOM | 2850 | CG2 | VAL B | 86 | −27.285 | −9.001 | −4.151 | 1.00 | 66.62 | C |
| ATOM | 2851 | C | VAL B | 86 | −25.218 | −0.516 | −2.337 | 1.00 | 88.28 | C |
| ATOM | 2852 | O | VAL B | 86 | −24.328 | −9.601 | −3.188 | 1.00 | 68.44 | O |

TABLE 11-continued

| | | | | | | | | | | |
|---|---|---|---|---|---|---|---|---|---|---|
| ATOM | 2853 | N | GLY B | 87 | −25.247 | −8.569 | −1.399 | 1.00 | 67.72 | N |
| ATOM | 2854 | CA | GLY B | 87 | −24.204 | −7.546 | −1.359 | 1.00 | 67.09 | C |
| ATOM | 2855 | C | GLY B | 87 | −23.670 | −7.306 | 0.030 | 1.00 | 66.36 | C |
| ATOM | 2856 | O | GLY B | 87 | −24.349 | −7.619 | 1.039 | 1.00 | 66.62 | O |
| ATOM | 2857 | N | GLU B | 88 | −22.455 | −6.763 | 0.086 | 1.00 | 64.68 | N |
| ATOM | 2858 | CA | GLU B | 88 | −21.901 | −6.349 | 1.350 | 1.00 | 63.84 | C |
| ATOM | 2859 | CB | GLU B | 88 | −21.897 | −7.504 | 2.310 | 1.00 | 64.44 | C |
| ATOM | 2860 | CG | GLU B | 88 | −21.390 | −7.148 | 3.651 | 1.00 | 67.65 | C |
| ATOM | 2861 | CD | GLU B | 88 | −20.437 | −8.211 | 4.091 | 1.00 | 74.37 | C |
| ATOM | 2862 | OE1 | GLU B | 88 | −20.284 | −9.183 | 3.261 | 1.00 | 76.00 | O |
| ATOM | 2863 | OE2 | GLU B | 88 | −19.844 | −8.070 | 5.214 | 1.00 | 72.63 | O |
| ATOM | 2864 | C | GLU B | 88 | −20.513 | −5.792 | 1.236 | 1.00 | 62.51 | C |
| ATOM | 2865 | O | GLU B | 88 | −19.673 | −6.346 | 0.555 | 1.00 | 62.58 | O |
| ATOM | 2866 | N | PHE B | 89 | −20.294 | −4.675 | 1.919 | 1.00 | 61.13 | N |
| ATOM | 2867 | CA | PHE B | 89 | −19.021 | −3.984 | 1.941 | 1.00 | 59.83 | C |
| ATOM | 2868 | CB | PHE B | 89 | −18.844 | −3.050 | 0.724 | 1.00 | 59.89 | C |
| ATOM | 2869 | CG | PHE B | 89 | −19.537 | −1.705 | 0.855 | 1.00 | 59.74 | C |
| ATOM | 2870 | CD1 | PHE B | 89 | −18.838 | −0.581 | 1.263 | 1.00 | 59.70 | C |
| ATOM | 2871 | CE1 | PHE B | 89 | −19.499 | 0.697 | 1.415 | 1.00 | 61.17 | C |
| ATOM | 2872 | CZ | PHE B | 89 | −20.865 | 0.835 | 1.105 | 1.00 | 58.21 | C |
| ATOM | 2873 | CE2 | PHE B | 89 | −21.559 | −0.283 | 0.658 | 1.00 | 59.52 | C |
| ATOM | 2874 | CD2 | PHE B | 89 | −20.893 | −1.563 | 0.554 | 1.00 | 60.20 | C |
| ATOM | 2875 | C | PHE B | 89 | −18.932 | −3.188 | 3.227 | 1.00 | 59.07 | C |
| ATOM | 2876 | O | PHE B | 89 | −19.963 | −2.827 | 3.826 | 1.00 | 58.82 | O |
| ATOM | 2877 | N | SER B | 90 | −17.687 | −2.896 | 3.615 | 1.00 | 57.42 | N |
| ATOM | 2878 | CA | SER B | 90 | −17.377 | −2.103 | 4.789 | 1.00 | 55.56 | C |
| ATOM | 2879 | CB | SER B | 90 | −16.461 | −2.910 | 5.681 | 1.00 | 55.44 | C |
| ATOM | 2880 | OG | SER B | 90 | −17.207 | −3.971 | 6.228 | 1.00 | 56.22 | O |
| ATOM | 2881 | C | SER B | 90 | −16.722 | −0.783 | 4.434 | 1.00 | 54.39 | C |
| ATOM | 2882 | O | SER B | 90 | −16.080 | 0.656 | 3.418 | 1.00 | 53.14 | O |
| ATOM | 2883 | N | GLY B | 91 | −16.907 | 0.203 | 5.289 | 1.00 | 53.74 | N |
| ATOM | 2884 | CA | GLY B | 91 | −16.211 | 1.459 | 5.146 | 1.00 | 53.82 | C |
| ATOM | 2885 | C | GLY B | 91 | −17.211 | 2.567 | 4.957 | 1.00 | 53.49 | C |
| ATOM | 2886 | O | GLY B | 91 | −18.219 | 2.346 | 4.345 | 1.00 | 52.93 | O |
| ATOM | 2887 | N | ALA B | 92 | −16.914 | 3.776 | 5.428 | 1.00 | 54.15 | N |
| ATOM | 2888 | CA | ALA B | 92 | −17.855 | 4.909 | 5.267 | 1.00 | 54.74 | C |
| ATOM | 2889 | CB | ALA B | 92 | −17.684 | 5.948 | 6.386 | 1.00 | 53.84 | C |
| ATOM | 2890 | C | ALA B | 92 | −17.765 | 5.581 | 3.939 | 1.00 | 54.75 | C |
| ATOM | 2891 | O | ALA B | 92 | −17.407 | 6.700 | 3.879 | 1.00 | 57.10 | O |
| ATOM | 2892 | N | ASN B | 93 | −18.131 | 4.947 | 2.859 | 1.00 | 55.04 | N |
| ATOM | 2893 | CA | ASN B | 93 | −17.968 | 5.598 | 1.585 | 1.00 | 55.05 | C |
| ATOM | 2894 | CB | ASN B | 93 | −17.094 | 4.674 | 0.752 | 1.00 | 55.34 | C |
| ATOM | 2895 | CG | ASN B | 93 | −16.867 | 5.154 | −0.668 | 1.00 | 57.90 | C |
| ATOM | 2896 | OD1 | ASN B | 93 | −17.589 | 6.008 | −1.228 | 1.00 | 60.79 | O |
| ATOM | 2897 | ND2 | ASN B | 93 | −15.857 | 4.584 | −1.274 | 1.00 | 59.37 | N |
| ATOM | 2898 | C | ASN B | 93 | −19.354 | 5.838 | 0.962 | 1.00 | 55.29 | C |
| ATOM | 2899 | O | ASN B | 93 | −19.979 | 4.907 | 0.448 | 1.00 | 55.01 | O |
| ATOM | 2900 | N | LYS B | 94 | −19.861 | 7.072 | 1.019 | 1.00 | 55.65 | N |
| ATOM | 2901 | CA | LYS B | 94 | −21.230 | 7.328 | 0.493 | 1.00 | 56.25 | C |
| ATOM | 2902 | CB | LYS B | 94 | −21.583 | 8.821 | 0.379 | 1.00 | 56.68 | C |
| ATOM | 2903 | CG | LYS B | 94 | −20.934 | 9.760 | 1.378 | 1.00 | 59.95 | C |
| ATOM | 2904 | CD | LYS B | 94 | −21.357 | 11.190 | 1.118 | 1.00 | 62.63 | C |
| ATOM | 2905 | CE | LYS B | 94 | −20.933 | 11.640 | −0.264 | 1.00 | 66.03 | C |
| ATOM | 2906 | NZ | LYS B | 94 | −19.462 | 11.886 | −0.322 | 1.00 | 67.17 | N |
| ATOM | 2907 | C | LYS B | 94 | −21.413 | 6.722 | 0.900 | 1.00 | 55.93 | C |
| ATOM | 2908 | O | LYS B | 94 | −22.328 | 5.906 | −1.117 | 1.00 | 55.38 | O |
| ATOM | 2909 | N | GLU B | 95 | −20.508 | 7.140 | −1.811 | 1.00 | 55.35 | N |
| ATOM | 2910 | CA | GLU B | 95 | −20.532 | 6.866 | −3.259 | 1.00 | 53.86 | C |
| ATOM | 2911 | CB | GLU B | 95 | −19.241 | 7.331 | −3.936 | 1.00 | 54.51 | C |
| ATOM | 2912 | CG | GLU B | 95 | −19.011 | 8.829 | −4.092 | 1.00 | 56.81 | C |
| ATOM | 2913 | CD | GLU B | 95 | −18.692 | 9.562 | −2.772 | 1.00 | 62.75 | C |
| ATOM | 2914 | OE1 | GLU B | 95 | −18.269 | 8.917 | −1.725 | 1.00 | 62.27 | O |
| ATOM | 2915 | OE2 | GLU B | 95 | −18.886 | 10.806 | −2.806 | 1.00 | 63.45 | C |
| ATOM | 2916 | C | GLU B | 95 | −20.656 | 5.407 | −3.521 | 1.00 | 52.59 | C |
| ATOM | 2917 | O | GLU B | 95 | −21.527 | 4.971 | −4.285 | 1.00 | 51.94 | O |
| ATOM | 2918 | N | LYS B | 96 | −19.769 | 4.660 | −2.885 | 1.00 | 51.98 | N |
| ATOM | 2919 | CA | LYS B | 96 | −19.813 | 3.220 | −2.933 | 1.00 | 52.85 | C |
| ATOM | 2920 | CB | LYS B | 96 | −18.726 | 2.604 | −2.069 | 1.00 | 52.61 | C |
| ATOM | 2921 | CG | LYS B | 96 | −18.936 | 1.093 | −1.886 | 1.00 | 56.22 | C |
| ATOM | 2922 | CD | LYS B | 96 | −18.908 | 0.286 | −3.199 | 1.00 | 61.19 | C |
| ATOM | 2923 | CE | LYS B | 96 | −18.247 | −1.111 | −3.028 | 1.00 | 65.06 | C |
| ATOM | 2924 | NZ | LYS B | 96 | −17.092 | −1.110 | −1.997 | 1.00 | 65.93 | N |
| ATOM | 2925 | C | LYS B | 96 | −21.167 | 2.702 | −2.487 | 1.00 | 52.65 | C |
| ATOM | 2926 | O | LYS B | 96 | −21.731 | 1.821 | −3.114 | 1.00 | 52.01 | O |
| ATOM | 2927 | N | LEU B | 97 | −21.695 | 3.275 | −1.422 | 1.00 | 52.99 | N |
| ATOM | 2928 | CA | LEU B | 97 | −22.996 | 2.849 | −0.935 | 1.00 | 54.91 | C |
| ATOM | 2929 | CB | LEU B | 97 | −23.305 | 3.514 | 0.422 | 1.00 | 55.37 | C |
| ATOM | 2930 | CG | LEU B | 97 | −24.692 | 3.296 | 1.011 | 1.00 | 54.82 | C |
| ATOM | 2931 | CD1 | LEU B | 97 | −25.019 | 1.826 | 1.344 | 1.00 | 53.94 | C |
| ATOM | 2932 | CD2 | LEU B | 97 | −24.170 | 4.150 | 2.235 | 1.00 | 56.12 | C |

TABLE 11-continued

| | | | | | | | | | | |
|---|---|---|---|---|---|---|---|---|---|---|
| ATOM | 2933 | C | LEU B | 97 | −24.170 | 3.062 | −1.924 | 1.00 | 55.37 | C |
| ATOM | 2934 | O | LEU B | 97 | −24.958 | 2.124 | −2.146 | 1.00 | 56.40 | O |
| ATOM | 2935 | N | GLU B | 98 | −24.311 | 4.279 | −2.477 | 1.00 | 54.79 | N |
| ATOM | 2936 | CA | GLU B | 98 | −25.309 | 4.533 | −3.511 | 1.00 | 53.86 | C |
| ATOM | 2937 | CB | GLU B | 98 | −25.332 | 5.990 | −3.929 | 1.00 | 52.67 | C |
| ATOM | 2938 | CG | GLU B | 98 | −20.527 | 8.338 | −4.704 | 1.00 | 51.49 | C |
| ATOM | 2939 | CD | GLU B | 98 | −26.657 | 7.837 | −5.076 | 1.00 | 52.10 | C |
| ATOM | 2940 | OE1 | GLU B | 98 | −25.683 | 8.617 | −4.814 | 1.00 | 49.63 | O |
| ATOM | 2941 | OE2 | GLU B | 98 | −27.754 | 8.214 | −5.604 | 1.00 | 49.85 | O |
| ATOM | 2942 | C | GLU B | 98 | −24.968 | 3.657 | −4.672 | 1.00 | 54.48 | C |
| ATOM | 2943 | O | GLU B | 98 | −25.761 | 2.842 | −5.088 | 1.00 | 54.84 | O |
| ATOM | 2944 | N | ALA B | 99 | −23.749 | 3.775 | −5.166 | 1.00 | 55.74 | N |
| ATOM | 2945 | CA | ALA B | 99 | −23.321 | 2.879 | −6.244 | 1.00 | 56.58 | C |
| ATOM | 2946 | CB | ALA B | 99 | −21.816 | 2.965 | −6.502 | 1.00 | 55.73 | C |
| ATOM | 2947 | C | ALA B | 99 | −23.751 | 1.438 | −5.989 | 1.00 | 56.75 | C |
| ATOM | 2948 | O | ALA B | 99 | −24.317 | 0.831 | −6.878 | 1.00 | 57.76 | O |
| ATOM | 2949 | N | THR B | 100 | −23.531 | 0.897 | −4.792 | 1.00 | 56.49 | N |
| ATOM | 2950 | CA | THR B | 100 | −23.860 | −0.512 | −4.588 | 1.00 | 56.63 | C |
| ATOM | 2951 | CB | THR B | 100 | −23.239 | −1.145 | −3.276 | 1.00 | 56.27 | C |
| ATOM | 2952 | OG1 | THR B | 100 | 20.803 | 1.125 | 3.314 | 1.00 | 54.67 | O |
| ATOM | 2953 | CG2 | THR B | 100 | −23.680 | −2.564 | −3.088 | 1.00 | 54.47 | C |
| ATOM | 2954 | C | THR B | 100 | −25.366 | −0.651 | −4.585 | 1.00 | 58.00 | C |
| ATOM | 2955 | O | THR B | 100 | −25.897 | −1.631 | −5.112 | 1.00 | 58.08 | O |
| ATOM | 2956 | N | ILE B | 101 | −26.053 | 0.345 | −4.011 | 1.00 | 59.59 | N |
| ATOM | 2957 | CA | ILE B | 101 | −27.507 | 0.284 | −3.859 | 1.00 | 61.09 | C |
| ATOM | 2958 | CB | ILE B | 101 | −28.079 | 1.537 | −3.221 | 1.00 | 61.03 | C |
| ATOM | 2959 | CG1 | ILE B | 101 | −27.997 | 1.406 | −1.702 | 1.00 | 61.72 | C |
| ATOM | 2960 | CD1 | ILE B | 101 | −28.500 | 2.625 | −0.956 | 1.00 | 61.71 | C |
| ATOM | 2961 | CG2 | ILE B | 101 | −29.560 | 1.799 | −3.739 | 1.00 | 60.08 | C |
| ATOM | 2962 | C | ILE B | 101 | −28.133 | 0.171 | −5.207 | 1.00 | 62.58 | C |
| ATOM | 2963 | O | ILE B | 101 | −28.837 | −0.805 | −5.488 | 1.00 | 62.03 | O |
| ATOM | 2964 | N | ASN B | 102 | −27.874 | 1.189 | −6.029 | 1.00 | 64.00 | N |
| ATOM | 2965 | CA | ASN B | 102 | −28.311 | 1.192 | −7.389 | 1.00 | 65.67 | C |
| ATOM | 2966 | CB | ASN B | 102 | −27.591 | 2.284 | −8.184 | 1.00 | 65.88 | C |
| ATOM | 2967 | CG | ASN B | 102 | −28.010 | 3.670 | −7.778 | 1.00 | 64.99 | C |
| ATOM | 2968 | OD1 | ASN B | 102 | −29.187 | 3.970 | −7.703 | 1.00 | 65.08 | O |
| ATOM | 2969 | ND2 | ASN B | 102 | −27.042 | 4.527 | −7.530 | 1.00 | 66.16 | N |
| ATOM | 2970 | C | ASN B | 102 | −27.903 | −0.163 | −7.910 | 1.00 | 66.91 | C |
| ATOM | 2971 | O | ASN B | 102 | −28.760 | −1.019 | −8.120 | 1.00 | 67.39 | O |
| ATOM | 2972 | N | GLU B | 103 | −26.591 | −0.380 | −8.035 | 1.00 | 67.88 | N |
| ATOM | 2973 | CA | GLU B | 103 | −26.053 | −1.579 | −8.686 | 1.00 | 69.22 | C |
| ATOM | 2974 | CB | GLU B | 103 | −24.510 | −1.558 | −9.707 | 1.00 | 69.23 | C |
| ATOM | 2975 | CG | GLU B | 103 | −23.865 | −2.555 | −9.683 | 1.00 | 69.78 | C |
| ATOM | 2976 | CD | GLU B | 103 | −22.897 | −3.560 | −9.008 | 1.00 | 70.95 | C |
| ATOM | 2977 | OE1 | GLU B | 103 | −22.548 | −4.585 | −9.681 | 1.00 | 72.18 | O |
| ATOM | 2978 | OE2 | GLU B | 103 | −22.495 | −3.341 | −7.832 | 1.00 | 65.86 | O |
| ATOM | 2979 | C | GLU B | 103 | 26.582 | 2.913 | 8.106 | 1.00 | 69.80 | C |
| ATOM | 2980 | O | GLU B | 103 | −26.040 | −3.974 | −8.406 | 1.00 | 70.03 | O |
| ATOM | 2981 | N | LEU B | 104 | −27.629 | −2.871 | −7.288 | 1.00 | 70.27 | N |
| ATOM | 2982 | CA | LEU B | 104 | −28.179 | −4.099 | −6.744 | 1.00 | 70.90 | C |
| ATOM | 2983 | CB | LEU B | 104 | −27.584 | −4.383 | −5.378 | 1.00 | 70.69 | C |
| ATOM | 2984 | CG | LEU B | 104 | −26.374 | −5.298 | −5.240 | 1.00 | 70.93 | C |
| ATOM | 2985 | CD1 | LEU B | 104 | −26.346 | −5.656 | −3.758 | 1.00 | 71.78 | C |
| ATOM | 2986 | CD2 | LEU B | 104 | −26.419 | −6.558 | −6.125 | 1.00 | 67.86 | C |
| ATOM | 2987 | C | LEU B | 104 | −29.687 | −4.137 | −6.627 | 1.00 | 71.68 | C |
| ATOM | 2988 | O | LEU B | 104 | −30.239 | −5.227 | −6.470 | 1.00 | 71.72 | O |
| ATOM | 2989 | N | VAL B | 105 | −30.336 | −2.961 | −6.667 | 1.00 | 72.70 | N |
| ATOM | 2990 | CA | VAL B | 105 | −31.801 | −2.833 | −6.545 | 1.00 | 73.71 | C |
| ATOM | 2991 | CB | VAL B | 105 | −32.353 | −1.557 | −7.236 | 1.00 | 73.47 | C |
| ATOM | 2992 | CG1 | VAL B | 105 | −33.831 | −1.423 | −6.979 | 1.00 | 73.70 | C |
| ATOM | 2993 | CG2 | VAL B | 105 | −31.660 | −0.326 | −6.73 | 1.00 | 73.88 | C |
| ATOM | 2994 | C | VAL B | 105 | −32.476 | −4.043 | −7.192 | 1.00 | 74.56 | C |
| ATOM | 2995 | O | VAL B | 105 | −33.424 | −4.644 | −6.652 | 1.00 | 75.13 | O |
| ATOM | 2996 | OXT | VAL B | 105 | −32.060 | −4.448 | −8.289 | 1.00 | 75.02 | O |
| TER | | | | | | | | | | |
| ATOM | 2997 | N | LYS C | 8 | 25.142 | 3.286 | 6.181 | 1.00 | 65.61 | N |
| ATOM | 2998 | CA | LYS C | 8 | 25.219 | 4.732 | 5.770 | 1.00 | 66.40 | C |
| ATOM | 2999 | CB | LYS C | 8 | 23.895 | 5.178 | 5.169 | 1.00 | 66.52 | C |
| ATOM | 3000 | CG | LYS C | 8 | 23.985 | 6.495 | 4.380 | 1.00 | 68.27 | C |
| ATOM | 3001 | CD | LYS C | 8 | 23.576 | 7.741 | 5.210 | 1.00 | 68.57 | C |
| ATOM | 3002 | CE | LYS C | 8 | 23.269 | 8.914 | 4.268 | 1.00 | 70.26 | C |
| ATOM | 3003 | NZ | LYS C | 8 | 22.638 | 10.100 | 4.933 | 1.00 | 69.87 | N |
| ATOM | 3004 | C | LYS C | 8 | 25.748 | 5.761 | 6.839 | 1.00 | 66.46 | C |
| ATOM | 3005 | O | LYS C | 8 | 26.891 | 6.192 | 6.729 | 1.00 | 67.19 | O |
| ATOM | 3006 | N | SER C | 9 | 24.932 | 6.203 | 7.810 | 1.00 | 65.61 | N |
| ATOM | 3007 | CA | SER C | 9 | 25.466 | 6.883 | 9.015 | 1.00 | 64.77 | C |
| ATOM | 3008 | CB | SER C | 9 | 24.759 | 8.203 | 9.379 | 1.00 | 64.46 | C |
| ATOM | 3009 | OG | SER C | 9 | 24.001 | 8.731 | 8.313 | 1.00 | 64.95 | O |
| ATOM | 3010 | C | SER C | 9 | 25.214 | 5.914 | 10.148 | 1.00 | 64.52 | C |

TABLE 11-continued

| ATOM | 3011 | O | SER C | 9 | 24.187 | 5.217 | 10.149 | 1.00 | 65.30 | O |
|---|---|---|---|---|---|---|---|---|---|---|
| ATOM | 3012 | N | PHE C | 10 | 26.135 | 5.894 | 11.108 | 1.00 | 63.18 | N |
| ATOM | 3013 | CA | PHE C | 10 | 26.089 | 5.036 | 12.272 | 1.00 | 61.98 | C |
| ATOM | 3014 | CB | PHE C | 10 | 26.543 | 3.631 | 11.906 | 1.00 | 61.36 | C |
| ATOM | 3015 | CG | PHE C | 10 | 26.554 | 2.666 | 13.068 | 1.00 | 60.31 | C |
| ATOM | 3016 | CD1 | PHE C | 10 | 25.445 | 2.544 | 13.911 | 1.00 | 60.33 | C |
| ATOM | 3017 | CE1 | PHE C | 10 | 25.462 | 1.633 | 14.980 | 1.00 | 59.24 | C |
| ATOM | 3018 | CZ | PHE C | 10 | 26.598 | 0.829 | 15.190 | 1.00 | 58.49 | C |
| ATOM | 3019 | CE2 | PHE C | 10 | 27.692 | 0.936 | 14.341 | 1.00 | 55.96 | C |
| ATOM | 3020 | CD2 | PHE C | 10 | 27.663 | 1.856 | 13.208 | 1.00 | 57.76 | C |
| ATOM | 3021 | C | PHE C | 10 | 27.042 | 5.656 | 13.294 | 1.00 | 62.21 | C |
| ATOM | 3022 | O | PHE C | 10 | 28.260 | 5.370 | 13.314 | 1.00 | 62.66 | O |
| ATOM | 3023 | N | GLU B | 11 | 26.496 | 6.498 | 14.158 | 1.00 | 61.20 | N |
| ATOM | 3024 | CA | GLU C | 11 | 27.350 | 7.428 | 14.851 | 1.00 | 60.30 | C |
| ATOM | 3025 | CB | GLU C | 11 | 27.209 | 8.763 | 14.129 | 1.00 | 60.69 | C |
| ATOM | 3026 | CG | GLU C | 11 | 28.504 | 9.345 | 13.580 | 1.00 | 65.18 | C |
| ATOM | 3027 | CD | GLU C | 11 | 29.038 | 10.535 | 14.429 | 1.00 | 68.62 | C |
| ATOM | 3028 | OE1 | GLU C | 11 | 28.267 | 11.625 | 14.666 | 1.00 | 64.56 | O |
| ATOM | 3029 | OE2 | GLU C | 11 | 30.236 | 10.460 | 14.841 | 1.00 | 68.46 | O |
| ATOM | 3030 | C | GLU C | 11 | 26.980 | 7.497 | 16.359 | 1.00 | 58.73 | C |
| ATOM | 3031 | O | GLU C | 11 | 25.793 | 7.508 | 16.722 | 1.00 | 58.61 | O |
| ATOM | 3032 | N | VAL C | 12 | 28.004 | 7.462 | 17.226 | 1.00 | 56.26 | N |
| ATOM | 3033 | CA | VAL C | 12 | 27.817 | 7.605 | 18.663 | 1.00 | 52.74 | C |
| ATOM | 3034 | CB | VAL C | 12 | 28.909 | 6.899 | 19.443 | 1.00 | 52.34 | C |
| ATOM | 3035 | CG1 | VAL C | 12 | 28.812 | 7.272 | 20.903 | 1.00 | 53.26 | C |
| ATOM | 3036 | CG2 | VAL C | 12 | 28.755 | 5.438 | 10.315 | 1.00 | 49.64 | C |
| ATOM | 3037 | C | VAL C | 12 | 27.879 | 9.087 | 18.968 | 1.00 | 51.52 | C |
| ATOM | 3038 | O | VAL C | 12 | 28.867 | 9.742 | 18.692 | 1.00 | 51.35 | O |
| ATOM | 3039 | N | VAL C | 13 | 26.816 | 9.617 | 19.539 | 1.00 | 49.38 | N |
| ATOM | 3040 | CA | VAL C | 13 | 26.682 | 11.036 | 19.710 | 1.00 | 46.89 | C |
| ATOM | 3041 | CB | VAL C | 13 | 25.560 | 11.527 | 18.799 | 1.00 | 46.93 | C |
| ATOM | 3042 | CG1 | VAL C | 13 | 25.348 | 13.021 | 18.911 | 1.00 | 45.24 | C |
| ATOM | 3043 | CG2 | VAL C | 13 | 25.932 | 11.168 | 17.395 | 1.00 | 48.95 | C |
| ATOM | 3044 | C | VAL C | 13 | 26.350 | 11.311 | 21.154 | 1.00 | 45.52 | C |
| ATOM | 3045 | O | VAL C | 13 | 25.299 | 10.942 | 21.642 | 1.00 | 44.42 | O |
| ATOM | 3046 | N | PHE C | 14 | 27.256 | 11.994 | 21.824 | 1.00 | 44.89 | N |
| ATOM | 3047 | CA | PHE C | 14 | 27.057 | 12.415 | 23.207 | 1.00 | 44.59 | C |
| ATOM | 3048 | CB | PHE C | 14 | 28.417 | 12.650 | 23.879 | 1.00 | 43.98 | C |
| ATOM | 3049 | CG | PHE C | 14 | 29.274 | 11.449 | 23.887 | 1.00 | 41.20 | C |
| ATOM | 3050 | CD1 | PHE C | 14 | 29.112 | 10.471 | 24.904 | 1.00 | 38.77 | C |
| ATOM | 3051 | CE1 | PHE C | 14 | 29.884 | 9.321 | 24.943 | 1.00 | 38.49 | C |
| ATOM | 3052 | CZ | PHE C | 14 | 30.847 | 9.081 | 23.937 | 1.00 | 38.65 | C |
| ATOM | 3053 | CE2 | PHE C | 14 | 30.982 | 10.053 | 22.864 | 1.00 | 43.21 | C |
| ATOM | 3054 | CD2 | PHE C | 14 | 30.179 | 11.238 | 22.863 | 1.00 | 38.86 | C |
| ATOM | 3055 | C | PHE C | 14 | 26.252 | 13.686 | 23.316 | 1.00 | 44.73 | C |
| ATOM | 3056 | O | PHE C | 14 | 26.345 | 14.567 | 22.452 | 1.00 | 44.66 | O |
| ATOM | 3057 | N | ASN C | 15 | 25.494 | 13.791 | 24.404 | 1.00 | 44.85 | N |
| ATOM | 3058 | CA | ASN C | 15 | 24.764 | 15.00 | 24.694 | 1.00 | 44.72 | C |
| ATOM | 3059 | CB | ASN C | 15 | 23.856 | 14.745 | 25.825 | 1.00 | 44.06 | C |
| ATOM | 3060 | CG | ASN C | 15 | 22.810 | 13.735 | 25.466 | 1.00 | 45.37 | C |
| ATOM | 3061 | OD1 | ASN C | 15 | 22.114 | 13.235 | 26.324 | 1.00 | 45.11 | O |
| ATOM | 3062 | ND2 | ASN C | 15 | 22.689 | 13.416 | 24.166 | 1.00 | 50.89 | N |
| ATOM | 3063 | C | ASN C | 15 | 25.590 | 16.206 | 24.966 | 1.00 | 46.03 | C |
| ATOM | 3064 | O | ASN C | 15 | 25.199 | 17.256 | 24.569 | 1.00 | 47.48 | O |
| ATOM | 3065 | N | ASP C | 16 | 26.732 | 16.062 | 25.634 | 1.00 | 47.48 | N |
| ATOM | 3066 | CA | ASP C | 16 | 27.702 | 17.136 | 25.847 | 1.00 | 48.28 | C |
| ATOM | 3067 | CB | ASP C | 16 | 27.051 | 17.311 | 27.334 | 1.00 | 50.03 | C |
| ATOM | 3068 | CG | ASP C | 16 | 26.648 | 17.307 | 28.140 | 1.00 | 54.67 | C |
| ATOM | 3069 | OD1 | ASP C | 16 | 26.514 | 16.520 | 29.131 | 1.00 | 59.51 | O |
| ATOM | 3070 | OD2 | ASP C | 16 | 25.737 | 18.088 | 27.756 | 1.00 | 60.86 | O |
| ATOM | 3071 | C | ASP C | 16 | 28.983 | 16.773 | 25.127 | 1.00 | 48.08 | C |
| ATOM | 3072 | O | ASP C | 16 | 29.883 | 16.114 | 25.654 | 1.00 | 48.19 | O |
| ATOM | 3073 | N | PRO C | 17 | 29.042 | 17.092 | 23.856 | 1.00 | 48.13 | N |
| ATOM | 3074 | CA | PRO C | 17 | 30.243 | 16.633 | 23.157 | 1.00 | 48.11 | C |
| ATOM | 3075 | CB | PRO C | 17 | 30.043 | 17.203 | 21.762 | 1.00 | 47.97 | C |
| ATOM | 3076 | CG | PRO C | 17 | 28.527 | 17.235 | 21.638 | 1.00 | 46.87 | C |
| ATOM | 3077 | CD | PRO C | 17 | 28.065 | 17.718 | 22.952 | 1.00 | 47.68 | C |
| ATOM | 3078 | C | PRO C | 17 | 31.556 | 17.121 | 23.754 | 1.00 | 48.66 | C |
| ATOM | 3379 | O | PRO C | 17 | 32.602 | 16.511 | 23.508 | 1.00 | 48.31 | O |
| ATOM | 3080 | N | GLU C | 18 | 31.534 | 18.219 | 24.514 | 1.00 | 41.84 | N |
| ATOM | 3081 | CA | GLU C | 18 | 32.806 | 18.716 | 25.063 | 1.00 | 49.29 | C |
| ATOM | 3082 | CB | GLU C | 18 | 33.087 | 20.155 | 24.623 | 1.00 | 49.04 | C |
| ATOM | 3083 | CG | GLU C | 18 | 33.776 | 20.214 | 23.295 | 1.00 | 49.59 | C |
| ATOM | 3084 | CD | GLU C | 18 | 32.896 | 19.661 | 22.182 | 1.00 | 53.55 | C |
| ATOM | 3085 | OE1 | GLU C | 18 | 31.876 | 20.318 | 21.898 | 1.00 | 54.45 | O |
| ATOM | 3086 | OE2 | GLU C | 18 | 33.193 | 18.569 | 21.610 | 1.00 | 54.62 | O |
| ATOM | 3087 | C | GLU C | 18 | 33.091 | 18.519 | 26.557 | 1.00 | 49.46 | C |
| ATOM | 3088 | O | GLU C | 18 | 34.069 | 19.079 | 27.103 | 1.00 | 50.74 | O |
| ATOM | 3089 | N | LYS C | 19 | 32.283 | 17.723 | 27.248 | 1.00 | 48.71 | N |
| ATOM | 3090 | CA | LYS C | 19 | 32.416 | 17.668 | 28.665 | 1.00 | 48.95 | C |

TABLE 11-continued

| | | | | | | | | | | |
|---|---|---|---|---|---|---|---|---|---|---|
| ATOM | 3091 | CB | LYS C | 19 | 31.131 | 17.169 | 29.286 | 1.00 | 49.63 | C |
| ATOM | 3292 | CG | LYS C | 19 | 31.138 | 17.280 | 30.800 | 1.00 | 51.20 | C |
| ATOM | 3093 | CD | LYS C | 19 | 29.992 | 16.534 | 31.432 | 1.00 | 52.14 | C |
| ATOM | 3094 | CE | LYS C | 19 | 30.110 | 16.704 | 32.920 | 1.00 | 54.92 | C |
| ATOM | 3095 | NZ | LYS C | 19 | 29.002 | 15.960 | 33.506 | 1.00 | 56.54 | N |
| ATOM | 3076 | C | LYS C | 19 | 33.596 | 16.801 | 29.056 | 1.00 | 49.16 | C |
| ATOM | 3097 | O | LYS C | 19 | 33.912 | 15.813 | 28.361 | 1.00 | 50.15 | O |
| ATOM | 3098 | N | VAL C | 20 | 34.288 | 17.186 | 30.124 | 1.00 | 47.92 | N |
| ATOM | 3099 | CA | VAL C | 20 | 35.197 | 16.241 | 30.769 | 1.00 | 46.76 | C |
| ATOM | 3100 | CB | VAL C | 20 | 36.482 | 16.880 | 31.295 | 1.00 | 45.98 | C |
| ATOM | 3101 | CG1 | VAL C | 20 | 37.449 | 15.757 | 31.716 | 1.00 | 43.11 | C |
| ATOM | 3102 | CG2 | VAL C | 20 | 37.083 | 17.810 | 30.268 | 1.00 | 44.31 | C |
| ATOM | 3103 | C | VAL C | 20 | 34.452 | 15.653 | 31.979 | 1.00 | 47.16 | C |
| ATOM | 3104 | O | VAL C | 20 | 34.139 | 16.366 | 32.923 | 1.00 | 47.98 | O |
| ATOM | 3105 | N | TYR C | 21 | 34.174 | 14.358 | 31.963 | 1.00 | 46.32 | N |
| ATOM | 3106 | CA | TYR C | 21 | 33.354 | 13.771 | 32.992 | 1.00 | 44.87 | C |
| ATOM | 3107 | CB | TYR C | 21 | 32.604 | 12.537 | 32.463 | 1.00 | 44.46 | C |
| ATOM | 3108 | CG | TYR C | 21 | 31.676 | 12.807 | 31.288 | 1.00 | 43.69 | C |
| ATOM | 3109 | CD1 | TYR C | 21 | 30.300 | 13.042 | 31.473 | 1.00 | 42.79 | C |
| ATOM | 3110 | CE1 | TYR C | 21 | 29.463 | 13.303 | 30.406 | 1.00 | 43.11 | C |
| ATOM | 3111 | CZ | TYR C | 21 | 29.993 | 13.340 | 29.105 | 1.00 | 47.87 | C |
| ATOM | 3112 | OH | TYR C | 21 | 29.204 | 13.580 | 27.988 | 1.00 | 53.35 | O |
| ATOM | 3113 | CE2 | TYR C | 21 | 31.338 | 13.132 | 28.891 | 1.00 | 45.49 | C |
| ATOM | 3114 | CD2 | TYR C | 21 | 32.176 | 12.859 | 29.989 | 1.00 | 43.71 | C |
| ATOM | 3115 | C | TYR C | 21 | 34.196 | 13.487 | 34.231 | 1.00 | 44.97 | C |
| ATOM | 3116 | O | TYR C | 21 | 35.384 | 13.129 | 34.142 | 1.00 | 44.83 | O |
| ATOM | 3117 | N | GLY C | 22 | 33.581 | 13.689 | 35.391 | 1.00 | 44.74 | N |
| ATOM | 3118 | CA | GLY C | 22 | 34.258 | 13.512 | 36.637 | 1.00 | 45.59 | C |
| ATOM | 3119 | C | GLY C | 22 | 33.813 | 12.230 | 37.291 | 1.00 | 46.88 | C |
| ATOM | 3120 | O | GLY C | 22 | 32.796 | 11.623 | 36.918 | 1.00 | 46.46 | O |
| ATOM | 3121 | N | SER C | 23 | 34.571 | 11.793 | 38.279 | 1.00 | 48.05 | N |
| ATOM | 3122 | CA | SER C | 23 | 34.136 | 10.626 | 38.994 | 1.00 | 50.45 | C |
| ATOM | 3123 | CB | SER C | 23 | 35.018 | 10.397 | 40.202 | 1.00 | 50.58 | C |
| ATOM | 3124 | OG | SER C | 23 | 34.642 | 9.154 | 40.751 | 1.00 | 54.76 | O |
| ATOM | 3125 | C | SER C | 23 | 32.664 | 10.766 | 39.386 | 1.00 | 50.97 | C |
| ATOM | 3126 | O | SER C | 23 | 32.204 | 11.869 | 39.663 | 1.00 | 51.65 | O |
| ATOM | 3127 | N | GLY C | 24 | 31.919 | 9.669 | 39.347 | 1.00 | 52.08 | N |
| ATOM | 3128 | CA | GLY C | 24 | 30.492 | 9.670 | 39.690 | 1.00 | 52.62 | C |
| ATOM | 3129 | C | GLY C | 24 | 29.434 | 10.124 | 38.694 | 1.00 | 53.69 | C |
| ATOM | 3130 | O | GLY C | 24 | 28.351 | 9.556 | 38.679 | 1.00 | 54.76 | O |
| ATOM | 3131 | N | GLU C | 25 | 29.725 | 11.142 | 37.870 | 1.00 | 54.18 | N |
| ATOM | 3132 | CA | GLU C | 25 | 28.785 | 11.686 | 36.855 | 1.00 | 53.74 | C |
| ATOM | 3133 | CB | GLU C | 25 | 29.398 | 12.837 | 36.017 | 1.00 | 53.04 | C |
| ATOM | 3134 | CG | GLU C | 25 | 30.539 | 13.640 | 36.650 | 1.00 | 54.55 | C |
| ATOM | 3135 | CD | GLU C | 25 | 30.639 | 15.106 | 36.177 | 1.00 | 59.28 | C |
| ATOM | 3136 | OE1 | GLU C | 25 | 31.690 | 15.553 | 35.645 | 1.00 | 61.08 | O |
| ATOM | 3137 | OE2 | GLU C | 25 | 29.659 | 15.859 | 36.371 | 1.00 | 62.63 | O |
| ATOM | 3138 | C | GLU C | 25 | 28.205 | 10.615 | 35.919 | 1.00 | 54.22 | C |
| ATOM | 3139 | O | GLU C | 25 | 28.670 | 9.470 | 35.872 | 1.00 | 54.27 | O |
| ATOM | 3143 | N | ARG C | 26 | 27.180 | 11.013 | 35.172 | 1.00 | 55.00 | N |
| ATOM | 3144 | CA | ARG C | 26 | 26.452 | 10.148 | 34.229 | 1.00 | 55.91 | C |
| ATOM | 3142 | CB | ARG C | 26 | 24.978 | 10.548 | 34.280 | 1.00 | 57.03 | C |
| ATOM | 3143 | CG | ARG C | 26 | 24.009 | 9.750 | 33.440 | 1.00 | 61.79 | C |
| ATOM | 3144 | CD | ARG C | 26 | 22.714 | 9.585 | 34.233 | 1.00 | 70.33 | C |
| ATOM | 3145 | NE | ARG C | 26 | 21.622 | 8.942 | 33.495 | 1.00 | 77.58 | N |
| ATOM | 3146 | CZ | ARG C | 26 | 21.442 | 7.615 | 33.369 | 1.00 | 82.23 | C |
| ATOM | 3147 | NH1 | ARG C | 26 | 22.312 | 6.738 | 33.899 | 1.00 | 82.18 | N |
| ATOM | 3148 | NH2 | ARG C | 26 | 20.380 | 7.153 | 32.688 | 1.00 | 83.63 | N |
| ATOM | 3149 | C | ARG C | 26 | 26.973 | 10.415 | 32.839 | 1.00 | 54.68 | C |
| ATOM | 3150 | O | ARG C | 26 | 27.194 | 11.579 | 32.490 | 1.00 | 54.96 | O |
| ATOM | 3151 | N | VAL C | 27 | 27.185 | 9.382 | 32.030 | 1.00 | 52.98 | N |
| ATOM | 3152 | CA | VAL C | 27 | 27.550 | 9.686 | 30.628 | 1.00 | 51.68 | C |
| ATOM | 3153 | CB | VAL C | 27 | 28.838 | 9.017 | 30.131 | 1.00 | 50.79 | C |
| ATOM | 3154 | CG1 | VAL C | 27 | 28.929 | 9.042 | 28.586 | 1.00 | 48.86 | C |
| ATOM | 3155 | CG2 | VAL C | 27 | 30.003 | 9.696 | 30.731 | 1.00 | 50.50 | C |
| ATOM | 3156 | C | VAL C | 27 | 26.415 | 9.271 | 29.762 | 1.00 | 51.52 | C |
| ATOM | 3157 | O | VAL C | 27 | 25.956 | 8.123 | 29.888 | 1.00 | 51.71 | O |
| ATOM | 3158 | N | ALA C | 28 | 25.964 | 10.196 | 28.902 | 1.00 | 50.84 | N |
| ATOM | 3159 | CA | ALA C | 28 | 24.737 | 9.991 | 28.105 | 1.00 | 50.02 | C |
| ATOM | 3160 | CB | ALA C | 28 | 23.482 | 10.517 | 28.865 | 1.00 | 49.24 | C |
| ATOM | 3161 | C | ALA C | 28 | 24.774 | 10.565 | 26.708 | 1.00 | 49.26 | C |
| ATOM | 3162 | O | ALA C | 28 | 25.387 | 11.636 | 26.447 | 1.00 | 49.46 | O |
| ATOM | 3163 | N | GLY C | 29 | 24.078 | 9.850 | 25.829 | 1.00 | 47.90 | N |
| ATOM | 3164 | CA | GLY C | 29 | 24.011 | 10.200 | 24.448 | 1.00 | 47.39 | C |
| ATOM | 3165 | C | GLY C | 29 | 22.993 | 9.374 | 23.708 | 1.00 | 47.49 | C |
| ATOM | 3166 | O | GLY C | 29 | 22.013 | 8.913 | 24.282 | 1.00 | 48.09 | O |
| ATOM | 3167 | N | ARG C | 30 | 23.241 | 9.212 | 22.418 | 1.00 | 47.50 | N |
| ATOM | 3168 | CA | ARG C | 30 | 22.377 | 8.531 | 21.507 | 1.00 | 48.20 | C |
| ATOM | 3169 | CB | ARG C | 30 | 21.515 | 9.573 | 20.780 | 1.00 | 48.63 | C |
| ATOM | 3170 | CG | ARG C | 30 | 20.186 | 10.023 | 21.463 | 1.00 | 49.48 | C |

TABLE 11-continued

| | | | | | | | | | | |
|---|---|---|---|---|---|---|---|---|---|---|
| ATOM | 3171 | CD | ARG C | 30 | 19.953 | 11.554 | 21.411 | 1.00 | 51.20 | C |
| ATOM | 3172 | NE | ARG C | 30 | 20.489 | 12.149 | 20.190 | 1.00 | 54.87 | N |
| ATOM | 3173 | CZ | ARG C | 30 | 21.075 | 13.343 | 20.103 | 1.00 | 58.26 | C |
| ATOM | 3174 | NH1 | ARG C | 30 | 21.201 | 14.120 | 21.184 | 1.00 | 61.61 | N |
| ATOM | 3175 | NH2 | ARG C | 30 | 21.562 | 13.761 | 18.932 | 1.00 | 56.46 | N |
| ATOM | 3176 | C | ARG C | 30 | 23.271 | 7.785 | 20.504 | 1.00 | 49.22 | C |
| ATOM | 3177 | O | ARG C | 30 | 24.392 | 8.206 | 20.209 | 1.00 | 50.00 | O |
| ATOM | 3178 | N | VAL C | 31 | 22.821 | 6.642 | 19.997 | 1.00 | 50.31 | N |
| ATOM | 3179 | CA | VAL C | 31 | 23.464 | 6.074 | 18.813 | 1.00 | 50.61 | C |
| ATOM | 3180 | CB | VAL C | 31 | 23.715 | 4.614 | 18.912 | 1.00 | 49.93 | C |
| ATOM | 3181 | CG1 | VAL C | 31 | 24.722 | 4.260 | 17.881 | 1.00 | 49.83 | C |
| ATOM | 3182 | CG2 | VAL C | 31 | 24.285 | 4.302 | 20.232 | 1.00 | 48.37 | C |
| ATOM | 3183 | C | VAL C | 31 | 22.559 | 6.369 | 17.640 | 1.00 | 52.13 | C |
| ATOM | 3184 | O | VAL C | 31 | 21.355 | 6.164 | 17.701 | 1.00 | 51.23 | O |
| ATOM | 3185 | N | ILE C | 32 | 23.125 | 6.935 | 16.590 | 1.00 | 54.77 | N |
| ATOM | 3186 | CA | ILE C | 32 | 22.256 | 7.496 | 15.580 | 1.00 | 57.26 | C |
| ATOM | 3187 | CB | ILE C | 32 | 22.202 | 9.044 | 15.569 | 1.00 | 57.01 | C |
| ATOM | 3188 | CG1 | ILE C | 32 | 21.923 | 9.605 | 16.989 | 1.00 | 55.35 | C |
| ATOM | 3189 | CD1 | ILE C | 32 | 21.540 | 11.096 | 17.059 | 1.00 | 50.23 | C |
| ATOM | 3190 | CG2 | ILE C | 32 | 21.144 | 9.493 | 14.544 | 1.00 | 57.10 | C |
| ATOM | 3191 | C | ILE C | 32 | 22.559 | 6.878 | 14.224 | 1.00 | 59.25 | C |
| ATOM | 3192 | O | ILE C | 32 | 23.689 | 6.971 | 13.686 | 1.00 | 59.63 | O |
| ATOM | 3193 | N | VAL C | 33 | 21.463 | 6.258 | 13.710 | 1.00 | 60.77 | N |
| ATOM | 3194 | CA | VAL C | 33 | 21.541 | 5.329 | 12.615 | 1.00 | 62.90 | C |
| ATOM | 3195 | CB | VAL C | 33 | 21.008 | 3.942 | 13.003 | 1.00 | 62.80 | C |
| ATOM | 3196 | CG1 | VAL C | 33 | 21.601 | 2.882 | 12.087 | 1.00 | 64.18 | C |
| ATOM | 3197 | CG2 | VAL C | 33 | 21.361 | 3.591 | 14.418 | 1.00 | 62.29 | C |
| ATOM | 3198 | C | VAL C | 33 | 20.715 | 5.853 | 11.478 | 1.00 | 64.71 | C |
| ATOM | 3199 | O | VAL C | 33 | 19.532 | 6.146 | 11.629 | 1.00 | 64.77 | O |
| ATOM | 3200 | N | GLU C | 34 | 21.367 | 5.996 | 10.335 | 1.00 | 67.71 | N |
| ATOM | 3201 | CA | GLU C | 34 | 20.700 | 6.427 | 9.125 | 1.00 | 70.37 | C |
| ATOM | 3202 | CB | GLU C | 34 | 21.073 | 7.846 | 8.790 | 1.00 | 70.04 | C |
| ATOM | 3203 | CG | GLU C | 34 | 20.576 | 8.787 | 9.839 | 1.00 | 71.68 | C |
| ATOM | 3204 | CD | GLU C | 34 | 19.889 | 9.991 | 9.244 | 1.00 | 75.42 | C |
| ATOM | 3205 | OE1 | GLU C | 34 | 19.924 | 10.138 | 7.989 | 1.00 | 76.03 | O |
| ATOM | 3206 | OE2 | GLU C | 34 | 19.306 | 10.778 | 10.030 | 1.00 | 75.08 | O |
| ATOM | 3207 | C | GLU C | 34 | 21.051 | 5.475 | 8.016 | 1.00 | 72.05 | C |
| ATOM | 3208 | O | GLU C | 34 | 22.138 | 4.872 | 8.034 | 1.00 | 72.02 | O |
| ATOM | 3209 | N | VAL C | 35 | 20.106 | 5.336 | 7.078 | 1.00 | 74.59 | N |
| ATOM | 3210 | CA | VAL C | 35 | 20.136 | 4.321 | 5.988 | 1.00 | 76.82 | C |
| ATOM | 3211 | CB | VAL C | 35 | 19.426 | 2.965 | 6.426 | 1.00 | 76.59 | C |
| ATOM | 3212 | CG1 | VAL C | 35 | 18.488 | 2.408 | 5.351 | 1.00 | 75.94 | C |
| ATOM | 3213 | CG2 | VAL C | 35 | 20.468 | 1.929 | 6.809 | 1.00 | 76.17 | C |
| ATOM | 3214 | C | VAL C | 35 | 19.641 | 4.849 | 4.605 | 1.00 | 78.41 | C |
| ATOM | 3215 | O | VAL C | 35 | 18.710 | 5.696 | 4.534 | 1.00 | 78.49 | O |
| ATOM | 3216 | N | CYS C | 36 | 20.270 | 4.346 | 3.529 | 1.00 | 80.11 | N |
| ATOM | 3217 | CA | CYS C | 36 | 19.890 | 4.681 | 2.131 | 1.00 | 81.59 | C |
| ATOM | 3218 | CB | CYS C | 36 | 21.081 | 5.193 | 1.311 | 1.00 | 81.79 | C |
| ATOM | 3219 | SG | CYS C | 36 | 21.168 | 7.008 | 1.503 | 1.00 | 84.12 | S |
| ATOM | 3220 | C | CYS C | 36 | 19.036 | 3.676 | 1.352 | 1.00 | 81.73 | C |
| ATOM | 3221 | O | CYS C | 36 | 18.489 | 4.017 | 0.293 | 1.00 | 81.19 | O |
| ATOM | 3222 | N | GLU C | 37 | 18.940 | 2.454 | 1.893 | 1.00 | 82.45 | N |
| ATOM | 3223 | CA | GLU C | 37 | 17.682 | 1.478 | 1.536 | 1.00 | 82.95 | C |
| ATOM | 3224 | CB | GLU C | 37 | 18.205 | 0.726 | 0.235 | 1.00 | 83.26 | C |
| ATOM | 3225 | CG | GLU C | 37 | 18.208 | −0.796 | 0.360 | 1.00 | 83.42 | C |
| ATOM | 3226 | CD | GLU C | 37 | 19.596 | −1.312 | 0.617 | 1.00 | 83.26 | C |
| ATOM | 3227 | OE1 | GLU C | 37 | 19.909 | −1.634 | 1.789 | 1.00 | 81.07 | O |
| ATOM | 3228 | OE2 | GLU C | 37 | 20.388 | −1.349 | −0.362 | 1.00 | 83.07 | O |
| ATOM | 3229 | C | GLU C | 37 | 17.474 | 0.499 | 2.667 | 1.00 | 83.01 | C |
| ATOM | 3230 | O | GLU C | 37 | 18.325 | −0.015 | 3.399 | 1.00 | 83.13 | O |
| ATOM | 3231 | N | VAL C | 38 | 16.153 | 0.310 | 2.791 | 1.00 | 82.80 | N |
| ATOM | 3232 | CA | VAL C | 38 | 15.460 | −0.683 | 3.638 | 1.00 | 82.43 | C |
| ATOM | 3233 | CB | VAL C | 38 | 14.170 | −1.225 | 2.866 | 1.00 | 82.37 | C |
| ATOM | 3234 | CG1 | VAL C | 38 | 15.549 | −2.117 | 1.655 | 1.00 | 83.13 | C |
| ATOM | 3235 | CG2 | VAL C | 38 | 13.173 | −1.941 | 3.792 | 1.00 | 81.46 | C |
| ATOM | 3236 | C | VAL C | 38 | 16.331 | −1.833 | 4.230 | 1.00 | 82.52 | C |
| ATOM | 3237 | O | VAL C | 38 | 16.924 | −2.627 | 3.477 | 1.00 | 82.90 | O |
| ATOM | 3238 | N | THR C | 39 | 16.379 | −1.930 | 5.571 | 1.00 | 81.97 | N |
| ATOM | 3239 | CA | THR C | 39 | 17.199 | −2.938 | 6.279 | 1.00 | 31.29 | C |
| ATOM | 3240 | CB | THR C | 39 | 18.474 | −2.282 | 6.770 | 1.00 | 81.21 | C |
| ATOM | 3241 | OG1 | THR C | 39 | 18.948 | −1.378 | 5.758 | 1.00 | 80.61 | O |
| ATOM | 3242 | CG2 | THR C | 39 | 19.532 | −3.336 | 7.135 | 1.00 | 80.34 | C |
| ATOM | 3243 | C | THR C | 39 | 16.551 | −3.576 | 7.518 | 1.00 | 81.42 | C |
| ATOM | 3244 | O | THR C | 39 | 15.840 | −2.898 | 8.275 | 1.00 | 82.11 | O |
| ATOM | 3245 | N | ARG C | 40 | 16.835 | −4.858 | 7.760 | 1.00 | 80.86 | N |
| ATOM | 3246 | CA | ARG C | 40 | 16.335 | −5.541 | 8.968 | 1.00 | 80.09 | C |
| ATOM | 3247 | CB | ARG C | 40 | 15.752 | −6.909 | 8.603 | 1.00 | 79.83 | C |
| ATOM | 3248 | CG | ARG C | 40 | 14.522 | −7.257 | 9.400 | 1.00 | 81.03 | C |
| ATOM | 3249 | CD | ARG C | 40 | 13.555 | −8.202 | 8.657 | 1.00 | 81.48 | C |
| ATOM | 3250 | NE | ARG C | 40 | 12.529 | −8.729 | 9.569 | 1.00 | 80.92 | N |

TABLE 11-continued

| | | | | | | | | | | |
|---|---|---|---|---|---|---|---|---|---|---|
| ATOM | 3251 | CZ | ARG C | 40 | 12.583 | −9.935 | 10.144 | 1.00 | 80.35 | C |
| ATOM | 3252 | NH1 | ARG C | 40 | 13.606 | −10.751 | 9.890 | 1.00 | 81.18 | N |
| ATOM | 3253 | NH2 | ARG C | 40 | 11.620 | −10.333 | 10.970 | 1.00 | 78.18 | N |
| ATOM | 3254 | C | ARG C | 40 | 17.424 | −5.660 | 10.065 | 1.00 | 79.20 | C |
| ATOM | 3255 | O | ARG C | 40 | 18.472 | −6.278 | 9.827 | 1.00 | 79.63 | O |
| ATOM | 3256 | N | VAL C | 41 | 17.168 | −5.105 | 11.260 | 1.00 | 77.03 | N |
| ATOM | 3257 | CA | VAL C | 41 | 18.180 | −5.054 | 12.326 | 1.00 | 74.77 | C |
| ATOM | 3258 | CB | VAL C | 41 | 18.346 | −3.622 | 12.826 | 1.00 | 74.92 | C |
| ATOM | 3259 | CG1 | VAL C | 41 | 19.221 | −3.581 | 14.090 | 1.00 | 74.58 | C |
| ATOM | 3260 | CG2 | VAL C | 41 | 18.932 | −2.762 | 11.715 | 1.00 | 74.79 | C |
| ATOM | 3261 | C | VAL C | 41 | 17.958 | −5.959 | 13.532 | 1.00 | 73.69 | C |
| ATOM | 3262 | O | VAL C | 41 | 17.042 | −5.757 | 14.325 | 1.00 | 73.53 | O |
| ATOM | 3263 | N | LYS C | 42 | 18.838 | −6.937 | 13.695 | 1.00 | 72.60 | N |
| ATOM | 3264 | CA | LYS C | 42 | 18.734 | −7.888 | 14.817 | 1.00 | 71.56 | C |
| ATOM | 3265 | CB | LYS C | 42 | 19.659 | −9.108 | 14.586 | 1.00 | 71.52 | C |
| ATOM | 3266 | CG | LYS C | 42 | 19.871 | −10.044 | 15.827 | 1.00 | 72.46 | C |
| ATOM | 3267 | CD | LYS C | 42 | 20.684 | −11.334 | 15.521 | 1.00 | 71.90 | C |
| ATOM | 3268 | CE | LYS C | 42 | 19.802 | −12.513 | 15.093 | 1.00 | 71.43 | C |
| ATOM | 3269 | NZ | LYS C | 42 | 20.607 | −13.647 | 14.526 | 1.00 | 71.72 | N |
| ATOM | 3270 | C | LYS C | 42 | 18.933 | −7.248 | 16.223 | 1.00 | 70.38 | C |
| ATOM | 3271 | O | LYS C | 42 | 18.282 | −7.651 | 17.204 | 1.00 | 69.66 | O |
| ATOM | 3272 | N | ALA C | 43 | 19.817 | −6.247 | 16.293 | 1.00 | 69.16 | N |
| ATOM | 3273 | CA | ALA C | 43 | 20.196 | −5.587 | 17.548 | 1.00 | 67.46 | C |
| ATOM | 3274 | CB | ALA C | 43 | 20.973 | −8.558 | 18.458 | 1.00 | 67.24 | C |
| ATOM | 3275 | C | ALA C | 43 | 21.022 | −4.329 | 17.299 | 1.00 | 66.80 | C |
| ATOM | 3276 | O | ALA C | 43 | 21.814 | −4.721 | 16.332 | 1.00 | 67.21 | O |
| ATOM | 3277 | N | VAL C | 44 | 20.829 | −3.320 | 18.159 | 1.00 | 65.70 | N |
| ATOM | 3278 | CA | VAL C | 44 | 21.849 | −2.237 | 18.374 | 1.00 | 64.19 | C |
| ATOM | 3279 | CB | VAL C | 44 | 21.333 | −0.811 | 17.925 | 1.00 | 63.82 | C |
| ATOM | 3280 | CG1 | VAL C | 44 | 22.041 | 0.313 | 18.620 | 1.00 | 63.42 | C |
| ATOM | 3281 | CG2 | VAL C | 44 | 21.507 | −0.648 | 16.450 | 1.00 | 62.70 | C |
| ATOM | 3282 | C | VAL C | 44 | 22.436 | −2.299 | 19.820 | 1.00 | 63.52 | C |
| ATOM | 3283 | O | VAL C | 44 | 21.700 | −2.099 | 20.809 | 1.00 | 63.37 | O |
| ATOM | 3284 | N | ARG C | 45 | 23.738 | −2.623 | 19.932 | 1.00 | 62.65 | N |
| ATOM | 3285 | CA | ARG C | 45 | 24.430 | −2.808 | 21.251 | 1.00 | 62.10 | C |
| ATOM | 3286 | CB | ARG C | 45 | 25.141 | −4.174 | 21.341 | 1.00 | 62.63 | C |
| ATOM | 3287 | CG | ARG C | 45 | 24.369 | −5.336 | 21.987 | 1.00 | 64.95 | C |
| ATOM | 3288 | CD | ARG C | 45 | 24.978 | −6.699 | 21.568 | 1.00 | 68.67 | C |
| ATOM | 3289 | NE | ARG C | 45 | 25.324 | −6.703 | 20.131 | 1.00 | 72.60 | N |
| ATOM | 3290 | CZ | ARG C | 45 | 26.546 | −6.927 | 19.628 | 1.00 | 72.51 | C |
| ATOM | 3291 | NH1 | ARG C | 45 | 27.565 | −7.225 | 20.430 | 1.00 | 70.72 | N |
| ATOM | 3292 | NH2 | ARG C | 45 | 26.737 | −6.880 | 18.304 | 1.00 | 72.66 | N |
| ATOM | 3293 | C | ARG C | 45 | 25.478 | −1.739 | 21.510 | 1.00 | 60.35 | C |
| ATOM | 3294 | O | ARG C | 45 | 25.989 | −1.137 | 20.570 | 1.00 | 60.22 | C |
| ATOM | 3295 | N | ILE C | 46 | 25.809 | −1.537 | 22.778 | 1.00 | 58.58 | N |
| ATOM | 3296 | CA | ILE C | 46 | 26.993 | −0.793 | 23.145 | 1.00 | 57.59 | C |
| ATOM | 3297 | CB | ILE C | 46 | 26.700 | 0.655 | 23.617 | 1.00 | 57.45 | C |
| ATOM | 3298 | CG | ILE C | 46 | 25.780 | 0.672 | 24.837 | 1.00 | 56.96 | C |
| ATOM | 3299 | CD1 | ILE C | 46 | 25.939 | 1.933 | 25.649 | 1.00 | 54.85 | C |
| ATOM | 3300 | CG2 | ILE C | 46 | 26.238 | 1.558 | 22.491 | 1.00 | 57.08 | C |
| ATOM | 3301 | C | ILE C | 46 | 27.805 | −1.407 | 24.280 | 1.00 | 57.63 | C |
| ATOM | 3302 | O | ILE C | 46 | 27.280 | −1.967 | 25.260 | 1.00 | 58.44 | O |
| ATOM | 3303 | N | LEU C | 47 | 29.111 | −1.232 | 24.154 | 1.00 | 56.58 | N |
| ATOM | 3304 | CA | LEU C | 47 | 30.019 | −1.422 | 25.276 | 1.00 | 54.45 | C |
| ATOM | 3305 | CB | LEU C | 47 | 30.908 | −2.598 | 24.965 | 1.00 | 54.06 | C |
| ATOM | 3306 | CG | LEU C | 47 | 32.267 | −2.680 | 25.599 | 1.00 | 55.67 | C |
| ATOM | 3307 | CD1 | LEU C | 47 | 32.241 | 2.962 | 27.097 | 1.00 | 55.37 | C |
| ATOM | 3308 | CD2 | LEU C | 47 | 33.002 | −3.755 | 24.861 | 1.00 | 58.09 | C |
| ATOM | 3309 | C | LEU C | 47 | 30.805 | −0.119 | 25.458 | 1.00 | 53.60 | C |
| ATOM | 3310 | O | LEU C | 47 | 31.172 | 0.555 | 24.475 | 1.00 | 52.48 | O |
| ATOM | 3311 | N | ALA C | 48 | 31.011 | 0.236 | 26.725 | 1.00 | 53.23 | N |
| ATOM | 3312 | CA | ALA C | 48 | 31.700 | 1.432 | 27.130 | 1.00 | 53.46 | C |
| ATOM | 3313 | CB | ALA C | 48 | 30.710 | 2.399 | 27.755 | 1.00 | 53.18 | C |
| ATOM | 3314 | C | ALA C | 48 | 32.805 | 1.092 | 28.116 | 1.00 | 53.83 | C |
| ATOM | 3315 | O | ALA C | 48 | 32.546 | 0.562 | 29.182 | 1.00 | 54.60 | O |
| ATOM | 3316 | N | CYS C | 49 | 34.043 | 1.414 | 27.796 | 1.00 | 54.03 | N |
| ATOM | 3317 | CA | CYS C | 49 | 35.122 | 1.031 | 28.698 | 1.00 | 54.96 | C |
| ATOM | 3318 | CB | CYS C | 49 | 36.090 | 0.050 | 28.028 | 1.00 | 55.82 | C |
| ATOM | 3319 | SG | CYS C | 49 | 35.204 | −1.388 | 27.438 | 1.00 | 63.42 | S |
| ATOM | 3320 | C | CYS C | 49 | 35.917 | 2.175 | 29.156 | 1.00 | 53.97 | C |
| ATOM | 3321 | O | CYS C | 49 | 35.902 | 3.264 | 28.537 | 1.00 | 55.05 | O |
| ATOM | 3322 | N | GLY C | 50 | 36.640 | 1.911 | 30.232 | 1.00 | 52.34 | N |
| ATOM | 3323 | CA | GLY C | 50 | 37.665 | 2.810 | 30.715 | 1.00 | 51.76 | C |
| ATOM | 3324 | C | GLY C | 50 | 38.772 | 1.915 | 31.196 | 1.00 | 51.47 | C |
| ATOM | 3325 | O | GLY C | 50 | 38.555 | 0.978 | 31.978 | 1.00 | 51.25 | O |
| ATOM | 3326 | N | VAL C | 51 | 39.969 | 2.166 | 30.704 | 1.00 | 51.06 | N |
| ATOM | 3327 | CA | VAL C | 51 | 41.066 | 1.331 | 31.121 | 1.00 | 49.84 | C |
| ATOM | 3328 | CB | VAL C | 51 | 41.139 | 0.057 | 30.286 | 1.00 | 49.36 | C |
| ATOM | 3329 | CG1 | VAL C | 51 | 40.946 | 0.389 | 28.868 | 1.00 | 48.39 | C |
| ATOM | 3330 | CG2 | VAL C | 51 | 42.472 | −0.637 | 30.542 | 1.00 | 48.57 | C |

TABLE 11-continued

| ATOM | 3331 | C | VAL C | 51 | 42.365 | 2.082 | 31.140 | 1.00 | 49.25 | C |
|---|---|---|---|---|---|---|---|---|---|---|
| ATOM | 3332 | O | VAL C | 51 | 42.584 | 2.936 | 30.327 | 1.00 | 49.22 | O |
| ATOM | 3333 | N | ALA C | 52 | 43.189 | 1.777 | 32.133 | 1.00 | 50.07 | N |
| ATOM | 3334 | CA | ALA C | 52 | 44.584 | 2.265 | 32.259 | 1.00 | 50.14 | C |
| ATOM | 3335 | CB | ALA C | 52 | 44.818 | 2.904 | 33.616 | 1.00 | 48.93 | C |
| ATOM | 3336 | C | ALA C | 52 | 45.613 | 1.170 | 32.016 | 1.00 | 50.32 | C |
| ATOM | 3337 | O | ALA C | 52 | 45.430 | 0.028 | 32.385 | 1.00 | 49.84 | O |
| ATOM | 3338 | N | LYS C | 53 | 40.680 | 1.535 | 31.335 | 1.00 | 52.12 | N |
| ATOM | 3339 | CA | LYS C | 53 | 47.858 | 0.684 | 31.226 | 1.00 | 54.27 | C |
| ATOM | 3340 | CB | LYS C | 53 | 48.136 | 0.298 | 29.779 | 1.00 | 54.07 | C |
| ATOM | 3341 | CG | LYS C | 53 | 47.260 | −0.772 | 29.291 | 1.00 | 55.87 | C |
| ATOM | 3342 | CD | LYS C | 53 | 46.798 | −0.497 | 27.880 | 1.00 | 59.13 | C |
| ATOM | 3343 | CE | LYS C | 53 | 45.825 | −1.590 | 27.424 | 1.00 | 61.21 | C |
| ATOM | 3344 | NZ | LYS C | 53 | 44.835 | −1.004 | 26.454 | 1.00 | 63.09 | N |
| ATOM | 3345 | C | LYS C | 53 | 49.028 | 1.481 | 31.739 | 1.00 | 54.97 | C |
| ATOM | 3346 | O | LYS C | 53 | 49.391 | 2.475 | 31.136 | 1.00 | 56.22 | O |
| ATOM | 3347 | N | VAL C | 54 | 49.602 | 1.082 | 32.861 | 1.00 | 55.46 | N |
| ATOM | 3348 | CA | VAL C | 54 | 50.912 | 1.601 | 33.213 | 1.00 | 55.67 | C |
| ATOM | 3349 | CB | VAL C | 54 | 51.020 | 1.914 | 34.768 | 1.00 | 56.13 | C |
| ATOM | 3350 | CG1 | VAL C | 54 | 52.076 | 2.972 | 34.938 | 1.00 | 56.04 | C |
| ATOM | 3351 | CG2 | VAL C | 54 | 49.663 | 2.414 | 35.283 | 1.00 | 57.02 | C |
| ATOM | 3352 | C | VAL C | 54 | 51.985 | 0.590 | 32.731 | 1.00 | 55.38 | C |
| ATOM | 3353 | O | VAL C | 54 | 51.840 | −0.620 | 32.893 | 1.00 | 56.02 | O |
| ATOM | 3354 | N | LEU C | 55 | 53.048 | 1.080 | 32.114 | 1.00 | 54.72 | N |
| ATOM | 3355 | CA | LEU C | 55 | 53.978 | 0.238 | 31.375 | 1.00 | 53.94 | C |
| ATOM | 3356 | CB | LEU C | 55 | 53.506 | 0.181 | 29.912 | 1.00 | 54.63 | C |
| ATOM | 3357 | CG | LEU C | 55 | 54.168 | −0.775 | 28.907 | 1.00 | 57.13 | C |
| ATOM | 3358 | CD1 | LEU C | 55 | 53.241 | −2.010 | 28.526 | 1.00 | 59.14 | C |
| ATOM | 3359 | CD2 | LEU C | 55 | 54.634 | −0.023 | 27.647 | 1.00 | 57.35 | C |
| ATOM | 3360 | C | LEU C | 55 | 55.399 | 0.842 | 31.495 | 1.00 | 52.47 | C |
| ATOM | 3361 | O | LEU C | 55 | 55.561 | 2.065 | 31.349 | 1.00 | 52.56 | O |
| ATOM | 3362 | N | TRP C | 56 | 56.409 | 0.020 | 31.800 | 1.00 | 50.14 | N |
| ATOM | 3363 | CA | TRP C | 56 | 57.807 | 0.522 | 31.981 | 1.00 | 48.22 | C |
| ATOM | 3364 | CB | TRP C | 56 | 58.015 | 1.321 | 33.282 | 1.00 | 47.27 | C |
| ATOM | 3365 | CG | TRP C | 56 | 58.069 | 0.513 | 34.535 | 1.00 | 48.16 | C |
| ATOM | 3366 | CD1 | TRP C | 56 | 59.182 | 0.126 | 35.181 | 1.00 | 47.10 | C |
| ATOM | 3367 | NE1 | TRP C | 56 | 58.842 | −0.598 | 36.312 | 1.00 | 48.88 | N |
| ATOM | 3368 | CE2 | TRP C | 56 | 57.478 | −0.688 | 36.410 | 1.00 | 46.72 | C |
| ATOM | 3369 | CD2 | TRP C | 56 | 56.944 | 0.005 | 35.329 | 1.00 | 48.59 | C |
| ATOM | 3370 | CE3 | TRP C | 56 | 55.558 | 0.030 | 35.185 | 1.00 | 49.39 | C |
| ATOM | 3371 | CZ3 | TRP C | 56 | 54.769 | −0.622 | 36.148 | 1.00 | 50.11 | C |
| ATOM | 3372 | CH2 | TRP C | 56 | 55.336 | −1.289 | 37.205 | 1.00 | 46.96 | C |
| ATOM | 3373 | CZ2 | TRP C | 56 | 56.631 | −1.323 | 37.365 | 1.00 | 47.41 | C |
| ATOM | 3374 | C | TRP C | 56 | 58.857 | −0.558 | 31.840 | 1.00 | 47.18 | C |
| ATOM | 3375 | O | TRP C | 56 | 58.558 | −1.734 | 31.927 | 1.00 | 46.72 | O |
| ATOM | 3376 | N | MET C | 57 | 60.080 | −0.149 | 31.569 | 1.00 | 46.85 | N |
| ATOM | 3377 | CA | MET C | 57 | 61.196 | −1.089 | 31.586 | 1.00 | 46.16 | C |
| ATOM | 3378 | CB | MET C | 57 | 62.215 | −0.677 | 30.548 | 1.00 | 46.37 | C |
| ATOM | 3379 | CG | MET C | 57 | 61.677 | −0.635 | 29.155 | 1.00 | 42.05 | C |
| ATOM | 3380 | SD | MET C | 57 | 61.057 | −2.244 | 28.674 | 1.00 | 42.59 | S |
| ATOM | 3381 | CE | MET C | 57 | 62.344 | −3.459 | 28.609 | 1.00 | 38.37 | C |
| ATOM | 3382 | C | MET C | 57 | 61.855 | −1.096 | 32.947 | 1.00 | 45.84 | C |
| ATOM | 3383 | O | MET C | 57 | 61.945 | −0.056 | 33.598 | 1.00 | 45.49 | O |
| ATOM | 3384 | N | GLN C | 58 | 62.260 | −2.274 | 33.393 | 1.00 | 45.62 | N |
| ATOM | 3385 | CA | GLN C | 58 | 63.022 | −2.408 | 34.613 | 1.00 | 46.63 | C |
| ATOM | 3386 | CB | GLN C | 58 | 62.240 | −3.175 | 35.694 | 1.00 | 48.13 | C |
| ATOM | 3387 | CG | GLN C | 58 | 62.686 | −2.928 | 37.184 | 1.00 | 53.10 | C |
| ATOM | 3388 | CD | GLN C | 58 | 62.076 | −1.632 | 37.779 | 1.00 | 60.41 | C |
| ATOM | 3389 | OE1 | GLN C | 58 | 60.852 | −1.538 | 38.042 | 1.00 | 63.53 | O |
| ATOM | 3390 | NE2 | GLN C | 58 | 62.929 | −0.640 | 38.020 | 1.00 | 61.93 | N |
| ATOM | 3391 | C | GLN C | 58 | 64.153 | −3.225 | 34.072 | 1.00 | 45.85 | C |
| ATOM | 3392 | O | GLN C | 58 | 64.027 | −4.441 | 33.884 | 1.00 | 45.91 | O |
| ATOM | 3393 | N | GLY C | 59 | 65.240 | −2.530 | 33.742 | 1.00 | 45.58 | N |
| ATOM | 3394 | CA | GLY C | 59 | 66.317 | −3.102 | 32.985 | 1.00 | 44.83 | C |
| ATOM | 3395 | C | GLY C | 59 | 65.775 | −3.769 | 31.755 | 1.00 | 45.66 | C |
| ATOM | 3396 | O | GLY C | 59 | 65.038 | −3.176 | 30.978 | 1.00 | 45.61 | O |
| ATOM | 3397 | N | SER C | 60 | 66.135 | −5.024 | 31.578 | 1.00 | 46.72 | N |
| ATOM | 3398 | CA | SER C | 60 | 65.921 | −5.756 | 30.332 | 1.00 | 47.45 | C |
| ATOM | 3399 | CB | SER C | 60 | 66.816 | −6.992 | 30.402 | 1.00 | 46.96 | C |
| ATOM | 3400 | OG | SER C | 60 | 66.356 | −8.042 | 29.556 | 1.00 | 51.41 | O |
| ATOM | 3401 | C | SER C | 60 | 64.462 | −6.159 | 30.084 | 1.00 | 47.85 | C |
| ATOM | 3402 | O | SER C | 60 | 64.128 | −6.665 | 29.030 | 1.00 | 47.71 | O |
| ATOM | 3403 | N | GLN C | 61 | 63.604 | −5.912 | 31.076 | 1.00 | 49.41 | N |
| ATOM | 3404 | CA | GLN C | 61 | 62.313 | −6.578 | 31.257 | 1.00 | 50.11 | C |
| ATOM | 3405 | CB | GLN C | 61 | 62.424 | −7.405 | 32.546 | 1.00 | 50.96 | C |
| ATOM | 3406 | CG | GLN C | 61 | 61.195 | −8.228 | 32.930 | 1.00 | 56.54 | C |
| ATOM | 3407 | CD | GLN C | 61 | 61.340 | −9.702 | 32.630 | 1.00 | 63.01 | C |
| ATOM | 3408 | OE1 | GLN C | 61 | 60.477 | −10.335 | 31.981 | 1.00 | 65.40 | O |
| ATOM | 3409 | NE2 | GLN C | 61 | 62.470 | −10.271 | 33.094 | 1.00 | 63.85 | N |
| ATOM | 3410 | C | GLN C | 61 | 61.212 | −5.531 | 31.434 | 1.00 | 49.73 | C |

TABLE 11-continued

| ATOM | 3411 | O | GLN C | 61 | 61.387 | −4.535 | 37.163 | 1.00 | 49.60 | O |
|------|------|-----|-------|----|--------|--------|--------|------|-------|---|
| ATOM | 3412 | N | GLN C | 62 | 60.067 | −5.768 | 30.812 | 1.00 | 49.53 | N |
| ATOM | 3413 | CA | GLN C | 62 | 58.951 | −4.821 | 30.871 | 1.00 | 49.21 | C |
| ATOM | 3414 | CB | GLN C | 62 | 58.224 | −4.813 | 29.548 | 1.00 | 49.19 | C |
| ATOM | 3415 | CG | GLN C | 62 | 57.192 | −3.745 | 29.418 | 1.00 | 53.09 | C |
| ATOM | 3416 | CD | GLN C | 62 | 56.507 | −3.842 | 28.086 | 1.00 | 58.79 | C |
| ATOM | 3417 | OE1 | GLN C | 62 | 56.476 | −4.925 | 27.486 | 1.00 | 61.73 | O |
| ATOM | 3418 | NE2 | GLN C | 62 | 55.987 | −2.724 | 27.584 | 1.00 | 57.61 | N |
| ATOM | 3419 | C | GLN C | 62 | 57.980 | −5.203 | 31.952 | 1.00 | 48.58 | C |
| ATOM | 3420 | O | GLN C | 62 | 57.730 | −5.380 | 32.151 | 1.00 | 49.15 | O |
| ATOM | 3421 | N | CYS C | 63 | 57.425 | −4.214 | 32.644 | 1.00 | 48.01 | N |
| ATOM | 3422 | CA | CYS C | 63 | 56.469 | 4.471 | 33.701 | 1.00 | 48.38 | C |
| ATOM | 3423 | CB | CYS C | 63 | 57.016 | −4.067 | 35.089 | 1.00 | 48.34 | C |
| ATOM | 3424 | SG | CYS C | 63 | 58.576 | −4.896 | 35.398 | 1.00 | 54.27 | S |
| ATOM | 3425 | C | CYS C | 63 | 55.234 | −3.690 | 33.367 | 1.00 | 47.87 | C |
| ATOM | 3426 | O | CYS C | 63 | 55.306 | −2.496 | 33.090 | 1.00 | 48.41 | O |
| ATOM | 3427 | N | LYS C | 64 | 54.093 | −4.359 | 33.431 | 1.00 | 47.10 | N |
| ATOM | 3428 | CA | LYS C | 64 | 52.821 | −3.748 | 33.069 | 1.00 | 47.10 | C |
| ATOM | 3429 | CB | LYS C | 64 | 52.368 | −4.407 | 31.769 | 1.00 | 48.33 | C |
| ATOM | 3430 | CG | LYS C | 64 | 51.100 | −3.875 | 31.159 | 1.00 | 52.63 | C |
| ATOM | 3431 | CD | LYS C | 64 | 50.796 | −4.700 | 29.942 | 1.00 | 57.56 | C |
| ATOM | 3432 | CE | LYS C | 64 | 49.542 | −4.179 | 29.251 | 1.00 | 61.76 | C |
| ATOM | 3433 | NZ | LYS C | 64 | 49.490 | −4.717 | 27.930 | 1.00 | 64.92 | N |
| ATOM | 3434 | C | LYS C | 64 | 51.762 | −3.937 | 34.158 | 1.00 | 45.24 | C |
| ATOM | 3435 | O | LYS C | 64 | 51.586 | −5.039 | 34.625 | 1.00 | 44.63 | O |
| ATOM | 3436 | N | GLN C | 65 | 51.114 | −2.859 | 34.596 | 1.00 | 44.14 | N |
| ATOM | 3437 | CA | GLN C | 65 | 49.840 | −2.964 | 35.330 | 1.00 | 43.46 | C |
| ATOM | 3438 | CB | GLN C | 65 | 49.888 | −2.184 | 36.532 | 1.00 | 43.01 | C |
| ATOM | 3439 | CG | GLN C | 65 | 48.650 | −2.409 | 37.491 | 1.00 | 43.29 | C |
| ATOM | 3440 | CD | GLN C | 65 | 48.074 | −1.658 | 38.824 | 1.00 | 42.89 | C |
| ATOM | 3441 | OE1 | GLN C | 65 | 49.513 | −0.818 | 39.044 | 1.00 | 45.08 | O |
| ATOM | 3442 | NE2 | GLN C | 65 | 47.716 | −1.949 | 39.691 | 1.00 | 37.89 | N |
| ATOM | 3443 | C | GLN C | 65 | 48.659 | −2.470 | 34.472 | 1.00 | 43.52 | C |
| ATOM | 3444 | O | GLN C | 65 | 48.738 | −1.378 | 33.865 | 1.00 | 42.72 | O |
| ATOM | 3445 | N | THR C | 66 | 47.579 | −3.271 | 34.424 | 1.00 | 42.90 | N |
| ATOM | 3446 | CA | THR C | 66 | 46.335 | −2.897 | 33.715 | 1.00 | 42.21 | C |
| ATOM | 3447 | CB | THR C | 66 | 45.956 | −3.983 | 32.705 | 1.00 | 41.70 | C |
| ATOM | 3448 | OG1 | THR C | 66 | 46.932 | −4.059 | 31.661 | 1.00 | 43.99 | O |
| ATOM | 3449 | CG2 | THR C | 66 | 44.671 | −3.686 | 32.072 | 1.00 | 40.96 | C |
| ATOM | 3450 | C | THR C | 66 | 45.141 | −2.622 | 34.698 | 1.00 | 42.66 | C |
| ATOM | 3451 | O | THR C | 66 | 44.869 | −3.403 | 35.579 | 1.00 | 43.66 | O |
| ATOM | 3452 | N | SER C | 67 | 44.445 | −1.511 | 34.568 | 1.00 | 42.47 | N |
| ATOM | 3453 | CA | SER C | 67 | 43.310 | −1.262 | 35.396 | 1.00 | 43.17 | C |
| ATOM | 3454 | CB | SER C | 67 | 43.613 | −0.089 | 36.236 | 1.00 | 41.95 | C |
| ATOM | 3455 | OG | SER C | 67 | 44.647 | −0.428 | 37.053 | 1.00 | 43.75 | O |
| ATOM | 3456 | C | SER C | 67 | 42.031 | −0.902 | 34.644 | 1.00 | 45.58 | C |
| ATOM | 3457 | O | SER C | 67 | 42.007 | 0.136 | 33.977 | 1.00 | 46.64 | O |
| ATOM | 3458 | N | GLU C | 68 | 40.955 | −1.594 | 34.809 | 1.00 | 47.05 | N |
| ATOM | 3459 | CA | GLU C | 68 | 39.630 | −1.345 | 34.289 | 1.00 | 48.39 | C |
| ATOM | 3460 | CB | GLU C | 68 | 38.795 | −2.579 | 34.037 | 1.00 | 47.72 | C |
| ATOM | 3461 | CG | GLU C | 68 | 39.055 | −3.164 | 32.716 | 1.00 | 49.07 | C |
| ATOM | 3462 | CD | GLU C | 68 | 38.175 | −4.342 | 32.446 | 1.00 | 53.27 | C |
| ATOM | 3463 | OE1 | GLU C | 68 | 36.979 | −4.171 | 32.104 | 1.00 | 55.15 | O |
| ATOM | 3464 | OE2 | GLU C | 68 | 38.700 | −5.463 | 32.573 | 1.00 | 55.68 | O |
| ATOM | 3465 | C | GLU C | 68 | 38.905 | −0.470 | 35.283 | 1.00 | 49.98 | C |
| ATOM | 3466 | O | GLU C | 68 | 38.798 | −0.844 | 36.474 | 1.00 | 50.96 | O |
| ATOM | 3467 | N | TYR C | 69 | 38.428 | 0.695 | 34.819 | 1.00 | 50.78 | N |
| ATOM | 3468 | CA | TYR C | 69 | 37.596 | 1.569 | 35.666 | 1.00 | 50.93 | C |
| ATOM | 3469 | CB | TYR C | 69 | 38.043 | 3.000 | 35.612 | 1.00 | 50.40 | C |
| ATOM | 3470 | CG | TYR C | 69 | 39.355 | 3.126 | 36.249 | 1.00 | 50.00 | C |
| ATOM | 3471 | CD1 | TYR C | 69 | 40.523 | 2.933 | 33.518 | 1.00 | 50.03 | C |
| ATOM | 3472 | CE1 | TYR C | 69 | 41.786 | 3.022 | 36.120 | 1.00 | 47.81 | C |
| ATOM | 3473 | CZ | TYR C | 69 | 41.844 | 3.262 | 37.468 | 1.00 | 47.36 | C |
| ATOM | 3474 | OH | TYR C | 69 | 43.007 | 3.322 | 38.073 | 1.00 | 49.68 | O |
| ATOM | 3475 | CE2 | TYR C | 69 | 40.713 | 3.429 | 38.241 | 1.00 | 50.52 | C |
| ATOM | 3476 | CD2 | TYR C | 69 | 39.454 | 3.362 | 37.614 | 1.00 | 51.90 | C |
| ATOM | 3477 | C | TYR C | 69 | 33.135 | 1.498 | 35.353 | 1.00 | 52.36 | C |
| ATOM | 3478 | O | TYR C | 69 | 35.327 | 1.958 | 36.175 | 1.00 | 52.91 | O |
| ATOM | 3479 | N | LEU C | 70 | 35.792 | 0.888 | 34.207 | 1.00 | 53.31 | N |
| ATOM | 3480 | CA | LEU C | 70 | 34.457 | 0.951 | 33.706 | 1.00 | 54.33 | C |
| ATOM | 3481 | CB | LEU C | 70 | 34.220 | 2.303 | 33.033 | 1.00 | 53.87 | C |
| ATOM | 3482 | CG | LEU C | 70 | 32.890 | 2.304 | 32.246 | 1.00 | 53.85 | C |
| ATOM | 3483 | CD1 | LEU C | 70 | 31.647 | 2.385 | 33.216 | 1.00 | 53.57 | C |
| ATOM | 3484 | CD2 | LEU C | 70 | 32.840 | 3.359 | 31.182 | 1.00 | 49.92 | C |
| ATOM | 3485 | C | LEU C | 70 | 34.185 | −0.118 | 32.704 | 1.00 | 56.35 | C |
| ATOM | 3486 | O | LEU C | 70 | 34.473 | 0.050 | 31.547 | 1.00 | 57.55 | O |
| ATOM | 3487 | N | ARG C | 71 | 33.580 | −1.209 | 33.132 | 1.00 | 59.53 | N |
| ATOM | 3488 | CA | ARG C | 71 | 33.131 | −2.235 | 32.210 | 1.00 | 62.40 | C |
| ATOM | 3489 | CB | ARG C | 71 | 33.709 | −3.603 | 32.501 | 1.00 | 61.41 | C |
| ATOM | 3490 | CG | ARG C | 71 | 33.572 | −4.399 | 31.261 | 1.00 | 61.72 | C |

TABLE 11-continued

| | | | | | | | | | |
|---|---|---|---|---|---|---|---|---|---|
| ATOM | 3491 | CD | ARG C | 71 | 33.758 | −5.805 | 31.510 | 1.00 | 62.30 | C |
| ATOM | 3492 | NE | ARG C | 71 | 34.929 | −6.030 | 32.314 | 1.00 | 60.02 | N |
| ATOM | 3493 | CZ | ARG C | 71 | 34.987 | −6.976 | 33.229 | 1.00 | 61.57 | C |
| ATOM | 3494 | NH1 | ARG C | 71 | 33.939 | −7.746 | 33.456 | 1.00 | 62.86 | N |
| ATOM | 3495 | NH2 | ARG C | 71 | 36.062 | −7.140 | 33.934 | 1.00 | 62.89 | N |
| ATOM | 3496 | C | ARG C | 71 | 31.613 | −2.321 | 32.184 | 1.00 | 65..01 | C |
| ATOM | 3497 | O | ARG C | 71 | 30.965 | −2.895 | 33.086 | 1.00 | 66.24 | O |
| ATOM | 3498 | N | TYR C | 72 | 31.254 | −1.778 | 31.114 | 1.00 | 87.10 | N |
| ATOM | 3499 | CA | TYR C | 72 | 29.642 | −1.477 | 31.066 | 1.00 | 68.54 | C |
| ATOM | 3500 | CB | TYR C | 72 | 29.441 | 0.058 | 31.291 | 1.00 | 68.97 | C |
| ATOM | 3501 | CG | TYR C | 72 | 27.997 | 0.463 | 31.149 | 1.00 | 71.00 | C |
| ATOM | 3502 | CD1 | TYR C | 72 | 27.126 | 0.654 | 32.269 | 1.00 | 72.26 | C |
| ATOM | 3503 | CE1 | TYR C | 72 | 25.819 | 0.959 | 32.089 | 1.00 | 74.59 | C |
| ATOM | 3504 | CZ | TYR C | 72 | 25.290 | 1.066 | 30.777 | 1.00 | 72.67 | C |
| ATOM | 3505 | OH | TYR C | 72 | 23.984 | 1.358 | 30.515 | 1.00 | 71.08 | O |
| ATOM | 3506 | CE2 | TYR C | 72 | 26.084 | 0.868 | 29.694 | 1.00 | 72.89 | C |
| ATOM | 3507 | CD2 | TYR C | 72 | 27.423 | 0.564 | 29.878 | 1.00 | 71.95 | C |
| ATOM | 3508 | C | TYR C | 72 | 29.198 | −1.954 | 29.694 | 1.00 | 68.76 | C |
| ATOM | 3509 | O | TYR C | 72 | 29.708 | −1.466 | 28.695 | 1.00 | 69.53 | O |
| ATOM | 3510 | N | GLU C | 73 | 28.314 | −2.919 | 29.623 | 1.00 | 69.22 | N |
| ATOM | 3511 | CA | GLU C | 73 | 27.804 | −3.423 | 28.312 | 1.00 | 69.26 | C |
| ATOM | 3512 | CB | GLU C | 73 | 28.214 | −4.876 | 27.993 | 1.00 | 69.96 | C |
| ATOM | 3513 | CG | GLU C | 73 | 27.954 | −5.304 | 26.487 | 1.00 | 73.17 | C |
| ATOM | 3514 | CD | GLU C | 73 | 28.956 | −6.358 | 25.908 | 1.00 | 77.31 | C |
| ATOM | 3515 | OE1 | GLU C | 73 | 29.755 | 7.020 | 26.653 | 1.00 | 76.90 | O |
| ATOM | 3516 | OE2 | GLU C | 73 | 28.968 | −6.504 | 24.664 | 1.00 | 78.85 | O |
| ATOM | 3517 | C | GLU C | 73 | 26.294 | −3.260 | 28.323 | 1.00 | 68.35 | C |
| ATOM | 3518 | O | GLU C | 73 | 25.721 | −3.021 | 29.383 | 1.00 | 68.47 | O |
| ATOM | 3519 | N | ASP C | 74 | 25.638 | −3.327 | 27.161 | 1.00 | 67.16 | N |
| ATOM | 3520 | CA | ASP C | 74 | 24.178 | −3.146 | 27.158 | 1.00 | 65.94 | C |
| ATOM | 3521 | CB | ASP C | 74 | 23.797 | −1.874 | 27.932 | 1.00 | 66.23 | C |
| ATOM | 3522 | CG | ASP C | 74 | 22.320 | −1.811 | 28.230 | 1.00 | 66.08 | C |
| ATOM | 3523 | OD1 | ASP C | 74 | 21.593 | −2.697 | 27.683 | 1.00 | 63.28 | O |
| ATOM | 3524 | OD2 | ASP C | 74 | 21.910 | −0.882 | 28.980 | 1.00 | 63.79 | O |
| ATOM | 3525 | C | ASP C | 74 | 23.554 | −3.126 | 25.759 | 1.00 | 64.66 | C |
| ATOM | 3526 | O | ASP C | 74 | 24.257 | −2.757 | 24.825 | 1.00 | 65.56 | O |
| ATOM | 3527 | N | THR C | 75 | 22.267 | −3.537 | 25.648 | 1.00 | 62.22 | N |
| ATOM | 3528 | CA | THR C | 75 | 21.521 | −3.494 | 24.352 | 1.00 | 60.05 | C |
| ATOM | 3529 | CB | THR C | 75 | 20.661 | −4.721 | 24.954 | 1.00 | 59.92 | C |
| ATOM | 3530 | OG1 | THR C | 75 | 21.253 | −5.893 | 24.616 | 1.00 | 59.86 | O |
| ATOM | 3531 | CG2 | THR C | 75 | 20.484 | −4.867 | 22.547 | 1.00 | 59.61 | C |
| ATOM | 3532 | C | THR C | 75 | 20.511 | −2.389 | 24.329 | 1.00 | 58.72 | C |
| ATOM | 3533 | O | THR C | 75 | 19.658 | −2.318 | 25.207 | 1.00 | 58.22 | O |
| ATOM | 3534 | N | LEU C | 76 | 20.574 | −1.571 | 23.285 | 1.00 | 57.09 | N |
| ATOM | 3535 | CA | LEU C | 76 | 19.689 | −0.427 | 23.133 | 1.00 | 55.22 | C |
| ATOM | 3536 | CB | LEU C | 76 | 20.411 | 0.646 | 22.366 | 1.00 | 55.17 | C |
| ATOM | 3537 | CG | LEU C | 76 | 21.274 | 1.594 | 23.183 | 1.00 | 54.81 | C |
| ATOM | 3538 | CD1 | LEU C | 76 | 21.937 | 0.961 | 24.418 | 1.00 | 53.46 | C |
| ATOM | 3539 | CD2 | LEU C | 76 | 22.250 | 2.152 | 22.238 | 1.00 | 50.16 | C |
| ATOM | 3540 | C | LEU C | 76 | 18.360 | −0.712 | 22.445 | 1.00 | 54.62 | C |
| ATOM | 3541 | O | LEU C | 76 | 18.288 | −1.393 | 21.428 | 1.00 | 53.45 | O |
| ATOM | 3542 | N | LEU C | 77 | 17.318 | −0.130 | 23.035 | 1.00 | 54.98 | N |
| ATOM | 3543 | CA | LEU C | 77 | 15.917 | −0.243 | 22.608 | 1.00 | 54.70 | C |
| ATOM | 3544 | CB | LEU C | 77 | 15.053 | −0.584 | 23. 834 | 1.00 | 54.75 | C |
| ATOM | 3545 | CG | LEU C | 77 | 14.583 | −2.037 | 23.982 | 1.00 | 54.77 | C |
| ATOM | 3546 | CD1 | LEU C | 77 | 13.224 | −2.073 | 24.717 | 1.00 | 55.20 | C |
| ATOM | 3547 | CD2 | LEU C | 77 | 14.495 | −2.714 | 22.587 | 1.00 | 55.15 | C |
| ATOM | 3548 | C | LEU C | 77 | 15.378 | 1.057 | 22.047 | 1.00 | 53.92 | C |
| ATOM | 3549 | O | LEU C | 77 | 15.572 | 2.084 | 22.558 | 1.00 | 54.56 | O |
| ATOM | 3550 | N | LEU C | 78 | 14.681 | 1.018 | 20.926 | 1.00 | 53.61 | N |
| ATOM | 3551 | CA | LEU C | 78 | 13.972 | 2.201 | 20.448 | 1.00 | 53.92 | C |
| ATOM | 3552 | CB | LEU C | 78 | 13.830 | 2.223 | 18.918 | 1.00 | 54.06 | C |
| ATOM | 3553 | CG | LEU C | 78 | 14.097 | 3.535 | 18.126 | 1.00 | 56.30 | C |
| ATOM | 3554 | CD1 | LEU C | 78 | 14.070 | 4.901 | 18.955 | 1.00 | 56.22 | C |
| ATOM | 3555 | CD2 | LEU C | 78 | 15.396 | 3.443 | 17.322 | 1.00 | 55.39 | C |
| ATOM | 3556 | C | LEU C | 78 | 12.590 | 2.251 | 21.044 | 1.00 | 54.23 | C |
| ATOM | 3557 | O | LEU C | 78 | 11.953 | 1.198 | 21.284 | 1.00 | 54.65 | O |
| ATOM | 3558 | N | GLU C | 79 | 12.112 | 3.477 | 21.261 | 1.00 | 54.35 | N |
| ATOM | 3559 | CA | GLU C | 79 | 10.734 | 3.758 | 21.707 | 1.00 | 54.31 | C |
| ATOM | 3560 | CB | GLU C | 79 | 10.506 | 5.230 | 21.534 | 1.00 | 54.16 | C |
| ATOM | 3561 | CG | GLU C | 79 | 10.773 | 6.001 | 22.748 | 1.00 | 53.81 | C |
| ATOM | 3562 | CD | GLU C | 79 | 9.645 | 6.993 | 22.964 | 1.00 | 66.65 | C |
| ATOM | 3563 | OE1 | GLU C | 79 | 9.606 | 8.046 | 22.231 | 1.00 | 67.69 | O |
| ATOM | 3564 | OE2 | GLU C | 79 | 8.770 | 6.689 | 23.833 | 1.00 | 67.00 | C |
| ATOM | 3565 | C | GLU C | 79 | 9.620 | 3.000 | 20.939 | 1.00 | 53.23 | C |
| ATOM | 3566 | O | GLU C | 79 | 8.601 | 2.654 | 21.489 | 1.00 | 52.59 | O |
| ATOM | 3567 | N | ASP C | 80 | 9.833 | 2.763 | 19.655 | 1.00 | 52.85 | N |
| ATOM | 3568 | CA | ASP C | 80 | 8.857 | 2.081 | 18.828 | 1.00 | 52.69 | C |
| ATOM | 3569 | CB | ASP C | 80 | 9.006 | 2.569 | 17.376 | 1.00 | 52.69 | C |
| ATOM | 3570 | CG | ASP C | 80 | 7.697 | 2.489 | 16.578 | 1.00 | 53. 49 | C |

TABLE 11-continued

| | | | | | | | | | | |
|---|---|---|---|---|---|---|---|---|---|---|
| ATOM | 3571 | OD1 | ASP C | 80 | 6.584 | 2.547 | 17.174 | 1.00 | 52.19 | O |
| ATOM | 3572 | OD2 | ASP C | 80 | 7.792 | 2.389 | 15.327 | 1.00 | 55.34 | O |
| ATOM | 3573 | C | ASP C | 80 | 8.971 | 0.535 | 18.906 | 1.00 | 52.27 | C |
| ATOM | 3574 | O | ASP C | 80 | 8.251 | −0.163 | 18.211 | 1.00 | 51.05 | O |
| ATOM | 3575 | N | GLN C | 81 | 9.877 | 0.027 | 19.754 | 1.00 | 52.59 | N |
| ATOM | 3576 | CA | GLN C | 81 | 10.409 | −1.427 | 19.979 | 1.00 | 52.60 | C |
| ATOM | 3577 | CB | GLN C | 81 | 11.623 | −1.706 | 20.130 | 1.00 | 52.87 | C |
| ATOM | 3578 | CG | GLN C | 81 | 12.509 | −1.806 | 18.867 | 1.00 | 55.34 | C |
| ATOM | 3579 | CD | GLN C | 8I | 13.989 | −2.210 | 19.223 | 1.00 | 50.23 | C |
| ATOM | 3580 | OE1 | GLN C | 81 | 14.949 | −1.457 | 18.953 | 1.00 | 55.97 | O |
| ATOM | 3581 | NE2 | GLN C | 81 | 14.154 | −3.407 | 19.843 | 1.00 | 61.16 | N |
| ATOM | 3582 | C | GLN C | 81 | 9.505 | −1.852 | 21.310 | 1.00 | 51.44 | C |
| ATOM | 3583 | O | GLN C | 81 | 10.242 | −2.284 | 22.186 | 1.00 | 51.41 | O |
| ATOM | 3584 | N | PRO C | 82 | 8.198 | −1.717 | 21.500 | 1.00 | 50.60 | N |
| ATOM | 3585 | CA | PRO C | 82 | 7.745 | −1.904 | 22.863 | 1.00 | 50.96 | C |
| ATOM | 3586 | CB | PRO C | 82 | 6.328 | −1.380 | 22.814 | 1.00 | 50.70 | C |
| ATOM | 3587 | CG | PRO C | 82 | 5.889 | −1.659 | 21.450 | 1.00 | 50.52 | C |
| ATOM | 3588 | CD | PRO C | 82 | 7.083 | −1.445 | 20.591 | 1.00 | 50.97 | C |
| ATOM | 3589 | C | PRO C | 82 | 7.774 | −3.366 | 23.358 | 1.00 | 51.60 | C |
| ATOM | 3590 | O | PRO C | 82 | 7.771 | −3.617 | 24.563 | 1.00 | 51.41 | O |
| ATOM | 3591 | N | THR C | 83 | 7.851 | −4.310 | 22.432 | 1.00 | 52.81 | N |
| ATOM | 3592 | CA | THR C | 83 | 7.948 | −5.729 | 22.761 | 1.00 | 54.21 | C |
| ATOM | 3593 | CB | THR C | 83 | 7.397 | −6.573 | 21.631 | 1.00 | 53.69 | C |
| ATOM | 3594 | OG1 | THR C | 83 | 7.750 | −5.932 | 20.393 | 1.00 | 53.97 | O |
| ATOM | 3595 | CG2 | THR C | 83 | 5.875 | −6.659 | 21.758 | 1.00 | 51.88 | C |
| ATOM | 3596 | C | THR C | 83 | 9.384 | −6.120 | 23.019 | 1.00 | 55.28 | C |
| ATOM | 3597 | O | THR C | 83 | 9.724 | −7.292 | 23.074 | 1.00 | 54.99 | O |
| ATOM | 3598 | N | GLY C | 84 | 10.228 | −5.120 | 23.168 | 1.00 | 57.26 | N |
| ATOM | 3599 | CA | GLY C | 84 | 11.613 | −5.343 | 23.502 | 1.00 | 60.55 | C |
| ATOM | 3600 | C | GLY C | 84 | 12.480 | −5.913 | 22.403 | 1.00 | 63.20 | C |
| ATOM | 3601 | O | GLY C | 84 | 12.201 | −5.797 | 21.192 | 1.00 | 63.02 | O |
| ATOM | 3602 | N | GLU C | 85 | 13.527 | −6.586 | 22.861 | 1.00 | 66.43 | N |
| ATOM | 3603 | CA | GLU C | 85 | 14.759 | −6.755 | 22.093 | 1.00 | 69.68 | C |
| ATOM | 3604 | CB | GLU C | 85 | 15.942 | −6.383 | 22.998 | 1.00 | 69.84 | C |
| ATOM | 3605 | CG | GLU C | 85 | 15.921 | −7.131 | 24.363 | 1.00 | 70.73 | C |
| ATOM | 3606 | CD | GLU C | 85 | 16.089 | −6.193 | 25.532 | 1.00 | 70.07 | C |
| ATOM | 3607 | OE1 | GLU C | 85 | 17.229 | −6.118 | 26.022 | 1.00 | 71.35 | O |
| ATOM | 3608 | OE2 | GLU C | 85 | 15.102 | −5.528 | 25.942 | 1.00 | 68.22 | O |
| ATOM | 3609 | C | GLU C | 85 | 14.988 | −8.140 | 21.466 | 1.00 | 71.92 | C |
| ATOM | 3610 | O | GLU C | 85 | 15.849 | −8.276 | 20.573 | 1.00 | 72.28 | O |
| ATOM | 3611 | N | ASN C | 86 | 14.266 | −9.176 | 21.928 | 1.00 | 74.98 | N |
| ATOM | 3612 | CA | ASN C | 86 | 14.200 | −10.404 | 21.085 | 1.00 | 77.11 | C |
| ATOM | 3613 | CB | ASN C | 86 | 13.979 | −11.703 | 21.861 | 1.00 | 77.50 | C |
| ATOM | 3614 | CG | ASN C | 86 | 15.232 | −12.602 | 21.852 | 1.00 | 80.05 | C |
| ATOM | 3615 | OD1 | ASN C | 86 | 15.363 | 13.509 | 22.684 | 1.00 | 83.36 | O |
| ATOM | 3616 | ND2 | ASN C | 86 | 16.151 | −12.351 | 20.909 | 1.00 | 80.91 | N |
| ATOM | 3617 | C | ASN C | 86 | 13.240 | −10.234 | 19.922 | 1.00 | 77.71 | C |
| ATOM | 3618 | O | ASN C | 86 | 12.862 | −11.213 | 19.262 | 1.00 | 77.77 | O |
| ATOM | 3619 | N | GLU C | 87 | 12.917 | −8.956 | 19.670 | 1.00 | 78.47 | N |
| ATOM | 3620 | CA | GLU C | 87 | 12.096 | −8.536 | 18.567 | 1.00 | 79.01 | C |
| ATOM | 3621 | CB | GLU C | 87 | 10.936 | −7.750 | 19.115 | 1.00 | 78.99 | C |
| ATOM | 3622 | CG | GLU C | 87 | 10.491 | −8.344 | 20.411 | 1.00 | 80.51 | C |
| ATOM | 3623 | CD | GLU C | 87 | 9.540 | −9.502 | 20.199 | 1.00 | 83.50 | C |
| ATOM | 3624 | OE1 | GLU C | 87 | 8.332 | −9.193 | 20.141 | 1.00 | 84.85 | O |
| ATOM | 3625 | OE2 | GLU C | 87 | 9.964 | −10.690 | 20.078 | 1.00 | 83.44 | O |
| ATOM | 3626 | C | GLU C | 87 | 12.963 | −7.668 | 17.690 | 1.00 | 79.12 | C |
| ATOM | 3627 | O | GLU C | 87 | 13.949 | −7.074 | 18.160 | 1.00 | 79.06 | O |
| ATOM | 3628 | N | MET C | 88 | 12.564 | −7.602 | 16.426 | 1.00 | 79.48 | N |
| ATOM | 3629 | CA | MET C | 88 | 13.382 | −7.073 | 15.353 | 1.00 | 79.89 | C |
| ATOM | 3630 | CB | MET C | 88 | 13.642 | −8.168 | 14.335 | 1.00 | 80.30 | C |
| ATOM | 3631 | CG | MET C | 88 | 14.894 | −8.950 | 14.637 | 1.00 | 81.51 | C |
| ATOM | 3632 | SD | MET C | 88 | 15.727 | −9.462 | 13.114 | 1.00 | 85.07 | S |
| ATOM | 3633 | CE | MET C | 88 | 15.387 | −8.083 | 12.009 | 1.00 | 83.08 | C |
| ATOM | 3634 | C | MET C | 88 | 12.759 | −5.899 | 14.645 | 1.00 | 79.64 | C |
| ATOM | 3635 | O | MET C | 88 | 11.536 | −5.773 | 14.557 | 1.00 | 79.46 | O |
| ATOM | 3636 | N | VAL C | 89 | 13.637 | −5.073 | 14.099 | 1.00 | 79.50 | N |
| ATOM | 3637 | CA | VAL C | 89 | 13.276 | −3.774 | 13.558 | 1.00 | 79.70 | C |
| ATOM | 3638 | CB | VAL C | 89 | 14.072 | −2.653 | 14.254 | 1.00 | 79.54 | C |
| ATOM | 3639 | CG1 | VAL C | 89 | 15.264 | −3.233 | 14.993 | 1.00 | 79.53 | C |
| ATOM | 3640 | CG2 | VAL C | 89 | 14.511 | −1.562 | 13.256 | 1.00 | 78.92 | C |
| ATOM | 3641 | C | VAL C | 89 | 13.476 | −3.702 | 12.055 | 1.00 | 80.22 | C |
| ATOM | 3642 | O | VAL C | 89 | 14.063 | −4.618 | 11.455 | 1.00 | 80.37 | O |
| ATOM | 3643 | N | ILE C | 90 | 13.014 | −2.580 | 11.481 | 1.00 | 80.59 | N |
| ATOM | 3644 | CA | ILE C | 90 | 12.709 | −2.420 | 10.046 | 1.00 | 80.82 | C |
| ATOM | 3645 | CB | ILE C | 90 | 11.190 | −2.796 | 9.758 | 1.00 | 80.80 | C |
| ATOM | 3646 | CG1 | ILE C | 90 | 11.029 | −4.287 | 0.304 | 1.00 | 80.70 | C |
| ATOM | 3647 | CD1 | ILE C | 90 | 11.116 | −5.349 | 10.509 | 1.00 | 80.02 | C |
| ATOM | 3648 | CG2 | ILE C | 90 | 10.568 | −1.865 | 8.712 | 1.00 | 80.67 | C |
| ATOM | 3649 | C | ILE C | 90 | 13.026 | −0.989 | 9.569 | 1.00 | 80.87 | C |
| ATOM | 3650 | O | ILE C | 90 | 12.193 | −0.082 | 9.703 | 1.00 | 80.49 | O |

TABLE 11-continued

| | | | | | | | | | | |
|---|---|---|---|---|---|---|---|---|---|---|
| ATOM | 3651 | N | MET C | 91 | 14.222 | −0.803 | 8.997 | 1.00 | 81.34 | N |
| ATOM | 3652 | CA | MET C | 91 | 14.760 | 0.550 | 8.736 | 1.00 | 81.80 | C |
| ATOM | 3653 | CB | MET C | 91 | 16.181 | 0.711 | 9.389 | 1.00 | 82.08 | C |
| ATOM | 3654 | CG | MET C | 91 | 16.163 | 1.310 | 10.852 | 1.00 | 82.64 | C |
| ATOM | 3655 | SD | MET C | 91 | 17.730 | 1.871 | 11.641 | 1.00 | 82.34 | S |
| ATOM | 3656 | CE | MET C | 91 | 18.552 | 0.308 | 11.852 | 1.00 | 80.42 | C |
| ATOM | 3657 | C | MET C | 91 | 14.749 | 1.106 | 7.282 | 1.00 | 82.06 | C |
| ATOM | 3658 | O | MET C | 91 | 15.641 | 0.843 | 6.451 | 1.00 | 81.97 | O |
| ATOM | 3659 | N | ARG C | 92 | 13.715 | 1.902 | 7.015 | 1.00 | 82.29 | N |
| ATOM | 3660 | CA | ARG C | 92 | 13.558 | 2.620 | 5.749 | 1.00 | 82.63 | C |
| ATOM | 3661 | CB | ARG C | 92 | 12.055 | 2.877 | 5.428 | 1.00 | 83.18 | C |
| ATOM | 3662 | CG | ARG C | 92 | 11.357 | 4.122 | 6.092 | 1.00 | 84.36 | C |
| ATOM | 3663 | CD | ARG C | 92 | 9.907 | 3.819 | 6.612 | 1.00 | 86.30 | C |
| ATOM | 3664 | NE | ARG C | 92 | 9.020 | 3.184 | 5.615 | 1.00 | 88.83 | N |
| ATOM | 3665 | CZ | ARG C | 92 | 8.658 | 1.889 | 5.599 | 1.00 | 88.50 | C |
| ATOM | 3666 | NH1 | ARG C | 92 | 9.107 | 1.048 | 6.532 | 1.00 | 87.95 | N |
| ATOM | 3667 | NH2 | ARG C | 92 | 7.839 | 1.428 | 4.642 | 1.00 | 86.82 | N |
| ATOM | 3668 | C | ARG C | 92 | 14.341 | 3.928 | 5.788 | 1.00 | 82.13 | C |
| ATOM | 3669 | O | ARG C | 92 | 14.524 | 4.503 | 6.873 | 1.00 | 82.14 | O |
| ATOM | 3670 | N | PRO C | 93 | 14.829 | 4.390 | 4.614 | 1.00 | 81.70 | N |
| ATOM | 3671 | CA | PRO C | 93 | 15.481 | 5.716 | 4.468 | 1.00 | 81.23 | C |
| ATOM | 3672 | CB | PRO C | 93 | 15.684 | 5.833 | 2.949 | 1.00 | 81.06 | C |
| ATOM | 3673 | CG | PRO C | 93 | 15.865 | 4.414 | 2.504 | 1.00 | 81.00 | C |
| ATOM | 3674 | CD | PRO C | 93 | 14.876 | 3.624 | 3.349 | 1.00 | 81.53 | C |
| ATOM | 3675 | C | PRO C | 93 | 14.685 | 6.913 | 5.014 | 1.00 | 80.54 | C |
| ATOM | 3676 | O | PRO C | 93 | 13.553 | 6.750 | 5.461 | 1.00 | 80.70 | O |
| ATOM | 3677 | N | GLY C | 94 | 15.301 | 8.091 | 5.021 | 1.00 | 79.83 | N |
| ATOM | 3678 | CA | GLY C | 94 | 14.580 | 9.339 | 5.284 | 1.00 | 78.56 | C |
| ATOM | 3679 | C | GLY C | 94 | 14.190 | 9.756 | 6.704 | 1.00 | 78.03 | C |
| ATOM | 3680 | O | GLY C | 94 | 13.670 | 10.869 | 6.864 | 1.00 | 77.91 | O |
| ATOM | 3681 | N | ASN C | 95 | 14.395 | 8.904 | 7.727 | 1.00 | 77.07 | N |
| ATOM | 3682 | CA | ASN C | 95 | 14.225 | 9.346 | 9.161 | 1.00 | 76.43 | C |
| ATOM | 3683 | CB | ASN C | 95 | 12.881 | 8.917 | 9.796 | 1.00 | 76.59 | C |
| ATOM | 3684 | CG | ASN C | 95 | 11.681 | 9.174 | 8.889 | 1.00 | 76.62 | C |
| ATOM | 3685 | OD1 | ASN C | 95 | 10.830 | 10.029 | 9.187 | 1.00 | 77.19 | O |
| ATOM | 3686 | ND2 | ASN C | 95 | 11.608 | 8.433 | 7.776 | 1.00 | 73.77 | N |
| ATOM | 3687 | C | ASN C | 95 | 15.357 | 8.913 | 10.087 | 1.00 | 75.45 | C |
| ATOM | 3688 | O | ASN C | 95 | 15.950 | 7.843 | 9.902 | 1.00 | 75.76 | O |
| ATOM | 3689 | N | LYS C | 96 | 15.651 | 9.728 | 11.096 | 1.00 | 73.93 | N |
| ATOM | 3690 | CA | LYS C | 96 | 16.826 | 9.450 | 11.948 | 1.00 | 72.12 | C |
| ATOM | 3691 | CB | LYS C | 96 | 17.485 | 10.750 | 12.460 | 1.00 | 72.08 | C |
| ATOM | 3692 | CG | LYS C | 96 | 16.796 | 12.083 | 12.046 | 1.00 | 72.68 | C |
| ATOM | 3693 | CD | LYS C | 96 | 17.592 | 13.369 | 12.441 | 1.00 | 73.01 | C |
| ATOM | 3694 | CE | LYS C | 96 | 19.133 | 13.332 | 12.111 | 1.00 | 73.76 | C |
| ATOM | 3695 | NZ | LYS C | 96 | 19.512 | 13.481 | 10.648 | 1.00 | 72.53 | N |
| ATOM | 3696 | C | LYS C | 96 | 16.471 | 8.491 | 13.097 | 1.00 | 70.62 | C |
| ATOM | 3697 | O | LYS C | 96 | 15.564 | 8.786 | 13.885 | 1.00 | 70.66 | O |
| ATOM | 3698 | N | TYR C | 97 | 17.158 | 7.349 | 13.169 | 1.00 | 68.25 | N |
| ATOM | 3699 | CA | TYR C | 97 | 16.933 | 6.378 | 14.248 | 1.00 | 66.85 | C |
| ATOM | 3700 | CB | TYR C | 97 | 16.967 | 4.918 | 13.739 | 1.00 | 67.68 | C |
| ATOM | 3701 | CG | TYR C | 97 | 16.108 | 4.724 | 12.513 | 1.00 | 71.85 | C |
| ATOM | 3702 | CD1 | TYR C | 97 | 14.705 | 4.644 | 12.613 | 1.00 | 74.20 | C |
| ATOM | 3703 | CE1 | TYR C | 97 | 13.896 | 4.510 | 11.457 | 1.00 | 75.34 | C |
| ATOM | 3704 | CZ | TYR C | 97 | 14.493 | 4.455 | 10.186 | 1.00 | 76.48 | C |
| ATOM | 3705 | OH | TYR C | 97 | 13.709 | 4.813 | 9.052 | 1.00 | 78.11 | O |
| ATOM. | 3706 | CE2 | TYR C | 97 | 15.878 | 4.541 | 10.056 | 1.00 | 74.86 | C |
| ATOM | 3707 | CD2 | TYR C | 97 | 16.682 | 4.692 | 11.226 | 1.00 | 74.57 | C |
| ATOM | 3708 | C | TYR C | 97 | 17.878 | 6.607 | 15.437 | 1.00 | 64.68 | C |
| ATOM | 3709 | O | TYR C | 97 | 19.090 | 6.487 | 15.349 | 1.00 | 64.07 | O |
| ATOM | 3710 | N | GLU C | 98 | 17.277 | 6.957 | 16.560 | 1.00 | 62.78 | N |
| ATOM | 3711 | CA | GLU C | 98 | 18.000 | 7.387 | 17.730 | 1.00 | 60.61 | C |
| ATOM | 3712 | CB | GLU C | 98 | 17.531 | 8.761 | 18.130 | 1.00 | 60.09 | C |
| ATOM | 3713 | CG | GLU C | 98 | 17.759 | 9.802 | 17.074 | 1.00 | 61.12 | C |
| ATOM | 3714 | CD | GLU C | 98 | 17.327 | 11.161 | 17.585 | 1.00 | 65.82 | C |
| ATOM | 3715 | OE1 | GLU C | 98 | 16.503 | 11.212 | 18.531 | 1.00 | 64.15 | O |
| ATOM | 3716 | OE2 | GLU C | 98 | 17.826 | 12.192 | 17.072 | 1.00 | 69.28 | O |
| ATOM | 3717 | C | GLU C | 98 | 17.800 | 6.423 | 18.878 | 1.00 | 59.04 | C |
| ATOM | 3718 | O | GLU C | 98 | 16.730 | 6.331 | 19.421 | 1.00 | 58.95 | O |
| ATOM | 3719 | N | TYR C | 99 | 18.862 | 5.716 | 19.238 | 1.00 | 57.27 | N |
| ATOM | 3720 | CA | TYR C | 99 | 18.894 | 4.831 | 20.377 | 1.00 | 55.39 | C |
| ATOM | 3721 | CB | TYR C | 99 | 19.792 | 3.600 | 19.998 | 1.00 | 55.11 | C |
| ATOM | 3722 | CG | TYR C | 99 | 19.170 | 2.720 | 19.067 | 1.00 | 55.94 | C |
| ATOM | 3723 | CD1 | TYR C | 99 | 18.546 | 1.586 | 19.579 | 1.00 | 57.31 | C |
| ATOM | 3724 | CE1 | TYR C | 99 | 17.965 | 0.665 | 18.760 | 1.00 | 57.28 | C |
| ATOM | 3725 | CZ | TYR C | 99 | 17.985 | 0.857 | 17.396 | 1.00 | 56.39 | C |
| ATOM | 3726 | OH | TYR C | 99 | 17.385 | −0.134 | 16.664 | 1.00 | 57.55 | O |
| ATOM | 3727 | CE2 | TYR C | 99 | 18.607 | 1.971 | 16.827 | 1.00 | 54.18 | C |
| ATOM | 3728 | CD2 | TYR C | 99 | 19.196 | 2.906 | 17.671 | 1.00 | 55.16 | C |
| ATOM | 3729 | C | TYR C | 99 | 19.495 | 5.524 | 21.606 | 1.00 | 54.25 | C |
| ATOM | 3730 | O | TYR C | 99 | 20.652 | 5.892 | 21.608 | 1.00 | 54.72 | O |

TABLE 11-continued

| | | | | | | | | | |
|---|---|---|---|---|---|---|---|---|---|
| ATOM | 3731 | N    | LYS C | 100 | 18.747 | 5.686 | 22.674 | 1.00 | 53.19 | N |
| ATOM | 3732 | CA   | LYS C | 100 | 19.309 | 6.397 | 23.838 | 1.00 | 52.49 | C |
| ATOM | 3733 | CB   | LYS C | 100 | 18.215 | 7.073 | 24.667 | 1.00 | 52.53 | C |
| ATOM | 3734 | CG   | LYS C | 100 | 17.797 | 8.401 | 24.107 | 1.00 | 55.32 | C |
| ATOM | 3735 | CD   | LYS C | 100 | 16.296 | 8.581 | 24.334 | 1.00 | 62.11 | C |
| ATOM | 3736 | CE   | LYS C | 100 | 16.021 | 9.349 | 25.633 | 1.00 | 65.31 | C |
| ATOM | 3737 | NZ   | LYS C | 100 | 14.630 | 9.853 | 25.612 | 1.00 | 66.70 | N |
| ATOM | 3738 | C    | LYS C | 100 | 20.141 | 5.510 | 24.742 | 1.00 | 50.93 | C |
| ATOM | 3739 | O    | LYS C | 100 | 19.794 | 4.344 | 24.936 | 1.00 | 49.91 | O |
| ATOM | 3740 | N    | PHE C | 101 | 21.229 | 6.057 | 25.302 | 1.00 | 49.62 | N |
| ATOM | 3741 | CA   | PHE C | 101 | 22.022 | 5.292 | 26.260 | 1.00 | 48.44 | C |
| ATOM | 3742 | CB   | PHE C | 101 | 23.204 | 4.593 | 25.589 | 1.00 | 47.38 | C |
| ATOM | 3743 | CG   | PHE C | 101 | 24.250 | 5.524 | 25.150 | 1.00 | 44.17 | C |
| ATOM | 3744 | CD1  | PHE C | 101 | 25.228 | 5.961 | 26.050 | 1.00 | 41.16 | C |
| ATOM | 3745 | CE1  | PHE C | 101 | 26.251 | 6.847 | 25.542 | 1.00 | 40.96 | C |
| ATOM | 3746 | CZ   | PHE C | 101 | 26.290 | 7.335 | 24.309 | 1.00 | 39.99 | C |
| ATOM | 3747 | CE2  | PHE C | 101 | 25.314 | 5.889 | 23.387 | 1.00 | 42.01 | C |
| ATOM | 3748 | CD2  | PHE C | 101 | 24.298 | 5.985 | 23.387 | 1.00 | 42.01 | C |
| ATOM | 3749 | C    | PHE C | 101 | 22.554 | 6.177 | 27.328 | 1.00 | 48.92 | C |
| ATOM | 3750 | O    | PHE C | 101 | 22.805 | 7.354 | 27.099 | 1.00 | 48.40 | O |
| ATOM | 3751 | N    | GLY C | 102 | 22.765 | 5.582 | 28.486 | 1.00 | 49.57 | N |
| ATOM | 3752 | CA   | GLY C | 102 | 23.326 | 6.247 | 29.648 | 1.00 | 50.95 | C |
| ATOM | 3753 | C    | GLY C | 102 | 24.038 | 5.281 | 30.585 | 1.00 | 52.08 | C |
| ATOM | 3754 | O    | GLY C | 102 | 23.835 | 4.063 | 30.519 | 1.00 | 52.41 | O |
| ATOM | 3255 | N    | PHE C | 103 | 24.932 | 5.822 | 31.410 | 1.00 | 52.93 | N |
| ATOM | 3756 | CA   | PHE C | 103 | 25.570 | 5.077 | 32.523 | 1.00 | 53.21 | C |
| ATOM | 3757 | CB   | PHE C | 103 | 26.489 | 4.007 | 32.017 | 1.00 | 51.32 | C |
| ATOM | 3758 | CG   | PHE C | 103 | 27.437 | 4.517 | 31.014 | 1.00 | 50.46 | C |
| ATOM | 3759 | CD1  | PHE C | 103 | 28.617 | 5.176 | 31.422 | 1.00 | 46.74 | C |
| ATOM | 3760 | CE1  | PHE C | 103 | 29.468 | 5.697 | 30.479 | 1.00 | 43.59 | C |
| ATOM | 3761 | CZ   | PHE C | 103 | 29.161 | 5.566 | 29.117 | 1.00 | 42.34 | C |
| ATOM | 3762 | CE2  | PHE C | 103 | 28.007 | 4.961 | 28.705 | 1.00 | 39.94 | C |
| ATOM | 3763 | CD2  | PHE C | 103 | 27.139 | 4.433 | 29.650 | 1.00 | 45.32 | C |
| ATOM | 3764 | C    | PHE C | 103 | 26.346 | 6.006 | 33.181 | 1.00 | 54.70 | C |
| ATOM | 3765 | O    | PHE C | 103 | 26.655 | 7.230 | 32.981 | 1.00 | 53.72 | O |
| ATOM | 3766 | N    | GLU C | 104 | 26.648 | 5.609 | 34.580 | 1.00 | 57.09 | N |
| ATOM | 3767 | CA   | GLU C | 104 | 27.466 | 6.434 | 35.430 | 1.00 | 59.43 | C |
| ATOM | 3768 | CB   | GLU C | 104 | 26.876 | 6.570 | 36.813 | 1.00 | 60.21 | C |
| ATOM | 3769 | CG   | GLU C | 104 | 25.475 | 7.221 | 36.787 | 1.00 | 64.49 | C |
| ATOM | 3770 | CD   | GLU C | 104 | 24.787 | 7.157 | 38.150 | 1.00 | 69.78 | C |
| ATOM | 3771 | OE1  | GLU C | 104 | 25.523 | 7.190 | 39.196 | 1.00 | 72.47 | O |
| ATOM | 3772 | OE2  | GLU C | 104 | 23.527 | 7.053 | 38.167 | 1.00 | 69.52 | O |
| ATOM | 3773 | C    | GLU C | 104 | 28.887 | 5.904 | 35.491 | 1.00 | 59.67 | C |
| ATOM | 3774 | O    | GLU C | 104 | 29.224 | 4.797 | 35.254 | 1.00 | 59.67 | O |
| ATOM | 3775 | N    | LEU C | 105 | 29.737 | 6.923 | 35.777 | 1.00 | 60.38 | N |
| ATOM | 3776 | CA   | LEU C | 105 | 31.082 | 6.597 | 36.083 | 1.00 | 60.93 | C |
| ATOM | 3777 | CB   | LEU C | 105 | 31.972 | 7.808 | 35.830 | 1.00 | 60.25 | C |
| ATOM | 3778 | CG   | LEU C | 105 | 31.996 | 8.164 | 34.339 | 1.00 | 57.95 | C |
| ATOM | 3779 | CD1  | LEU C | 105 | 32.873 | 9.364 | 34.098 | 1.00 | 54.30 | C |
| ATOM | 3780 | CD2  | LEU C | 105 | 32.455 | 6.937 | 33.556 | 1.00 | 55.41 | C |
| ATOM | 3781 | C    | LEU C | 105 | 31.109 | 6.129 | 37.547 | 1.00 | 62.50 | C |
| ATOM | 3782 | O    | LEU C | 105 | 30.470 | 6.754 | 38.441 | 1.00 | 61.79 | O |
| ATOM | 3783 | N    | PRO C | 106 | 31.836 | 5.024 | 37.778 | 1.00 | 63.83 | N |
| ATOM | 3784 | CA   | PRO C | 106 | 32.108 | 4.484 | 39.089 | 1.00 | 64.61 | C |
| ATOM | 3785 | CB   | PRO C | 106 | 33.266 | 3.485 | 38.850 | 1.00 | 64.87 | C |
| ATOM | 3786 | CG   | PRO C | 106 | 33.111 | 3.031 | 37.476 | 1.00 | 65.07 | C |
| ATOM | 3787 | CD   | PRO C | 106 | 32.516 | 4.247 | 36.721 | 1.00 | 64.58 | C |
| ATOM | 3788 | C    | PRO C | 106 | 32.569 | 5.570 | 40.034 | 1.00 | 64.85 | C |
| ATOM | 3789 | O    | PRO C | 106 | 32.935 | 6.884 | 39.626 | 1.00 | 63.83 | O |
| ATOM | 3790 | N    | GLN C | 107 | 32.556 | 5.178 | 41.298 | 1.00 | 66.15 | N |
| ATOM | 3791 | CA   | GLN C | 107 | 32.639 | 6.061 | 42.243 | 1.00 | 67.65 | C |
| ATOM | 3792 | CB   | GLN C | 107 | 32.193 | 5.323 | 43.694 | 1.00 | 67.88 | C |
| ATOM | 3793 | CG   | GLN C | 107 | 30.787 | 5.704 | 44.065 | 1.00 | 70.88 | C |
| ATOM | 3794 | CD   | GLN C | 107 | 30.517 | 7.164 | 43.656 | 1.00 | 74.97 | C |
| ATOM | 3795 | OE1  | GLN C | 107 | 31.366 | 8.036 | 43.877 | 1.00 | 76.74 | O |
| ATOM | 3796 | NE2  | GLN C | 107 | 29.363 | 7.423 | 43.010 | 1.00 | 74.96 | N |
| ATOM | 3797 | C    | GLN C | 107 | 34.007 | 6.595 | 42.641 | 1.00 | 68.31 | C |
| ATOM | 3798 | O    | GLN C | 107 | 34.152 | 7.763 | 43.025 | 1.00 | 68.16 | O |
| ATOM | 3799 | N    | GLY C | 108 | 34.986 | 5.738 | 42.365 | 1.00 | 68.68 | N |
| ATOM | 3800 | CA   | GLY C | 108 | 36.241 | 5.795 | 43.071 | 1.00 | 70.32 | C |
| ATOM | 3801 | C    | GLY C | 108 | 37.159 | 6.791 | 42.447 | 1.00 | 70.91 | C |
| ATOM | 3802 | O    | GLY C | 108 | 36.739 | 7.847 | 42.041 | 1.00 | 71.41 | O |
| ATOM | 3803 | N    | PRO C | 109 | 38.435 | 6.448 | 42.376 | 1.00 | 71.38 | N |
| ATOM | 3804 | CA   | PRO C | 109 | 39.366 | 7.224 | 41.593 | 1.00 | 71.30 | C |
| ATOM | 3805 | CB   | PRO C | 109 | 40.675 | 6.985 | 42.327 | 1.00 | 71.48 | C |
| ATOM | 3806 | CG   | PRO C | 109 | 40.553 | 5.521 | 42.801 | 1.00 | 71.54 | C |
| ATOM | 3807 | CD   | PRO C | 109 | 39.064 | 5.283 | 43.041 | 1.00 | 71.54 | C |
| ATOM | 3808 | C    | PRO C | 109 | 39.428 | 6.616 | 40.192 | 1.00 | 71.67 | C |
| ATOM | 3809 | O    | PRO C | 109 | 39.608 | 5.401 | 40.044 | 1.00 | 72.36 | O |
| ATOM | 3810 | N    | LEU C | 110 | 39.273 | 7.435 | 39.164 | 1.00 | 71.44 | N |

TABLE 11-continued

| | | | | | | | | | | |
|---|---|---|---|---|---|---|---|---|---|---|
| ATOM | 3811 | CA | LEU C | 110 | 39.367 | 6.957 | 37.786 | 1.00 | 71.16 | C |
| ATOM | 3812 | CB | LEU C | 110 | 38.278 | 7.610 | 36.984 | 1.00 | 70.57 | C |
| ATOM | 3813 | CG | LEU C | 110 | 36.962 | 7.742 | 37.746 | 1.00 | 69.24 | C |
| ATOM | 3814 | CD1 | LEU C | 110 | 35.924 | 8.200 | 36.768 | 1.00 | 66.33 | C |
| ATOM | 3815 | CD2 | LEU C | 110 | 36.525 | 6.446 | 38.464 | 1.00 | 69.61 | C |
| ATOM | 3816 | C | LEU C | 110 | 40.746 | 7.276 | 37.184 | 1.00 | 72.11 | C |
| ATOM | 3817 | O | LEU C | 110 | 41.407 | 8.230 | 37.617 | 1.00 | 73.89 | O |
| ATOM | 3818 | N | GLY C | 111 | 41.200 | 6.525 | 36.182 | 1.00 | 71.40 | N |
| ATOM | 3819 | CA | GLY C | 111 | 42.634 | 6.603 | 35.803 | 1.00 | 70.36 | C |
| ATOM | 3820 | C | GLY C | 111 | 43.135 | 8.008 | 35.442 | 1.00 | 69.70 | C |
| ATOM | 3821 | O | GLY C | 111 | 44.350 | 8.316 | 35.541 | 1.00 | 71.10 | O |
| ATOM | 3822 | N | THR C | 112 | 42.184 | 8.838 | 35.011 | 1.00 | 67.54 | N |
| ATOM | 3823 | CA | THR C | 112 | 42.359 | 10.227 | 34.515 | 1.00 | 64.72 | C |
| ATOM | 3824 | CB | THR C | 112 | 42.902 | 11.180 | 35.606 | 1.00 | 60.42 | C |
| ATOM | 3825 | OG1 | THR C | 112 | 43.638 | 12.255 | 34.990 | 1.00 | 52.98 | O |
| ATOM | 3826 | CG2 | THR C | 112 | 43.814 | 10.459 | 36.588 | 1.00 | 57.22 | C |
| ATOM | 3827 | C | THR C | 112 | 43.002 | 10.546 | 33.119 | 1.00 | 67.58 | C |
| ATOM | 3828 | O | THR C | 112 | 44.123 | 11.091 | 33.077 | 1.00 | 68.92 | O |
| ATOM | 3829 | N | SER C | 113 | 42.270 | 10.271 | 32.010 | 1.00 | 69.02 | N |
| ATOM | 3830 | CA | SER C | 113 | 42.717 | 10.535 | 30.605 | 1.00 | 70.72 | C |
| ATOM | 3831 | CB | SER C | 113 | 41.625 | 11.315 | 29.837 | 1.00 | 71.14 | C |
| ATOM | 3832 | OG | SER C | 113 | 40.533 | 10.463 | 29.460 | 1.00 | 68.29 | O |
| ATOM | 3833 | C | SER C | 113 | 44.147 | 11.127 | 30.395 | 1.00 | 72.20 | C |
| ATOM | 3834 | O | SER C | 113 | 44.402 | 12.285 | 30.747 | 1.00 | 72.69 | O |
| ATOM | 3835 | N | PHE C | 114 | 45.048 | 10.312 | 29.808 | 1.00 | 73.66 | N |
| ATOM | 3836 | CA | PHE C | 114 | 46.531 | 10.455 | 29.881 | 1.00 | 75.31 | C |
| ATOM | 3837 | CB | PHE C | 114 | 47.046 | 9.634 | 31.118 | 1.00 | 75.99 | C |
| ATOM | 3838 | CG | PHE C | 114 | 48.491 | 9.925 | 31.612 | 1.00 | 77.50 | C |
| ATOM | 3839 | CD1 | PHE C | 114 | 49.615 | 9.764 | 30.789 | 1.00 | 79.29 | C |
| ATOM | 3840 | CE1 | PHE C | 114 | 50.059 | 9.992 | 31.294 | 1.00 | 79.68 | C |
| ATOM | 3841 | CZ | PHE C | 114 | 51.166 | 10.336 | 32.646 | 1.00 | 79.73 | C |
| ATOM | 3842 | CE2 | PHE C | 114 | 50.048 | 10.452 | 33.499 | 1.00 | 78.82 | C |
| ATOM | 3843 | CD2 | PHE C | 114 | 48.714 | 10.224 | 32.975 | 1.00 | 79.21 | C |
| ATOM | 3844 | C | PHE C | 114 | 46.994 | 9.816 | 28.567 | 1.00 | 75.64 | C |
| ATOM | 3845 | O | PHE C | 114 | 46.277 | 9.006 | 27.983 | 1.00 | 75.61 | O |
| ATOM | 3846 | N | LYS C | 115 | 46.173 | 10.194 | 28.084 | 1.00 | 76.50 | N |
| ATOM | 3847 | CA | LYS C | 115 | 48.884 | 9.492 | 26.997 | 1.00 | 76.75 | C |
| ATOM | 3848 | CB | LYS C | 115 | 48.325 | 9.828 | 25.614 | 1.00 | 76.52 | C |
| ATOM | 3849 | CG | LYS C | 115 | 47.398 | 8.789 | 25.070 | 1.00 | 77.93 | C |
| ATOM | 3850 | CD | LYS C | 115 | 47.149 | 9.078 | 23.624 | 1.00 | 81.30 | C |
| ATOM | 3851 | CE | LYS C | 115 | 47.675 | 7.948 | 22.776 | 1.00 | 83.69 | C |
| ATOM | 3852 | NZ | LYS C | 115 | 48.696 | 8.498 | 21.834 | 1.00 | 84.76 | N |
| ATOM | 3853 | C | LYS C | 115 | 50.294 | 9.992 | 27.110 | 1.00 | 76.44 | C |
| ATOM | 3854 | O | LYS C | 115 | 50.740 | 10.754 | 26.278 | 1.00 | 77.13 | O |
| ATOM | 3855 | N | GLY C | 116 | 50.975 | 9.572 | 28.167 | 1.00 | 76.50 | N |
| ATOM | 3856 | CA | GLY C | 116 | 52.252 | 10.175 | 28.587 | 1.00 | 75.56 | C |
| ATOM | 3857 | C | GLY C | 116 | 53.353 | 9.145 | 28.772 | 1.00 | 74.62 | C |
| ATOM | 3858 | O | GLY C | 116 | 53.466 | 8.189 | 27.977 | 1.00 | 74.69 | O |
| ATOM | 3859 | N | LYS C | 117 | 54.176 | 9.319 | 29.806 | 1.00 | 73.15 | N |
| ATOM | 3860 | CA | LYS C | 117 | 55.423 | 8.567 | 29.780 | 1.00 | 71.10 | C |
| ATOM | 3861 | CB | LYS C | 117 | 56.478 | 9.144 | 30.733 | 1.00 | 71.95 | C |
| ATOM | 3862 | CG | LYS C | 117 | 57.909 | 9.040 | 30.143 | 1.00 | 72.74 | C |
| ATOM | 3863 | CD | LYS C | 117 | 58.992 | 8.848 | 31.206 | 1.00 | 75.34 | C |
| ATOM | 3864 | CE | LYS C | 117 | 59.295 | 10.144 | 31.985 | 1.00 | 77.68 | C |
| ATOM | 3865 | NZ | LYS C | 117 | 60.769 | 10.272 | 32.326 | 1.00 | 79.77 | N |
| ATOM | 3866 | C | LYS C | 117 | 55.192 | 7.061 | 29.966 | 1.00 | 69.00 | C |
| ATOM | 3867 | O | LYS C | 117 | 55.496 | 6.253 | 29.064 | 1.00 | 68.15 | O |
| ATOM | 3868 | N | TYR C | 118 | 54.609 | 6.681 | 31.092 | 1.00 | 66.25 | N |
| ATOM | 3869 | CA | TYR C | 118 | 54.375 | 5.260 | 31.300 | 1.00 | 64.60 | C |
| ATOM | 3870 | CB | TYR C | 118 | 54.825 | 4.872 | 32.686 | 1.00 | 63.86 | C |
| ATOM | 3871 | CG | TYR C | 118 | 56.153 | 5.465 | 33.088 | 1.00 | 61.09 | C |
| ATOM | 3872 | CD1 | TYR C | 118 | 57.332 | 4.805 | 32.827 | 1.00 | 60.77 | C |
| ATOM | 3873 | CE1 | TYR C | 118 | 58.552 | 5.339 | 33.229 | 1.00 | 62.59 | C |
| ATOM | 3874 | CZ | TYR C | 118 | 58.569 | 6.544 | 33.903 | 1.00 | 61.30 | C |
| ATOM | 3875 | OH | TYR C | 118 | 59.760 | 7.079 | 34.302 | 1.00 | 63.79 | O |
| ATOM | 3876 | CE2 | TYR C | 118 | 57.407 | 7.210 | 34.171 | 1.00 | 58.58 | C |
| ATOM | 3877 | CD2 | TYR C | 118 | 56.217 | 6.674 | 33.760 | 1.00 | 59.77 | C |
| ATOM | 3878 | C | TYR C | 118 | 52.952 | 4.782 | 30.990 | 1.00 | 63.95 | C |
| ATOM | 3879 | O | TYR C | 118 | 52.330 | 4.089 | 31.747 | 1.00 | 63.02 | O |
| ATOM | 3880 | N | GLY C | 119 | 52.455 | 5.180 | 29.832 | 1.00 | 64.94 | N |
| ATOM | 3381 | CA | GLY C | 119 | 51.171 | 4.712 | 29.318 | 1.00 | 64.90 | C |
| ATOM | 3882 | C | GLY C | 119 | 49.999 | 5.659 | 29.442 | 1.00 | 64.79 | C |
| ATOM | 3883 | O | GLY C | 119 | 50.143 | 6.853 | 29.765 | 1.00 | 64.88 | O |
| ATOM | 3884 | N | CYS C | 120 | 48.819 | 5.086 | 29.226 | 1.00 | 64.30 | N |
| ATOM | 3885 | CA | CYS C | 120 | 47.597 | 5.862 | 28.997 | 1.00 | 63.51 | C |
| ATOM | 3886 | CB | CYS C | 120 | 47.295 | 5.787 | 27.520 | 1.00 | 64.05 | C |
| ATOM | 3887 | SG | CYS C | 120 | 47.729 | 4.172 | 27.035 | 1.00 | 66.89 | S |
| ATOM | 3888 | C | CYS C | 120 | 46.352 | 5.384 | 29.714 | 1.00 | 61.75 | C |
| ATOM | 3889 | O | CYS C | 120 | 46.345 | 4.343 | 30.358 | 1.00 | 62.02 | O |
| ATOM | 3890 | N | VAL C | 121 | 45.293 | 6.164 | 29.566 | 1.00 | 59.81 | N |

TABLE 11-continued

| ATOM | 3891 | CA | VAL C | 121 | 43.984 | 5.830 | 30.097 | 1.00 | 58.13 | C |
|---|---|---|---|---|---|---|---|---|---|---|
| ATOM | 3892 | CB | VAL C | 121 | 43.655 | 6.693 | 31.313 | 1.00 | 58.51 | C |
| ATOM | 3893 | CG1 | VAL C | 121 | 42.387 | 6.211 | 31.917 | 1.00 | 58.28 | C |
| ATOM | 3894 | CG2 | VAL C | 121 | 44.790 | 6.678 | 32.341 | 1.00 | 58.83 | C |
| ATOM | 3895 | C | VAL C | 121 | 42.985 | 6.239 | 29.051 | 1.00 | 56.78 | C |
| ATOM | 3896 | O | VAL C | 121 | 42.912 | 7.440 | 28.748 | 1.00 | 57.99 | O |
| ATOM | 3897 | N | ASP C | 122 | 42.211 | 5.308 | 28.494 | 1.00 | 54.23 | N |
| ATOM | 3898 | CA | ASP C | 122 | 41.167 | 5.688 | 27.537 | 1.00 | 52.37 | C |
| ATOM | 3899 | CB | ASP C | 122 | 41.447 | 5.125 | 26.150 | 1.00 | 53.50 | C |
| ATOM | 3900 | CG | ASP C | 122 | 42.889 | 4.853 | 25.951 | 1.00 | 58.27 | C |
| ATOM | 3901 | OD1 | ASP C | 122 | 43.371 | 3.783 | 26.443 | 1.00 | 62.91 | O |
| ATOM | 3902 | OD2 | ASP C | 122 | 43.566 | 5.740 | 25.381 | 1.00 | 61.37 | O |
| ATOM | 3903 | C | ASP C | 122 | 39.800 | 5.224 | 27.980 | 1.00 | 50.57 | C |
| ATOM | 3904 | O | ASP C | 122 | 39.644 | 4.102 | 28.509 | 1.00 | 50.09 | O |
| ATOM | 3905 | N | TYR C | 123 | 38.822 | 6.110 | 27.774 | 1.00 | 47.73 | N |
| ATOM | 3906 | CA | TYR C | 123 | 37.434 | 5.793 | 27.905 | 1.00 | 45.25 | C |
| ATOM | 3907 | CB | TYR C | 123 | 36.796 | 6.683 | 28.947 | 1.00 | 45.06 | C |
| ATOM | 3908 | CG | TYR C | 123 | 37.291 | 6.549 | 30.379 | 1.00 | 45.34 | C |
| ATOM | 3909 | CD1 | TYR C | 123 | 36.482 | 5.987 | 31.346 | 1.00 | 46.89 | O |
| ATOM | 3910 | CE1 | TYR C | 123 | 36.885 | 5.885 | 32.698 | 1.00 | 47.45 | C |
| ATOM | 3911 | CZ | TYR C | 123 | 36.098 | 6.334 | 33.061 | 1.00 | 48.35 | C |
| ATOM | 3912 | OH | TYR C | 123 | 38.441 | 6.176 | 34.416 | 1.00 | 49.81 | O |
| ATOM | 3913 | CE2 | TYR C | 123 | 38.955 | 6.939 | 32.133 | 1.00 | 46.77 | C |
| ATOM | 3914 | CD2 | TYR C | 123 | 38.541 | 7.040 | 30.792 | 1.00 | 46.41 | C |
| ATOM | 3915 | C | TYR C | 123 | 36.844 | 6.108 | 26.539 | 1.00 | 44.64 | C |
| ATOM | 3916 | O | TYR C | 123 | 37.243 | 7.087 | 25.875 | 1.00 | 42.85 | O |
| ATOM | 3917 | N | TRP C | 124 | 35.899 | 5.263 | 26.127 | 1.00 | 43.75 | N |
| ATOM | 3918 | CA | TRP C | 124 | 35.227 | 5.371 | 24.843 | 1.00 | 43.34 | C |
| ATOM | 3919 | CB | TRP C | 124 | 36.105 | 4.814 | 23.714 | 1.00 | 43.22 | C |
| ATOM | 3920 | CG | TRP C | 124 | 36.821 | 3.513 | 24.072 | 1.00 | 48.58 | C |
| ATOM | 3921 | CD1 | TRP C | 124 | 38.099 | 3.412 | 24.467 | 1.00 | 50.75 | C |
| ATOM | 3922 | NE1 | TRP C | 124 | 38.422 | 2.117 | 24.747 | 1.00 | 50.01 | N |
| ATOM | 3923 | CE2 | TRP C | 124 | 37.353 | 1.316 | 24.527 | 1.00 | 49.87 | C |
| ATOM | 3924 | CD2 | TRP C | 124 | 36.297 | 2.154 | 24.109 | 1.00 | 51.73 | C |
| ATOM | 3925 | CE3 | TRP C | 124 | 30.051 | 1.572 | 23.833 | 1.00 | 53.92 | C |
| ATOM | 3926 | CZ3 | TRP C | 124 | 34.929 | 0.153 | 23.964 | 1.00 | 55.30 | C |
| ATOM | 3927 | CH2 | TRP C | 124 | 36.036 | −0.641 | 24.359 | 1.00 | 52.97 | C |
| ATOM | 3928 | CZ2 | TRP C | 124 | 37.235 | −0.070 | 24.661 | 1.00 | 51.53 | C |
| ATOM | 3929 | C | TRP C | 124 | 33.930 | 4.562 | 24.909 | 1.00 | 42.58 | C |
| ATOM | 3930 | O | TRP C | 124 | 33.703 | 3.798 | 25.815 | 1.00 | 41.67 | O |
| ATOM | 3931 | N | VAL C | 125 | 33.086 | 4.722 | 23.916 | 1.00 | 43.35 | N |
| ATOM | 3932 | CA | VAL C | 125 | 31.884 | 3.923 | 23.814 | 1.00 | 44.35 | C |
| ATOM | 3933 | CB | VAL C | 125 | 30.632 | 4.774 | 23.970 | 1.00 | 43.69 | C |
| ATOM | 3934 | CG1 | VAL C | 125 | 29.456 | 4.054 | 23.491 | 1.00 | 40.89 | C |
| ATOM | 3935 | CG2 | VAL C | 125 | 30.491 | 5.256 | 25.417 | 1.00 | 41.24 | C |
| ATOM | 3936 | C | VAL C | 125 | 31.914 | 3.321 | 22.431 | 1.00 | 46.68 | C |
| ATOM | 3937 | O | VAL C | 125 | 32.238 | 4.012 | 21.456 | 1.00 | 46.14 | O |
| ATOM | 3938 | N | LYS C | 126 | 31.651 | 2.014 | 22.398 | 1.00 | 49.76 | N |
| ATOM | 3939 | CA | LYS C | 126 | 31.643 | 1.209 | 21.188 | 1.00 | 53.17 | C |
| ATOM | 3940 | CB | LYS C | 126 | 32.431 | −0.091 | 21.407 | 1.00 | 53.89 | C |
| ATOM | 3941 | CG | LYS C | 126 | 33.256 | −0.601 | 20.202 | 1.00 | 55.39 | C |
| ATOM | 3942 | CD | LYS C | 126 | 34.694 | −0.041 | 20.177 | 1.00 | 59.62 | C |
| ATOM | 3943 | CE | LYS C | 126 | 35.743 | −1.005 | 20.762 | 1.00 | 62.42 | C |
| ATOM | 3944 | NZ | LYS C | 126 | 36.447 | −1.846 | 19.714 | 1.00 | 65.94 | N |
| ATOM | 3945 | C | LYS C | 126 | 30.189 | 0.846 | 20.908 | 1.00 | 54.77 | C |
| ATOM | 3946 | O | LYS C | 126 | 29.438 | 0.418 | 21.641 | 1.00 | 54.35 | O |
| ATOM | 3947 | N | ALA C | 127 | 29.778 | 1.049 | 19.645 | 1.00 | 55.97 | N |
| ATOM | 3948 | CA | ALA C | 127 | 28.443 | 0.693 | 19.176 | 1.00 | 57.69 | C |
| ATOM | 3949 | CB | ALA C | 127 | 17.722 | 1.892 | 16.679 | 1.00 | 56.66 | C |
| ATOM | 3950 | C | ALA C | 127 | 28.531 | −0.373 | 18.086 | 1.00 | 59.47 | C |
| ATOM | 3951 | O | ALA C | 127 | 29.095 | −0.150 | 16.999 | 1.00 | 59.70 | O |
| ATOM | 3952 | N | PHE C | 128 | 28.005 | −1.546 | 18.398 | 1.00 | 61.21 | N |
| ATOM | 3953 | CA | PHE C | 128 | 27.931 | −2.612 | 17.427 | 1.00 | 63.27 | C |
| ATOM | 3954 | CB | PHE C | 128 | 27.991 | −3.917 | 18.168 | 1.00 | 64.28 | C |
| ATOM | 3955 | CG | PHE C | 128 | 29.083 | −3.984 | 19.170 | 1.00 | 65.50 | C |
| ATOM | 3956 | CD1 | PHE C | 128 | 30.275 | −4.619 | 18.860 | 1.00 | 65.96 | C |
| ATOM | 3957 | CE1 | PHE C | 128 | 31.279 | −4.715 | 19.792 | 1.00 | 67.73 | C |
| ATOM | 3958 | CZ | PHE C | 128 | 31.104 | −4.170 | 21.048 | 1.00 | 67.08 | C |
| ATOM | 3959 | CE2 | PHE C | 128 | 29.914 | −3.526 | 21.360 | 1.00 | 67.14 | C |
| ATOM | 3960 | CD2 | PHE C | 128 | 28.915 | −3.433 | 20.418 | 1.00 | 65.33 | C |
| ATOM | 3961 | C | PHE C | 128 | 26.593 | −2.608 | 16.777 | 1.00 | 64.20 | C |
| ATOM | 3962 | O | PHE C | 128 | 25.593 | −2.509 | 17.476 | 1.00 | 65.10 | O |
| ATOM | 3963 | N | LEU C | 129 | 26.540 | −2.751 | 15.458 | 1.00 | 65.52 | N |
| ATOM | 3964 | CA | LEU C | 129 | 25.250 | −2.988 | 14.768 | 1.00 | 66.51 | C |
| ATOM | 3965 | CB | LEU C | 129 | 25.044 | −1.893 | 13.734 | 1.00 | 85.69 | C |
| ATOM | 3966 | CG | LEU C | 129 | 24.264 | −2.266 | 12.492 | 1.00 | 66.65 | C |
| ATOM | 3967 | CD1 | LEU C | 129 | 22.818 | −2.208 | 12.866 | 1.00 | 67.48 | C |
| ATOM | 3968 | CD2 | LEU C | 129 | 24.569 | −1.273 | 11.363 | 1.00 | 68.54 | C |
| ATOM | 3969 | C | LEU C | 129 | 25.099 | −4.445 | 14.158 | 1.00 | 67.56 | C |
| ATOM | 3970 | O | LEU C | 129 | 26.091 | −5.127 | 13.847 | 1.00 | 67.07 | O |

TABLE 11-continued

| ATOM | 3971 | N | ASP C | 130 | 23.868 | −4.934 | 14.024 | 1.00 | 68.88 | N |
|---|---|---|---|---|---|---|---|---|---|---|
| ATOM | 3972 | CA | ASP C | 130 | 23.634 | −6.274 | 13.417 | 1.00 | 70.03 | C |
| ATOM | 3973 | CB | ASP C | 130 | 23.443 | −7.347 | 14.519 | 1.00 | 69.57 | C |
| ATOM | 3974 | CG | ASP C | 130 | 24.411 | −7.142 | 15.693 | 1.00 | 71.20 | C |
| ATOM | 3975 | OD1 | ASP C | 130 | 24.281 | −7.768 | 16.789 | 1.00 | 71.74 | O |
| ATOM | 3976 | OD2 | ASP C | 130 | 25.324 | −6.313 | 15.516 | 1.00 | 70.44 | O |
| ATOM | 3977 | C | ASP C | 130 | 22.516 | −6.296 | 12.326 | 1.00 | 70.10 | C |
| ATOM | 3978 | O | ASP C | 130 | 21.353 | −6.566 | 12.640 | 1.00 | 70.47 | O |
| ATOM | 3979 | N | ARG C | 131 | 22.896 | −5.968 | 11.075 | 1.00 | 70.10 | N |
| ATOM | 3980 | CA | ARG C | 131 | 22.058 | −6.053 | 9.849 | 1.00 | 69.96 | C |
| ATOM | 3981 | CB | ARG C | 131 | 22.899 | −5.637 | 8.611 | 1.00 | 70.35 | C |
| ATOM | 3982 | CG | ARG C | 131 | 22.887 | −4.151 | 8.160 | 1.00 | 70.91 | C |
| ATOM | 3983 | CD | ARG C | 131 | 23.320 | −4.036 | 6.646 | 1.00 | 75.14 | C |
| ATOM | 3984 | NE | ARG C | 131 | 23.206 | −2.666 | 6.057 | 1.00 | 76.51 | N |
| ATOM | 3985 | CZ | ARG C | 131 | 22.624 | −2.340 | 4.576 | 1.00 | 77.84 | C |
| ATOM | 3986 | NH1 | ARG C | 131 | 22.091 | −3.278 | 4.094 | 1.00 | 75.88 | N |
| ATOM | 3987 | NH2 | ARG C | 131 | 22.576 | −1.059 | 4.461 | 1.00 | 76.34 | N |
| ATOM | 3988 | C | ARG C | 131 | 21.452 | −7.501 | 9.612 | 1.00 | 69.96 | C |
| ATOM | 3989 | O | ARG C | 131 | 21.644 | −8.432 | 10.478 | 1.00 | 70.20 | O |
| ATOM | 3990 | N | PRO C | 132 | 20.070 | −7.703 | 8.473 | 1.00 | 08.56 | N |
| ATOM | 3991 | CA | PRO C | 132 | 20.060 | −8.987 | 7.983 | 1.00 | 68.38 | C |
| ATOM | 3992 | CB | PRO C | 132 | 20.206 | −8.869 | 6.449 | 1.00 | 60.50 | C |
| ATOM | 3993 | CG | PRO C | 132 | 19.905 | −7.349 | 6.175 | 1.00 | 60.50 | C |
| ATOM | 3994 | CD | PRO C | 132 | 20.247 | −6.604 | 7.571 | 1.00 | 60.50 | C |
| ATOM | 3995 | C | PRO C | 132 | 20.706 | −10.294 | 8.443 | 1.00 | 68.79 | C |
| ATOM | 3996 | O | PRO C | 132 | 20.269 | −10.910 | 9.453 | 1.00 | 68.93 | O |
| ATOM | 3997 | N | SER C | 133 | 21.736 | −10.682 | 7.689 | 1.00 | 68.93 | N |
| ATOM | 3998 | CA | SER C | 133 | 22.491 | −11.885 | 7.930 | 1.00 | 69.27 | C |
| ATOM | 3999 | CB | SER C | 133 | 22.086 | −12.926 | 6.886 | 1.00 | 69.75 | C |
| ATOM | 4000 | OG | SER C | 133 | 20.949 | −13.672 | 7.313 | 1.00 | 70.68 | O |
| ATOM | 4001 | C | SER C | 133 | 23.974 | −11.587 | 7.821 | 1.00 | 68.93 | C |
| ATOM | 4002 | O | SER C | 133 | 24.694 | −12.254 | 7.080 | 1.00 | 69.19 | O |
| ATOM | 4003 | N | GLN C | 134 | 24.427 | −10.605 | 8.592 | 1.00 | 68.61 | N |
| ATOM | 4004 | CA | GLN C | 134 | 25.708 | −9.927 | 8.362 | 1.00 | 68.28 | C |
| ATOM | 4005 | CB | GLN C | 134 | 25.411 | −8.487 | 7.960 | 1.00 | 68.20 | C |
| ATOM | 4006 | CG | GLN C | 134 | 24.464 | −8.376 | 6.801 | 1.00 | 67.75 | C |
| ATOM | 4007 | CD | GLN C | 134 | 25.207 | −8.241 | 5.500 | 1.00 | 67.32 | C |
| ATOM | 4008 | OE1 | GLN C | 134 | 24.859 | −8.877 | 4.509 | 1.00 | 62.72 | O |
| ATOM | 4009 | NE2 | GLN C | 134 | 26.267 | −7.410 | 5.503 | 1.00 | 68.89 | N |
| ATOM | 4010 | C | GLN C | 134 | 26.632 | −9.918 | 9.592 | 1.00 | 68.24 | C |
| ATOM | 4011 | O | GLN C | 134 | 26.162 | −10.072 | 10.735 | 1.00 | 68.54 | O |
| ATOM | 4012 | N | PRO C | 135 | 27.946 | −9.670 | 0.388 | 1.00 | 68.07 | N |
| ATOM | 4013 | CA | PRO C | 135 | 28.695 | −9.675 | 10.634 | 1.00 | 67.71 | C |
| ATOM | 4014 | CB | PRO C | 135 | 30.148 | −9.898 | 10.201 | 1.00 | 67.67 | C |
| ATOM | 4015 | CG | PRO C | 135 | 30.197 | −9.586 | 8.718 | 1.00 | 67.65 | C |
| ATOM | 4016 | CD | PRO C | 135 | 28.784 | −9.327 | 8.225 | 1.00 | 68.11 | C |
| ATOM | 4017 | C | PRO C | 135 | 28.477 | −8.286 | 11.261 | 1.00 | 67.81 | C |
| ATOM | 4018 | O | PRO C | 135 | 27.882 | −7.351 | 10.616 | 1.00 | 67.71 | O |
| ATOM | 4019 | N | THR C | 136 | 28.907 | −8.155 | 12.511 | 1.00 | 66.41 | N |
| ATOM | 4020 | CA | THR C | 136 | 28.459 | −7.036 | 13.307 | 1.00 | 65.05 | C |
| ATOM | 4021 | CB | THR C | 136 | 28.327 | −7.407 | 14.852 | 1.00 | 65.71 | C |
| ATOM | 4022 | OG1 | THR C | 136 | 29.624 | −7.397 | 15.491 | 1.00 | 66.29 | O |
| ATOM | 4023 | CG2 | THR C | 136 | 27.558 | −8.797 | 15.093 | 1.00 | 64.86 | C |
| ATOM | 4024 | C | THR C | 136 | 29.370 | −5.860 | 13.030 | 1.00 | 63.93 | C |
| ATOM | 4025 | O | THR C | 136 | 30.558 | −5.896 | 13.386 | 1.00 | 63.74 | O |
| ATOM | 4026 | N | GLN C | 137 | 28.842 | −4.837 | 12.371 | 1.00 | 62.53 | N |
| ATOM | 4027 | CA | GLN C | 137 | 29.570 | −3.590 | 12.118 | 1.00 | 61.48 | C |
| ATOM | 4028 | CB | GLN C | 137 | 28.737 | −2.713 | 11.197 | 1.00 | 60.93 | C |
| ATOM | 4029 | CG | GLN C | 137 | 29.361 | −1.377 | 10.879 | 1.00 | 59.58 | C |
| ATOM | 4030 | CD | GLN C | 137 | 28.591 | −0.727 | 9.824 | 1.00 | 58.66 | C |
| ATOM | 4031 | OE1 | GLN C | 137 | 27.601 | −1.290 | 9.384 | 1.00 | 63.24 | O |
| ATOM | 4032 | NE2 | GLN C | 137 | 29.001 | 0.455 | 9.387 | 1.00 | 57.36 | N |
| ATOM | 4033 | C | GLN C | 137 | 29.956 | −2.802 | 13.406 | 1.00 | 61.04 | C |
| ATOM | 4034 | O | GLN C | 137 | 29.366 | −3.042 | 14.473 | 1.00 | 61.24 | O |
| ATOM | 4035 | N | GLU C | 138 | 30.912 | −1.860 | 13.291 | 1.00 | 59.93 | N |
| ATOM | 4036 | CA | GLU C | 137 | 31.431 | −1.091 | 14.447 | 1.00 | 59.53 | C |
| ATOM | 4037 | CB | GLU C | 138 | 32.791 | −1.604 | 14.850 | 1.00 | 60.07 | C |
| ATOM | 4038 | CG | GLU C | 138 | 32.738 | −2.660 | 15.916 | 1.00 | 63.64 | C |
| ATOM | 4039 | CD | GLU C | 138 | 34.104 | −2.891 | 16.509 | 1.00 | 67.53 | C |
| ATOM | 4040 | OE1 | GLU C | 138 | 34.507 | −4.072 | 16.571 | 1.00 | 70.10 | O |
| ATOM | 4041 | OE2 | GLU C | 138 | 34.774 | −1.894 | 16.685 | 1.00 | 68.42 | O |
| ATOM | 4042 | C | GLU C | 138 | 31.592 | 0.414 | 14.290 | 1.00 | 58.31 | C |
| ATOM | 4043 | O | GLU C | 138 | 31.828 | 0.929 | 13.203 | 1.00 | 58.95 | O |
| ATOM | 4044 | N | THR C | 139 | 31.448 | 1.113 | 15.407 | 1.00 | 56.52 | N |
| ATOM | 4045 | CA | THR C | 139 | 31.836 | 2.512 | 15.541 | 1.00 | 54.19 | C |
| ATOM | 4046 | CB | THR C | 139 | 30.703 | 3.492 | 15.122 | 1.00 | 54.27 | C |
| ATOM | 4047 | OG1 | THR C | 139 | 31.190 | 4.825 | 15.161 | 1.00 | 54.78 | O |
| ATOM | 4048 | CC2 | THR C | 139 | 29.540 | 3.448 | 16.064 | 1.00 | 53.03 | C |
| ATOM | 4049 | C | THR C | 139 | 32.237 | 2.701 | 17.006 | 1.00 | 53.00 | C |
| ATOM | 4050 | O | THR C | 139 | 31.611 | 2.133 | 17.913 | 1.00 | 54.06 | O |

TABLE 11-continued

| | | | | | | | | | | |
|---|---|---|---|---|---|---|---|---|---|---|
| ATOM | 4051 | N | LYS C | 140 | 33.288 | 3.473 | 17.240 | 1.00 | 51.10 | N |
| ATOM | 4052 | CA | LYS C | 140 | 33.846 | 3.712 | 18.588 | 1.00 | 49.42 | C |
| ATOM | 4053 | CB | LYS C | 140 | 35.160 | 2.956 | 18.711 | 1.00 | 48.81 | C |
| ATOM | 4054 | CG | LYS C | 140 | 36.156 | 3.617 | 19.553 | 1.00 | 50.75 | C |
| ATOM | 4055 | CD | LYS C | 140 | 37.177 | 2.617 | 20.081 | 1.00 | 54.82 | C |
| ATOM | 4056 | CE | LYS C | 140 | 38.509 | 3.298 | 20.358 | 1.00 | 59.13 | C |
| ATOM | 4057 | NZ | LYS C | 140 | 39.615 | 2.320 | 20.373 | 1.00 | 65.33 | N |
| ATOM | 4058 | C | LYS C | 140 | 34.059 | 5.232 | 18.818 | 1.00 | 47.50 | C |
| ATOM | 4059 | O | LYS C | 140 | 34.537 | 5.807 | 17.932 | 1.00 | 48.36 | O |
| ATOM | 4060 | N | LYS C | 141 | 33.706 | 5.807 | 19.959 | 1.00 | 44.75 | N |
| ATOM | 4061 | CA | LYS C | 141 | 34.014 | 7.240 | 20.110 | 1.00 | 42.08 | C |
| ATOM | 4062 | CB | LYS C | 141 | 32.796 | 8.059 | 19.765 | 1.00 | 41.85 | C |
| ATOM | 4063 | CG | LYS C | 141 | 33.119 | 9.448 | 19.566 | 1.00 | 41.48 | C |
| ATOM | 4064 | CD | LYS C | 141 | 31.910 | 10.303 | 19.412 | 1.00 | 40.54 | C |
| ATOM | 4065 | CE | LYS C | 141 | 31.520 | 10.322 | 17.942 | 1.00 | 42.71 | C |
| ATOM | 4066 | NZ | LYS C | 141 | 30.650 | 11.481 | 17.556 | 1.00 | 42.29 | N |
| ATOM | 4067 | C | LYS C | 141 | 34.529 | 7.588 | 21.511 | 1.00 | 40.84 | C |
| ATOM | 4068 | O | LYS C | 141 | 33.963 | 7.142 | 22.511 | 1.00 | 40.35 | O |
| ATOM | 4069 | N | ASN C | 142 | 35.626 | 8.313 | 21.599 | 1.00 | 39.32 | N |
| ATOM | 4070 | CA | ASN C | 142 | 36.209 | 8.557 | 22.912 | 1.00 | 39.51 | C |
| ATOM | 4071 | CB | ASN C | 142 | 37.653 | 8.993 | 22.833 | 1.00 | 38.60 | C |
| ATOM | 4072 | CG | ASN C | 142 | 38.534 | 7.945 | 22.234 | 1.00 | 42.96 | C |
| ATOM | 4073 | OD1 | ASN C | 142 | 38.679 | 6.840 | 22.768 | 1.00 | 46.73 | O |
| ATOM | 4074 | ND2 | ASN C | 142 | 39.134 | 8.277 | 21.092 | 1.00 | 49.68 | N |
| ATOM | 4075 | C | ASN C | 142 | 35.438 | 9.592 | 23.686 | 1.00 | 39.04 | C |
| ATOM | 4076 | O | ASN C | 142 | 34.738 | 10.419 | 23.099 | 1.00 | 39.34 | O |
| ATOM | 4077 | N | PHE C | 143 | 35.626 | 9.490 | 25.001 | 1.00 | 37.77 | N |
| ATOM | 4078 | CA | PHE C | 143 | 35.205 | 10.579 | 25.845 | 1.00 | 37.06 | C |
| ATOM | 4079 | CB | PHE C | 143 | 33.802 | 10.430 | 28.418 | 1.00 | 37.22 | C |
| ATOM | 4080 | CG | PHE C | 143 | 33.635 | 9.294 | 27.360 | 1.00 | 34.90 | C |
| ATOM | 4081 | CD | PHE C | 143 | 33.399 | 7.983 | 26.875 | 1.00 | 35.02 | C |
| ATOM | 4082 | CE1 | PHE C | 143 | 33.247 | 6.931 | 27.728 | 1.00 | 29.36 | C |
| ATOM | 4083 | CZ | PHE C | 143 | 33.300 | 7.168 | 29.107 | 1.00 | 30.29 | C |
| ATOM | 4084 | CE2 | PHE C | 143 | 33.546 | 8.448 | 29.600 | 1.00 | 28.80 | C |
| ATOM | 4085 | CD2 | PHE C | 143 | 33.685 | 9.509 | 28.707 | 1.00 | 30.80 | C |
| ATOM | 4086 | C | PHE C | 143 | 36.309 | 10.797 | 26.913 | 1.00 | 38.52 | C |
| ATOM | 4087 | O | PHE C | 143 | 37.150 | 9.915 | 27.167 | 1.00 | 35.89 | O |
| ATOM | 4088 | N | GLU C | 144 | 36.308 | 12.028 | 27.458 | 1.00 | 40.77 | N |
| ATOM | 4089 | CA | GLU C | 144 | 37.310 | 12.540 | 28.404 | 1.00 | 42.24 | C |
| ATOM | 4090 | CB | GLU C | 144 | 37.735 | 13.937 | 28.015 | 1.00 | 41.78 | C |
| ATOM | 4091 | CG | GLU C | 144 | 38.538 | 13.947 | 26.716 | 1.00 | 48.03 | C |
| ATOM | 4092 | CD | GLU C | 144 | 39.820 | 13.058 | 26.748 | 1.00 | 50.83 | C |
| ATOM | 4093 | OE1 | GLU C | 144 | 40.767 | 13.330 | 27.565 | 1.00 | 48.66 | O |
| ATOM | 4094 | OE2 | GLU C | 144 | 39.840 | 12.110 | 25.936 | 1.00 | 51.81 | O |
| ATOM | 4095 | C | GLU C | 144 | 36.838 | 12.514 | 29.836 | 1.00 | 42.99 | C |
| ATOM | 4096 | O | GLU C | 144 | 35.673 | 12.675 | 30.119 | 1.00 | 41.61 | O |
| ATOM | 4097 | N | VAL C | 145 | 37.788 | 12.291 | 30.732 | 1.00 | 46.23 | N |
| ATOM | 4098 | CA | VAL C | 145 | 37.517 | 11.909 | 32.106 | 1.00 | 49.67 | C |
| ATOM | 4099 | CB | VAL C | 145 | 37.538 | 10.377 | 32.257 | 1.00 | 48.91 | C |
| ATOM | 4100 | CG1 | VAL C | 145 | 37.810 | 9.970 | 33.678 | 1.00 | 49.31 | C |
| ATOM | 4101 | CG2 | VAL C | 145 | 36.230 | 9.804 | 31.802 | 1.00 | 48.21 | C |
| ATOM | 4102 | C | VAL C | 145 | 38.626 | 12.542 | 32.907 | 1.00 | 52.61 | C |
| ATOM | 4103 | O | VAL C | 145 | 39.684 | 12.749 | 32.325 | 1.00 | 53.17 | O |
| ATOM | 4104 | N | VAL C | 146 | 38.390 | 12.852 | 34.202 | 1.00 | 56.02 | N |
| ATOM | 4105 | CA | VAL C | 146 | 39.365 | 13.554 | 35.040 | 1.00 | 59.52 | C |
| ATOM | 4106 | CB | VAL C | 146 | 39.262 | 15.069 | 34.888 | 1.00 | 59.14 | C |
| ATOM | 4107 | CG1 | VAL C | 146 | 37.885 | 15.595 | 35.386 | 1.00 | 60.24 | C |
| ATOM | 4108 | CG2 | VAL C | 146 | 40.372 | 15.724 | 35.661 | 1.00 | 58.99 | C |
| ATOM | 4109 | C | VAL C | 146 | 39.230 | 13.308 | 36.525 | 1.00 | 62.86 | C |
| ATOM | 4110 | O | VAL C | 146 | 38.239 | 13.682 | 37.154 | 1.00 | 63.24 | O |
| ATOM | 4111 | N | ASP C | 147 | 40.272 | 12.764 | 37.129 | 1.00 | 67.18 | N |
| ATOM | 4112 | CA | ASP C | 147 | 40.213 | 12.586 | 38.576 | 1.00 | 70.75 | C |
| ATOM | 4113 | CB | ASP C | 147 | 40.968 | 11.334 | 39.053 | 1.00 | 70.73 | C |
| ATOM | 4114 | CG | ASP C | 147 | 40.202 | 10.610 | 40.151 | 1.00 | 73.03 | C |
| ATOM | 4115 | OD1 | ASP C | 147 | 39.120 | 10.052 | 39.669 | 1.00 | 73.09 | O |
| ATOM | 4116 | OD2 | ASP C | 147 | 40.467 | 10.652 | 41.321 | 1.00 | 78.34 | O |
| ATOM | 4117 | C | ASP C | 147 | 40.734 | 13.890 | 39.325 | 1.00 | 72.10 | C |
| ATOM | 4118 | O | ASP C | 147 | 41.550 | 14.564 | 38.935 | 1.00 | 72.84 | O |
| ATOM | 4119 | N | LEU C | 148 | 39.783 | 14.210 | 40.369 | 1.00 | 73.84 | N |
| ATOM | 4120 | CA | LEU C | 148 | 39.559 | 15.575 | 40.961 | 1.00 | 75.07 | C |
| ATOM | 4121 | CB | LEU C | 148 | 38.221 | 15.585 | 41.790 | 1.00 | 75.76 | C |
| ATOM | 4122 | CG | LEU C | 148 | 37.710 | 16.609 | 42.855 | 1.00 | 77.02 | C |
| ATOM | 4123 | CD1 | LEU C | 148 | 37.889 | 18.084 | 42.410 | 1.00 | 76.39 | C |
| ATOM | 4124 | CD2 | LEU C | 148 | 36.227 | 16.341 | 43.303 | 1.00 | 75.11 | C |
| ATOM | 4125 | C | LEU C | 148 | 40.734 | 16.160 | 41.777 | 1.00 | 75.27 | C |
| ATOM | 4126 | O | LEU C | 148 | 41.862 | 15.639 | 41.748 | 1.00 | 75.09 | O |
| ATOM | 4127 | N | PRO C | 154 | 52.732 | 13.255 | 39.944 | 1.00 | 68.29 | N |
| ATOM | 4128 | CA | PRO C | 154 | 53.924 | 12.615 | 40.526 | 1.00 | 67.68 | C |
| ATOM | 4129 | CB | PRO C | 154 | 53.385 | 11.956 | 41.807 | 1.00 | 67.30 | C |
| ATOM | 4130 | CG | PRO C | 154 | 51.940 | 11.609 | 41.485 | 1.00 | 68.82 | C |

TABLE 11-continued

| | | | | | | | | | |
|---|---|---|---|---|---|---|---|---|---|
| ATOM | 4131 | CD | PRO C | 154 | 51.491 | 12.532 | 40.288 | 1.00 | 68.72 | C |
| ATOM | 4132 | C | PRO C | 154 | 54.436 | 11.544 | 39.572 | 1.00 | 66.93 | C |
| ATOM | 4133 | O | PRO C | 154 | 53.612 | 10.757 | 39.077 | 1.00 | 67.56 | O |
| ATOM | 4134 | N | ASP C | 155 | 55.756 | 11.521 | 39.312 | 1.00 | 65.48 | N |
| ATOM | 4135 | CA | ASP C | 155 | 56.345 | 10.614 | 36.323 | 1.00 | 63.79 | C |
| ATOM | 4136 | CB | ASP C | 155 | 57.680 | 11.113 | 37.754 | 1.00 | 63.68 | C |
| ATOM | 4137 | CG | ASP C | 155 | 58.412 | 10.004 | 36.939 | 1.00 | 63.52 | C |
| ATOM | 4138 | OD1 | ASP C | 155 | 57.721 | 9.364 | 36.115 | 1.00 | 66.21 | O |
| ATOM | 4139 | OD2 | ASP C | 155 | 59.628 | 9.734 | 37.110 | 1.00 | 58.70 | O |
| ATOM | 4140 | C | ASP C | 155 | 56.623 | 9.253 | 38.907 | 1.00 | 6.22 | C |
| ATOM | 4141 | O | ASP C | 155 | 57.349 | 9.129 | 39.895 | 1.00 | 65.07 | O |
| ATOM | 4142 | N | LEU C | 156 | 56.127 | 8.232 | 36.228 | 1.00 | 60.68 | N |
| ATOM | 4143 | CA | LEU C | 156 | 56.372 | 6.837 | 38.542 | 1.00 | 58.32 | C |
| ATOM | 4144 | CB | LEU C | 156 | 56.142 | 5.998 | 37.289 | 1.00 | 58.23 | C |
| ATOM | 4145 | CG | LEU C | 156 | 55.915 | 4.500 | 37.439 | 1.00 | 58.41 | C |
| ATOM | 4146 | CD1 | LEU C | 156 | 54.855 | 4.197 | 38.463 | 1.00 | 58.35 | C |
| ATOM | 4147 | CD2 | LEU C | 156 | 55.472 | 3.927 | 36.157 | 1.00 | 58.93 | C |
| ATOM | 4148 | C | LEU C | 156 | 57.725 | 6.467 | 39.084 | 1.00 | 57.08 | C |
| ATOM | 4149 | O | LEU C | 156 | 57.844 | 5.489 | 39.798 | 1.00 | 57.60 | O |
| ATOM | 4150 | N | MET C | 157 | 58.763 | 7.194 | 38.735 | 1.00 | 55.85 | N |
| ATOM | 4151 | CA | MET C | 157 | 60.078 | 6.730 | 39.155 | 1.00 | 55.20 | C |
| ATOM | 4152 | CB | MET C | 157 | 60.985 | 6.485 | 37.958 | 1.00 | 54.81 | C |
| ATOM | 4153 | CG | MET C | 157 | 60.489 | 5.429 | 37.036 | 1.00 | 57.32 | C |
| ATOM | 4154 | SD | MET C | 157 | 60.967 | 3.725 | 37.430 | 1.00 | 62.32 | S |
| ATOM | 4155 | CE | MET C | 157 | 59.490 | 3.090 | 38.229 | 1.00 | 62.46 | C |
| ATOM | 4156 | C | MET C | 157 | 60.749 | 7.632 | 40.189 | 1.00 | 54.64 | C |
| ATOM | 4157 | O | MET C | 157 | 61.839 | 7.323 | 40.664 | 1.00 | 53.78 | O |
| ATOM | 4158 | N | ALA C | 158 | 60.084 | 8.726 | 40.561 | 1.00 | 54.32 | N |
| ATOM | 4159 | CA | ALA C | 158 | 60.585 | 9.583 | 41.635 | 1.00 | 54.22 | C |
| ATOM | 4160 | CB | ALA C | 158 | 59.887 | 10.926 | 41.584 | 1.00 | 53.28 | C |
| ATOM | 4161 | C | ALA C | 158 | 60.454 | 8.896 | 43.042 | 1.00 | 54.33 | C |
| ATOM | 4162 | O | ALA C | 158 | 59.663 | 7.996 | 43.233 | 1.00 | 53.70 | O |
| ATOM | 4163 | N | PRO C | 159 | 61.217 | 9.343 | 44.029 | 1.00 | 54.71 | N |
| ATOM | 4164 | CA | PRO C | 159 | 61.114 | 8.712 | 45.291 | 1.00 | 55.14 | C |
| ATOM | 4165 | CB | PRO C | 159 | 62.300 | 9.280 | 46.056 | 1.00 | 54.86 | C |
| ATOM | 4166 | CG | PRO C | 159 | 63.078 | 10.052 | 45.138 | 1.00 | 54.79 | C |
| ATOM | 4167 | CD | PRO C | 159 | 62.158 | 10.468 | 44.070 | 1.00 | 55.65 | C |
| ATOM | 4168 | C | PRO C | 159 | 59.852 | 9.200 | 45.949 | 1.00 | 56.77 | C |
| ATOM | 4169 | O | PRO C | 159 | 59.467 | 10.341 | 45.735 | 1.00 | 57.98 | O |
| ATOM | 4170 | N | VAL C | 160 | 59.221 | 8.346 | 46.747 | 1.00 | 57.61 | N |
| ATOM | 4171 | CA | VAL C | 160 | 57.998 | 8.666 | 47.467 | 1.00 | 58.36 | C |
| ATOM | 4172 | CB | VAL C | 160 | 56.880 | 7.635 | 47.120 | 1.00 | 58.99 | C |
| ATOM | 4173 | CG1 | VAL C | 160 | 55.605 | 7.825 | 47.968 | 1.00 | 59.53 | C |
| ATOM | 4174 | CG2 | VAL C | 160 | 56.538 | 7.683 | 45.653 | 1.00 | 60.38 | C |
| ATOM | 4175 | C | VAL C | 160 | 58.237 | 8.613 | 48.955 | 1.00 | 58.37 | C |
| ATOM | 4176 | O | VAL C | 160 | 51.197 | 7.646 | 49.397 | 1.00 | 58.44 | O |
| ATOM | 4177 | N | SER C | 161 | 57.632 | 9.419 | 49.738 | 1.00 | 58.66 | N |
| ATOM | 4178 | CA | SER C | 161 | 58.026 | 9.595 | 51.555 | 1.00 | 58.94 | C |
| ATOM | 4179 | CB | SER C | 161 | 59.362 | 10.285 | 51.212 | 1.00 | 58.35 | C |
| ATOM | 4180 | OG | SER C | 161 | 59.125 | 11.614 | 50.867 | 1.00 | 57.56 | O |
| ATOM | 4181 | C | SER C | 161 | 57.043 | 10.448 | 51.961 | 1.00 | 58.67 | C |
| ATOM | 4182 | O | SER C | 161 | 56.343 | 11.307 | 51.419 | 1.00 | 59.48 | O |
| ATOM | 4183 | N | ALA C | 162 | 57.033 | 10.248 | 53.262 | 1.00 | 57.28 | N |
| ATOM | 4184 | CA | ALA C | 162 | 56.891 | 10.891 | 54.085 | 1.00 | 56.19 | C |
| ATOM | 4185 | CB | ALA C | 162 | 54.679 | 10.142 | 53.973 | 1.00 | 54.65 | C |
| ATOM | 4186 | C | ALA C | 162 | 56.572 | 10.844 | 55.499 | 1.00 | 55.55 | C |
| ATOM | 4187 | O | ALA C | 162 | 54.578 | 10.108 | 55.745 | 1.00 | 54.98 | O |
| ATOM | 4188 | N | LYS C | 163 | 55.992 | 11.649 | 56.389 | 1.00 | 54.94 | N |
| ATOM | 4189 | CA | LYS C | 163 | 56.281 | 11.572 | 57.805 | 1.00 | 55.85 | C |
| ATOM | 4190 | CB | LYS C | 163 | 57.472 | 12.464 | 58.243 | 1.00 | 57.26 | C |
| ATOM | 4191 | CG | LYS C | 163 | 57.575 | 13.887 | 57.630 | 1.00 | 59.16 | C |
| ATOM | 4192 | CD | LYS C | 163 | 56.279 | 14.725 | 57.891 | 1.00 | 63.79 | C |
| ATOM | 4193 | CE | LYS C | 163 | 56.515 | 16.235 | 57.920 | 1.00 | 66.70 | C |
| ATOM | 4194 | NZ | LYS C | 163 | 57.258 | 16.740 | 56.703 | 1.00 | 68.21 | N |
| ATOM | 4195 | C | LYS C | 163 | 55.044 | 11.894 | 58.602 | 1.00 | 55.77 | C |
| ATOM | 4196 | O | LYS C | 163 | 54.167 | 12.646 | 58.155 | 1.00 | 55.98 | O |
| ATOM | 4197 | N | LYS C | 164 | 54.955 | 11.303 | 59.782 | 1.00 | 54.89 | N |
| ATOM | 4198 | CA | LYS C | 164 | 53.832 | 11.568 | 60.536 | 1.00 | 53.90 | C |
| ATOM | 4199 | CB | LYS C | 164 | 52.690 | 10.607 | 60.321 | 1.00 | 64.68 | C |
| ATOM | 4200 | CG | LYS C | 164 | 51.453 | 10.783 | 61.190 | 1.00 | 55.73 | C |
| ATOM | 4201 | CD | LYS C | 164 | 50.238 | 10.829 | 60.321 | 1.00 | 58.96 | C |
| ATOM | 4202 | CE | LYS C | 164 | 49.711 | 9.448 | 60.091 | 1.00 | 60.49 | C |
| ATOM | 4203 | NZ | LYS C | 164 | 48.458 | 9.535 | 59.320 | 1.00 | 62.54 | N |
| ATOM | 4204 | C | LYS C | 164 | 54.239 | 11.501 | 62.087 | 1.00 | 52.88 | C |
| ATOM | 4205 | O | LYS C | 164 | 55.174 | 10.815 | 62.442 | 1.00 | 52.25 | O |
| ATOM | 4206 | N | GLU C | 165 | 53.516 | 12.249 | 62.901 | 1.00 | 52.21 | N |
| ATOM | 4207 | CA | GLU C | 165 | 53.791 | 12.434 | 64.297 | 1.00 | 52.22 | C |
| ATOM | 4208 | CB | GLU C | 165 | 54.556 | 13.742 | 64.426 | 1.00 | 51.97 | C |
| ATOM | 4209 | CB | GLU C | 165 | 54.999 | 14.097 | 65.828 | 1.00 | 58.09 | C |
| ATOM | 4210 | CD | GLU C | 165 | 56.376 | 14.758 | 65.867 | 1.00 | 63.78 | C |

TABLE 11-continued

| | | | | | | | | | |
|---|---|---|---|---|---|---|---|---|---|
| ATOM | 4211 | OE1 | GLU C | 165 | 56.641 | 15.616 | 64.993 | 1.00 | 67.01 | O |
| ATOM | 4212 | OE2 | GLU C | 165 | 57.192 | 14.404 | 66.751 | 1.00 | 66.02 | O |
| ATOM | 4213 | C | GLU C | 165 | 52.441 | 12.387 | 65.105 | 1.00 | 51.69 | C |
| ATOM | 4214 | O | GLU C | 165 | 51.446 | 12.989 | 64.728 | 1.00 | 51.53 | O |
| ATOM | 4215 | N | LYS C | 166 | 52.339 | 11.601 | 66.174 | 1.00 | 51.96 | N |
| ATOM | 4216 | CA | LYS C | 166 | 51.226 | 11.568 | 67.083 | 1.00 | 51.27 | C |
| ATOM | 4217 | CB | LYS C | 166 | 50.378 | 10.296 | 66.927 | 1.00 | 51.34 | C |
| ATOM | 4218 | CG | LYS C | 166 | 48.899 | 10.491 | 67.367 | 1.00 | 55.64 | C |
| ATOM | 4219 | CD | LYS C | 166 | 47.987 | 9.242 | 67.232 | 1.00 | 61.12 | C |
| ATOM | 4220 | CE | LYS C | 166 | 48.465 | 8.033 | 68.107 | 1.00 | 64.27 | C |
| ATOM | 4221 | NZ | LYS C | 166 | 47.375 | 7.458 | 69.009 | 1.00 | 65.09 | N |
| ATOM | 4222 | C | LYS C | 166 | 51.677 | 11.717 | 68.530 | 1.00 | 50.43 | C |
| ATOM | 4223 | O | LYS C | 166 | 52.729 | 11.222 | 68.952 | 1.00 | 50.85 | O |
| ATOM | 4224 | N | LYS C | 167 | 50.581 | 12.442 | 69.265 | 1.00 | 49.67 | N |
| ATOM | 4225 | CA | LYS C | 167 | 51.025 | 12.776 | 70.649 | 1.00 | 48.77 | C |
| ATOM | 4226 | CB | LYS C | 167 | 50.114 | 13.959 | 70.956 | 1.00 | 48.49 | C |
| ATOM | 4227 | CG | LYS C | 167 | 50.611 | 14.847 | 72.092 | 1.00 | 55.24 | C |
| ATOM | 4228 | CD | LYS C | 167 | 49.932 | 16.259 | 72.120 | 1.00 | 59.10 | C |
| ATOM | 4229 | CE | LYS C | 167 | 48.793 | 16.346 | 73.175 | 1.00 | 61.87 | C |
| ATOM | 4230 | NZ | LYS C | 167 | 49.251 | 16.875 | 74.523 | 1.00 | 65.09 | N |
| ATOM | 4231 | C | LYS C | 167 | 50.551 | 11.512 | 71.335 | 1.00 | 47.21 | C |
| ATOM | 4232 | O | LYS C | 167 | 49.440 | 11.091 | 71.089 | 1.00 | 47.40 | O |
| ATOM | 4233 | N | VAL C | 168 | 51.411 | 10.870 | 72.28 | 1.00 | 45.80 | N |
| ATOM | 4234 | CA | VAL C | 168 | 51.023 | 9.723 | 72.939 | 1.00 | 44.07 | C |
| ATOM | 4235 | CB | VAL C | 168 | 51.753 | 8.417 | 72.546 | 1.00 | 44.05 | C |
| ATOM | 4236 | CG1 | VAL C | 168 | 51.309 | 7.297 | 73.473 | 1.00 | 44.68 | C |
| ATOM | 4237 | CG2 | VAL C | 168 | 51.478 | 8.023 | 71.115 | 1.00 | 41.57 | C |
| ATOM | 4238 | C | VAL C | 168 | 51.350 | 10.075 | 74.366 | 1.00 | 44.14 | C |
| ATOM | 4239 | O | VAL C | 168 | 52.472 | 9.908 | 74.831 | 1.00 | 44.52 | O |
| ATOM | 4240 | N | SER C | 169 | 50.395 | 10.625 | 75.086 | 1.00 | 44.69 | N |
| ATOM | 4241 | CA | SER C | 169 | 50.823 | 11.276 | 76.303 | 1.00 | 44.63 | C |
| ATOM | 4242 | CB | SER C | 169 | 50.161 | 12.608 | 76.499 | 1.00 | 44.58 | C |
| ATOM | 4243 | OG | SER C | 169 | 48.819 | 12.366 | 76.658 | 1.00 | 45.12 | O |
| ATOM | 4244 | C | SER C | 169 | 50.580 | 10.403 | 77.466 | 1.00 | 44.59 | C |
| ATOM | 4245 | O | SER C | 169 | 49.895 | 9.387 | 77.356 | 1.00 | 44.94 | O |
| ATOM | 4246 | N | SER C | 170 | 51.130 | 10.862 | 78.579 | 1.00 | 44.73 | N |
| ATOM | 4247 | CA | SER C | 170 | 51.475 | 10.099 | 79.751 | 1.00 | 44.62 | C |
| ATOM | 4248 | CB | SER C | 170 | 52.985 | 9.841 | 79.680 | 1.00 | 44.98 | C |
| ATOM | 4249 | OG | SER C | 170 | 53.428 | 8.641 | 80.273 | 1.00 | 46.07 | O |
| ATOM | 4250 | C | SER C | 170 | 51.200 | 11.154 | 80.801 | 1.00 | 44.78 | C |
| ATOM | 4251 | O | SER C | 170 | 51.318 | 12.368 | 80.544 | 1.00 | 45.41 | O |
| ATOM | 4252 | N | MET C | 171 | 50.821 | 10.736 | 81.989 | 1.00 | 45.22 | N |
| ATOM | 4253 | CA | MET C | 171 | 50.805 | 11.700 | 83.080 | 1.00 | 45.70 | C |
| ATOM | 4254 | CB | MET C | 171 | 50.209 | 11.100 | 84.338 | 1.00 | 45.61 | C |
| ATOM | 4255 | CG | MET C | 171 | 50.337 | 12.069 | 85.529 | 1.00 | 46.88 | C |
| ATOM | 4256 | SD | MET C | 171 | 49.792 | 11.420 | 87.095 | 1.00 | 48.12 | S |
| ATOM | 4257 | CE | MET C | 171 | 50.201 | 12.843 | 88.150 | 1.00 | 51.92 | C |
| ATOM | 4258 | C | MET C | 171 | 52.212 | 12.281 | 83.359 | 1.00 | 45.86 | C |
| ATOM | 4259 | O | MET C | 171 | 52.360 | 13.473 | 83.650 | 1.00 | 45.25 | O |
| ATOM | 4260 | N | PHE C | 172 | 53.236 | 11.440 | 83.240 | 1.00 | 46.45 | N |
| ATOM | 4261 | CA | PHE C | 172 | 54.596 | 11.889 | 83.529 | 1.00 | 46.88 | C |
| ATOM | 4262 | CB | PHE C | 172 | 55.326 | 10.875 | 84.414 | 1.00 | 47.89 | C |
| ATOM | 4263 | CG | PHE C | 172 | 54.698 | 10.712 | 85.784 | 1.00 | 50.13 | C |
| ATOM | 4264 | CD1 | PHE C | 172 | 54.661 | 11.795 | 86.694 | 1.00 | 52.87 | C |
| ATOM | 4265 | CE1 | PHE C | 172 | 54.071 | 11.676 | 87.971 | 1.00 | 52.30 | C |
| ATOM | 4266 | CZ | PHE C | 172 | 53.516 | 10.457 | 88.366 | 1.00 | 54.33 | C |
| ATOM | 4267 | CE2 | PHE C | 172 | 53.541 | 9.354 | 87.478 | 1.00 | 53.87 | C |
| ATOM | 4268 | CD2 | PHE C | 172 | 54.138 | 9.499 | 86.175 | 1.00 | 52.04 | C |
| ATOM | 4269 | C | PHE C | 172 | 55.371 | 12.257 | 82.276 | 1.00 | 46.20 | C |
| ATOM | 4270 | O | PHE C | 172 | 56.383 | 12.929 | 82.340 | 1.00 | 45.27 | O |
| ATOM | 4271 | N | ILE C | 173 | 54.866 | 11.868 | 81.114 | 1.00 | 46.03 | N |
| ATOM | 4272 | CA | ILE C | 173 | 55.404 | 12.464 | 79.890 | 1.00 | 45.35 | C |
| ATOM | 4273 | CB | ILE C | 173 | 56.250 | 11.431 | 79.936 | 1.00 | 45.14 | C |
| ATOM | 4274 | CG1 | ILE C | 173 | 57.266 | 10.699 | 79.921 | 1.00 | 43.90 | C |
| ATOM | 4275 | CD1 | ILE C | 173 | 57.560 | 9.283 | 79.432 | 1.00 | 41.52 | C |
| ATOM | 4276 | CG2 | ILE C | 173 | 57.048 | 12.128 | 77.938 | 1.00 | 43.38 | C |
| ATOM | 4277 | C | ILE C | 173 | 54.298 | 13.198 | 79.086 | 1.00 | 45.02 | C |
| ATOM | 4278 | O | ILE C | 173 | 53.851 | 12.693 | 78.079 | 1.00 | 45.42 | O |
| ATOM | 4279 | N | PRO C | 174 | 53.847 | 14.395 | 79.535 | 1.00 | 45.01 | N |
| ATOM | 4280 | CA | PRO C | 174 | 52.739 | 15.003 | 78.769 | 1.00 | 44.87 | C |
| ATOM | 4281 | CB | PRO C | 174 | 52.486 | 16.319 | 79.502 | 1.00 | 43.47 | C |
| ATOM | 4282 | CG | PRO C | 174 | 52.958 | 16.027 | 80.864 | 1.00 | 44.23 | C |
| ATOM | 4283 | CD | PRO C | 174 | 54.187 | 15.230 | 80.705 | 1.00 | 44.31 | C |
| ATOM | 4284 | C | PRO C | 174 | 53.058 | 15.250 | 77.312 | 1.00 | 45.10 | C |
| ATOM | 4285 | O | PRO C | 174 | 52.188 | 15.164 | 76.493 | 1.00 | 44.59 | O |
| ATOM | 4286 | N | ASP C | 175 | 54.310 | 15.526 | 76.977 | 1.00 | 47.27 | N |
| ATOM | 4287 | CA | ASP C | 175 | 54.653 | 15.886 | 75.598 | 1.00 | 47.71 | C |
| ATOM | 4288 | CB | ASP C | 175 | 55.721 | 17.004 | 75.600 | 1.00 | 49.22 | C |
| ATOM | 4289 | CG | ASP C | 175 | 55.290 | 18.247 | 76.445 | 1.00 | 53.40 | C |
| ATOM | 4290 | OD1 | ASP C | 175 | 56.136 | 18.798 | 77.204 | 1.00 | 58.49 | O |

TABLE 11-continued

| | | | | | | | | | | |
|---|---|---|---|---|---|---|---|---|---|---|
| ATOM | 4291 | OD2 | ASP C | 175 | 54.122 | 18.694 | 76.639 | 1.00 | 58.39 | O |
| ATOM | 4292 | C | ASP C | 175 | 55.136 | 14.649 | 74.861 | 1.00 | 48.84 | C |
| ATOM | 4293 | O | ASP C | 175 | 55.768 | 14.757 | 73.830 | 1.00 | 46.79 | O |
| ATOM | 4294 | N | GLY C | 176 | 54.825 | 13.479 | 75.400 | 1.00 | 46.12 | N |
| ATOM | 4295 | CA | GLY C | 176 | 55.118 | 12.232 | 74.744 | 1.00 | 47.04 | C |
| ATOM | 4296 | C | GLY C | 176 | 54.630 | 12.164 | 73.303 | 1.00 | 48.29 | C |
| ATOM | 4297 | O | GLY C | 176 | 53.469 | 12.535 | 72.969 | 1.00 | 48.61 | O |
| ATOM | 4298 | N | ARG C | 177 | 55.515 | 11.720 | 72.416 | 1.00 | 49.32 | N |
| ATOM | 4299 | CA | ARG C | 177 | 55.201 | 11.656 | 70.979 | 1.00 | 49.37 | C |
| ATOM | 4300 | CB | ARG C | 177 | 55.680 | 12.008 | 70.299 | 1.00 | 49.90 | C |
| ATOM | 4301 | CG | ARG C | 177 | 54.915 | 14.119 | 70.831 | 1.00 | 55.95 | C |
| ATOM | 4302 | CD | ARG C | 177 | 55.450 | 15.461 | 70.371 | 1.00 | 63.91 | C |
| ATOM | 4303 | NE | ARG C | 177 | 54.398 | 16.500 | 70.361 | 1.00 | 70.13 | N |
| ATOM | 4304 | CZ | ARG C | 177 | 53.472 | 16.649 | 69.397 | 1.00 | 73.58 | C |
| ATOM | 4305 | NH1 | ARG C | 177 | 53.404 | 15.817 | 68.344 | 1.00 | 72.02 | N |
| ATOM | 4306 | NH2 | ARG C | 177 | 52.595 | 17.643 | 69.491 | 1.00 | 75.95 | N |
| ATOM | 4307 | C | ARG C | 177 | 55.793 | 10.410 | 70.324 | 1.00 | 48.61 | C |
| ATOM | 4308 | O | ARG C | 177 | 56.787 | 9.853 | 70.799 | 1.00 | 48.98 | O |
| ATOM | 4309 | N | VAL C | 178 | 55.115 | 9.937 | 69.285 | 1.00 | 47.21 | N |
| ATOM | 4310 | CA | VAL C | 178 | 55.614 | 8.872 | 68.427 | 1.00 | 45.09 | C |
| ATOM | 4311 | CB | VAL C | 178 | 54.743 | 7.614 | 68.523 | 1.00 | 44.87 | C |
| ATOM | 4312 | CG1 | VAL C | 178 | 55.239 | 6.535 | 67.600 | 1.00 | 42.90 | C |
| ATOM | 4313 | CG2 | VAL C | 178 | 54.760 | 7.112 | 69.924 | 1.00 | 45.07 | C |
| ATOM | 4314 | C | VAL C | 178 | 55.554 | 9.414 | 67.029 | 1.00 | 43.91 | C |
| ATOM | 4315 | O | VAL C | 178 | 54.589 | 10.060 | 66.657 | 1.00 | 42.30 | O |
| ATOM | 4316 | N | SER C | 179 | 56.608 | 9.167 | 66.289 | 1.00 | 43.21 | N |
| ATOM | 4317 | CA | SER C | 179 | 56.686 | 9.688 | 64.923 | 1.00 | 42.87 | C |
| ATOM | 4318 | CB | SER C | 179 | 57.420 | 11.017 | 64.884 | 1.00 | 42.32 | C |
| ATOM | 4319 | OG | SER C | 179 | 58.715 | 10.705 | 64.427 | 1.00 | 45.07 | O |
| ATOM | 4320 | C | SER C | 179 | 57.481 | 8.748 | 64.086 | 1.00 | 42.57 | C |
| ATOM | 4321 | O | SER C | 179 | 58.237 | 8.015 | 64.617 | 1.00 | 42.21 | O |
| ATOM | 4322 | N | VAL C | 180 | 57.423 | 8.841 | 62.769 | 1.00 | 42.24 | N |
| ATOM | 4323 | CA | VAL C | 180 | 57.878 | 8.000 | 61.784 | 1.00 | 42.44 | C |
| ATOM | 4324 | CB | VAL C | 180 | 57.025 | 6.720 | 61.535 | 1.00 | 42.93 | C |
| ATOM | 4325 | CG1 | VAL C | 180 | 55.541 | 7.052 | 61.527 | 1.00 | 41.43 | C |
| ATOM | 4326 | CG2 | VAL C | 180 | 57.482 | 5.928 | 60.285 | 1.00 | 41.33 | C |
| ATOM | 4327 | C | VAL C | 180 | 58.059 | 8.738 | 60.493 | 1.00 | 43.70 | C |
| ATOM | 4328 | O | VAL C | 180 | 57.169 | 9.464 | 60.044 | 1.00 | 45.95 | O |
| ATOM | 4329 | N | SER C | 181 | 59.181 | 8.563 | 59.834 | 1.00 | 43.90 | N |
| ATOM | 4330 | CA | SER C | 181 | 59.156 | 8.983 | 58.467 | 1.00 | 44.68 | C |
| ATOM | 4331 | CB | SER C | 181 | 59.723 | 10.365 | 58.316 | 1.00 | 43.92 | C |
| ATOM | 4332 | OG | SER C | 181 | 61.052 | 10.353 | 58.709 | 1.00 | 44.69 | O |
| ATOM | 4333 | C | SER C | 181 | 59.905 | 7.983 | 57.654 | 1.00 | 45.43 | C |
| ATOM | 4334 | O | SER C | 181 | 60.887 | 7.411 | 58.129 | 1.00 | 46.92 | O |
| ATOM | 4335 | N | ALA C | 182 | 59.460 | 7.794 | 56.424 | 1.00 | 45.74 | N |
| ATOM | 4336 | CA | ALA C | 182 | 59.964 | 6.746 | 55.565 | 1.00 | 45.72 | C |
| ATOM | 4337 | CB | ALA C | 182 | 59.023 | 5.660 | 55.505 | 1.00 | 44.57 | C |
| ATOM | 4338 | C | ALA C | 182 | 60.077 | 7.318 | 54.200 | 1.00 | 47.36 | C |
| ATOM | 4339 | O | ALA C | 182 | 59.346 | 8.288 | 53.842 | 1.00 | 48.32 | O |
| ATOM | 4340 | N | ARG C | 183 | 60.938 | 6.652 | 53.421 | 1.00 | 47.94 | N |
| ATOM | 4341 | CA | ARG C | 183 | 61.235 | 6.958 | 52.028 | 1.00 | 47.55 | C |
| ATOM | 4342 | CB | ARG C | 183 | 62.467 | 7.850 | 51.985 | 1.00 | 47.47 | C |
| ATOM | 4343 | CG | ARG C | 183 | 62.849 | 8.392 | 50.586 | 1.00 | 52.45 | C |
| ATOM | 4344 | CD | ARG C | 183 | 64.376 | 8.550 | 50.561 | 1.00 | 59.71 | C |
| ATOM | 4345 | NE | ARG C | 183 | 65.011 | 8.732 | 49.239 | 1.00 | 66.28 | N |
| ATOM | 4346 | CZ | ARG C | 183 | 64.894 | 9.798 | 48.434 | 1.00 | 68.16 | C |
| ATOM | 4347 | NH1 | ARG C | 183 | 64.078 | 10.819 | 48.742 | 1.00 | 69.93 | N |
| ATOM | 4348 | NH2 | ARG C | 183 | 65.582 | 9.827 | 47.286 | 1.00 | 66.34 | N |
| ATOM | 4349 | C | ARG C | 183 | 61.465 | 5.636 | 51.239 | 1.00 | 46.85 | C |
| ATOM | 4350 | O | ARG C | 183 | 62.059 | 4.693 | 51.759 | 1.00 | 46.88 | O |
| ATOM | 4351 | N | ILE C | 184 | 60.951 | 5.569 | 50.005 | 1.00 | 46.15 | N |
| ATOM | 4352 | CA | ILE C | 184 | 61.278 | 4.510 | 49.039 | 1.00 | 45.21 | C |
| ATOM | 4353 | CB | ILE C | 184 | 60.095 | 3.588 | 48.792 | 1.00 | 43.65 | C |
| ATOM | 4354 | CG1 | ILE C | 184 | 58.861 | 4.414 | 48.426 | 1.00 | 43.71 | C |
| ATOM | 4355 | CD1 | IEL C | 184 | 57.675 | 3.658 | 47.815 | 1.00 | 37.08 | C |
| ATOM | 4356 | CG2 | ILE C | 184 | 59.819 | 2.827 | 50.051 | 1.00 | 43.77 | C |
| ATOM | 4357 | C | ILE C | 184 | 61.772 | 5.151 | 47.734 | 1.00 | 45.89 | C |
| ATOM | 4358 | O | ILE C | 184 | 61.499 | 6.325 | 47.502 | 1.00 | 44.97 | O |
| ATOM | 4359 | N | ASP C | 185 | 62.495 | 4.396 | 46.898 | 1.00 | 47.38 | N |
| ATOM | 4360 | CA | ASP C | 185 | 63.178 | 5.006 | 45.742 | 1.00 | 49.29 | C |
| ATOM | 4361 | CB | ASP C | 185 | 64.541 | 4.352 | 45.413 | 1.00 | 50.09 | C |
| ATOM | 4362 | CG | ASP C | 185 | 64.440 | 3.068 | 44.568 | 1.00 | 57.04 | C |
| ATOM | 4363 | OD1 | ASP C | 185 | 63.966 | 3.109 | 43.381 | 1.00 | 53.43 | O |
| ATOM | 4364 | OD2 | ASP C | 185 | 64.927 | 2.006 | 45.058 | 1.00 | 62.75 | O |
| ATOM | 4365 | C | ASP C | 185 | 62.304 | 5.400 | 44.500 | 1.00 | 49.20 | C |
| ATOM | 4366 | O | ASP C | 185 | 62.522 | 6.460 | 43.897 | 1.00 | 51.02 | O |
| ATOM | 4367 | N | ARG C | 186 | 61.303 | 4.580 | 44.190 | 1.00 | 47.57 | N |
| ATOM | 4368 | CA | ARG C | 186 | 60.365 | 4.836 | 43.107 | 1.00 | 45.47 | C |
| ATOM | 4369 | CB | ARG C | 186 | 60.763 | 3.996 | 41.914 | 1.00 | 45.17 | C |
| ATOM | 4370 | CG | ARG C | 186 | 61.000 | 2.592 | 42.291 | 1.00 | 44.01 | C |

TABLE 11-continued

| | | | | | | | | | | |
|---|---|---|---|---|---|---|---|---|---|---|
| ATOM | 4371 | CD | ARG C | 186 | 61.746 | 1.892 | 41.229 | 1.00 | 46.16 | C |
| ATOM | 4372 | NE | ARG C | 186 | 62.284 | 0.654 | 41.812 | 1.00 | 50.63 | N |
| ATOM | 4373 | CZ | ARG C | 186 | 61.939 | −0.585 | 41.441 | 1.00 | 50.56 | C |
| ATOM | 4374 | NH1 | ARG C | 186 | 61.057 | −0.786 | 40.446 | 1.00 | 52.67 | N |
| ATOM | 4375 | NH2 | ARG C | 186 | 62.476 | −1.835 | 42.062 | 1.00 | 46.71 | N |
| ATOM | 4376 | C | ARG C | 186 | 58.971 | 4.424 | 43.608 | 1.00 | 44.39 | C |
| ATOM | 4377 | O | ARG C | 186 | 58.834 | 3.951 | 44.755 | 1.00 | 44.16 | O |
| ATOM | 4378 | N | LYS C | 187 | 57.955 | 4.572 | 42.773 | 1.00 | 41.92 | N |
| ATOM | 4379 | CA | LYS C | 187 | 56.666 | 4.088 | 43.166 | 1.00 | 42.03 | C |
| ATOM | 4380 | CB | LYS C | 187 | 55.077 | 5.207 | 42.893 | 1.00 | 42.45 | C |
| ATOM | 4381 | CG | LYS C | 187 | 54.216 | 4.787 | 42.750 | 1.00 | 48.24 | C |
| ATOM | 4382 | CD | LYS C | 187 | 53.359 | 5.946 | 42.182 | 1.00 | 50.66 | C |
| ATOM | 4383 | CE | LYS C | 187 | 51.916 | 5.801 | 42.536 | 1.00 | 53.40 | C |
| ATOM | 4384 | NZ | LYS C | 187 | 51.433 | 7.193 | 42.609 | 1.00 | 56.86 | N |
| ATOM | 4385 | C | LYS C | 187 | 56.255 | 2.778 | 42.428 | 1.00 | 41.46 | C |
| ATOM | 4386 | O | LYS C | 187 | 55.282 | 2.128 | 42.787 | 1.00 | 41.54 | O |
| ATOM | 4387 | N | GLY C | 188 | 57.066 | 2.383 | 41.405 | 1.00 | 40.37 | N |
| ATOM | 4388 | CA | GLY C | 188 | 56.602 | 1.296 | 40.566 | 1.00 | 38.82 | C |
| ATOM | 4389 | C | GLY C | 188 | 57.526 | 0.134 | 40.798 | 1.00 | 38.47 | C |
| ATOM | 4390 | O | GLY C | 188 | 58.734 | 0.242 | 40.671 | 1.00 | 37.90 | O |
| ATOM | 4391 | N | PHE C | 189 | 56.956 | −1.004 | 41.136 | 1.00 | 38.32 | N |
| ATOM | 4392 | CA | PHE C | 189 | 57.750 | −2.210 | 41.270 | 1.00 | 37.92 | C |
| ATOM | 4393 | CB | PHE C | 189 | 57.840 | −2.613 | 42.705 | 1.00 | 36.06 | C |
| ATOM | 4394 | CG | PHE C | 189 | 58.413 | −1.551 | 43.562 | 1.00 | 35.58 | C |
| ATOM | 4395 | CD1 | PHE C | 189 | 59.800 | −1.482 | 43.785 | 1.00 | 34.82 | C |
| ATOM | 4396 | CE1 | PHE C | 189 | 60.381 | −0.493 | 44.554 | 1.00 | 27.14 | C |
| ATOM | 4397 | CZ | PHE C | 189 | 59.618 | 0.430 | 45.114 | 1.00 | 28.75 | C |
| ATOM | 4398 | CE2 | PHE C | 189 | 58.206 | 0.376 | 44.935 | 1.00 | 30.90 | C |
| ATOM | 4399 | CD2 | PHE C | 189 | 57.613 | −0.598 | 44.142 | 1.00 | 31.05 | C |
| ATOM | 4400 | C | PHE C | 189 | 57.153 | −3.292 | 40.431 | 1.00 | 38.62 | C |
| ATOM | 4401 | O | PHE C | 189 | 55.977 | −3.236 | 40.120 | 1.00 | 39.85 | O |
| ATOM | 4402 | N | CYS C | 190 | 58.005 | −4.185 | 39.975 | 1.00 | 39.95 | N |
| ATOM | 4403 | CA | CSY C | 190 | 57.606 | −5.402 | 39.327 | 1.00 | 42.85 | C |
| ATOM | 4404 | CB | CYS C | 190 | 58.674 | −5.852 | 38.328 | 1.00 | 43.30 | C |
| ATOM | 4405 | SG | CYS C | 190 | 59.344 | −4.529 | 37.295 | 1.00 | 52.38 | S |
| ATOM | 4406 | C | CYS C | 190 | 57.461 | −6.495 | 40.359 | 1.00 | 42.23 | C |
| ATOM | 4407 | O | CYS C | 190 | 58.266 | −6.565 | 41.290 | 1.00 | 40.69 | O |
| ATOM | 4408 | N | GLU C | 191 | 56.537 | −7.397 | 40.139 | 1.00 | 43.33 | N |
| ATOM | 4409 | CA | GLU C | 191 | 56.384 | −8.526 | 41.044 | 1.00 | 44.50 | C |
| ATOM | 4410 | CB | GLU C | 191 | 55.272 | −9.461 | 40.610 | 1.00 | 44.11 | C |
| ATOM | 4411 | CG | GLU C | 191 | 55.761 | −10.605 | 39.783 | 1.00 | 50.19 | C |
| ATOM | 4412 | CD | GLU C | 191 | 54.691 | −11.134 | 38.830 | 1.00 | 55.95 | C |
| ATOM | 4413 | OE1 | GLU C | 191 | 54.914 | −11.088 | 37.563 | 1.00 | 54.81 | O |
| ATOM | 4414 | OE2 | GLU C | 191 | 53.641 | −11.580 | 39.378 | 1.00 | 57.07 | O |
| ATOM | 4415 | C | GLU C | 191 | 57.737 | −9.190 | 41.056 | 1.00 | 44.04 | C |
| ATOM | 4416 | O | GLU C | 191 | 58.323 | −9.367 | 40.002 | 1.00 | 44.35 | O |
| ATOM | 4417 | N | GLY C | 192 | 58.248 | −9.457 | 42.256 | 1.00 | 43.73 | N |
| ATOM | 4418 | CA | GLY C | 192 | 59.498 | −10.112 | 42.465 | 1.00 | 44.34 | C |
| ATOM | 4419 | C | GLY C | 192 | 60.573 | −9.230 | 43.047 | 1.00 | 45.66 | C |
| ATOM | 4420 | O | GLY C | 192 | 61.458 | −9.702 | 43.753 | 1.00 | 45.93 | O |
| ATOM | 4421 | N | ASP C | 193 | 60.523 | −7.941 | 42.753 | 1.00 | 47.44 | N |
| ATOM | 4422 | CA | ASP C | 193 | 61.545 | −7.028 | 43.230 | 1.00 | 48.38 | C |
| ATOM | 4423 | CB | ASP C | 193 | 61.425 | −5.632 | 42.602 | 1.00 | 49.25 | C |
| ATOM | 4424 | CG | ASP C | 193 | 61.830 | −5.566 | 41.116 | 1.00 | 52.15 | C |
| ATOM | 4425 | OD1 | ASP C | 193 | 62.631 | −6.412 | 40.620 | 1.00 | 52.16 | O |
| ATOM | 4426 | OD2 | ASP C | 193 | 61.337 | −4.598 | 40.461 | 1.00 | 56.42 | O |
| ATOM | 4427 | C | ASP C | 193 | 61.243 | −6.878 | 44.670 | 1.00 | 48.71 | C |
| ATOM | 4428 | O | ASP C | 193 | 60.145 | −7.215 | 45.133 | 1.00 | 47.89 | O |
| ATOM | 4429 | N | GLU C | 194 | 62.197 | −6.336 | 45.401 | 1.00 | 49.63 | N |
| ATOM | 4430 | CA | GLU C | 194 | 61.871 | −5.976 | 46.757 | 1.00 | 50.47 | C |
| ATOM | 4431 | CB | GLU C | 194 | 62.919 | −6.495 | 47.705 | 1.00 | 51.98 | C |
| ATOM | 4432 | CG | GLU C | 194 | 64.338 | −6.283 | 47.279 | 1.00 | 56.28 | C |
| ATOM | 4433 | CD | GLU C | 194 | 65.285 | −7.062 | 48.185 | 1.00 | 61.47 | C |
| ATOM | 4434 | OE1 | GLU C | 194 | 65.116 | −8.316 | 48.268 | 1.00 | 60.38 | O |
| ATOM | 4435 | OE2 | GLU C | 194 | 66.162 | −6.407 | 48.822 | 1.00 | 62.72 | O |
| ATOM | 4436 | C | GLU C | 194 | 61.740 | −4.508 | 46.934 | 1.00 | 49.50 | C |
| ATOM | 4437 | O | GLU C | 194 | 62.364 | −3.741 | 46.224 | 1.00 | 49.56 | O |
| ATOM | 4438 | N | ILE C | 195 | 60.909 | −4.093 | 47.884 | 1.00 | 48.67 | N |
| ATOM | 4439 | CA | ILE C | 195 | 60.929 | −2.687 | 48.275 | 1.00 | 46.80 | C |
| ATOM | 4440 | CB | ILE C | 195 | 59.575 | −2.197 | 48.664 | 1.00 | 46.11 | C |
| ATOM | 4441 | CG1 | ILE C | 195 | 58.633 | −2.425 | 47.506 | 1.00 | 45.23 | C |
| ATOM | 4442 | CD1 | ILE C | 195 | 57.243 | −2.109 | 47.843 | 1.00 | 46.05 | C |
| ATOM | 4443 | CG2 | ILE C | 195 | 59.638 | −0.683 | 48.973 | 1.00 | 46.33 | C |
| ATOM | 4444 | C | ILE C | 195 | 61.907 | −2.533 | 49.413 | 1.00 | 46.32 | C |
| ATOM | 4445 | O | ILE C | 195 | 61.787 | −3.187 | 50.437 | 1.00 | 46.85 | O |
| ATOM | 4446 | N | SER C | 196 | 62.822 | −1.673 | 49.196 | 1.00 | 45.67 | N |
| ATOM | 4447 | CA | SER C | 196 | 63.959 | −1.314 | 50.126 | 1.00 | 45.19 | C |
| ATOM | 4448 | CB | SER C | 196 | 65.146 | −0.887 | 49.221 | 1.00 | 44.67 | C |
| ATOM | 4449 | OG | SER C | 196 | 66.384 | −1.067 | 49.814 | 1.00 | 46.62 | O |
| ATOM | 4450 | C | SER C | 196 | 63.465 | −0.101 | 50.923 | 1.00 | 44.73 | C |

TABLE 11-continued

| ATOM | 4451 | O | SER C | 196 | 63.364 | 1.018 | 50.381 | 1.00 | 46.01 | O |
|---|---|---|---|---|---|---|---|---|---|---|
| ATOM | 4452 | N | ILE C | 197 | 63.094 | −0.277 | 52.180 | 1.00 | 44.56 | N |
| ATOM | 4453 | CA | ILE C | 197 | 62.530 | 0.881 | 52.964 | 1.00 | 44.38 | C |
| ATOM | 4454 | CB | ILE C | 197 | 61.317 | 0.502 | 53.847 | 1.00 | 43.47 | C |
| ATOM | 4455 | CG1 | ILE C | 197 | 60.355 | −0.412 | 53.075 | 1.00 | 44.02 | C |
| ATOM | 4456 | CD1 | ILE C | 197 | 59.127 | −0.845 | 58.859 | 1.00 | 44.28 | C |
| ATOM | 4457 | CG2 | ILE C | 197 | 60.628 | 1.757 | 54.373 | 1.00 | 39.61 | C |
| ATOM | 4458 | C | ILE C | 197 | 63.584 | 1.565 | 53.887 | 1.00 | 45.45 | C |
| ATOM | 4459 | O | ILE C | 197 | 64.229 | 0.901 | 54.734 | 1.00 | 44.44 | O |
| ATOM | 4460 | N | HIS C | 198 | 63.735 | 2.875 | 53.689 | 1.00 | 45.98 | N |
| ATOM | 4461 | CA | HIS C | 198 | 64.522 | 3.770 | 54.564 | 1.00 | 46.98 | C |
| ATOM | 4462 | CB | HIS C | 198 | 65.342 | 4.758 | 53.709 | 1.00 | 47.54 | C |
| ATOM | 4463 | CG | HIS C | 198 | 66.525 | 4.117 | 53.032 | 1.00 | 51.03 | C |
| ATOM | 4464 | ND1 | HIS C | 198 | 66.411 | 3.379 | 51.869 | 1.00 | 53.10 | N |
| ATOM | 4465 | CE1 | HIS C | 198 | 67.607 | 2.933 | 51.514 | 1.00 | 53.17 | C |
| ATOM | 4466 | NE2 | HIS C | 198 | 68.490 | 3.332 | 52.416 | 1.00 | 52.26 | N |
| ATOM | 4467 | CD2 | HIS C | 198 | 67.842 | 4.075 | 53.379 | 1.00 | 51.87 | C |
| ATOM | 4468 | C | HIS C | 198 | 63.597 | 4.517 | 55.498 | 1.00 | 45.81 | C |
| ATOM | 4469 | O | HIS C | 198 | 62.736 | 5.244 | 55.030 | 1.00 | 46.64 | O |
| ATOM | 4470 | N | ALA C | 199 | 63.707 | 4.290 | 56.801 | 1.00 | 45.12 | N |
| ATOM | 4471 | CA | ALA C | 199 | 62.733 | 4.853 | 57.791 | 1.00 | 44.32 | C |
| ATOM | 4472 | CB | ALA C | 199 | 61.568 | 3.903 | 58.020 | 1.00 | 42.66 | C |
| ATOM | 4473 | C | ALA C | 199 | 63.378 | 5.224 | 59.123 | 1.00 | 44.28 | C |
| ATOM | 4474 | O | ALA C | 199 | 64.273 | 4.538 | 59.623 | 1.00 | 44.35 | O |
| ATOM | 4475 | N | ASP C | 200 | 62.955 | 6.346 | 59.677 | 1.00 | 44.58 | N |
| ATOM | 4476 | CA | ASP C | 200 | 63.426 | 6.762 | 60.995 | 1.00 | 43.72 | C |
| ATOM | 4477 | CB | ASP C | 200 | 64.186 | 8.074 | 60.936 | 1.00 | 43.41 | C |
| ATOM | 4478 | CG | ASP C | 200 | 65.442 | 7.970 | 60.163 | 1.00 | 45.88 | C |
| ATOM | 4479 | OD1 | ASP C | 200 | 66.047 | 6.881 | 60.065 | 1.00 | 48.66 | O |
| ATOM | 4480 | OD2 | ASP C | 200 | 65.839 | 9.017 | 59.646 | 1.00 | 51.23 | O |
| ATOM | 4481 | C | ASP C | 200 | 62.231 | 6.934 | 61.875 | 1.00 | 42.92 | C |
| ATOM | 4482 | O | ASP C | 200 | 61.289 | 7.578 | 61.500 | 1.00 | 42.34 | O |
| ATOM | 4483 | N | PHE C | 201 | 62.314 | 6.311 | 63.038 | 1.00 | 43.39 | N |
| ATOM | 4484 | CA | PHE C | 201 | 61.288 | 6.246 | 54.058 | 1.00 | 44.08 | C |
| ATOM | 4485 | CB | PHE C | 201 | 60.941 | 4.791 | 64.342 | 1.00 | 43.85 | C |
| ATOM | 4486 | CG | PHE C | 201 | 60.678 | 3.943 | 63.117 | 1.00 | 44.28 | C |
| ATOM | 4487 | CD1 | PHE C | 201 | 50.411 | 3.819 | 65.291 | 1.00 | 45.71 | C |
| ATOM | 4488 | CE1 | PHE C | 201 | 59.161 | 3.017 | 61.485 | 1.00 | 45.02 | C |
| ATOM | 4489 | CZ | PHE C | 201 | 60.159 | 2.307 | 60.909 | 1.00 | 45.36 | C |
| ATOM | 4490 | CE2 | PHE C | 201 | 61.421 | 2.417 | 61.405 | 1.00 | 48.56 | C |
| ATOM | 4491 | CD2 | PHE C | 201 | 61.676 | 3.233 | 62.528 | 1.00 | 46.48 | C |
| ATOM | 4492 | C | PHE C | 201 | 61.838 | 6.839 | 65.379 | 1.00 | 44.61 | C |
| ATOM | 4493 | O | PHE C | 201 | 62.910 | 6.458 | 65.799 | 1.00 | 44.66 | O |
| ATOM | 4494 | N | GLU C | 202 | 61.074 | 7.745 | 66.004 | 1.00 | 44.93 | N |
| ATOM | 4495 | CA | GLU C | 202 | 61.354 | 8.358 | 67.290 | 1.00 | 45.52 | C |
| ATOM | 4496 | CB | GLU C | 202 | 61.534 | 9.878 | 67.090 | 1.00 | 46.84 | C |
| ATOM | 4497 | CG | GLU C | 202 | 61.612 | 10.727 | 68.381 | 1.00 | 50.84 | C |
| ATOM | 4498 | CD | GLU C | 202 | 82.134 | 12.147 | 89.095 | 1.00 | 57.00 | C |
| ATOM | 4499 | OE1 | GLU C | 202 | 61.864 | 13.076 | 68.902 | 1.00 | 56.71 | C |
| ATOM | 4500 | OE2 | GLU C | 202 | 62.793 | 12.337 | 67.037 | 1.00 | 60.29 | O |
| ATOM | 4501 | C | GLU C | 202 | 60.198 | 8.077 | 68.271 | 1.00 | 44.64 | C |
| ATOM | 4502 | O | GLU C | 202 | 59.013 | 8.221 | 67.931 | 1.00 | 44.47 | O |
| ATOM | 4503 | N | ASN C | 203 | 60.539 | 7.689 | 69.492 | 1.00 | 43.40 | N |
| ATOM | 4504 | CA | ASN C | 203 | 59.533 | 7.403 | 70.512 | 1.00 | 41.28 | C |
| ATOM | 4505 | CB | ASN C | 203 | 59.389 | 5.888 | 70.708 | 1.00 | 40.25 | C |
| ATOM | 4506 | CG | ASN C | 203 | 58.491 | 5.510 | 71.920 | 1.00 | 39.48 | C |
| ATOM | 4507 | OD1 | ASN C | 203 | 57.800 | 6.348 | 72.525 | 1.00 | 35.04 | O |
| ATOM | 4508 | ND2 | ASN C | 203 | 58.485 | 4.233 | 72.246 | 1.00 | 34.76 | N |
| ATOM | 4509 | C | ASN C | 203 | 59.916 | 8.061 | 71.824 | 1.00 | 40.61 | C |
| ATOM | 4510 | O | ASN C | 203 | 60.814 | 7.552 | 72.521 | 1.00 | 40.70 | O |
| ATOM | 4511 | N | THR C | 204 | 59.277 | 9.186 | 72.149 | 1.00 | 39.31 | N |
| ATOM | 4512 | CA | THR C | 204 | 59.465 | 9.626 | 73.472 | 1.00 | 39.28 | C |
| ATOM | 4513 | CB | THR C | 204 | 59.634 | 11.359 | 73.359 | 1.00 | 38.80 | C |
| ATOM | 4514 | OG1 | THR C | 204 | 58.498 | 11.899 | 72.672 | 1.00 | 41.18 | O |
| ATOM | 4515 | CG2 | THR C | 204 | 60.881 | 11.719 | 72.614 | 1.00 | 36.44 | C |
| ATOM | 4516 | C | THR C | 204 | 58.272 | 9.553 | 74.406 | 1.00 | 39.70 | C |
| ATOM | 4517 | O | THR C | 204 | 58.042 | 10.257 | 75.388 | 1.00 | 39.06 | O |
| ATOM | 4518 | N | SER C | 205 | 57.480 | 8.551 | 74.047 | 1.00 | 40.53 | N |
| ATOM | 4519 | CA | SER C | 205 | 56.273 | 8.317 | 74.805 | 1.00 | 41.47 | C |
| ATOM | 4520 | CB | SER C | 205 | 55.277 | 7.705 | 73.876 | 1.00 | 40.65 | C |
| ATOM | 4521 | OG | SER C | 205 | 55.449 | 6.297 | 73.931 | 1.00 | 41.44 | O |
| ATOM | 4522 | C | SER C | 205 | 56.659 | 7.306 | 75.877 | 1.00 | 42.89 | C |
| ATOM | 4523 | O | SER C | 205 | 57.821 | 6.904 | 75.959 | 1.00 | 43.50 | O |
| ATOM | 4524 | N | SER C | 206 | 55.705 | 6.871 | 76.693 | 1.00 | 43.94 | N |
| ATOM | 4525 | CA | SER C | 206 | 56.042 | 5.970 | 77.781 | 1.00 | 45.02 | C |
| ATOM | 4526 | CB | SER C | 206 | 55.173 | 6.262 | 78.980 | 1.00 | 44.69 | C |
| ATOM | 4527 | OG | SER C | 206 | 53.926 | 5.696 | 78.720 | 1.00 | 46.69 | O |
| ATOM | 4528 | C | SER C | 206 | 55.850 | 4.525 | 77.365 | 1.00 | 46.30 | C |
| ATOM | 4529 | O | SER C | 206 | 56.159 | 3.593 | 78.135 | 1.00 | 46.51 | O |
| ATOM | 4530 | N | ARG C | 207 | 55.332 | 4.312 | 76.152 | 1.00 | 47.23 | N |

TABLE 11-continued

| | | | | | | | | | |
|---|---|---|---|---|---|---|---|---|---|
| ATOM | 4531 | CA | ARG C | 207 | 55.176 | 2.943 | 75.716 | 1.00 | 48.05 | C |
| ATOM | 4532 | CB | ARG C | 207 | 53.863 | 2.667 | 74.984 | 1.00 | 48.63 | C |
| ATOM | 4533 | CG | ARG C | 207 | 52.989 | 3.823 | 74.700 | 1.00 | 50.40 | C |
| ATOM | 4534 | CD | ARG C | 207 | 51.889 | 3.912 | 75.737 | 1.00 | 55.06 | C |
| ATOM | 4535 | NE | ARG C | 207 | 51.755 | 5.336 | 76.066 | 1.00 | 60.93 | N |
| ATOM | 4536 | CZ | ARG C | 207 | 50.717 | 5.917 | 76.652 | 1.00 | 62.89 | C |
| ATOM | 4537 | NH1 | ARG C | 207 | 49.653 | 5.197 | 77.002 | 1.00 | 61.37 | N |
| ATOM | 4538 | NH2 | ARG C | 207 | 50.760 | 7.229 | 76.877 | 1.00 | 63.82 | N |
| ATOM | 4539 | C | ARG C | 207 | 56.634 | 2.433 | 74.923 | 1.00 | 47.90 | C |
| ATOM | 4540 | O | ARG C | 207 | 57.205 | 3.208 | 74.492 | 1.00 | 47.89 | O |
| ATOM | 4541 | N | ILE C | 208 | 56.418 | 1.108 | 74.802 | 1.00 | 46.88 | N |
| ATOM | 4542 | CA | ILE C | 208 | 57.261 | 0.425 | 73.888 | 1.00 | 45.85 | C |
| ATOM | 4543 | CB | ILE C | 208 | 57.582 | −0.942 | 74.420 | 1.00 | 46.24 | C |
| ATOM | 4544 | CG1 | ILE C | 208 | 58.462 | −0.823 | 75.678 | 1.00 | 45.23 | C |
| ATOM | 4545 | CD1 | ILE C | 208 | 58.558 | −2.110 | 78.489 | 1.00 | 48.82 | C |
| ATOM | 4546 | CG2 | ILE C | 208 | 58.098 | −1.827 | 73.274 | 1.00 | 44.11 | C |
| ATOM | 4547 | C | ILE C | 208 | 58.453 | 0.237 | 72.630 | 1.00 | 45.66 | C |
| ATOM | 4548 | O | ILE C | 208 | 55.376 | −0.335 | 72.660 | 1.00 | 46.72 | O |
| ATOM | 4549 | N | VAL C | 209 | 56.983 | 0.707 | 71.513 | 1.00 | 44.53 | N |
| ATOM | 4550 | CA | VAL C | 209 | 56.253 | 0.746 | 70.264 | 1.00 | 42.19 | C |
| ATOM | 4551 | CB | VAL C | 209 | 56.167 | 2.196 | 69.751 | 1.00 | 41.96 | C |
| ATOM | 4552 | CG1 | VAL C | 209 | 55.361 | 3.076 | 70.754 | 1.00 | 38.46 | C |
| ATOM | 4553 | CG2 | VAL C | 209 | 57.546 | 2.773 | 69.495 | 1.00 | 38.21 | C |
| ATOM | 4554 | C | VAL C | 209 | 56.938 | −0.166 | 69.281 | 1.00 | 43.21 | C |
| ATOM | 4555 | O | VAL C | 209 | 58.109 | −0.511 | 69.437 | 1.00 | 44.88 | O |
| ATOM | 4556 | N | VAL C | 210 | 56.201 | −0.607 | 68.287 | 1.00 | 43.47 | N |
| ATOM | 4557 | CA | VAL C | 210 | 56.697 | −1.583 | 67.352 | 1.00 | 43.25 | C |
| ATOM | 4558 | CB | VAL C | 210 | 55.976 | −2.897 | 67.540 | 1.00 | 42.44 | C |
| ATOM | 4559 | CG1 | VAL C | 210 | 56.597 | −3.962 | 66.609 | 1.00 | 42.23 | C |
| ATOM | 4560 | CG2 | VAL C | 210 | 56.010 | −3.288 | 66.962 | 1.00 | 39.19 | C |
| ATOM | 4561 | C | VAL C | 210 | 56.441 | −1.107 | 65.907 | 1.00 | 44.59 | C |
| ATOM | 4562 | O | VAL C | 210 | 55.274 | −1.055 | 65.462 | 1.00 | 45.48 | O |
| ATOM | 4563 | N | PRO C | 211 | 57.520 | −0.796 | 55.167 | 1.00 | 44.90 | N |
| ATOM | 4564 | CA | PRO C | 211 | 57.366 | −0.398 | 63.765 | 1.00 | 45.33 | C |
| ATOM | 4565 | CB | PRO C | 211 | 58.691 | 0.263 | 63.448 | 1.00 | 44.78 | C |
| ATOM | 4566 | CG | PRO C | 211 | 59.697 | −0.490 | 64.332 | 1.00 | 44.36 | C |
| ATOM | 4567 | CD | PRO C | 211 | 58.942 | −0.880 | 85.579 | 1.00 | 44.68 | C |
| ATOM | 4568 | C | PRO C | 211 | 57.153 | −1.660 | 62.888 | 1.00 | 46.23 | C |
| ATOM | 4569 | O | PRO C | 211 | 57.789 | −2.689 | 63.119 | 1.00 | 46.87 | O |
| ATOM | 4570 | N | LYS C | 212 | 56.261 | −1.556 | 61.902 | 1.00 | 45.95 | N |
| ATOM | 4571 | CA | LYS C | 212 | 55.876 | −2.640 | 61.042 | 1.00 | 44.21 | C |
| ATOM | 4572 | CB | LYS C | 212 | 54.558 | −3.114 | 61.479 | 1.00 | 43.29 | C |
| ATOM | 4573 | CG | LYS C | 212 | 54.682 | −3.753 | 62.785 | 1.00 | 43.68 | C |
| ATOM | 4574 | CD | LYS C | 212 | 53.449 | −4.600 | 63.019 | 1.00 | 40.46 | N |
| ATOM | 4575 | CE | LYS C | 212 | 53.530 | −5.077 | 64.392 | 1.00 | 41.34 | C |
| ATOM | 4576 | NZ | LYS C | 212 | 52.143 | −5.015 | 64.816 | 1.00 | 47.57 | N |
| ATOM | 4577 | C | LYS C | 212 | 55.722 | 2.050 | 59.663 | 1.00 | 44.45 | C |
| ATOM | 4578 | O | LYS C | 212 | 55.535 | −0.860 | 59.598 | 1.00 | 44.99 | O |
| ATOM | 4579 | N | ALA C | 213 | 55.831 | −2.856 | 58.617 | 1.00 | 44.60 | N |
| ATOM | 4580 | CA | ALA C | 213 | 55.402 | −2.426 | 57.277 | 1.00 | 44.31 | C |
| ATOM | 4581 | CB | ALA C | 213 | 56.521 | −1.811 | 56.485 | 1.00 | 44.08 | C |
| ATOM | 4582 | C | ALA C | 213 | 54.743 | −3.566 | 56.539 | 1.00 | 44.07 | C |
| ATOM | 4583 | O | ALA C | 213 | 54.812 | −4.659 | 56.996 | 1.00 | 44.68 | O |
| ATOM | 4584 | N | ALA C | 214 | 54.065 | −3.291 | 55.426 | 1.00 | 44.23 | N |
| ATOM | 4585 | CA | ALA C | 214 | 53.143 | −4.245 | 54.776 | 1.00 | 43.54 | C |
| ATOM | 4586 | CB | ALA C | 214 | 51.890 | −4.508 | 55.636 | 1.00 | 43.49 | C |
| ATOM | 4587 | C | ALA C | 214 | 52.687 | −3.689 | 53.472 | 1.00 | 42.97 | O |
| ATOM | 4588 | O | ALA C | 214 | 52.396 | −2.509 | 53.344 | 1.00 | 42.50 | O |
| ATOM | 4589 | N | ILE C | 215 | 52.623 | −4.565 | 52.491 | 1.00 | 43.46 | N |
| ATOM | 4590 | CA | ILE C | 215 | 51.959 | −4.219 | 51.258 | 1.00 | 43.64 | C |
| ATOM | 4591 | CB | ILE C | 215 | 52.577 | −4.968 | 50.088 | 1.00 | 43.39 | C |
| ATOM | 4592 | CG1 | ILE C | 215 | 54.015 | −4.487 | 49.864 | 1.00 | 42.60 | C |
| ATOM | 4593 | CD1 | ILE C | 215 | 54.723 | −5.190 | 48.699 | 1.00 | 44.17 | C |
| ATOM | 4594 | CG2 | ILE C | 215 | 51.760 | −4.749 | 48.869 | 1.00 | 42.66 | C |
| ATOM | 4595 | C | ILE C | 215 | 50.491 | −4.543 | 51.390 | 1.00 | 43.34 | C |
| ATOM | 4596 | O | ILE C | 215 | 50.124 | −5.667 | 51.701 | 1.00 | 44.24 | O |
| ATOM | 4597 | N | VAL C | 216 | 49.627 | −3.590 | 51.173 | 1.00 | 43.21 | N |
| ATOM | 4598 | CA | VAL C | 216 | 48.230 | −3.975 | 51.156 | 1.00 | 44.20 | C |
| ATOM | 4599 | CB | VAL C | 216 | 47.519 | −3.334 | 52.271 | 1.00 | 45.16 | C |
| ATOM | 4600 | CG1 | VAL C | 216 | 46.001 | −3.514 | 52.087 | 1.00 | 47.14 | C |
| ATOM | 4601 | CG2 | VAL C | 216 | 46.003 | −3.986 | 53.579 | 1.00 | 43.68 | C |
| ATOM | 4602 | C | VAL C | 216 | 47.529 | −3.734 | 49.821 | 1.00 | 44.44 | C |
| ATOM | 4603 | O | VAL C | 216 | 47.680 | −2.671 | 49.220 | 1.00 | 44.89 | O |
| ATOM | 4604 | N | ALA C | 217 | 46.779 | −4.731 | 49.344 | 1.00 | 44.91 | N |
| ATOM | 4605 | CA | ALA C | 217 | 46.152 | −4.663 | 47.998 | 1.00 | 44.85 | C |
| ATOM | 4606 | CB | ALA C | 217 | 46.485 | −5.927 | 47.183 | 1.00 | 45.61 | C |
| ATOM | 4607 | C | ALA C | 217 | 44.665 | −4.503 | 48.068 | 1.00 | 44.69 | C |
| ATOM | 4608 | O | ALA C | 217 | 43.998 | −5.242 | 48.768 | 1.00 | 45.11 | O |
| ATOM | 4609 | N | ARG C | 218 | 44.116 | −3.544 | 47.351 | 1.00 | 45.19 | N |
| ATOM | 4610 | CA | ARG C | 218 | 42.639 | −3.507 | 47.214 | 1.00 | 45.93 | C |

TABLE 11-continued

| | | | | | | | | | |
|---|---|---|---|---|---|---|---|---|---|
| ATOM | 4611 | CB | ARG C | 218 | 42.101 | −2.144 | 47.585 | 1.00 | 46.35 | C |
| ATOM | 4612 | CG | ARG C | 218 | 42.546 | −1.734 | 48.987 | 1.00 | 53.22 | C |
| ATOM | 4613 | CD | ARG C | 218 | 42.504 | −0.207 | 49.253 | 1.00 | 61.86 | C |
| ATOM | 4614 | NE | ARG C | 218 | 43.509 | 0.577 | 48.482 | 1.00 | 69.77 | N |
| ATOM | 4615 | CZ | ARG C | 218 | 44.722 | 0.959 | 48.921 | 1.00 | 69.28 | C |
| ATOM | 4616 | NH1 | ARG C | 218 | 45.146 | 0.616 | 50.140 | 1.00 | 69.55 | N |
| ATOM | 4617 | NH2 | ARG C | 218 | 45.507 | 1.692 | 48.132 | 1.00 | 66.20 | N |
| ATOM | 4618 | C | ARG C | 218 | 42.179 | −3.958 | 45.835 | 1.00 | 44.29 | C |
| ATOM | 4619 | O | ARG C | 218 | 42.470 | −3.323 | 44.837 | 1.00 | 43.71 | O |
| ATOM | 4620 | N | HIS C | 219 | 41.537 | −5.133 | 45.799 | 1.00 | 43.27 | N |
| ATOM | 4621 | CA | HIS C | 219 | 41.004 | −5.722 | 44.561 | 1.00 | 42.59 | C |
| ATOM | 4622 | CB | HIS C | 219 | 41.024 | −7.264 | 44.611 | 1.00 | 41.06 | C |
| ATOM | 4623 | CG | HIS C | 219 | 42.376 | −7.822 | 44.910 | 1.00 | 38.58 | C |
| ATOM | 4624 | ND1 | HIS C | 219 | 42.879 | 7.897 | 46.198 | 1.00 | 39.18 | N |
| ATOM | 4625 | CE1 | HIS C | 219 | 44.106 | −8.330 | 46.165 | 1.00 | 35.06 | C |
| ATOM | 4626 | NE2 | HIS C | 219 | 44.417 | −8.624 | 44.906 | 1.00 | 37.17 | N |
| ATOM | 4627 | CD2 | HIS C | 219 | 43.347 | −8.298 | 44.099 | 1.00 | 35.37 | C |
| ATOM | 4628 | C | HIS C | 219 | 39.583 | −5.230 | 44.327 | 1.00 | 42.49 | C |
| ATOM | 4629 | O | HIS C | 219 | 38.758 | −5.434 | 45.202 | 1.00 | 41.67 | O |
| ATOM | 4630 | N | THR C | 220 | 39.334 | −4.564 | 43.185 | 1.00 | 42.83 | N |
| ATOM | 4631 | CA | THR C | 220 | 37.994 | −4.080 | 42.849 | 1.00 | 44.06 | C |
| ATOM | 4632 | CB | THR C | 220 | 37.957 | −2.759 | 42.153 | 1.00 | 42.80 | C |
| ATOM | 4633 | OG1 | THR C | 220 | 38.396 | −1.751 | 43.056 | 1.00 | 43.64 | O |
| ATOM | 4634 | CG2 | THR C | 220 | 36.584 | −2.444 | 41.830 | 1.00 | 41.01 | C |
| ATOM | 4635 | C | THR C | 220 | 37.408 | −5.050 | 41.904 | 1.00 | 45.80 | C |
| ATOM | 4636 | O | THR C | 220 | 38.037 | −5.428 | 40.926 | 1.00 | 46.40 | O |
| ATOM | 4637 | N | TYR C | 221 | 36.224 | −5.557 | 42.199 | 1.00 | 47.19 | N |
| ATOM | 4638 | CA | TYR C | 221 | 35.740 | −6.596 | 41.331 | 1.00 | 49.61 | C |
| ATOM | 4639 | CB | TYR C | 221 | 36.249 | −7.955 | 41.823 | 1.00 | 49.09 | C |
| ATOM | 4640 | CG | TYR C | 221 | 35.563 | −8.311 | 43.091 | 1.00 | 51.70 | C |
| ATOM | 4641 | CD1 | TYR C | 221 | 35.957 | −7.741 | 44.315 | 1.00 | 51.15 | C |
| ATOM | 4642 | CE1 | TYR C | 221 | 35.274 | −8.050 | 45.498 | 1.00 | 51.84 | C |
| ATOM | 4643 | CZ | TYR C | 221 | 34.174 | −8.942 | 45.447 | 1.00 | 52.54 | C |
| ATOM | 4644 | OH | TYR C | 221 | 33.473 | −9.298 | 46.578 | 1.00 | 52.79 | O |
| ATOM | 4645 | CE2 | TYR C | 221 | 33.750 | −9.485 | 44.247 | 1.00 | 52.12 | O |
| ATOM | 4646 | CD2 | TYR C | 221 | 34.430 | −9.153 | 43.068 | 1.00 | 53.64 | C |
| ATOM | 4647 | C | TYR C | 221 | 34.239 | −6.497 | 41.286 | 1.00 | 50.27 | C |
| ATOM | 4648 | O | TYR C | 221 | 33.662 | −5.772 | 42.105 | 1.00 | 50.77 | O |
| ATOM | 4649 | N | LEU C | 222 | 33.624 | −7.196 | 40.329 | 1.00 | 52.48 | N |
| ATOM | 4650 | CA | LEU C | 222 | 32.134 | −7.197 | 40.096 | 1.00 | 54.33 | C |
| ATOM | 4651 | CB | LEU C | 222 | 31.745 | −7.110 | 38.609 | 1.00 | 52.92 | C |
| ATOM | 4652 | CG | LEU C | 222 | 32.235 | −5.887 | 37.833 | 1.00 | 54.46 | C |
| ATOM | 4653 | CD1 | LEU C | 222 | 31.891 | −5.918 | 38.355 | 1.00 | 55.19 | C |
| ATOM | 4654 | CD2 | LEU C | 222 | 31.821 | −4.510 | 38.432 | 1.00 | 56.30 | C |
| ATOM | 4655 | C | LEU C | 222 | 31.508 | −8.343 | 40.692 | 1.00 | 58.00 | C |
| ATOM | 4656 | O | LEU C | 222 | 31.796 | −9.559 | 40.218 | 1.00 | 55.88 | O |
| ATOM | 4657 | N | ALA C | 223 | 30.801 | −8.226 | 41.789 | 1.00 | 58.93 | N |
| ATOM | 4658 | CA | ALA C | 223 | 29.907 | −9.246 | 42.296 | 1.00 | 62.24 | C |
| ATOM | 4659 | CB | ALA C | 223 | 30.144 | −9.543 | 43.771 | 1.00 | 61.93 | C |
| ATOM | 4660 | C | ALA C | 223 | 28.622 | −8.516 | 42.079 | 1.00 | 64.48 | C |
| ATOM | 4661 | O | ALA C | 223 | 28.631 | −7.372 | 41.567 | 1.00 | 64.70 | O |
| ATOM | 4662 | N | ASN C | 224 | 27.519 | −9.140 | 42.461 | 1.00 | 66.66 | N |
| ATOM | 4663 | CA | ASN C | 224 | 26.257 | −8.645 | 41.963 | 1.00 | 68.87 | C |
| ATOM | 4664 | CB | ASN C | 224 | 25.603 | −9.745 | 41.145 | 1.00 | 69.51 | C |
| ATOM | 4665 | CG | ASN C | 224 | 26.641 | −10.577 | 40.427 | 1.00 | 72.44 | C |
| ATOM | 4666 | OD1 | ASN C | 224 | 27.447 | −10.031 | 39.643 | 1.00 | 76.08 | O |
| ATOM | 4667 | ND2 | ASN C | 224 | 26.689 | −11.887 | 40.739 | 1.00 | 73.69 | N |
| ATOM | 4668 | C | ASN C | 224 | 25.306 | −7.964 | 42.960 | 1.00 | 69.51 | C |
| ATOM | 4669 | O | ASN C | 224 | 25.154 | −8.390 | 44.131 | 1.00 | 70.27 | O |
| ATOM | 4670 | N | GLY C | 225 | 24.701 | −6.870 | 42.480 | 1.00 | 69.52 | N |
| ATOM | 4671 | CA | GLY C | 225 | 25.032 | −6.325 | 41.149 | 1.00 | 67.80 | C |
| ATOM | 4672 | C | GLY C | 225 | 25.932 | −5.163 | 41.445 | 1.00 | 66.84 | C |
| ATOM | 4673 | O | GLY C | 225 | 25.543 | −4.012 | 41.307 | 1.00 | 67.25 | O |
| ATOM | 4674 | N | GLN C | 226 | 27.123 | −5.442 | 41.932 | 1.00 | 65.63 | N |
| ATOM | 4675 | CA | GLN C | 226 | 27.937 | −4.331 | 42.363 | 1.00 | 64.81 | C |
| ATOM | 4676 | CB | GLN C | 226 | 27.638 | −3.936 | 43.837 | 1.00 | 65.59 | C |
| ATOM | 4677 | CG | GLN C | 226 | 26.720 | −4.943 | 44.682 | 1.00 | 66.80 | C |
| ATOM | 4678 | CD | GLN C | 226 | 26.709 | −4.680 | 46.225 | 1.00 | 66.22 | C |
| ATOM | 4679 | OE1 | GLN C | 226 | 26.078 | −5.425 | 46.996 | 1.00 | 66.98 | O |
| ATOM | 4680 | NE2 | GLN C | 226 | 27.401 | −3.634 | 46.658 | 1.00 | 64.96 | N |
| ATOM | 4681 | C | GLN C | 226 | 29.429 | −4.457 | 42.083 | 1.00 | 63.90 | C |
| ATOM | 4682 | O | GLN C | 226 | 29.960 | −5.504 | 41.676 | 1.00 | 62.64 | O |
| ATOM | 4683 | N | THR C | 227 | 30.062 | −3.311 | 42.238 | 1.00 | 63.36 | N |
| ATOM | 4684 | CA | THR C | 227 | 31.487 | −3.201 | 42.313 | 1.00 | 63.45 | C |
| ATOM | 4685 | CB | THR C | 227 | 31.882 | −1.787 | 41.916 | 1.00 | 63.34 | C |
| ATOM | 4686 | OG1 | THR C | 227 | 31.143 | −1.416 | 40.754 | 1.00 | 65.96 | O |
| ATOM | 4687 | CG2 | THR C | 727 | 33.354 | −1.694 | 41.618 | 1.00 | 63.33 | C |
| ATOM | 4688 | C | THR C | 227 | 31.791 | −3.353 | 43.797 | 1.00 | 62.64 | C |
| ATOM | 4689 | O | THR C | 227 | 31.435 | −2.455 | 44.588 | 1.00 | 62.89 | O |
| ATOM | 4690 | N | LYS C | 228 | 32.408 | −4.467 | 44.198 | 1.00 | 60.68 | N |

TABLE 11-continued

| | | | | | | | | | |
|---|---|---|---|---|---|---|---|---|---|
| ATOM | 4691 | CA | LYS C | 228 | 32.882 | −4.561 | 45.608 | 1.00 | 59.23 | C |
| ATOM | 4692 | CB | LYS C | 228 | 32.417 | 5.871 | 46.285 | 1.00 | 59.22 | C |
| ATOM | 4693 | CG | LYS C | 228 | 31.045 | −6.335 | 45.784 | 1.00 | 60.04 | C |
| ATOM | 4694 | CD | LYS C | 228 | 30.551 | −7.519 | 46.559 | 1.00 | 62.29 | C |
| ATOM | 4695 | CE | LYS C | 228 | 29.487 | −7.192 | 47.534 | 1.00 | 66.59 | C |
| ATOM | 4696 | NZ | LYS C | 228 | 29.382 | −8.059 | 48.702 | 1.00 | 71.19 | N |
| ATOM | 4697 | C | LYS C | 228 | 34.408 | −4.297 | 45.711 | 1.00 | 56.88 | C |
| ATOM | 4698 | O | LYS C | 228 | 35.059 | −4.066 | 44.691 | 1.00 | 57.42 | O |
| ATOM | 4699 | N | VAL C | 229 | 34.962 | −4.261 | 46.917 | 1.00 | 53.70 | N |
| ATOM | 4700 | CA | VAL C | 229 | 36.401 | −4.090 | 47.090 | 1.00 | 51.04 | C |
| ATOM | 4701 | CB | VAL C | 229 | 36.774 | −2.679 | 47.617 | 1.00 | 51.14 | C |
| ATOM | 4702 | CG1 | VAL C | 279 | 38.086 | −2.680 | 48.388 | 1.00 | 50.25 | C |
| ATOM | 4703 | CG2 | VAL C | 279 | 36.841 | −1.676 | 46.480 | 1.00 | 49.37 | C |
| ATOM | 4704 | C | VAL C | 229 | 36.855 | −5.138 | 48.057 | 1.00 | 49.71 | C |
| ATOM | 4705 | O | VAL C | 229 | 36.364 | −5.145 | 49.156 | 1.00 | 50.46 | O |
| ATOM | 4706 | N | LEU C | 230 | 37.756 | −6.034 | 47.646 | 1.00 | 47.76 | N |
| ATOM | 4707 | CA | LEU C | 230 | 38.394 | −6.978 | 48.561 | 1.00 | 45.96 | C |
| ATOM | 4708 | CB | LEU C | 230 | 38.473 | −8.372 | 47.950 | 1.00 | 44.87 | C |
| ATOM | 4709 | CG | LEU C | 230 | 39.492 | −9.223 | 48.725 | 1.00 | 44.92 | C |
| ATOM | 4710 | OD1 | LEU C | 230 | 38.942 | −9.611 | 50.054 | 1.00 | 46.17 | C |
| ATOM | 4711 | CD2 | LEU C | 230 | 39.959 | −10.454 | 48.029 | 1.00 | 43.74 | C |
| ATOM | 4712 | C | LEU C | 230 | 39.811 | −6.477 | 48.911 | 1.00 | 44.80 | C |
| ATOM | 4713 | O | LEU C | 230 | 40.586 | −6.214 | 48.033 | 1.00 | 46.13 | O |
| ATOM | 4714 | N | THR C | 231 | 40.130 | −6.389 | 50.188 | 1.00 | 43.16 | N |
| ATOM | 4715 | CA | THR C | 231 | 41.419 | −5.944 | 50.717 | 1.00 | 42.18 | C |
| ATOM | 4716 | CB | THR C | 231 | 41.192 | −4.839 | 51.768 | 1.00 | 41.73 | C |
| ATOM | 4717 | OG1 | THR C | 231 | 40.618 | −3.698 | 51.130 | 1.00 | 41.34 | O |
| ATOM | 4718 | CG2 | THR C | 231 | 42.440 | −4.413 | 52.329 | 1.00 | 41.04 | C |
| ATOM | 4719 | C | THR C | 231 | 42.230 | −7.098 | 51.344 | 1.00 | 42.34 | C |
| ATOM | 4720 | O | THR C | 231 | 41.720 | −7.982 | 52.022 | 1.00 | 42.53 | O |
| ATOM | 4721 | N | GLN C | 232 | 43.516 | −7.095 | 51.099 | 1.00 | 43.01 | N |
| ATOM | 4722 | CA | GLN C | 232 | 44.341 | −8.223 | 51.405 | 1.00 | 44.35 | C |
| ATOM | 4723 | CB | GLN C | 232 | 44.489 | −9.042 | 50.126 | 1.00 | 44.22 | C |
| ATOM | 4724 | CG | GLN C | 232 | 44.660 | −10.512 | 50.307 | 1.00 | 49.24 | C |
| ATOM | 4725 | CD | GLN C | 232 | 45.181 | −11.223 | 49.023 | 1.00 | 56.59 | C |
| ATOM | 4726 | OE1 | GLN C | 232 | 45.003 | −10.740 | 47.893 | 1.00 | 58.58 | O |
| ATOM | 4727 | NE2 | GLN C | 232 | 45.826 | −12.383 | 49.206 | 1.00 | 57.96 | N |
| ATOM | 4728 | C | GLN C | 232 | 45.700 | −7.687 | 51.852 | 1.00 | 44.63 | C |
| ATOM | 4729 | O | GLN C | 232 | 46.335 | −6.859 | 51.154 | 1.00 | 45.29 | O |
| ATOM | 4730 | N | LYS C | 233 | 46.143 | −8.132 | 53.016 | 1.00 | 45.00 | N |
| ATOM | 4731 | CA | LYS C | 233 | 47.497 | −7.903 | 53.433 | 1.00 | 45.76 | C |
| ATOM | 4732 | CB | LYS C | 233 | 47.817 | −7.968 | 54.926 | 1.00 | 46.53 | C |
| ATOM | 4733 | CG | LYS C | 233 | 49.093 | −7.855 | 55.432 | 1.00 | 48.93 | C |
| ATOM | 4734 | CD | LYS C | 233 | 49.115 | −7.643 | 56.944 | 1.00 | 49.37 | C |
| ATOM | 4735 | CE | LYS C | 233 | 50.052 | −8.641 | 57.560 | 1.00 | 48.87 | C |
| ATOM | 4736 | NZ | LYS C | 233 | 49.680 | −8.680 | 58.994 | 1.00 | 52.67 | N |
| ATOM | 4737 | C | LYS C | 233 | 48.399 | −8.949 | 52.784 | 1.00 | 46.25 | C |
| ATOM | 4738 | O | LYS C | 233 | 48.229 | −10.171 | 52.949 | 1.00 | 46.23 | O |
| ATOM | 4739 | N | LEU C | 234 | 49.379 | −8.450 | 52.067 | 1.00 | 45.84 | N |
| ATOM | 4740 | CA | LEU C | 234 | 50.015 | −9.253 | 51.101 | 1.00 | 46.35 | C |
| ATOM | 4741 | CB | LEU C | 234 | 50.031 | −8.505 | 49.785 | 1.00 | 44.59 | C |
| ATOM | 4742 | CG | LEU C | 234 | 49.081 | −8.811 | 48.632 | 1.00 | 43.25 | C |
| ATOM | 4743 | CD1 | LEU C | 234 | 49.633 | −8.093 | 47.419 | 1.00 | 36.40 | C |
| ATOM | 4744 | CD2 | LEU C | 234 | 49.011 | −10.366 | 48.402 | 1.00 | 41.22 | C |
| ATOM | 4745 | C | LEU C | 234 | 51.463 | −9.481 | 51.372 | 1.00 | 48.91 | C |
| ATOM | 4746 | O | LEU C | 234 | 52.135 | −9.833 | 50.424 | 1.00 | 52.62 | O |
| ATOM | 4747 | N | SER C | 235 | 51.997 | −9.279 | 52.575 | 1.00 | 48.16 | N |
| ATOM | 4748 | CA | SER C | 235 | 53.440 | −9.319 | 52.678 | 1.00 | 47.0 | C |
| ATOM | 4749 | CB | SER C | 235 | 54.040 | −8.839 | 51.356 | 1.00 | 46.55 | C |
| ATOM | 4750 | OG | SER C | 235 | 55.471 | −9.053 | 51.290 | 1.00 | 41.07 | O |
| ATOM | 4751 | C | SER C | 235 | 53.876 | −8.281 | 53.652 | 1.00 | 48.65 | C |
| ATOM | 4757 | O | SER C | 235 | 53.578 | −7.086 | 53.424 | 1.00 | 49.57 | O |
| ATOM | 4753 | N | SER C | 236 | 54.585 | −8.682 | 54.710 | 1.00 | 48.39 | N |
| ATOM | 4754 | CA | SER C | 236 | 54.945 | −7.698 | 55.734 | 1.00 | 49.35 | C |
| ATOM | 4755 | CB | SER C | 236 | 53.778 | −7.388 | 56.647 | 1.00 | 48.07 | C |
| ATOM | 4756 | OG | SER C | 236 | 53.332 | −8.569 | 57.230 | 1.00 | 49 06 | O |
| ATOM | 4757 | C | SER C | 236 | 56.184 | −8.023 | 56.548 | 1.00 | 49.92 | C |
| ATOM | 4758 | O | SER C | 236 | 56.782 | −9.106 | 56.402 | 1.00 | 49.78 | O |
| ATOM | 4759 | N | VAL C | 237 | 56.590 | −7.031 | 57.340 | 1.00 | 50.81 | N |
| ATOM | 4760 | CA | VAL C | 237 | 57.788 | −7.086 | 58.149 | 1.00 | 52.16 | C |
| ATOM | 4761 | CB | VAL C | 237 | 59.042 | −0.409 | 57.473 | 1.00 | 51.76 | C |
| ATOM | 4762 | CG1 | VAL C | 237 | 59.593 | −7.390 | 56.440 | 1.00 | 53.23 | C |
| ATOM | 4763 | CG2 | VAL C | 237 | 58.746 | −5.168 | 56.850 | 1.00 | 51.13 | C |
| ATOM | 4764 | C | VAL C | 237 | 57.558 | −6.423 | 59.463 | 1.00 | 53.29 | C |
| A TOM | 4765 | O | VAL C | 237 | 56.648 | −5.616 | 59.648 | 1.00 | 53.07 | O |
| ATOM | 4766 | N | ARG C | 238 | 58.432 | −6.792 | 60.380 | 1.00 | 54.86 | N |
| ATOM | 4767 | CA | ARG C | 238 | 58.325 | −6.375 | 61.763 | 1.00 | 56.82 | C |
| ATOM | 4768 | CB | ARG C | 238 | 57.841 | −7.578 | 62.575 | 1.00 | 57.74 | C |
| ATOM | 4769 | CG | ARG C | 238 | 57.349 | −7.224 | 63.962 | 1.00 | 62.19 | C |
| ATOM | 4772 | CD | ARG C | 238 | 57.255 | −8.483 | 64.795 | 1.00 | 68.29 | C |

TABLE 11-continued

| | | | | | | | | | | |
|---|---|---|---|---|---|---|---|---|---|---|
| ATOM | 4771 | NE | ARG C | 238 | 56.974 | −8.162 | 66.186 | 1.00 | 73.99 | N |
| ATOM | 4772 | CZ | ARG C | 238 | 57.891 | −7.728 | 67.062 | 1.00 | 77.70 | C |
| ATOM | 4773 | NH1 | ARG C | 238 | 59.176 | −7.555 | 66.690 | 1.00 | 76.06 | N |
| ATOM | 4774 | NH2 | ARG C | 238 | 57.510 | −7.462 | 68.324 | 1.00 | 78.36 | N |
| ATOM | 4775 | C | ARG C | 238 | 59.714 | −5.966 | 62.231 | 1.00 | 56.04 | C |
| ATOM | 4776 | O | ARG C | 238 | 60.644 | −6.778 | 62.164 | 1.00 | 56.69 | O |
| ATOM | 4777 | N | GLY C | 239 | 59.884 | −4.721 | 62.664 | 1.00 | 55.34 | N |
| ATOM | 4778 | CA | GLY C | 239 | 61.179 | −4.281 | 63.172 | 1.00 | 53.79 | C |
| ATOM | 4779 | C | GLY C | 239 | 61.301 | −4.685 | 64.628 | 1.00 | 53.44 | C |
| ATOM | 4780 | O | GLY C | 239 | 60.401 | −5.284 | 65.179 | 1.00 | 53.78 | O |
| ATOM | 4781 | N | ASN C | 240 | 62.426 | −4.366 | 65.245 | 1.00 | 52.98 | N |
| ATOM | 4782 | CA | ASN C | 240 | 62.570 | −4.367 | 66.694 | 1.00 | 52.84 | C |
| ATOM | 4783 | CB | ASN C | 240 | 63.978 | 3.946 | 66.962 | 1.00 | 53.76 | O |
| ATOM | 4784 | CG | ASN C | 240 | 64.920 | −4.985 | 66.643 | 1.00 | 56.63 | C |
| ATOM | 4785 | OD1 | ASN C | 240 | 64.612 | −6.184 | 66.823 | 1.00 | 61.48 | O |
| ATOM | 4786 | ND2 | ASN C | 240 | 66.112 | −4.579 | 66.190 | 1.00 | 57.05 | N |
| ATOM | 4787 | C | ASN C | 240 | 61.723 | −3.409 | 67.536 | 1.00 | 51.35 | C |
| ATOM | 4788 | O | ASN C | 240 | 61.616 | −2.246 | 67.174 | 1.00 | 50.97 | O |
| ATOM | 4789 | N | HIS C | 241 | 61.215 | −3.894 | 68.680 | 1.00 | 50.29 | N |
| ATOM | 4790 | CA | HIS C | 241 | 60.539 | −3.081 | 69.709 | 1.00 | 50.41 | C |
| ATOM | 4791 | CB | HIS C | 241 | 60.493 | −3.821 | 71.069 | 1.00 | 51.94 | C |
| ATOM | 4792 | CG | HIS C | 241 | 59.616 | −5.048 | 71.100 | 1.00 | 58.76 | C |
| ATOM | 4793 | ND1 | HIS C | 241 | 58.605 | −5.222 | 72.029 | 1.00 | 64.79 | N |
| ATOM | 4794 | CE1 | HIS C | 241 | 58.014 | −6.390 | 71.838 | 1.00 | 64.41 | C |
| ATOM | 4795 | NE2 | HIS C | 241 | 58.610 | −6.991 | 70.822 | 1.00 | 64.29 | N |
| ATOM | 4796 | CD2 | HIS C | 241 | 59.618 | −6.179 | 70.346 | 1.00 | 63.33 | C |
| ATOM | 4797 | C | HIS C | 241 | 61.376 | −1.807 | 69.894 | 1.00 | 48.60 | C |
| ATOM | 4798 | O | HIS C | 241 | 62.585 | −1.902 | 70.079 | 1.00 | 48.63 | O |
| ATOM | 4799 | N | ILE C | 242 | 60.776 | −0.630 | 69.812 | 1.00 | 46.01 | N |
| ATOM | 4800 | CA | ILE C | 242 | 61.532 | 0.581 | 70.104 | 1.00 | 44.85 | C |
| ATOM | 4801 | CB | ILE C | 242 | 61.235 | 1.720 | 89.113 | 1.00 | 45.55 | C |
| ATOM | 4802 | CG1 | ILE C | 242 | 61.639 | 1.324 | 67.680 | 1.00 | 46.33 | C |
| ATOM | 4803 | CD1 | ILE C | 242 | 60.949 | 2.140 | 68.625 | 1.00 | 43.63 | C |
| ATOM | 4804 | CG2 | ILE C | 242 | 61.936 | 3.022 | 69.548 | 1.00 | 43.08 | C |
| ATOM | 4805 | C | ILE C | 242 | 61.137 | 1.062 | 71.478 | 1.00 | 44.00 | C |
| ATOM | 4806 | O | ILE C | 242 | 59.970 | 1.375 | 71.710 | 1.00 | 43.93 | O |
| ATOM | 4807 | N | ILE C | 243 | 62.090 | 1.101 | 72.406 | 1.00 | 42.69 | N |
| ATOM | 4808 | CA | ILE C | 243 | 61.718 | 1.375 | 73.797 | 1.00 | 40.40 | C |
| ATOM | 4809 | CB | ILE C | 243 | 62.702 | 0.786 | 74.869 | 1.00 | 40.16 | C |
| ATOM | 4810 | CG1 | ILE C | 243 | 63.940 | 1.688 | 75.062 | 1.00 | 37.19 | C |
| ATOM | 4811 | CD1 | ILE C | 243 | 64.850 | 1.264 | 75.739 | 1.00 | 34.71 | C |
| ATOM | 4812 | CG2 | ILE C | 243 | 62.948 | −0.717 | 74.670 | 1.00 | 36.37 | C |
| ATOM | 4813 | C | ILE C | 243 | 61.620 | 2.849 | 74.032 | 1.00 | 41.15 | C |
| ATOM | 4814 | O | ILE C | 243 | 62.237 | 3.661 | 73.324 | 1.00 | 40.83 | O |
| ATOM | 4815 | N | SER C | 244 | 60.883 | 3.184 | 75.088 | 1.00 | 41.65 | N |
| ATOM | 4816 | CA | SER C | 244 | 60.655 | 4.566 | 75.474 | 1.00 | 40.97 | C |
| ATOM | 4817 | CB | SER C | 244 | 59.958 | 4.600 | 76.796 | 1.00 | 40.81 | C |
| ATOM | 4818 | OG | SER C | 244 | 59.921 | 5.950 | 77.189 | 1.00 | 44.29 | O |
| ATOM | 4819 | C | SER C | 244 | 61.935 | 5.361 | 75.573 | 1.00 | 40.42 | C |
| ATOM | 4820 | O | SER C | 244 | 62.926 | 4.891 | 76.060 | 1.00 | 40.12 | O |
| ATOM | 4821 | N | GLY C | 245 | 61.917 | 6.567 | 75.055 | 1.00 | 41.10 | N |
| ATOM | 4822 | CA | GLY C | 245 | 63.105 | 7.415 | 75.037 | 1.00 | 41.74 | C |
| ATOM | 4823 | C | GLY C | 245 | 64.193 | 7.035 | 74.048 | 1.00 | 42.59 | C |
| ATOM | 4824 | O | GLY C | 245 | 65.370 | 7.155 | 73.394 | 1.00 | 43.02 | O |
| ATOM | 4825 | N | THR C | 246 | 63.833 | 6.600 | 72.838 | 1.00 | 42.49 | N |
| ATOM | 4826 | CA | THR C | 246 | 64.824 | 6.288 | 71.835 | 1.00 | 43.97 | C |
| ATOM | 4827 | CB | THR C | 246 | 65.368 | 4.831 | 71.926 | 1.00 | 44.66 | C |
| ATOM | 4828 | OG1 | THR C | 246 | 64.401 | 3.934 | 71.406 | 1.00 | 46.09 | O |
| ATOM | 4829 | CG2 | THR C | 246 | 65.694 | 4.405 | 73.328 | 1.00 | 43.95 | C |
| ATOM | 4830 | C | THR C | 246 | 64.332 | 6.459 | 70.410 | 1.00 | 45.44 | C |
| ATOM | 4831 | O | THR C | 246 | 63.114 | 6.624 | 70.141 | 1.00 | 45.91 | O |
| ATOM | 4832 | N | CYS C | 247 | 65.284 | 6.397 | 69.488 | 1.00 | 46.25 | N |
| ATOM | 4833 | CA | CYS C | 247 | 64.999 | 6.430 | 68.073 | 1.00 | 47.43 | C |
| ATOM | 4834 | CB | CYS C | 247 | 65.569 | 7.688 | 67.419 | 1.00 | 47.76 | C |
| ATOM | 4835 | SG | CYS C | 247 | 65.096 | 9.272 | 68.207 | 1.00 | 51.78 | S |
| ATOM | 4836 | C | CYS C | 247 | 65.643 | 5.207 | 67.483 | 1.00 | 48.16 | C |
| ATOM | 4837 | O | CYS C | 247 | 66.445 | 4.534 | 68.151 | 1.00 | 49.38 | O |
| ATOM | 4838 | N | ALA C | 248 | 65.278 | 4.895 | 66.245 | 1.00 | 48.62 | N |
| ATOM | 4839 | CA | ALA C | 248 | 65.821 | 3.719 | 65.539 | 1.00 | 48.92 | C |
| ATOM | 4840 | CB | ALA C | 248 | 65.156 | 2.439 | 66.027 | 1.00 | 48.39 | C |
| ATOM | 4841 | C | ALA C | 248 | 65.611 | 3.946 | 64.037 | 1.00 | 49.09 | C |
| ATOM | 4842 | O | ALA C | 248 | 64.826 | 4.804 | 63.672 | 1.00 | 48.80 | O |
| ATOM | 4843 | N | SER C | 249 | 66.318 | 3.228 | 63.166 | 1.00 | 49.31 | N |
| ATOM | 4844 | CA | SER C | 249 | 66.210 | 3.513 | 61.743 | 1.00 | 49.99 | C |
| ATOM | 4845 | CB | SER C | 249 | 67.380 | 4.342 | 61.293 | 1.00 | 50.10 | C |
| ATOM | 4846 | OG | SER C | 249 | 67.508 | 5.493 | 62.070 | 1.00 | 52.54 | O |
| ATOM | 4847 | C | SER C | 249 | 66.277 | 2.293 | 60.887 | 1.00 | 50.63 | C |
| ATOM | 4848 | O | SER C | 249 | 67.710 | 1.462 | 61.081 | 1.00 | 52.68 | O |
| ATOM | 4849 | N | TRP C | 250 | 65.422 | 2.203 | 59.870 | 1.00 | 49.69 | N |
| ATOM | 4850 | CA | TRP C | 250 | 65.634 | 1.188 | 58.839 | 1.00 | 48.02 | C |

TABLE 11-continued

| | | | | | | | | | | |
|---|---|---|---|---|---|---|---|---|---|---|
| ATOM | 4851 | CB | TRP C | 250 | 64.301 | 0.698 | 58.311 | 1.00 | 48.07 | C |
| ATOM | 4852 | CG | TRP C | 250 | 63.487 | −0.047 | 59.291 | 1.00 | 46.88 | C |
| ATOM | 4853 | CD1 | TRP C | 250 | 63.883 | −0.510 | 60.508 | 1.00 | 45.00 | C |
| ATOM | 4854 | NE1 | TRP C | 250 | 62.855 | −1.189 | 61.107 | 1.00 | 44.90 | N |
| ATOM | 4855 | CE2 | TRP C | 250 | 61.774 | −1.191 | 60.270 | 1.00 | 44.86 | C |
| ATOM | 4856 | CD2 | TRP C | 250 | 62.132 | −0.477 | 59.120 | 1.00 | 45.66 | C |
| ATOM | 4857 | CE3 | TRP C | 250 | 61.182 | −0.313 | 58.106 | 1.00 | 43.95 | C |
| ATOM | 4858 | CZ3 | TRP C | 250 | 59.924 | −0.857 | 58.267 | 1.00 | 41.26 | C |
| ATOM | 4859 | CH2 | TRP C | 250 | 59.580 | −1.540 | 59.431 | 1.00 | 44.14 | C |
| ATOM | 4860 | CZ2 | TRP C | 250 | 60.495 | −1.124 | 60.446 | 1.00 | 46.44 | C |
| ATOM | 4861 | C | TRP C | 250 | 66.500 | 1.725 | 57.714 | 1.00 | 47.72 | C |
| ATOM | 4862 | O | TRP C | 250 | 66.226 | 2.778 | 57.153 | 1.00 | 46.73 | O |
| ATOM | 4863 | N | ARG C | 251 | 67.582 | 1.025 | 57.413 | 1.00 | 48.77 | N |
| ATOM | 4864 | CA | ARG C | 251 | 68.484 | 1.483 | 56.334 | 1.00 | 49.88 | C |
| ATOM | 4865 | CB | ARG C | 251 | 69.938 | 1.517 | 56.771 | 1.00 | 48.50 | C |
| ATOM | 4866 | CG | ARG C | 251 | 70.216 | 2.543 | 57.859 | 1.00 | 50.60 | C |
| ATOM | 4867 | CD | ARG C | 251 | 71.684 | 2.488 | 58.435 | 1.00 | 53.75 | C |
| ATOM | 4868 | NE | ARG C | 251 | 71.800 | 2.975 | 59.824 | 1.00 | 57.92 | N |
| ATOM | 4869 | CZ | ARG C | 251 | 71.765 | 4.267 | 60.215 | 1.00 | 59.30 | C |
| ATOM | 4870 | NH1 | ARG C | 251 | 71.611 | 5.273 | 59.335 | 1.00 | 52.63 | N |
| ATOM | 4871 | NH2 | ARG C | 251 | 71.867 | 4.547 | 61.518 | 1.00 | 60.77 | N |
| ATOM | 4872 | C | ARG C | 251 | 68.312 | 0.537 | 55.171 | 1.00 | 50.89 | C |
| ATOM | 4873 | O | ARG C | 251 | 69.152 | −0.336 | 54.895 | 1.00 | 51.20 | O |
| ATOM | 4874 | N | GLY C | 252 | 67.170 | 0.668 | 54.512 | 1.00 | 51.17 | N |
| ATOM | 4875 | CA | GLY C | 252 | 66.878 | −0.233 | 53.402 | 1.00 | 51.21 | C |
| ATOM | 4876 | C | GLY C | 252 | 66.387 | −1.600 | 53.839 | 1.00 | 50.63 | C |
| ATOM | 4877 | O | GLY C | 252 | 66.753 | −2.605 | 53.248 | 1.00 | 50.88 | O |
| ATOM | 4878 | N | LYS C | 253 | 65.529 | −1.627 | 54.854 | 1.00 | 50.62 | N |
| ATOM | 4879 | CA | LYS C | 253 | 64.816 | −2.843 | 55.253 | 1.00 | 50.68 | C |
| ATOM | 4880 | CB | LYS C | 253 | 63.942 | −2.557 | 56.492 | 1.00 | 50.42 | C |
| ATOM | 4881 | CG | LYS C | 253 | 62.904 | −3.619 | 56.940 | 1.00 | 52.13 | C |
| ATOM | 4882 | CD | LYS C | 253 | 63.432 | −4.762 | 57.894 | 1.00 | 56.71 | C |
| ATOM | 4883 | CE | LYS C | 253 | 63.502 | −4.404 | 59.386 | 1.00 | 57.46 | C |
| ATOM | 4884 | NZ | LYS C | 253 | 64.935 | −4.185 | 59.875 | 1.00 | 59.11 | N |
| ATOM | 4885 | C | LYS C | 253 | 64.008 | −3.260 | 54.019 | 1.00 | 51.14 | C |
| ATOM | 4886 | O | LYS C | 253 | 63.291 | −2.447 | 53.390 | 1.00 | 51.10 | O |
| ATOM | 4887 | N | SER C | 254 | 64.160 | −4.509 | 53.630 | 1.00 | 50.23 | N |
| ATOM | 4888 | CA | SER C | 254 | 63.662 | −4.863 | 52.365 | 1.00 | 50.10 | C |
| ATOM | 4889 | CB | SER C | 254 | 64.747 | −5.625 | 51.627 | 1.00 | 50.46 | C |
| ATOM | 4890 | OG | SER C | 254 | 64.322 | −6.947 | 51.430 | 1.00 | 53.18 | O |
| ATOM | 4891 | C | SER C | 254 | 62.341 | −5.637 | 52.492 | 1.00 | 49.93 | C |
| ATOM | 4892 | O | SER C | 254 | 62.088 | −6.278 | 53.513 | 1.00 | 49.11 | O |
| ATOM | 4893 | N | LEU C | 255 | 61.505 | −5.570 | 51.451 | 1.00 | 49.73 | N |
| ATOM | 4894 | CA | LEU C | 255 | 60.162 | −6.139 | 51.485 | 1.00 | 49.91 | C |
| ATOM | 4895 | CB | LEU C | 255 | 59.184 | −5.107 | 52.010 | 1.00 | 49.21 | C |
| ATOM | 4896 | CG | LEU C | 255 | 57.700 | −5.417 | 52.001 | 1.00 | 49.21 | C |
| ATOM | 4897 | CD1 | LEU C | 255 | 57.477 | −6.839 | 52.478 | 1.00 | 51.91 | C |
| ATOM | 4898 | CD2 | LEU C | 255 | 56.915 | −4.462 | 52.890 | 1.00 | 47.71 | C |
| ATOM | 4899 | C | LEU C | 255 | 59.749 | −6.612 | 50.111 | 1.00 | 50.77 | C |
| ATOM | 4900 | O | LEU C | 255 | 59.542 | −5.821 | 49.228 | 1.00 | 50.87 | O |
| ATOM | 4901 | N | ARG C | 256 | 59.648 | −7.916 | 49.941 | 1.00 | 52.72 | N |
| ATOM | 4902 | CA | ARG C | 256 | 59.407 | −8.500 | 48.648 | 1.00 | 55.23 | C |
| ATOM | 4903 | CB | ARG C | 256 | 59.652 | −10.004 | 48.682 | 1.00 | 55.99 | C |
| ATOM | 4904 | CG | ARG C | 256 | 59.845 | −10.582 | 47.279 | 1.00 | 58.84 | C |
| ATOM | 4905 | CD | ARG C | 256 | 60.905 | −11.648 | 47.204 | 1.00 | 64.89 | C |
| ATOM | 4906 | NE | ARG C | 256 | 62.272 | −11.191 | 47.509 | 1.00 | 66.56 | N |
| ATOM | 4907 | CZ | ARG C | 256 | 63.131 | −10.702 | 45.612 | 1.00 | 68.67 | C |
| ATOM | 4908 | NH1 | ARG C | 256 | 64.347 | −10.346 | 46.988 | 1.00 | 69.68 | N |
| ATOM | 4909 | NH2 | ARG C | 256 | 62.769 | −10.549 | 45.343 | 1.00 | 69.16 | N |
| ATOM | 4910 | C | ARG C | 256 | 58.008 | −8.250 | 48.173 | 1.00 | 56.44 | C |
| ATOM | 4911 | O | ARG C | 256 | 57.091 | −8.143 | 48.991 | 1.00 | 57.75 | O |
| ATOM | 4912 | N | VAL C | 257 | 57.854 | −8.148 | 46.848 | 1.00 | 57.50 | N |
| ATOM | 4913 | CA | VAL C | 257 | 56.559 | −8.023 | 46.163 | 1.00 | 58.48 | C |
| ATOM | 4914 | CB | VAL C | 257 | 56.662 | −6.949 | 45.063 | 1.00 | 58.37 | C |
| ATOM | 4915 | CG1 | VAL C | 257 | 55.368 | −6.817 | 44.347 | 1.00 | 58.53 | C |
| ATOM | 4916 | CG2 | VAL C | 257 | 57.107 | −5.607 | 45.611 | 1.00 | 57.39 | C |
| ATOM | 4917 | C | VAL C | 257 | 56.201 | −9.308 | 45.413 | 1.00 | 59.93 | C |
| ATOM | 4918 | O | VAL C | 257 | 57.017 | −9.602 | 44.510 | 1.00 | 60.30 | O |
| ATOM | 4919 | N | GLN C | 258 | 55.231 | −10.086 | 45.736 | 1.00 | 62.14 | N |
| ATOM | 4920 | CA | GLN C | 258 | 54.858 | −11.237 | 44.834 | 1.00 | 64.64 | C |
| ATOM | 4921 | CB | GLN C | 258 | 55.118 | −12.674 | 45.410 | 1.00 | 65.31 | C |
| ATOM | 4922 | CG | GLN C | 258 | 55.208 | −12.833 | 46.939 | 1.00 | 68.69 | C |
| ATOM | 4923 | CD | GLN C | 258 | 54.224 | −11.956 | 47.705 | 1.00 | 74.17 | C |
| ATOM | 4924 | OE1 | GLN C | 258 | 54.285 | −11.880 | 48.937 | 1.00 | 77.25 | O |
| ATOM | 4925 | NE2 | GLN C | 258 | 53.315 | −11.278 | 46.985 | 1.00 | 75.55 | N |
| ATOM | 4926 | C | GLN C | 258 | 53.484 | −11.155 | 44.130 | 1.00 | 65.06 | C |
| ATOM | 4927 | O | GLN C | 258 | 53.228 | −11.925 | 43.169 | 1.00 | 65.61 | O |
| ATOM | 4928 | N | LEU C | 265 | 40.078 | −13.758 | 43.199 | 1.00 | 76.04 | N |
| ATOM | 4929 | CA | LEU C | 265 | 38.836 | −14.188 | 42.530 | 1.00 | 76.22 | C |
| ATOM, | 4930 | CB | LEU C | 265 | 37.609 | −13.373 | 43.014 | 1.00 | 76.65 | C |

TABLE 11-continued

| ATOM | 4931 | CG | LEU C | 265 | 37.467 | −11.841 | 43.117 | 1.00 | 76.24 | C |
|---|---|---|---|---|---|---|---|---|---|---|
| ATOM | 4932 | CD1 | LEU C | 265 | 36.023 | −11.534 | 42.856 | 1.00 | 75.36 | C |
| ATOM | 4933 | CD2 | LEU C | 265 | 37.890 | −11.270 | 44.473 | 1.00 | 74.52 | C |
| ATOM | 4934 | C | LEU C | 265 | 38.960 | −14.340 | 40.976 | 1.00 | 75.49 | C |
| ATOM | 4935 | O | LEU C | 265 | 40.001 | −14.836 | 40.515 | 1.00 | 76.08 | O |
| ATOM | 4936 | N | GLY C | 266 | 37.950 | −13.942 | 40.183 | 1.00 | 74.22 | N |
| ATOM | 4937 | CA | GLY C | 266 | 37.959 | −14.221 | 38.715 | 1.00 | 72.66 | C |
| ATOM | 4938 | C | GLY C | 266 | 38.118 | −13.083 | 37.715 | 1.00 | 71.19 | C |
| ATOM | 4939 | O | GLY C | 266 | 38.612 | −12.038 | 38.051 | 1.00 | 71.56 | O |
| ATOM | 4940 | N | SER C | 267 | 37.678 | −13.282 | 36.473 | 1.00 | 70.43 | N |
| ATOM | 4941 | CA | SER C | 267 | 37.717 | −12.206 | 35.423 | 1.00 | 68.98 | C |
| ATOM | 4942 | CB | SER C | 267 | 37.620 | −12.785 | 33.992 | 1.00 | 69.03 | C |
| ATOM | 4943 | OG | SER C | 267 | 36.282 | −13.080 | 33.631 | 1.00 | 67.00 | O |
| ATOM | 4944 | C | SER C | 267 | 36.639 | −11.108 | 35.628 | 1.00 | 67.98 | C |
| ATOM | 4945 | O | SER C | 267 | 36.404 | −10.245 | 34.758 | 1.00 | 67.85 | O |
| ATOM | 4946 | N | ASN C | 268 | 35.955 | −11.195 | 36.761 | 1.00 | 66.20 | N |
| ATOM | 4947 | CA | ASN C | 268 | 35.224 | −10.077 | 37.322 | 1.00 | 63.91 | C |
| ATOM | 4948 | CB | ASN C | 268 | 34.063 | −10.577 | 38.211 | 1.00 | 64.43 | C |
| ATOM | 4949 | CG | ASN C | 268 | 34.395 | −11.903 | 38.970 | 1.00 | 65.45 | C |
| ATOM | 4950 | OD1 | ASN C | 268 | 35.552 | −12.389 | 38.997 | 1.00 | 64.20 | O |
| ATOM | 4951 | ND2 | ASN C | 268 | 33.365 | −12.482 | 39.586 | 1.00 | 65.40 | N |
| ATOM | 4952 | C | ASN C | 268 | 36.190 | −9.138 | 38.085 | 1.00 | 61.63 | C |
| ATOM | 4953 | O | ASN C | 268 | 35.749 | −8.094 | 38.553 | 1.00 | 61.56 | O |
| ATOM | 4954 | N | ILE C | 269 | 37.485 | −9.516 | 38.181 | 1.00 | 58.39 | N |
| ATOM | 4955 | CA | ILE C | 269 | 38.598 | −8.672 | 38.716 | 1.00 | 55.86 | C |
| ATOM | 4956 | CB | ILE C | 269 | 39.803 | −9.583 | 39.009 | 1.00 | 55.77 | C |
| ATOM | 4957 | CG1 | ILE C | 269 | 40.885 | −8.856 | 39.788 | 1.00 | 55.53 | C |
| ATOM | 4958 | CD1 | ILE C | 269 | 42.245 | −9.595 | 39.675 | 1.00 | 58.00 | C |
| ATOM | 4959 | CG2 | ILE C | 269 | 40.392 | −10.182 | 37.675 | 1.00 | 56.51 | C |
| ATOM | 4960 | C | ILE C | 269 | 39.043 | −7.421 | 37.819 | 1.00 | 53.25 | C |
| ATOM | 4961 | O | ILE C | 269 | 39.755 | −7.568 | 36.830 | 1.00 | 52.54 | O |
| ATOM | 4962 | N | LEU C | 270 | 38.637 | −6.212 | 39.198 | 1.00 | 49.85 | N |
| ATOM | 4963 | CA | LEU C | 270 | 38.784 | −5.032 | 37.350 | 1.00 | 46.60 | C |
| ATOM | 4964 | CB | LEU C | 270 | 37.725 | −3.975 | 37.665 | 1.00 | 46.84 | C |
| ATOM | 4965 | CG | LEU C | 270 | 36.586 | −3.933 | 36.637 | 1.00 | 49.37 | C |
| ATOM | 4966 | CD1 | LEU C | 270 | 35.874 | −5.305 | 36.633 | 1.00 | 47.59 | C |
| ATOM | 4967 | CD2 | LEU C | 270 | 35.603 | −2.723 | 36.836 | 1.00 | 49.44 | C |
| ATOM | 4968 | C | LEU C | 270 | 40.110 | −4.388 | 37.427 | 1.00 | 44.55 | C |
| ATOM | 4969 | O | LEU C | 270 | 40.708 | −4.065 | 36.407 | 1.00 | 43.53 | O |
| ATOM | 4970 | N | ARG C | 271 | 40.538 | −4.150 | 38.651 | 1.00 | 42.99 | N |
| ATOM | 4971 | CA | ARG C | 271 | 41.830 | −3.562 | 38.939 | 1.00 | 42.72 | C |
| ATOM | 4972 | CB | ARG C | 271 | 41.767 | −2.071 | 38.717 | 1.00 | 43.47 | C |
| ATOM | 4973 | CG | ARG C | 271 | 40.669 | −1.398 | 39.446 | 1.00 | 46.05 | C |
| ATOM | 4974 | CD | ARG C | 271 | 40.823 | 0.101 | 39.247 | 1.00 | 55.00 | C |
| ATOM | 4975 | NE | ARG C | 271 | 40.016 | 0.842 | 40.217 | 1.00 | 56.44 | N |
| ATOM | 4976 | CZ | ARG C | 271 | 38.686 | 0.826 | 40.238 | 1.00 | 57.13 | C |
| ATOM | 4977 | NH1 | ARG C | 271 | 37.989 | 0.120 | 39.327 | 1.00 | 49.61 | N |
| ATOM | 4978 | NH2 | ARG C | 271 | 38.061 | 1.526 | 41.188 | 1.00 | 61.98 | N |
| ATOM | 4979 | C | ARG C | 271 | 42.216 | −3.840 | 40.373 | 1.00 | 41.28 | C |
| ATOM | 4980 | O | ARG C | 271 | 41.396 | −4.274 | 41.764 | 1.00 | 39.46 | O |
| ATOM | 4981 | N | VAL C | 272 | 43.479 | −3.613 | 40.688 | 1.00 | 41.40 | N |
| ATOM | 4982 | CA | VAL C | 272 | 44.000 | −3.838 | 42.047 | 1.00 | 41.96 | C |
| ATOM | 4983 | CB | VAL C | 272 | 44.963 | −5.127 | 42.182 | 1.00 | 41.79 | C |
| ATOM | 4984 | CG1 | VAL C | 272 | 45.074 | −5.523 | 43.607 | 1.00 | 39.31 | C |
| ATOM | 4985 | CG2 | VAL C | 272 | 44.435 | −6.377 | 41.414 | 1.00 | 39.62 | C |
| ATOM | 4986 | C | VAL C | 272 | 44.724 | −2.550 | 42.436 | 1.00 | 42.65 | C |
| ATOM | 4987 | O | VAL C | 272 | 45.402 | −2.011 | 41.637 | 1.00 | 43.34 | O |
| ATOM | 4988 | N | GLU C | 273 | 44.537 | −2.019 | 43.618 | 1.00 | 44.33 | N |
| ATOM | 4989 | CA | GLU C | 273 | 45.374 | −0.851 | 43.995 | 1.00 | 46.71 | C |
| ATOM | 4990 | CB | GLU C | 273 | 44.531 | 0.338 | 44.305 | 1.00 | 46.27 | C |
| ATOM | 4991 | CG | GLU C | 273 | 43.720 | 0.673 | 43.139 | 1.00 | 52.49 | C |
| ATOM | 4992 | CD | GLU C | 273 | 42.754 | 1.730 | 43.473 | 1.00 | 62.98 | C |
| ATOM | 4993 | OE1 | GLU C | 273 | 42.867 | 2.194 | 44.631 | 1.00 | 58.31 | O |
| ATOM | 4994 | OE2 | GLU C | 273 | 41.898 | 2.095 | 42.616 | 1.00 | 67.66 | O |
| ATOM | 4995 | C | GLU C | 273 | 40.285 | −1.185 | 45.156 | 1.00 | 46.36 | C |
| ATOM | 4996 | O | GLU C | 273 | 45.936 | −2.014 | 45.963 | 1.00 | 47.77 | O |
| ATOM | 4997 | N | TYR C | 274 | 47.468 | −0.609 | 45.217 | 1.00 | 46.18 | N |
| ATOM | 4998 | CA | TYR C | 274 | 48.427 | −1.071 | 46.215 | 1.00 | 46.57 | C |
| ATOM | 4999 | CB | TYR C | 274 | 49.570 | −1.830 | 45.574 | 1.00 | 44.99 | C |
| ATOM | 5000 | CG | TYR C | 274 | 49.297 | −3.066 | 44.735 | 1.00 | 43.21 | C |
| ATOM | 5001 | CD1 | TYR C | 274 | 49.458 | −4.357 | 45.277 | 1.00 | 44.02 | C |
| ATOM | 5002 | CE1 | TYR C | 274 | 49.232 | −5.536 | 44.494 | 1.00 | 42.34 | C |
| ATOM | 5003 | CZ | TYR C | 274 | 48.912 | −5.360 | 43.151 | 1.00 | 42.03 | C |
| ATOM | 5004 | OH | TYR C | 274 | 48.721 | −6.432 | 42.367 | 1.00 | 40.55 | O |
| ATOM | 5005 | CE2 | TYR C | 274 | 48.775 | −4.092 | 42.594 | 1.00 | 39.31 | C |
| ATOM | 5005 | CD2 | TYR C | 274 | 48.977 | −2.958 | 43.386 | 1.00 | 42.08 | C |
| ATOM | 5007 | C | TYR C | 274 | 49.001 | 0.075 | 47.024 | 1.00 | 46.16 | C |
| ATOM | 5008 | O | TYR C | 274 | 49.254 | 1.174 | 46.528 | 1.00 | 46.73 | O |
| ATOM | 5009 | N | SER C | 275 | 49.178 | −0.167 | 48.307 | 1.00 | 46.56 | N |
| ATOM | 5010 | CA | SER C | 275 | 49.876 | 0.784 | 49.139 | 1.00 | 46.09 | C |

TABLE 11-continued

| ATOM | 5011 | CB | SER C | 275 | 48.917 | 1.396 | 50.128 | 1.00 | 46.18 | C |
| --- | --- | --- | --- | --- | --- | --- | --- | --- | --- | --- |
| ATOM | 5012 | OG | SER C | 275 | 47.764 | 1.733 | 49.411 | 1.00 | 48.21 | O |
| ATOM | 5013 | C | SER C | 275 | 50.928 | 0.039 | 49.875 | 1.00 | 45.28 | C |
| ATOM | 5014 | O | SER C | 275 | 50.730 | −1.119 | 50.250 | 1.00 | 43.95 | O |
| ATOM | 5015 | N | LEU C | 276 | 52.068 | 0.699 | 50.052 | 1.00 | 45.60 | N |
| ATOM | 5016 | CA | LEU C | 276 | 52.961 | 0.286 | 51.095 | 1.00 | 45.67 | C |
| ATOM | 5017 | CB | LEU C | 276 | 54.379 | 0.562 | 50.716 | 1.00 | 45.44 | C |
| ATOM | 5018 | CG | LEU C | 276 | 55.352 | 0.364 | 51.883 | 1.00 | 46.60 | C |
| ATOM | 5019 | CD1 | LEU C | 276 | 55.248 | −1.011 | 52.508 | 1.00 | 47.17 | C |
| ATOM | 5020 | CD2 | LEU C | 276 | 56.722 | 0.609 | 51.390 | 1.00 | 44.49 | C |
| ATOM | 5021 | C | LEU C | 276 | 52.566 | 1.016 | 52.385 | 1.00 | 46.03 | C |
| ATOM | 5022 | O | LEU C | 276 | 52.454 | 2.251 | 52.433 | 1.00 | 46.02 | O |
| ATOM | 5023 | N | LEU C | 277 | 52.319 | 0.235 | 53.421 | 1.00 | 45.84 | N |
| ATOM | 5024 | CA | LEU C | 277 | 51.999 | 0.810 | 54.708 | 1.00 | 45.93 | C |
| ATOM | 5025 | CB | LEU C | 277 | 50.869 | 0.050 | 55.397 | 1.00 | 45.20 | C |
| ATOM | 5026 | CG | LEU C | 277 | 49.568 | 0.216 | 54.646 | 1.00 | 45.26 | C |
| ATOM | 5027 | CD1 | LEU C | 277 | 48.533 | −0.262 | 55.520 | 1.00 | 46.31 | C |
| ATOM | 5028 | CD2 | LEU C | 277 | 49.288 | 1.677 | 54.310 | 1.00 | 44.94 | C |
| ATOM | 5029 | C | LEU C | 277 | 53.216 | 0.647 | 55.513 | 1.00 | 46.03 | C |
| ATOM | 5030 | O | LEU C | 277 | 53.740 | −0.463 | 55.572 | 1.00 | 45.38 | O |
| ATOM | 5031 | N | ILE C | 278 | 53.666 | 1.762 | 56.096 | 1.00 | 46.19 | N |
| ATOM | 5032 | CA | ILE C | 278 | 54.704 | 1.771 | 57.086 | 1.00 | 46.62 | C |
| ATOM | 5033 | CB | ILE C | 278 | 55.869 | 2.561 | 56.650 | 1.00 | 47.01 | C |
| ATOM | 5034 | CG1 | ILE C | 278 | 56.325 | 2.052 | 55.277 | 1.00 | 48.70 | C |
| ATOM | 5035 | CD1 | ILE C | 278 | 56.999 | 3.064 | 54.447 | 1.00 | 49.30 | C |
| ATOM | 5036 | CG2 | ILE C | 278 | 56.950 | 2.394 | 57.662 | 1.00 | 47.18 | C |
| ATOM | 5037 | C | ILE C | 278 | 54.097 | 2.472 | 58.248 | 1.00 | 47.50 | C |
| ATOM | 5038 | O | ILE C | 278 | 53.829 | 3.695 | 58.192 | 1.00 | 48.42 | O |
| ATOM | 5039 | N | TYR C | 279 | 53.819 | 1.684 | 59.291 | 1.00 | 47.54 | N |
| ATOM | 5040 | CA | TYR C | 279 | 53.205 | 2.205 | 60.507 | 1.00 | 47.27 | C |
| ATOM | 5041 | CB | TYR C | 279 | 51.768 | 1.802 | 60.545 | 1.00 | 46.12 | C |
| ATOM | 5042 | CG | TYR C | 279 | 51.536 | 0.331 | 60.545 | 1.00 | 46.57 | C |
| ATOM | 5043 | CD1 | TYR C | 279 | 51.903 | −0.403 | 59.396 | 1.00 | 46.39 | C |
| ATOM | 5044 | CE1 | TYR C | 279 | 51.769 | −1.811 | 59.403 | 1.00 | 45.95 | C |
| ATOM | 5045 | CZ | TYR C | 279 | 51.377 | −2.460 | 60.561 | 1.00 | 44.95 | C |
| ATOM | 5046 | OH | TYR C | 279 | 51.281 | −3.832 | 60.555 | 1.00 | 48.41 | O |
| ATOM | 5047 | CE2 | TYR C | 279 | 51.128 | −1.740 | 61.717 | 1.00 | 42.75 | C |
| ATOM | 5048 | CD2 | TYR C | 279 | 51.262 | −0.365 | 61.771 | 1.00 | 44.60 | C |
| ATOM | 5049 | C | TYR C | 279 | 53.929 | 1.760 | 61.816 | 1.00 | 48.06 | C |
| ATOM | 5050 | O | TYR C | 279 | 54.819 | 0.866 | 61.815 | 1.00 | 47.20 | O |
| ATOM | 5051 | N | VAL C | 280 | 53.557 | 2.440 | 62.909 | 1.0 | 48.12 | N |
| ATOM | 5052 | CA | VAL C | 280 | 54.011 | 2.120 | 64.238 | 1.00 | 48.05 | C |
| ATOM | 5053 | CB | VAL C | 280 | 54.761 | 3.262 | 64.822 | 1.00 | 47.41 | C |
| ATOM | 5054 | CG1 | VAL C | 280 | 55.063 | 2.975 | 66.277 | 1.00 | 46.80 | C |
| ATOM | 5055 | CG2 | VAL C | 280 | 56.055 | 3.369 | 64.086 | 1.00 | 48.24 | C |
| ATOM | 5056 | C | VAL C | 280 | 52.878 | 1.756 | 65.165 | 1.00 | 48.84 | C |
| ATOM | 5057 | O | VAL C | 280 | 51.898 | 2.489 | 65.264 | 1.00 | 48.05 | O |
| ATOM | 5058 | N | SER C | 281 | 53.023 | 0.627 | 65.855 | 1.00 | 50.09 | N |
| ATOM | 5059 | CA | SER C | 281 | 52.010 | 0.229 | 66.831 | 1.00 | 51.91 | C |
| ATOM | 5060 | CB | SER C | 281 | 51.873 | −1.290 | 66.930 | 1.00 | 52.23 | C |
| ATOM | 5061 | OG | SER C | 281 | 51.616 | −1.878 | 65.652 | 1.00 | 55.75 | O |
| ATOM | 5062 | C | SER C | 281 | 52.361 | 0.783 | 68.186 | 1.00 | 51.98 | C |
| ATOM | 5063 | O | SER C | 281 | 53.460 | 0.570 | 68.657 | 1.00 | 52.61 | O |
| ATOM | 5064 | N | VAL C | 282 | 51.407 | 1.479 | 68.790 | 1.00 | 51.65 | N |
| ATOM | 5065 | CA | VAL C | 282 | 51.491 | 1.991 | 70.120 | 1.00 | 51.57 | C |
| ATOM | 5066 | CB | VAL C | 282 | 51.015 | 3.480 | 70.104 | 1.00 | 51.75 | C |
| ATOM | 5067 | CG1 | VAL C | 282 | 51.146 | 4.104 | 71.485 | 1.00 | 51.47 | C |
| ATOM | 5068 | CG2 | VAL C | 282 | 51.748 | 4.307 | 69.018 | 1.00 | 49.13 | C |
| ATOM | 5069 | C | VAL C | 282 | 50.506 | 1.169 | 70.972 | 1.00 | 52.78 | C |
| ATOM | 5070 | O | VAL C | 282 | 49.323 | 1.290 | 70.771 | 1.00 | 53.23 | O |
| ATOM | 5071 | N | PRO C | 283 | 50.062 | 0.331 | 71.925 | 1.00 | 54.14 | N |
| ATOM | 5072 | CA | PRO C | 283 | 49.918 | −0.352 | 72.740 | 1.00 | 55.23 | C |
| ATOM | 5073 | CB | PRO C | 283 | 50.737 | −1.210 | 73.313 | 1.00 | 54.84 | C |
| ATOM | 5074 | CG | PRO C | 283 | 52.053 | −1.417 | 73.000 | 1.00 | 53.86 | C |
| ATOM | 5075 | CD | PRO C | 283 | 52.314 | −0.097 | 72.323 | 1.00 | 53.78 | C |
| ATOM | 5076 | C | PRO C | 283 | 48.972 | 0.613 | 73.502 | 1.00 | 56.31 | C |
| ATOM | 5077 | O | PRO C | 283 | 49.440 | 1.565 | 74.125 | 1.00 | 57.07 | O |
| ATOM | 5078 | N | GLY C | 284 | 47.654 | 0.380 | 43.413 | 1.00 | 57.00 | N |
| ATOM | 5079 | CA | GLY C | 284 | 46.647 | 1.226 | 74.071 | 1.00 | 57.78 | C |
| ATOM | 5080 | C | GLY C | 284 | 46.496 | 2.635 | 73.500 | 1.00 | 58.36 | C |
| ATOM | 5081 | O | GLY C | 284 | 46.403 | 3.620 | 74.235 | 1.00 | 59.77 | O |
| ATOM | 5082 | N | SER C | 285 | 26.454 | 2.739 | 72.178 | 1.00 | 57.95 | N |
| ATOM | 5083 | CA | SER C | 285 | 46.380 | 4.035 | 71.487 | 1.00 | 56.72 | C |
| ATOM | 5084 | CB | SER C | 285 | 47.563 | 4.903 | 71.887 | 1.00 | 55.90 | C |
| ATOM | 5085 | OG | SER C | 285 | 47.972 | 5.947 | 70.972 | 1.00 | 58.26 | O |
| ATOM | 5086 | C | SER C | 285 | 46.316 | 3.764 | 69.970 | 1.00 | 55.39 | C |
| ATOM | 5087 | O | SER C | 285 | 46.641 | 2.685 | 69.531 | 1.00 | 55.11 | O |
| ATOM | 5088 | N | LYS C | 286 | 45.854 | 4.689 | 69.158 | 1.00 | 54.78 | N |
| ATOM | 5089 | CA | LYS C | 286 | 45.786 | 4.339 | 67.718 | 1.00 | 55.48 | C |
| ATOM | 5090 | CB | LYS C | 286 | 44.785 | 5.226 | 66.925 | 1.00 | 55.50 | C |

TABLE 11-continued

| | | | | | | | | | | |
|---|---|---|---|---|---|---|---|---|---|---|
| ATOM | 5091 | CG | LYS C | 286 | 43.332 | 4.765 | 67.133 | 1.00 | 57.44 | C |
| ATOM | 5092 | CD | LYS C | 286 | 42.291 | 5.563 | 66.310 | 1.00 | 83.71 | C |
| ATOM | 5093 | CE | LYS C | 266 | 42.033 | 6.988 | 66.846 | 1.00 | 63.81 | C |
| ATOM | 5094 | NZ | LYS C | 286 | 43.092 | 7.928 | 66.364 | 1.00 | 67.28 | N |
| ATOM | 5095 | C | LYS C | 286 | 47.177 | 4.227 | 67.017 | 1.00 | 53.80 | C |
| ATOM | 5096 | O | LYS C | 286 | 48.111 | 4.918 | 67.405 | 1.00 | 53.55 | O |
| ATOM | 5097 | N | LYS C | 287 | 47.288 | 3.351 | 56.016 | 1.00 | 51.76 | N |
| ATOM | 5098 | CA | LYS C | 287 | 48.488 | 3.257 | 65.176 | 1.00 | 50.28 | C |
| ATOM | 5099 | CB | LYS C | 287 | 48.306 | 2.191 | 64.070 | 1.00 | 50.03 | C |
| ATOM | 5100 | CG | LYS C | 287 | 48.356 | 0.748 | 64.522 | 1.00 | 49.90 | C |
| ATOM | 5101 | CD | LYS C | 287 | 47.792 | −0.095 | 63.459 | 1.00 | 54.00 | C |
| ATOM | 5102 | CE | LYS C | 287 | 47.723 | −1.539 | 63.843 | 1.00 | 57.12 | C |
| ATOM | 5103 | NZ | LYS C | 287 | 46.761 | −1.752 | 64.928 | 1.00 | 60.32 | N |
| ATOM | 5104 | C | LYS C | 287 | 48.900 | 4.607 | 64.540 | 1.00 | 49.09 | C |
| ATOM | 5105 | O | LYS C | 287 | 48.072 | 5.561 | 64.327 | 1.00 | 48.95 | O |
| ATOM | 5106 | N | VAL C | 288 | 50.183 | 4.762 | 64.247 | 1.00 | 47.97 | N |
| ATOM | 5107 | CA | VAL C | 288 | 50.597 | 5.859 | 63.359 | 1.00 | 46.75 | C |
| ATOM | 5108 | CB | VAL C | 288 | 51.500 | 6.962 | 64.039 | 1.00 | 46.41 | C |
| ATOM | 5109 | CG1 | VAL C | 288 | 51.921 | 6.545 | 65.397 | 1.00 | 45.07 | C |
| ATOM | 5110 | CG2 | VAL C | 288 | 52.670 | 7.343 | 63.211 | 1.00 | 48.77 | C |
| ATOM | 5111 | C | VAL C | 288 | 51.044 | 5.317 | 62.024 | 1.00 | 46.03 | C |
| ATOM | 5112 | O | VAL C | 288 | 51.995 | 4.529 | 61.933 | 1.00 | 45.26 | O |
| ATOM | 5113 | N | ILE C | 289 | 50.298 | 5.746 | 61.002 | 1.00 | 46.31 | N |
| ATOM | 5114 | CA | ILE C | 289 | 50.321 | 5.186 | 59.642 | 1.00 | 46.22 | C |
| ATOM | 5115 | CB | ILE C | 289 | 48.942 | 4.674 | 59.284 | 1.00 | 46.13 | C |
| ATOM | 5116 | CG1 | ILE C | 289 | 48.583 | 3.535 | 60.243 | 1.00 | 46.03 | C |
| ATOM | 5117 | CD1 | ILE C | 289 | 47.174 | 3.430 | 50.585 | 1.00 | 44.04 | C |
| ATOM | 5118 | CG2 | ILE C | 289 | 48.910 | 4.206 | 57.833 | 1.00 | 46.41 | C |
| ATOM | 5119 | C | ILE C | 289 | 50.796 | 6.145 | 58.542 | 1.00 | 46.86 | C |
| ATOM | 5120 | O | ILE C | 289 | 50.254 | 7.234 | 58.358 | 1.00 | 47.16 | O |
| ATOM | 5121 | N | LEU C | 290 | 51.826 | 5.747 | 57.810 | 1.00 | 47.01 | N |
| ATOM | 5122 | CA | LEU C | 290 | 52.132 | 6.428 | 56.582 | 1.00 | 46.04 | C |
| ATOM | 5123 | CB | LEU C | 290 | 53.635 | 6.489 | 56.375 | 1.00 | 45.88 | C |
| ATOM | 5124 | CG | LEU C | 290 | 54.549 | 7.048 | 57.480 | 1.00 | 43.35 | C |
| ATOM | 5125 | CD1 | LEU C | 290 | 55.900 | 7.133 | 56.923 | 1.00 | 38.85 | C |
| ATOM | 5126 | CD2 | LEU C | 290 | 54.169 | 8.448 | 57.918 | 1.00 | 42.00 | C |
| ATOM | 5127 | C | LEU C | 290 | 51.528 | 5.481 | 55.614 | 1.00 | 47.25 | C |
| ATOM | 5128 | O | LEU C | 290 | 51.579 | 4.279 | 55.825 | 1.00 | 48.33 | O |
| ATOM | 5129 | N | ASP C | 291 | 50.935 | 8.008 | 54.554 | 1.00 | 48.26 | N |
| ATOM | 5130 | CA | ASP C | 291 | 50.450 | 5.212 | 53.442 | 1.00 | 48.27 | C |
| ATOM | 5131 | CB | ASP C | 291 | 48.936 | 5.265 | 53.438 | 1.00 | 49.04 | C |
| ATOM | 5132 | CG | ASP C | 291 | 48.315 | 4.479 | 52.288 | 1.00 | 52.76 | C |
| ATOM | 5133 | OD1 | ASP C | 291 | 48.896 | 4.412 | 51.177 | 1.00 | 56.06 | O |
| ATOM | 5134 | OD2 | ASP C | 291 | 47.202 | 3.947 | 52.490 | 1.00 | 58.49 | O |
| ATOM | 5135 | C | ASP C | 291 | 51.015 | 5.746 | 52.128 | 1.00 | 47.79 | C |
| ATOM | 5136 | O | ASP C | 291 | 50.759 | 6.842 | 51.705 | 1.00 | 48.10 | O |
| ATOM | 5137 | N | LEU C | 292 | 51.788 | 4.935 | 51.455 | 1.00 | 48.53 | N |
| ATOM | 5138 | CA | LEU C | 292 | 52.439 | 5.349 | 50.221 | 1.00 | 48.01 | C |
| ATOM | 5139 | CB | LEU C | 292 | 53.940 | 5.055 | 50.336 | 1.00 | 47.59 | C |
| ATOM | 5140 | CG | LEU C | 292 | 54.715 | 5.498 | 51.560 | 1.00 | 45.17 | C |
| ATOM | 5141 | CD1 | LEU C | 292 | 56.120 | 5.495 | 51.148 | 1.00 | 40.02 | C |
| ATOM | 5142 | CD2 | LEU C | 292 | 54.327 | 6.873 | 51.914 | 1.00 | 44.65 | C |
| ATOM | 5143 | C | LEU C | 292 | 51.918 | 4.529 | 49.069 | 1.00 | 48.09 | C |
| ATOM | 5144 | O | LEU C | 292 | 52.166 | 3.313 | 49.041 | 1.00 | 50.59 | O |
| ATOM | 5145 | N | PRO C | 293 | 51.259 | 5.156 | 48.084 | 1.00 | 46.99 | N |
| ATOM | 5146 | CA | PRO C | 293 | 50.642 | 4.336 | 47.050 | 1.00 | 46.12 | C |
| ATOM | 5147 | CB | PRO C | 293 | 49.771 | 5.365 | 46.314 | 1.00 | 47.27 | C |
| ATOM | 5148 | CG | PRO C | 293 | 49.559 | 6.523 | 47.384 | 1.00 | 46.65 | C |
| ATOM | 5149 | CD | PRO C | 293 | 51.009 | 6.571 | 47.825 | 1.00 | 46.64 | C |
| ATOM | 5150 | C | PRO C | 293 | 51.689 | 3.688 | 46.128 | 1.00 | 45.31 | C |
| ATOM | 5151 | O | PRO C | 293 | 52.836 | 4.062 | 46.143 | 1.00 | 46.21 | O |
| ATOM | 5152 | N | LEU C | 294 | 51.332 | 2.654 | 45.402 | 1.00 | 53.44 | N |
| ATOM | 5153 | CA | LEU C | 294 | 52.279 | 1.998 | 44.507 | 1.00 | 43.38 | C |
| ATOM | 5154 | CB | LEU C | 294 | 52.992 | 0.818 | 45.153 | 1.00 | 43.14 | C |
| ATOM | 5155 | CG | LEU C | 294 | 53.381 | 0.800 | 46.637 | 1.00 | 45.84 | C |
| ATOM | 5156 | CD1 | LEU C | 294 | 53.172 | −0.592 | 47.143 | 1.00 | 48.40 | C |
| ATOM | 5157 | CD2 | LEU C | 294 | 54.799 | 1.184 | 46.872 | 1.00 | 44.03 | C |
| ATOM | 5158 | C | LEU C | 294 | 51.568 | 1.499 | 43.260 | 1.00 | 43.04 | C |
| ATOM | 5159 | O | LEU C | 294 | 50.313 | 1.501 | 43.161 | 1.00 | 42.76 | O |
| ATOM | 5160 | N | VAL C | 295 | 52.391 | 1.123 | 42.282 | 1.00 | 41.49 | N |
| ATOM | 5161 | CA | VAL C | 295 | 51.908 | 0.576 | 41.051 | 1.00 | 39.21 | C |
| ATOM | 5162 | CB | VAL C | 295 | 52.373 | 1.420 | 39.897 | 1.00 | 39.23 | C |
| ATOM | 5163 | CG1 | VAL C | 295 | 52.294 | 0.689 | 38.571 | 1.00 | 35.04 | C |
| ATOM | 5164 | CG2 | VAL C | 295 | 51.592 | 2.768 | 39.883 | 1.00 | 37.17 | C |
| ATOM | 5165 | C | VAL C | 295 | 52.585 | −0.733 | 41.051 | 1.00 | 39.77 | C |
| ATOM | 5166 | O | VAL C | 295 | 53.766 | −0.793 | 41.381 | 1.00 | 39.60 | O |
| ATOM | 5167 | N | ILE C | 296 | 51.880 | −1.821 | 40.733 | 1.00 | 40.37 | N |
| ATOM | 5168 | CA | ILE C | 296 | 52.632 | −3.074 | 40.706 | 1.00 | 41.02 | C |
| ATOM | 5169 | CB | ILE C | 296 | 52.523 | −3.901 | 42.035 | 1.00 | 41.49 | C |
| ATOM | 5170 | CG1 | ILE C | 296 | 53.465 | −3.301 | 43.060 | 1.00 | 41.15 | C |

TABLE 11-continued

| | | | | | | | | | | |
|---|---|---|---|---|---|---|---|---|---|---|
| ATOM | 5171 | CD1 | ILE C | 296 | 52.855 | −3.090 | 44.347 | 1.00 | 43.44 | C |
| ATOM | 5172 | CG2 | ILE C | 296 | 53.048 | −5.298 | 41.851 | 1.00 | 42.80 | C |
| ATOM | 5173 | C | ILE C | 296 | 52.333 | −3.844 | 39.492 | 1.00 | 40.08 | C |
| ATOM | 5174 | O | ILE C | 296 | 51.253 | −4.350 | 39.326 | 1.00 | 39.84 | O |
| ATOM | 5175 | N | GLY C | 297 | 53.315 | −3.896 | 38.624 | 1.00 | 40.43 | N |
| ATOM | 5176 | CA | GLY C | 297 | 53.124 | −4.606 | 37.375 | 1.00 | 41.99 | C |
| ATOM | 5177 | C | GLY C | 297 | 53.720 | −5.997 | 37.351 | 1.00 | 42.78 | C |
| ATOM | 5178 | O | GLY C | 297 | 54.540 | −6.346 | 38.223 | 1.00 | 43.43 | O |
| ATOM | 5179 | N | SER C | 298 | 53.316 | −6.786 | 36.374 | 1.00 | 43.47 | N |
| ATOM | 5180 | CA | SER C | 298 | 53.825 | −8.133 | 36.203 | 1.00 | 44.56 | C |
| ATOM | 5181 | CB | SER C | 298 | 52.667 | −9.103 | 35.933 | 1.00 | 44.96 | C |
| ATOM | 5182 | OG | SER C | 298 | 51.597 | −8.436 | 35.300 | 1.00 | 44.35 | O |
| ATOM | 5183 | C | SER C | 298 | 54.903 | −8.229 | 35.107 | 1.00 | 45.65 | C |
| ATOM | 5184 | O | SER C | 298 | 55.099 | −7.280 | 34.304 | 1.00 | 43.89 | O |
| ATOM | 5185 | N | ARG C | 299 | 55.604 | −9.381 | 35.119 | 1.00 | 47.58 | N |
| ATOM | 5186 | CA | ARG C | 299 | 56.668 | −9.702 | 34.165 | 1.00 | 49.19 | C |
| ATOM | 5187 | CB | ARG C | 299 | 57.621 | −10.764 | 34.701 | 1.00 | 50.08 | C |
| ATOM | 5188 | CG | ARG C | 299 | 58.068 | −10.516 | 36.150 | 1.00 | 34.28 | C |
| ATOM | 5189 | CD | ARG C | 299 | 59.466 | −11.050 | 36.458 | 1.00 | 59.46 | C |
| ATOM | 5190 | NE | ARG C | 299 | 60.482 | −9.982 | 36.510 | 1.00 | 63.34 | N |
| ATOM | 5191 | CZ | ARG C | 299 | 60.823 | −9.296 | 37.607 | 1.00 | 62.88 | C |
| ATOM | 5192 | NH1 | ARG C | 299 | 60.231 | −9.548 | 38.772 | 1.00 | 62.72 | N |
| ATOM | 5193 | NH2 | ARG C | 299 | 61.760 | −8.349 | 37.537 | 1.00 | 62.07 | N |
| ATOM | 5194 | C | ARG C | 299 | 56.042 | −10.204 | 32.917 | 1.00 | 49.11 | C |
| ATOM | 5195 | O | ARG C | 299 | 56.052 | −9.480 | 31.937 | 1.00 | 50.56 | O |
| TER | | | | | | | | | | |
| ATOM | 5196 | N | MET D | 1 | 84.926 | 16.828 | 78.667 | 1.00 | 56.17 | N |
| ATOM | 5197 | CA | MET D | 1 | 84.714 | 16.943 | 77.187 | 1.00 | 56.17 | C |
| ATOM | 5198 | CB | MET D | 1 | 85.951 | 17.520 | 76.502 | 1.00 | 56.37 | C |
| ATOM | 5199 | CG | MET D | 1 | 86.196 | 18.980 | 76.860 | 1.00 | 60.17 | C |
| ATOM | 5200 | SD | MET D | 1 | 84.935 | 20.190 | 76.305 | 1.00 | 66.37 | S |
| ATOM | 5201 | CE | MET D | 1 | 84.882 | 19.827 | 74.543 | 1.00 | 63.97 | C |
| ATOM | 5202 | C | MET D | 1 | 84.440 | 15.597 | 76.594 | 1.00 | 55.10 | C |
| ATOM | 5203 | O | MET D | 1 | 84.957 | 14.607 | 77.098 | 1.00 | 54.50 | O |
| ATOM | 5204 | N | VAL D | 2 | 83.624 | 15.563 | 75.534 | 1.00 | 54.62 | N |
| ATOM | 5205 | CA | VAL D | 2 | 83.408 | 14.337 | 74.756 | 1.00 | 53.80 | C |
| ATOM | 5206 | CB | VAL D | 2 | 81.929 | 14.130 | 74.496 | 1.00 | 53.98 | C |
| ATOM | 5207 | CG1 | VAL D | 2 | 81.681 | 12.780 | 73.812 | 1.00 | 53.51 | C |
| ATOM | 5208 | CG2 | VAL D | 2 | 81.155 | 14.208 | 75.805 | 1.00 | 53.18 | C |
| ATOM | 5209 | C | VAL D | 2 | 84.201 | 14.317 | 73.429 | 1.00 | 53.44 | C |
| ATOM | 5210 | O | VAL D | 2 | 84.171 | 15.270 | 72.681 | 1.00 | 52.78 | O |
| ATOM | 5211 | N | LYS D | 3 | 84.909 | 13.224 | 73.133 | 1.00 | 53.18 | N |
| ATOM | 5212 | CA | LYS D | 3 | 85.642 | 13.126 | 71.864 | 1.00 | 52.42 | C |
| ATOM | 5213 | CB | LYS D | 3 | 86.879 | 12.260 | 72.024 | 1.00 | 52.53 | C |
| ATOM | 5214 | CG | LYS D | 3 | 87.937 | 12.544 | 70.367 | 1.00 | 53.99 | C |
| ATOM | 5215 | CD | LYS D | 3 | 88.625 | 11.271 | 70.451 | 1.00 | 55.01 | C |
| ATOM | 5216 | CE | LYS D | 3 | 89.936 | 11.640 | 69.740 | 1.00 | 57.63 | C |
| ATOM | 5217 | NZ | LYS D | 3 | 89.732 | 11.934 | 68.295 | 1.00 | 58.41 | N |
| ATOM | 5218 | C | LYS D | 3 | 84.763 | 12.497 | 70.800 | 1.00 | 52.20 | C |
| ATOM | 5219 | O | LYS D | 3 | 84.127 | 11.469 | 71.065 | 1.00 | 52.81 | O |
| ATOM | 5220 | N | GLN D | 4 | 84.761 | 13.092 | 69.609 | 1.00 | 51.37 | N |
| ATOM | 5221 | CA | GLN D | 4 | 83.937 | 12.681 | 68.499 | 1.00 | 52.23 | C |
| ATOM | 5222 | CB | GLN D | 4 | 88.518 | 13.913 | 67.694 | 1.00 | 51.41 | C |
| ATOM | 5223 | CG | GLN D | 4 | 82.511 | 13.668 | 66.528 | 1.00 | 56.43 | C |
| ATOM | 5224 | CD | GLN D | 4 | 80.989 | 13.494 | 66.929 | 1.00 | 60.49 | C |
| ATOM | 5225 | OE1 | GLN D | 4 | 80.346 | 14.420 | 67.460 | 1.00 | 62.53 | O |
| ATOM | 5226 | NE2 | GLN D | 4 | 80.425 | 12.307 | 66.633 | 1.00 | 59.61 | N |
| ATOM | 5227 | C | GLN D | 4 | 84.617 | 11.598 | 67.623 | 1.00 | 52.97 | C |
| ATOM | 5228 | O | GLN D | 4 | 85.594 | 11.866 | 66.948 | 1.00 | 53.85 | O |
| ATOM | 5229 | N | ILE D | 5 | 84.125 | 10.364 | 67.622 | 1.00 | 53.57 | N |
| ATOM | 5230 | CA | ILE D | 5 | 84.792 | 9.400 | 66.776 | 1.00 | 54.47 | C |
| ATOM | 5231 | CB | ILE D | 5 | 84.546 | 8.007 | 67.194 | 1.00 | 53.54 | C |
| ATOM | 5252 | CG1 | ILE D | 5 | 85.291 | 7.759 | 68.502 | 1.00 | 53.46 | C |
| ATOM | 5233 | CD1 | ILE D | 5 | 86.665 | 8.289 | 68.561 | 1.00 | 52.27 | C |
| ATOM | 5234 | CG2 | ILE D | 5 | 84.932 | 7.064 | 66.067 | 1.00 | 52.29 | C |
| ATOM | 5235 | C | ILE D | 5 | 84.386 | 9.582 | 65.323 | 1.00 | 56.14 | C |
| ATOM | 5236 | O | ILE D | 5 | 83.203 | 9.646 | 65.003 | 1.00 | 57.33 | O |
| ATOM | 5237 | N | GLU D | 6 | 85.349 | 9.692 | 64.430 | 1.00 | 56.99 | N |
| ATOM | 5238 | CA | GLU D | 6 | 84.927 | 9.906 | 63.080 | 1.00 | 57.59 | C |
| ATOM | 5239 | CB | GLU D | 6 | 85.691 | 11.075 | 62.437 | 1.00 | 58.86 | C |
| ATOM | 5240 | CG | GLU D | 6 | 85.101 | 12.489 | 62.726 | 1.00 | 61.95 | C |
| ATOM | 5241 | CD | GLU D | 6 | 83.568 | 12.618 | 62.464 | 1.00 | 67.13 | C |
| ATOM | 5242 | OE1 | GLU D | 6 | 83.047 | 12.007 | 61.502 | 1.00 | 68.15 | O |
| ATOM | 5243 | OE2 | GLU D | 6 | 82.877 | 13.350 | 63.222 | 1.00 | 68.59 | O |
| ATOM | 5244 | C | GLU D | 6 | 84.981 | 8.639 | 62.255 | 1.00 | 57.09 | C |
| ATOM | 5245 | O | GLU D | 6 | 84.503 | 8.640 | 61.138 | 1.00 | 56.42 | O |
| ATOM | 5246 | N | SER D | 7 | 85.525 | 7.555 | 62.821 | 1.00 | 57.32 | N |
| ATOM | 5247 | CA | SER D | 7 | 85.713 | 8.306 | 82.066 | 1.00 | 57.19 | C |
| ATOM | 5248 | CB | SER D | 7 | 86.797 | 6.487 | 61.024 | 1.00 | 57.14 | C |

TABLE 11-continued

| | | | | | | | | | |
|---|---|---|---|---|---|---|---|---|---|
| ATOM | 5249 | OG | SER D | 7 | 88.013 | 6.765 | 61.682 | 1.00 | 57.59 | O |
| ATOM | 5250 | C | SER D | 7 | 86.112 | 5.089 | 52.885 | 1.00 | 56.89 | C |
| ATOM | 5251 | O | SER D | 7 | 86.435 | 5.187 | 64.054 | 1.00 | 56.55 | O |
| ATOM | 5252 | N | LYS D | 8 | 86.121 | 3.942 | 62.209 | 1.00 | 56.60 | N |
| ATOM | 5253 | CA | LYS D | 8 | 86.557 | 2.693 | 62.795 | 1.00 | 56.35 | C |
| ATOM | 5254 | CB | LYS D | 8 | 86.420 | 1.587 | 61.758 | 1.00 | 55.96 | C |
| ATOM | 5255 | CG | LYS D | 8 | 86.105 | 0.237 | 62.402 | 1.00 | 56.40 | C |
| ATOM | 5256 | CD | LYS D | 8 | 84.882 | −0.463 | 61.738 | 1.00 | 54.35 | C |
| ATOM | 5257 | CE | LYS D | 8 | 85.281 | −1.432 | 60.660 | 1.00 | 53.97 | C |
| ATOM | 5258 | NZ | LYS D | 8 | 86.250 | −2.402 | 61.233 | 1.00 | 55.13 | N |
| ATOM | 5259 | C | LYS D | 8 | 88.004 | 2.786 | 63.294 | 1.00 | 56.25 | C |
| ATOM | 5260 | O | LYS D | 8 | 88.356 | 2.301 | 64.368 | 1.00 | 56.14 | O |
| ATOM | 5261 | N | THR D | 9 | 88.854 | 3.417 | 62.507 | 1.00 | 55.88 | N |
| ATOM | 5232 | CA | THR D | 9 | 90.199 | 3.698 | 62.979 | 1.00 | 55.54 | C |
| ATOM | 5263 | CB | THR D | 9 | 91.015 | 4.353 | 61.863 | 1.00 | 55.07 | C |
| ATOM | 5264 | OG1 | THR D | 9 | 81.053 | 3.441 | 60.770 | 1.00 | 55.00 | O |
| ATOM | 5265 | CG2 | THR D | 9 | 92.434 | 4.651 | 62.285 | 1.00 | 54.98 | C |
| ATOM | 5266 | C | THR D | 9 | 90.174 | 4.527 | 64. 273 | 1.00 | 55.74 | C |
| ATOM | 5267 | O | THR D | 9 | 90.660 | 4.072 | 65.306 | 1.00 | 55.70 | O |
| ATOM | 5268 | N | ALA D | 10 | 89.561 | 5.715 | 64.232 | 1.00 | 56.37 | N |
| ATOM | 5269 | CA | ALA D | 10 | 89.572 | 6.640 | 65.387 | 1.00 | 55.94 | C |
| ATOM | 5270 | CB | ALA D | 10 | 88.661 | 7.880 | 65.152 | 1.00 | 55.95 | C |
| ATOM | 5271 | C | ALA D | 10 | 89.133 | 5.861 | 66.603 | 1.00 | 55.45 | C |
| ATOM | 5272 | O | ALA D | 10 | 89.663 | 6.058 | 67.688 | 1.00 | 55.29 | O |
| ATOM | 5273 | N | PHE D | 11 | 88.198 | 4.945 | 66.372 | 1.00 | 55.09 | N |
| ATOM | 5274 | CA | PHE D | 11 | 87.647 | 4.119 | 67.399 | 1.00 | 55.04 | C |
| ATOM | 5275 | CB | PHE D | 11 | 86.645 | 3.183 | 66.823 | 1.00 | 55.04 | C |
| ATOM | 5276 | CG | PHE D | 11 | 85.674 | 2.713 | 67.821 | 1.00 | 57.35 | C |
| ATOM | 5277 | CD1 | PHE D | 11 | 85.190 | 3.614 | 68.811 | 1.00 | 59.38 | C |
| ATOM | 5278 | CE1 | PHE D | 11 | 84.244 | 3.196 | 89.770 | 1.00 | 59.84 | C |
| ATOM | 5279 | CZ | PHE D | 11 | 83.781 | 1.879 | 69.735 | 1.00 | 59.09 | C |
| ATOM | 5280 | CE2 | PHE D | 11 | 84.262 | 0.986 | 68.745 | 1.00 | 57.90 | C |
| ATOM | 5281 | CD2 | PHE D | 11 | 85.200 | 1.406 | 67.791 | 1.00 | 56.60 | C |
| ATOM | 5282 | C | PHE D | 11 | 88.653 | 3.244 | 68.063 | 1.00 | 55.14 | C |
| ATOM | 5283 | O | PHE D | 11 | 88.701 | 3.196 | 69.291 | 1.00 | 55.58 | O |
| ATOM | 5284 | N | GLN D | 12 | 89.424 | 2.520 | 67.251 | 1.00 | 54.83 | N |
| ATOM | 5285 | CA | GLN D | 12 | 90.423 | 1.601 | 67.753 | 1.00 | 54.13 | C |
| ATOM | 5286 | CB | GLN D | 12 | 91.084 | 0.841 | 66.605 | 1.00 | 54.12 | C |
| ATOM | 5287 | CG | GLN D | 12 | 91.643 | −0.495 | 67.080 | 1.00 | 54.56 | C |
| ATOM | 5288 | CD | GLN D | 12 | 90.661 | −1.219 | 67.985 | 1.00 | 55.86 | C |
| ATOM | 5289 | OE1 | GLN D | 12 | 90.147 | −2.282 | 67.656 | 1.00 | 56.41 | O |
| ATOM | 5290 | NE2 | GLN D | 12 | 90.362 | −0.611 | 69.128 | 1.00 | 56.61 | N |
| ATOM | 5291 | C | GLN D | 12 | 91.475 | 2.341 | 68.571 | 1.00 | 53.81 | C |
| ATOM | 5292 | O | GLN D | 12 | 91.822 | 1.946 | 69.683 | 1.00 | 53.46 | O |
| ATOM | 5293 | N | GLU D | 13 | 91.958 | 3.438 | 68.015 | 1.00 | 53.38 | N |
| ATOM | 5294 | CA | GLU D | 13 | 92.946 | 4.225 | 68.675 | 1.00 | 53.17 | C |
| ATOM | 5295 | CB | GLU D | 13 | 93.381 | 5.377 | 67.788 | 1.00 | 53.04 | C |
| ATOM | 5296 | CG | GLU D | 13 | 94.196 | 4.824 | 66.631 | 1.00 | 53.93 | C |
| ATOM | 5297 | CD | GLU D | 13 | 95.481 | 4.079 | 67.112 | 1.00 | 56.83 | C |
| ATOM | 5298 | OE1 | GLU D | 13 | 96.260 | 4.723 | 67.871 | 1.00 | 53.76 | O |
| ATOM | 5299 | OE2 | GLU D | 13 | 95.715 | 2.877 | 66.733 | 1.00 | 57.02 | O |
| ATOM | 5300 | C | GLU D | 13 | 92.421 | 4.675 | 70.014 | 1.00 | 53.34 | C |
| ATOM | 5301 | O | GLU D | 13 | 93.093 | 4.507 | 71.040 | 1.00 | 53.94 | O |
| ATOM | 5302 | N | ALA D | 14 | 91.208 | 5.199 | 70.031 | 1.00 | 53.06 | N |
| ATOM | 5303 | CA | ALA D | 14 | 90.601 | 5.553 | 71.298 | 1.00 | 52.99 | C |
| ATOM | 5304 | CB | ALA D | 14 | 89.167 | 6.046 | 71.108 | 1.00 | 52.36 | C |
| ATOM | 5305 | C | ALA D | 14 | 90.677 | 4.384 | 72.296 | 1.00 | 53.31 | C |
| ATOM | 5306 | O | ALA D | 14 | 91.226 | 4.558 | 73.387 | 1.00 | 53.88 | O |
| ATOM | 5307 | N | LEU D | 15 | 90.169 | 3.209 | 71.913 | 1.00 | 53.70 | N |
| ATOM | 5308 | CA | LEU D | 15 | 90.025 | 2.047 | 72.813 | 1.00 | 54.88 | C |
| ATOM | 5309 | CB | LEU D | 15 | 89.455 | 0.861 | 72.028 | 1.00 | 54.83 | C |
| ATOM | 5310 | CG | LEU D | 15 | 87.987 | 0.451 | 72.212 | 1.00 | 56.20 | C |
| ATOM | 5311 | CD1 | LEU D | 15 | 87.042 | 1.715 | 73.302 | 1.00 | 57.43 | C |
| ATOM | 5312 | CD2 | LEU D | 15 | 87.503 | −0.591 | 71.161 | 1.00 | 52.76 | C |
| ATOM | 5313 | C | LEU D | 15 | 91.314 | 1.587 | 73.521 | 1.00 | 56.19 | C |
| ATOM | 5314 | O | LEU D | 15 | 91.274 | 1.114 | 74.658 | 1.00 | 56.18 | O |
| ATOM | 5315 | N | ASP D | 16 | 92.444 | 1.723 | 72.623 | 1.00 | 57.06 | N |
| ATOM | 5316 | CA | ASP D | 16 | 93.714 | 1.188 | 73.257 | 1.00 | 57.59 | C |
| ATOM | 5317 | CB | ASP D | 16 | 94.496 | 0.657 | 72.036 | 1.00 | 58.11 | C |
| ATOM | 5318 | CG | ASP D | 16 | 93.690 | −0.340 | 71.168 | 1.00 | 58.95 | C |
| ATOM | 5319 | OD1 | ASP D | 16 | 92.719 | −0.961 | 71.682 | 1.00 | 60.38 | O |
| ATOM | 5320 | OD2 | APS D | 16 | 94.054 | −0.512 | 89.971 | 1.00 | 57.04 | O |
| ATOM | 5321 | C | ASP D | 16 | 94.517 | 2.295 | 73.927 | 1.00 | 57.68 | C |
| ATOM | 5322 | O | ASP D | 16 | 95.254 | 2.046 | 74.876 | 1.00 | 57.48 | O |
| ATOM | 5323 | N | ALA D | 17 | 94.401 | 3.515 | 73.401 | 1.00 | 57.95 | N |
| ATOM | 5324 | CA | ALA D | 17 | 95.081 | 4.667 | 74.020 | 1.00 | 58.27 | C |
| ATOM | 5325 | CB | ALA D | 17 | 95.009 | 5.919 | 73.134 | 1.00 | 58.12 | C |
| ATOM | 5326 | C | ALA D | 17 | 94.441 | 4.926 | 75.375 | 1.00 | 58.49 | C |
| ATOM | 5327 | O | ALA D | 17 | 95.051 | 5.539 | 76.239 | 1.00 | 58.41 | O |
| ATOM | 5328 | N | ALA D | 18 | 93.202 | 4.461 | 75.549 | 1.00 | 58.72 | N |

TABLE 11-continued

| | | | | | | | | | | |
|---|---|---|---|---|---|---|---|---|---|---|
| ATOM | 5329 | CA | ALA D | 18 | 92.588 | 4.413 | 76.866 | 1.00 | 59.00 | C |
| ATOM | 5330 | CB | ALA D | 18 | 91.193 | 3.809 | 76.769 | 1.00 | 58.39 | C |
| ATOM | 5331 | C | ALA D | 18 | 93.524 | 3.540 | 77.694 | 1.00 | 59.33 | C |
| ATOM | 5332 | O | ALA D | 18 | 94.454 | 2.937 | 77.153 | 1.00 | 59.90 | O |
| ATOM | 5333 | N | GLY D | 19 | 93.342 | 3.436 | 78.989 | 1.00 | 59.40 | N |
| ATOM | 5334 | CA | GLY D | 19 | 94.376 | 2.660 | 79.670 | 1.00 | 60.53 | C |
| ATOM | 5335 | C | GLY D | 19 | 93.712 | 1.481 | 80.280 | 1.00 | 60.94 | C |
| ATOM | 5336 | O | GLY D | 19 | 93.041 | 0.689 | 79.594 | 1.00 | 61.44 | O |
| ATOM | 5337 | N | ASP D | 20 | 93.880 | 1.375 | 81.588 | 1.00 | 60.45 | N |
| ATOM | 5338 | CA | ASP C | 20 | 92.881 | 0.637 | 82.330 | 1.00 | 60.27 | C |
| ATOM | 5339 | CB | ASP C | 20 | 93.455 | 0.236 | 83.704 | 1.00 | 60.19 | C |
| ATOM | 5340 | CG | ASP D | 20 | 94.033 | −1.234 | 83.693 | 1.00 | 63.17 | C |
| ATOM | 5341 | OD1 | ASP D | 20 | 95.051 | −1.575 | 84.433 | 1.00 | 61.37 | O |
| ATOM | 5342 | OD2 | ASP D | 20 | 93.406 | −2.047 | 82.938 | 1.00 | 63.37 | O |
| ATOM | 5343 | C | ASP C | 20 | 91.534 | 1.437 | 82.403 | 1.00 | 59.19 | C |
| ATOM | 5344 | O | ASP C | 20 | 90.525 | 8.979 | 82.973 | 1.00 | 58.99 | C |
| ATOM | 5345 | N | LYS D | 21 | 91.491 | 2.618 | 81.797 | 1.00 | 57.84 | N |
| ATOM | 5346 | CA | LYS D | 21 | 90.390 | 3.537 | 82.104 | 1.00 | 57.43 | C |
| ATOM | 5347 | CB | LYS D | 21 | 90.744 | 4.950 | 81.650 | 1.00 | 57.30 | C |
| ATOM | 5348 | CG | LYS D | 21 | 92.225 | 5.251 | 81.565 | 1.00 | 58.95 | C |
| ATOM | 5349 | CD | LYS D | 21 | 92.524 | 6.654 | 82.106 | 1.00 | 61.20 | C |
| ATOM | 5350 | CE | LYS D | 21 | 92.351 | 7.762 | 81.051 | 1.00 | 64.85 | C |
| ATOM | 5351 | NZ | LYS D | 21 | 93.404 | 7.758 | 79.945 | 1.00 | 65.74 | N |
| ATOM | 5352 | C | LYS D | 21 | 89.015 | 3.117 | 81.525 | 1.00 | 57.07 | C |
| ATOM | 5353 | O | LYS D | 21 | 88.920 | 2.380 | 80.517 | 1.00 | 58.78 | O |
| ATOM | 5354 | N | LEU D | 22 | 87.937 | 3.566 | 82.158 | 1.00 | 56.08 | N |
| ATOM | 5355 | CA | LEU D | 22 | 86.629 | 3.249 | 81.633 | 1.00 | 55.27 | C |
| ATOM | 5356 | CB | LEU D | 22 | 85.587 | 3.348 | 82.729 | 1.00 | 55.02 | C |
| ATOM | 5357 | CG | LEU D | 22 | 84.106 | 3.286 | 82.439 | 1.00 | 53.83 | C |
| ATOM | 5358 | CD1 | LEU D | 22 | 83.501 | 1.874 | 82.280 | 1.00 | 48.52 | C |
| ATOM | 5359 | CD2 | LEU D | 22 | 83.431 | 4.100 | 83.391 | 1.00 | 55.25 | C |
| ATOM | 5360 | C | LEU D | 22 | 86.316 | 4.209 | 80.476 | 1.00 | 55.90 | C |
| ATOM | 5361 | O | LEU D | 22 | 86.544 | 5.416 | 80.591 | 1.00 | 56.11 | O |
| ATOM | 5362 | N | VAL D | 23 | 85.836 | 3.647 | 79.362 | 1.00 | 55.16 | N |
| ATOM | 5363 | CA | VAL D | 23 | 85.412 | 4.403 | 78.199 | 1.00 | 55.20 | C |
| ATOM | 5364 | CB | VAL D | 23 | 85.906 | 3.764 | 76.873 | 1.00 | 55.38 | C |
| ATOM | 5365 | CG1 | VAL D | 23 | 85.744 | 4.756 | 75.737 | 1.00 | 56.04 | C |
| ATOM | 5366 | CG2 | VAL D | 23 | 87.299 | 3.282 | 76.964 | 1.00 | 54.35 | C |
| ATOM | 5367 | C | VAL D | 23 | 83.88 | 4.324 | 78.080 | 1.00 | 54.52 | C |
| ATOM | 5368 | O | VAL D | 23 | 83.324 | 3.231 | 78.036 | 1.00 | 54.43 | O |
| ATOM | 5369 | N | VAL D | 24 | 83.225 | 5.455 | 77.977 | 1.00 | 52.97 | N |
| ATOM | 5370 | CA | VAL D | 24 | 81.837 | 5.363 | 77.661 | 1.00 | 53.70 | C |
| ATOM | 5371 | CB | VAL D | 24 | 80.983 | 5.915 | 78.832 | 1.00 | 53.19 | C |
| ATOM | 5372 | CG1 | VAL D | 24 | 81.566 | 7.178 | 79.332 | 1.00 | 54.84 | C |
| ATOM | 5373 | CG2 | VAL D | 24 | 79.577 | 6.142 | 78.416 | 1.00 | 52.72 | C |
| ATOM | 5374 | C | VAL D | 24 | 81.608 | 5.958 | 76.236 | 1.00 | 53.85 | C |
| ATOM | 5375 | O | VAL D | 24 | 82.339 | 6.854 | 75.839 | 1.00 | 54.76 | O |
| ATOM | 5376 | N | VAL D | 25 | 80.678 | 5.397 | 75.455 | 1.00 | 53.72 | N |
| ATOM | 5377 | CA | VAL D | 25 | 80.417 | 5.777 | 74.054 | 1.00 | 53.32 | C |
| ATOM | 5378 | CB | VAL D | 25 | 80.647 | 4.602 | 73.096 | 1.00 | 53.49 | C |
| ATOM | 5379 | CG1 | VAL D | 25 | 80.584 | 5.073 | 71.656 | 1.00 | 53.16 | C |
| ATOM | 5380 | CG2 | VAL D | 25 | 81.956 | 3.925 | 73.373 | 1.00 | 55.46 | C |
| ATOM | 5381 | C | VAL D | 25 | 78.951 | 5.993 | 73.919 | 1.00 | 53.11 | C |
| ATOM | 5382 | O | VAL D | 25 | 78.154 | 5.104 | 74.144 | 1.00 | 53.83 | O |
| ATOM | 5383 | N | ASP D | 26 | 78.569 | 7.170 | 73.509 | 1.00 | 53.46 | N |
| ATOM | 5384 | CA | ASP D | 26 | 77.159 | 7.435 | 73.311 | 1.00 | 52.88 | C |
| ATOM | 5385 | CB | ASP D | 26 | 76.859 | 8.826 | 73.852 | 1.00 | 53.22 | C |
| ATOM | 5386 | CG | ASP D | 26 | 75.676 | 9.489 | 73.217 | 1.00 | 55.17 | C |
| ATOM | 5387 | OD1 | ASP D | 26 | 74.760 | 8.803 | 72.747 | 1.00 | 60.41 | O |
| ATOM | 5388 | OD2 | ASPD | 26 | 75.665 | 10.738 | 73.208 | 1.00 | 59.37 | O |
| ATOM | 5389 | C | ASP D | 26 | 76.925 | 7.366 | 71.824 | 1.00 | 51.94 | C |
| ATOM | 5390 | O | ASP D | 26 | 77.364 | 8.171 | 71.063 | 1.00 | 51.87 | O |
| ATOM | 5391 | N | PHE D | 27 | 76.319 | 6.197 | 71.410 | 1.00 | 50.79 | N |
| ATOM | 5392 | CA | PHE D | 27 | 75.920 | 6.053 | 70.018 | 1.00 | 50.81 | C |
| ATOM | 5393 | CB | PHE D | 27 | 75.677 | 4.621 | 69.596 | 1.00 | 50.46 | C |
| ATOM | 5394 | CG | PHE D | 27 | 76.924 | 3.793 | 69.559 | 1.00 | 51.58 | C |
| ATOM | 5395 | CD1 | PHE D | 27 | 77.685 | 3.696 | 68.421 | 1.00 | 51.28 | C |
| ATOM | 5396 | CE1 | PHE D | 27 | 78.799 | 2.922 | 68.368 | 1.00 | 48.60 | C |
| ATOM | 5397 | CZ | PHE D | 27 | 79.199 | 2.208 | 69.491 | 1.00 | 53.08 | C |
| ATOM | 5398 | CE2 | PHE D | 27 | 78.481 | 2.290 | 70.650 | 1.00 | 54.56 | C |
| ATOM | 5399 | CD2 | PHE D | 27 | 77.339 | 3.102 | 70.691 | 1.00 | 53.28 | C |
| ATOM | 5400 | C | PHE D | 27 | 74.692 | 6.855 | 69.870 | 1.00 | 51.10 | C |
| ATOM | 5401 | O | PHE D | 27 | 73.699 | 6.629 | 70.554 | 1.00 | 50.88 | O |
| ATOM | 5402 | N | SER D | 28 | 74.812 | 7.816 | 68.957 | 1.00 | 51.51 | N |
| ATOM | 5403 | CA | SER D | 28 | 73.947 | 8.945 | 68.813 | 1.00 | 50.87 | C |
| ATOM | 5404 | CB | SER D | 28 | 74.704 | 10.128 | 69.372 | 1.00 | 50.53 | C |
| ATOM | 5405 | OG | SER D | 28 | 73.787 | 11.137 | 69.635 | 1.00 | 53.39 | O |
| ATOM | 5406 | C | SER D | 28 | 73.560 | 9.199 | 67.326 | 1.00 | 51.48 | C |
| ATOM | 5407 | O | SER D | 28 | 74.178 | 8.584 | 65.349 | 1.00 | 50.82 | O |
| ATOM | 5408 | N | ALA D | 29 | 72.569 | 10.108 | 67.156 | 1.00 | 50.35 | N |

TABLE 11-continued

| | | | | | | | | | |
|---|---|---|---|---|---|---|---|---|---|
| ATOM | 5409 | CA | ALA D | 29 | 72.146 | 10.583 | 65.850 | 1.00 | 49.99 | C |
| ATOM | 5410 | CB | ALA D | 29 | 71.057 | 9.754 | 65.355 | 1.00 | 49.96 | C |
| ATOM | 5411 | C | ALA D | 29 | 71.677 | 12.015 | 65.994 | 1.00 | 50.87 | C |
| ATOM | 5412 | O | ALA D | 29 | 71.048 | 12.322 | 67.012 | 1.00 | 50.76 | O |
| ATOM | 5413 | N | THR D | 30 | 71.926 | 12.896 | 65.001 | 1.00 | 50.54 | N |
| ATOM | 5414 | CA | THR D | 30 | 71.659 | 14.328 | 65.255 | 1.00 | 50.57 | C |
| ATOM | 5415 | CB | THR D | 30 | 72.502 | 15.315 | 54.391 | 1.00 | 51.01 | C |
| ATOM | 5416 | OG1 | THR D | 30 | 71.823 | 15.536 | 63.152 | 1.00 | 55.61 | O |
| ATOM | 5417 | CG2 | THR D | 30 | 73.932 | 14.831 | 64.091 | 1.00 | 52.12 | C |
| ATOM | 5418 | C | THR D | 30 | 70.192 | 14.727 | 65.126 | 1.00 | 49.93 | C |
| ATOM | 5419 | O | THR D | 30 | 69.839 | 15.866 | 65.499 | 1.00 | 49.69 | O |
| ATOM | 5420 | N | TRP D | 31 | 69.349 | 13.822 | 64.590 | 1.00 | 49.71 | N |
| ATOM | 5421 | CA | TRP D | 31 | 67.900 | 14.073 | 64.375 | 1.00 | 49.75 | C |
| ATOM | 5422 | CB | TRP D | 31 | 67.469 | 13.532 | 63.016 | 1.00 | 48.99 | C |
| ATOM | 5423 | CG | TRP D | 31 | 67.898 | 12.098 | 62.808 | 1.00 | 49.36 | C |
| ATOM | 5424 | CD1 | TRP D | 31 | 69.038 | 11.662 | 62.182 | 1.00 | 48.16 | C |
| ATOM | 5425 | NE1 | TPR D | 31 | 69.104 | 10.289 | 62.204 | 1.00 | 47.61 | N |
| ATOM | 5426 | CE2 | TRP D | 31 | 67.996 | 9.796 | 62.834 | 1.00 | 48.46 | C |
| ATOM | 5427 | CD2 | TRP D | 31 | 67.200 | 10.916 | 63.231 | 1.00 | 47.73 | C |
| ATOM | 5428 | CE3 | TRP D | 31 | 65.994 | 10.692 | 63.918 | 1.00 | 45.51 | C |
| ATOM | 5429 | CZ3 | TRP D | 31 | 65.603 | 9.360 | 64.161 | 1.00 | 49.17 | C |
| ATOM | 5430 | CH2 | TRP D | 31 | 66.433 | 8.255 | 63.762 | 1.00 | 48.38 | C |
| ATOM | 5431 | CZ2 | TRP D | 31 | 67.630 | 8.461 | 63.106 | 1.00 | 48.67 | C |
| ATOM | 5432 | C | TRP D | 31 | 66.969 | 13.528 | 65.492 | 1.00 | 50.57 | C |
| ATOM | 5433 | O | TRP D | 31 | 65.779 | 13.873 | 65.557 | 1.00 | 50.88 | O |
| ATOM | 5434 | N | CYS D | 32 | 67.539 | 12.685 | 66.357 | 1.00 | 51.78 | N |
| ATOM | 5435 | CA | CYS D | 32 | 66.879 | 11.982 | 67.494 | 1.00 | 52.83 | C |
| ATOM | 5436 | CB | CYS D | 32 | 61.753 | 10.792 | 67.962 | 1.00 | 52.74 | C |
| ATOM | 5437 | SG | CYS D | 32 | 66.902 | 9.798 | 69.266 | 1.00 | 56.81 | S |
| ATOM | 5438 | C | CYS D | 32 | 66.637 | 12.843 | 68.746 | 1.00 | 52.75 | C |
| ATOM | 5439 | O | CY3 D | 32 | 67.584 | 13.190 | 69.464 | 1.00 | 53.54 | O |
| ATOM | 5440 | N | GLY D | 33 | 65.382 | 13.135 | 69.050 | 1.00 | 52.48 | N |
| ATOM | 5441 | CA | GLY D | 33 | 65.064 | 13.967 | 70.193 | 1.00 | 52.19 | C |
| ATOM | 5442 | C | GLY D | 33 | 65.790 | 13.450 | 71.400 | 1.00 | 52.61 | C |
| ATOM | 5443 | O | GLY D | 33 | 66.593 | 14.198 | 71.980 | 1.00 | 54.02 | O |
| ATOM | 5444 | N | PRO D | 34 | 65.550 | 12.177 | 71.776 | 1.00 | 51.66 | N |
| ATOM | 5445 | CA | PRO D | 34 | 66.189 | 11.656 | 72.988 | 1.00 | 51.96 | C |
| ATOM | 5446 | CB | PRO D | 34 | 65.729 | 10.178 | 73.073 | 1.00 | 52.97 | C |
| ATOM | 5447 | CG | PRO D | 34 | 64.796 | 9.943 | 71.891 | 1.00 | 51.56 | C |
| ATOM | 5448 | CD | PRO D | 34 | 64.648 | 11.212 | 71.120 | 1.00 | 51.30 | C |
| ATOM | 5449 | C | PRO D | 34 | 67.698 | 11.740 | 72.93 | 1.00 | 52.36 | C |
| ATOM | 5450 | O | PRO D | 34 | 60.325 | 12.181 | 73.896 | 1.00 | 52.23 | O |
| ATOM | 5451 | N | ALA D | 35 | 68.315 | 11.314 | 71.842 | 1.00 | 52.96 | N |
| ATOM | 5452 | CA | ALA D | 35 | 69.777 | 11.547 | 71.744 | 1.00 | 53.85 | C |
| ATOM | 5453 | CB | ALA D | 35 | 70.379 | 10.993 | 70.472 | 1.00 | 52.59 | C |
| ATOM | 5454 | C | ALA D | 35 | 70.160 | 13.035 | 71.948 | 1.00 | 54.03 | C |
| ATOM | 5455 | O | ALA D | 35 | 71.084 | 13.307 | 72.685 | 1.00 | 55.17 | O |
| ATOM | 5456 | N | LYS D | 36 | 69.448 | 13.970 | 71.321 | 1.00 | 54.27 | N |
| ATOM | 5457 | CA | LYS D | 36 | 69.672 | 15.409 | 71.556 | 1.00 | 54.70 | C |
| ATOM | 5458 | CB | LYS D | 36 | 68.710 | 16.295 | 70.742 | 1.00 | 54.65 | C |
| ATOM | 5459 | CG | LYS D | 36 | 69.233 | 16.812 | 69.429 | 1.00 | 53.33 | C |
| ATOM | 5450 | CD | LYS D | 36 | 68.138 | 17.699 | 68.773 | 1.00 | 59.83 | C |
| ATOM | 5461 | CE | LYS D | 36 | 66.912 | 16.895 | 63.187 | 1.00 | 59.98 | C |
| ATOM | 5462 | NZ | LYS D | 36 | 65.801 | 17.763 | 67.578 | 1.00 | 60.44 | N |
| ATOM | 5463 | C | LYS D | 36 | 69.493 | 15.799 | 73.019 | 1.00 | 54.76 | C |
| ATOM | 5464 | O | LYS D | 36 | 70.277 | 16.601 | 73.555 | 1.00 | 55.69 | O |
| ATOM | 5465 | N | MET D | 37 | 68.457 | 15.271 | 73.559 | 1.00 | 53.61 | N |
| ATOM | 5466 | CA | MET D | 37 | 68.190 | 15.663 | 75.027 | 1.00 | 53.28 | C |
| ATOM | 5467 | CB | MET D | 37 | 66.879 | 15.048 | 75.531 | 1.00 | 52.61 | C |
| ATOM | 5468 | CG | MET D | 37 | 66.504 | 15.416 | 76.952 | 1.00 | 56.86 | C |
| ATOM | 5469 | SD | MET D | 37 | 67.118 | 14.241 | 78.255 | 1.00 | 63.69 | S |
| ATOM | 5470 | CE | MET D | 37 | 65.951 | 12.899 | 77.970 | 1.00 | 63.61 | C |
| ATOM | 5471 | C | MET D | 37 | 69.393 | 15.346 | 75.929 | 1.00 | 52.83 | C |
| ATOM | 5472 | O | MET D | 37 | 69.857 | 16.188 | 76.660 | 1.00 | 53.88 | O |
| ATOM | 5473 | N | ILE D | 38 | 69.929 | 14.146 | 75.848 | 1.00 | 52.21 | N |
| ATOM | 5474 | CA | ILE D | 38 | 70.894 | 13.701 | 76.834 | 1.00 | 50.67 | C |
| ATOM | 5475 | CB | ILE D | 38 | 70.871 | 12.175 | 76.871 | 1.00 | 50.66 | C |
| ATOM | 5476 | CG1 | ILE D | 38 | 71.504 | 11.667 | 78.161 | 1.00 | 51.70 | C |
| ATOM | 5477 | CD1 | ILE D | 38 | 70.844 | 10.461 | 78.738 | 1.00 | 52.77 | C |
| ATOM | 5478 | CG2 | ILE D | 38 | 71.554 | 11.630 | 75.673 | 1.00 | 47.00 | C |
| ATOM | 5479 | C | ILE D | 38 | 72.308 | 14.205 | 76.524 | 1.00 | 50.76 | C |
| ATOM | 5480 | O | ILE D | 38 | 73.235 | 14.059 | 77.345 | 1.00 | 49.88 | O |
| ATOM | 5481 | N | LYS D | 39 | 72.495 | 14.821 | 75.350 | 1.00 | 50.70 | N |
| ATOM | 5482 | CA | LYS D | 39 | 73.864 | 15.267 | 75.005 | 1.00 | 50.79 | C |
| ATOM | 5483 | CB | LYS D | 39 | 73.998 | 15.807 | 73.609 | 1.00 | 50.54 | C |
| ATOM | 5484 | CG | LYS D | 39 | 74.211 | 14.693 | 72.611 | 1.00 | 55.21 | C |
| ATOM | 5485 | CD | LYS D | 39 | 74.688 | 15.278 | 71.306 | 1.00 | 61.91 | C |
| ATOM | 5486 | CE | LYS D | 39 | 75.390 | 16.600 | 71.570 | 1.00 | 63.46 | C |
| ATOM | 5487 | NZ | LYS D | 39 | 76.537 | 16.908 | 70.638 | 1.00 | 67.52 | N |
| ATOM | 5488 | C | LYS D | 39 | 74.496 | 16.176 | 76.025 | 1.00 | 49.05 | C |

TABLE 11-continued

| | | | | | | | | | | |
|---|---|---|---|---|---|---|---|---|---|---|
| ATOM | 5489 | O | LYS D | 39 | 75.572 | 15.869 | 76.492 | 1.00 | 48.83 | O |
| ATOM | 5490 | N | PRO D | 40 | 73.798 | 17.250 | 76.420 | 1.00 | 48.57 | N |
| ATOM | 5491 | CA | PRO D | 40 | 74.426 | 18.103 | 77.415 | 1.00 | 48.67 | C |
| ATOM | 5492 | CB | PRO D | 40 | 73.387 | 19.174 | 77.707 | 1.00 | 47.77 | C |
| ATOM | 5393 | CG | PRO D | 40 | 72.278 | 18.977 | 76.751 | 1.00 | 47.56 | C |
| ATOM | 5494 | CD | PRO D | 40 | 72.473 | 17.730 | 75.989 | 1.00 | 48.01 | C |
| ATOM | 5495 | C | PRO D | 40 | 74.778 | 17.321 | 78.686 | 1.00 | 49.76 | C |
| ATOM | 5496 | O | PRO D | 40 | 75.791 | 17.600 | 79.339 | 1.00 | 50.57 | O |
| ATOM | 5497 | N | PHE D | 41 | 73.976 | 16.320 | 79.040 | 1.00 | 49.71 | N |
| ATOM | 5498 | CA | PHE D | 41 | 74.241 | 15.642 | 80.280 | 1.00 | 47.87 | C |
| ATOM | 5499 | CB | PHE D | 41 | 73.024 | 14.927 | 80.859 | 1.00 | 47.97 | C |
| ATOM | 5500 | CG | PHE D | 41 | 71.888 | 15.866 | 81.169 | 1.00 | 49.45 | C |
| ATOM | 5501 | CD1 | PHE D | 41 | 72.071 | 16.954 | 82.070 | 1.00 | 51.29 | C |
| ATOM | 5502 | OE1 | PHE D | 41 | 71.068 | 17.858 | 82.337 | 1.00 | 47.29 | C |
| ATOM | 5503 | CZ | PHE D | 41 | 69.833 | 17.720 | 81.700 | 1.00 | 50.49 | C |
| ATOM | 5504 | CE2 | PHE D | 41 | 69.620 | 16.664 | 80.791 | 1.00 | 53 96 | C |
| ATOM | 5505 | CD2 | PHE D | 41 | 70.662 | 15.742 | 80.525 | 1.00 | 52.61 | C |
| ATOM | 5506 | C | PHE D | 41 | 75.399 | 14.783 | 80.058 | 1.00 | 47.69 | C |
| ATOM | 5507 | O | PHE D | 41 | 76.268 | 14.737 | 80.918 | 1.00 | 48.95 | O |
| ATOM | 5508 | N | PHE D | 42 | 75.495 | 14.160 | 78.697 | 1.00 | 47.26 | N |
| ATOM | 5509 | CA | PHE D | 42 | 76.656 | 13.297 | 78.675 | 1.00 | 48.24 | C |
| ATOM | 5510 | CB | PHE D | 42 | 76.716 | 12.831 | 77.268 | 1.00 | 48.34 | C |
| ATOM | 5511 | CG | PHE D | 42 | 77.610 | 11.686 | 77.041 | 1.00 | 47.88 | C |
| ATOM | 5512 | CD1 | PHE D | 42 | 77.363 | 10.467 | 77.659 | 1.00 | 52.38 | C |
| ATOM | 5513 | CE1 | PHE D | 42 | 78.187 | 9.331 | 77.430 | 1.00 | 52.87 | C |
| ATOM | 5514 | CZ | PHE D | 42 | 79.229 | 9.421 | 76.501 | 1.00 | 54.20 | C |
| ATOM | 5515 | CE2 | PHE D | 42 | 79.448 | 10.658 | 75.816 | 1.00 | 53.86 | C |
| ATOM | 5516 | CD2 | PHR D | 42 | 78.638 | 11.773 | 76.110 | 1.00 | 49.91 | C |
| ATOM | 5517 | C | PHE D | 42 | 77.882 | 14.107 | 78.893 | 1.00 | 49.17 | C |
| ATOM | 5518 | O | PHE D | 42 | 78.839 | 13.644 | 79.528 | 1.00 | 50.59 | O |
| ATOM | 5519 | N | HIS D | 43 | 77.830 | 15.338 | 78.384 | 1.00 | 49.13 | N |
| ATOM | 5520 | CA | HIS D | 43 | 78.920 | 16.297 | 78.483 | .00 | 48.98 | C |
| ATOM | 5521 | CB | HIS D | 43 | 78.637 | 17.503 | 77.605 | 1.00 | 48.42 | C |
| ATOM | 5522 | CG | HIS D | 43 | 79.721 | 18.503 | 77.687 | 1.00 | 49.56 | C |
| ATOM | 5523 | ND1 | HIS D | 43 | 80.878 | 18.395 | 76.940 | 1.00 | 52.17 | N |
| ATOM | 5524 | CE1 | HIS D | 43 | 81.690 | 19.389 | 77.266 | 1.00 | 55.13 | C |
| ATOM | 5525 | NE2 | HIS D | 43 | 81.112 | 20.116 | 78.212 | 1.00 | 53.01 | N |
| ATOM | 5526 | CD2 | HIS D | 43 | 79.889 | 19.556 | 78.512 | 1.00 | 51.94 | C |
| ATOM | 5527 | C | HIS D | 43 | 79.267 | 16.844 | 79.881 | 1.00 | 49.21 | C |
| ATOM | 5528 | O | HIS D | 43 | 8.442 | 17.048 | 80.198 | 1.00 | 50.46 | O |
| ATOM | 5529 | N | SER D | 44 | 78.267 | 17.175 | 80.685 | 1.00 | 48.47 | N |
| ATOM | 5530 | CA | SER D | 44 | 78.535 | 17.601 | 82.036 | 1.00 | 48.64 | C |
| ATOM | 5531 | CB | SER D | 44 | 77.213 | 17.892 | 82.716 | 1.00 | 49.39 | C |
| ATOM | 5532 | OG | SER D | 44 | 76.539 | 18.968 | 82.122 | 1.00 | 50.57 | O |
| ATOM | 5533 | C | SER D | 44 | 79.290 | 16.481 | 82.816 | 1.00 | 48.67 | C |
| ATOM | 5534 | O | SER D | 44 | 80.299 | 16.740 | 83.506 | 1.00 | 47.70 | O |
| ATOM | 5535 | N | LEU D | 45 | 78.780 | 15.248 | 82.668 | 1.00 | 47.77 | N |
| ATOM | 5536 | CA | LEU D | 45 | 79.422 | 14.052 | 83.158 | 1.00 | 47.19 | C |
| ATOM | 5537 | CB | LEU D | 45 | 78.632 | 12.816 | 82.712 | 1.00 | 47.66 | C |
| ATOM | 5538 | CG | LEU D | 45 | 77.667 | 2.046 | 83.686 | 1.00 | 46.76 | C |
| ATOM | 5539 | CD1 | LEU D | 45 | 77.138 | 12.824 | 84.893 | 1.00 | 42.70 | C |
| ATOM | 5540 | CD2 | LEU D | 45 | 76.499 | 11.398 | 82.949 | 1.00 | 43.82 | C |
| ATOM | 5541 | C | LEU D | 45 | 80.880 | 13.933 | 82.742 | 1.00 | 47.13 | C |
| ATOM | 5542 | O | LEU D | 45 | 81.758 | 13.696 | 83.588 | 1.00 | 47.07 | O |
| ATOM | 5543 | N | SER D | 46 | 81.154 | 14.136 | 81.460 | 1.00 | 46.91 | N |
| ATOM | 5544 | CB | SER D | 46 | 82.531 | 14.040 | 80.980 | 1.00 | 46.63 | C |
| ATOM | 5545 | CB | SER D | 46 | 82.640 | 14.204 | 79.454 | 1.00 | 45.34 | C |
| ATOM | 5546 | OG | SER D | 46 | 82.707 | 15.583 | 79.103 | 1.00 | 47.63 | O |
| ATOM | 5547 | C | SER D | 46 | 83.449 | 15.019 | 81.726 | 1.00 | 47.13 | C |
| ATOM | 5548 | O | SER D | 46 | 84.587 | 14.659 | 82.085 | 1.00 | 46.18 | O |
| ATOM | 5549 | N | GLU D | 47 | 82.964 | 16.250 | 81.930 | 1.00 | 47.82 | N |
| ATOM | 5550 | CA | GLU D | 47 | 83.707 | 17.207 | 82.728 | 1.00 | 48.08 | C |
| ATOM | 5551 | CB | GLU D | 47 | 83.120 | 18.631 | 82.685 | 1.00 | 48.59 | C |
| ATOM | 5552 | CG | GLU D | 47 | 83.299 | 19.402 | 81.381 | 1.00 | 46.93 | C |
| ATOM | 5553 | CD | GLU D | 47 | 84.779 | 19.614 | 81.052 | 1.00 | 51.39 | C |
| ATOM | 5554 | OE1 | GLU D | 47 | 85.534 | 20.045 | 81.959 | 1.00 | 55.58 | O |
| ATOM | 5555 | OE2 | GLU D | 47 | 85.225 | 19.359 | 79.899 | 1.00 | 52.22 | O |
| ATOM | 5556 | C | GLU D | 47 | 83.803 | 16.692 | 84.151 | 1.00 | 48.80 | C |
| ATOM | 5557 | O | GLU D | 47 | 84.891 | 16.743 | 84.725 | 1.00 | 50.09 | O |
| ATOM | 5558 | N | LYS D | 48 | 82.736 | 16.148 | 84.735 | 1.00 | 48.96 | N |
| ATOM | 5559 | CA | LYS D | 48 | 82.910 | 15.649 | 86.126 | 1.00 | 49.83 | C |
| ATOM | 5560 | CB | LYS D | 48 | 81.606 | 15.487 | 86.912 | 1.00 | 49.59 | C |
| ATOM | 5561 | CG | LYS D | 48 | 81.753 | 14.829 | 88.308 | 1.00 | 47.62 | C |
| ATOM | 5562 | CD | LYS D | 48 | 80.460 | 13.976 | 88.572 | 1.00 | 48.60 | C |
| ATOM | 5563 | CE | LYS D | 48 | 80.006 | 13.843 | 90.090 | 1.00 | 48.31 | C |
| ATOM | 5564 | NZ | LYS D | 48 | 80.111 | 15.045 | 90.964 | 1.00 | 45.74 | N |
| ATOM | 5565 | C | LYS D | 48 | 83.793 | 14.424 | 86.277 | 1.00 | 50.49 | C |
| ATOM | 5566 | O | LYS D | 48 | 84.713 | 14.453 | 87.038 | 1.00 | 51.24 | O |
| ATOM | 5567 | N | TYR D | 49 | 83.522 | 13.360 | 85.557 | 1.00 | 51.22 | N |
| ATOM | 5568 | CA | TYR D | 49 | 84.287 | 12.143 | 85.729 | 1.00 | 53.15 | C |

TABLE 11-continued

| ATOM | 5569 | CB | TYR D | 49 | 83.418 | 10.907 | 85.435 | 1.00 | 53.73 | C |
|---|---|---|---|---|---|---|---|---|---|---|
| ATOM | 5570 | CG | TYR D | 49 | 82.295 | 10.770 | 86.439 | 1.00 | 55.99 | C |
| ATOM | 5571 | CD1 | TYR D | 49 | 82.497 | 10.134 | 87.654 | 1.00 | 55.45 | C |
| ATOM | 5572 | CE1 | TYR D | 49 | 81.457 | 10.029 | 88.602 | 1.00 | 55.08 | C |
| ATOM | 5573 | CZ | TYR D | 49 | 80.212 | 10.547 | 88.323 | 1.00 | 54.40 | C |
| ATOM | 5574 | PH | TYR D | 49 | 79.177 | 10.436 | 89.225 | 1.00 | 50.49 | O |
| ATOM | 5575 | CE2 | TYR D | 49 | 79.996 | 11.173 | 87.121 | 1.00 | 57.43 | C |
| ATOM | 5576 | CD2 | TYR D | 49 | 81.034 | 11.290 | 86.176 | 1.00 | 56.58 | C |
| ATOM | 5577 | C | TYR D | 49 | 85.504 | 12.143 | 84.851 | 1.00 | 53.50 | C |
| ATOM | 5578 | O | TYR D | 49 | 85.596 | 11.370 | 83.894 | 1.00 | 53.88 | O |
| ATOM | 5579 | N | SER D | 50 | 86.451 | 12.993 | 85.195 | 1.00 | 54.64 | N |
| ATOM | 5580 | CA | SER D | 50 | 87.593 | 13.240 | 84.337 | 1.00 | 56.41 | C |
| ATOM | 5581 | CB | SER D | 50 | 88.346 | 14.476 | 84.820 | 1.00 | 56.92 | C |
| ATOM | 5582 | OG | SER D | 50 | 88.731 | 14.315 | 86.183 | 1.00 | 59.07 | O |
| ATOM | 5583 | C | SER D | 50 | 88.562 | 12.068 | 84.213 | 1.00 | 56.95 | C |
| ATOM | 5584 | O | SER D | 50 | 89.534 | 12.156 | 83.429 | 1.00 | 57.07 | O |
| ATOM | 5585 | N | ASN D | 51 | 88.300 | 10.995 | 84.972 | 1.00 | 57.07 | N |
| ATOM | 5586 | CA | ASN D | 51 | 89.066 | 9.733 | 84.890 | 1.00 | 57.19 | C |
| ATOM | 5587 | CB | ASN D | 51 | 89.302 | 9.172 | 86.287 | 1.00 | 58.46 | C |
| ATOM | 5588 | CG | ASN D | 51 | 88.166 | 9.535 | 87.280 | 1.00 | 52.00 | C |
| ATOM | 5589 | OD1 | ASN D | 51 | 86.967 | 9.648 | 86.907 | 1.00 | 60.93 | O |
| ATOM | 5590 | ND2 | ASN D | 51 | 88.560 | 9.743 | 88.560 | 1.00 | 63.33 | N |
| ATOM | 5591 | C | ASN D | 51 | 88.410 | 8.646 | 84.060 | 1.00 | 56.21 | C |
| ATOM | 5592 | O | ASN D | 51 | 88.815 | 7.499 | 84.096 | 1.00 | 56.50 | O |
| ATOM | 5593 | N | VAL D | 52 | 87.388 | 9.014 | 83.316 | 1.00 | 55.25 | N |
| ATOM | 5594 | CA | VAL D | 52 | 86.630 | 8.098 | 82.511 | 1.00 | 54.26 | C |
| ATOM | 5595 | CB | VAL D | 52 | 85.166 | 8.158 | 82.941 | 1.00 | 53.99 | C |
| ATOM | 5596 | CG1 | VAL D | 52 | 84.252 | 7.451 | 81.973 | 1.00 | 54.27 | C |
| ATOM | 5597 | CG2 | VAL D | 52 | 84.991 | 7.560 | 84.284 | 1.00 | 53.01 | C |
| ATOM | 5598 | C | VAL D | 52 | 86.786 | 8.786 | 81.184 | 1.00 | 54.70 | C |
| ATOM | 5599 | O | VAL D | 52 | 86.930 | 10.008 | 81.161 | 1.00 | 55.86 | O |
| ATOM | 5600 | N | ILE D | 53 | 86.812 | 8.024 | 80.089 | 1.00 | 54.03 | N |
| ATOM | 5601 | CA | ILE D | 53 | 86.920 | 8.585 | 78.737 | 1.00 | 53.20 | C |
| ATOM | 5602 | CB | ILE D | 53 | 88.096 | 7.932 | 77.891 | 1.00 | 53.71 | C |
| ATOM | 5603 | CG1 | ILE D | 53 | 89.452 | 8.585 | 78.312 | 1.00 | 52.53 | C |
| ATOM | 5604 | CD1 | ILE D | 53 | 90.611 | 7.606 | 77.887 | 1.00 | 53.56 | C |
| ATOM | 5605 | CG2 | ILE D | 53 | 87.932 | 8.161 | 76.384 | 1.00 | 51.53 | C |
| ATOM | 5606 | C | IEL D | 53 | 85.581 | 8.470 | 78.017 | 1.00 | 52.66 | C |
| ATOM | 5607 | O | ILE D | 53 | 84.901 | 7.422 | 78.078 | 1.00 | 52.46 | O |
| ATOM | 5608 | N | PHE D | 54 | 85.238 | 9.554 | 77.323 | 1.00 | 51.30 | N |
| ATOM | 5609 | CA | PHE D | 54 | 83.921 | 9.759 | 76.811 | 1.00 | 51.11 | C |
| ATOM | 5610 | CB | PHE D | 54 | 83.325 | 11.003 | 77.452 | 1.00 | 50.89 | C |
| ATOM | 5611 | CG | PHE D | 54 | 82.936 | 10.840 | 78.883 | 1.00 | 51.47 | C |
| ATOM | 5612 | CD1 | PHE D | 54 | 83.883 | 10.842 | 79.889 | 1.00 | 51.39 | C |
| ATOM | 5613 | CE1 | PHE D | 54 | 83.501 | 10.704 | 81.220 | 1.00 | 48.37 | C |
| ATOM | 5614 | CZ | PHE D | 54 | 82.154 | 10.588 | 87.572 | 1.00 | 48.88 | C |
| ATOM | 5615 | CE2 | PHE D | 54 | 81.213 | 10.599 | 80.635 | 1.00 | 50.38 | C |
| ATOM | 5616 | CD2 | PHE D | 54 | 81.600 | 10.728 | 79.249 | 1.00 | 4.14 | C |
| ATOM | 5617 | C | PHE D | 54 | 83.961 | 9.946 | 75.305 | 1.00 | 51.64 | C |
| ATOM | 5618 | O | PHE D | 54 | 84.545 | 10.918 | 74.769 | 1.00 | 52.31 | O |
| ATOM | 5619 | N | LEU D | 55 | 83.315 | 9.050 | 74.599 | 1.00 | 51.54 | N |
| ATOM | 5620 | CA | LEU D | 55 | 83.318 | 9.161 | 73.160 | 1.00 | 53.26 | C |
| ATOM | 5621 | CB | LEU D | 55 | 83.927 | 7.907 | 72.494 | 1.00 | 53.85 | C |
| ATOM | 5622 | CG | LEU D | 55 | 85.248 | 7.430 | 73.120 | 1.00 | 53.84 | C |
| ATOM | 5623 | CD1 | LEU D | 55 | 85.861 | 6.195 | 72.443 | 1.00 | 49.51 | C |
| ATOM | 5624 | CD2 | LEU D | 55 | 86.194 | 8.650 | 73.096 | 1.00 | 54.23 | C |
| ATOM | 5625 | C | LEU D | 55 | 81.897 | 9.345 | 72.694 | 1.00 | 53.94 | C |
| ATOM | 5626 | O | LEU D | 55 | 80.933 | 8.965 | 73.399 | 1.00 | 54.07 | O |
| ATOM | 5627 | N | GLU D | 56 | 81.763 | 9.968 | 71.528 | 1.00 | 54.12 | N |
| ATOM | 5628 | CA | GLU D | 56 | 80.503 | 9.954 | 70.840 | 1.00 | 54.71 | C |
| ATOM | 5629 | CB | GLU D | 56 | 79.949 | 11.331 | 70.739 | 1.00 | 54.09 | C |
| ATOM | 5630 | CG | GLU D | 56 | 78.471 | 11.277 | 70.523 | 1.00 | 59.81 | C |
| ATOM | 5631 | CD | GLU D | 56 | 77.937 | 12.453 | 69.746 | 1.00 | 65.24 | C |
| ATOM | 5632 | OE1 | GLU D | 56 | 77.354 | 13.383 | 70.351 | 1.00 | 68.48 | O |
| ATOM | 5633 | OE2 | GLU D | 56 | 78.107 | 12.444 | 68.521 | 1.00 | 69.99 | O |
| ATOM | 5634 | C | GLU D | 56 | 80.769 | 9.366 | 69.428 | 1.00 | 54.92 | C |
| ATOM | 5635 | O | GLU D | 56 | 81.742 | 9.593 | 68.745 | 1.00 | 55.38 | O |
| ATOM | 5636 | N | VAL D | 57 | 79.655 | 8.615 | 69.000 | 1.00 | 52.70 | N |
| ATOM | 5637 | CA | VAL D | 57 | 79.611 | 8.097 | 67.661 | 1.00 | 51.63 | C |
| ATOM | 5638 | CB | VAL D | 57 | 79.828 | 6.581 | 67.642 | 1.00 | 51.25 | C |
| ATOM | 5639 | CG1 | VAL D | 57 | 79.586 | 6.048 | 66.259 | 1.00 | 48.88 | C |
| ATOM | 5640 | CG2 | VAL D | 57 | 81.202 | 6.232 | 68.130 | 1.00 | 48.90 | C |
| ATOM | 5641 | C | VAL D | 57 | 78.285 | 8.404 | 66.965 | 1.00 | 52.21 | C |
| ATOM | 5642 | O | VAL D | 57 | 77.221 | 8.004 | 67.417 | 1.00 | 51.86 | O |
| ATOM | 5643 | N | ASP D | 58 | 78.361 | 9.071 | 65.824 | 1.00 | 52.60 | N |
| ATOM | 5644 | CA | ASP D | 58 | 77.181 | 9.242 | 65.027 | 1.00 | 53.08 | C |
| ATOM | 5645 | CB | ASP D | 58 | 77.307 | 10.437 | 64.128 | 1.00 | 52.74 | C |
| ATOM | 5646 | CG | ASP D | 58 | 75.966 | 10.912 | 63.643 | 1.00 | 54.45 | C |
| ATOM | 5647 | OD1 | ASP D | 58 | 75.441 | 10.319 | 62.695 | 1.00 | 57.86 | O |
| ATOM | 5648 | OD2 | ASP D | 58 | 75.423 | 11.881 | 64.220 | 1.00 | 57.66 | O |

TABLE 11-continued

| ATOM | 5649 | C | ASP D | 58 | 76.906 | 8.007 | 64.205 | 1.00 | 53.32 | C |
|---|---|---|---|---|---|---|---|---|---|---|
| ATOM | 5650 | O | ASP D | 58 | 77.706 | 7.636 | 63.330 | 1.00 | 53.70 | O |
| ATOM | 5651 | N | VAL D | 59 | 75.776 | 7.365 | 64.496 | 1.00 | 53.07 | N |
| ATOM | 5652 | CA | VAL D | 59 | 75.404 | 6.138 | 63.782 | 1.00 | 52.07 | C |
| ATOM | 5653 | CB | VAL D | 59 | 74.150 | 5.450 | 64.383 | 1.00 | 51.85 | C |
| ATOM | 5654 | CG1 | VAL D | 59 | 74.380 | 5.191 | 65.846 | 1.00 | 50.21 | C |
| ATOM | 5655 | CG2 | VAL D | 59 | 72.859 | 6.317 | 64.179 | 1.00 | 49.76 | C |
| ATOM | 5656 | C | VAL D | 59 | 75.170 | 6.415 | 62.312 | 1.00 | 52.59 | C |
| ATOM | 5657 | O | VAL D | 59 | 75.222 | 5.479 | 61.511 | 1.00 | 53.63 | O |
| ATOM | 5658 | N | ASP D | 60 | 74.887 | 7.668 | 61.938 | 1.00 | 52.02 | N |
| ATOM | 5659 | CA | ASP D | 60 | 74.704 | 7.953 | 60.514 | 1.00 | 52.50 | C |
| ATOM | 5660 | CB | ASP D | 60 | 73.659 | 9.009 | 60.223 | 1.00 | 51.18 | C |
| ATOM | 5661 | CG | ASP D | 60 | 72.246 | 8.536 | 60.581 | 1.00 | 52.96 | C |
| ATOM | 5662 | OD1 | ASP D | 60 | 71.433 | 9.287 | 61.133 | 1.00 | 53.06 | O |
| ATOM | 5663 | OD2 | ASP D | 60 | 71.915 | 7.374 | 60.336 | 1.00 | 56.80 | O |
| ATOM | 5664 | C | ASP D | 60 | 76.048 | 8.190 | 59.851 | 1.00 | 53.67 | C |
| ATOM | 5665 | O | ASP D | 60 | 76.281 | 7.731 | 58.721 | 1.00 | 54.41 | O |
| ATOM | 5666 | N | ASP D | 61 | 76.962 | 8.836 | 60.563 | 1.00 | 54.52 | N |
| ATOM | 5667 | CA | ASP D | 61 | 78.277 | 9.053 | 60.000 | 1.00 | 56.24 | C |
| ATOM | 5668 | CB | ASP D | 61 | 79.035 | 10.124 | 60.770 | 1.00 | 56.09 | C |
| ATOM | 5669 | CG | ASP D | 61 | 78.313 | 11.461 | 60.763 | 1.00 | 55.67 | C |
| ATOM | 5670 | OD1 | ASP D | 61 | 77.468 | 11.723 | 59.867 | 1.00 | 55.35 | O |
| ATOM | 5671 | OD2 | ASP D | 61 | 78.611 | 12.258 | 61.666 | 1.00 | 53.18 | O |
| ATOM | 5672 | C | ASP D | 61 | 79.061 | 7.750 | 59.922 | 1.00 | 57.82 | C |
| ATOM | 5673 | O | ASP D | 61 | 79.621 | 7.412 | 58.863 | 1.00 | 58.69 | O |
| ATOM | 5674 | N | CYS D | 62 | 79.063 | 6.994 | 66.013 | 1.00 | 58.77 | N |
| ATOM | 5675 | CA | CYS D | 62 | 79.756 | 5.733 | 61.025 | 1.00 | 60.30 | C |
| ATOM | 5676 | CB | CYS D | 62 | 80.703 | 5.722 | 62.211 | 1.00 | 61.16 | C |
| ATOM | 5677 | SG | CYS D | 62 | 81.637 | 7.235 | 62.260 | 1.00 | 67.60 | S |
| ATOM | 5678 | C | CYS D | 62 | 78.842 | 4.567 | 61.187 | 1.00 | 60.03 | C |
| ATOM | 5679 | O | CYS D | 62 | 78.886 | 3.917 | 62.216 | 1.00 | 60.25 | O |
| ATOM | 5680 | N | GLN D | 63 | 78.023 | 4.240 | 60.205 | 1.00 | 60.29 | N |
| ATOM | 5681 | CA | GLN D | 63 | 77.216 | 3.047 | 60.413 | 1.00 | 60.93 | C |
| ATOM | 5682 | CB | GLN D | 63 | 76.225 | 2.794 | 59.299 | 1.00 | 60.82 | C |
| ATOM | 5683 | CG | GLN D | 63 | 75.410 | 3.979 | 58.936 | 1.00 | 65.33 | C |
| ATOM | 5684 | CD | GLN D | 63 | 75.780 | 4.552 | 57.567 | 1.00 | 70.28 | C |
| ATOM | 5685 | OE1 | GLN D | 63 | 74.908 | 4.672 | 56.685 | 1.00 | 66.63 | O |
| ATOM | 5686 | NE2 | GLN D | 63 | 77.086 | 4.926 | 57.401 | 1.00 | 71.94 | N |
| ATOM | 5687 | C | GLN D | 63 | 78.058 | 1.805 | 60.632 | 1.00 | 60.15 | C |
| ATOM | 5688 | O | GLN D | 63 | 77.553 | 0.787 | 61.071 | 1.00 | 60.32 | O |
| ATOM | 5689 | N | ASP D | 64 | 79.338 | 1.865 | 60.323 | 1.00 | 60.42 | N |
| ATOM | 5690 | CA | ASP D | 64 | 80.133 | 0.625 | 60.395 | 1.00 | 60.90 | C |
| ATOM | 5691 | CB | ASP D | 64 | 81.280 | 0.535 | 59.369 | 1.00 | 60.73 | C |
| ATOM | 5692 | CG | ASP D | 64 | 82.071 | 1.807 | 59.258 | 1.00 | 62.29 | C |
| ATOM | 5693 | OD1 | ASP D | 64 | 81.601 | 2.856 | 59.757 | 1.00 | 62.78 | O |
| ATOM | 5694 | OD2 | ASP D | 64 | 83.186 | 1.736 | 58.669 | 1.00 | 62.93 | O |
| ATOM | 5695 | C | ASP D | 64 | 80.567 | 0.333 | 61.807 | 1.00 | 60.29 | C |
| ATOM | 5696 | O | ASP D | 64 | 80.475 | −0.830 | 62.252 | 1.00 | 60.27 | O |
| ATOM | 5697 | N | VAL D | 65 | 80.959 | 1.396 | 62.525 | 1.00 | 59.76 | N |
| ATOM | 5698 | CA | VAL D | 65 | 81.217 | 1.309 | 63.968 | 1.00 | 58.82 | C |
| ATOM | 5699 | CB | VAL D | 65 | 81.729 | 2.638 | 64.556 | 1.00 | 58.76 | C |
| ATOM | 5700 | CG1 | VAL D | 65 | 81.872 | 2.552 | 66.072 | 1.00 | 59.87 | C |
| ATOM | 5701 | CG2 | VAL D | 65 | 83.064 | 2.985 | 63.977 | 1.00 | 60.11 | C |
| ATOM | 5702 | C | VAL D | 65 | 79.905 | 0.858 | 64.594 | 1.00 | 57.96 | C |
| ATOM | 5703 | O | VAL D | 65 | 79.865 | −0.158 | 65.297 | 1.00 | 58.12 | O |
| ATOM | 5704 | N | ALA D | 66 | 78.836 | 1.579 | 64.263 | 1.00 | 56.97 | N |
| ATOM | 5705 | CA | ALA D | 66 | 77.461 | 1.248 | 64.664 | 1.00 | 56.69 | C |
| ATOM | 5706 | CB | ALA D | 66 | 76.482 | 2.120 | 63.900 | 1.00 | 56.28 | C |
| ATOM | 5707 | C | ALA D | 66 | 77.038 | −0.236 | 64.568 | 1.00 | 56.48 | C |
| ATOM | 5708 | O | ALA D | 66 | 76.461 | −0.800 | 65.505 | 1.00 | 56.74 | O |
| ATOM | 5709 | N | SER D | 67 | 77.301 | −0.889 | 63.456 | 1.00 | 56.29 | N |
| ATOM | 5710 | CA | SER D | 67 | 76.835 | −2.248 | 63.340 | 1.00 | 56.81 | C |
| ATOM | 5711 | CB | SER D | 67 | 76.484 | −2.563 | 61.900 | 1.00 | 56.77 | C |
| ATOM | 5712 | OG | SER D | 67 | 77.647 | −2.429 | 61.170 | 1.00 | 57.21 | O |
| ATOM | 5713 | C | SER D | 67 | 77.869 | −3.244 | 63.825 | 1.00 | 57.00 | C |
| ATOM | 5714 | O | SER D | 67 | 77.552 | −4.428 | 64.105 | 1.00 | 57.13 | O |
| ATOM | 5715 | N | GLU D | 68 | 79.114 | −2.803 | 63.889 | 1.00 | 56.34 | N |
| ATOM | 5716 | CA | GLU D | 68 | 80.085 | −3.700 | 64.409 | 1.00 | 56.84 | C |
| ATOM | 5717 | CB | GLU D | 68 | 81.459 | −3.171 | 64.132 | 1.00 | 58.05 | C |
| ATOM | 5718 | CG | GLU D | 68 | 82.552 | −4.223 | 64.103 | 1.00 | 60.94 | C |
| ATOM | 5719 | CD | GLU D | 68 | 83.703 | −3.756 | 63.242 | 1.00 | 66.23 | C |
| ATOM | 5720 | OE1 | GLU D | 68 | 83.448 | 3.668 | 62.003 | 1.00 | 68.99 | O |
| ATOM | 5721 | OE1 | GLU D | 68 | 84.823 | −3.463 | 63.797 | 1.00 | 66.63 | O |
| ATOM | 5722 | C | GLU D | 68 | 79.823 | −3.807 | 65.896 | 1.00 | 56.34 | C |
| ATOM | 5723 | O | GLU D | 68 | 79.937 | −4.888 | 66.483 | 1.00 | 56.42 | O |
| ATOM | 5724 | N | CYS D | 69 | 79.420 | −2.683 | 66.486 | 1.00 | 55.42 | N |
| ATOM | 5725 | CA | CYS D | 69 | 78.966 | −2.650 | 67.848 | 1.00 | 54.16 | C |
| ATOM | 5726 | CB | CYS D | 69 | 79.156 | −1.263 | 68.362 | 1.00 | 54.59 | C |
| ATOM | 5727 | SG | CYS D | 69 | 80.897 | −0.770 | 68.434 | 1.00 | 56.88 | S |
| ATOM | 5728 | C | CYS D | 69 | 77.521 | −3.074 | 68.053 | 1.00 | 53.87 | C |

TABLE 11-continued

| | | | | | | | | | |
|---|---|---|---|---|---|---|---|---|---|
| ATOM | 5729 | O | CYS D | 69 | 77.044 | −3.143 | 69.186 | 1.00 | 54.10 | O |
| ATOM | 5730 | N | GLU D | 70 | 76.792 | −3.352 | 66.985 | 1.00 | 83.86 | N |
| ATOM | 5731 | CA | GLU D | 70 | 75.419 | −3.886 | 67.145 | 1.00 | 54.36 | C |
| ATOM | 5732 | CB | GLU D | 70 | 75.389 | −5.226 | 67.928 | 1.00 | 54.60 | C |
| ATOM | 5733 | CG | GLU D | 70 | 76.094 | −6.402 | 67.232 | 1.00 | 56.17 | C |
| ATOM | 5734 | CD | GLU D | 70 | 75.864 | −7.748 | 67.960 | 1.00 | 58.13 | C |
| ATOM | 5735 | OE1 | GLU D | 70 | 76.416 | −7.495 | 69.068 | 1.00 | 56.94 | O |
| ATOM | 5736 | OE2 | GLU D | 70 | 75.121 | −8.602 | 67.421 | 1.00 | 59.03 | O |
| ATOM | 5737 | C | GLU D | 70 | 74.430 | −2.868 | 67.762 | 1.00 | 53.54 | C |
| ATOM | 5738 | O | GLU D | 70 | 73.419 | −3.229 | 68.365 | 1.00 | 53.70 | O |
| ATOM | 5739 | N | VAL D | 71 | 74.696 | −1.594 | 67.552 | 1.00 | 52.32 | N |
| ATOM | 5740 | CA | VAL D | 71 | 73.760 | −0.591 | 67.982 | 1.00 | 51.71 | C |
| ATOM | 5741 | CB | VAL D | 71 | 74.380 | 0.773 | 67.856 | 1.00 | 50.93 | C |
| ATOM | 5742 | CG1 | VAL D | 71 | 73.449 | 1.841 | 68.317 | 1.00 | 50.05 | C |
| ATOM | 5743 | CG2 | VAL D | 71 | 75.572 | 0.781 | 68.740 | 1.00 | 52.33 | C |
| ATOM | 5744 | C | VAL D | 71 | 72.444 | −0.736 | 67.223 | 1.00 | 51.53 | C |
| ATOM | 5745 | O | VAL D | 71 | 72.439 | −0.949 | 66.017 | 1.00 | 51.25 | O |
| ATOM | 5746 | N | LYS D | 72 | 71.335 | −0.671 | 67.943 | 1.00 | 51.68 | N |
| ATOM | 5747 | CA | LYS D | 72 | 70.036 | −0.846 | 67.292 | 1.00 | 52.83 | C |
| ATOM | 5748 | CB | LYS D | 72 | 69.351 | −2.148 | 67.745 | 1.00 | 53.15 | C |
| ATOM | 5749 | CG | LYS D | 72 | 69.937 | −3.351 | 67.024 | 1.00 | 54.90 | C |
| ATOM | 5750 | CD | LYS D | 72 | 69.954 | −4.606 | 67.861 | 1.00 | 57.92 | C |
| ATOM | 5751 | CE | LYS D | 72 | 70.158 | −5.780 | 66.902 | 1.00 | 59.33 | C |
| ATOM | 5752 | NZ | LYS D | 72 | 70.461 | −7.006 | 67.655 | 1.00 | 62.16 | N |
| ATOM | 5753 | C | LYS D | 72 | 69.101 | 0.348 | 67.390 | 1.00 | 52.36 | C |
| ATOM | 5754 | O | LYS D | 72 | 68.194 | 0.515 | 66.567 | 1.00 | 53.06 | O |
| ATOM | 5755 | N | CYS D | 73 | 69.324 | 1.168 | 68.394 | 1.00 | 50.96 | N |
| ATOM | 5756 | CA | CYS D | 73 | 68.547 | 2.336 | 68.559 | 1.00 | 50.77 | C |
| ATOM | 5757 | CB | CYS D | 73 | 67.388 | 2.060 | 69.466 | 1.00 | 50.71 | C |
| ATOM | 5758 | SG | CYS D | 73 | 67.937 | 1.464 | 71.013 | 1.00 | 53.98 | S |
| ATOM | 5759 | C | CYS D | 73 | 69.444 | 3.319 | 69.218 | 1.00 | 50.46 | C |
| ATOM | 5760 | O | CYS D | 73 | 70.560 | 2.991 | 69.616 | 1.00 | 49.67 | O |
| ATOM | 5761 | N | MEY D | 74 | 68.948 | 4.532 | 69.331 | 1.00 | 50.26 | N |
| ATOM | 5762 | CA | MET D | 74 | 69.708 | 5.585 | 69.961 | 1.00 | 50.87 | C |
| ATOM | 5763 | CB | MET D | 74 | 70.290 | 6.547 | 68.893 | 1.00 | 51.40 | C |
| ATOM | 5764 | CG | MET D | 74 | 71.246 | 5.901 | 67.867 | 1.00 | 53.25 | C |
| ATOM | 5765 | SD | MET D | 74 | 70.493 | 4.839 | 66.572 | 1.00 | 58.32 | S |
| ATOM | 5766 | CE | MET D | 74 | 69.711 | 8.035 | 65.493 | 1.00 | 49.70 | C |
| ATOM | 5767 | C | MET D | 74 | 68.810 | 6.353 | 70.957 | 1.00 | 50.14 | C |
| ATOM | 5768 | O | MET D | 74 | 67.586 | 6.430 | 70.754 | 1.00 | 50.11 | O |
| ATOM | 5769 | N | PRO D | 75 | 69.421 | 6.948 | 72.003 | 1.00 | 49.13 | N |
| ATOM | 5770 | CA | PRO D | 75 | 70.845 | 6.754 | 72.298 | 1.00 | 48.61 | C |
| ATOM | 5771 | CB | PRO D | 75 | 71.137 | 7.812 | 73.380 | 1.00 | 48.35 | C |
| ATOM | 5772 | CG | PRO D | 75 | 69.867 | 7.993 | 74.095 | 1.00 | 49.14 | C |
| ATOM | 5773 | CD | PRO D | 75 | 68.798 | 7.904 | 72.937 | 1.00 | 49.18 | C |
| ATOM | 5774 | C | PRO D | 75 | 71.079 | 5.384 | 72.912 | 1.00 | 48.02 | C |
| ATOM | 5775 | O | PRO D | 75 | 70.300 | 4.995 | 73.780 | 1.00 | 47.47 | O |
| ATOM | 5776 | N | THR D | 76 | 72.150 | 4.701 | 72.485 | 1.00 | 47.60 | N |
| ATOM | 5777 | CA | THR D | 76 | 72.684 | 3.523 | 73.165 | 1.00 | 47.90 | C |
| ATOM | 5778 | CB | THR D | 76 | 72.668 | 2.260 | 72.218 | 1.00 | 48.33 | C |
| ATOM | 5779 | OG1 | THR D | 76 | 71.324 | 1.773 | 72.081 | 1.00 | 47.31 | O |
| ATOM | 5780 | CG2 | THR D | 76 | 73.564 | 1.112 | 72.751 | 1.00 | 46.92 | C |
| ATOM | 5781 | C | THR D | 76 | 74.099 | 3.796 | 73.717 | 1.00 | 48.50 | C |
| ATOM | 5782 | O | THR D | 76 | 74.953 | 4.343 | 73.015 | 1.00 | 47.95 | O |
| ATOM | 5783 | N | PHE D | 77 | 74.348 | 3.353 | 74.955 | 1.00 | 48.91 | N |
| ATOM | 5784 | CA | PHE D | 77 | 75.596 | 3.621 | 75.669 | 1.00 | 48.90 | C |
| ATOM | 5785 | CB | PHE D | 77 | 75.291 | 4.267 | 77.016 | 1.00 | 48.48 | C |
| ATOM | 5786 | CG | PHE D | 77 | 74.780 | 5.611 | 76.885 | 1.00 | 47.74 | C |
| ATOM | 5787 | CD1 | PHE D | 77 | 75.640 | 6.659 | 76.670 | 1.00 | 45.29 | C |
| ATOM | 5788 | CE1 | PHE D | 77 | 75.149 | 7.942 | 76.495 | 1.00 | 48.52 | C |
| ATOM | 5789 | CZ | PHE D | 77 | 73.780 | 8.202 | 76.472 | 1.00 | 45.47 | C |
| ATOM | 5790 | CE2 | PHE D | 77 | 72.915 | 7.169 | 76.660 | 1.00 | 51.08 | C |
| ATOM | 5791 | CD2 | PHE D | 77 | 73.414 | 5.838 | 76.857 | 1.00 | 50.16 | C |
| ATOM | 5792 | C | PHE D | 77 | 76.368 | 2.351 | 75.930 | 1.00 | 50.39 | C |
| ATOM | 5793 | O | PHE D | 77 | 75.815 | 1.428 | 76.516 | 1.00 | 50.67 | O |
| ATOM | 5794 | N | GLN D | 78 | 77.629 | 2.324 | 75.508 | 1.00 | 50.75 | N |
| ATOM | 5795 | CA | GLN D | 78 | 78.397 | 1.133 | 75.689 | 1.00 | 52.73 | C |
| ATOM | 5796 | CB | GLN D | 78 | 78.759 | 0.509 | 74.359 | 1.00 | 52.89 | C |
| ATOM | 5797 | CG | GLN D | 78 | 77.575 | 0.029 | 73.632 | 1.00 | 54.38 | C |
| ATOM | 5798 | CD | GLN D | 78 | 77.896 | −0.859 | 72.469 | 1.00 | 54.32 | C |
| ATOM | 5799 | OE1 | GLN D | 78 | 78.977 | −0.796 | 71.875 | 1.00 | 54.25 | O |
| ATOM | 5800 | NE2 | GLN D | 78 | 76.933 | −1.689 | 72.118 | 1.00 | 50.87 | N |
| ATOM | 5801 | C | GLN D | 78 | 79.647 | 1.487 | 76.447 | 1.00 | 54.25 | C |
| ATOM | 5802 | O | GLN D | 78 | 80.155 | 2.636 | 76.331 | 1.00 | 54.29 | O |
| ATOM | 5803 | N | PHE D | 79 | 80.141 | 0.492 | 77.192 | 1.00 | 54.63 | N |
| ATOM | 5804 | CA | PHE D | 79 | 81.132 | 0.710 | 78.225 | 1.00 | 55.50 | C |
| ATOM | 5805 | CB | PHE D | 79 | 80.521 | 0.394 | 79.552 | 1.00 | 55.49 | C |
| ATOM | 5806 | CG | PHE D | 79 | 79.539 | 1.376 | 79.956 | 1.00 | 55.96 | C |
| ATOM | 5807 | CD1 | PHE D | 79 | 78.233 | 1.253 | 79.564 | 1.00 | 57.44 | C |
| ATOM | 5808 | CE1 | PHE D | 79 | 77.313 | 2.245 | 70.937 | 1.00 | 60.12 | C |

TABLE 11-continued

| | | | | | | | | | |
|---|---|---|---|---|---|---|---|---|---|
| ATOM | 5809 | CZ | PHE D | 79 | 77.722 | 3.366 | 80.768 | 1.00 | 54.67 | C |
| ATOM | 5810 | CE2 | PHE D | 79 | 79.011 | 3.459 | 81.059 | 1.00 | 54.58 | C |
| ATOM | 5811 | CD2 | PHE D | 79 | 79.925 | 2.490 | 80.570 | 1.00 | 54.16 | C |
| ATOM | 5812 | C | PHE D | 79 | 82.260 | −0.218 | 78.042 | 1.00 | 56.64 | C |
| ATOM | 5813 | O | PHE D | 79 | 82.082 | −1.439 | 77.967 | 1.00 | 57.51 | O |
| ATOM | 5814 | N | PHE D | 80 | 83.447 | 0.335 | 77.981 | 1.00 | 57.48 | N |
| ATOM | 5815 | CA | PHE D | 80 | 84.581 | −0.497 | 77.664 | 1.00 | 58.12 | C |
| ATOM | 5816 | CB | PHE D | 80 | 85.084 | −0.123 | 76.302 | 1.00 | 57.71 | C |
| ATOM | 5817 | CG | PHE D | 80 | 84.134 | −0.398 | 75.199 | 1.00 | 55.33 | C |
| ATOM | 5818 | CD1 | PHE D | 80 | 83.174 | 0.544 | 74.686 | 1.00 | 53.34 | C |
| ATOM | 5819 | CE1 | PHE D | 80 | 82.317 | 0.305 | 73.762 | 1.00 | 53.29 | C |
| ATOM | 5820 | CZ | PHE D | 80 | 82.425 | −0.885 | 73.030 | 1.00 | 51.47 | C |
| ATOM | 5821 | CE2 | PHE D | 80 | 83.388 | −1.842 | 73.386 | 1.00 | 50.55 | C |
| ATOM | 5822 | CD2 | PHE D | 80 | 84.241 | −1.582 | 74.455 | 1.00 | 54.07 | C |
| ATOM | 5823 | C | PHE D | 80 | 85.724 | −0.396 | 78.668 | 1.00 | 59.53 | C |
| ATOM | 5824 | O | PHE D | 80 | 85.707 | 0.445 | 79.573 | 1.00 | 60.43 | O |
| ATOM | 5825 | N | LYS D | 81 | 86.705 | −1.281 | 78.483 | 1.00 | 61.27 | N |
| ATOM | 5826 | CA | LYS D | 81 | 87.858 | −1.530 | 79.376 | 1.00 | 62.09 | C |
| ATOM | 5827 | CB | LYS D | 81 | 87.439 | −2.216 | 80.681 | 1.00 | 61.83 | C |
| ATOM | 5828 | CG | LYS D | 81 | 87.411 | −1.301 | 81.892 | 1.00 | 63.24 | C |
| ATOM | 5829 | CD | LYS D | 81 | 86.857 | −1.996 | 83.182 | 1.00 | 65.11 | C |
| ATOM | 5830 | CE | LYS D | 81 | 86.763 | −0.972 | 84.348 | 1.00 | 65.69 | C |
| ATOM | 5831 | NZ | LYS D | 81 | 88.157 | −0.573 | 84.862 | 1.00 | 65.82 | N |
| ATOM | 5832 | C | LYS D | 81 | 88.778 | 2.469 | 70.609 | 1.00 | 62.40 | C |
| ATOM | 5833 | O | LYS D | 81 | 88.368 | −3.581 | 78.240 | 1.00 | 62.20 | O |
| ATOM | 5834 | N | LYS D | 82 | 90.002 | −2.006 | 78.335 | 1.00 | 63.21 | N |
| ATOM | 5835 | CA | LYS D | 82 | 91.013 | −2.855 | 77.725 | 1.00 | 63.42 | C |
| ATOM | 5836 | CB | LYS D | 82 | 91.346 | −3.973 | 78.717 | 1.00 | 63.27 | C |
| ATOM | 5837 | CG | LYS D | 82 | 92.369 | −3.608 | 79.807 | 1.00 | 61.93 | C |
| ATOM | 5838 | CD | LYS D | 82 | 93.679 | −4.401 | 79.606 | 1.00 | 59.09 | C |
| ATOM | 5839 | CE | LYS D | 82 | 93.384 | −5.868 | 79.183 | 1.00 | 57.82 | C |
| ATOM | 5840 | NZ | LYS D | 82 | 94.366 | −6.859 | 79.716 | 1.00 | 57.22 | N |
| ATOM | 5841 | C | LYS D | 82 | 90.552 | 3.435 | 76.369 | 1.00 | 63.93 | C |
| ATOM | 5842 | O | LYS D | 82 | 90.937 | −4.545 | 75.992 | 1.00 | 64.21 | O |
| ATOM | 5843 | N | GLY D | 83 | 89.713 | −2.677 | 75.654 | 1.00 | 64.61 | N |
| ATOM | 5844 | CA | GLY D | 83 | 89.190 | −3.068 | 74.327 | 1.00 | 65.06 | C |
| ATOM | 5845 | C | GLY D | 83 | 87.875 | −3.845 | 74.334 | 1.00 | 65.10 | C |
| ATOM | 5846 | O | GLY D | 83 | 81.357 | −4.211 | 73.269 | 1.00 | 64.87 | O |
| ATOM | 5847 | N | GLN D | 84 | 87.319 | −4.041 | 75.532 | 1.00 | 65.14 | N |
| ATOM | 5848 | CA | GLN D | 84 | 86.332 | −5.079 | 75.806 | 1.00 | 65.29 | C |
| ATOM | 5849 | CB | GLN D | 84 | 86.970 | −6.108 | 76.705 | 1.00 | 65.39 | C |
| ATOM | 5850 | CG | GLN D | 84 | 88.000 | −6.942 | 76.030 | 1.00 | 67.85 | C |
| ATOM | 5851 | CD | GLN D | 84 | 87.376 | −8.208 | 75.468 | 1.00 | 71.15 | C |
| ATOM | 5852 | OE1 | GLN D | 84 | 86.806 | −8.196 | 74.372 | 1.00 | 71.43 | O |
| ATOM | 5853 | NE2 | GLN D | 84 | 87.460 | −9.306 | 76.227 | 1.00 | 70.30 | N |
| ATOM | 5854 | C | GLN D | 84 | 85.085 | −4.561 | 76.533 | 1.00 | 64.76 | C |
| ATOM | 5855 | O | GLN D | 84 | 85.209 | −3.866 | 77.552 | 1.00 | 65.15 | O |
| ATOM | 5855 | N | LYS D | 85 | 83.880 | −4.942 | 76.057 | 1.00 | 63.56 | N |
| ATOM | 5857 | CA | LYS D | 85 | 82.607 | −4.391 | 76.586 | 1.00 | 62.26 | C |
| ATOM | 5858 | CB | LYS D | 85 | 81.480 | 4.573 | 75.595 | 1.00 | 62.32 | C |
| ATOM | 5859 | CG | LYS D | 85 | 80.075 | −4.547 | 76.241 | 1.00 | 61.63 | C |
| ATOM | 5860 | CD | LYS D | 85 | 79.023 | −4.071 | 75.282 | 1.00 | 60.95 | C |
| ATOM | 5861 | CE | LYS D | 85 | 78.644 | −5.165 | 74.312 | 1.00 | 63.54 | C |
| ATOM | 5862 | NZ | LYS D | 85 | 78.477 | −4.524 | 72.934 | 1.00 | 66.61 | N |
| ATOM | 5863 | C | LYS D | 85 | 82.173 | −4.955 | 77.917 | 1.00 | 61.47 | C |
| ATOM | 5864 | O | LYS D | 85 | 82.017 | −6.164 | 78.065 | 1.00 | 61.44 | O |
| ATOM | 5865 | N | VAL D | 86 | 81.932 | −4.071 | 78.875 | 1.00 | 60.81 | N |
| ATOM | 5866 | CA | VAL D | 86 | 81.552 | −4.493 | 80.225 | 1.00 | 60.19 | C |
| ATOM | 5867 | CB | VAL D | 86 | 82.570 | −4.030 | 81.269 | 1.00 | 59.86 | C |
| ATOM | 5868 | CG1 | VAL D | 86 | 83.862 | −4.823 | 81.140 | 1.00 | 60.18 | C |
| ATOM | 5869 | CG2 | VAL D | 86 | 82.853 | −2.557 | 91.111 | 1.00 | 60.12 | O |
| ATOM | 5870 | C | VAL D | 86 | 80.173 | −3.979 | 80.597 | 1.00 | 59.88 | C |
| ATOM | 5871 | O | VAL D | 86 | 79.628 | −4.270 | 81.679 | 1.00 | 60.59 | O |
| ATOM | 5872 | N | GLY D | 87 | 79.593 | −3.222 | 79.694 | 1.00 | 59.15 | N |
| ATOM | 5873 | CA | GLY D | 87 | 78.340 | −2.595 | 80.008 | 1.00 | 59.02 | C |
| ATOM | 5874 | C | GLY D | 87 | 77.649 | −2.097 | 78.770 | 1.00 | 58.64 | C |
| ATOM | 5875 | O | GLY D | 87 | 78.292 | −1.805 | 77.727 | 1.00 | 58.30 | O |
| ATOM | 5876 | N | GLU D | 88 | 76.328 | −1.994 | 78.911 | 1.00 | 58.03 | N |
| ATOM | 5877 | CA | GLU D | 88 | 75.471 | −1.496 | 77.857 | 1.00 | 57.61 | C |
| ATOM | 5878 | CB | GLU D | 88 | 75.423 | −2.472 | 76.701 | 1.00 | 58.22 | C |
| ATOM | 5879 | CG | GLU D | 88 | 75.126 | −1.764 | 75.406 | 1.00 | 62.56 | C |
| ATOM | 5880 | CD | GLU D | 88 | 74.986 | −2.712 | 74.232 | 1.00 | 65.54 | C |
| ATOM | 5881 | OE1 | GLU D | 88 | 75.475 | −3.875 | 74.330 | 1.00 | 66.13 | O |
| ATOM | 5882 | OE2 | GLU D | 88 | 74.363 | −2.291 | 73.224 | 1.00 | 65.37 | O |
| ATOM | 5883 | C | GLU D | 88 | 74.065 | −1.297 | 78.299 | 1.00 | 55.80 | C |
| ATOM | 5884 | O | GLU D | 88 | 73.513 | −2.126 | 78.998 | 1.00 | 56.63 | O |
| ATOM | 5885 | N | PHE D | 89 | 73.464 | −0.210 | 77.846 | 1.00 | 54.42 | N |
| ATOM | 5886 | CA | PHE D | 89 | 72.032 | −0.059 | 77.944 | 1.00 | 52.06 | C |
| ATOM | 5887 | CB | PHE D | 89 | 71.637 | 0.382 | 79.325 | 1.00 | 52.42 | C |
| ATOM | 5888 | CG | PHE D | 89 | 71.895 | 1.814 | 79.584 | 1.00 | 52.00 | C |

TABLE 11-continued

| | | | | | | | | | | |
|---|---|---|---|---|---|---|---|---|---|---|
| ATOM | 5889 | CD1 | PHE D | 89 | 70.955 | 2.792 | 79.176 | 1.00 | 50.26 | C |
| ATOM | 5890 | CE1 | PHE D | 89 | 71.186 | 4.102 | 79.424 | 1.00 | 49.97 | C |
| ATOM | 5891 | CZ | PHE D | 89 | 72.386 | 4.489 | 80.120 | 1.00 | 51.53 | C |
| ATOM | 5892 | CE2 | PHE D | 89 | 73.314 | 3.531 | 80.499 | 1.00 | 49.22 | C |
| ATOM | 5893 | CD2 | PHE D | 89 | 73.059 | 2.198 | 80.232 | 1.00 | 49.15 | C |
| ATOM | 5894 | C | PHE D | 89 | 71.635 | 0.978 | 76.988 | 1.00 | 50.51 | N |
| ATOM | 5895 | O | PHE D | 89 | 72.500 | 1.668 | 76.445 | 1.00 | 49.81 | O |
| ATOM | 5896 | N | SER D | 90 | 70.328 | 1.097 | 76.784 | 1.00 | 49.48 | N |
| ATOM | 5897 | CA | SER D | 90 | 69.825 | 2.083 | 75.840 | 1.00 | 49.88 | C |
| ATOM | 5898 | CB | SER D | 90 | 69.277 | 1.388 | 74.606 | 1.00 | 50.04 | C |
| ATOM | 5899 | OG | SER D | 90 | 70.150 | 0.339 | 74.238 | 1.00 | 52.42 | O |
| ATOM | 5900 | C | SER D | 90 | 68.818 | 3.071 | 76.420 | 1.00 | 49.43 | C |
| ATOM | 5901 | O | SER D | 90 | 68.161 | 2.797 | 77.441 | 1.00 | 49.36 | O |
| ATOM | 5902 | N | GLY D | 91 | 68.735 | 4.243 | 75.816 | 1.00 | 49.13 | N |
| ATOM | 5903 | CA | GLY D | 91 | 67.703 | 5.189 | 76.198 | 1.00 | 51.25 | C |
| ATOM | 5904 | C | GLY D | 91 | 68.195 | 6.435 | 76.855 | 1.00 | 52.38 | C |
| ATOM | 5905 | O | GLY D | 91 | 69.226 | 6.435 | 77.607 | 1.00 | 52.15 | O |
| ATOM | 5906 | N | ALA D | 92 | 67.471 | 7.528 | 76.673 | 1.00 | 54.23 | N |
| ATOM | 5907 | CA | ALA D | 92 | 67.956 | 8.786 | 77.201 | 1.00 | 56.43 | C |
| ATOM | 5908 | CB | ALA D | 92 | 67.345 | 9.900 | 76.481 | 1.00 | 56.17 | C |
| ATOM | 5909 | C | ALA D | 92 | 67.679 | 8.886 | 78.709 | 1.00 | 58.45 | C |
| ATOM | 5910 | O | ALA D | 92 | 66.704 | 9.538 | 79.122 | 1.00 | 60.93 | O |
| ATOM | 5911 | N | ASN D | 93 | 68.540 | 8.272 | 79.531 | 1.00 | 58.67 | N |
| ATOM | 5912 | CA | ASN D | 93 | 68.312 | 8.183 | 80.971 | 1.00 | 58.16 | C |
| ATOM | 5913 | CB | ASN D | 93 | 67.950 | 6.741 | 81.289 | 1.00 | 58.71 | C |
| ATOM | 5914 | CG | ASN D | 93 | 57.436 | 6.584 | 82.698 | 1.00 | 59.03 | C |
| ATOM | 5915 | OD1 | ASN D | 93 | 67.736 | 7.335 | 83.604 | 1.00 | 62.54 | O |
| ATOM | 5916 | ND2 | ASN D | 93 | 66.655 | 5.547 | 82.886 | 1.00 | 57.97 | N |
| ATOM | 5917 | C | ASN D | 93 | 69.506 | 8.624 | 81.848 | 1.00 | 58.11 | C |
| ATOM | 5918 | O | ASN D | 93 | 70.332 | 7.803 | 82.235 | 1.00 | 57.60 | O |
| ATOM | 5919 | N | LYS D | 94 | 69.565 | 9.914 | 82.182 | 1.00 | 58.70 | N |
| ATOM | 5920 | CA | LYS D | 94 | 70.670 | 10.488 | 82.964 | 1.00 | 59.28 | C |
| ATOM | 5921 | CB | LYS D | 94 | 70.319 | 11.883 | 83.490 | 1.00 | 59.85 | C |
| ATOM | 5922 | CG | LYS D | 94 | 69.861 | 12.903 | 82.463 | 1.00 | 62.94 | C |
| ATOM | 5923 | CD | LYS D | 94 | 69.251 | 14.137 | 83.172 | 1.00 | 65.98 | C |
| ATOM | 5924 | CE | LYS D | 94 | 67.809 | 13.901 | 83.697 | 1.00 | 68.13 | C |
| ATOM | 5925 | NZ | LYS D | 94 | 67.455 | 14.912 | 84.744 | 1.00 | 66.83 | N |
| ATOM | 5926 | C | LYS D | 94 | 71.019 | 9.618 | 84.155 | 1.00 | 58.66 | C |
| ATOM | 5927 | O | LYS D | 94 | 72.186 | 9.261 | 84.356 | 1.00 | 59.82 | O |
| ATOM | 5928 | N | GLU D | 95 | 70.008 | 9.290 | 84.949 | 1.00 | 57.29 | N |
| ATOM | 5929 | CA | GLU D | 95 | 70.212 | 8.578 | 86.197 | 1.00 | 56.70 | C |
| ATOM | 5930 | CB | GLU D | 95 | 68.889 | 8.383 | 86.962 | 1.00 | 57.79 | C |
| ATOM | 5931 | CG | GLU D | 95 | 68.291 | 9.646 | 87.593 | 1.00 | 59.74 | C |
| ATOM | 5932 | CD | GLU D | 95 | 68.015 | 10.747 | 86.588 | 1.00 | 63.88 | C |
| ATOM | 5933 | OE1 | GLU D | 95 | 67.885 | 10.479 | 85.373 | 1.00 | 66.59 | O |
| ATOM | 5934 | OE2 | GLU D | 95 | 67.930 | 11.909 | 87.004 | 1.00 | 66.66 | O |
| ATOM | 5935 | C | GLU D | 95 | 70.851 | 7.242 | 85.916 | 1.00 | 55.08 | C |
| ATOM | 5936 | O | GLU D | 95 | 71.867 | 6.925 | 86.496 | 1.00 | 55.47 | O |
| ATOM | 5937 | N | LYS D | 96 | 70.286 | 6.478 | 84.990 | 1.00 | 53.68 | N |
| ATOM | 5938 | CA | LYS D | 96 | 70.831 | 5.151 | 84.674 | 1.00 | 52.31 | C |
| ATOM | 5939 | CB | LYS D | 96 | 69.941 | 4.380 | 83.670 | 1.00 | 52.51 | C |
| ATOM | 5940 | CG | LYS D | 96 | 70.480 | 2.987 | 83.441 | 1.00 | 52.99 | C |
| ATOM | 5941 | CD | LYS D | 96 | 69.561 | 2.081 | 82.736 | 1.00 | 56.79 | C |
| ATOM | 5942 | CE | LYS D | 96 | 69.954 | 0.634 | 83.061 | 1.00 | 59.97 | C |
| ATOM | 5943 | NZ | LYS D | 96 | 69.106 | −0.245 | 82.198 | 1.00 | 62.61 | N |
| ATOM | 5944 | C | LYS D | 96 | 72.276 | 5.211 | 84.204 | 1.00 | 50.88 | C |
| ATOM | 5945 | O | LYS D | 96 | 73.117 | 4.372 | 84.614 | 1.00 | 49.57 | O |
| ATOM | 5946 | N | LEU D | 97 | 72.520 | 6.204 | 83.346 | 1.00 | 49.96 | N |
| ATOM | 5947 | CA | LEU D | 97 | 73.838 | 6.604 | 82.866 | 1.00 | 50.42 | C |
| ATOM | 5948 | CB | LEU D | 97 | 73.704 | 7.847 | 82.017 | 1.00 | 50.62 | C |
| ATOM | 5949 | CG | LEU D | 97 | 74.967 | 8.457 | 81.455 | 1.00 | 52.10 | C |
| ATOM | 5950 | CD1 | LEU D | 97 | 75.760 | 7.485 | 80.629 | 1.00 | 51.91 | C |
| ATOM | 5951 | CD2 | LEU D | 97 | 74.642 | 9.697 | 80.636 | 1.00 | 51.62 | C |
| ATOM | 5952 | C | IEU D | 97 | 74.848 | 6.858 | 83.987 | 1.00 | 50.58 | C |
| ATOM | 5953 | O | LEU D | 97 | 75.971 | 6.271 | 83.993 | 1.00 | 51.34 | O |
| ATOM | 5954 | N | GLU D | 98 | 74.460 | 7.666 | 84.974 | 1.00 | 49.73 | N |
| ATOM | 5955 | CA | GLU D | 98 | 75.428 | 7.970 | 86.052 | 1.00 | 49.17 | C |
| ATOM | 5956 | CB | GLU D | 98 | 75.055 | 9.225 | 86.877 | 1.00 | 48.36 | C |
| ATOM | 5957 | CG | GLU D | 98 | 76.154 | 9.632 | 87.778 | 1.00 | 47.29 | C |
| ATOM | 5958 | CD | GLU D | 98 | 75.996 | 11.044 | 88.410 | 1.00 | 51.19 | C |
| ATOM | 5959 | OE1 | GLU D | 98 | 74.875 | 11.659 | 88.371 | 1.00 | 47.07 | O |
| ATOM | 5960 | OE2 | GLU D | 98 | 77.025 | 11.514 | 89.006 | 1.00 | 49.07 | O |
| ATOM | 5961 | C | GLU D | 98 | 75.709 | 6.741 | 86.913 | 1.00 | 48.25 | C |
| ATOM | 5962 | O | GLU D | 98 | 76.859 | 6.468 | 87.268 | 1.00 | 48.38 | O |
| ATOM | 5963 | N | ALA D | 99 | 74.663 | 5.985 | 87.215 | 1.00 | 47.76 | N |
| ATOM | 5964 | CA | ALA D | 99 | 74.814 | 4.721 | 87.944 | 1.00 | 47.05 | C |
| ATOM | 5965 | CB | ALA D | 99 | 73.439 | 4.047 | 88.203 | 1.00 | 46.09 | C |
| ATOM | 5966 | C | ALA D | 99 | 75.781 | 3.778 | 87.224 | 1.00 | 46.64 | C |
| ATOM | 5967 | O | ALA D | 99 | 76.777 | 3.359 | 87.776 | 1.00 | 46.05 | O |
| ATOM | 5968 | N | THR D | 100 | 75.533 | 3.461 | 85.975 | 1.00 | 47.99 | N |

TABLE 11-continued

| ATOM | 5969 | CA | THR D | 100 | 76.444 | 2.494 | 85.328 | 1.00 | 49.30 | C |
|---|---|---|---|---|---|---|---|---|---|---|
| ATOM | 5970 | CB | THR D | 100 | 76.097 | 2.232 | 83.809 | 1.00 | 49.38 | C |
| ATOM | 5971 | OG1 | THR D | 100 | 74.692 | 2.050 | 83.631 | 1.00 | 47.48 | O |
| ATOM | 5972 | CG2 | THR D | 100 | 76.831 | 1.045 | 83.292 | 1.00 | 47.31 | C |
| ATOM | 5973 | C | THR D | 100 | 77.874 | 3.034 | 85.405 | 1.00 | 50.78 | C |
| ATOM | 5974 | O | THR D | 100 | 78.811 | 2.251 | 85.542 | 1.00 | 51.20 | O |
| ATOM | 5975 | N | ILE D | 101 | 78.052 | 4.366 | 85.252 | 1.00 | 52.31 | N |
| ATOM | 5976 | CA | ILE D | 101 | 79.402 | 4.933 | 85.282 | 1.00 | 52.23 | C |
| ATOM | 5977 | CB | ILE D | 101 | 79.432 | 6.432 | 85.020 | 1.00 | 51.92 | C |
| ATOM | 5978 | CG1 | ILE D | 101 | 79.168 | 6.702 | 85.533 | 1.00 | 52.53 | C |
| ATOM | 5979 | CD1 | ILE D | 101 | 79.231 | 8.184 | 83.138 | 1.00 | 52.28 | C |
| ATOM | 5980 | CG2 | ILE D | 101 | 80.799 | 7.006 | 85.385 | 1.00 | 48.34 | C |
| ATOM | 5981 | C | ILE D | 101 | 80.077 | 4.571 | 86.593 | 1.00 | 53.40 | C |
| ATOM | 5982 | O | ILE D | 101 | 81.122 | 3.871 | 86.601 | 1.00 | 53.33 | O |
| ATOM | 5983 | N | ASN D | 102 | 79.470 | 5.027 | 87.690 | 1.00 | 54.06 | N |
| ATOM | 5984 | CA | ASN D | 102 | 79.939 | 4.710 | 89.043 | 1.00 | 54.90 | C |
| ATOM | 5985 | CB | ASN D | 102 | 79.823 | 5.333 | 90.053 | 1.00 | 54.21 | C |
| ATOM | 5986 | CG | ASN D | 102 | 79.026 | 6.783 | 89.963 | 1.00 | 55.14 | C |
| ATOM | 5987 | OD1 | ASN D | 102 | 80.104 | 7.417 | 89.928 | 1.00 | 55.37 | O |
| ATOM | 5988 | ND2 | ASN D | 102 | 77.823 | 7.367 | 89.930 | 1.00 | 54.04 | N |
| ATOM | 5989 | C | ASN D | 102 | 79.933 | 3.248 | 89.377 | 1.00 | 55.63 | C |
| ATOM | 5990 | O | ASN D | 102 | 80.447 | 2.825 | 90.432 | 1.00 | 57.03 | O |
| ATOM | 5991 | N | GLU D | 103 | 79.303 | 2.463 | 88.543 | 1.00 | 55.76 | N |
| ATOM | 5992 | CA | GLU D | 103 | 79.184 | 1.085 | 88.991 | 1.00 | 57.11 | C |
| ATOM | 5993 | CB | GLU D | 103 | 77.753 | 0.580 | 88.690 | 1.00 | 56.79 | C |
| ATOM | 5994 | CG | GLU D | 103 | 77.547 | −0.872 | 88.506 | 1.00 | 58.03 | C |
| ATOM | 5995 | CD | GLU D | 103 | 76.070 | −1.175 | 88.168 | 1.00 | 63.41 | C |
| ATOM | 5996 | OE1 | GLU D | 103 | 75.620 | −0.914 | 87.007 | 1.00 | 62.66 | O |
| ATOM | 5997 | OE2 | GLU D | 103 | 75.357 | −1.684 | 89.084 | 1.00 | 65.97 | O |
| ATOM | 5998 | C | GLU D | 103 | 80.249 | 0.332 | 88.185 | 1.00 | 57.20 | C |
| ATOM | 5999 | O | GLU D | 103 | 80.565 | −0.772 | 88.552 | 1.00 | 58.40 | O |
| ATOM | 6000 | N | LEU D | 104 | 80.868 | 0.961 | 87.215 | 1.00 | 57.70 | N |
| ATOM | 6001 | CA | LEU D | 104 | 81.794 | 0.248 | 85.359 | 1.00 | 58.96 | C |
| ATOM | 6002 | CB | LEU D | 104 | 81.135 | 0.000 | 84.987 | 1.00 | 58.33 | C |
| ATOM | 6003 | CG | LEU D | 104 | 80.080 | −1.124 | 84.865 | 1.00 | 57.19 | C |
| ATOM | 6004 | CD1 | LEU D | 104 | 79.249 | −1.065 | 83.561 | 1.00 | 58.38 | C |
| ATOM | 6005 | CD2 | LEU D | 104 | 80.696 | −2.476 | 84.972 | 1.00 | 52.65 | C |
| ATOM | 6006 | C | LEU D | 104 | 83.185 | 0.921 | 86.219 | 1.00 | 60.49 | C |
| ATOM | 6007 | O | LEU D | 104 | 84.089 | 0.348 | 85.599 | 1.00 | 60.81 | O |
| ATOM | 6008 | N | VAL D | 105 | 83.345 | 2.137 | 86.762 | 1.00 | 61.89 | N |
| ATOM | 6009 | CA | VAL D | 105 | 84.660 | 2.744 | 86.881 | 1.00 | 63.12 | C |
| ATOM | 6010 | CB | VAL D | 105 | 84.705 | 4.009 | 87.804 | 1.00 | 63.14 | C |
| ATOM | 6011 | CG1 | VAL D | 105 | 84.377 | 5.220 | 87.024 | 1.00 | 62.92 | C |
| ATOM | 6012 | CG2 | VAL D | 105 | 83.774 | 3.891 | 89.027 | 1.00 | 83.19 | C |
| ATOM | 6013 | C | VAL D | 105 | 85.545 | 1.684 | 87.488 | 1.00 | 64.48 | C |
| ATOM | 6014 | O | VAL D | 105 | 85.188 | 1.144 | 88.551 | 1.00 | 65.43 | O |
| ATOM | 6015 | OXT | VAL D | 105 | 86.607 | 1.324 | 86.944 | 1.00 | 65.61 | O |
| TER | | | | | | | | | | |
| ATOM | 6016 | O | HOH W | 1 | 47.966 | −6.060 | 35.393 | 1.00 | 48.18 | O |
| ATOM | 6017 | O | HOH W | 2 | 63.204 | 15.546 | 66.578 | 1.00 | 47.81 | O |
| ATOM | 6018 | O | HOH W | 3 | −15.844 | −5.890 | 15.377 | 1.00 | 41.81 | O |
| ATOM | 6019 | O | HOH W | 4 | 6.672 | 0.388 | 14.030 | 1.00 | 41.55 | O |
| ATOM | 6020 | O | HOH W | 5 | 5.628 | −0.439 | 4.663 | 1.00 | 55.87 | O |
| ATOM | 6021 | O | HOH W | 6 | −6.657 | −1.075 | 39.601 | 1.00 | 48.41 | O |
| ATOM | 6022 | O | HOH W | 7 | 77.795 | 17.771 | 74.566 | 1.00 | 41.95 | O |
| ATOM | 6023 | O | HOH W | 8 | 45.358 | −3.554 | 38.212 | 1.00 | 34.07 | O |
| ATOM | 6024 | O | HOH W | 9 | 45.121 | 7.285 | 70.045 | 1.00 | 64.82 | O |
| ATOM | 6025 | O | HOH W | 10 | 81.720 | 8.777 | 92.289 | 1.00 | 49.47 | O |
| ATOM | 6026 | O | HOH W | 11 | 3.726 | −1.516 | 11.028 | 1.00 | 49.02 | O |
| ATOM | 6027 | O | HOH W | 12 | −5.447 | 10.545 | 23.498 | 1.00 | 60.19 | O |
| ATOM | 6028 | O | HOH W | 13 | 47.749 | 8.547 | 75.599 | 1.00 | 59.35 | O |
| ATOM | 6029 | O | HOH W | 14 | 3.940 | −2.384 | 35.612 | 1.00 | 56.99 | O |
| ATOM | 6030 | O | HOH W | 15 | 39.596 | 8.994 | 27.527 | 1.00 | 43.19 | O |
| ATOM | 6031 | O | HOH W | 16 | 68.676 | −1.114 | 77.523 | 1.00 | 59.81 | O |
| ATOM | 6032 | O | HOH W | 17 | 43.617 | −6.151 | 35.157 | 1.00 | 57.64 | O |
| ATOM | 6033 | O | HOH W | 18 | 37.186 | 9.325 | 18.814 | 1.00 | 40.10 | O |
| ATOM | 6034 | O | HOH W | 19 | 48.846 | 7.560 | 43.080 | 1.00 | 50.65 | O |
| ATOM | 6035 | O | HOH W | 20 | 32.939 | 9.613 | 56.336 | 1.00 | 56.41 | O |
| ATOM | 6036 | O | HOH W | 21 | 8.127 | 3.993 | 45.577 | 1.00 | 61.50 | O |
| ATOM | 6037 | O | HOH W | 22 | −11.862 | −2.809 | 8.483 | 1.00 | 37.42 | O |
| ATOM | 6038 | O | HOH W | 23 | 1.888 | 5.546 | 21.102 | 1.00 | 52.27 | O |
| ATOM | 6039 | O | HOH W | 24 | 29.653 | 20.246 | 25.483 | 1.00 | 61.05 | O |
| ATOM | 6040 | O | HOH W | 25 | 70.724 | 2.059 | 62.594 | 1.00 | 48.47 | O |
| ATOM | 6041 | O | HOH W | 26 | 48.180 | 0.154 | 42.773 | 1.00 | 55.63 | O |
| ATOM | 6042 | O | HOH W | 27 | 48.272 | 6.898 | 61.888 | 1.00 | 41.18 | O |
| ATOM | 6043 | O | HOH W | 28 | −18.515 | 9.366 | 2.804 | 1.00 | 47.74 | O |
| ATOM | 6044 | O | HOH W | 29 | 26.922 | −5.894 | 61.506 | 1.00 | 58.23 | O |
| ATOM | 6045 | O | HOH W | 30 | 35.195 | −14.459 | 41.813 | 1.00 | 60.27 | O |
| ATOM | 6046 | O | HOH W | 31 | 35.666 | −7.168 | 58.643 | 1.00 | 49.17 | O |

TABLE 11-continued

| ATOM | 6047 | O | HOH W | 32 | 39.646 | 13.154 | 43.227 | 1.00 | 61.49 | O |
|---|---|---|---|---|---|---|---|---|---|---|
| ATOM | 6048 | O | HOH W | 33 | 68.062 | -2.357 | 57.650 | 1.00 | 54.39 | O |
| ATOM | 6049 | O | HOH W | 34 | 34.313 | -3.508 | 73.662 | 1.00 | 64.71 | O |
| ATOM | 6050 | O | HOH W | 35 | -3.958 | -9.288 | 11.266 | 1.00 | 36.47 | O |
| ATOM | 6051 | O | HOH W | 36 | 67.097 | -5.607 | 58.150 | 1.00 | 57.46 | O |
| ATOM | 6052 | O | HOH W | 37 | 2.265 | -8.666 | 19.774 | 1.00 | 43.62 | O |
| ATOM | 6053 | O | HOH W | 38 | 17.083 | -3.214 | 17.851 | 1.00 | 53.84 | O |
| ATOM | 6054 | O | HOH W | 39 | -17.084 | 0.827 | 23.894 | 1.00 | 61.02 | O |
| ATOM | 6055 | O | HOH W | 40 | 4.919 | -5.480 | 15.458 | 1.00 | 50.27 | O |
| ATOM | 6056 | O | HOH W | 41 | 80.578 | 10.353 | 64.873 | 1.00 | 47.77 | O |
| ATOM | 6057 | O | HOH W | 42 | -13.896 | -11.885 | 22.190 | 1.00 | 57.91 | O |
| ATOM | 6058 | O | HOH W | 43 | 27.378 | -3.564 | 33.013 | 1.00 | 63.91 | O |
| ATOM | 6059 | O | HOH W | 44 | 49.295 | -5.449 | 62.385 | 1.00 | 55.41 | O |
| ATOM | 6060 | O | HOH W | 45 | 8.206 | -3.817 | 18.442 | 1.00 | 46.33 | O |
| ATOM | 6061 | O | HOH W | 46 | 46.111 | 9.126 | 37.252 | 1.00 | 54.06 | O |
| ATOM | 6062 | O | HOH W | 47 | -11.652 | 9.545 | 14.652 | 1.00 | 53.68 | O |
| ATOM | 6063 | O | HOH W | 48 | 84.343 | 0.018 | 90.735 | 1.00 | 61.39 | O |
| ATOM | 6064 | O | HOH W | 49 | 4.655 | -7.555 | 16.943 | 1.00 | 47.96 | O |
| ATOM | 6065 | O | HOH W | 50 | 58.934 | -5.185 | 25.295 | 1.00 | 56.46 | O |
| ATOM | 6066 | O | HOH W | 51 | 42.687 | -14.538 | 40.831 | 1.00 | 51.18 | O |
| ATOM | 6067 | O | HOH W | 52 | 66.416 | -3.356 | 61.916 | 1.00 | 72.73 | O |
| ATOM | 6068 | O | HOH W | 53 | -40.824 | -11.103 | 2.765 | 1.00 | 73.03 | O |
| ATOM | 6069 | O | HOH W | 54 | 68.754 | 1.887 | 64.409 | 1.00 | 37.37 | O |
| ATOM | 6070 | O | HOH W | 55 | 34.377 | -15.491 | 79.535 | 1.00 | 51.16 | O |
| ATOM | 6071 | O | HOH W | 56 | 39.907 | -8.439 | 59.469 | 1.00 | 52.78 | O |
| ATOM | 6072 | O | HOH W | 57 | 22.813 | -6.800 | 69.133 | 1.00 | 64.46 | O |
| ATOM | 6073 | O | HOH W | 58 | 26.192 | 13.054 | 29.194 | 1.00 | 55.35 | O |
| ATOM | 6074 | O | HOH W | 59 | -21.804 | -17.554 | 11.518 | 1.00 | 55.95 | O |

Example 7: NMR Spectroscopy

NMR interaction experiments were carried out by recording $^1$H-$^{15}$N NMR HSQC spectra of $^{15}$N-labeled N-TXNIP upon addition of unlabeled TRX or its mutant, which was reduced with 5 mM DTT and dialyzed against 50 mM potassium phosphate (pH 6.6) prior to the interaction study to remove excess DTT.

The $^1$H-$^{15}$N HSQC spectra of all proteins were measured on a Bruker 900 MHz NMR spectrometer at the Korea Basic Science Institute (Ochang, Korea). The NMR measurements were performed using 0.3 mM $^{15}$N-labeled protein in 50 mM potassium phosphate (pH 6.6) containing 10% D$_2$O at 25° C. All NMR spectra were processed with Topspin 2.1 and analyzed with the program SPARKY 3.1.

Example 8: TRX Activity Assay

TRX activity was assayed using the insulin disulfide reduction assay. The transiently transfected HEK 293T cells were lysed in lysis buffer containing 20 mM HEPES (pH 7.9), 100 mM KCl, 300 mM NaCl, 10 mM EDTA, 0.1% Nonidet P-40, and protease inhibitors. To reduce TRX, cell extracts (20 μg) were incubated at 37° C. for 20 minutes with 2 μl of DTT activation buffer containing 50 mM HEPES(pH 7.6), 1 mM EDTA, 1 mg/ml BSA, and 2 mM DTT in a total volume of 70 μl. 40 μl of reaction mixture taken from a solution containing 200 μl of 1 M HEPES (pH 7.6), 40 μl of 0.2 M EDTA, 40 μl of NADPH (40 mg/ml), and 500 μl of insulin (10 mg/ml) was then added. Rat thioredoxin reductase (100 U/ml) was added to reaction and incubated at 37° C. for 20 minutes. The reaction was stopped with 6 M guanidine-HCl and 1 mM DNTB (3-carboxy-4-nitrophenyl disulfide), and absorbance was measured at 412 nm.

Example 9: ROS (Reactive Oxygen Species) Assay

The TRX and T-TXNIP(C120S/C170S/C205S/C267S) (SEQ ID NO: 6) complex was used to circumvent non-functional cysteine-induced aggregation. The complex (at a concentration of 0.05 mM) was incubated with H$_2$O$_2$ at concentrations in the range of 0 to 10 mM in 50 mM Tris-HCl (pH 8.0), 500 mM NaCl, and 10% glycerol at 37° C. The TRX(C37A) and T-TXNIP(C36S/C49S/C120S/C170S/C205S/C267S) complex was also used to avoid TRX dimerization and non-functional cysteine-induced aggregation. This complex was incubated with 0 to 3 mM diamide in 50 mM Tris-HCl(pH 8.0), 500 mM NaCl, and 10% glycerol at 37° C. After a 30-minute reaction, the samples were injected onto a HiLoad™ 16/60 Superdex™ 75 gel filtration column (GE Healthcare) installed on an AKTA purifier FPLC system at a flow rate of 1 ml/min at room temperature. To examine the role of TRX Cys35 for dissociation between TRX and TXNIP, the TRX(C35A)(SEQ ID NO:3)-T-TXNIP(C120S/C170S/C205S/C267S)(SEQ ID NO: 6) complex was incubated at room temperature for 1 hour with 3.3 mM diamide and then injected onto the Superdex™ 75 10/300 GL gel filtration column. All fractions were subjected to SDS-PAGE.

Example 10: Mass Spectrometry

Example 10-1: Sample Preparation for Mass Spectrometric Analysis

For the analysis of interprotomer disulfide bond between TXNIP molecules by mass spectrometry in vivo, HEK 293T cell were transfected with expression plasmid expressing TXNIP fused with GST. 24 hours later, the transfected cells were harvested and lysed in lysis buffer containing 0.5% Triton X-100, 150 mM NaCl, 10% glycerol and 20 mM HEPES (pH 7.2) supplemented with complete protease inhibitor cocktail (Roche). After incubation at 4° C. for 30 minutes, lysates were centrifuged at 16,000 g for 20 minutes. The supernatants were overnight-incubated at 4° C. with Glutathione Sepharose 4FF (GE Healthcare) and centrifuged at 10,000 g for 5 minutes. Next, the supernatant was discarded and the resin was washed five times with lysis buffer. Bound proteins to resin were eluted by boiling in an LDS-PAGE loading buffer (life technologies).

For analysis by mass spectrometry in vitro, purified TRX(C73A)-T-TXNIP(C36S/C49S/C120S/C170S/C205S/C267S) complex was incubated with 100 mM DTT for 1 hour at room temperature and injected to the Superdex™ 200 10/300 GL gel filtration column installed on an AKTA purifier FPLC system to obtain T-TXNIP(C36S/C49S/C120S/C170S/C205S/C267S) from remained protein complex and TRX(C73A). The fractions containing T-TXNIP (C36S/C49S/C120S/C170S/C205S/C267S) were dialyzed against 50 mM Tris-HCl (pH 8.0), 500 mM NaCl and 10% glycerol to induce the formation of disulfide bonds between TXNIP molecules through air oxidation. Dialyzed proteins were then subjected to SDS-PAGE under non-reducing conditions.

Example 10-2: In Gel Digestion

The high molecular TXNIP complex-containing gel pieces were destained in the 25 mM ammonium bicarbonate and 50% acetonitrile solution, dehydrated with 100% acetonitrile and dried at room temperature. Alkylation of free cysteines was performed by addition of 55 mM iodoacetamide in 25 mM ammonium bicarbonate, followed by incubation at 25° C. for 1 hour in the dark. The gel was washed with 25 mM ammonium bicarbonate and 50% acetonitrile solution, dehydrated with 100% acetonitrile and dried at room temperature. The gel pieces were rehydrated with a solution of sequencing-grade trypsin (12.5 ng/µL; Promega, Madison, Wis., U.S.A.) in 25 mM ammonium bicarbonate and incubated at 37° C. for 16 hours for protein digestion. Next, supernatants were transferred to fresh tubes, and the remaining peptides were sequentially extracted by incubating gel pieces with 50% acetonitrile in 25 mM ammonium bicarbonate, 50% acetonitrile in 0.5% trifluoroacetic acid (TFA), and 70% acetonitrile in 0.5% TFA. The extracted peptides were combined and dried in a vacuum evaporator (MIVAC DUO, Genevac, Ipswich, England). The peptides were stored at −20° C. until use.

Example 10-3: Mass Spectrometric Analysis

The peptides obtained in 10-2 were diluted with 0.4% acetic acid to achieve concentrations of 1 µg/µL and an aliquot (~1 µg) was injected to a reversed-phase Magic C18aq column (15 cm×75 µm) on an Eksigent nanoLC-ultra 1D plus system at a flow rate of 300 nL/min. The column was equilibrated with 95% buffer A (0.1% formic acid in $H_2O$)+5% buffer B (0.1% formic acid in acetonitrile) prior to use. Peptides were eluted with a linear gradient from 10% buffer B to 40% buffer B over 40 minutes. The HPLC system was coupled to a Q Exactive quadrupole mass spectrometer (Thermo Scientific, San Jose, Calif., USA). The Q Exactive instrument was operated in data dependent mode. Survey full-scan MS spectra (m/z 300-2,000) were acquired in the Orbitrap with a resolution of 75,000, MS/MS spectra of the twelve most intense ions from the MS1 scan with charge state ≥2 were acquired with the following settings: resolution, 17,500; isolation width, 2 m/z; normalized collision energy, 27%; dynamic exclusion duration, 30s. ion selection threshold, 4.00E+03 counts.

Example 10-4: Database Searching and Validation

The acquired MS/MS spectra were searched using X!Tandem (open source software, available fromproteome.ca/opensource.html) against the SwissProt database. Briefly, peptide mass tolerance was set to ±15 ppm, cleavage specificity was set to trypsin, allowing for a maximum of one missed cleavages. A variable modification of methionine oxidation (+15.9949 Da) and carbamidomethylated cysteine (+57.0215 Da) was allowed. Peptide assignment was performed with the Trans Proteomics Pipeline provided by Institute for Systems Biology (TPP, version 4.5 RAPTURE rev 2, roteomecenter.org). From the X!Tandem search output, peptides with probabilities greater than 0.9 were included in the subsequent Protein-Prophet, and proteins having protein probability of more than 0.9 were gathered. From the results, the contaminants (e.g. Keratin and trypsin artificial) were removed. Analysis for identification of disulfide linkages was performed using DBond software (version 3.02, prix.hanyang.ac.kr/download/dbond.j sp) (PMID: 19902913).

Experimental Example 1: Structure Determination and Molecular Architecture of TRX-TXNIP Complex Repeated experiments aimed at the overexpression of the recombinant full-length TXNIP protein as a soluble protein have been tried. However, when only TXNIP was expressed, it behaved as a molten globular protein showing a low binding activity. Under these circumstances, it was tried to express TXNIP as a soluble protein by carrying out constructional changes in TXNIP protein and co-expressing TRX and TXNIP.

Figure 5:
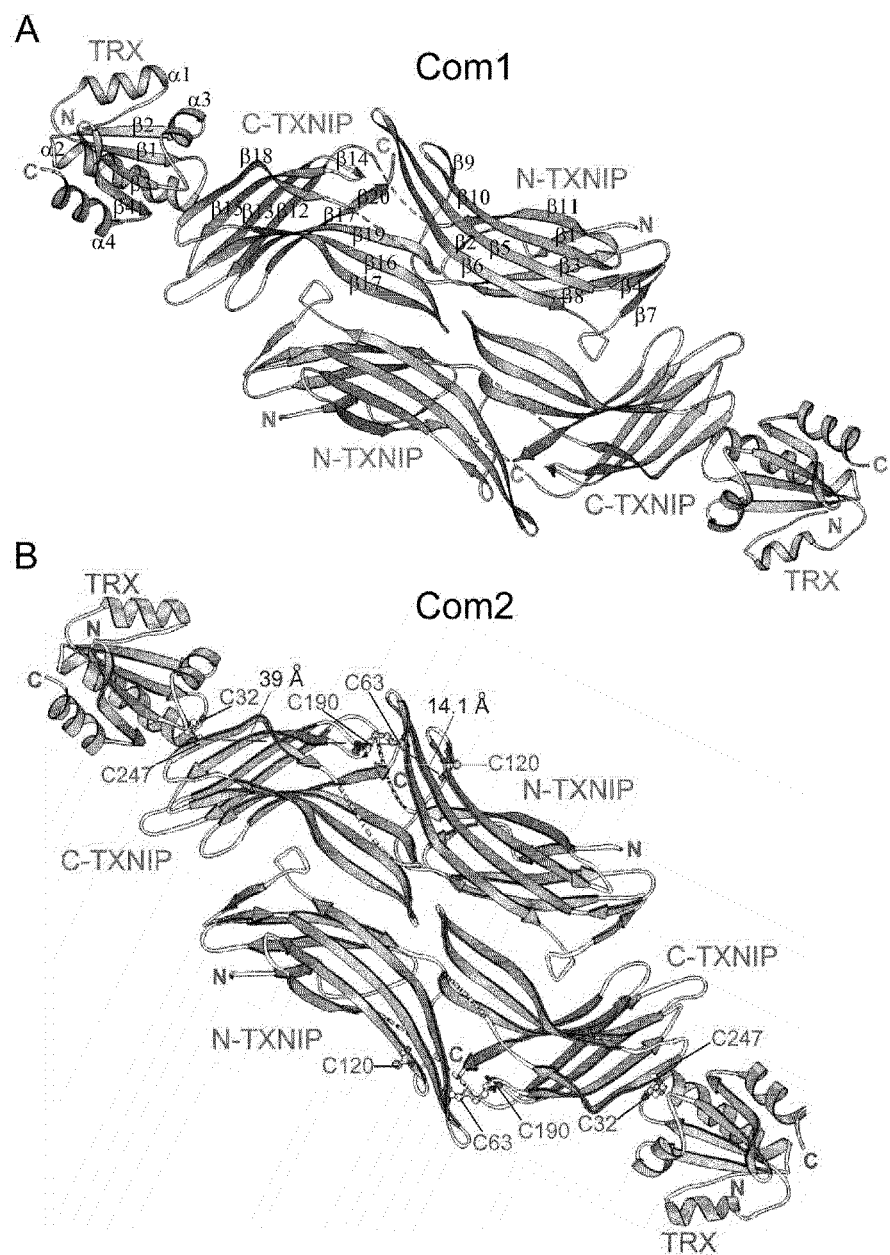
FIG. 5 shows the overall structure of TRX and TXNIP complex: (A) Ribbon representation of COM1 is shown, the structure of TRX(C35A)(SEQ ID NO: 3)-T-TXNIP(C120S/C170S/C205S/C267S)(SEQ ID NO:6) complex (COM1) was determined at a resolution of 2.0 Å. There are two heterodimeric complexes of TRX and TXNIP in the asymmetric unit. The N-terminal TXNIP (N-TXNIP) and C-terminal TXNIP (C-TXNIP) domains are indicated. (B) Ribbon representation of COM2 is shown, the structure of TRX (C35A)(SEQ ID NO:3)-T-TXNIP(C170S/C205S/C267S) (SEQ ID NO: 5) complex (COM2) was determined at a resolution of 2.7 Å. The intermolecular disulfide bond between TRX Cys32 and TXNIP Cys247 and the interdomain disulfide bond between TXNIP Cys63 and Cys190 are displayed. The location of Cys120 in TXNIP is indicated.

In particular, because TRX (containing five cysteines) and TXNIP (containing 11 cysteines) are redox proteins whose properties make them difficult to handle in vitro, the present inventors engineered a cysteine(Cys35) to alanine (Ala) mutation in TRX to prevent further reactions after interaction between the two proteins, as well as combinatorial cysteine mutations in the tandem arrestin-like domain of TXNIP (T-TXNIP, amino acid 3 to 317) to prevent non-specific aggregation and to generate crystals suitable for X-ray diffraction. Two mutant complexes, TRX(C35A)-T-TXNIP(C120S/C170S/C205S/C267S)(SEQ ID NO: 6) complex (COM1) and TRX(C35A)(SEQ ID NO:3)-T-TXNIP(C170S/C205S/C267S)(SEQ ID NO: 5) complex (COM2), were crystallized for X-ray diffraction and their structures were determined using the multiple anomalous wavelength dispersion method, together with the molecular replacement method. The structures of COM1 and COM2, which were refined to resolutions of 2.0 Å and 2.7 Å, respectively, are shown in FIG. 5.

Figure 6A:
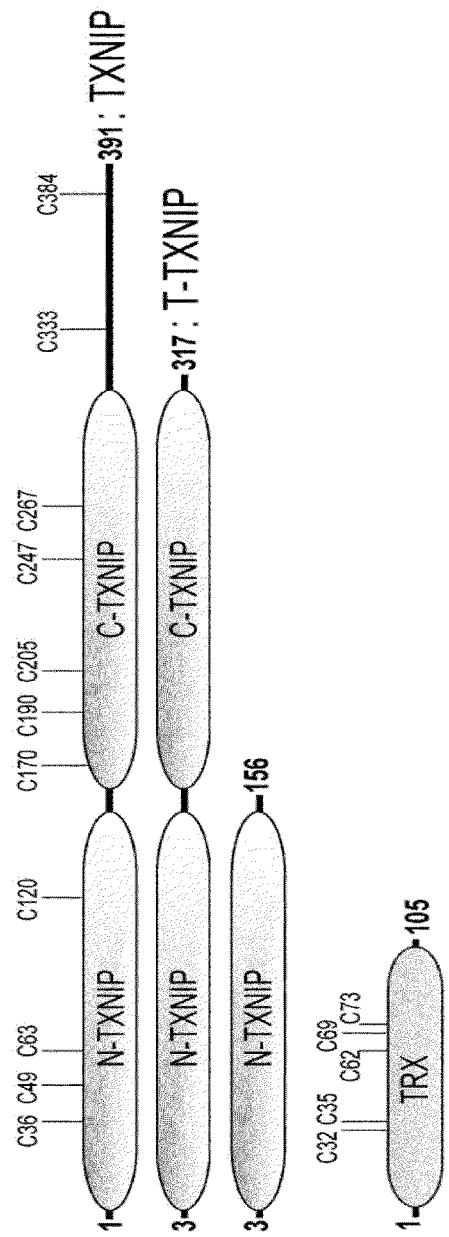
FIG. 6a is a schematic representation of the TXNIP and TRX constructs used in the present invention, showing the locations of the cysteines.
Figure 6B:
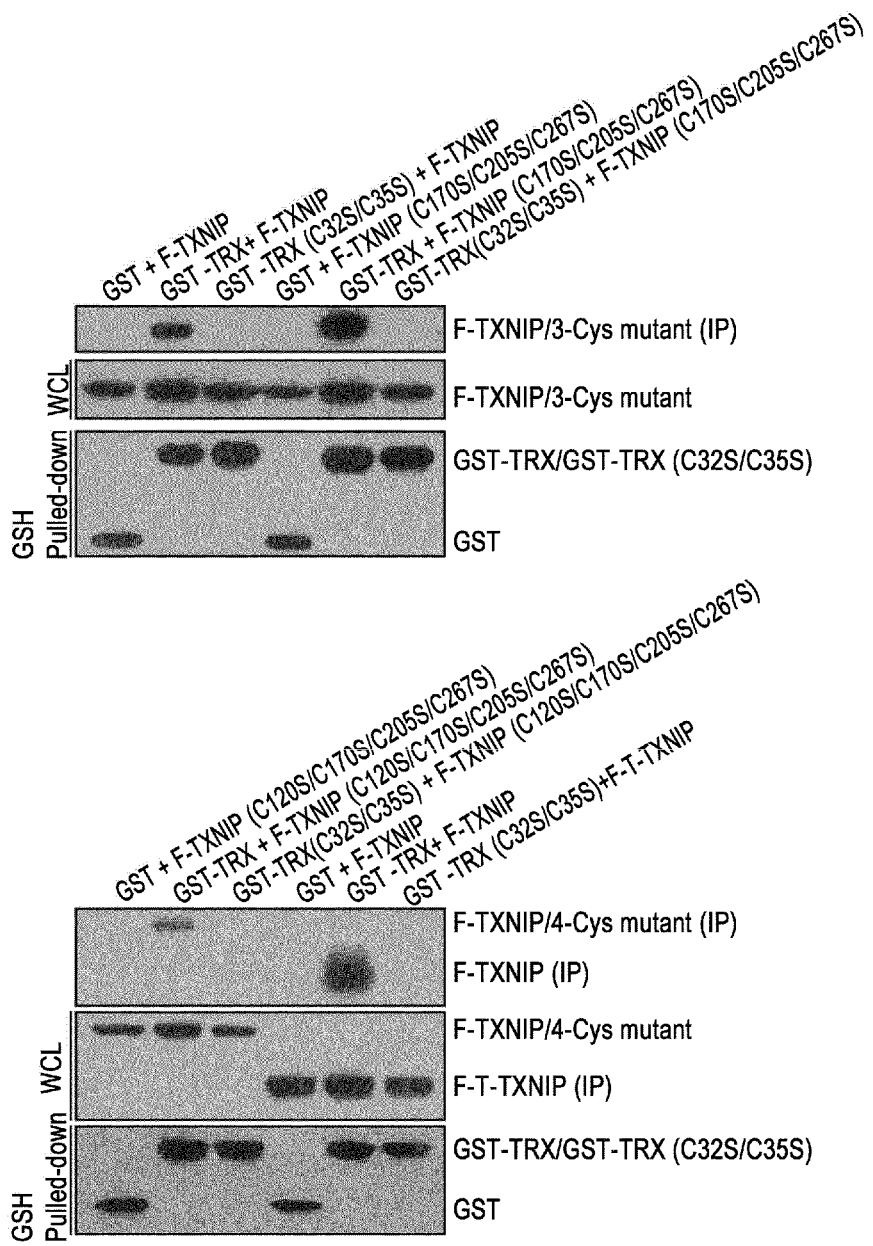
FIGS. 6b and c show that native T-TXNIP and its mutants were indistinguishable from full-length TXNIP in their ability to negatively regulate TRX. In detail.
Figure 6C:
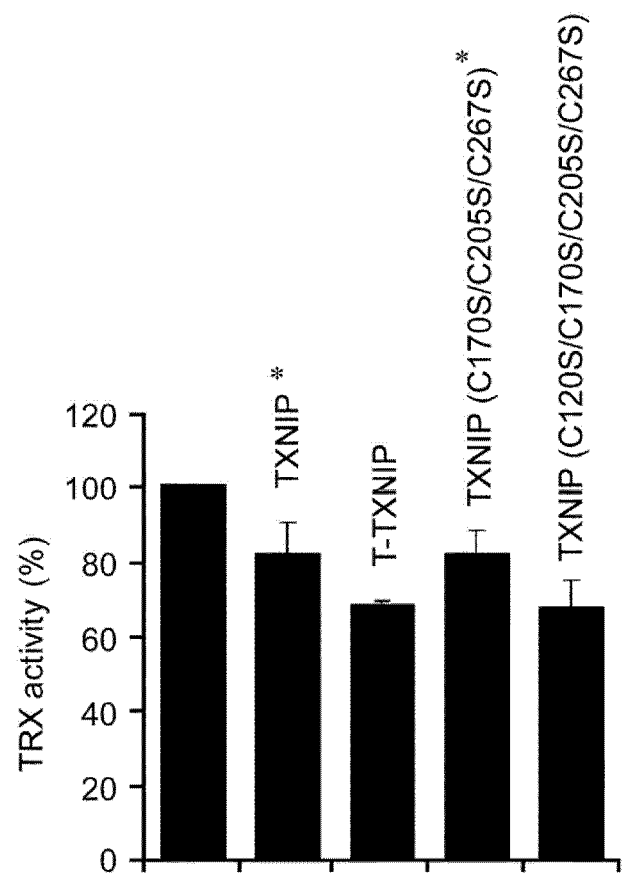
FIG. 6c shows that the TRX-interacting activities of T-TXNIP and its mutants are the same as that of full-length TXNIP. HEK 293T cells were transfected with the expression plasmids indicated in FIG. 6b and the cells were lysed. GST and GST-fusion proteins were pulled down with glutathione beads and immunoblotted with anti-FLAG or anti-GST antibodies. One percent of each whole cell lysate (WCL) was used as the input.

Further, T-TXNIP was comparable to the native TXNIP and its mutant in their ability to bind TRX and inhibit TRX activity (FIGS. 6B and C). This result suggests that the crystal structures of COM1 and COM2 using the modified TXNIP protein resulting from mutagenesis of TXNIP protein represents the TRX-TXNIP complex crystal through interactions between TRX and TXNIP.

Figure 6D:
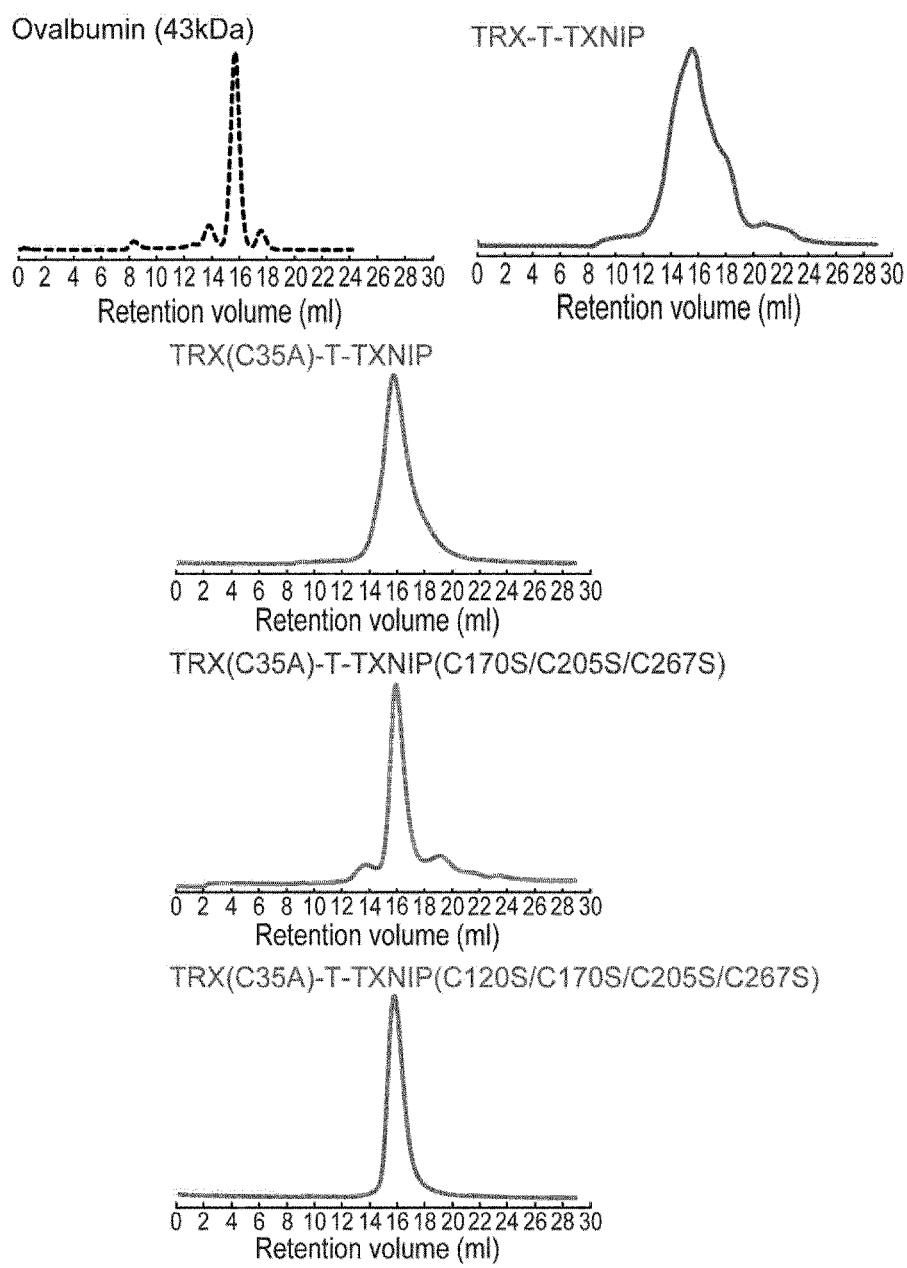
FIG. 6d shows that TRX and T-TXNIP complex exists as single heterodimeric species in solution. The wild type complex and its modified complexes are indicated by different colors. Ovalbumin, shown by the black dashed line, was used as a size marker.

The structures of COM1 and COM2 are essentially identical, each contains two heterodimeric complexes of TRX and T-TXNIP in an asymmetric unit, with a large interface between the two T-TXNIP molecules (FIGS. 5A and B). However, size-exclusion chromatography of TRX-T-TXNIP, TRX(C35A)(SEQ ID NO:3)-T-TXNIP(C170S/C205S/C267S)(SEQ ID NO: 5) and TRX(C35A)(SEQ ID NO:3)-T-TXNIP(C120S/C170S/C205S/C267S)(SEQ ID NO: 6) showed that all the complexes exist as single heterodimeric species in solution (FIG. 6D). Thus, the interfaces between the T-TXNIP molecules in the crystal structures merely constitute large crystal contacts.

Since the structures of COM1 and COM2 are essentially identical and the TRX and T-TXNIP complex exists as a single heterodimeric species in solution, the T-TXNIP (chain C) and TRX (chain D) complex (FIG. 6E) of COM1 was chosen as a representative structure. The final structure of the heterodimeric complex contains residues 8-299 of the expressed protein residues 3-317 of T-TXNIP and all residues of TRX. Residues 148-153 and 260-265 of T-TXNIP are not included in the final model because they are invisible in the electron density map; these regions are presumably very flexible.

Figure 6E:
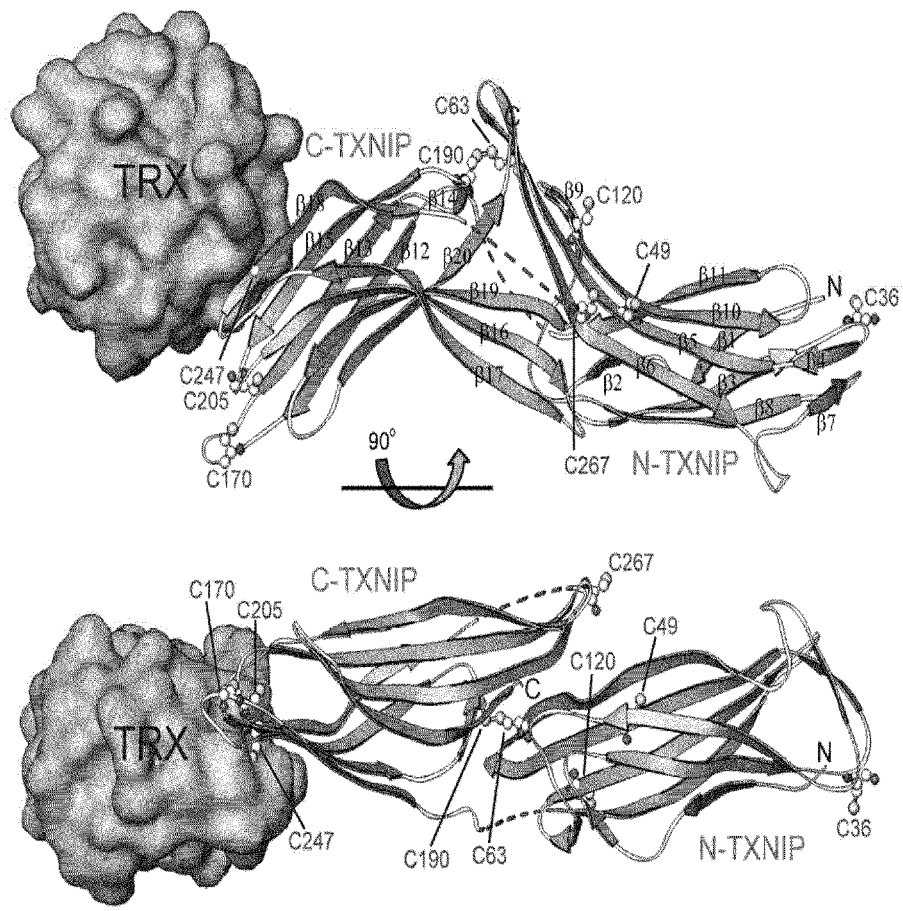
FIG. 6e shows a representative structure of the TRX and TXNIP complex. The β-sheets of TXNIP are numbered. Disordered regions in TXNIP are depicted as gray dashed lines. The N-terminal domain of TXNIP is indicated by N-TXNIP and the C-terminal domain of TXNIP is indicated by C-TXNIP. Cysteine locations on the TXNIP structure are displayed with white carbon atoms.
Figure 7:
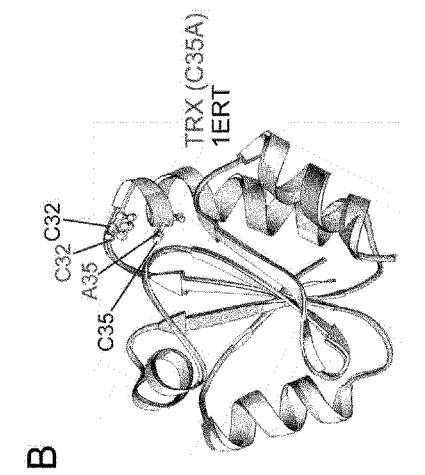
FIG. 7 shows a structural analysis of T-TXNIP domain and a comparison of the T-TXNIP-bound TRX and Free TRX. (A) Superimposition of the C-TXNIP and N-TXNIP structures is shown. (B) No significant structural changes are found in the structure of TRX(C35A)(SEQ ID NO:3) complexed with T-TXNIP compared to the free TRX (PDB ID 1ERT) structure.
Figure 7:
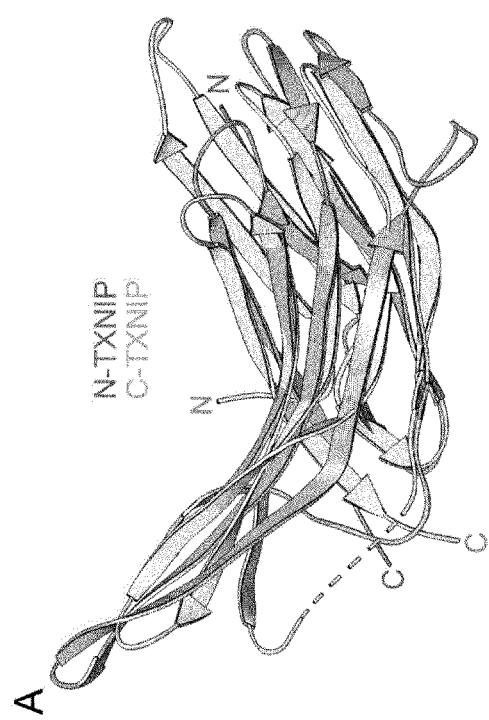
Figure 8A:
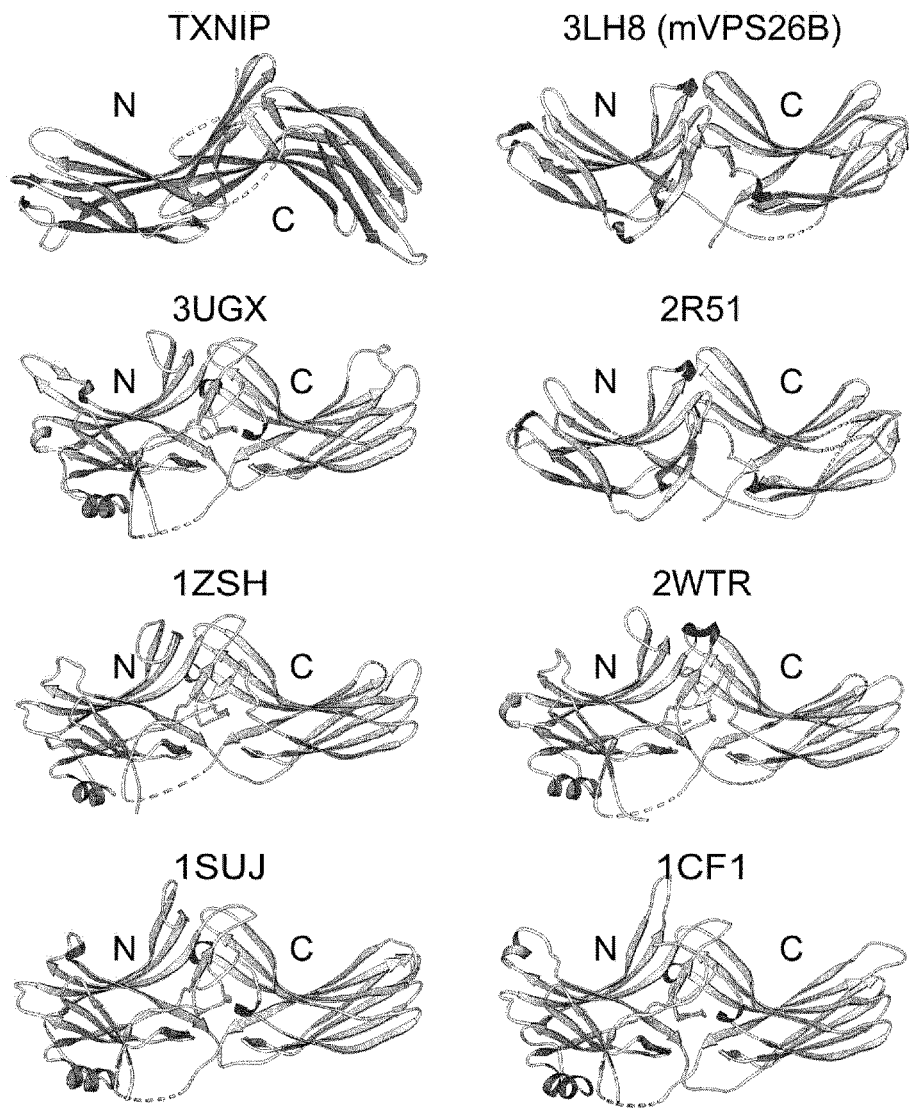
FIG. 8a shows distinctiveness of the domain assembly of TXNIP. TRX-bound TXNIP has an entirely different domain arrangement fold from the previously reported arrestin family proteins. Representative arrestin structures with their PDB accession IDs are displayed and compared with TXNIP. The N-terminal (N) and C-terminal (C) domains for each structure are indicated.
Figure 8B:
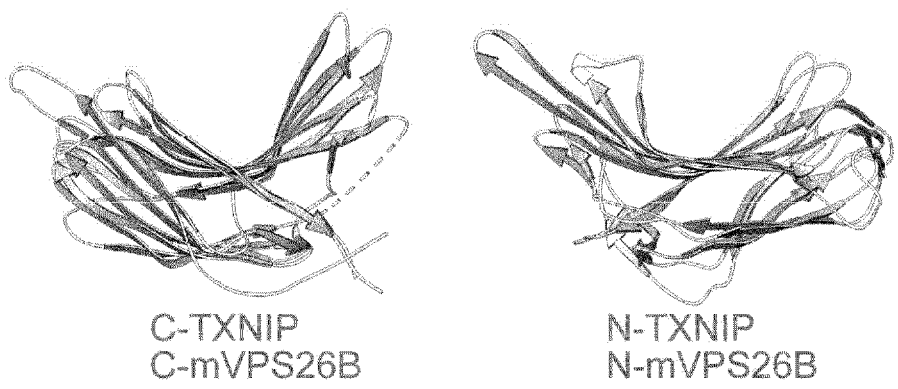
FIG. 8b shows superimposition of N-TXNIP and C-TXNIP domain structures onto N-mVPS26B and C-mVPS26B domain structures, respectively.
Figure 8C:
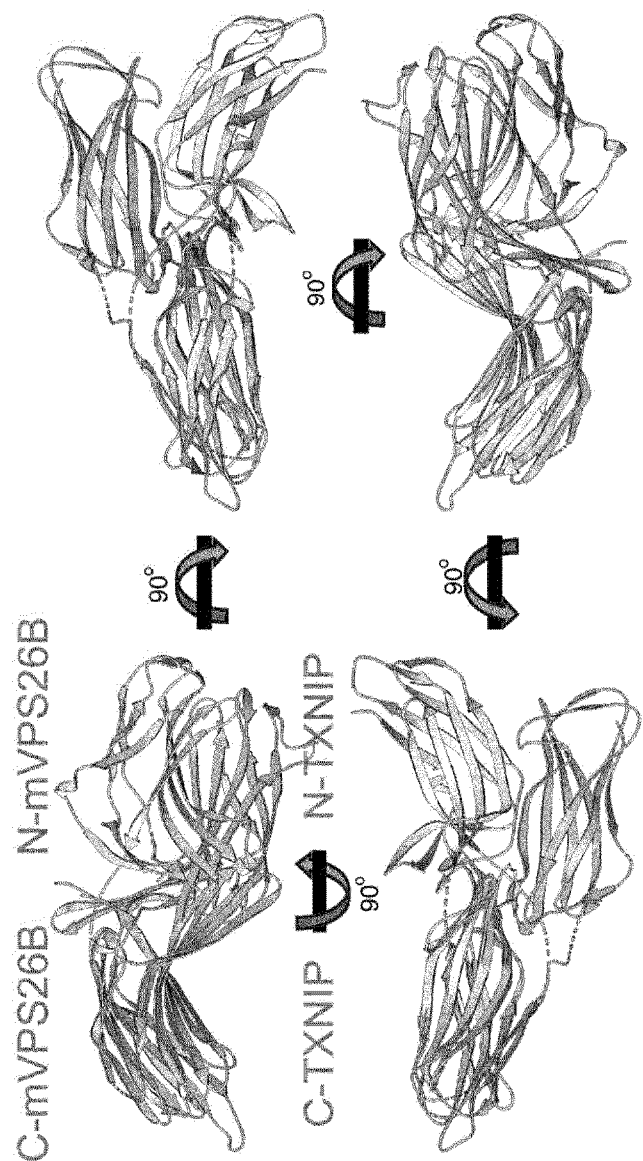
FIG. 8c shows that TRX-bound TXNIP has a different domain arrangement fold from the previously reported arrestin family proteins. Representative arrestin structures (mVPS26B, PDB ID 3LH8) are displayed and compared with TXNIP. Superimposition of TXNIP onto mVPS26B based on the C-terminal domain, is shown.
Figure 8D:
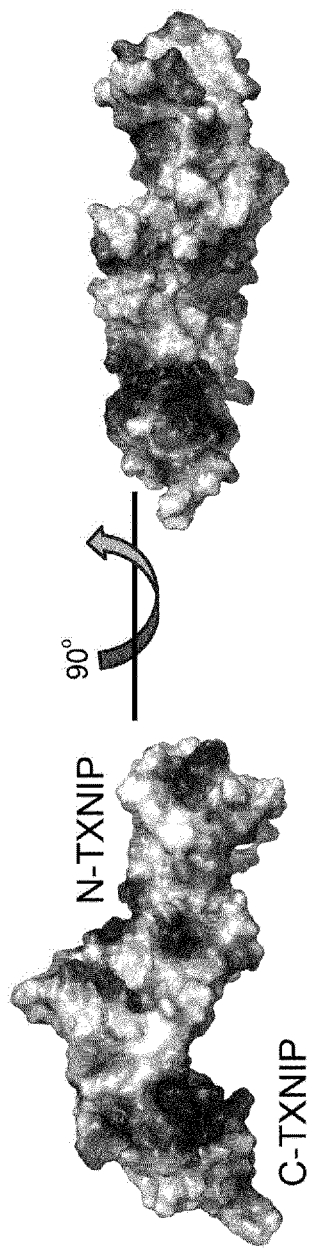
FIG. 8d shows that the electrostatic surface potential of TXNIP reveals a highly basic C-terminal domain and a relatively negative electrostatic N-terminal domain.

As shown in FIG. 6E, T-TXNIP is composed entirely of β strands, which form two deeply curved β-sandwich domains. Further, T-TXNIP is composed of an N-terminal domain comprising β1 to β11 (N-TXNIP, residues 8-147) and a C-terminal domain including β12 to β20 (C-TXNIP, residues 154-299). It folds into an elongated S-shaped domain arrangement with pseudo-two-fold symmetry in which C-TXNIP is inverted relative to N-TXNIP. The two domains can be superimposed with a root-mean-square deviation (r.m.s.d.) of 1.88 for 60 Cα atoms (FIG. 7A). Although the overall structure of T-TXNIP has 13% amino acid homology to that of proteins in the arrestin superfamily comprising mVPS26B (mouse vacuolar protein sorting-associated protein 26B, PDB ID code 3LH8), they are very similar in the structure. However, domain arrangement of T-TXNIP interacting with TRX is completely different from that of all other arrestin structures reported, which have ω-shaped domains (FIG. 8A). Thus, tandem T-TXNIP composed of two domains cannot be superimposed onto mVPS26B (FIG. 8B), while each N-TXNIP (r.m.s.d.=1.33 for 82 Cα atoms; Z=12.3) and C-TXNIP (r.m.s.d.=1.42 for 84 Cα atoms; Z=12.5) domain of TXNIP can be superimposed onto each N-mVPS26B and C-mVPS26B, respectively (FIG. 8C). Structural analysis also revealed that T-TXNIP is electrically polarized (FIG. 8D). In particular, the inside of the curved-sandwich of the C-TXNIP domain contains a prominent basic region, while N-TXNIP has a negative electrostatic potential. No significant structural changes are found in the structure of TRX complexed with T-TXNIP compared to the previously reported free TRX structure (FIG. 7B).

Experimental Example 2: Characterization of TRX-TXNIP Interaction

Cys247 in TXNIP is the most important residue for the interaction with TRX Cys32. Examination of the intermolecular disulfide bond between TRX Cys32 and T-TXNIP Cys247 provides insight into how TXNIP negatively regulates TRX (FIG. 9A). According to the structure of TXNIP and TRX complex shown in FIG. 9, the disulfide bond is located in the center of the interaction interface between the two proteins. The β18 strand of T-TXNIP in combination with β15 is a critical component of the interaction between TRX and TXNIP, and the overall conformation of bound β18 is extended and follows the cleft formed by residues in the active site of TRX. Further, intermolecular backbone-backbone interactions between TRX and residues in the β18 strand of T-TXNIP (TRX Ala92 and T-TXNIP Gly245, and TRX Met74 and T-TXNIP Cys247), stabilize the intermolecular disulfide bond. There are also intermolecular hydrogen bonds and hydrophobic interactions between the proteins. In particular, the side-chain amino group of T-TXNIP Arg251 forms a salt bridge with the side-chain carboxyl group of TRX Asp60, which further supports the interaction between TRX and T-TXNIP (FIG. 9B). This interaction pattern is similar to that of TRX complexes with the peptides of NF-κB and Ref-1, which are implicated in TRX-mediated disulfide bond reduction of cellular substrates (FIG. 9C). The intermolecular backbone-backbone interactions stabilizing the intermolecular disulfide bond are strictly conserved in each of these complexes.

Experimental Example 3: Formation of Head-to-Tail Interprotomer Disulfide Bond by TXNIP The interaction between TXNIP and TRX requires oxidized TXNIP, which was thought to contain an intramolecular disulfide bond between Cys63 and Cys247, and reduced TRX32. According to the T-TXNIP structure shown in FIG. 5, Cys63 is located 39 Å from Cys247. Given this distance, there is not much likelihood of an intramolecular disulfide bond between the two residues. Instead, it was hypothesized that rather than forming an intramolecular disulfide, Cys63 and Cys247 might form interprotomer disulfide bonds between TXNIP molecules. To test this hypothesis, the following experiments were performed.

First, the in vivo interprotomer interaction between TXNIP molecules was examined using 293T cells transfected with HA-tagged TXNIP and FLAG-tagged T-TXNIP-expressing plasmids. At this time, cysteine-blocking reagent iodoacetamide-containing lysis buffer was used to avoid non-specific extra redox reaction during cell lysis. The results are shown in FIG. 9D.

As shown in FIG. 9, an interprotomer interaction between TXNIP molecules was observed (left), and high molecular complex of T-TXNIP was detected dependent on the redox condition (right).

Further, coimmunoprecipitation assays were performed using lysates of 293T cells transfected with FLAG-tagged TXNIP and HA-tagged TXNIP-expressing plasmids, and the results are shown in FIG. 9E. To examine the domains involved in interprotomer disulfide bonds, Flag-tagged deletion mutants were prepared, and for immunoprecipitation of HA-tagged TXNIP, anti-HA antibody was used.

As shown in FIG. 9E (left), the immunoblot analysis using anti-HA antibody demonstrated that both the N- and C-terminal TXNIP domains are required for the interprotomer disulfide bonds.

Further, the roles of Cys63 in the N-terminal domain and Cys247 in the C-terminal domain in the formation of interprotomer disulfide bonds were evaluated using GST-fused- and FLAG-tagged-TXNIP. The substitution of Cys247 with serine in both the GST-fused- and the FLAG-tagged-TXNIP molecules abolished the formation of interprotomer disulfide bonds, unlike the substitution of Cys247 with serine in the GST-fused TXNIP (FIG. 9E, right). The same result was obtained upon substitution of Cys63 with serine. The results of structural analysis and these results indicated that TXNIP molecules form a head-to-tail interprotomer disulfide bond between Cys63 and Cys247 in vivo.

In addition, mass spectrometry was employed to analyze the interprotomer disulfide bond between Cys63 and Cys247. To achieve this, the non-specific covalent oligomerization-preventing T-TXNIP(C36S/C49S/C120S/C170S/C205S/C267S) protein was isolated from the TRX(C73A)-T-TXNIP(C36S/C49S/C120S/C170S/C205S/C267S) complex (FIG. 9g), and used to induce the interprotomer-interacting TXNIP molecules in vitro, and fractionated protein bands by SDS-PAGE under non-reducing condition were then used for mass spectrometric analysis (FIG. 9h). The disulfide bond and free cysteine of the two protein bands of ~32 kDa and ~60 kDa (as a monomeric T-TXNIP mutant and interprotomer-interacting protein complex, respectively) were analyzed by mass spectrometry, the results of which are shown in the following Table:

TABLE 12

|  |  | The number of spectra | |
|---|---|---|---|
|  |  | ~60 kDa | ~32 kDa |
| Disulfide bond | C63-C190 | 1 | 93 |
|  | C63-C247 | 5 | 3 |
|  | C63-C63 | 1 | 1 |
|  | C190-C247 | 1 | 3 |
|  | C247-C247 | 1 | 2 |
|  | Total | 9 | 102 |
| Free cysteine | C63 | 4 | 5 |
|  | C190 | 0 | 42 |
|  | C247 | 2 | 5 |
|  | Total | 6 | 52 |

As shown in Table 12, above, the sites of disulfide bonds were identified at residues Cys63-Cys190, Cys63-Cys247, Cys63-Cys63, Cys190-Cys247, and Cys247-Cys247 with Dbond score >20. However, the distribution of the disulfide bond site was significantly different between the bands. In ~60 kDa band, Cys63-Cys247 was identified with 5 spectra comprising the major disulfide bond while Cys63-Cys190 in ~32 kDa band appeared as the majority with 93 spectra out of 102. Furthermore, the sites of free cysteines which appeared as carbamidomethyl cysteines after alkylation were identified to have different distributions.

This demonstrates that the majority of Cys63 are disulfide-bonded with Cys190 in ~32 kDa band (a monomeric T-TXNIP) and with Cys247 in ~60 kDa band (an interprotomer-interacting T-TXNIP molecules), and a great amount of Cys190 remains as free cysteines at the ~32 kDa band.

A representative MS/MS spectrum for Cys63-Cys190 identified from ~32 kDa band and that for Cys63-Cys247 identified from ~60 kDa band are shown in FIGS. 9i and j, respectively. Doubly charged [M+2H]$^+$ peptide ions at m/z 1759.77 (FIG. 9i) and m/z 1353.64 (FIG. 9j) were fragmented via higher-energy collisional dissociation (HCD). As a result, the standard backbone fragments that occurred by amide bond cleavages are highly abundant, and the persulfide ion (P$^+$32) formed by S—S or C—S bond cleavage reactions was also identified in these spectra.

Therefore, these data collectively demonstrate that a head-to-tail interprotomer disulfide bond between Cys63 and Cys247 is present in TXNIP molecules.

As shown in FIG. 6D, TRX-bound TXNIP exists predominantly in a heterodimeric form in solution. To evaluate the effect of TRX on the interprotomer disulfide bond between TXNIP molecules, coimmunoprecipitation assays were performed using lysates of 293T cells transfected with FLAG-tagged TXNIP, HA-tagged TXNIP, and FLAG-tagged TRX-expressing plasmids. The interaction between TXNIP molecules through perhaps interprotomer disulfide bonds was significantly diminished by the overexpression of TRX (FIG. 9E).

These results suggest that the stable formation of TRX and T-TXNIP heterodimeric complexes appears to involve the transient interaction of TRX with the interprotomer disulfide bond between TXNIP molecules.

Experimental Example 4: Disulfide Bond Switching Mediated by Cys63 Involved in TRX-TXNIP Interaction As shown in FIG. 10, the present inventors demonstrated that N-terminal TXNIP, N-TXNIP, can be co-expressed and co-purified with TRX and TRX(C35A)(SEQ ID NO:3). To evaluate the involvement of N-TXNIP in the interaction of TXNIP with TRX, an NMR-titration experiment was performed by recording a series of $^1$H-$^{15}$N heteronuclear single quantum coherence (HSQC) spectra of $^{15}$N-labeled N-TXNIP after addition of unlabeled, reduced TRX.

Figure 10B:
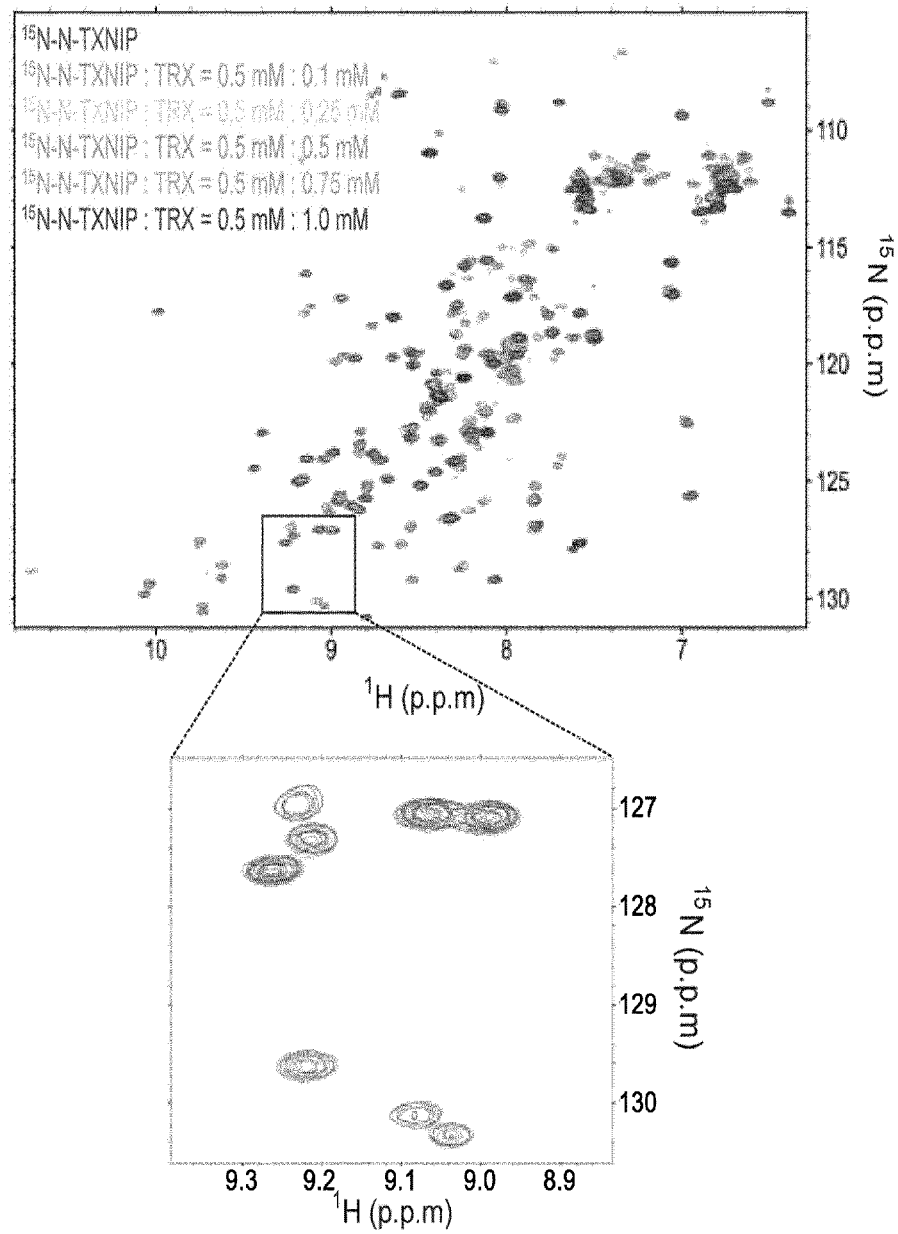

The addition of TRX caused substantial chemical shifts, pointing to a direct interaction between N-TXNIP and TRX (FIG. 10B). However, attempts to crystallize the complex between N-TXNIP and TRX(C35A)(SEQ ID NO:3) were unsuccessful, suggesting that the interaction between the two proteins is transient.

Further, TRX muteins were added and $^1$H-$^{15}$N HSQC spectra of $^{15}$N-labeled N-TXNIP were monitored to examine interaction between N-TXNIP and TRX. There were no significant chemical shift changes when C32A or C35A TRX mutants were added to $^{15}$N-labeled N-TXNIP (FIG. 12), indicating that these cysteine residues are involved in interaction between TRX and N-TXNIP. In contrast, C62A, C69A, and C73A mutants caused a chemical shift similar to the wild-type TRX (FIG. 12).

Because reduced TRX only binds to oxidized T-TXNIP having a disulfide bond, it was assumed that a disulfide bond might also be involved in the interaction between N-TXNIP and TRX. To test this assumption, the structure of N-TXNIP at 1.6 Å resolution was determined and shown in FIG. 11.

Figure 11A:
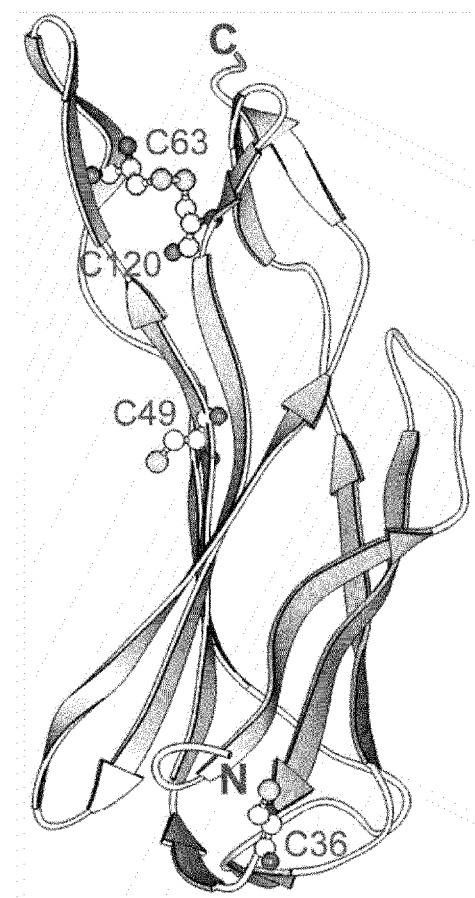

As a result, the structure of N-TXNIP is very similar to that of the corresponding domain in T-TXNIP. However, unlike the case of T-TXNIP, there is an unexpected intramolecular disulfide bond between Cys63 and Cys120 (FIG. 11A). In the COM2 structure, the distance between Cys63 and Cys120 is 14.1 Å (FIG. 5B), which is too large for the formation of a disulfide bond. Cys120 has been shown not to be greatly involved in TRX binding. Furthermore, alignment of the amino acid sequences of TXNIP from different species shows that while Cys190 and Cys247 are strictly conserved, Cys120 is not (FIG. 13). Thus, the unexpected disulfide bond between Cys63 and Cys120 in the N-TXNIP structure may be an artificial consequence due to crystallization. It is very likely that Cys63 requires, if not Cys120, then another orphan cysteine residue to form a stable disulfide bond. There are other cysteine residues at positions 36 and 49 in N-TXNIP. These are 49 Å and 22 Å distant from Cys63, respectively, which is too far for disulfide bond formation (FIG. 11A). These results suggest that TXNIP undergoes a Cys63-mediated conformational change during its interaction with TRX. The interaction between Cys63 and Cys120 in N-TXNIP results in a significant movement of approximately 96° in a clockwise direction and a 54° downward bending of strands β5 and β6. This movement leads to a change in the secondary structures of the β5 and β6 strands (FIG. 11B).

Figure 11B:
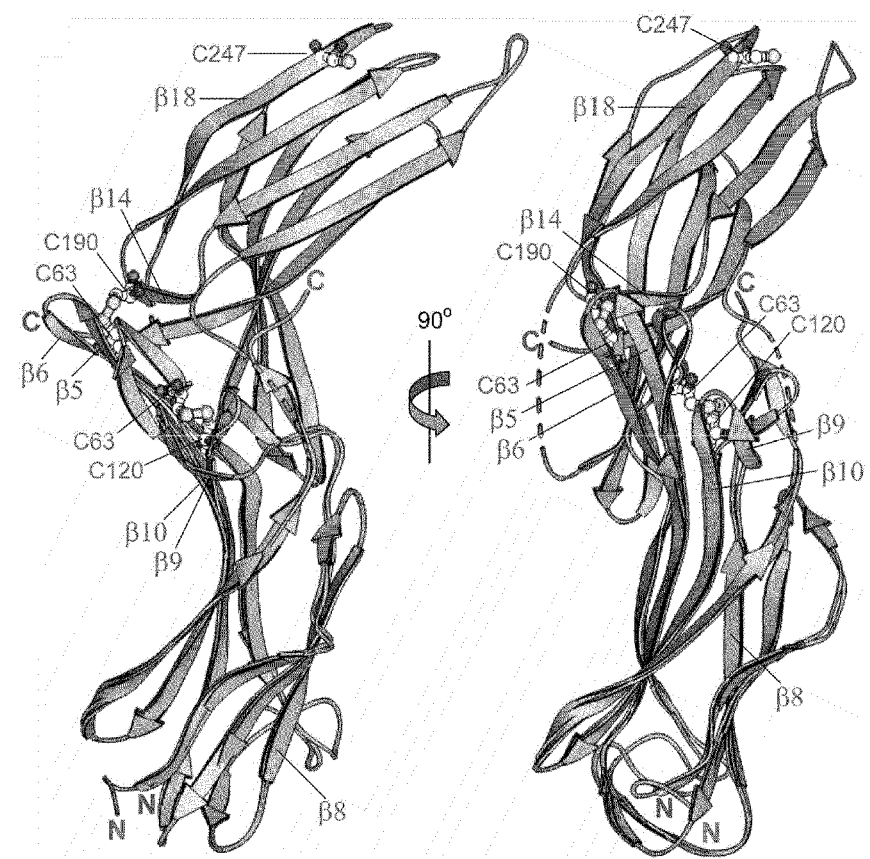
Figure 11C:
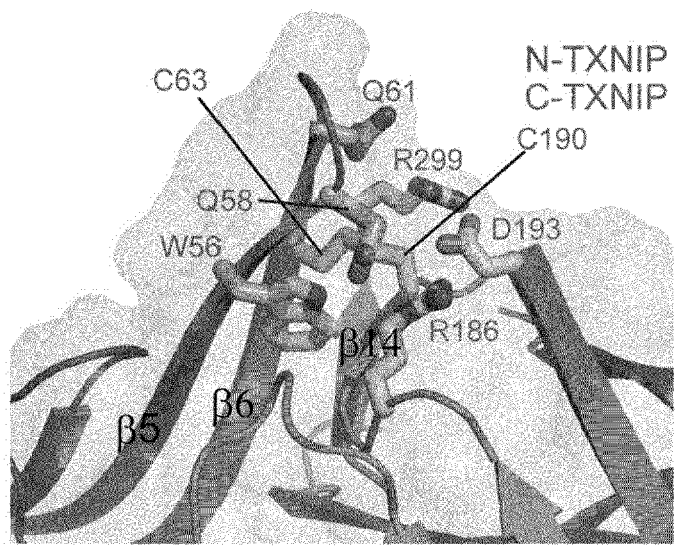
Figure 11D:
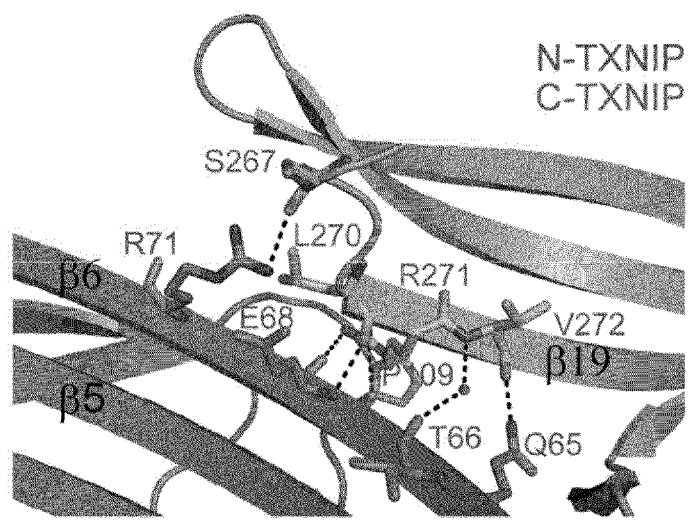

In addition, there is a significant change in the β8 to β10 region (FIG. 11B). To further test the importance of the Cys63-mediated disulfide bond for the interaction of TXNIP with TRX, NMR $^1$H-$^{15}$N HSQC experiments were performed with $^{15}$N-labeled N-TXNIP mutants and TRX. There were no significant chemical shifts in the spectra of either of the C63S or C120S N-TXNIP mutants in the presence of TRX (FIG. 14). This further supports that the interaction of TRX with TXNIP is initiated by a transient interaction between TRX and the interprotomer Cys63-Cys247 disulfide bond in TXNIP molecules.

The transient interaction of TRX with the interprotomer disulfide bond between Cys63 and Cys247 in TXNIP must result in the stable intermolecular interaction between TRX Cys32 and TXNIP Cys247, as seen in the complex structure of FIG. 11. Therefore, when TRX of the interprotomer interaction in TXNIP molecules, that is, a disulfide bond between Cys63 and Cys247 of TXNIP is inhibited, Cys63 becomes reactive again. One of the notable aspects of the TXNIP structure is the interdomain disulfide bond between N-TXNIP Cys63 and C-TXNIP Cys190 (FIG. 11C). This implies that the orphaned Cys63 immediately searches for a nearby cysteine residue with which to form a bond to stabilize it, and forms a disulfide bond with Cys190. This interaction causes the formation of a tight junction between the two domains, with the disulfide bond located in the center of the interdomain interface, between the β-sheets of each domain. The disulfide bond is then surrounded by other residues involved in the interface and is completely shielded from solvent. At this time, the long N-terminal strands, β5 and β6 cause the C-terminal strand β14 to rise (FIG. 11 C). Therefore, the atypical S-shaped domain conformation of TXNIP can be attributed to this unique mutual disposition of the two domains, which is mainly due to the disulfide bond between Cys63 and Cys190. In addition, there were other interdomain interactions between the N-terminal β6 strand and the β29 strand on the other side of the C-terminal β-sheets (FIG. 11D). The side-to-side interaction between the β-sheets of the two domains seems to confirm the S-shaped conformation. These interdomain interactions of TXNIP are entirely different from those reported for arrestin proteins. In general, the domain interface of arrestin family proteins merely contains clusters of buried polar interactions.

The above experiments suggest that interaction between TRX and TXNIP is related to a novel mechanism of disulfide bond switching: the replacement of a head-to-tail interprotomer TXNIP Cys63-TXNIP Cys247 disulfide bond with an interdomain TXNIP Cys63-Cys190 disulfide bond and a de novo intermolecular TXNIP Cys247-TRX Cys32 disulfide bond.

Experimental Example 5: Effect of ROS on TRX-TXNIP Interaction

The regulation of TRX by TXNIP is known to be redox-dependent. ROS are involved in activation of the oxidative stress-responsive pathway and can alter protein structure and/or function. To assess the effect of ROS on interaction between TRX and TXNIP, the TRX-T-TXNIP complexes were treated with ROS. To prevent non-functional cysteine-induced non-specific aggregation of T-TXNIP and dimerization of TRX, T-TXNIP(C120S/C170S/C205S/C267S)(SEQ ID NO: 6) complexed with native TRX, or T-TXNIP(C36S/C49S/C120S/C170S/C205S/C267S) complexed with TRX (C73A) were used. Both of them contain intermolecular disulfide bonds between TXNIP Cys247 and TRX Cys32 and intramolecular disulfide bonds between TXNIP Cys63 and Cys190. Treatment of TRX-T-TXNIP with $H_2O_2$ resulted in dissociation of the proteins in a dose-dependent manner (FIG. 15a) and the same effects were observed with the thiol-oxidizing agent diamide (FIG. 15b). It was observed that the dissociated T-TXNIP by ROS treatment exists as a monomer form, indicating that ROS may react with the intermolecular disulfide bond between TRX Cys32 and TXNIP Cys247, while the TXNIP interdomain disulfide bond between Cys63 and Cys190 persists in oxidizing conditions. Regulation of TRX-TXNIP interaction by ROS is shown in FIG. 15d.

Taken together, under normoxic conditions, TXNIP binds to TRX through an intermolecular disulfide bond and inhibits TRX activity, whereas in response to oxidative stress, ROS increases to disrupt the intermolecular disulfide bond between TRX and TXNIP. Therefore, high levels of ROS may cause the intermolecular disulfide to undergo further oxidation, leading to the formation of thiosulfinates. Such intermediates may react readily with any available thiol (e.g. TRX Cys35) to form disulfide bonds (e.g. between TRX Cys32 and Cys35) and sulfenic acid, which in turn, rapidly react with other thiol groups to form other disulfide bonds and water. Consequently, TXNIP is dissociated from TRX. Meanwhile, the ROS may trigger antioxidant pathways, which would then utilize the TRX system, comprising TRX reductase and NADPH, to restore a reducing environment, together with other antioxidant systems. This would lead to a reduction of the TXNIP interdomain disulfide bond between Cys63 and Cys190, making Cys63 available to form an interprotomer disulfide linkage with the Cys247 of another TXNIP molecule. TRX may interact through its active cysteines with the TXNIP interprotomer disulfide bond between Cys63 and Cys247, which would perturb the interprotomer interaction between TXNIP molecules and leave Cys63 orphaned and reactive. Consequently, Cys63 would couple with the C-terminal Cys190, producing S-shape from w-shape. This structure would eventually facilitate the formation of a stable interaction interface between TRX and TXNIP through TRX Cys32 and TXNIP Cys247 (FIG. 15d).

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

Effect of the Invention

Since TXNIP protein is a protein that regulates TRX activity through interaction with TRX protein, thereby exhibiting various physiological activities such as regulation of cell proliferation, blood glucose level, etc., a crystal of the TRX and TXNIP protein complex provided in the present invention, a crystallization method and a three-dimensional structure thereof can be usefully applied to development of new drugs for the treatment or diagnosis of diseases such as cancer or diabetes, which are associated with interaction between TRX and TXNIP proteins.

What is claimed is:

1. A method for screening a substance regulating interaction between thioredoxin (TRX) and thioredoxin-interacting protein (TXNIP), comprising:
   (a) preparing at least one crystal selected from the group consisting of
      (i) a crystal of a modified TXNIP protein consisting of an amino acid sequence of SEQ ID NO: 8;
      (ii) a crystal of a first protein complex of a modified TXNIP protein consisting of an amino acid sequence of SEQ ID NO: 6 and a modified TRX protein consisting of an amino acid sequence of SEQ ID NO: 3; and
      (iii) a crystal of a second protein complex of a modified TXNIP protein consisting of an amino acid sequence of SEQ ID NO: 5 and a modified TRX protein consisting of an amino acid sequence of SEQ ID NO: 3,
   (b) obtaining a three-dimensional structure of the at least one crystal using X-ray crystallography to generate a X-ray diffraction data;
   (c) synthesizing or selecting a candidate substance regulating interaction between TRX and TXNIP based on a three-dimensional structure of the at least one crystal, wherein the candidate substance is a compound or peptide;
   (d) contacting the candidate substance with the TRX and the TXNIP to examine whether the candidate substance regulates interaction between TRX and TXNIP.

2. The method according to claim 1, further comprising determining the candidate substance regulating interaction between TRX and TXNIP as an anticancer agent or a diabetes therapeutic agent when the candidate regulates the interaction between TRX and TXNIP, compared to control group treated with no candidates.

3. A method for screening an inhibitor of thioredoxin (TRX) activity, comprising:
   (a) preparing at least one crystal selected from the group consisting of
      (i) a crystal of a modified thioredoxin-interacting protein (TXNIP) protein consisting of an amino acid sequence of SEQ ID NO: 8;
      (ii) a crystal of a first protein complex of a modified TXNIP protein consisting of an amino acid sequence of SEQ ID NO: 6 and a modified TRX protein consisting of an amino acid sequence of SEQ ID NO: 3; and
      (iii) a crystal of a second protein complex of a modified TXNIP protein consisting of an amino acid sequence of SEQ ID NO: 5 and a modified TRX protein consisting of an amino acid sequence of SEQ ID NO: 3,
   (b) obtaining a three-dimensional structure of the at least one crystal using X-ray crystallography to generate a X-ray diffraction data;
   (c) synthesizing or selecting a to peptide of inhibiting TRX activity or a TRX-binding compound based on using a three-dimensional structure of the at least one crystal;

(d) contacting the peptide or the TRX-binding compound to with the TRX or TRX-TXNIP complex to examine whether the to peptide or the TRX-binding compound inhibits TRX activity.

4. The method according to claim 3, further comprising determining the peptide or compound as an anticancer agent when the peptide or compound exhibits higher TRX-binding ability than TXNIP so as to inhibit TRX activity.

5. A method for screening a substance regulating TXNIP function, comprising:
(a) preparing at least one crystal selected from the group consisting of
  (i) a crystal of a modified TXNIP protein consisting of an amino acid sequence of SEQ ID NO: 8;
  (ii) a crystal of a first protein complex of a modified TXNIP protein consisting of an amino acid sequence of SEQ ID NO: 6 and a modified TRX protein consisting of an amino acid sequence of SEQ ID NO: 3; and
  (iii) a crystal of a second protein complex of a modified TXNIP protein consisting of an amino acid sequence of SEQ ID NO: 5 and a modified TRX protein consisting of an amino acid sequence of SEQ ID NO: 3,
(b) obtaining a three-dimensional structure of the at least one crystal using X-ray crystallography to generate a X-ray diffraction data;
(c) synthesizing or selecting a candidate substance regulating TXNIP function based on a three-dimensional structure of the at least one crystal, wherein the candidate substance is a compound or peptide;
(d) contacting the candidate substance with the TXNIP or TRX-TXNIP complex to examine whether the candidate regulates TXNIP function.

6. The method according to claim 5, further comprising determining the candidate substance regulating TXNIP function as a diabetes therapeutic agent when the candidate regulates the TXNIP function.

7. The method according to claim 1, wherein
(i) the crystal of the modified TXNIP protein has a space group of $P2_12_12_1$, a unit-cell dimension of a=37.43 Å, b=56.62 Å, and c=67.66 Å, and $\alpha=\beta=\gamma=90°$, and the atomic coordinates shown in Table 8;
(ii) the crystal of the first protein complex has a space group of $P2_1$, a unit-cell dimension of a=80.14 Å, b=64.02 Å, c=88.30 Å, $\alpha=\gamma=90°$, and $\beta=91.28°$, and the atomic coordinates shown in Table 10; and
(iii) the crystal of the second protein complex has a space group of $P2_1$, a unit-cell dimension of a=79.83 Å, b=64.99 Å and c=88.42 Å, $\alpha=\gamma=90°$, and $\beta=90.88°$, and the atomic coordinates shown in Table 11.

8. The method according to claim 3, wherein
(i) the crystal of the modified TXNIP protein has a space group of $P2_12_12_1$, a unit-cell dimension of a=37.43 Å, b=56.62 Å, and c=67.66 Å, and $\alpha=\beta=\gamma=90°$, and the atomic coordinates shown in Table 8;
(ii) the crystal of the first protein complex has a space group of $P2_1$, a unit-cell dimension of a=80.14 Å, b=64.02 Å, c=88.30 Å, $\alpha=\gamma=90°$, and $\beta=91.28°$, and the atomic coordinates shown in Table 10; and
(iii) the crystal of the second protein complex has a space group of $P2_1$, a unit-cell dimension of a=79.83 Å, b=64.99 Å and c=88.42 Å, $\alpha=\gamma=90°$, and $\beta=90.88°$, and the atomic coordinates shown in Table 11.

9. The method according to claim 5, wherein
(i) the crystal of the modified TXNIP protein has a space group of $P2_12_12_1$, a unit-cell dimension of a=37.43 Å, b=56.62 Å, and c=67.66 Å, and $\alpha=\beta=\gamma=90°$, and the atomic coordinates shown in Table 8;
(ii) the crystal of the first protein complex has a space group of $P2_1$, a unit-cell dimension of a=80.14 Å, b=64.02 Å, c=88.30 Å, $\alpha=\gamma=90°$, and $\beta=91.28°$, and the atomic coordinates shown in Table 10; and
(iii) the crystal of the second protein complex has a space group of $P2_1$, a unit-cell dimension of a=79.83 Å, b=64.99 Å and c=88.42 Å, $\alpha=\gamma=90°$, and $\beta=90.88°$, and the atomic coordinates shown in Table 11.

10. A method for detecting interaction between TRX and TXNIP in the presence of a candidate substance regulating interaction between TRX and TXNIP, comprising:
(a) producing the candidate selected by using a three-dimensional structure of the at least one crystal selected from the group consisting of:
  (i) a crystal of a modified TXNIP protein consisting of an amino acid sequence of SEQ ID NO: 8, wherein the crystal has a space group of $P2_12_12_1$, a unit-cell dimension of a=37.43 Å, b=56.62 Å, and c=67.66 Å, and $\alpha=\beta=\gamma=90°$, and the atomic coordinates shown in Table 9;
  (ii) a crystal of a protein complex of a modified TXNIP protein consisting of an amino acid sequence of SEQ ID NO: 6 and a modified TRX protein consisting of an amino acid sequence of SEQ ID NO: 3, wherein the crystal has a space group of $P2_1$, a unit-cell dimension of a=80.14 Å, b=64.02 Å, c=88.30 Å, $\alpha=\gamma=90°$, and $\beta=91.28°$, and the atomic coordinates shown in Table 10; and
  (iii) a crystal of a protein complex of a modified TXNIP protein consisting of an amino acid sequence of SEQ ID NO: 5 and a modified TRX protein consisting of an amino acid sequence of SEQ ID NO. 3, wherein the crystal has a space group of $P2_1$, a unit-cell dimension of a=79.83 Å, b=64.99 Å and c=88.42 Å, $\alpha=\gamma=90°$, and $\beta=90.88°$, and the atomic coordinates shown in Table 11;
(b) preparing at least one crystal selected from the group consisting of
  (i) a first crystal of a modified TXNIP protein consisting of an amino acid sequence of SEQ ID NO: 8;
  (ii) a second crystal of a first protein complex of a modified TXNIP protein consisting of an amino acid sequence of SEQ ID NO: 6 and a modified TRX protein consisting of an amino acid sequence of comprising SEQ ID NO: 3; and
  (iii) a third crystal of a second protein complex of a modified TXNIP protein consisting of an amino acid sequence of SEQ ID NO: 5 and a modified TRX protein consisting of an amino acid sequence of SEQ ID NO: 3; and
(c) contacting the candidate substance with the at least one crystal selected from the first, second, and third crystals to detect interaction between TRX and TXNIP in the presence of the candidate substance,
wherein the candidate substance is a compound or peptide.

* * * * *

SEQUENCE LISTING

<160> NUMBER OF SEQ ID NOS: 27

<210> SEQ ID NO 1
<211> LENGTH: 391
<212> TYPE: PRT
<213> ORGANISM: Homo Sapiens

<400> SEQUENCE: 1

```
Met Val Met Phe Lys Lys Ile Lys Ser Phe Glu Val Val Phe Asn Asp
 1               5                  10                  15

Pro Glu Lys Val Tyr Gly Ser Gly Glu Arg Val Ala Gly Arg Val Ile
             20                  25                  30

Val Glu Val Cys Glu Val Thr Arg Val Lys Ala Val Arg Ile Leu Ala
         35                  40                  45

Cys Gly Val Ala Lys Val Leu Trp Met Gln Gly Ser Gln Gln Cys Lys
     50                  55                  60

Gln Thr Ser Glu Tyr Leu Arg Tyr Glu Asp Thr Leu Leu Glu Asp
 65                  70                  75                  80

Gln Pro Thr Gly Glu Asn Glu Met Val Ile Met Arg Pro Gly Asn Lys
             85                  90                  95

Tyr Glu Tyr Lys Phe Gly Phe Glu Leu Pro Gln Gly Pro Leu Gly Thr
            100                 105                 110

Ser Phe Lys Gly Lys Tyr Gly Cys Val Asp Tyr Trp Val Lys Ala Phe
        115                 120                 125

Leu Asp Arg Pro Ser Gln Pro Thr Gln Glu Thr Lys Lys Asn Phe Glu
    130                 135                 140

Val Val Asp Leu Val Asp Val Asn Thr Pro Asp Leu Met Ala Pro Val
145                 150                 155                 160

Ser Ala Lys Lys Glu Lys Lys Val Ser Cys Met Phe Ile Pro Asp Gly
                165                 170                 175

Arg Val Ser Val Ser Ala Arg Ile Asp Arg Lys Gly Phe Cys Glu Gly
            180                 185                 190

Asp Glu Ile Ser Ile His Ala Asp Phe Glu Asn Thr Cys Ser Arg Ile
        195                 200                 205

Val Val Pro Lys Ala Ala Ile Val Ala Arg His Thr Tyr Leu Ala Asn
    210                 215                 220

Gly Gln Thr Lys Val Leu Thr Gln Lys Leu Ser Ser Val Arg Gly Asn
225                 230                 235                 240

His Ile Ile Ser Gly Thr Cys Ala Ser Trp Arg Gly Lys Ser Leu Arg
                245                 250                 255

Val Gln Lys Ile Arg Pro Ser Ile Leu Gly Cys Asn Ile Leu Arg Val
            260                 265                 270

Glu Tyr Ser Leu Leu Ile Tyr Val Ser Val Pro Gly Ser Lys Lys Val
        275                 280                 285

Ile Leu Asp Leu Pro Leu Val Ile Gly Ser Arg Ser Gly Leu Ser Ser
    290                 295                 300

Arg Thr Ser Ser Met Ala Ser Arg Thr Ser Ser Glu Met Ser Trp Val
305                 310                 315                 320

Asp Leu Asn Ile Pro Asp Thr Pro Glu Ala Pro Pro Cys Tyr Met Asp
                325                 330                 335

Val Ile Pro Glu Asp His Arg Leu Glu Ser Pro Thr Thr Pro Leu Leu
            340                 345                 350

Asp Asp Met Asp Gly Ser Gln Asp Ser Pro Ile Phe Met Tyr Ala Pro
        355                 360                 365
```

```
Glu Phe Lys Phe Met Pro Pro Pro Thr Tyr Thr Glu Val Asp Pro Cys
        370             375                 380
Ile Leu Asn Asn Asn Val Gln
385                 390

<210> SEQ ID NO 2
<211> LENGTH: 105
<212> TYPE: PRT
<213> ORGANISM: Homo Sapiens

<400> SEQUENCE: 2

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Asp Cys Gln Asp
    50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 3
<211> LENGTH: 105
<212> TYPE: PRT
<213> ORGANISM: Artificial Sequence
<220> FEATURE:
<223> OTHER INFORMATION: TRX(C35A)

<400> SEQUENCE: 3

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
            20                  25                  30

Gly Pro Ala Lys Met Ile Lys Pro Phe Phe His Ser Leu Ser Glu Lys
        35                  40                  45

Tyr Ser Asn Val Ile Phe Leu Glu Val Asp Val Asp Asp Cys Gln Asp
    50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 4
<211> LENGTH: 315
<212> TYPE: PRT
<213> ORGANISM: Artificial Sequence
<220> FEATURE:
<223> OTHER INFORMATION: T-TXNIP

<400> SEQUENCE: 4

Met Phe Lys Lys Ile Lys Ser Phe Glu Val Val Phe Asn Asp Pro Glu
1               5                   10                  15
```

Lys Val Tyr Gly Ser Gly Glu Arg Val Ala Gly Arg Val Ile Val Glu
            20                  25                  30

Val Cys Glu Val Thr Arg Val Lys Ala Val Arg Ile Leu Ala Cys Gly
        35                  40                  45

Val Ala Lys Val Leu Trp Met Gln Gly Ser Gln Gln Cys Lys Gln Thr
    50                  55                  60

Ser Glu Tyr Leu Arg Tyr Glu Asp Thr Leu Leu Glu Asp Gln Pro
65                  70                  75                  80

Thr Gly Glu Asn Glu Met Val Ile Met Arg Pro Gly Asn Lys Tyr Glu
                85                  90                  95

Tyr Lys Phe Gly Phe Glu Leu Pro Gln Gly Pro Leu Gly Thr Ser Phe
            100                 105                 110

Lys Gly Lys Tyr Gly Cys Val Asp Tyr Trp Val Lys Ala Phe Leu Asp
        115                 120                 125

Arg Pro Ser Gln Pro Thr Gln Glu Thr Lys Lys Asn Phe Glu Val Val
    130                 135                 140

Asp Leu Val Asp Val Asn Thr Pro Asp Leu Met Ala Pro Val Ser Ala
145                 150                 155                 160

Lys Lys Glu Lys Lys Val Ser Cys Met Phe Ile Pro Asp Gly Arg Val
                165                 170                 175

Ser Val Ser Ala Arg Ile Asp Arg Lys Gly Phe Cys Glu Gly Asp Glu
            180                 185                 190

Ile Ser Ile His Ala Asp Phe Glu Asn Thr Cys Ser Arg Ile Val Val
        195                 200                 205

Pro Lys Ala Ala Ile Val Ala Arg His Thr Tyr Leu Ala Asn Gly Gln
    210                 215                 220

Thr Lys Val Leu Thr Gln Lys Leu Ser Ser Val Arg Gly Asn His Ile
225                 230                 235                 240

Ile Ser Gly Thr Cys Ala Ser Trp Arg Gly Lys Ser Leu Arg Val Gln
                245                 250                 255

Lys Ile Arg Pro Ser Ile Leu Gly Cys Asn Ile Leu Arg Val Glu Tyr
            260                 265                 270

Ser Leu Leu Ile Tyr Val Ser Val Pro Gly Ser Lys Lys Val Ile Leu
        275                 280                 285

Asp Leu Pro Leu Val Ile Gly Ser Arg Ser Gly Leu Ser Ser Arg Thr
    290                 295                 300

Ser Ser Met Ala Ser Arg Thr Ser Ser Glu Met
305                 310                 315

<210> SEQ ID NO 5
<211> LENGTH: 315
<212> TYPE: PRT
<213> ORGANISM: Artificial Sequence
<220> FEATURE:
<223> OTHER INFORMATION: T-TXNIP(C170S/C205S/C267S)

<400> SEQUENCE: 5

Met Phe Lys Lys Ile Lys Ser Phe Glu Val Val Phe Asn Asp Pro Glu
1               5                   10                  15

Lys Val Tyr Gly Ser Gly Glu Arg Val Ala Gly Arg Val Ile Val Glu
            20                  25                  30

Val Cys Glu Val Thr Arg Val Lys Ala Val Arg Ile Leu Ala Cys Gly
        35                  40                  45

Val Ala Lys Val Leu Trp Met Gln Gly Ser Gln Gln Cys Lys Gln Thr
    50                  55                  60

```
Ser Glu Tyr Leu Arg Tyr Glu Asp Thr Leu Leu Glu Asp Gln Pro
 65                  70                  75                  80

Thr Gly Glu Asn Glu Met Val Ile Met Arg Pro Gly Asn Lys Tyr Glu
                 85                  90                  95

Tyr Lys Phe Gly Phe Glu Leu Pro Gln Gly Pro Leu Gly Thr Ser Phe
            100                 105                 110

Lys Gly Lys Tyr Gly Cys Val Asp Tyr Trp Val Lys Ala Phe Leu Asp
        115                 120                 125

Arg Pro Ser Gln Pro Thr Gln Glu Thr Lys Lys Asn Phe Glu Val Val
130                 135                 140

Asp Leu Val Asp Val Asn Thr Pro Asp Leu Met Ala Pro Val Ser Ala
145                 150                 155                 160

Lys Lys Glu Lys Lys Val Ser Ser Met Phe Ile Pro Asp Gly Arg Val
                165                 170                 175

Ser Val Ser Ala Arg Ile Asp Arg Lys Gly Phe Cys Glu Gly Asp Glu
            180                 185                 190

Ile Ser Ile His Ala Asp Phe Glu Asn Thr Ser Ser Arg Ile Val Val
        195                 200                 205

Pro Lys Ala Ala Ile Val Ala Arg His Thr Tyr Leu Ala Asn Gly Gln
210                 215                 220

Thr Lys Val Leu Thr Gln Lys Leu Ser Ser Val Arg Gly Asn His Ile
225                 230                 235                 240

Ile Ser Gly Thr Cys Ala Ser Trp Arg Gly Lys Ser Leu Arg Val Gln
                245                 250                 255

Lys Ile Arg Pro Ser Ile Leu Gly Ser Asn Ile Leu Arg Val Glu Tyr
            260                 265                 270

Ser Leu Leu Ile Tyr Val Ser Val Pro Gly Ser Lys Lys Val Ile Leu
        275                 280                 285

Asp Leu Pro Leu Val Ile Gly Ser Arg Ser Gly Leu Ser Ser Arg Thr
290                 295                 300

Ser Ser Met Ala Ser Arg Thr Ser Ser Glu Met
305                 310                 315

<210> SEQ ID NO 6
<211> LENGTH: 315
<212> TYPE: PRT
<213> ORGANISM: Artificial Sequence
<220> FEATURE:
<223> OTHER INFORMATION: T-TXNIP(C120S/C170S/C205S/C267S)

<400> SEQUENCE: 6

Met Phe Lys Lys Ile Lys Ser Phe Glu Val Val Phe Asn Asp Pro Glu
  1               5                  10                  15

Lys Val Tyr Gly Ser Gly Glu Arg Val Ala Gly Arg Val Ile Val Glu
             20                  25                  30

Val Cys Glu Val Thr Arg Val Lys Ala Val Arg Ile Leu Ala Cys Gly
         35                  40                  45

Val Ala Lys Val Leu Trp Met Gln Gly Ser Gln Gln Cys Lys Gln Thr
     50                  55                  60

Ser Glu Tyr Leu Arg Tyr Glu Asp Thr Leu Leu Glu Asp Gln Pro
 65                  70                  75                  80

Thr Gly Glu Asn Glu Met Val Ile Met Arg Pro Gly Asn Lys Tyr Glu
                 85                  90                  95

Tyr Lys Phe Gly Phe Glu Leu Pro Gln Gly Pro Leu Gly Thr Ser Phe
            100                 105                 110
```

```
Lys Gly Lys Tyr Gly Ser Val Asp Tyr Trp Val Lys Ala Phe Leu Asp
            115                 120                 125

Arg Pro Ser Gln Pro Thr Gln Glu Thr Lys Lys Asn Phe Glu Val Val
130                 135                 140

Asp Leu Val Asp Val Asn Thr Pro Asp Leu Met Ala Pro Val Ser Ala
145                 150                 155                 160

Lys Lys Glu Lys Lys Val Ser Ser Met Phe Ile Pro Asp Gly Arg Val
                165                 170                 175

Ser Val Ser Ala Arg Ile Asp Arg Lys Gly Phe Cys Glu Gly Asp Glu
            180                 185                 190

Ile Ser Ile His Ala Asp Phe Glu Asn Thr Ser Ser Arg Ile Val Val
        195                 200                 205

Pro Lys Ala Ala Ile Val Ala Arg His Thr Tyr Leu Ala Asn Gly Gln
    210                 215                 220

Thr Lys Val Leu Thr Gln Lys Leu Ser Ser Val Arg Gly Asn His Ile
225                 230                 235                 240

Ile Ser Gly Thr Cys Ala Ser Trp Arg Gly Lys Ser Leu Arg Val Gln
                245                 250                 255

Lys Ile Arg Pro Ser Ile Leu Gly Ser Asn Ile Leu Arg Val Glu Tyr
            260                 265                 270

Ser Leu Leu Ile Tyr Val Ser Val Pro Gly Ser Lys Lys Val Ile Leu
        275                 280                 285

Asp Leu Pro Leu Val Ile Gly Ser Arg Ser Gly Leu Ser Ser Arg Thr
    290                 295                 300

Ser Ser Met Ala Ser Arg Thr Ser Ser Glu Met
305                 310                 315

<210> SEQ ID NO 7
<211> LENGTH: 154
<212> TYPE: PRT
<213> ORGANISM: Artificial Sequence
<220> FEATURE:
<223> OTHER INFORMATION: N-TXNIP

<400> SEQUENCE: 7

Met Phe Lys Lys Ile Lys Ser Phe Glu Val Val Phe Asn Asp Pro Glu
1               5                   10                  15

Lys Val Tyr Gly Ser Gly Glu Arg Val Ala Gly Arg Val Ile Val Glu
            20                  25                  30

Val Cys Glu Val Thr Arg Val Lys Ala Val Arg Ile Leu Ala Cys Gly
        35                  40                  45

Val Ala Lys Val Leu Trp Met Gln Gly Ser Gln Gln Cys Lys Gln Thr
    50                  55                  60

Ser Glu Tyr Leu Arg Tyr Glu Asp Thr Leu Leu Leu Glu Asp Gln Pro
65                  70                  75                  80

Thr Gly Glu Asn Glu Met Val Ile Met Arg Pro Gly Asn Lys Tyr Glu
                85                  90                  95

Tyr Lys Phe Gly Phe Glu Leu Pro Gln Gly Pro Leu Gly Thr Ser Phe
            100                 105                 110

Lys Gly Lys Tyr Gly Cys Val Asp Tyr Trp Val Lys Ala Phe Leu Asp
        115                 120                 125

Arg Pro Ser Gln Pro Thr Gln Glu Thr Lys Lys Asn Phe Glu Val Val
    130                 135                 140

Asp Leu Val Asp Val Asn Thr Pro Asp Leu
145                 150
```

<210> SEQ ID NO 8
<211> LENGTH: 154
<212> TYPE: PRT
<213> ORGANISM: Artificial Sequence
<220> FEATURE:
<223> OTHER INFORMATION: N-TXNIP(K5A/K6A)

<400> SEQUENCE: 8

```
Met Phe Ala Ala Ile Lys Ser Phe Glu Val Val Phe Asn Asp Pro Glu
 1               5                  10                  15

Lys Val Tyr Gly Ser Gly Glu Arg Val Ala Gly Arg Val Ile Val Glu
             20                  25                  30

Val Cys Glu Val Thr Arg Val Lys Ala Val Arg Ile Leu Ala Cys Gly
         35                  40                  45

Val Ala Lys Val Leu Trp Met Gln Gly Ser Gln Gln Cys Lys Gln Thr
     50                  55                  60

Ser Glu Tyr Leu Arg Tyr Glu Asp Thr Leu Leu Glu Asp Gln Pro
 65                  70                  75                  80

Thr Gly Glu Asn Glu Met Val Ile Met Arg Pro Gly Asn Lys Tyr Glu
                 85                  90                  95

Tyr Lys Phe Gly Phe Glu Leu Pro Gln Gly Pro Leu Gly Thr Ser Phe
            100                 105                 110

Lys Gly Lys Tyr Gly Cys Val Asp Tyr Trp Val Lys Ala Phe Leu Asp
        115                 120                 125

Arg Pro Ser Gln Pro Thr Gln Glu Thr Lys Lys Asn Phe Glu Val Val
    130                 135                 140

Asp Leu Val Asp Val Asn Thr Pro Asp Leu
145                 150
```

<210> SEQ ID NO 9
<211> LENGTH: 1176
<212> TYPE: DNA
<213> ORGANISM: Homo Sapiens

<400> SEQUENCE: 9

| | | |
|---|---|---|
| atggtgatgt tcaagaagat caagtctttt gaggtggtct ttaacgaccc tgaaaaggtg | 60 |
| tacggcagtg gcgagagggt ggctggccgg gtgatagtgg aggtgtgtga agttactcgt | 120 |
| gtcaaagccg ttaggatcct ggcttgcgga gtggctaaag tgctttggat gcagggatcc | 180 |
| cagcagtgca aacagacttc ggagtacctg cgctatgaag acacgcttct tctggaagac | 240 |
| cagccaacag gtgagaatga gatggtgatc atgagacctg gaaacaaata tgagtacaag | 300 |
| ttcggctttg agcttcctca ggggcctctg gaacatcctc tcaaaggaaa atatgggtgt | 360 |
| gtagactact gggtgaaggc ttttcttgac cgcccgagcc agccaactca agagacaaag | 420 |
| aaaaactttg aagtagtgga tctggtggat gtcaataccc ctgatttaat ggcacctgtg | 480 |
| tctgctaaaa aagaaaagaa agtttcctgc atgttcattc ctgatgggcg ggtgtctgtc | 540 |
| tctgctcgaa ttgacagaaa aggattctgt gaaggtgatg agatttccat ccatgctgac | 600 |
| tttgagaata catgttcccg aattgtggtc cccaaagctg ccattgtggc ccgccacact | 660 |
| taccttgcca atggccagac caaggtgctg actcagaagt tgtcatcagt cagaggcaat | 720 |
| catattatct cagggacatg cgcatcatgg cgtggcaaga gccttcgggt tcagaagatc | 780 |
| aggccttcta tcctgggctg caacatcctt cgagttgaat attccttact gatctatgtt | 840 |
| agcgttcctg gatccaagaa ggtcatcctt gacctgcccc tggtaattgg cagcagatca | 900 |
| ggtctaagca gcagaacatc cagcatggcc agccgaacca gctctgagat gagttgggta | 960 |

-continued

| | |
|---|---|
| gatctgaaca tccctgatac cccagaagct cctccctgct atatggatgt cattcctgaa | 1020 |
| gatcaccgat tggagagccc aacaactcct ctgctagatg acatggatgg ctctcaagac | 1080 |
| agccctatct ttatgtatgc ccctgagttc aagttcatgc caccaccgac ttatactgag | 1140 |
| gtggatccct gcatcctcaa caacaatgtg cagtga | 1176 |

<210> SEQ ID NO 10
<211> LENGTH: 318
<212> TYPE: DNA
<213> ORGANISM: Homo Sapiens

<400> SEQUENCE: 10

| | |
|---|---|
| atggtgaagc agatcgagag caagactgct tttcaggaag ccttggacgc tgcaggtgat | 60 |
| aaacttgtag tagttgactt ctcagccacg tggtgtgggc cttgcaaaat gatcaagcct | 120 |
| ttctttcatt ccctctctga aaagtattcc aacgtgatat tccttgaagt agatgtggat | 180 |
| gactgtcagg atgttgcttc agagtgtgaa gtcaaatgca tgccaacatt ccagtttttt | 240 |
| aagaagggac aaaaggtggg tgaattttct ggagccaata ggaaaagct tgaagccacc | 300 |
| attaatgaat tagtctaa | 318 |

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11

| | |
|---|---|
| catgccatgg tcaagaagat caag | 24 |

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12

| | |
|---|---|
| ataagaatgc ggccgctcac atctcagagc tgg | 33 |

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13

| | |
|---|---|
| ggaattccat atggtgaagc agat | 24 |

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14

| | |
|---|---|
| ccgctcgagt cagactaatt cattaat | 27 |

<210> SEQ ID NO 15

<210> SEQ ID NO 15
<211> LENGTH: 41
<212> TYPE: DNA
<213> ORGANISM: Artificial Sequence
<220> FEATURE:
<223> OTHER INFORMATION: Primer

<400> SEQUENCE: 15
cagccacgtg gtgtgggcct gccaaaatga tcaagccttt c         41

<210> SEQ ID NO 16
<211> LENGTH: 41
<212> TYPE: DNA
<213> ORGANISM: Artificial Sequence
<220> FEATURE:
<223> OTHER INFORMATION: Primer

<400> SEQUENCE: 16
gaaaggcttg atcattttgg caggcccaca ccacgtggct g         41

<210> SEQ ID NO 17
<211> LENGTH: 39
<212> TYPE: DNA
<213> ORGANISM: Artificial Sequence
<220> FEATURE:
<223> OTHER INFORMATION: Primer

<400> SEQUENCE: 17
ttcaaaggaa aatatgggtc tgtagactac tgggtgaag            39

<210> SEQ ID NO 18
<211> LENGTH: 39
<212> TYPE: DNA
<213> ORGANISM: Artificial Sequence
<220> FEATURE:
<223> OTHER INFORMATION: Primer

<400> SEQUENCE: 18
cttcacccag tagtctacag acccatattt tcctttgaa            39

<210> SEQ ID NO 19
<211> LENGTH: 39
<212> TYPE: DNA
<213> ORGANISM: Artificial Sequence
<220> FEATURE:
<223> OTHER INFORMATION: Primer

<400> SEQUENCE: 19
aaagaaaaga agtttcctc catgttcatt cctgatggg             39

<210> SEQ ID NO 20
<211> LENGTH: 396
<212> TYPE: PRT
<213> ORGANISM: Mus musculus

<400> SEQUENCE: 20

Met Val Met Phe Lys Lys Ile Lys Ser Phe Glu Val Val Phe Asn Asp
 1               5                  10                  15

Pro Glu Lys Val Tyr Gly Ser Gly Glu Lys Val Ala Gly Arg Val Ile
            20                  25                  30

Val Glu Val Cys Glu Val Thr Arg Val Lys Ala Val Arg Ile Leu Ala
        35                  40                  45

Cys Gly Val Ala Lys Val Leu Trp Met Gln Gly Ser Gln Gln Cys Lys
    50                  55                  60

Gln Thr Leu Asp Tyr Leu Arg Tyr Glu Asp Thr Leu Leu Leu Glu Glu

```
                65                  70                  75                  80
        Gln Pro Thr Gly Glu Asn Glu Met Val Ile Met Arg Pro Gly Asn Lys
                            85                  90                  95

Tyr Glu Tyr Lys Phe Gly Phe Glu Leu Pro Gln Gly Pro Leu Gly Thr
                           100                 105                 110

Ser Phe Lys Gly Lys Tyr Gly Cys Val Asp Tyr Trp Val Lys Ala Phe
                           115                 120                 125

Leu Asp Arg Pro Ser Gln Pro Thr Gln Glu Ala Lys Lys Asn Phe Glu
                130                 135                 140

Val Met Asp Leu Val Asp Val Asn Thr Pro Asp Leu Met Ala Pro Val
        145                 150                 155                 160

Ser Ala Lys Lys Glu Lys Lys Val Ser Cys Met Phe Ile Pro Asp Gly
                            165                 170                 175

Arg Val Ser Val Ser Ala Arg Ile Asp Arg Lys Gly Phe Cys Glu Gly
                           180                 185                 190

Asp Asp Ile Ser Ile His Ala Asp Phe Glu Asn Thr Cys Ser Arg Ile
                           195                 200                 205

Val Val Pro Lys Ala Ala Ile Val Ala Arg His Thr Tyr Leu Ala Asn
                210                 215                 220

Gly Gln Thr Lys Val Phe Thr Gln Lys Leu Ser Ser Val Arg Gly Asn
        225                 230                 235                 240

His Ile Ile Ser Gly Thr Cys Ala Ser Trp Arg Gly Lys Ser Leu Arg
                            245                 250                 255

Val Gln Lys Ile Arg Pro Ser Ile Leu Gly Cys Asn Ile Leu Lys Val
                           260                 265                 270

Glu Tyr Ser Leu Leu Ile Tyr Val Ser Val Pro Gly Ser Lys Lys Val
                           275                 280                 285

Ile Leu Asp Leu Pro Leu Val Ile Gly Ser Arg Ser Gly Leu Ser Ser
                290                 295                 300

Arg Thr Ser Ser Met Ala Ser Arg Thr Ser Ser Glu Met Ser Trp Ile
        305                 310                 315                 320

Asp Leu Asn Ile Pro Asp Thr Pro Glu Ala Pro Pro Cys Tyr Met Asp
                            325                 330                 335

Ile Ile Pro Glu Asp His Arg Leu Glu Ser Pro Thr Thr Pro Leu Leu
                           340                 345                 350

Asp Asp Val Asp Asp Ser Gln Asp Ser Pro Ile Phe Met Tyr Ala Pro
                           355                 360                 365

Glu Phe Gln Phe Met Pro Pro Thr Tyr Thr Glu Val Asp Pro Cys
                370                 375                 380

Val Leu Asn Asn Asn Asn Asn Asn Asn Val Gln
        385                 390                 395

<210> SEQ ID NO 21
<211> LENGTH: 39
<212> TYPE: DNA
<213> ORGANISM: Artificial Sequence
<220> FEATURE:
<223> OTHER INFORMATION: Primer

<400> SEQUENCE: 21
gctgactttg agaatacatc ttcccgaatt gtggtcccc                            39

<210> SEQ ID NO 22
<211> LENGTH: 39
<212> TYPE: DNA
<213> ORGANISM: Artificial Sequence
```

```
<220> FEATURE:
<223> OTHER INFORMATION: Primer

<400> SEQUENCE: 22
ggggaccaca attcgggaag atgtattctc aaagtcagc                          39

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
aggccttcta tcctgggctc caacatcctt cgagttgaa                          39

<210> SEQ ID NO 24
<211> LENGTH: 39
<212> TYPE: DNA
<213> ORGANISM: Artificial Sequence
<220> FEATURE:
<223> OTHER INFORMATION: Primer

<400> SEQUENCE: 24
ttcaactcga aggatgttgg agcccaggat agaaggcct                          39

<210> SEQ ID NO 25
<211> LENGTH: 396
<212> TYPE: PRT
<213> ORGANISM: Mus musculus

<400> SEQUENCE: 25
```

Met Val Met Phe Lys Lys Ile Lys Ser Phe Glu Val Val Phe Asn Asp
 1               5                  10                  15

Pro Glu Lys Val Tyr Gly Ser Gly Glu Lys Val Ala Gly Arg Val Ile
                20                  25                  30

Val Glu Val Cys Glu Val Thr Arg Val Lys Ala Val Arg Ile Leu Ala
            35                  40                  45

Cys Gly Val Ala Lys Val Leu Trp Met Gln Gly Ser Gln Gln Cys Lys
        50                  55                  60

Gln Thr Leu Asp Tyr Leu Arg Tyr Glu Asp Thr Leu Leu Glu Glu
 65                 70                  75                  80

Gln Pro Thr Gly Glu Asn Glu Met Val Ile Met Arg Pro Gly Asn Lys
                85                  90                  95

Tyr Glu Tyr Lys Phe Gly Phe Glu Leu Pro Gln Gly Pro Leu Gly Thr
            100                 105                 110

Ser Phe Lys Gly Lys Tyr Gly Cys Val Asp Tyr Trp Val Lys Ala Phe
        115                 120                 125

Leu Asp Arg Pro Ser Gln Pro Thr Gln Glu Ala Lys Lys Asn Phe Glu
    130                 135                 140

Val Met Asp Leu Val Asp Val Asn Thr Pro Asp Leu Met Ala Pro Val
145                 150                 155                 160

Ser Ala Lys Lys Glu Lys Lys Val Ser Cys Met Phe Ile Pro Asp Gly
                165                 170                 175

Arg Val Ser Val Ser Ala Arg Ile Asp Arg Lys Gly Phe Cys Glu Gly
            180                 185                 190

Asp Asp Ile Ser Ile His Ala Asp Phe Glu Asn Thr Cys Ser Arg Ile
        195                 200                 205

Val Val Pro Lys Ala Ala Ile Val Ala Arg His Thr Tyr Leu Ala Asn

```
              210                 215                 220
Gly Gln Thr Lys Val Phe Thr Gln Lys Leu Ser Ser Val Arg Gly Asn
225                 230                 235                 240

His Ile Ile Ser Gly Thr Cys Ala Ser Trp Arg Gly Lys Ser Leu Arg
                245                 250                 255

Val Gln Lys Ile Arg Pro Ser Ile Leu Gly Cys Asn Ile Leu Lys Val
                260                 265                 270

Glu Tyr Ser Leu Leu Ile Tyr Val Ser Val Pro Gly Ser Lys Lys Val
            275                 280                 285

Ile Leu Asp Leu Pro Leu Val Ile Gly Ser Arg Ser Gly Leu Ser Ser
        290                 295                 300

Arg Thr Ser Ser Met Ala Ser Arg Thr Ser Ser Glu Met Ser Trp Ile
305                 310                 315                 320

Asp Leu Asn Ile Pro Asp Thr Pro Glu Ala Pro Pro Cys Tyr Met Asp
                325                 330                 335

Ile Ile Pro Glu Asp His Arg Leu Glu Ser Pro Thr Thr Pro Leu Leu
            340                 345                 350

Asp Asp Val Asp Asp Ser Gln Asp Ser Pro Ile Phe Met Tyr Ala Pro
        355                 360                 365

Glu Phe Gln Phe Met Pro Pro Thr Tyr Thr Glu Val Asp Pro Cys
370                 375                 380

Val Leu Asn Asn Asn Asn Asn Asn Asn Val Gln
385                 390                 395

<210> SEQ ID NO 26
<211> LENGTH: 396
<212> TYPE: PRT
<213> ORGANISM: Salmo salar

<400> SEQUENCE: 26

Met Val Val Met Ser Lys Thr Val Lys Thr Phe Glu Val Ile Phe Ser
1               5                   10                  15

Asp Pro Ser Lys Thr Phe Tyr Cys Ser Gly Asp Lys Val Ala Gly Lys
                20                  25                  30

Ile Leu Val Glu Val Ala Glu Val Thr Arg Val Ser Ala Met Lys Val
            35                  40                  45

Leu Gly Val Gly Cys Ala Lys Val Glu Tyr Ala Lys Gly Lys Gln Lys
        50                  55                  60

Cys Arg Glu Glu Asn Glu Tyr Leu Arg Tyr Glu Glu Val Val Gln Leu
65                  70                  75                  80

Asp Asp His Pro Ala Asp His Asp Gly Ser Val Ile Leu Arg Pro Gly
                85                  90                  95

Asn Lys Tyr Glu Tyr Met Phe Gly Phe Glu Leu Pro Gln Gln Gly Gln
            100                 105                 110

Ile Val Ser Ser Tyr Lys Gly Lys Phe Gly Tyr Val Gln Tyr Tyr Val
        115                 120                 125

Lys Ala Phe Met Glu Arg Pro Ala Gln Pro Ala Leu Glu Cys Lys Lys
    130                 135                 140

His Phe Glu Val Glu Pro Leu Asp Val Asn Thr Pro Asp Leu Leu
145                 150                 155                 160

Ser Pro Thr Gly Gly Met Lys Glu Lys Lys Val Thr Cys Met Phe Ile
                165                 170                 175

Pro Asp Gly Gln Val Ser Leu Asn Ala Lys Ile Asp Arg Lys Gly Phe
            180                 185                 190
```

```
Cys Glu Gly Glu Asp Ile Cys Ile Cys Ala Lys Phe Glu Asn Thr Cys
            195                 200                 205

Ser Arg Ile Val Ile Pro Lys Ala Ala Ile Ile Ser Lys His Thr Tyr
210                 215                 220

Gln Ala Asn Gly Arg Thr Lys Val Phe Arg Gln Lys Leu Ser Ser Val
225                 230                 235                 240

Arg Gly Asn His Ile Ile Ser Gly Met Cys Asp Ala Trp Gln Gly Lys
            245                 250                 255

Thr Ile Arg Val Pro Lys Ile Lys Pro Ser Met Leu Gly Cys Asn Ile
            260                 265                 270

Ile Arg Val Glu Tyr Ala Leu Met Ile Tyr Met His Ile Pro Gly Ser
            275                 280                 285

Glu Lys Leu Ile Leu Glu Leu Pro Leu Val Ile Gly Thr Ala Gly Leu
290                 295                 300

Gly Ser Arg Thr Asn Ser Met Ser Ser Thr Asp Gly Ser Val Ser Asn
305                 310                 315                 320

Ala Ser Ala Ser Trp Val Ser Leu Arg Met Pro Ser Ala Pro Pro Ser
            325                 330                 335

Tyr Cys Asp Val Thr Arg Asp Cys Arg Leu Asp Gln Pro Leu Thr Pro
            340                 345                 350

Leu Leu Asn Asp Tyr Asp Gly Asp Ser Pro Ile Phe Met His Ala
            355                 360                 365

Ser Ala Phe Gln Phe Pro Asn Leu Pro Ala Tyr Ser Glu Val Asp Glu
370                 375                 380

Glu Phe Ser Gly Asn Ala His Met Leu Gln Val Cys
385                 390                 395

<210> SEQ ID NO 27
<211> LENGTH: 400
<212> TYPE: PRT
<213> ORGANISM: Danio rerio

<400> SEQUENCE: 27

Met Val Ala Met Thr Lys Arg Val Lys Val Phe Glu Ile Ala Phe Asn
1               5                   10                  15

Asp Pro Ser Lys Thr Phe Tyr Cys Ser Gly Asp Lys Val Ala Gly Lys
            20                  25                  30

Val Leu Val Glu Val Ser Glu Val Thr Arg Val Met Ala Met Lys Val
        35                  40                  45

Leu Gly Val Gly Cys Ala Lys Val Glu Tyr Ala Lys Gly Lys Gln Arg
    50                  55                  60

Cys Arg Glu Glu Val Asp Tyr Leu Lys Tyr Glu Asp Val Val Gln Leu
65                  70                  75                  80

Asp Glu His Pro Thr Asp Asn Asp Gly Ser Val Ile Leu Arg Pro Gly
            85                  90                  95

Asn Lys Tyr Glu Tyr Ser Phe Gly Phe Glu Leu Pro Ala Gln Gly Gln
            100                 105                 110

Leu Val Ser Ser Tyr Lys Gly Lys Phe Gly Phe Val Gln Tyr Tyr Val
        115                 120                 125

Lys Ala Leu Met Glu Arg Pro Cys Gln Pro Ala Leu Glu Cys Lys Lys
    130                 135                 140

His Phe Glu Val Glu Glu Pro Leu Asp Val Asn Thr Pro Asp Leu Leu
145                 150                 155                 160

Ser Pro Thr Gly Gly Met Lys Glu Lys Lys Val Thr Cys Met Phe Ile
            165                 170                 175
```

-continued

```
Pro Asp Gly Gln Val Ser Leu Asn Ala Lys Ile Asp Arg Arg Gly Phe
            180                 185                 190

Cys Glu Gly Glu Glu Ile Cys Ile Asp Ala Lys Phe Glu Asn Thr Cys
            195                 200                 205

Ser Arg Ile Val Val Pro Lys Ala Ala Ile Val Ala Lys Gln Thr Tyr
210                     215                 220

Gln Ala Asn Gly Arg Thr Lys Val Phe Arg Gln Lys Leu Ser Ser Val
225                 230                 235                 240

Arg Gly Asn His Ile Ile Ser Gly Met Cys Asp Ala Trp Gln Gly Lys
                245                 250                 255

Ser Ile Arg Val Pro Lys Ile Lys Pro Ser Ile Leu Gly Cys Asn Ile
            260                 265                 270

Ile Arg Val Glu Tyr Ala Leu Met Ile Tyr Met His Ile Pro Gly Ser
            275                 280                 285

Glu Lys Leu Ile Leu Glu Leu Pro Leu Val Ile Gly Thr Val Pro Tyr
    290                 295                 300

Asn Gly Phe Gly Ser Arg Thr Asn Ser Met Ser Ser Gln Asp Gly Ser
305                 310                 315                 320

Ile Ser Asn Ala Ser Asn Ser Trp Val Ser Leu Arg Met Pro Ser Ser
                325                 330                 335

Ala Pro Pro Ser Tyr Cys Asp Ile Thr Arg Asp Cys Cys Ile Asp Gln
            340                 345                 350

Pro Leu Thr Pro Leu Leu Asp Asp Tyr Asp Gly Gly Asp Ser Pro Ile
            355                 360                 365

Phe Met Asn Ala Ala Gln Phe Gln Phe Pro Pro Leu Pro Ala Tyr Ser
    370                 375                 380

Glu Val Glu Glu Glu Phe Asn Ala Asn Ala Arg Met Leu Pro Val Cys
385                 390                 395                 400
```